(12) United States Patent
Schnell et al.

(10) Patent No.: US 11,660,336 B2
(45) Date of Patent: May 30, 2023

(54) CORONAVIRUS DISEASE (COVID-19) VACCINE

(71) Applicant: Thomas Jefferson University, Philadelphia, PA (US)

(72) Inventors: Matthias Johannes Schnell, Harleysville, PA (US); Christoph Wirblich, Wernau (DE); Drishya Kurup, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 17/817,708

(22) Filed: Aug. 5, 2022

(65) Prior Publication Data

US 2023/0057428 A1 Feb. 23, 2023

Related U.S. Application Data

(62) Division of application No. 17/193,890, filed on Mar. 5, 2021, now Pat. No. 11,478,543.

(60) Provisional application No. 63/017,241, filed on Apr. 29, 2020, provisional application No. 62/986,396, filed on Mar. 6, 2020.

(51) Int. Cl.
| | |
|---|---|
| *A61K 39/215* | (2006.01) |
| *A61K 39/00* | (2006.01) |
| *A61K 39/42* | (2006.01) |
| *A61P 31/14* | (2006.01) |
| *C07K 16/10* | (2006.01) |
| *C12N 7/00* | (2006.01) |

(52) U.S. Cl.
CPC .............. *A61K 39/215* (2013.01); *C12N 7/00* (2013.01); *A61K 2039/5252* (2013.01); *A61K 2039/55572* (2013.01); *C12N 2760/20042* (2013.01); *C12N 2770/20034* (2013.01)

(58) Field of Classification Search
CPC ....... A61K 39/215; A61K 39/12; A61P 31/14; C12N 2770/20034; C12N 2760/16134
See application file for complete search history.

(56) References Cited

U.S. PATENT DOCUMENTS

2019/0062785 A1 2/2019 Johnson et al.

OTHER PUBLICATIONS

"International Search Report and Written Opinion dated Aug. 5, 2021 for International Appln. No. PCT/US21/21200".
Bhandari, et al., "A dose-escalation safety and immunogenicity study of live attenuated oral rotavirus vaccine 116E in infants: a randomized, double-blind, placebo-controlled trial", J Infect Dis., 200(3), Epub Jun. 24, 2009. doi: 10.1086/600104. PubMed PMID: 19545211, 2009, 421-9.
Bhandari, et al., "Efficacy of a monovalent human-bovine (116E) rotavirus vaccine in Indian children in the second year of life", Vaccine, 32 Suppl 1, doi: 10.1016/j.vaccine.2014.04.079. PubMed PMID: 25091663; PMCID: 25091663, 2014, A110-6.
Bhandari, et al., "Efficacy of a monovalent human-bovine (116E) rotavirus vaccine in Indian infants: a randomised, double-blind, placebo-controlled trial", Lancet, 383(9935), Epub Mar. 19, 2014. doi: 10.1016/s0140-6736(13)62630-6. PubMed PMID: 24629994; PMCID: PMC4532697, 2014, 2136-43.
Bhandari, et al., "Safety and immunogenicity of two live attenuated human rotavirus vaccine candidates, 116E and 321, in infants: results of a randomised controlled trial", Vaccine., 24(31-32), Epub Jun. 1, 2006. doi: 10.1016/j.vaccine.2006.05.001. PubMed PMID: 16735085, 2006, 5817-23.
Blaney, et al., "Antibody quality and protection from lethal Ebola virus challenge in nonhuman primates immunized with rabies virus based bivalent vaccine", PLoS pathogens, 9(5):e1003389. doi: 10.1371/journal.ppat.1003389. PubMed PMID: 23737747; PMCID: 3667758., 2013.
Blaney, et al., "Inactivated or live-attenuated bivalent vaccines that confer protection against rabies and Ebola viruses", J Virol., 85(20), Epub Aug. 19, 2011. doi: 10.1128/JVI.00558-11. PubMed PMID: 21849459; PMCID: 3187516., 2011, 10605-16.
Burkard, et al., "Coronavirus cell entry occurs through the endo-/lysosomal pathway in a proteolysis-dependent manner", PLoS pathogens, 10(11):e1004502. doi: 10.1371/journal.ppat.1004502. PubMed PMID: 25375324; PMCID: PMC422306, 2014.
Conzelmann, et al., "Molecular cloning and complete nucleotide sequence of the attenuated rabies virus SAD B19", Virology, 175(2), PubMed PMID: 2139267, 1990, 485-99.
Hudacek, et al., "Recombinant rabies virus particles presenting botulinum neurotoxin antigens elicit a protective humoral response

(56) References Cited

OTHER PUBLICATIONS

McGettigan, et al., "Functional human immunodeficiency virus type 1 (HIV-1) Gag-Pol or HIV-1 Gag-Pol and env expressed from a single rhabdovirus-based vaccine vector genome", J Virol., 77(20), Epub Sep. 27, 2003. PubMed PMID: 14512539; PMCID: 224996, 2003, 10889-99.

McGettigan, et al., "Second-generation rabies virus-based vaccine vectors expressing human immunodeficiency virus type 1 gag have greatly reduced pathogenicity but are highly immunogenic", J Virol.,77(1), Epub Dec. 13, 2002. PubMed PMID: 12477829; PMCID: 140592, 2003, 237-44.

Mohan, et al., "Safety and immunogenicity of a Vi polysaccharide-tetanus toxoid conjugate vaccine (Typbar-TCV) in healthy infants, children, and adults in typhoid endemic areas: a multicenter, 2-cohort, open-label, double-blind, randomized controlled phase 3 study", Clinical infectious diseases: an official publication of the Infectious Diseases Society of America, 61(3), Epub Apr. 15, 2015. doi: 10.1093/cid/civ295. PubMed PMID: 25870324, 2015, 393-402.

Muthumani, et al., "A synthetic consensus anti-spike protein DNA vaccine induces protective immunity against Middle East respiratory syndrome coronavirus in nonhuman primates", Sci Transl Med., 7(301):301ra132. doi: 10.1126/scitranslmed.aac7462. PubMed PMID: 26290414; PMCID: PMC4573558, 2015.

Papaneri, et al., "Alanine scanning of the rabies virus glycoprotein antigenic site III using recombinant rabies virus: implication for post-exposure treatment", Vaccine, 31(49), Epub Oct. 15, 2013. doi: 10.1016/j.vaccine.2013.09.038. PubMed PMID: 24120673, 2013, 5897-902.

Pfaller, et al., "Reverse genetics of Mononegavirales: How they work, new vaccines, and new cancer therapeutics", Virology, 479-480, doi: 10.1016/j.virol.2015.01.029. PubMed PMID: 25702088; PMCID: 4557643, 331-44.

Raj, et al., "Dipeptidyl peptidase 4 is a functional receptor for the emerging human coronavirus-EMC", Nature, 495 (7440), doi: 10.1038/nature12005. PubMed PMID: 23486063, 2013, 251-4.

Servat, et al., "A quantitative indirect ELISA to monitor the effectiveness of rabies vaccination in domestic and wild carnivores", J Immunol Methods., 318(1-2), doi: 10.1016/j.jim.2006.07.026. PubMed PMID: 17166510, 2007, 1-10.

Shakya, et al., "Phase 3 Efficacy Analysis of a Typhoid Conjugate Vaccine Trial in Nepal", New England Journal of Medicine, 381(23), doi: 10.1056/NEJMoa1905047, 2019, 2209-18.

Shi, et al., "Susceptibility of ferrets, cats, dogs, and other domesticated animals to SARS-coronavirus 2", Science, vol. 368, Issue 6494, May 29, 2020, 1016-1020.

Singh, et al., "A Japanese Encephalitis Vaccine From India Induces Durable and Cross-protective Immunity Against Temporally and Spatially Wide-ranging Global Field Strains", The Journal of Infectious Diseases, 212(5),. doi: 10.1093/infdis/jiv023, 2015, 715-25.

Sun, et al., "SARS-CoV-2 and SARS-CoV Spike-RBD Structure and Receptor Binding Comparison and Potential Implications on Neutralizing Antibody and Vaccine Development", bioRxiv, 1-18, Feb. 20, 2020 [online]. [Retrieved on Jun. 28, 2021]. Retrieved from the internet: <URL: https://www.biorxiv.org/contenUbiorxiv/early/2020/02/20/2020.02.16.951723.full.pdf>.

Vadrevu, et al., "Persistence of Immune Responses With an Inactivated Japanese Encephalitis Single-Dose Vaccine, JENVAC and Interchangeability With a Live-Attenuated Vaccine", The Journal of Infectious Diseases, doi: 10.1093/infdis/jiz672, 2019.

Volz, et al., "Protective Efficacy of Recombinant Modified Vaccinia Virus Ankara Delivering Middle East Respiratory Syndrome Coronavirus Spike Glycoprotein", J Virol., 89(16). doi: 10.1128/JVI.00614-15. PubMed PMID: 26018172; PMCID: PMC4524222, 2015, 8651-6.

Voysey, et al., "Seroefficacy of Vi Polysaccharide-Tetanus Toxoid Typhoid Conjugate Vaccine (Typbar TCV)", Clinical Infectious Diseases, 67(1), doi: 10.1093/cid/cix1145, 2018, 18-24.

Wasniewski, et al., "Evaluation of an ELISA to detect rabies antibodies in orally vaccinated foxes and raccoon dogs sampled in the field", J Virol Methods, 187(2):264-70. doi: 10.1016/j.jviromet.2012.11.022. PubMed PMID: 23201293, 2013, 264-70.

Wasniewski, et al., "Evaluation of ELISA for detection of rabies antibodies in domestic carnivores", J Virol Methods., 179(1), doi: 10.1016/j.jviromet.2011.10.019. PubMed PMID: 22080853, 2012, 166-75.

Willet, et al., "Preclinical Development of Inactivated Rabies Virus-Based Polyvalent Vaccine Against Rabies and Filoviruses", J Infect Dis., 212 Suppl 2:. doi: 10.1093/infdis/jiv251. PubMed PMID: 26063224; PMCID: 4564550, 2015, S414-24.

Wirblich, et al., "One-Health: a Safe, Efficient, Dual-Use Vaccine for Humans and Animals against Middle East Respiratory Syndrome Coronavirus and Rabies Virus", Journal of virology, 91(2). Epub Nov. 4, 2016. doi: 10.1128/JVI.02040-16. PubMed PMID: 27807241; PMCID: PMC5215356, 2017.

Zhao, et al., "Rapid generation of a mouse model for Middle East respiratory syndrome", Proc Natl Acad Sci U S A., 111(13), Epub Mar. 7, 2014. doi: 10.1073/pnas.1323279111. PubMed PMID: 24599590; PMCID: 3977243, 2014, 4970-5.

FIG. 1

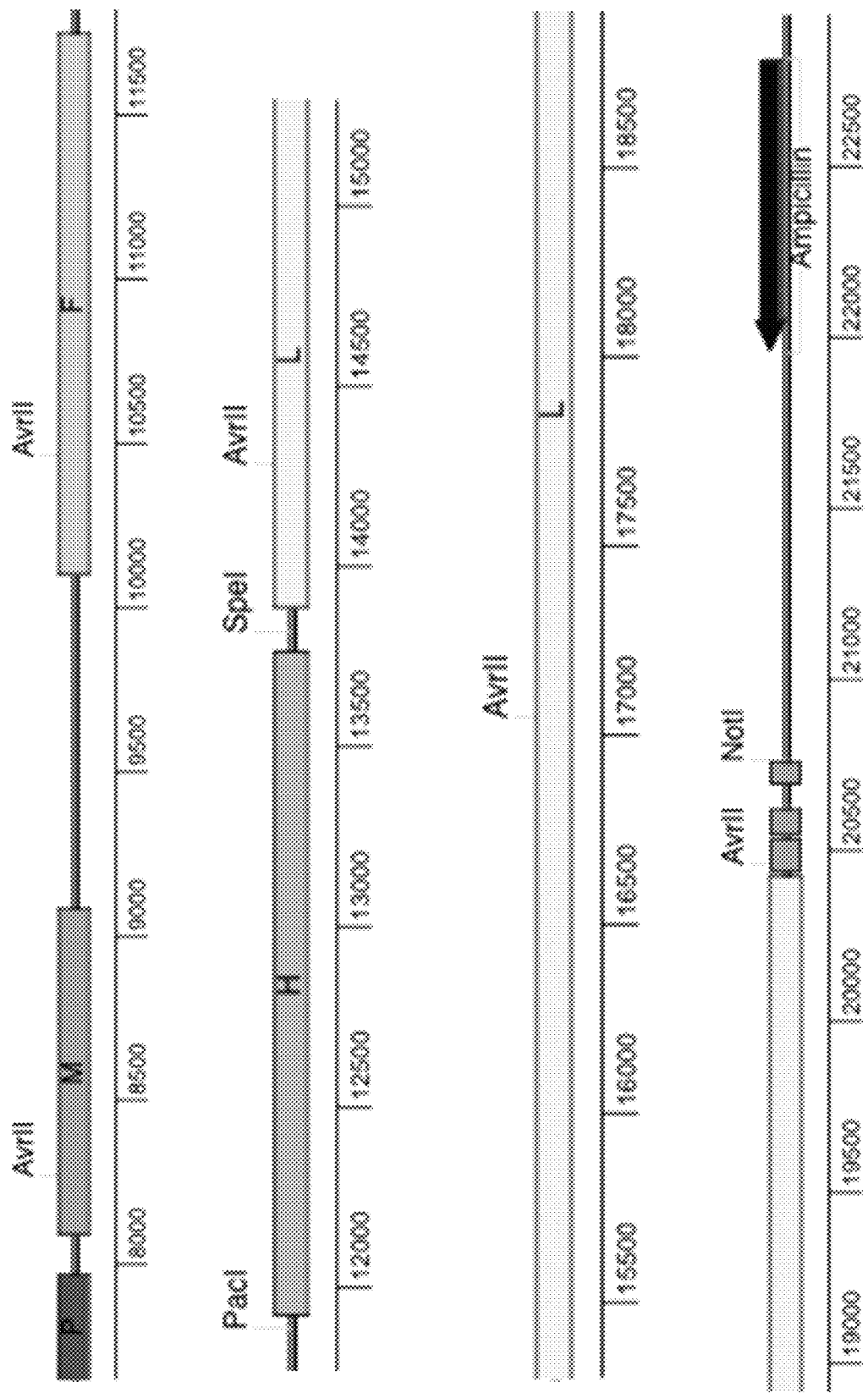
FIG. 3 - continued

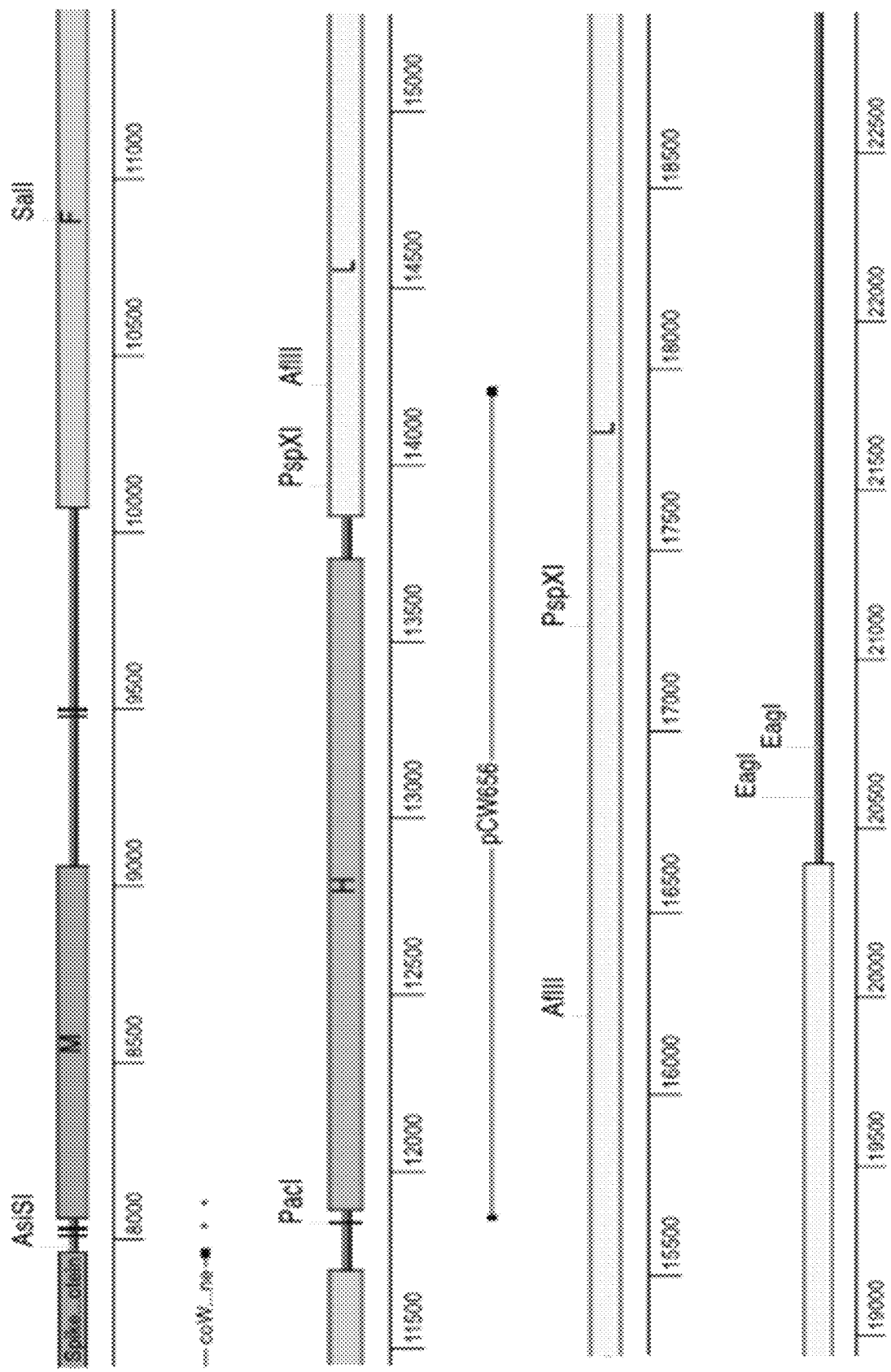
FIG. 4 - continued

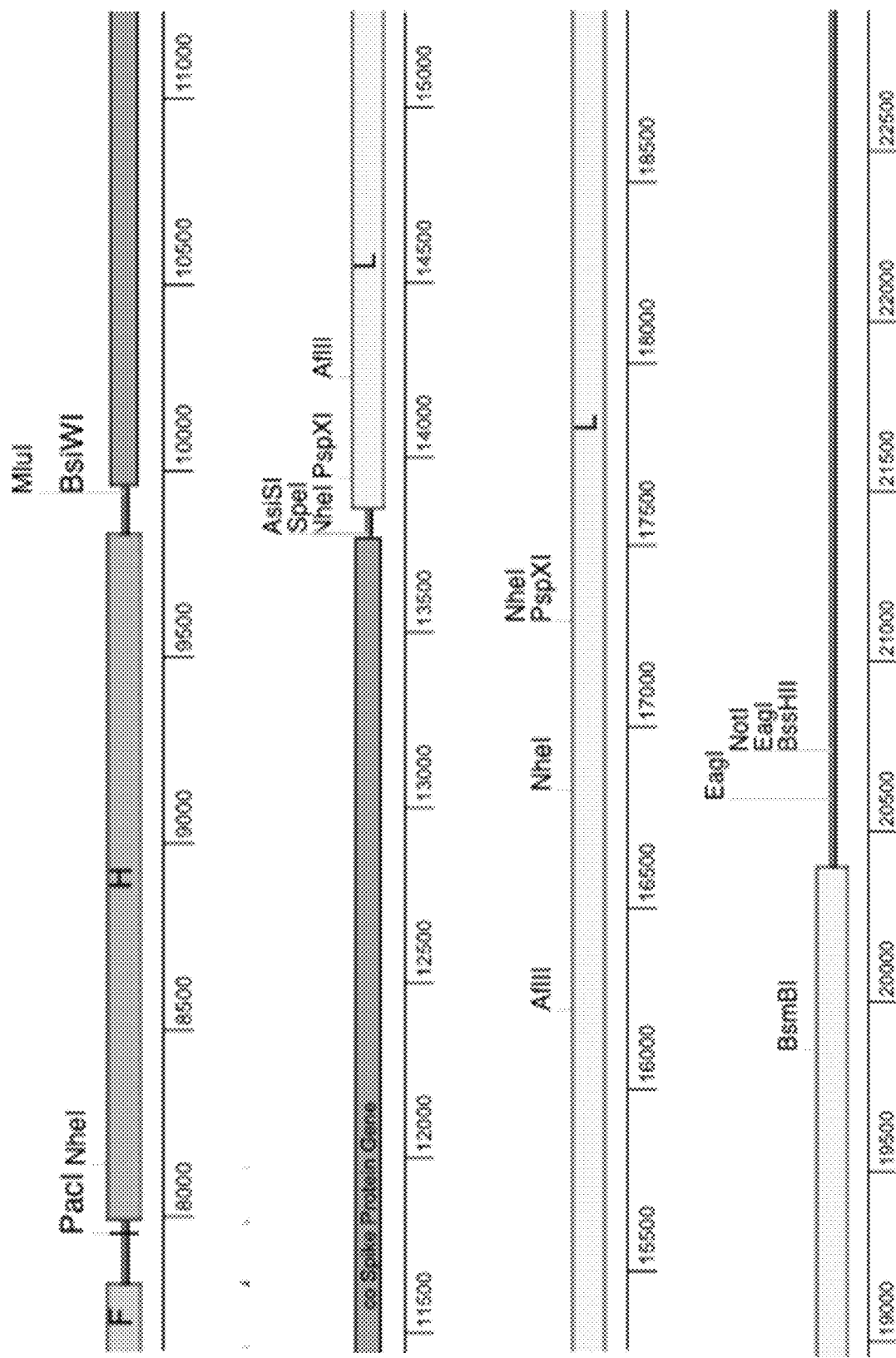
FIG. 5 - continued

| Show | | Type | Name | Range | Strand | Length | Description |
|---|---|---|---|---|---|---|---|
| ✓ | | misc_feature | Ampicillin | complement (16204..17061) | ◀ | 858 | Ampicillin |
| ✓ | | misc_feature | CMV promoter | 626..1206 | ▶ | 581 | CMV promoter |
| ✓ | | misc_feature | CP1685M | 8023..8041 | ▶ | 19 | CP1685M |
| ✓ | | misc_feature | HH ribozyme | 1276..1323 | ▶ | 48 | HH ribozyme |
| ✓ | | misc_feature | HdR | 14799..14894 | ▶ | 96 | HdR |
| ✓ | | misc_feature | Leader | 1324..1386 | ▶ | 63 | Leader |
| | | insert | PCR 676B+677 | 1324..3397 | ▶ | 2074 | |
| ✓ | | insert | PCW469-1 | 8048..8257 | ▶ | 210 | |
| ✓ | | misc_feature | RP659M | complement (2085..2104) | ◀ | 20 | RP659M |
| ✓ | | misc_feature | RP660 | 5051..5070 | ▶ | 20 | RP660 |
| ✓ | | misc_feature | RP77 | complement (3496..3516) | ◀ | 21 | RP77 |
| ✓ | | misc_feature | Signal Peptide | 5996..6040 | ▶ | 45 | Signal Peptide |
| ✓ | | misc_feature | Stop | 2700..2706 | ▶ | 7 | Stop |
| ✓ | | misc_feature | Stop | 8351..8357 | ▶ | 7 | Stop |
| ✓ | | misc_feature | T7 | 1238..1258 | ▶ | 21 | T7 |
| ✓ | | misc_feature | T7Term | 14965..15012 | ▶ | 48 | T7Term |
| ✓ | | misc_feature | TM | 8125..8193 | ▶ | 69 | TM |
| ✓ | | misc_feature | Trailer | 14700..14798 | ▶ | 99 | Trailer |
| ✓ | | misc_feature | VP1F | 1710..1729 | ▶ | 20 | VP1F |
| ✓ | | misc_feature | VP2F | 2196..2215 | ▶ | 20 | VP2F |
| ✓ | | misc_feature | VP3F | 3229..3248 | ▶ | 20 | VP3F |
| ✓ | | misc_feature | VP4F | 3710..3729 | ▶ | 20 | VP4F |
| ✓ | | misc_feature | VP5F | 4227..4246 | ▶ | 20 | VP5F |
| ✓ | | misc_feature | VP6F | 4693..4713 | ▶ | 21 | VP6F |

FIG. 7

| | | | | | | | |
|---|---|---|---|---|---|---|---|
| ✓ | | misc_feature | VP7F | 5228..5247 | ▶ | 20 | VP7F |
| ✓ | | misc_feature | VP8F | 5692..5712 | ▶ | 21 | VP8F |
| ✓ | | misc_feature | VSV-G | 4401..5936 | ▶ | 1536 | VSV-G |
| ✓ | | misc_feature | VSV-G | 8048..8257 | ▶ | 210 | VSV-G |
| ✓ | | misc_feature | VSV-L | 8370..14699 | ▶ | 6330 | VSV-L |
| ✓ | | misc_feature | VSV-M | 3573..4262 | ▶ | 690 | VSV-M |
| ✓ | | misc_feature | VSV-N | 1387..2655 | ▶ | 1269 | VSV-N |
| ✓ | | misc_feature | VSV-P | 2719..3516 | ▶ | 798 | VSV-P |
| ✓ | | misc_feature | WuV-S-Fwd1184 | 7159..7178 | ▶ | 20 | WuV-S-Fwd1184 |
| ✓ | | misc_feature | WuV-S-Fwd1814 | 7789..7808 | ▶ | 20 | WuV-S-Fwd1814 |
| ✓ | | misc_feature | WuV-S-Fwd581 | 6556..6575 | ▶ | 20 | WuV-S-Fwd581 |
| ✓ | | misc_feature | WuV-S1 | 5996..8041 | ▶ | 2046 | WuV-S1 |

FIG. 7 - continued

| Show | Type | Name | Range | Strand | Length | Description |
|---|---|---|---|---|---|---|
| ✓ | misc_feature | Ampicillin | complement(16626..17483) | ▼ | 858 | Ampicillin |
|  | coverage_below | Below threshold | 2772..4270 | ▲ | 1499 |  |
| ✓ | misc_feature | CMV promoter | 626..1206 | ▲ | 581 | CMV promoter |
| ✓ | contig | Contig 1(1>gt | 2772..4270 | ▲ | 1499 |  |
| ✓ | misc_feature | G | 6979..8553 | ▲ | 1575 | G |
| ✓ | misc_feature | G-tail | 4834..5124 | ▲ | 291 | G-tail |
| ✓ | misc_feature | HH ribozyme | 1277..1323 | ▲ | 47 | HH ribozyme |
| ✓ | misc_signal | Hammerhead ribozyme | 1277..1323 | ▲ | 47 | self-splicing site |
| ✓ | misc_feature | HdR | 15231..15322 | ▲ | 92 | HdR |
| ✓ | misc_feature | Helix I | 1277..1284 | ▲ | 8 | Helix I |
| ✓ | misc_feature | Helix I | 1324..1331 | ▲ | 8 | Helix I |
| ✓ | misc_feature | Helix II | 1292..1295 | ▲ | 4 | Helix II |
| ✓ | misc_feature | Helix II | 1300..1303 | ▲ | 4 | Helix II |
| ✓ | misc_feature | Helix III | 1307..1312 | ▲ | 6 | Helix III |
| ✓ | misc_feature | Helix III | 1317..1322 | ▲ | 6 | Helix III |
| ✓ | misc_feature | L | 8716..15093 | ▲ | 6384 | L |
| ✓ | misc_feature | M | 6158..6766 | ▲ | 609 | M |
|  | coverage_one | One_strand | 3382..3538 | ▲ | 157 |  |
|  | coverage_once | Only_once | 3539..4270 | ▲ | 732 |  |
|  | coverage_once | Only_once | 2772..3381 | ▲ | 610 |  |

FIG. 8

| Feature | Name | Location | | Length | Name |
|---|---|---|---|---|---|
| misc_feature | p | 5176..6069 | ▲ | 894 | p |
| misc_feature | RP381 | 1383..1401 | ▲ | 19 | RP381 |
| misc_feature | RP951 | 2630..2657 | ▲ | 28 | RP951 |
| misc_feature | RP952M | complement(5216..5244) | ▼ | 29 | RP952M |
| misc_feature | RTP-1 qPCR primer | 1421..1460 | ▲ | 30 | RTP-1 qPCR primer |
| misc_feature | RV leader | 1324..1381 | ▲ | 58 | RV leader |
| misc_feature | SAD-N | 1394..2746 | ▲ | 1353 | SAD-N |
| 5UTR | SPBN leader | 1324..1393 | ▲ | 70 | SPBN leader |
| misc_feature | T7 | 1239..1255 | ▲ | 17 | T7 |
| misc_feature | T7 promoter | 1238..1258 | ▲ | 21 | T7 promoter |
| misc_feature | T7Term | 15387..15434 | ▲ | 48 | T7Term |
| misc_feature | TM | 4927..4992 | ▲ | 66 | TM |
| misc_feature | Trailer | 15100..15230 | ▲ | 131 | Trailer |
| misc_feature | WuS1-RABVG | 2782..5127 | ▲ | 2346 | WuS1-RABVG |
| insert | cSPBN | 987..1519 | ▲ | 533 | |
| insert | pBS-CMV-N2C-HdR | 620..986, 15261..15442 | ▲ | 549 | |
| insert | pCW367 | 1520..2771, 5129..15260 | ▲ | 11384 | |
| insert | pCW761-2 plasmid sequence | 2772..5128 | ▲ | 2357 | |
| misc_feature | qPCR T7 standard forward primer | 1371..1392 | ▲ | 22 | qPCR T7 standard forward primer |

FIG. 8 - continued

| Show | | Type | Name | Range | Strand | Length | Description |
|---|---|---|---|---|---|---|---|
| ✓ | | misc_feature | | 4555..4560 | ▶ | 6 | |
| ✓ | | misc_feature | | 4546..4551 | ▶ | 6 | |
| ✓ | | misc_feature | Ampicillin | complement (21955..22815) | ◀ | 861 | Ampicillin |
| ✓ | | misc_feature | CP1685M | complement (4530..4561) | ◀ | 32 | CP1685M |
| ✓ | | misc_feature | F | 10095..11756 | ▶ | 1662 | F |
| ✓ | | misc_feature | H | 11917..13770 | ▶ | 1854 | H |
| ✓ | | misc_feature | HH Ribozyme | 667..716 | ▶ | 50 | HH Ribozyme |
| ✓ | | misc_feature | L | 13880..20431 | ▶ | 6552 | L |
| ✓ | | misc_feature | M | 8084..9091 | ▶ | 1008 | M |
| | | insert | MV-GFP corrected | 824..2471 | ▶ | 1648 | |
| | | insert | MV-GFP corrected | 6336..6689 | ▶ | 354 | |
| ✓ | | misc_feature | MV33F | 19986..20005 | ▶ | 20 | MV33F |
| ✓ | | misc_feature | MV4F | 2158..2177 | ▶ | 20 | MV4F |
| ✓ | | misc_feature | MV5F | 6573..6591 | ▶ | 19 | MV5F |
| ✓ | | misc_feature | N | 824..2398 | ▶ | 1575 | N |
| ✓ | | misc_feature | P | 6453..7976 | ▶ | 1524 | P |
| ✓ | | misc_feature | RP1686P | 4542..4569 | ▶ | 28 | RP1686P |
| ✓ | | misc_feature | RP602 | complement (20729..20746) | ◀ | 18 | RP602 |
| ✓ | | misc_feature | Signal peptide | 2503..2547 | ▶ | 45 | Signal peptide |
| ✓ | | misc_feature | Spike Protein | 2503..6321 | ▶ | 3819 | Spike Protein |
| ✓ | | misc_feature | T7 TERM | 20688..20763 | ▶ | 76 | T7 TERM |
| ✓ | | misc_feature | T7 promoter | 629..645 | ▶ | 17 | T7 promoter |
| ✓ | | misc_feature | UTR | 20432..20540 | ▶ | 109 | UTR |
| ✓ | | misc_feature | UTR | 717..820 | ▶ | 104 | UTR |
| ✓ | | insert | coWuhan-Virus Spike protein Gene | 2490..6335 | ▶ | 3846 | |
| ✓ | | misc_feature | hHdVRzym | 20541..20626 | ▶ | 86 | hHdVRzym |

FIG. 9

| Show | Type | Name | Range | Strand | Length | Description |
|---|---|---|---|---|---|---|
| ✓ | misc_feature | | 3870..3889 | ▲ | 20 | |
| ✓ | misc_feature | Ampicillin | complement (21925..22785) | ▼ | 861 | Ampicillin |
| ✓ | misc_feature | F | 10065..11726 | ▲ | 1662 | F |
| ✓ | misc_feature | GE | 2450..2460 | ▲ | 11 | GE |
| ✓ | misc_feature | GE | 758..768 | ▲ | 11 | GE |
| ✓ | misc_feature | GE | 9477..9487 | ▲ | 11 | GE |
| ✓ | misc_feature | GE | 4097..4107 | ▲ | 11 | GE |
| ✓ | misc_feature | GE | 11853..11858 | ▲ | 6 | GE |
| ✓ | misc_feature | GE | 8008..8018 | ▲ | 11 | GE |
| ✓ | misc_feature | GE | 20460..20470 | ▲ | 11 | GE |
| ✓ | misc_feature | GS | 2464..2480 | ▲ | 17 | GS |
| ✓ | misc_feature | GS | 772..788 | ▲ | 17 | GS |
| ✓ | misc_feature | GS | 9491..9507 | ▲ | 17 | GS |
| ✓ | misc_feature | GS | 20474..20490 | ▲ | 17 | GS |
| ✓ | misc_feature | GS | 8022..8038 | ▲ | 17 | GS |
| ✓ | misc_feature | GS | 4111..4127 | ▲ | 17 | GS |
| ✓ | misc_feature | H | 11887..13740 | ▲ | 1854 | H |
| ✓ | misc_feature | HH Ribozyme | 667..716 | ▲ | 50 | HH Ribozyme |
| ✓ | misc_feature | L | 13850..20401 | ▲ | 6552 | L |
| ✓ | misc_feature | M | 8054..9061 | ▲ | 1008 | M |
| ✓ | insert | MV-GFP corrected | 2523..2759 | | 237 | |
| ✓ | insert | MV-GFP corrected | 824..2401 | | 1578 | |

FIG. 10

| | | | | | |
|---|---|---|---|---|---|
| V | misc_feature | MV33F | 19956..19975 | ▲ | 20 | MV33F |
| V | misc_feature | MV4F | 2158..2177 | ▲ | 20 | MV4F |
| V | misc_feature | MV5F | 2643..2661 | ▲ | 19 | MV5F |
| V | misc_feature | MV6F | 3147..3166 | ▲ | 20 | MV6F |
| V | misc_feature | MV7F | 3639..3658 | ▲ | 20 | MV7F |
| V | misc_feature | MV8F | 8030..8049 | ▲ | 20 | MV8F |
| V | misc_feature | MVPos3 Rev | complement (8093..8111) | ▼ | 19 | MVPos3 Rev |
| V | misc_feature | N | 824..2398 | ▲ | 1575 | N |
| V | misc_feature | P | 2523..4046 | ▲ | 1524 | P |
| V | insert | PCR 240-1 | 713..820 | ▲ | 108 | |
| V | insert | PCR 240-2 | 713..823 | ▲ | 111 | |
| V | insert | PCR 245-3 | 713..2401 | ▲ | 1689 | |
| V | insert | PCR 254 | 2523..2759 | ▲ | 237 | |
| V | insert | PCR238-1 | 20740..20743 | ▲ | 4 | |
| V | misc_feature | RP602 | complement (20699..20716) | ▼ | 18 | RP602 |
| V | misc_feature | Spike Protein | 4150..7968 | ▲ | 3819 | Spike Protein |
| V | misc_feature | T7 TERM | 20658..20733 | ▲ | 76 | T7 TERM |
| V | misc_feature | T7 promoter | 629..645 | ▲ | 17 | T7 promoter |
| V | misc_feature | UTR | 717..820 | ▲ | 104 | UTR |
| V | misc_feature | UTR | 20402..20510 | ▲ | 109 | UTR |
| V | insert | coWuhan-Virus Spike protein Gene | 4137..7982 | ▲ | 3846 | |
| V | misc_feature | hHdVRzym | 20511..20596 | ▲ | 86 | hHdVRzym |
| V | ins

| | | | | | |
|---|---|---|---|---|---|
| > | misc_feature | Ampicillin | | | Ampicillin |
| > | misc_feature | F | 6165..7826 | 861 | F |
| > | PCR_primer | GCAGAGACGCGTCTCACTTGGTCCTAAGTTTTTATAACAATG | complement (21925..22769) | 1662 | RP1418MMVIGRPCR |
| > | PCR_primer | GCTATAACGCGTATCACTTGGTCCTAAGTTTTTATAACAATG | complement (9900..9943) | 44 | RP1424 MV full length |
| > | misc_feature | GE | 758..768 | 44 | GE |
| > | misc_feature | GE | 2450..2460 | 11 | GE |
| > | misc_feature | GE | 4108..4118 | 11 | GE |
| > | misc_feature | GE | 5577..5587 | 11 | GE |
| > | misc_feature | GE | 7953..7958 | 6 | GE |
| > | misc_feature | GE | 20460..20470 | 11 | GE |
| > | misc_feature | GS | 5591..5607 | 17 | GS |
| > | misc_feature | GS | 4122..4138 | 17 | GS |
| > | misc_feature | GS | 20474..20490 | 17 | GS |
| > | misc_feature | GS | 2464..2480 | 17 | GS |
| > | misc_feature | GS | 772..788 | 17 | GS |
| > | misc_feature | H | 7987..9837 | 1851 | H |
| > | insert | H-MCS-L | 9813..9943, 13788..13791 | 135 | |
| > | misc_feature | HH Ribozyme | 667..716 | 50 | HH Ribozyme |
| > | misc_feature | L | 13850..20401 | 6552 | L |
| > | misc_feature | M | 4154..5161 | 1008 | M |
| > | insert | MV Wu S in position 3 | 9944..13787 | 3844 | |
| > | insert | MV-GFP corrected | 2523..2759 | 237 | |
| > | insert | MV-GFP corrected | 824..2401 | 1578 | |

FIG. 11

| | | | | | | | |
|---|---|---|---|---|---|---|---|
| ✓ | ◌ | misc_feature | MV33F | 19956..19975 | ▶ | 20 | MV33F |
| ✓ | ◌ | misc_feature | MV4F | 2158..2177 | ▶ | 20 | MV4F |
| ✓ | ◌ | misc_feature | MV5F | 2643..2661 | ▶ | 19 | MV5F |
| ✓ | ◌ | misc_feature | N | 824..2398 | ▶ | 1575 | N |
| ✓ | ◌ | misc_feature | P | 2523..4046 | ▶ | 1524 | P |
| ✓ | ◌ | insert | PCR 240-1 | 713..820 | ▶ | 108 | |
| ✓ | ◌ | insert | PCR 240-2 | 713..823 | ▶ | 111 | |
| | ◌ | insert | PCR 245-3 | 713..2401 | ▶ | 1689 | |
| ✓ | ◌ | insert | PCR 254 | 2523..2759 | ▶ | 237 | |
| ✓ | ◌ | insert | PCR238-1 | 20740..20743 | ▶ | 4 | |
| ✓ | ◌ | misc_feature | RP602 | complement (20699..20716) | ◀ | 18 | RP602 |
| ✓ | ◌ | misc_feature | T7 TERM | 20658..20733 | ▶ | 76 | T7 TERM |
| ✓ | ◌ | misc_feature | T7 promoter | 629..645 | ▶ | 17 | T7 promoter |
| ✓ | ◌ | PCR_primer | TATCACTCTGTGTGGACCTGGTTCCTAAGTTTTTTATAACAATG | complement (9900..9943) | ◀ | 44 | RP1433:MV PCR |
| ✓ | ◌ | misc_feature | UTR | 717..820 | ▶ | 104 | UTR |
| ✓ | ◌ | misc_feature | UTR | 20402..20510 | ▶ | 109 | UTR |
| ✓ | ◌ | misc_feature | co Spike Protein Gene | 9957..13775 | ▶ | 3819 | co Spike Protein Gene |
| ✓ | ◌ | insert | coWuhan-Virus Spike protein Gene | 9944..13787 | ▶ | 3844 | |
| ✓ | ◌ | misc_feature | hHdVRzym | 20511..20596 | ▶ | 86 | hHdVRzym |
| ✓ | ◌ | insert | pCW640D1 | 2402..2522 | ▶ | 121 | |
| | ◌ | insert | pCW661 | 7959..9943, 13788..13791 | ▶ | 1989 | |

FIG. 11 - continued

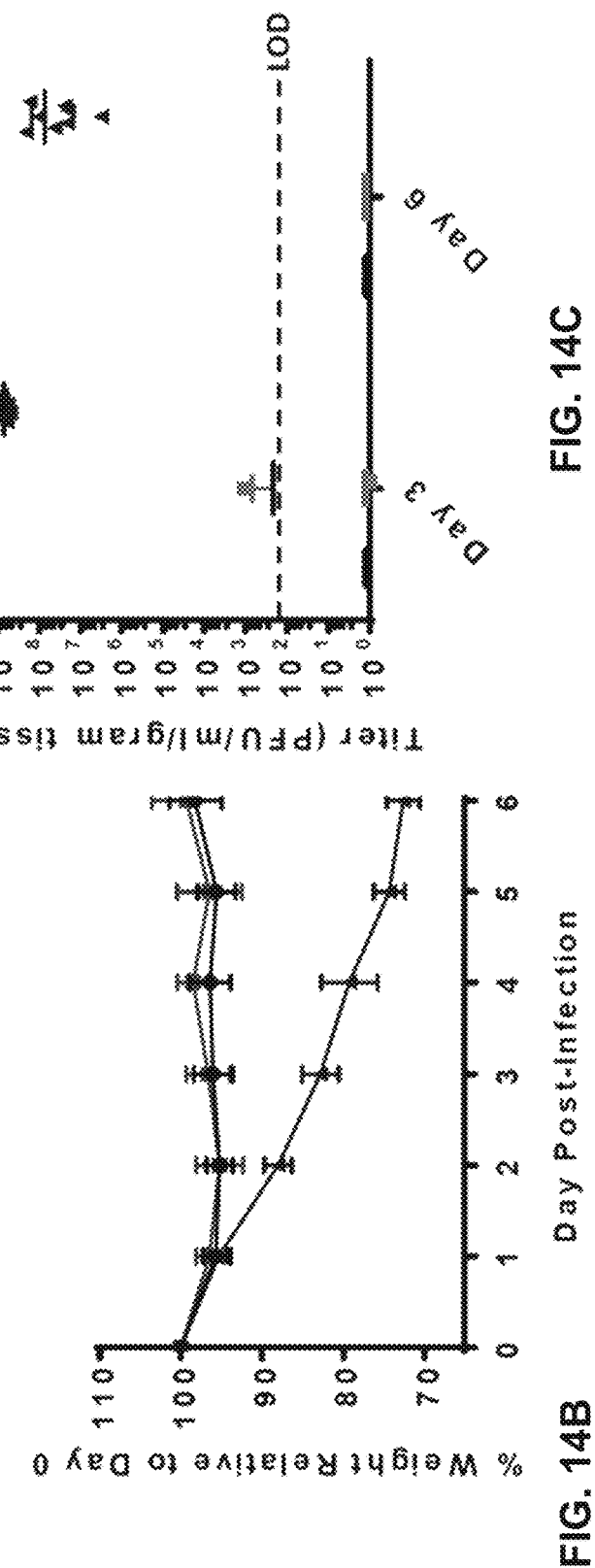
FIG. 14A
FIG. 14B
FIG. 14C

BBV151 Vaccine Presentations

BBV151 Vaccine Presentations

Antigen+SEPIVAC SWE (pre-mixed)

FIG. 17 – continued

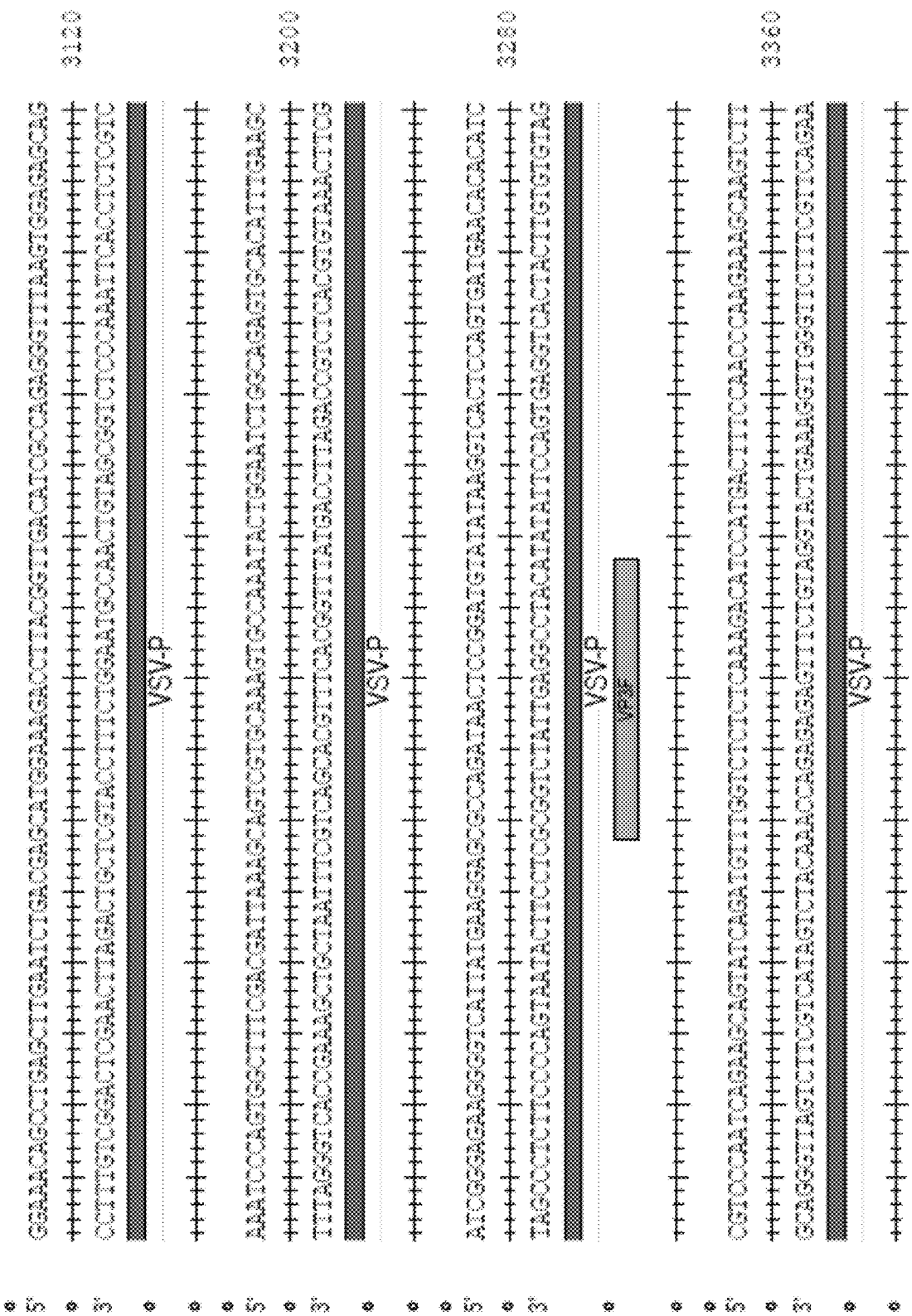
FIG. 17 – continued

FIG. 17 – continued

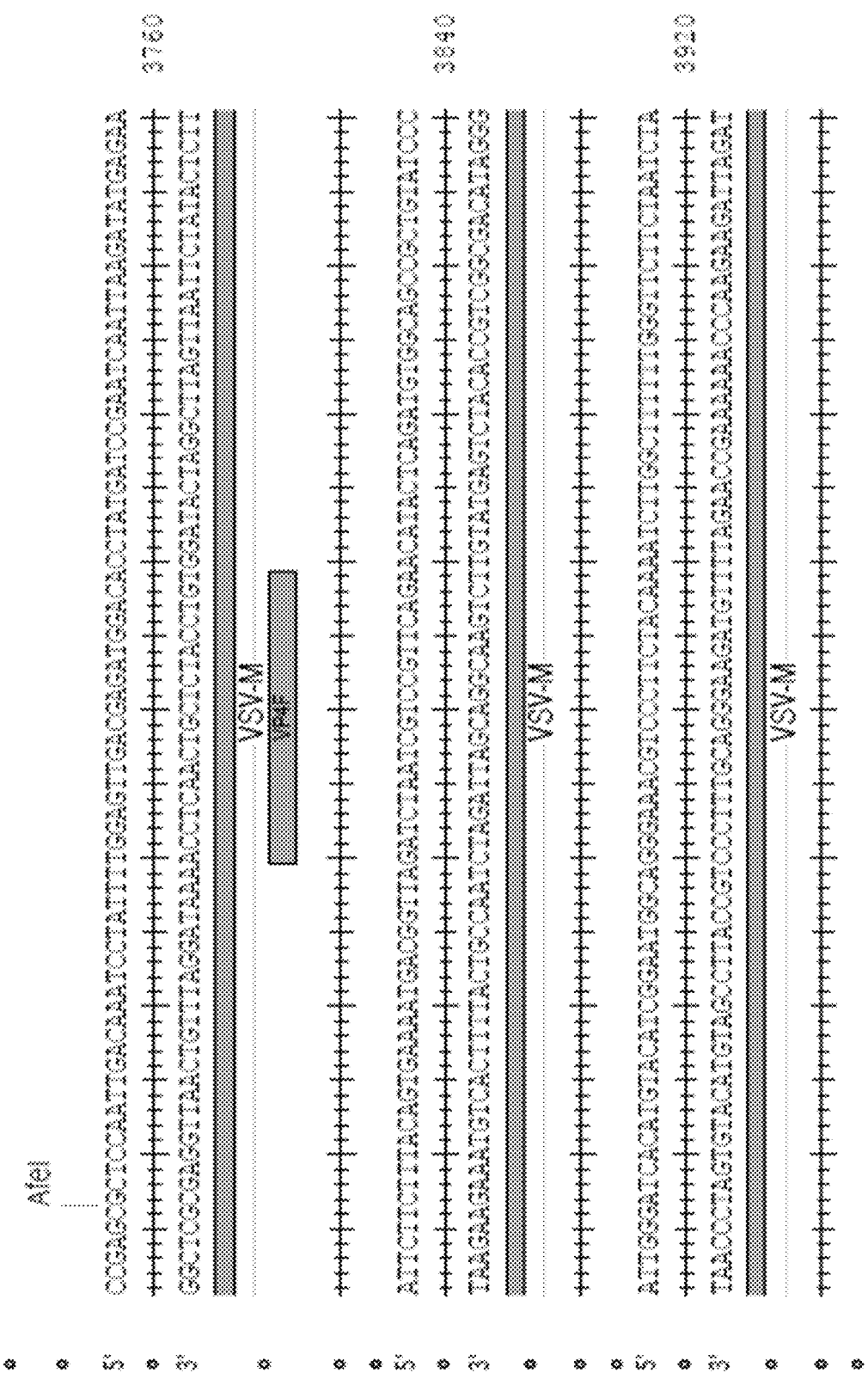
FIG. 17 – continued

FIG. 17 – continued

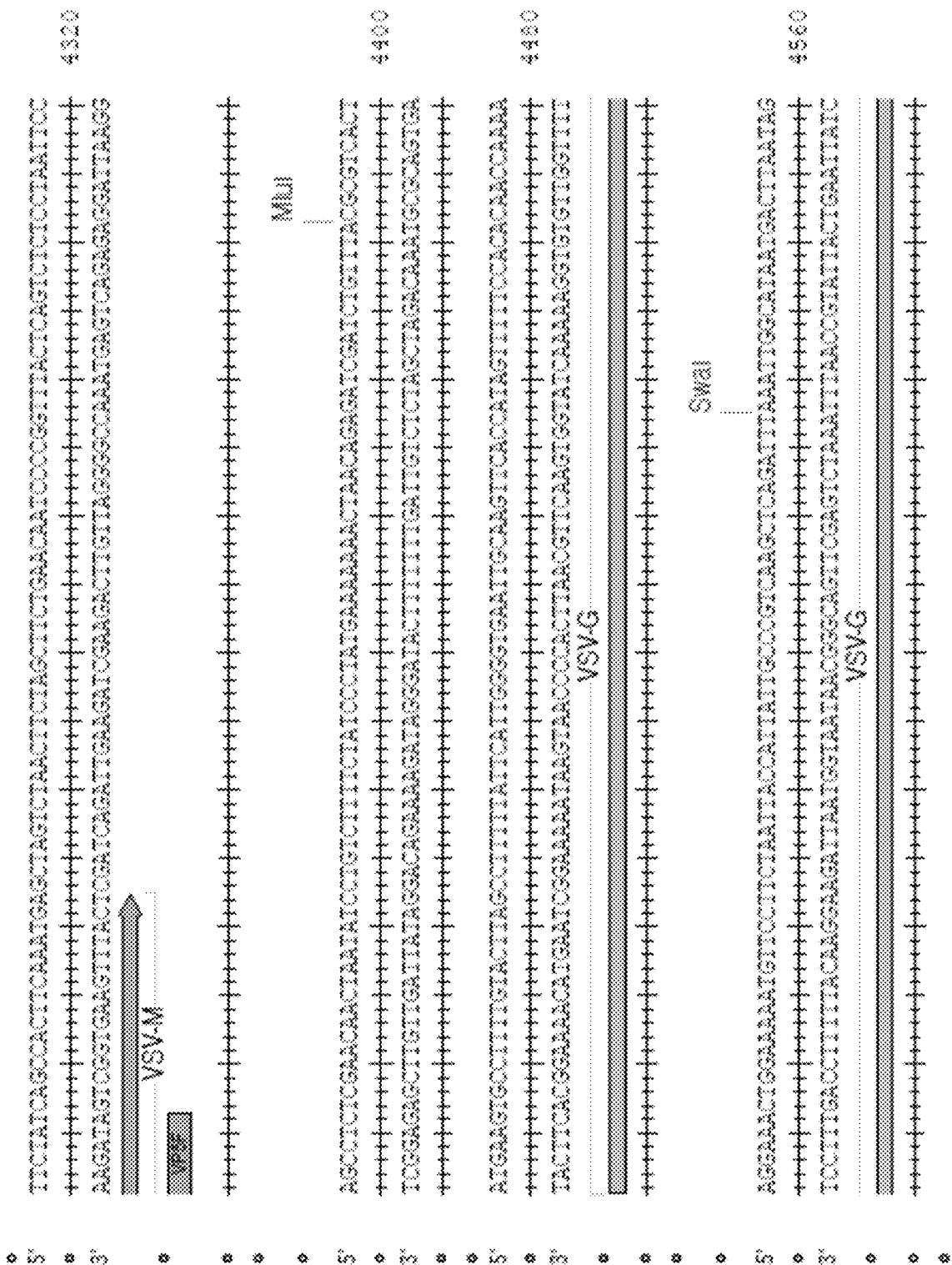
FIG. 17 – continued

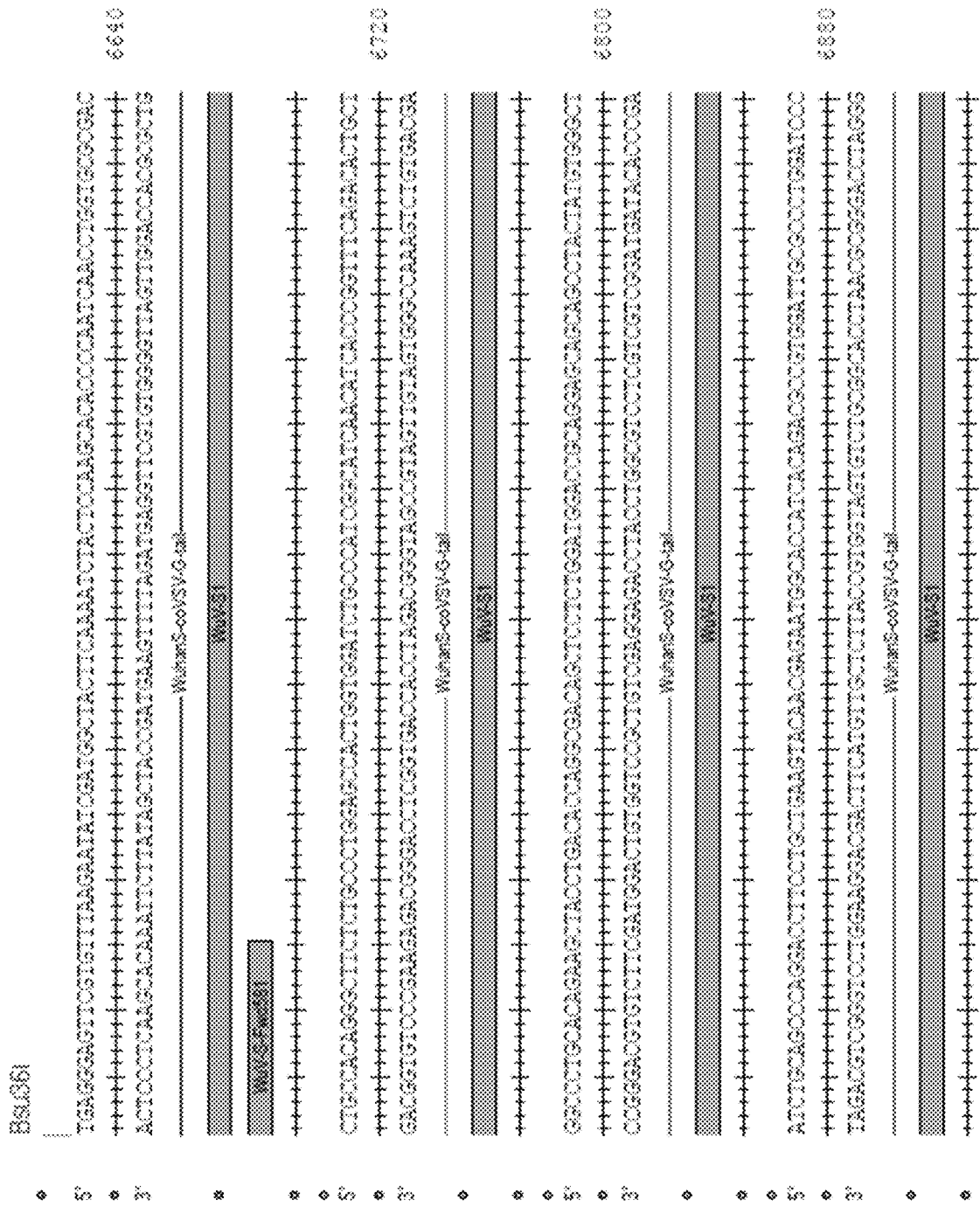
FIG. 17 – continued

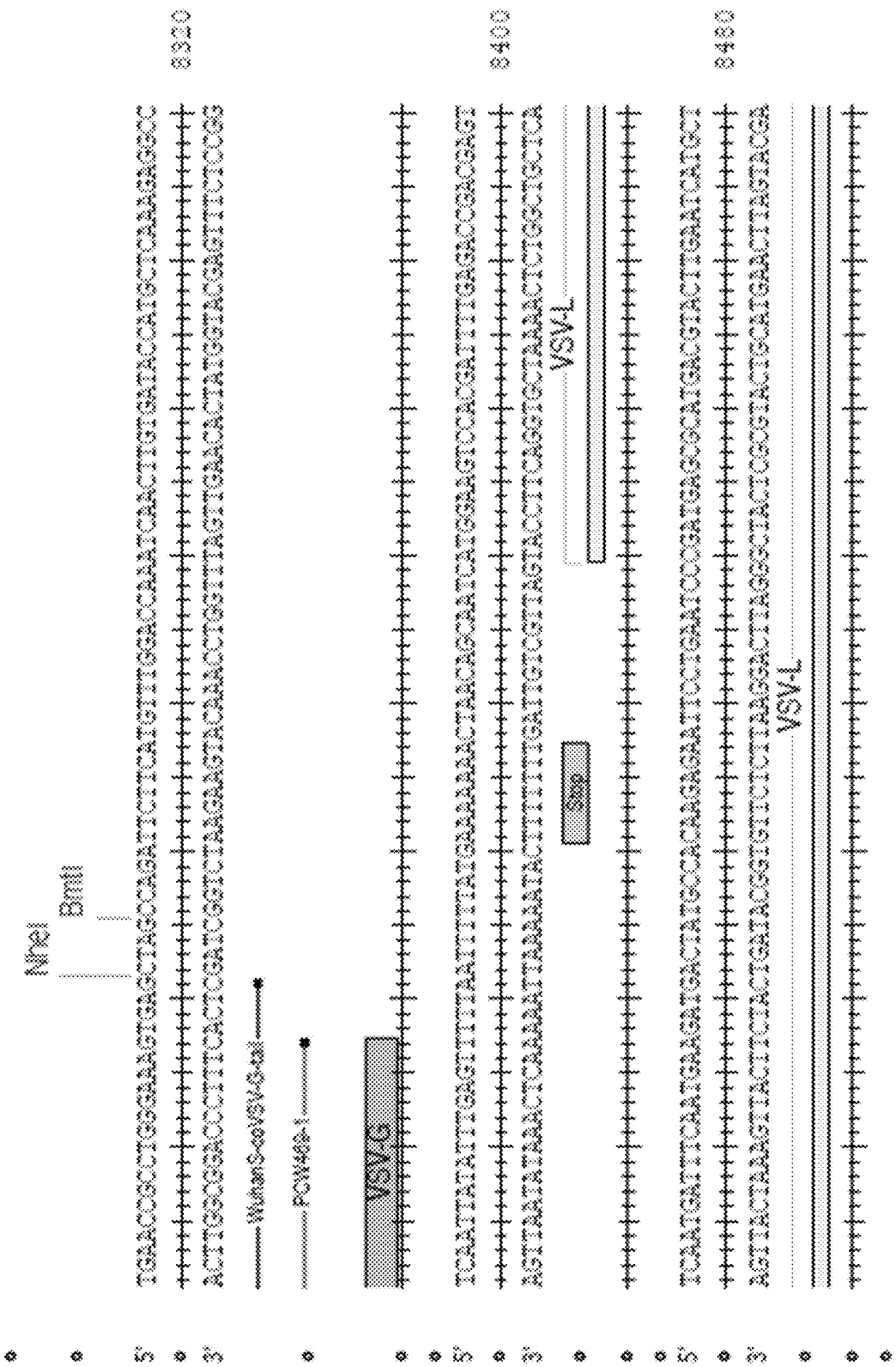
FIG. 17 – continued

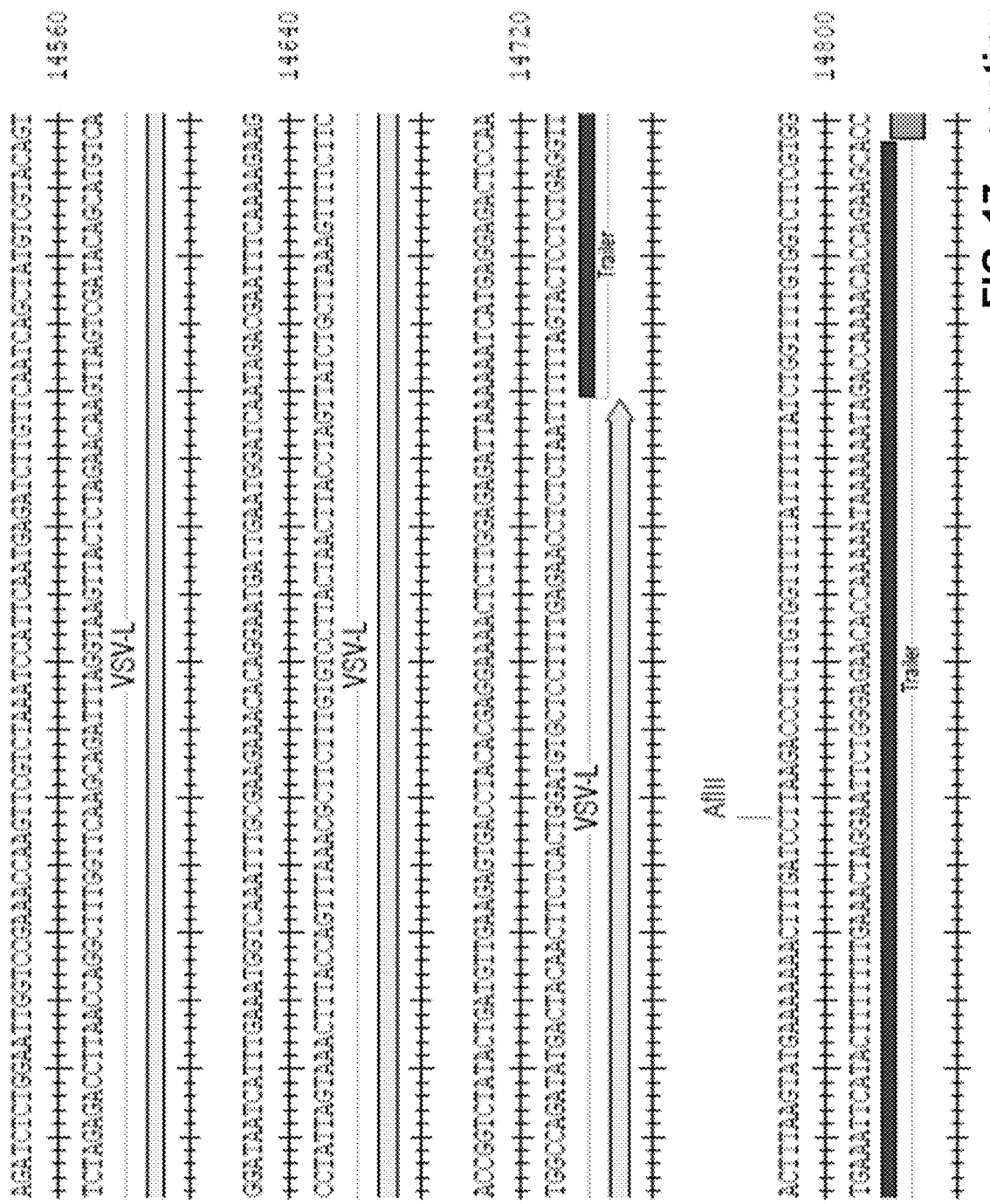
FIG. 17 – continued

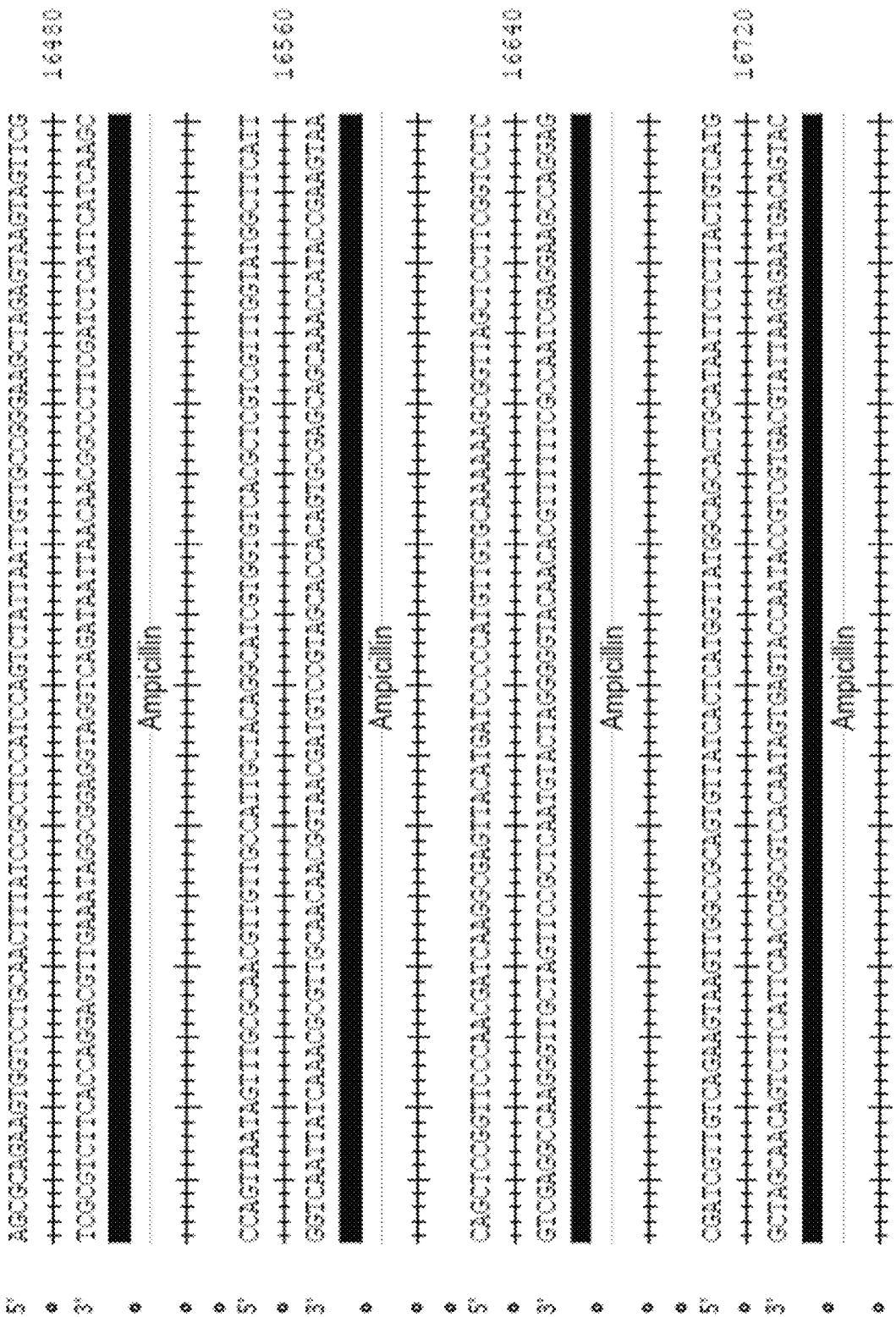
FIG. 17 – continued

FIG. 18 – continued

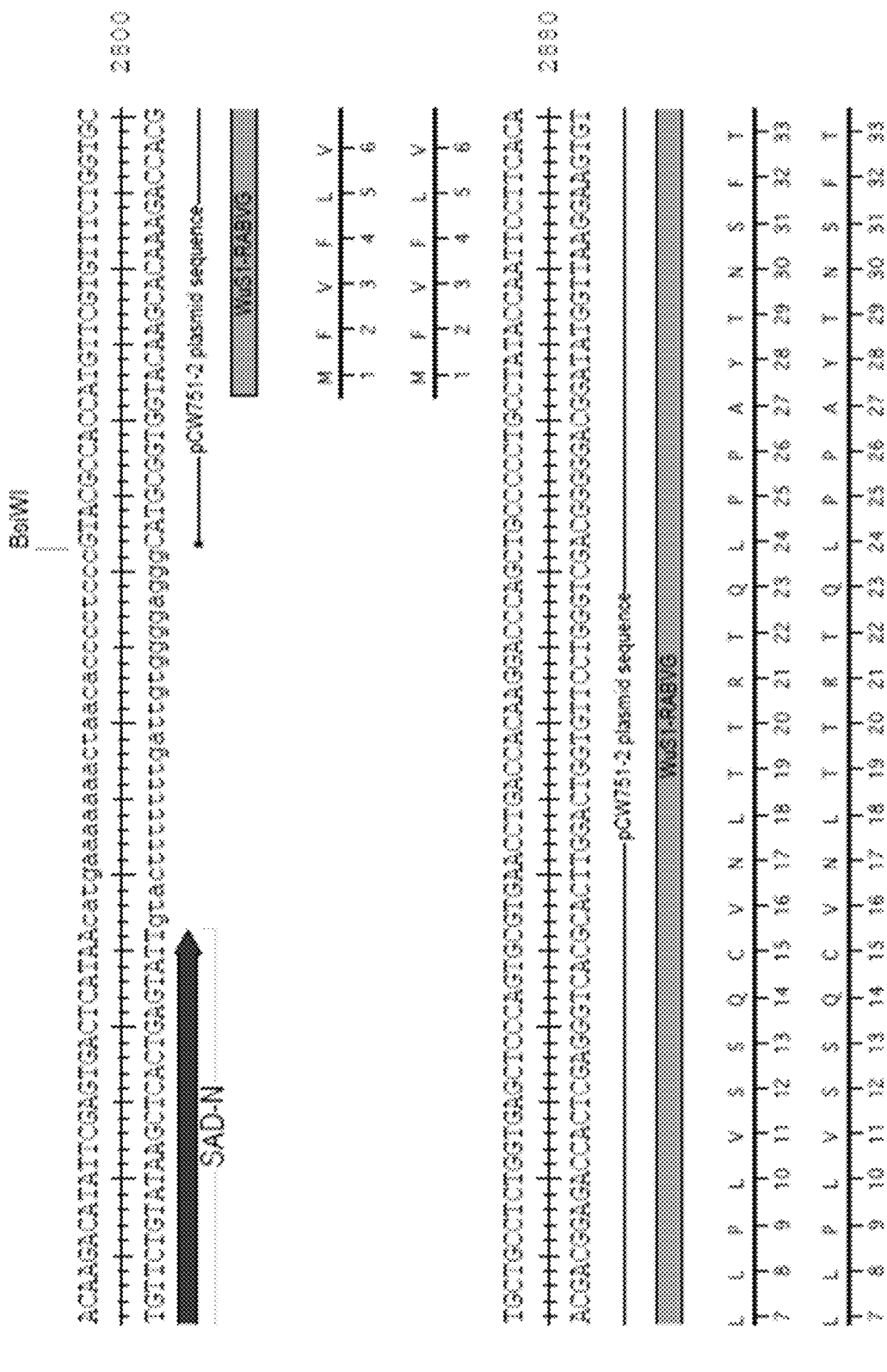
FIG. 18 – continued

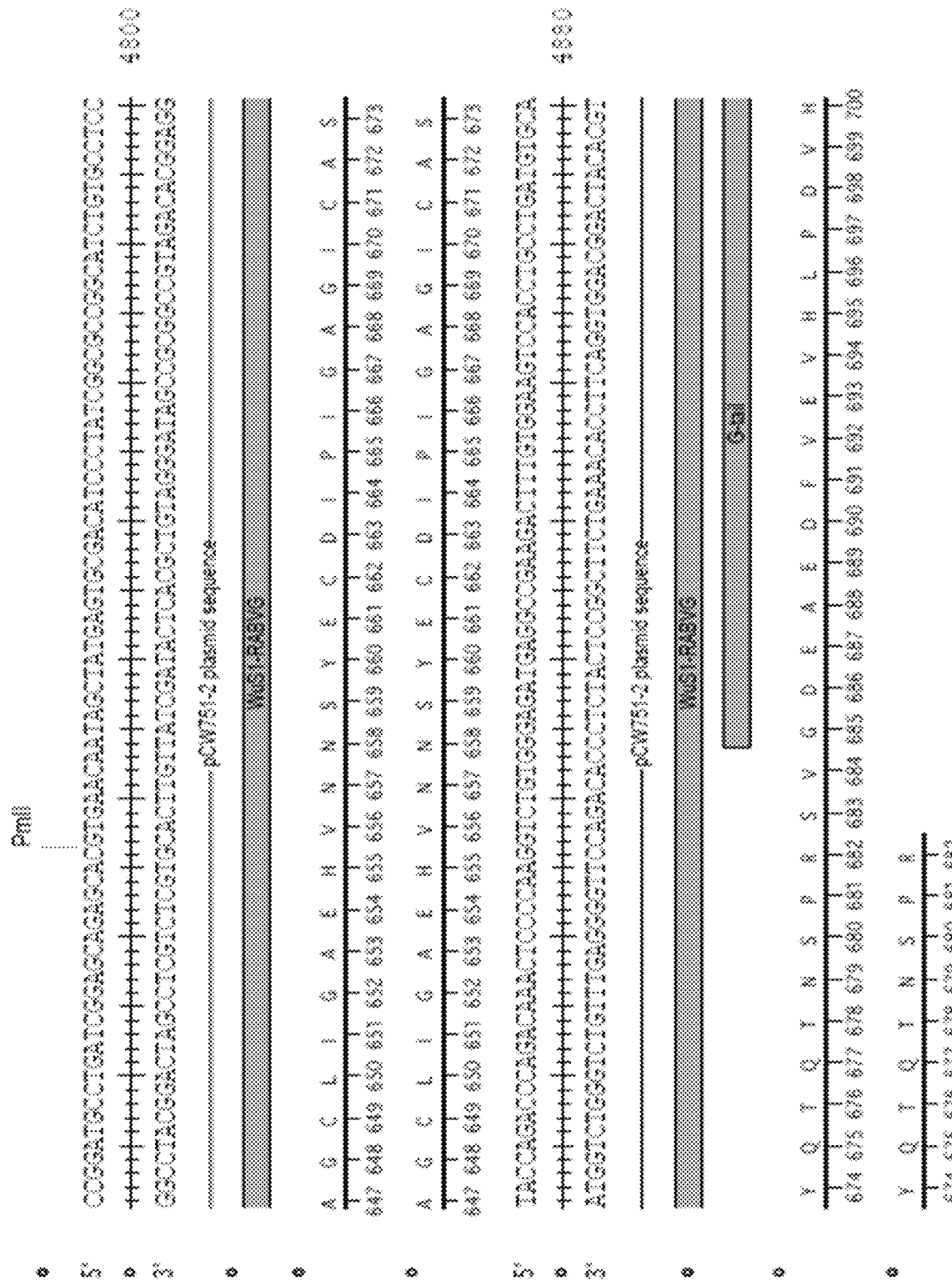
FIG. 18 – continued

FIG. 18 – continued

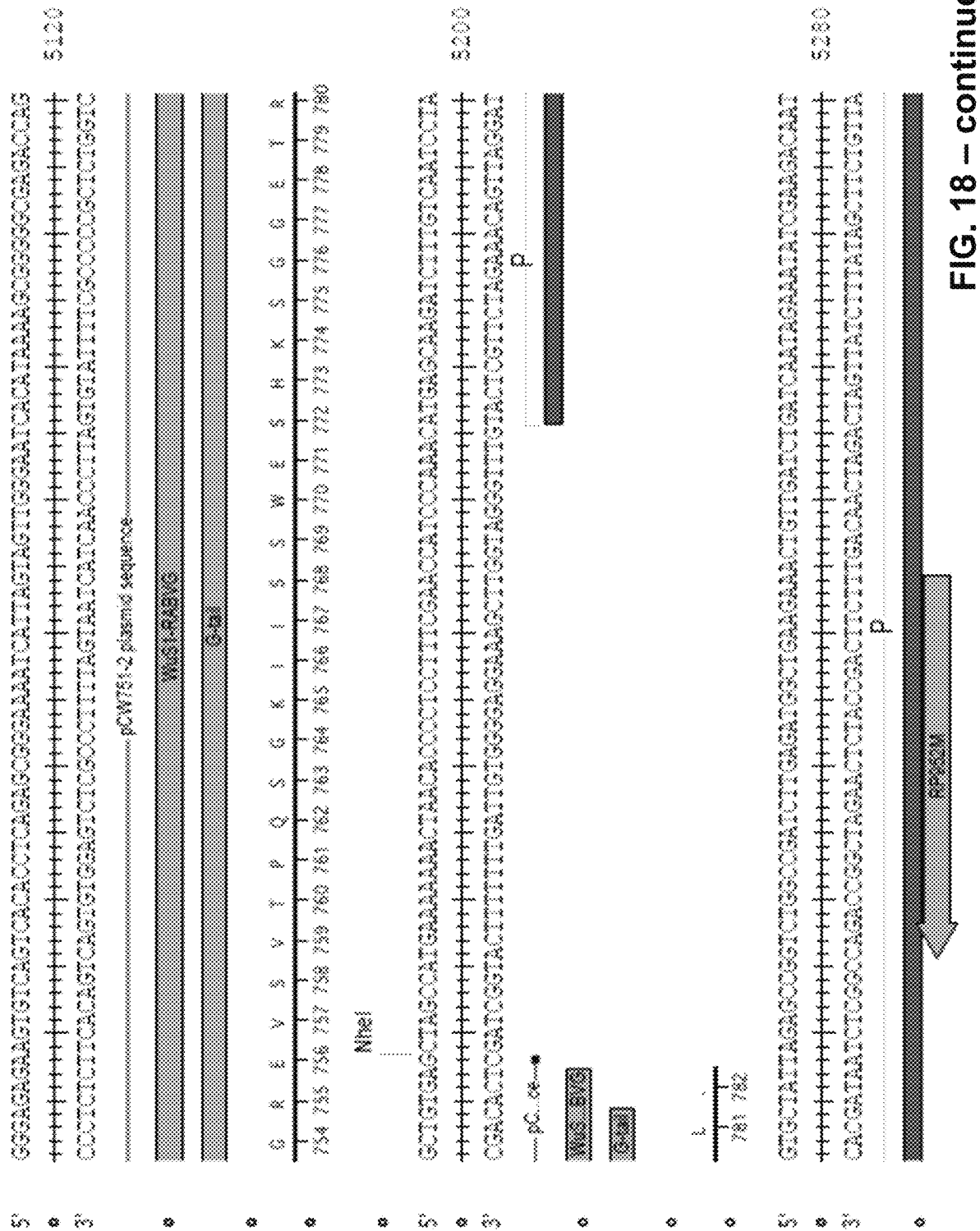
FIG. 18 – continued

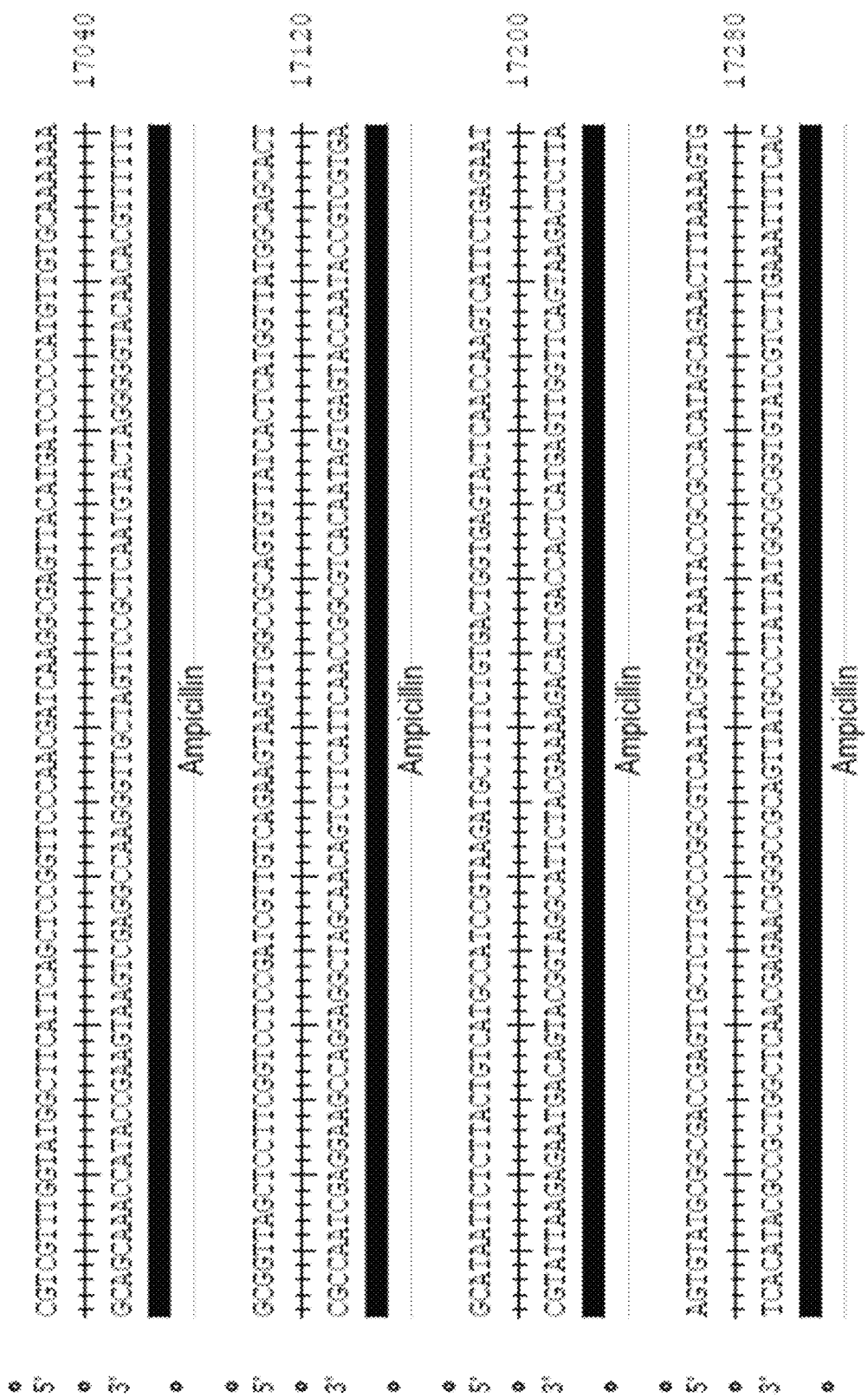
FIG. 18 – continued

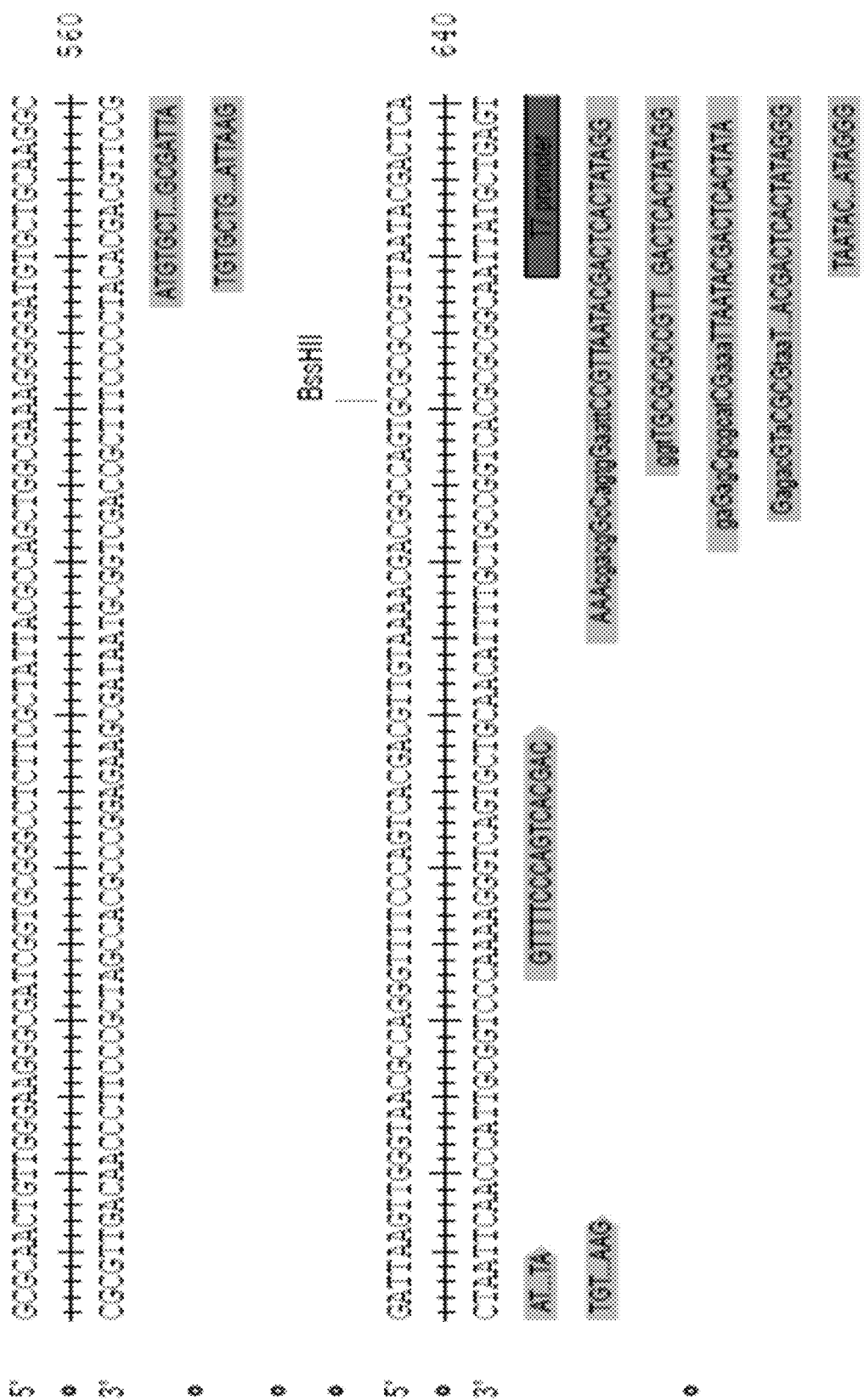
FIG. 19 – continued

FIG. 19 – continued

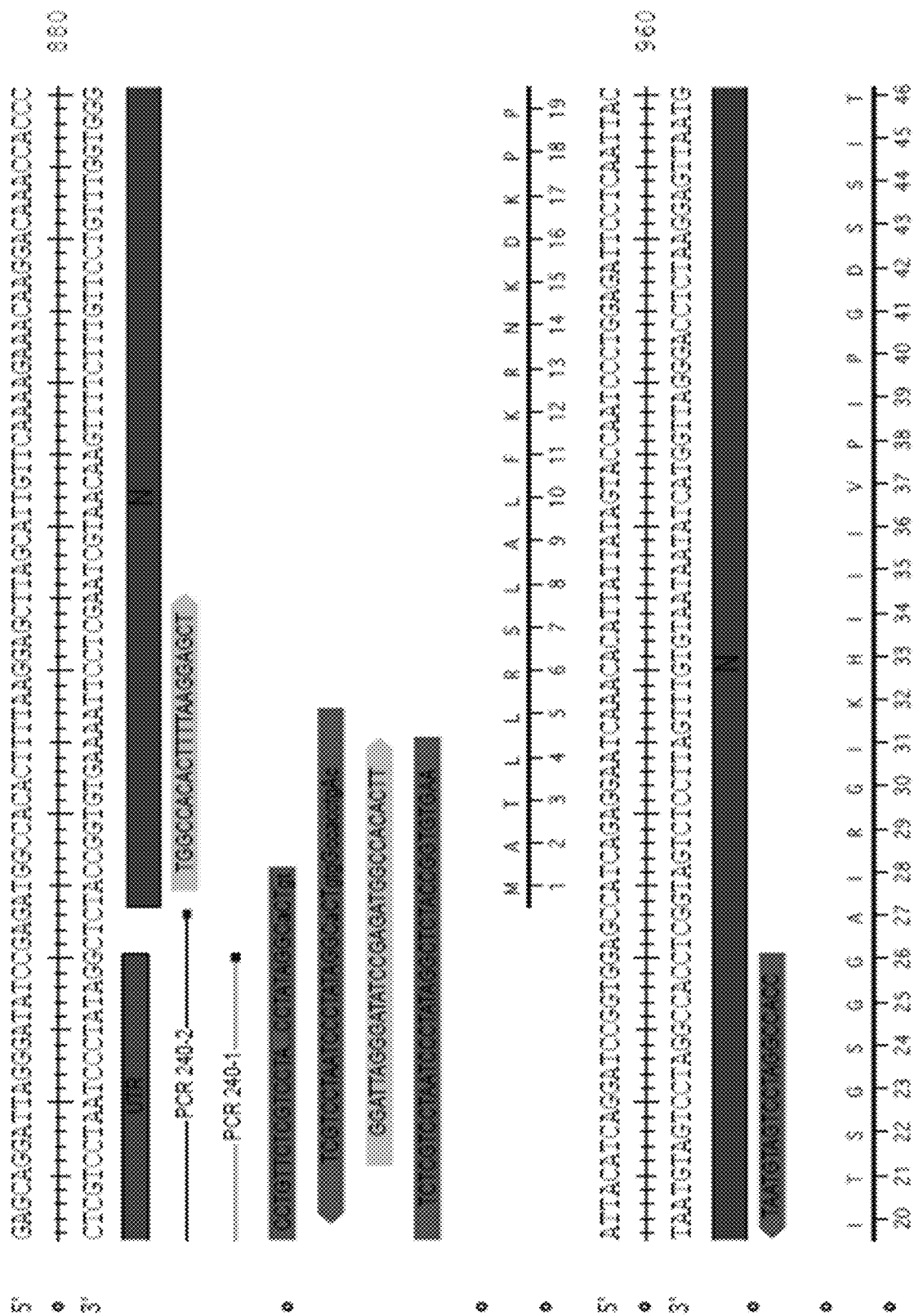
FIG. 19 – continued

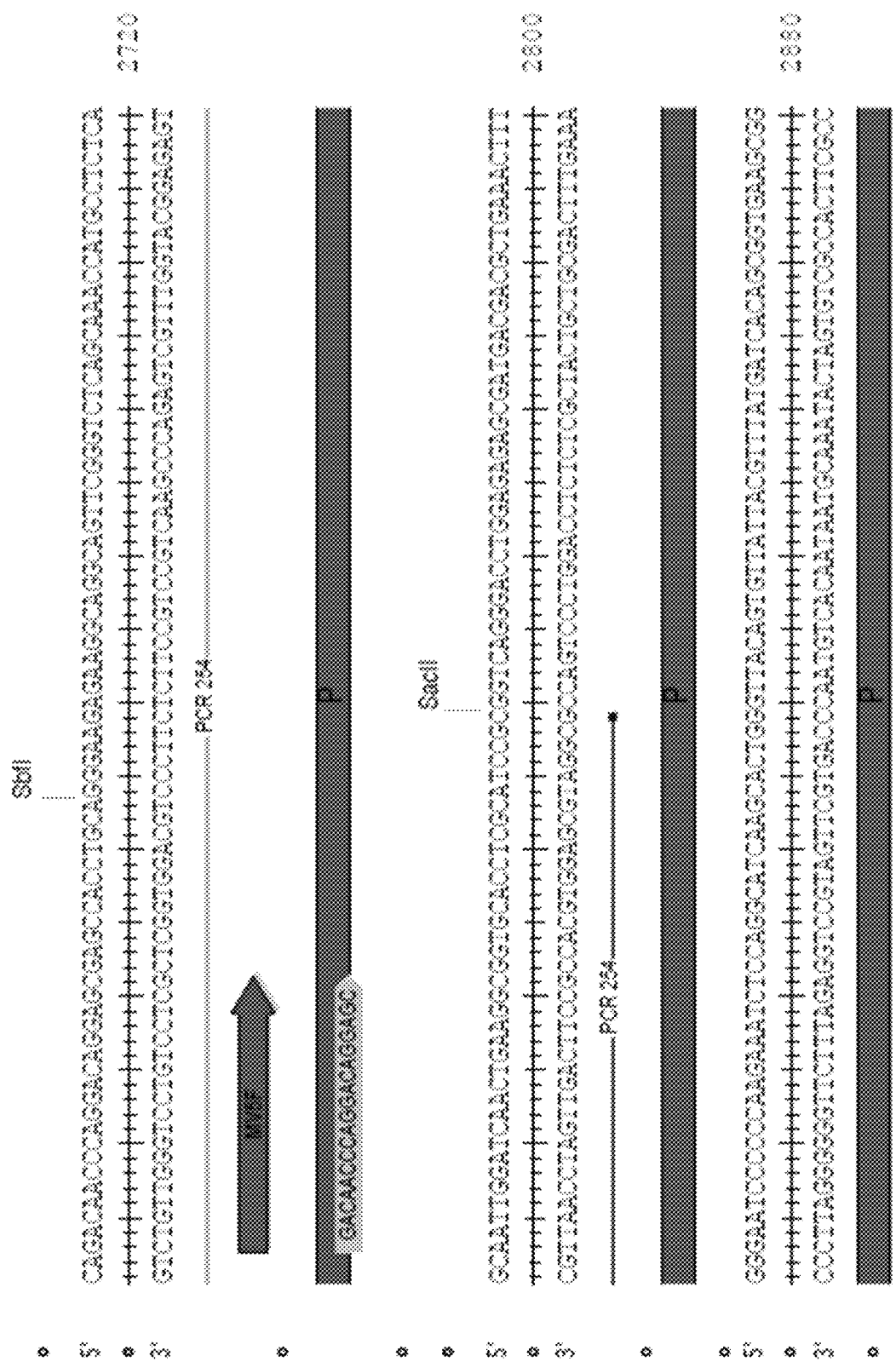
FIG. 19 – continued

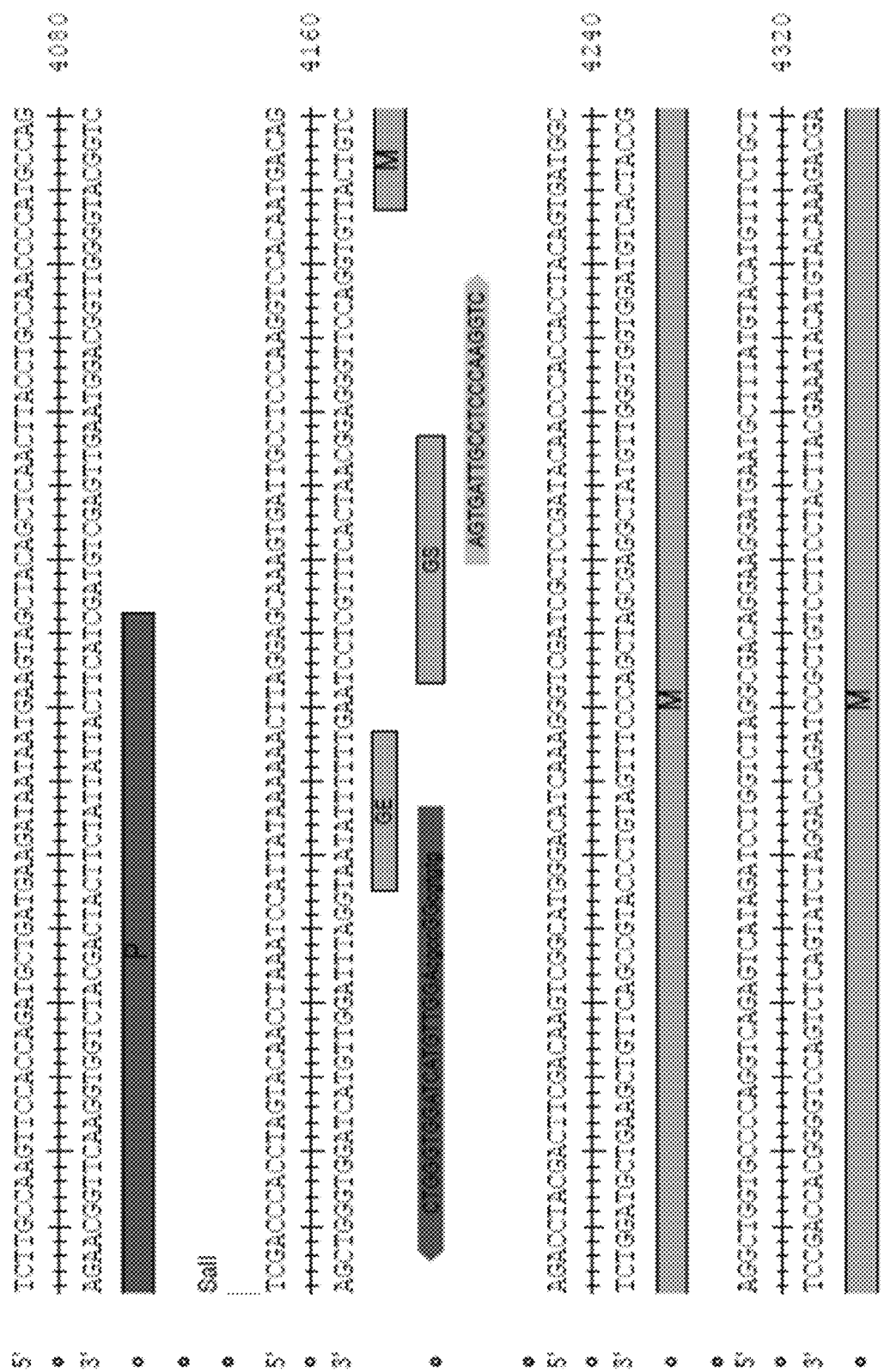
FIG. 19 – continued

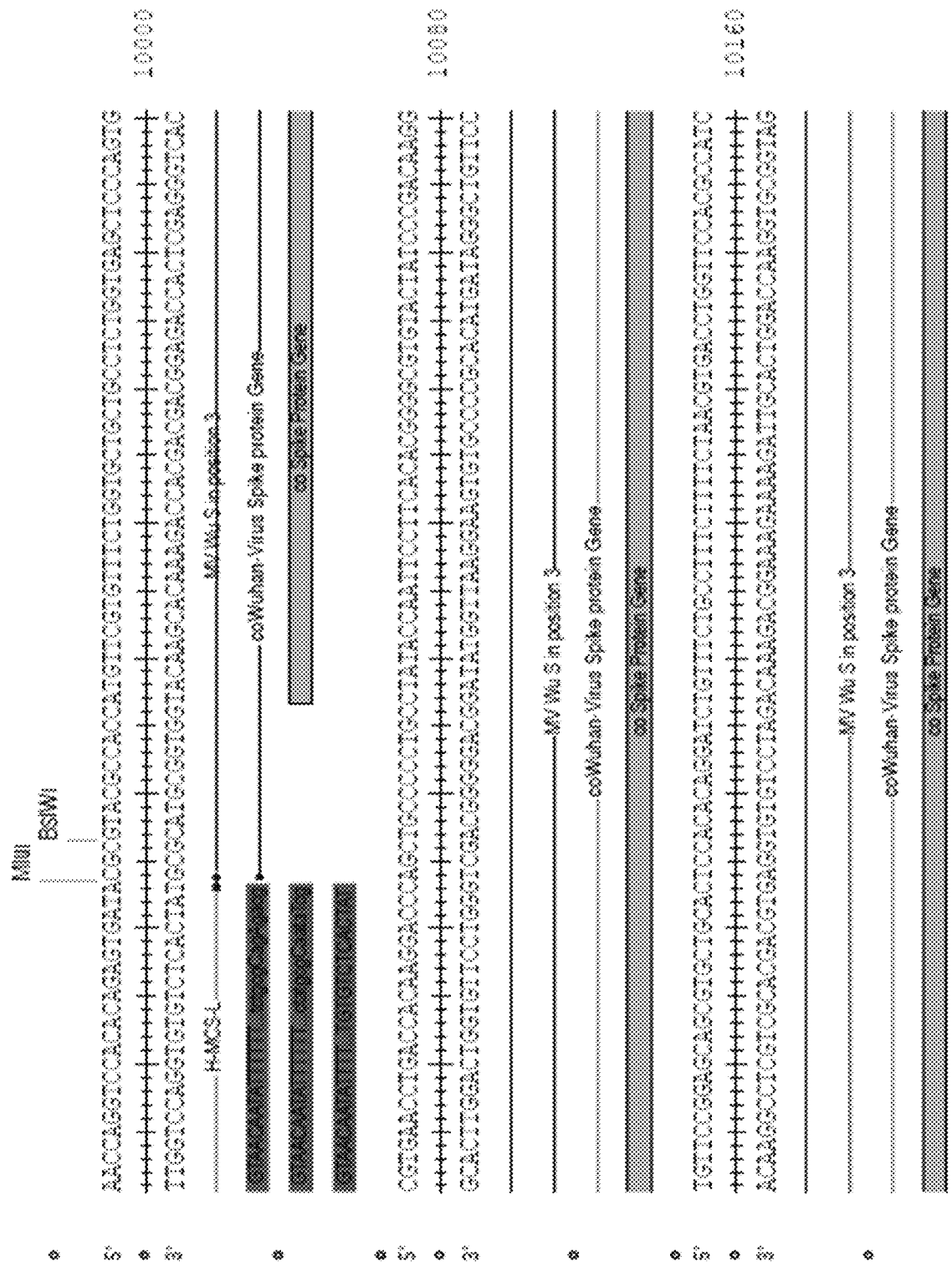
FIG. 19 – continued

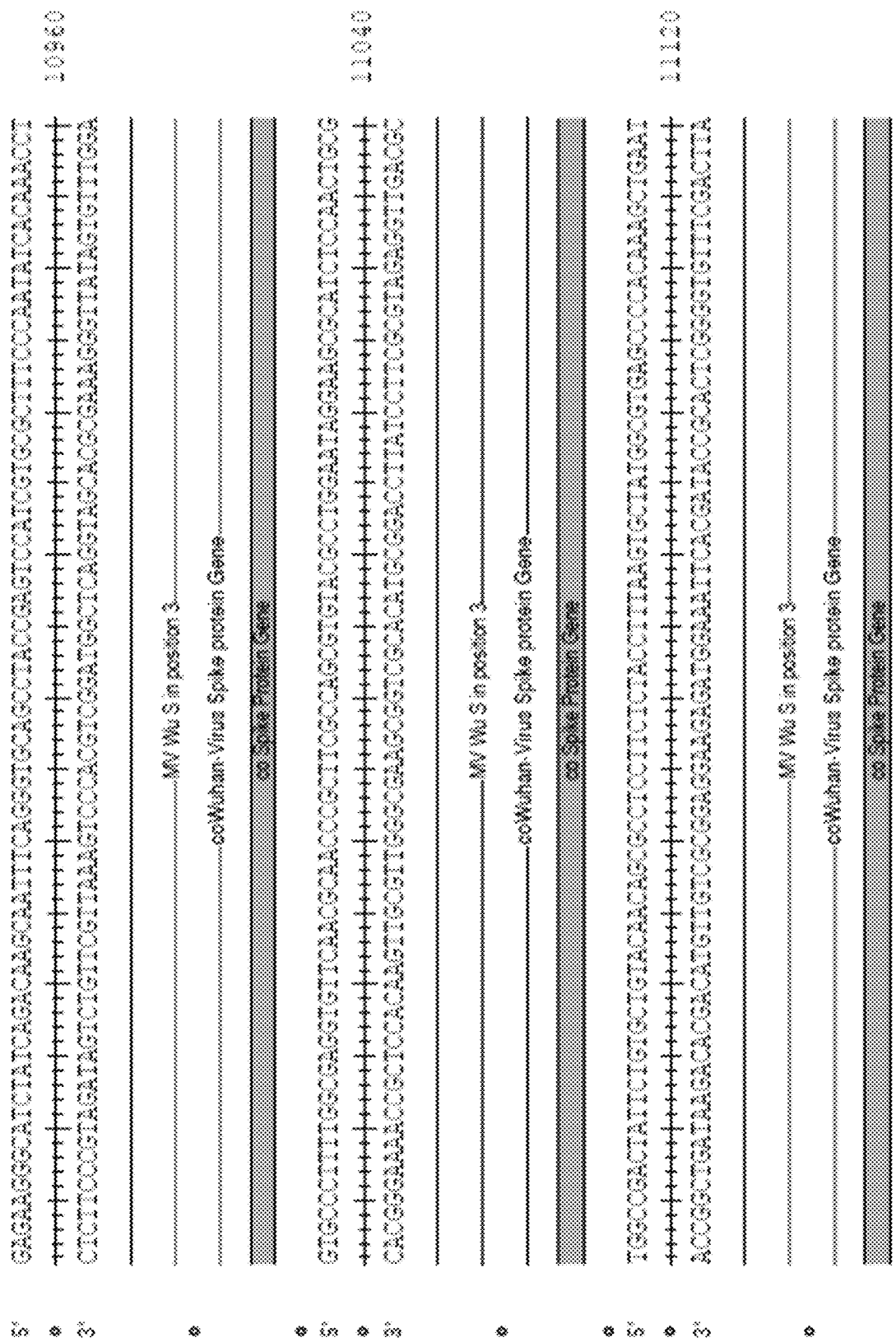
FIG. 19 – continued

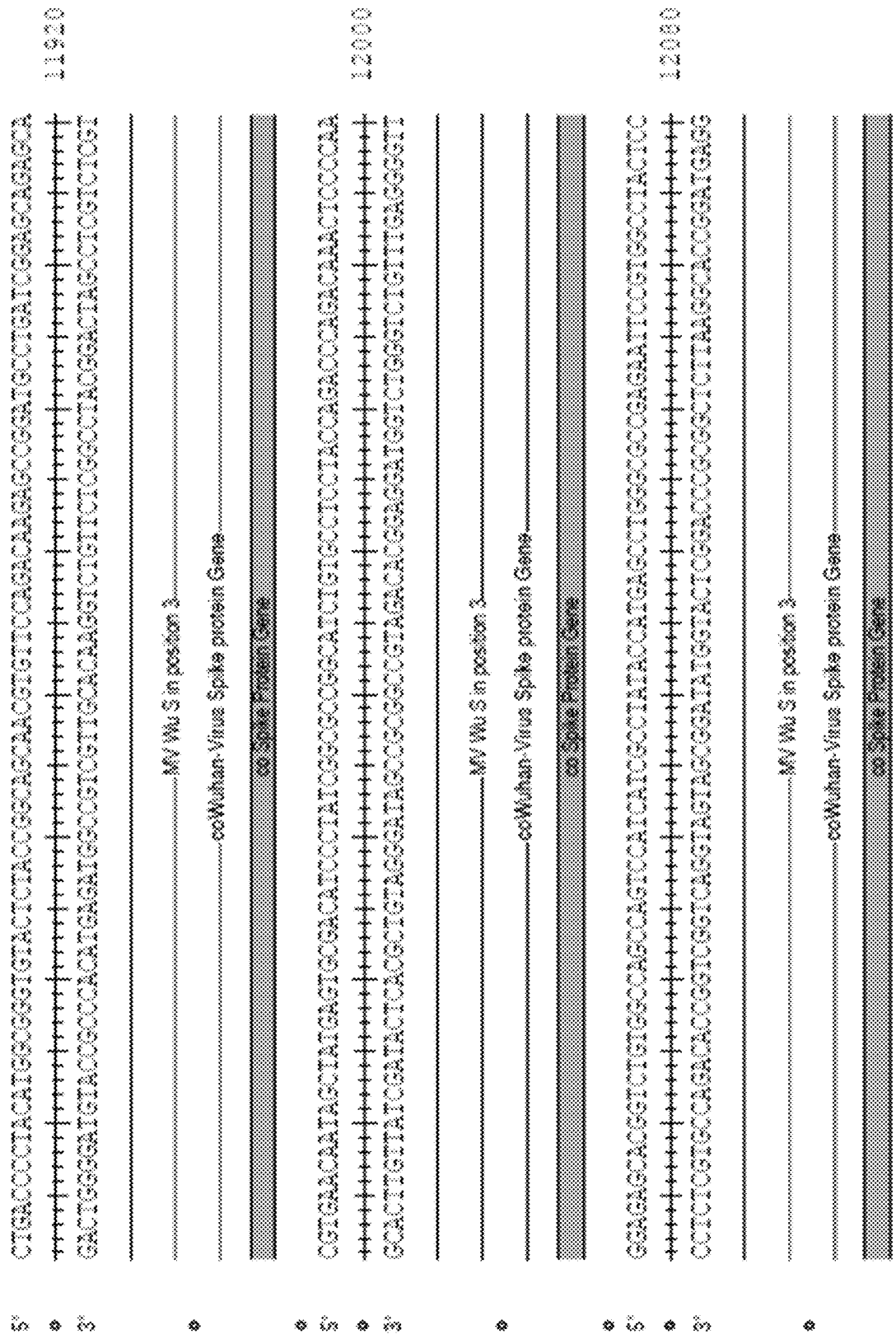
FIG. 19 – continued

FIG. 19 – continued

FIG. 19 – continued

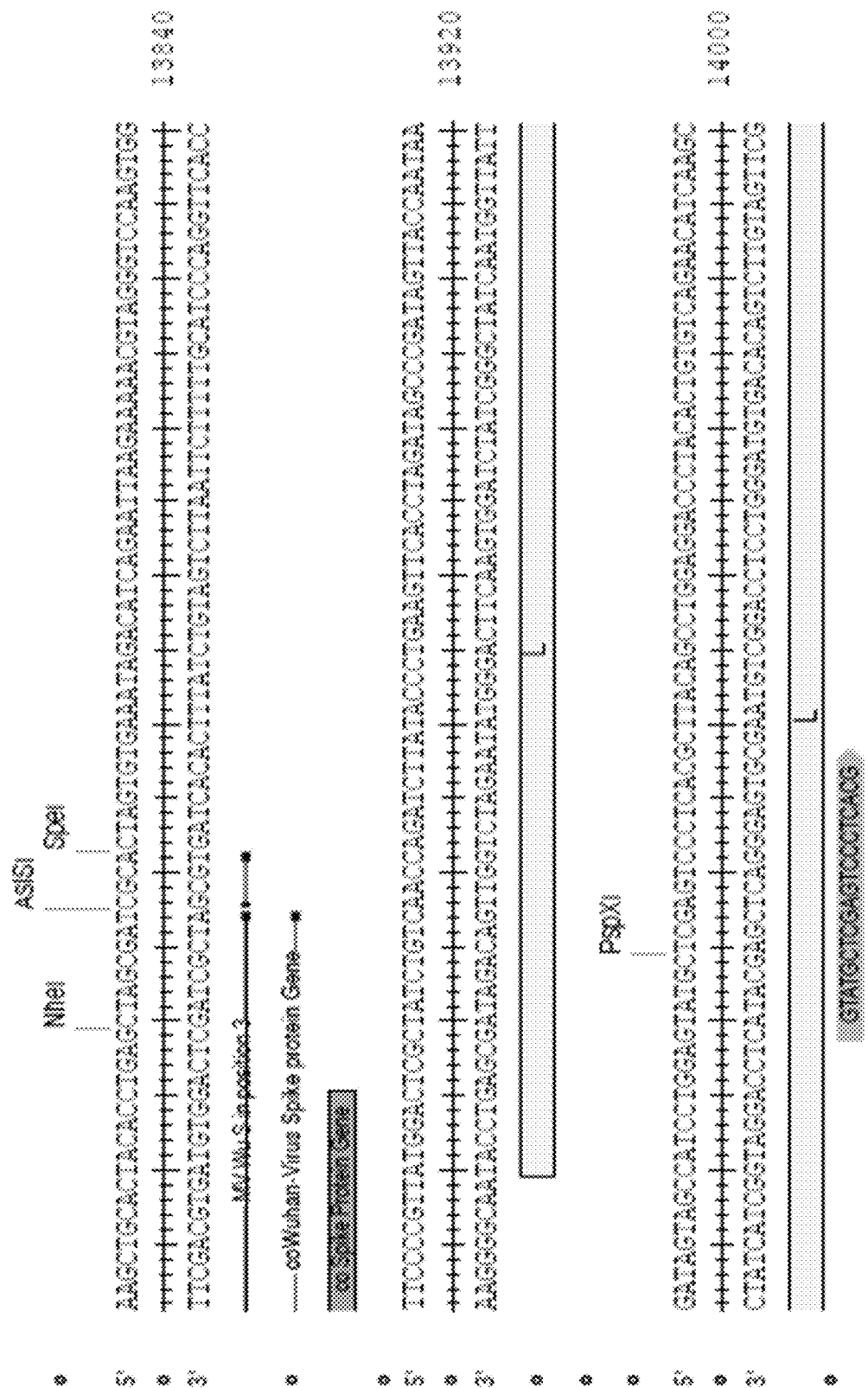
FIG. 19 – continued

FIG. 19 – continued

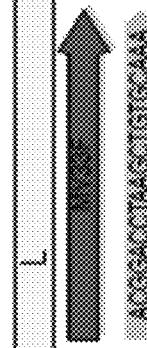
FIG. 19 – continued

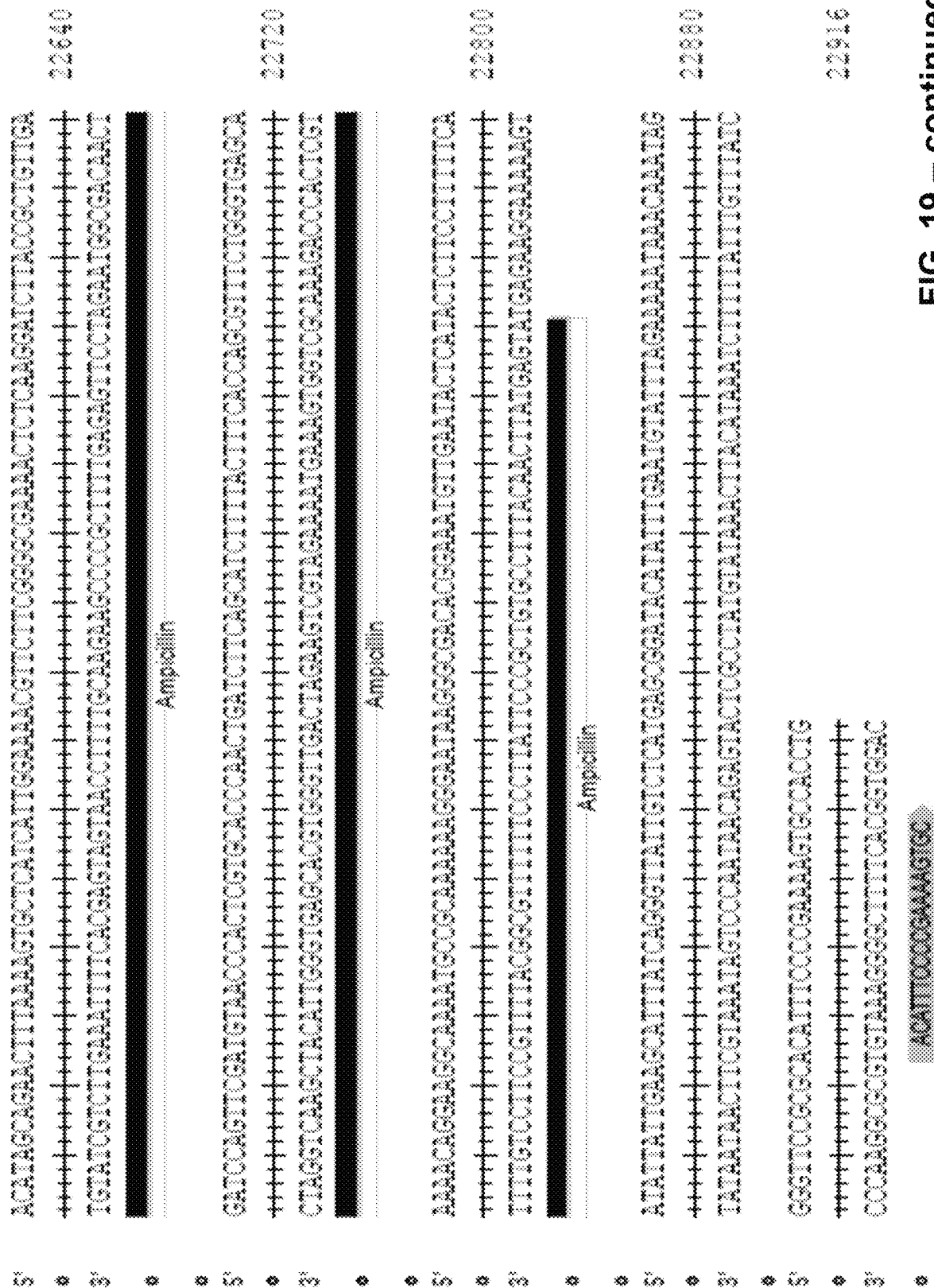
FIG. 19 – continued

FIG. 20

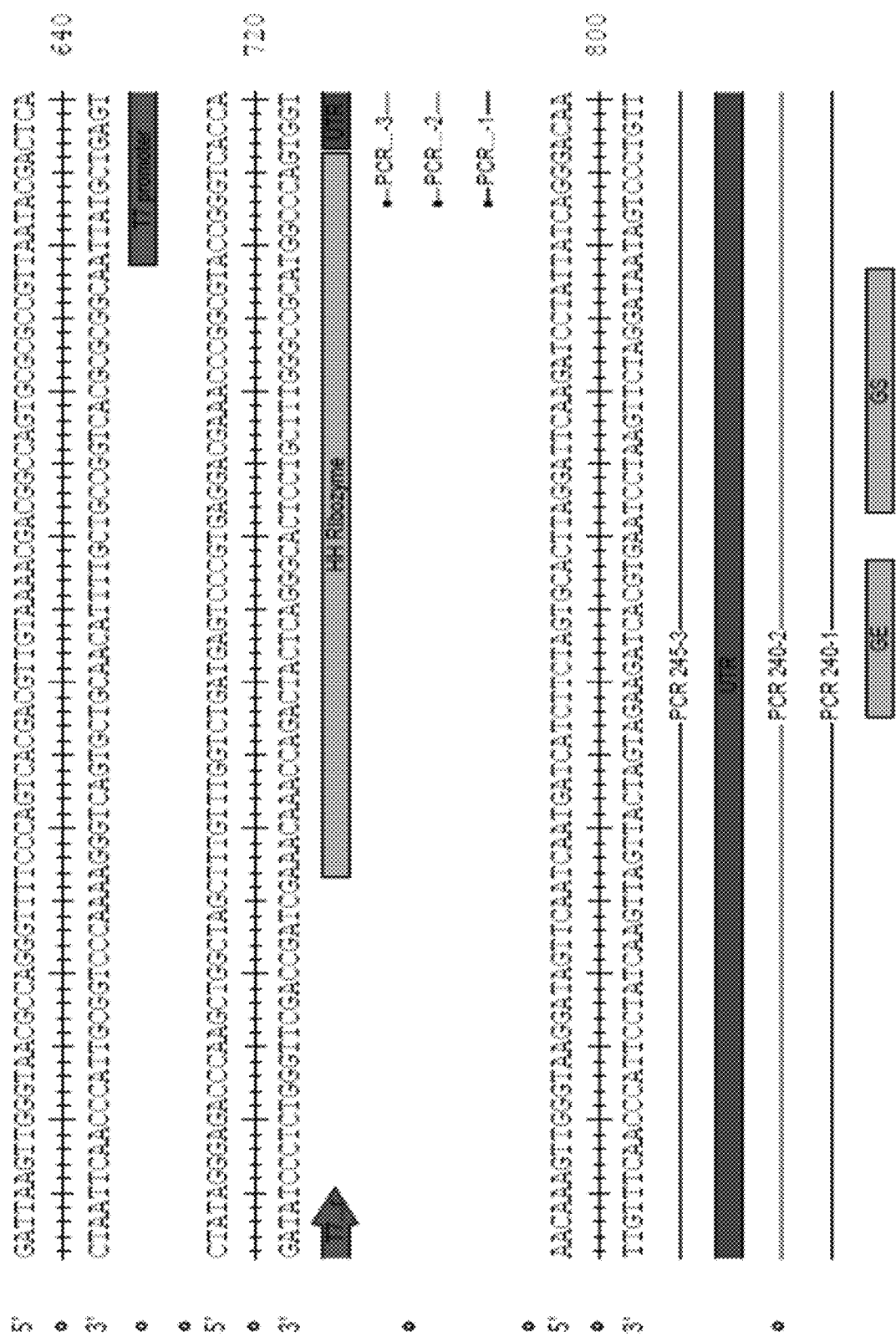
FIG. 20 – continued

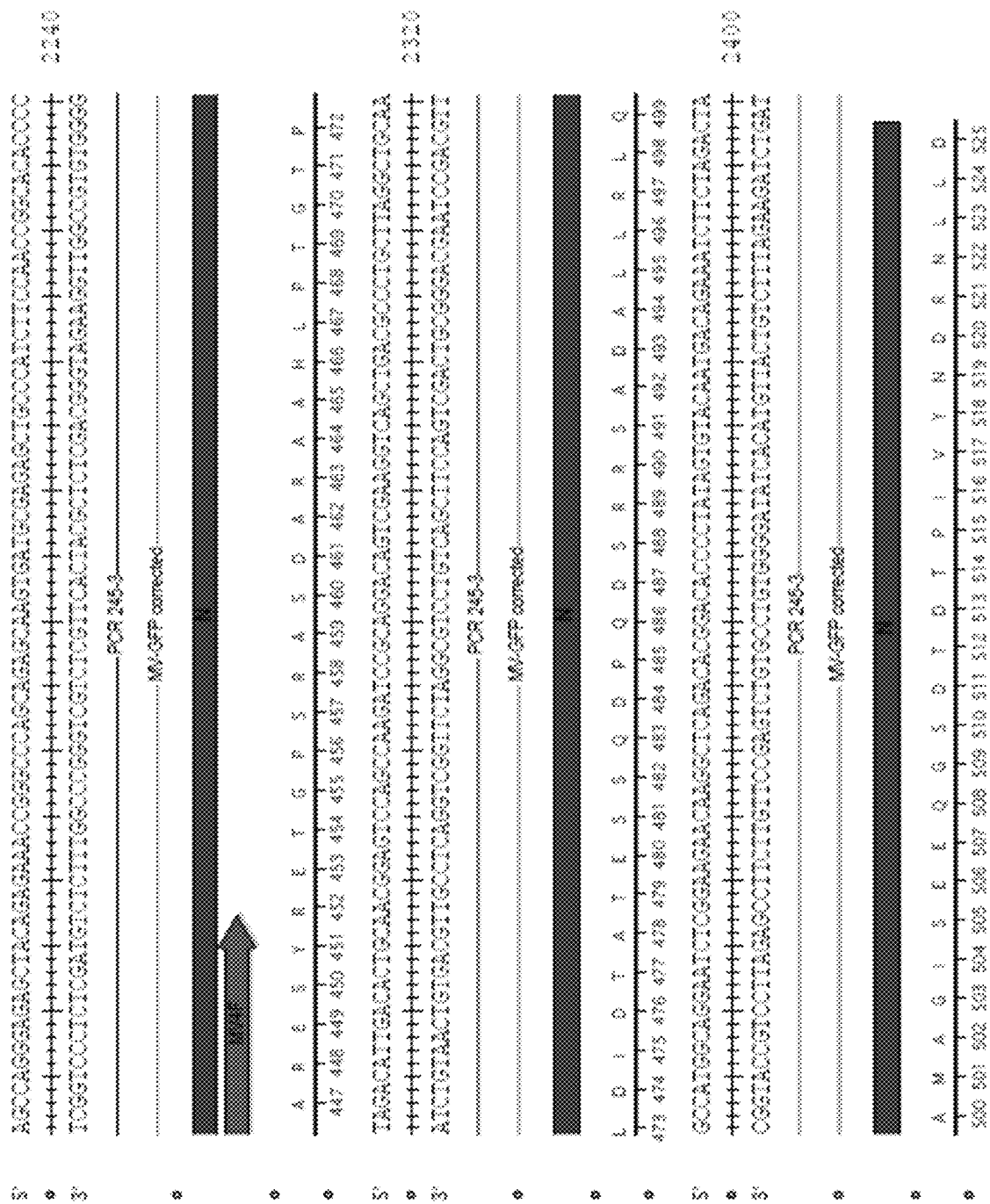
FIG. 20 – continued

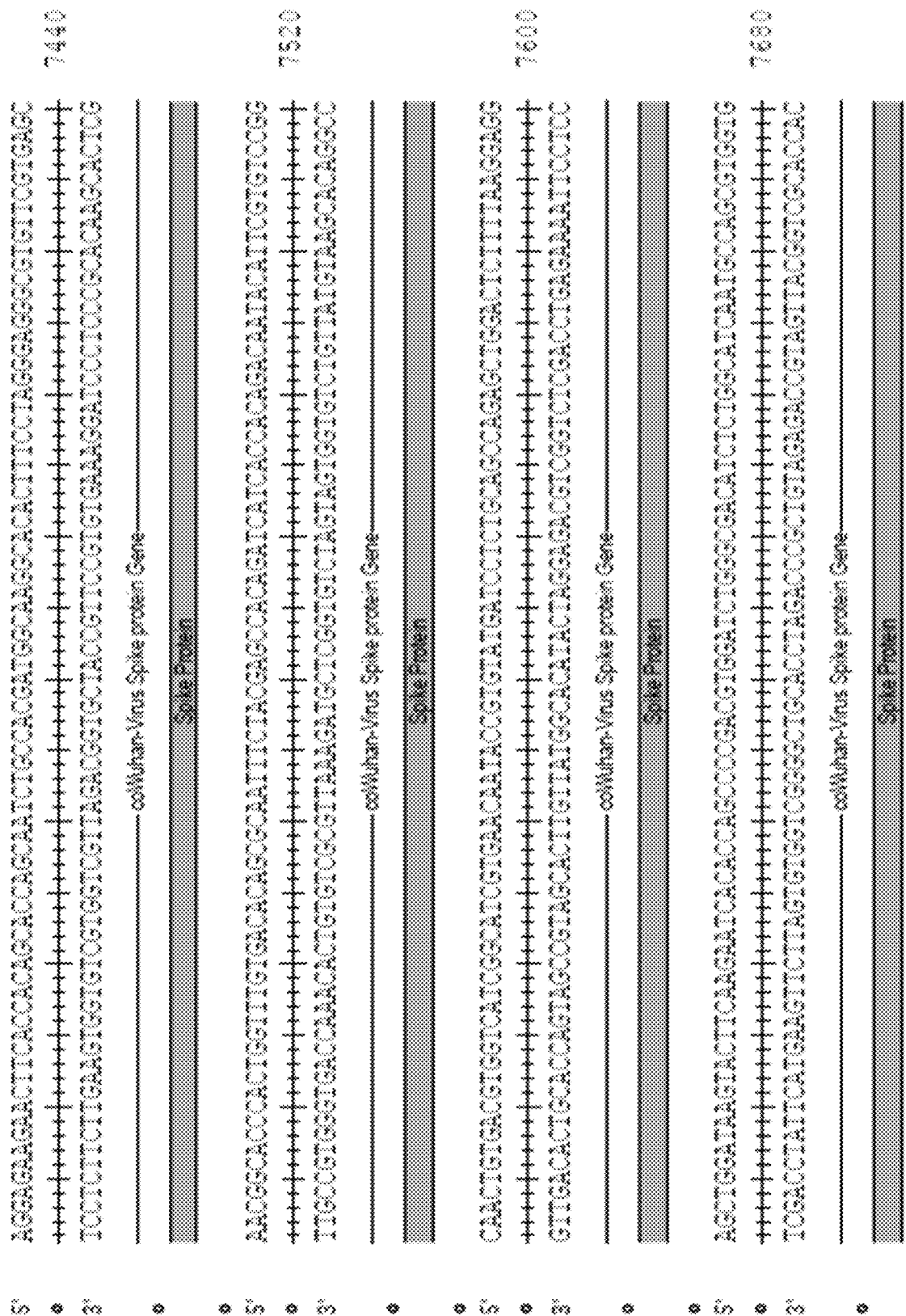
FIG. 20 – continued

FIG. 20 – continued

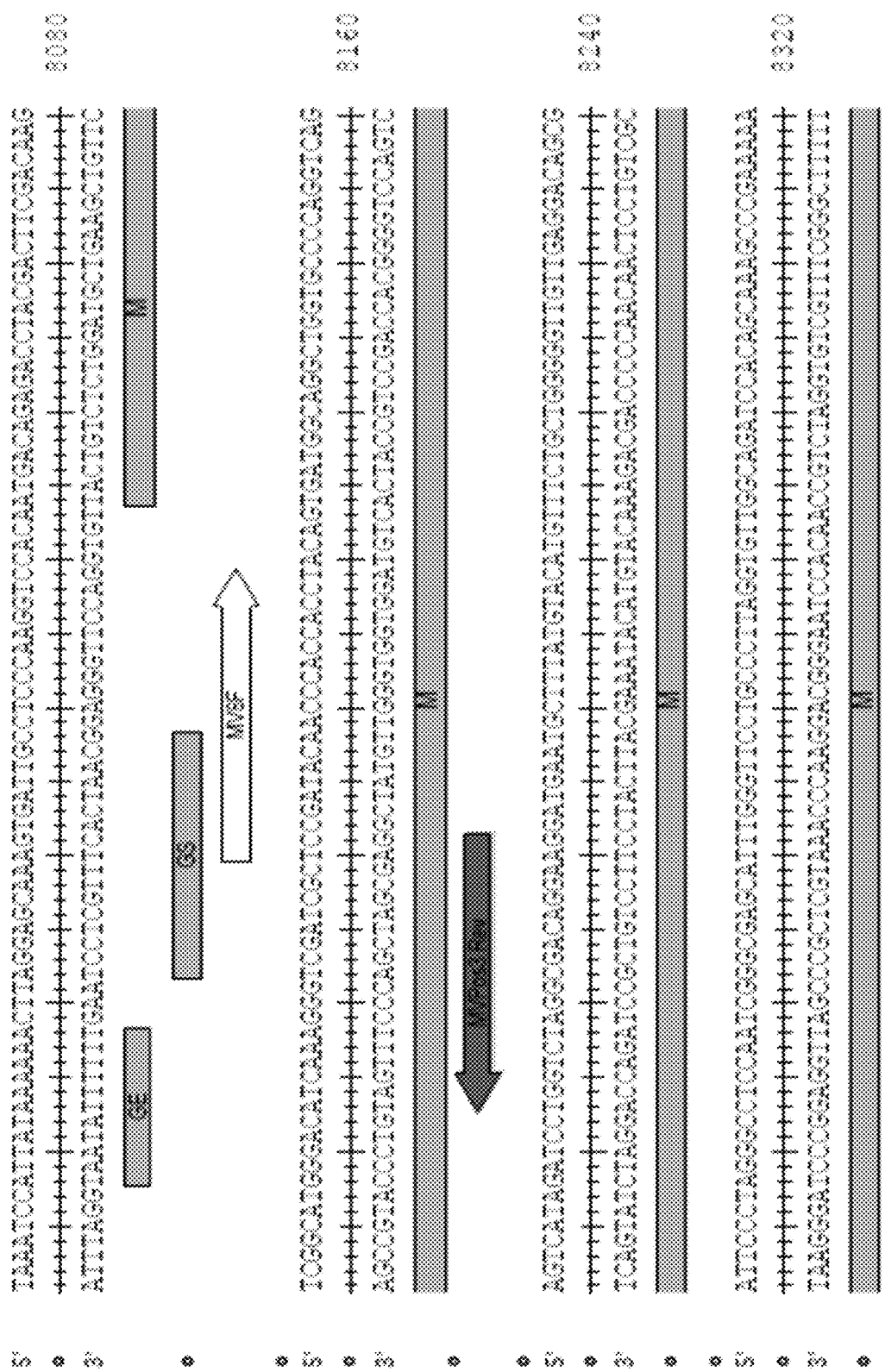
FIG. 20 – continued

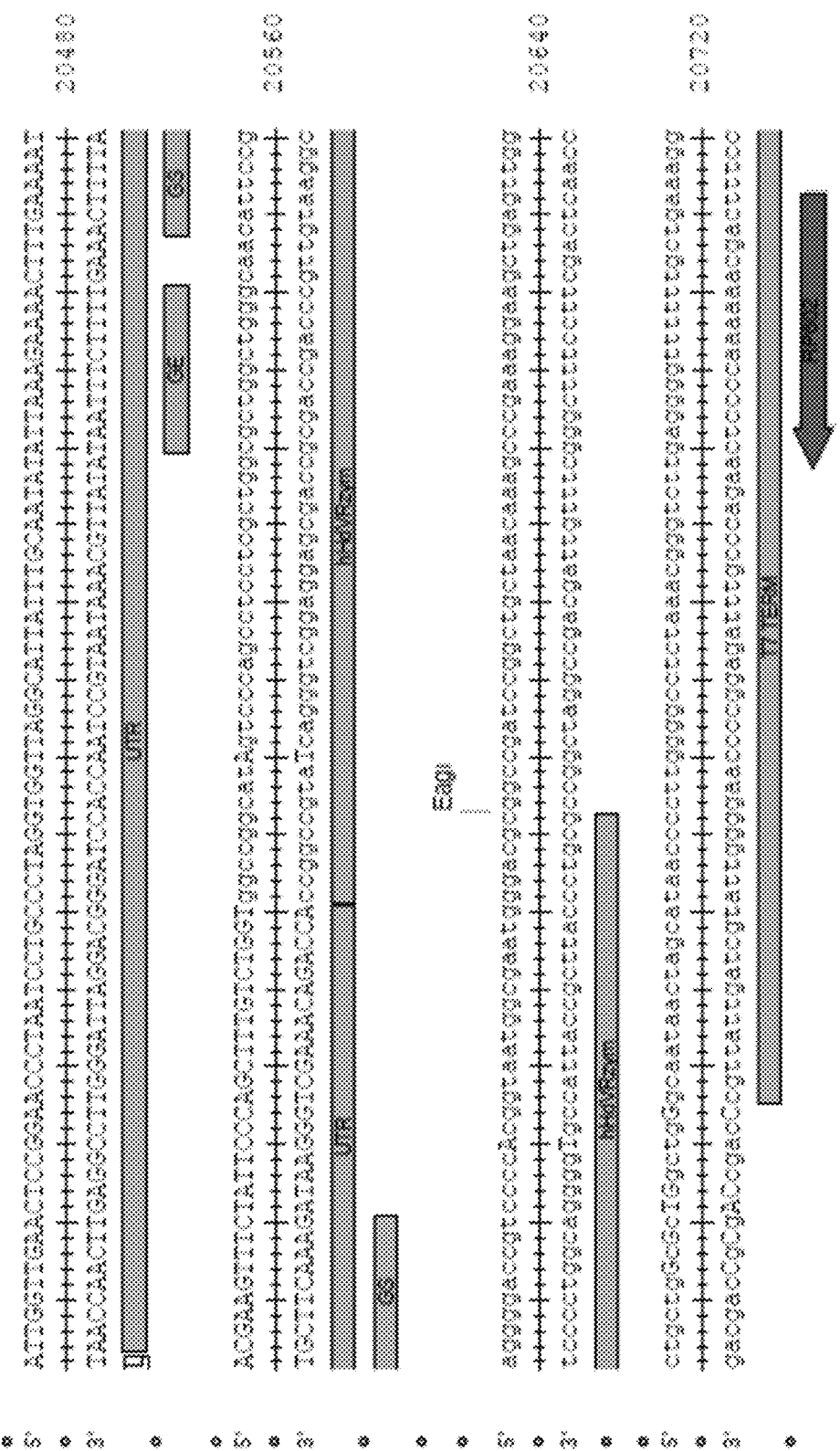
FIG. 20 – continued

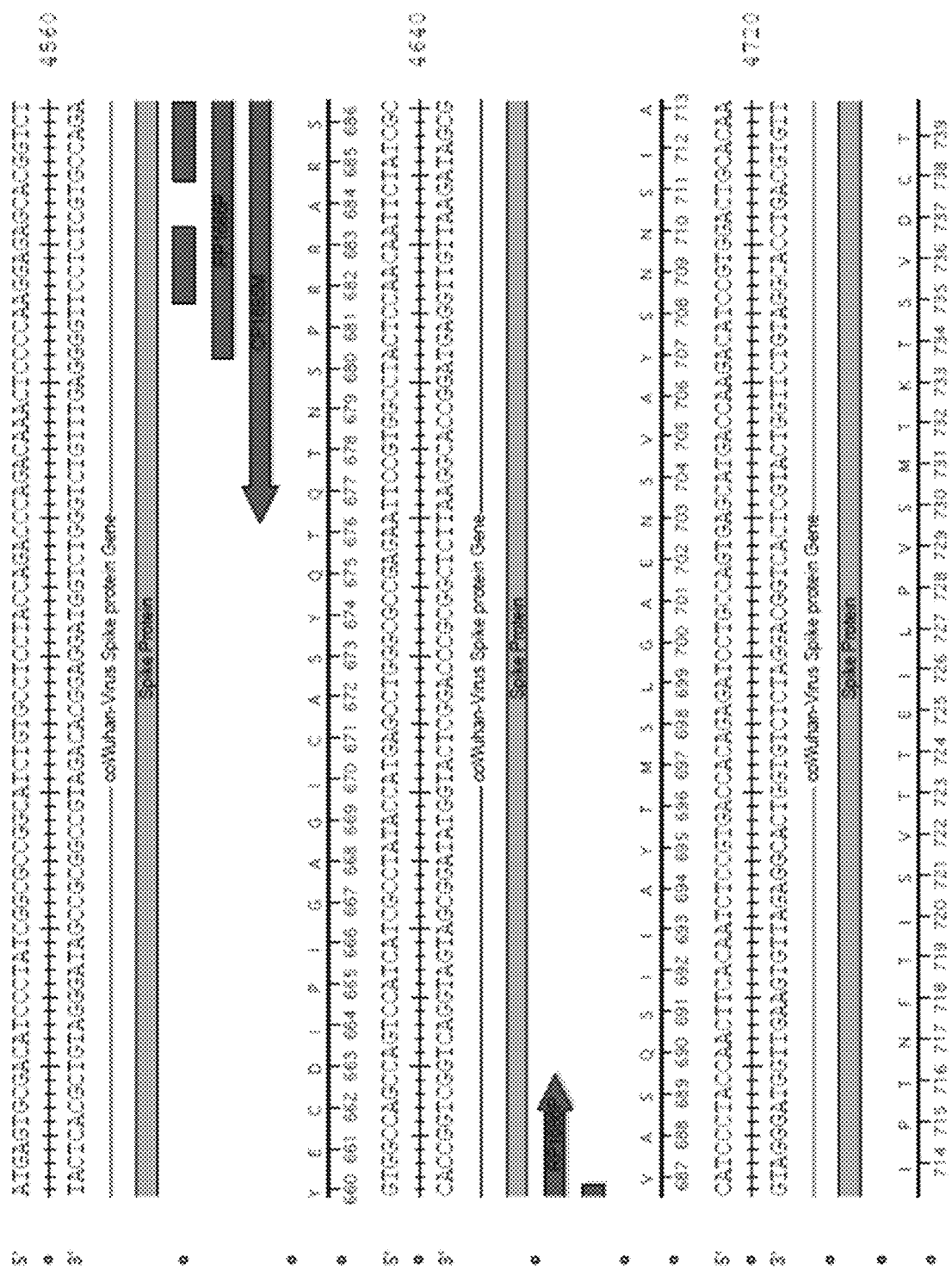
FIG. 21 – continued

CORONAVIRUS DISEASE (COVID-19) VACCINE

CROSS-REFERENCE TO RELATED APPLICATIONS

This application is a divisional of U.S. patent application Ser. No. 17/193,890 filed Mar. 5, 2021, which claims priority to U.S. Provisional Application No. 62/986,396 filed Mar. 6, 2020 and to U.S. Provisional Application No. 63/017,241 filed Apr. 29, 2020, each of which is herein incorporated by reference in its entirety.

STATEMENT REGARDING FEDERALLY SPONSORED RESEARCH OR DEVELOPMENT

This invention was made with government support under grant no. 1R21AI158044-01 awarded by the National Institute of Health. The government has certain rights in the invention.

REFERENCE TO SEQUENCE LISTING

The Sequence Listing concurrently submitted herewith as a text file named "205961_7055US2_Sequence_Listing.xml," created on Aug. 3, 2022 and having a size of 542,206 bytes is herein incorporated by reference pursuant to 37 C.F.R. § 1.52(e)(5).

BACKGROUND OF THE INVENTION

The recently emerged coronavirus, currently called 2019-nCoV or SARS-CoV-2 virus, is rapidly spreading in China and Asia with over 42,000 cases, 500 deaths and cases in 18 countries as of Feb. 10, 2020. This novel coronavirus is thought to have emerged from a live animal market in Wuhan, China, and has quickly spread in the community with large clusters of human to human transmission. The sequence of several isolates have been determined, and the closest strains are SARS-like bat coronavirus lineages. Little is known about this virus including its susceptibility to anti-viral compounds, ability to replicate in cell lines or host factors regulating replication. Importantly there are no therapeutics available to treat the virus, although investigational studies are underway. Modeling of the current outbreak suggests that the virus could infect >1 billion people and become a yearly epidemic.

A need exists for novel methods for generating vaccines to treat Coronaviruses, in particular, COVID-19. The present invention addresses and satisfies this need.

SUMMARY OF THE INVENTION

In some aspects, the present disclosure provides an isolated nucleic acid encoding a recombinant virus comprising a SARS-CoV-2 spike protein (S) or a portion thereof.

In other aspects, the present disclosure provides a recombinant virus comprising a SARS-CoV-2 spike protein (S) or a portion thereof.

In one aspect, the present disclosure provides a recombinant virus encoded by a nucleic acid described herein. In some embodiments, the nucleic acid encodes a recombinant virus comprising a SARS-CoV-2 spike protein (S) or a portion thereof.

In another aspect, the present disclosure provides a recombinant fusion protein comprising (a) a glycoprotein (G) of a virus or a portion thereof, and (b) a SARS-CoV-2 spike protein (S) or a portion thereof.

In some aspects, the present disclosure provides a vector comprising a nucleic acid described herein. In one embodiment, the nucleic acid encodes a recombinant virus comprising a SARS-CoV-2 spike protein (S) or a portion thereof.

In other aspects, the present disclosure provides a vaccine comprising a recombinant virus comprising a SARS-CoV-2 spike protein (S) or a portion thereof, and a pharmaceutically acceptable carrier.

In one aspect, the present disclosure provides a method of generating an immune response against a SARS-CoV-2 virus in a subject in need thereof, the method comprising administering to the subject an effective amount of a vaccine described herein. In some embodiments, the vaccine comprises a recombinant virus comprising a SARS-CoV-2 spike protein (S) or a portion thereof, and a pharmaceutically acceptable carrier.

In another aspect, the present disclosure provides a method of vaccinating a subject against a SARS-CoV-2 virus, the method comprising administering to the subject an effective amount of the vaccine described herein. In some embodiments, the vaccine comprises a recombinant virus comprising a SARS-CoV-2 spike protein (S) or a portion thereof, and a pharmaceutically acceptable carrier.

In other aspects, the present disclosure provides a method of providing immunity against a SARS-CoV-2 virus in a subject, the method comprising administering to the subject an effective amount of the vaccine described herein. In some embodiments, the vaccine comprises a recombinant virus comprising a SARS-CoV-2 spike protein (S) or a portion thereof, and a pharmaceutically acceptable carrier.

In some aspects, the present disclosure provides a method of treating and/or preventing a disease or disorder associated with a SARS-CoV-2 virus in a subject in need thereof, the method comprising administering to the subject an effective amount of the vaccine described herein. In some embodiments, the vaccine comprises a recombinant virus comprising a SARS-CoV-2 spike protein (S) or a portion thereof, and a pharmaceutically acceptable carrier.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

Figure 1:
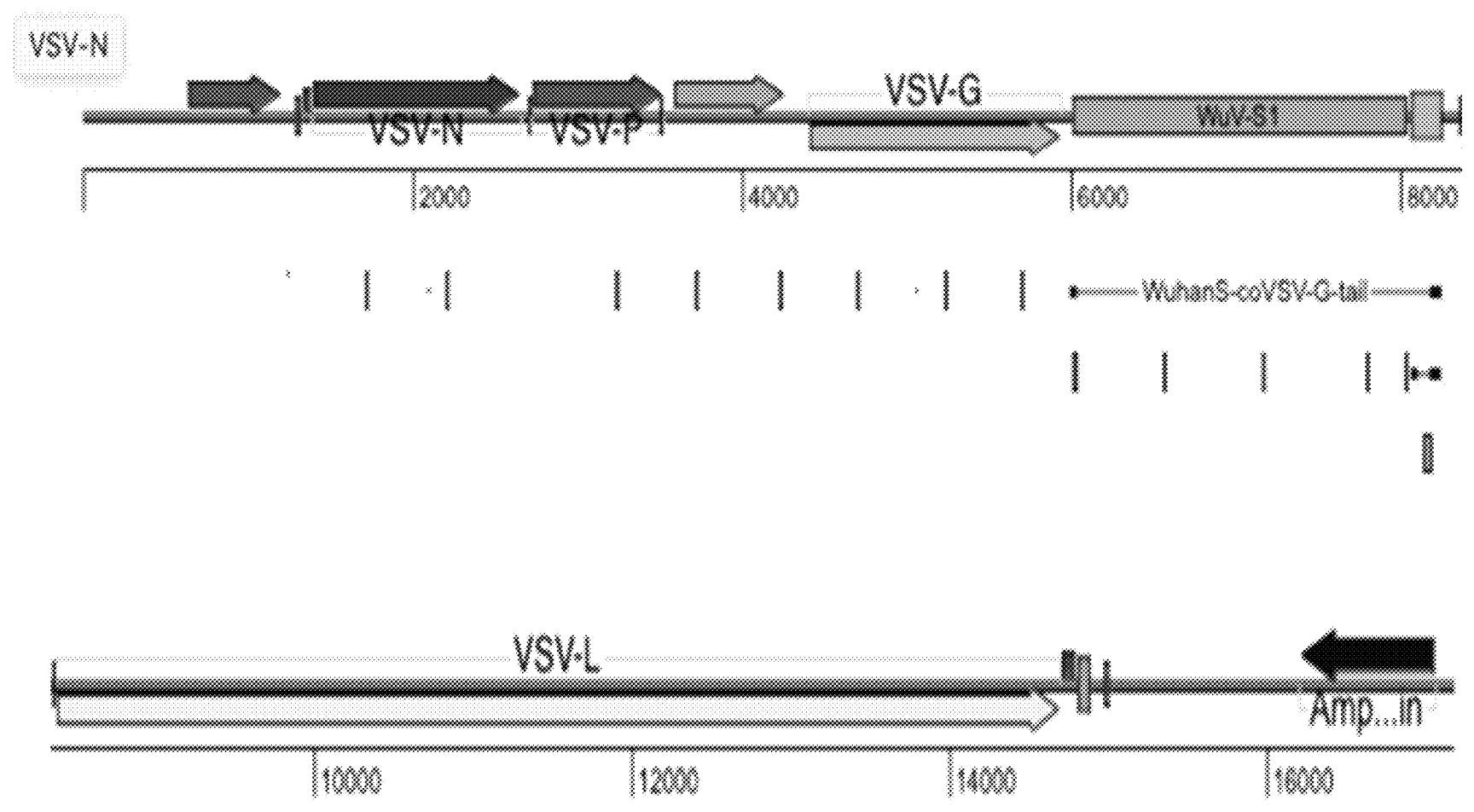

FIG. 1: VSV expressing codon-optimized Covid-S1. The map shows the viral sequence including the plasmids utilized to create the recombinant virus. The sequence is shown in SEQ ID NO: 1 and features are shown in FIG. 7. The sequence and features are also shown in FIG. 17 ("VSV-COVID19-S1-VSVG").

FIG. 7 shows the features of the map shown in FIG. 1.
FIG. 8 shows the features of the map shown in FIG. 2.
FIG. 9 shows the features of the map shown in FIG. 3.
FIG. 10 shows the features of the map shown in FIG. 4.
FIG. 11 shows the features of the map shown in FIG. 5.

FIGS. 14A-14C: Two or three inoculation with MERSRAB protect animals from weight loss and vaccine induce immune responses control the MERS-CoV challenge viruses to undetectable levels. Animals were immunized and challenge as outlined in FIG. 13.

FIGS. 16A-16B: FIG. 16A is a presentation showing formulation of BBV151-A vaccine (BBV151-A1 & BBV151-A2) and FIG. 16B is a presentation showing formulation of BBV-151-B vaccine.

FIG. 17 shows the sequence (SEQ ID NO: 1) and features of "VSV-COVID19-S1-VSVG.

FIG. 18 shows the sequence (SEQ ID NO: 2) and features of "BNSP333-COVID19-S1-RVG".

Figure 19:
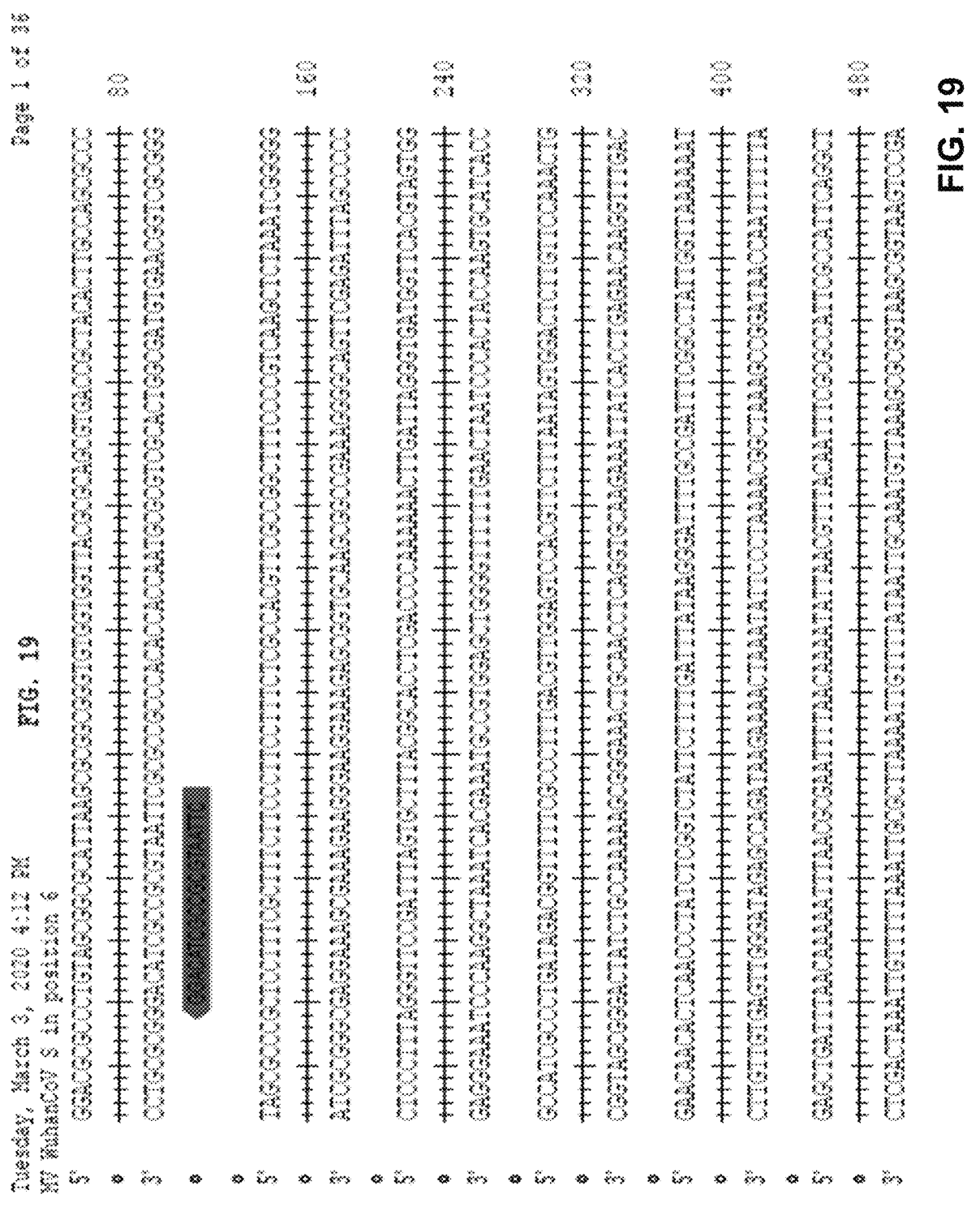
Figure 19:
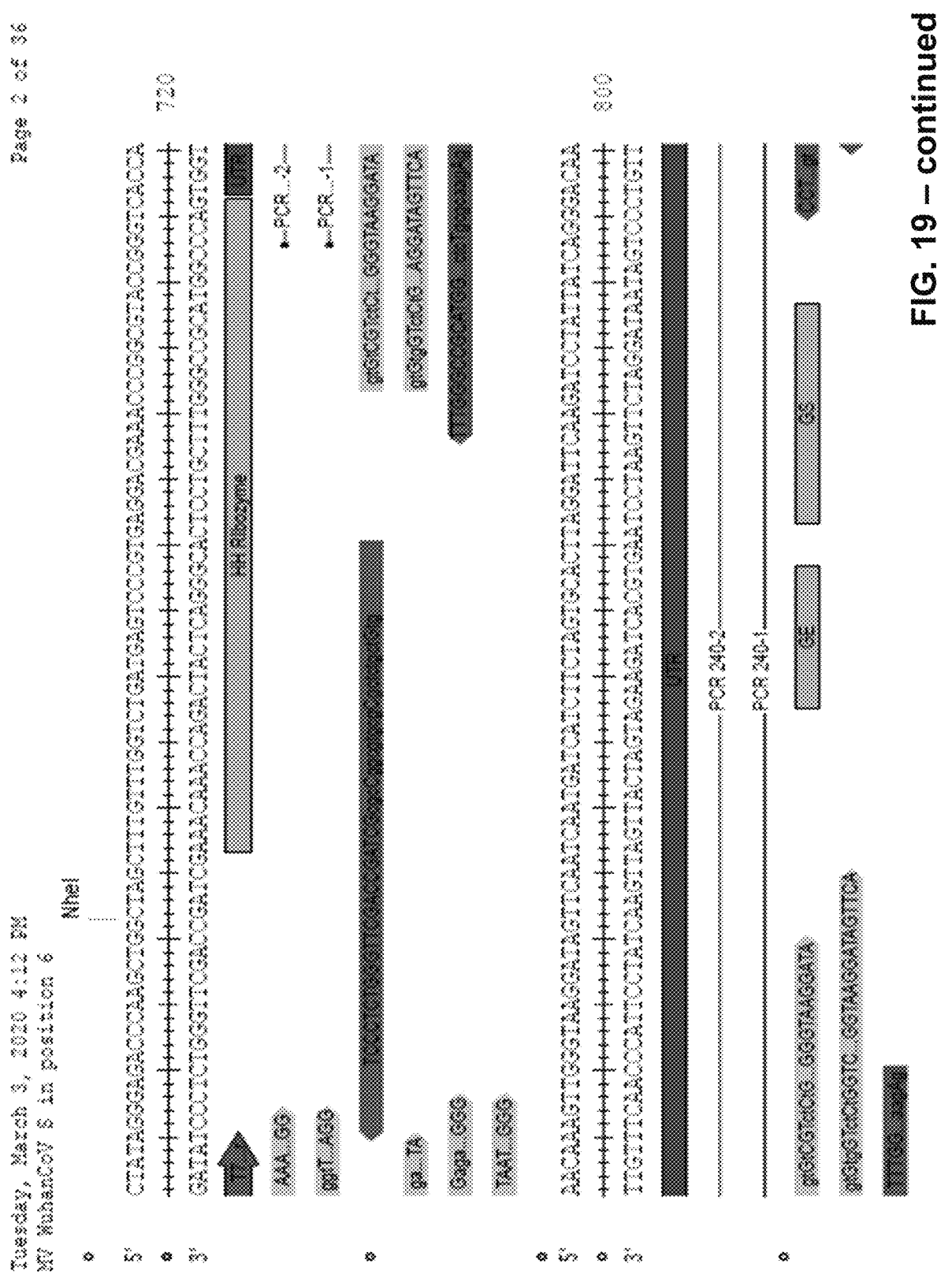
Figure 19:
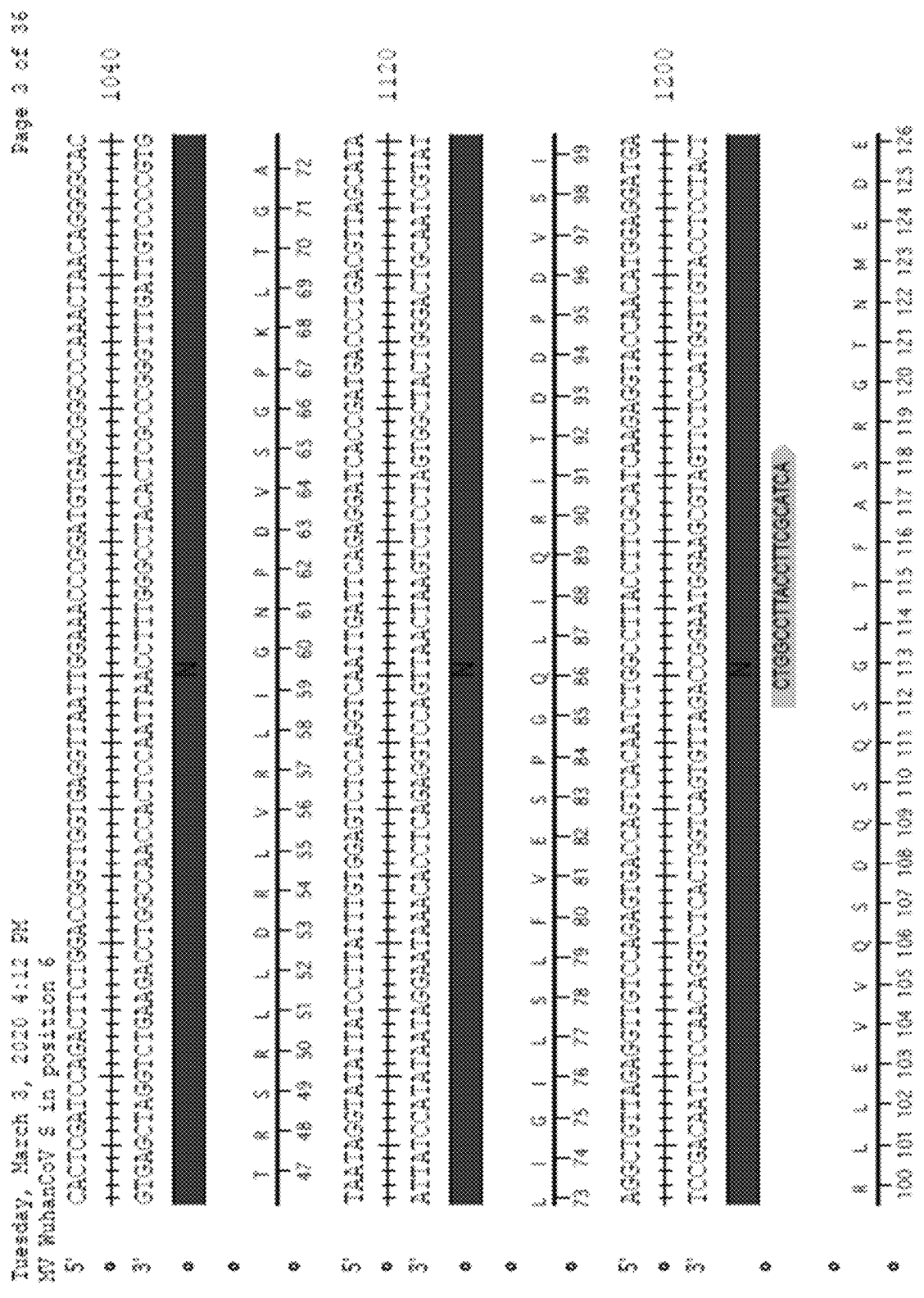
Figure 19:
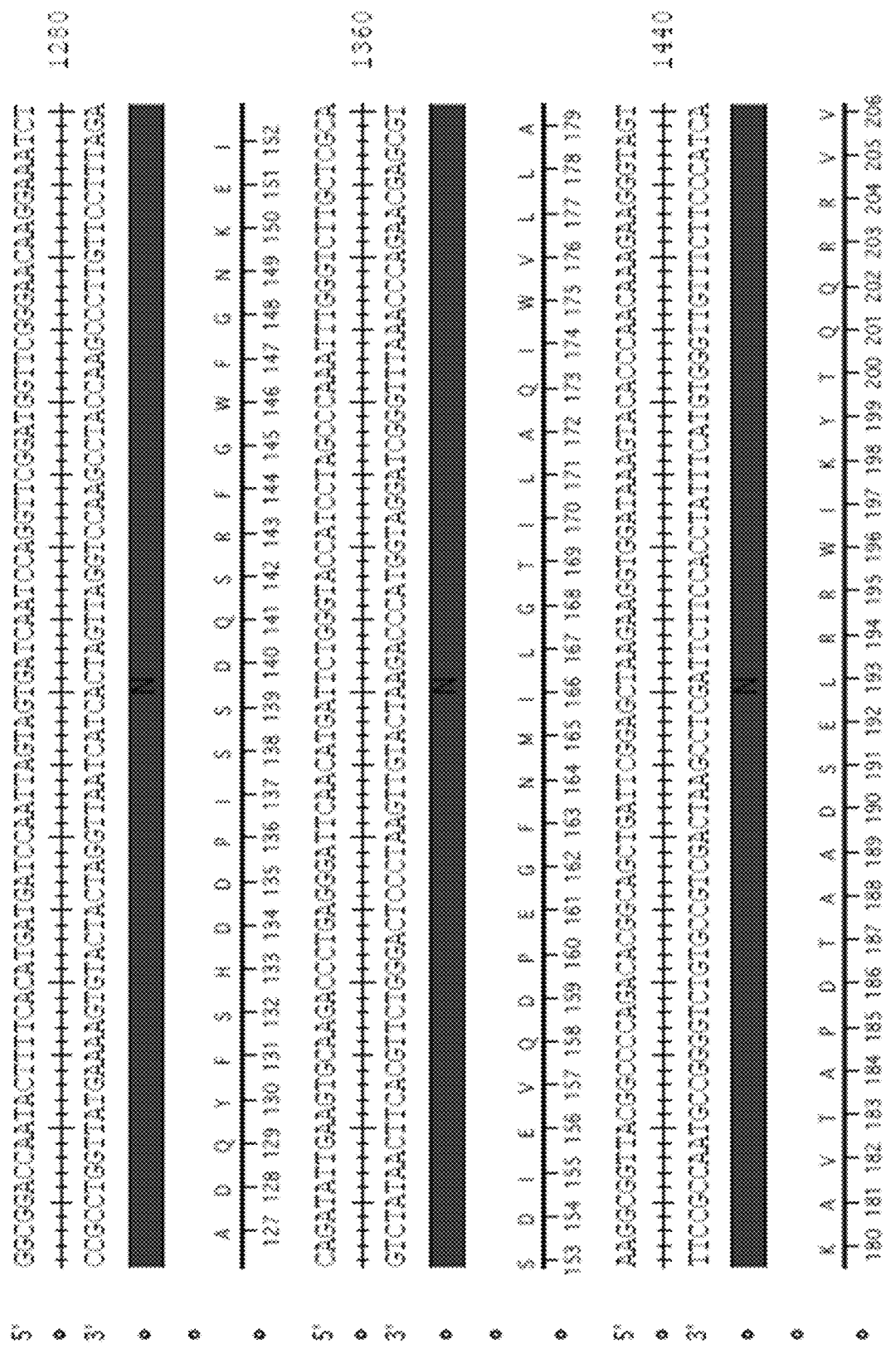
Figure 19:
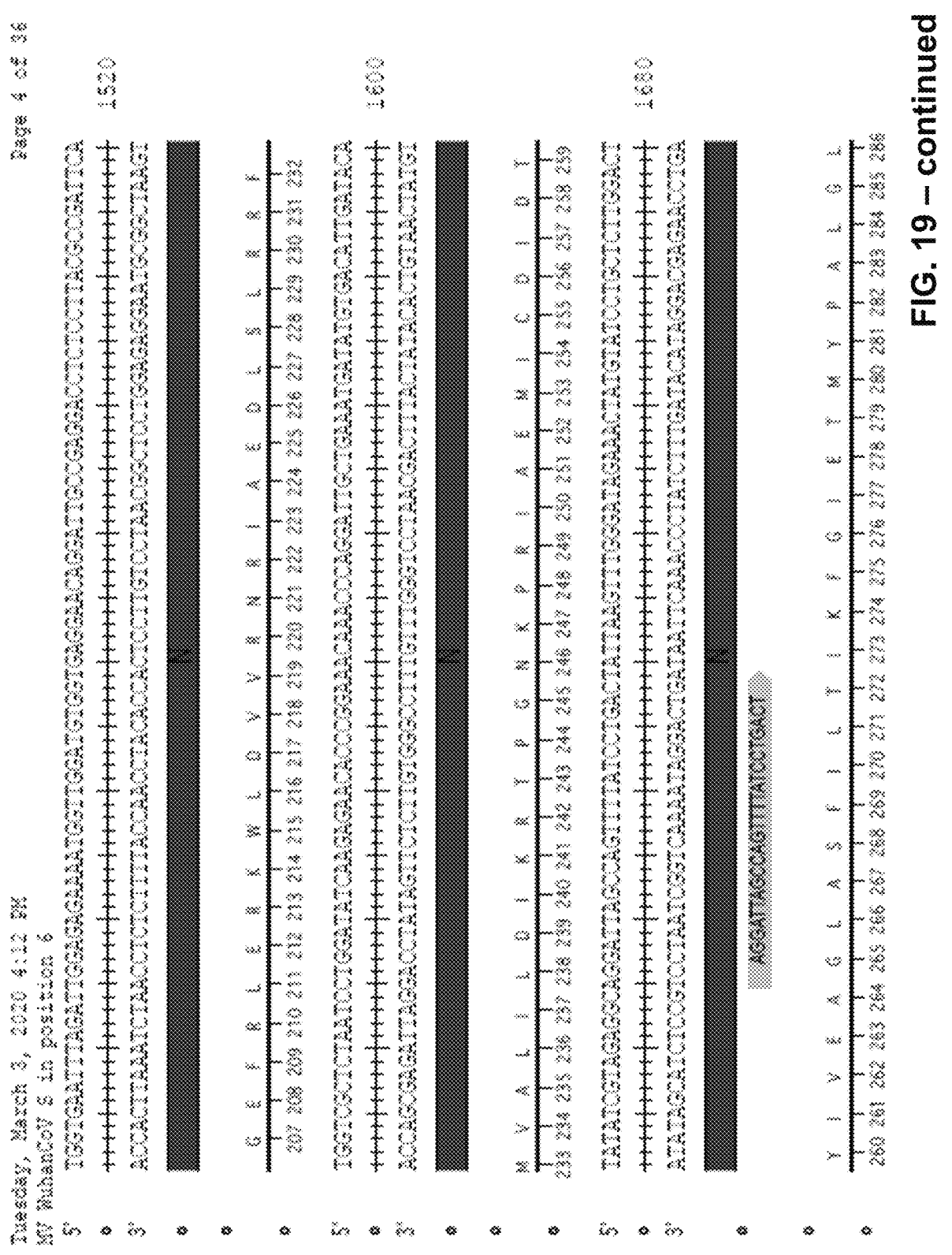
Figure 19:
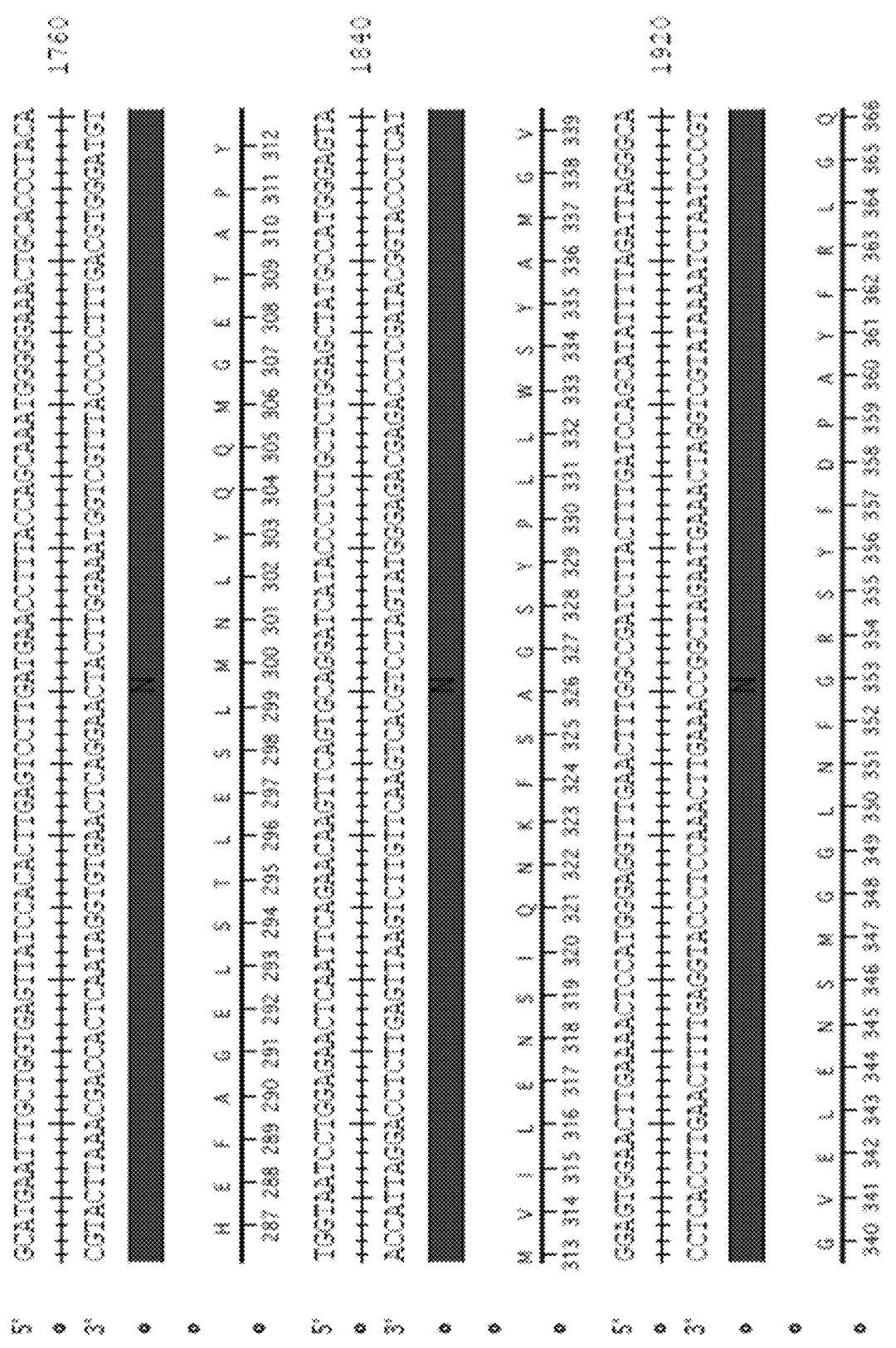
Figure 19:
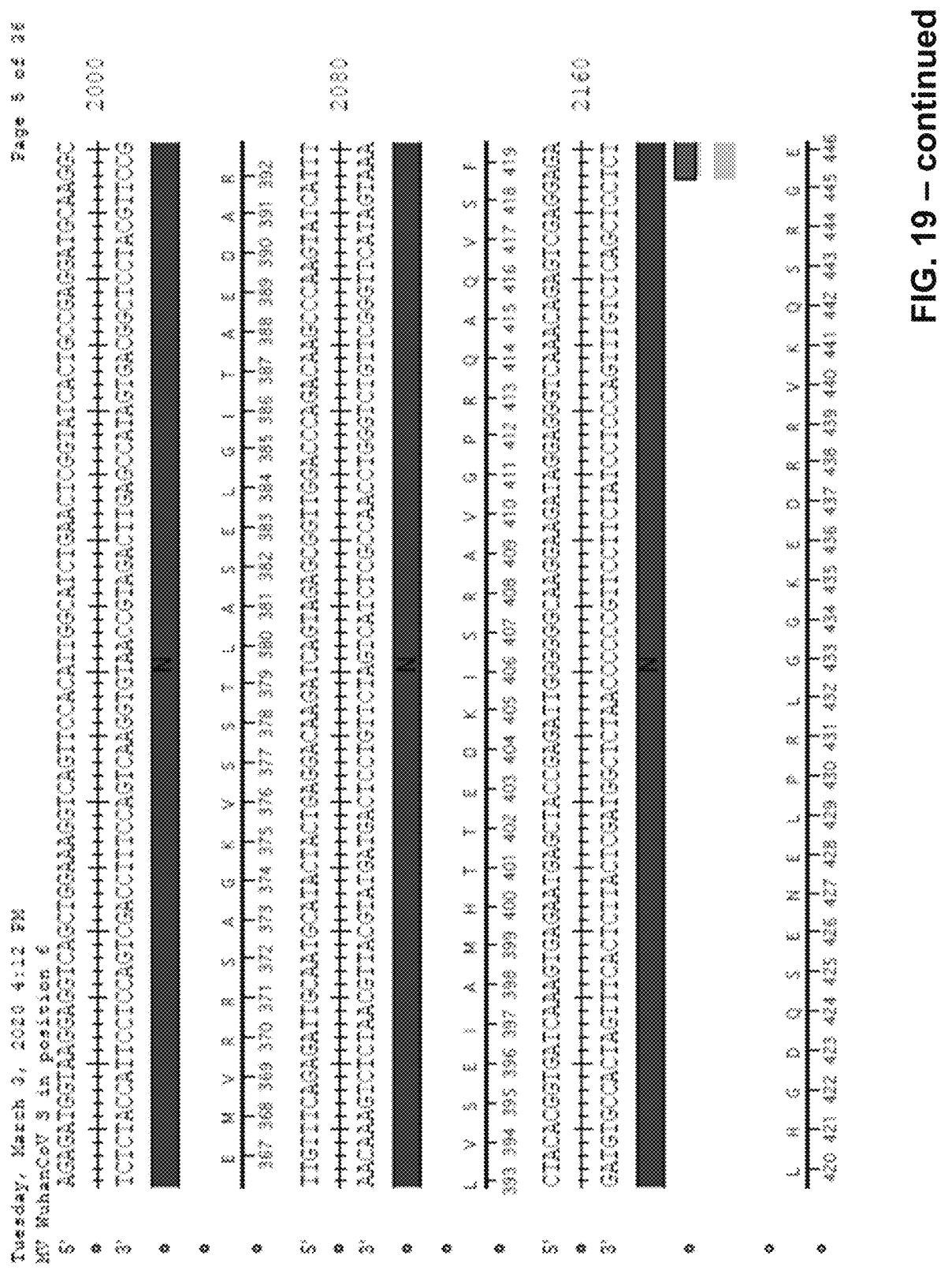
Figure 19:
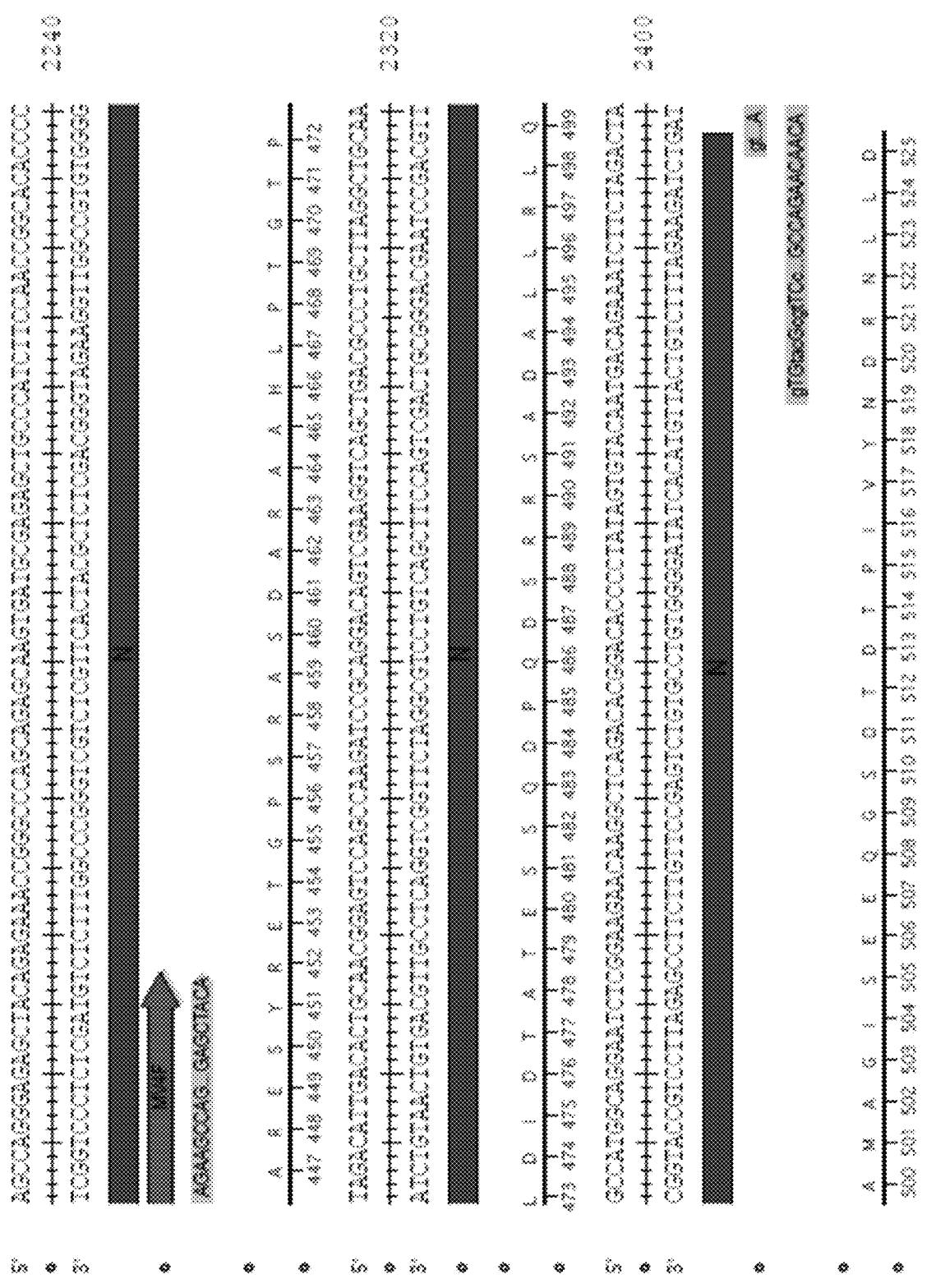
Figure 19:
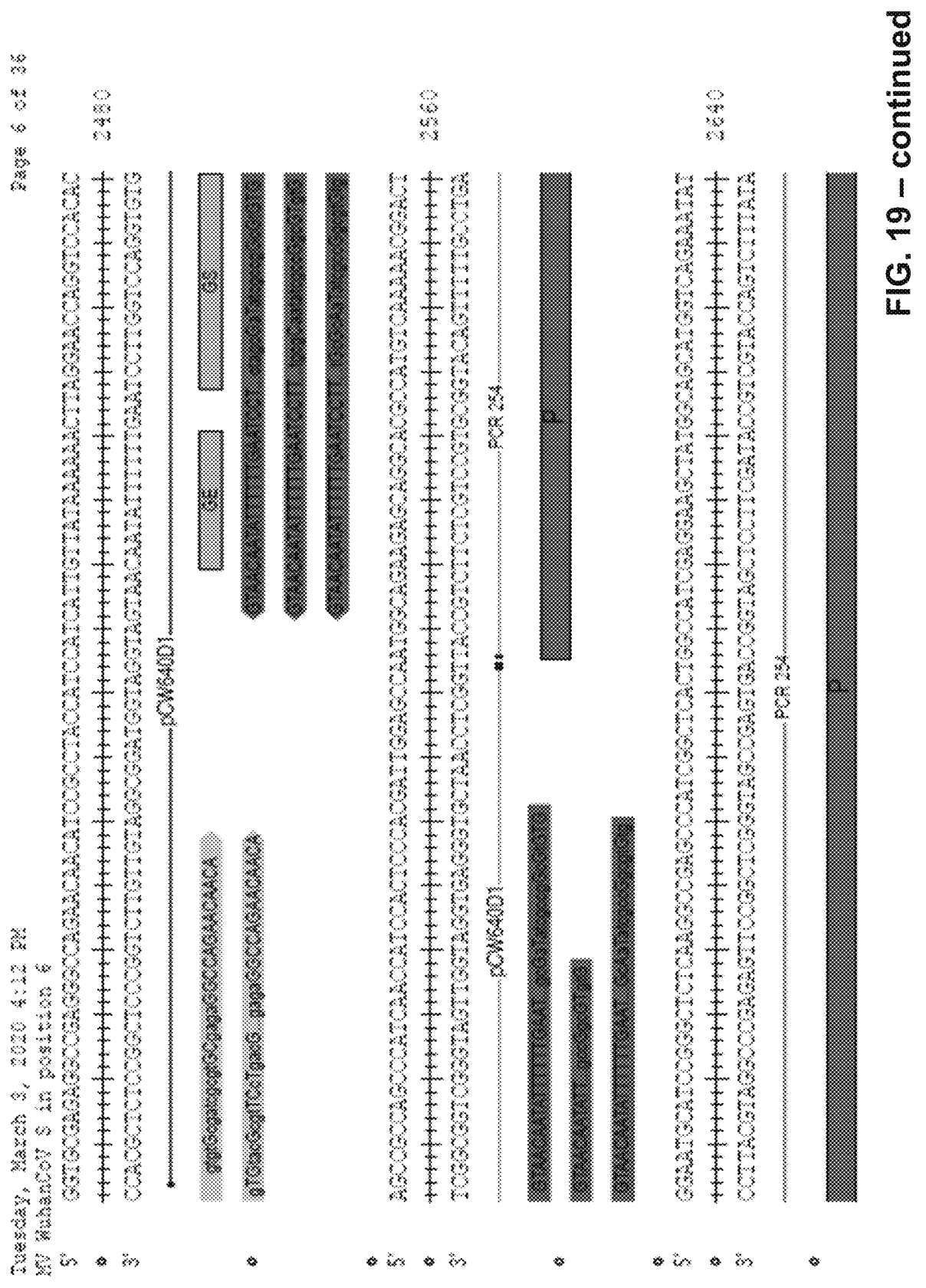
Figure 19:
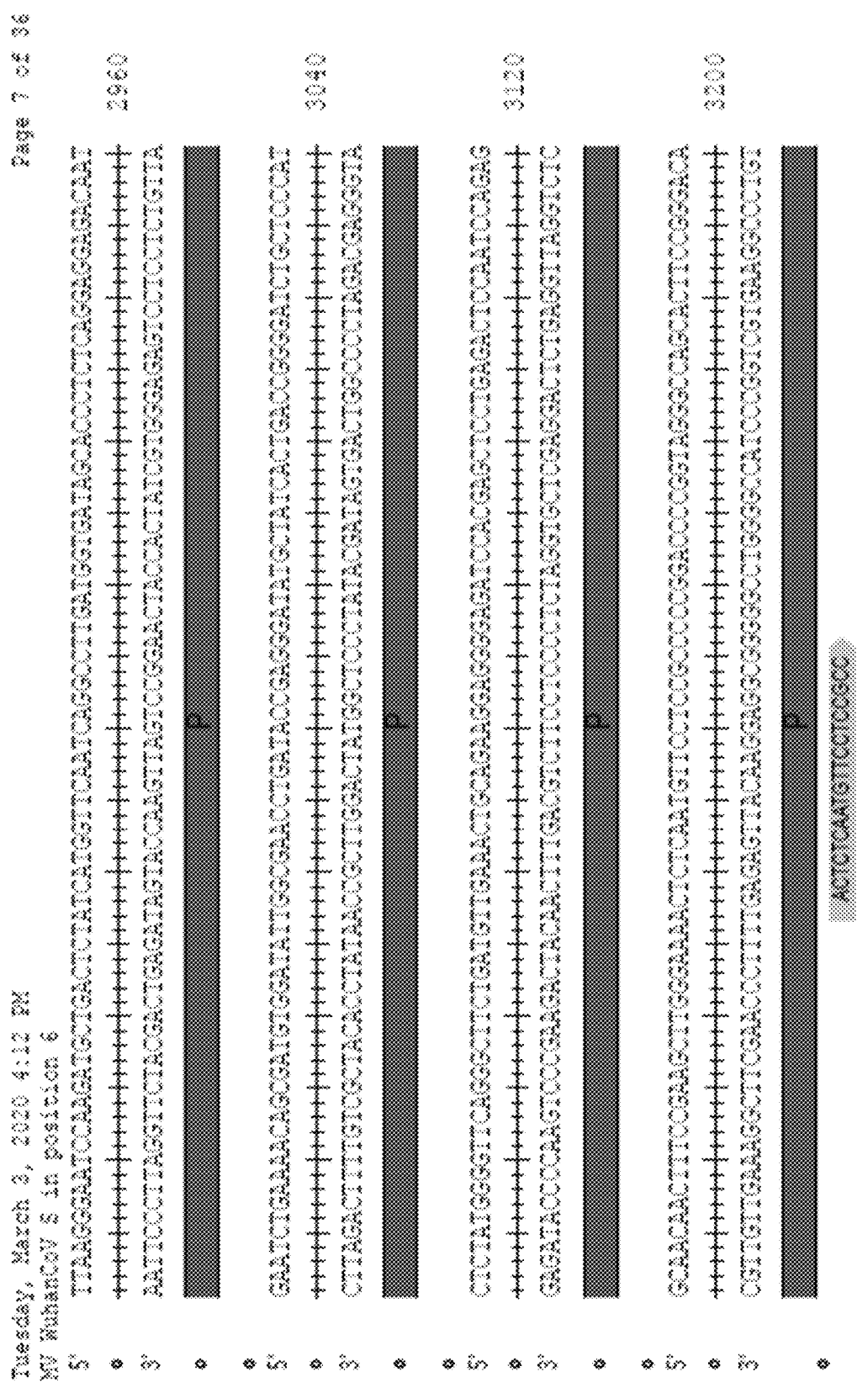
Figure 19:
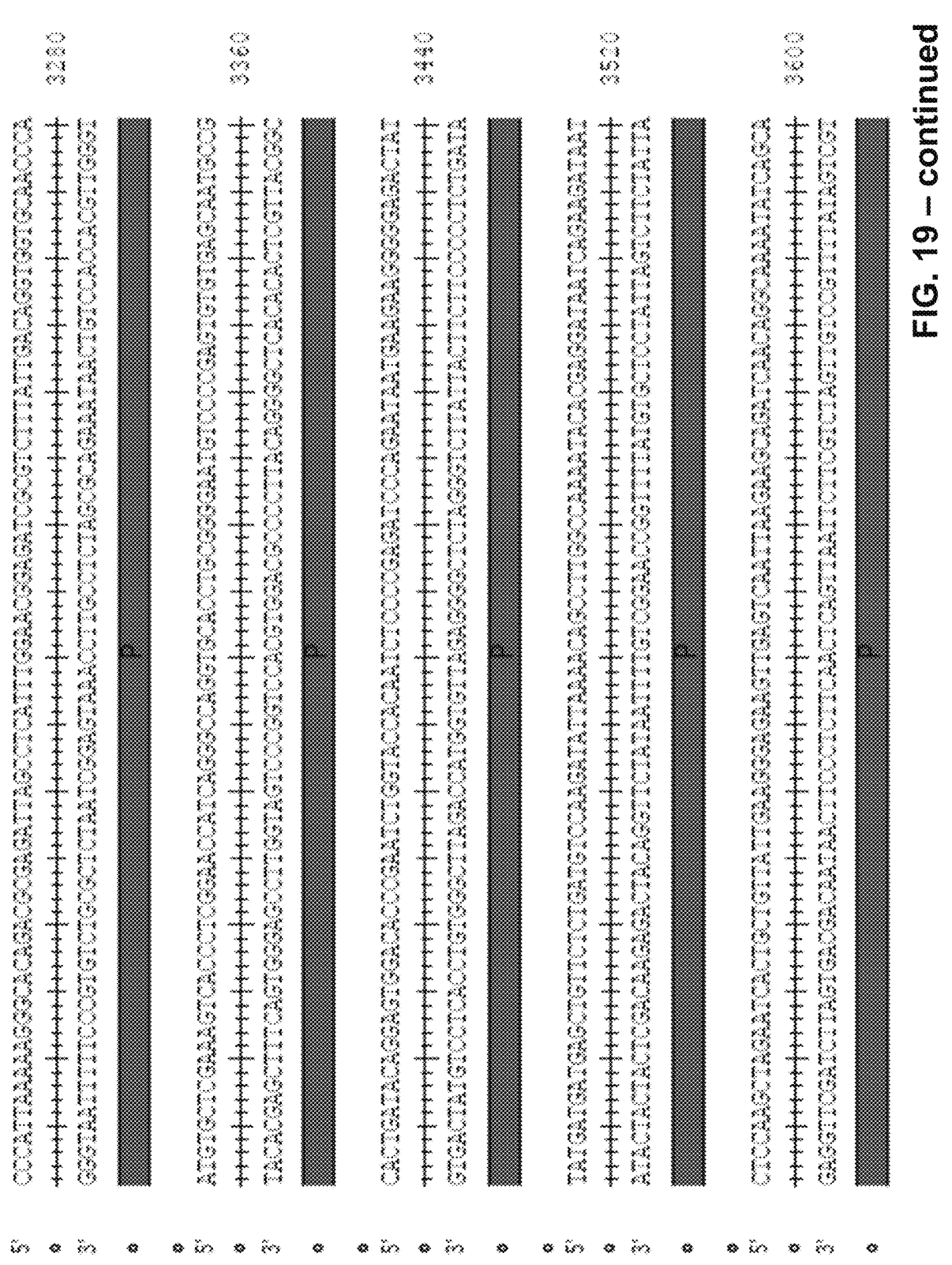
Figure 19:
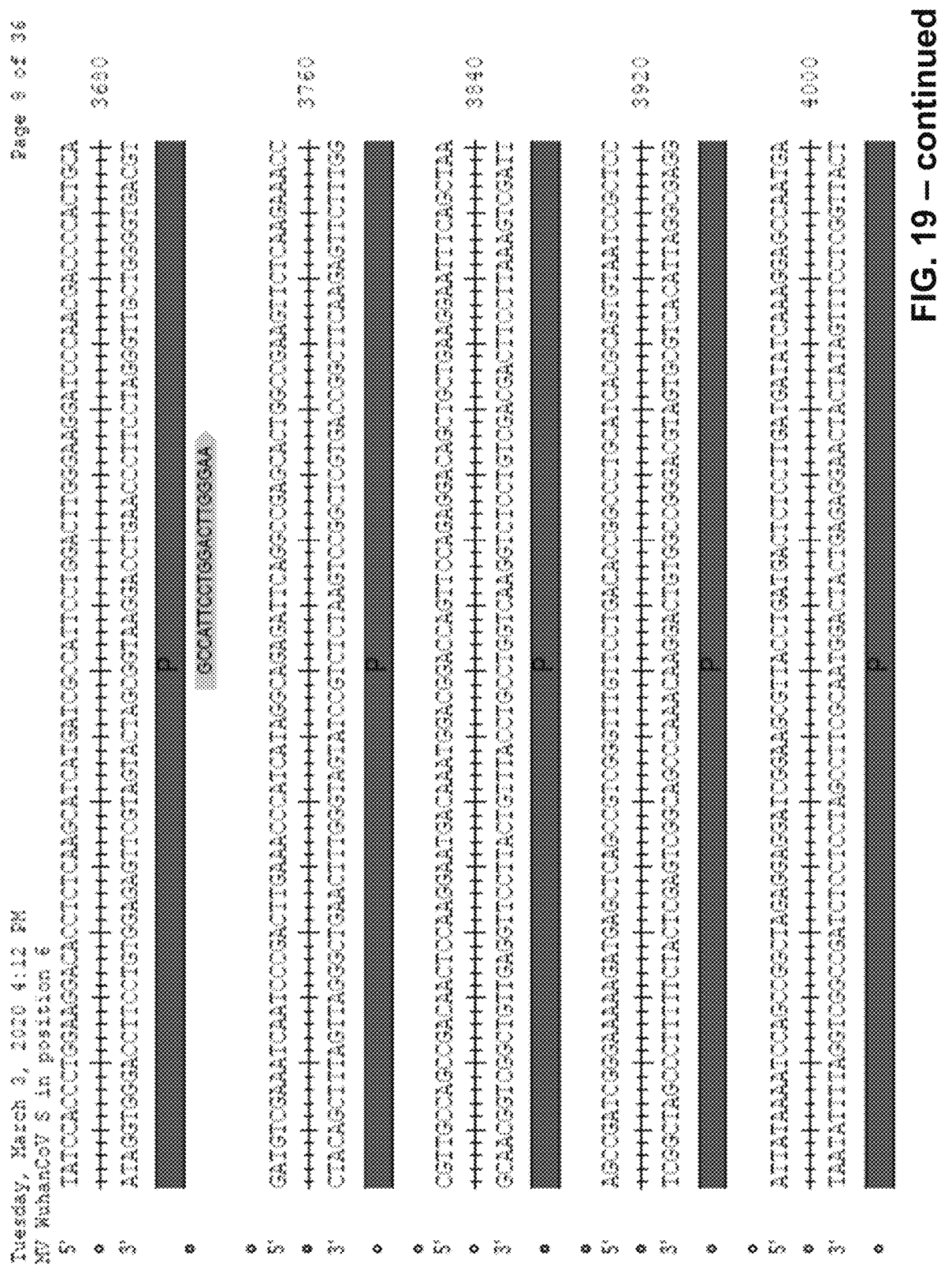
Figure 19:
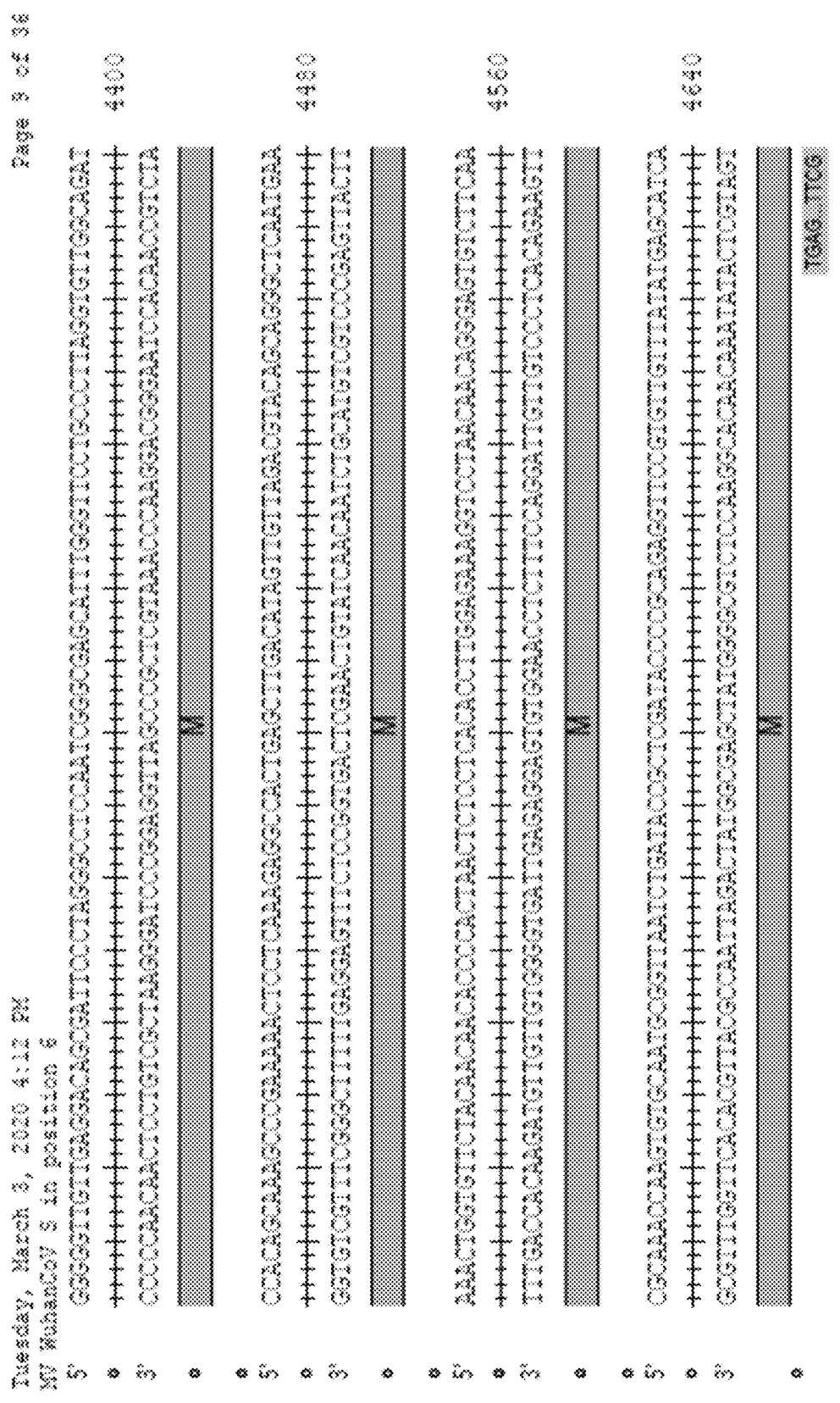
Figure 19:
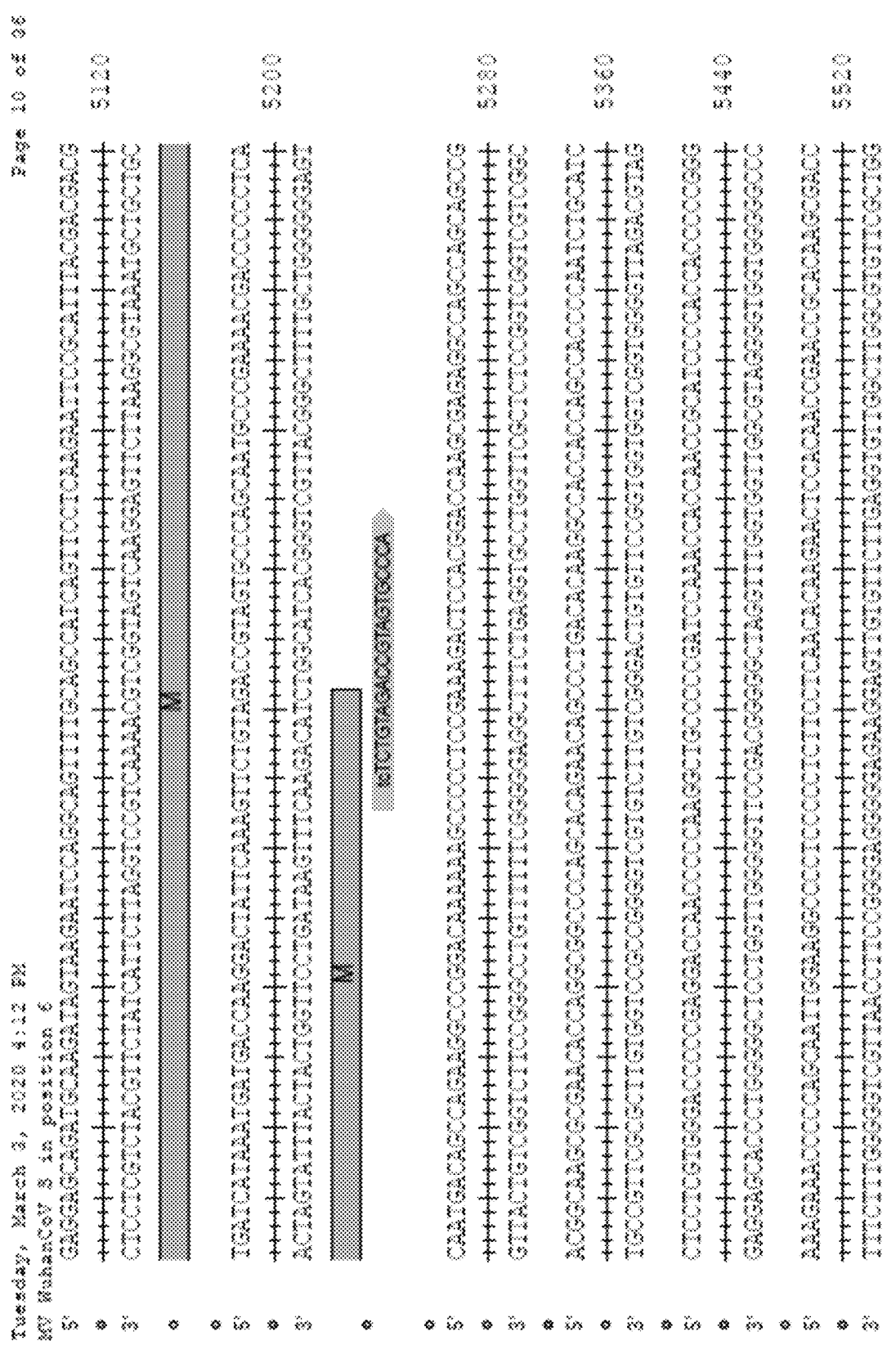
Figure 19:
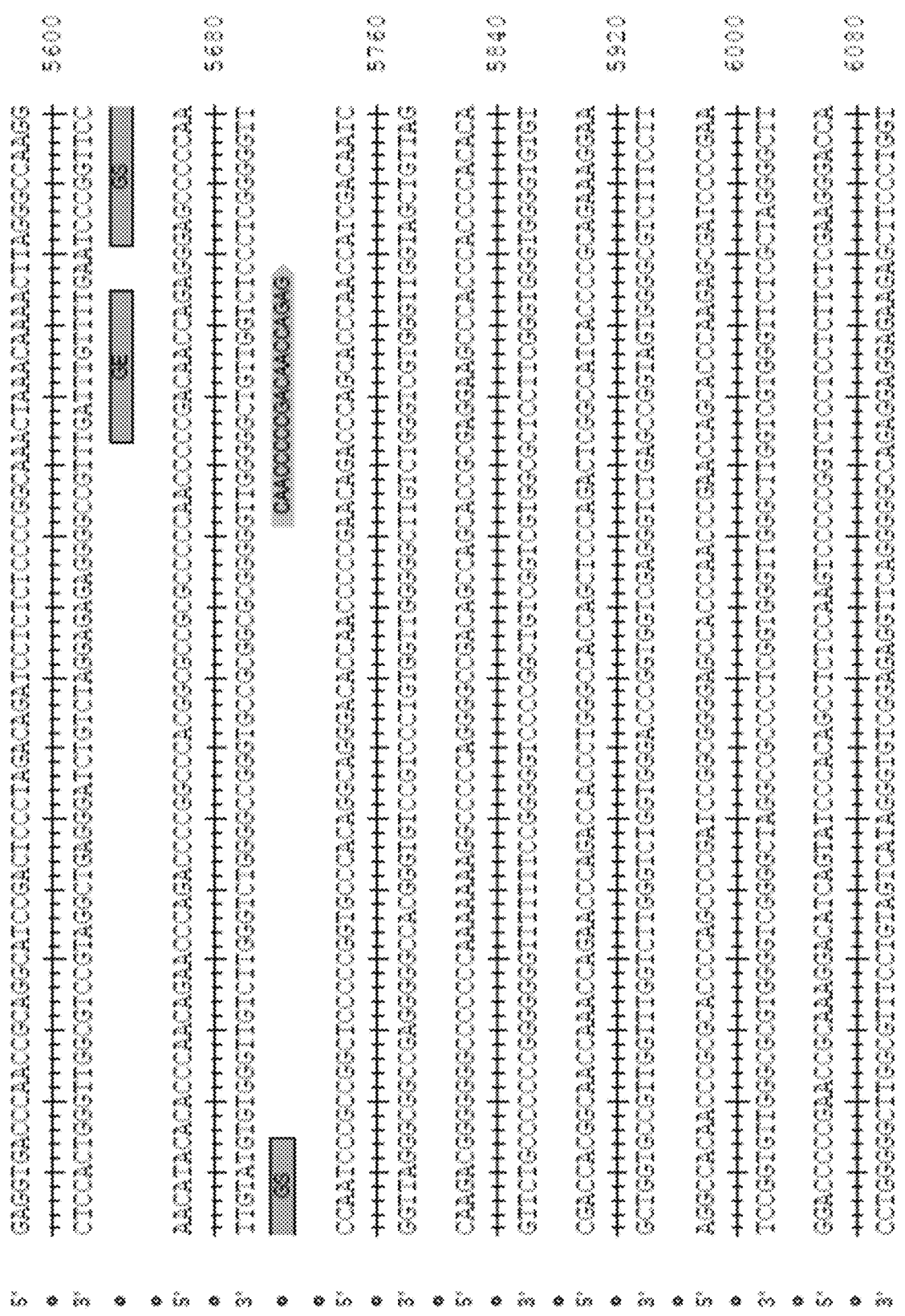
Figure 19:
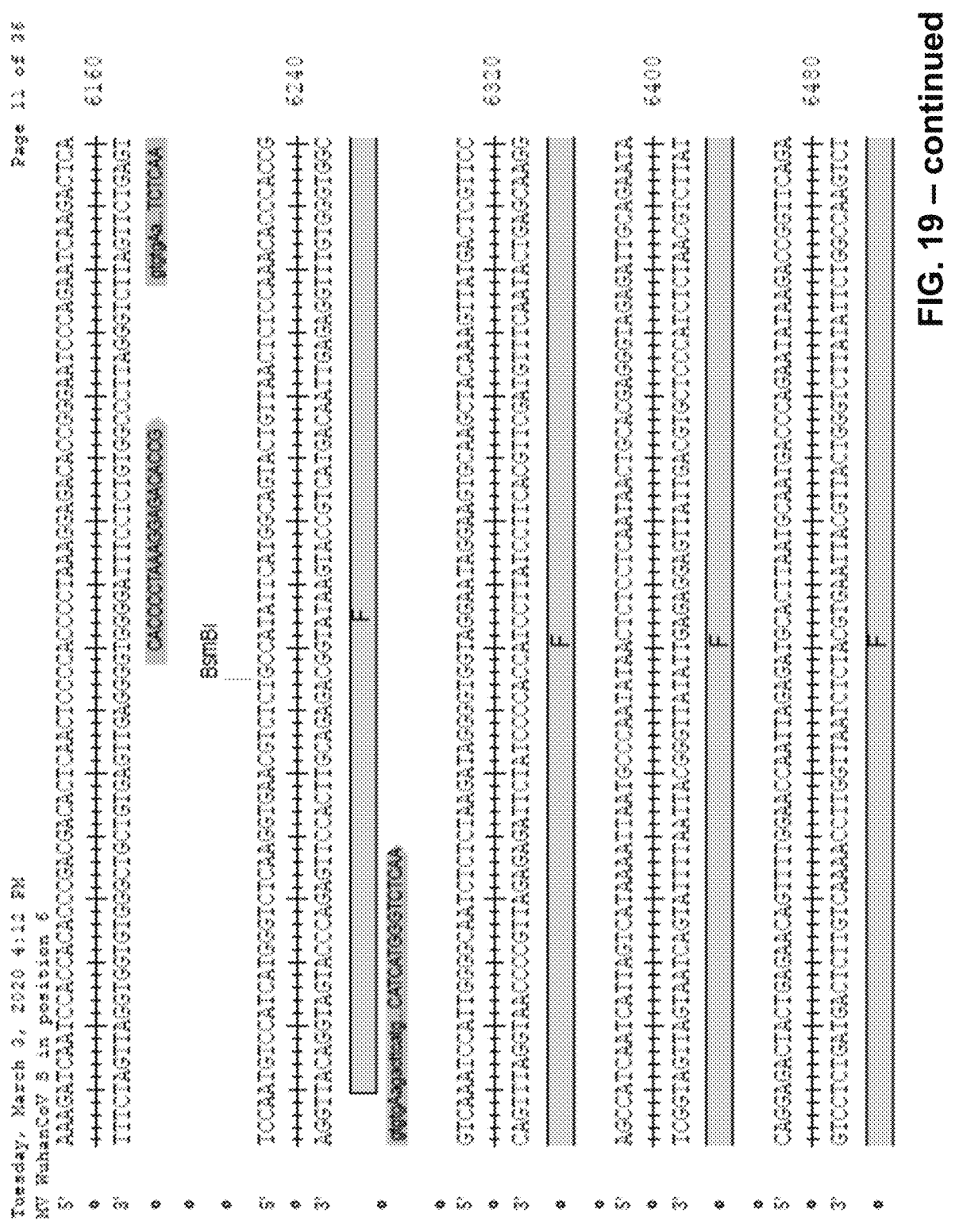
Figure 19:
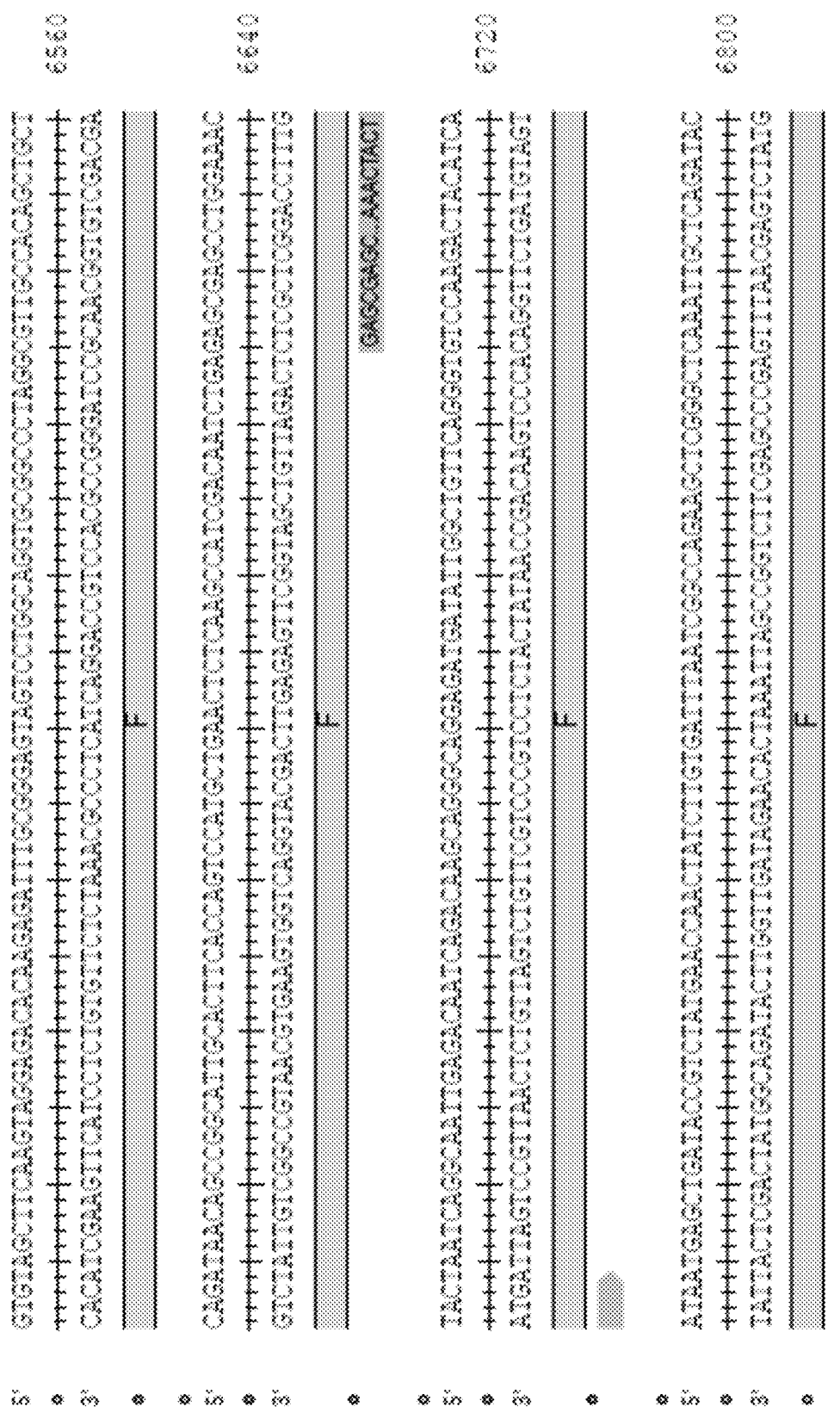
Figure 19:
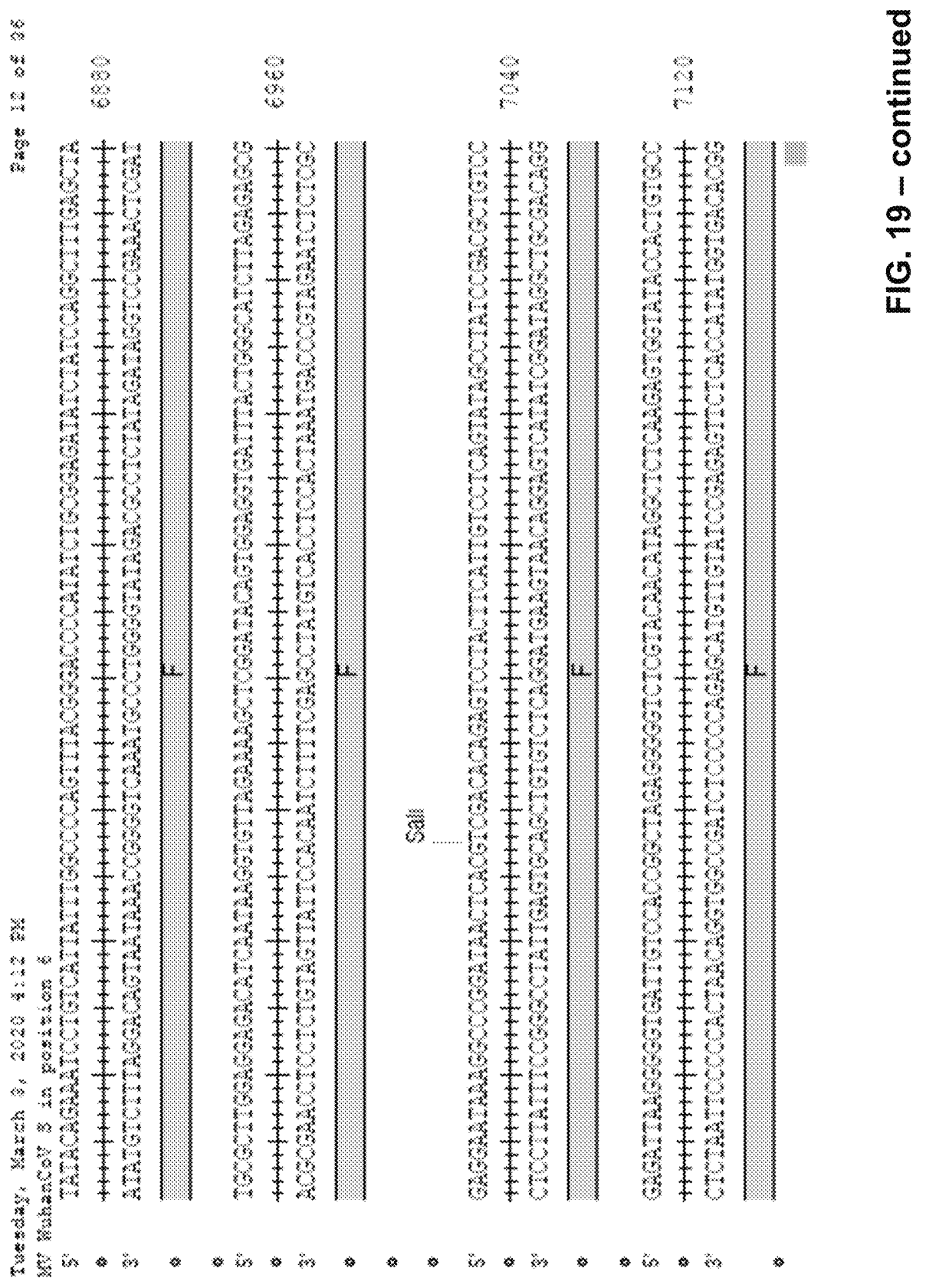
Figure 19:
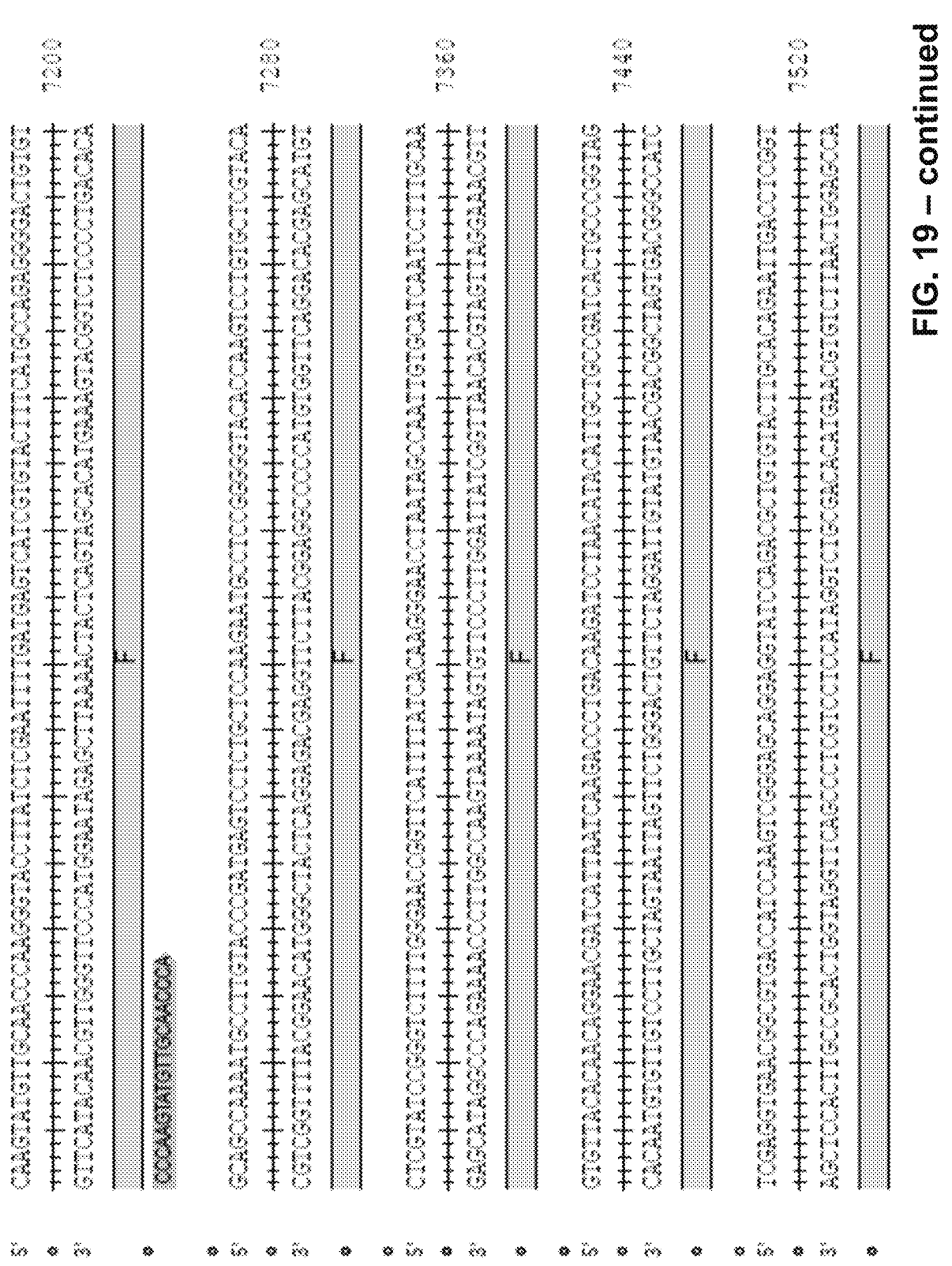
Figure 19:
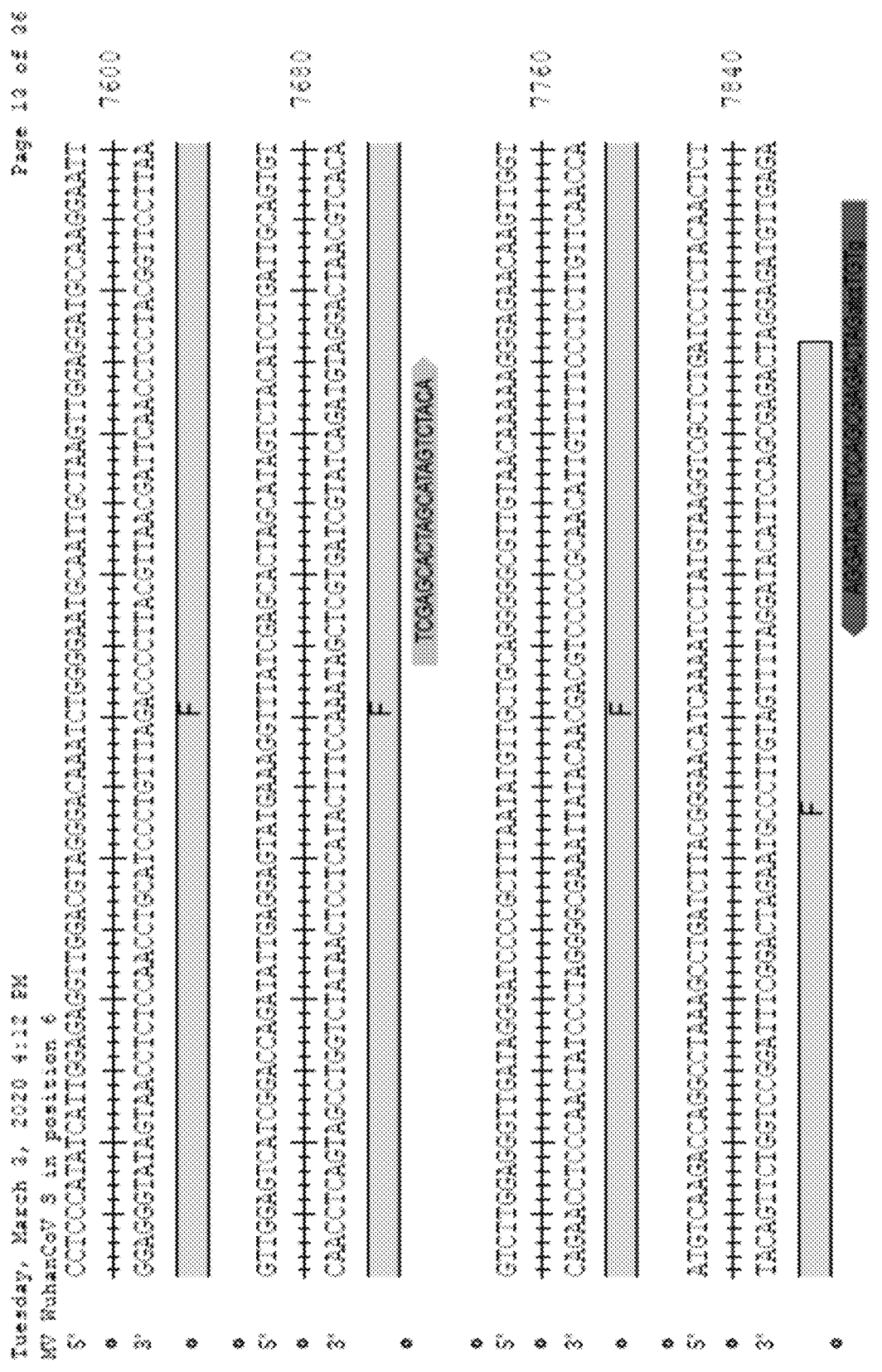
Figure 19:
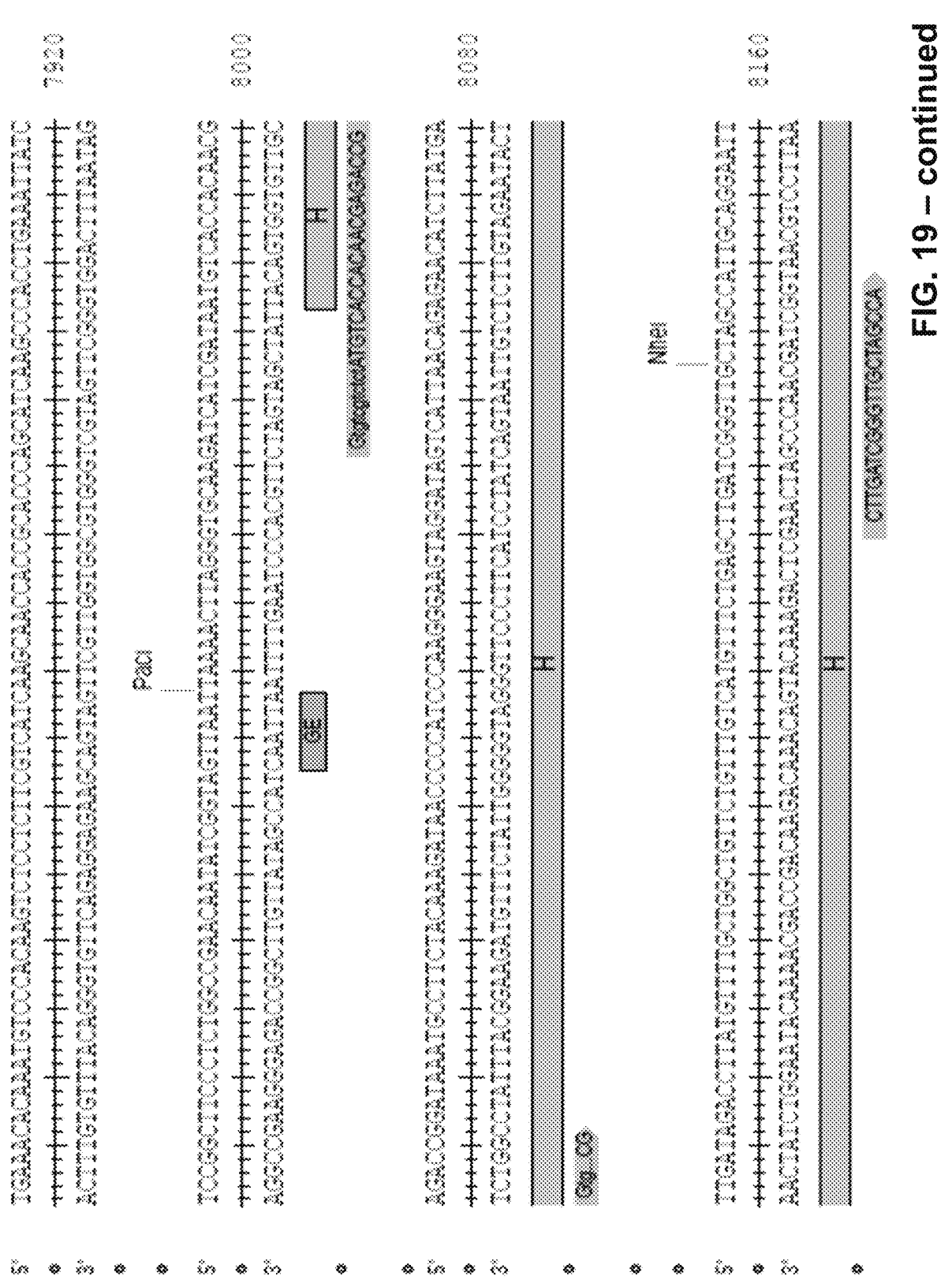
Figure 19:
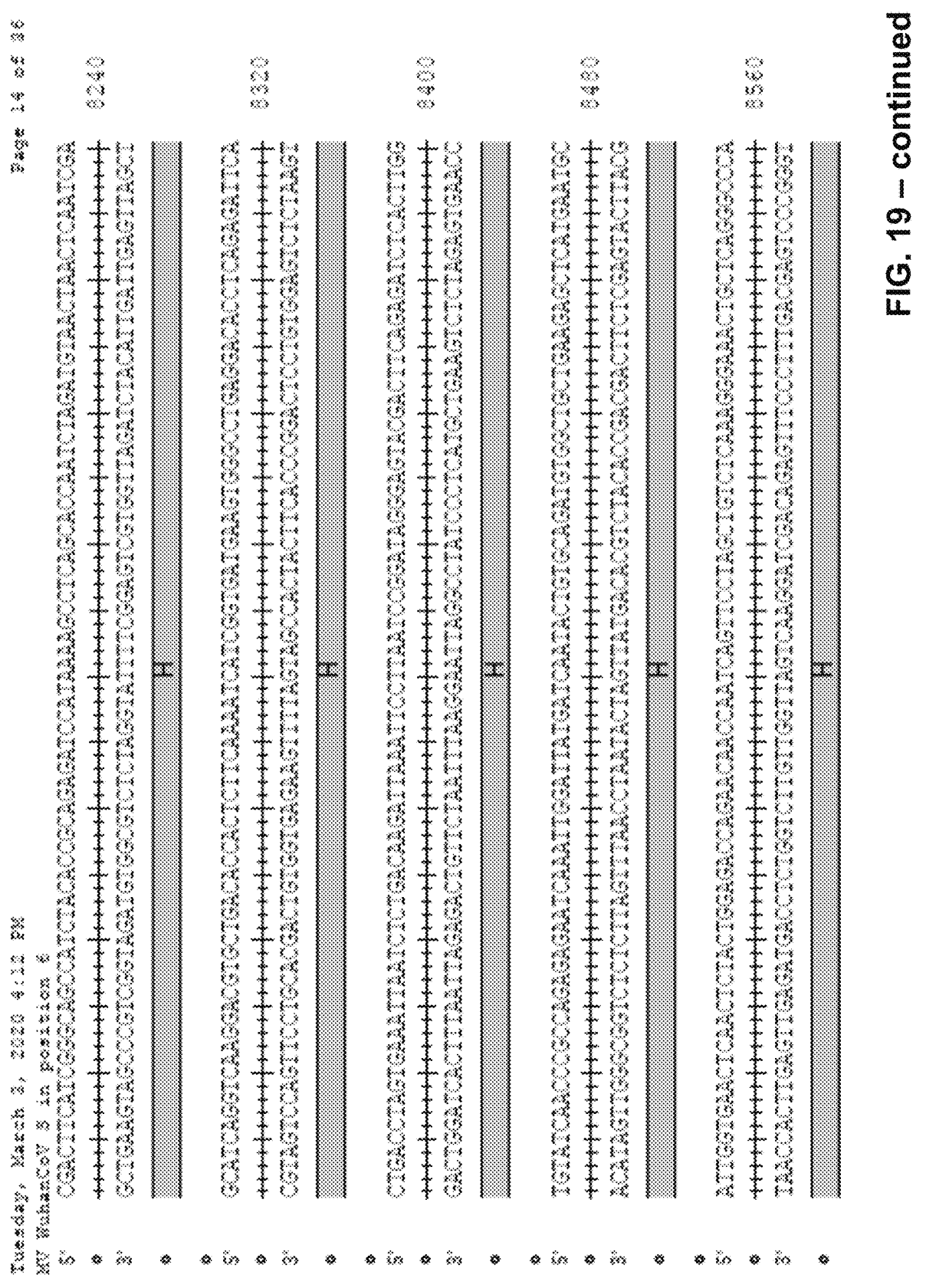
Figure 19:
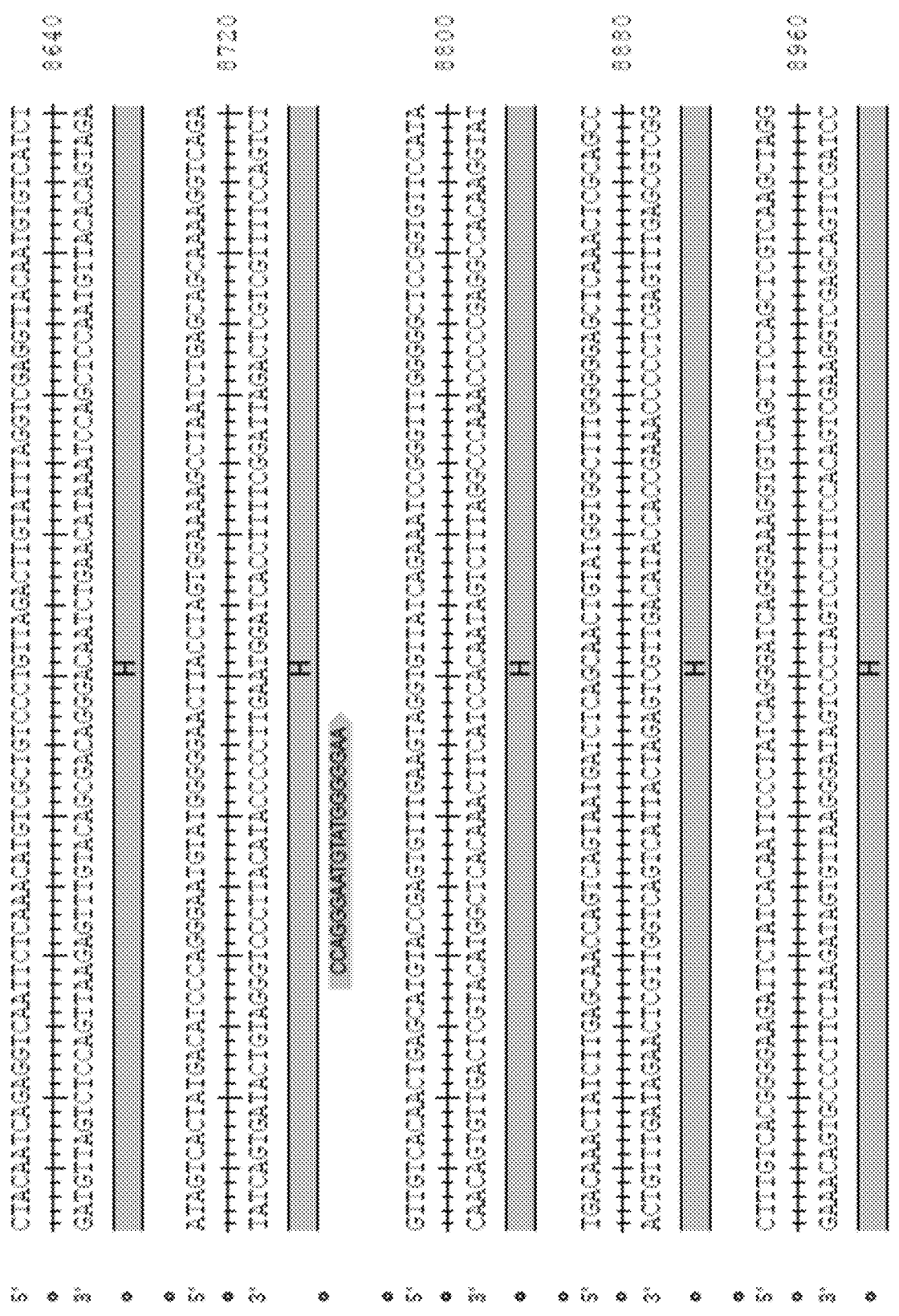
Figure 19:
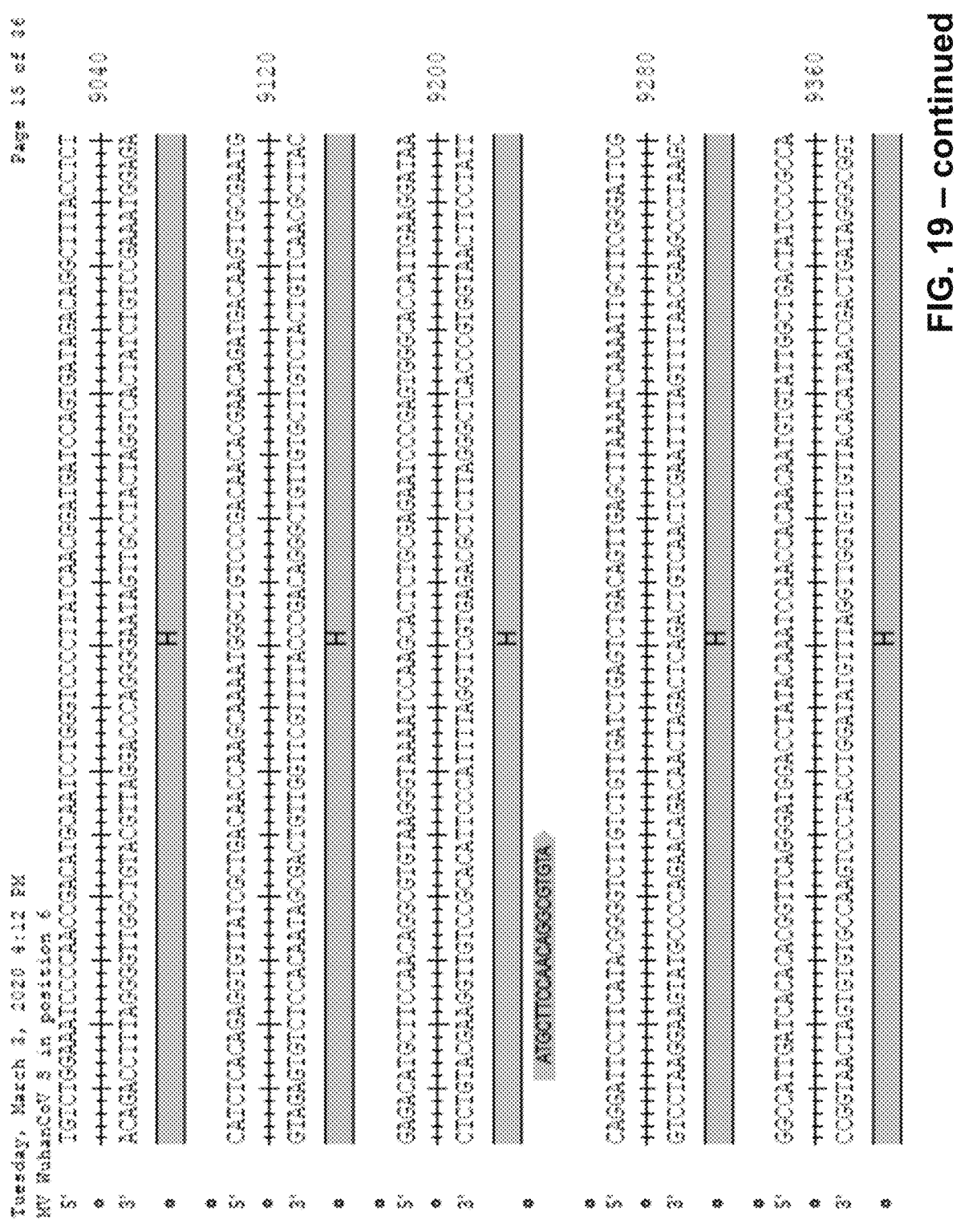
Figure 19:
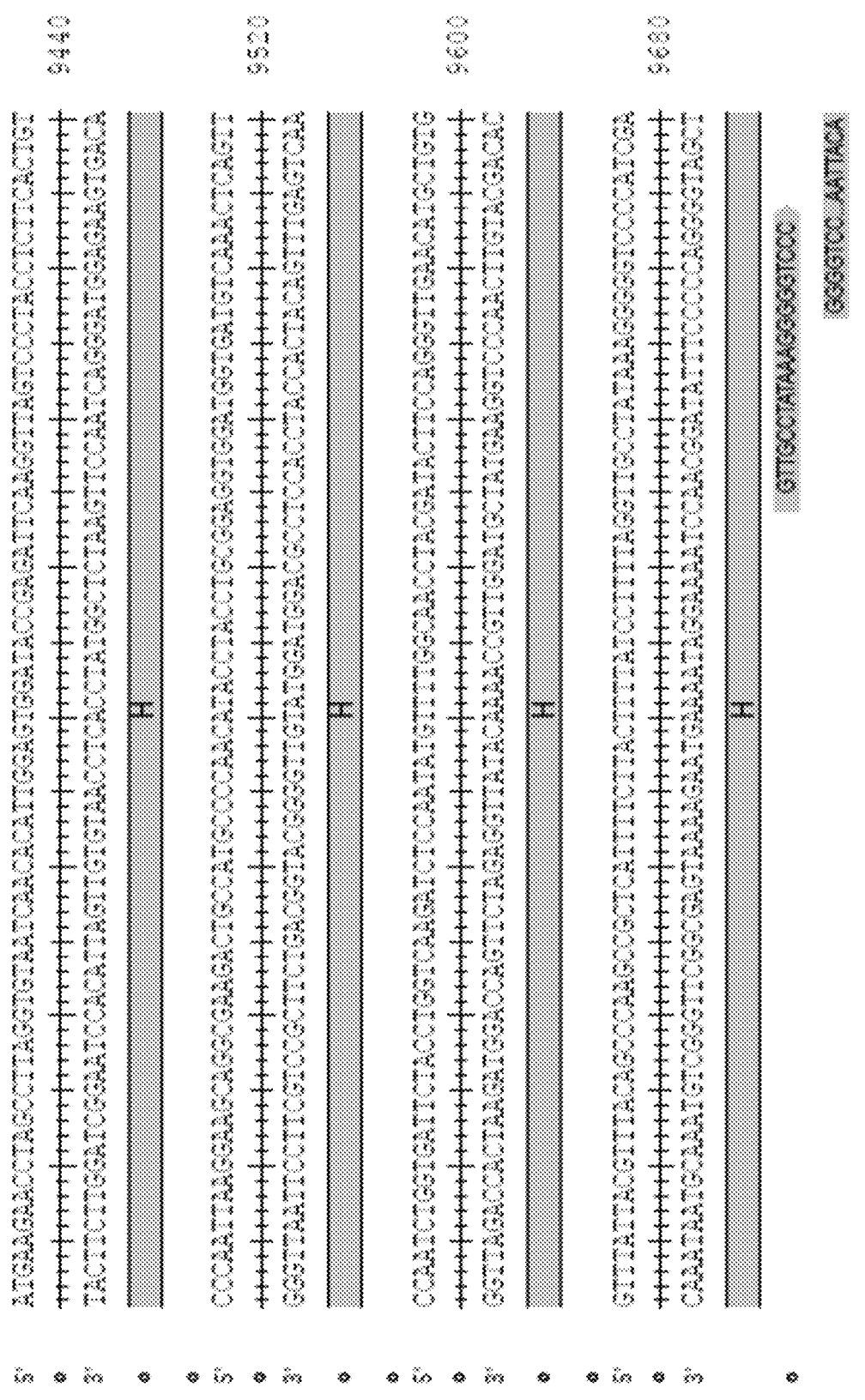
Figure 19:
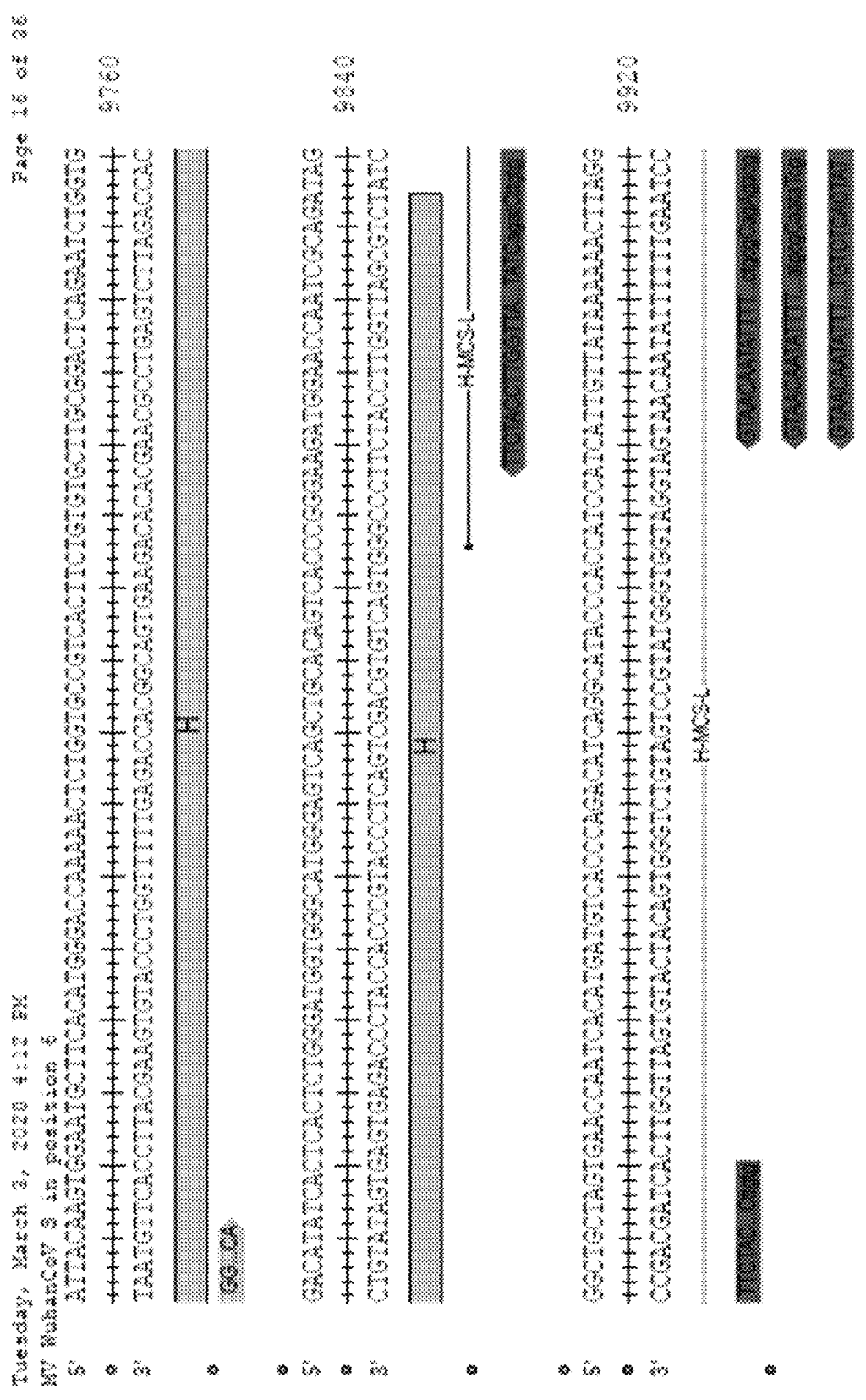
Figure 19:
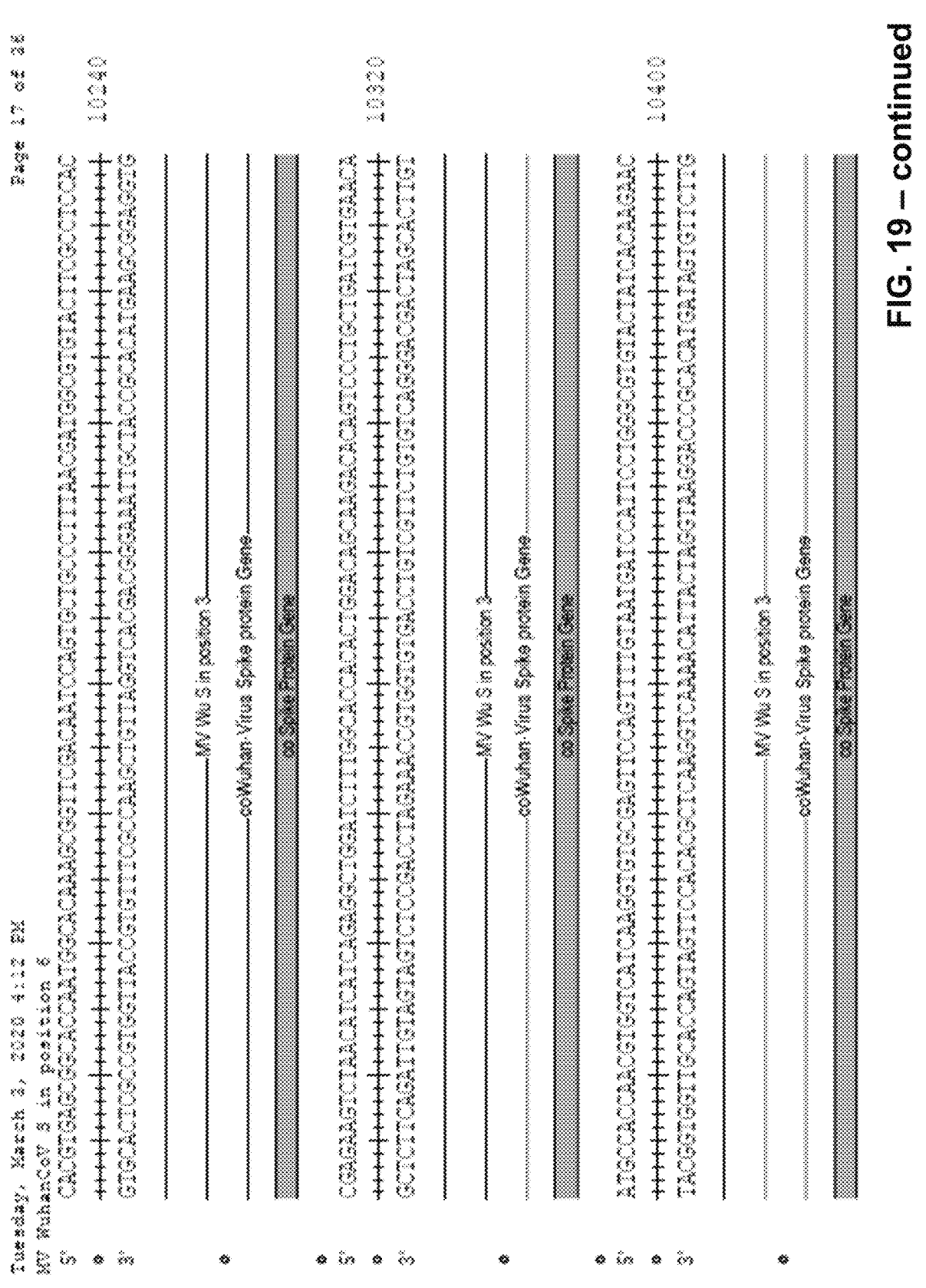
Figure 19:
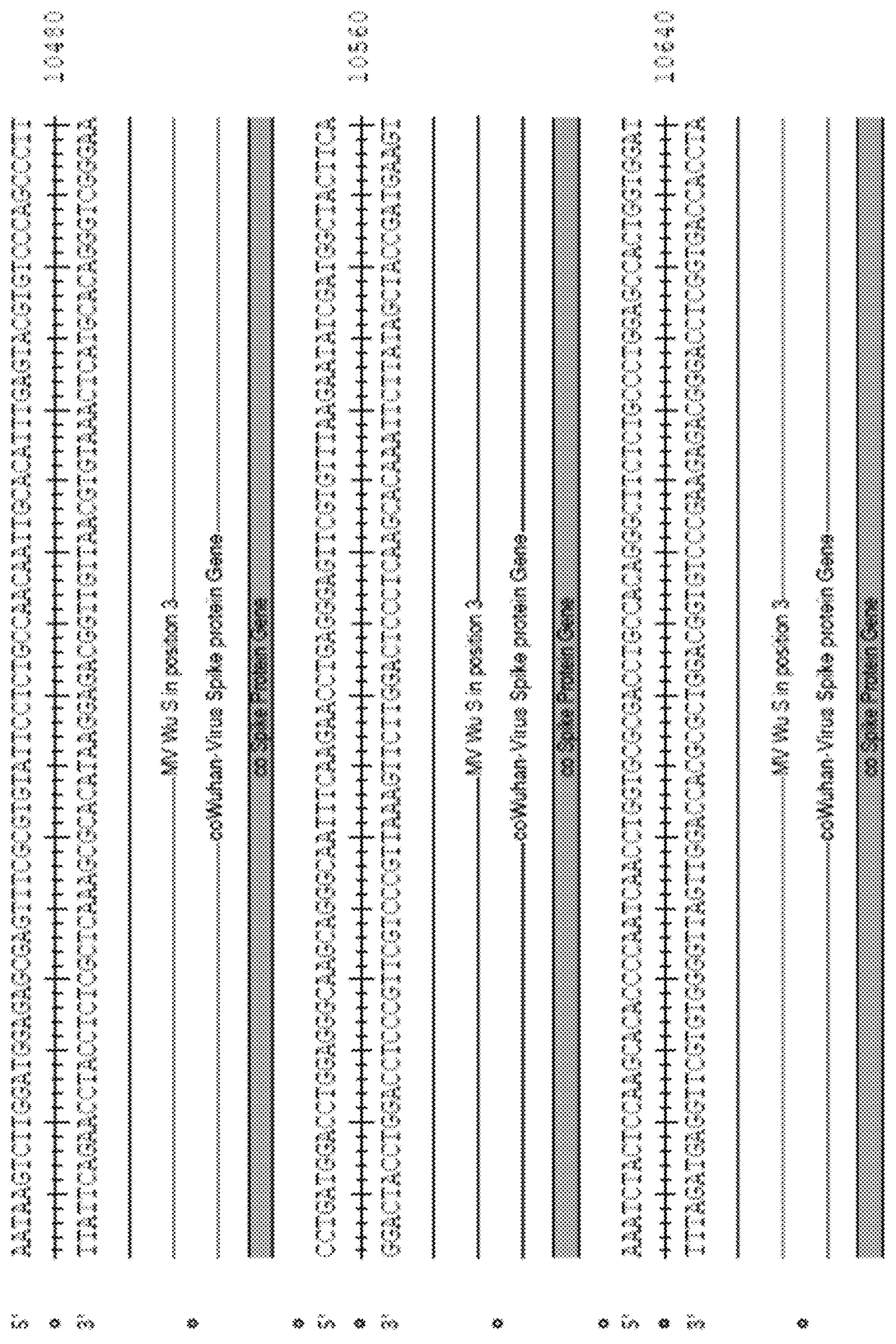
Figure 19:
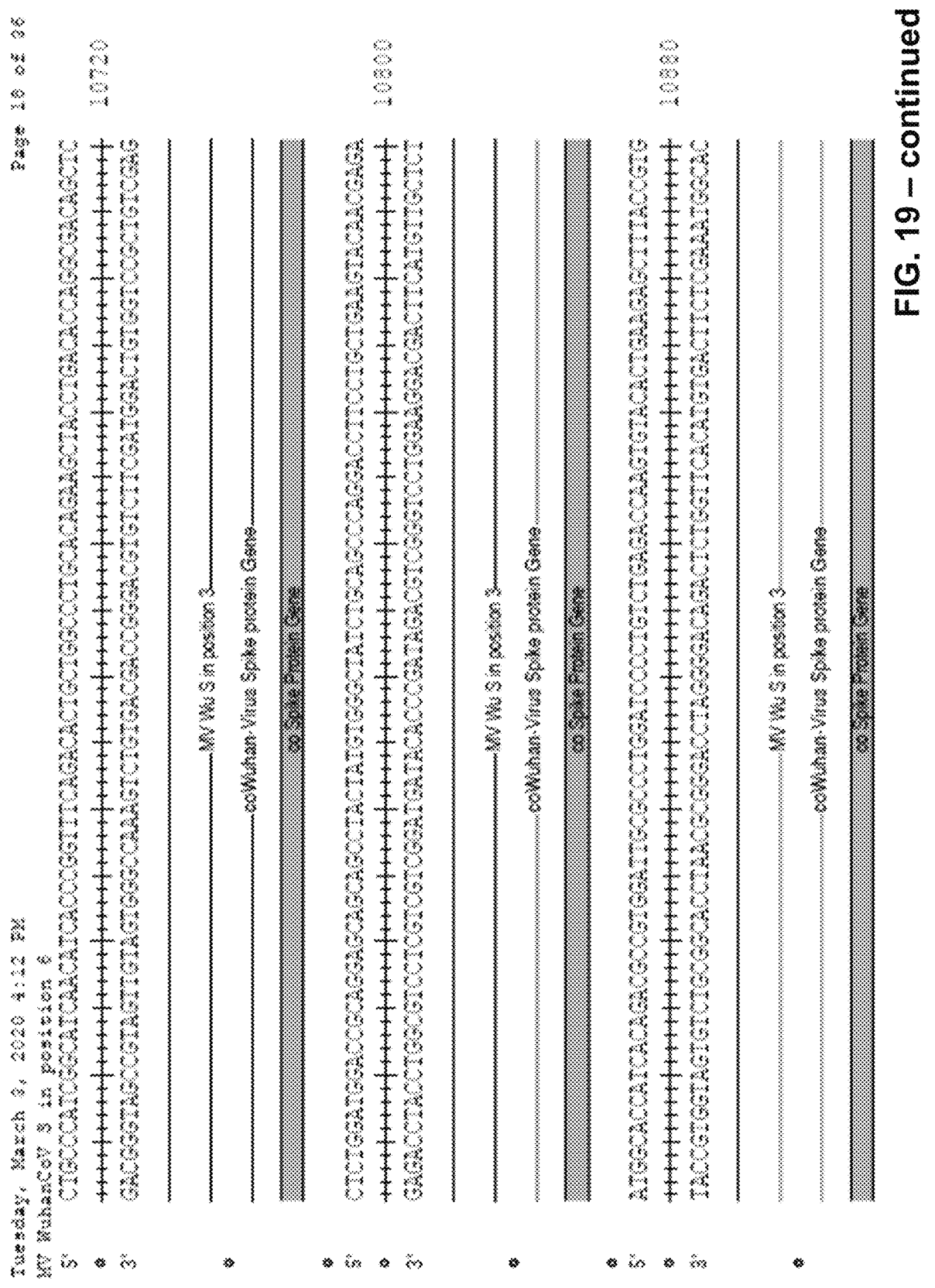
Figure 19:
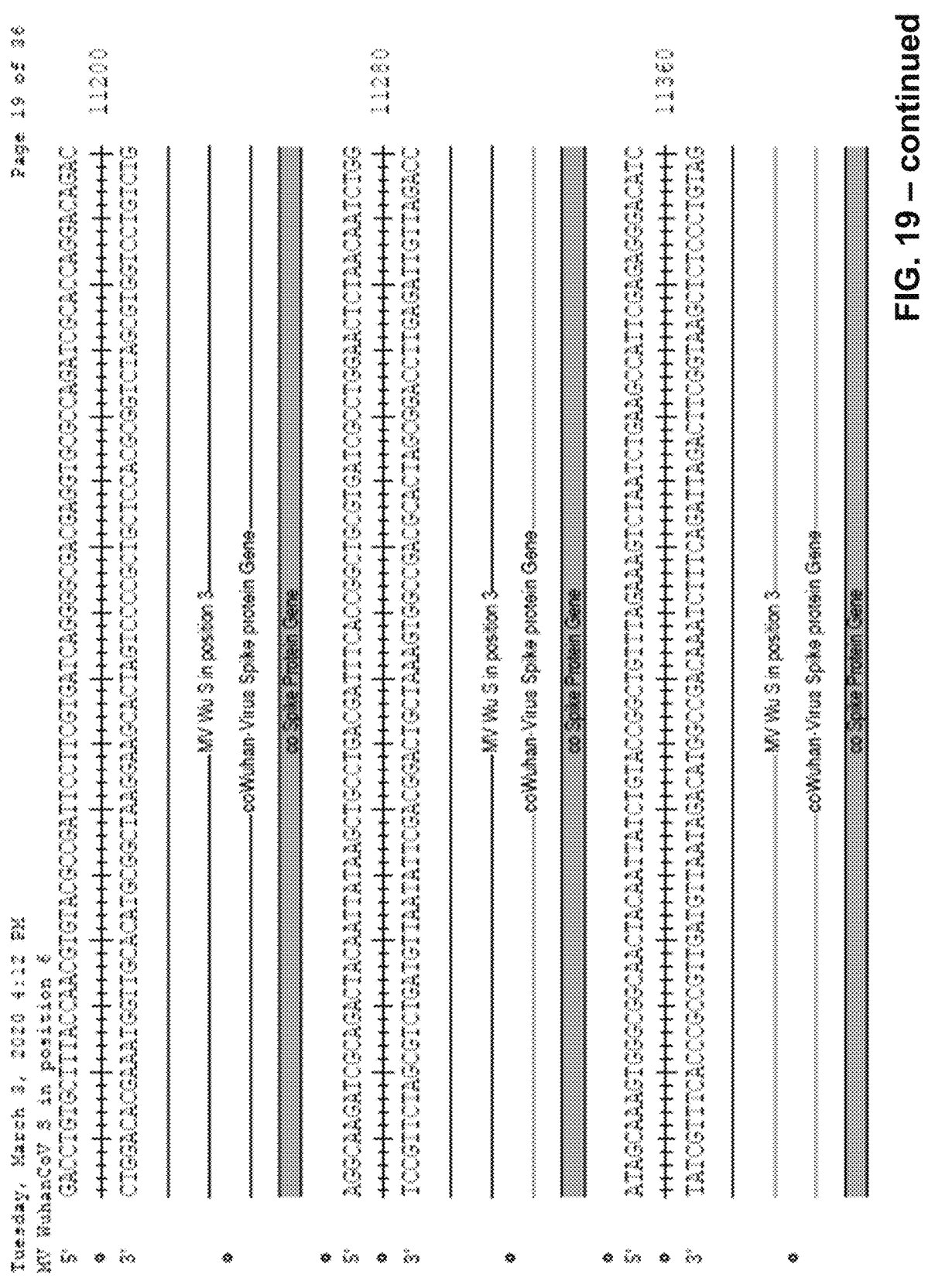
Figure 19:
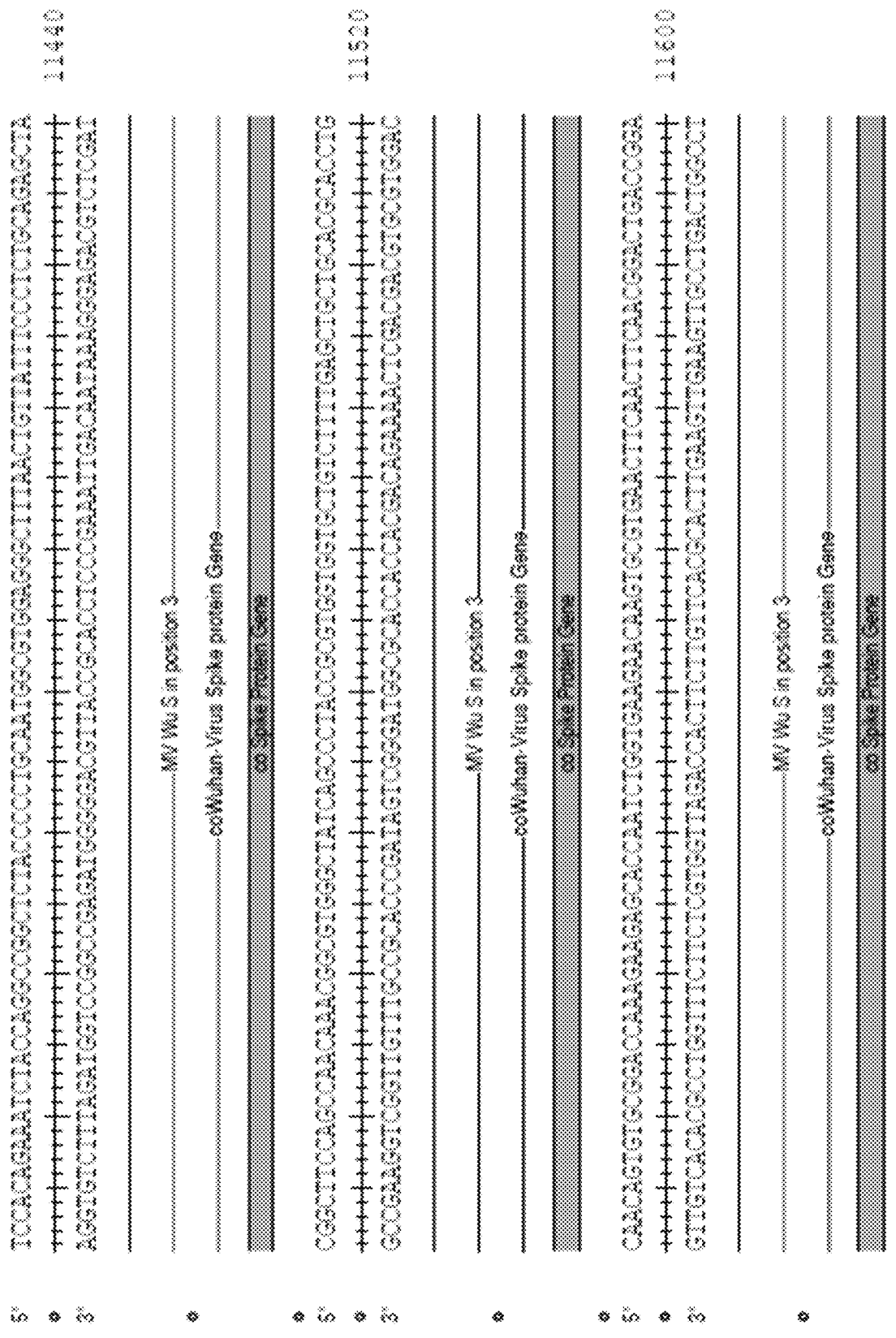
Figure 19:
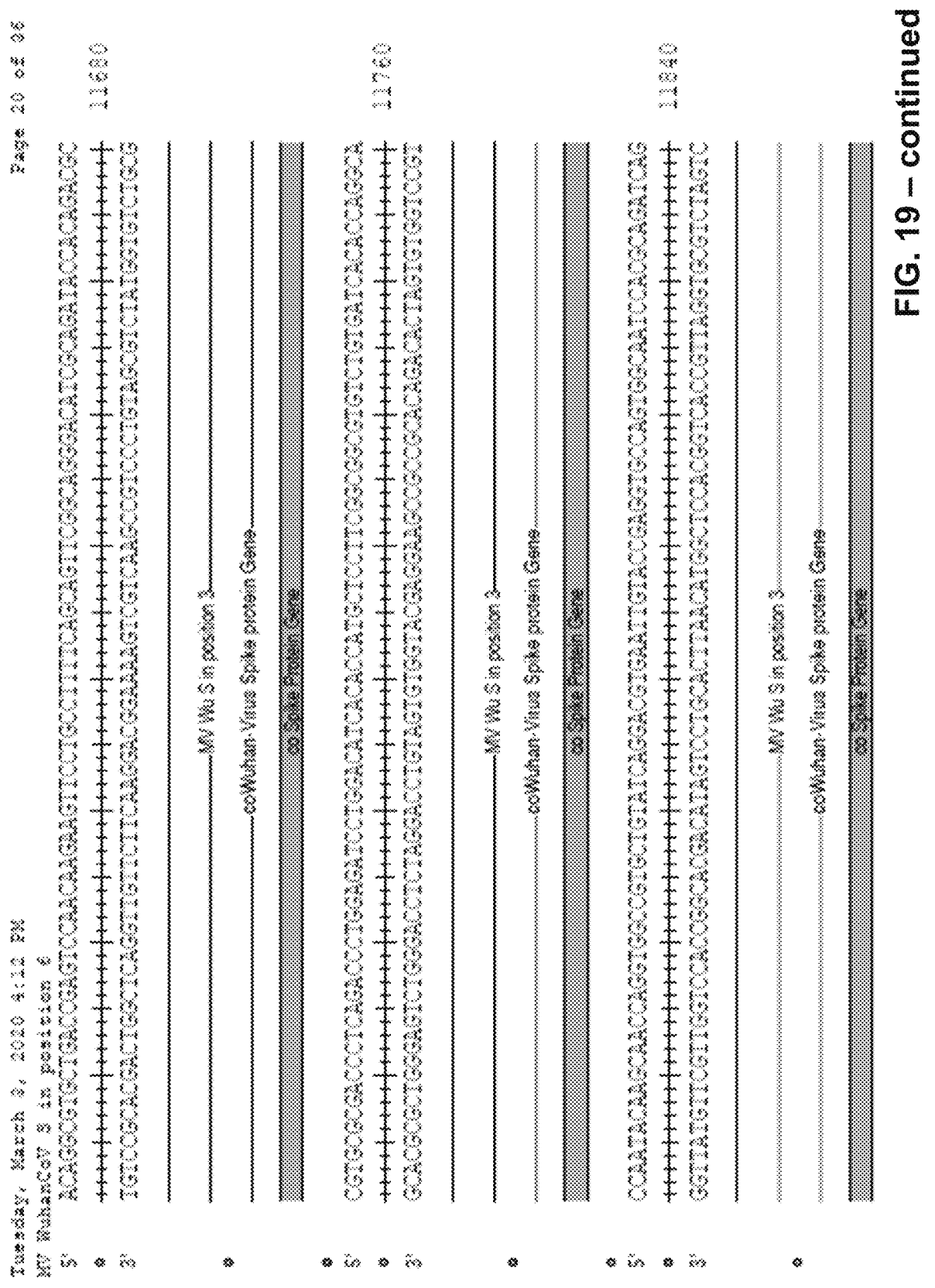
Figure 19:
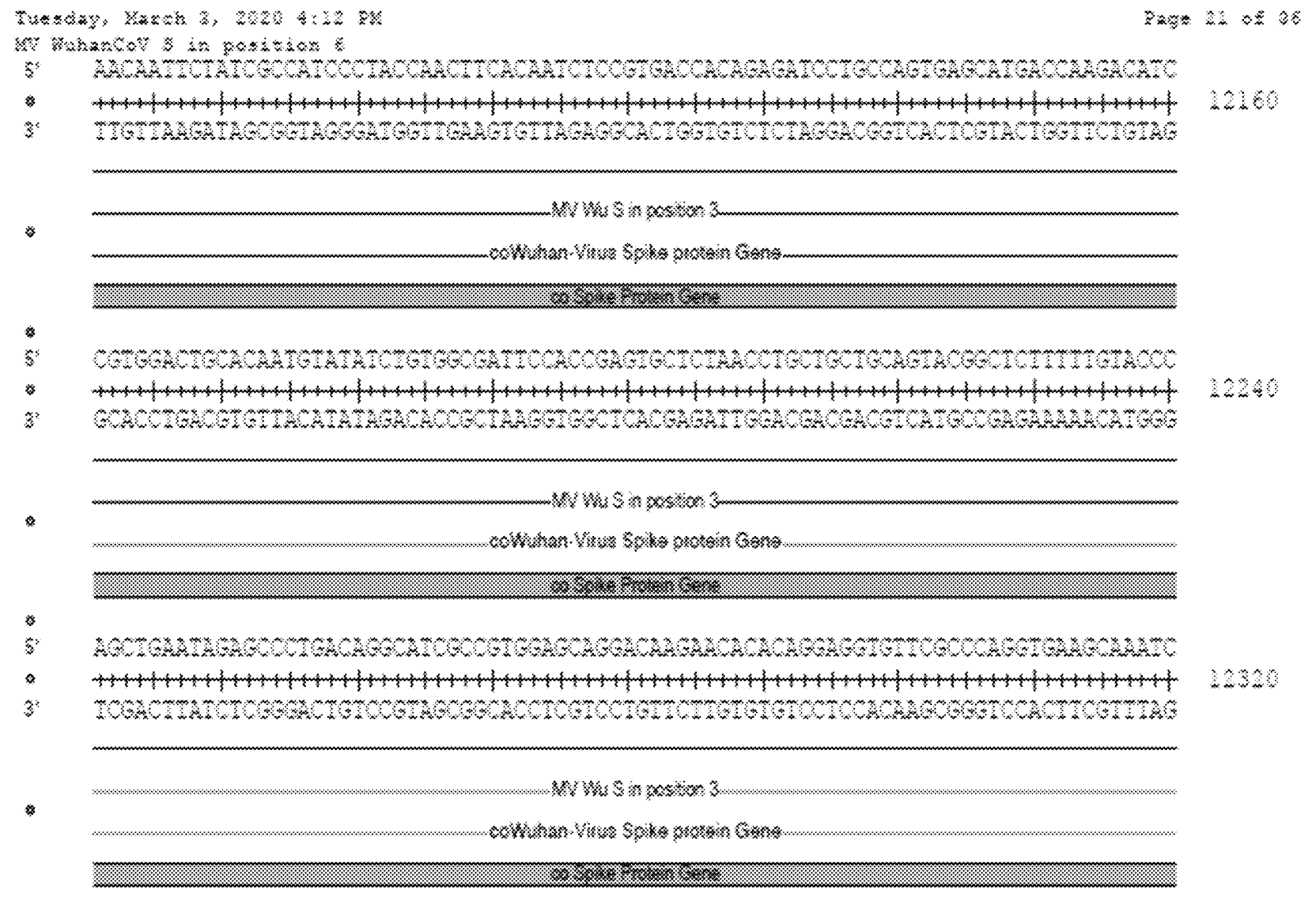
Figure 19:
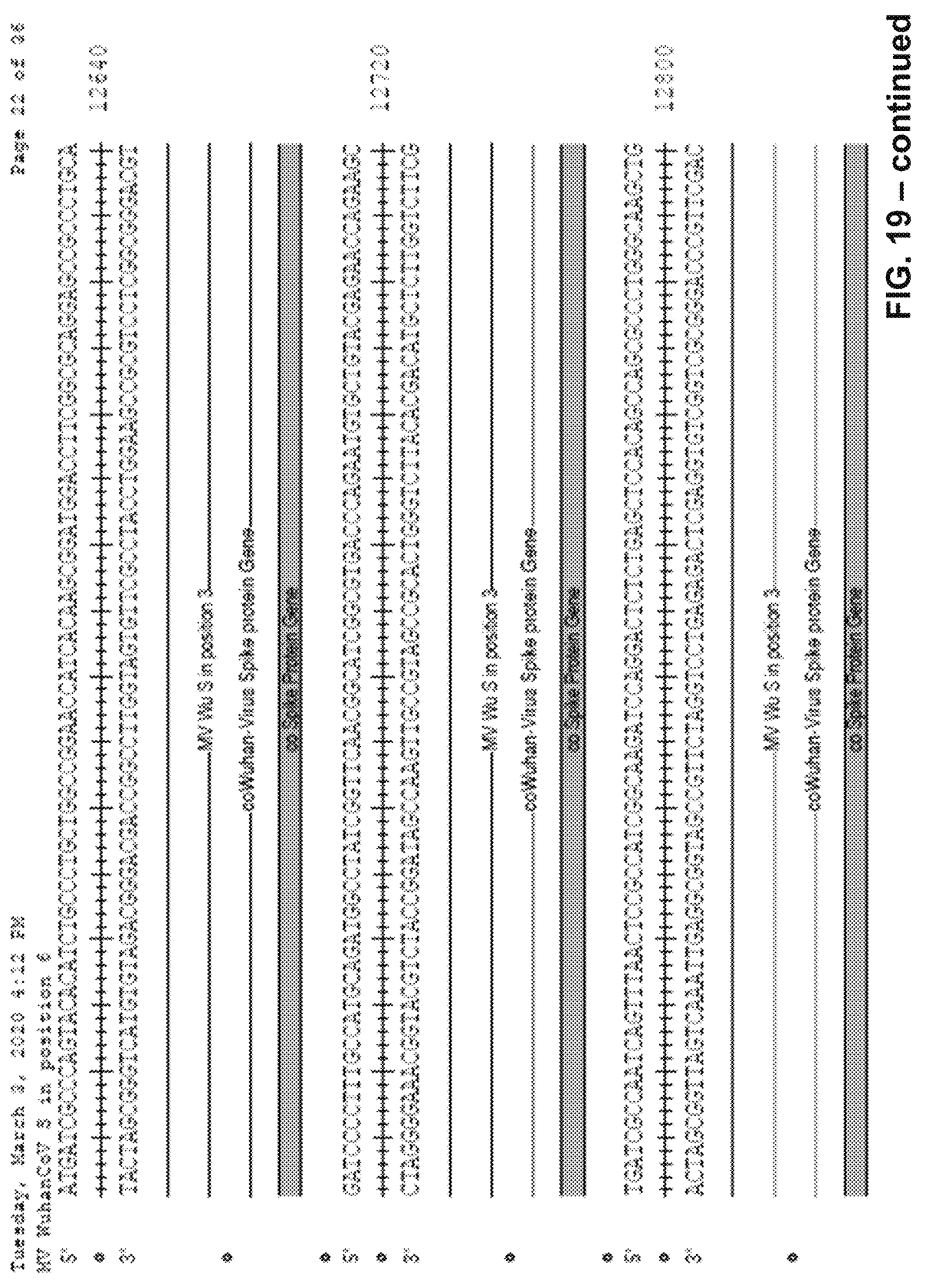
Figure 19:
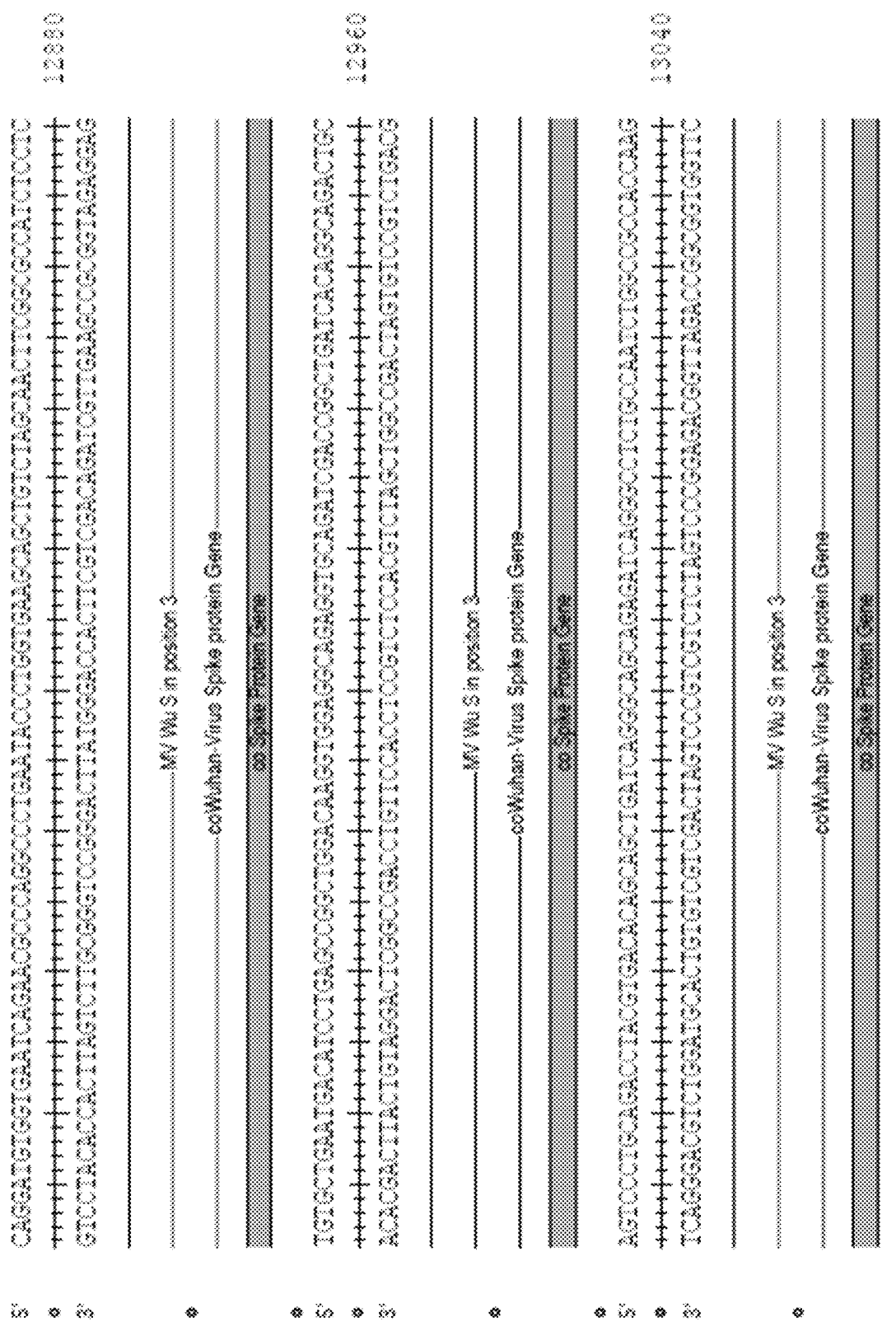
Figure 19:
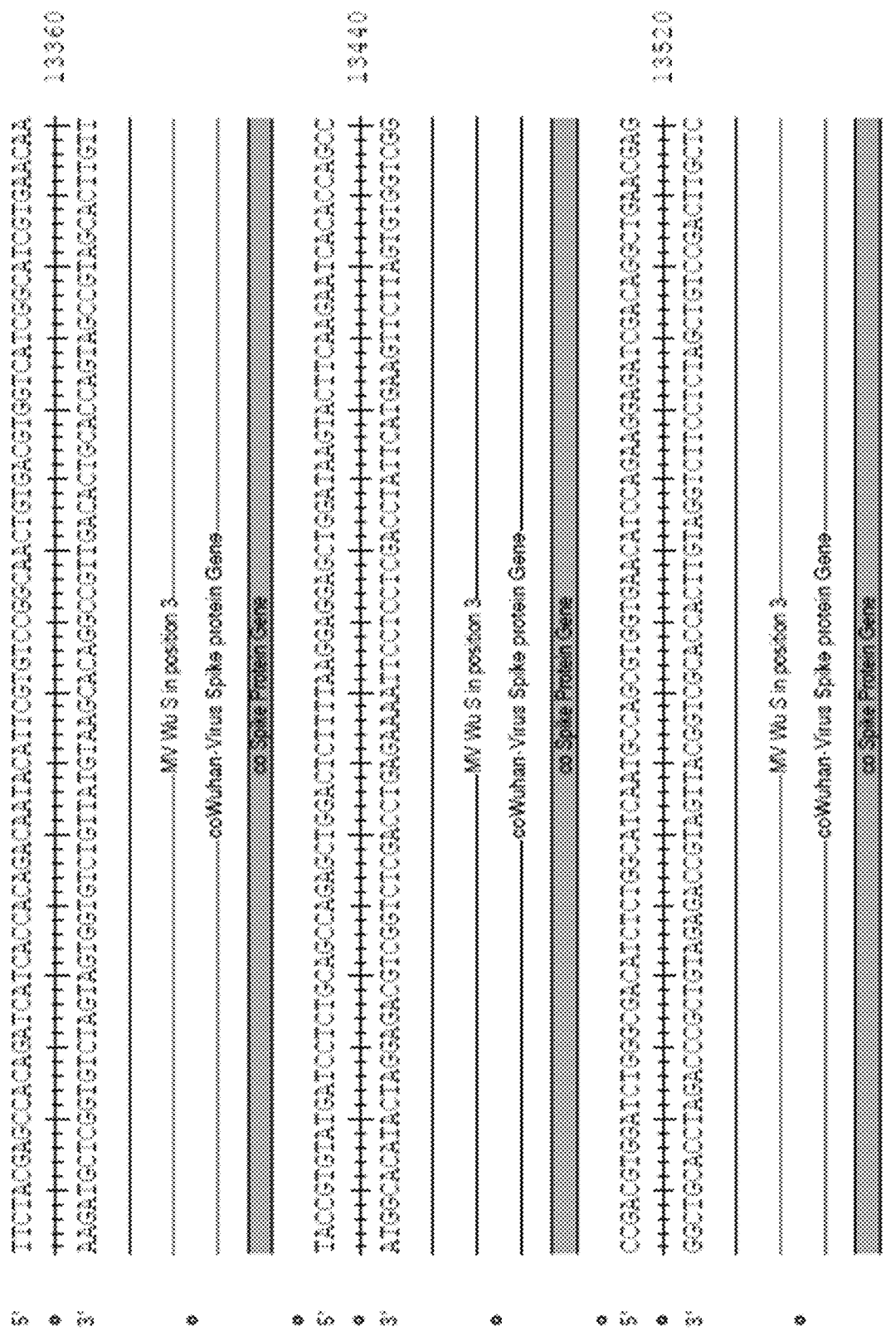
Figure 19:
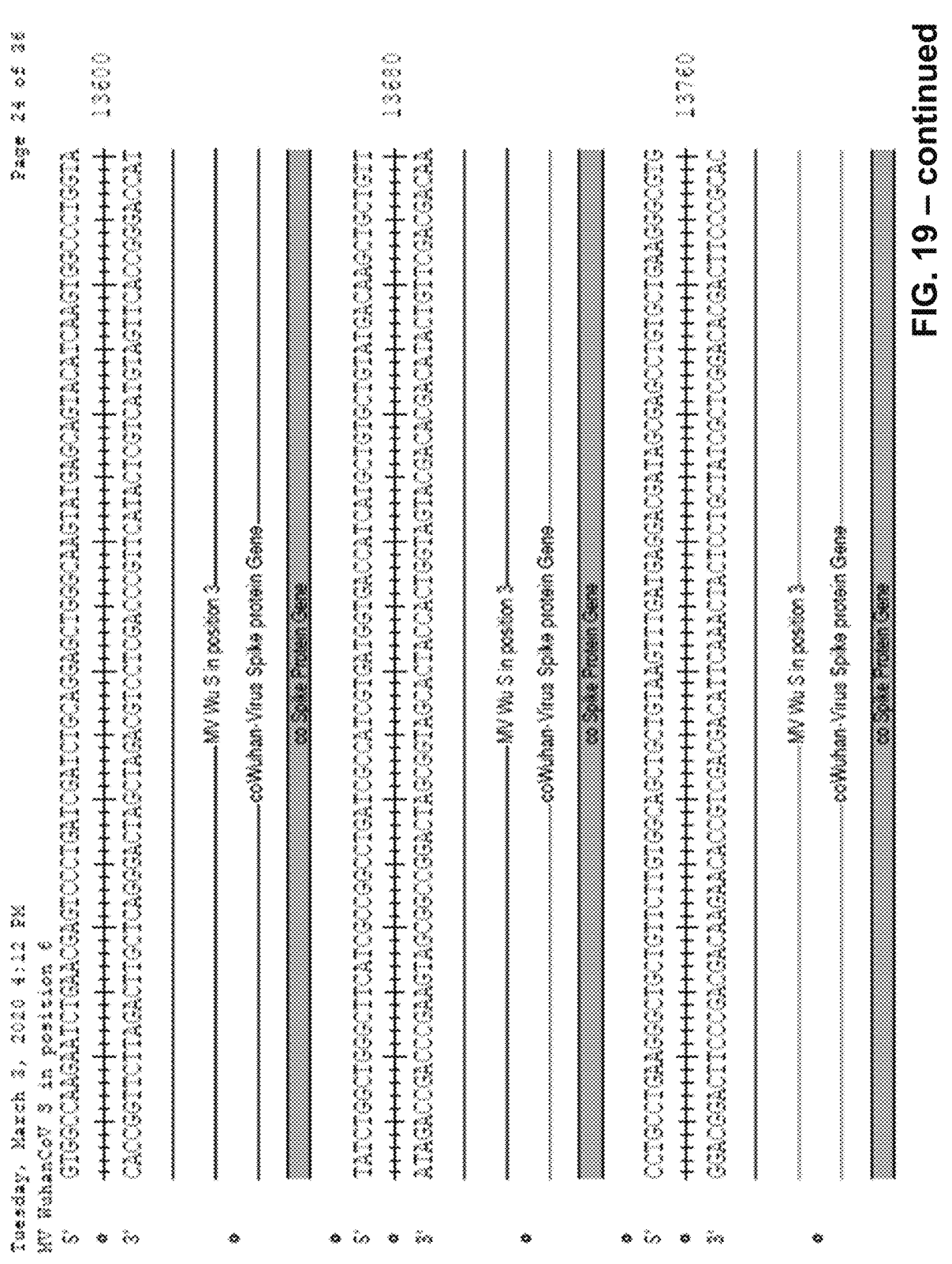
Figure 19:
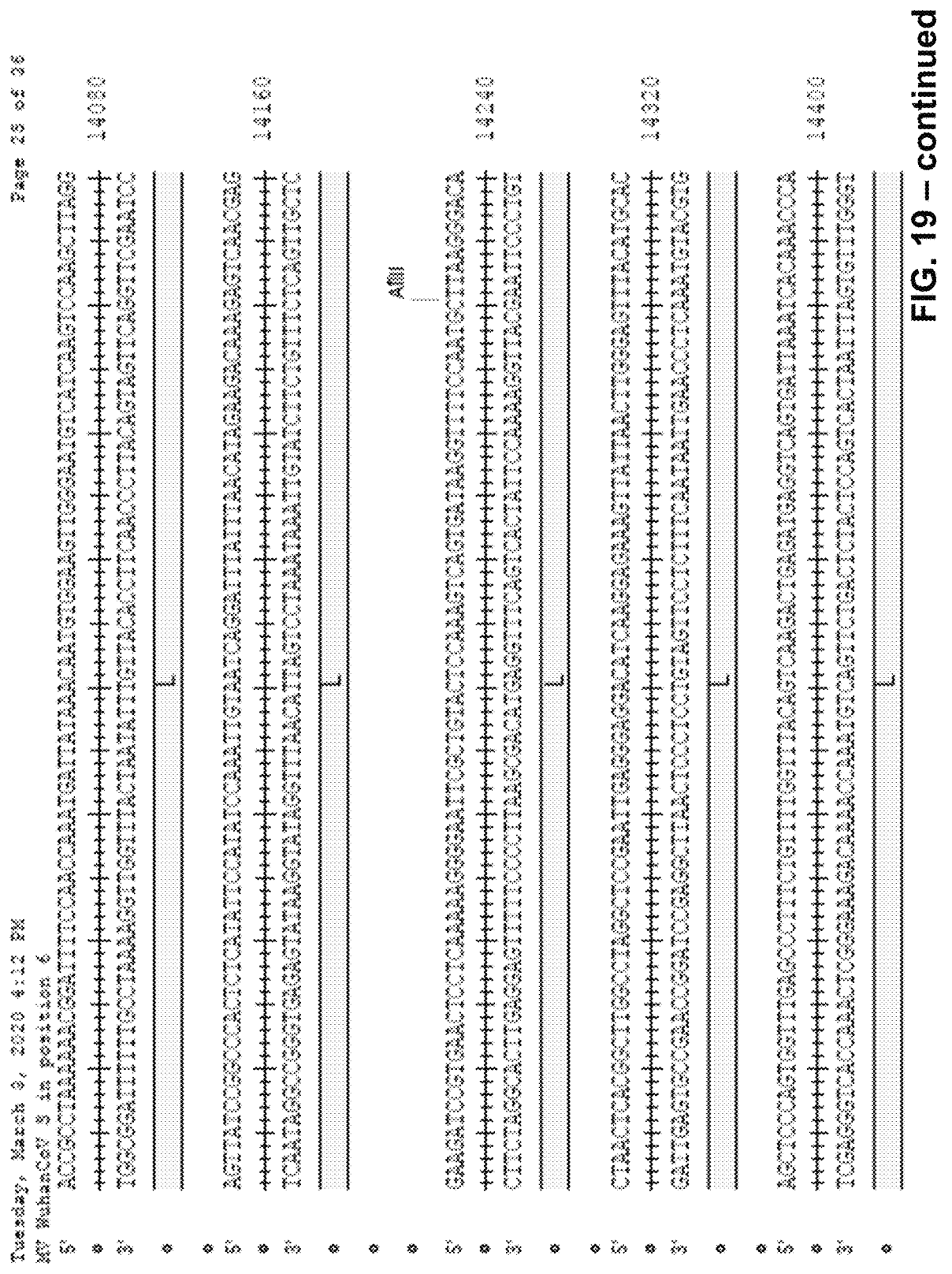
Figure 19:
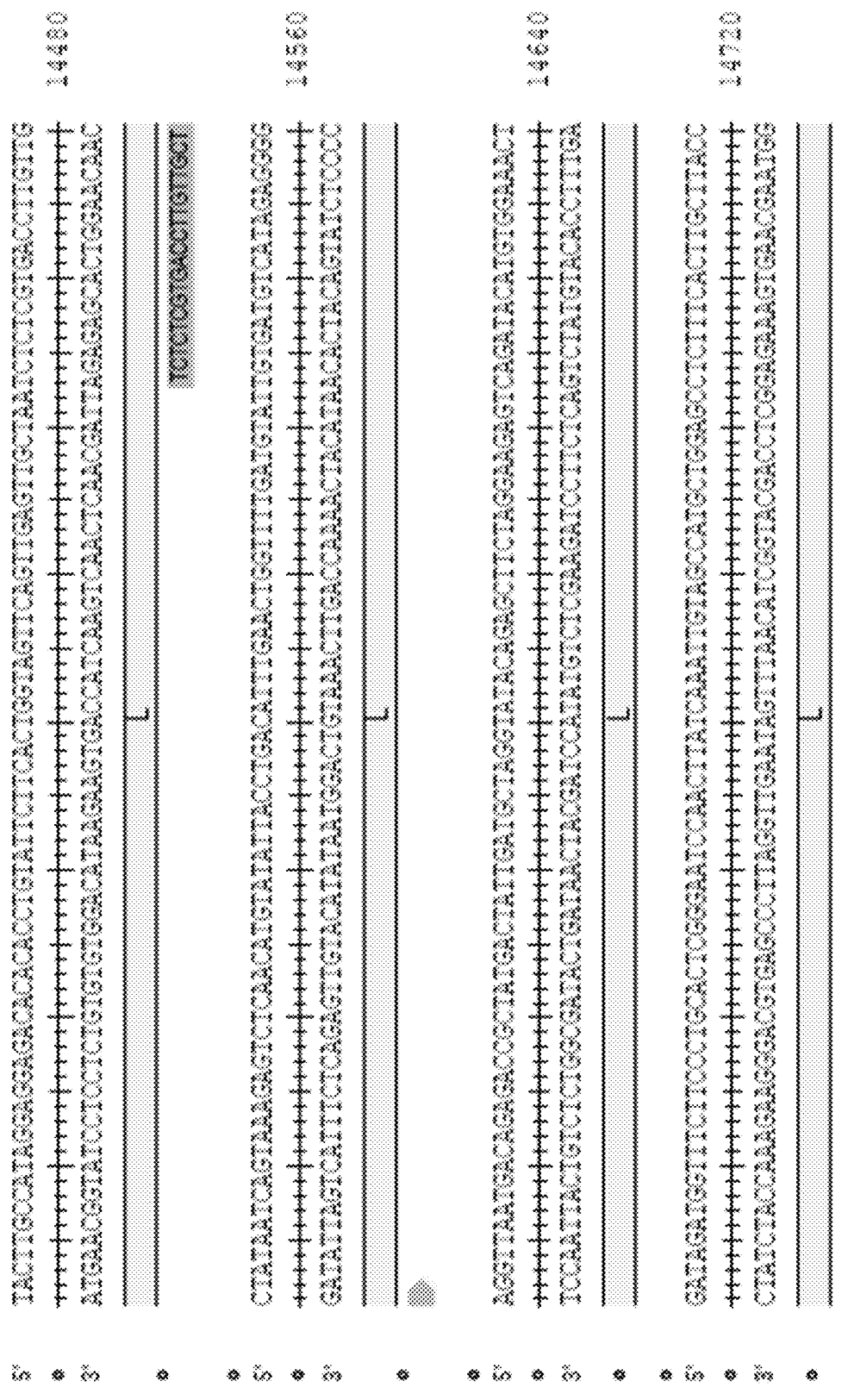
Figure 19:
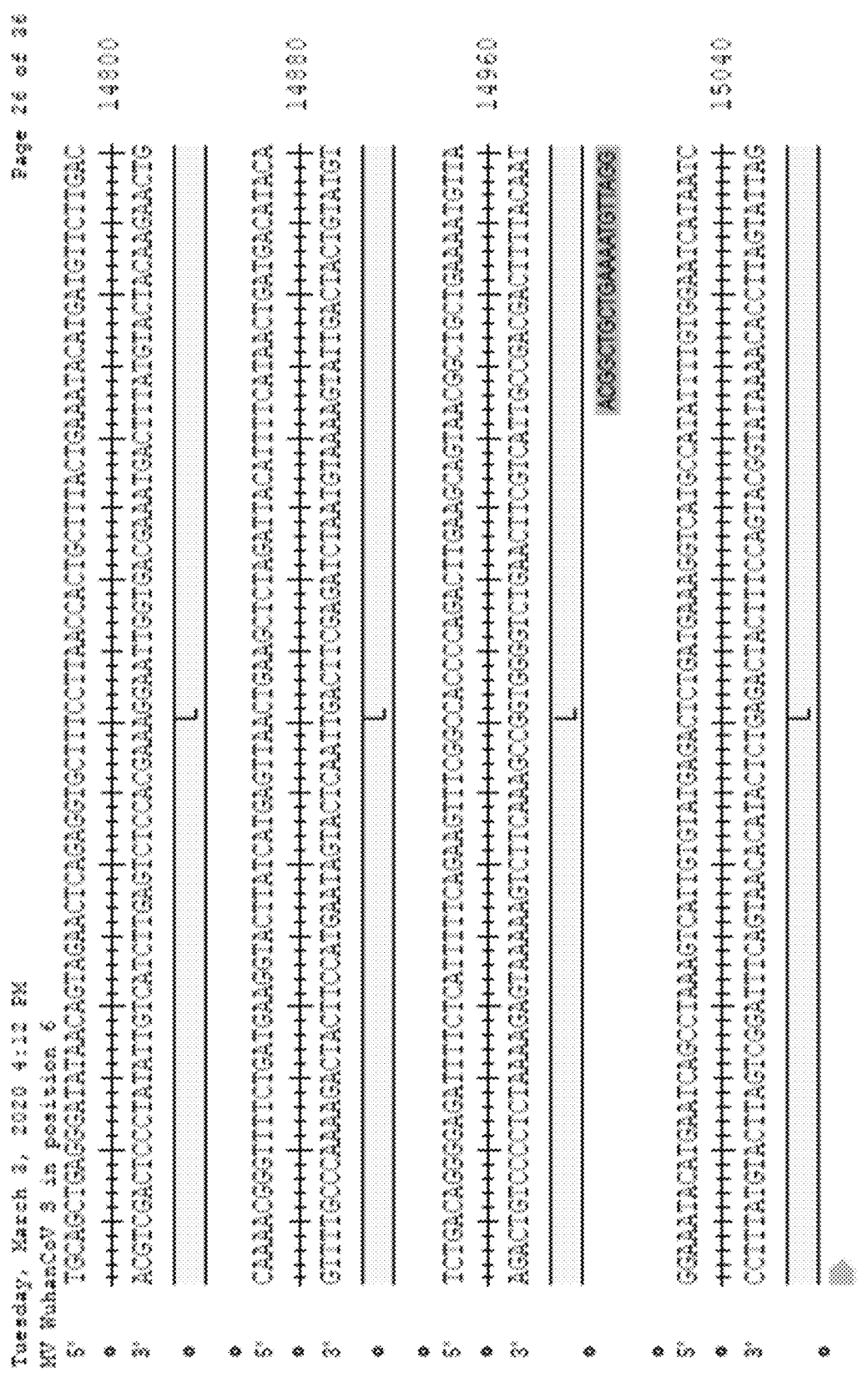
Figure 19:
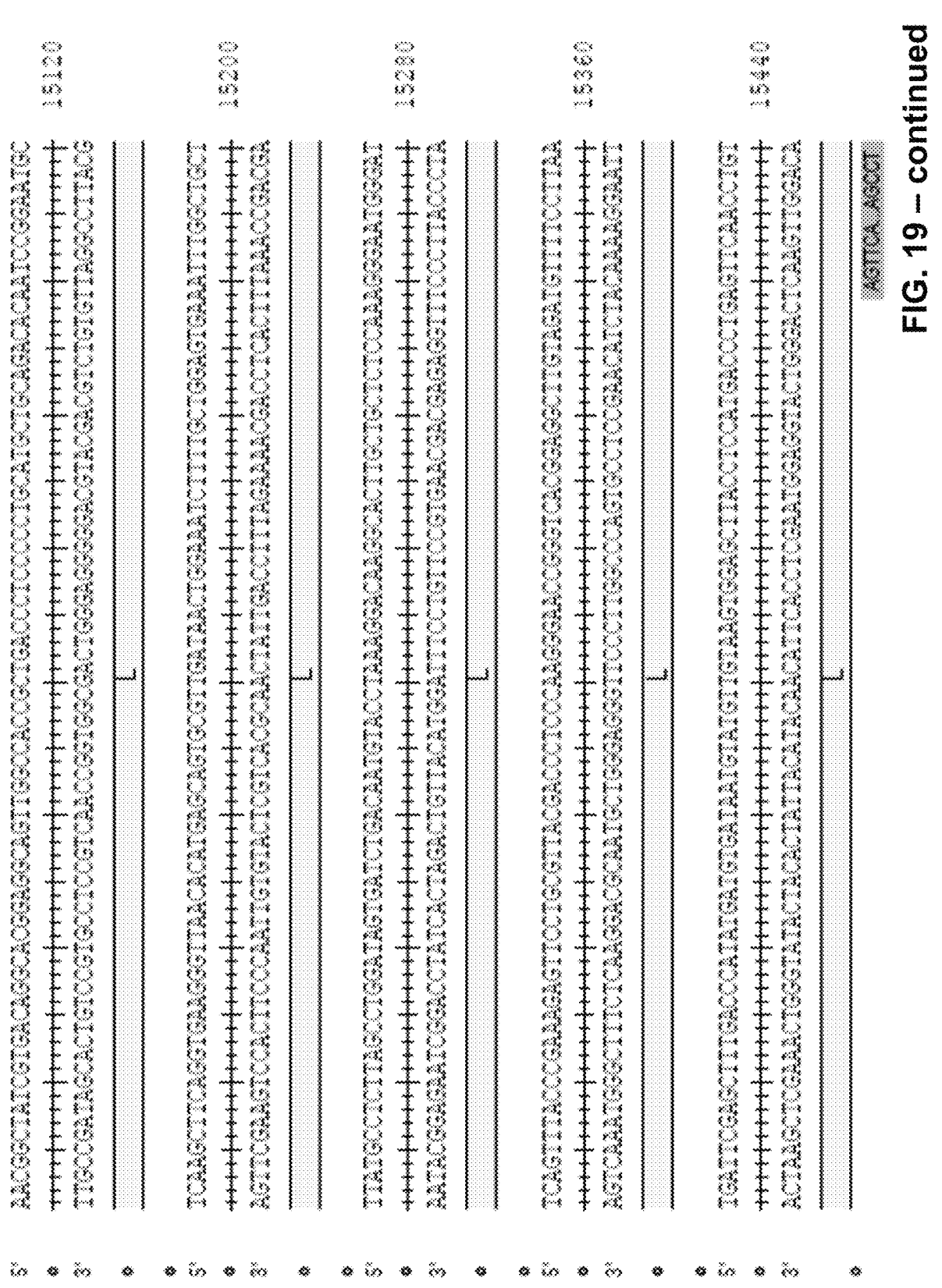
Figure 19:
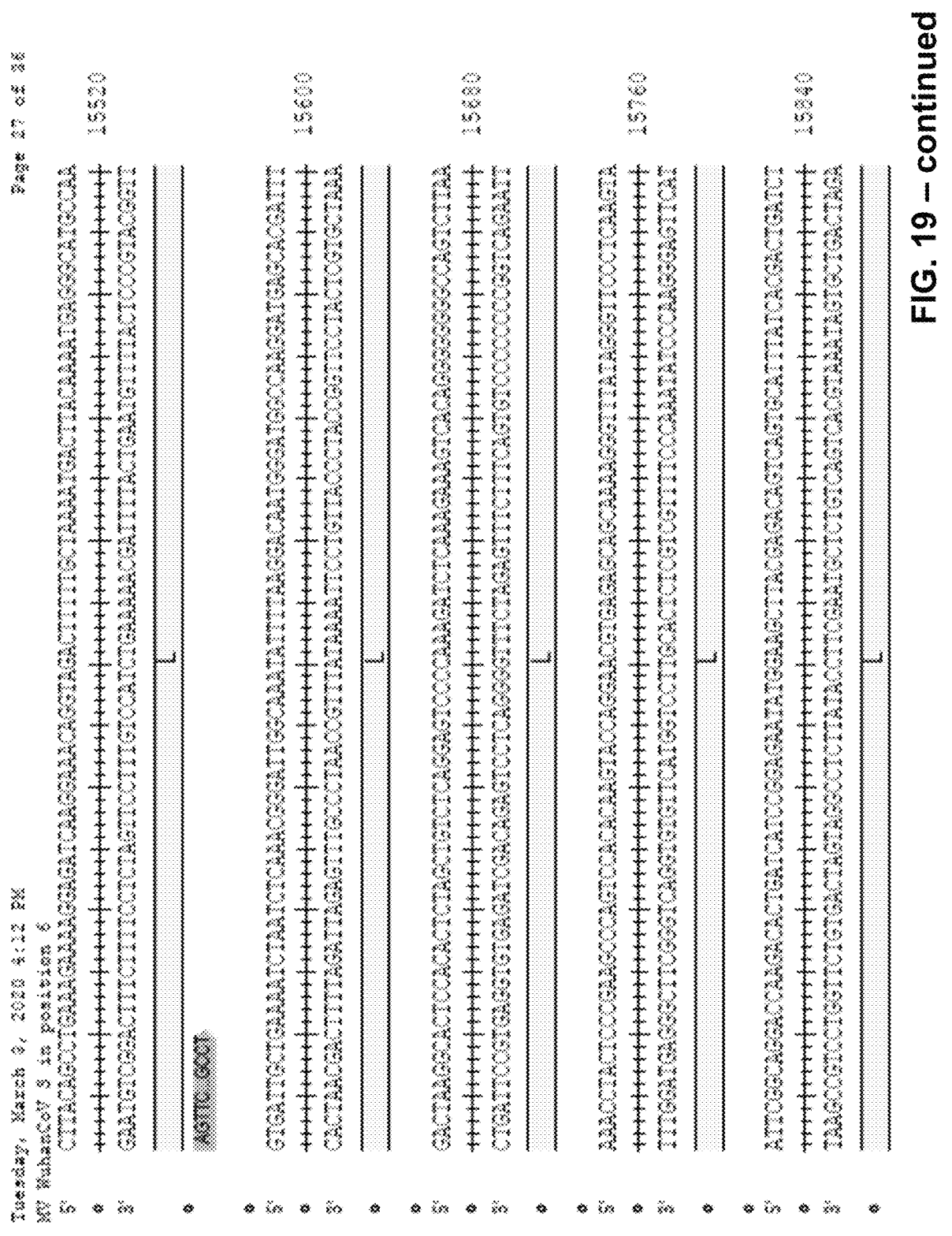
Figure 19:
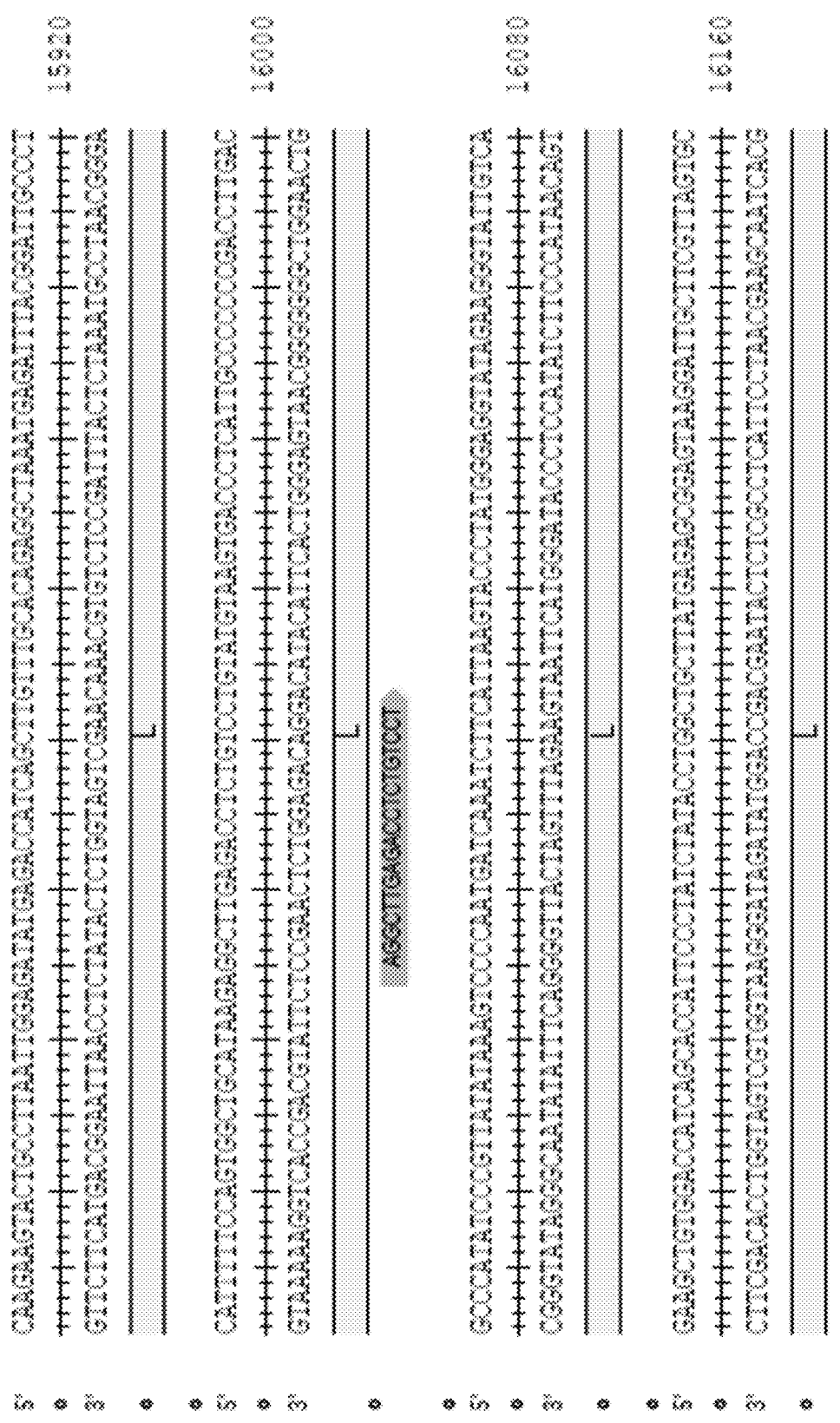
Figure 19:
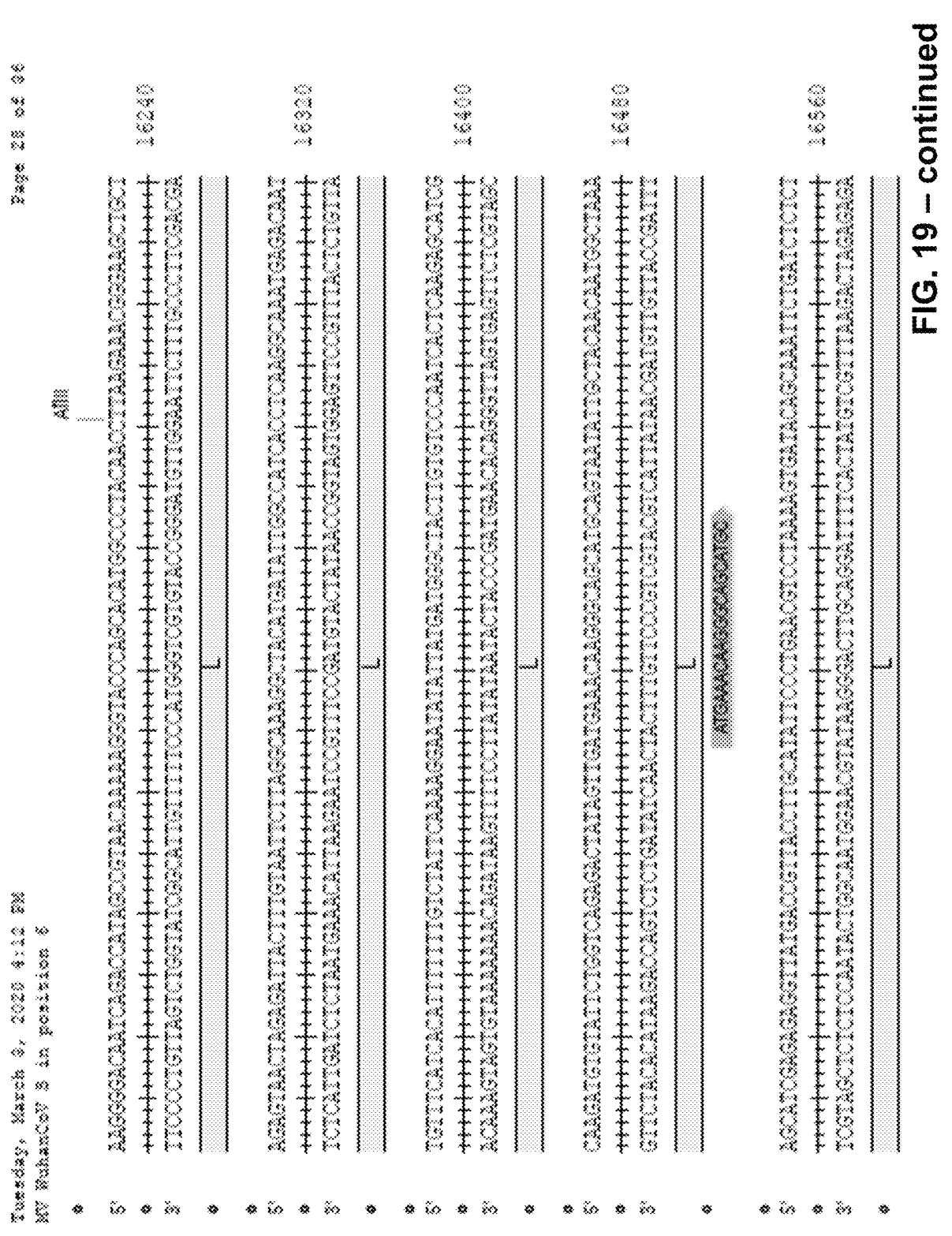
Figure 19:
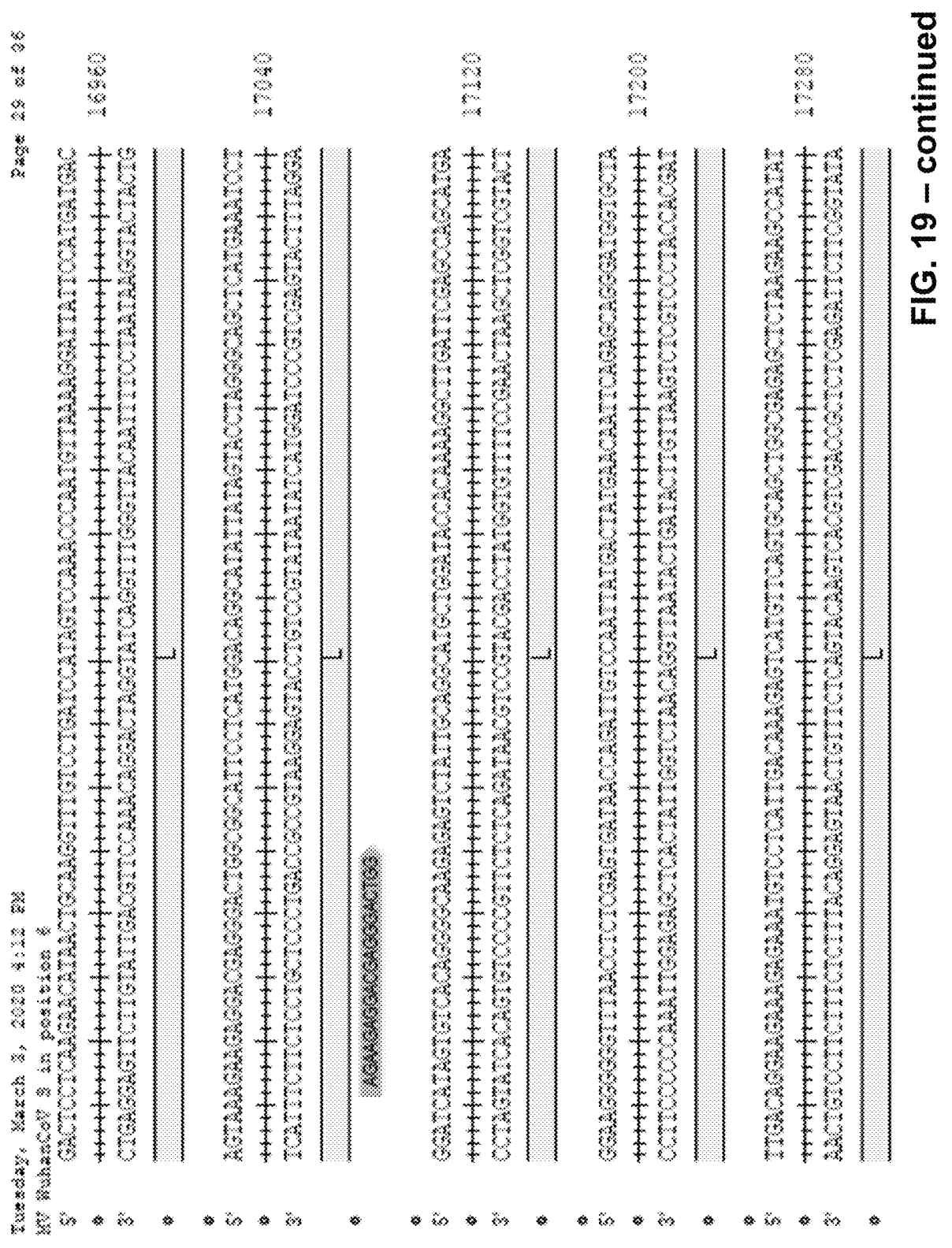
Figure 19:
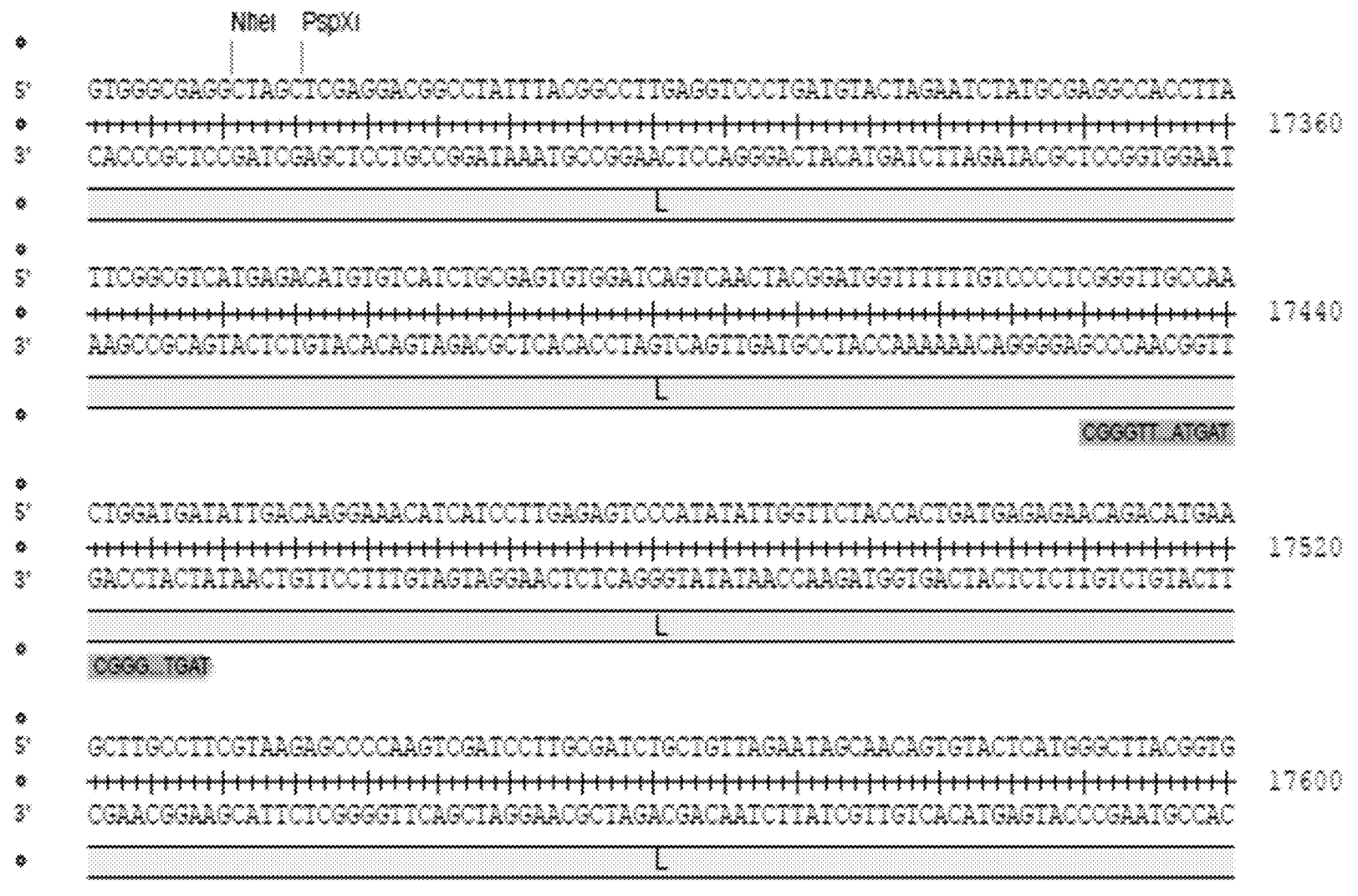
Figure 19:
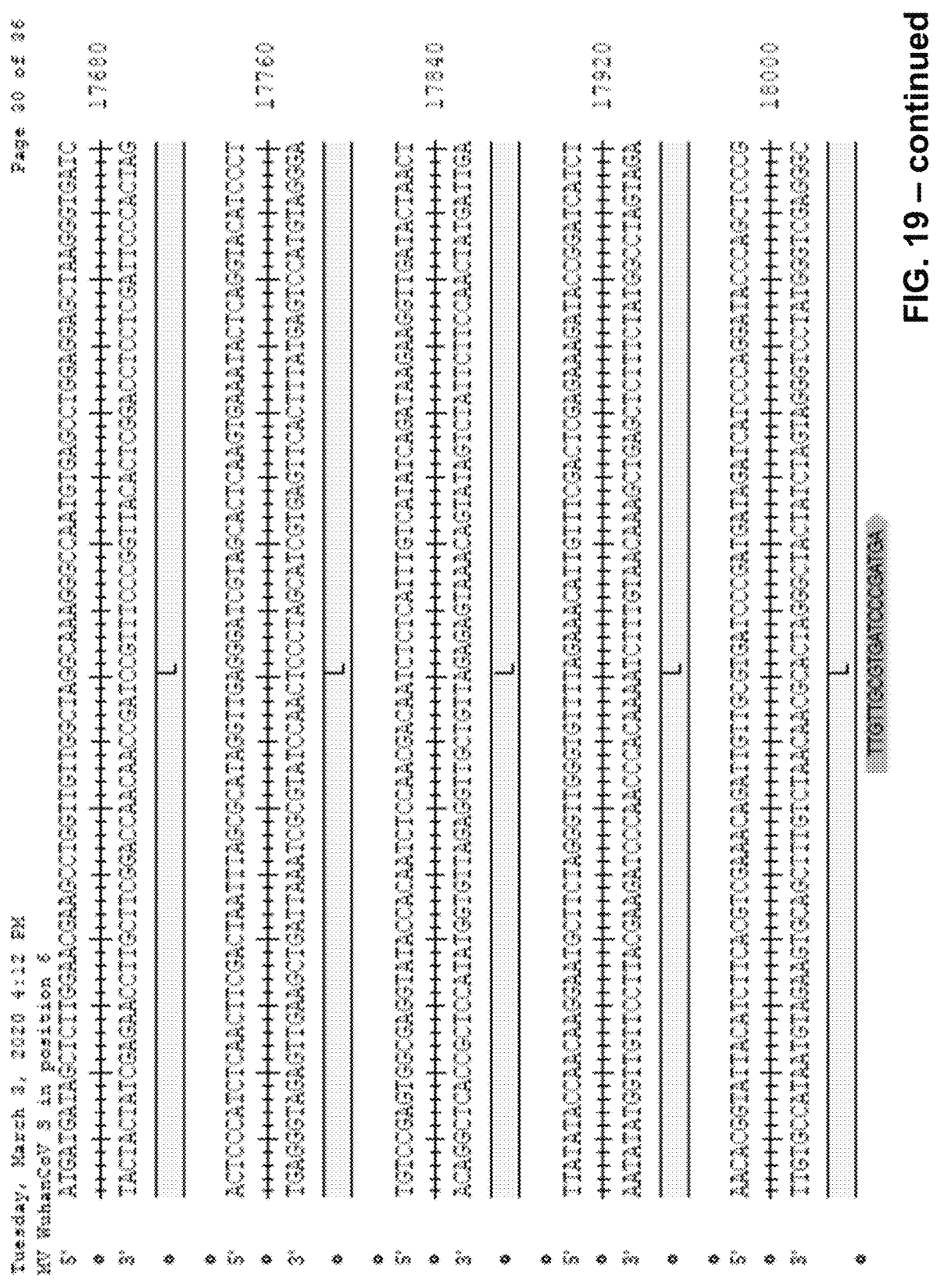
Figure 19:
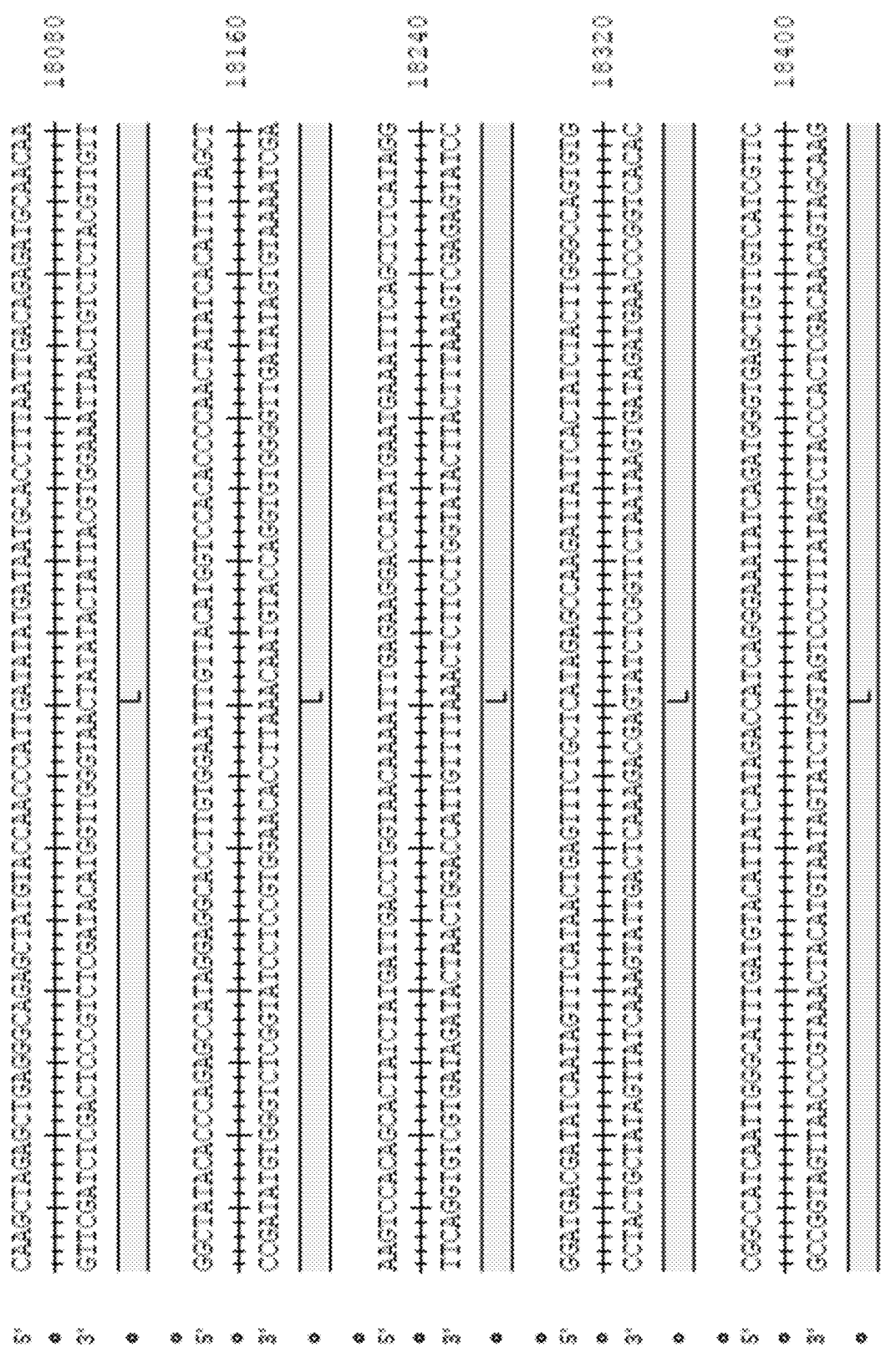
Figure 19:
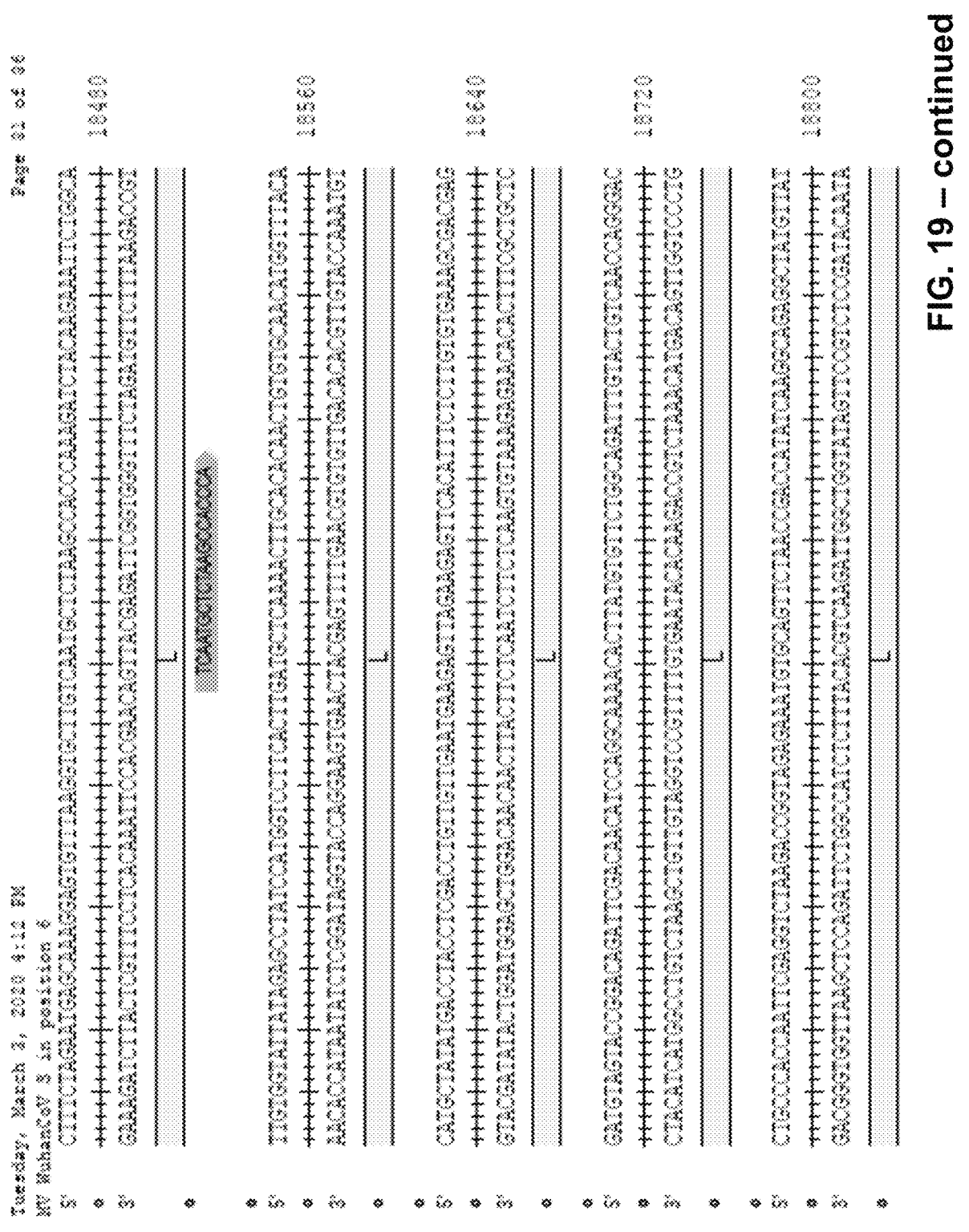
Figure 19:
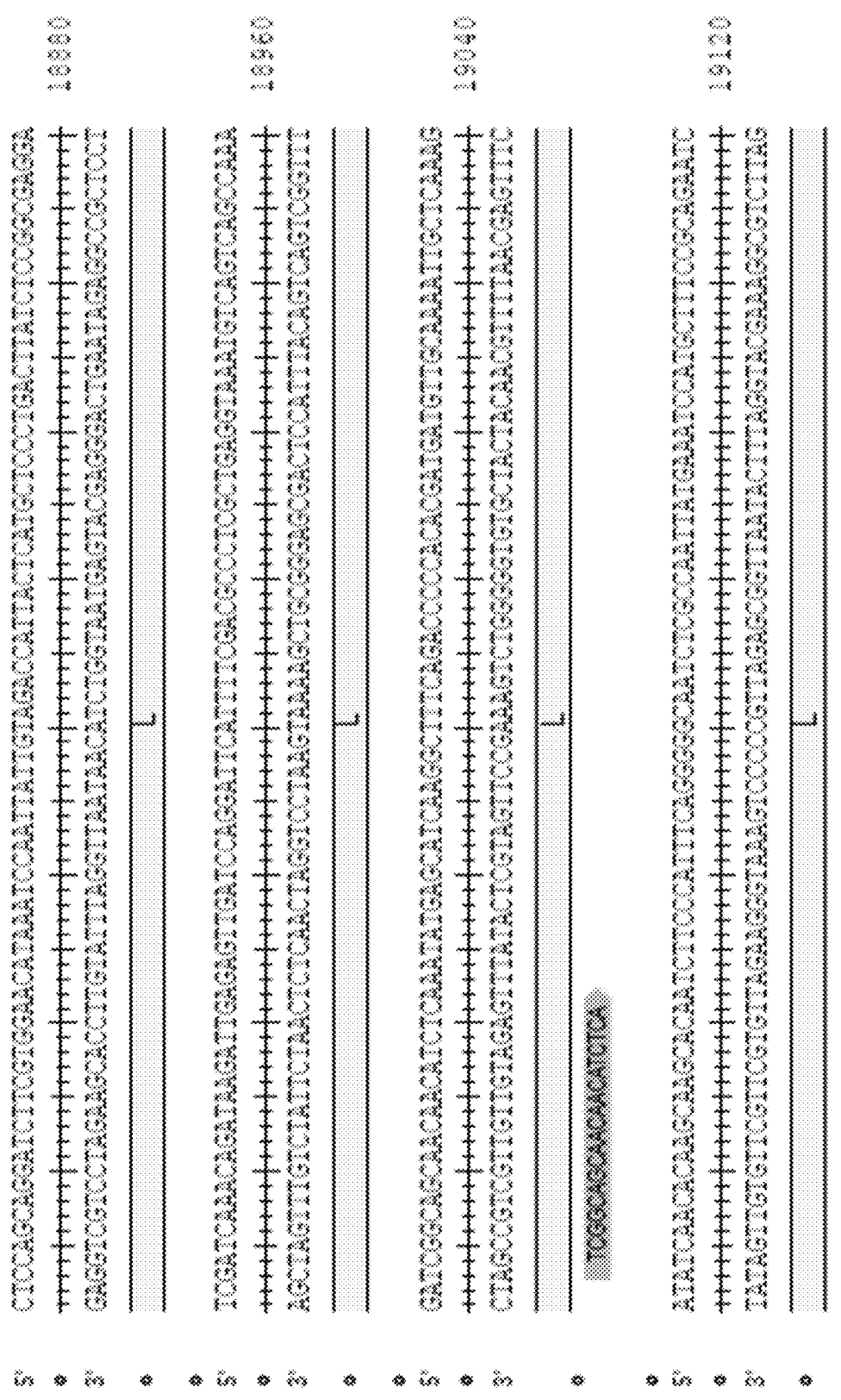
Figure 19:
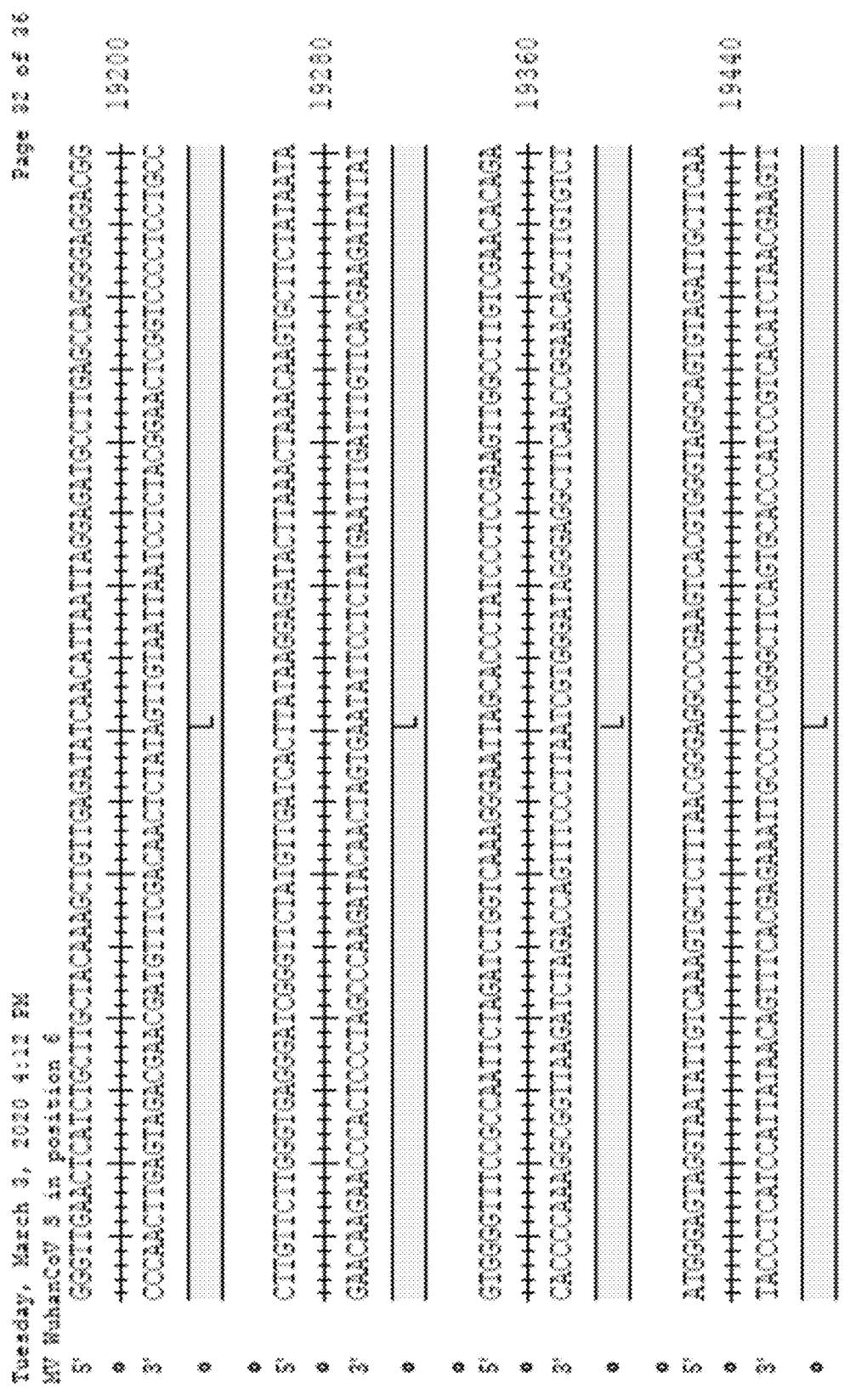
Figure 19:
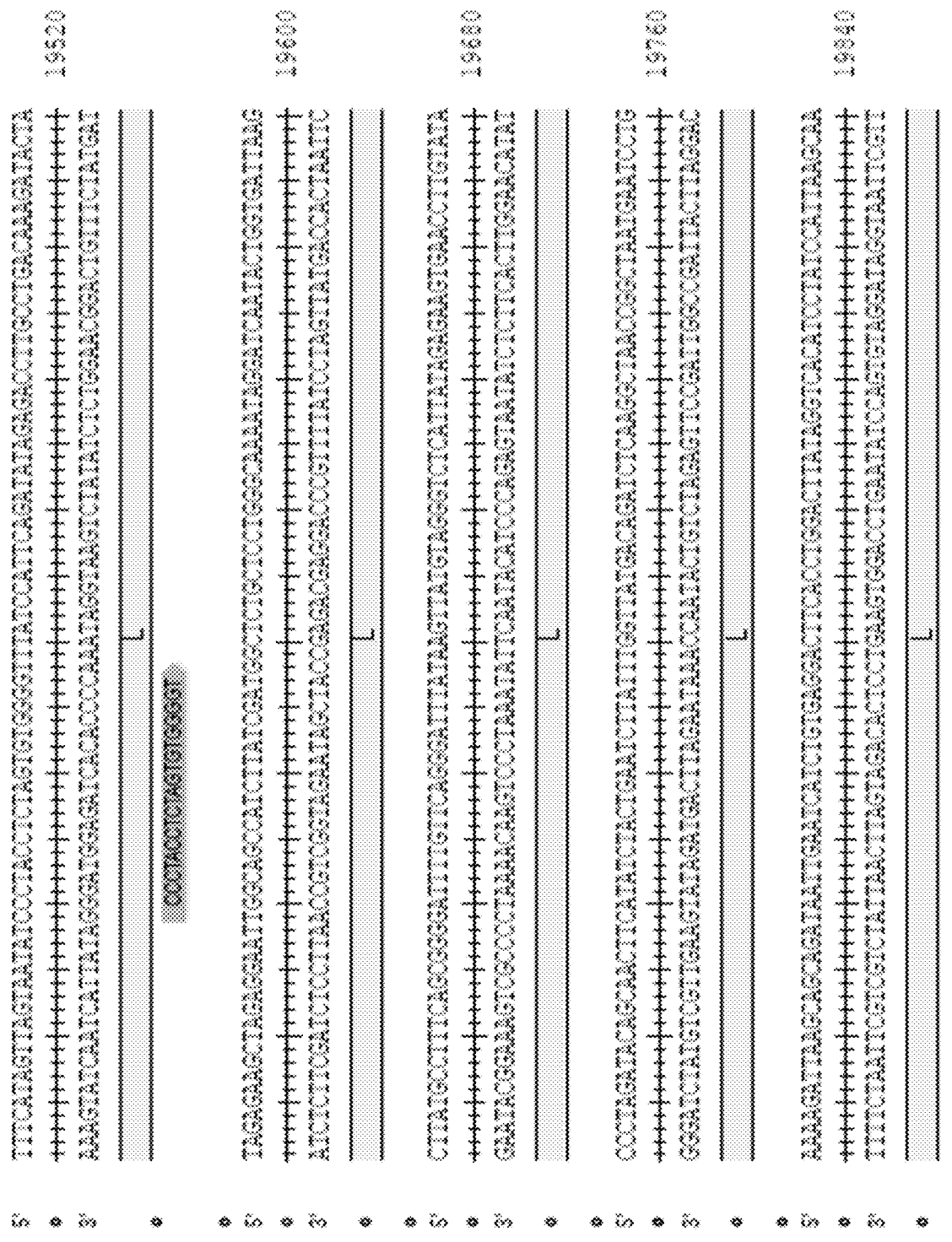
Figure 19:
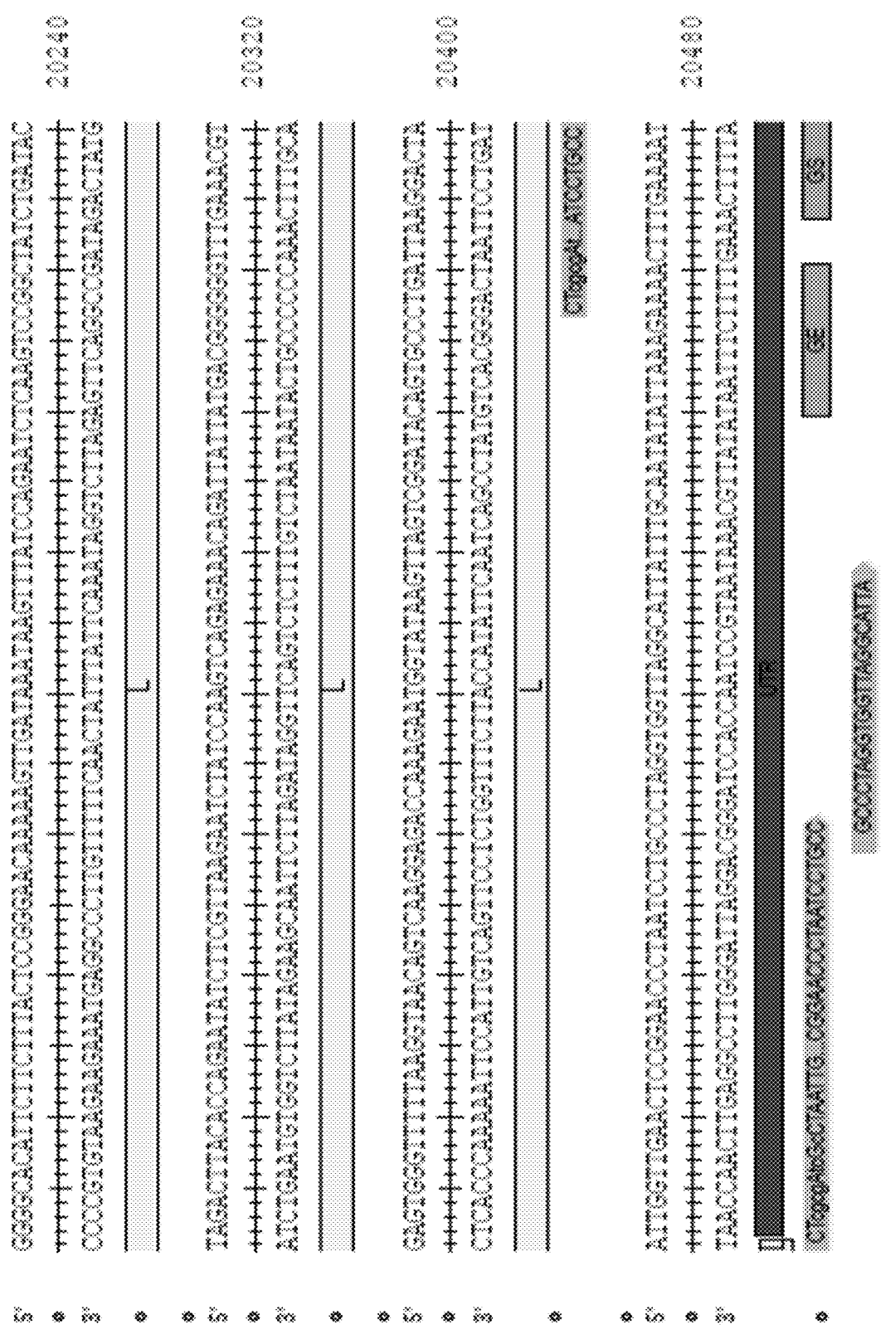
Figure 19:
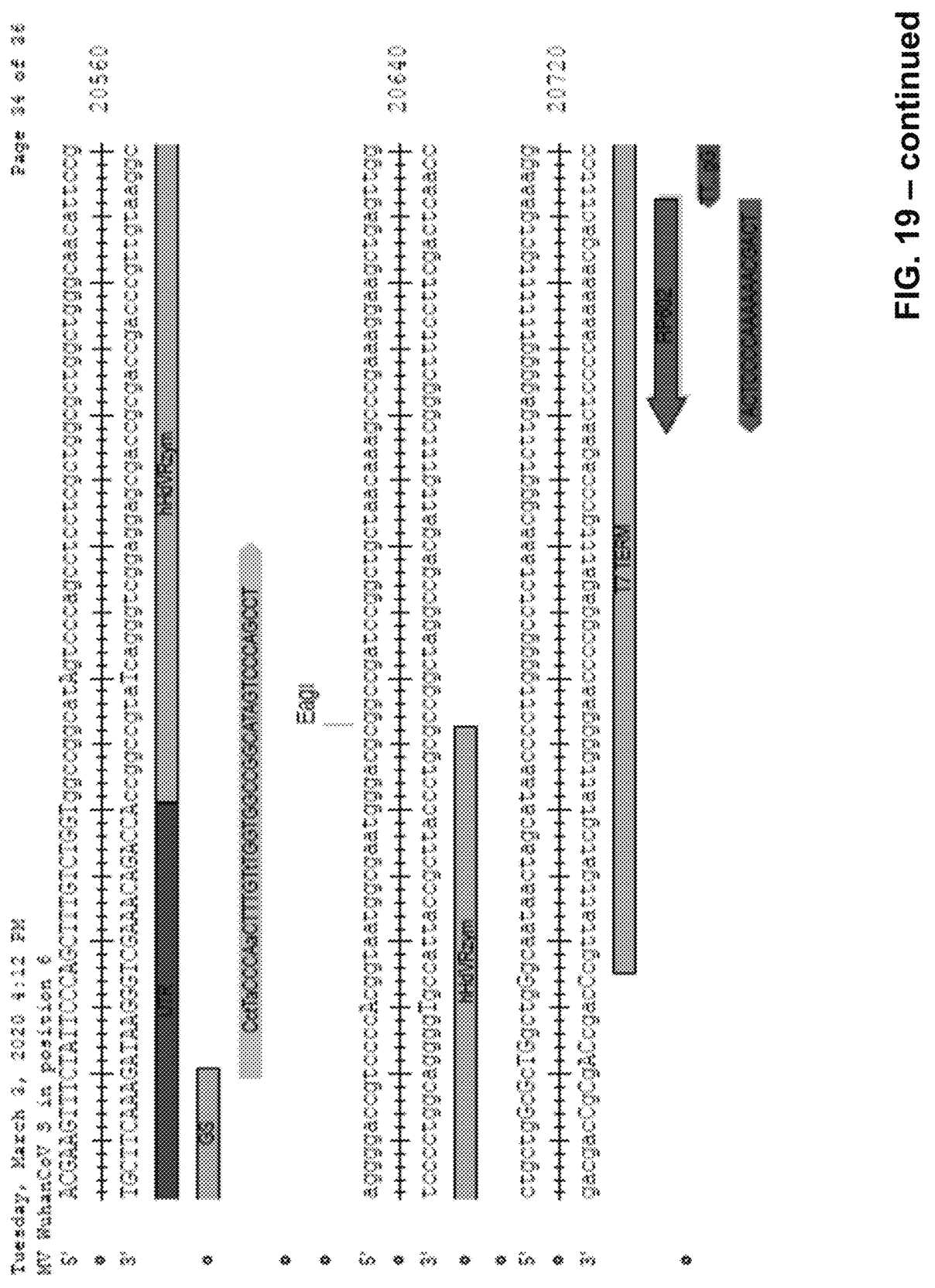
Figure 19:
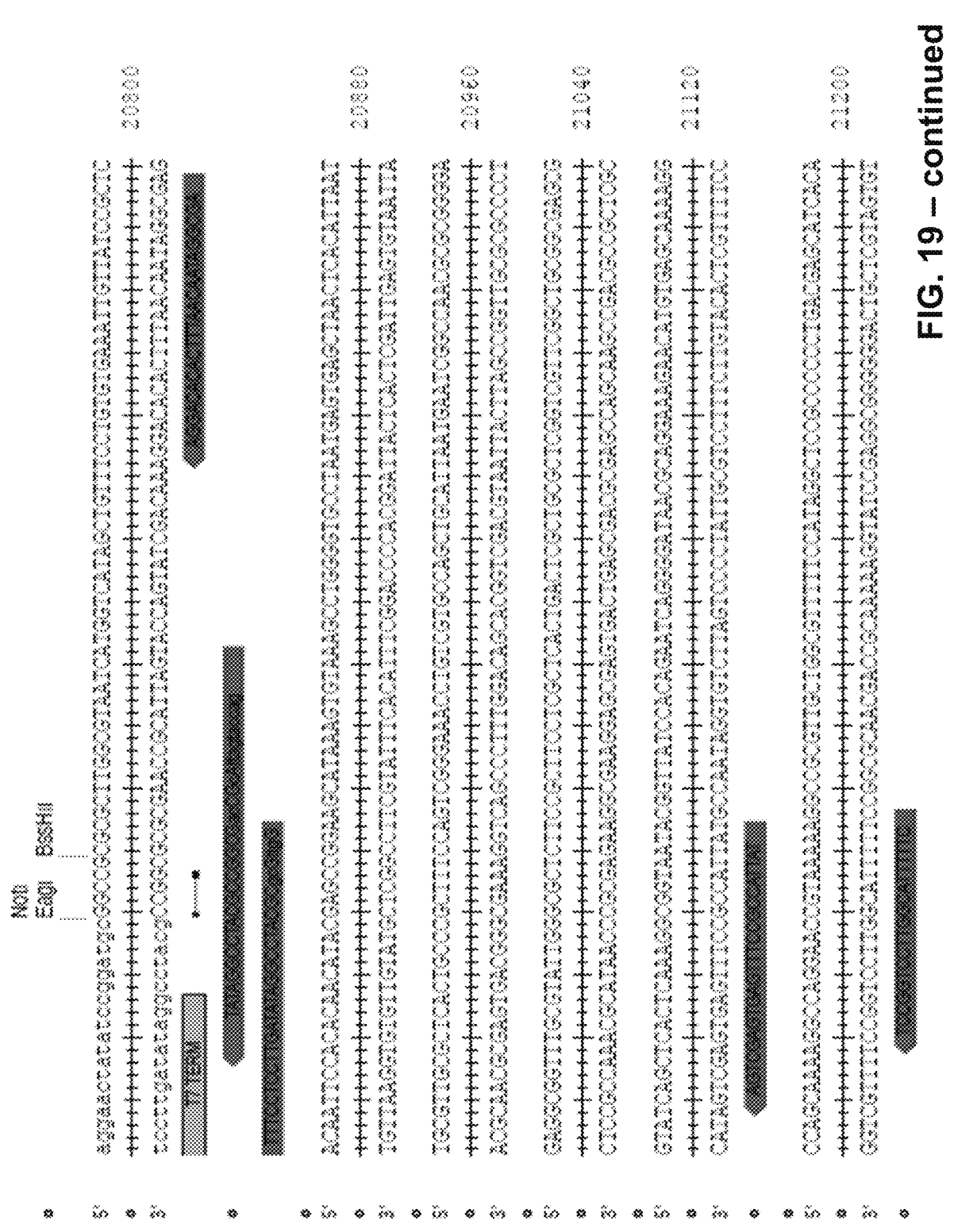
Figure 19:
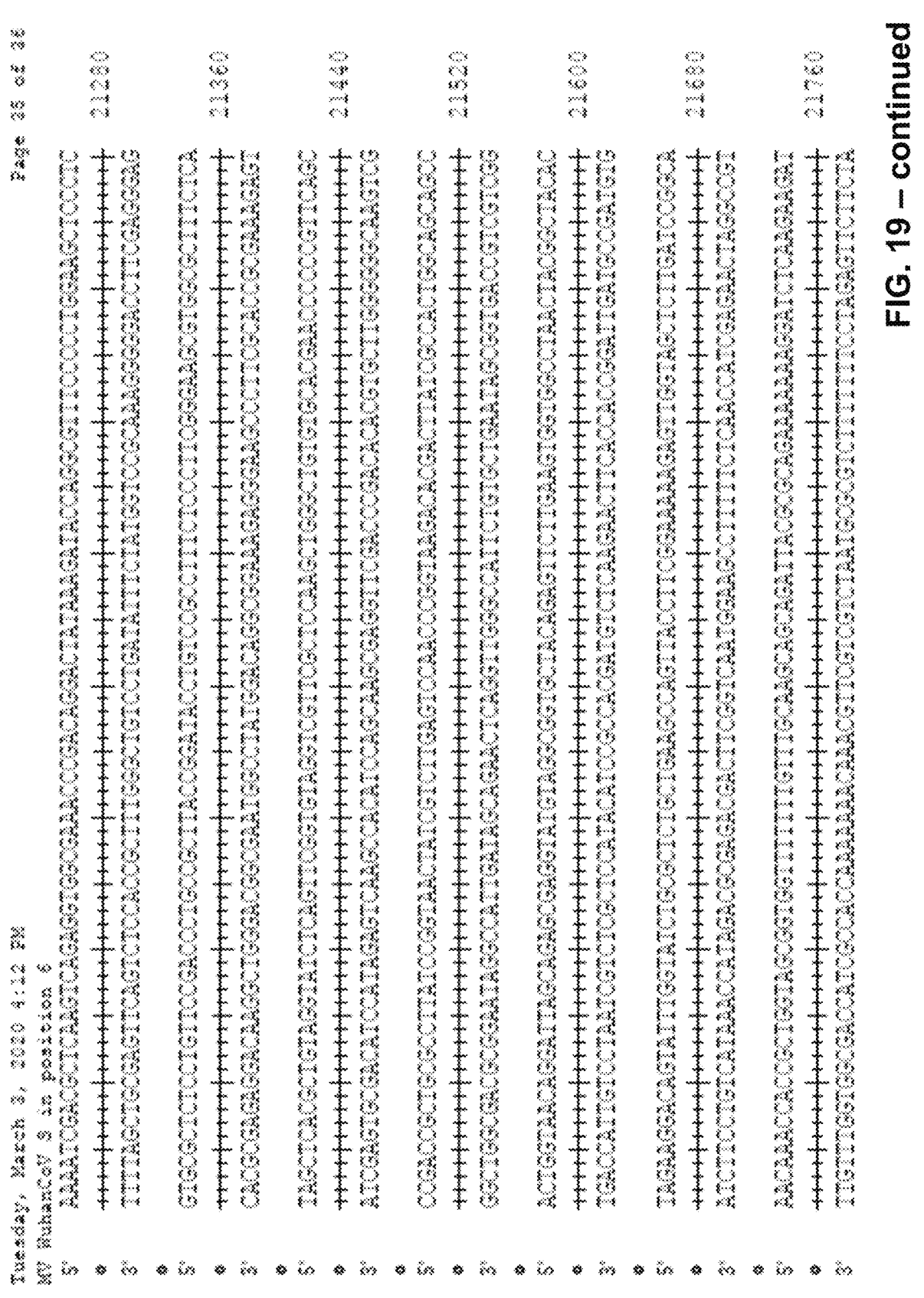
Figure 19:
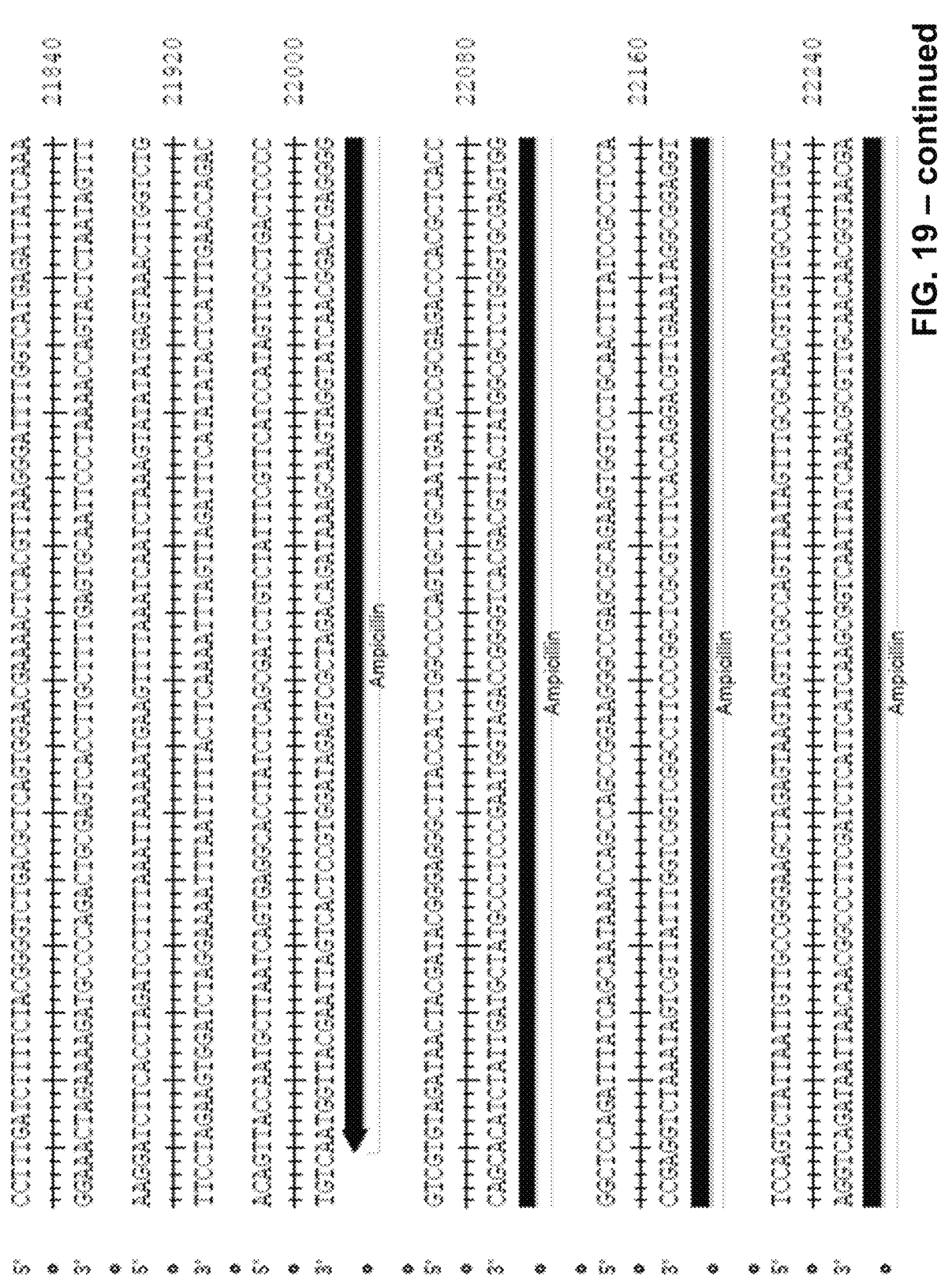
Figure 19:
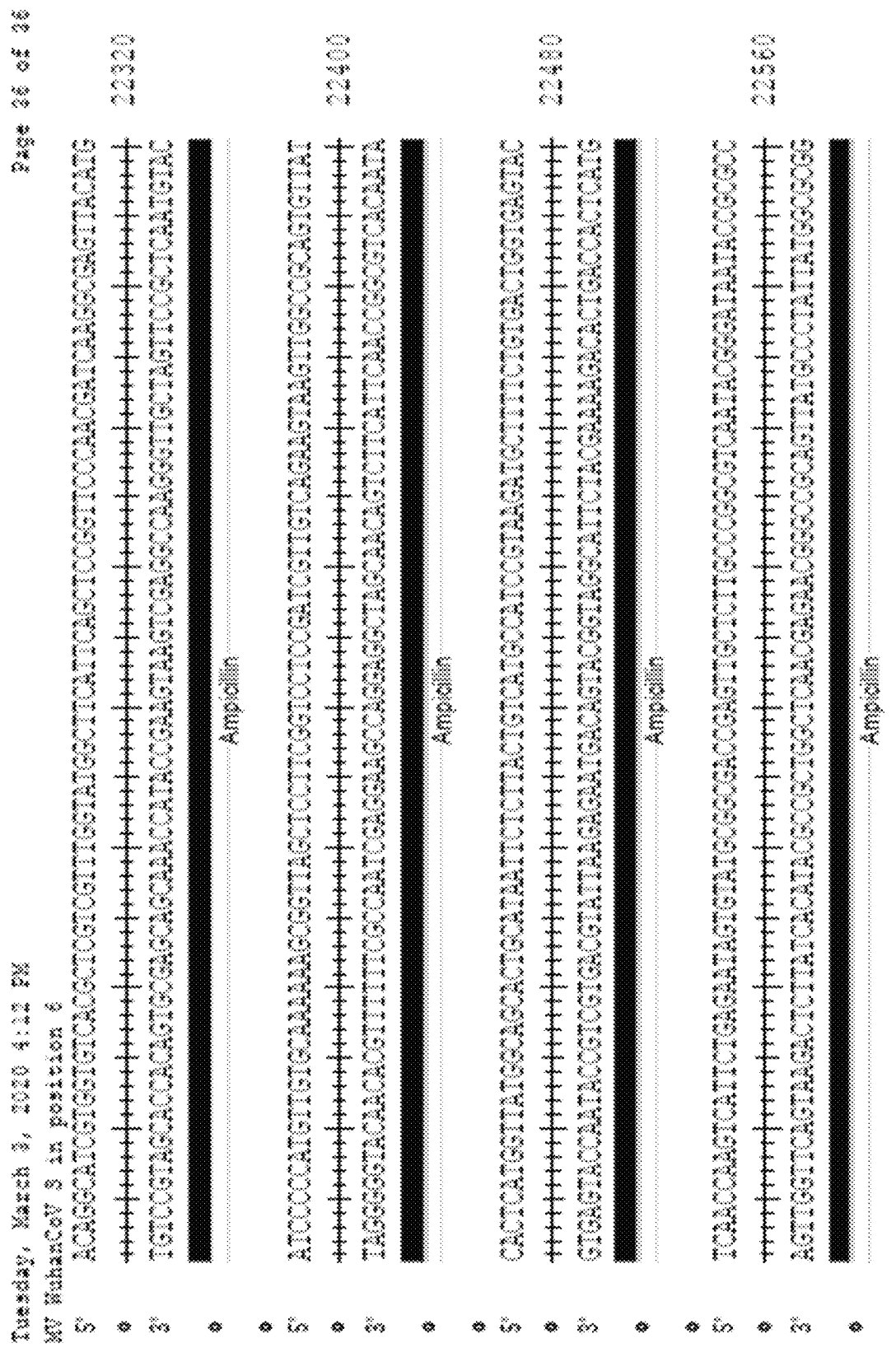

FIG. 19 shows the sequence (SEQ ID NO: 5) and features of "MV WuhanCoV S in position 6". FIG. 19 additionally shows the sequences of SEQ ID NOs: 33-106.

Figure 20:
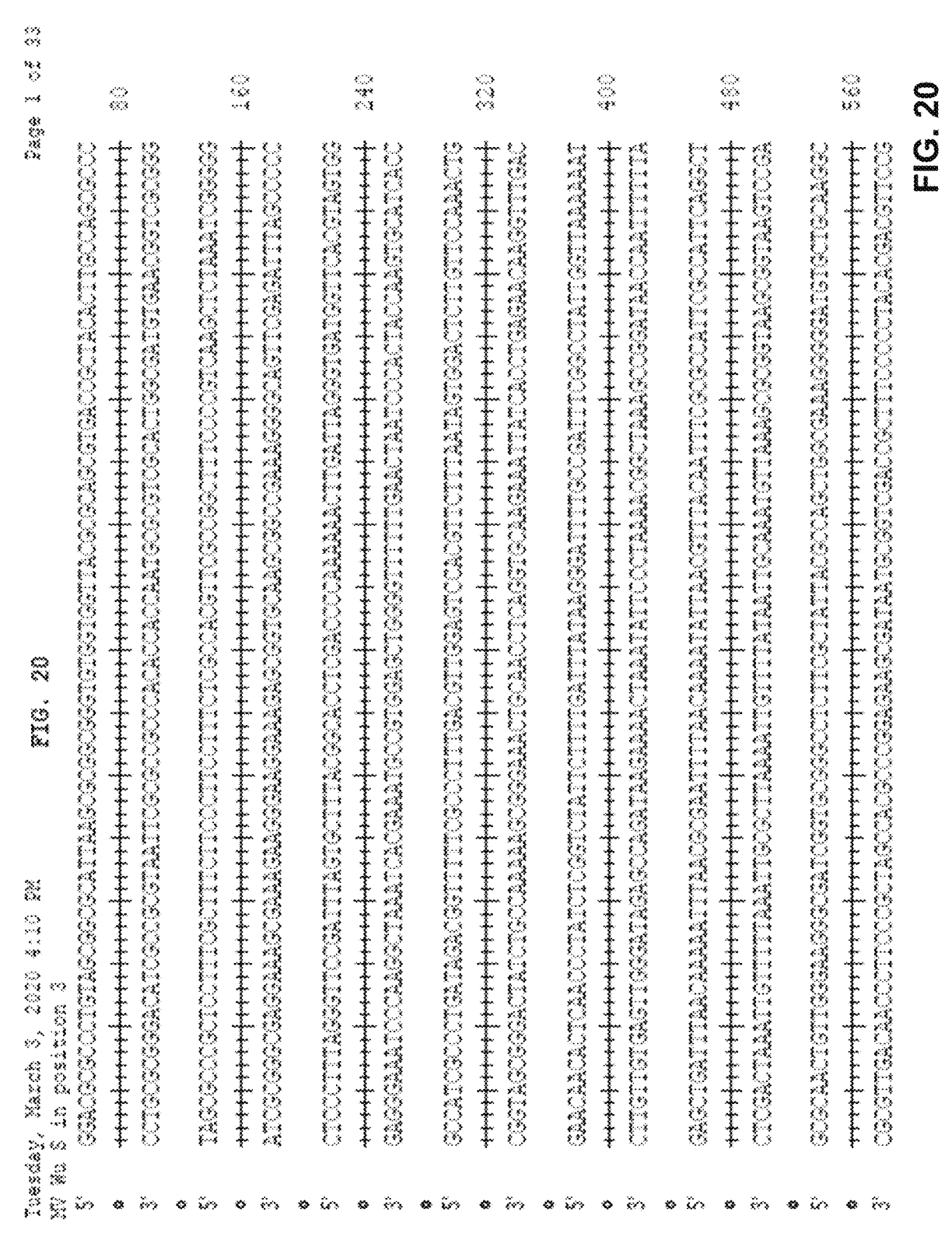
Figure 20:
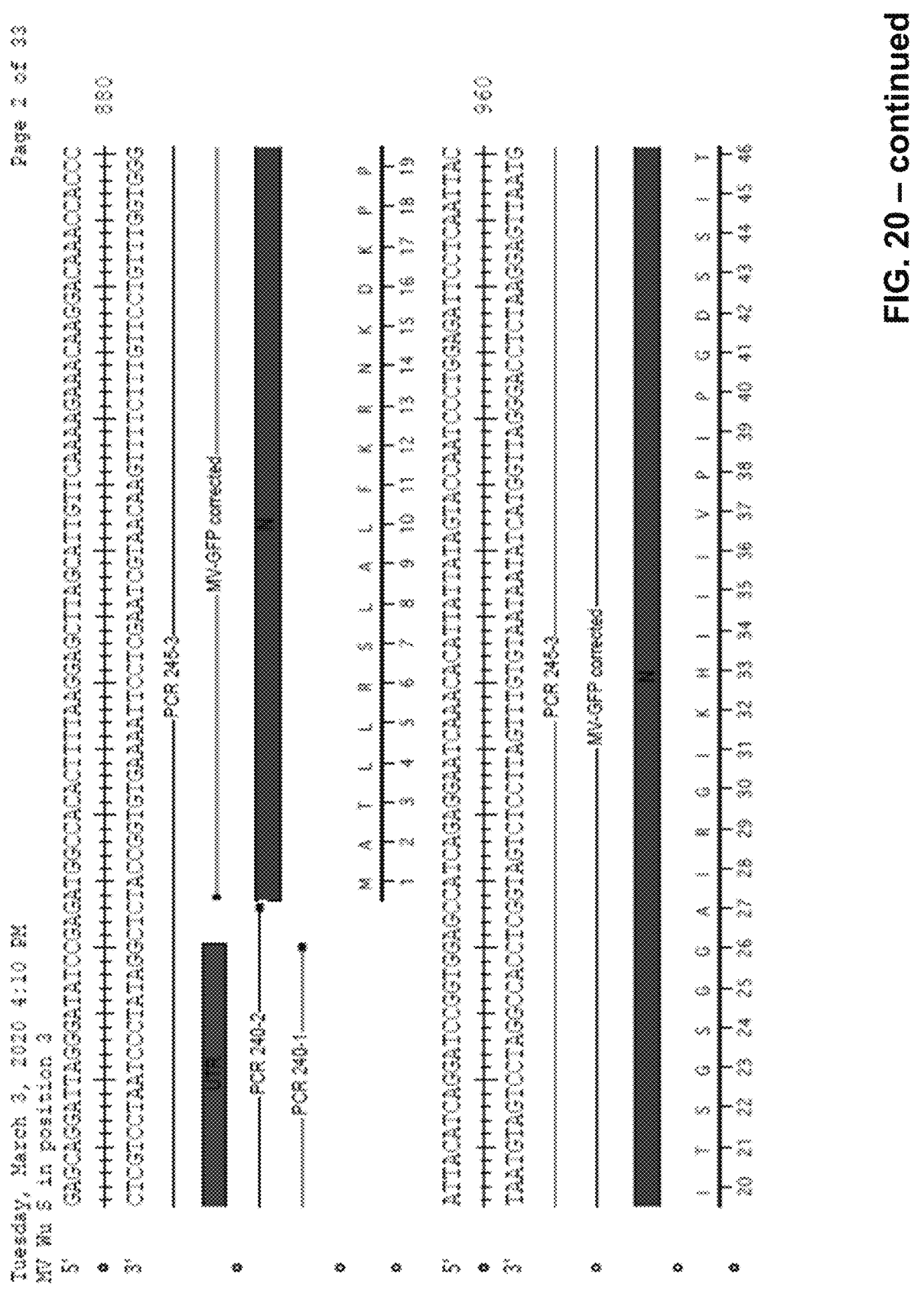
Figure 20:
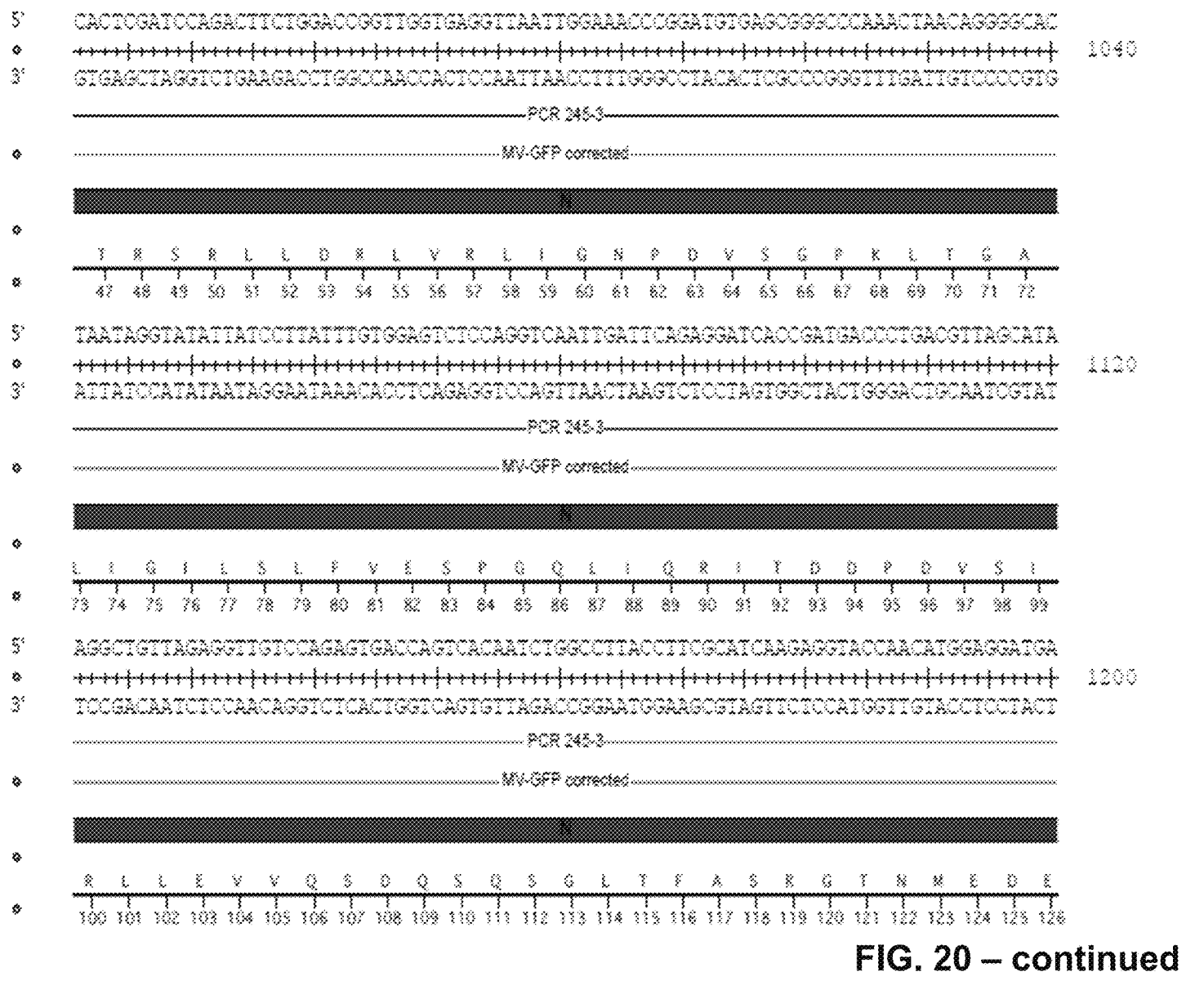
Figure 20:
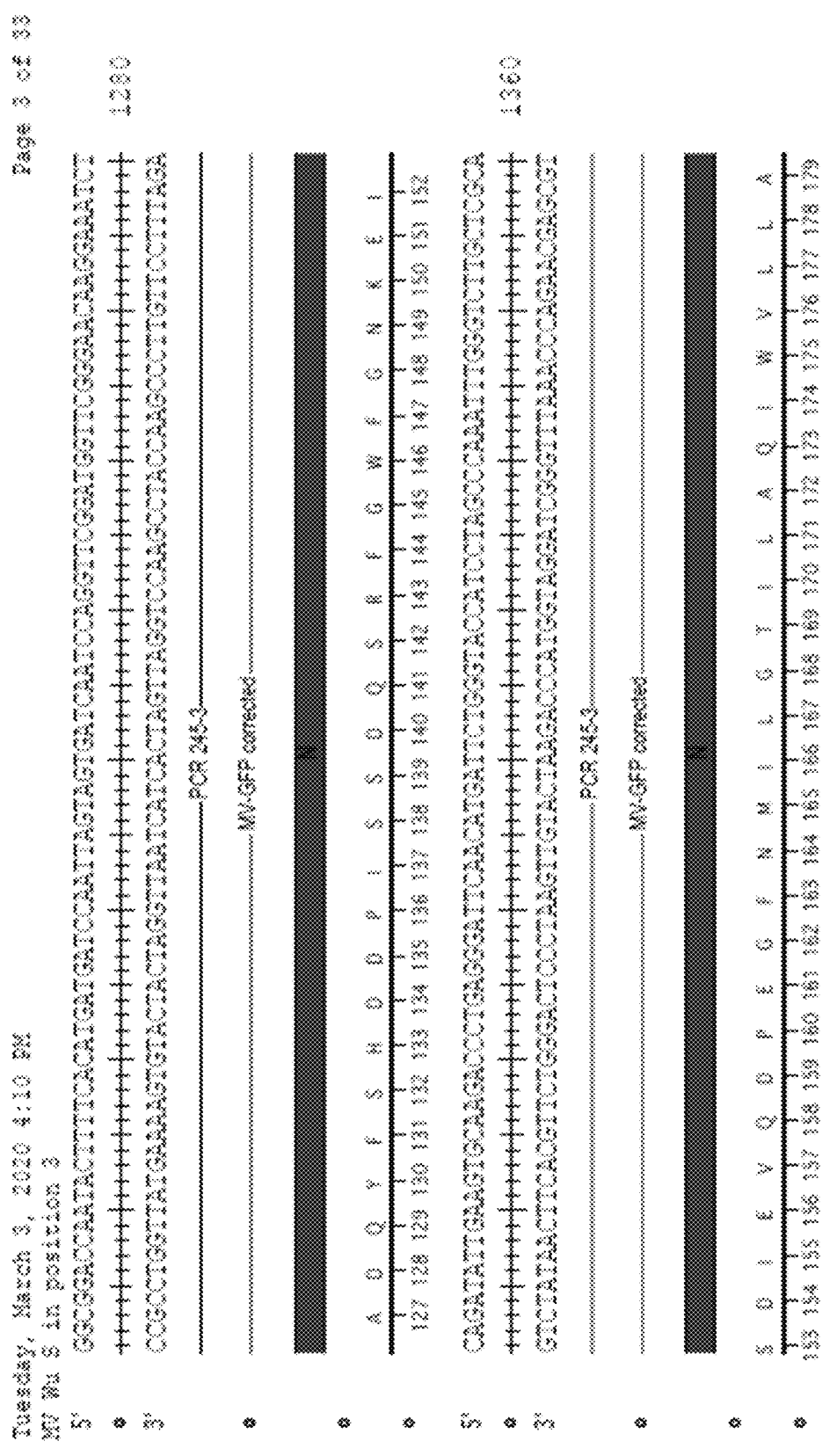
Figure 20:
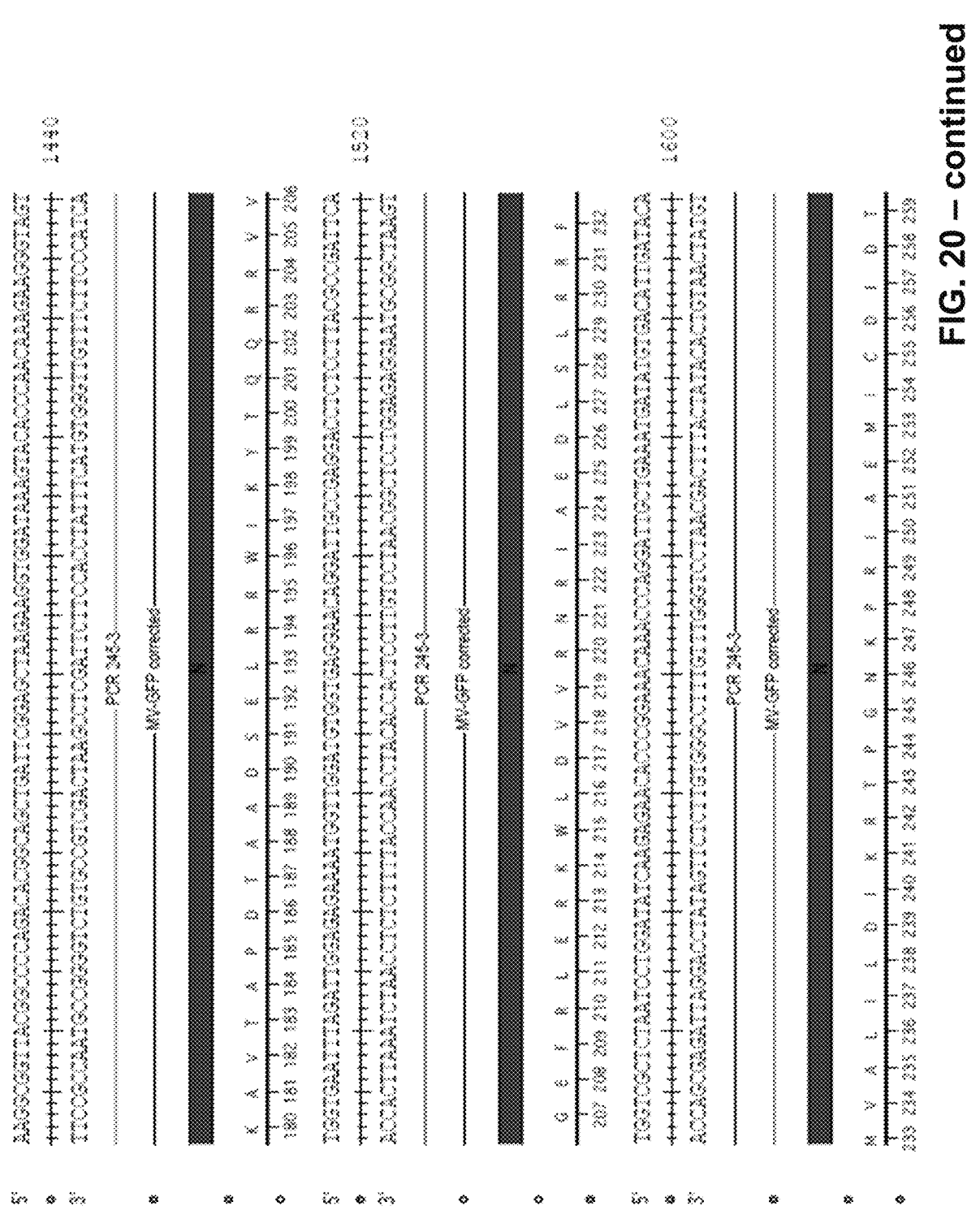
Figure 20:
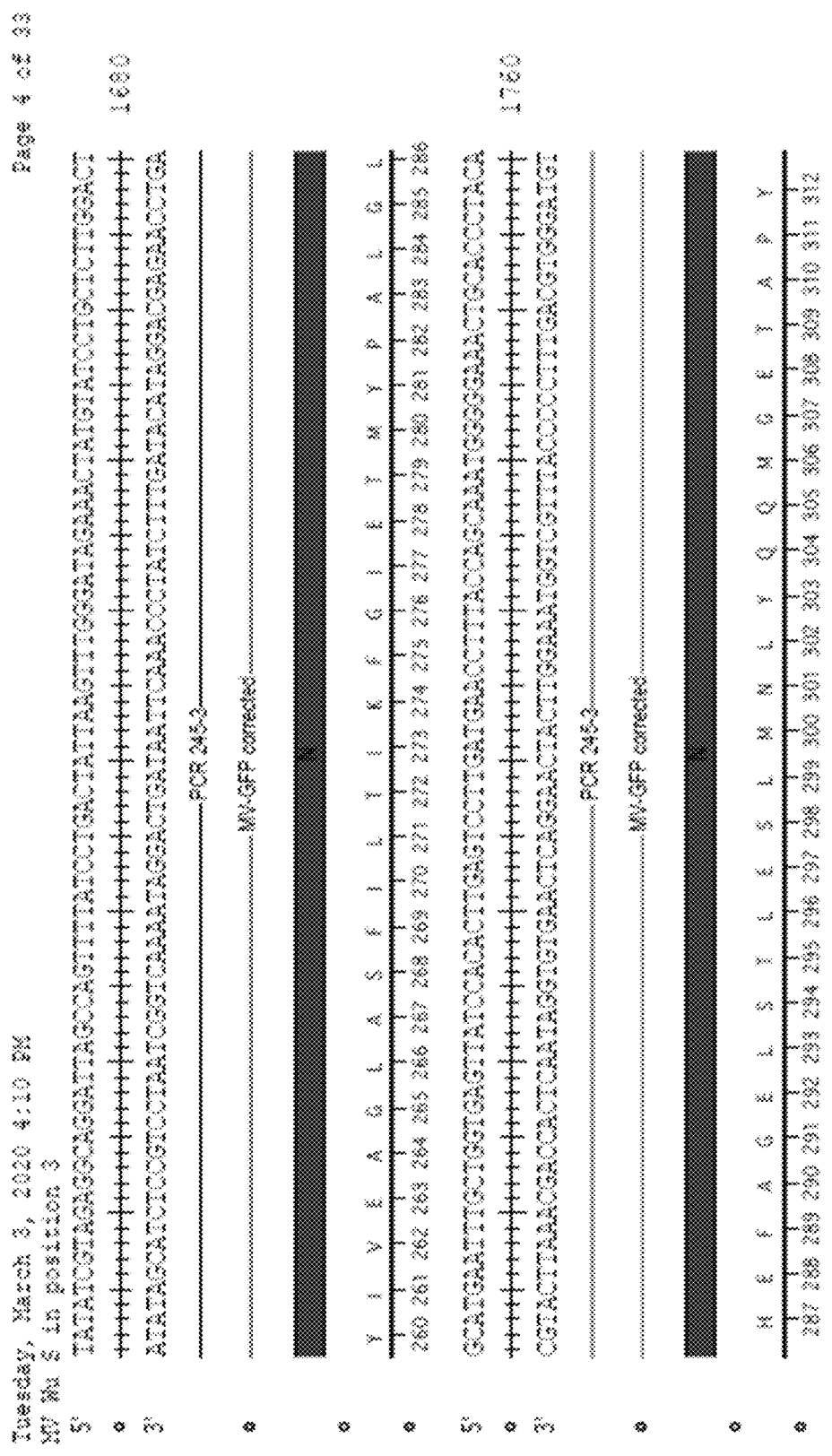
Figure 20:
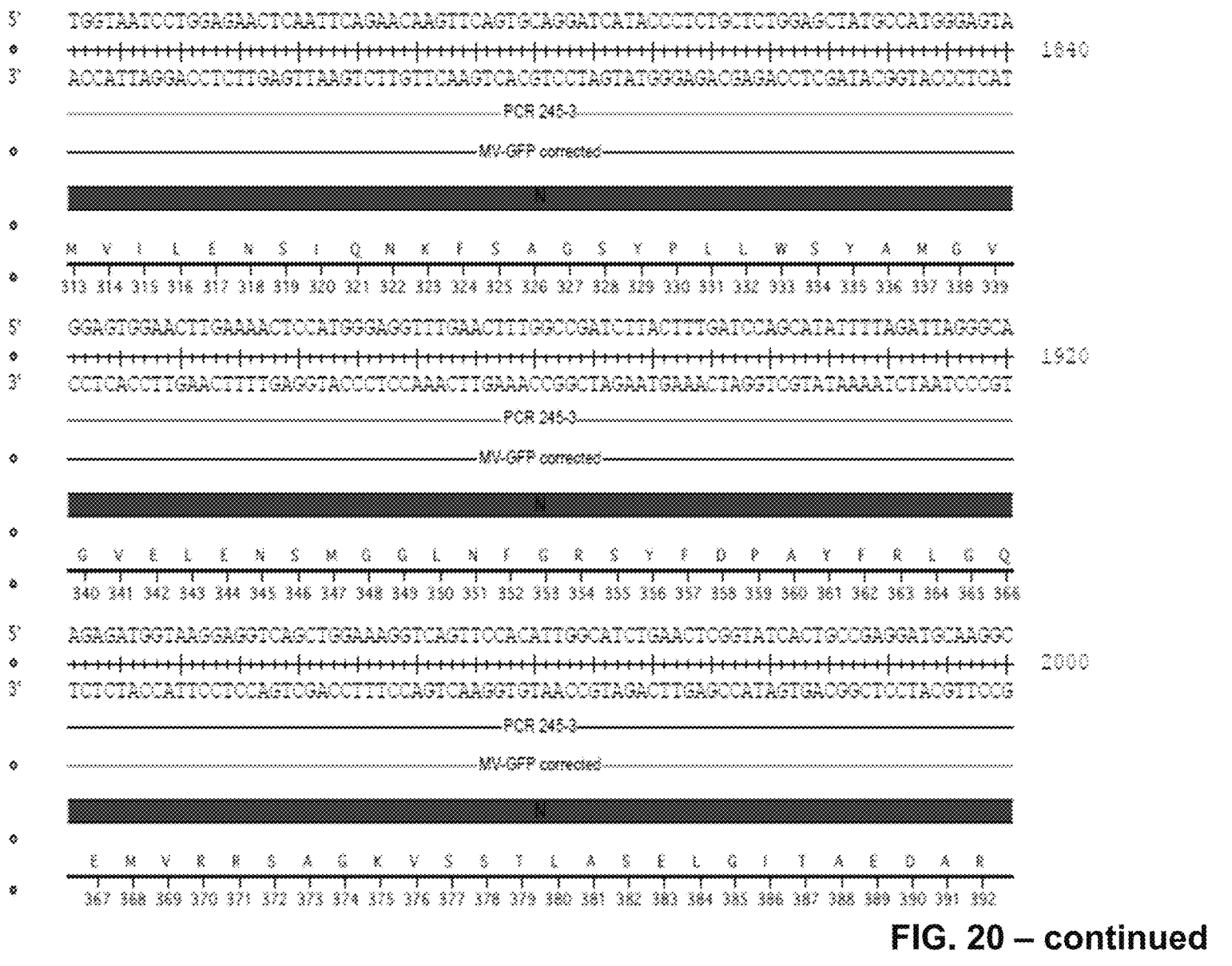
Figure 20:
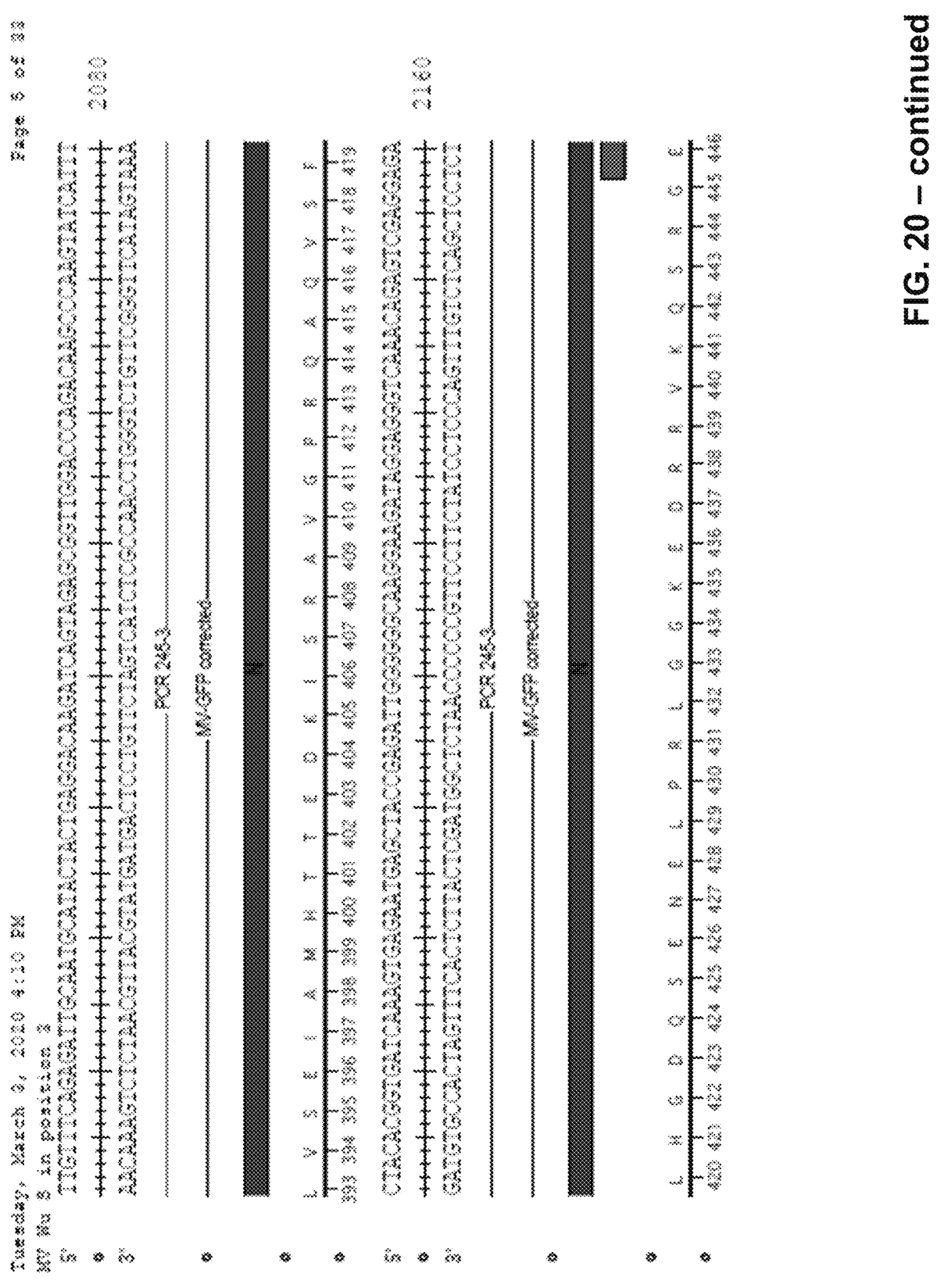
Figure 20:
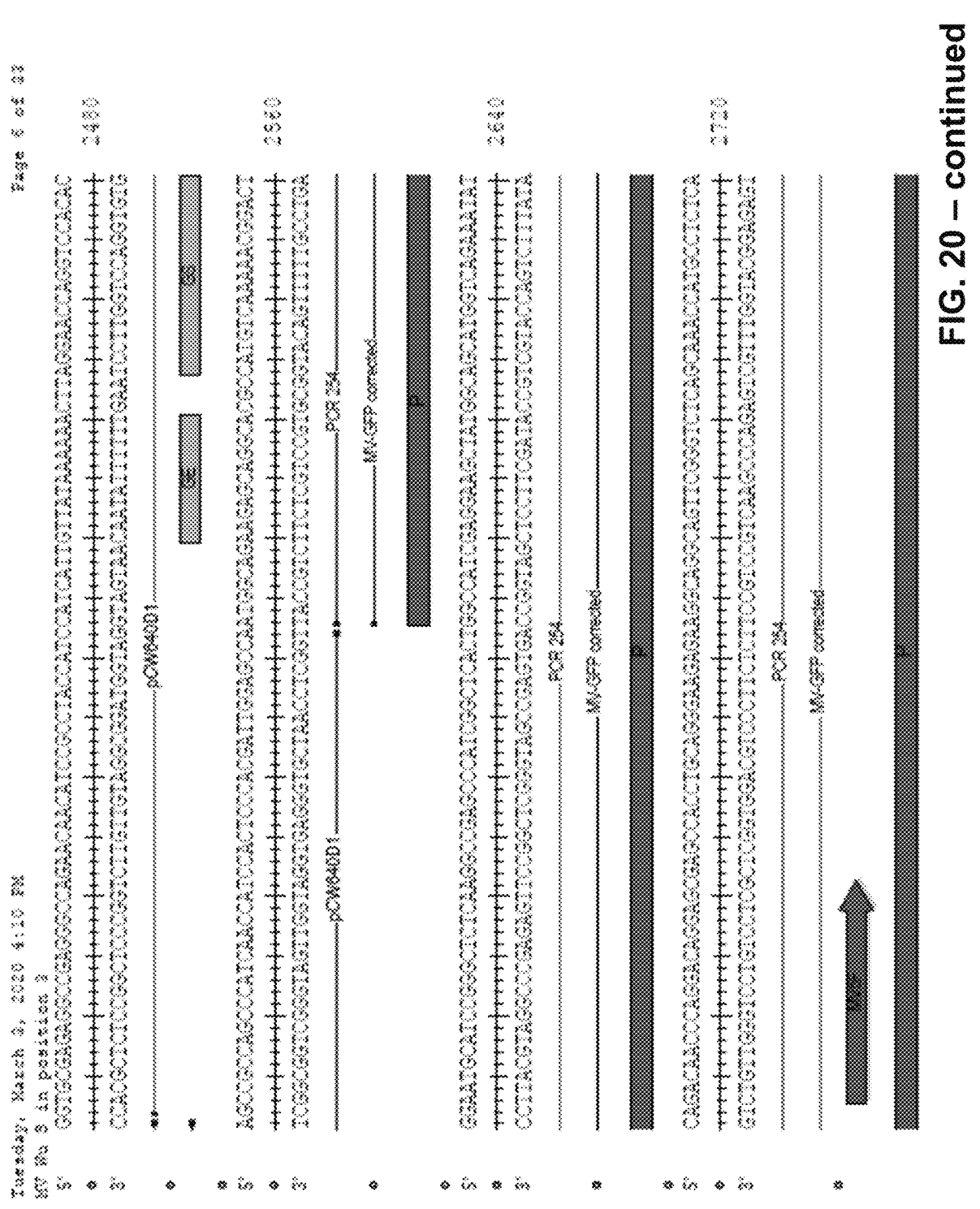
Figure 20:
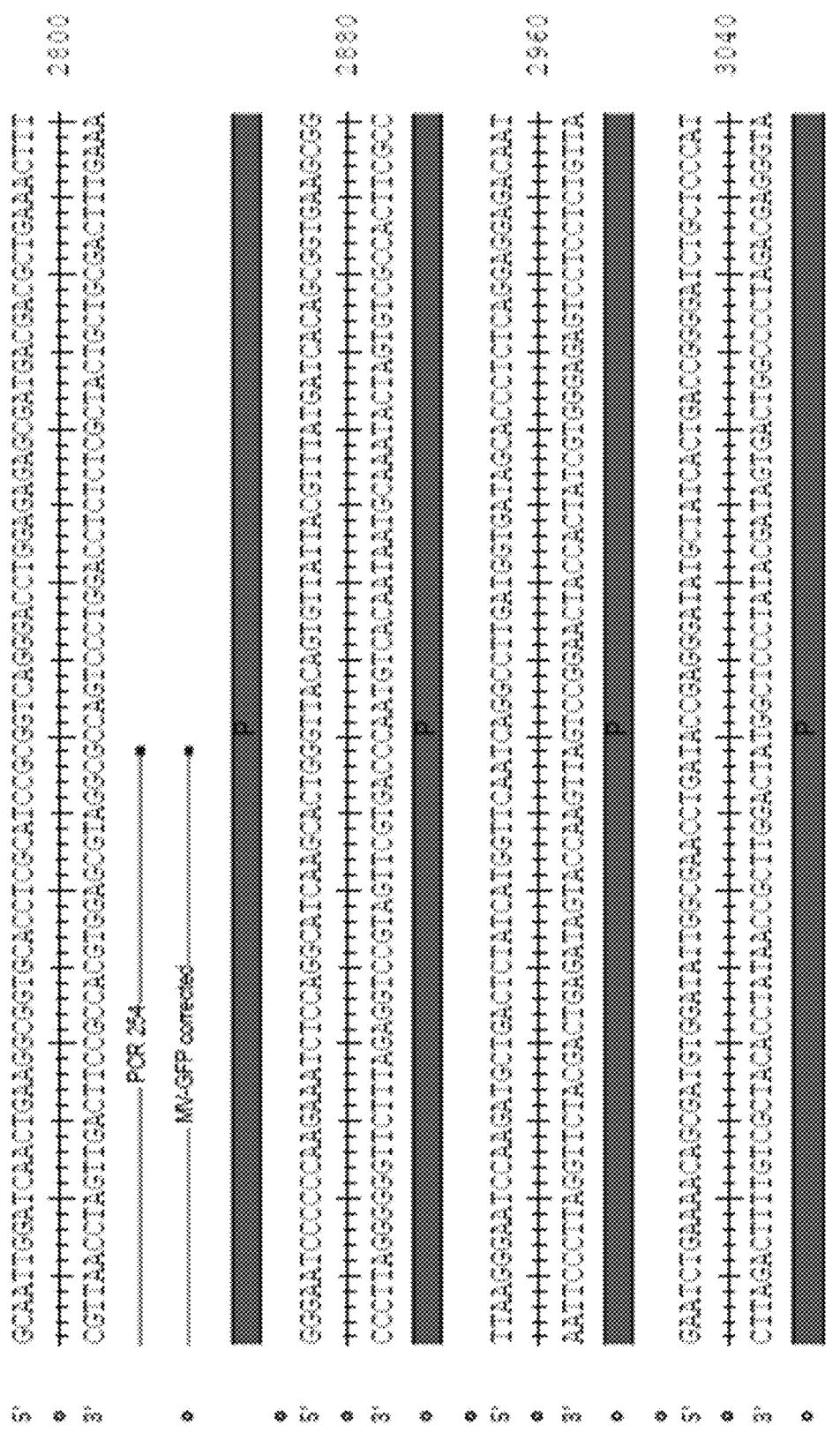
Figure 20:
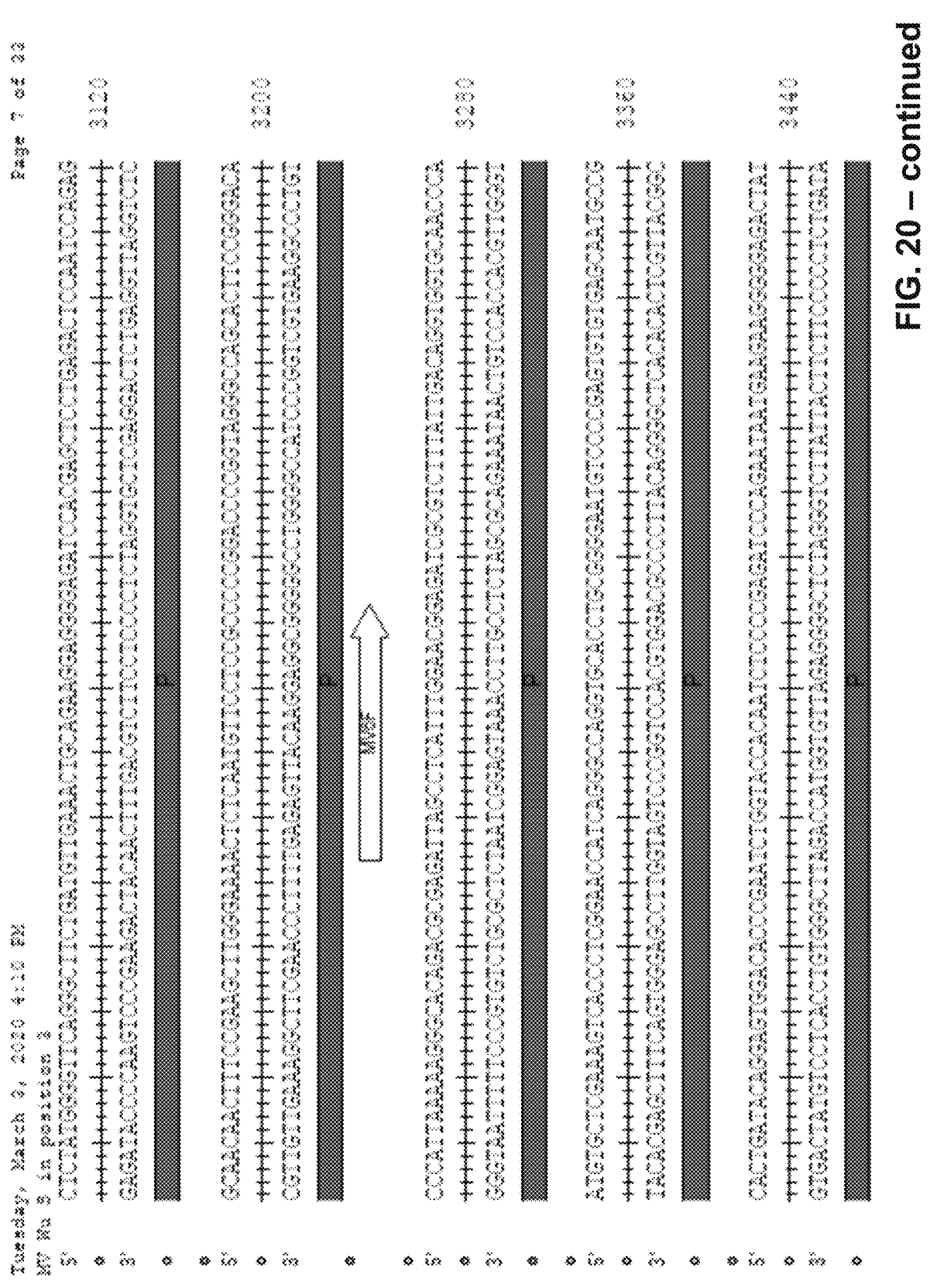
Figure 20:
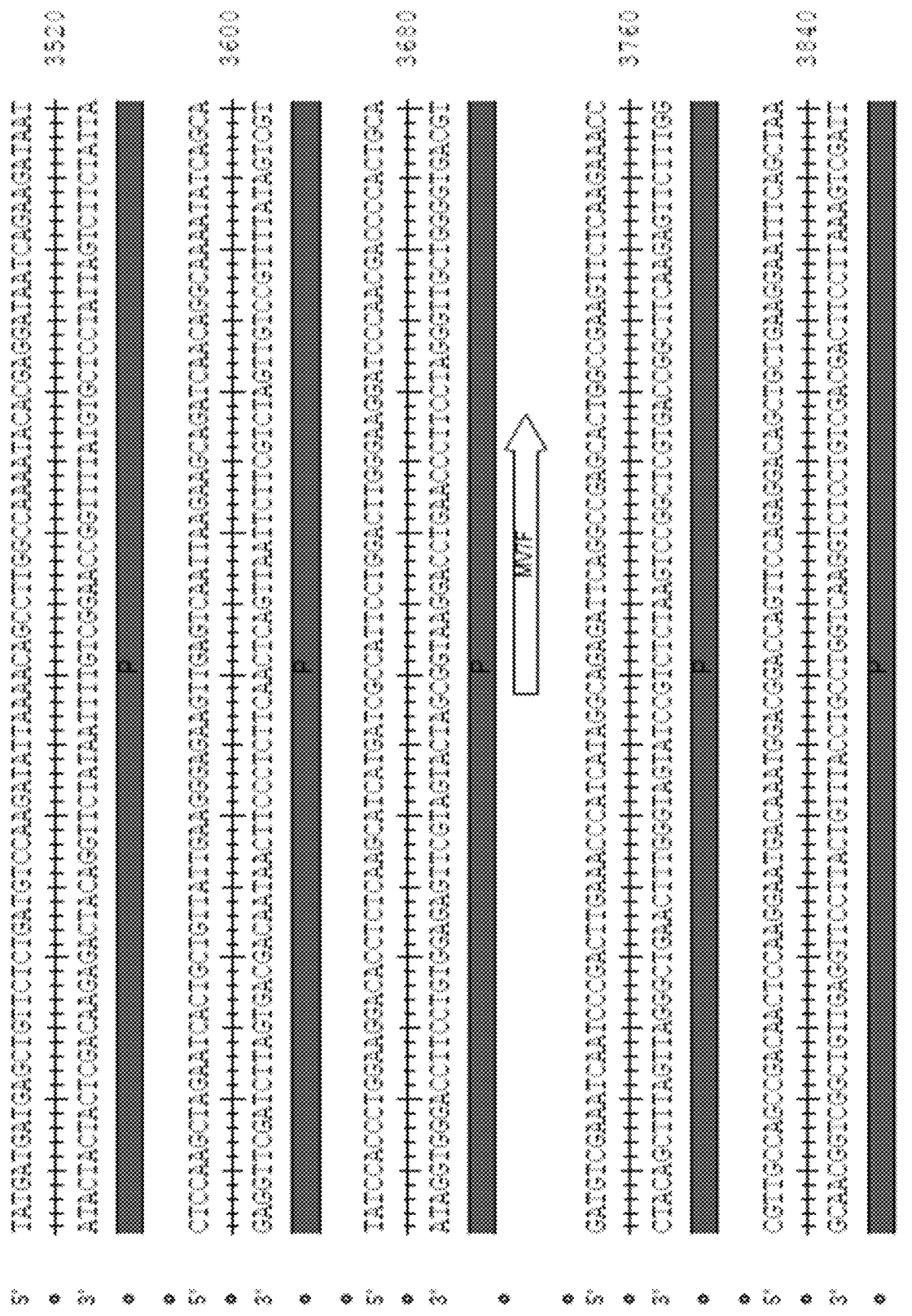
Figure 20:
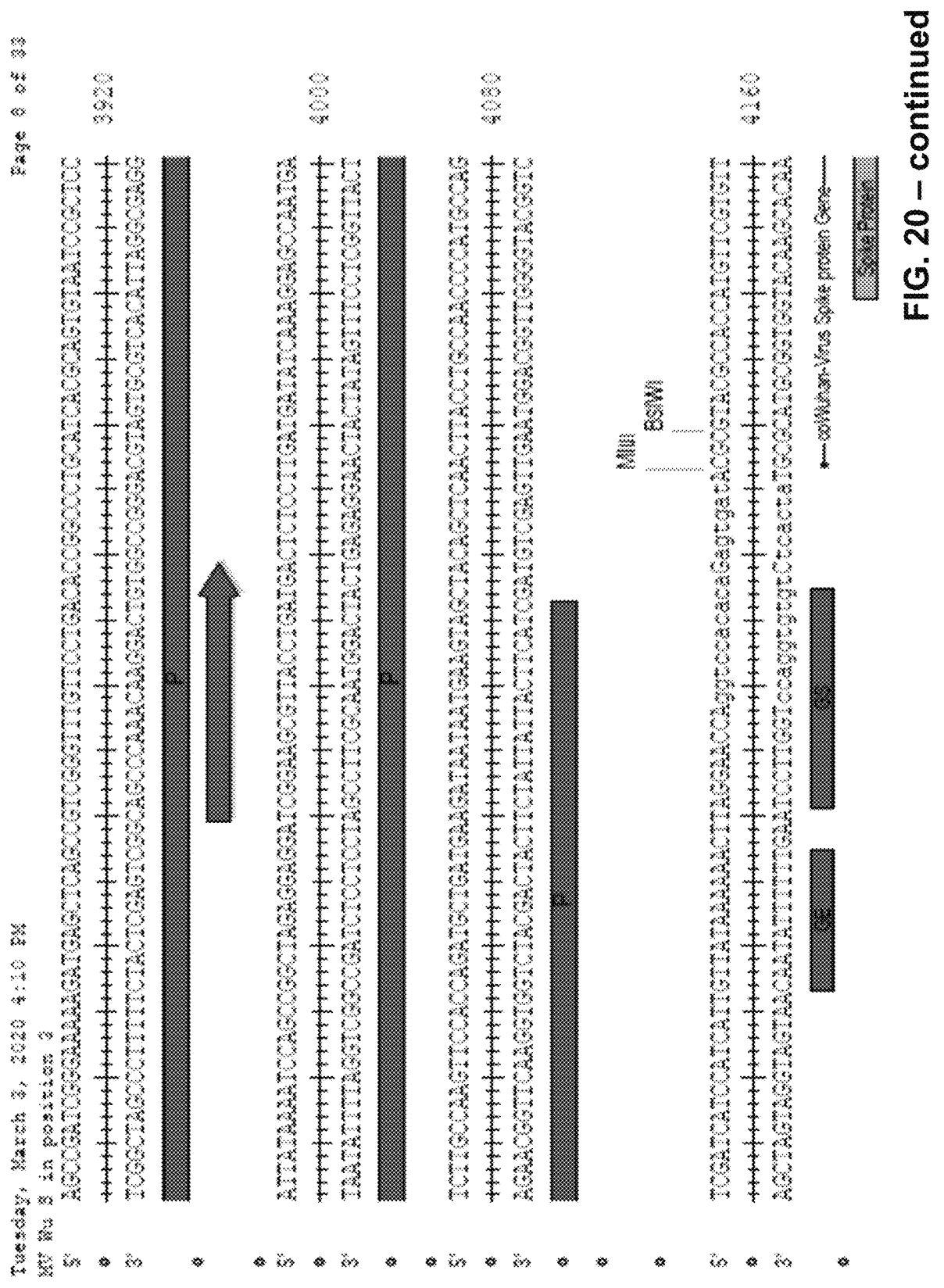
Figure 20:
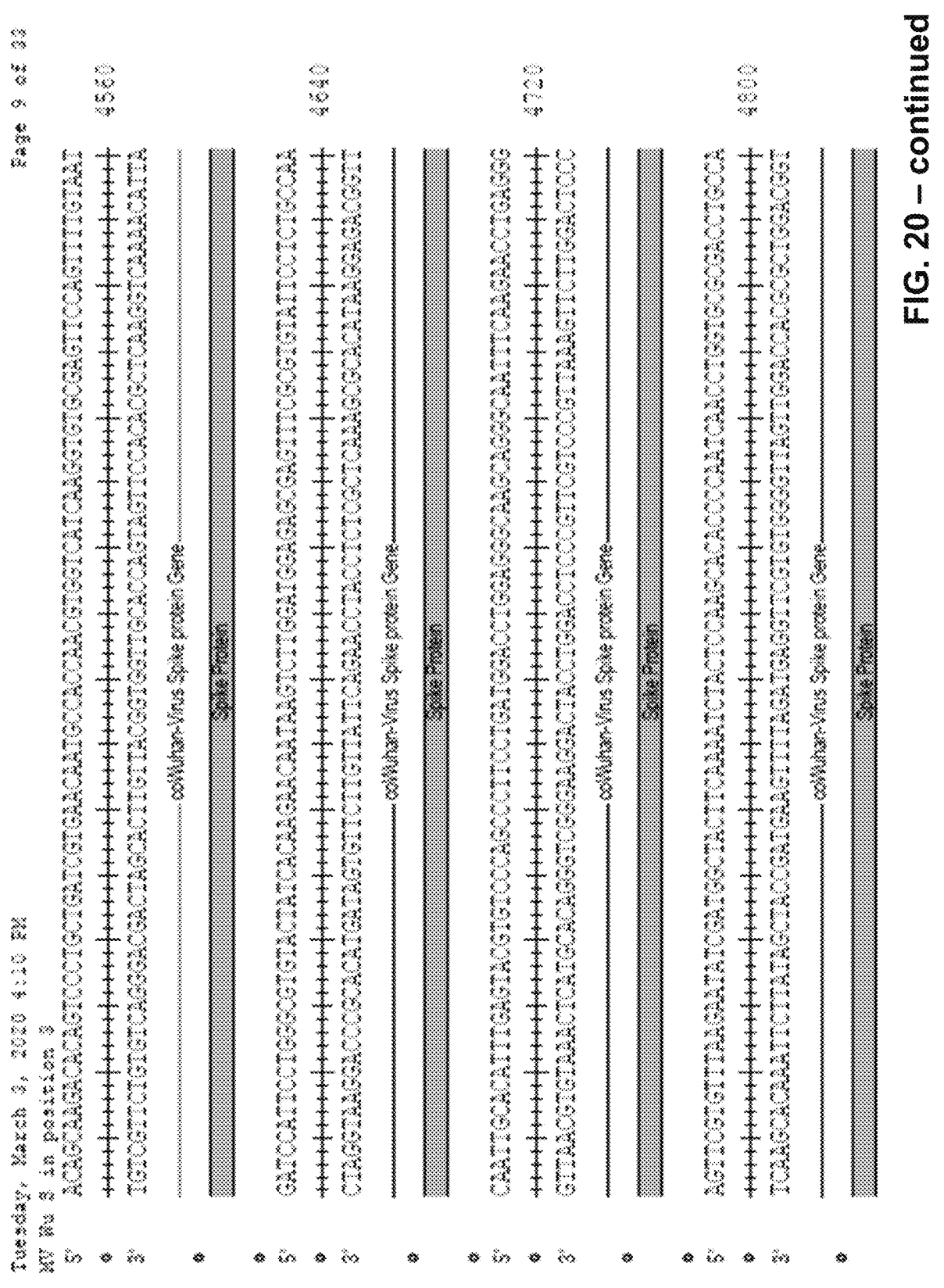
Figure 20:
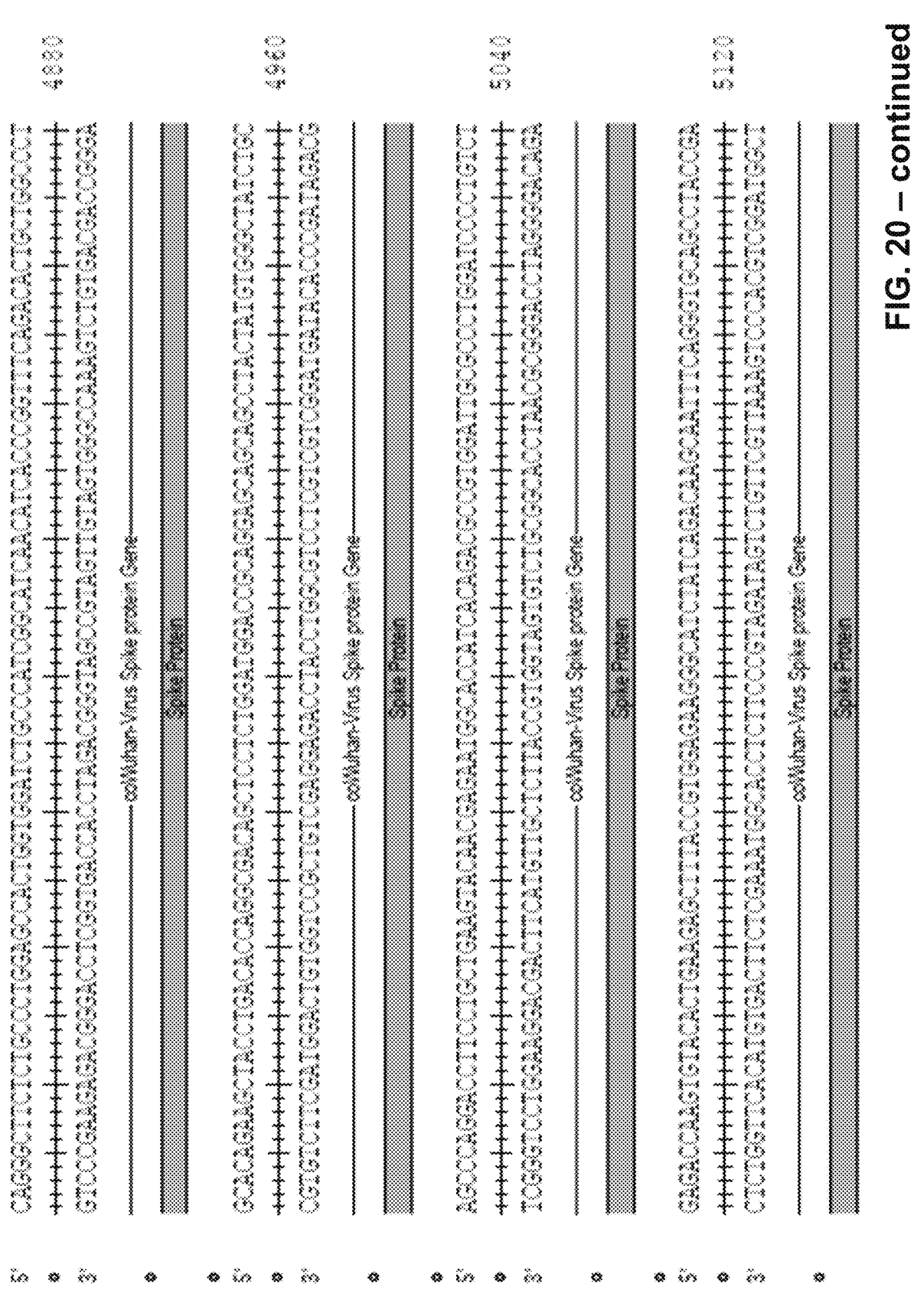
Figure 20:
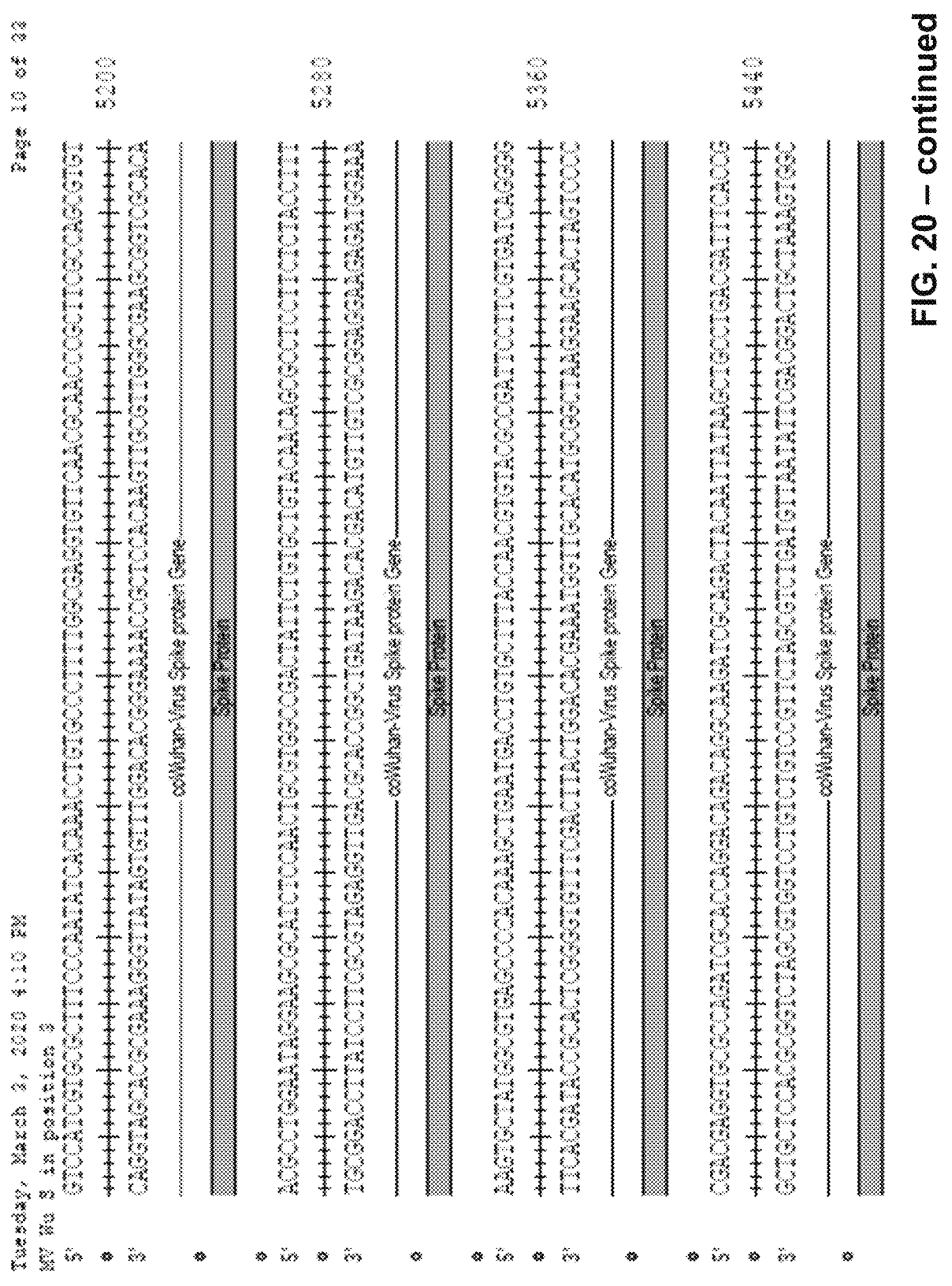
Figure 20:
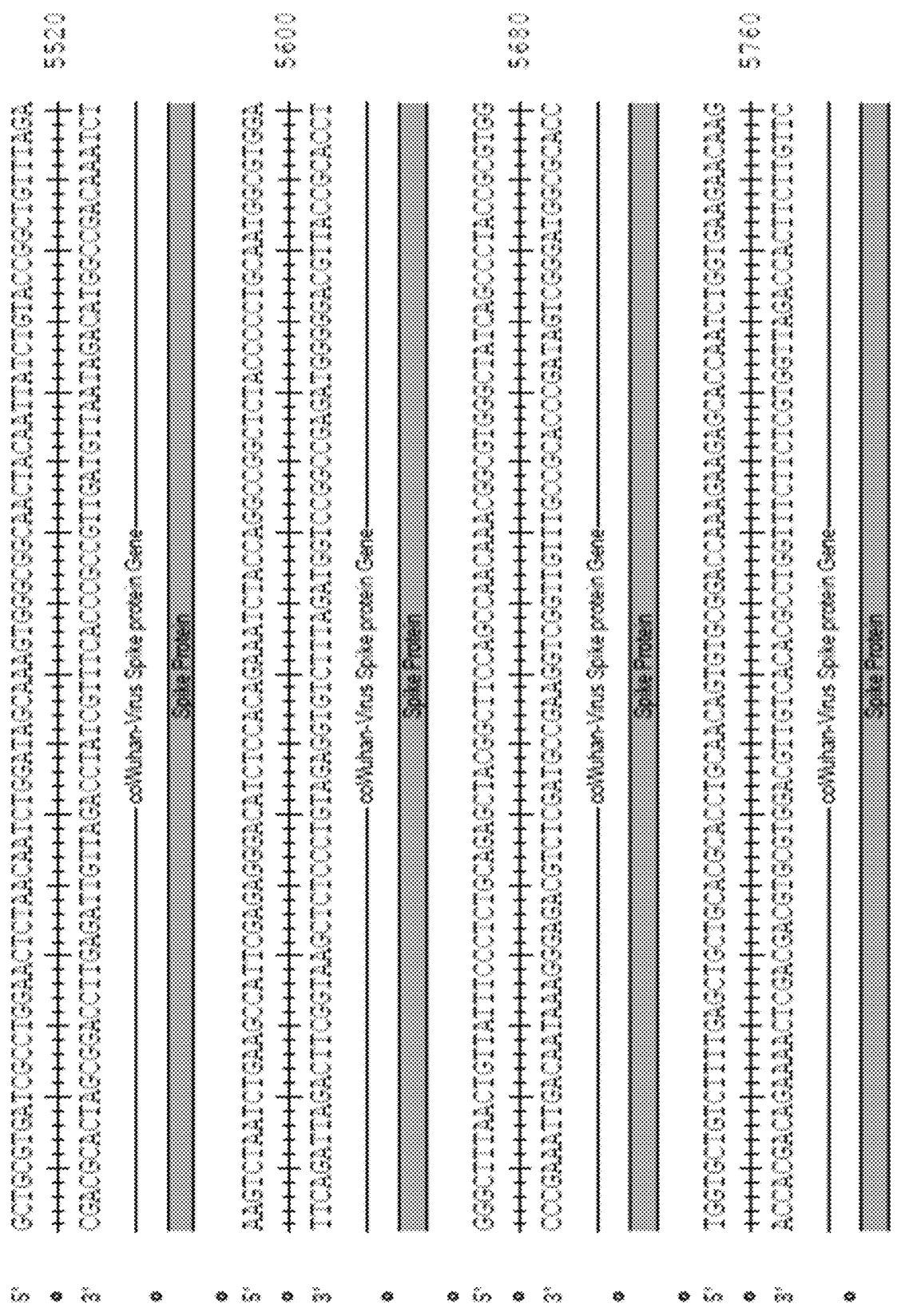
Figure 20:
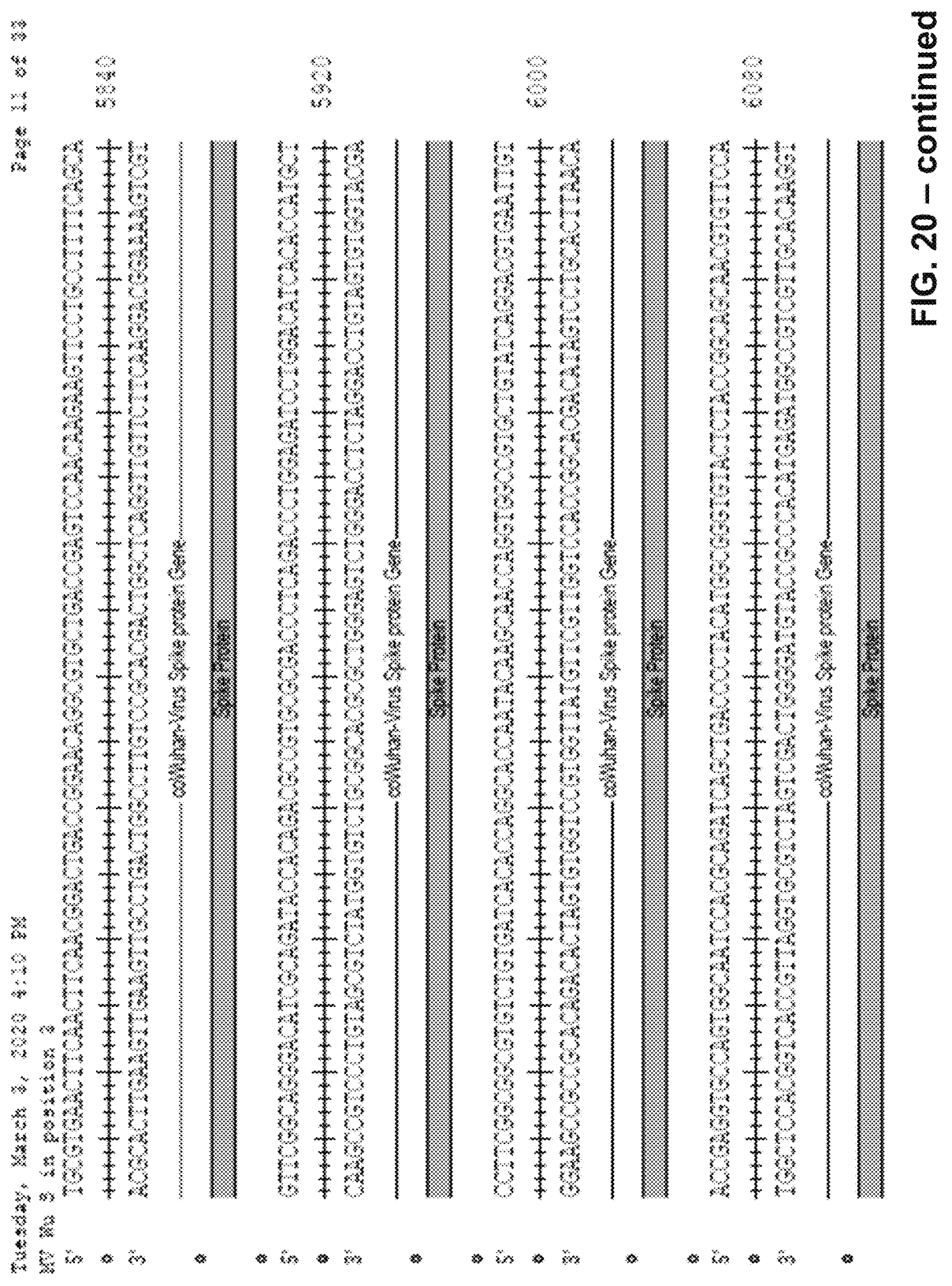
Figure 20:
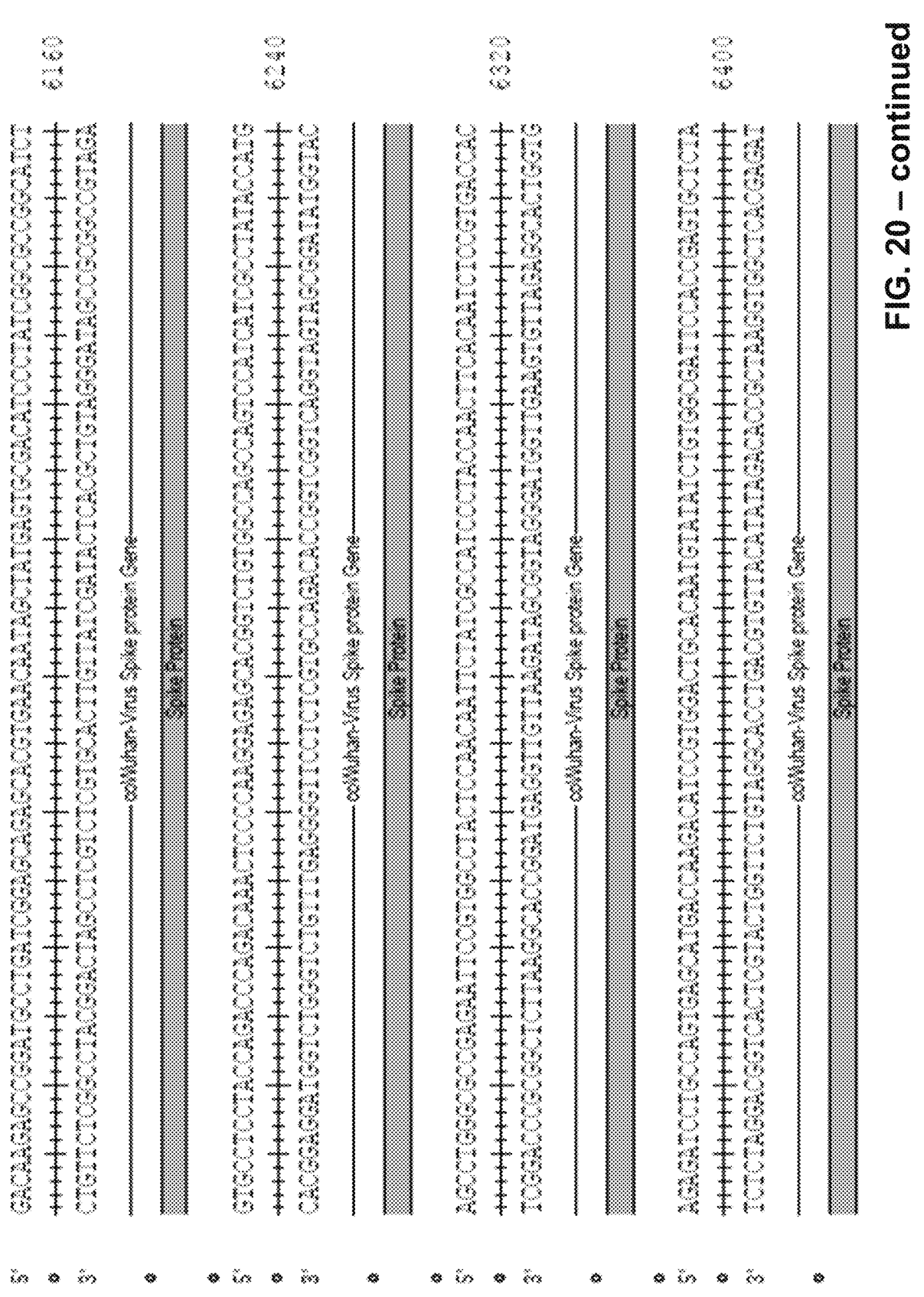
Figure 20:
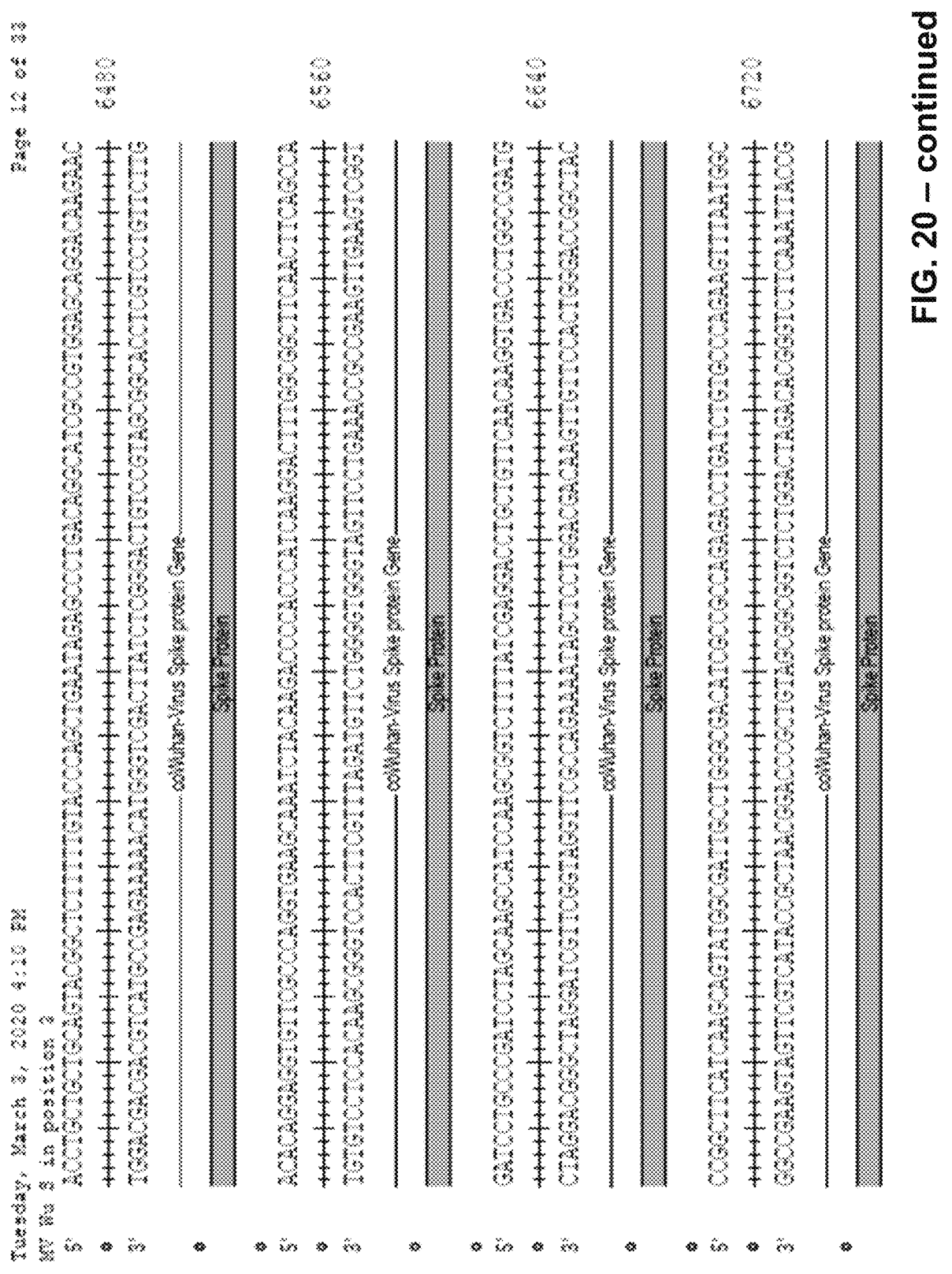
Figure 20:
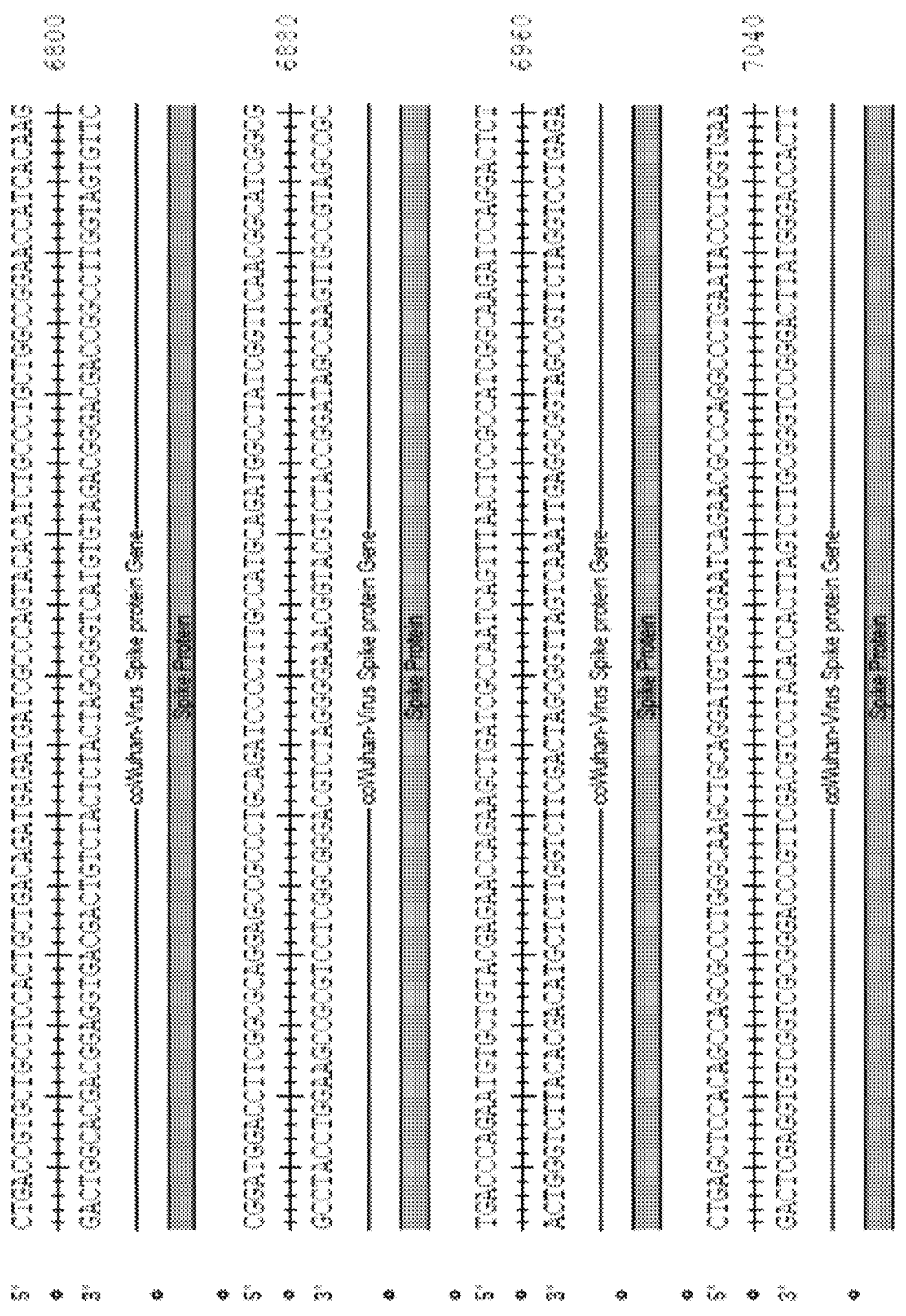
Figure 20:
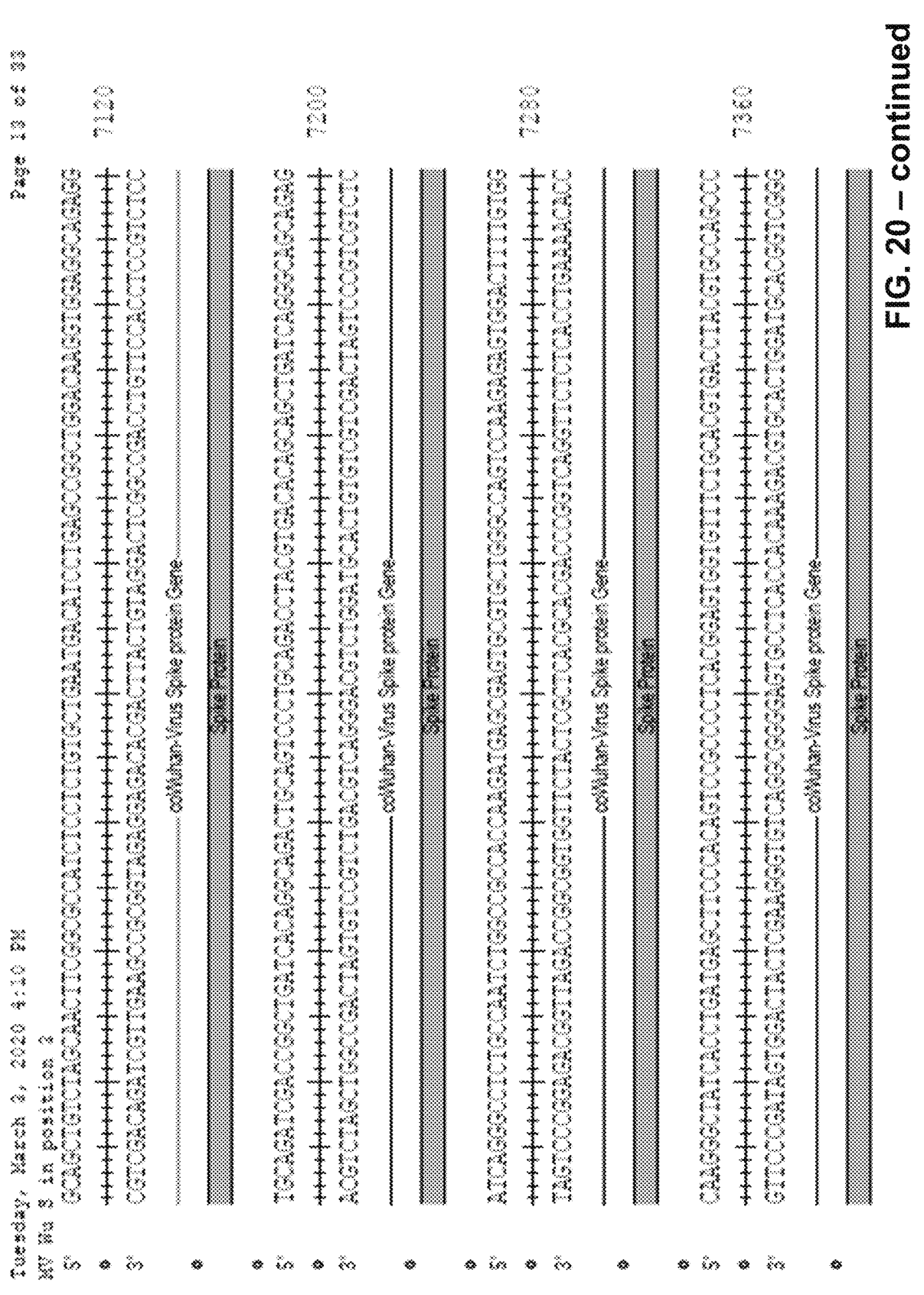
Figure 20:
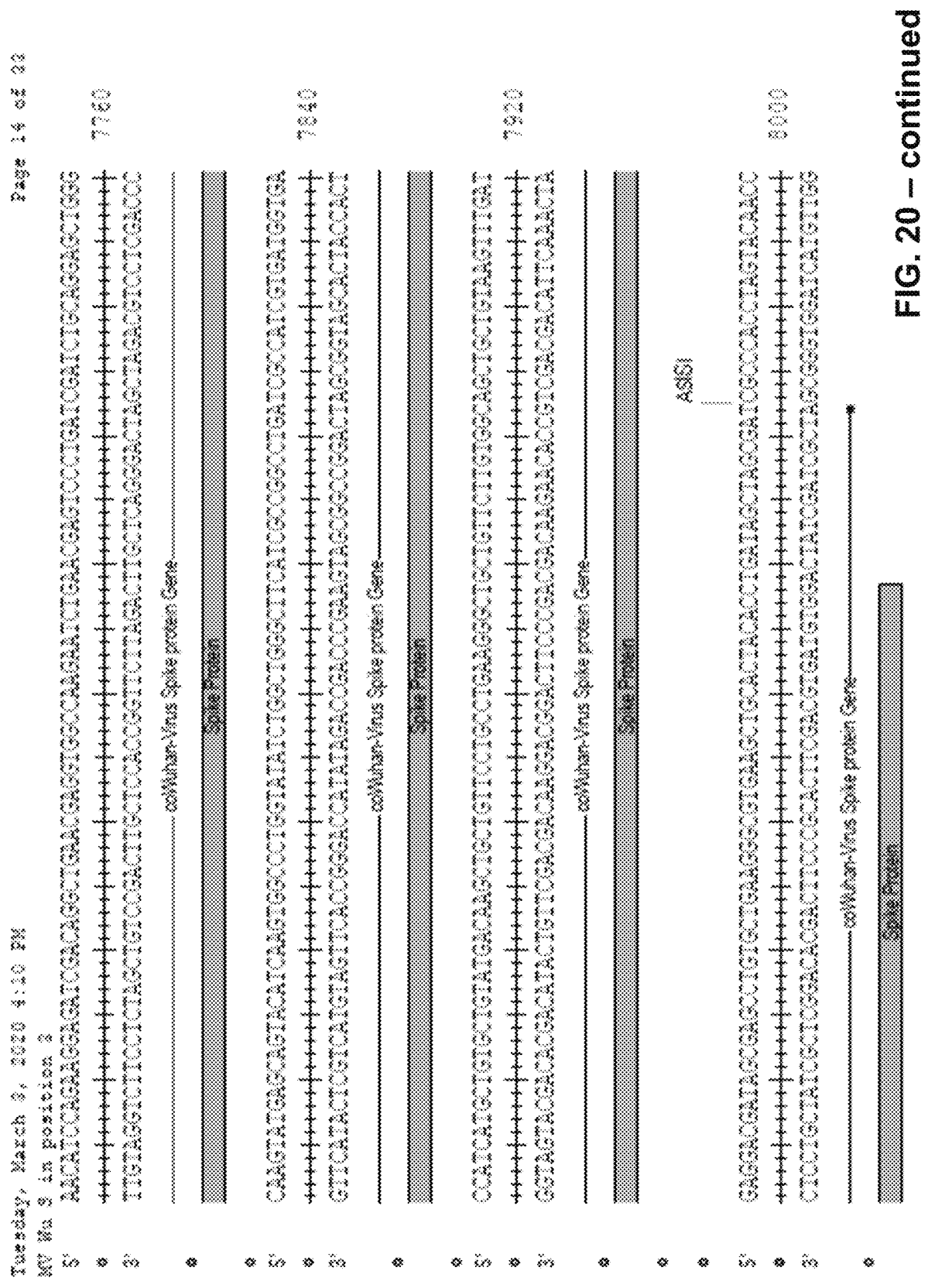
Figure 20:
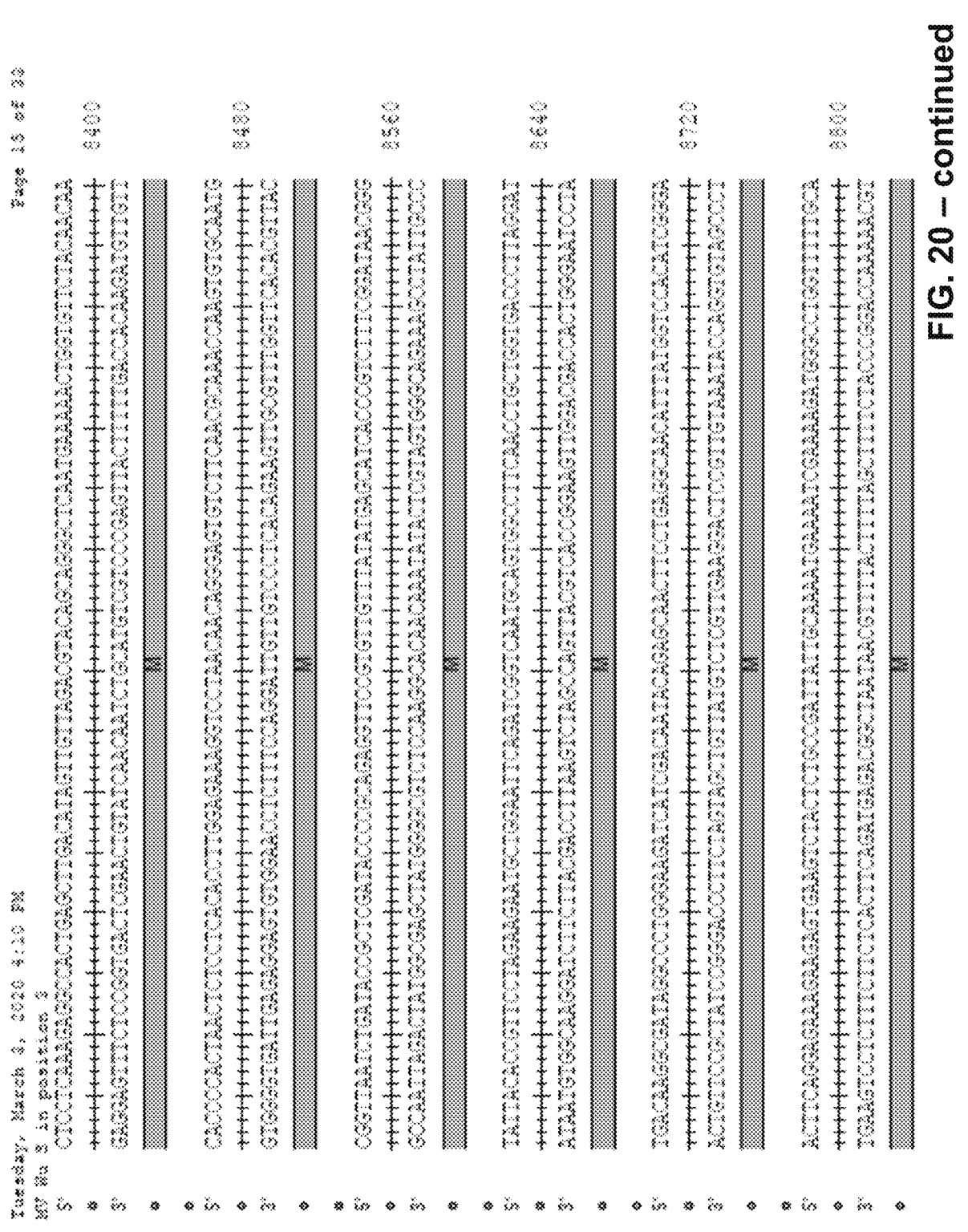
Figure 20:
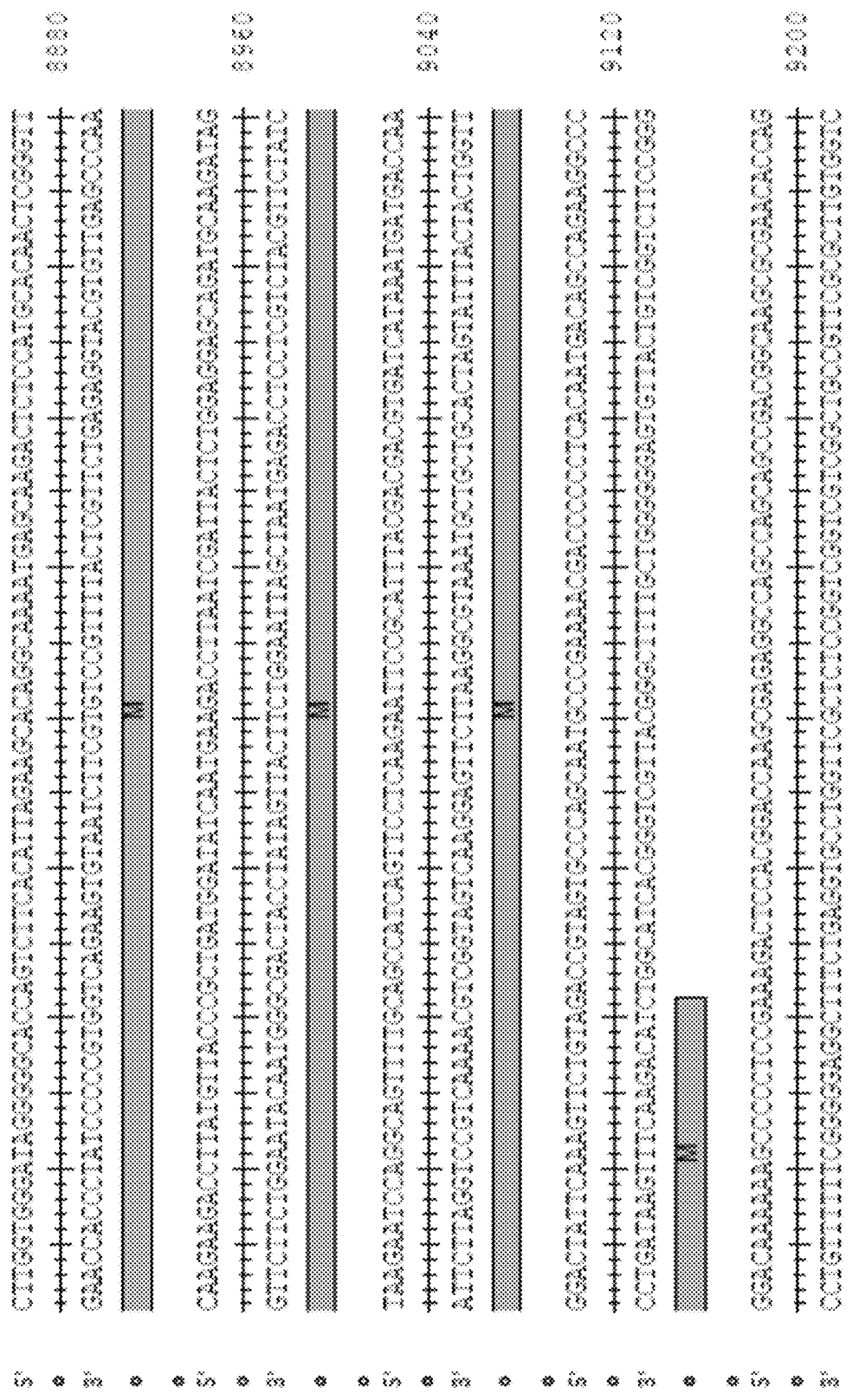
Figure 20:
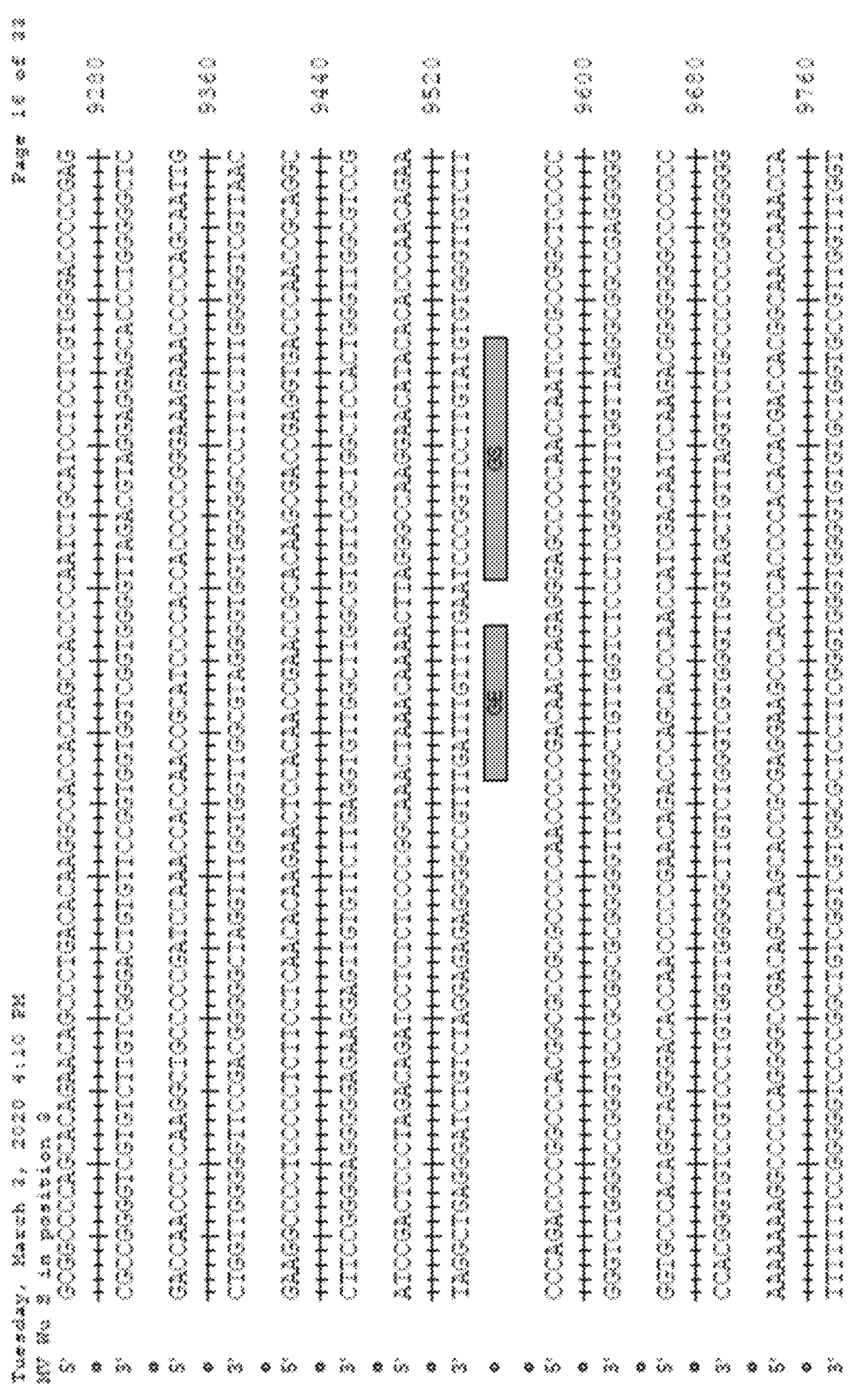
Figure 20:
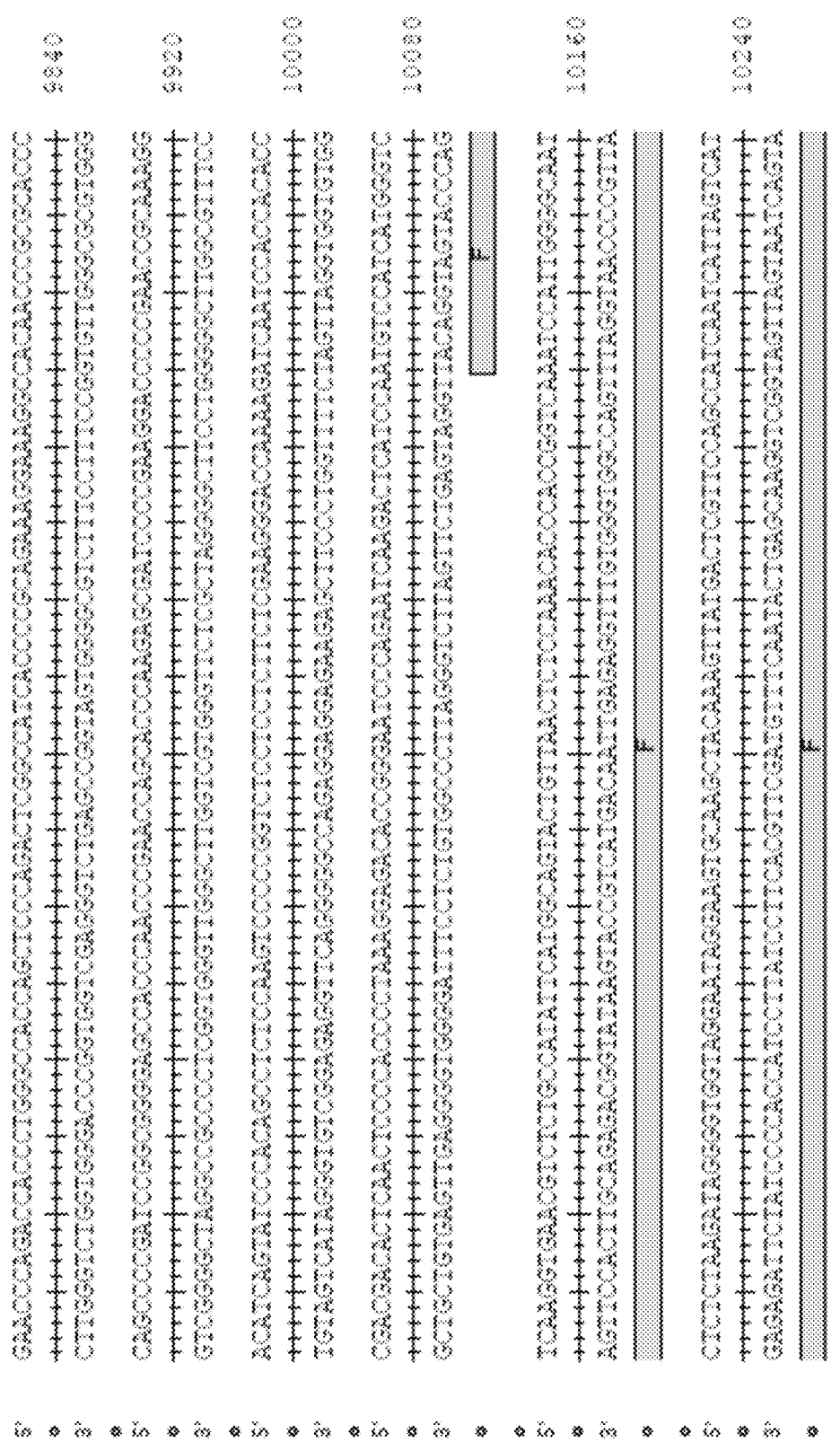
Figure 20:
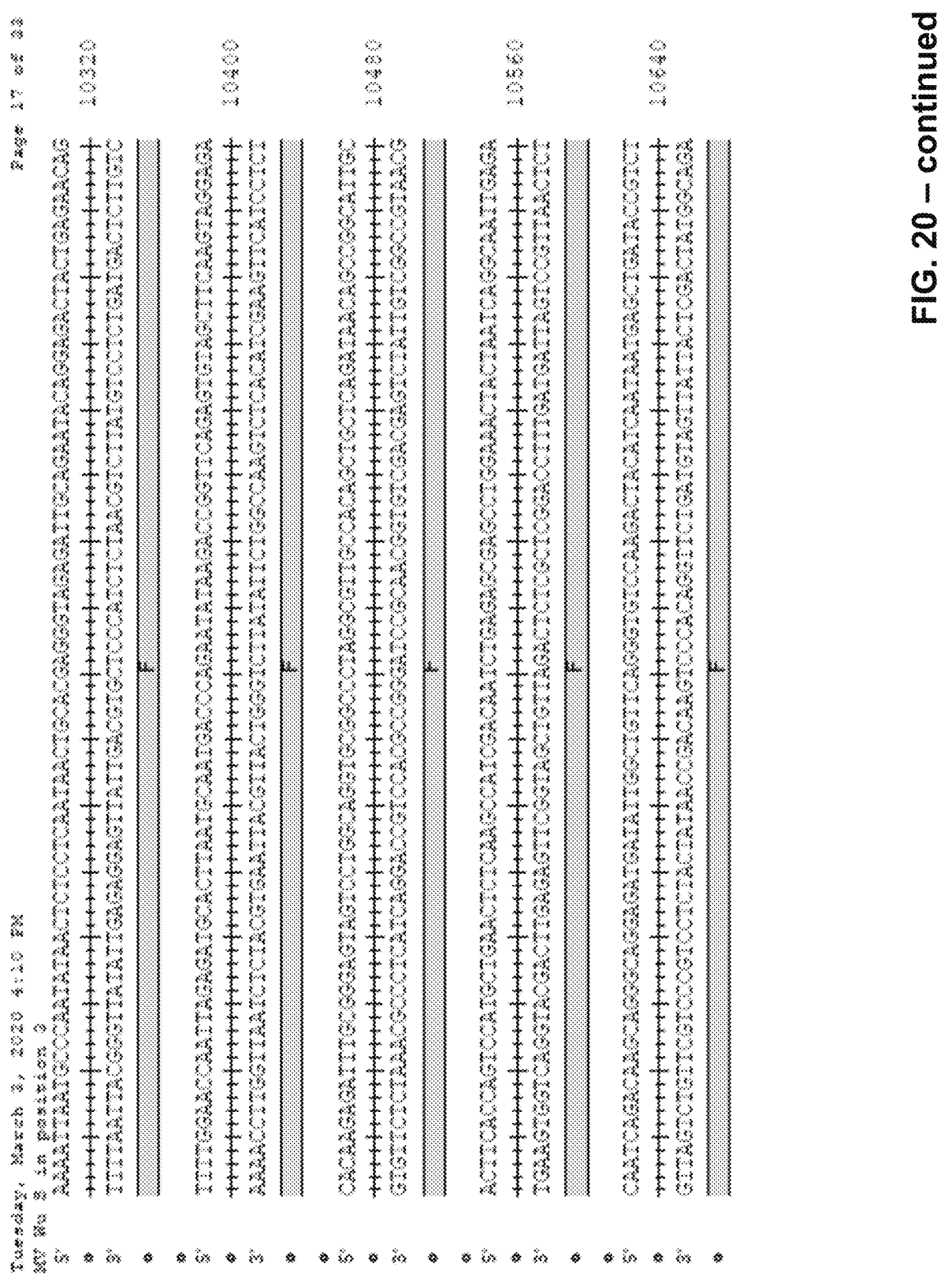
Figure 20:
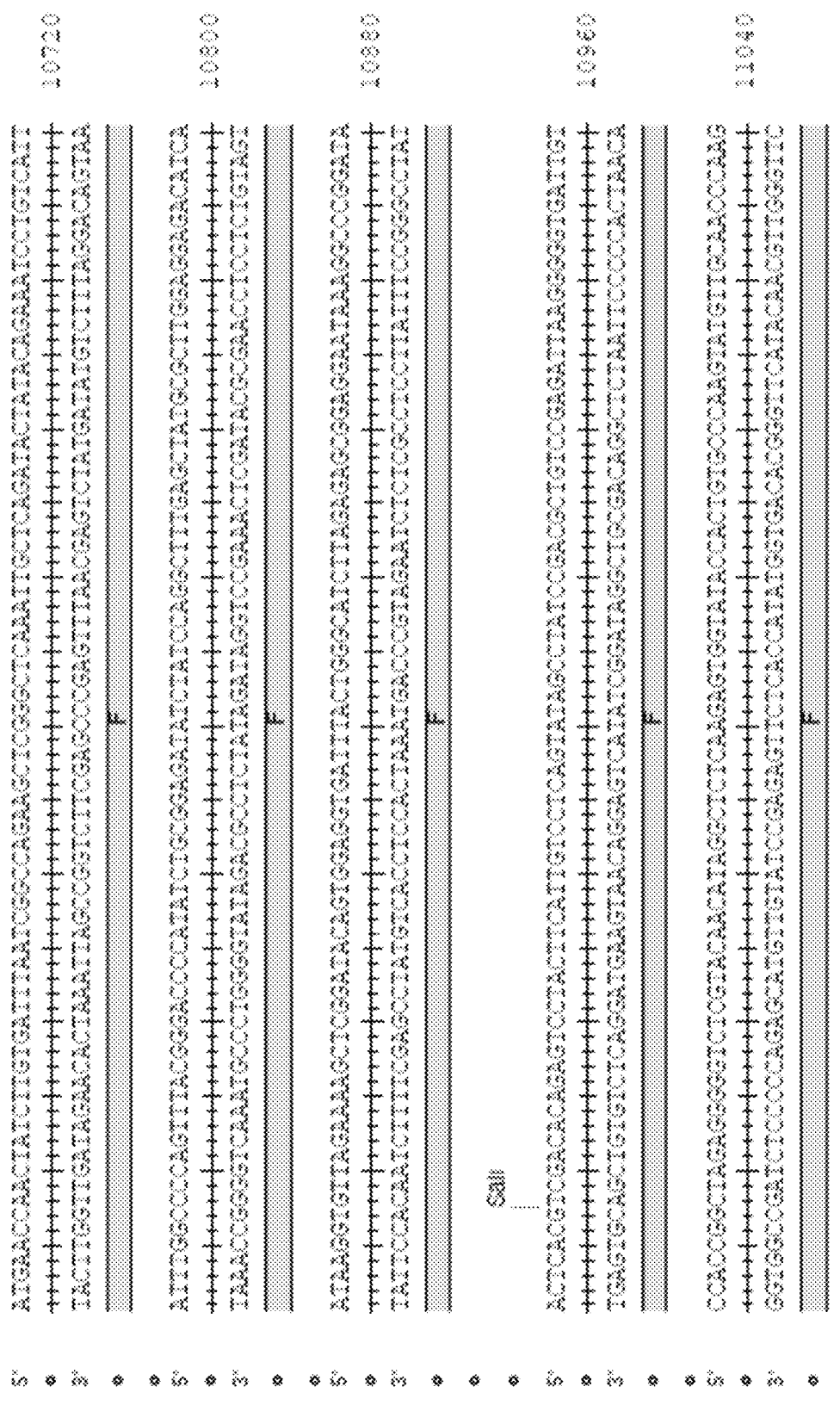
Figure 20:
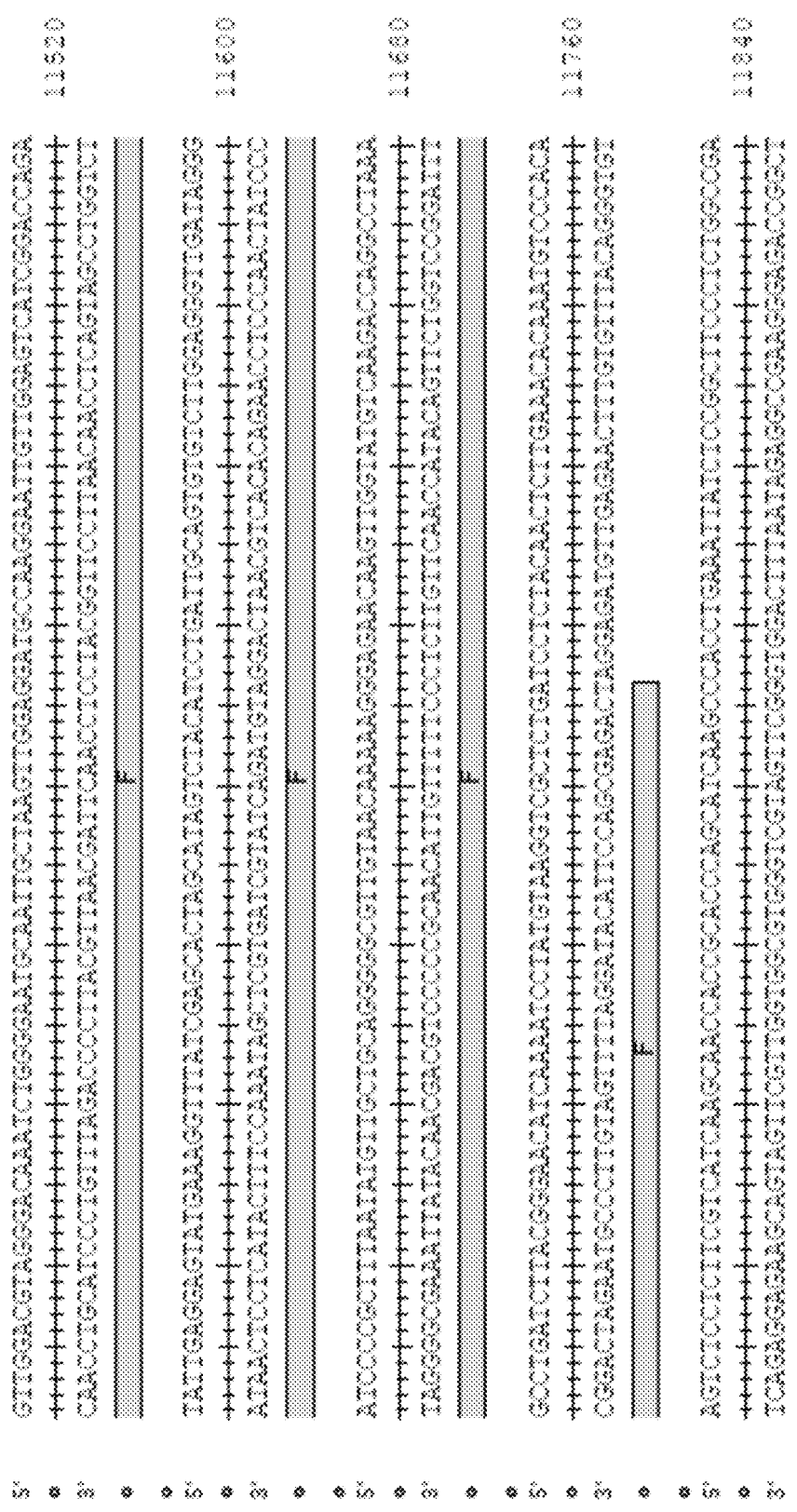
Figure 20:
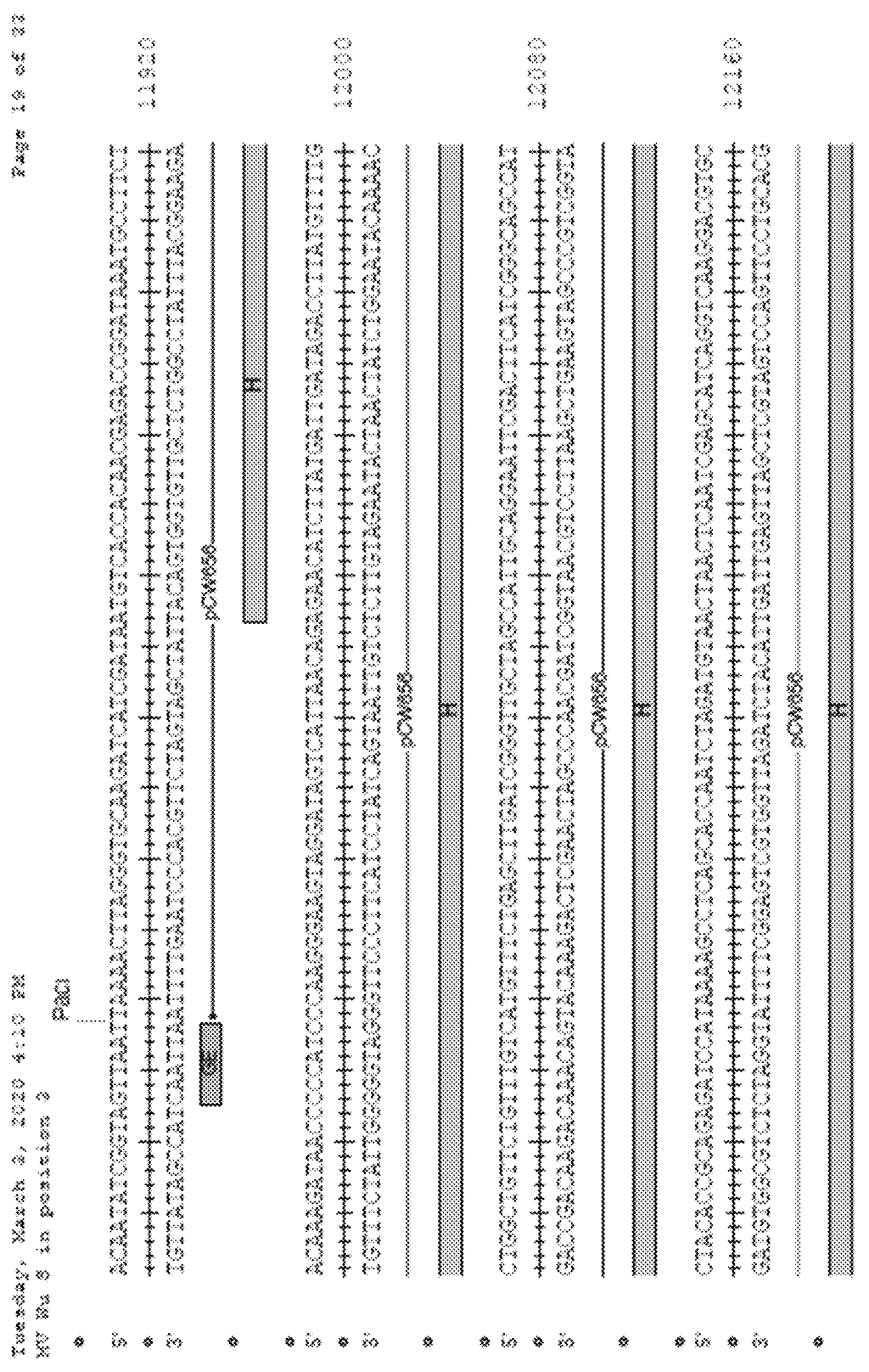
Figure 20:
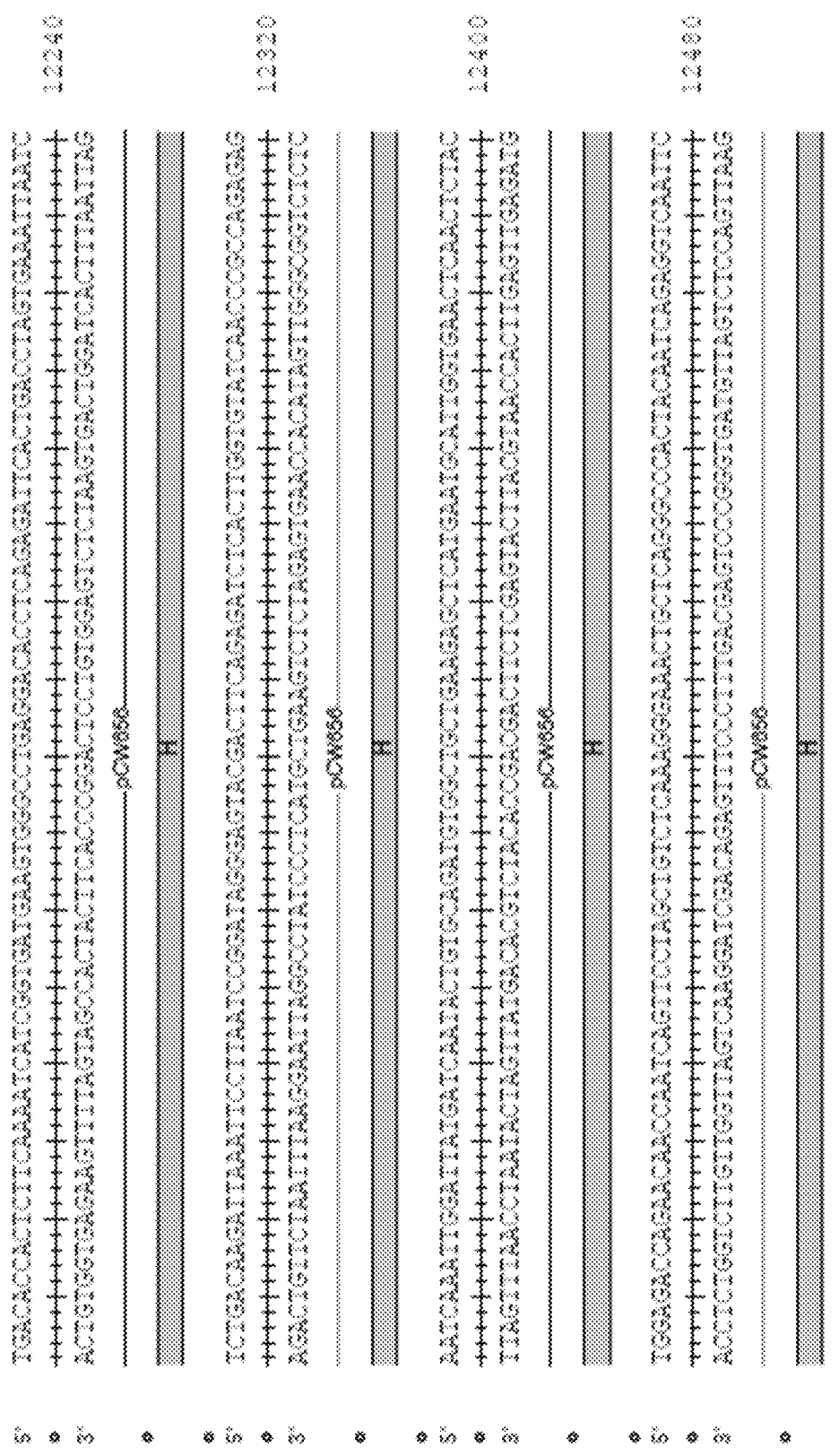
Figure 20:
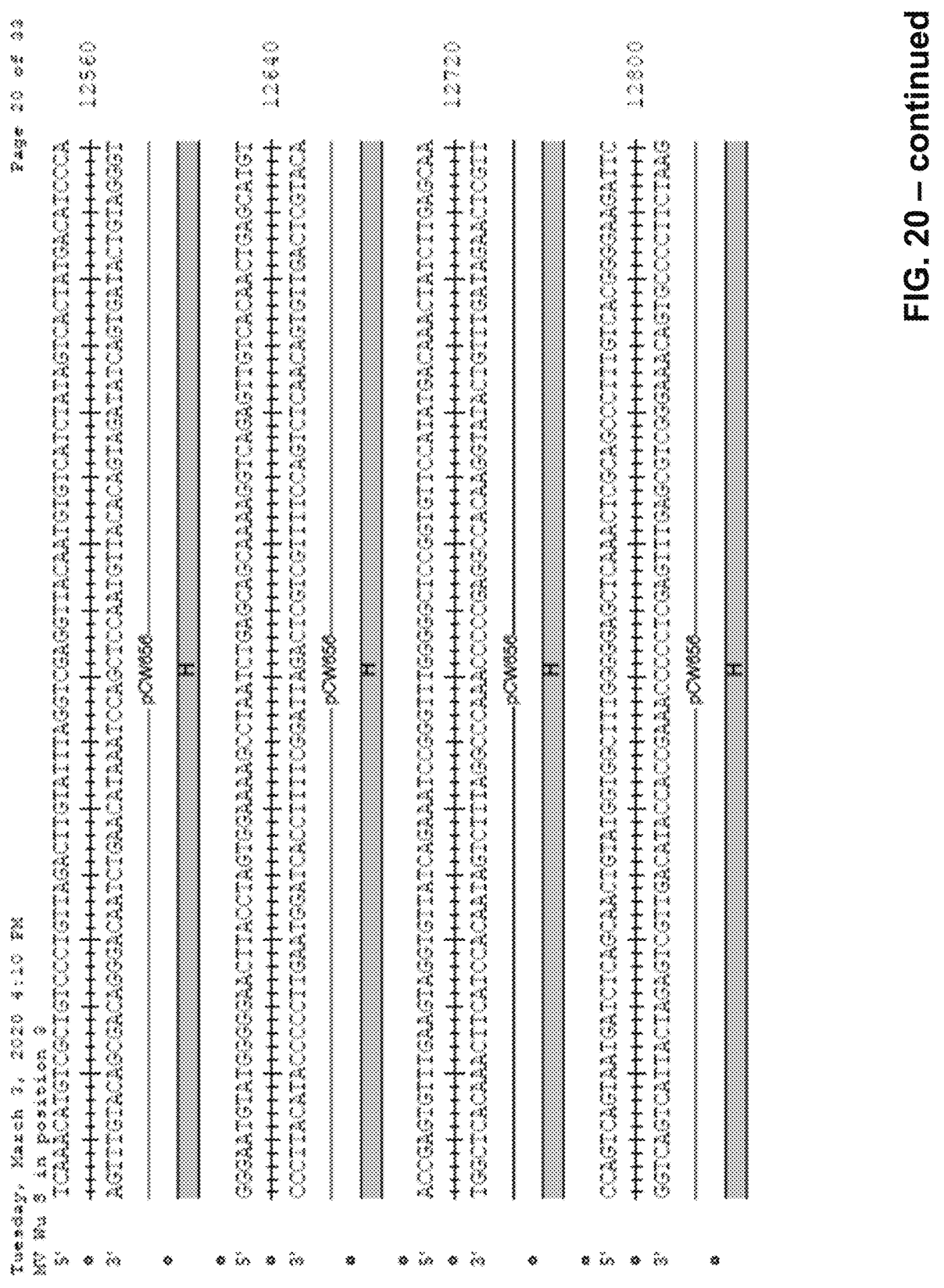
Figure 20:
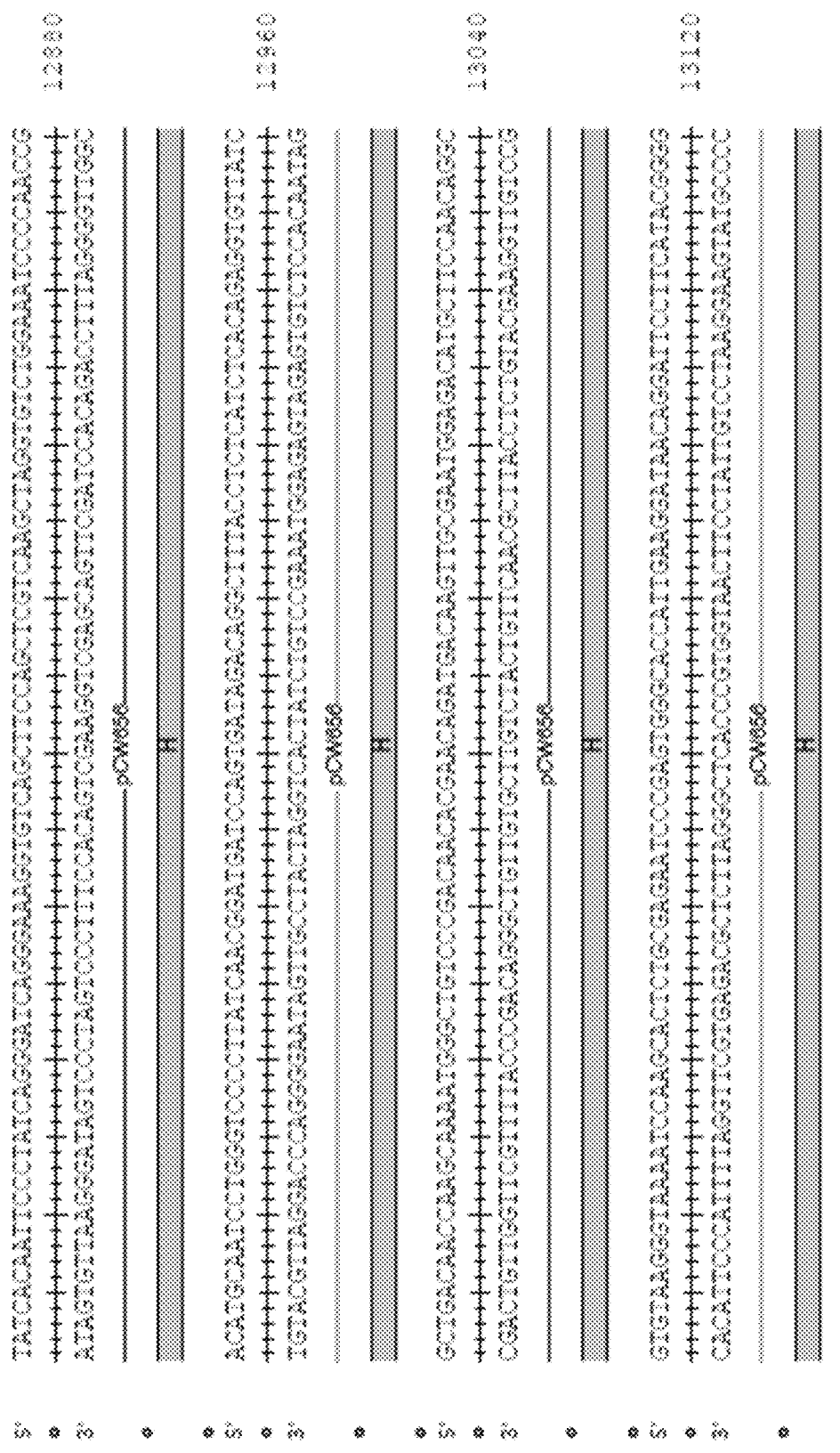
Figure 20:
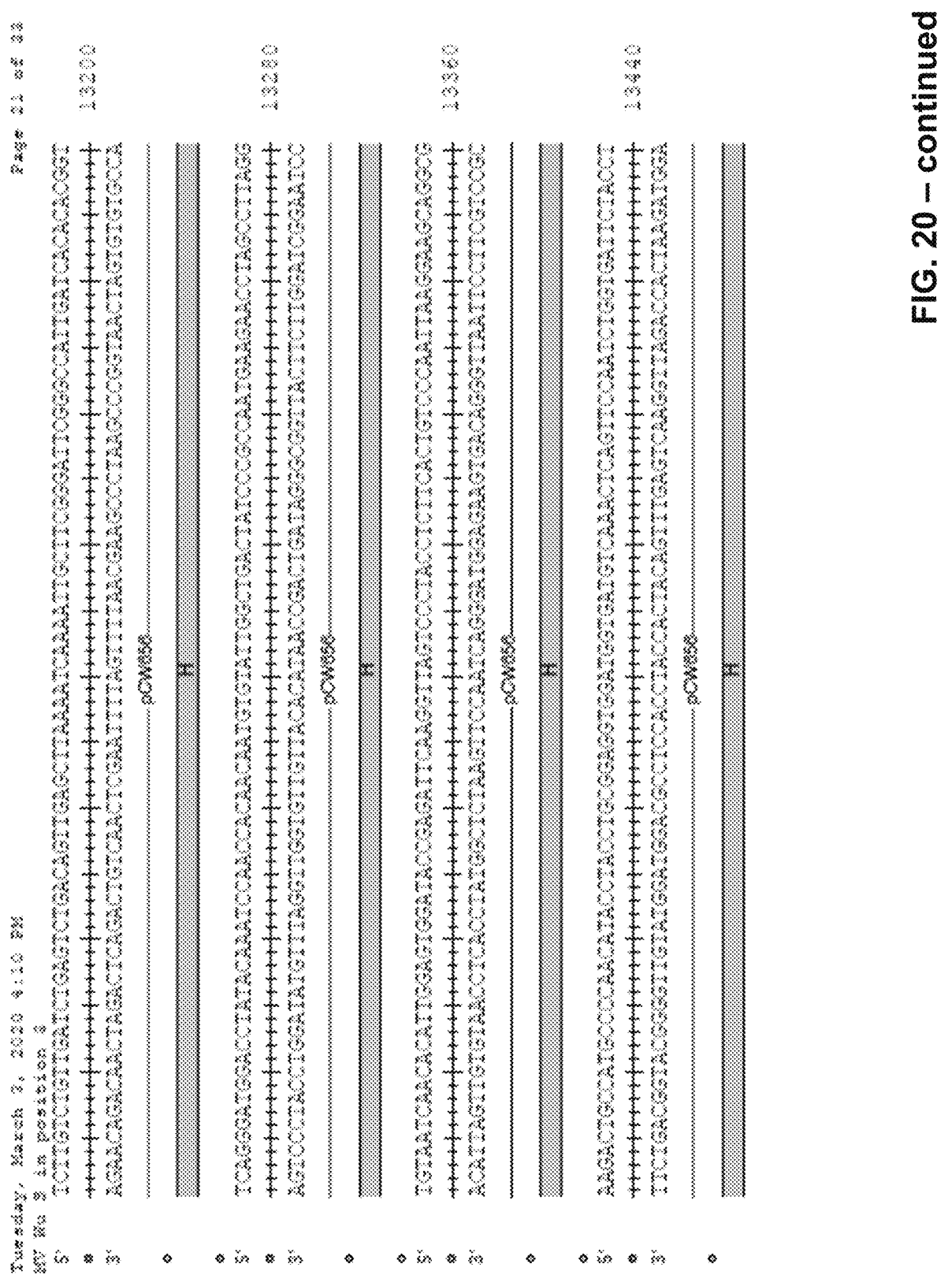
Figure 20:
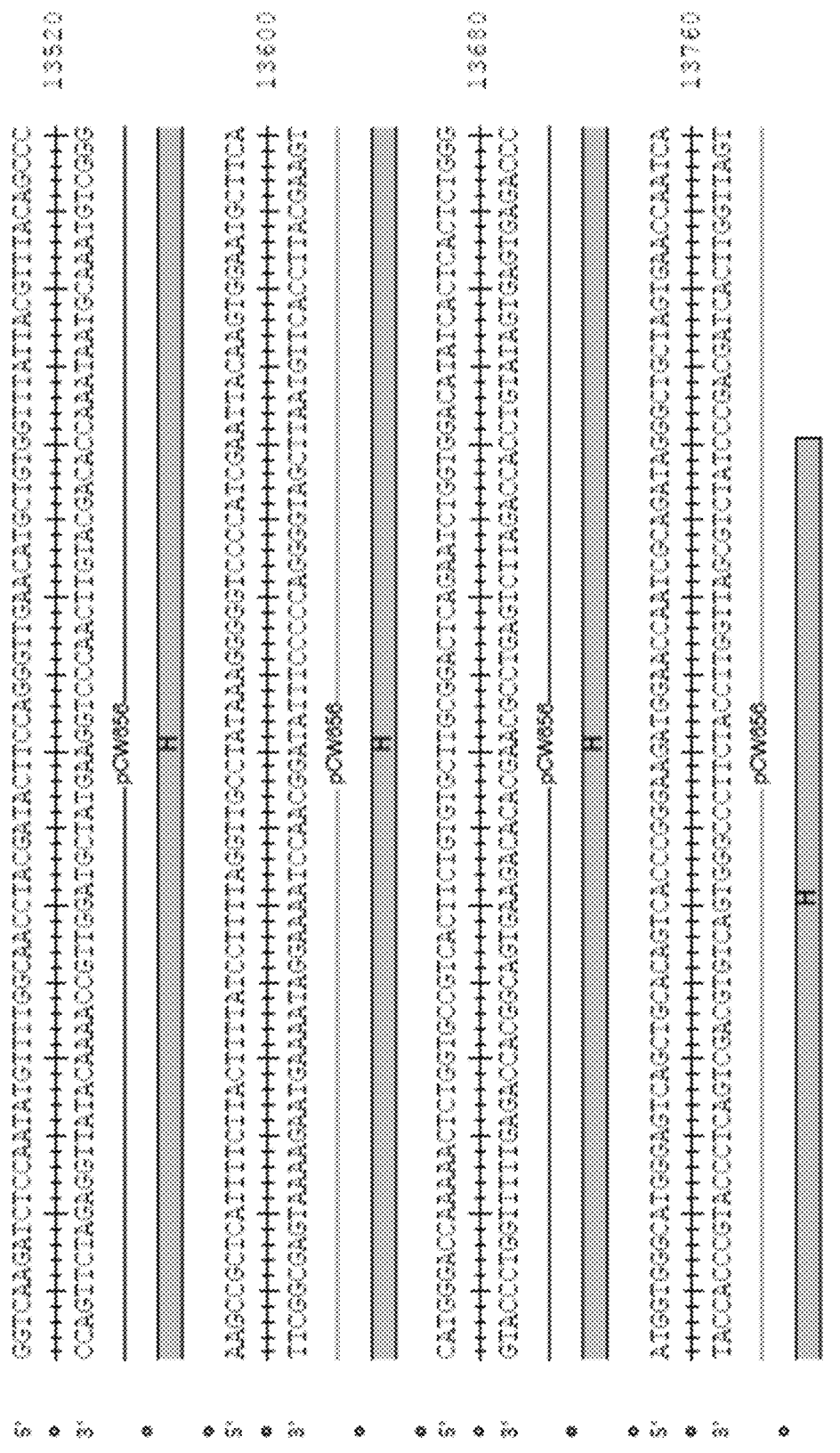
Figure 20:
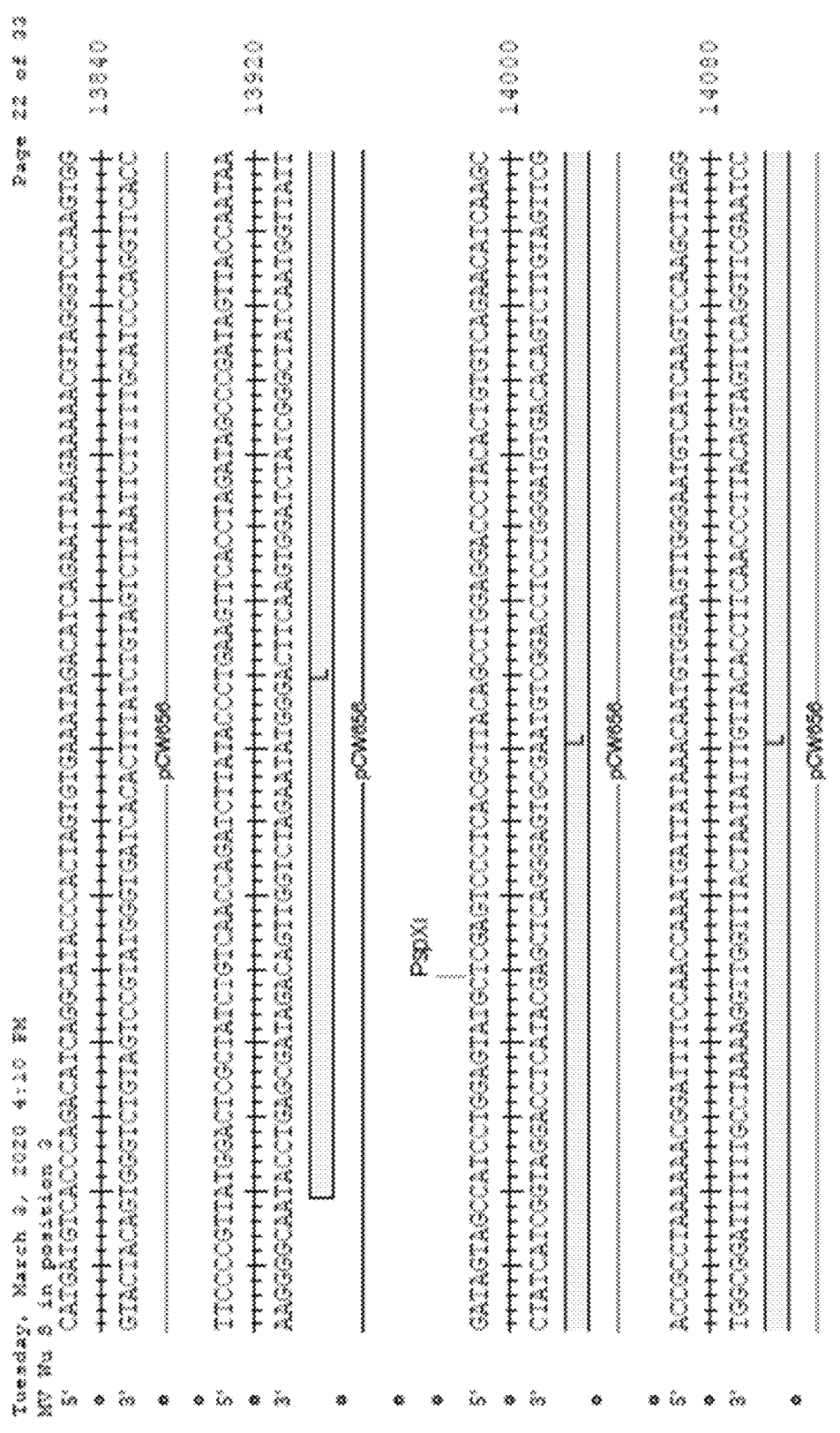
Figure 20:
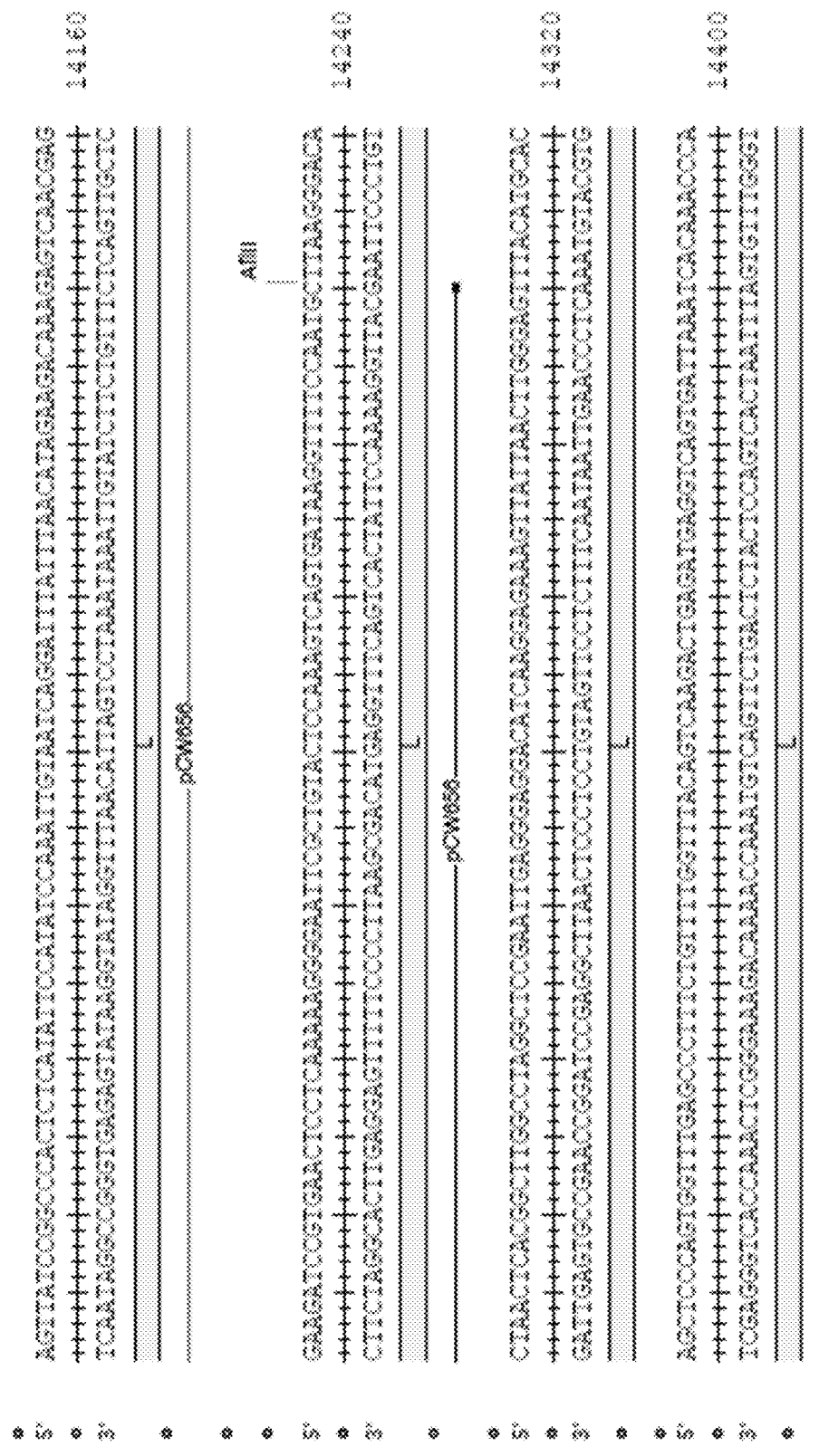
Figure 20:
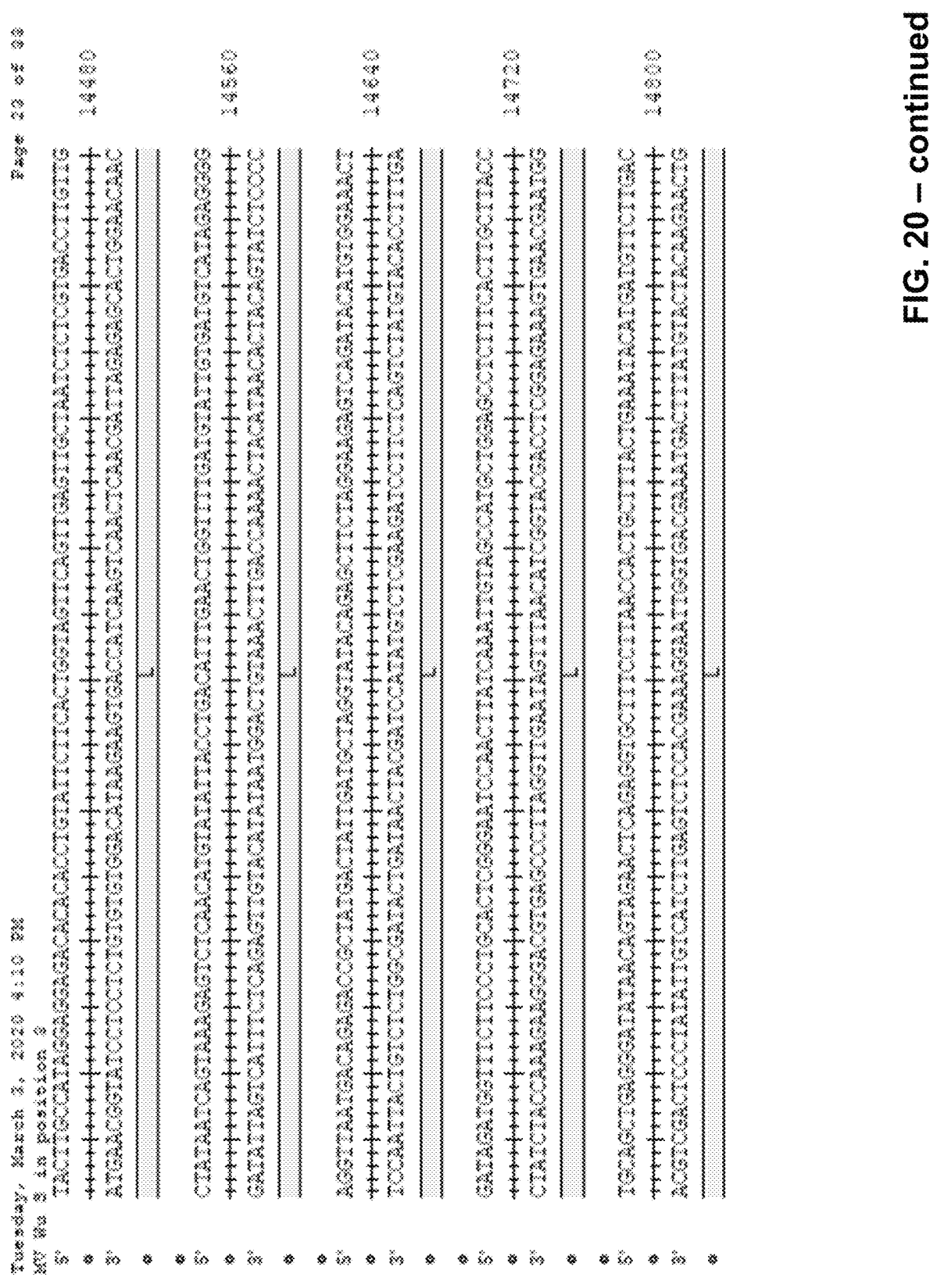
Figure 20:
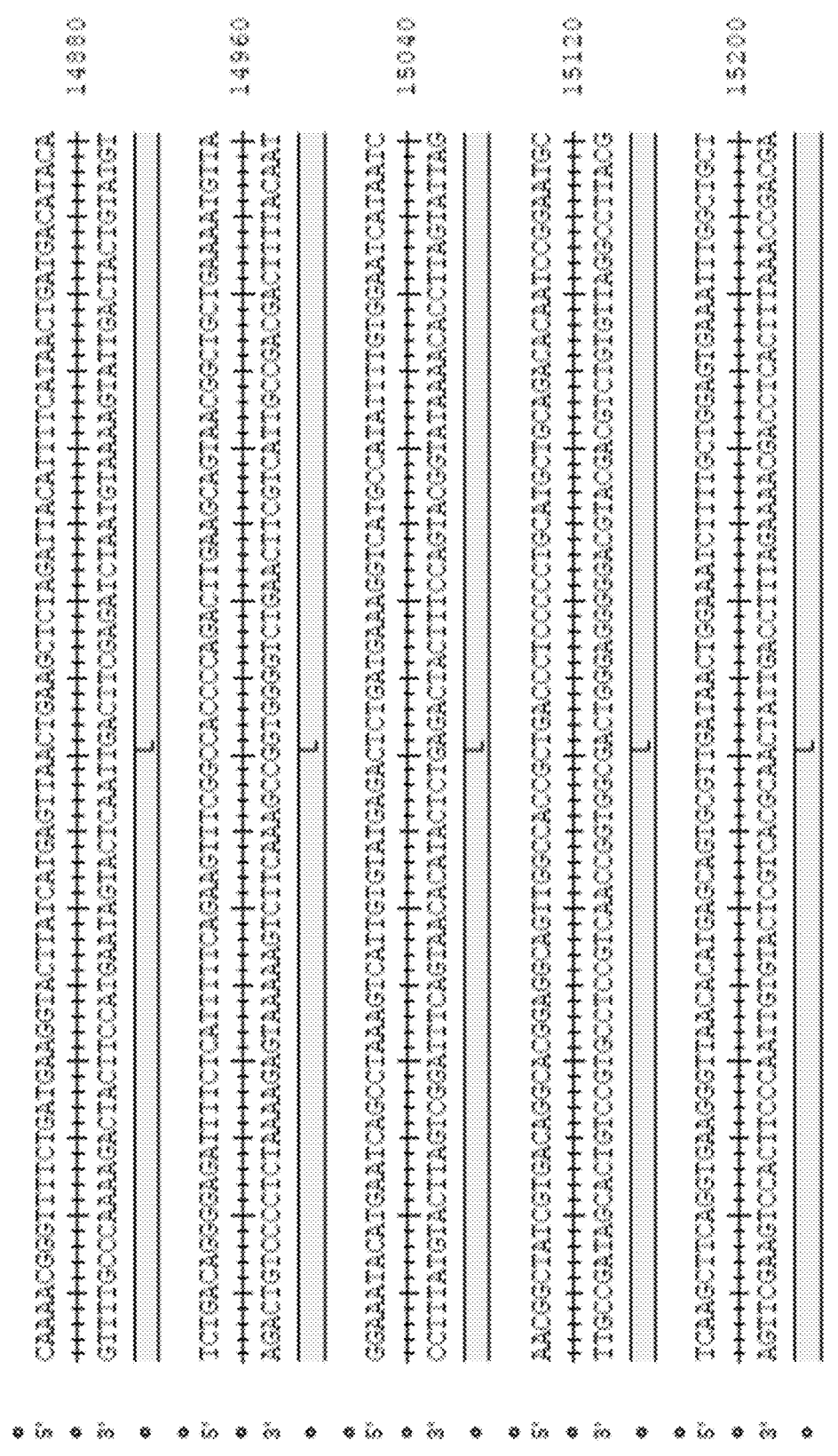
Figure 20:
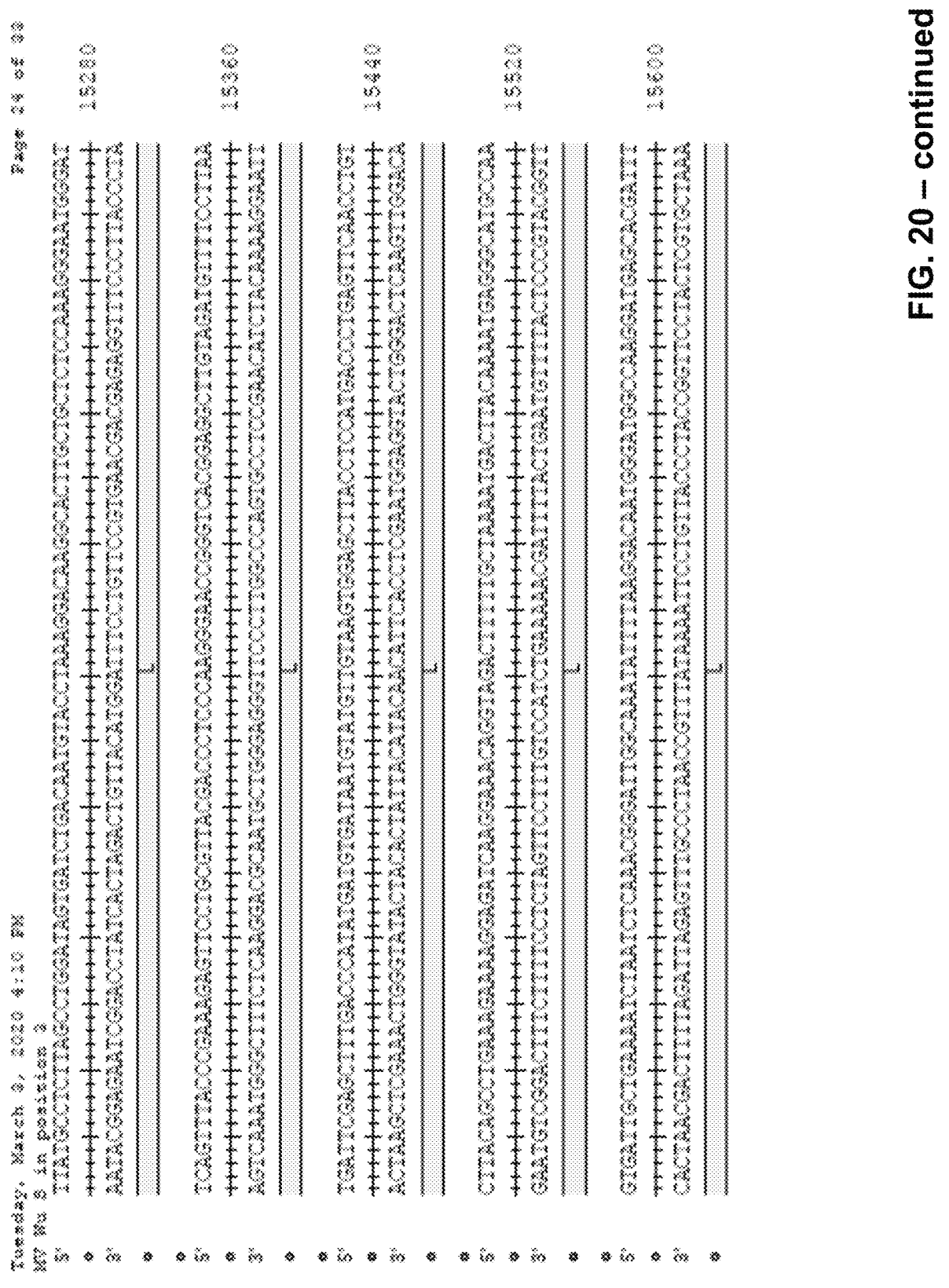
Figure 20:
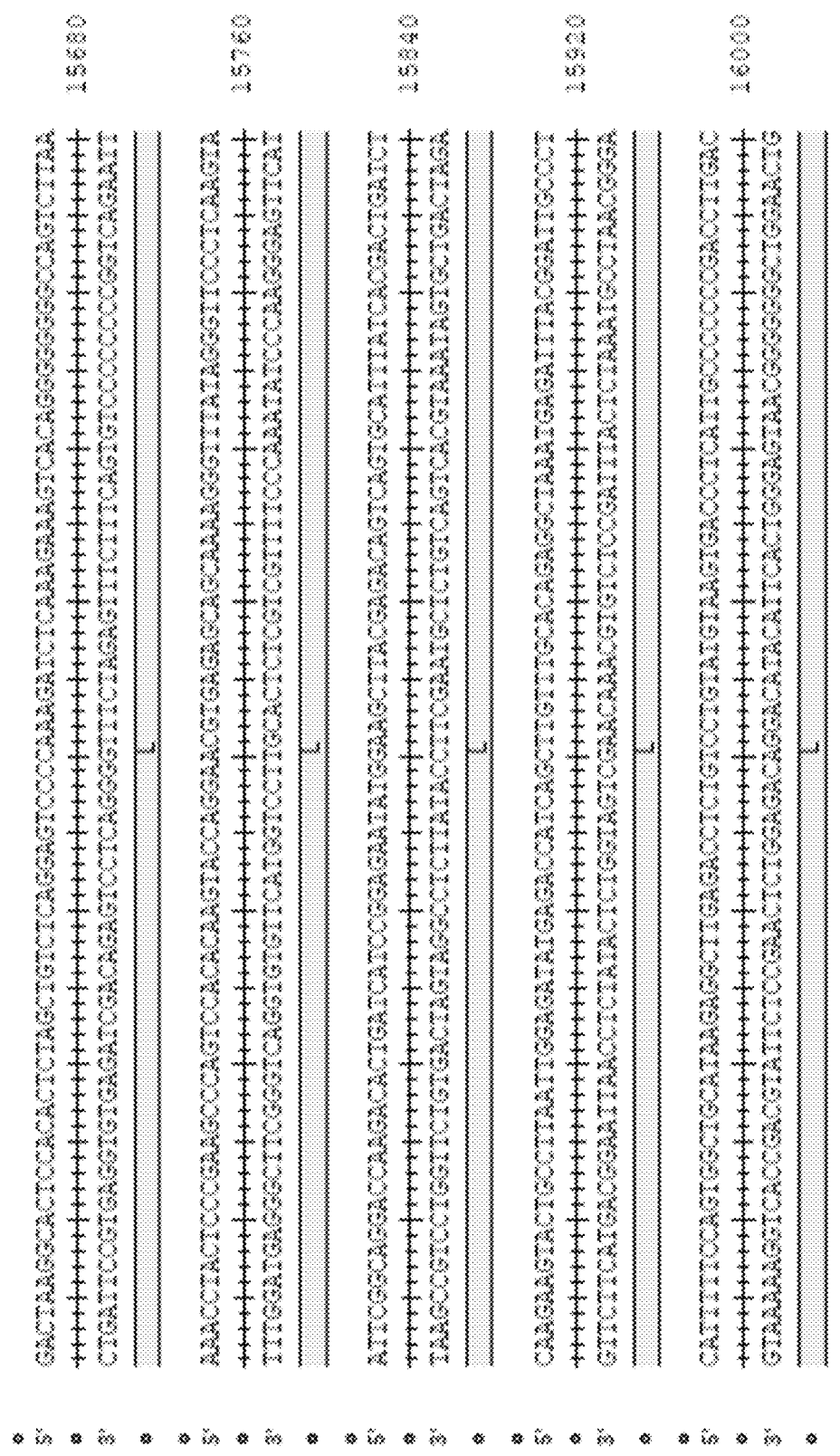
Figure 20:
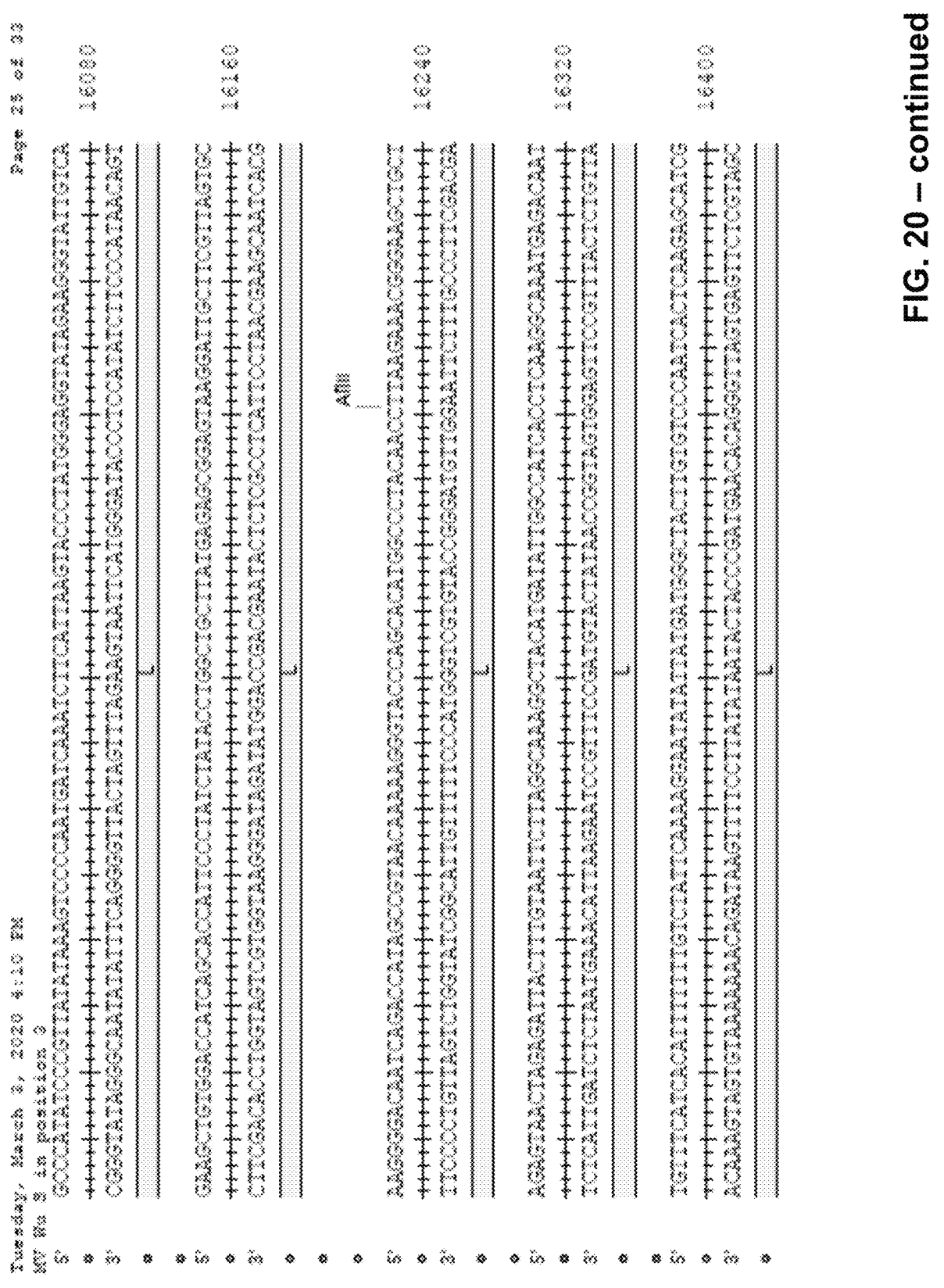
Figure 20:
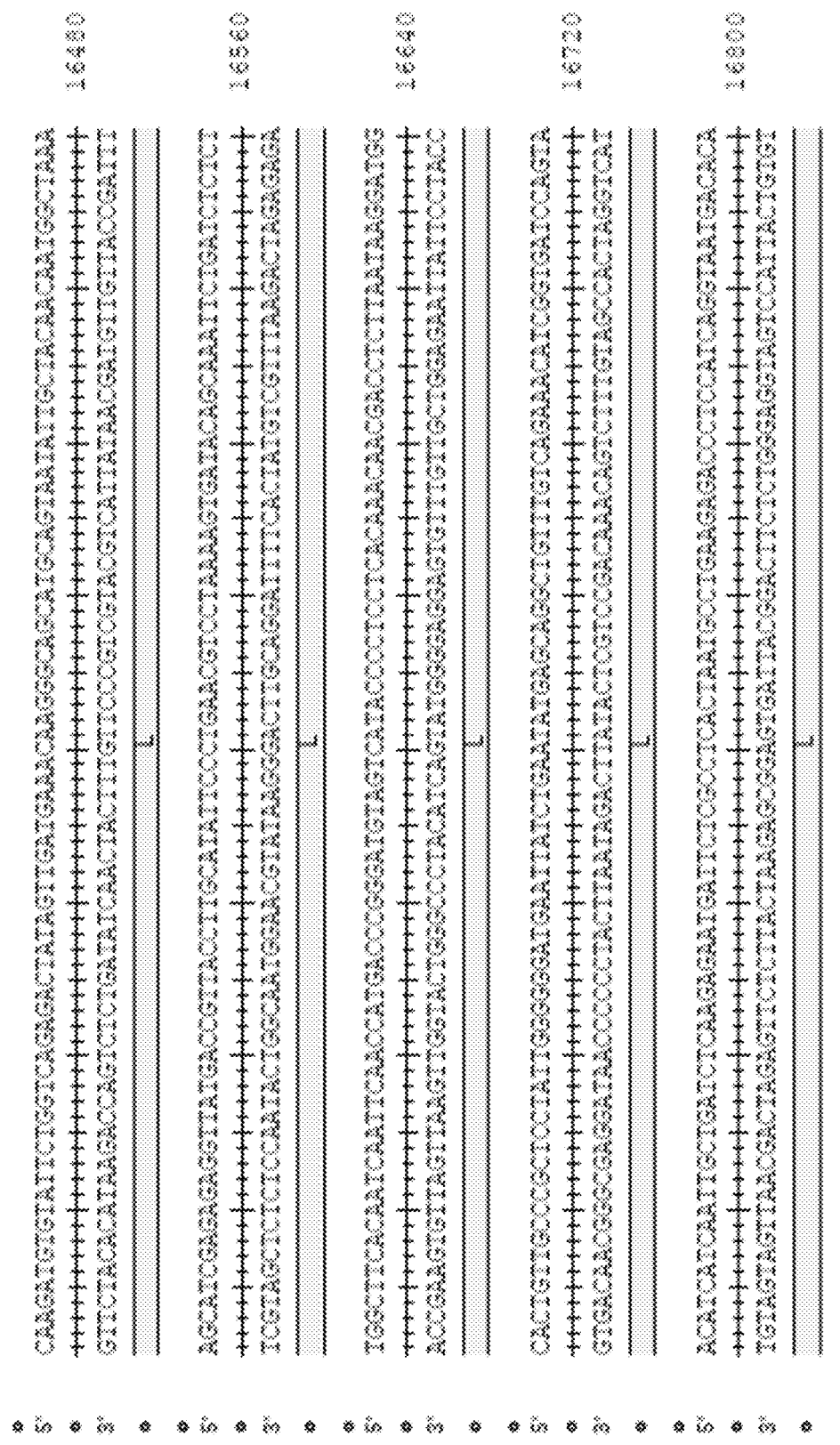
Figure 20:
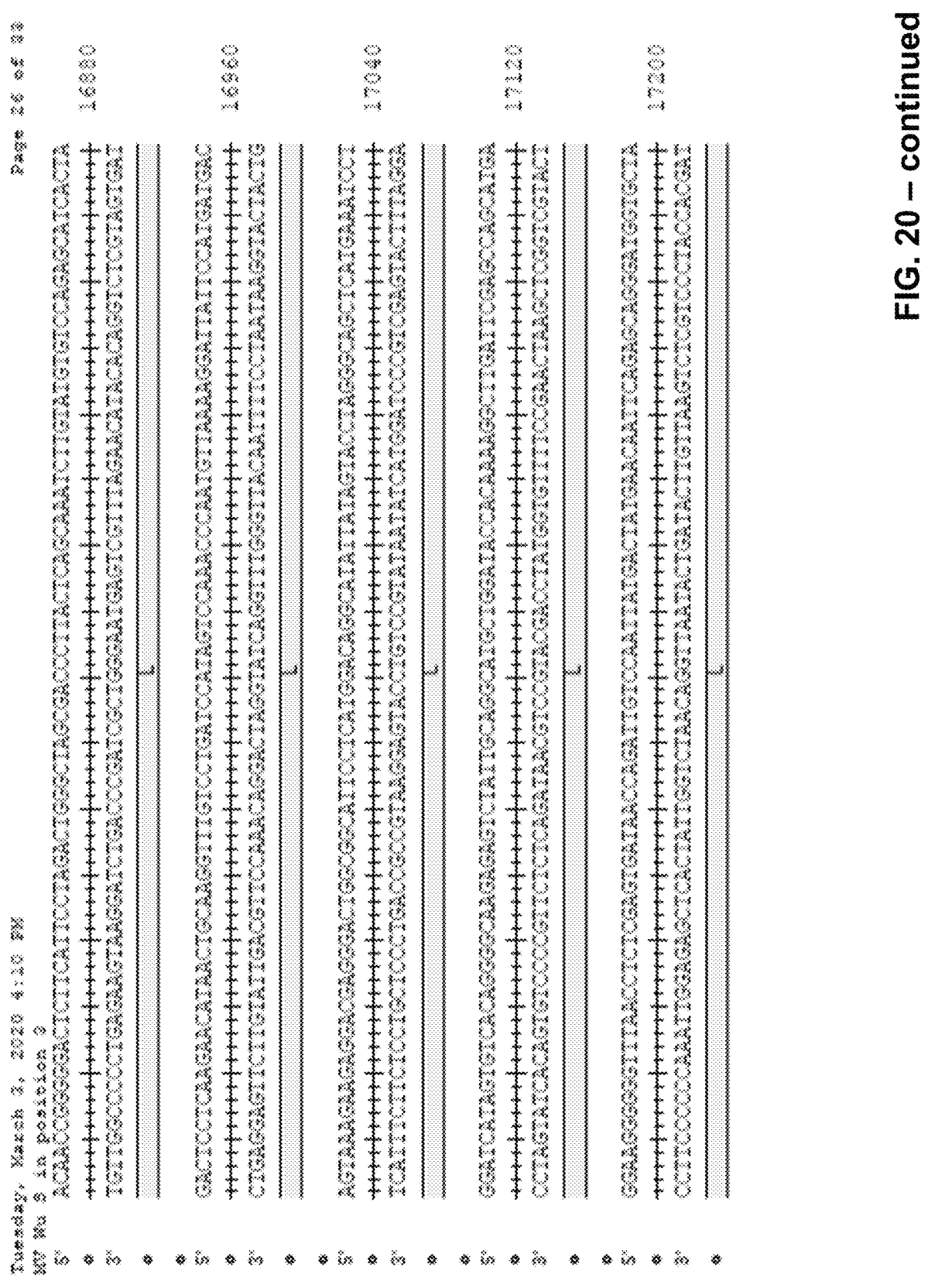
Figure 20:
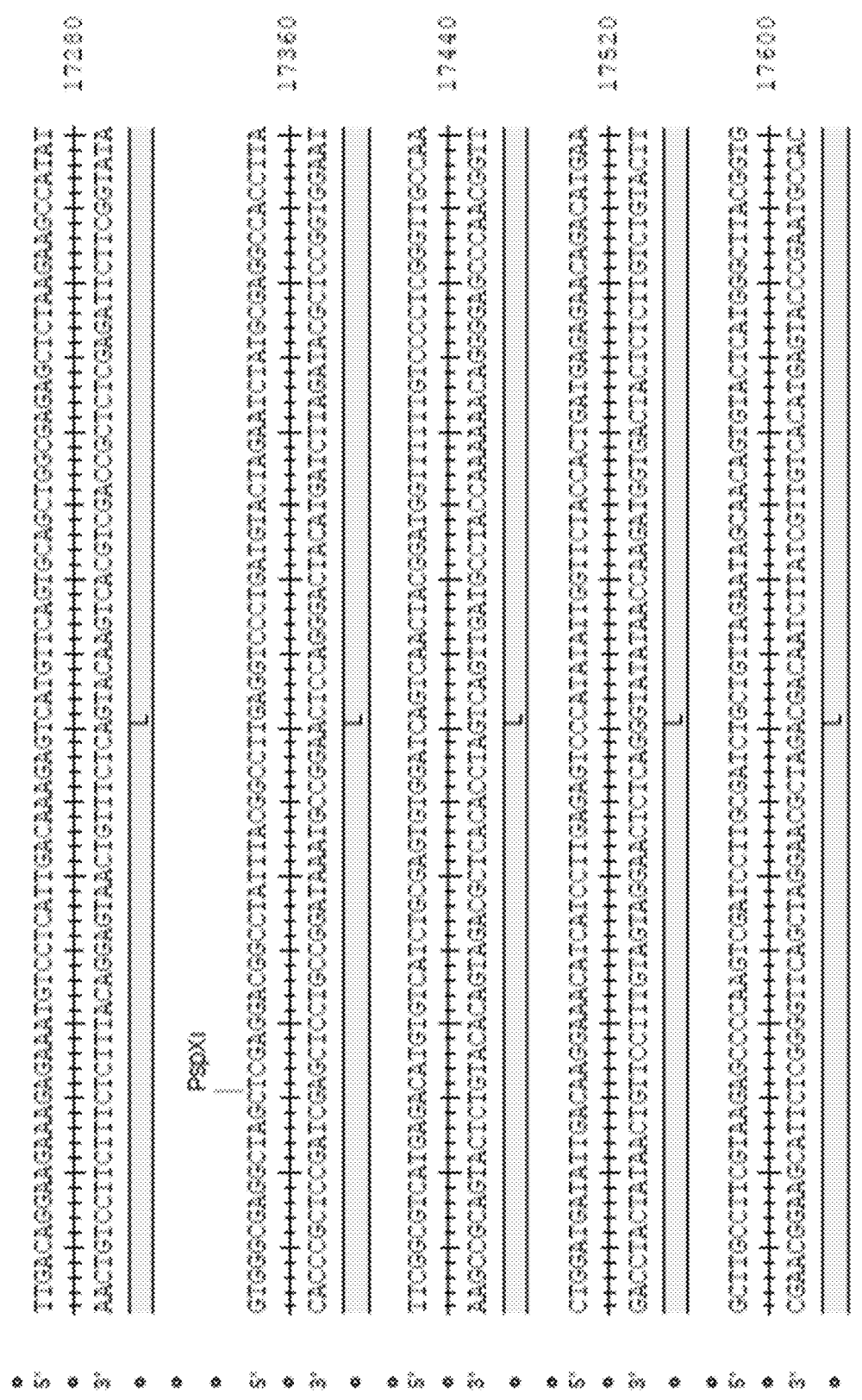
Figure 20:
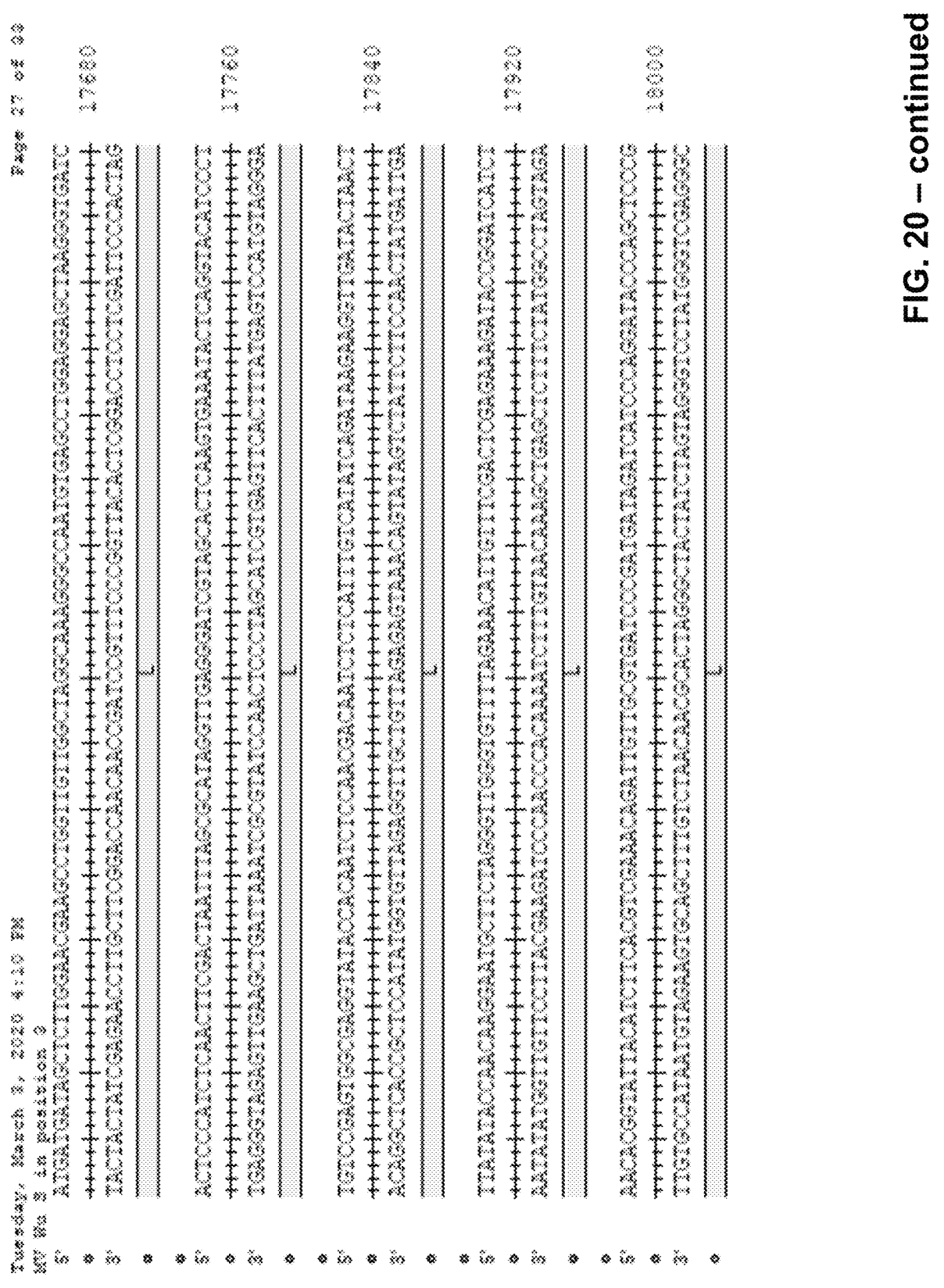
Figure 20:
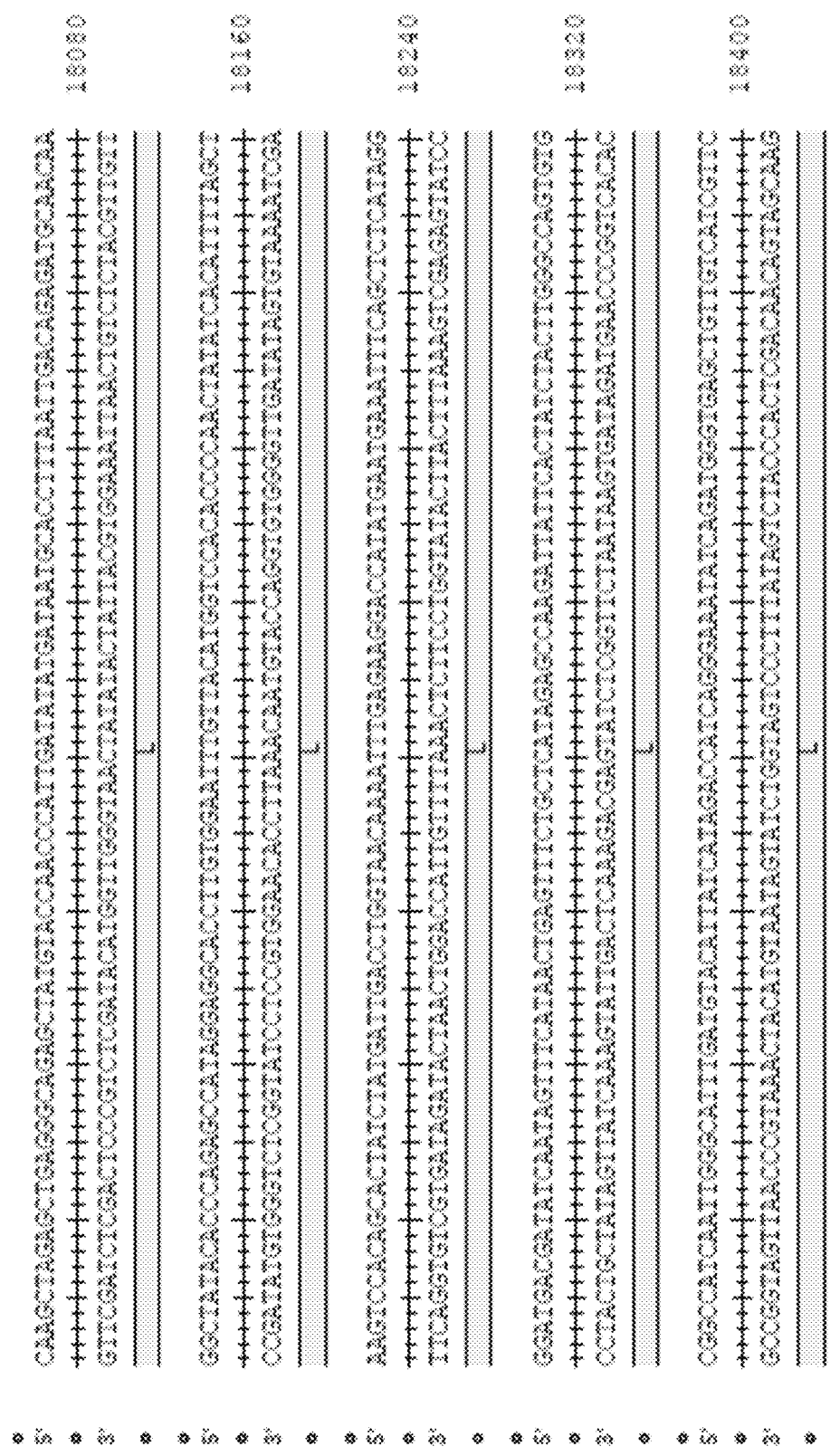
Figure 20:
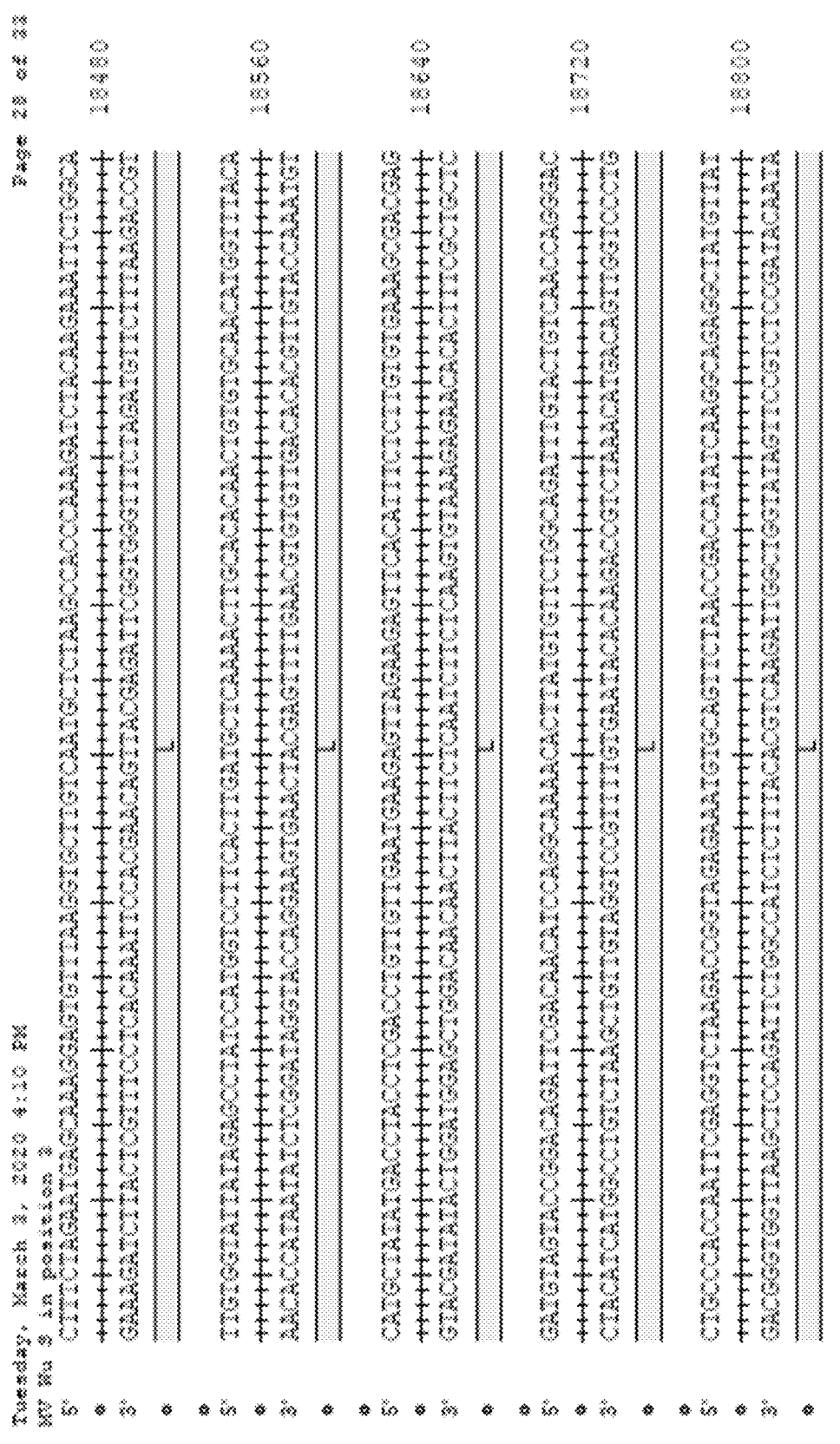
Figure 20:
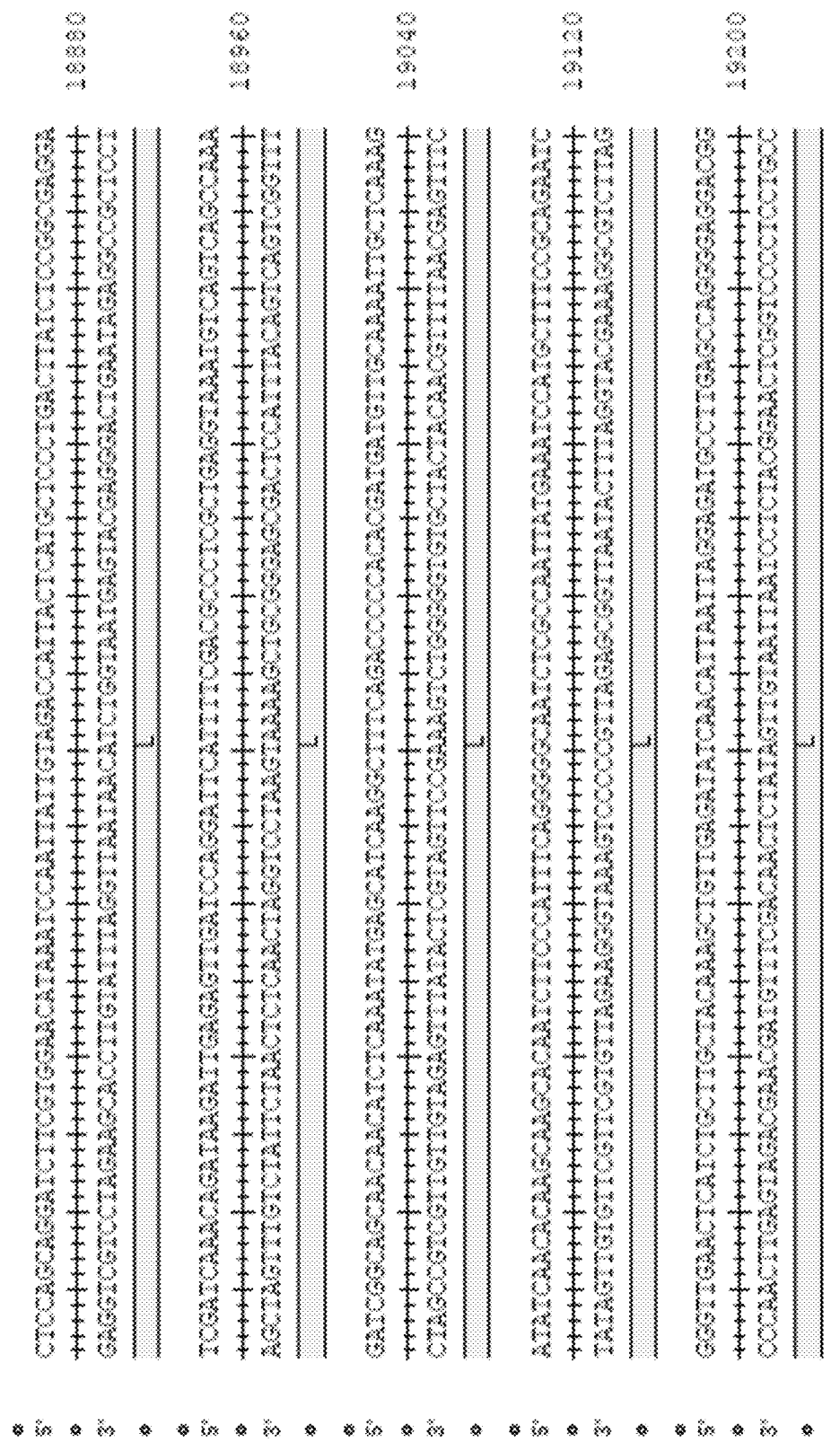
Figure 20:
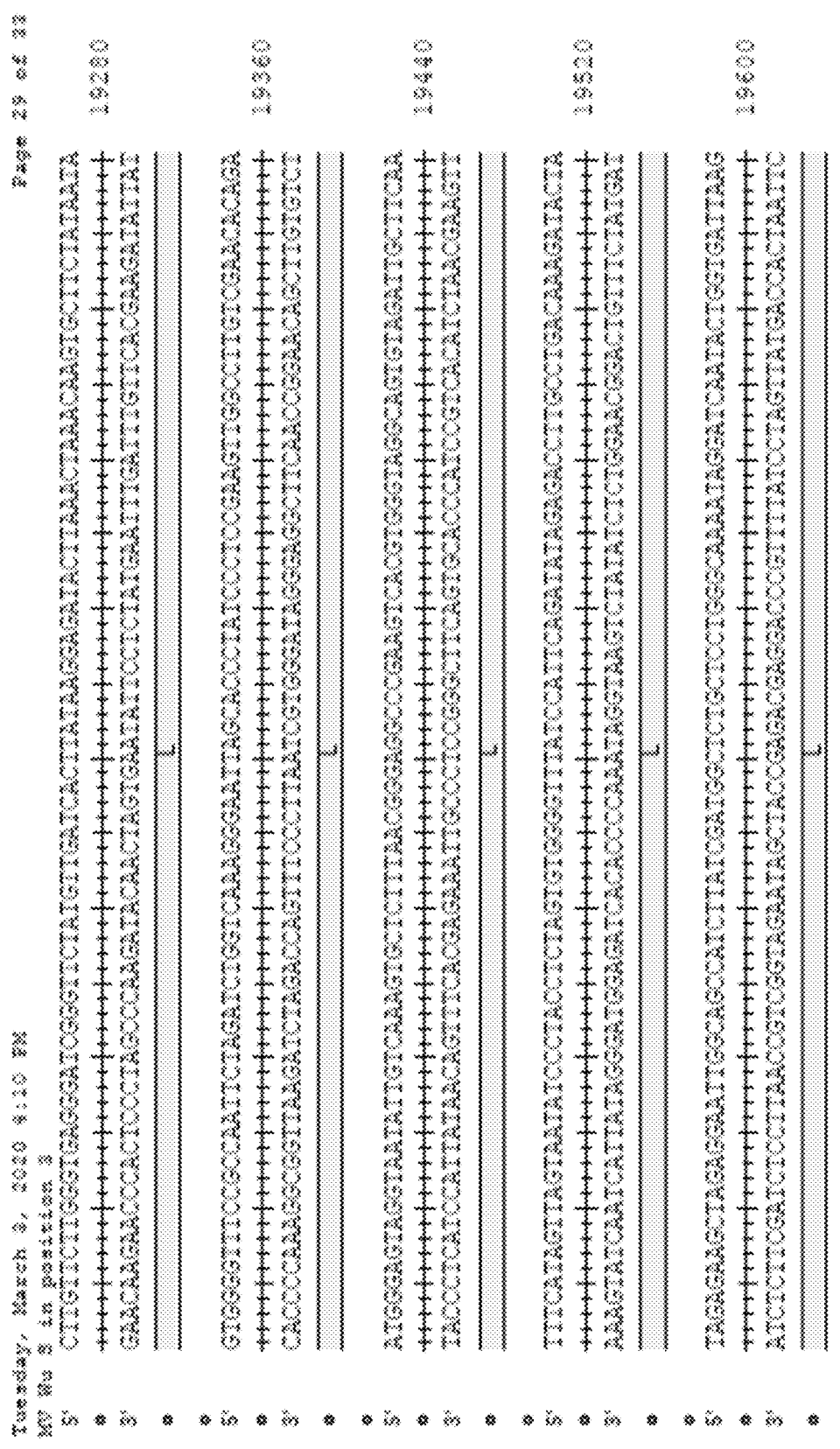
Figure 20:
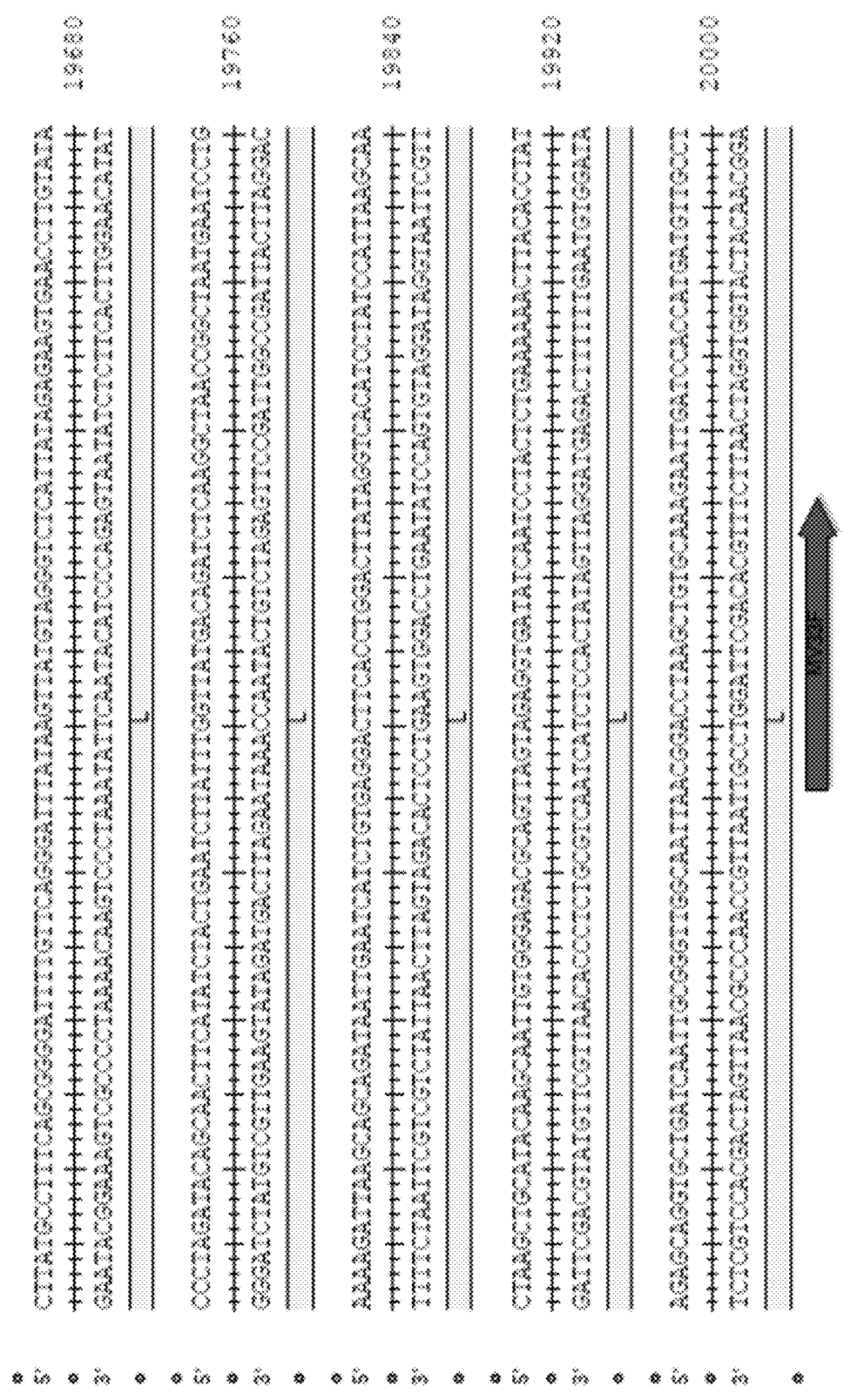
Figure 20:
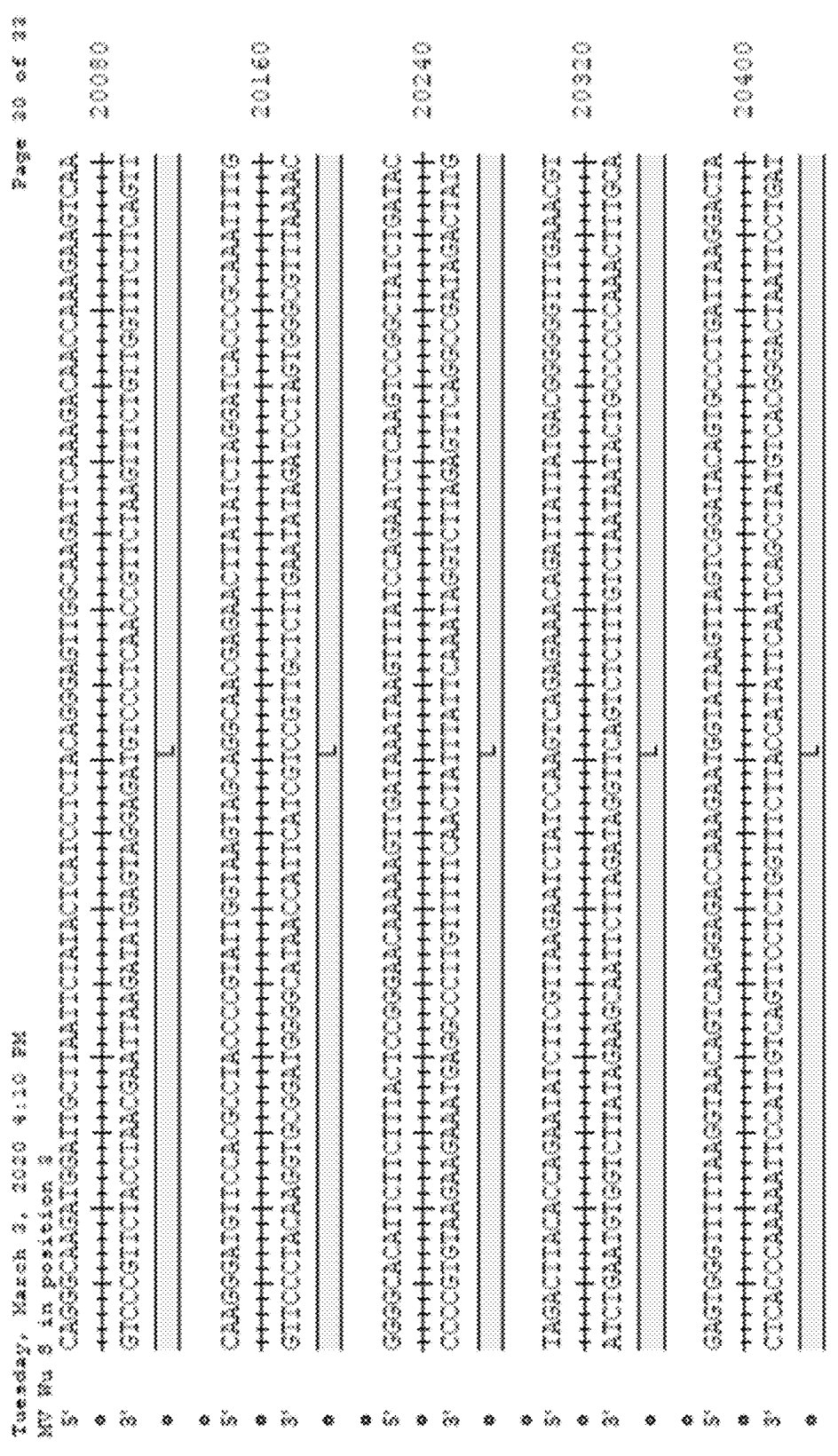
Figure 20:
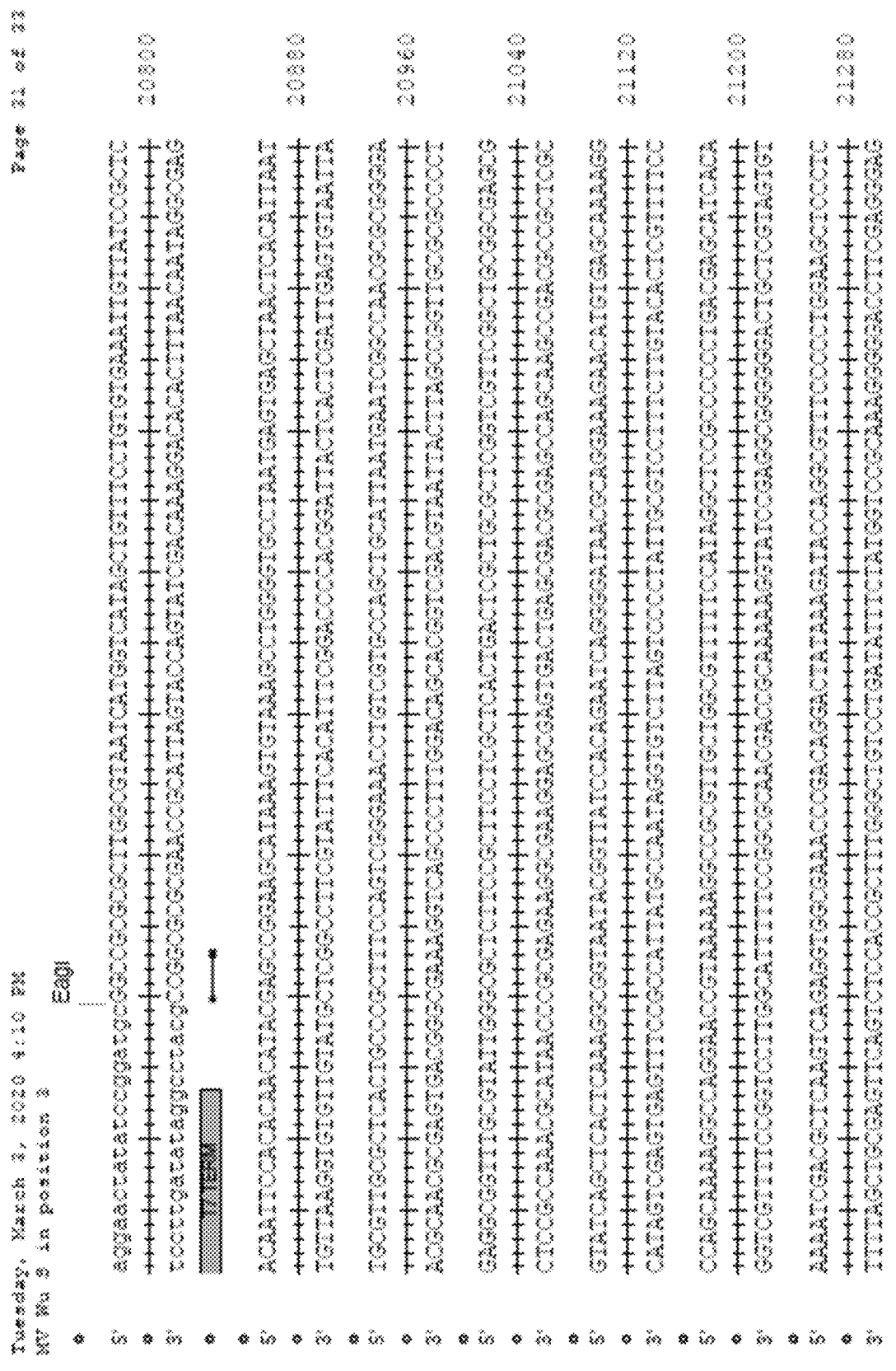
Figure 20:
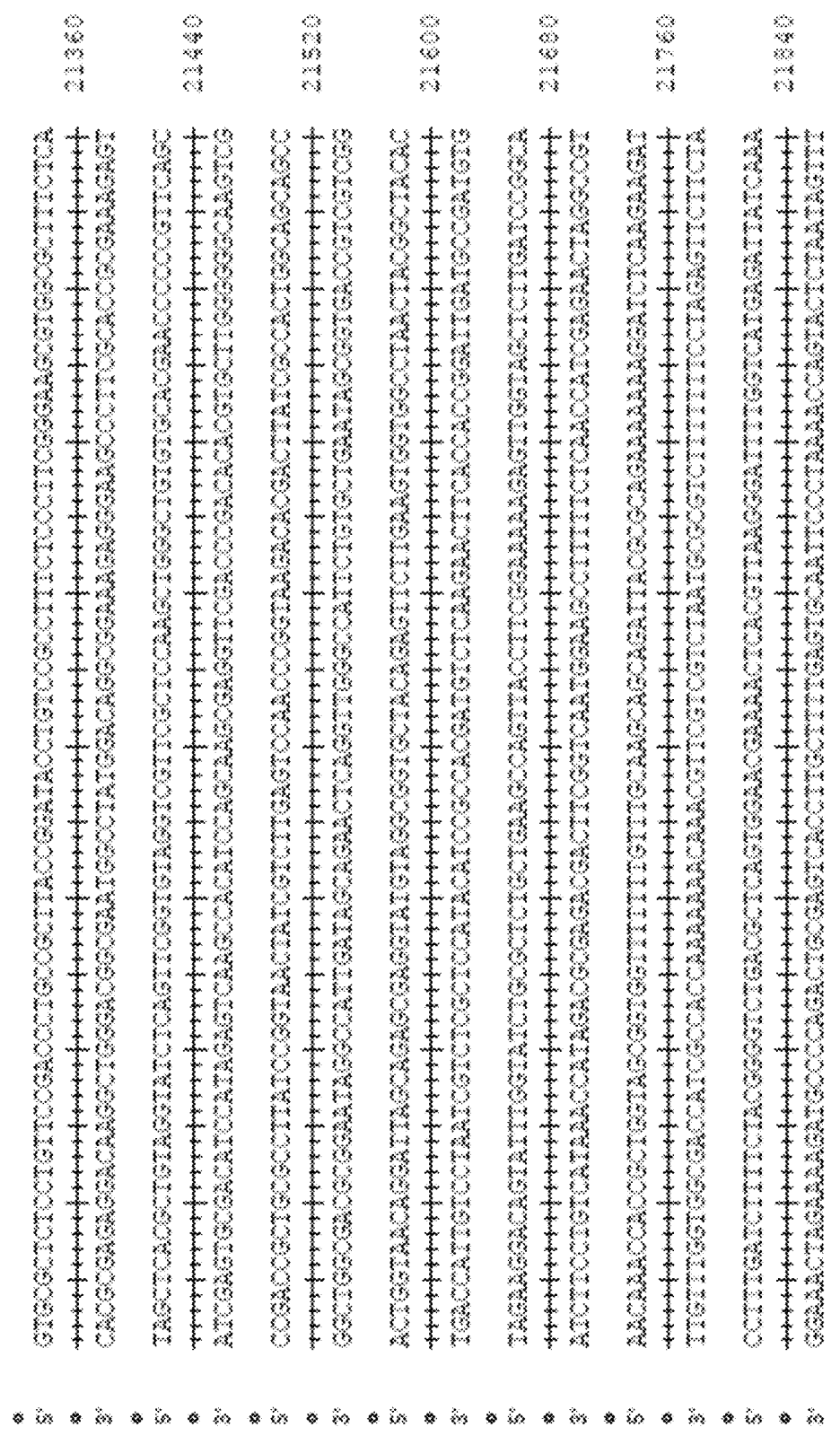
Figure 20:
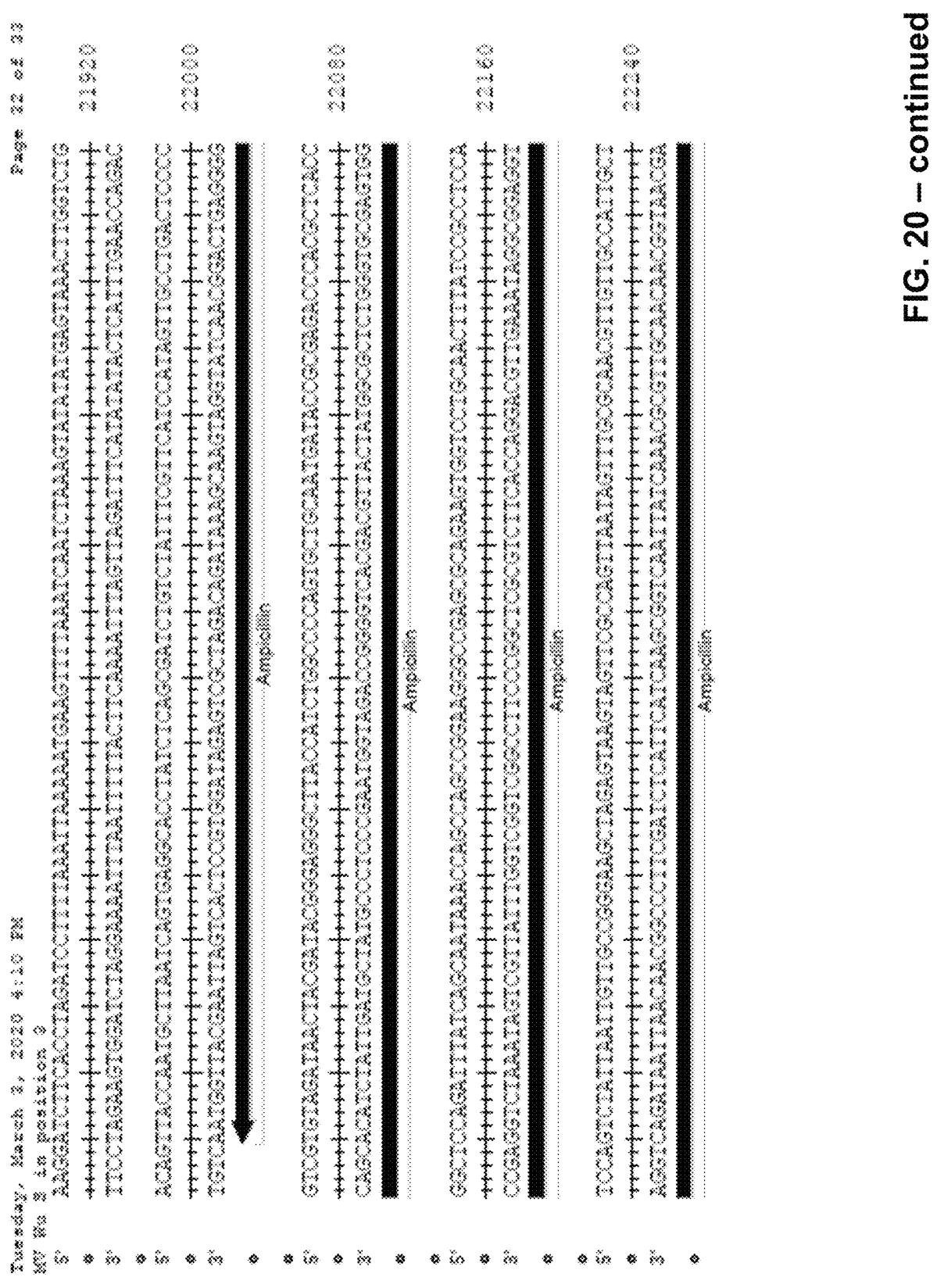
Figure 20:
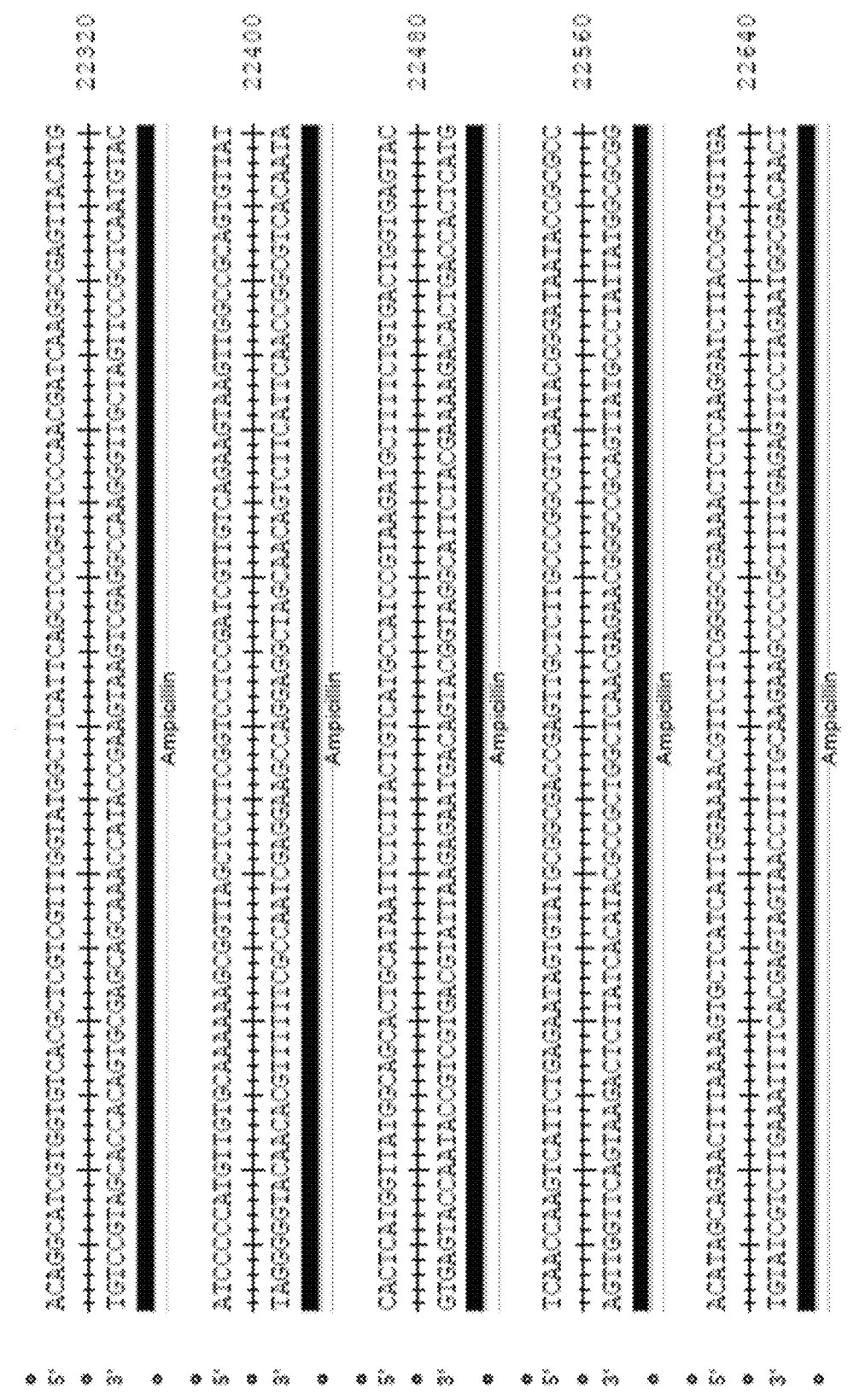
Figure 20:
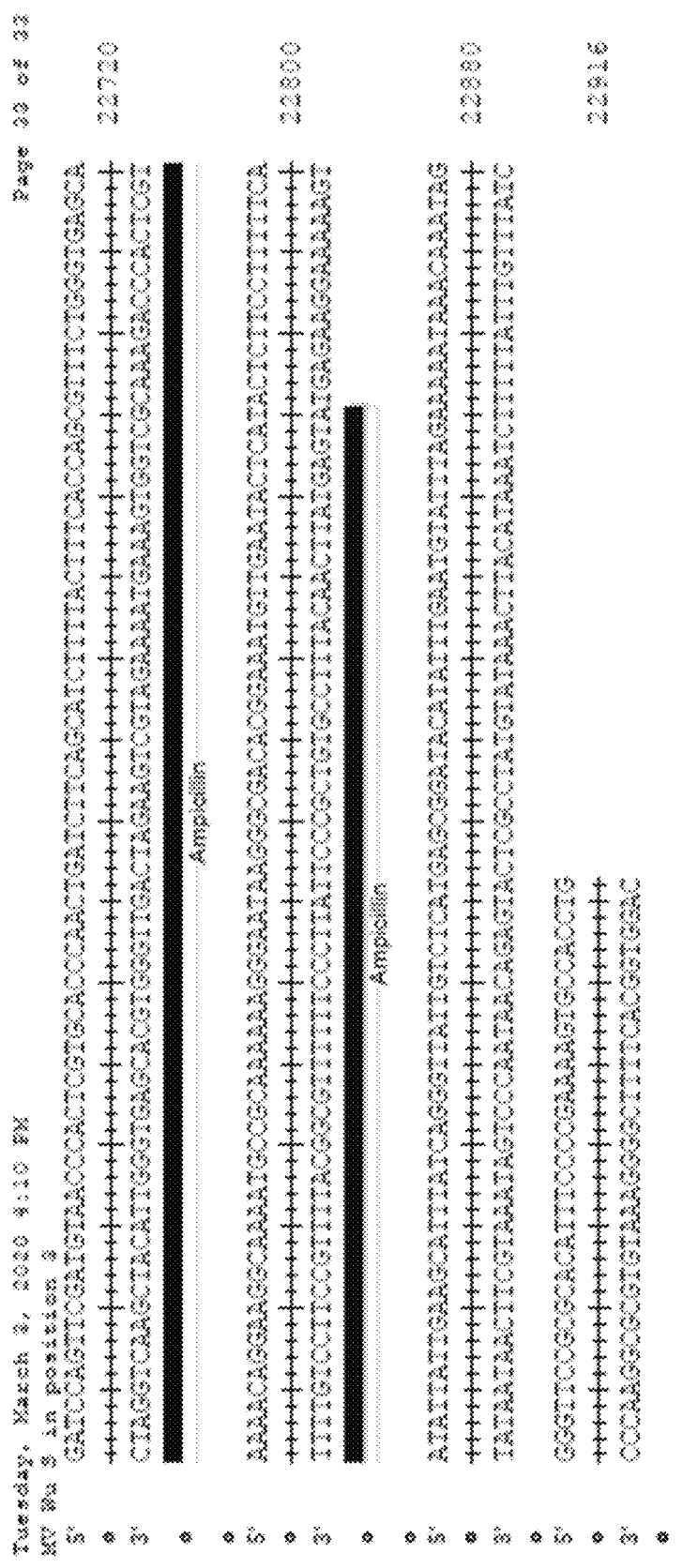

FIG. 20 shows the sequence (SEQ ID NO: 4) and features of "MV Wu S in position 3".

Figure 21:
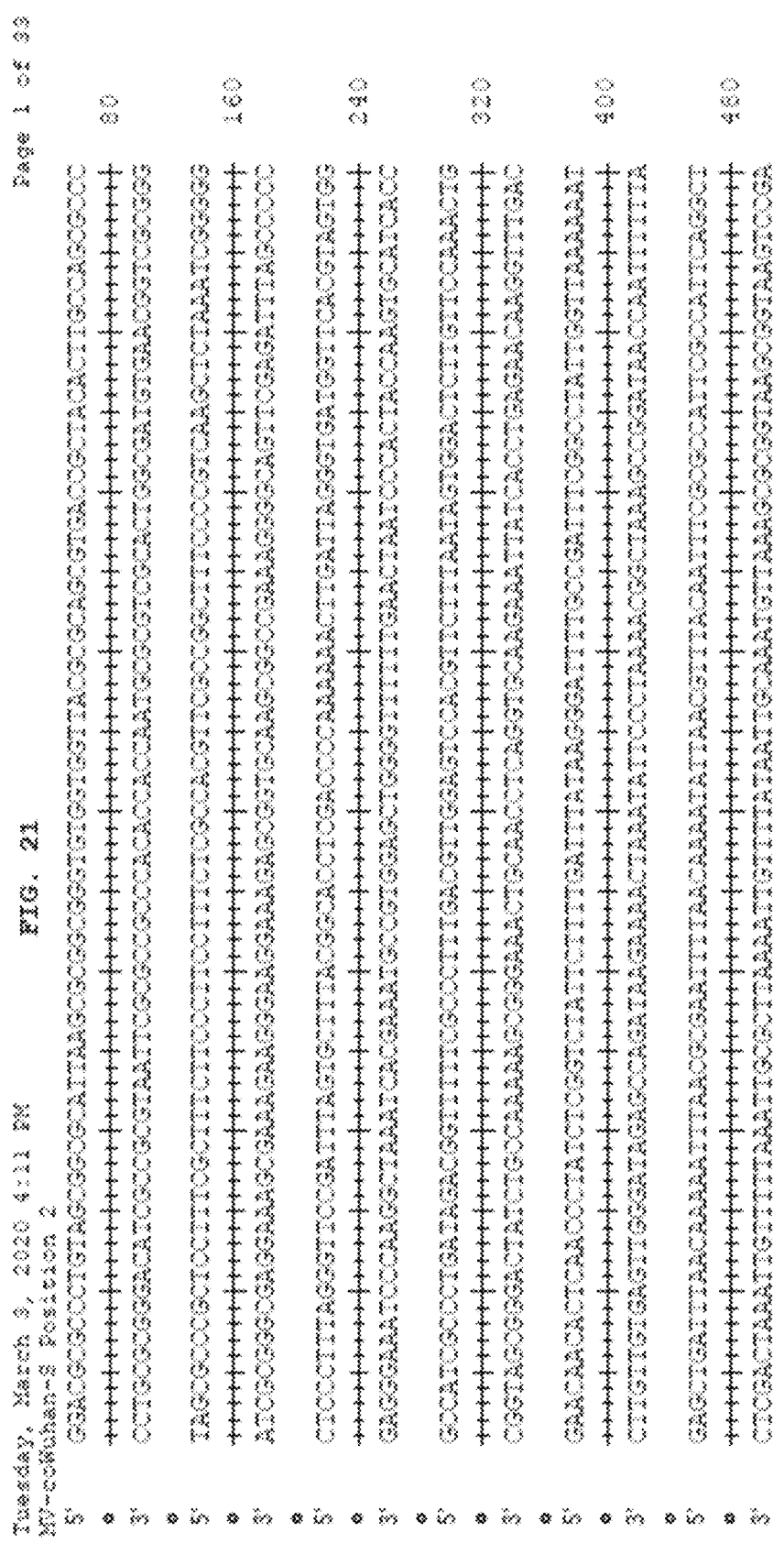
Figure 21:
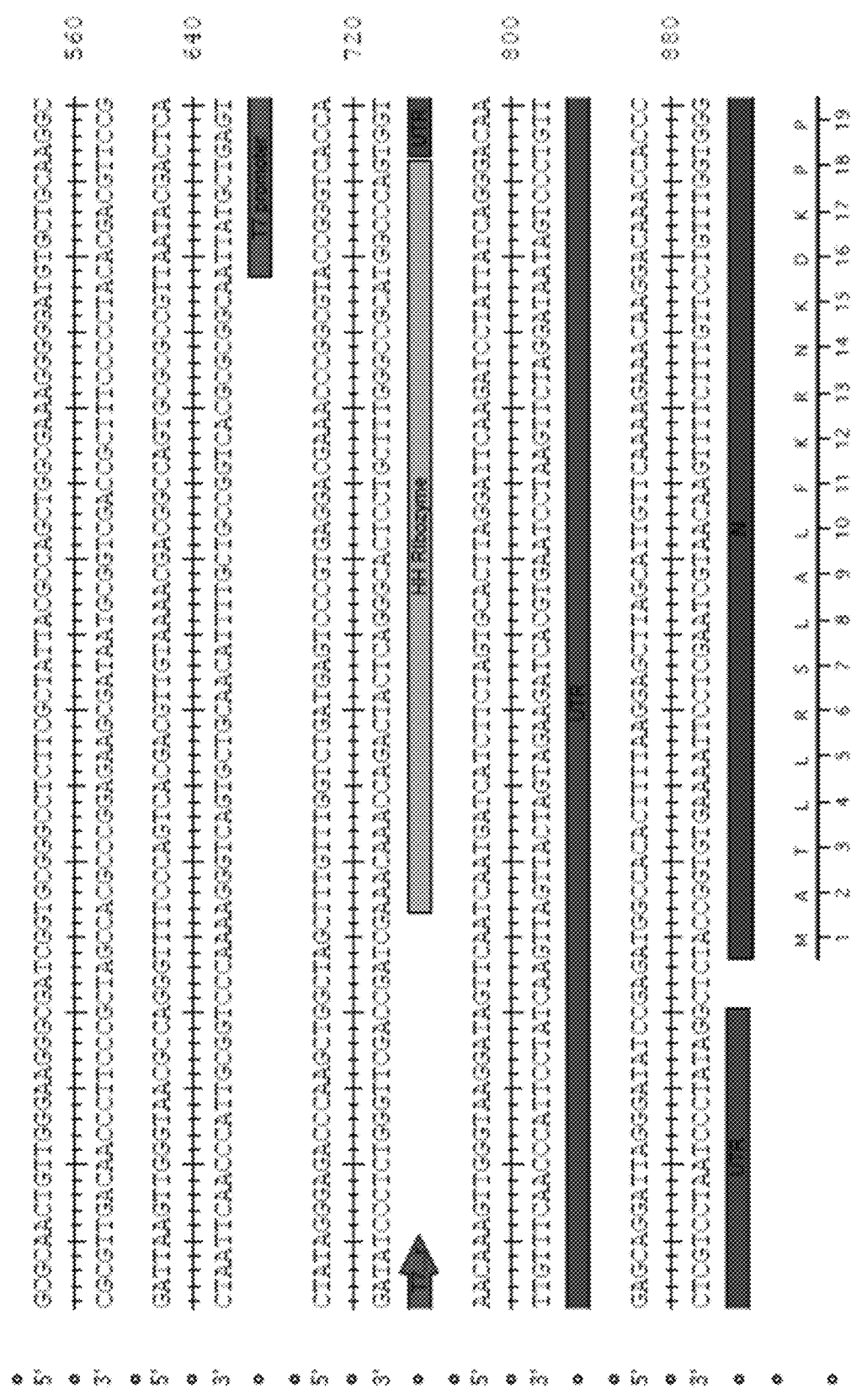
Figure 21:
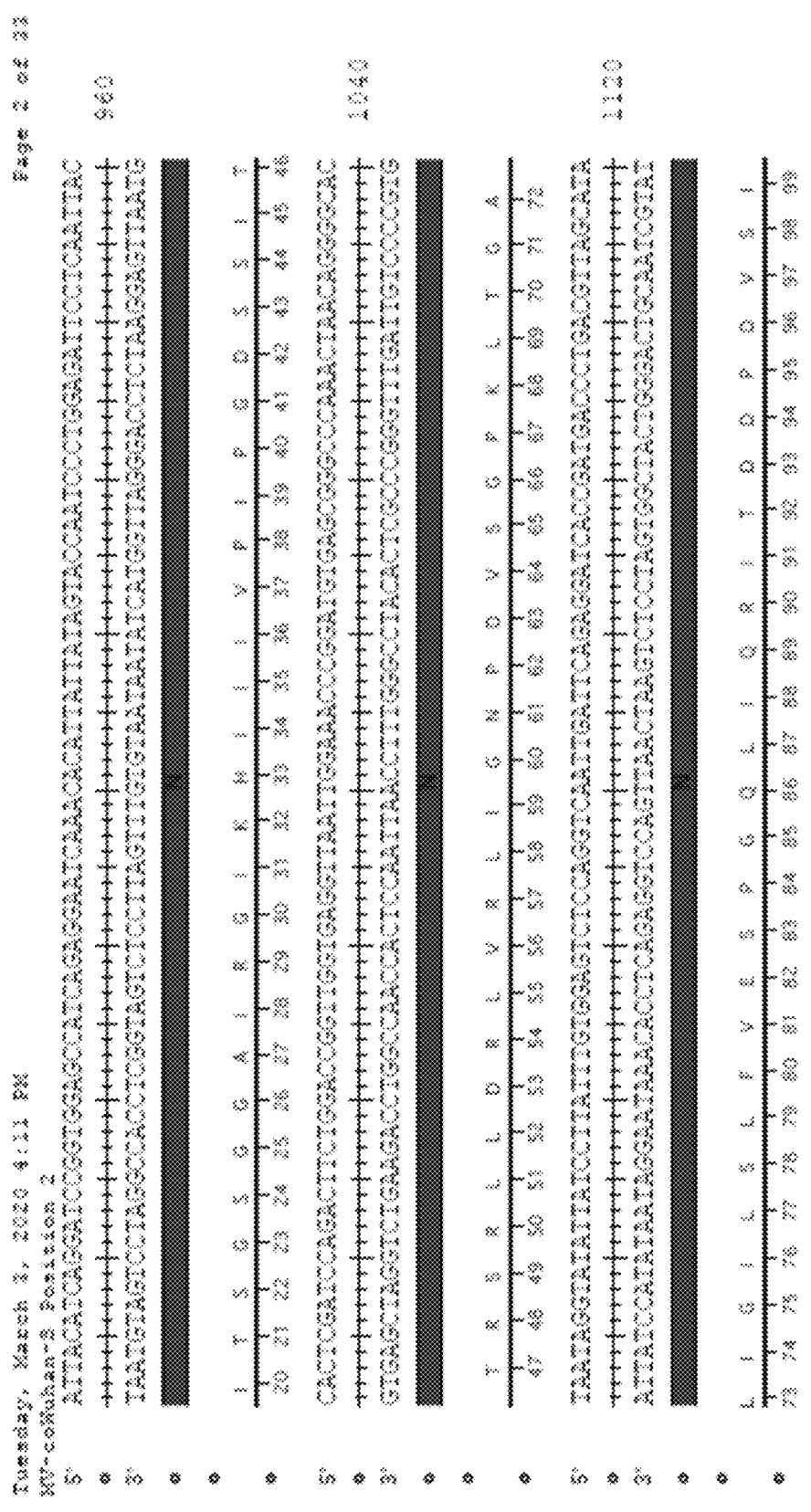
Figure 21:
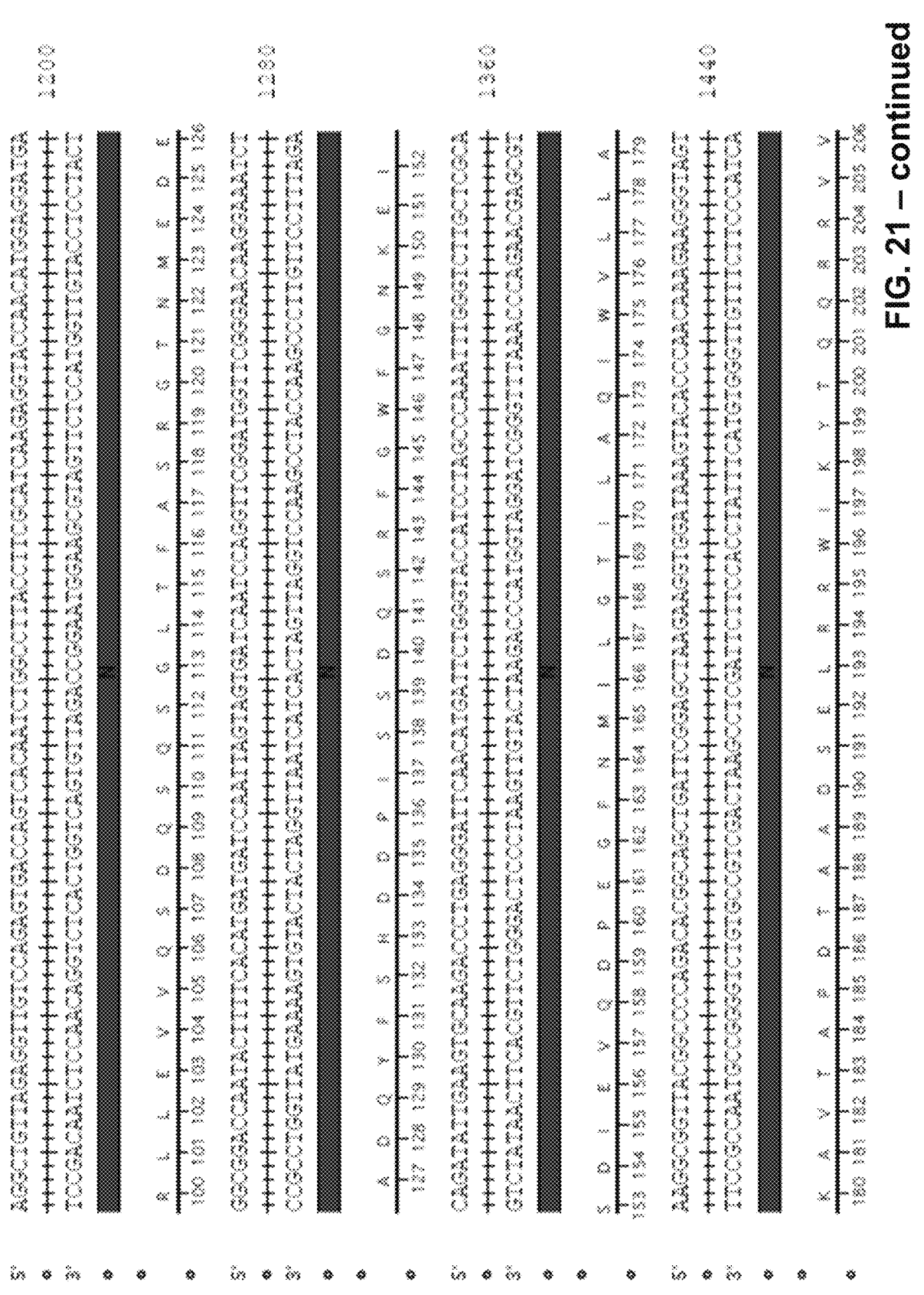
Figure 21:
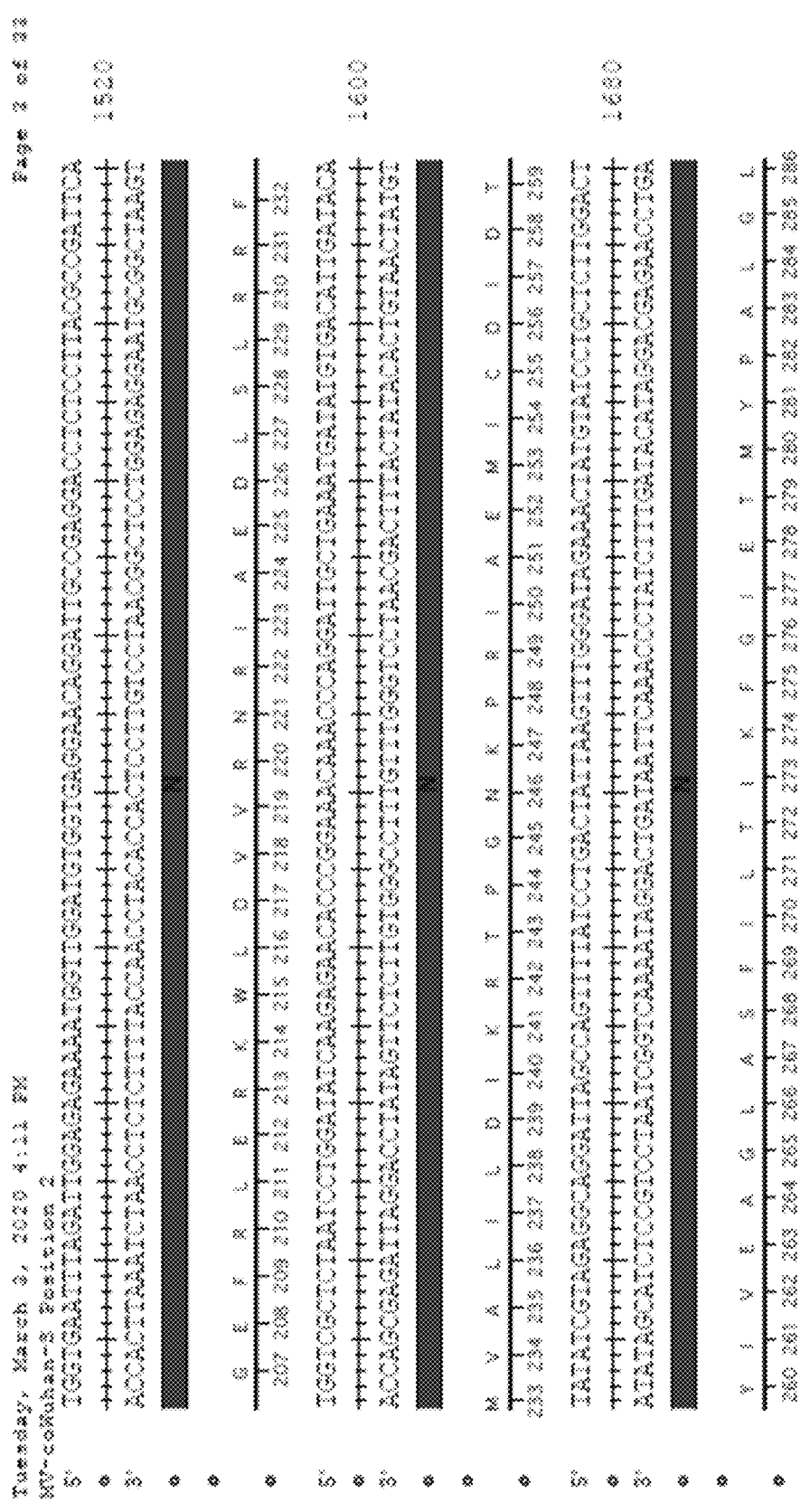
Figure 21:
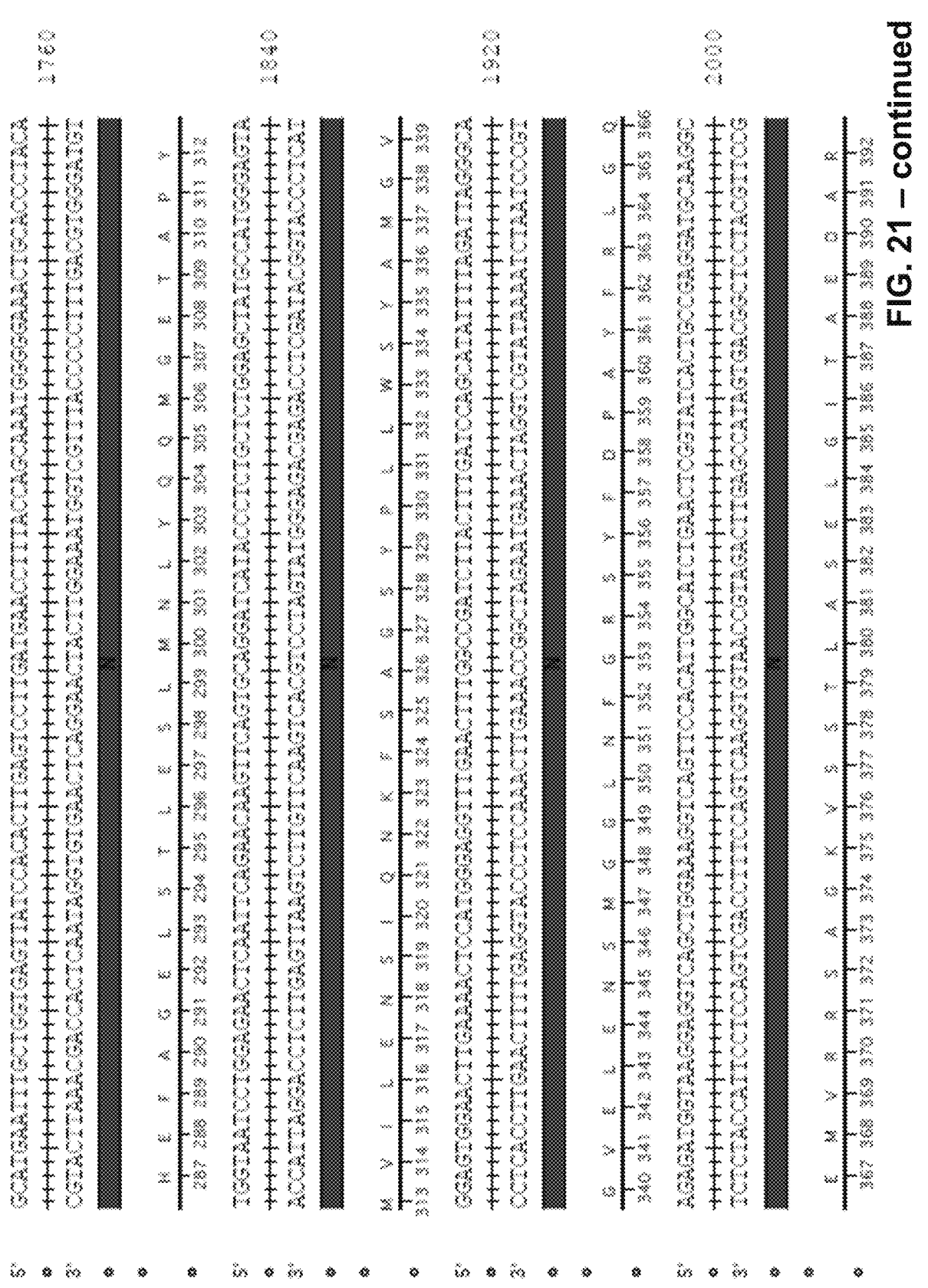
Figure 21:
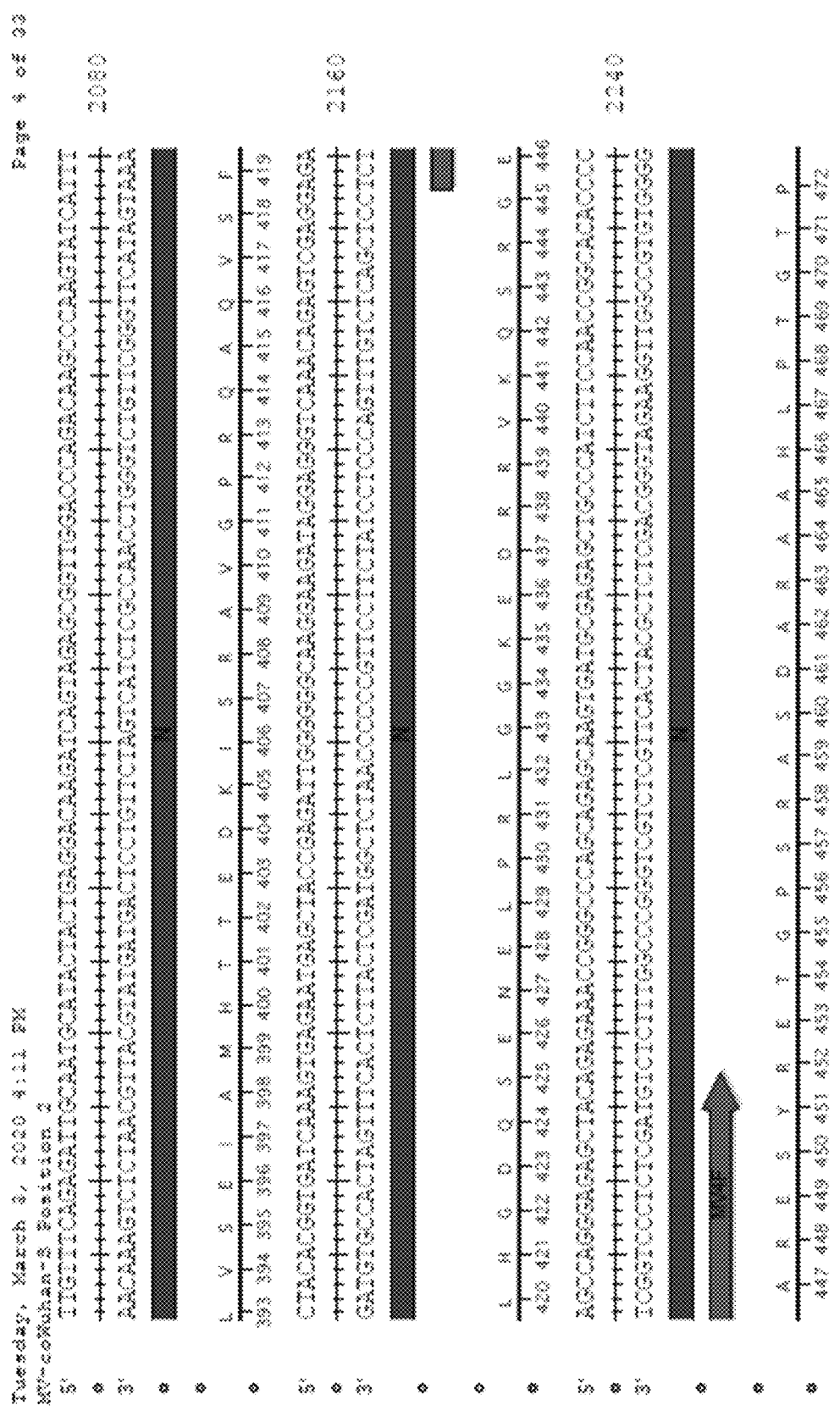
Figure 21:
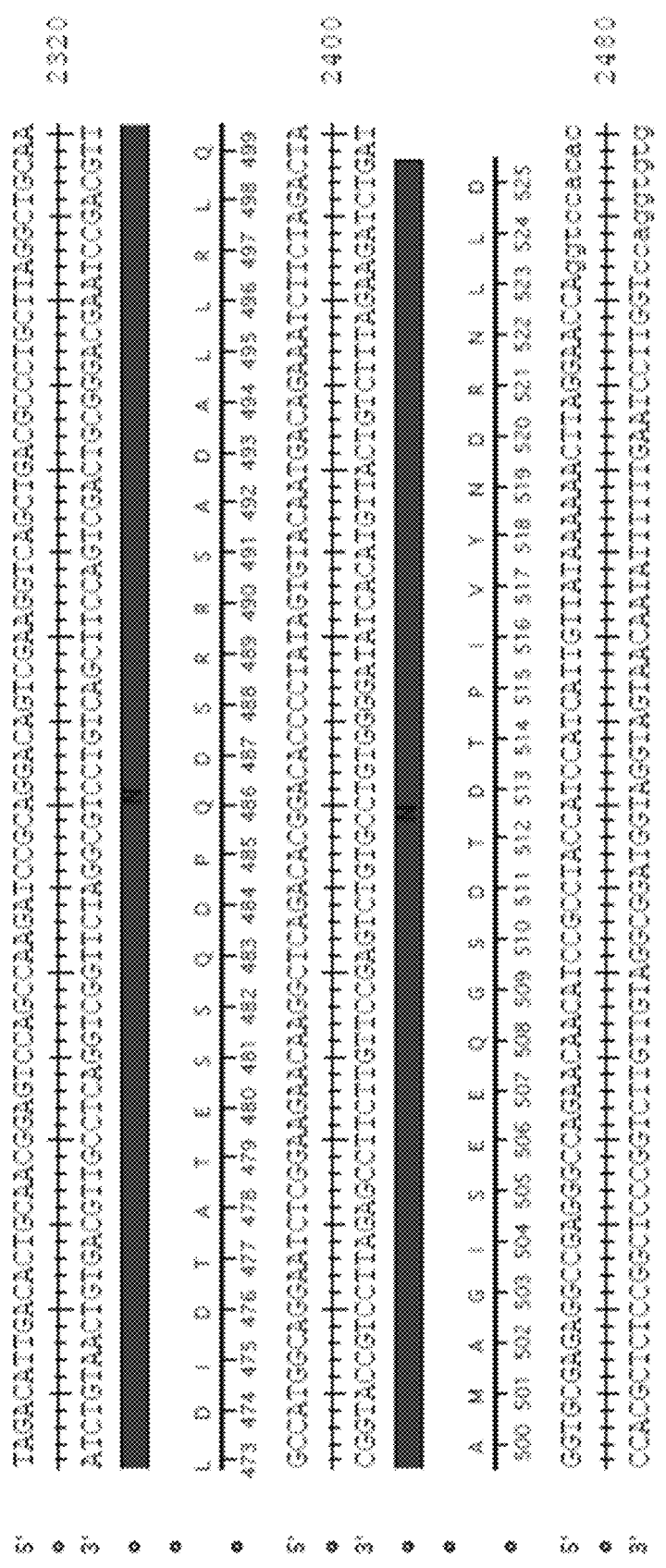
Figure 21:
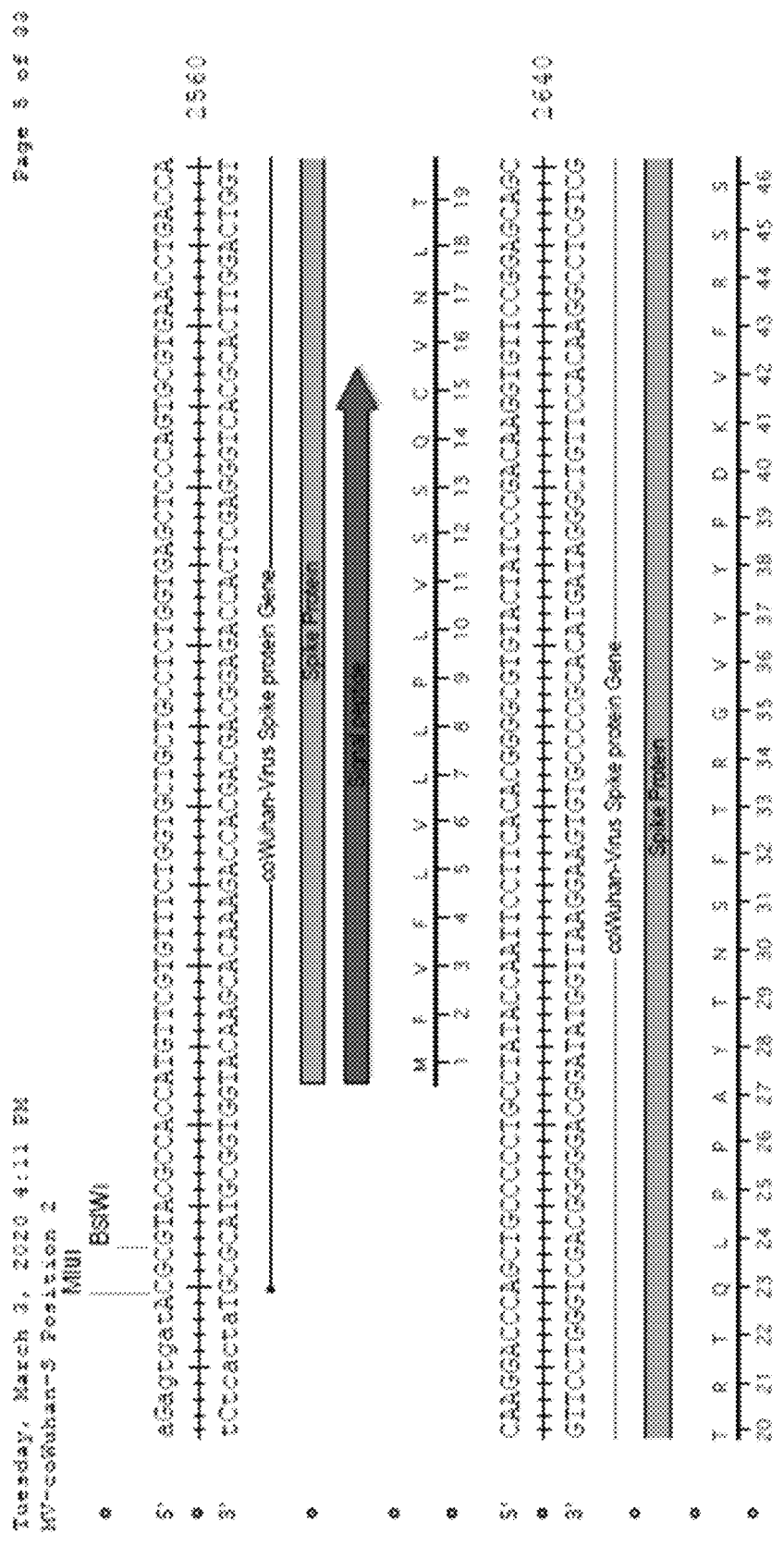
Figure 21:
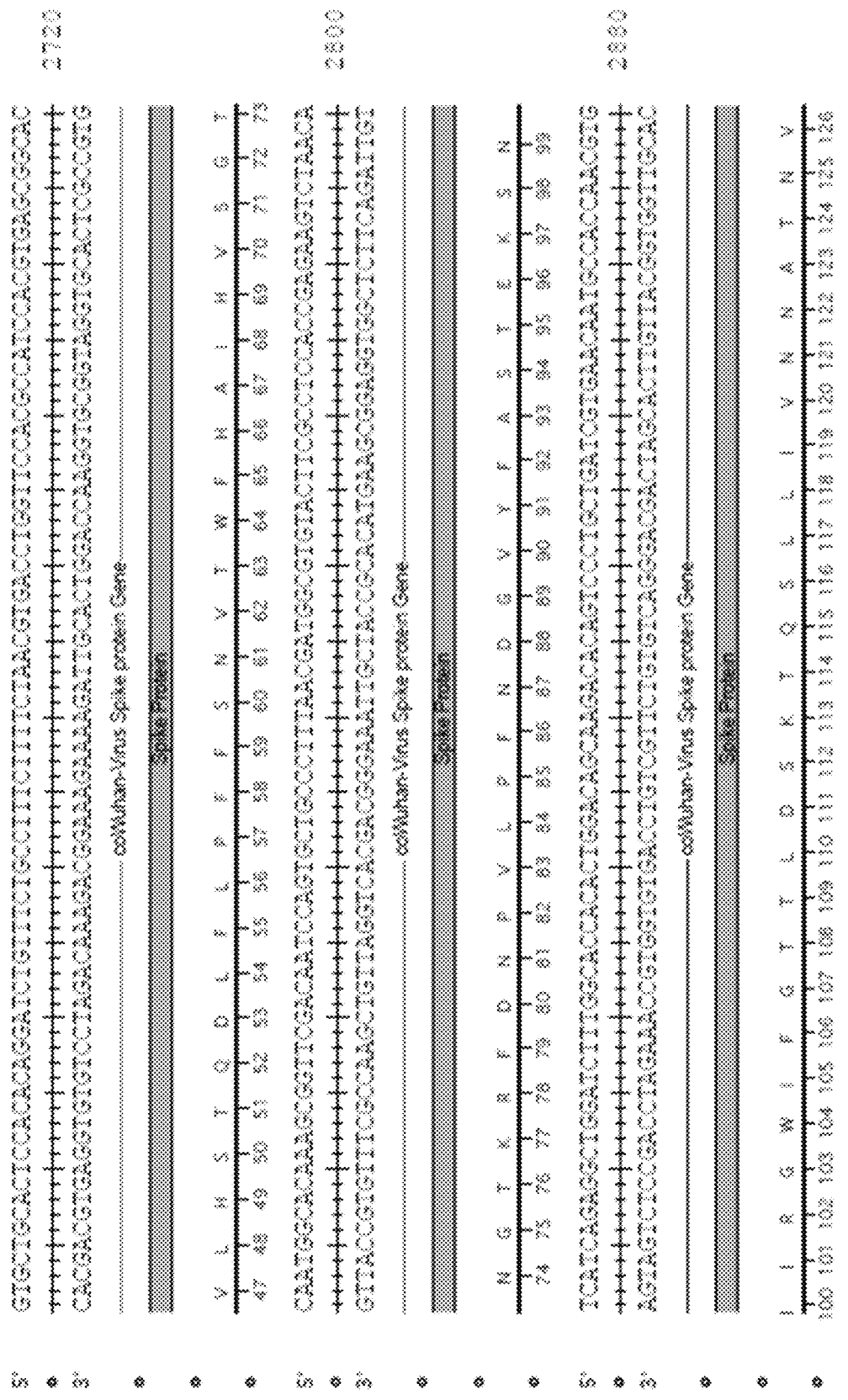
Figure 21:
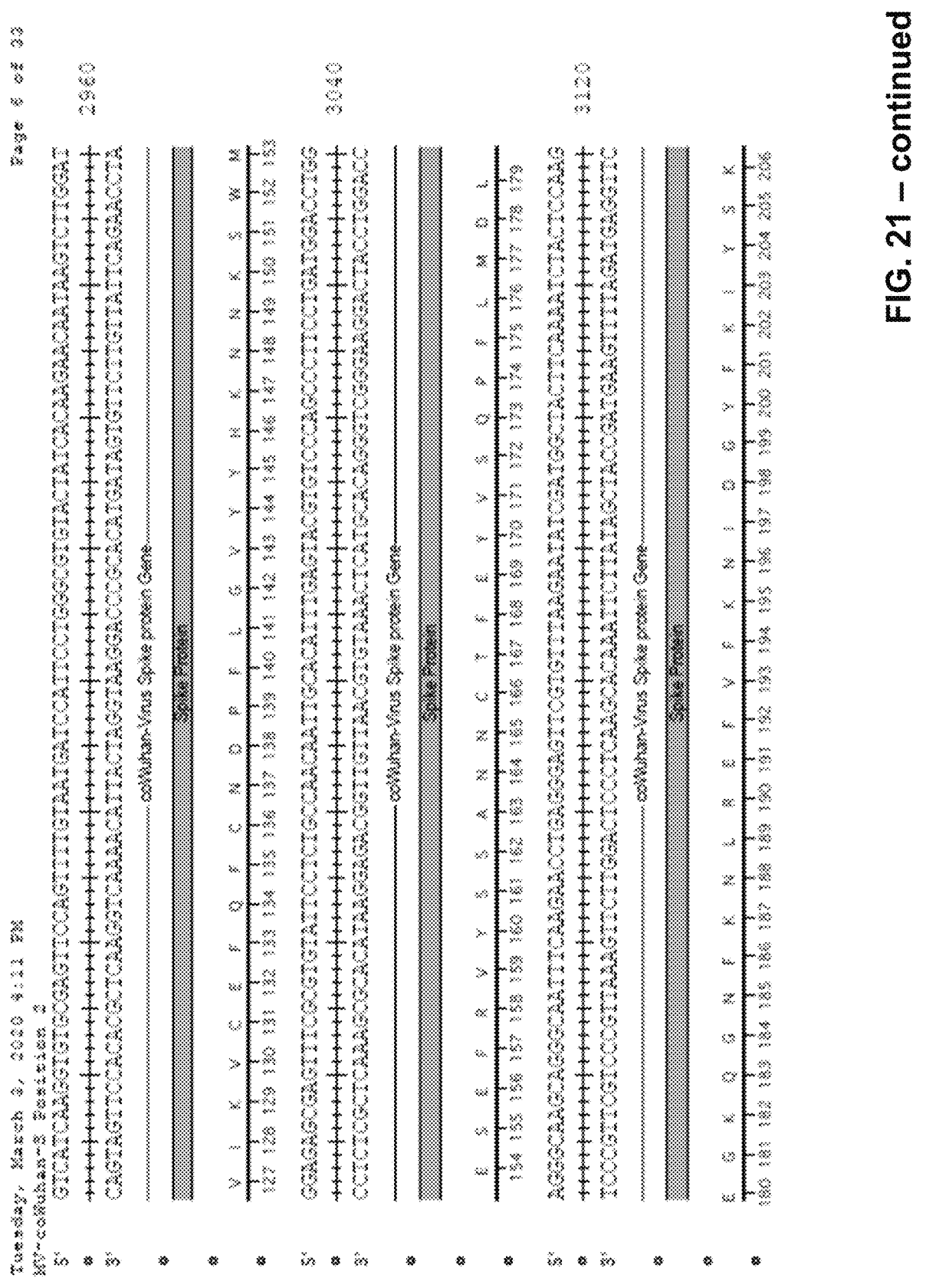
Figure 21:
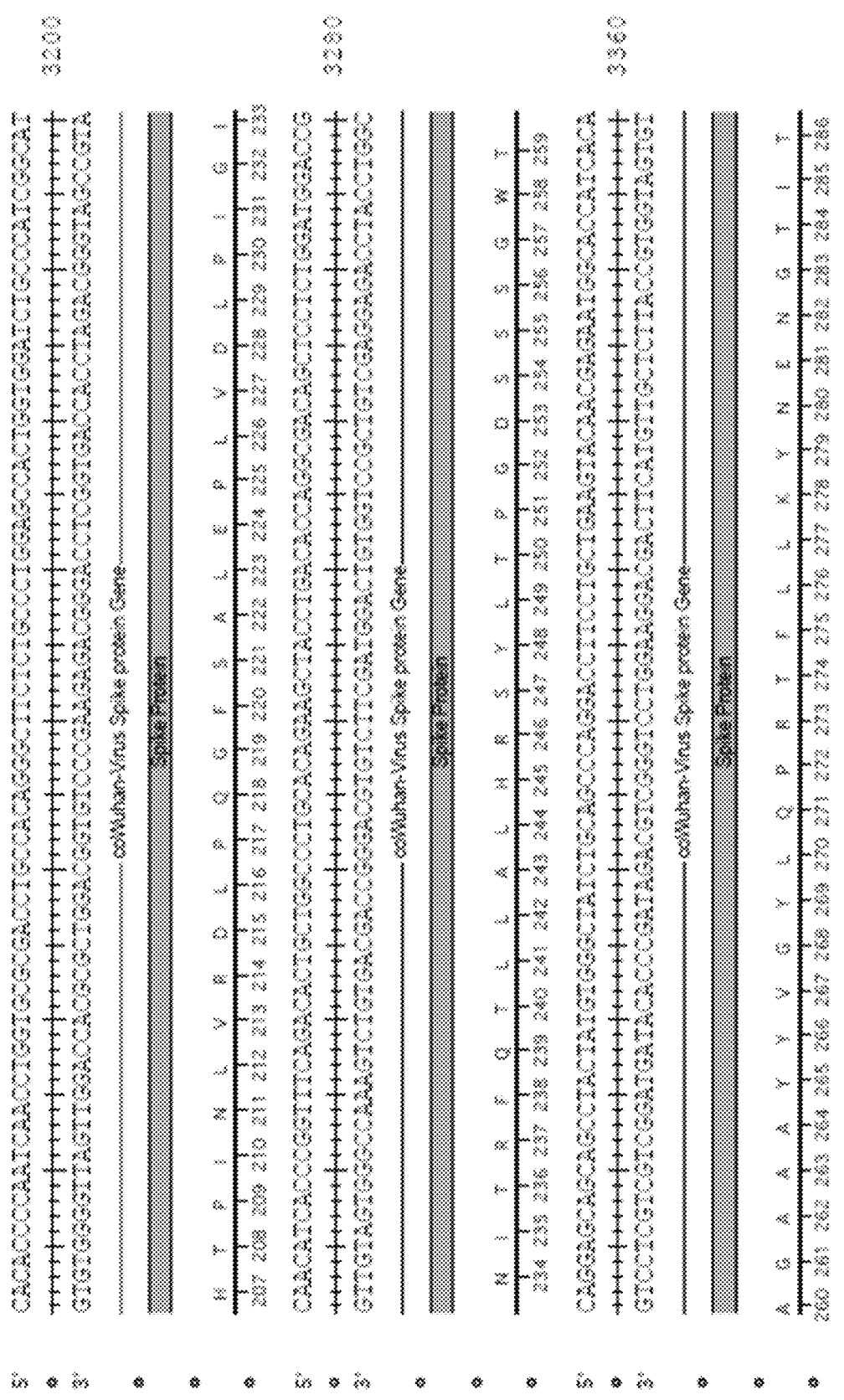
Figure 21:
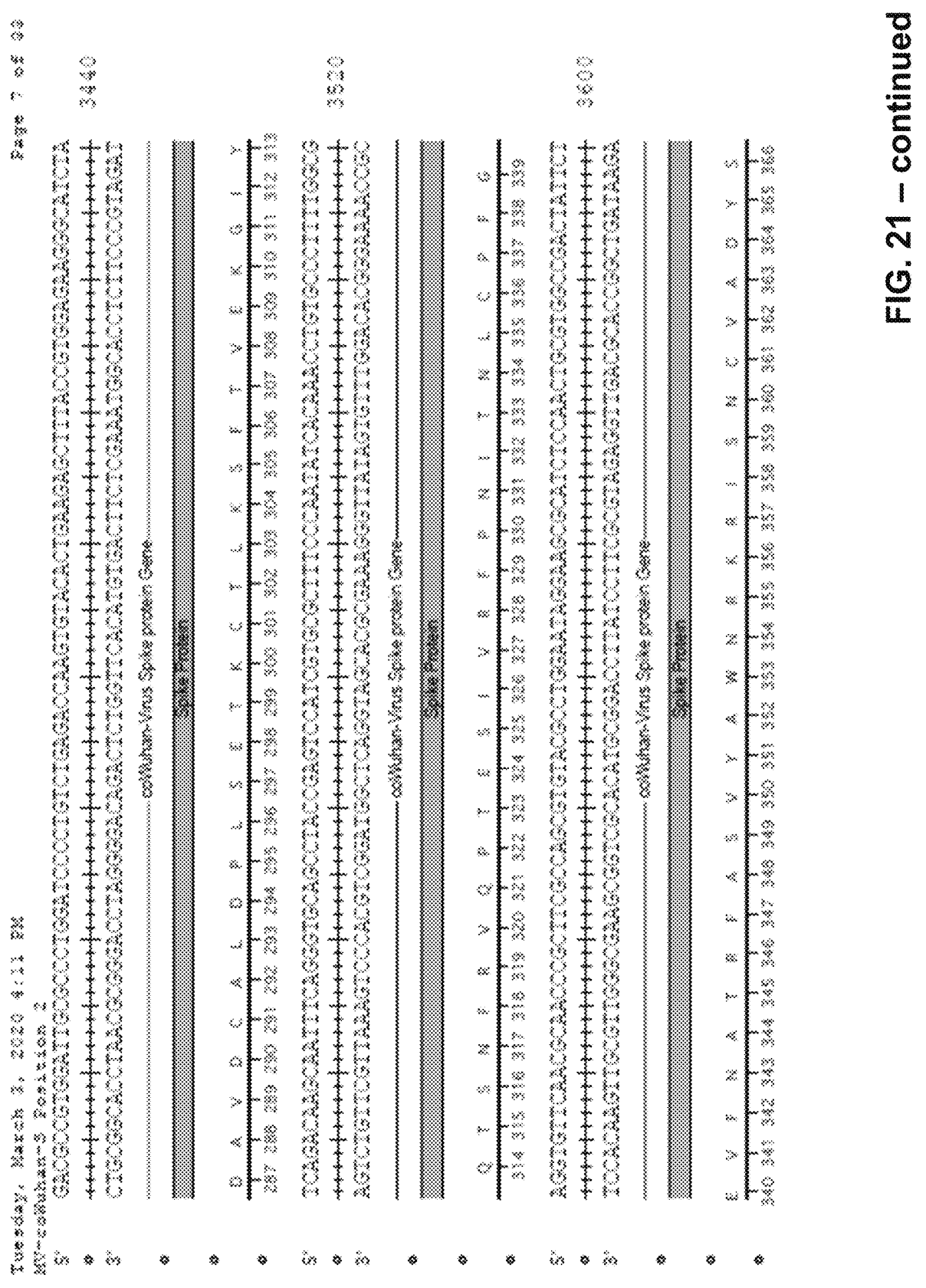
Figure 21:
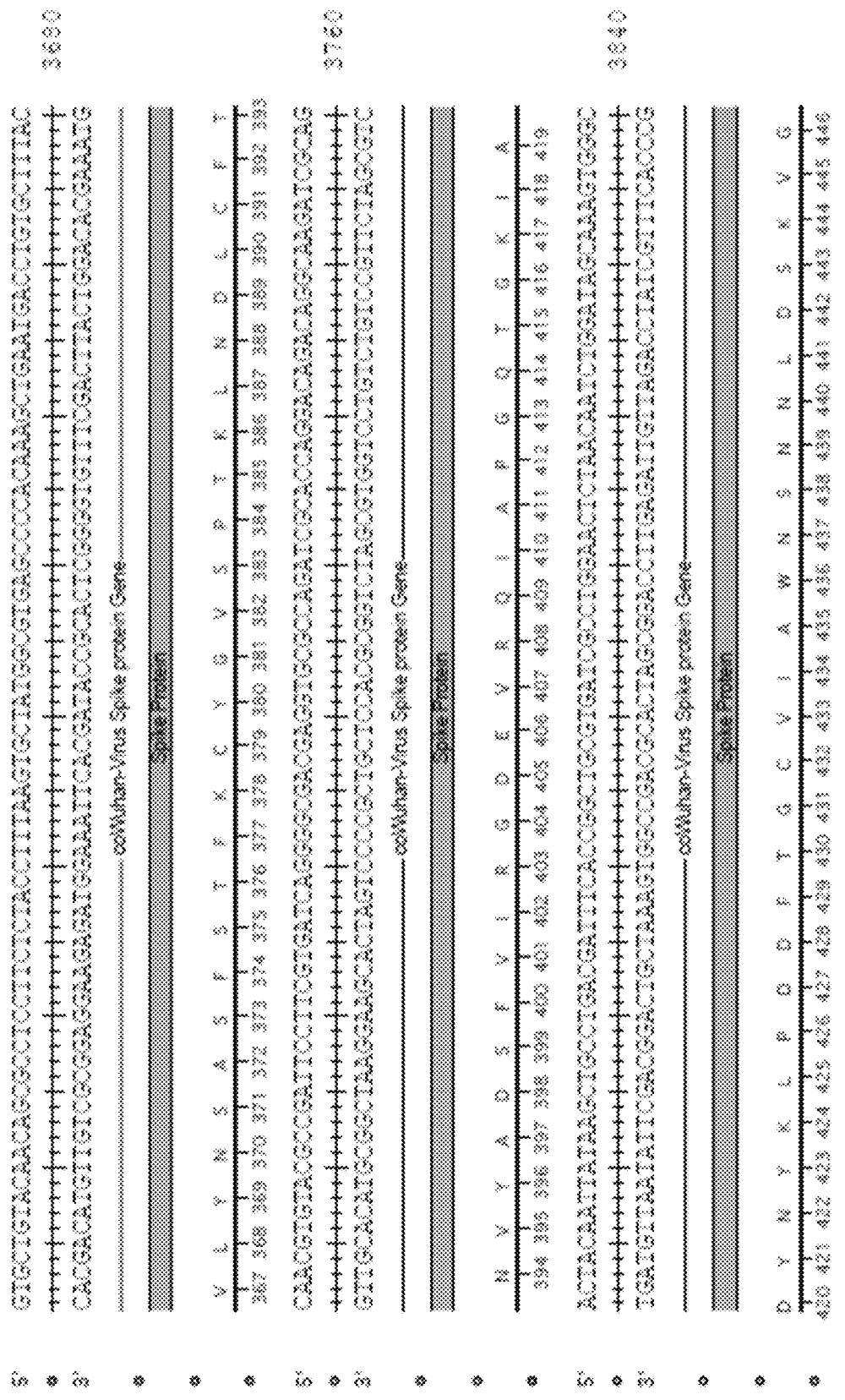
Figure 21:
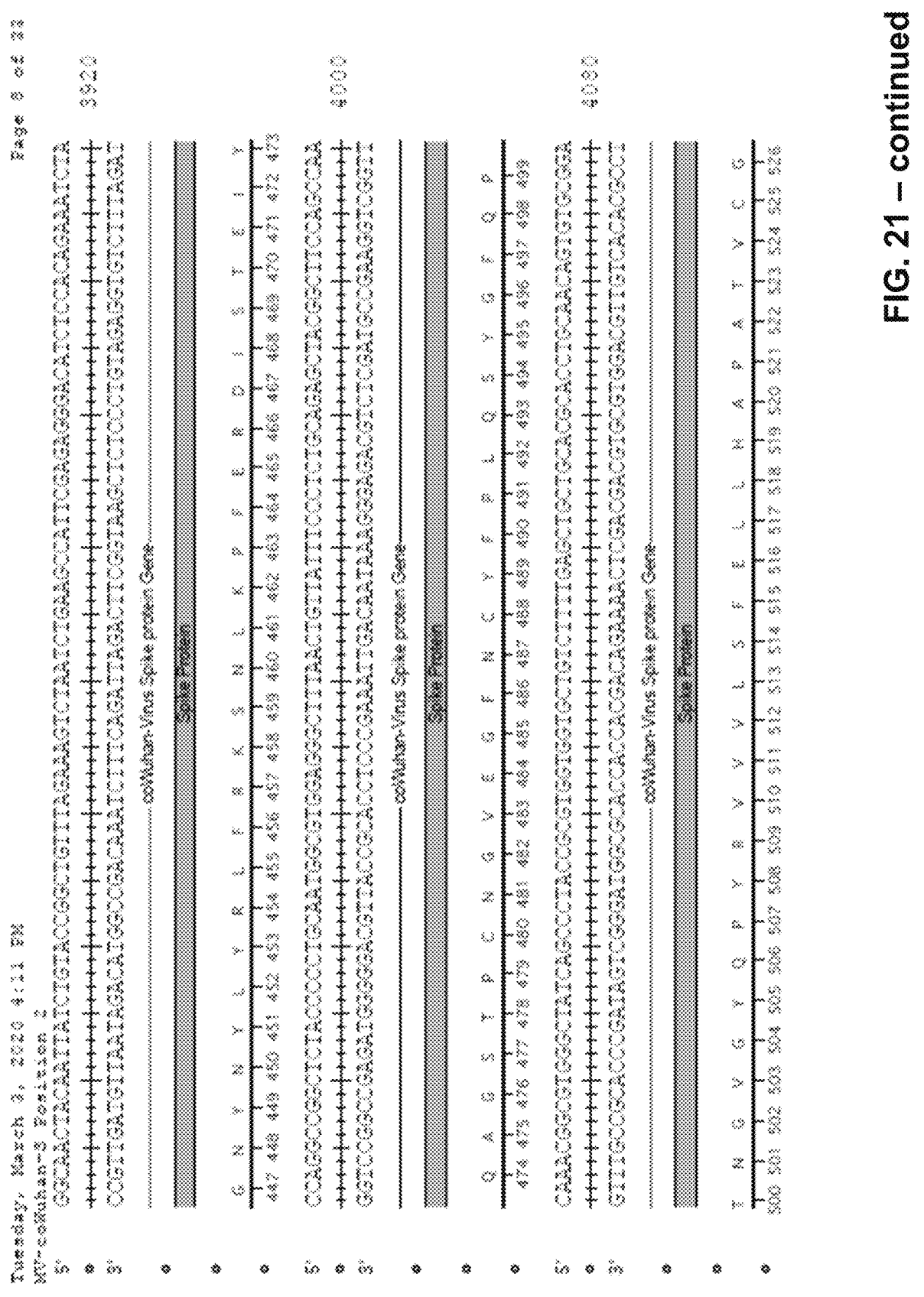
Figure 21:
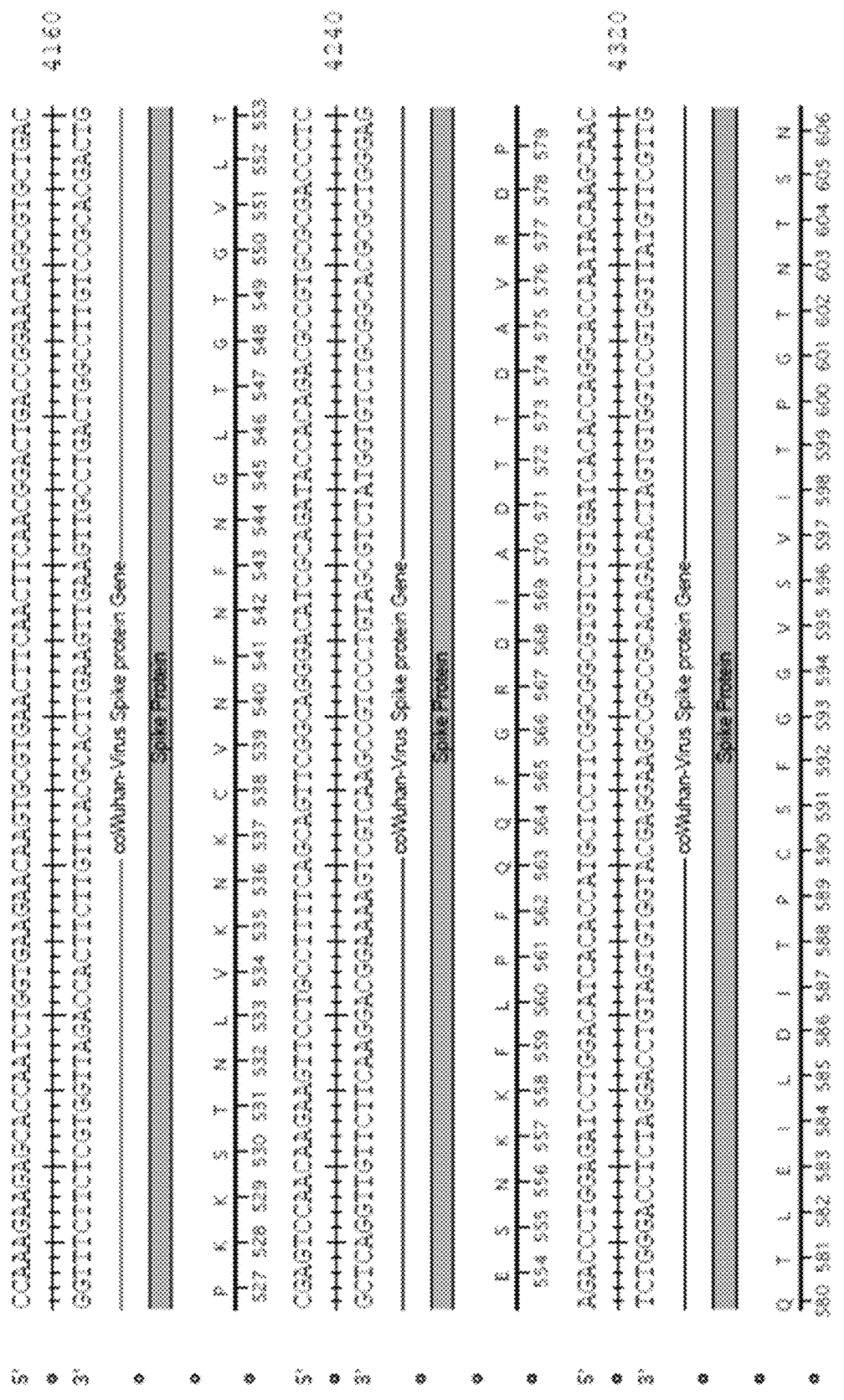
Figure 21:
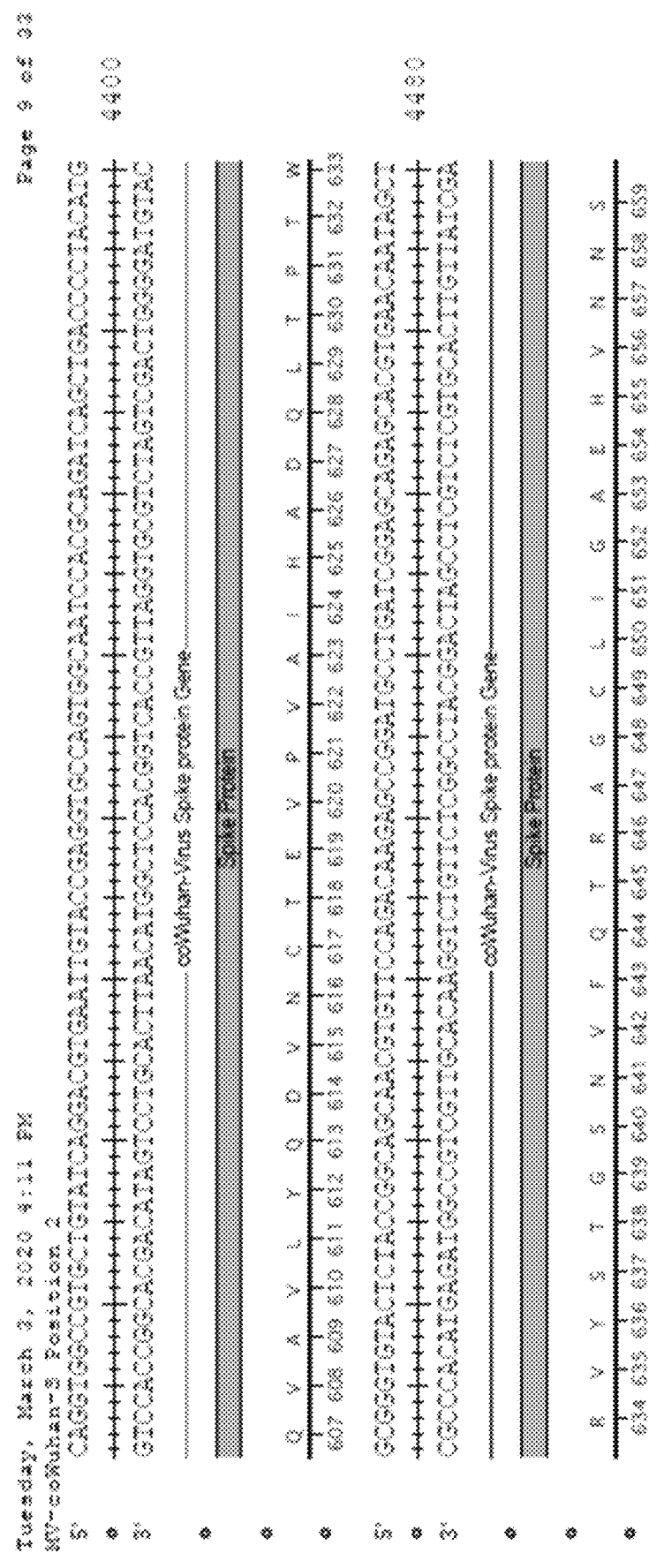
Figure 21:
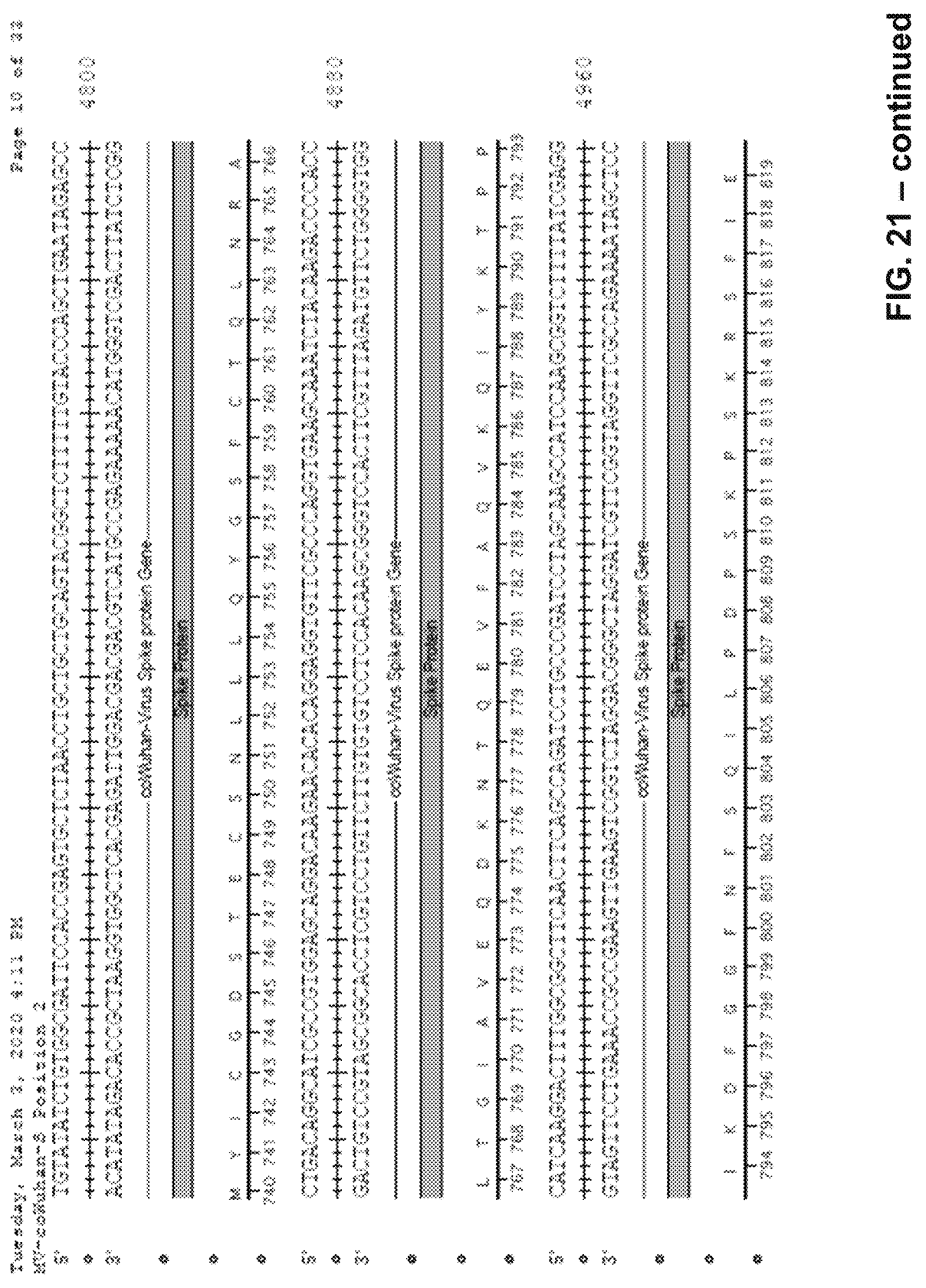
Figure 21:
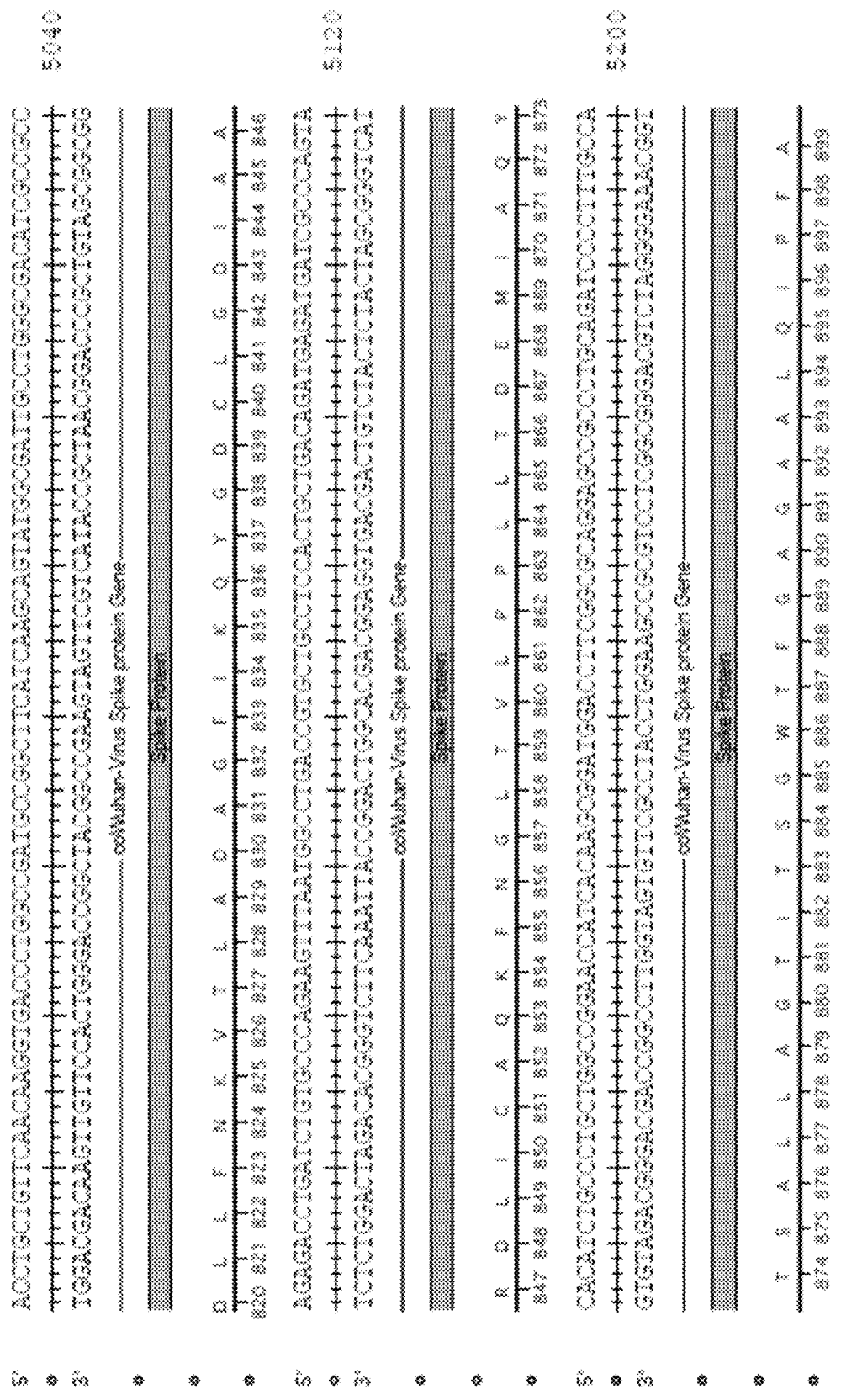
Figure 21:
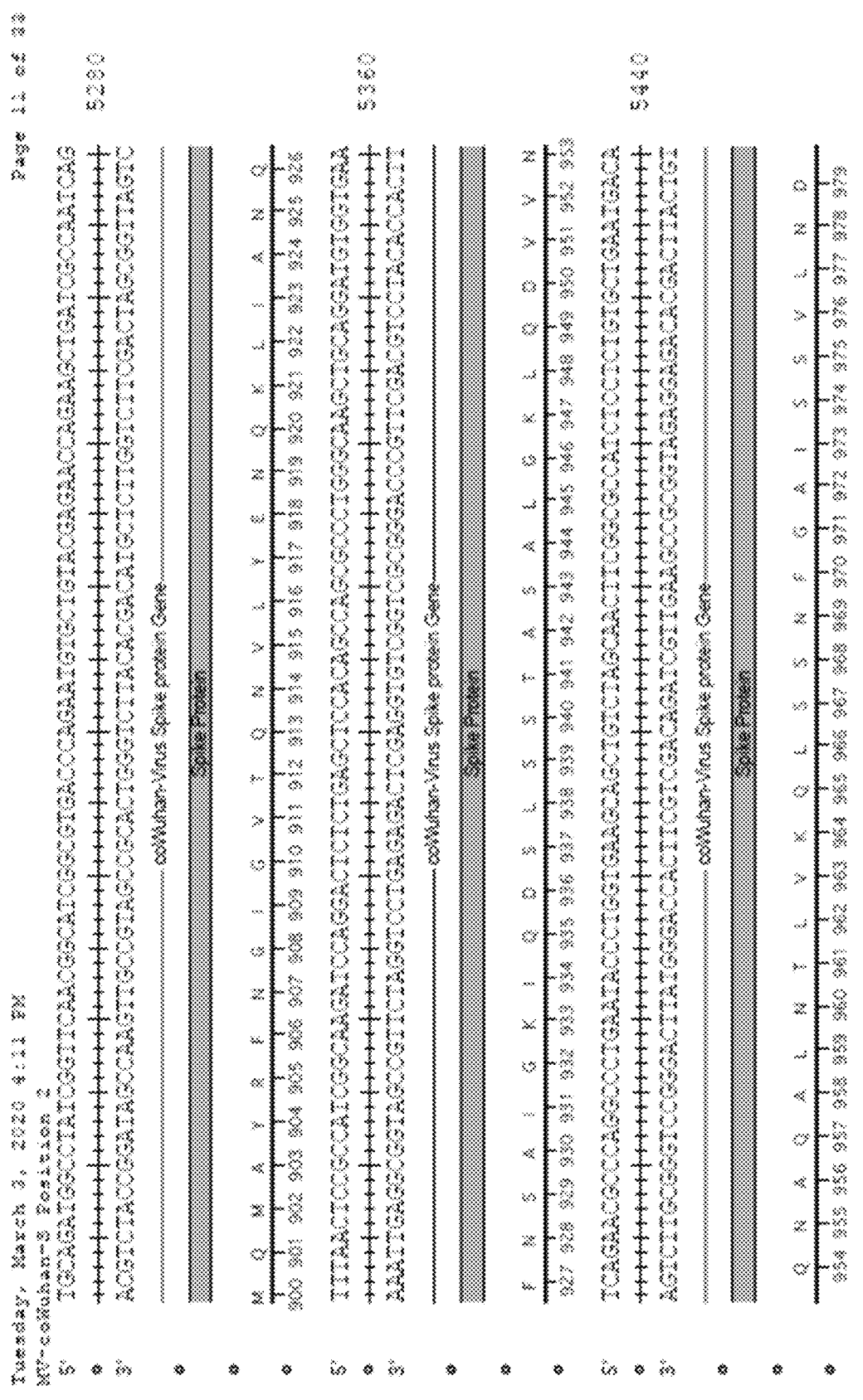
Figure 21:
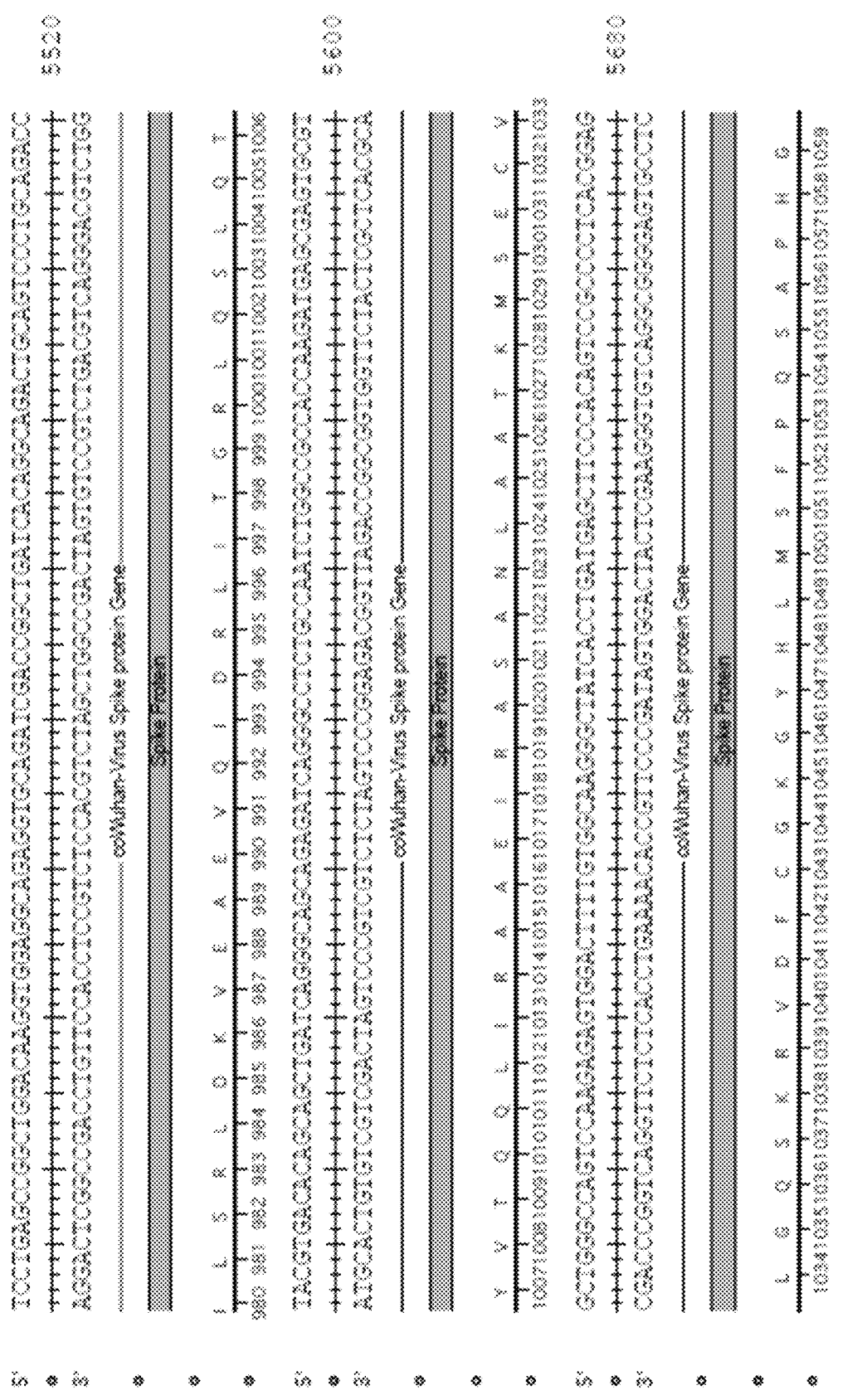
Figure 21:
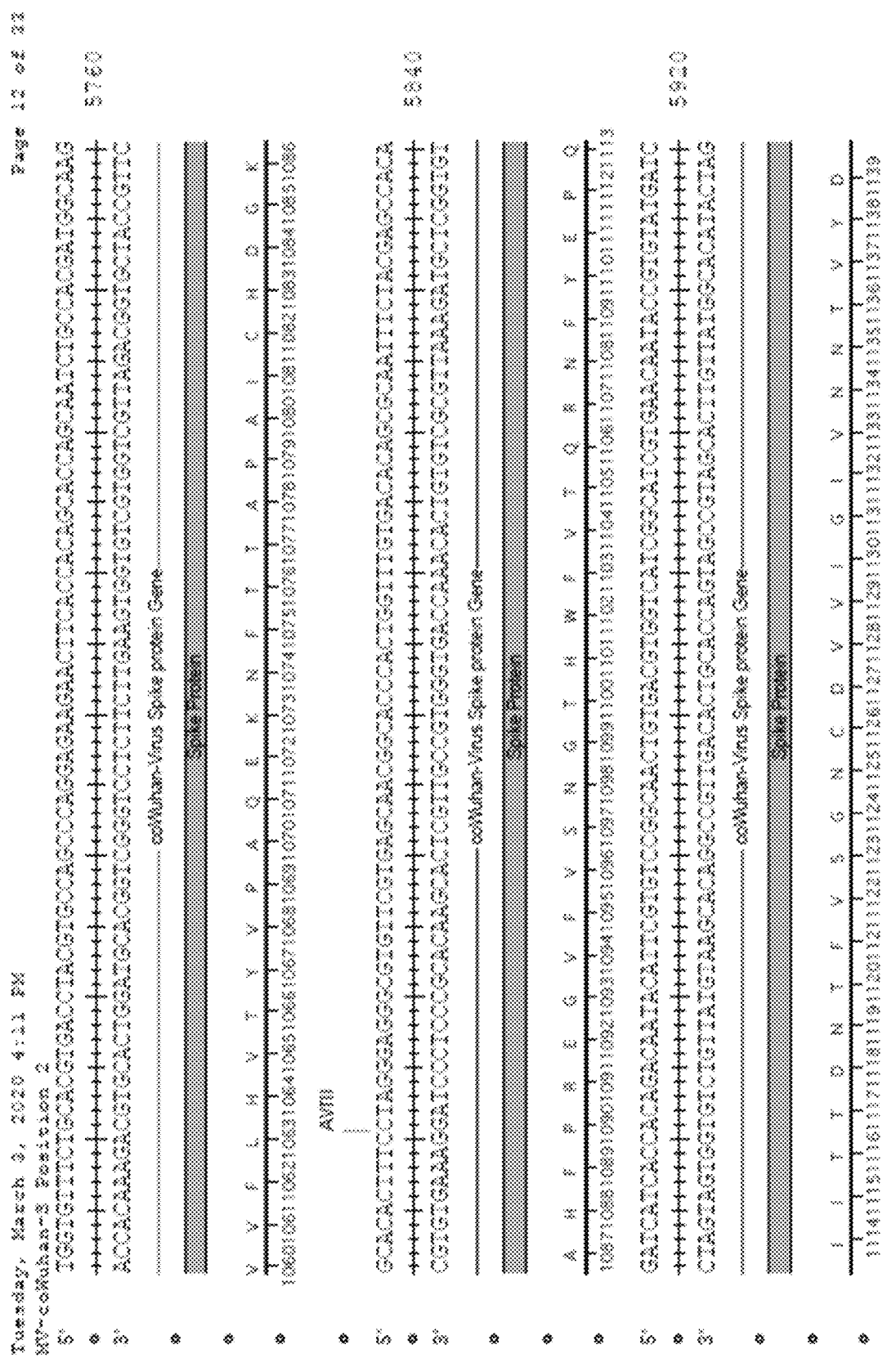
Figure 21:
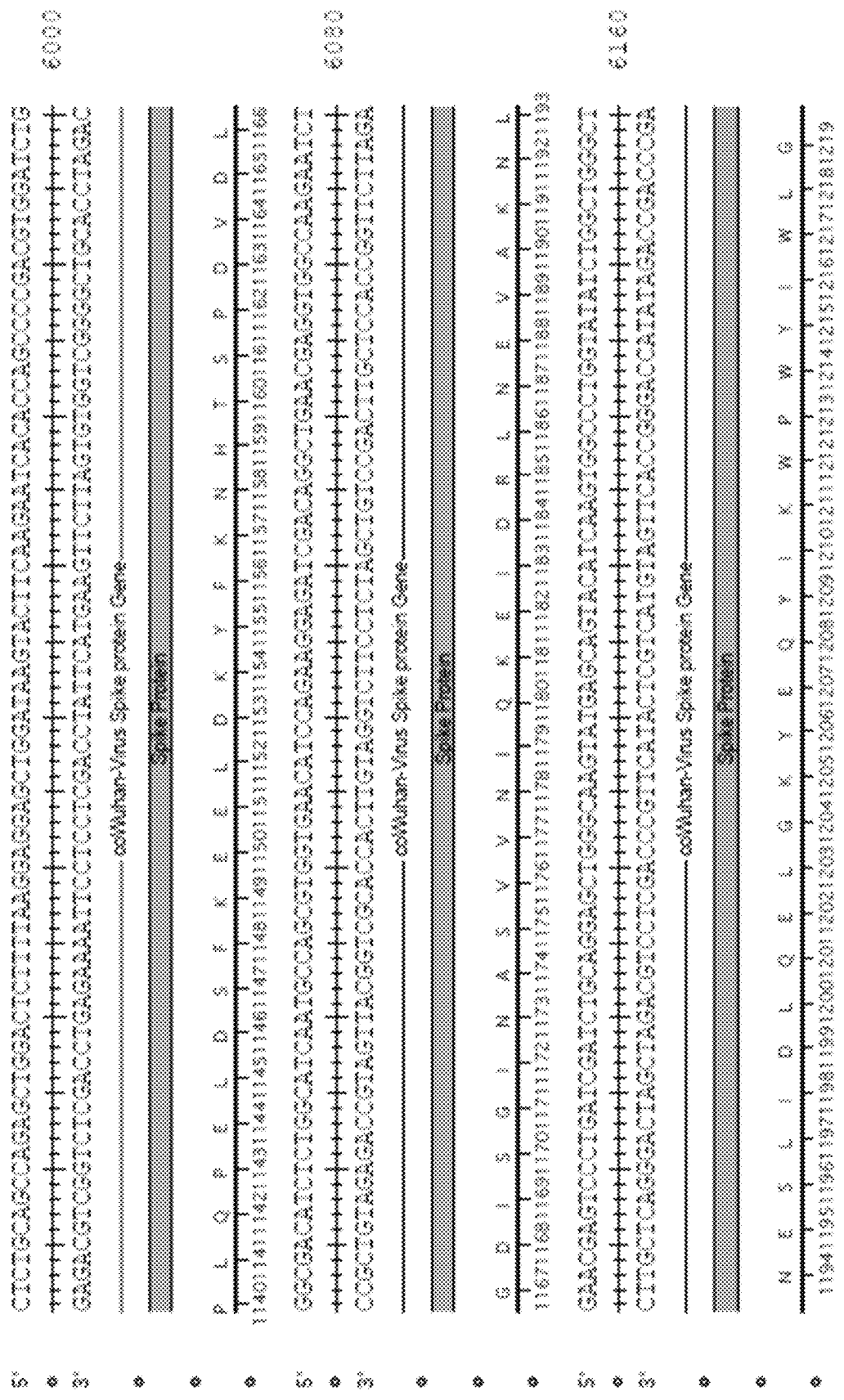
Figure 21:
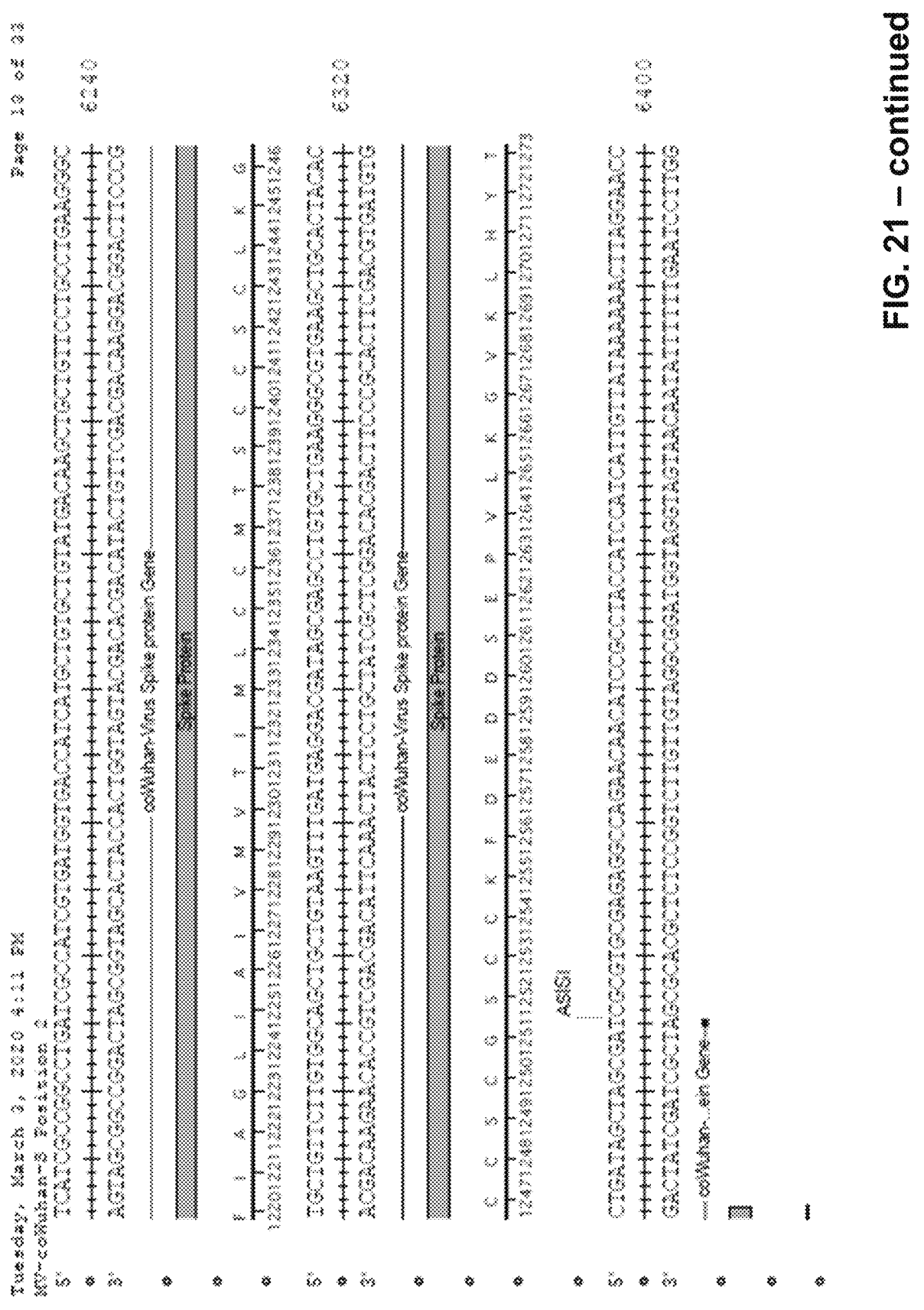
Figure 21:
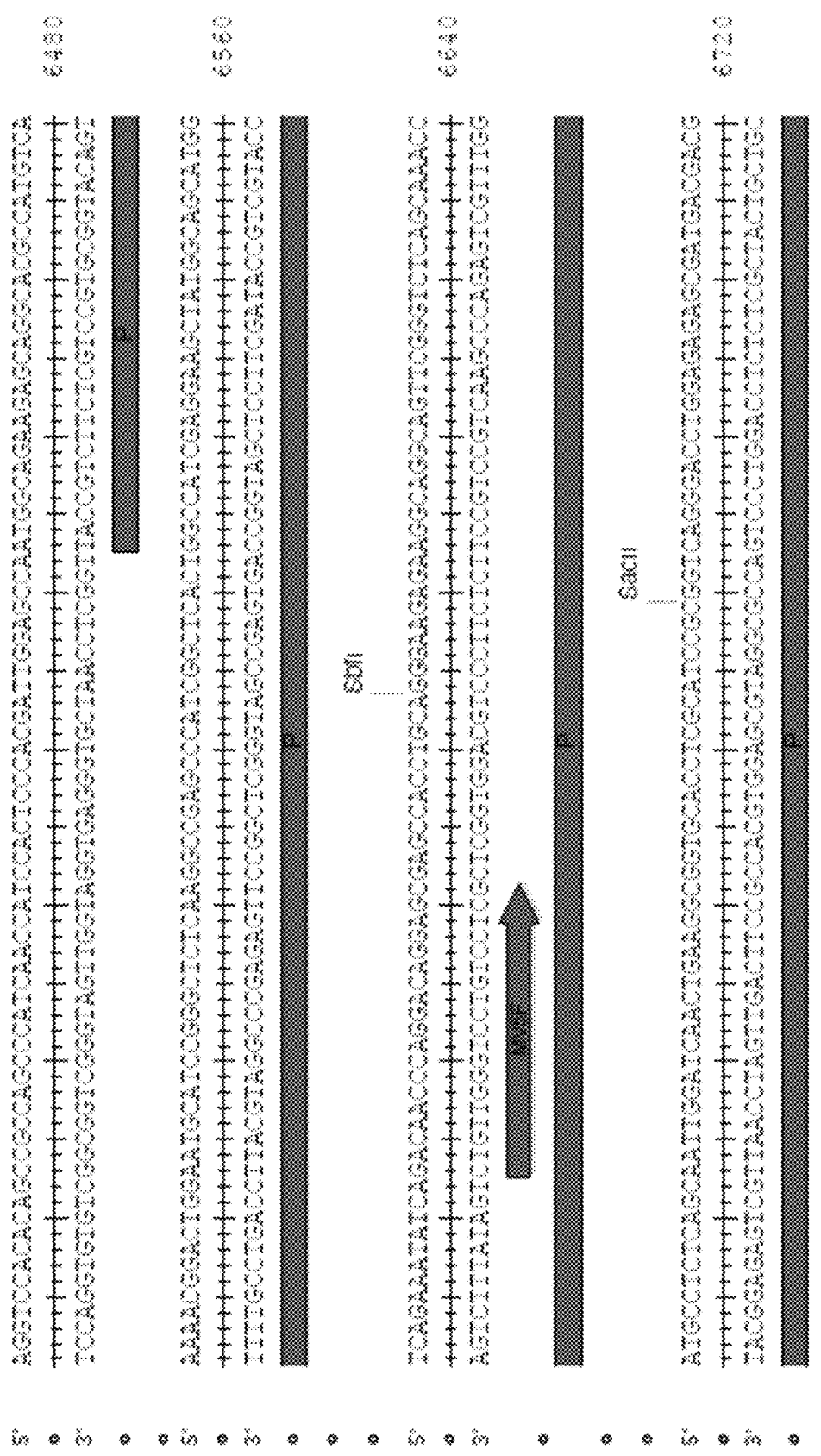
Figure 21:
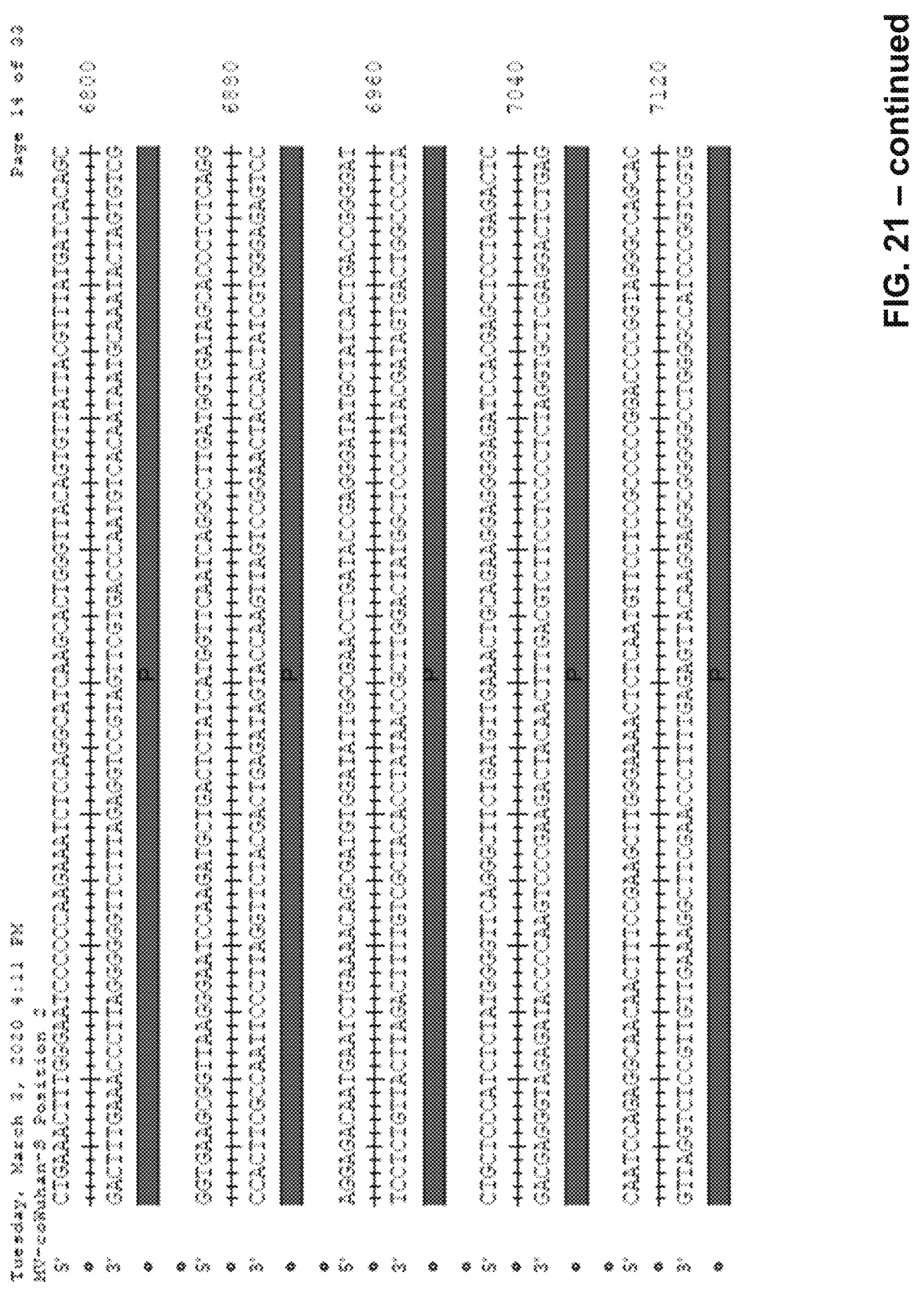
Figure 21:
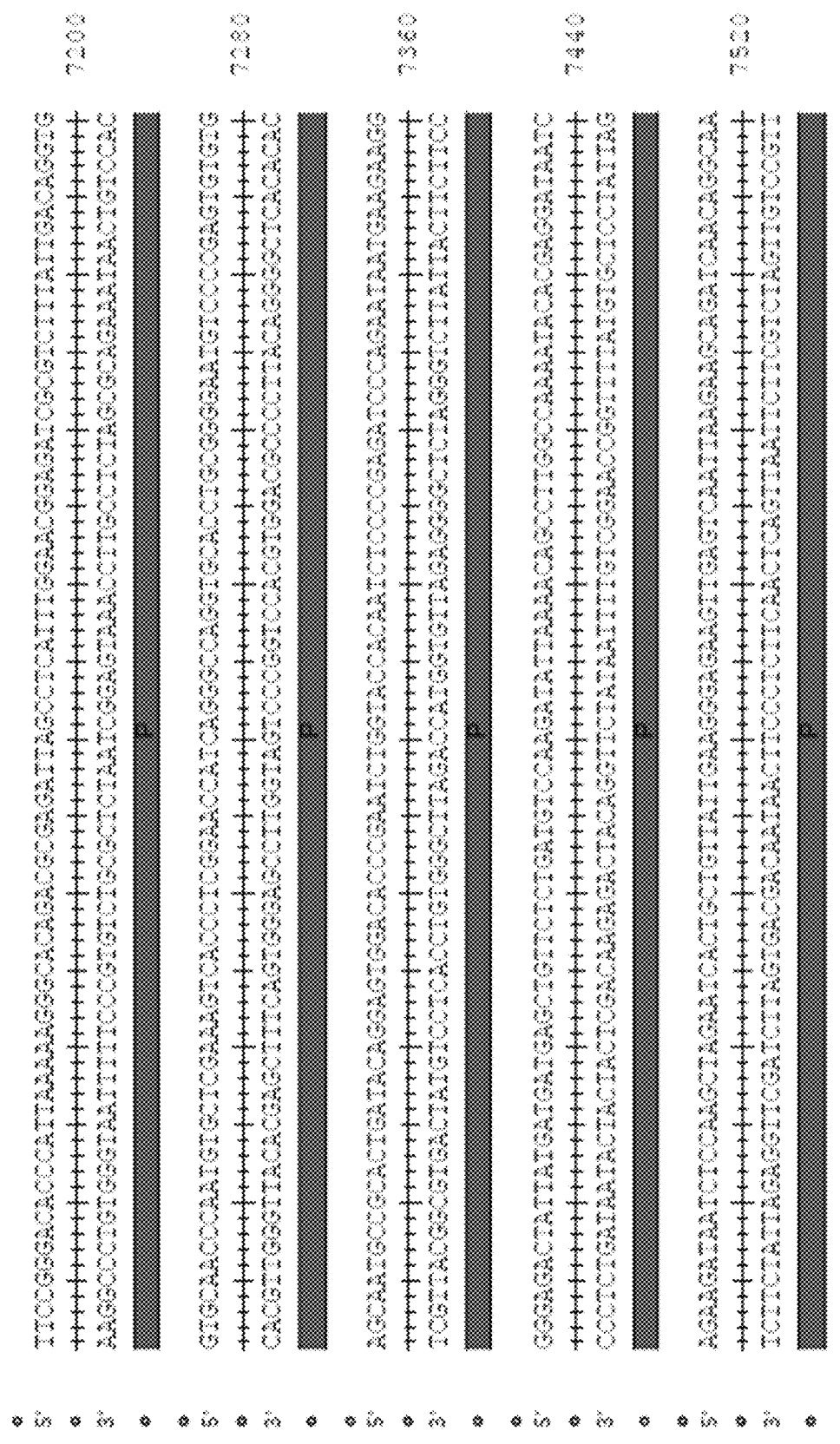
Figure 21:
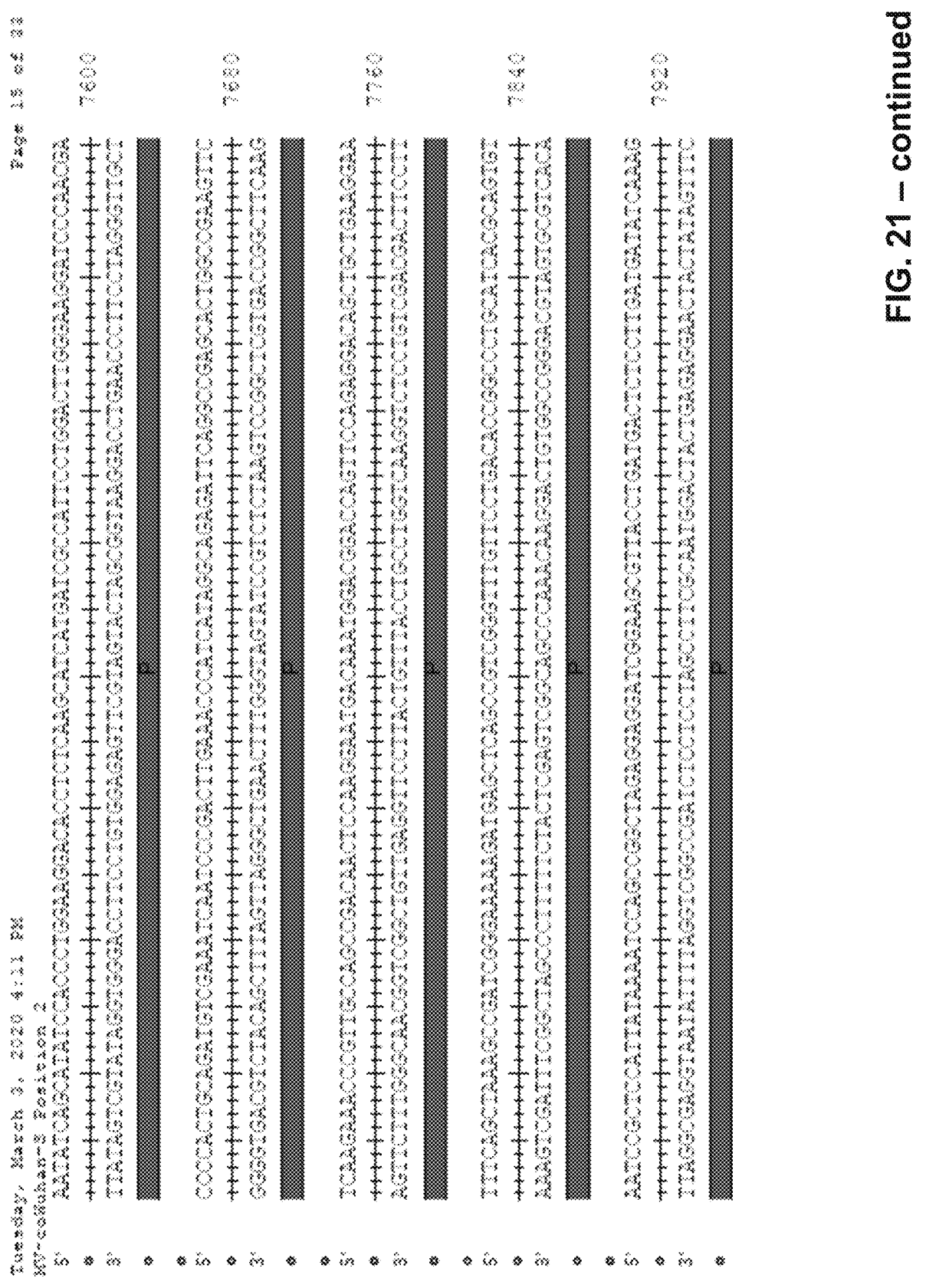
Figure 21:
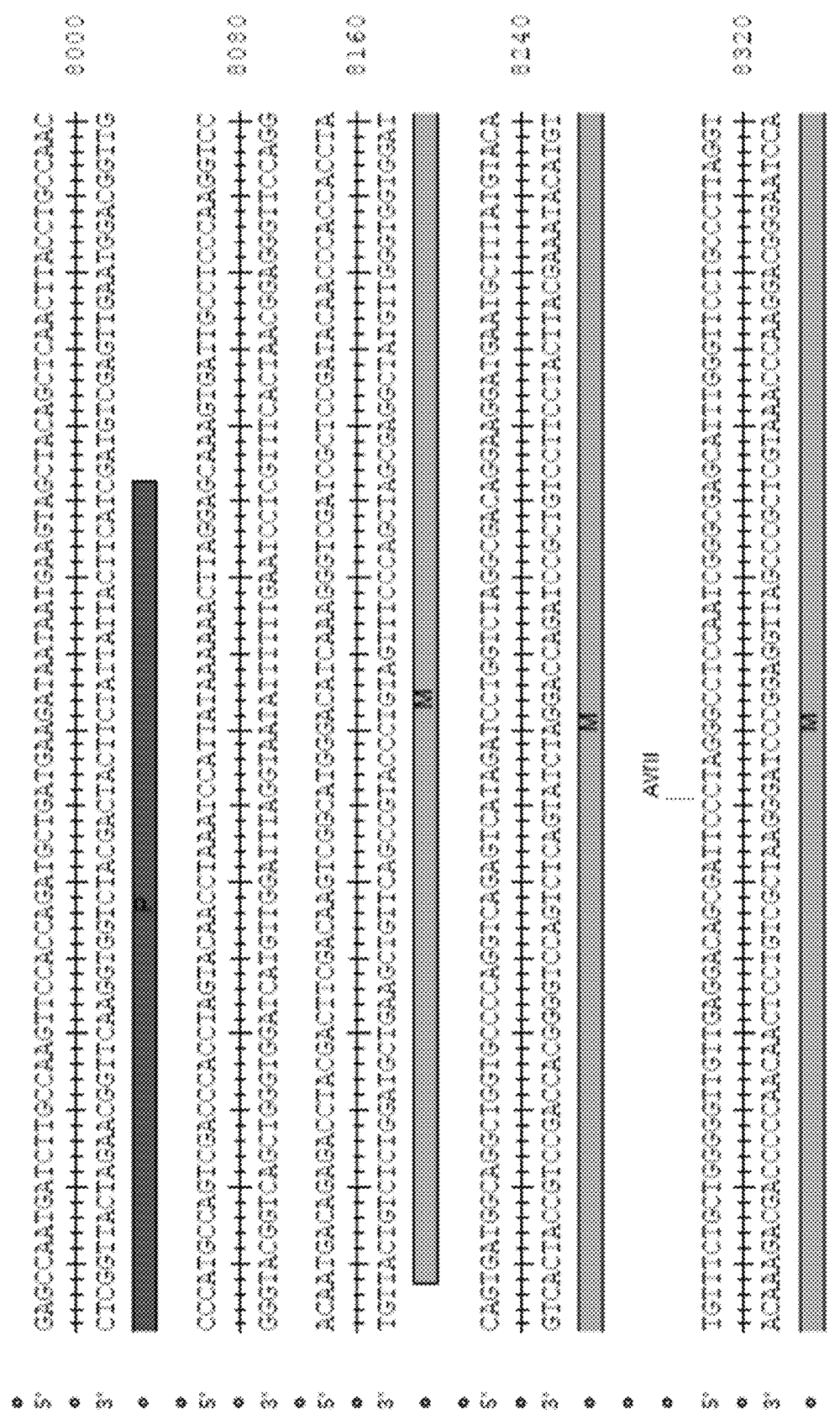
Figure 21:
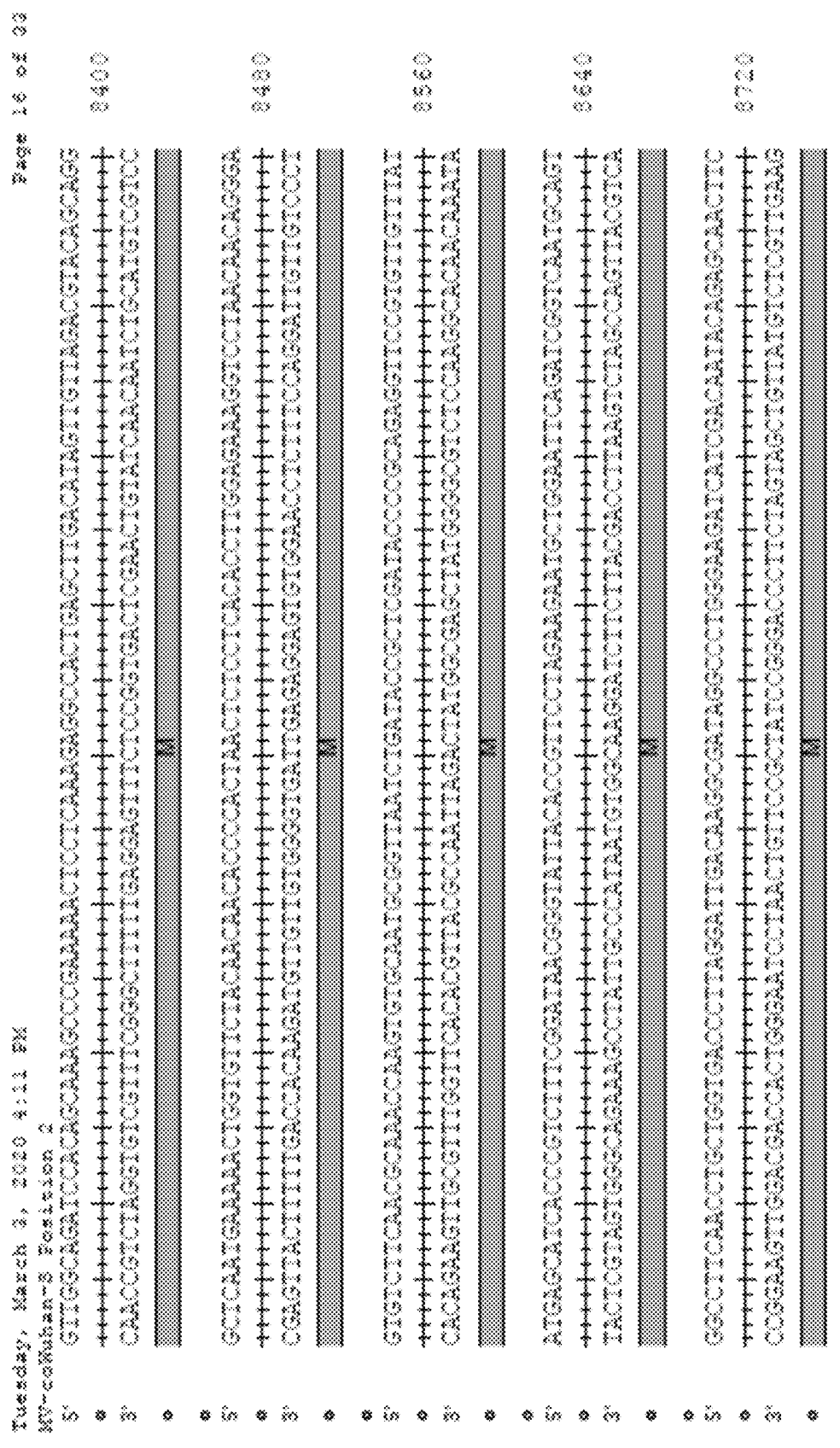
Figure 21:
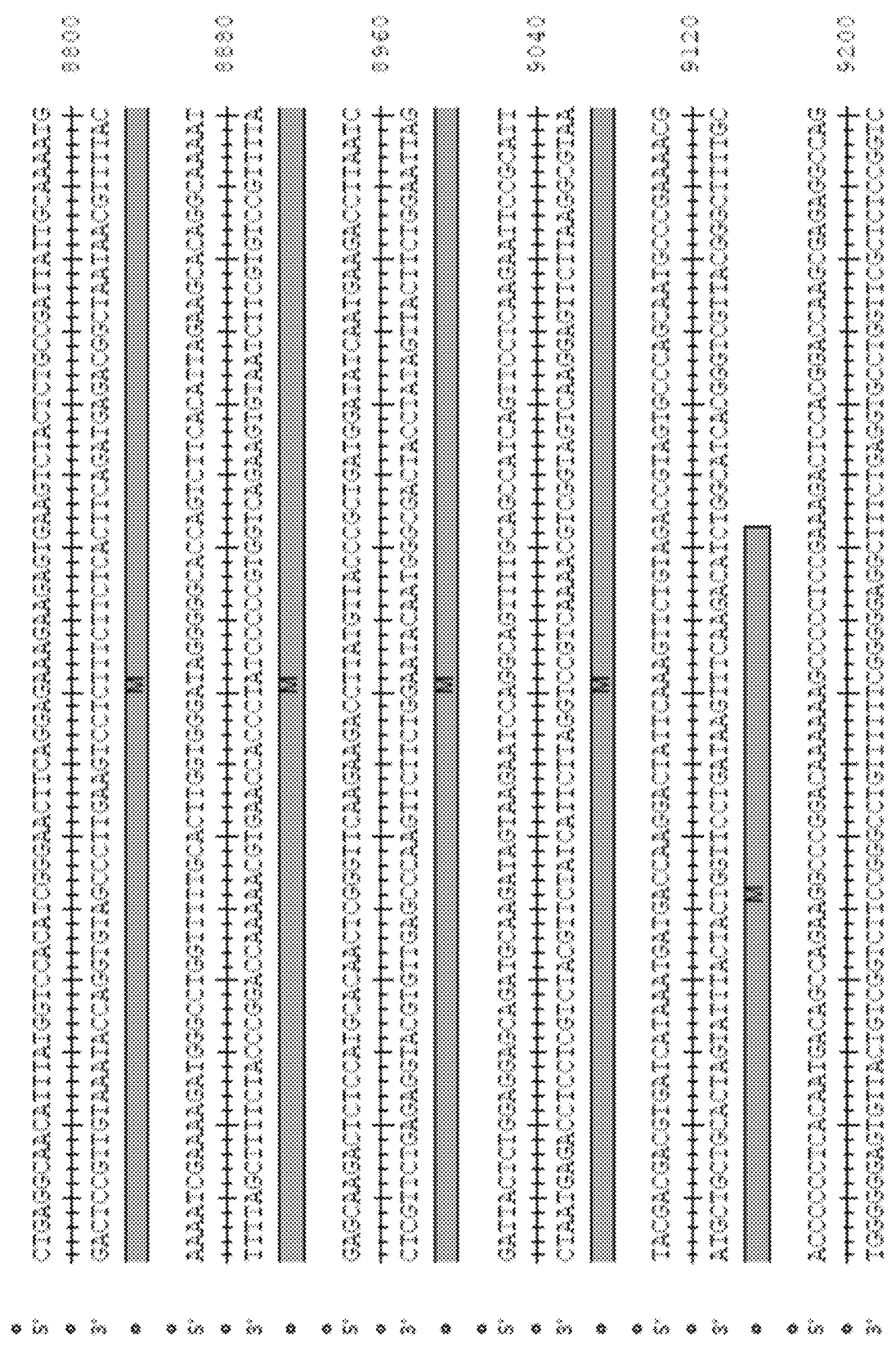
Figure 21:
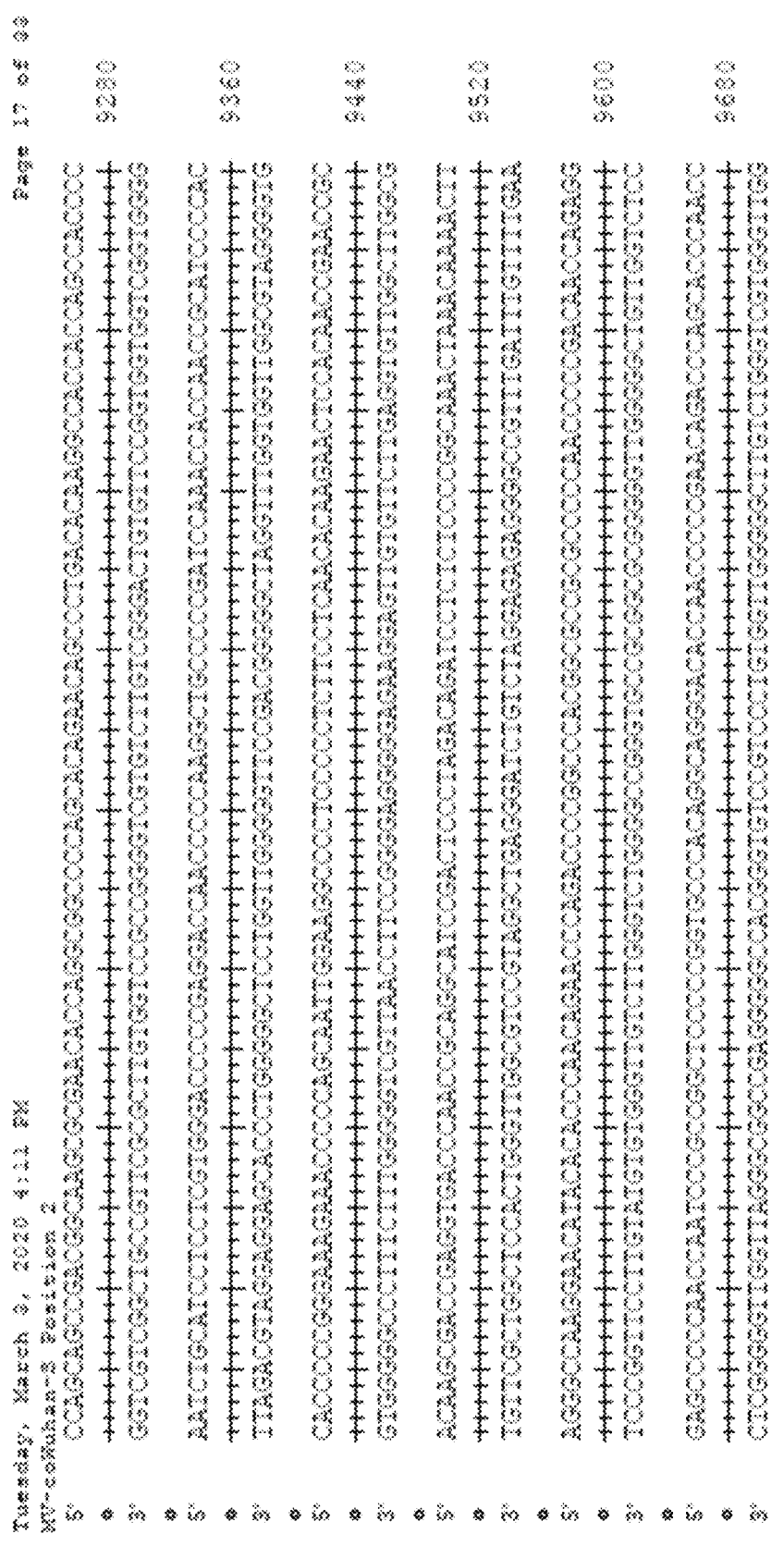
Figure 21:
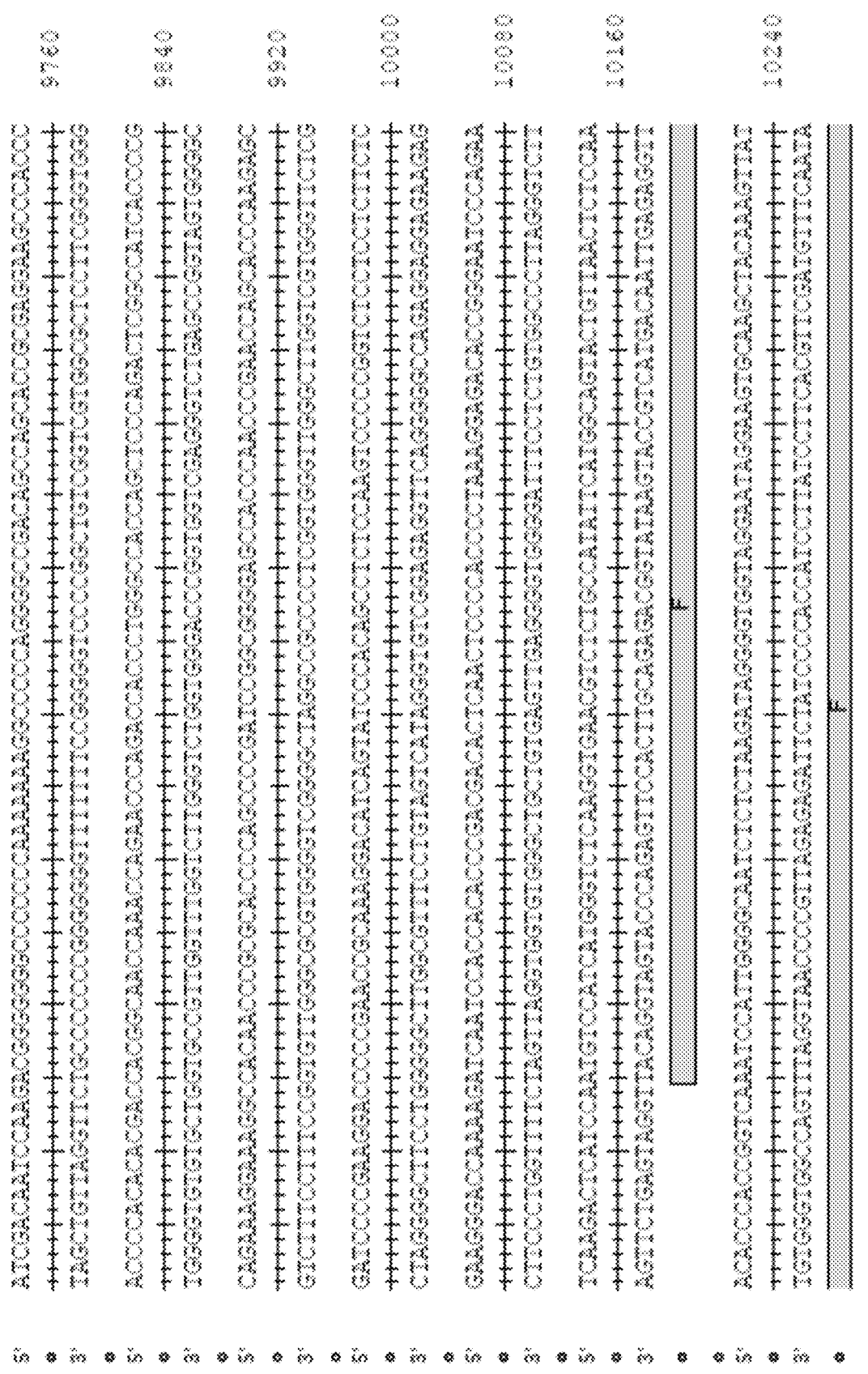
Figure 21:
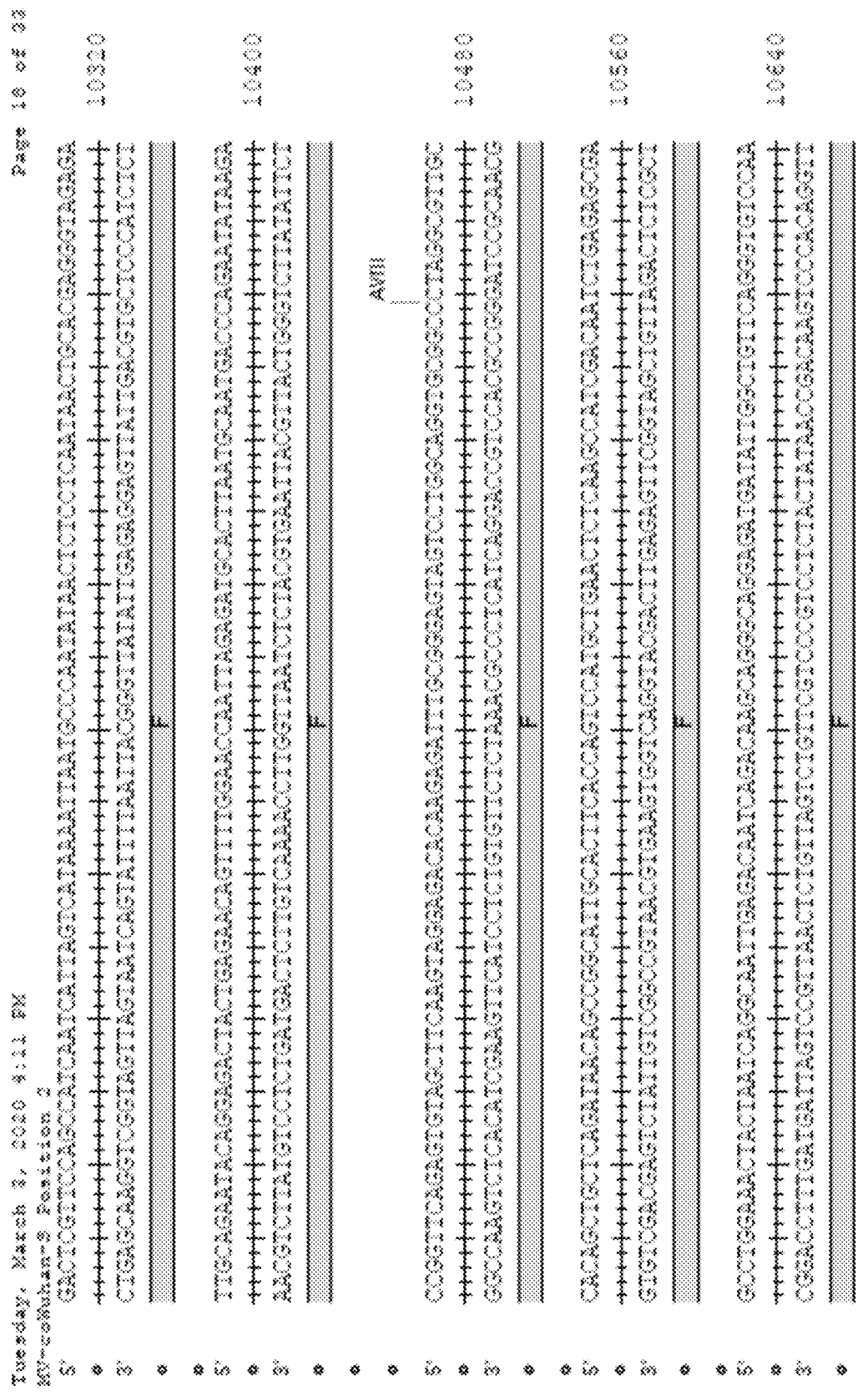
Figure 21:
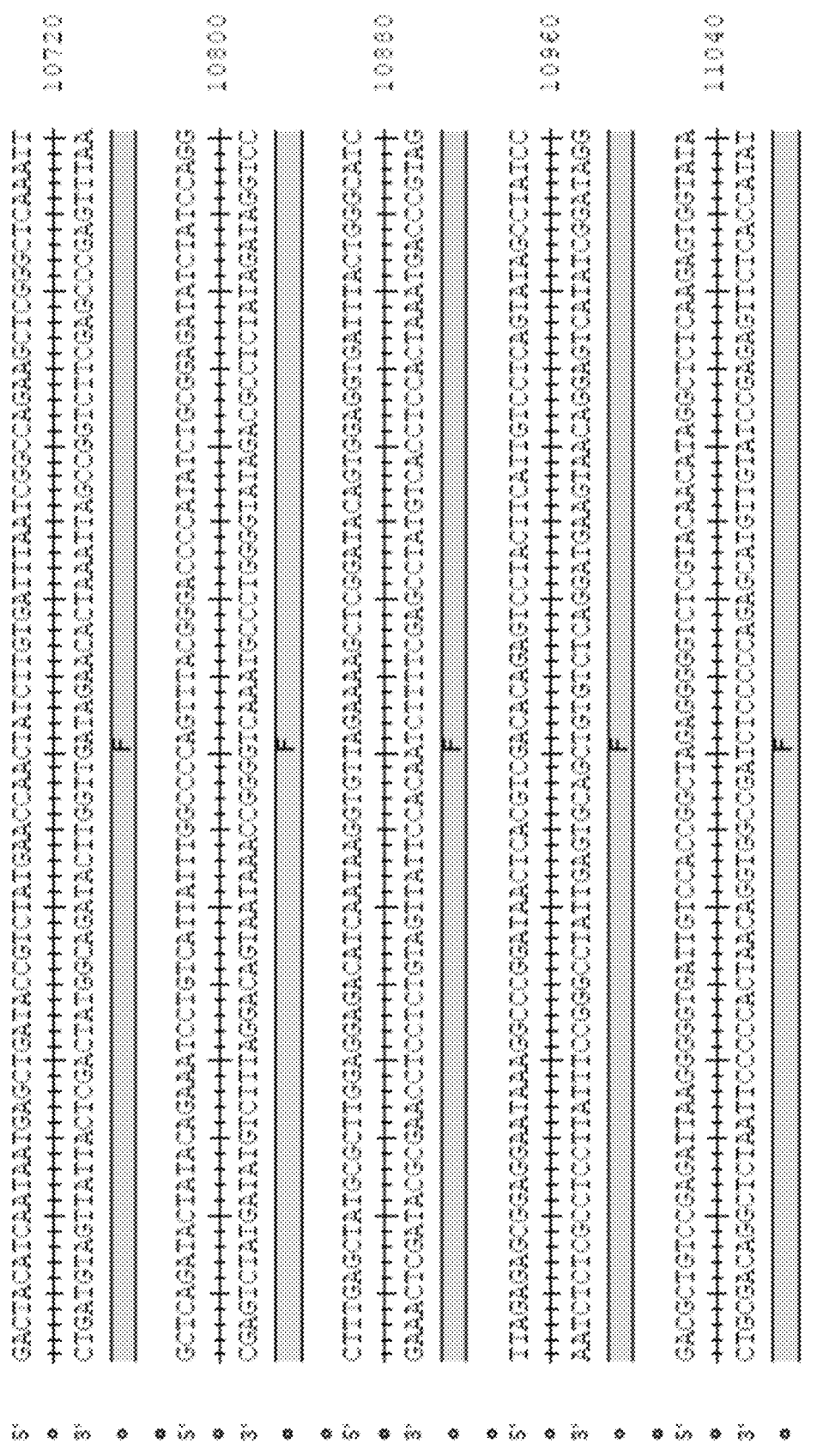
Figure 21:
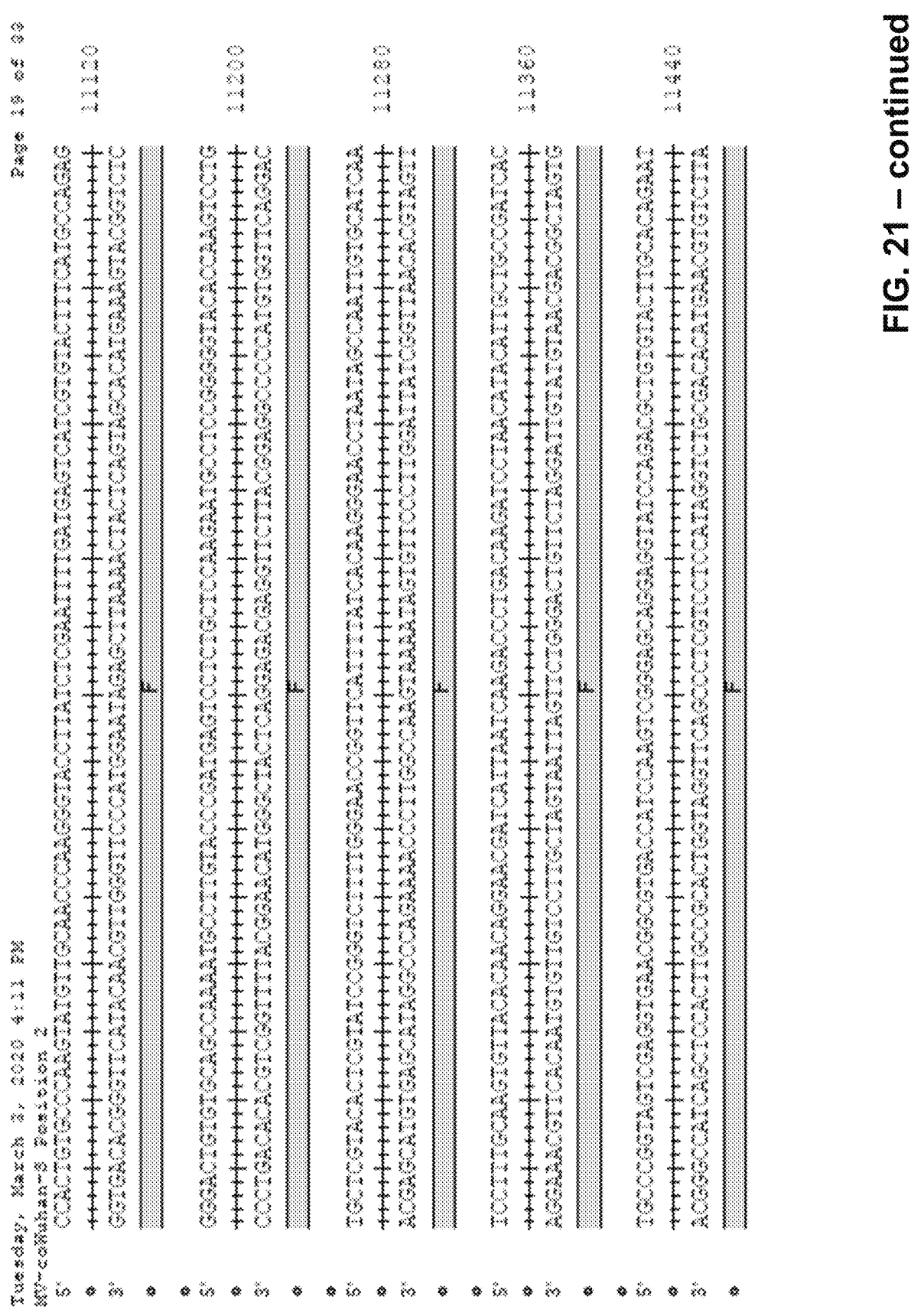
Figure 21:
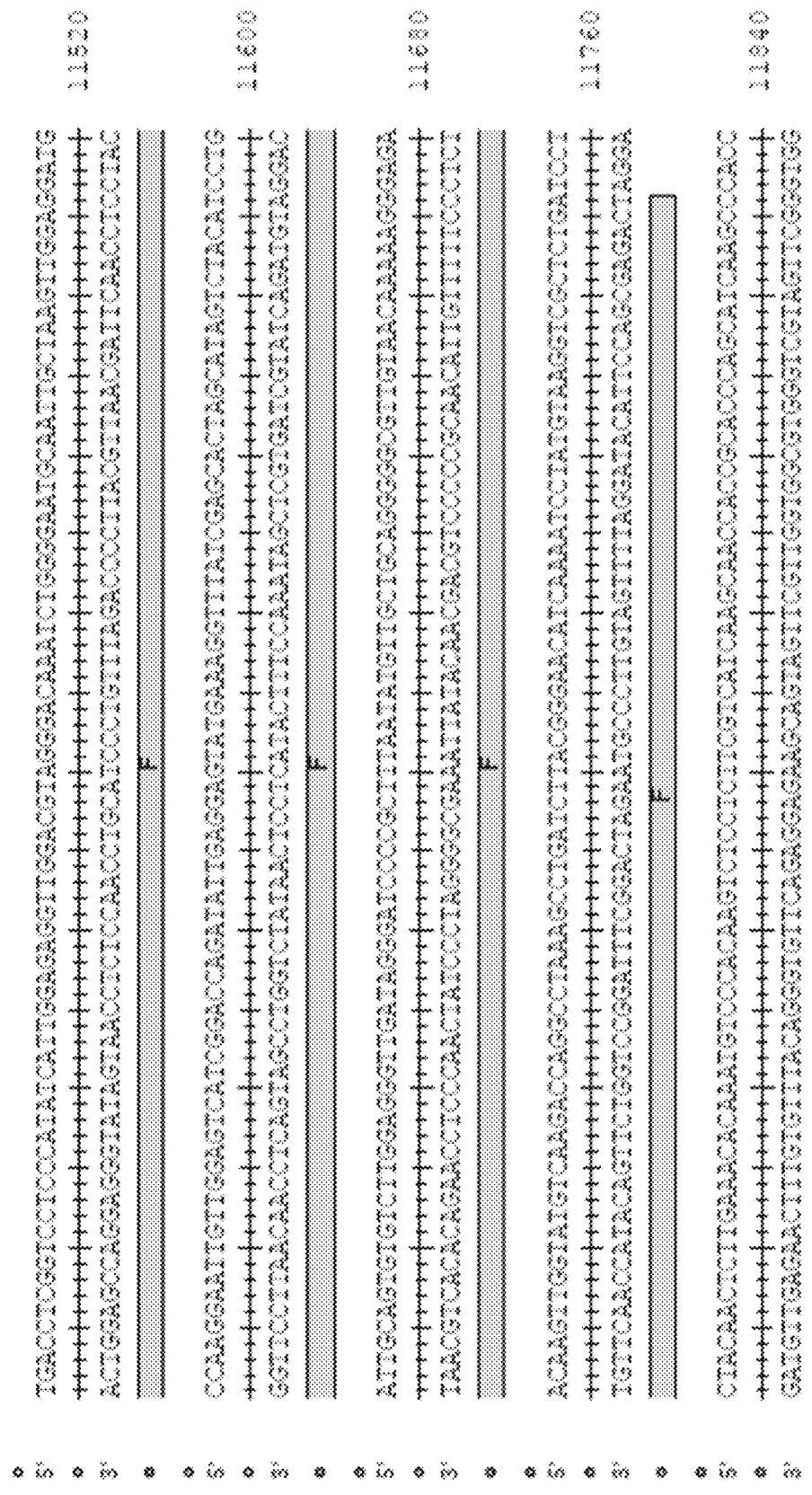
Figure 21:
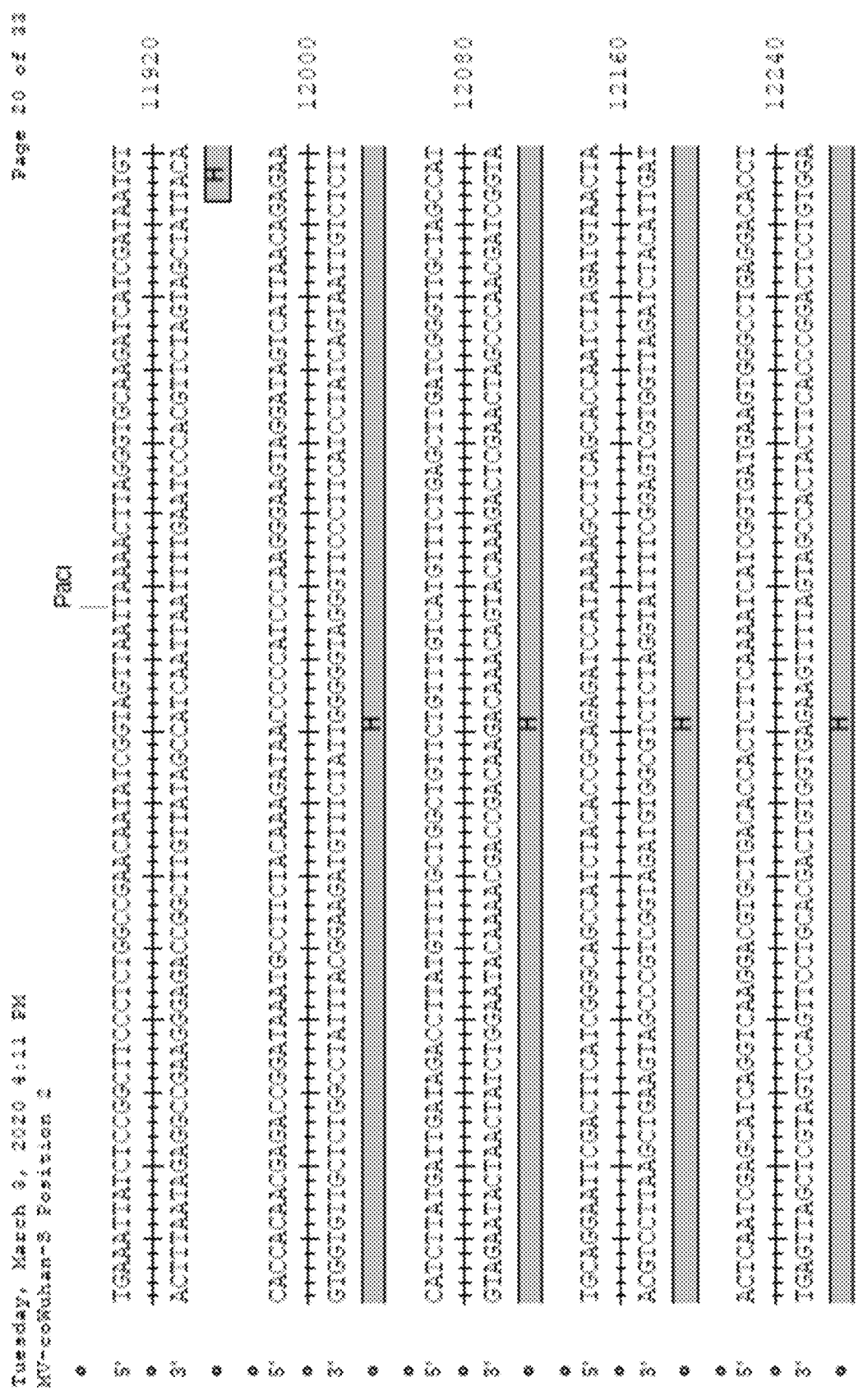
Figure 21:
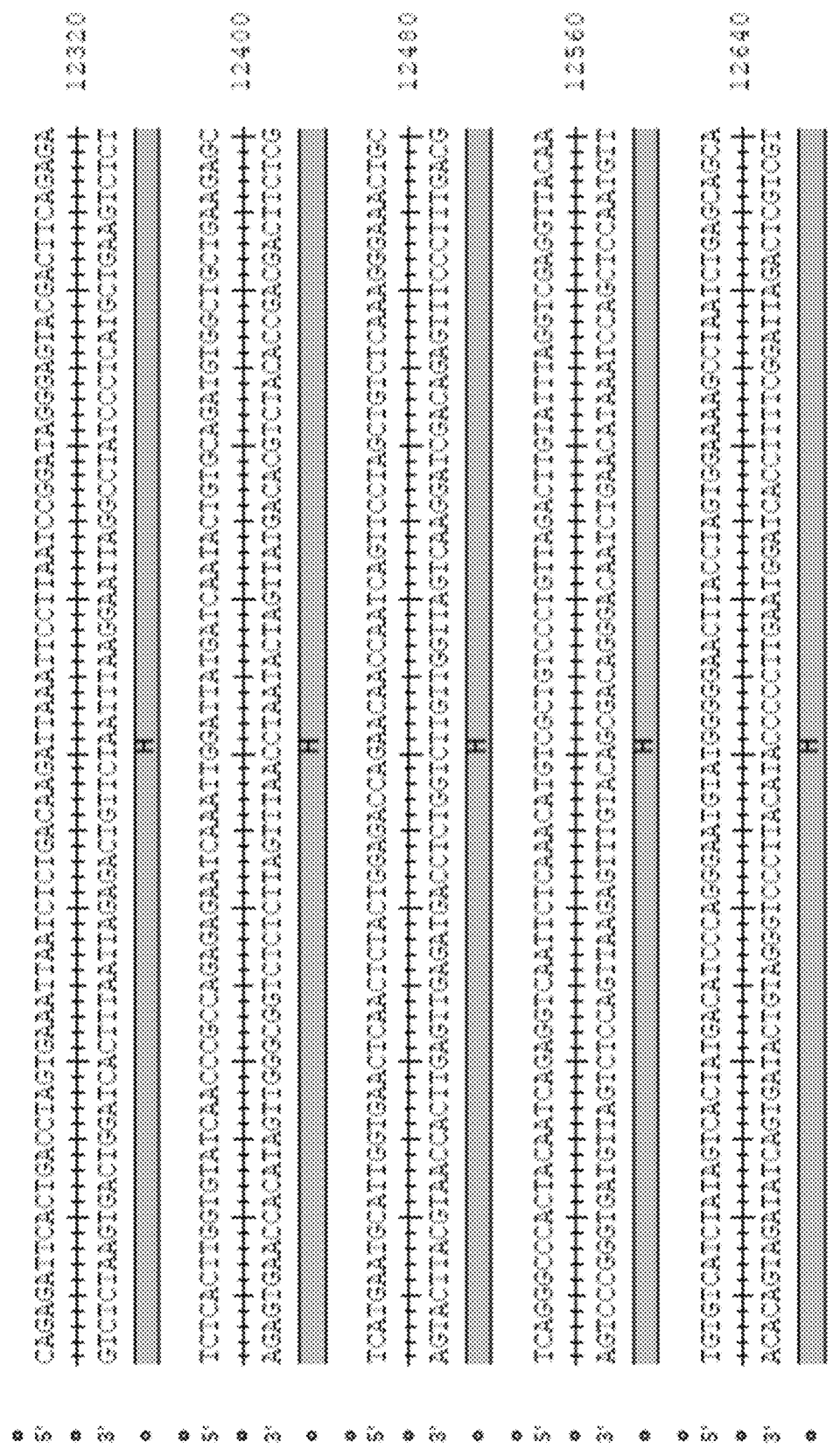
Figure 21:
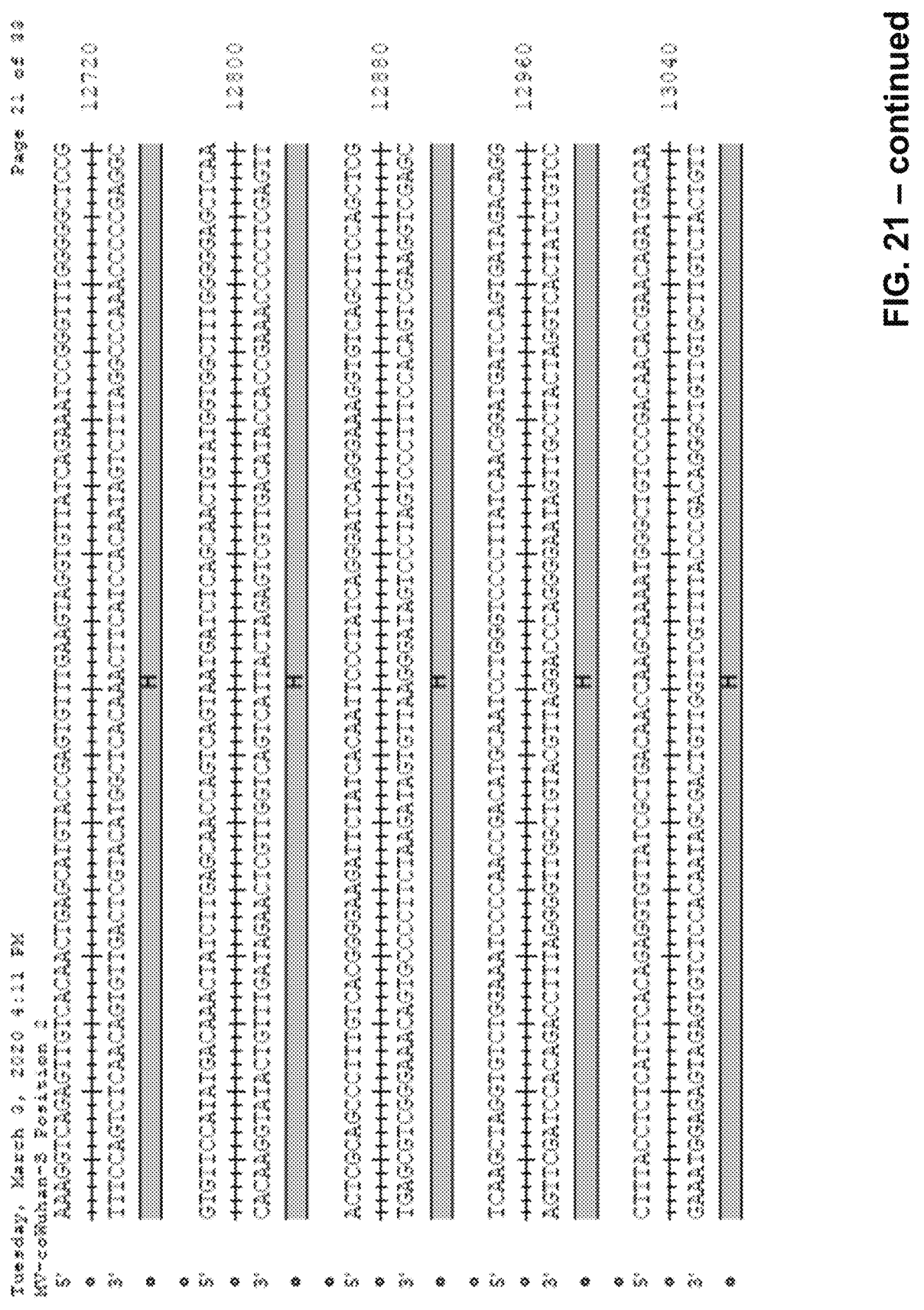
Figure 21:
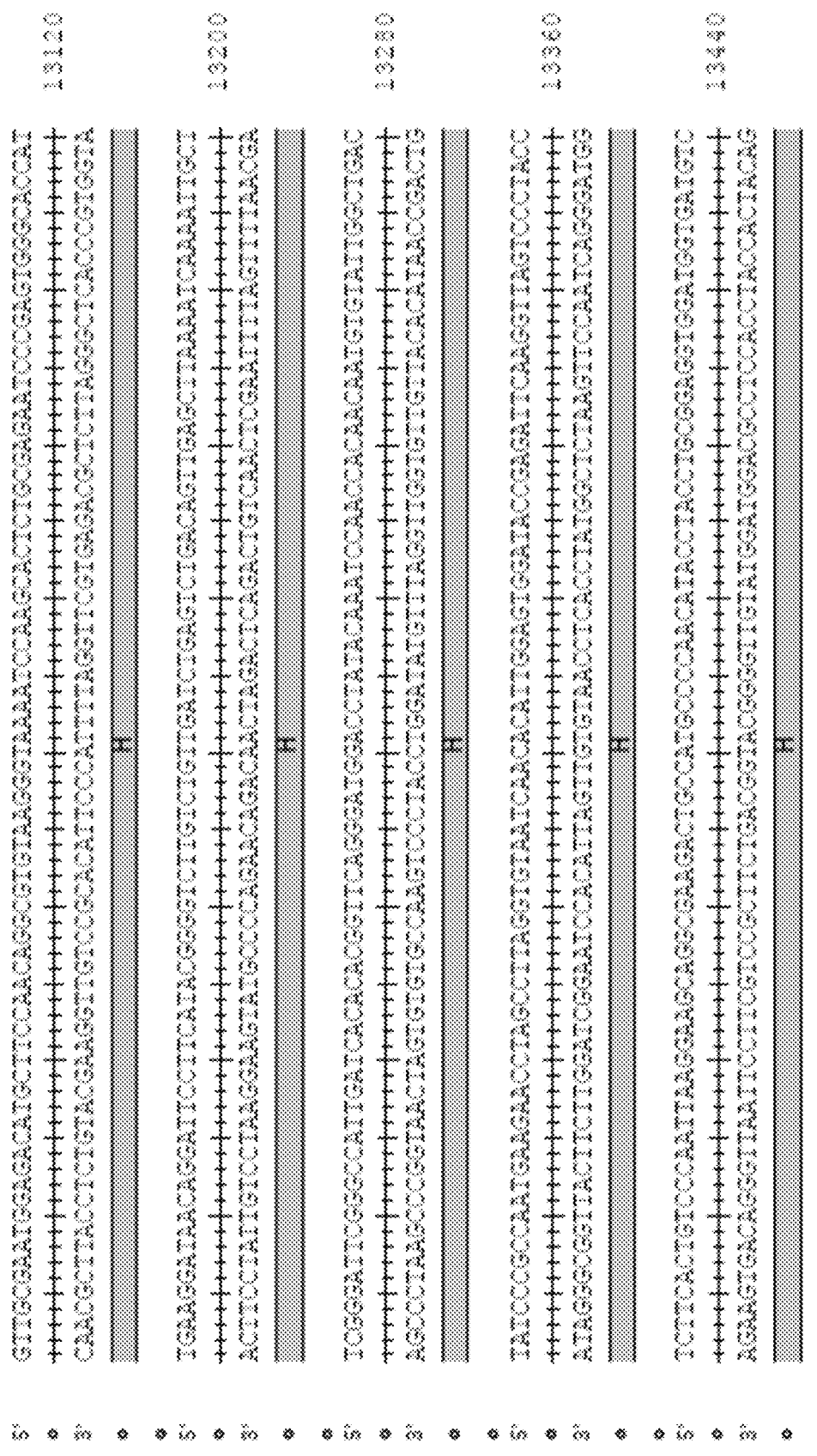
Figure 21:
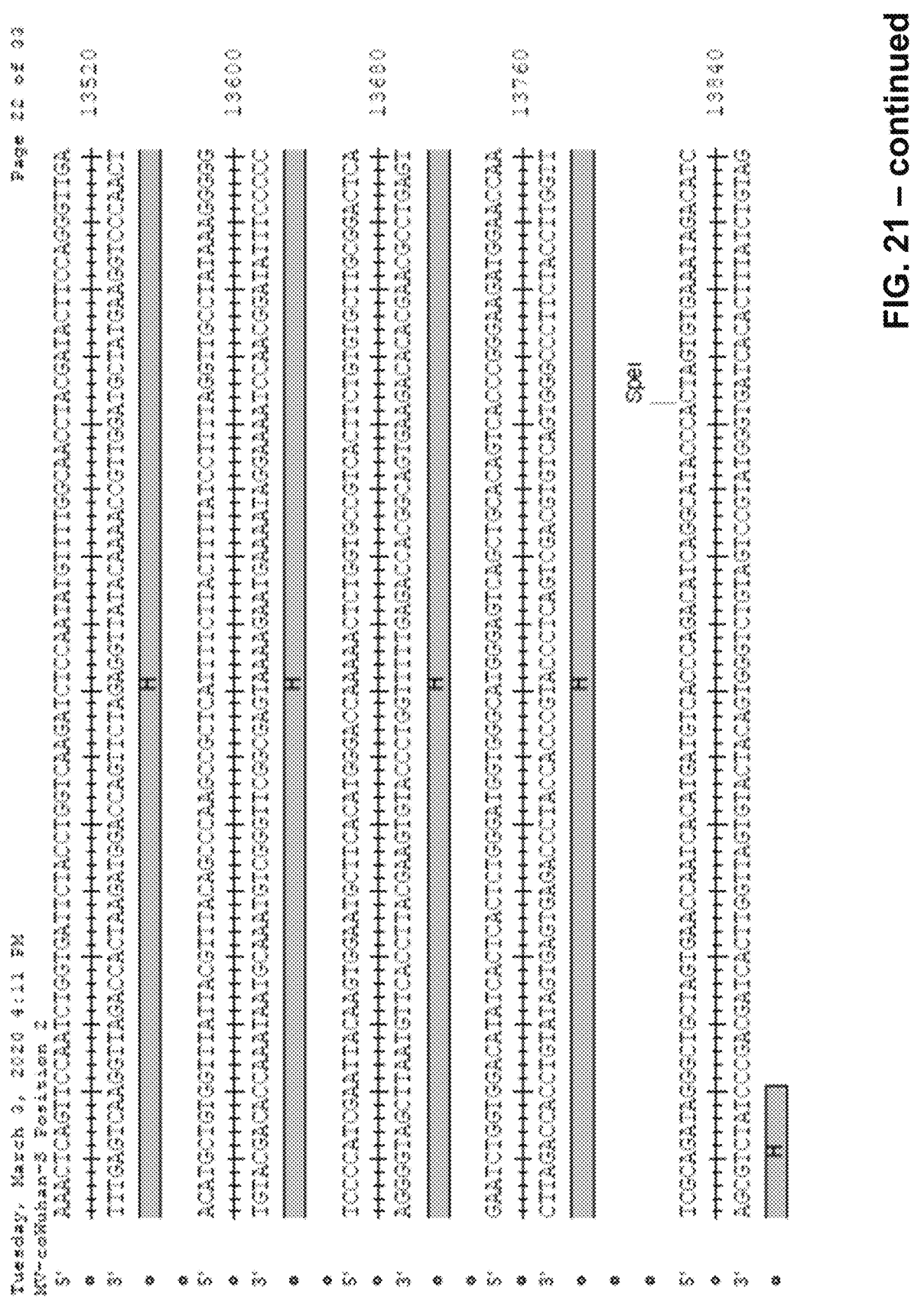
Figure 21:
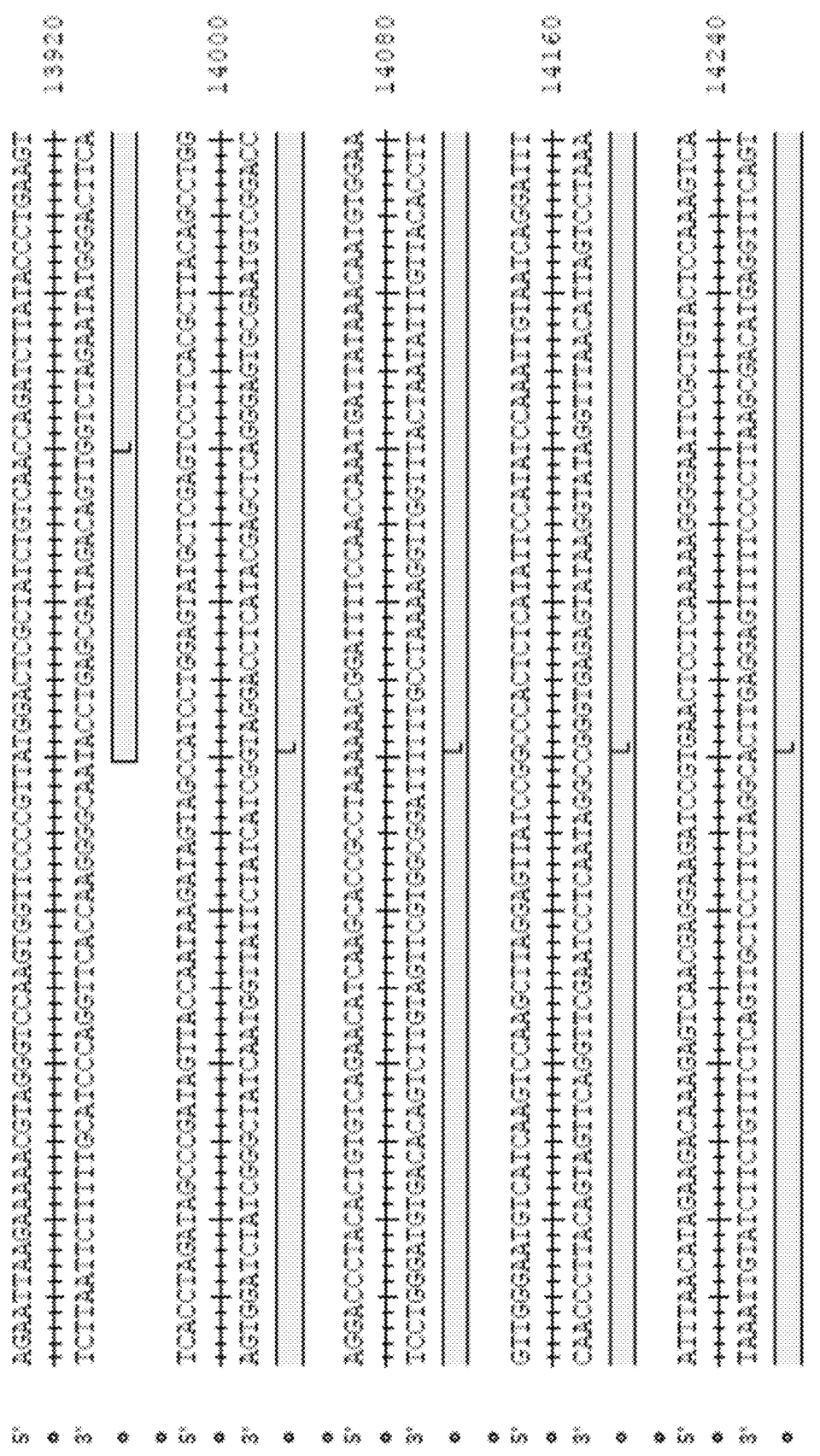
Figure 21:
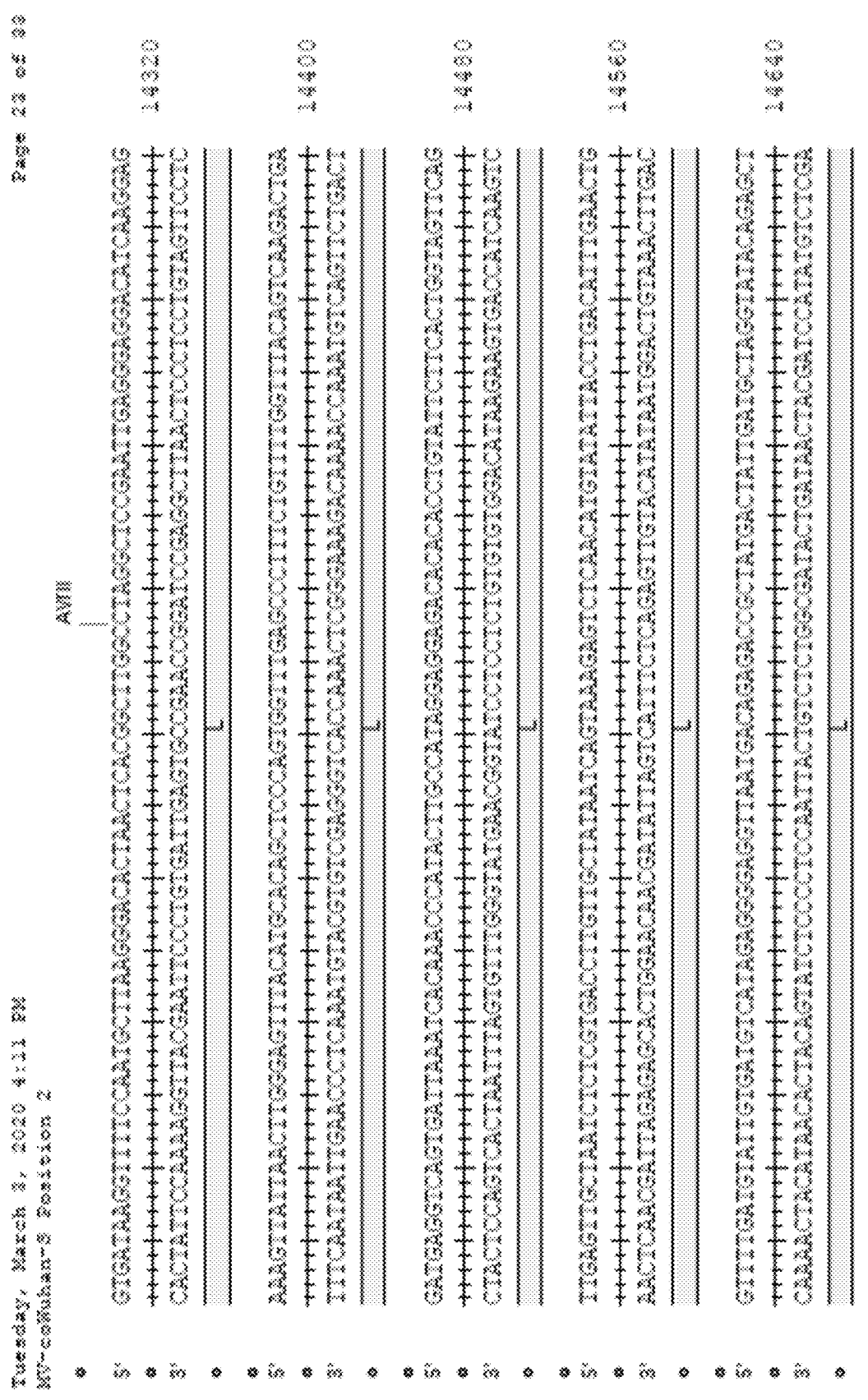
Figure 21:
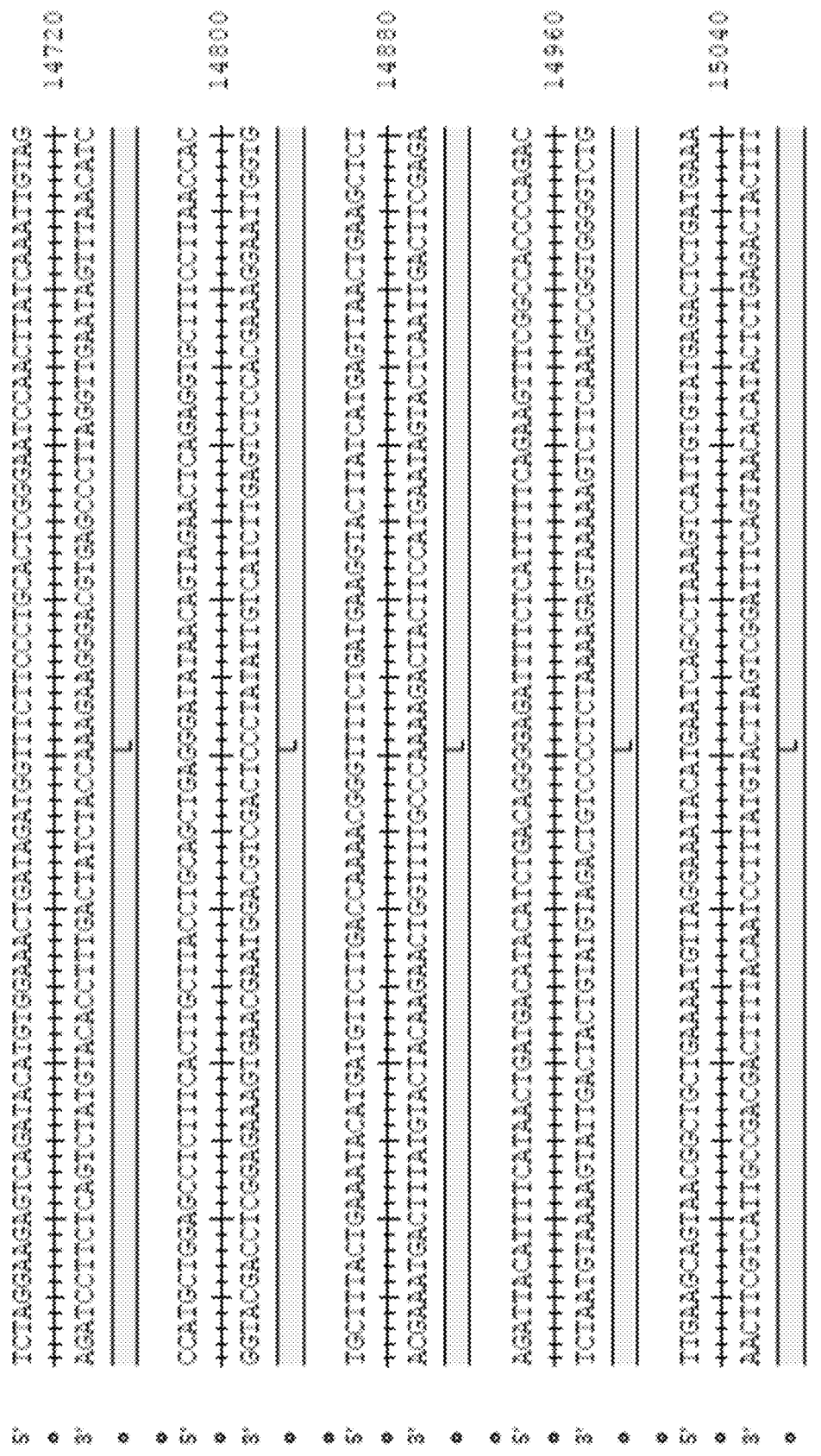
Figure 21:
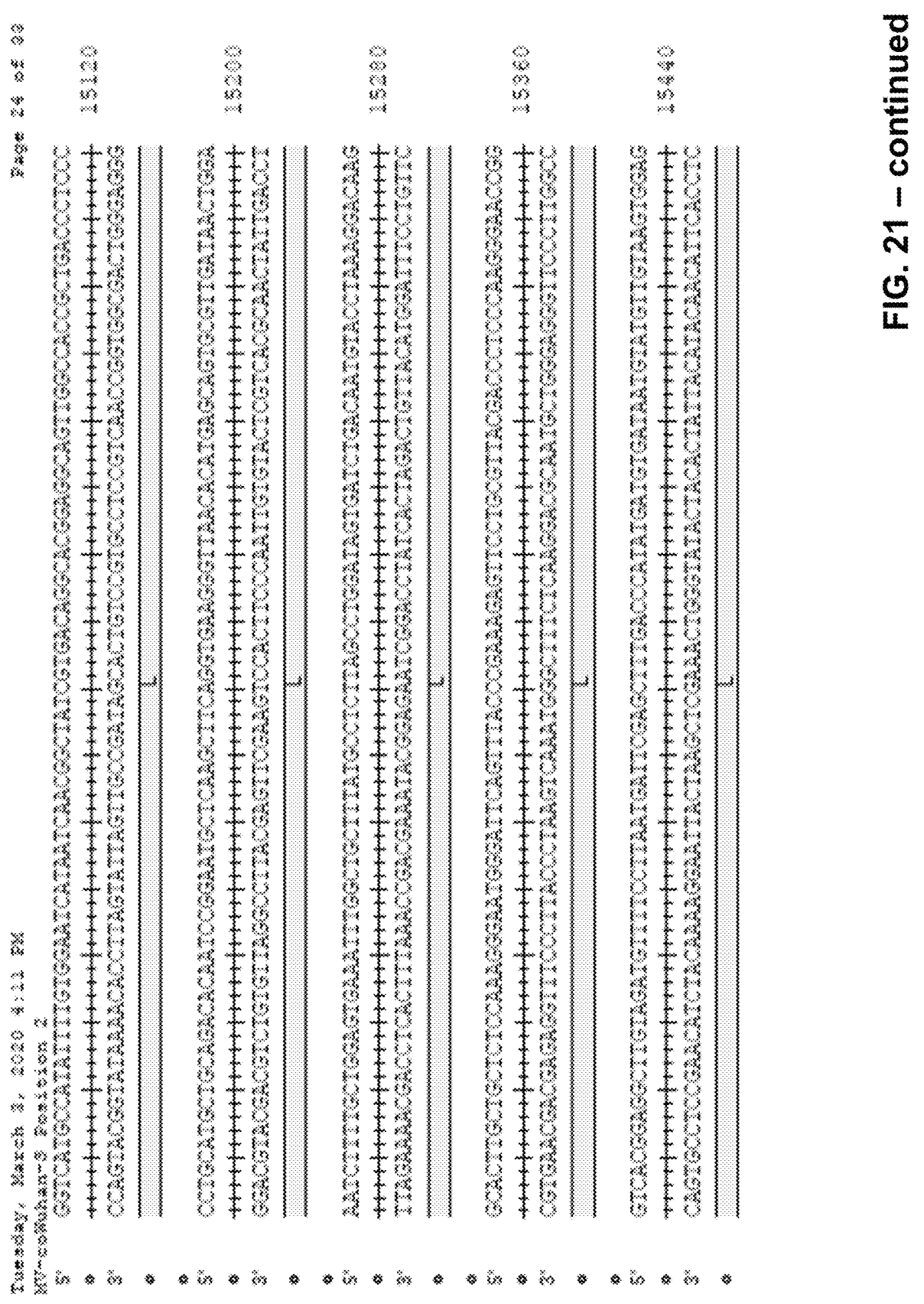
Figure 21:
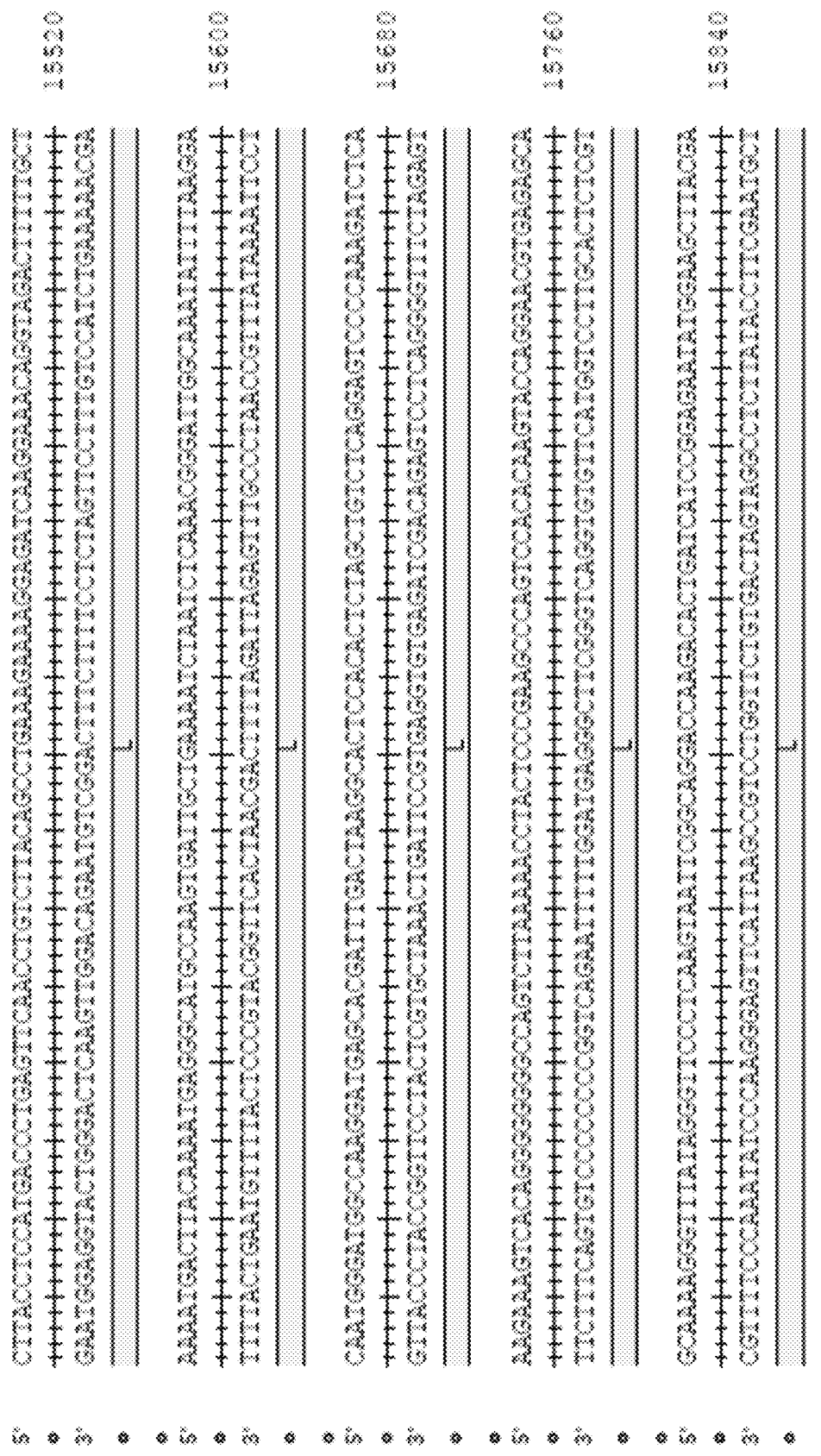
Figure 21:
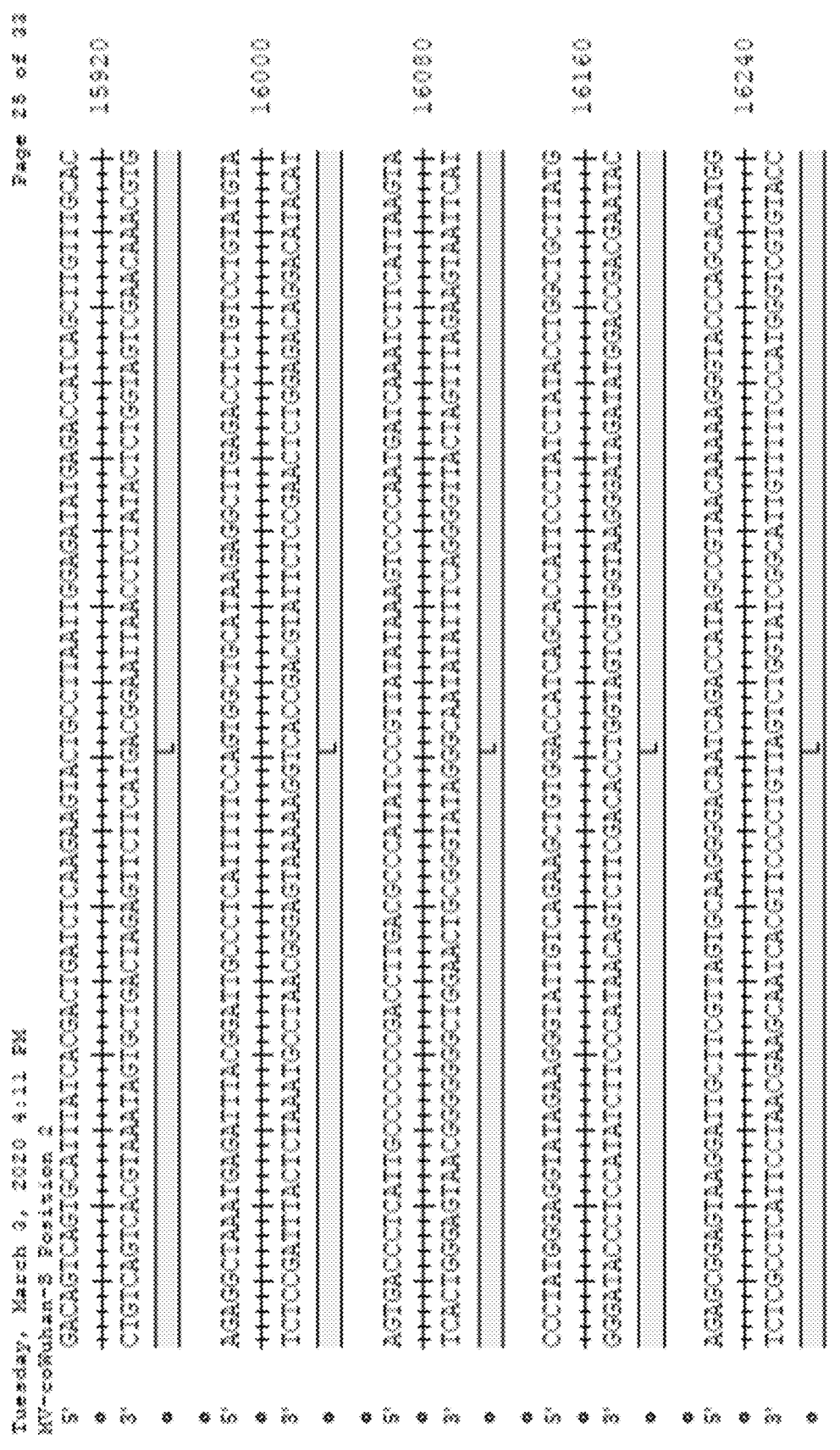
Figure 21:
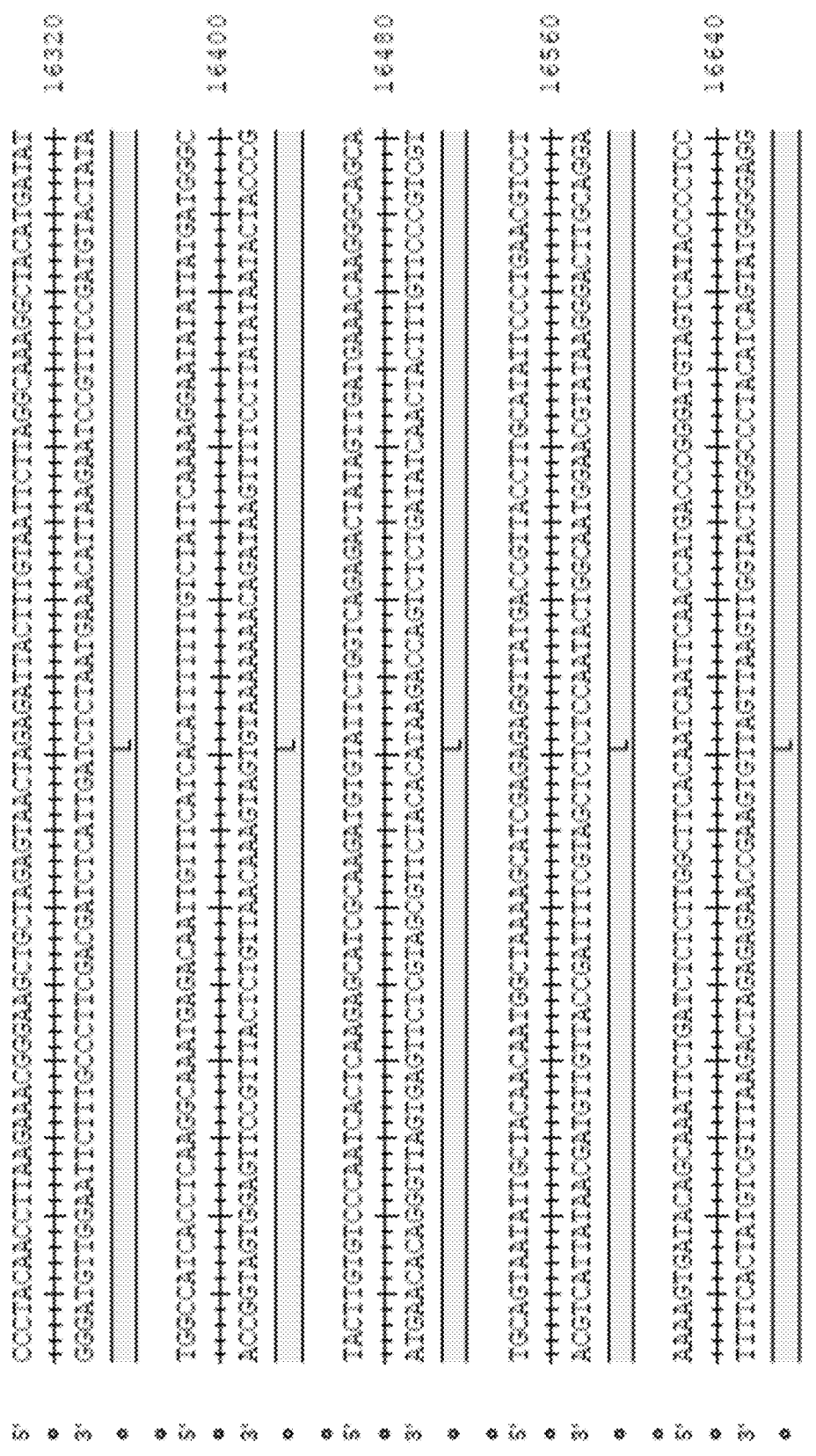
Figure 21:
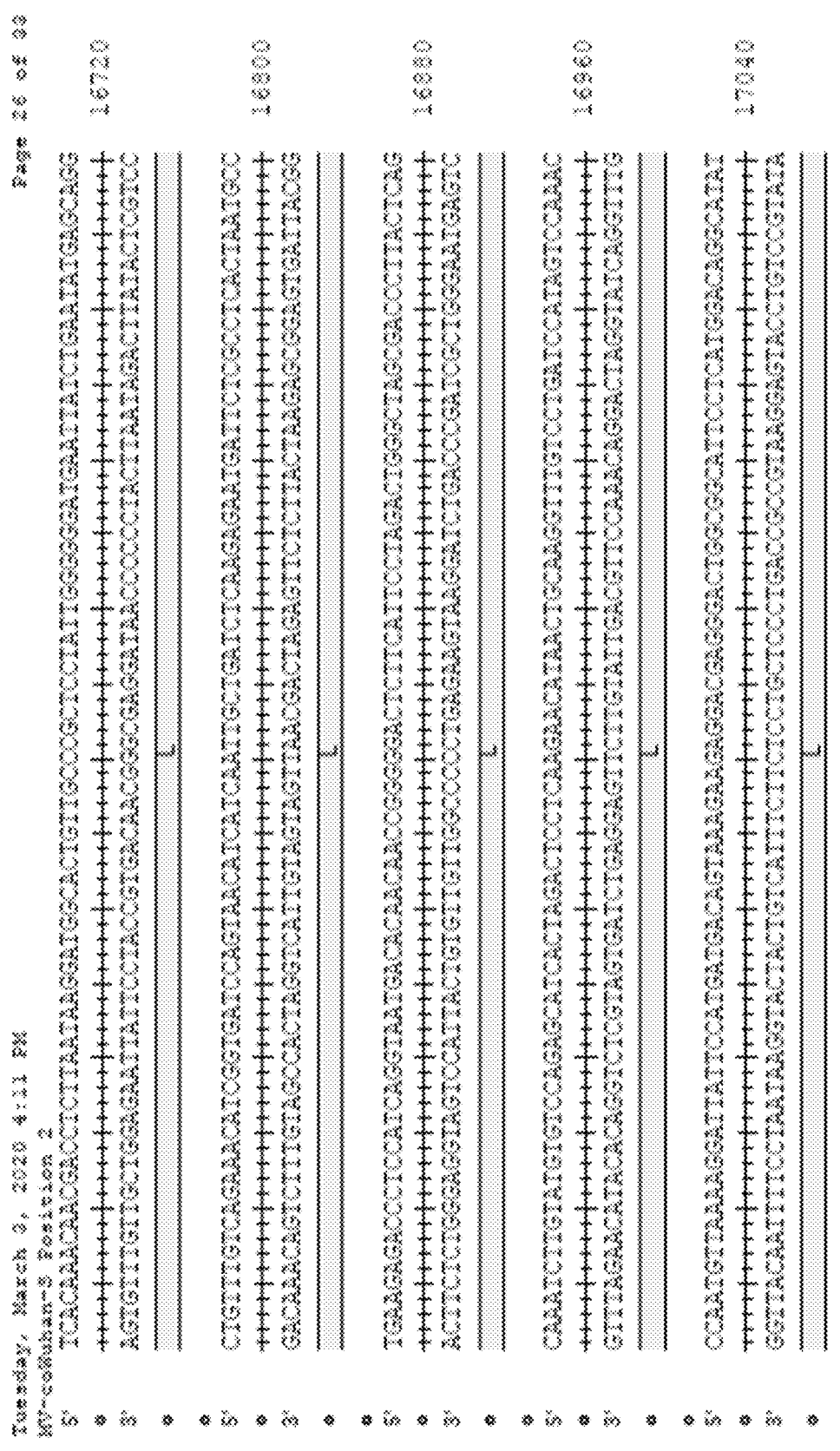
Figure 21:
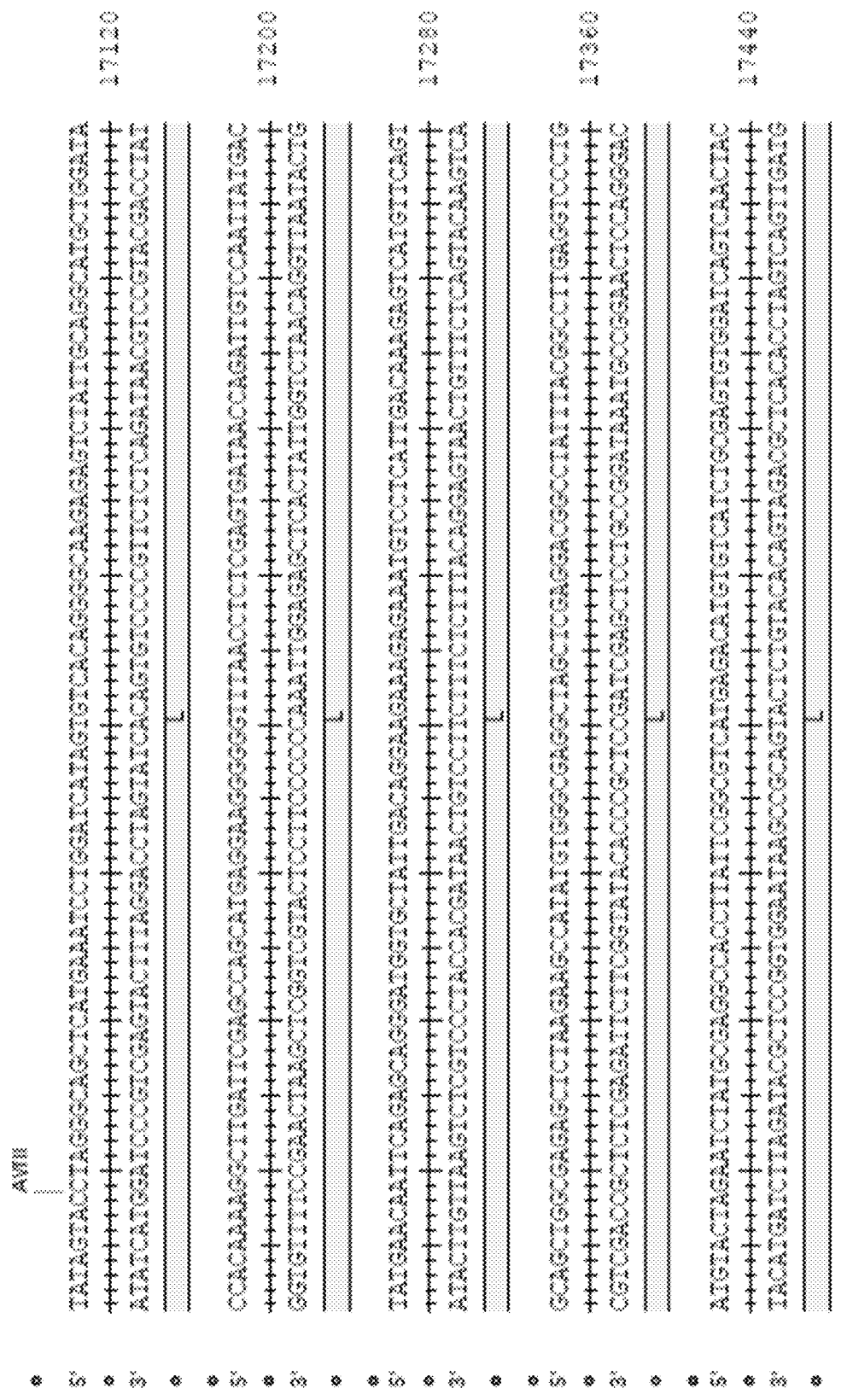
Figure 21:
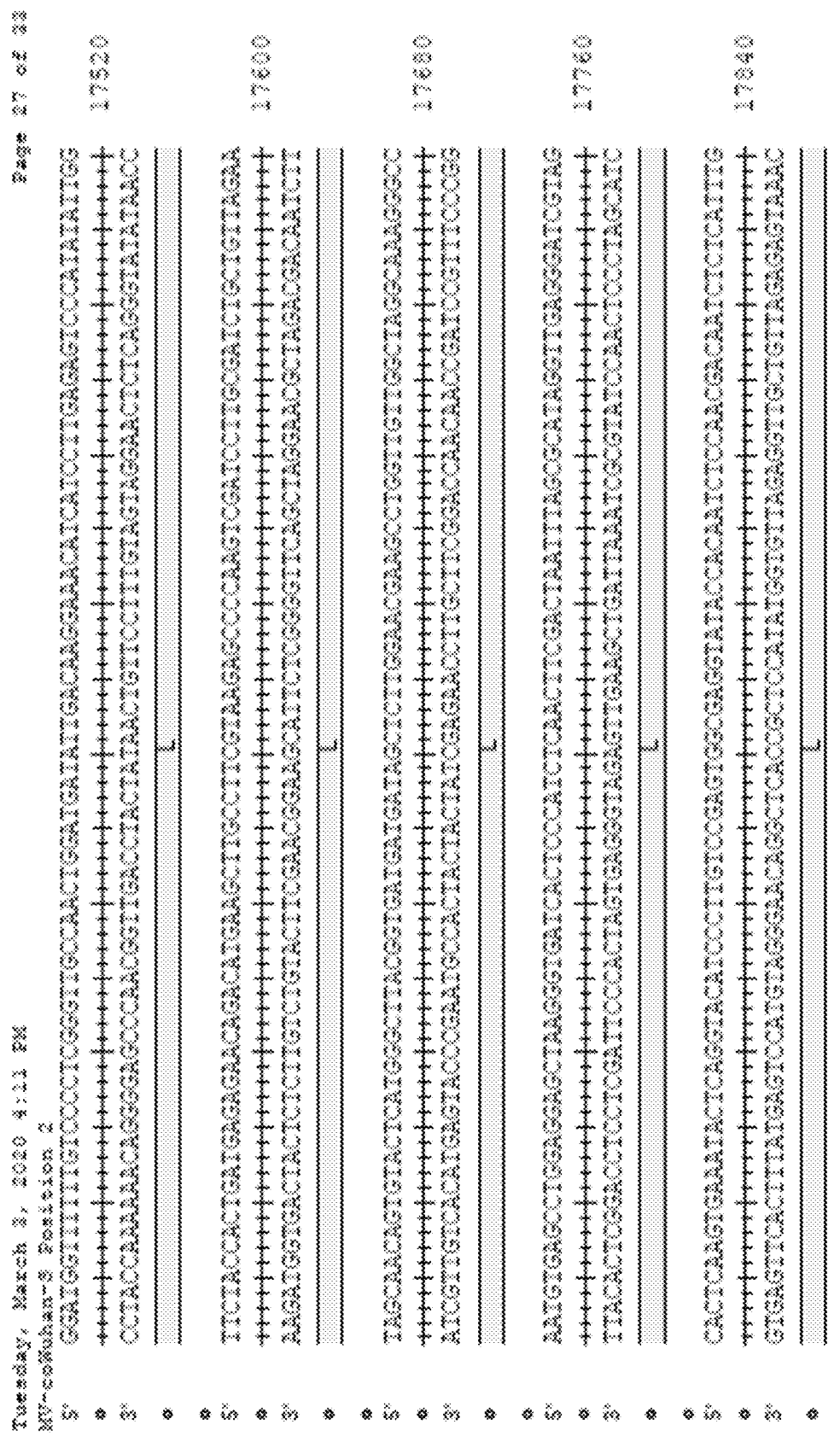
Figure 21:
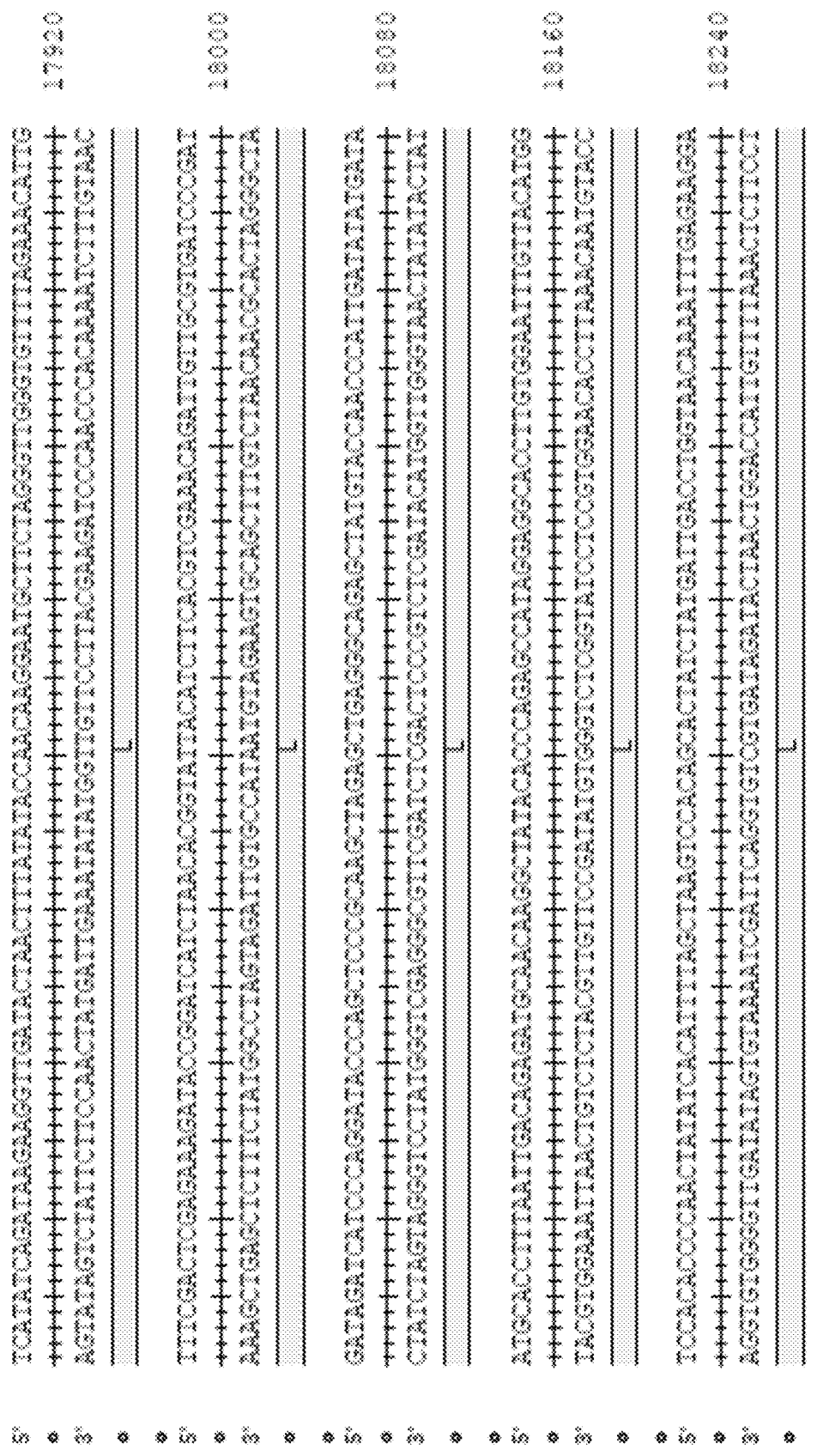
Figure 21:
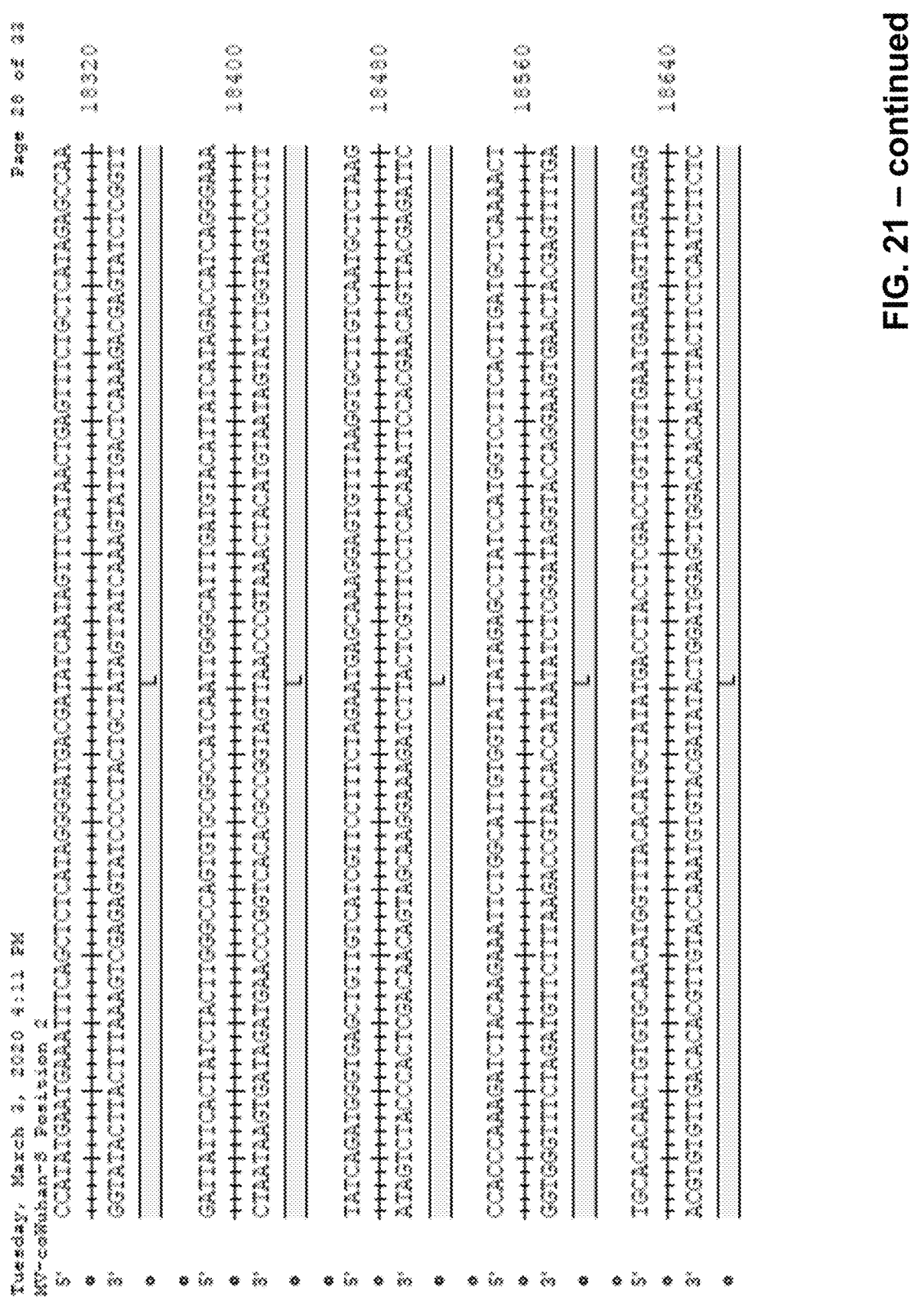
Figure 21:
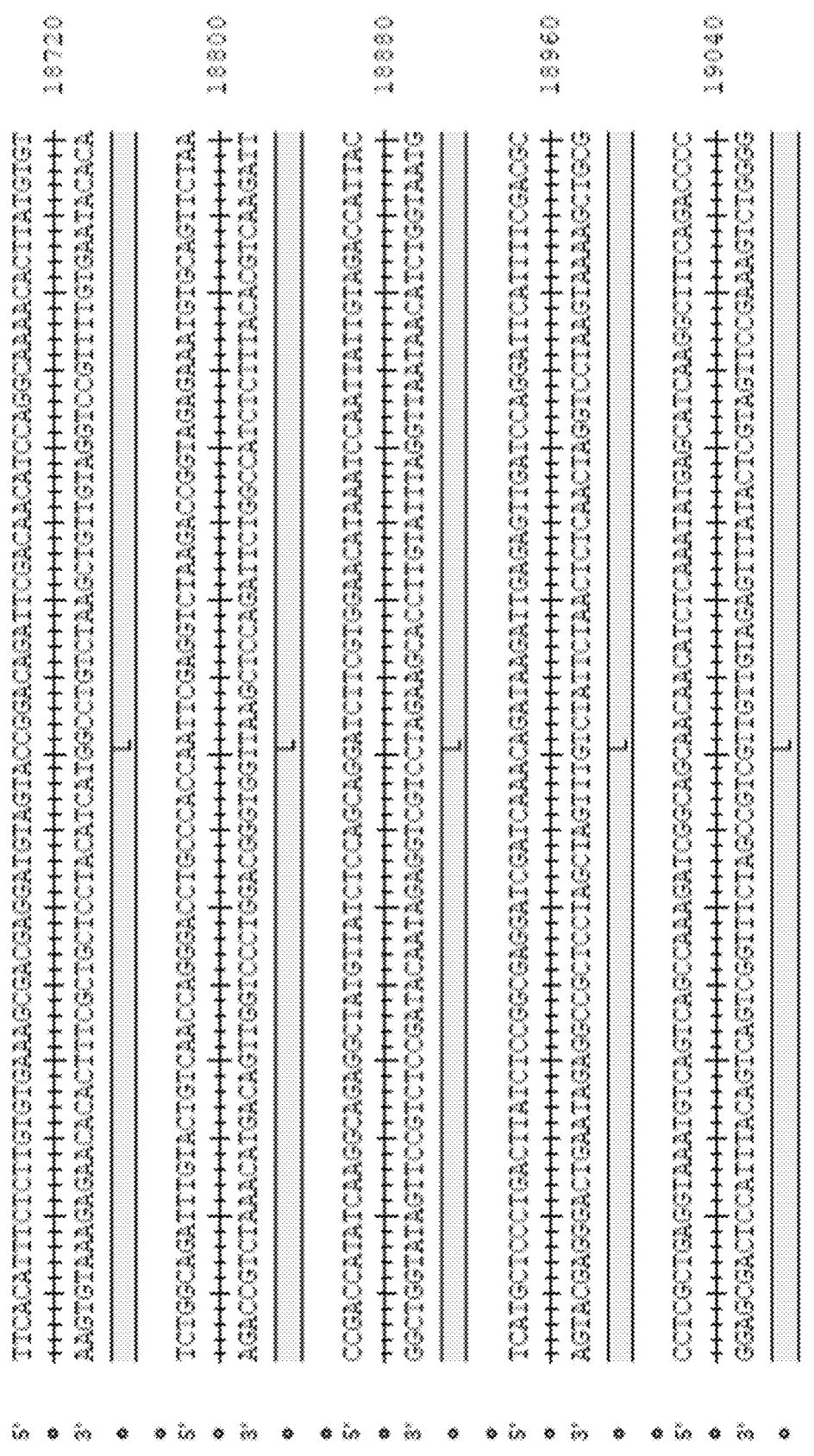
Figure 21:
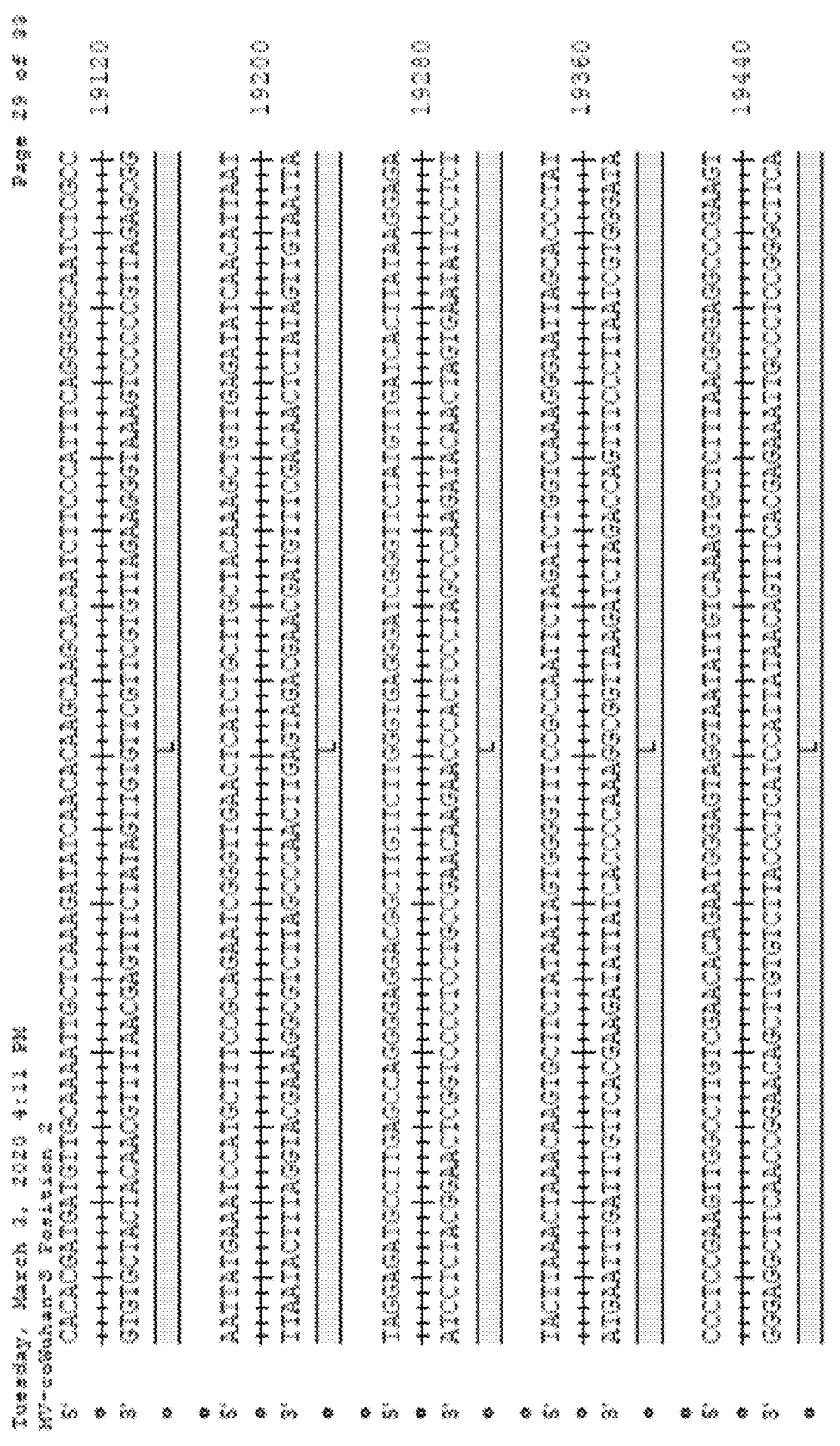
Figure 21:
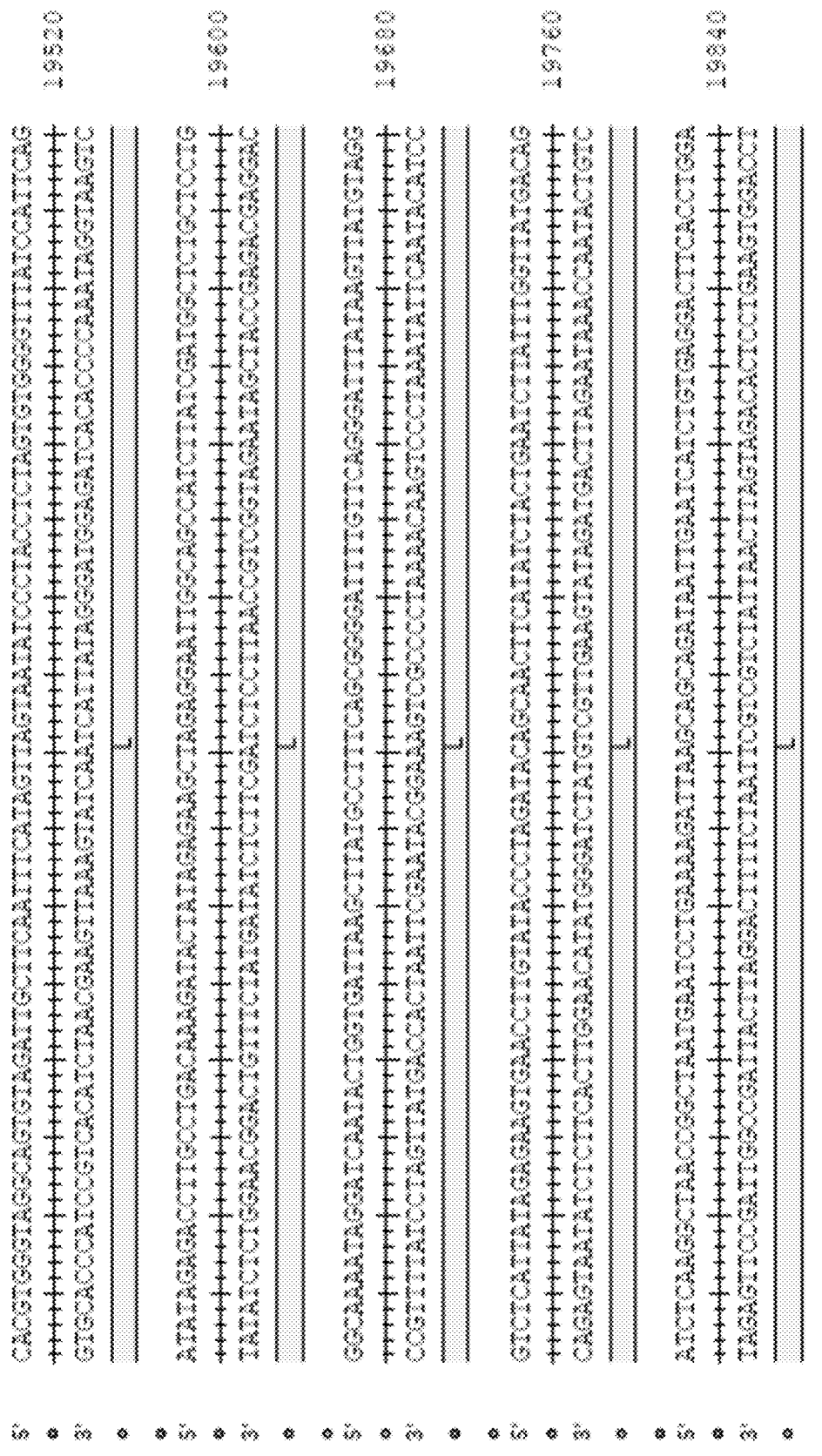
Figure 21:
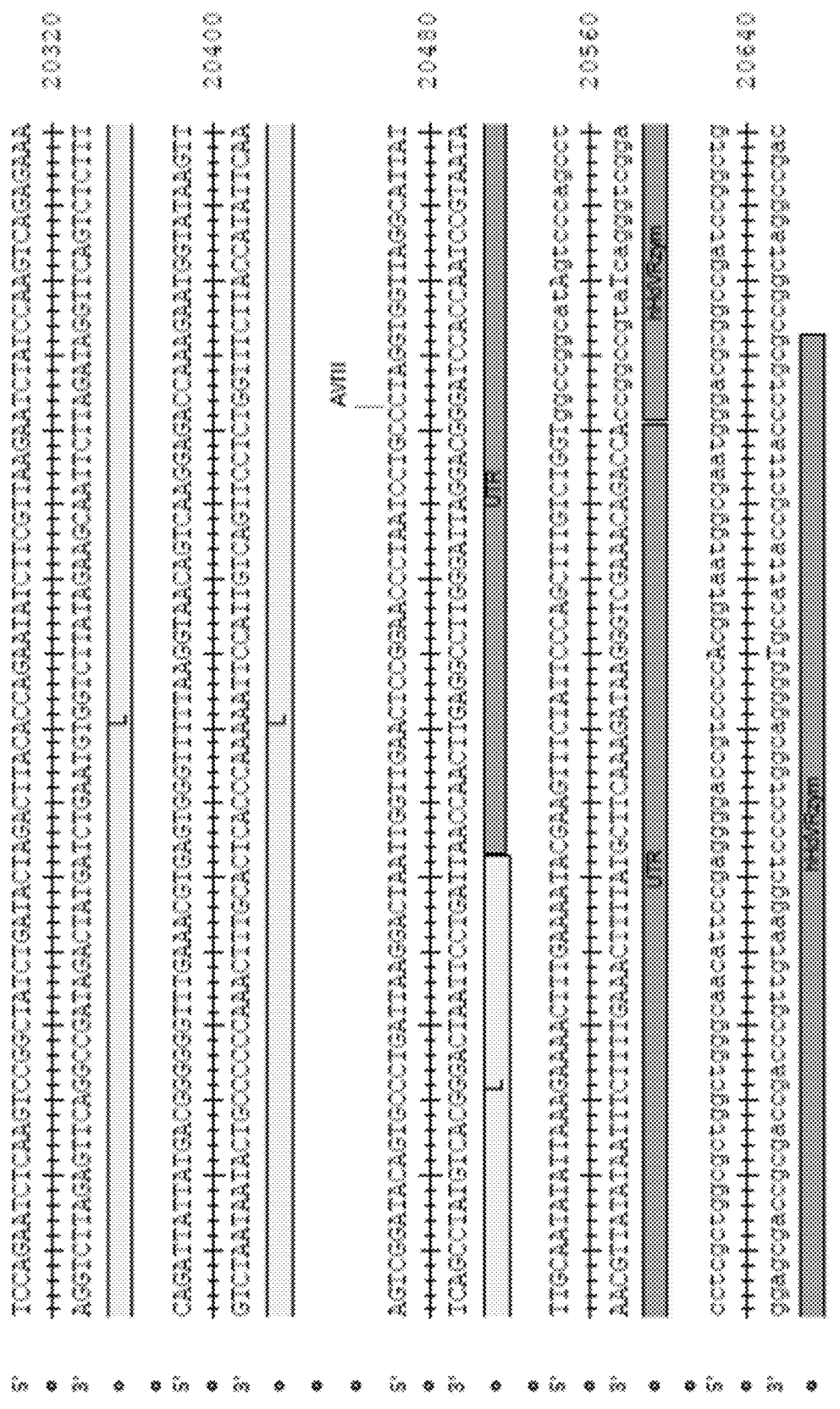
Figure 21:
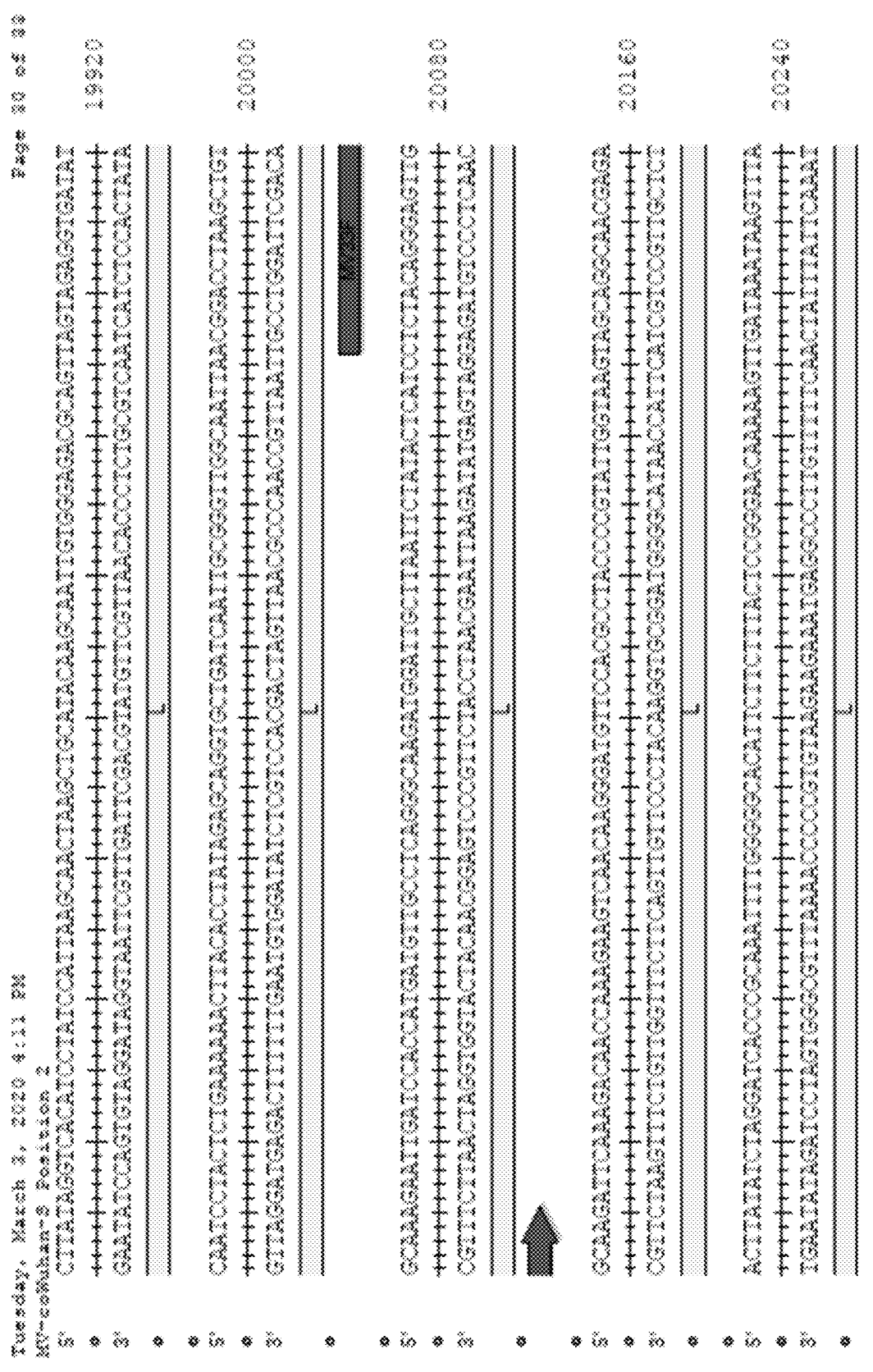
Figure 21:
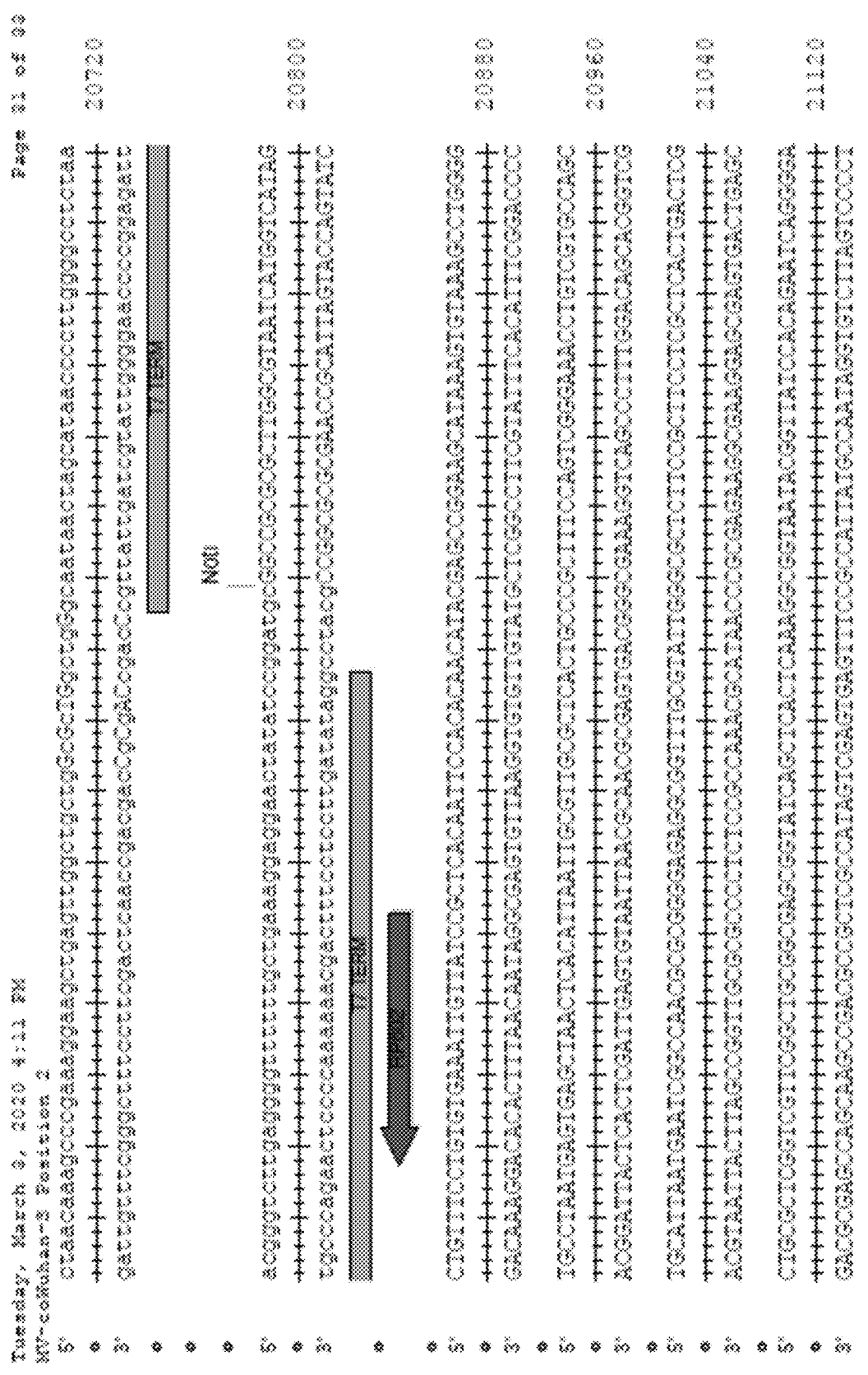
Figure 21:
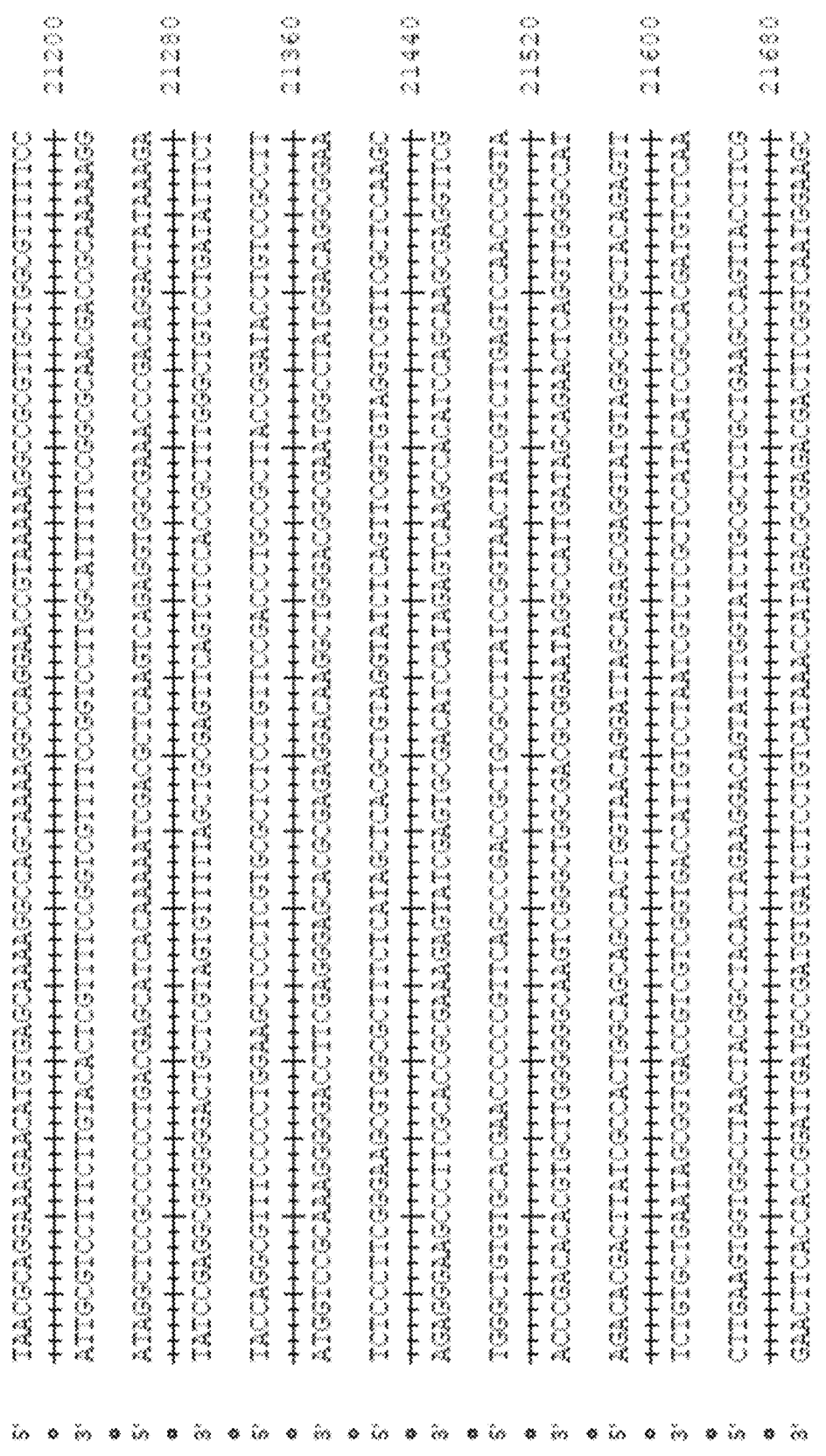
Figure 21:
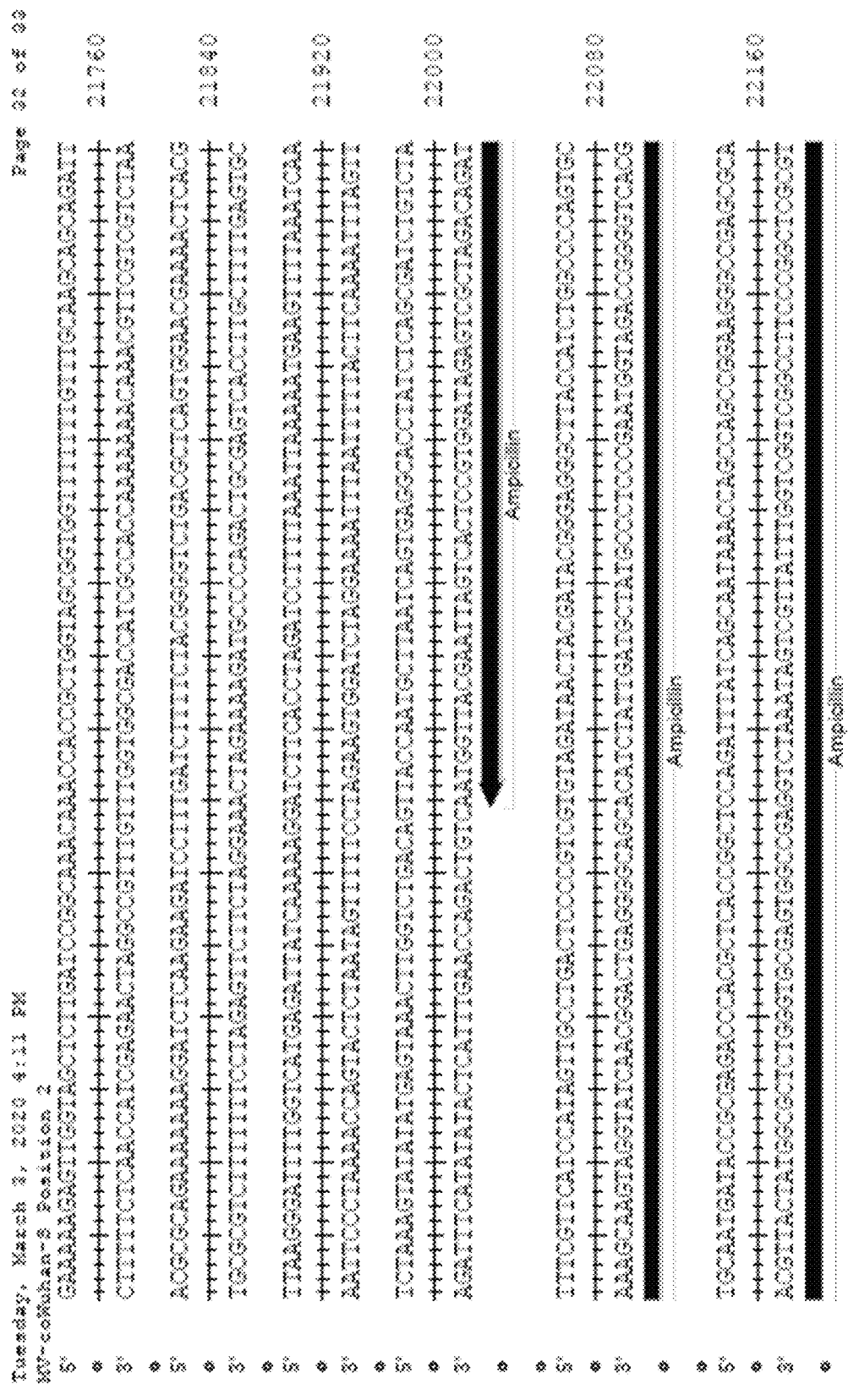
Figure 21:
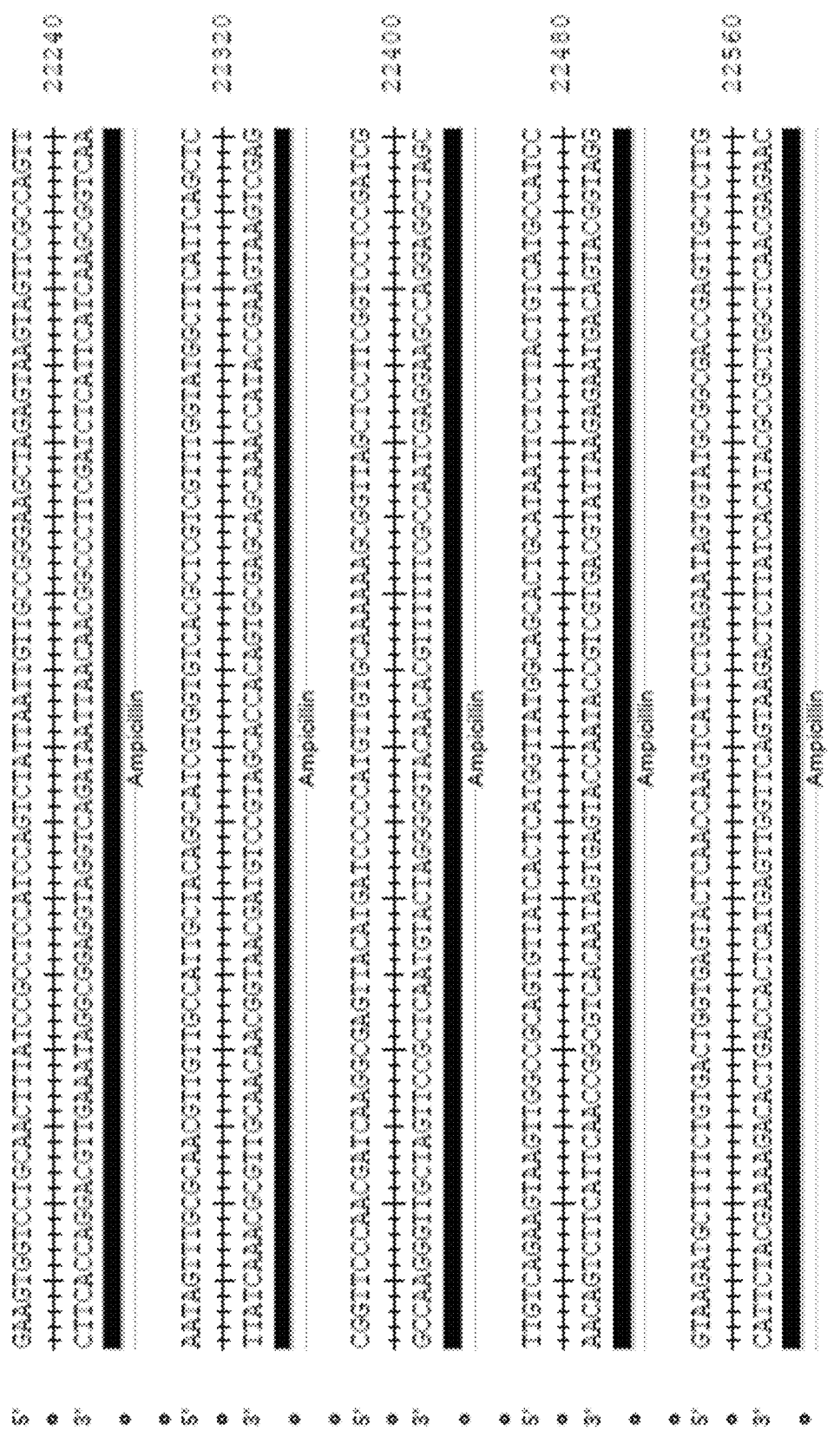
Figure 21:
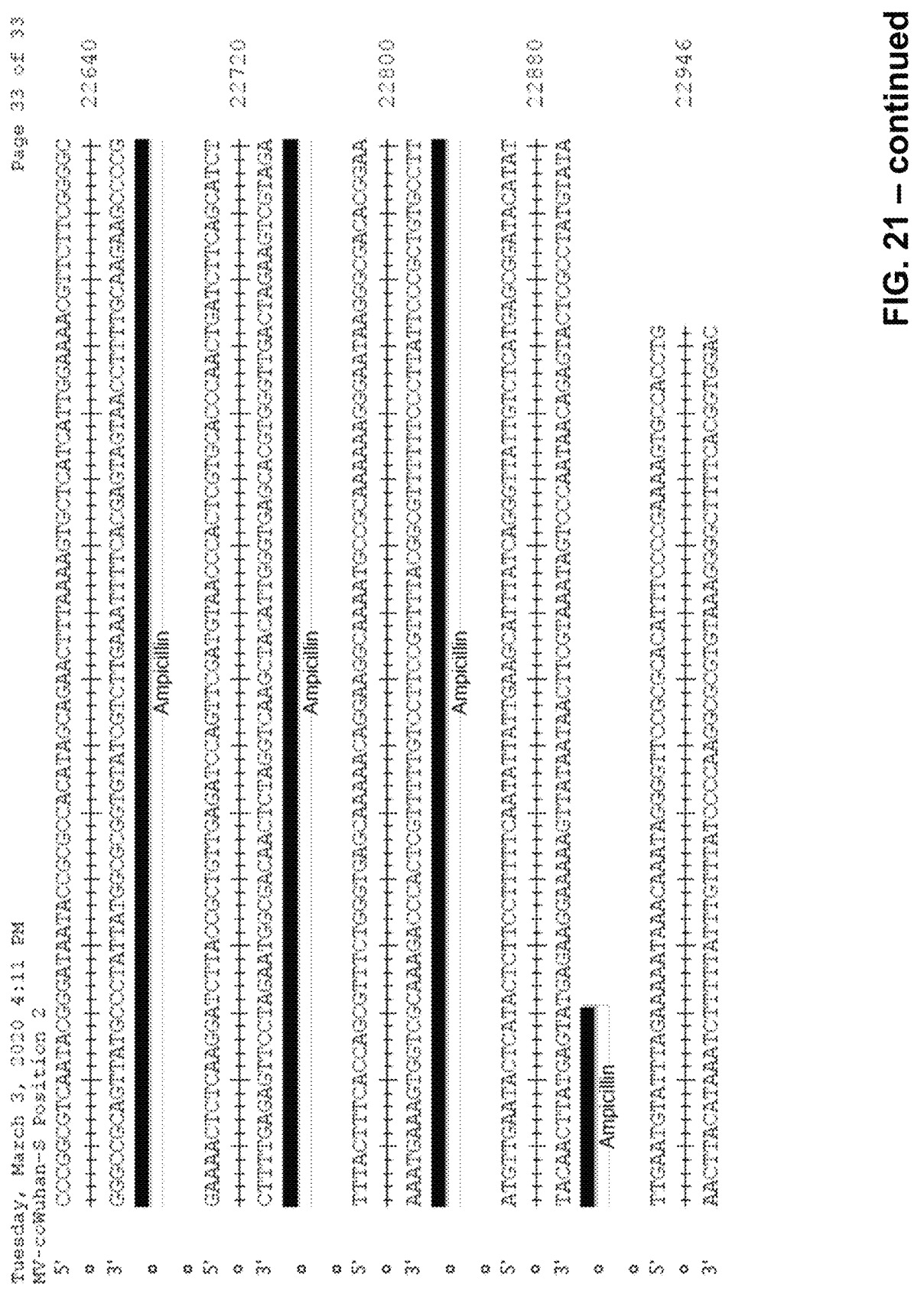

FIG. 21 shows the sequence (SEQ ID NO: 3) and features of "MV-coWuhan-S Position 2".

DETAILED DESCRIPTION

Definitions

Figure 2:
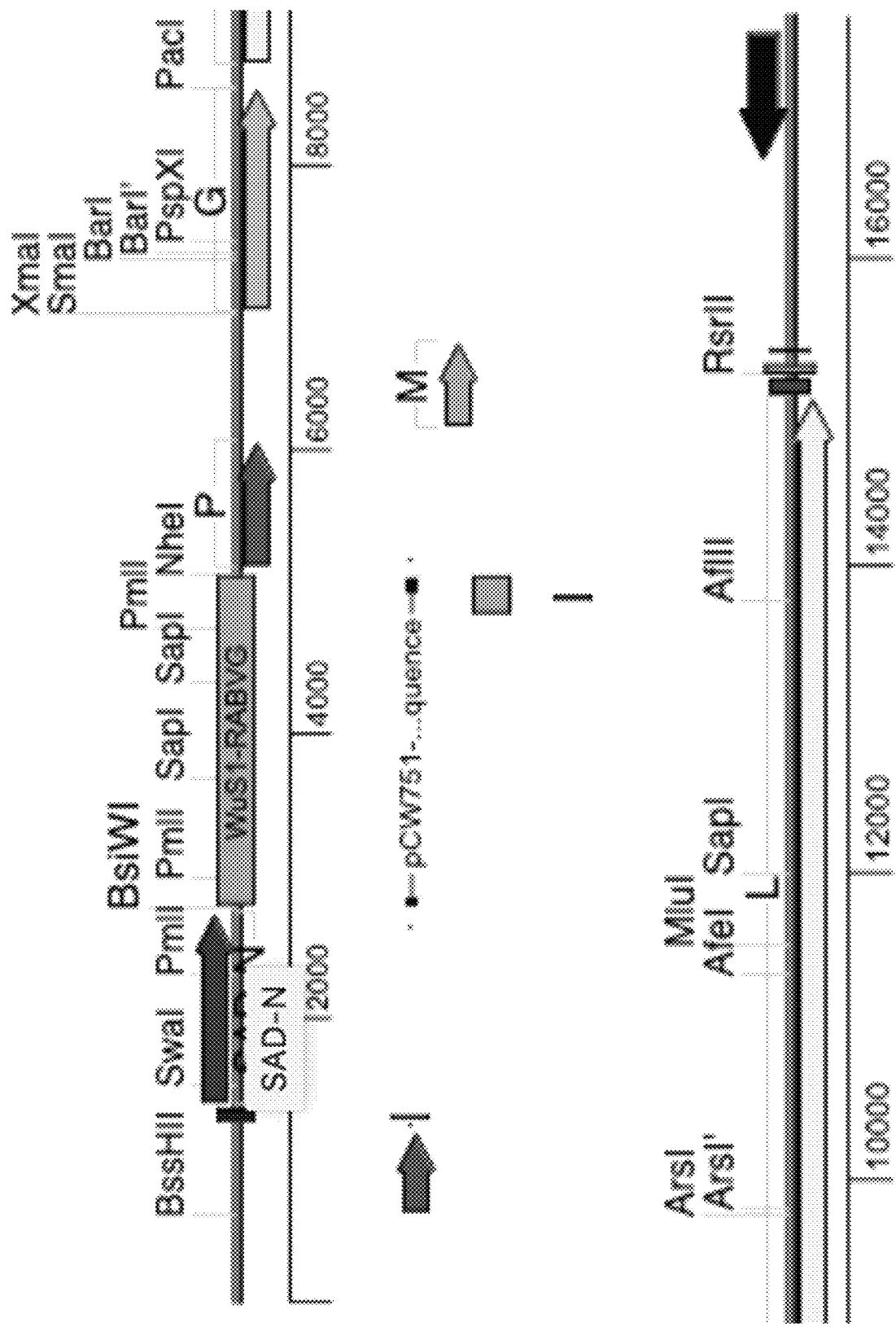
FIG. 2: RABV expressing codon-optimized Covid-S1. The map shows the viral sequence, including the plasmids utilized to create the recombinant virus. The sequence is shown in SEQ ID NO: 2 and features are shown in FIG. 8. The sequence and features are also shown in FIG. 18 ("BNSP333-COVID19-S1-RVG").
Figure 3:
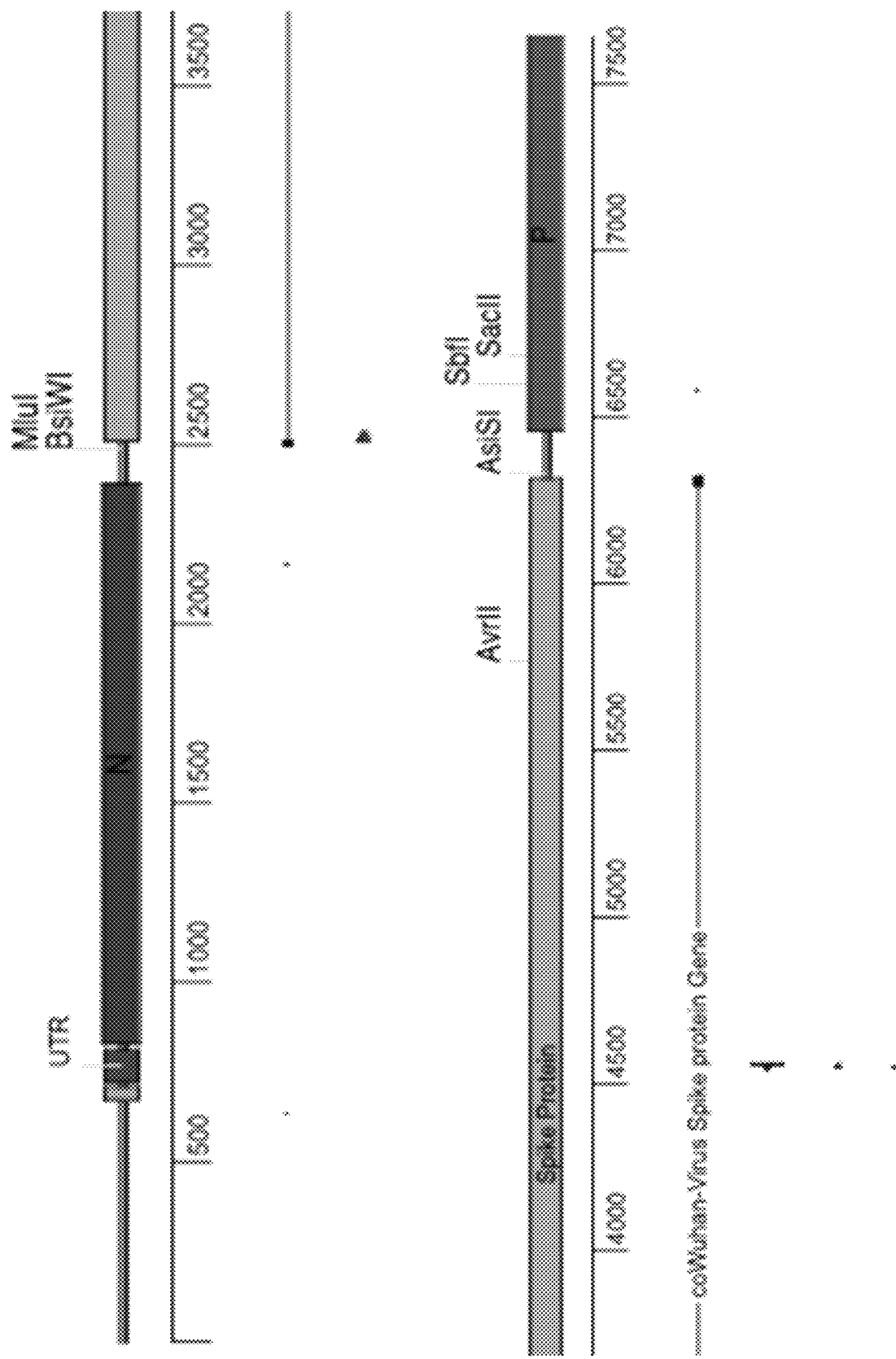
FIG. 3: MV expressing codon-optimized Covid-S from position 2 of the genome. The map shows the viral sequence, including the plasmids utilized to create the recombinant virus. The sequences is shown in SEQ ID NO: 3 and features are shown in FIG. 9. The sequence and features are also shown in FIG. 21 ("MV-coWuhan-S Position 2").
Figure 4:
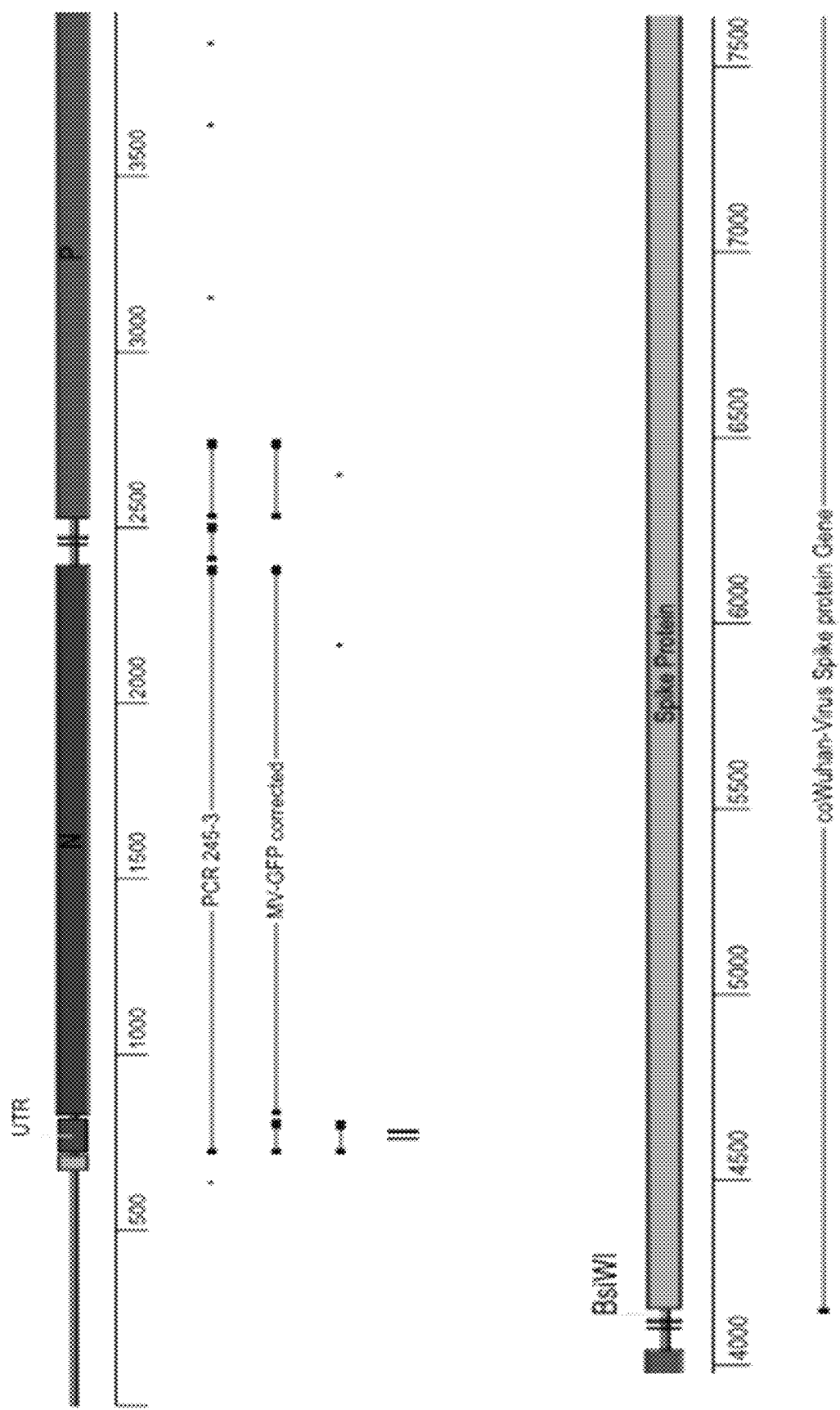
FIG. 4: MV expressing codon-optimized Covid-S from position 3 of the genome. The map shows the viral sequence, including the plasmids utilized to create the recombinant virus. The sequence is shown in SEQ ID NO: 4 and features are shown in FIG. 10. The sequence and features are also depicted in FIG. 20 ("MV Wu S in position 3").
Figure 5:
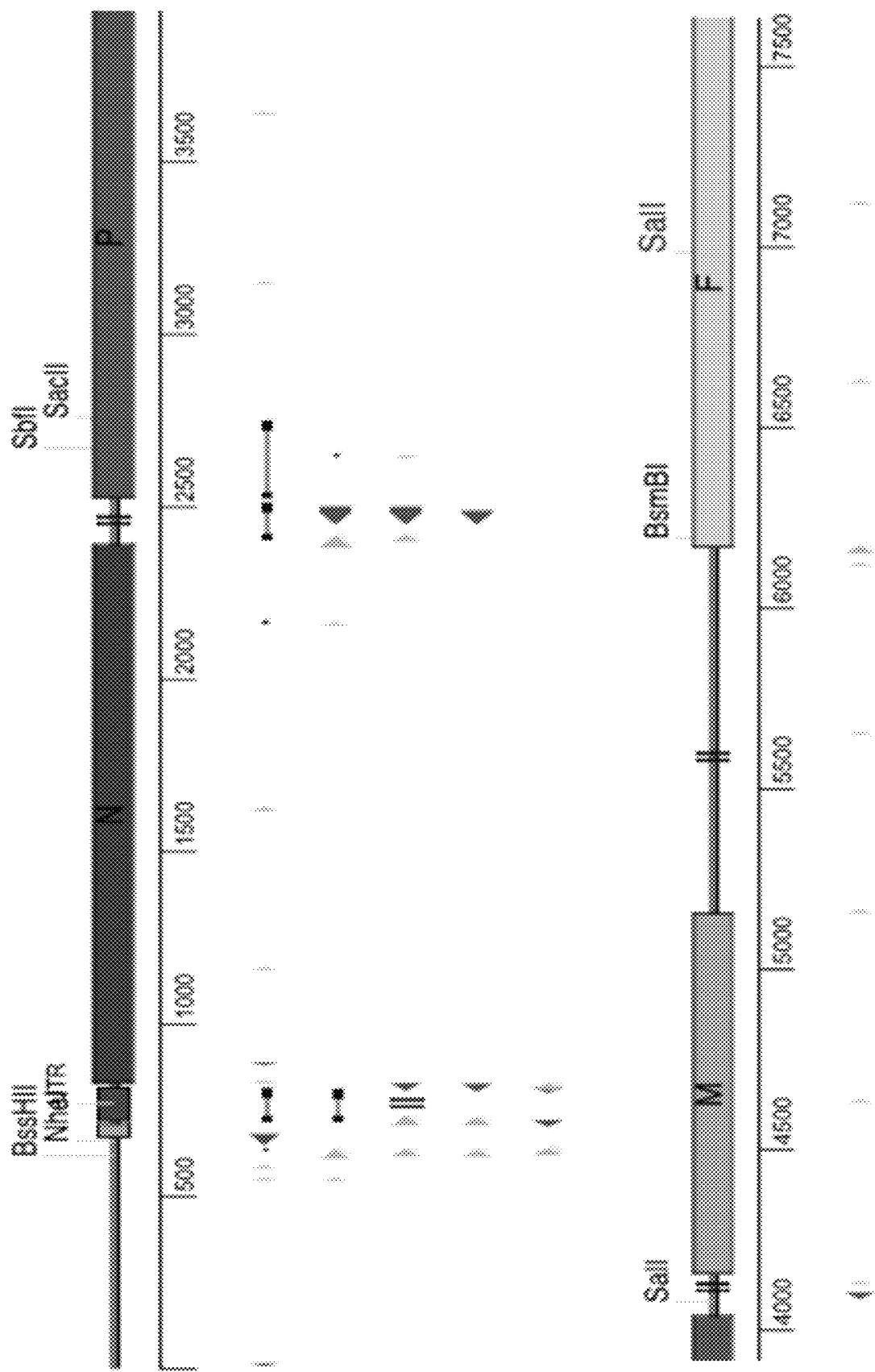
FIG. 5: MV expressing codon-optimized Covid-S from position 6 of the genome. The map shows the viral sequence, including the plasmids utilized to create the recombinant virus. The sequence is shown in SEQ ID NO: 5 and features are shown in FIG. 11. The sequence and features are also depicted in FIG. 19 ("MV WuhanCoV S in position 6").

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

The term "antibody" or "Ab" as used herein, refers to a protein, or polypeptide sequence derived from an immunoglobulin molecule, which specifically binds to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv) and humanized antibodies (Harlow et al., 1998, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426). An antibody may be derived from natural sources or from recombinant sources. Antibodies are typically tetramers of immunoglobulin molecules.

The term "ameliorating" or "treating" means that the clinical signs and/or the symptoms associated with a disease are lessened as a result of the actions performed. The signs or symptoms to be monitored will be well known to the skilled clinician.

As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

The term "biological" or "biological sample" refers to a sample obtained from an organism or from components (e.g., cells) of an organism. The sample may be of any biological tissue or fluid. Frequently the sample will be a "clinical sample" which is a sample derived from a patient. Such samples include, but are not limited to, bone marrow, cardiac tissue, sputum, blood, lymphatic fluid, blood cells (e.g., white cells), tissue or fine needle biopsy samples, urine, peritoneal fluid, and pleural fluid, or cells therefrom.

Biological samples may also include sections of tissues such as frozen sections taken for histological purposes.

As used herein, the terms "control," or "reference" are used interchangeably and refer to a value that is used as a standard of comparison.

The term "immunogenicity" as used herein, refers to the innate ability of an antigen or organism to elicit an immune response in an animal when the antigen or organism is administered to the animal. Thus, "enhancing the immunogenicity" refers to increasing the ability of an antigen or organism to elicit an immune response in an animal when the antigen or organism is administered to an animal. The increased ability of an antigen or organism to elicit an immune response can be measured by, among other things, a greater number of antibodies that bind to an antigen or organism, a greater diversity of antibodies to an antigen or organism, a greater number of T-cells specific for an antigen or organism, a greater cytotoxic or helper T-cell response to an antigen or organism, a greater expression of cytokines in response to an antigen, and the like.

As used herein, the terms "eliciting an immune response" or "immunizing" refer to the process of generating a B cell and/or a T cell response against a heterologous protein.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full-length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

"Heterologous antigens" used herein to refer to an antigen that is not endogenous to the organism comprising or expressing an antigen. As an example, a virus vaccine vector comprising or expressing a viral or tumor antigen comprises a heterologous antigen. The term "Heterologous protein" as used herein refers to a protein that elicits a beneficial immune response in a subject (i.e. mammal), irrespective of its source.

The term "specifically binds", "selectively binds" or "binding specificity" refers to the ability of the humanized antibodies or binding compounds of the invention to bind to a target epitope with a greater affinity than that which results when bound to a non-target epitope. In certain embodiments, specific binding refers to binding to a target with an affinity that is at least 10, 50, 100, 250, 500, or 1000 times greater than the affinity for a non-target epitope.

As used herein, by "combination therapy" is meant that a first agent is administered in conjunction with another agent. "In combination with" or "In conjunction with" refers to administration of one treatment modality in addition to another treatment modality. As such, "in combination with" refers to administration of one treatment modality before, during, or after delivery of the other treatment modality to the individual. Such combinations are considered to be part of a single treatment regimen or regime.

"Humoral immunity" or "humoral immune response" both refer to B-cell mediated immunity and are mediated by highly specific antibodies, produced and secreted by B-lymphocytes (B-cells).

"Prevention" refers to the use of a pharmaceutical compositions for the vaccination against a disorder.

"Adjuvant" refers to a substance that is capable of potentiating the immunogenicity of an antigen. Adjuvants can be one substance or a mixture of substances and function by acting directly on the immune system or by providing a slow release of an antigen. Examples of adjuvants include, but are not limited to, emulsions (e.g., oil in water (o/w) emulsions), aluminium salts, polyanions, bacterial glycopeptides and slow release agents such as Freund's incomplete.

"Delivery vehicle" refers to a composition that helps to target the antigen to specific cells and to facilitate the effective recognition of an antigen by the immune system. The best-known delivery vehicles are liposomes, virosomes, microparticles including microspheres and nanospheres, polymers, bacterial ghosts, bacterial polysaccharides, attenuated bacteria, virus like particles, attenuated viruses and ISCOMS.

The term "expression" as used herein is defined as the transcription and/or translation of a particular nucleotide sequence driven by its promoter.

As used herein, the term "expression cassette" means a nucleic acid sequence capable of directing the transcription and/or translation of a heterologous coding sequence. In some embodiments, the expression cassette comprises a promoter sequence operably linked to a sequence encoding a heterologous protein. In some embodiments, the expression cassette further comprises at least one regulatory sequence operably linked to the sequence encoding the heterologous protein.

"Incorporated into" or "encapsulated in" refers to an antigenic peptide and/or nucleic acid molecule that is/are within a delivery vehicle, such as microparticles, bacterial ghosts, attenuated bacteria, virus like particles, attenuated viruses, ISCOMs, liposomes and preferably virosomes.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that may comprise a protein or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A "fusion protein" as used herein refers to a protein wherein the protein comprises two or more proteins linked together by peptide bonds or other chemical bonds. The proteins can be linked together directly by a peptide or other chemical bond, or with one or more amino acids between the two or more proteins, referred to herein as a spacer.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "RNA" as used herein is defined as ribonucleic acid.

"Transform", "transforming", and "transformation" is used herein to refer to a process of introducing an isolated nucleic acid into the interior of an organism.

The term "treatment" as used within the context of the present invention is meant to include therapeutic treatment as well as prophylactic, or suppressive measures for the disease or disorder. As used herein, the term "treatment" and associated terms such as "treat" and "treating" means the reduction of the progression, severity and/or duration of a disease condition or at least one symptom thereof. The term 'treatment' therefore refers to any regimen that can benefit a subject. The treatment may be in respect of an existing condition or may be prophylactic (preventative treatment). Treatment may include curative, alleviative or prophylactic effects. References herein to "therapeutic" and "prophylactic" treatments are to be considered in their broadest context. The term "therapeutic" does not necessarily imply that a subject is treated until total recovery. Similarly, "prophylactic" does not necessarily mean that the subject will not eventually contract a disease condition. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease.

The term "equivalent," when used in reference to nucleotide sequences, is understood to refer to nucleotide sequences encoding functionally equivalent polypeptides. Equivalent nucleotide sequences will include sequences that differ by one or more nucleotide substitutions, additions- or deletions, such as allelic variants; and will, therefore, include sequences that differ from the nucleotide sequence of the nucleic acids described herein due to the degeneracy of the genetic code.

The term "isolated" as used herein with respect to nucleic acids, such as DNA or RNA, refers to molecules separated from other DNAs or RNAs, respectively that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments, which are not naturally occurring as fragments and would not be found in the natural state. The term "isolated" is also used herein to refer to polypeptides, which are isolated from other cellular proteins and is meant to encompass both purified and recombinant polypeptides. An "isolated cell" or "isolated population of cells" is a cell or population of cells that is not present in its natural environment.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

A "mutation" as used therein is a change in a DNA sequence resulting in an alteration from its natural state. The mutation can comprise a deletion and/or insertion and/or duplication and/or substitution of at least one deoxyribonucleic acid base such as a purine (adenine and/or thymine) and/or a pyrimidine (guanine and/or cytosine). Mutations may or may not produce discernible changes in the observable characteristics (phenotype) of an organism.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids. As used herein, nucleic acids include but are not limited to, all nucleic acid sequences which are obtained by any means available in the art, including, without limitation, recombinant means, i.e., the cloning of nucleic acid sequences from a recombinant library or a viral genome, using ordinary cloning technology and PCR™, and the like, and by synthetic means.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. There are numerous expression control sequences, including promoters which are native, constitutive, inducible and/or tissue-specific, are known in the art that may be used in the compositions of the invention. "Operably linked" should be construed to include RNA expression and control sequences in addition to DNA expression and control sequences.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence, which is required for expression of a gene product operably linked to the promoter/ regulatory sequence. In some instances, this sequence may be the core promoter sequence and in other instances, this sequence may also include an enhancer sequence and other regulatory elements, which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

As used herein, the term "pharmaceutical composition" refers to a mixture of at least one compound useful within the invention with other chemical components, such as carriers, stabilizers, diluents, adjuvants, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

As used herein, the term "effective amount" or "therapeutically effective amount" means that amount of a composition (e.g., vaccine composition) or active ingredient (e.g., virus like particles (VLPs), virions, viral vectors, antigen, nucleic acid molecule) necessary to achieve an intended result e.g., to produce an intended immunological, pharmacological, therapeutic and/or protective result (e.g., that amount of VLPs, virions, or viral vectors sufficient to induce a measurable immune response, to prevent a particular disease condition, to reduce the severity of and/or ameliorate the disease condition or at least one symptom and/or condition associated therewith).

A "subject" or "patient," as used therein, may be a human or non-human mammal. Non-human mammals include, for example, livestock and pets, such as ovine, bovine, porcine, canine, feline and murine mammals. Preferably, the subject is human. In some embodiments, the subject is a domestic pet or livestock. In some embodiments, the subject is a cat. In some embodiments, the subject is a dog. In some other embodiments, the subject is a ferret.

"Titers" are numerical measures of the concentration of a virus or viral vector compared to a reference sample, where the concentration is determined either by the activity of the virus, or by measuring the number of viruses in a unit volume of buffer. The titer of viral stocks are determined, e.g., by measuring the infectivity of a solution or solutions (typically serial dilutions) of the viruses, e.g., on HeLa cells using the soft agar method (see, Graham & Van Der eb (1973) Virology 52:456-467) or by monitoring resistance conferred to cells, e.g., G418 resistance encoded by the virus or vector, or by quantitating the viruses by UV spectrophotometry (see, Chardonnet & Dales (1970) Virology 40:462-477).

"Vaccination" refers to the process of inoculating a subject with an antigen to elicit an immune response in the subject, that helps to prevent or treat the disease or disorder the antigen is connected with. The term "immunization" is used interchangeably herein with vaccination.

A "vector" is a composition of matter which comprises a nucleic acid and which can be used to deliver the nucleic acid to the interior of a cell. Numerous vectors are known in the art including, but not limited to, linear polynucleotides, polynucleotides associated with ionic or amphiphilic compounds, plasmids, and viruses. In the present disclosure, the term "vector" includes an autonomously replicating virus.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to compositions and methods for generating vaccines against a SARS-CoV-2 virus. The SARS-CoV-2 virus is also referred to herein as 2019-nCoV or 2019 Novel Coronavirus.

Described herein is a vaccine against the SARS-CoV-2 virus that uses a rabies virus-based vector that has proven to be an efficient vector against emerging and re-emerging infectious diseases. It was previously demonstrated that inactivated rabies virus particles containing MERS-CoV spike S1 protein induce potent immune responses against MERS-CoV and RABV and provide protection in animal systems.

The 2019-nCoV vaccine described herein has the following advantages:

The construct is based on a currently available rabies vaccine product, and therefore will facilitate entry of a vaccine into a clinical phase one study to be prepared within a short time period. Bharat Biotech Ltd (BBIL) produce currently 20 million doses of the RABV vaccine a year.

The construct can be rapidly scaled, as needed, for additional clinical trials and commercial manufacture.

The construct can be manufactured at low cost-of-goods. Rabies vaccines have been commercially produced for decades, costs are well known and are inexpensive. The present vaccine uses the same manufacturing process as the current human rabies vaccine. When vaccinating millions of people in resource-limited areas, a low-cost vaccine is a significant advantage The vaccine should be safe for all population groups. In some embodiments, the vaccine is based on the killed rabies vaccine backbone since the rabies vaccine has decades of safe use across diverse populations.

Proof of concept has been demonstrated by protecting in animal models based on challenge studies with the related MERS-CoV in two mouse models and alpacas (camelid).

Long-term protection is expected since the RABV vaccine often provides life-long protection.

The vaccine can be produced by an experienced commercial-scale manufacturing partner, Bharat Biotech, who has successfully met WHO pre-qualification standards for other vaccines, and can move quickly into clinical trials and commercial production. Bharat Biotech meets the FDA, EMA, and WHO PQ standards for cGMP.

Utilises a unique polysaccharide adjuvant, Advax-SM, that has already been extensively tested in human clinical trials, being shown to enhance both humoral and cellular immunity. Most notably, addition of Advax-SM to prototype cGMP whole cell and recombinant spike protein SARS vaccines, not only enhanced neutralising antibody responses and prevented lung viral replication but also completely prevented vaccine-enhanced eosinophilic lung pathology in response to SARS virus exposure.

Both the RABV vector and the utilized adjuvant can be stabilized and stored at room temperature.

Constructs

In one aspect, the present invention includes an isolated nucleic acid encoding a recombinant virus comprising a SARS-CoV-2 spike protein (S) or a portion thereof. In some embodiments, the virus is a rhabdovirus. In some embodiments, the virus is a rabies virus, a vesicular stomatitis virus (VSV), or a measles virus. In a particular embodiment, the virus is a rabies virus. The nucleic acid can comprises sequences that are codon-optimized for expression in a cell (e.g., a mammalian cell, a human cell).

In one embodiment, the SARS-CoV-2 spike protein (S) or the portion thereof comprises the amino acid sequence as set forth in SEQ ID NO: 28:

MFVFLVLLPLVSSQCVNLTTRTQLPPAYTNSFTRGVYYPDKVFRSSVLH

STQDLFLPFFSNVTWFHAIHVSGTNGTKRFDNPVLPFNDGVYFASTEKS

NIIRGWIFGTTLDSKTQSLLIVNNATNVVIKVCEFQFCNDPFLGVYYHK

NNKSWMESEFRVYSSANNCTFEYVSQPFLMDLEGKQGNFKNLREFVFKN

IDGYFKIYSKHTPINLVRDLPQGFSALEPLVDLPIGINITRFQTLLALH

RSYLTPGDSSSGWTAGAAAYYVGYLQPRTFLLKYNENGTITDAVDCALD

PLSETKCTLKSFTVEKGIYQTSNFRVQPTESIVRFPNITNLCPFGEVFN

ATRFASVYAWNRKRISNCVADYSVLYNSASFSTFKCYGVSPTKLNDLCF

TNVYADSFVIRGDEVRQIAPGQTGKIADYNYKLPDDFTGCVIAWNSNNL

DSKVGGNYNYLYRLFRKSNLKPFERDISTEIYQAGSTPCNGVEGFNCYF

PLQSYGFQPTNGVGYQPYRVVVLSFELLHAPATVCGPKKSTNLVKNKCV

NFNFNGLTGTGVLTESNKKFLPFQQFGRDIADTTDAVRDPQTLEILDIT

PCSFGGVSVITPGTNTSNQVAVLYQDVNCTEVPVAIHADQLTPTWRVYS

TGSNVFQTRAGCLIGAEHVNNSYECDIPIGAGICASYQTQTNSPR.

In another embodiment, the SARS-CoV-2 spike protein (S) or the portion thereof comprises the amino acid sequence as set forth in SEQ ID NO: 29:

MFVFLVLLPLVSSQCVNLTTRTQLPPAYTNSFTRGVYYPDKVFRSSVLH

STQDLFLPFFSNVTWFHAIHVSGTNGTKRFDNPVLPFNDGVYFASTEKS

NIIRGWIFGTTLDSKTQSLLIVNNATNVVIKVCEFQFCNDPFLGVYYHK

NNKSWMESEFRVYSSANNCTFEYVSQPFLMDLEGKQGNFKNLREFVFKN

IDGYFKIYSKHTPINLVRDLPQGFSALEPLVDLPIGINITRFQTLLALH

RSYLTPGDSSSGWTAGAAAYYVGYLQPRTFLLKYNENGTITDAVDCALD

PLSETKCTLKSFTVEKGIYQTSNFRVQPTESIVRFPNITNLCPFGEVFN

ATRFASVYAWNRKRISNCVADYSVLYNSASFSTFKCYGVSPTKLNDLCF

TNVYADSFVIRGDEVRQIAPGQTGKIADYNYKLPDDFTGCVIAWNSNNL

DSKVGGNYNYLYRLFRKSNLKPFERDISTEIYQAGSTPCNGVEGFNCYF

PLQSYGFQPTNGVGYQPYRVVVLSFELLHAPATVCGPKKSTNLVKNKCV

NFNFNGLTGTGVLTESNKKFLPFQQFGRDIADTTDAVRDPQTLEILDIT

PCSFGGVSVITPGTNTSNQVAVLYQDVNCTEVPVAIHADQLTPTWRVYS

TGSNVFQTRAGCLIGAEHVNNSYECDIPIGAGICASYQTQTNSPRRARS

VASQSIIAYTMSLGAENSVAYSNNSIAIPTNFTISVTTEILPVSMTKTS

VDCTMYICGDSTECSNLLLQYGSFCTQLNRALTGIAVEQDKNTQEVFAQ

VKQIYKTPPIKDFGGFNFSQILPDPSKPSKRSFIEDLLFNKVTLADAGF

IKQYGDCLGDIAARDLICAQKFNGLTVLPPLLTDEMIAQYTSALLAGTI

TSGWTFGAGAALQIPFAMQMAYRFNGIGVTQNVLYENQKLIANQFNSAI

GKIQDSLSSTASALGKLQDVVNQNAQALNTLVKQLSSNFGAISSVLNDI

LSRLDKVEAEVQIDRLITGRLQSLQTYVTQQLIRAAEIRASANLAATKM

SECVLGQSKRVDFCGKGYHLMSFPQSAPHGVVFLHVTYVPAQEKNFTTA

PAICHDGKAHFPREGVFVSNGTHWFVTQRNFYEPQIITTDNTFVSGNCD

VVIGIVNNTVYDPLQPELDSFKEELDKYFKNHTSPDVDLGDISGINASV

-continued
VNIQKEIDRLNEVAKNLNESLIDLQELGKYEQYIKWPWYIWLGFIAGLI

AIVMVTIMLCCMTSCCSCLKGCCSCGSCCKFDEDDSEPVLKGVKLHYT.

In one embodiment, the SARS-CoV-2 spike protein (S) or the portion thereof comprises the amino acid sequence as set forth in SEQ ID NO: 30:

MFVFLVLLPLVSSQCVNLTTRTQLPPAYTNSFTRGVYYPDKVFRSSVLH

STQDLFLPFFSNVTWFHAIHVSGTNGTKRFDNPVLPFNDGVYFASTEKS

NIIRGWIFGTTLDSKTQSLLIVNNATNVVIKVCEFQFCNDPFLGVYYHK

NNKSWMESEFRVYSSANNCTFEYVSQPFLMDLEGKQGNFKNLREFVFKN

IDGYFKIYSKHTPINLVRDLPQGFSALEPLVDLPIGINITRFQTLLALH

RSYLTPGDSSSGWTAGAAAYYVGYLQPRTFLLKYNENGTITDAVDCALD

PLSETKCTLKSFTVEKGIYQTSNFRVQPTESIVRFPNITNLCPFGEVFN

ATRFASVYAWNRKRISNCVADYSVLYNSASFSTFKCYGVSPTKLNDLCF

TNVYADSFVIRGDEVRQIAPGQTGKIADYNYKLPDDFTGCVIAWNSNNL

DSKVGGNYNYLYRLFRKSNLKPFERDISTEIYQAGSTPCNGVEGFNCYF

PLQSYGFQPTNGVGYQPYRVVVLSFELLHAPATVCGPKKSTNLVKNKCV

NFNFNGLTGTGVLTESNKKFLPFQQFGRDIADTTDAVRDPQTLEILDIT

PCSFGGVSVITPGTNTSNQVAVLYQDVNCTEVPVAIHADQLTPTWRVYS

TGSNVFQTRAGCLIGAEHVNNSYECDIPIGAGICASYQTQTNSPRSVGD

EAEDFVEVHLPDVHNQVSGVDLGLPNWGKYVLLSAGALTALMLIIFLMT

CCRRVNRSEPTQHNLRGTGREVSVTPQSGKIISSWESHKSGGETRL.

In another embodiment, the SARS-CoV-2 spike protein (S) or the portion thereof comprises the amino acid sequence as set forth in SEQ ID NO: 31:

MFVFLVLLPLVSSQCVNLTTRTQLPPAYTNSFTRGVYYPDKVFRSSVLHS

TQDLFLPFFSNVTWFHAIHVSGTNGTKRFDNPVLPFNDGVYFASTEKSNI

IRGWIFGTTLDSKTQSLLIVNNATNVVIKVCEFQFCNDPFLGVYYHKNNK

SWMESEFRVYSSANNCTFEYVSQPFLMDLEGKQGNFKNLREFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSF

VIRGDEVRQIAPGQTGKIADYNYKLPDDFTGCVIAWNSNNLDSKVGGNYN

YLYRLFRKSNLKPFERDISTEIYQAGSTPCNGVEGFNCYFPLQSYGFQPT

NGVGYQPYRVVVLSFELLHAPATVCGPKKSTNLVKNKCVNFNFNGLTGTG

VLTESNKKFLPFQQFGRDIADTTDAVRDPQTLEILDITPCSFGGVSVITP

GTNTSNQVAVLYQDVNCTEVPVAIHADQLTPTWRVYSTGSNVFQTRAGCL

IGAEHVNNSYECDIPIGAGICASYQTQTNSPR.

In another embodiment, an N protein (N) or the portion thereof is provided, comprising the amino acid sequence as set forth in SEQ ID NO: 32:

MATLLRSLALFKRNKDKPPITSGSGGAIRGIKHIIIVPIPGDSSITTRSR

LLDRLVRLIGNPDVSGPKLTGALIGILSLFVESPGQLIQRITDDPDVSIR

LLEVVQSDQSQSGLTFASRGTNMEDEADQYFSHDDPISSDQSRFGWFGNK

EISDIEVQDPEGFNMILGTILAQIWVLLAKAVTAPDTAADSELRRWIKYT

QQRRVVGEFRLERKWLDVVRNRIAEDLSLRRFMVALILDIKRTPGNKPRI

AEMICDIDTYIVEAGLASFILTIKFGIETMYPALGLHEFAGELSTLESLM

NLYQQMGETAPYMVILENSIQNKFSAGSYPLLWSYAMGVGVELENSMGGL

NFGRSYFDPAYFRLGQEMVRRSAGKVSSTLASELGITAEDARLVSEIAMH

TTEDKISRAVGPRQAQVSFLHGDQSENELPRLGGKEDRRVKQSRGEARES

YRETGPSRASDARAAHLPTGTPLDIDTATESSQDPQDSRRSADALLRLQA

MAGISEEQGSDTDTPIVYNDRNLLD.

In another embodiment, the SARS-CoV-2 spike protein (S) or the portion thereof is a variant spike polypeptide comprising one or more alterations (e.g., substitution(s), insertion(s), deletion(s), addition(s), modification(s)) in its amino acid sequence relative to the amino acid sequence set forth as SEQ ID NO: 28, 29, 30, or 31.

In other embodiments, the SARS-CoV-2 spike protein (S) or the portion thereof is a variant spike polypeptide comprising, relative to the amino acid sequence set forth as SEQ ID NO: 28, 29, 30, or 31, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more alterations.

In one embodiment, the SARS-CoV-2 spike protein (S) or the portion thereof is a variant spike polypeptide comprising at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but not 100%, sequence identity to the amino acid sequence set forth as SEQ ID NO: 28, 29, 30, or 31. In another embodiment, the N protein (N) or the portion thereof is a variant N polypeptide comprising one or more alterations (e.g., substitution(s), insertion(s), deletion(s), addition(s), modification(s)) in its amino acid sequence relative to the amino acid sequence set forth as SEQ ID NO: 32.

In other embodiments, the N protein (N) or the portion thereof is a variant N polypeptide comprising, relative to the amino acid sequence set forth as SEQ ID NO: 32, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more alterations.

In one embodiment, the N protein (N) or the portion thereof is a variant N polypeptide comprising at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but not 100%, sequence identity to the amino acid sequence set forth as SEQ ID NO: 32.

In some embodiments, the recombinant virus expresses a full-length SARS-CoV-2 spike protein (S). In some other embodiments, the recombinant virus expresses a portion of the SARS-CoV-2 spike protein (S). In one embodiment, the portion of the SARS-CoV-2 spike protein (S) is a receptor binding site of the SARS-CoV-2 spike protein (S). In another embodiment, the portion of the SARS-CoV-2 spike protein (S) is the S1 domain. In another embodiment, the portion of the SARS-CoV-2 spike protein (S) is the N-terminal 750 amino acids of the SARS-CoV-2 spike protein (S).

In some embodiments, the SARS-CoV-2 spike protein (S) or portion thereof is fused to a glycoprotein (G) or a portion thereof. In some embodiments, the glycoprotein (G) comprises a mutation substituting arginine with glutamic acid at position 333. In some embodiments, the portion of glycoprotein (G) comprises an ectodomain, a cytoplasmic domain, and a transmembrane domain. In other embodiments, the portion of the glycoprotein (G) comprises 1 to about 100 amino acids of the ectodomain or a trimerization domain. In some embodiments, the portion of the glycoprotein (G) comprises 31 amino acids of the ectodomain. In some embodiments, the glycoprotein (G) comprises 31 amino acids of the ectodomain and the full-length cytoplasmic domain.

In some embodiments, the sequence encoding the SARS-CoV-2 spike protein (S) or portion thereof is codon-optimized for expression in a cell. In some embodiments, the sequence encoding the SARS-CoV-2 spike protein (S) or portion thereof fused to a glycoprotein (G) or portion thereof is codon-optimized for expression in a cell.

In some embodiments, the nucleic acid comprises a sequence encoding at least a portion of the genome of the virus. In some embodiments, the isolated nucleic acid comprises the full-length genome.

In one embodiment, the nucleic acid comprises (a) a sequence encoding at least a portion of the genome of a vesicular stomatitis virus (VSV), and (b) a sequence encoding a protein comprising a SARS-CoV-2 spike protein (S) or a portion thereof. In some embodiments, the protein comprising a SARS-CoV-2 spike protein (S) or a portion thereof is a fusion protein comprising a glycoprotein (G) or a portion thereof and a SARS-CoV-2 spike protein (S) or a portion thereof. In some embodiments, the fusion protein comprises a glycoprotein (G) or portion thereof fused to the S1 domain of a SARS-CoV-2 spike protein (S).

In another embodiment, the nucleic acid comprises the sequence of SEQ ID NO: 1, shown below:

CTGACGCGCCCTGTAGCGGCGCATTAAGCGCGGCGGGTGTGGTGGTTAC

GCGCAGCGTGACCGCTACACTTGCCAGCGCCCTAGCGCCCGCTCCTTTC

GCTTTCTTCCCTTCCTTTCTCGCCACGTTCGCCGGCTTTCCCCGTCAAG

CTCTAAATCGGGGGCTCCCTTTAGGGTTCCGATTTAGTGCTTTACGGCA

CCTCGACCCCAAAAAACTTGATTAGGGTGATGGTTCACGTAGTGGGCCA

TCGCCCTGATAGACGGTTTTTCGCCCTTTGACGTTGGAGTCCACGTTCT

TTAATAGTGGACTCTTGTTCCAAACTGGAACAACACTCAACCCTATCTC

GGTCTATTCTTTTGATTTATAAGGGATTTTGCCGATTTCGGCCTATTGG

TTAAAAAATGAGCTGATTTAACAAAAATTTAACGCGAATTTTAACAAAA

TATTAACGCTTACAATTTCCATTCGCCATTCAGGCTGCGCAACTGTTGG

GAAGGGCGATCGGTGCGGGCCTCTTCGCTATTACGCCAGCTGGCGAAAG

GGGGATGTGCTGCAAGGCGATTAAGTTGGGTAACGCCAGGGTTTTCCCA

GTCACGACGTTGTAAAACGACGGCCAGTGAGcgcgccCTAGTTATTAAT

AGTAATCAATTACGGGGTCATTAGTTCATAGCCCATATATGGAGTTCCG

CGTTACATAACTTACGGTAAATGGCCCGCCTGGCTGACCGCCCAACGAC

CCCCGCCCATTGACGTCAATAATGACGTATGTTCCCATAGTAACGCCAA

TAGGGACTTTCCATTGACGTCAATGGGTGGAGTATTTACGGTAAACTGC

CCACTTGGCAGTACATCAAGTGTATCATATGCCAAGTACGCCCCCTATT

GACGTCAATGACGGTAAATGGCCCGCCTGGCATTATGCCCAGTACATGA

CCTTATGGGACTTTCCTACTTGGCAGTACATCTACGTATTAGTCATCGC

TATTACCATGGTGATGCGGTTTTGGCAGTACATCAATGGGCGTGGATAG

CGGTTTGACTCACGGGGATTTCCAAGTCTCCACCCCATTGACGTCAATG

GGAGTTTGTTTTGGCACCAAAATCAACGGGACTTTCCAAAATGTCGTAA

CAACTCCGCCCCATTGACGCAAATGGGCGGTAGGCGTGTACGGTGGGAG

GTCTATATAAGCAGAGCTCTCTGGCTAACTAGAGAACCCACTGCTTACT

GGCTTATCGAAATTAATACGACTCACTATAGGGAGACCCAAGCTGGCTA

GGGTCTTCGTCTGATGAGTCCGTGAGGACGAAACCCGGCGTACCGGGTC

ACGAAGACAAACAAACCATTATTATCATTAAAAGGCTCAGGAGAAACTT

TAACAGTAATCAAAATGTCTGTTACAGTCAAGAGAATCATTGACAACAC

AGTCATAGTTCCAAAACTTCCTGCAAATGAGGATCCAGTGGAATACCCG

GCAGATTACTTCAGAAAATCAAAGGAGATTCCTCTTTACATCAATACTA

CAAAAAGTTTGTCAGATCTAAGAGGATATGTCTACCAAGGCCTCAAATC

CGGAAATGTATCAATCATACATGTCAACAGCTACTTGTATGGAGCATTA

AAGGACATCCGGGGTAAGTTGGATAAAGATTGGTCAAGTTTCGGAATAA

ACATCGGGAAAGCAGGGGATACAATCGGAATATTTGACCTTGTATCCTT

GAAAGCCCTGGACGGCGTACTTCCAGATGGAGTATCGGATGCTTCCAGA

ACCAGCGCAGATGACAAATGGTTGCCTTTGTATCTACTTGGCTTATACA

GAGTGGGCAGAACACAAATGCCTGAATACAGAAAAAAGCTCATGGATGG

GCTGACAAATCAATGCAAAATGATCAATGAACAGTTTGAACCTCTTGTG

CCAGAAGGTCGTGACATTTTTGATGTGTGGGGAAATGACAGTAATTACA

CAAAAATTGTCGCTGCAGTGGACATGTTCTTCCACATGTTCAAAAAACA

TGAATGTGCCTCGTTCAGATACGGAACTATTGTTTCCAGATTCAAAGAT

TGTGCTGCATTGGCAACATTTGGACACCTCTGCAAAATAACCGGAATGT

CTACAGAAGATGTAACGACCTGGATCTTGAACCGAGAAGTTGCAGATGA

AATGGTCCAAATGATGCTTCCAGGCCAAGAAATTGACAAGGCCGATTCA

TACATGCCTTATTTGATCGACTTTGGATTGTCTTCTAAGTCTCCATATT

CTTCCGTCAAAAACCCTGCCTTCCACTTCTGGGGGCAATTGACAGCTCT

TCTGCTCAGATCCACCAGAGCAAGGAATGCCCGACAGCCTGATGACATT

GAGTATACATCTCTTACTACAGCAGGTTTGTTGTACGCTTATGCAGTAG

GATCCTCTGCCGACTTGGCACAACAGTTTTGTGTTGGAGATAACAAATA

CACTCCAGATGATAGTACCGGAGGATTGACGACTAATGCACCGCCACAA

GGCAGAGATGTGGTCGAATGGCTCGGATGGTTTGAAGATCAAAACAGAA

AACCGACTCCTGATATGATGCAGTATGCGAAAAGAGCAGTCATGTCACT

GCAAGGCCTAAGAGAGAAGACAATTGGCAAGTATGCTAAGTCAGAATTT

GACAAATGACCCTATAATTCTCAGATCACCTATTATATATTATGCTACA

-continued

TATGAAAAAAACTAACAGATATCATGGATAATCTCACAAAAGTTCGTGA

GTATCTCAAGTCCTATTCTCGTCTGGATCAGGCGGTAGGAGAGATAGAT

GAGATCGAAGCACAACGAGCTGAAAAGTCCAATTATGAGTTGTTCCAAG

AGGATGGAGTGGAAGAGCATACTAAGCCCTCTTATTTTCAGGCAGCAGA

TGATTCTGACACAGAATCTGAACCAGAAATTGAAGACAATCAAGGTTTG

TATGCACCAGATCCAGAAGCTGAGCAAGTTGAAGGCTTTATACAGGGGC

CTTTAGATGACTATGCAGATGAGGAAGTGGATGTTGTATTTACTTCGGA

CTGGAAACAGCCTGAGCTTGAATCTGACGAGCATGGAAAGACCTTACGG

TTGACATCGCCAGAGGGTTTAAGTGGAGAGCAGAAATCCCAGTGGCTTT

CGACGATTAAAGCAGTCGTGCAAAGTGCCAAATACTGGAATCTGGCAGA

GTGCACATTTGAAGCATCGGGAGAAGGGGTCATTATGAAGGAGCGCCAG

ATAACTCCGGATGTATATAAGGTCACTCCAGTGATGAACACACATCCGT

CCCAATCAGAAGCAGTATCAGATGTTTGGTCTCTCAAAGACATCCAT

GACTTTCCAACCCAAGAAAGCAAGTCTTCAGCCTCTCACCATATCCTTG

GATGAATTGTTCTCATCTAGAGGAGAGTTCATCTCTGTCGGAGGTGACG

GACGAATGTCTCATAAAGAGGCCATCCTGCTCGGCCTGAGATACAAAAA

GTTGTACAATCAGGCGAGAGTCAAATATTCTCTGTAGACTATGAAAAAA

AGTAACAGATATCACGATCTAAGTGTTATCCCAATCCATTCATCATGAG

TTCCTTAAAGAAGATTCTCGGTCTGAAGGGGAAAGGTAAGAAATCTAAG

AAATTAGGGATCGCACCACCCCCTTATGAAGAGGACACTAGCATGGAGT

ATGCTCCGAGCGCTCCAATTGACAAATCCTATTTTGGAGTTGACGAGAT

GGACACCTATGATCCGAATCAATTAAGATATGAGAAATTCTTCTTTACA

GTGAAAATGACGGTTAGATCTAATCGTCCGTTCAGAACATACTCAGATG

TGGCAGCCGCTGTATCCCATTGGGATCACATGTACATCGGAATGGCAGG

GAAACGTCCCTTCTACAAAATCTTGGCTTTTTTGGGTTCTTCTAATCTA

AAGGCCACTCCAGCGGTATTGGCAGATCAAGGTCAACCAGAGTATCACA

CTCACTGCGAAGGCAGGGCTTATTTGCCACATAGGATGGGGAAGACCCC

TCCCATGCTCAATGTACCAGAGCACTTCAGAAGACCATTCAATATAGGT

CTTTACAAGGGAACGATTGAGCTCACAATGACCATCTACGATGATGAGT

CACTGGAAGCAGCTCCTATGATCTGGGATCATTTCAATTCTTCCAAATT

TTCTGATTTCAGAGAGAAGGCCTTAATGTTTGGCCTGATTGTCGAGAAA

AAGGCATCTGGAGCGTGGGTCCTGGATTCTATCAGCCACTTCAAATGAG

CTAGTCTAACTTCTAGCTTCTGAACAATCCCCGGTTTACTCAGTCTCTC

CTAATTCCAGCCTCTCGAACAACTAATATCCTGTCTTTTCTATCCCTAT

GAAAAAAACTAACAGAGATCGATCTGTTTACGCGTCACTATGAAGTGCC

TTTTGTACTTAGCCTTTTTATTCATTGGGGTGAATTGCAAGTTCACCAT

AGTTTTTCCACACAACCAAAAAGGAAACTGGAAAAATGTTCCTTCTAAT

TACCATTATTGCCCGTCAAGCTCAGATTTAAATTGGCATAATGACTTAA

TAGGCACAGCCATACAAGTCAAAATGCCCAAGAGTCACAAGGCTATTCA

AGCAGACGGTTGGATGTGTCATGCTTCCAAATGGGTCACTACTTGTGAT

-continued

TTCCGCTGGTATGGACCGAAGTATATAACACAGTCCATCCGATCCTTCA

CTCCATCTGTAGAACAATGCAAGGAAAGCATTGAACAAACGAAACAAGG

AACTTGGCTGAATCCAGGCTTCCCTCCTCAAAGTTGTGGATATGCAACT

GTGACGGATGCCGAAGCAGTGATTGTCCAGGTGACTCCTCACCATGTGC

TGGTTGATGAATACACAGGAGAATGGGTTGATTCACAGTTCATCAACGG

AAAATGCAGCAATTACATATGCCCCACTGTCCATAACTCTACAACCTGG

CATTCTGACTATAAGGTCAAAGGGCTATGTGATTCTAACCTCATTTCCA

TGGACATCACCTTCTTCTCAGAGGACGGAGAGCTATCATCCCTGGGAAA

GGAGGGCACAGGGTTCAGAAGTAACTACTTTGCTTATGAAACTGGAGGC

AAGGCCTGCAAAATGCAATACTGCAAGCATTGGGGAGTCAGACTCCCAT

CAGGTGTCTGGTTCGAGATGGCTGATAAGGATCTCTTTGCTGCAGCCAG

ATTCCCTGAATGCCCAGAAGGGTCAAGTATCTCTGCTCCATCTCAGACC

TCAGTGGATGTAAGTCTAATTCAGGACGTTGAGAGGATCTTGGATTATT

CCCTCTGCCAAGAAACCTGGAGCAAAATCAGAGCGGGTCTTCCAATCTC

TCCAGTGGATCTCAGCTATCTTGCTCCTAAAAACCCAGGAACCGGTCCT

GCTTTCACCATAATCAATGGTACCCTAAAATACTTTGAGACCAGATACA

TCAGAGTCGATATTGCTGCTCCAATCCTCTCAAGAATGGTCGGAATGAT

CAGTGGAACTACCACAGAAAGGGAACTGTGGGATGACTGGGCACCATAT

GAAGACGTGGAAATTGGACCCAATGGAGTTCTGAGGACCAGTTCAGGAT

ATAAGTTTCCTTTATACATGATTGGACATGGTATGTTGGACTCCGATCT

TCATCTTAGCTCAAAGGCTCAGGTGTTCGAACATCCTCACATTCAAGAC

GCTGCTTCGCAACTTCCTGATGATGAGAGTTTATTTTTTGGTGATACTG

GGCTATCCAAAAATCCAATCGAGCTTGTAGAAGGTTGGTTCAGTAGTTG

GAAAAGCTCTATTGCCTCTTTTTTCTTTATCATAGGGTTAATCATTGGA

CTATTCTTGGTTCTCCGAGTTGGTATCCATCTTTGCATTAAATTAAAGC

ACACCAAGAAAAGACAGATTTATACAGACATAGAGATGAACCGACTTGG

AAAGTAACTCAAATCCTGCTAGGTATGAAAAAAACTAACaGATATCACG

CTCGAGCGTACGCCACCATGTTCGTGTTTCTGGTGCTGCTGCCTCTGGT

GAGCTCCCAGTGCGTGAACCTGACCACAAGGACCCAGCTGCCCCCTGCC

TATACCAATTCCTTCACACGGGGCGTGTACTATCCCGACAAGGTGTTCC

GGAGCAGCGTGCTGCACTCCACACAGGATCTGTTTCTGCCTTTCTTTTC

TAACGTGACCTGGTTCCACGCCATCCACGTGAGCGGCACCAATGGCACA

AAGCGGTTCGACAATCCAGTGCTGCCCTTTAACGATGGCGTGTACTTCG

CCTCCACCGAGAAGTCTAACATCATCAGAGGCTGGATCTTTGGCACCAC

ACTGGACAGCAAGACACAGTCCCTGCTGATCGTGAACAATGCCACCAAC

GTGGTCATCAAGGTGTGCGAGTTCCAGTTTTGTAATGATCCATTCCTGG

GCGTGTACTATCACAAGAACAATAAGTCTTGGATGGAGAGCGAGTTTCG

CGTGTATTCCTCTGCCAACAATTGCACATTTGAGTACGTGTCCCAGCCC

TTCCTGATGGACCTGGAGGGCAAGCAGGGCAATTTCAAGAACCTGAGGG

AGTTCGTGTTTAAGAATATCGATGGCTACTTCAAAATCTACTCCAAGCA

CACCCCAATCAACCTGGTGCGCGACCTGCCACAGGGCTTCTCTGCCCTG

```
GAGCCACTGGTGGATCTGCCCATCGGCATCAACATCACCCGGTTTCAGA
CACTGCTGGCCCTGCACAGAAGCTACCTGACACCAGGCGACAGCTCCTC
TGGATGGACCGCAGGAGCAGCAGCCTACTATGTGGGCTATCTGCAGCCC
AGGACCTTCCTGCTGAAGTACAACGAGAATGGCACCATCACAGACGCCG
TGGATTGCGCCCTGGATCCCCTGTCTGAGACCAAGTGTACACTGAAGAG
CTTTACCGTGGAGAAGGGCATCTATCAGACAAGCAATTTCAGGGTGCAG
CCTACCGAGTCCATCGTGCGCTTTCCCAATATCACAAACCTGTGCCCTT
TTGGCGAGGTGTTCAACGCAACCCGCTTCGCCAGCGTGTACGCCTGGAA
TAGGAAGCGCATCTCCAACTGCGTGGCCGACTATTCTGTGCTGTACAAC
AGCGCCTCCTTCTCTACCTTTAAGTGCTATGGCGTGAGCCCCACAAAGC
TGAATGACCTGTGCTTTACCAACGTGTACGCCGATTCCTTCGTGATCAG
GGGCGACGAGGTGCGCCAGATCGCACCAGGACAGACAGGCAAGATCGCA
GACTACAATTATAAGCTGCCTGACGATTTCACCGGCTGCGTGATCGCCT
GGAACTCTAACAATCTGGATAGCAAAGTGGGCGGCAACTACAATTATCT
GTACCGGCTGTTTAGAAAGTCTAATCTGAAGCCATTCGAGAGGGACATC
TCCACAGAAATCTACCAGGCCGGCTCTACCCCCTGCAATGGCGTGGAGG
GCTTTAACTGTTATTTCCCTCTGCAGAGCTACGGCTTCCAGCCAACAAA
CGGCGTGGGCTATCAGCCCTACCGCGTGGTGGTGCTGTCTTTTGAGCTG
CTGCACGCACCTGCAACAGTGTGCGGACCAAAGAAGAGCACCAATCTGG
TGAAGAACAAGTGCGTGAACTTCAACTTCAACGGACTGACCGGAACAGG
CGTGCTGACCGAGTCCAACAAGAAGTTCCTGCCTTTTCAGCAGTTCGGC
AGGGACATCGCAGATACCACAGACGCCGTGCGCGACCCTCAGACCCTGG
AGATCCTGGACATCACACCATGCTCCTTCGGCGGCGTGTCTGTGATCAC
ACCAGGCACCAATACAAGCAACCAGGTGGCCGTGCTGTATCAGGACGTG
AATTGTACCGAGGTGCCAGTGGCAATCCACGCAGATCAGCTGACCCCTA
CATGGCGGGTGTACTCTACCGGCAGCAACGTGTTCCAGACAAGAGCCGG
ATGCCTGATCGGAGCAGAGCACGTGAACAATAGCTATGAGTGCGACATC
CCTATCGGCGCCGGCATCTGTGCCTCCTACCAGACCCAGACAAACTCCC
CAAGGTCTGTGGGCGATACAGGCCTGTCCAAGAATCCAATCGAGCTGGT
AGAGGGCTGGTTCAGCAGTTGGAAAAGCTCCATCGCCTCCTTTTTCTTT
ATCATCGGCCTGATCATCGGACTGTTCCTGGTGCTCCGCGTGGGTATCC
ACCTGTGCATCAAGCTGAAGCACACCAAGAAAAGACAGATTTATACAGA
CATCGAGATGAACCGCCTGGGAAAGTGAGCTAGCCAGATTCTTCATGTT
TGGACCAAATCAACTTGTGATACCATGCTCAAAGAGGCCTCAATTATAT
TTGAGTTTTAATTTTTATGAAAAAAACTAACAGCAATCATGGAAGTCC
ACGATTTTGAGACCGACGAGTTCAATGATTTCAATGAAGATGACTATGC
CACAAGAGAATTCCTGAATCCCGATGAGCGCATGACGTACTTGAATCAT
GCTGATTACAATTTGAATTCTCCTCTAATTAGTGATGATATTGACAATT
TGATCAGGAAATTCAATTCTCTTCCGATTCCCTCGATGTGGGATAGTAA
GAACTGGGATGGAGTTCTTGAGATGTTAACATCATGTCAAGCCAATCCC
ATCTCAACATCTCAGATGCATAAATGGATGGGAAGTTGGTTAATGTCTG
ATAATCATGATGCCAGTCAAGGGTATAGTTTTTTACATGAAGTGGACAA
AGAGGCAGAAATAACATTTGACGTGGTGGAGACCTTCATCCGCGGCTGG
GGCAACAAACCAATTGAATACATCAAAAAGGAAAGATGGACTGACTCAT
TCAAAATTCTCGCTTATTTGTGTCAAAAGTTTTTGGACTTACACAAGTT
GACATTAATCTTAAATGCTGTCTCTGAGGTGGAATTGCTCAACTTGGCG
AGGACTTTCAAAGGCAAAGTCAGAAGAAGTTCTCATGGAACGAACATAT
GCAGGATTAGGGTTCCCAGCTTGGGTCCTACTTTTATTTCAGAAGGATG
GGCTTACTTCAAGAAACTTGATATTCTAATGGACCGAAACTTTCTGTTA
ATGGTCAAAGATGTGATTATAGGGAGGATGCAAACGGTGCTATCCATGG
TATGTAGAATAGACAACCTGTTCTCAGAGCAAGACATCTTCTCCCTTCT
AAATATCTACAGAATTGGAGATAAAATTGTGGAGAGGCAGGGAAATTTT
TCTTATGACTTGATTAAAATGGTGGAACCGATATGCAACTTGAAGCTGA
TGAAATTAGCAAGAGAATCAAGGCCTTTAGTCCCACAATTCCCTCATTT
TGAAAATCATATCAAGACTTCTGTTGATGAAGGGGCAAAATTGACCGA
GGTATAAGATTCCTCCATGATCAGATAATGAGTGTGAAAACAGTGGATC
TCACACTGGTGATTTATGGATCGTTCAGACATTGGGTCATCCTTTTAT
AGATTATTACACTGGACTAGAAAATTACATTCCCAAGTAACCATGAAG
AAAGATATTGATGTGTCATATGCAAAAGCACTTGCAAGTGATTTAGCTC
GGATTGTTCTATTTCAACAGTTCAATGATCATAAAAAGTGGTTCGTGAA
TGGAGACTTGCTCCCTCATGATCATCCCTTTAAAAGTCATGTTAAAGAA
AATACATGGCCCACAGCTGCTCAAGTTCAAGATTTTGGAGATAAATGGC
ATGAACTTCCGCTGATTAAATGTTTTGAAATACCCGACTTACTAGACCC
ATCGATAATATACTCTGACAAAAGTCATTCAATGAATAGGTCAGAGGTG
TTGAAACATGTCCGAATGAATCCGAACACTCCTATCCCTAGTAAAAAGG
TGTTGCAGACTATGTTGGACACAAAGGCTACCAATTGGAAAGAATTTCT
TAAAGAGATTGATGAGAAGGGCTTAGATGATGATGATCTAATTATTGGT
CTTAAAGGAAAGGAGAGGGAACTGAAGTTGGCAGGTAGATTTTCTCCC
TAATGTCTTGGAAATTGCGAGAATACTTTGTAATTACCGAATATTTGAT
AAAGACTCATTTCGTCCCTATGTTTAAAGGCCTGACAATGGCGGACGAT
CTAACTGCAGTCATTAAAAGATGTTAGATTCCTCATCCGGCCAAGGAT
TGAAGTCATATGAGGCAATTTGCATAGCCAATCACATTGATTACGAAAA
ATGGAATAACCACCAAAGGAAGTTATCAAACGGCCCAGTGTTCCGAGTT
ATGGGCCAGTTCTTAGGTTATCCATCCTTAATCGAGAGAACTCATGAAT
TTTTTGAGAAAAGTCTTATATACTACAATGGAAGACCAGACTTGATGCG
TGTTCACAACAACACACTGATCAATTCAACCTCCCAACGAGTTTGTTGG
CAAGGACAAGAGGGTGGACTGGAAGGTCTACGGCAAAAAGGATGGACTA
TCCTCAATCTACTGGTTATTCAAAGAGAGGCTAAAATCAGAAACACTGC
TGTCAAAGTCTTGGCACAAGGTGATAATCAAGTTATTTGCACACAGTAT
AAAAACGAAGAAATCGAGAAACGTTGTAGAATTACAGGGTGCTCTCAATC
AAATGGTTTCTAATAATGAGAAAATTATGACTGCAATCAAAATAGGGAC
```

-continued

AGGGAAGTTAGGACTTTTGATAAATGACGATGAGACTATGCAATCTGCA
GATTACTTGAATTATGGAAAAATACCGATTTTCCGTGGAGTGATTAGAG
GGTTAGAGACCAAGAGATGGTCACGAGTGACTTGTGTCACCAATGACCA
AATACCCACTTGTGCTAATATAATGAGCTCAGTTTCCACAAATGCTCTC
ACCGTAGCTCATTTTGCTGAGAACCCAATCAATGCCATGATACAGTACA
ATTATTTTGGGACATTTGCTAGACTCTTGTTGATGATGCATGATCCTGC
TCTTCGTCAATCATTGTATGAAGTTCAAGATAAGATACCGGGCTTGCAC
AGTTCTACTTTCAAATACGCCATGTTGTATTTGGACCCTTCCATTGGAG
GAGTGTCGGGCATGTCTTTGTCCAGGTTTTTGATTAGAGCCTTCCCAGA
TCCCGTAACAGAAAGTCTCTCATTCTGGAGATTCATCCATGTACATGCT
CGAAGTGAGCATCTGAAGGAGATGAGTGCAGTATTTGGAAACCCCGAGA
TAGCCAAGTTTCGAATAACTCACATAGACAAGCTAGTAGAAGATCCAAC
CTCTCTGAACATCGCTATGGGAATGAGTCCAGCGAACTTGTTAAAGACT
GAGGTTAAAAAATGCTTAATCGAATCAAGACAAACCATCAGGAACCAGG
TGATTAAGGATGCAACCATATATTTGTATCATGAAGAGGATCGGCTCAG
AAGTTTCTTATGGTCAATAAATCCTCTGTTCCCTAGATTTTTAAGTGAA
TTCAAATCAGGCACTTTTTTGGGAGTCGCAGACGGGCTCATCAGTCTAT
TTCAAAATTCTCGTACTATTCGGAACTCCTTTAAGAAAAAGTATCATAG
GGAATTGGATGATTTGATTGTGAGGAGTGAGGTATCCTCTTTGACACAT
TTAGGGAAACTTCATTTGAGAAGGGGATCATGTAAAATGTGGACATGTT
CAGCTACTCATGCTGACACATTAAGATACAAATCCTGGGGCCGTACAGT
TATTGGGACAACTGTACCCCATCCATTAGAAATGTTGGGTCCACAACAT
CGAAAAGAGACTCCTTGTGCACCATGTAACACATCAGGGTTCAATTATG
TTTCTGTGCATTGTCCAGACGGGATCCATGACGTCTTTAGTTCACGGGG
ACCATTGCCTGCTTATCTAGGGTCTAAAACATCTGAATCTACATCTATT
TTGCAGCCTTGGGAAAGGGAAAGCAAAGTCCCACTGATTAAAAGAGCTA
CACGTCTTAGAGATGCTATCTCTTGGTTTGTTGAACCCGACTCTAAACT
AGCAATGACTATACTTTCTAACATCCACTCTTTAACAGGCGAAGAATGG
ACCAAAAGGCAGCATGGGTTCAAAAGAACAGGGTCTGCCCTTCATAGGT
TTTCGACATCTCGGATGAGCCATGGTGGGTTCGCATCTCAGAGCACTGC
AGCATTGACCAGGTTGATGGCAACTACAGACACCATGAGGGATCTGGGA
GATCAGAATTTCGACTTTTTATTCCAAGCAACGTTGCTCTATGCTCAAA
TTACCACCACTGTTGCAAGAGACGGATGGATCACCAGTTGTACAGATCA
TTATCATATTGCCTGTAAGTCCTGTTTGAGACCCATAGAAGAGATCACC
CTGGACTCAAGTATGGACTACACGCCCCAGATGTATCCCATGTGCTGA
AGACATGGAGGAATGGGAAGGTTCGTGGGACAAGAGATAAAACAGAT
CTATCCTTTAGAAGGGAATTGGAAGAATTTAGCACCTGCTGAGCAATCC
TATCAAGTCGGCAGATGTATAGGTTTTCTATATGGAGACTTGGCGTATA
GAAAATCTACTCATGCCGAGGACAGTTCTCTATTTCCTCTATCTATACA
AGGTCGTATTAGAGGTCGAGGTTTCTTAAAAGGGTTGCTAGACGGATTA

ATGAGAGCAAGTTGCTGCCAAGTAATACACCGGAGAAGTCTGGCTCATT
TGAAGAGGCCGGCCAACGCAGTGTACGGAGGTTTGATTTACTTGATTGA
TAAATTGAGTGTATCACCTCCATTCCTTTCTCTTACTAGATCAGGACCT
ATTAGAGACGAATTAGAAACGATTCCCCACAAGATCCCAACCTCCTATC
CGACAAGCAACCGTGATATGGGGGTGATTGTCAGAAATTACTTCAAATA
CCAATGCCGTCTAATTGAAAAGGGAAAATACAGATCACATTATTCACAA
TTATGGTTATTCTCAGATGTCTTATCCATAGACTTCATTGGACCATTCT
CTATTTCCACCACCCTCTTGCAAATCCTATACAAGCCATTTTTATCTGG
GAAAGATAAGAATGAGTTGAGAGAGCTGGCAAATCTTTCTTCATTGCTA
AGATCAGGAGAGGGTGGGAAGACATACATGTGAAATTCTTCACCAAGG
ACATATTATTGTGTCCAGAGGAAATCAGACATGCTTGCAAGTTCGGGAT
TGCTAAGGATAATAATAAAGACATGAGCTATCCCCCTTGGGGAAGGGAA
TCCAGAGGGACAATTACAACAATCCCTGTTTATTATACGACCACCCCTT
ACCCAAAGATGCTAGAGATGCCTCCAAGAATCCAAAATCCCCTGCTGTC
CGGAATCAGGTTGGGCCAATTACCAACTGGCGCTCATTATAAAATTCGG
AGTATATTACATGGAATGGGAATCCATTACAGGGACTTCTTGAGTTGTG
GAGACGGCTCCGGAGGGATGACTGCTGCATTACTACGAGAAAATGTGCA
TAGCAGAGGAATATTCAATAGTCTGTTAGAATTATCAGGGTCAGTCATG
CGAGGCGCCTCTCCTGAGCCCCCCAGTGCCCTAGAAACTTTAGGAGGAG
ATAAATCGAGATGTGTAAATGGTGAAACATGTTGGGAATATCCATCTGA
CTTATGTGACCCAAGGACTTGGGACTATTTCCTCCGACTCAAAGCAGGC
TTGGGGCTTCAAATTGATTTAATTGTAATGGATATGGAAGTTCGGGATT
CTTCTACTAGCCTGAAAATTGAGACGAATGTTAGAAATTATGTGCACCG
GATTTTGGATGAGCAAGGAGTTTTAATCTACAAGACTTATGGAACATAT
ATTTGTGAGAGCGAAAAGAATGCAGTAACAATCCTTGGTCCCATGTTCA
AGACGGTCGACTTAGTTCAAACAGAATTTAGTAGTTCTCAAACGTCTGA
AGTATATATGGTATGTAAAGGTTTGAAGAAATTAATCGATGAACCCAAT
CCCGATTGGTCTTCCATCAATGAATCCTGGAAAAACCTGTACGCATTCC
AGTCATCAGAACAGGAATTTGCCAGAGCAAAGAAGGTTAGTACATACTT
TACCTTGACAGGTATTCCCTCCCAATTCATTCCTGATCCTTTTGTAAAC
ATTGAGACTATGCTACAAATATTCGGAGTACCCACGGGTGTGTCTCATG
CGGCTGCCTTAAAATCATCTGATAGACCTGCAGATTTATTGACCATTAG
CCTTTTTTATATGGCGATTATATCGTATTATAACATCAATCATATCGAGA
GTAGGACCGATACCTCCGAACCCCCCATCAGATGGAATTGCACAAAATG
TGGGGATCGCTATAACTGGTATAAGCTTTTGGCTGAGTTTGATGGAGAA
AGACATTCCACTATATCAACAGTGTTTAGCAGTTATCCAGCAATCATTC
CCGATTAGGTGGGAGGCTGTTTCAGTAAAAGGAGGATACAAGCAGAAGT
GGAGTACTAGAGGTGATGGGCTCCCAAAAGATACCCGAACTTCAGACTC
CTTGGCCCCAATCGGGAACTGGATCAGATCTCTGGAATTGGTCCGAAAC
CAAGTTCGTCTAAATCCATTCAATGAGATCTTGTTCAATCAGCTATGTC
GTACAGTGGATAATCATTTGAAATGGTCAAATTTGCGAAGAAACACAGG

-continued

```
AATGATTGAATGGATCAATAGACGAATTTCAAAAGAAGACCGGTCTATA
CTGATGTTGAAGAGTGACCTACACGAGGAAAACTCTTGGAGAGATTAAA
AAATCATGAGGAGACTCCAAACTTTAAGTATGAAAAAAACTTTGATCCT
TAAGACCCTCTTGTGGTTTTTATTTTTTATCTGGTTTTGTGGTCTTCGT
GGGTCGGCATGGCATCTCCACCTCCTCGCGGTCCGACCTGGGCATCCGA
AGGAGGACGCACGTCCACTCGGATGGCTAAGGGAGAGCCAGAAAATAAC
TAGTGGATCCGGCTGCTAACAAAGCCCGAAAGGAAGCTGAGTTGGCTGC
TGCCACCGCTGAGCAATAACTAGCATAACCCCTTGGGGCCTCTAAACGG
GTCTTGAGGGGTTTTTTGCTGAAAGtCGCGCTTGGCGTAATCATGGTCA
TAGCTGTTTCCTGTGTGAAATTGTTATCCGCTCACAATTCCACACAACA
TACGAGCCGGAAGCATAAAGTGTAAAGCCTGGGGTGCCTAATGAGTGAG
CTAACTCACATTAATTGCGTTGCGCTCACTGCCCGCTTTCCAGTCGGGA
AACCTGTCGTGCCAGCTGCATTAATGAATCGGCCAACGCGCGGGGAGAG
GCGGTTTGCGTATTGGGCGCTCTTCCGCTTCCTCGCTCACTGACTCGCT
GCGCTCGGTCGTTCGGCTGCGGCGAGCGGTATCAGCTCACTCAAAGGCG
GTAATACGGTTATCCACAGAATCAGGGGATAACGCAGGAAAGAACATGT
GAGCAAAAGGCCAGCAAAAGGCCAGGAACCGTAAAAAGGCCGCGTTGCT
GGCGTTTTTCCATAGGCTCCGCCCCCCTGACGAGCATCACAAAAATCGA
CGCTCAAGTCAGAGGTGGCGAAACCCGACAGGACTATAAAGATACCAGG
CGTTTCCCCCTGGAAGCTCCCTCGTGCGCTCTCCTGTTCCGACCCTGCC
GCTTACCGGATACCTGTCCGCCTTTCTCCCTTCGGGAAGCGTGGCGCTT
TCTCATAGCTCACGCTGTAGGTATCTCAGTTCGGTGTAGGTCGTTCGCT
CCAAGCTGGGCTGTGTGCACGAACCCCCCGTTCAGCCCGACCGCTGCGC
CTTATCCGGTAACTATCGTCTTGAGTCCAACCCGGTAAGACACGACTTA
TCGCCACTGGCAGCAGCCACTGGTAACAGGATTAGCAGAGCGAGGTATG
TAGGCGGTGCTACAGAGTTCTTGAAGTGGTGGCCTAACTACGGCTACAC
TAGAAGGACAGTATTTGGTATCTGCGCTCTGCTGAAGCCAGTTACCTTC
GGAAAAAGAGTTGGTAGCTCTTGATCCGGCAAACAAACCACCGCTGGTA
GCGGTGGTTTTTTTGTTTGCAAGCAGCAGATTACGCGCAGAAAAAAAGG
ATCTCAAGAAGATCCTTTGATCTTTTCTACGGGGTCTGACGCTCAGTGG
AACGAAAACTCACGTTAAGGGATTTTGGTCATGAGATTATCAAAAAGGA
TCTTCACCTAGATCCTTTTAAATTAAAAATGAAGTTTTAAATCAATCTA
AAGTATATATGAGTAAACTTGGTCTGACAGTTACCAATGCTTAATCAGT
GAGGCACCTATCTCAGCGATCTGTCTATTTCGTTCATCCATAGTTGCCT
GACTCCCCGTCGTGTAGATAACTACGATACGGGAGGGCTTACCATCTGG
CCCCAGTGCTGCAATGATACCGCGAGACCCACGCTCACCGGCTCCAGAT
TTATCAGCAATAAACCAGCCAGCCGGAAGGGCCGAGCGCAGAAGTGGTC
CTGCAACTTTATCCGCCTCCATCCAGTCTATTAATTGTTGCCGGGAAGC
TAGAGTAAGTAGTTCGCCAGTTAATAGTTTGCGCAACGTTGTTGCCATT
GCTACAGGCATCGTGGTGTCACGCTCGTCGTTTGGTATGGCTTCATTCA
GCTCCGGTTCCCAACGATCAAGGCGAGTTACATGATCCCCCATGTTGTG
CAAAAAAGCGGTTAGCTCCTTCGGTCCTCCGATCGTTGTCAGAAGTAAG
TTGGCCGCAGTGTTATCACTCATGGTTATGGCAGCACTGCATAATTCTC
TTACTGTCATGCCATCCGTAAGATGCTTTTCTGTGACTGGTGAGTACTC
AACCAAGTCATTCTGAGAATAGTGTATGCGGCGACCGAGTTGCTCTTGC
CCGGCGTCAATACGGGATAATACCGCGCCACATAGCAGAACTTTAAAAG
TGCTCATCATTGGAAAACGTTCTTCGGGGCGAAAACTCTCAAGGATCTT
ACCGCTGTTGAGATCCAGTTCGATGTAACCCACTCGTGCACCCAACTGA
TCTTCAGCATCTTTTACTTTCACCAGCGTTTCTGGGTGAGCAAAAACAG
GAAGGCAAAATGCCGCAAAAAAGGGAATAAGGGCGACACGGAAATGTTG
AATACTCATACTCTTCCTTTTTCAATATTATTGAAGCATTTATCAGGGT
TATTGTCTCATGAGCGGATACATATTTGAATGTATTTAGAAAAATAAAC
AAATAGGGGTTCCGCGCACATTTCCCCGAAAAGTGCCAC.
```

In one embodiment, the nucleic acid comprises (a) a sequence encoding at least a portion of the genome of a rabies virus and (b) a sequence encoding a protein comprising a SARS-CoV-2 spike protein (S) or a portion thereof. In some embodiments, the at least a portion of the genome of the rabies virus comprises an N gene and a P gene, and the sequence encoding the protein comprising the SARS-CoV-2 spike protein (S) or portion thereof is inserted into a position between the N gene and P gene. In some embodiments, the protein comprising a SARS-CoV-2 spike protein (S) or a portion thereof is a fusion protein comprising a glycoprotein (G) or a portion thereof and a SARS-CoV-2 spike protein (S) or a portion thereof. In some embodiments, the fusion protein comprises a glycoprotein (G) or portion thereof fused to the S1 domain of a SARS-CoV-2 spike protein (S).

In another embodiment, the nucleic acid comprises the sequence of SEQ ID NO: 2, shown below:

```
CTGACGCGCCCTGTAGCGGCGCATTAAGCGCGGCGGGTGTGGTGGTTACGCGCA
GCGTGACCGCTACACTTGCCAGCGCCCTAGCGCCCGCTCCTTTCGCTTTCTTCCCT
TCCTTTCTCGCCACGTTCGCCGGCTTTCCCCGTCAAGCTCTAAATCGGGGCTCC
CTTTAGGGTTCCGATTTAGTGCTTTACGGCACCTCGACCCCAAAAAACTTGATTA
GGGTGATGGTTCACGTAGTGGGCCATCGCCCTGATAGACGGTTTTTCGCCCTTTG
ACGTTGGAGTCCACGTTCTTTAATAGTGGACTCTTGTTCCAAACTGGAACAACAC
TCAACCCTATCTCGGTCTATTCTTTTGATTTATAAGGGATTTTGCCGATTTCGGCC
```

-continued

```
TATTGGTTAAAAAATGAGCTGATTTAACAAAAATTTAACGCGAATTTTAACAAA
ATATTAACGCTTACAATTTCCATTCGCCATTCAGGCTGCGCAACTGTTGGGAAGG
GCGATCGGTGCGGGCCTCTTCGCTATTACGCCAGCTGGCGAAAGGGGGATGTGC
TGCAAGGCGATTAAGTTGGGTAACGCCAGGGTTTTCCCAGTCACGACGTTGTAA
AACGACGGCCAGTGAGcgcgccCTAGTTATTAATAGTAATCAATTACGGGGTCATT
AGTTCATAGCCCATATATGGAGTTCCGCGTTACATAACTTACGGTAAATGGCCCG
CCTGGCTGACCGCCCAACGACCCCCGCCCATTGACGTCAATAATGACGTATGTTC
CCATAGTAACGCCAATAGGGACTTTCCATTGACGTCAATGGGTGGAGTATTTACG
GTAAACTGCCCACTTGGCAGTACATCAAGTGTATCATATGCCAAGTACGCCCCCT
ATTGACGTCAATGACGGTAAATGGCCCGCCTGGCATTATGCCCAGTACATGACCT
TATGGGACTTTCCTACTTGGCAGTACATCTACGTATTAGTCATCGCTATTACCATG
GTGATGCGGTTTTGGCAGTACATCAATGGGCGTGGATAGCGGTTTGACTCACGG
GGATTTCCAAGTCTCCACCCCATTGACGTCAATGGGAGTTTGTTTTGGCACCAAA
ATCAACGGGACTTTCCAAAATGTCGTAACAACTCCGCCCCATTGACGCAAATGG
GCGGTAGGCGTGTACGGTGGGAGGTCTATATAAGCAGAGCTCTCTGGCTAACTA
GAGAACCCACTGCTTACTGGCTTATCGAAATTAATACGACTCACTATAGGGAGA
CCCAAGCTGGCTAGATTAAGCGTCTGATGAGTCCGTGAGGACGAAACCCGGCGT
ACCGGGTCACGCTTAACAACCAGATCAAAGAAAAAACAGACATTGTCAATTGCA
AAGCAAAAATGTAACACCCCTACAATGGATGCCGACAAGATTGTATTCAAAGTC
AATAATCAGGTGGTCTCTTTGAAGCCTGAGATTATCGTGGATCAATATGAGTACA
AGTACCCTGCCATCAAAGATTTGAAAAAGCCCTGTATAACCCTAGGAAAGGCTC
CCGATTTAAATAAAGCATACAAGTCAGTTTTGTCAGGCATGAGCGCCGCCAAAC
TTAATCCTGACGATGTATGTTCCTATTTGGCAGCGGCAATGCAGTTTTTTGAGGG
GACATGTCCGGAAGACTGGACCAGCTATGGAATTGTGATTGCACGAAAAGGAGA
TAAGATCACCCCAGGTTCTCTGGTGGAGATAAAACGTACTGATGTAGAAGGGAA
TTGGGCTCTGACAGGAGGCATGGAACTGACAAGAGACCCCACTGTCCCTGAGCA
TGCGTCCTTAGTCGGTCTTCTCTTGAGTCTGTATAGGTTGAGCAAAATATCCGGG
CAAAACACTGGTAACTATAAGACAAACATTGCAGACAGGATAGAGCAGATTTTT
GAGACAGCCCCTTTTGTTAAAATCGTGGAACACCATACTCTAATGACAACTCACA
AaATGTGTGCTAATTGGAGTACTATACCAAACTTCAGATTTTTGGCCGGAACCTA
TGACATGTTTTTCTCCCGGATTGAGCATCTATATTCAGCAATCAGAGTGGGCACA
GTTGTCACTGCTTATGAAGACTGTTCAGGACTGGTATCATTTACTGGGTTCATAA
AACAAATCAATCTCACCGCTAGAGAGGCAATACTATATTTCTTCCACAAGAACTT
TGAGGAAGAGATAAGAAGAATGTTTGAGCCAGGGCAGGAGACAGCTGTTCCTCA
CTCTTATTTCATCCACTTCCGTTCACTAGGCTTGAGTGGGAAATCTCCTTATTCAT
CAAATGCTGTTGGTCACGTGTTCAATCTCATTCACTTTGTAGGATGCTATATGGG
TCAAGTCAGATCCCTAAATGCAACGGTTATTGCTGCATGTGCTCCTCATGAAATG
TCTGTTCTAGGGGGCTATCTGGGAGAGGAATTCTTCGGGAAAGGGACATTTGAA
AGAAGATTCTTCAGAGATGAGAAAGAACTTCAAGAATACGAGGCGGCTGAACTG
ACAAAGACTGACGTAGCACTGGCAGATGATGGAACTGTCAACTCTGACGACGAG
GACTACTTTTCAGGTGAAACCAGAAGTCCGGAGGCTGTTTATACTCGAATCATGA
```

-continued

```
TGAATGGAGGTCGACTAAAGAGATCTCACATACGGAGATATGTCTCAGTCAGTT

CCAATCATCAAGCCCGTCCAAACTCATTCGCCGAGTTTCTAAACAAGACATATTC

GAGTGACTCATAAcatgaaaaaaactaacacccctcccGTACGCCACCATGTTCGTGTTTCTGG

TGCTGCTGCCTCTGGTGAGCTCCCAGTGCGTGAACCTGACCACAAGGACCCAGCT

GCCCCCTGCCTATACCAATTCCTTCACACGGGGCGTGTACTATCCCGACAAGGTG

TTCCGGAGCAGCGTGCTGCACTCCACACAGGATCTGTTTCTGCCTTTCTTTTCTAA

CGTGACCTGGTTCCACGCCATCCACGTGAGCGGCACCAATGGCACAAAGCGGTT

CGACAATCCAGTGCTGCCCTTTAACGATGGCGTGTACTTCGCCTCCACCGAGAAG

TCTAACATCATCAGAGGCTGGATCTTTGGCACCACACTGGACAGCAAGACACAG

TCCCTGCTGATCGTGAACAATGCCACCAACGTGGTCATCAAGGTGTGCGAGTTCC

AGTTTTGTAATGATCCATTCCTGGGCGTGTACTATCACAAGAACAATAAGTCTTG

GATGGAGAGCGAGTTTCGCGTGTATTCCTCTGCCAACAATTGCACATTTGAGTAC

GTGTCCCAGCCCTTCCTGATGGACCTGGAGGGCAAGCAGGGCAATTTCAAGAAC

CTGAGGGAGTTCGTGTTTAAGAATATCGATGGCTACTTCAAAATCTACTCCAAGC

ACACCCCAATCAACCTGGTGCGCGACCTGCCACAGGGCTTCTCTGCCCTGGAGCC

ACTGGTGGATCTGCCCATCGGCATCAACATCACCCGGTTTCAGACACTGCTGGCC

CTGCACAGAAGCTACCTGACACCAGGCGACAGCTCCTCTGGATGGACCGCAGGA

GCAGCAGCCTACTATGTGGGCTATCTGCAGCCCAGGACCTTCCTGCTGAAGTACA

ACGAGAATGGCACCATCACAGACGCCGTGGATTGCGCCCTGGATCCCCTGTCTG

AGACCAAGTGTACACTGAAGAGCTTTACCGTGGAGAAGGGCATCTATCAGACAA

GCAATTTCAGGGTGCAGCCTACCGAGTCCATCGTGCGCTTTCCCAATATCACAAA

CCTGTGCCCTTTTGGCGAGGTGTTCAACGCAACCCGCTTCGCCAGCGTGTACGCC

TGGAATAGGAAGCGCATCTCCAACTGCGTGGCCGACTATTCTGTGCTGTACAACA

GCGCCTCCTTCTCTACCTTTAAGTGCTATGGCGTGAGCCCCACAAAGCTGAATGA

CCTGTGCTTTACCAACGTGTACGCCGATTCCTTCGTGATCAGGGGCGACGAGGTG

CGCCAGATCGCACCAGGACAGACAGGCAAGATCGCAGACTACAATTATAAGCTG

CCTGACGATTTCACCGGCTGCGTGATCGCCTGGAACTCTAACAATCTGGATAGCA

AAGTGGGCGGCAACTACAATTATCTGTACCGGCTGTTTAGAAAGTCTAATCTGAA

GCCATTCGAGAGGGACATCTCCACAGAAATCTACCAGGCCGGCTCTACCCCCTG

CAATGGCGTGGAgGGCTTTAACTGTTATTTCCCTCTGCAGAgCTACgGCTTCCAGC

CAACAAACGGCGTGGGCTATCAGCCCTACCGCGTGGTGGTGCTGTCTTTTGAGCT

GCTGCACGCACCTGCAACAGTGTGCGGACCAAAGAAGAGCACCAATCTGGTGAA

GAACAAGTGCGTGAACTTCAACTTCAACGGACTGACCGGAACAGGCGTGCTGAC

CGAGTCCAACAAGAAGTTCCTGCCTTTTCAGCAGTTCGGCAGGGACATCGCAGA

TACCACAGACGCCGTGCGCGACCCTCAGACCCTGGAGATCCTGGACATCACACC

ATGCTCCTTCGGCGGCGTGTCTGTGATCACACCAGGCACCAATACAAGCAACCA

GGTGGCCGTGCTGTATCAGGACGTGAATTGTACCGAGGTGCCAGTGGCAATCCA

CGCAGATCAGCTGACCCCTACATGGCGGGTGTACTCTACCGGCAGCAACGTGTT

CCAGACAAGAGCCGGATGCCTGATCGGAGCAGAGCACGTGAACAATAGCTATG

AGTGCGACATCCCTATCGGCGCCGGCATCTGTGCCTCCTACCAGACCCAGACAA
```

-continued

```
ACTCCCCAAGGTCTGTGGGAGATGAGGCCGAAGACTTTGTGGAAGTCCACCTGC

CTGATGTGCATAACCAGGTGTCTGGCGTCGACCTGGGACTGCCAAATTGGGGCA

AGTACGTGCTGCTGAGTGCTGGAGCACTGACTGCCCTGATGCTGATCATTTTCCT

GATGACCTGCTGTCGGCGCGTGAACAGAAGTGAGCCCACTCAGCACAATCTGCG

AGGAACCGGGAGAGAAGTGTCAGTCACACCTCAGAGCGGGAAAATCATTAGTA

GTTGGGAATCACATAAAAGCGGGGGCGAGACCAGGCTGTGAGCTAGCCATGAA

AAAAACTAACACCCCTCCTTTCGAACCATCCCAAACATGAGCAAGATCTTTGTCA

ATCCTAGTGCTATTAGAGCCGGTCTGGCCGATCTTGAGATGGCTGAAGAAACTGT

TGATCTGATCAATAGAAATATCGAAGACAATCAGGCTCATCTCCAAGGGGAACC

CATAGAGGTGGACAATCTCCCTGAGGATATGGGGCGACTTCACCTGGATGATGG

AAAATCGCCCAACCATGGTGAGATAGCCAAGGTGGGAGAAGGCAAGTATCGAG

AGGACTTTCAGATGGATGAAGGAGAGGATCCTAGCTTCCTGTTCCAGTCATACCT

GGAAAATGTTGGAGTCCAAATAGTCAGACAAATGAGGTCAGGAGAGAGATTTCT

CAAGATATGGTCACAGACCGTAGAAGAGATTATATCCTATGTCGCGGTCAACTTT

CCCAACCCTCCAGGAAAGTCTTCAGAGGATAAATCAACCCAGACTACTGGCCGA

GAGCTCAAGAAGGAGACAACACCCACTCCTTCTCAGAGAGAAAGCCAATCATCG

AAAGCCAGGATGGCGGCTCAAATTGCTTCTGGCCCTCCAGCCCTTGAATGGTCG

GCTACCAATGAAGAGGATGATCTATCAGTGGAGGCTGAGATCGCTCACCAGATT

GCAGAAAGTTTCTCCAAAAAATATAAGTTTCCCTCTCGATCCTCAGGGATACTCT

TGTATAATTTTGAGCAATTGAAAATGAACCTTGATGATATAGTTAAAGAGGCAA

AAAATGTACCAGGTGTGACCCGTTTAGCCCATGACGGGTCCAAACTCCCCCTAA

GATGTGTACTGGGATGGGTCGCTTTGGCCAACTCTAAGAAATTCCAGTTGTTAGT

CGAATCCGACAAGCTGAGTAAAATCATGCAAGATGACTTGAATCGCTATACATC

TTGCTAACCGAACCTCTCCCCTCAGTCCCTCTAGACAATAAAATCCGAGATGTCC

CAAAGTCAACATGAAAAAAACAGGCAACACCACTGATAAAATGAACCTCCTACG

TAAGATAGTGAAAAACCGCAGGGACGAGGACACTCAAAAATCCTCTCCCGCGTC

AGCCCCTCTGGATGACGATGACTTGTGGCTTCCACCCCCTGAATACGTCCCGCTG

AAAGAACTTACAGGCAAGAAGAACATGAGGAACTTTTGTATCAACGGAAGGGTT

AAAGTGTGTAGCCCGAATGGTTACTCGTTCAGGATCCTGCGGCACATTCTGAAAT

CATTCGACGAGATATATTCTGGGAATCATAGGATGATCGGGTTAGTCAAAGTGG

TTATTGGACTGGCTTTGTCAGGATCTCCAGTCCCTGAGGGCCTGAACTGGGTATA

CAAATTGAGGAGAACCTTTATCTTCCAGTGGGCTGATTCCAGGGGCCCTCTTGAA

GGGGAGGAGTTGGAATACTCTCAGGAGATCACTTGGGATGATGATACTGAGTTC

GTCGGATTGCAAATAAGAGTGATTGCAAAACAGTGTCATATCCAGGGCAGAGTC

TGGTGTATCAACATGAACCCGAGAGCATGTCAACTATGGTCTGACATGTCTCTTC

AGACACAAAGGTCCGAAGAGGACAAAGATTCCTCTCTGCTTCTAGAATAATCAG

ATTATATCCCGCAAATTTATCACTTGTTTACCTCTGGAGGAGAGAACATATGGGC

TCAACTCCAACCCTTGGGAGCAATATAACAAAAAACATGTTATGGTGCCATTAA

ACCGCTGCATTTCATCAAAGTCAAGTTGATTACCTTTACATTTTGATCCTCTTGGA

TGTGAAAAAAACTATTAACATCCCTCAAAAGACcccgggAAAGATGGTTCCTCAGG

CTCTCCTGTTTGTACCCCTTCTGGTTTTTCCATTGTGTTTTGGGAAATTCCCTATTT
```

```
ACACGATACCAGACAAGCTTGGTCCCTGGAGTCCGATTGACATACATCACCTCA
GCTGCCCAAACAATTTGGTAGTGGAGGACGAAGGATGCACCAACCTGTCAGGGT
TCTCCTACATGGAACTTAAAGTTGGATACATCTTAGCCATAAAAGTGAACGGGTT
CACTTGCACAGGCGTTGTGACGGAGGCTGAAACCTACACTAACTTCGTTGGTTAT
GTCACAACCACGTTCAAAAGAAAGCATTTCCGCCCAACACCAGATGCATGTAGA
GCCGCGTACAACTGGAAGATGGCCGGTGACCCCAGATATGAAGAGTCTCTACAC
AATCCGTACCCTGACTACCGCTGGCTTCGAACTGTAAAAACCACCAAGGAGTCT
CTCGTTATCATATCTCCAAGTGTGGCAGATTTGGACCCATATGACAGATCCCTTC
ACTCGAGGGTCTTCCCTAGCGGGAAGTGCTCAGGAGTAGCGGTGTCTTCTACCTA
CTGCTCCACTAACCACGATTACACCATTTGGATGCCCGAGAATCCGAGACTAGG
GATGTCTTGTGACATTTTTACCAATAGTAGAGGGAAGAGAGCATCCAAAGGGAG
TGAGACTTGCGGCTTTGTAGATGAAAGAGGCCTATATAAGTCTTTAAAAGGAGC
ATGCAAACTCAAGTTATGTGGAGTTCTAGGACTTAGACTTATGGATGGAACATG
GGTCTCGATGCAAACATCAAATGAAACCAAATGGTGCCCTCCCGATAAGTTGGT
GAACCTGCACGACTTTCGCTCAGACGAAATTGAGCACCTTGTTGTAGAGGAGTTG
GTCAGGAAGAGAGAGGAGTGTCTGGATGCACTAGAGTCCATCATGACAACCAAG
TCAGTGAGTTTCAGACGTCTCAGTCATTTAAGAAAACTTGTCCCTGGGTTTGGAA
AAGCATATACCATATTCAACAAGACCTTGATGGAAGCCGATGCTCACTACAAGT
CAGTCgagACTTGGAATGAGATCCTCCCTTCAAAAGGGTGTTTAAGAGTTGGGGG
GAGGTGTCATCCTCATGTGAACGGGGTGTTTTTCAATGGTATAATATTAGGACCT
GACGGCAATGTCTTAATCCCAGAGATGCAATCATCCCTCCTCCAGCAACATATGG
AGTTGTTGGAATCCTCGGTTATCCCCCTTGTGCACCCCCTGGCAGACCCGTCTAC
CGTTTTCAAGGACGGTGACGAGGCTGAGGATTTTGTTGAAGTTCACCTTCCCGAT
GTGCACAATCAGGTCTCAGGAGTTGACTTGGGTCTCCCGAACTGGGGGAAGTAT
GTATTACTGAGTGCAGGGGCCCTGACTGCCTTGATGTTGATAATTTTCCTGATGA
CATGTTGTAGAAGAGTCAATCGATCAGAACCTACGCAACACAATCTCAGAGGGA
CAGGGAGGGAGGTGTCAGTCACTCCCCAAAGCGGGAAGATCATATCTTCATGGG
AATCACACAAGAGTGGGGGTGAGACCAGACTGTAAttaattaaCGTCCTTTCAACGAT
CCAAGTCcatgaaaaaaactaacaccccctcccgtacctagcTTATAAAGTGCTGGGTCATCTAAGCTT
TTCAGTCGAGAAAAAAACATTAGATCAGAAGAACAACTGGCAACACTTCTCAAC
CTGAGACTTACTTCAAGATGCTCGATCCTGGAGAGGTCTATGATGACCCTATTGA
CCCAATCGAGTTAGAGGCTGAACCCAGAGGAACCCCCATTGTCCCCAACATCTT
GAGGAACTCTGACTACAATCTCAACTCTCCTTTGATAGAAGATCCTGCTAGACTA
ATGTTAGAATGGTTAAAAACAGGGAATAGACCTTATCGGATGACTCTAACAGAC
AATTGCTCCAGGTCTTTCAGAGTTTTGAAAGATTATTTCAAGAAGGTAGATTTGG
GTTCTCTCAAGGTGGGCGGAATGGCTGCACAGTCAATGATTTCTCTCTGGTTATA
TGGTGCCCACTCTGAATCCAACAGGAGCCGGAGATGTATAACAGACTTGGCCCA
TTTCTATTCCAAGTCGTCCCCCATAGAGAAGCTGTTGAATCTCACGCTAGGAAAT
AGAGGGCTGAGAATCCCCCAGAGGGAGTGTTAAGTTGCCTTGAGAGGGTTGAT
TATGATAATGCATTTGGAAGGTATCTTGCCAACACGTATTCCTCTTACTTGTTCTT
```

-continued

```
CCATGTAATCACCTTATACATGAACGCCCTAGACTGGGATGAAGAAAAGACCAT

CCTAGCATTATGGAAAGATTTAACCTCAGTGGACATCGGGAAGGACTTGGTAAA

GTTCAAAGACCAAATATGGGGACTGCTGATCGTGACAAAGGACTTTGTTTACTCC

CAAAGTTCCAATTGTCTTTTTGACAGAAACTACACACTTATGCTAAAAGATCTTT

TCTTGTCTCGCTTCAACTCCTTAATGGTCTTGCTCTCTCCCCCAGAGCCCCGATAC

TCAGATGACTTGATATCTCAACTATGCCAGCTGTACATTGCTGGGGATCAAGTCT

TGTCTATGTGTGGAAACTCCGGCTATGAAGTCATCAAAATATTGGAGCCATATGT

CGTGAATAGTTTAGTCCAGAGAGCAGAAAAGTTTAGGCCTCTCATTCATTCCTTG

GGAGACTTTCCTGTATTTATAAAAGACAAGGTAAGTCAACTTGAAGAGACGTTC

GGTCCCTGTGCAAGAAGGTTCTTTAGGGCTCTGGATCAATTCGACAACATACATG

ACTTGGTTTTTGTGTTTGGCTGTTACAGGCATTGGGGGCACCCATATATAGATTA

TCGAAAGGGTCTGTCAAAACTATATGATCAGGTTCACCTTAAAAAAATGATAGA

TAAGTCCTACCAGGAGTGCTTAGCAAGCGACCTAGCCAGGAGGATCCTTAGATG

GGGTTTTGATAAGTACTCCAAGTGGTATCTGGATTCAAGATTCCTAGCCCGAGAC

CACCCCTTGACTCCTTATATCAAAACCCAAACATGGCCACCCAAACATATTGTAG

ACTTGGTGGGGATACATGGCACAAGCTCCCGATCACGCAGATCTTTGAGATTCC

TGAATCAATGGATCCGTCAGAAATATTGGATGACAAATCACATTCTTTCACCAGA

ACGAGACTAGCTTCTTGGCTGTCAGAAAACCGAGGGGGGCCTGTTCCTAGCGAA

AAAGTTATTATCACGGCCCTGTCTAAGCCGCCTGTCAATCCCCGAGAGTTTCTGA

GGTCTATAGACCTCGGAGGATTGCCAGATGAAGACTTGATAATTGGCCTCAAGC

CAAAGGAACGGGAATTGAAGATTGAAGGTCGATTCTTTGCTCTAATGTCATGGA

ATCTAAGATTGTATTTTGTCATCACTGAAAAACTCTTGGCCAACTACATCTTGCC

ACTTTTTGACGCGCTGACTATGACAGACAACCTGAACAAGGTGTTTAAAAAGCT

GATCGACAGGGTCACCGGGCAAGGGCTTTTGGACTATTCAAGGGTCACATATGC

ATTTCACCTGGACTATGAAAAGTGGAACAACCATCAAAGATTAGAGTCAACAGA

GGATGTATTTTCTGTCCTAGATCAAGTGTTTGGATTGAAGAGAGTGTTTTCTAGA

ACACACGAGTTTTTTCAAAAGGCCTGGATCTATTATTCAGACAGATCAGACCTCA

TCGGGTTACGGGAGGATCAAATATACTGCTTAGATGCGTCCAACGGCCCAACCT

GTTGGAATGGCCAGGATGGCGGGCTAGAAGGCTTACGGCAGAAGGGCTGGAGTC

TAGTCAGCTTATTGATGATAGATAGAGAATCTCAAATCAGGAACACAAGAACCA

AAATACTAGCTCAAGGAGACAACCAGGTTTTATGTCCGACATACATGTTGTCGCC

AGGGCTATCTCAAGAGGGGCTCCTCTATGAATTGGAGAGAATATCAAGGAATGC

ACTTTCGATATACAGAGCCGTCGAGGAAGGGGCATCTAAGCTAGGGCTGATCAT

CAAGAAAGAAGAGACCATGTGTAGTTATGACTTCCTCATCTATGGAAAAACCCC

TTTGTTTAGAGGTAACATATTGGTGCCTGAGTCCAAAAGATGGGCCAGAGTCTCT

TGCGTCTCTAATGACCAAATAGTCAACCTCGCCAATATAATGTCGACAGTGTCCA

CCAATGCGCTAACAGTGGCACAACACTCTCAATCTTTGATCAAACCGATGAGGG

ATTTTCTGCTCATGTCAGTACAGGCAGTCTTTCACTACCTGCTATTTAGCCCAATC

TTAAAGGGAAGAGTTTACAAGATTCTGAGCGCTGAAGGGGAGAGCTTTCTCCTA

GCCATGTCAAGGATAATCTATCTAGATCCTTCTTTGGGAGGGATATCTGGAATGT

CCCTCGGAAGATTCCATATACGACAGTTCTCAGACCCTGTCTCTGAAGGGTTATC
```

```
CTTCTGGAGAGAGATCTGGTTAAGCTCCCAAGAGTCCTGGATTCACGCGTTGTGT

CAAGAGGCTGGAAACCCAGATCTTGGAGAGAGAACACTCGAGAGCTTCACTCGC

CTTCTAGAAGATCCGACCACCTTAAATATCAGAGGAGGGGCCAGTCCTACCATT

CTACTCAAGGATGCAATCAGAAAGGCTTTATATGACGAGGTGGACAAGGTGGAA

AATTCAGAGTTTCGAGAGGCAATCCTGTTGTCCAAGACCCATAGAGATAATTTTA

TACTCTTCTTAATATCTGTTGAGCCTCTGTTTCCTCGATTTCTCAGTGAGCTATTC

AGTTCGTCTTTTTTGGGAATCCCCGAGTCAATCATTGGATTGATACAAAACTCCC

GAACGATAAGAAGGCAGTTTAGAAAGAGTCTCTCAAAAACTTTAGAAGAATCCT

TCTACAACTCAGAGATCCACGGGATTAGTCGGATGACCCAGACACCTCAGAGGG

TTGGGGGGGTGTGGCCTTGCTCTTCAGAGAGGGCAGATCTACTTAGGGAGATCTC

TTGGGGAAGAAAAGTGGTAGGCACGACAGTTCCTCACCCTTCTGAGATGTTGGG

ATTACTTCCCAAGTCCTCTATTTCTTGCACTTGTGGAGCAACAGGAGGAGGCAAT

CCTAGAGTTTCTGTATCAGTACTCCCGTCCTTTGATCAGTCATTTTTTTCACGAGG

CCCCCTAAAGGGATACTTGGGCTCGTCCACCTCTATGTCGACCCAGCTATTCCAT

GCATGGGAAAAAGTCACTAATGTTCATGTGGTGAAGAGAGCTCTATCGTTAAAA

GAATCTATAAACTGGTTCATTACTAGAGATTCCAACTTGGCTCAAGCTCTAATTA

GGAACATTATGTCTCTGACAGGCCCTGATTTCCCTCTAGAGGAGGCCCCTGTCTT

CAAAAGGACGGGGTCAGCCTTGCATAGGTTCAAGTCTGCCAGATACAGCGAAGG

AGGGTATTCTTCTGTCTGCCCGAACCTCCTCTCTCATATTTCTGTTAGTACAGACA

CCATGTCTGATTTGACCCAAGACGGGAAGAACTACGATTTCATGTTCCAGCCATT

GATGCTTTATGCACAGACATGGACATCAGAGCTGGTACAGAGAGACACAAGGCT

AAGAGACTCTACGTTTCATTGGCACCTCCGATGCAACAGGTGTGTGAGACCCATT

GACGACGTGACCCTGGAGACCTCTCAGATCTTCGAGTTTCCGGATGTGTCGAAAA

GAATATCCAGAATGGTTTCTGGGGCTGTGCCTCACTTCCAGAGGCTTCCCGATAT

CCGTCTGAGACCAGGAGATTTTGAATCTCTAAGCGGTAGAGAAAAGTCTCACCA

TATCGGATCAGCTCAGGGGCTCTTATACTCAATCTTAGTGGCAATTCACGACTCA

GGATACAATGATGGAACCATCTTCCCTGTCAACATATACGGCAAGGTTTCCCCTA

GAGACTATTTGAGAGGGCTCGCAAGGGGAGTATTGATAGGATCCTCGATTTGCTT

CTTGACAAGAATGACAAATATCAATATTAATAGACCTCTTGAATTGGTCTCAGGG

GTAATCTCATATATTCTCCTGAGGCTAGATAACCATCCCTCCTTGTACATAATGCT

CAGAGAACCGTCTCTTAGAGGAGAGATATTTTCTATCCCTCAGAAAATCCCCGCC

GCTTATCCAACCACTATGAAAGAAGGCAACAGATCAATCTTGTGTTATCTCCAAC

ATGTGCTACGCTATGAGCGAGAGATAATCACGGCGTCTCCAGAGAATGACTGGC

TATGGATCTTTTCAGACTTTAGAAGTGCCAAAATGACGTACCTATCCCTCATTAC

TTACCAGTCTCATCTTCTACTCCAGAGGGTTGAGAGAAACCTATCTAAGAGTATG

AGAGATAACCTGCGACAATTGAGTTCTTTGATGAGGCAGGTGCTGGGCGGGCAC

GGAGAAGATACCTTAGAGTCAGACGACAACATTCAACGACTGCTAAAAGACTCT

TTACGAAGGACAAGATGGGTGGATCAAGAGGTGCGCCATGCAGCTAGAACCATG

ACTGGAGATTACAGCCCCAACAAGAAGGTGTCCCGTAAGGTAGGATGTTCAGAA

TGGGTCTGCTCTGCTCAACAGGTTGCAGTCTCTACCTCAGCAAACCCGGCCCCTG
```

-continued

```
TCTCGGAGCTTGACATAAGGGCCCTCTCTAAGAGGTTCCAGAACCCTTTGATCTC

GGGCTTGAGAGTGGTTCAGTGGGCAACCGGTGCTCATTATAAGCTTAAGCCTATT

CTAGATGATCTCAATGTTTTCCCATCTCTCTGCCTTGTAGTTGGGGACGGGTCAG

GGGGGATATCAAGGGCAGTCCTCAACATGTTTCCAGATGCCAAGCTTGTGTTCAA

CAGTCTTTTAGAGGTGAATGACCTGATGGCTTCCGGAACACATCCACTGCCTCCT

TCAGCAATCATGAGGGGAGGAAATGATATCGTCTCCAGAGTGATAGATCTTGAC

TCAATCTGGGAAAAACCGTCCGACTTGAGAAACTTGGCAACCTGGAAATACTTC

CAGTCAGTCCAAAAGCAGGTCAACATGTCCTATGACCTCATTATTTGCGATGCAG

AAGTTACTGACATTGCATCTATCAACCGGATCACCCTGTTAATGTCCGATTTTGC

ATTGTCTATAGATGGACCACTCTATTTGGTCTTCAAAACTTATGGGACTATGCTA

GTAAATCCAAACTACAAGGCTATTCAACACCTGTCAAGAGCGTTCCCCTCGGTCA

CAGGGTTTATCACCCAAGTAACTTCGTCTTTTTCATCTGAGCTCTACCTCCGATTC

TCCAAACGAGGGAAGTTTTTCAGAGATGCTGAGTACTTGACCTCTTCCACCCTTC

GAGAAATGAGCCTTGTGTTATTCAATTGTAGCAGCCCCAAGAGTGAGATGCAGA

GAGCTCGTTCCTTGAACTATCAGGATCTTGTGAGAGGATTTCCTGAAGAAATCAT

ATCAAATCCTTACAATGAGATGATCATAACTCTGATTGACAGTGATGTAGAATCT

TTTCTAGTCCACAAGATGGTTGATGATCTTGAGTTACAGAGGGGAACTCTGTCTA

AAGTGGCTATCATTATAGCCATCATGATAGTTTTCTCCAACAGAGTCTTCAACGT

TTCCAAACCCCTAACTGACCCCTCGTTCTATCCACCGTCTGATCCCAAAATCCTG

AGGCACTTCAACATATGTTGCAGTACTATGATGTATCTATCTACTGCTTTAGGTG

ACGTCCCTAGCTTCGCAAGACTTCACGACCTGTATAACAGACCTATAACTTATTA

CTTCAGAAAGCAAGTCATTCGAGGGAACGTTTATCTATCTTGGAGTTGGTCCAAC

GACACCTCAGTGTTCAAAAGGGTAGCCTGTAATTCTAGCCTGAGTCTGTCATCTC

ACTGGATCAGGTTGATTTACAAGATAGTGAAGACTACCAGACTCGTTGGCAGCA

TCAAGGATCTATCCAGAGAAGTGGAAAGACACCTTCATAGGTACAACAGGTGGA

TCACCCTAGAGGATATCAGATCTAGATCATCCCTACTAGACTACAGTTGCCTGTG

AACCGGATACTCCTGGAAGCCTGCCCATGCTAAGACTCTTGTGTGATGTATCTTG

AAAAAAACAAGATCCTAAATCTGAACCTTTGGTTGTTTGATTGTTTTTCTCAttttttgtt gtttatttgttaagcgtGGGTCGGCATGGCATCTCCACCTCCTCGCGGTCCGACCTGGGCAT CCGAAGGAGGACGCACGTCCACTCGGATGGCTAAGGGAGagccagaaGGATCCGGC

TGCTAACAAAGCCCGAAAGGAAGCTGAGTTGGCTGCTGCCACCGCTGAGCAATA

ACTAGCATAACCCCTTGGGGCCTCTAAACGGGTCTTGAGGGGTTTTTTGCTGAAA

GtCGCGCTTGGCGTAATCATGGTCATAGCTGTTTCCTGTGTGAAATTGTTATCCGC

TCACAATTCCACACAACATACGAGCCGGAAGCATAAAGTGTAAAGCCTGGGGTG

CCTAATGAGTGAGCTAACTCACATTAATTGCGTTGCGCTCACTGCCCGCTTTCCA

GTCGGGAAACCTGTCGTGCCAGCTGCATTAATGAATCGGCCAACGCGCGGGGAG

AGGCGGTTTGCGTATTGGGCGCTCTTaCGCTTCCTCGCTCACTGACTCGCTGCGCT

CGGTCGTTCGGCTGCGGCGAGCGGTATCAGCTCACTCAAAGGCGGTAATACGGT

TATCCACAGAATCAGGGGATAACGCAGGAAAGAACATGTGAGCAAAAGGCCAG

CAAAAGGCCAGGAACCGTAAAAAGGCCGCGTTGCTGGCGTTTTTCCATAGGCTC

CGCCCCCCTGACGAGCATCACAAAAATCGACGCTCAAGTCAGAGGTGGCGAAAC
```

-continued

```
CCGACAGGACTATAAAGATACCAGGCGTTTCCCCCTGGAAGCTCCCTCGTGCGCT

CTCCTGTTCCGACCCTGCCGCTTACCGGATACCTGTCCGCCTTTCTCCCTTCGGGA

AGCGTGGCGCTTTCTCATAGCTCACGCTGTAGGTATCTCAGTTCGGTGTAGGTCG

TTCGCTCCAAGCTGGGCTGTGTGCACGAACCCCCCGTTCAGCCCGACCGCTGCGC

CTTATCCGGTAACTATCGTCTTGAGTCCAACCCGGTAAGACACGACTTATCGCCA

CTGGCAGCAGCCACTGGTAACAGGATTAGCAGAGCGAGGTATGTAGGCGGTGCT

ACAGAGTTCTTGAAGTGGTGGCCTAACTACGGCTACACTAGAAGGACAGTATTT

GGTATCTGCGCTCTGCTGAAGCCAGTTACCTTCGGAAAAAGAGTTGGTAGCTCTT

GATCCGGCAAACAAACCACCGCTGGTAGCGGTGGTTTTTTTGTTTGCAAGCAGCA

GATTACGCGCAGAAAAAAAGGATCTCAAGAAGATCCTTTGATCTTTTCTACGGG

GTCTGACGCTCAGTGGAACGAAAACTCACGTTAAGGGATTTTGGTCATGAGATT

ATCAAAAAGGATCTTCACCTAGATCCTTTTAAATTAAAAATGAAGTTTTAAATCA

ATCTAAAGTATATATGAGTAAACTTGGTCTGACAGTTACCAATGCTTAATCAGTG

AGGCACCTATCTCAGCGATCTGTCTATTTCGTTCATCCATAGTTGCCTGACTCCCC

GTCGTGTAGATAACTACGATACGGGAGGGCTTACCATCTGGCCCCAGTGCTGCA

ATGATACCGCGAGACCCACGCTCACCGGCTCCAGATTTATCAGCAATAAACCAG

CCAGCCGGAAGGGCCGAGCGCAGAAGTGGTCCTGCAACTTTATCCGCCTCCATC

CAGTCTATTAATTGTTGCCGGGAAGCTAGAGTAAGTAGTTCGCCAGTTAATAGTT

TGCGCAACGTTGTTGCCATTGCTACAGGCATCGTGGTGTCACGCTCGTCGTTTGG

TATGGCTTCATTCAGCTCCGGTTCCCAACGATCAAGGCGAGTTACATGATCCCCC

ATGTTGTGCAAAAAAGCGGTTAGCTCCTTCGGTCCTCCGATCGTTGTCAGAAGTA

AGTTGGCCGCAGTGTTATCACTCATGGTTATGGCAGCACTGCATAATTCTCTTAC

TGTCATGCCATCCGTAAGATGCTTTTCTGTGACTGGTGAGTACTCAACCAAGTCA

TTCTGAGAATAGTGTATGCGGCGACCGAGTTGCTCTTGCCCGGCGTCAATACGGG

ATAATACCGCGCCACATAGCAGAACTTTAAAAGTGCTCATCATTGGAAAACGTT

CTTCGGGGCGAAAACTCTCAAGGATCTTACCGCTGTTGAGATCCAGTTCGATGTA

ACCCACTCGTGCACCCAACTGATCTTCAGCATCTTTTACTTTCACCAGCGTTTCTG

GGTGAGCAAAAACAGGAAGGCAAAATGCCGCAAAAAAGGGAATAAGGGCGACA

CGGAAATGTTGAATACTCATACTCTTCCTTTTTCAATATTATTGAAGCATTTATCA

GGGTTATTGTCTCATGAGCGGATACATATTTGAATGTATTTAGAAAAATAAACAA

ATAGGGGTTCCGCGCACATTTCCCCGAAAAGTGCCAC.
```

In one embodiment, the nucleic acid comprises a sequence encoding at least a portion of the genome of a measles virus and (b) a sequence encoding a SARS-CoV-2 spike protein (S) or a portion thereof. In some embodiments, the sequence encoding the SARS-CoV-2 spike protein (S) or portion thereof is inserted into position 2, 3, or 6 of the genome of the measles virus.

In one embodiment, the nucleic acid comprises the sequence of SEQ ID NO: 3, shown below:

```
GGACGCGCCCTGTAGCGGCGCATTAAGCGCGGCGGGTGTGGTGGTTACGCGCAG

CGTGACCGCTACACTTGCCAGCGCCCTAGCGCCCGCTCCTTTCGCTTTCTTCCCTT

CCTTTCTCGCCACGTTCGCCGGCTTTCCCCGTCAAGCTCTAAATCGGGGGCTCCC

TTTAGGGTTCCGATTTAGTGCTTTACGGCACCTCGACCCCAAAAAACTTGATTAG

GGTGATGGTTCACGTAGTGGGCCATCGCCCTGATAGACGGTTTTTCGCCCTTTGA
```

-continued

```
CGTTGGAGTCCACGTTCTTTAATAGTGGACTCTTGTTCCAAACTGGAACAACACT

CAACCCTATCTCGGTCTATTCTTTTGATTTATAAGGGATTTTGCCGATTTCGGCCT

ATTGGTTAAAAAATGAGCTGATTTAACAAAAATTTAACGCGAATTTTAACAAAA

TATTAACGTTTACAATTTCGCGCCATTCGCCATTCAGGCTGCGCAACTGTTGGGA

AGGGCGATCGGTGCGGGCCTCTTCGCTATTACGCCAGCTGGCGAAAGGGGGATG

TGCTGCAAGGCGATTAAGTTGGGTAACGCCAGGGTTTTCCCAGTCACGACGTTGT

AAAACGACGGCCAGTGCGCGCCGTTAATACGACTCACTATAGGGAGACCCAAGC

TGGCTAGCTTTGTTTGGTCTGATGAGTCCCGTGAGGACGAAACCCGGCGTACCGG

GTCACCAAACAAAGTTGGGTAAGGATAGTTCAATCAATGATCATCTTCTAGTGCA

CTTAGGATTCAAGATCCTATTATCAGGGACAAGAGCAGGATTAGGGATATCCGA

GATGGCCACACTTTTAAGGAGCTTAGCATTGTTCAAAAGAAACAAGGACAAACC

ACCCATTACATCAGGATCCGGTGGAGCCATCAGAGGAATCAAACACATTATTAT

AGTACCAATCCCTGGAGATTCCTCAATTACCACTCGATCCAGACTTCTGGACCGG

TTGGTGAGGTTAATTGGAAACCCGGATGTGAGCGGGCCCAAACTAACAGGGGCA

CTAATAGGTATATTATCCTTATTTGTGGAGTCTCCAGGTCAATTGATTCAGAGGA

TCACCGATGACCCTGACGTTAGCATAAGGCTGTTAGAGGTTGTCCAGAGTGACC

AGTCACAATCTGGCCTTACCTTCGCATCAAGAGGTACCAACATGGAGGATGAGG

CGGACCAATACTTTTCACATGATGATCCAATTAGTAGTGATCAATCCAGGTTCGG

ATGGTTCGGGAACAAGGAAATCTCAGATATTGAAGTGCAAGACCCTGAGGGATT

CAACATGATTCTGGGTACCATCCTAGCCCAAATTTGGGTCTTGCTCGCAAAGGCG

GTTACGGCCCCAGACACGGCAGCTGATTCGGAGCTAAGAAGGTGGATAAAGTAC

ACCCAACAAAGAAGGGTAGTTGGTGAATTTAGATTGGAGAGAAAATGGTTGGAT

GTGGTGAGGAACAGGATTGCCGAGGACCTCTCCTTACGCCGATTCATGGTCGCTC

TAATCCTGGATATCAAGAGAACACCCGGAAACAAACCCAGGATTGCTGAAATGA

TATGTGACATTGATACATATATCGTAGAGGCAGGATTAGCCAGTTTTATCCTGAC

TATTAAGTTTGGGATAGAAACTATGTATCCTGCTCTTGGACTGCATGAATTTGCT

GGTGAGTTATCCACACTTGAGTCCTTGATGAACCTTTACCAGCAAATGGGGGAA

ACTGCACCCTACATGGTAATCCTGGAGAACTCAATTCAGAACAAGTTCAGTGCA

GGATCATACCCTCTGCTCTGGAGCTATGCCATGGGAGTAGGAGTGGAACTTGAA

AACTCCATGGGAGGTTTGAACTTTGGCCGATCTTACTTTGATCCAGCATATTTTA

GATTAGGGCAAGAGATGGTAAGGAGGTCAGCTGGAAAGGTCAGTTCCACATTGG

CATCTGAACTCGGTATCACTGCCGAGGATGCAAGGCTTGTTTCAGAGATTGCAAT

GCATACTACTGAGGACAAGATCAGTAGAGCGGTTGGACCCAGACAAGCCCAAGT

ATCATTTCTACACGGTGATCAAAGTGAGAATGAGCTACCGAGATTGGGGGCAA

GGAAGATAGGAGGGTCAAACAGAGTCGAGGAGAAGCCAGGGAGAGCTACAGAG

AAACCGGGCCCAGCAGAGCAAGTGATGCGAGAGCTGCCCATCTTCCAACCGGCA

CACCCCTAGACATTGACACTGCAACGGAGTCCAGCCAAGATCCGCAGGACAGTC

GAAGGTCAGCTGACGCCCTGCTTAGGCTGCAAGCCATGGCAGGAATCTCGGAAG

AACAAGGCTCAGACACGGACACCCCTATAGTGTACAATGACAGAAATCTTCTAG

ACTAGGTGCGAGAGGCCGAGGGCCAGAACAACATCCGCCTACCATCCATCATTG
```

-continued

```
TTATAAAAAACTTAGGAACCAggtccacacaGagtgatACGCGTACGCCACCATGTTCGT

GTTTCTGGTGCTGCTGCCTCTGGTGAGCTCCCAGTGCGTGAACCTGACCACAAGG

ACCCAGCTGCCCCCTGCCTATACCAATTCCTTCACACGGGGCGTGTACTATCCCG

ACAAGGTGTTCCGGAGCAGCGTGCTGCACTCCACACAGGATCTGTTTCTGCCTTT

CTTTTCTAACGTGACCTGGTTCCACGCCATCCACGTGAGCGGCACCAATGGCACA

AAGCGGTTCGACAATCCAGTGCTGCCCTTTAACGATGGCGTGTACTTCGCCTCCA

CCGAGAAGTCTAACATCATCAGAGGCTGGATCTTTGGCACCACACTGGACAGCA

AGACACAGTCCCTGCTGATCGTGAACAATGCCACCAACGTGGTCATCAAGGTGT

GCGAGTTCCAGTTTTGTAATGATCCATTCCTGGGCGTGTACTATCACAAGAACAA

TAAGTCTTGGATGGAGAGCGAGTTTCGCGTGTATTCCTCTGCCAACAATTGCACA

TTTGAGTACGTGTCCCAGCCCTTCCTGATGGACCTGGAGGGCAAGCAGGGCAATT

TCAAGAACCTGAGGGAGTTCGTGTTTAAGAATATCGATGGCTACTTCAAAATCTA

CTCCAAGCACACCCCAATCAACCTGGTGCGCGACCTGCCACAGGGCTTCTCTGCC

CTGGAGCCACTGGTGGATCTGCCCATCGGCATCAACATCACCCGGTTTCAGACAC

TGCTGGCCCTGCACAGAAGCTACCTGACACCAGGCGACAGCTCCTCTGGATGGA

CCGCAGGAGCAGCAGCCTACTATGTGGGCTATCTGCAGCCCAGGACCTTCCTGCT

GAAGTACAACGAGAATGGCACCATCACAGACGCCGTGGATTGCGCCCTGGATCC

CCTGTCTGAGACCAAGTGTACACTGAAGAGCTTTACCGTGGAGAAGGGCATCTA

TCAGACAAGCAATTTCAGGGTGCAGCCTACCGAGTCCATCGTGCGCTTTCCCAAT

ATCACAAACCTGTGCCCTTTTGGCGAGGTGTTCAACGCAACCCGCTTCGCCAGCG

TGTACGCCTGGAATAGGAAGCGCATCTCCAACTGCGTGGCCGACTATTCTGTGCT

GTACAACAGCGCCTCCTTCTCTACCTTTAAGTGCTATGGCGTGAGCCCCACAAAG

CTGAATGACCTGTGCTTTACCAACGTGTACGCCGATTCCTTCGTGATCAGGGGCG

ACGAGGTGCGCCAGATCGCACCAGGACAGACAGGCAAGATCGCAGACTACAAT

TATAAGCTGCCTGACGATTTCACCGGCTGCGTGATCGCCTGGAACTCTAACAATC

TGGATAGCAAAGTGGGCGGCAACTACAATTATCTGTACCGGCTGTTTAGAAAGT

CTAATCTGAAGCCATTCGAGAGGGACATCTCCACAGAAATCTACCAGGCCGGCT

CTACCCCCTGCAATGGCGTGGAGGGCTTTAACTGTTATTTCCCTCTGCAGAGCTA

CGGCTTCCAGCCAACAAACGGCGTGGGCTATCAGCCCTACCGCGTGGTGGTGCT

GTCTTTTGAGCTGCTGCACGCACCTGCAACAGTGTGCGGACCAAAGAAGAGCAC

CAATCTGGTGAAGAACAAGTGCGTGAACTTCAACTTCAACGGACTGACCGGAAC

AGGCGTGCTGACCGAGTCCAACAAGAAGTTCCTGCCTTTTCAGCAGTTCGGCAG

GGACATCGCAGATACCACAGACGCCGTGCGCGACCCTCAGACCCTGGAGATCCT

GGACATCACACCATGCTCCTTCGGCGGCGTGTCTGTGATCACACCAGGCACCAAT

ACAAGCAACCAGGTGGCCGTGCTGTATCAGGACGTGAATTGTACCGAGGTGCCA

GTGGCAATCCACGCAGATCAGCTGACCCCTACATGGCGGGTGTACTCTACCGGC

AGCAACGTGTTCCAGACAAGAGCCGGATGCCTGATCGGAGCAGAGCACGTGAAC

AATAGCTATGAGTGCGACATCCCTATCGGCGCCGGCATCTGTGCCTCCTACCAGA

CCCAGACAAACTCCCCAAGGAGAGCACGGTCTGTGGCCAGCCAGTCCATCATCG

CCTATACCATGAGCCTGGGCGCCGAGAATTCCGTGGCCTACTCCAACAATTCTAT

CGCCATCCCTACCAACTTCACAATCTCCGTGACCACAGAGATCCTGCCAGTGAGC
```

-continued

```
ATGACCAAGACATCCGTGGACTGCACAATGTATATCTGTGGCGATTCCACCGAGT
GCTCTAACCTGCTGCTGCAGTACGGCTCTTTTTGTACCCAGCTGAATAGAGCCCT
GACAGGCATCGCCGTGGAGCAGGACAAGAACACACAGGAGGTGTTCGCCCAGG
TGAAGCAAATCTACAAGACCCCACCCATCAAGGACTTTGGCGGCTTCAACTTCA
GCCAGATCCTGCCCGATCCTAGCAAGCCATCCAAGCGGTCTTTTATCGAGGACCT
GCTGTTCAACAAGGTGACCCTGGCCGATGCCGGCTTCATCAAGCAGTATGGCGA
TTGCCTGGGCGACATCGCCGCCAGAGACCTGATCTGTGCCCAGAAGTTTAATGG
CCTGACCGTGCTGCCTCCACTGCTGACAGATGAGATGATCGCCCAGTACACATCT
GCCCTGCTGGCCGGAACCATCACAAGCGGATGGACCTTCGGCGCAGGAGCCGCC
CTGCAGATCCCCTTTGCCATGCAGATGGCCTATCGGTTCAACGGCATCGGCGTGA
CCCAGAATGTGCTGTACGAGAACCAGAAGCTGATCGCCAATCAGTTTAACTCCG
CCATCGGCAAGATCCAGGACTCTCTGAGCTCCACAGCCAGCGCCCTGGGCAAGC
TGCAGGATGTGGTGAATCAGAACGCCCAGGCCCTGAATACCCTGGTGAAGCAGC
TGTCTAGCAACTTCGGCGCCATCTCCTCTGTGCTGAATGACATCCTGAGCCGGCT
GGACAAGGTGGAGGCAGAGGTGCAGATCGACCGGCTGATCACAGGCAGACTGC
AGTCCCTGCAGACCTACGTGACACAGCAGCTGATCAGGGCAGCAGAGATCAGGG
CCTCTGCCAATCTGGCCGCCACCAAGATGAGCGAGTGCGTGCTGGGCCAGTCCA
AGAGAGTGGACTTTTGTGGCAAGGGCTATCACCTGATGAGCTTCCCACAGTCCGC
CCCTCACGGAGTGGTGTTTCTGCACGTGACCTACGTGCCAGCCCAGGAGAAGAA
CTTCACCACAGCACCAGCAATCTGCCACGATGGCAAGGCACACTTTCCTAGGGA
GGGCGTGTTCGTGAGCAACGGCACCCACTGGTTTGTGACACAGCGCAATTTCTAC
GAGCCACAGATCATCACCACAGACAATACATTCGTGTCCGGCAACTGTGACGTG
GTCATCGGCATCGTGAACAATACCGTGTATGATCCTCTGCAGCCAGAGCTGGACT
CTTTTAAGGAGGAGCTGGATAAGTACTTCAAGAATCACACCAGCCCCGACGTGG
ATCTGGGCGACATCTCTGGCATCAATGCCAGCGTGGTGAACATCCAGAAGGAGA
TCGACAGGCTGAACGAGGTGGCCAAGAATCTGAACGAGTCCCTGATCGATCTGC
AGGAGCTGGGCAAGTATGAGCAGTACATCAAGTGGCCCTGGTATATCTGGCTGG
GCTTCATCGCCGGCCTGATCGCCATCGTGATGGTGACCATCATGCTGTGCTGTAT
GACAAGCTGCTGTTCCTGCCTGAAGGGCTGCTGTTCTTGTGGCAGCTGCTGTAAG
TTTGATGAGGACGATAGCGAGCCTGTGCTGAAGGGCGTGAAGCTGCACTACACC
TGATAGCTAGCGATCGCGTGCGAGAGGCCAGAACAACATCCGCCTACCATCCAT
CATTGTTATAAAAAACTTAGGAACCAGGTCCACACAGCCGCCAGCCCATCAACC
ATCCACTCCCACGATTGGAGCCAATGGCAGAAGAGCAGGCACGCCATGTCAAAA
ACGGACTGGAATGCATCCGGGCTCTCAAGGCCGAGCCCATCGGCTCACTGGCCA
TCGAGGAAGCTATGGCAGCATGGTCAGAAATATCAGACAACCCAGGACAGGAG
CGAGCCACCTGCAGGGAAGAGAAGGCAGGCAGTTCGGGTCTCAGCAAACCATG
CCTCTCAGCAATTGGATCAACTGAAGGCGGTGCACCTCGCATCCGCGGTCAGGG
ACCTGGAGAGAGCGATGACGACGCTGAAACTTTGGGAATCCCCCCAAGAAATCT
CCAGGCATCAAGCACTGGGTTACAGTGTTATTACGTTTATGATCACAGCGGTGAA
GCGGTTAAGGGAATCCAAGATGCTGACTCTATCATGGTTCAATCAGGCCTTGATG
```

-continued

```
GTGATAGCACCCTCTCAGGAGGAGACAATGAATCTGAAAACAGCGATGTGGATA
TTGGCGAACCTGATACCGAGGGATATGCTATCACTGACCGGGGATCTGCTCCCAT
CTCTATGGGGTTCAGGGCTTCTGATGTTGAAACTGCAGAAGGAGGGGAGATCCA
CGAGCTCCTGAGACTCCAATCCAGAGGCAACAACTTTCCGAAGCTTGGGAAAAC
TCTCAATGTTCCTCCGCCCCCGGACCCCGGTAGGGCCAGCACTTCCGGGACACCC
ATTAAAAAGGGCACAGACGCGAGATTAGCCTCATTTGGAACGGAGATCGCGTCT
TTATTGACAGGTGGTGCAACCCAATGTGCTCGAAAGTCACCCTCGGAACCATCA
GGGCCAGGTGCACCTGCGGGGAATGTCCCCGAGTGTGTGAGCAATGCCGCACTG
ATACAGGAGTGGACACCCGAATCTGGTACCACAATCTCCCCGAGATCCCAGAAT
AATGAAGAAGGGGGAGACTATTATGATGATGAGCTGTTCTCTGATGTCCAAGAT
ATTAAAACAGCCTTGGCCAAAATACACGAGGATAATCAGAAGATAATCTCCAAG
CTAGAATCACTGCTGTTATTGAAGGGAGAAGTTGAGTCAATTAAGAAGCAGATC
AACAGGCAAAATATCAGCATATCCACCCTGGAAGGACACCTCTCAAGCATCATG
ATCGCCATTCCTGGACTTGGGAAGGATCCCAACGACCCCACTGCAGATGTCGAA
ATCAATCCCGACTTGAAACCCATCATAGGCAGAGATTCAGGCCGAGCACTGGCC
GAAGTTCTCAAGAAACCCGTTGCCAGCCGACAACTCCAAGGAATGACAAATGGA
CGGACCAGTTCCAGAGGACAGCTGCTGAAGGAATTTCAGCTAAAGCCGATCGGG
AAAAAGATGAGCTCAGCCGTCGGGTTTGTTCCTGACACCGGCCCTGCATCACGC
AGTGTAATCCGCTCCATTATAAAATCCAGCCGGCTAGAGGAGGATCGGAAGCGT
TACCTGATGACTCTCCTTGATGATATCAAAGGAGCCAATGATCTTGCCAAGTTCC
ACCAGATGCTGATGAAGATAATAATGAAGTAGCTACAGCTCAACTTACCTGCCA
ACCCCATGCCAGTCGACCCACCTAGTACAACCTAAATCCATTATAAAAAACTTA
GGAGCAAAGTGATTGCCTCCCAAGGTCCACAATGACAGAGACCTACGACTTCGA
CAAGTCGGCATGGGACATCAAAGGGTCGATCGCTCCGATACAACCCACCACCTA
CAGTGATGGCAGGCTGGTGCCCCAGGTCAGAGTCATAGATCCTGGTCTAGGCGA
CAGGAAGGATGAATGCTTTATGTACATGTTTCTGCTGGGGGTTGTTGAGGACAGC
GATTCCCTAGGGCCTCCAATCGGGCGAGCATTTGGGTTCCTGCCCTTAGGTGTTG
GCAGATCCACAGCAAAGCCCGAAAAACTCCTCAAAGAGGCCACTGAGCTTGACA
TAGTTGTTAGACGTACAGCAGGGCTCAATGAAAAACTGGTGTTCTACAACAACA
CCCCACTAACTCTCCTCACACCTTGGAGAAAGGTCCTAACAACAGGGAGTGTCTT
CAACGCAAACCAAGTGTGCAATGCGGTTAATCTGATACCGCTCGATACCCCGCA
GAGGTTCCGTGTTGTTTATATGAGCATCACCCGTCTTTCGGATAACGGGTATTAC
ACCGTTCCTAGAAGAATGCTGGAATTCAGATCGGTCAATGCAGTGGCCTTCAACC
TGCTGGTGACCCTTAGGATTGACAAGGCGATAGGCCCTGGGAAGATCATCGACA
ATACAGAGCAACTTCCTGAGGCAACATTTATGGTCCACATCGGGAACTTCAGGA
GAAAGAAGAGTGAAGTCTACTCTGCCGATTATTGCAAAATGAAAATCGAAAAGA
TGGGCCTGGTTTTTGCACTTGGTGGGATAGGGGGCACCAGTCTTCACATTAGAAG
CACAGGCAAAATGAGCAAGACTCTCCATGCACAACTCGGGTTCAAGAAGACCTT
ATGTTACCCGCTGATGGATATCAATGAAGACCTTAATCGATTACTCTGGAGGAGC
AGATGCAAGATAGTAAGAATCCAGGCAGTTTTGCAGCCATCAGTTCCTCAAGAA
TTCCGCATTTACGACGACGTGATCATAAATGATGACCAAGGACTATTCAAAGTTC
```

-continued

```
TGTAGACCGTAGTGCCCAGCAATGCCCGAAAACGACCCCCCTCACAATGACAGC
CAGAAGGCCCGGACAAAAAAGCCCCCTCCGAAAGACTCCACGGACCAAGCGAG
AGGCCAGCCAGCAGCCGACGGCAAGCGCGAACACCAGGCGGCCCCAGCACAGA
ACAGCCCTGACACAAGGCCACCACCAGCCACCCCAATCTGCATCCTCCTCGTGG
GACCCCCGAGGACCAACCCCCAAGGCTGCCCCCGATCCAAACCACCAACCGCAT
CCCCACCACCCCGGGAAAGAAACCCCCAGCAATTGGAAGGCCCCTCCCCCTCT
TCCTCAACACAAGAACTCCACAACCGAACCGCACAAGCGACCGAGGTGACCCAA
CCGCAGGCATCCGACTCCCTAGACAGATCCTCTCTCCCCGGCAAACTAAACAAA
ACTTAGGGCCAAGGAACATACACACCCAACAGAACCCAGACCCCGGCCCACGGC
GCCGCGCCCCAACCCCCGACAACCAGAGGGAGCCCCCAACCAATCCCGCCGGC
TCCCCCGGTGCCCACAGGCAGGGACACCAACCCCCGAACAGACCCAGCACCCAA
CCATCGACAATCCAAGACGGGGGGGCCCCCCCAAAAAAAGGCCCCCAGGGGCC
GACAGCCAGCACCGCGAGGAAGCCCACCCACCCCACACACGACCACGGCAACC
AAACCAGAACCCAGACCACCCTGGGCCACCAGCTCCCAGACTCGGCCATCACCC
CGCAGAAAGGAAAGGCCACAACCCGCGCACCCCAGCCCCGATCCGGCGGGGAG
CCACCCAACCCGAACCAGCACCCAAGAGCGATCCCCGAAGGACCCCCGAACCGC
AAAGGACATCAGTATCCCACAGCCTCTCCAAGTCCCCCGGTCTCCTCCTCTTCTC
GAAGGGACCAAAAGATCAATCCACCACACCCGACGACACTCAACTCCCCACCCC
TAAAGGAGACACCGGGAATCCCAGAATCAAGACTCATCCAATGTCCATCATGGG
TCTCAAGGTGAACGTCTCTGCCATATTCATGGCAGTACTGTTAACTCTCCAAACA
CCCACCGGTCAAATCCATTGGGGCAATCTCTCTAAGATAGGGGTGGTAGGAATA
GGAAGTGCAAGCTACAAAGTTATGACTCGTTCCAGCCATCAATCATTAGTCATAA
AATTAATGCCCAATATAACTCTCCTCAATAACTGCACGAGGGTAGAGATTGCAG
AATACAGGAGACTACTGAGAACAGTTTTGGAACCAATTAGAGATGCACTTAATG
CAATGACCCAGAATATAAGACCGGTTCAGAGTGTAGCTTCAAGTAGGAGACACA
AGAGATTTGCGGGAGTAGTCCTGGCAGGTGCGGCCCTAGGCGTTGCCACAGCTG
CTCAGATAACAGCCGGCATTGCACTTCACCAGTCCATGCTGAACTCTCAAGCCAT
CGACAATCTGAGAGCGAGCCTGGAAACTACTAATCAGGCAATTGAGACAATCAG
ACAAGCAGGGCAGGAGATGATATTGGCTGTTCAGGGTGTCCAAGACTACATCAA
TAATGAGCTGATACCGTCTATGAACCAACTATCTTGTGATTTAATCGGCCAGAAG
CTCGGGCTCAAATTGCTCAGATACTATACAGAAATCCTGTCATTATTTGGCCCCA
GTTTACGGGACCCCATATCTGCGGAGATATCTATCCAGGCTTTGAGCTATGCGCT
TGGAGGAGACATCAATAAGGTGTTAGAAAAGCTCGGATACAGTGGAGGTGATTT
ACTGGGCATCTTAGAGAGCGGAGGAATAAAGGCCCGGATAACTCACGTCGACAC
AGAGTCCTACTTCATTGTCCTCAGTATAGCCTATCCGACGCTGTCCGAGATTAAG
GGGGTGATTGTCCACCGGCTAGAGGGGGTCTCGTACAACATAGGCTCTCAAGAG
TGGTATACCACTGTGCCCAAGTATGTTGCAACCCAAGGGTACCTTATCTCGAATT
TTGATGAGTCATCGTGTACTTTCATGCCAGAGGGGACTGTGTGCAGCCAAAATGC
CTTGTACCCGATGAGTCCTCTGCTCCAAGAATGCCTCCGGGGTACACCAAGTCC
TGTGCTCGTACACTCGTATCCGGGTCTTTTGGGAACCGGTTCATTTTATCACAAG
```

-continued

```
GGAACCTAATAGCCAATTGTGCATCAATCCTTTGCAAGTGTTACACAACAGGAA

CGATCATTAATCAAGACCCTGACAAGATCCTAACATACATTGCTGCCGATCACTG

CCCGGTAGTCGAGGTGAACGGCGTGACCATCCAAGTCGGGAGCAGGAGGTATCC

AGACGCTGTGTACTTGCACAGAATTGACCTCGGTCCTCCCATATCATTGGAGAGG

TTGGACGTAGGGACAAATCTGGGGAATGCAATTGCTAAGTTGGAGGATGCCAAG

GAATTGTTGGAGTCATCGGACCAGATATTGAGGAGTATGAAAGGTTTATCGAGC

ACTAGCATAGTCTACATCCTGATTGCAGTGTGTCTTGGAGGGTTGATAGGGATCC

CCGCTTTAATATGTTGCTGCAGGGGGCGTTGTAACAAAAAGGGAGAACAAGTTG

GTATGTCAAGACCAGGCCTAAAGCCTGATCTTACGGGAACATCAAAATCCTATG

TAAGGTCGCTCTGATCCTCTACAACTCTTGAAACACAAATGTCCCACAAGTCTCC

TCTTCGTCATCAAGCAACCACCGCACCCAGCATCAAGCCCACCTGAAATTATCTC

CGGCTTCCCTCTGGCCGAACAATATCGGTAGTTAATTAAAACTTAGGGTGCAAGA

TCATCGATAATGTCACCACAACGAGACCGGATAAATGCCTTCTACAAAGATAAC

CCCCATCCCAAGGGAAGTAGGATAGTCATTAACAGAGAACATCTTATGATTGAT

AGACCTTATGTTTTGCTGGCTGTTCTGTTTGTCATGTTTCTGAGCTTGATCGGGTT

GCTAGCCATTGCAGGAATTCGACTTCATCGGGCAGCCATCTACACCGCAGAGAT

CCATAAAAGCCTCAGCACCAATCTAGATGTAACTAACTCAATCGAGCATCAGGT

CAAGGACGTGCTGACACCACTCTTCAAAATCATCGGTGATGAAGTGGGCCTGAG

GACACCTCAGAGATTCACTGACCTAGTGAAATTAATCTCTGACAAGATTAAATTC

CTTAATCCGGATAGGGAGTACGACTTCAGAGATCTCACTTGGTGTATCAACCCGC

CAGAGAGAATCAAATTGGATTATGATCAATACTGTGCAGATGTGGCTGCTGAAG

AGCTCATGAATGCATTGGTGAACTCAACTCTACTGGAGACCAGAACAACCAATC

AGTTCCTAGCTGTCTCAAAGGGAAACTGCTCAGGGCCCACTACAATCAGAGGTC

AATTCTCAAACATGTCGCTGTCCCTGTTAGACTTGTATTTAGGTCGAGGTTACAA

TGTGTCATCTATAGTCACTATGACATCCCAGGGAATGTATGGGGGAACTTACCTA

GTGGAAAAGCCTAATCTGAGCAGCAAAAGGTCAGAGTTGTCACAACTGAGCATG

TACCGAGTGTTTGAAGTAGGTGTTATCAGAAATCCGGGTTTGGGGGCTCCGGTGT

TCCATATGACAAACTATCTTGAGCAACCAGTCAGTAATGATCTCAGCAACTGTAT

GGTGGCTTTGGGGGAGCTCAAACTCGCAGCCCTTTGTCACGGGGAAGATTCTATC

ACAATTCCCTATCAGGGATCAGGGAAAGGTGTCAGCTTCCAGCTCGTCAAGCTA

GGTGTCTGGAAATCCCCAACCGACATGCAATCCTGGGTCCCCTTATCAACGGATG

ATCCAGTGATAGACAGGCTTTACCTCTCATCTCACAGAGGTGTTATCGCTGACAA

CCAAGCAAAATGGGCTGTCCCGACAACACGAACAGATGACAAGTTGCGAATGG

AGACATGCTTCCAACAGGCGTGTAAGGGTAAAATCCAAGCACTCTGCGAGAATC

CCGAGTGGGCACCATTGAAGGATAACAGGATTCCTTCATACGGGGTCTTGTCTGT

TGATCTGAGTCTGACAGTTGAGCTTAAAATCAAAATTGCTTCGGGATTCGGGCCA

TTGATCACACACGGTTCAGGGATGGACCTATACAAATCCAACCACAACAATGTG

TATTGGCTGACTATCCCGCCAATGAAGAACCTAGCCTTAGGTGTAATCAACACAT

TGGAGTGGATACCGAGATTCAAGGTTAGTCCCTACCTCTTCACTGTCCCAATTAA

GGAAGCAGGCGAAGACTGCCATGCCCCAACATACCTACCTGCGGAGGTGGATGG

TGATGTCAAACTCAGTTCCAATCTGGTGATTCTACCTGGTCAAGATCTCCAATAT
```

-continued

```
GTTTTGGCAACCTACGATACTTCCAGGGTTGAACATGCTGTGGTTTATTACGTTT

ACAGCCCAAGCCGCTCATTTTCTTACTTTTATCCTTTTAGGTTGCCTATAAAGGGG

GTCCCCATCGAATTACAAGTGGAATGCTTCACATGGGACCAAAAACTCTGGTGC

CGTCACTTCTGTGTGCTTGCGGACTCAGAATCTGGTGGACATATCACTCACTCTG

GGATGGTGGGCATGGGAGTCAGCTGCACAGTCACCCGGGAAGATGGAACCAATC

GCAGATAGGGCTGCTAGTGAACCAATCACATGATGTCACCCAGACATCAGGCAT

ACCCACTAGTGTGAAATAGACATCAGAATTAAGAAAAACGTAGGGTCCAAGTGG

TTCCCCGTTATGGACTCGCTATCTGTCAACCAGATCTTATACCCTGAAGTTCACCT

AGATAGCCCGATAGTTACCAATAAGATAGTAGCCATCCTGGAGTATGCTCGAGT

CCCTCACGCTTACAGCCTGGAGGACCCTACACTGTGTCAGAACATCAAGCACCG

CCTAAAAAACGGATTTTCCAACCAAATGATTATAAACAATGTGGAAGTTGGGAA

TGTCATCAAGTCCAAGCTTAGGAGTTATCCGGCCCACTCTCATATTCCATATCCA

AATTGTAATCAGGATTTATTTAACATAGAAGACAAAGAGTCAACGAGGAAGATC

CGTGAACTCCTCAAAAAGGGGAATTCGCTGTACTCCAAAGTCAGTGATAAGGTT

TTCCAATGCTTAAGGGACACTAACTCACGGCTTGGCCTAGGCTCCGAATTGAGGG

AGGACATCAAGGAGAAAGTTATTAACTTGGGAGTTTACATGCACAGCTCCCAGT

GGTTTGAGCCCTTTCTGTTTTGGTTTACAGTCAAGACTGAGATGAGGTCAGTGAT

TAAATCACAAACCCATACTTGCCATAGGAGGAGACACACACCTGTATTCTTCACT

GGTAGTTCAGTTGAGTTGCTAATCTCTCGTGACCTTGTTGCTATAATCAGTAAAG

AGTCTCAACATGTATATTACCTGACATTTGAACTGGTTTTGATGTATTGTGATGTC

ATAGAGGGGAGGTTAATGACAGAGACCGCTATGACTATTGATGCTAGGTATACA

GAGCTTCTAGGAAGAGTCAGATACATGTGGAAACTGATAGATGGTTTCTTCCCTG

CACTCGGGAATCCAACTTATCAAATTGTAGCCATGCTGGAGCCTCTTTCACTTGC

TTACCTGCAGCTGAGGGATATAACAGTAGAACTCAGAGGTGCTTTCCTTAACCAC

TGCTTTACTGAAATACATGATGTTCTTGACCAAAACGGGTTTTCTGATGAAGGTA

CTTATCATGAGTTAACTGAAGCTCTAGATTACATTTTCATAACTGATGACATACA

TCTGACAGGGGAGATTTTCTCATTTTTCAGAAGTTTCGGCCACCCCAGACTTGAA

GCAGTAACGGCTGCTGAAAATGTTAGGAAATACATGAATCAGCCTAAAGTCATT

GTGTATGAGACTCTGATGAAAGGTCATGCCATATTTTGTGGAATCATAATCAACG

GCTATCGTGACAGGCACGGAGGCAGTTGGCCACCGCTGACCCTCCCCCTGCATG

CTGCAGACACAATCCGGAATGCTCAAGCTTCAGGTGAAGGGTTAACACATGAGC

AGTGCGTTGATAACTGGAAATCTTTTGCTGGAGTGAAATTTGGCTGCTTTATGCC

TCTTAGCCTGGATAGTGATCTGACAATGTACCTAAAGGACAAGGCACTTGCTGCT

CTCCAAAGGGAATGGGATTCAGTTTACCCGAAAGAGTTCCTGCGTTACGACCCTC

CCAAGGGAACCGGGTCACGGAGGCTTGTAGATGTTTTCCTTAATGATTCGAGCTT

TGACCCATATGATGTGATAATGTATGTTGTAAGTGGAGCTTACCTCCATGACCCT

GAGTTCAACCTGTCTTACAGCCTGAAAGAAAGGAGATCAAGGAAACAGGTAGA

CTTTTTGCTAAAATGACTTACAAAATGAGGGCATGCCAAGTGATTGCTGAAAATC

TAATCTCAAACGGGATTGGCAAATATTTTAAGGACAATGGGATGGCCAAGGATG

AGCACGATTTGACTAAGGCACTCCACACTCTAGCTGTCTCAGGAGTCCCCAAAG
```

-continued
```
ATCTCAAAGAAAGTCACAGGGGGGGGCCAGTCTTAAAAACCTACTCCCGAAGCC

CAGTCCACACAAGTACCAGGAACGTGAGAGCAGCAAAAGGGTTTATAGGGTTCC

CTCAAGTAATTCGGCAGGACCAAGACACTGATCATCCGGAGAATATGGAAGCTT

ACGAGACAGTCAGTGCATTTATCACGACTGATCTCAAGAAGTACTGCCTTAATTG

GAGATATGAGACCATCAGCTTGTTTGCACAGAGGCTAAATGAGATTTACGGATT

GCCCTCATTTTTCCAGTGGCTGCATAAGAGGCTTGAGACCTCTGTCCTGTATGTA

AGTGACCCTCATTGCCCCCCCGACCTTGACGCCCATATCCCGTTATATAAAGTCC

CCAATGATCAAATCTTCATTAAGTACCCTATGGGAGGTATAGAAGGGTATTGTCA

GAAGCTGTGGACCATCAGCACCATTCCCTATCTATACCTGGCTGCTTATGAGAGC

GGAGTAAGGATTGCTTCGTTAGTGCAAGGGGACAATCAGACCATAGCCGTAACA

AAAAGGGTACCCAGCACATGGCCCTACAACCTTAAGAAACGGGAAGCTGCTAGA

GTAACTAGAGATTACTTTGTAATTCTTAGGCAAAGGCTACATGATATTGGCCATC

ACCTCAAGGCAAATGAGACAATTGTTTCATCACATTTTTTGTCTATTCAAAAGG

AATATATTATGATGGGCTACTTGTGTCCCAATCACTCAAGAGCATCGCAAGATGT

GTATTCTGGTCAGAGACTATAGTTGATGAAACAAGGGCAGCATGCAGTAATATT

GCTACAACAATGGCTAAAAGCATCGAGAGAGGTTATGACCGTTACCTTGCATAT

TCCCTGAACGTCCTAAAAGTGATACAGCAAATTCTGATCTCTCTTGGCTTCACAA

TCAATTCAACCATGACCCGGGATGTAGTCATACCCCTCCTCACAAACAACGACCT

CTTAATAAGGATGGCACTGTTGCCCGCTCCTATTGGGGGATGAATTATCTGAAT

ATGAGCAGGCTGTTTGTCAGAAACATCGGTGATCCAGTAACATCATCAATTGCTG

ATCTCAAGAGAATGATTCTCGCCTCACTAATGCCTGAAGAGACCCTCCATCAGGT

AATGACACAACAACCGGGGACTCTTCATTCCTAGACTGGGCTAGCGACCCTTA

CTCAGCAAATCTTGTATGTGTCCAGAGCATCACTAGACTCCTCAAGAACATAACT

GCAAGGTTTGTCCTGATCCATAGTCCAAACCCAATGTTAAAAGGATTATTCCATG

ATGACAGTAAAGAAGAGGACGAGGGACTGGCGGCATTCCTCATGGACAGGCAT

ATTATAGTACCTAGGGCAGCTCATGAAATCCTGGATCATAGTGTCACAGGGGCA

AGAGAGTCTATTGCAGGCATGCTGGATACCACAAAAGGCTTGATTCGAGCCAGC

ATGAGGAAGGGGGTTTAACCTCTCGAGTGATAACCAGATTGTCCAATTATGAC

TATGAACAATTCAGAGCAGGGATGGTGCTATTGACAGGAAGAAAGAGAAATGTC

CTCATTGACAAAGAGTCATGTTCAGTGCAGCTGGCGAGAGCTCTAAGAAGCCAT

ATGTGGGCGAGGCTAGCTCGAGGACGGCCTATTTACGGCCTTGAGGTCCCTGAT

GTACTAGAATCTATGCGAGGCCACCTTATTCGGCGTCATGAGACATGTGTCATCT

GCGAGTGTGGATCAGTCAACTACGGATGGTTTTTTGTCCCCTCGGGTTGCCAACT

GGATGATATTGACAAGGAAACATCATCCTTGAGAGTCCCATATATTGGTTCTACC

ACTGATGAGAGAACAGACATGAAGCTTGCCTTCGTAAGAGCCCCAAGTCGATCC

TTGCGATCTGCTGTTAGAATAGCAACAGTGTACTCATGGGCTTACGGTGATGATG

ATAGCTCTTGGAACGAAGCCTGGTTGTTGGCTAGGCAAAGGGCCAATGTGAGCC

TGGAGGAGCTAAGGGTGATCACTCCCATCTCAACTTCGACTAATTTAGCGCATAG

GTTGAGGGATCGTAGCACTCAAGTGAAATACTCAGGTACATCCCTTGTCCGAGTG

GCGAGGTATACCACAATCTCCAACGACAATCTCTCATTTGTCATATCAGATAAGA

AGGTTGATACTAACTTTATATACCAACAAGGAATGCTTCTAGGGTTGGGTGTTTT
```

-continued

```
AGAAACATTGTTTCGACTCGAGAAAGATACCGGATCATCTAACACGGTATTACA

TCTTCACGTCGAAACAGATTGTTGCGTGATCCCGATGATAGATCATCCCAGGATA

CCCAGCTCCCGCAAGCTAGAGCTGAGGGCAGAGCTATGTACCAACCCATTGATA

TATGATAATGCACCTTTAATTGACAGAGATGCAACAAGGCTATACACCCAGAGC

CATAGGAGGCACCTTGTGGAATTTGTTACATGGTCCACACCCCAACTATATCACA

TTTTAGCTAAGTCCACAGCACTATCTATGATTGACCTGGTAACAAAATTTGAGAA

GGACCATATGAATGAAATTTCAGCTCTCATAGGGGATGACGATATCAATAGTTTC

ATAACTGAGTTTCTGCTCATAGAGCCAAGATTATTCACTATCTACTTGGGCCAGT

GTGCGGCCATCAATTGGGCATTTGATGTACATTATCATAGACCATCAGGGAAATA

TCAGATGGGTGAGCTGTTGTCATCGTTCCTTTCTAGAATGAGCAAAGGAGTGTTT

AAGGTGCTTGTCAATGCTCTAAGCCACCCAAAGATCTACAAGAAATTCTGGCATT

GTGGTATTATAGAGCCTATCCATGGTCCTTCACTTGATGCTCAAAACTTGCACAC

AACTGTGTGCAACATGGTTTACACATGCTATATGACCTACCTCGACCTGTTGTTG

AATGAAGAGTTAGAAGAGTTCACATTTCTCTTGTGTGAAAGCGACGAGGATGTA

GTACCGGACAGATTCGACAACATCCAGGCAAAACACTTATGTGTTCTGGCAGAT

TTGTACTGTCAACCAGGGACCTGCCCACCAATTCGAGGTCTAAGACCGGTAGAG

AAATGTGCAGTTCTAACCGACCATATCAAGGCAGAGGCTATGTTATCTCCAGCA

GGATCTTCGTGGAACATAAATCCAATTATTGTAGACCATTACTCATGCTCCCTGA

CTTATCTCCGGCGAGGATCGATCAAACAGATAAGATTGAGAGTTGATCCAGGAT

TCATTTTCGACGCCCTCGCTGAGGTAAATGTCAGTCAGCCAAAGATCGGCAGCA

ACAACATCTCAAATATGAGCATCAAGGCTTTCAGACCCCCACACGATGATGTTG

CAAAATTGCTCAAAGATATCAACACAAGCAAGCACAATCTTCCCATTTCAGGGG

GCAATCTCGCCAATTATGAAATCCATGCTTTCCGCAGAATCGGGTTGAACTCATC

TGCTTGCTACAAAGCTGTTGAGATATCAACATTAATTAGGAGATGCCTTGAGCCA

GGGGAGGACGGCTTGTTCTTGGGTGAGGGATCGGGTTCTATGTTGATCACTTATA

AGGAGATACTTAAACTAAACAAGTGCTTCTATAATAGTGGGGTTTCCGCCAATTC

TAGATCTGGTCAAAGGGAATTAGCACCCTATCCCTCCGAAGTTGGCCTTGTCGAA

CACAGAATGGGAGTAGGTAATATTGTCAAAGTGCTCTTTAACGGGAGGCCCGAA

GTCACGTGGGTAGGCAGTGTAGATTGCTTCAATTTCATAGTTAGTAATATCCCTA

CCTCTAGTGTGGGGTTTATCCATTCAGATATAGAGACCTTGCCTGACAAAGATAC

TATAGAGAAGCTAGAGGAATTGGCAGCCATCTTATCGATGGCTCTGCTCCTGGGC

AAAATAGGATCAATACTGGTGATTAAGCTTATGCCTTTCAGCGGGGATTTTGTTC

AGGGATTTATAAGTTATGTAGGGTCTCATTATAGAGAAGTGAACCTTGTATACCC

TAGATACAGCAACTTCATATCTACTGAATCTTATTTGGTTATGACAGATCTCAAG

GCTAACCGGCTAATGAATCCTGAAAAGATTAAGCAGCAGATAATTGAATCATCT

GTGAGGACTTCACCTGGACTTATAGGTCACATCCTATCCATTAAGCAACTAAGCT

GCATACAAGCAATTGTGGGAGACGCAGTTAGTAGAGGTGATATCAATCCTACTC

TGAAAAAACTTACACCTATAGAGCAGGTGCTGATCAATTGCGGGTTGGCAATTA

ACGGACCTAAGCTGTGCAAAGAATTGATCCACCATGATGTTGCCTCAGGGCAAG

ATGGATTGCTTAATTCTATACTCATCCTCTACAGGGAGTTGGCAAGATTCAAAGA
```

-continued

```
CAACCAAAGAAGTCAACAAGGGATGTTCCACGCCTACCCCGTATTGGTAAGTAG

CAGGCAACGAGAACTTATATCTAGGATCACCCGCAAATTTTGGGGGCACATTCTT

CTTTACTCCGGGAACAAAAAGTTGATAAATAAGTTTATCCAGAATCTCAAGTCCG

GCTATCTGATACTAGACTTACACCAGAATATCTTCGTTAAGAATCTATCCAAGTC

AGAGAAACAGATTATTATGACGGGGGGTTTGAAACGTGAGTGGGTTTTTAAGGT

AACAGTCAAGGAGACCAAAGAATGGTATAAGTTAGTCGGATACAGTGCCCTGAT

TAAGGACTAATTGGTTGAACTCCGGAACCCTAATCCTGCCCTAGGTGGTTAGGCA

TTATTTGCAATATATTAAAGAAAACTTTGAAAATACGAAGTTTCTATTCCCAGCT

TTGTCTGGTggccggcatAgtcccagcctcctcgctggcgctggctgggcaacattccgaggggaccgtccccAcggtaa tggcgaatgggacgcggccgatccggctgctaacaaagcccgaaaggaagctgagttggctgctgGcGcTGgctgGgcaata actagcataaccccttggggcctctaaacgggtcttgaggggttttttgctgaaaggaggaactatatccggatgcGGCCGCGC

GCTTGGCGTAATCATGGTCATAGCTGTTTCCTGTGTGAAATTGTTATCCGCTCAC

AATTCCACACAACATACGAGCCGGAAGCATAAAGTGTAAAGCCTGGGGTGCCTA

ATGAGTGAGCTAACTCACATTAATTGCGTTGCGCTCACTGCCCGCTTTCCAGTCG

GGAAACCTGTCGTGCCAGCTGCATTAATGAATCGGCCAACGCGCGGGGAGAGGC

GGTTTGCGTATTGGGCGCTCTTCCGCTTCCTCGCTCACTGACTCGCTGCGCTCGGT

CGTTCGGCTGCGGCGAGCGGTATCAGCTCACTCAAAGGCGGTAATACGGTTATC

CACAGAATCAGGGGATAACGCAGGAAAGAACATGTGAGCAAAAGGCCAGCAAA

AGGCCAGGAACCGTAAAAAGGCCGCGTTGCTGGCGTTTTTCCATAGGCTCCGCC

CCCCTGACGAGCATCACAAAAATCGACGCTCAAGTCAGAGGTGGCGAAACCCGA

CAGGACTATAAAGATACCAGGCGTTTCCCCCTGGAAGCTCCCTCGTGCGCTCTCC

TGTTCCGACCCTGCCGCTTACCGGATACCTGTCCGCCTTTCTCCCTTCGGGAAGC

GTGGCGCTTTCTCATAGCTCACGCTGTAGGTATCTCAGTTCGGTGTAGGTCGTTC

GCTCCAAGCTGGGCTGTGTGCACGAACCCCCCGTTCAGCCCGACCGCTGCGCCTT

ATCCGGTAACTATCGTCTTGAGTCCAACCCGGTAAGACACGACTTATCGCCACTG

GCAGCAGCCACTGGTAACAGGATTAGCAGAGCGAGGTATGTAGGCGGTGCTACA

GAGTTCTTGAAGTGGTGGCCTAACTACGGCTACACTAGAAGGACAGTATTTGGT

ATCTGCGCTCTGCTGAAGCCAGTTACCTTCGGAAAAAGAGTTGGTAGCTCTTGAT

CCGGCAAACAAACCACCGCTGGTAGCGGTGGTTTTTTTGTTTGCAAGCAGCAGAT

TACGCGCAGAAAAAAAGGATCTCAAGAAGATCCTTTGATCTTTTCTACGGGTCT

GACGCTCAGTGGAACGAAAACTCACGTTAAGGGATTTTGGTCATGAGATTATCA

AAAAGGATCTTCACCTAGATCCTTTTAAATTAAAAATGAAGTTTTAAATCAATCT

AAAGTATATATGAGTAAACTTGGTCTGACAGTTACCAATGCTTAATCAGTGAGGC

ACCTATCTCAGCGATCTGTCTATTTCGTTCATCCATAGTTGCCTGACTCCCCGTCG

TGTAGATAACTACGATACGGGAGGGCTTACCATCTGGCCCCAGTGCTGCAATGA

TACCGCGAGACCCACGCTCACCGGCTCCAGATTTATCAGCAATAAACCAGCCAG

CCGGAAGGGCCGAGCGCAGAAGTGGTCCTGCAACTTTATCCGCCTCCATCCAGT

CTATTAATTGTTGCCGGGAAGCTAGAGTAAGTAGTTCGCCAGTTAATAGTTTGCG

CAACGTTGTTGCCATTGCTACAGGCATCGTGGTGTCACGCTCGTCGTTTGGTATG

GCTTCATTCAGCTCCGGTTCCCAACGATCAAGGCGAGTTACATGATCCCCCATGT

TGTGCAAAAAAGCGGTTAGCTCCTTCGGTCCTCCGATCGTTGTCAGAAGTAAGTT
```

```
GGCCGCAGTGTTATCACTCATGGTTATGGCAGCACTGCATAATTCTCTTACTGTC

ATGCCATCCGTAAGATGCTTTTCTGTGACTGGTGAGTACTCAACCAAGTCATTCT

GAGAATAGTGTATGCGGCGACCGAGTTGCTCTTGCCCGGCGTCAATACGGGATA

ATACCGCGCCACATAGCAGAACTTTAAAAGTGCTCATCATTGGAAAACGTTCTTC

GGGGCGAAAACTCTCAAGGATCTTACCGCTGTTGAGATCCAGTTCGATGTAACCC

ACTCGTGCACCCAACTGATCTTCAGCATCTTTTACTTTCACCAGCGTTTCTGGGTG

AGCAAAAACAGGAAGGCAAAATGCCGCAAAAAAGGGAATAAGGGCGACACGG

AAATGTTGAATACTCATACTCTTCCTTTTTCAATATTATTGAAGCATTTATCAGGG

TTATTGTCTCATGAGCGGATACATATTTGAATGTATTTAGAAAAATAAACAAATA

GGGGTTCCGCGCACATTTCCCCGAAAAGTGCCACCTG.
```

In another embodiment, the nucleic acid comprises the sequence of SEQ ID NO: 4, shown below:

```
GGACGCGCCCTGTAGCGGCGCATTAAGCGCGGCGGGTGTGGTGGTTACGCGCAG

CGTGACCGCTACACTTGCCAGCGCCCTAGCGCCCGCTCCTTTCGCTTTCTTCCCTT

CCTTTCTCGCCACGTTCGCCGGCTTTCCCCGTCAAGCTCTAAATCGGGGCTCCC

TTTAGGGTTCCGATTTAGTGCTTTACGGCACCTCGACCCCAAAAAACTTGATTAG

GGTGATGGTTCACGTAGTGGGCCATCGCCCTGATAGACGGTTTTTCGCCCTTTGA

CGTTGGAGTCCACGTTCTTTAATAGTGGACTCTTGTTCCAAACTGGAACAACACT

CAACCCTATCTCGGTCTATTCTTTTGATTTATAAGGGATTTTGCCGATTTCGGCCT

ATTGGTTAAAAAATGAGCTGATTTAACAAAAATTTAACGCGAATTTTAACAAAA

TATTAACGTTTACAATTTCGCGCCATTCGCCATTCAGGCTGCGCAACTGTTGGGA

AGGGCGATCGGTGCGGGCCTCTTCGCTATTACGCCAGCTGGCGAAAGGGGGATG

TGCTGCAAGGCGATTAAGTTGGGTAACGCCAGGGTTTTCCCAGTCACGACGTTGT

AAAACGACGGCCAGTGCGCGCCGTTAATACGACTCACTATAGGGAGACCCAAGC

TGGCTAGCTTTGTTTGGTCTGATGAGTCCCGTGAGGACGAAACCCGGCGTACCGG

GTCACCAAACAAAGTTGGGTAAGGATAGTTCAATCAATGATCATCTTCTAGTGCA

CTTAGGATTCAAGATCCTATTATCAGGGACAAGAGCAGGATTAGGGATATCCGA

GATGGCCACACTTTTAAGGAGCTTAGCATTGTTCAAAAGAAACAAGGACAAACC

ACCCATTACATCAGGATCCGGTGGAGCCATCAGAGGAATCAAACACATTATTAT

AGTACCAATCCCTGGAGATTCCTCAATTACCACTCGATCCAGACTTCTGGACCGG

TTGGTGAGGTTAATTGGAAACCCGGATGTGAGCGGGCCCAAACTAACAGGGGCA

CTAATAGGTATATTATCCTTATTTGTGGAGTCTCCAGGTCAATTGATTCAGAGGA

TCACCGATGACCCTGACGTTAGCATAAGGCTGTTAGAGGTTGTCCAGAGTGACC

AGTCACAATCTGGCCTTACCTTCGCATCAAGAGGTACCAACATGGAGGATGAGG

CGGACCAATACTTTTCACATGATGATCCAATTAGTAGTGATCAATCCAGGTTCGG

ATGGTTCGGGAACAAGGAAATCTCAGATATTGAAGTGCAAGACCCTGAGGGATT

CAACATGATTCTGGGTACCATCCTAGCCCAAATTTGGGTCTTGCTCGCAAAGGCG

GTTACGGCCCCAGACACGGCAGCTGATTCGGAGCTAAGAAGGTGGATAAAGTAC

ACCCAACAAAGAAGGGTAGTTGGTGAATTTAGATTGGAGAGAAAATGGTTGGAT
```

-continued

```
GTGGTGAGGAACAGGATTGCCGAGGACCTCTCCTTACGCCGATTCATGGTCGCTC

TAATCCTGGATATCAAGAGAACACCCGGAAACAAACCCAGGATTGCTGAAATGA

TATGTGACATTGATACATATATCGTAGAGGCAGGATTAGCCAGTTTTATCCTGAC

TATTAAGTTTGGGATAGAAACTATGTATCCTGCTCTTGGACTGCATGAATTTGCT

GGTGAGTTATCCACACTTGAGTCCTTGATGAACCTTTACCAGCAAATGGGGGAA

ACTGCACCCTACATGGTAATCCTGGAGAACTCAATTCAGAACAAGTTCAGTGCA

GGATCATACCCTCTGCTCTGGAGCTATGCCATGGGAGTAGGAGTGGAACTTGAA

AACTCCATGGGAGGTTTGAACTTTGGCCGATCTTACTTTGATCCAGCATATTTTA

GATTAGGGCAAGAGATGGTAAGGAGGTCAGCTGGAAAGGTCAGTTCCACATTGG

CATCTGAACTCGGTATCACTGCCGAGGATGCAAGGCTTGTTTCAGAGATTGCAAT

GCATACTACTGAGGACAAGATCAGTAGAGCGGTTGGACCCAGACAAGCCCAAGT

ATCATTTCTACACGGTGATCAAAGTGAGAATGAGCTACCGAGATTGGGGGGCAA

GGAAGATAGGAGGGTCAAACAGAGTCGAGGAGAAGCCAGGGAGAGCTACAGAG

AAACCGGGCCCAGCAGAGCAAGTGATGCGAGAGCTGCCCATCTTCCAACCGGCA

CACCCCTAGACATTGACACTGCAACGGAGTCCAGCCAAGATCCGCAGGACAGTC

GAAGGTCAGCTGACGCCCTGCTTAGGCTGCAAGCCATGGCAGGAATCTCGGAAG

AACAAGGCTCAGACACGGACACCCCTATAGTGTACAATGACAGAAATCTTCTAG

ACTAGGTGCGAGAGGCCGAGGGCCAGAACAACATCCGCCTACCATCCATCATTG

TTATAAAAAACTTAGGAACCAGGTCCACACAGCCGCCAGCCCATCAACCATCCA

CTCCCACGATTGGAGCCAATGGCAGAAGAGCAGGCACGCCATGTCAAAAACGG

ACTGGAATGCATCCGGGCTCTCAAGGCCGAGCCCATCGGCTCACTGGCCATCGA

GGAAGCTATGGCAGCATGGTCAGAAATATCAGACAACCCAGGACAGGAGCGAG

CCACCTGCAGGGAAGAGAAGGCAGGCAGTTCGGGTCTCAGCAAACCATGCCTCT

CAGCAATTGGATCAACTGAAGGCGGTGCACCTCGCATCCGCGGTCAGGGACCTG

GAGAGAGCGATGACGACGCTGAAACTTTGGGAATCCCCCCAAGAAATCTCCAGG

CATCAAGCACTGGGTTACAGTGTTATTACGTTTATGATCACAGCGGTGAAGCGGT

TAAGGGAATCCAAGATGCTGACTCTATCATGGTTCAATCAGGCCTTGATGGTGAT

AGCACCCTCTCAGGAGGAGACAATGAATCTGAAAACAGCGATGTGGATATTGGC

GAACCTGATACCGAGGGATATGCTATCACTGACCGGGGATCTGCTCCCATCTCTA

TGGGGTTCAGGGCTTCTGATGTTGAAACTGCAGAAGGAGGGGAGATCCACGAGC

TCCTGAGACTCCAATCCAGAGGCAACAACTTTCCGAAGCTTGGGAAAACTCTCA

ATGTTCCTCCGCCCCCGGACCCCGGTAGGGCCAGCACTTCCGGGACACCCATTAA

AAAGGGCACAGACGCGAGATTAGCCTCATTTGGAACGGAGATCGCGTCTTTATT

GACAGGTGGTGCAACCCAATGTGCTCGAAAGTCACCCTCGGAACCATCAGGGCC

AGGTGCACCTGCGGGGAATGTCCCCGAGTGTGTGAGCAATGCCGCACTGATACA

GGAGTGGACACCCGAATCTGGTACCACAATCTCCCCGAGATCCCAGAATAATGA

AGAAGGGGAGACTATTATGATGATGAGCTGTTCTCTGATGTCCAAGATATTAA

AACAGCCTTGGCCAAAATACACGAGGATAATCAGAAGATAATCTCCAAGCTAGA

ATCACTGCTGTTATTGAAGGGAGAAGTTGAGTCAATTAAGAAGCAGATCAACAG

GCAAAATATCAGCATATCCACCCTGGAAGGACACCTCTCAAGCATCATGATCGC

CATTCCTGGACTTGGGAAGGATCCCAACGACCCCACTGCAGATGTCGAAATCAA
```

-continued

TCCCGACTTGAAACCCATCATAGGCAGAGATTCAGGCCGAGCACTGGCCGAAGT

TCTCAAGAAACCCGTTGCCAGCCGACAACTCCAAGGAATGACAAATGGACGGAC

CAGTTCCAGAGGACAGCTGCTGAAGGAATTTCAGCTAAAGCCGATCGGGAAAAA

GATGAGCTCAGCCGTCGGGTTTGTTCCTGACACCGGCCCTGCATCACGCAGTGTA

ATCCGCTCCATTATAAAATCCAGCCGGCTAGAGGAGGATCGGAAGCGTTACCTG

ATGACTCTCCTTGATGATATCAAAGGAGCCAATGATCTTGCCAAGTTCCACCAGA

TGCTGATGAAGATAATAATGAAGTAGCTACAGCTCAACTTACCTGCCAACCCCAT

GCCAGTCGATCATCCATCATTGTTATAAAAAACTTAGGAACCAggtccacacaGagtgat

ACGCGTACGCCACCATGTTCGTGTTTCTGGTGCTGCTGCCTCTGGTGAGCTCCCA

GTGCGTGAACCTGACCACAAGGACCCAGCTGCCCCCTGCCTATACCAATTCCTTC

ACACGGGCGTGTACTATCCCGACAAGGTGTTCCGGAGCAGCGTGCTGCACTCC

ACACAGGATCTGTTTCTGCCTTTCTTTTCTAACGTGACCTGGTTCCACGCCATCCA

CGTGAGCGGCACCAATGGCACAAAGCGGTTCGACAATCCAGTGCTGCCCTTTAA

CGATGGCGTGTACTTCGCCTCCACCGAGAAGTCTAACATCATCAGAGGCTGGAT

CTTTGGCACCACACTGGACAGCAAGACACAGTCCCTGCTGATCGTGAACAATGC

CACCAACGTGGTCATCAAGGTGTGCGAGTTCCAGTTTTGTAATGATCCATTCCTG

GGCGTGTACTATCACAAGAACAATAAGTCTTGGATGGAGAGCGAGTTTCGCGTG

TATTCCTCTGCCAACAATTGCACATTTGAGTACGTGTCCCAGCCCTTCCTGATGG

ACCTGGAGGGCAAGCAGGGCAATTTCAAGAACCTGAGGGAGTTCGTGTTTAAGA

ATATCGATGGCTACTTCAAAATCTACTCCAAGCACACCCCAATCAACCTGGTGCG

CGACCTGCCACAGGGCTTCTCTGCCCTGGAGCCACTGGTGGATCTGCCCATCGGC

ATCAACATCACCCGGTTTCAGACACTGCTGGCCCTGCACAGAAGCTACCTGACA

CCAGGCGACAGCTCCTCTGGATGGACCGCAGGAGCAGCAGCCTACTATGTGGGC

TATCTGCAGCCCAGGACCTTCCTGCTGAAGTACAACGAGAATGGCACCATCACA

GACGCCGTGGATTGCGCCCTGGATCCCCTGTCTGAGACCAAGTGTACACTGAAG

AGCTTTACCGTGGAGAAGGGCATCTATCAGACAAGCAATTTCAGGGTGCAGCCT

ACCGAGTCCATCGTGCGCTTTCCCAATATCACAAACCTGTGCCCTTTTGGCGAGG

TGTTCAACGCAACCCGCTTCGCCAGCGTGTACGCCTGGAATAGGAAGCGCATCT

CCAACTGCGTGGCCGACTATTCTGTGCTGTACAACAGCGCCTCCTTCTCTACCTTT

AAGTGCTATGGCGTGAGCCCCACAAAGCTGAATGACCTGTGCTTTACCAACGTGT

ACGCCGATTCCTTCGTGATCAGGGGCGACGAGGTGCGCCAGATCGCACCAGGAC

AGACAGGCAAGATCGCAGACTACAATTATAAGCTGCCTGACGATTTCACCGGCT

GCGTGATCGCCTGGAACTCTAACAATCTGGATAGCAAAGTGGGCGGCAACTACA

ATTATCTGTACCGGCTGTTTAGAAAGTCTAATCTGAAGCCATTCGAGAGGGACAT

CTCCACAGAAATCTACCAGGCCGGCTCTACCCCCTGCAATGGCGTGGAGGGCTTT

AACTGTTATTTCCCTCTGCAGAGCTACGGCTTCCAGCCAACAAACGGCGTGGGCT

ATCAGCCCTACCGCGTGGTGGTGCTGTCTTTTGAGCTGCTGCACGCACCTGCAAC

AGTGTGCGGACCAAAGAAGAGCACCAATCTGGTGAAGAACAAGTGCGTGAACTT

CAACTTCAACGGACTGACCGGAACAGGCGTGCTGACCGAGTCCAACAAGAAGTT

CCTGCCTTTTCAGCAGTTCGGCAGGGACATCGCAGATACCACAGACGCCGTGCG

-continued

```
CGACCCTCAGACCCTGGAGATCCTGGACATCACACCATGCTCCTTCGGCGGCGTG

TCTGTGATCACACCAGGCACCAATACAAGCAACCAGGTGGCCGTGCTGTATCAG

GACGTGAATTGTACCGAGGTGCCAGTGGCAATCCACGCAGATCAGCTGACCCCT

ACATGGCGGGTGTACTCTACCGGCAGCAACGTGTTCCAGACAAGAGCCGGATGC

CTGATCGGAGCAGAGCACGTGAACAATAGCTATGAGTGCGACATCCCTATCGGC

GCCGGCATCTGTGCCTCCTACCAGACCCAGACAAACTCCCCAAGGAGAGCACGG

TCTGTGGCCAGCCAGTCCATCATCGCCTATACCATGAGCCTGGGCGCCGAGAATT

CCGTGGCCTACTCCAACAATTCTATCGCCATCCCTACCAACTTCACAATCTCCGT

GACCACAGAGATCCTGCCAGTGAGCATGACCAAGACATCCGTGGACTGCACAAT

GTATATCTGTGGCGATTCCACCGAGTGCTCTAACCTGCTGCTGCAGTACGGCTCT

TTTTGTACCCAGCTGAATAGAGCCCTGACAGGCATCGCCGTGGAGCAGGACAAG

AACACACAGGAGGTGTTCGCCCAGGTGAAGCAAATCTACAAGACCCCACCCATC

AAGGACTTTGGCGGCTTCAACTTCAGCCAGATCCTGCCCGATCCTAGCAAGCCAT

CCAAGCGGTCTTTTATCGAGGACCTGCTGTTCAACAAGGTGACCCTGGCCGATGC

CGGCTTCATCAAGCAGTATGGCGATTGCCTGGGCGACATCGCCGCCAGAGACCT

GATCTGTGCCCAGAAGTTTAATGGCCTGACCGTGCTGCCTCCACTGCTGACAGAT

GAGATGATCGCCCAGTACACATCTGCCCTGCTGGCCGGAACCATCACAAGCGGA

TGGACCTTCGGCGCAGGAGCCGCCCTGCAGATCCCCTTTGCCATGCAGATGGCCT

ATCGGTTCAACGGCATCGGCGTGACCCAGAATGTGCTGTACGAGAACCAGAAGC

TGATCGCCAATCAGTTTAACTCCGCCATCGGCAAGATCCAGGACTCTCTGAGCTC

CACAGCCAGCGCCCTGGGCAAGCTGCAGGATGTGGTGAATCAGAACGCCCAGGC

CCTGAATACCCTGGTGAAGCAGCTGTCTAGCAACTTCGGCGCCATCTCCTCTGTG

CTGAATGACATCCTGAGCCGGCTGGACAAGGTGGAGGCAGAGGTGCAGATCGAC

CGGCTGATCACAGGCAGACTGCAGTCCCTGCAGACCTACGTGACACAGCAGCTG

ATCAGGGCAGCAGAGATCAGGGCCTCTGCCAATCTGGCCGCCACCAAGATGAGC

GAGTGCGTGCTGGGCCAGTCCAAGAGAGTGGACTTTTGTGGCAAGGGCTATCAC

CTGATGAGCTTCCCACAGTCCGCCCCTCACGGAGTGGTGTTTCTGCACGTGACCT

ACGTGCCAGCCCAGGAGAAGAACTTCACCACAGCACCAGCAATCTGCCACGATG

GCAAGGCACACTTTCCTAGGGAGGGCGTGTTCGTGAGCAACGGCACCCACTGGT

TTGTGACACAGCGCAATTTCTACGAGCCACAGATCATCACCACAGACAATACAT

TCGTGTCCGGCAACTGTGACGTGGTCATCGGCATCGTGAACAATACCGTGTATGA

TCCTCTGCAGCCAGAGCTGGACTCTTTTAAGGAGGAGCTGGATAAGTACTTCAAG

AATCACACCAGCCCCGACGTGGATCTGGGCGACATCTCTGGCATCAATGCCAGC

GTGGTGAACATCCAGAAGGAGATCGACAGGCTGAACGAGGTGGCCAAGAATCT

GAACGAGTCCCTGATCGATCTGCAGGAGCTGGGCAAGTATGAGCAGTACATCAA

GTGGCCCTGGTATATCTGGCTGGGCTTCATCGCCGGCCTGATCGCCATCGTGATG

GTGACCATCATGCTGTGCTGTATGACAAGCTGCTGTTCCTGCCTGAAGGGCTGCT

GTTCTTGTGGCAGCTGCTGTAAGTTTGATGAGGACGATAGCGAGCCTGTGCTGAA

GGGCGTGAAGCTGCACTACACCTGATAGCTAGCGATCGCCCACCTAGTACAACC

TAAATCCATTATAAAAAACTTAGGAGCAAAGTGATTGCCTCCCAAGGTCCACAA

TGACAGAGACCTACGACTTCGACAAGTCGGCATGGGACATCAAAGGGTCGATCG
```

```
CTCCGATACAACCCACCACCTACAGTGATGGCAGGCTGGTGCCCCAGGTCAGAG
TCATAGATCCTGGTCTAGGCGACAGGAAGGATGAATGCTTTATGTACATGTTTCT
GCTGGGGGTTGTTGAGGACAGCGATTCCCTAGGGCCTCCAATCGGGCGAGCATT
TGGGTTCCTGCCCTTAGGTGTTGGCAGATCCACAGCAAAGCCCGAAAAACTCCTC
AAAGAGGCCACTGAGCTTGACATAGTTGTTAGACGTACAGCAGGGCTCAATGAA
AAACTGGTGTTCTACAACAACACCCCACTAACTCTCCTCACACCTTGGAGAAAG
GTCCTAACAACAGGGAGTGTCTTCAACGCAAACCAAGTGTGCAATGCGGTTAAT
CTGATACCGCTCGATACCCCGCAGAGGTTCCGTGTTGTTTATATGAGCATCACCC
GTCTTTCGGATAACGGGTATTACACCGTTCCTAGAAGAATGCTGGAATTCAGATC
GGTCAATGCAGTGGCCTTCAACCTGCTGGTGACCCTTAGGATTGACAAGGCGAT
AGGCCCTGGGAAGATCATCGACAATACAGAGCAACTTCCTGAGGCAACATTTAT
GGTCCACATCGGGAACTTCAGGAGAAAGAAGAGTGAAGTCTACTCTGCCGATTA
TTGCAAAATGAAAATCGAAAAGATGGGCCTGGTTTTTGCACTTGGTGGGATAGG
GGGCACCAGTCTTCACATTAGAAGCACAGGCAAAATGAGCAAGACTCTCCATGC
ACAACTCGGGTTCAAGAAGACCTTATGTTACCCGCTGATGGATATCAATGAAGA
CCTTAATCGATTACTCTGGAGGAGCAGATGCAAGATAGTAAGAATCCAGGCAGT
TTTGCAGCCATCAGTTCCTCAAGAATTCCGCATTTACGACGACGTGATCATAAAT
GATGACCAAGGACTATTCAAAGTTCTGTAGACCGTAGTGCCCAGCAATGCCCGA
AAACGACCCCCTCACAATGACAGCCAGAAGGCCCGGACAAAAAAGCCCCCTCC
GAAAGACTCCACGGACCAAGCGAGAGGCCAGCCAGCAGCCGACGGCAAGCGCG
AACACCAGGCGGCCCCAGCACAGAACAGCCCTGACACAAGGCCACCACCAGCC
ACCCCAATCTGCATCCTCCTCGTGGGACCCCCGAGGACCAACCCCCAAGGCTGC
CCCCGATCCAAACCACCAACCGCATCCCCACCACCCCGGGAAAGAAACCCCCA
GCAATTGGAAGGCCCCTCCCCCTCTTCCTCAACACAAGAACTCCACAACCGAAC
CGCACAAGCGACCGAGGTGACCCAACCGCAGGCATCCGACTCCCTAGACAGATC
CTCTCTCCCCGGCAAACTAAACAAAACTTAGGGCCAAGGAACATACACACCCAA
CAGAACCCAGACCCCGGCCCACGGCGCCGCGCCCCAACCCCCGACAACCAGAG
GGAGCCCCCAACCAATCCCGCCGGCTCCCCCGGTGCCCACAGGCAGGGACACCA
ACCCCCGAACAGACCCAGCACCCAACCATCGACAATCCAAGACGGGGGGCCCC
CCCAAAAAAAGGCCCCCAGGGGCCGACAGCCAGCACCGCGAGGAAGCCCACCC
ACCCCACACACGACCACGGCAACCAAACCAGAACCCAGACCACCCTGGGCCACC
AGCTCCCAGACTCGGCCATCACCCCGCAGAAAGGAAAGGCCACAACCCGCGCAC
CCCAGCCCCGATCCGGCGGGAGCCACCCAACCCGAACCAGCACCCAAGAGCG
ATCCCCGAAGGACCCCCGAACCGCAAAGGACATCAGTATCCCACAGCCTCTCCA
AGTCCCCCGGTCTCCTCCTCTTCTCGAAGGGACCAAAAGATCAATCCACCACACC
CGACGACACTCAACTCCCCACCCCTAAAGGAGACACCGGGAATCCCAGAATCAA
GACTCATCCAATGTCCATCATGGGTCTCAAGGTGAACGTCTCTGCCATATTCATG
GCAGTACTGTTAACTCTCCAAACACCCACCGGTCAAATCCATTGGGCAATCTCT
CTAAGATAGGGGTGGTAGGAATAGGAAGTGCAAGCTACAAAGTTATGACTCGTT
CCAGCCATCAATCATTAGTCATAAAATTAATGCCCAATATAACTCTCCTCAATAA
```

-continued

```
CTGCACGAGGGTAGAGATTGCAGAATACAGGAGACTACTGAGAACAGTTTTGGA

ACCAATTAGAGATGCACTTAATGCAATGACCCAGAATATAAGACCGGTTCAGAG

TGTAGCTTCAAGTAGGAGACACAAGAGATTTGCGGGAGTAGTCCTGGCAGGTGC

GGCCCTAGGCGTTGCCACAGCTGCTCAGATAACAGCCGGCATTGCACTTCACCA

GTCCATGCTGAACTCTCAAGCCATCGACAATCTGAGAGCGAGCCTGGAAACTAC

TAATCAGGCAATTGAGACAATCAGACAAGCAGGGCAGGAGATGATATTGGCTGT

TCAGGGTGTCCAAGACTACATCAATAATGAGCTGATACCGTCTATGAACCAACT

ATCTTGTGATTTAATCGGCCAGAAGCTCGGGCTCAAATTGCTCAGATACTATACA

GAAATCCTGTCATTATTTGGCCCCAGTTTACGGGACCCCATATCTGCGGAGATAT

CTATCCAGGCTTTGAGCTATGCGCTTGGAGGAGACATCAATAAGGTGTTAGAAA

AGCTCGGATACAGTGGAGGTGATTTACTGGGCATCTTAGAGAGCGGAGGAATAA

AGGCCCGGATAACTCACGTCGACACAGAGTCCTACTTCATTGTCCTCAGTATAGC

CTATCCGACGCTGTCCGAGATTAAGGGGGTGATTGTCCACCGGCTAGAGGGGGT

CTCGTACAACATAGGCTCTCAAGAGTGGTATACCACTGTGCCCAAGTATGTTGCA

ACCCAAGGGTACCTTATCTCGAATTTTGATGAGTCATCGTGTACTTTCATGCCAG

AGGGGACTGTGTGCAGCCAAAATGCCTTGTACCCGATGAGTCCTCTGCTCCAAG

AATGCCTCCGGGGGTACACCAAGTCCTGTGCTCGTACACTCGTATCCGGGTCTTT

TGGGAACCGGTTCATTTTATCACAAGGGAACCTAATAGCCAATTGTGCATCAATC

CTTTGCAAGTGTTACACAACAGGAACGATCATTAATCAAGACCCTGACAAGATC

CTAACATACATTGCTGCCGATCACTGCCCGGTAGTCGAGGTGAACGGCGTGACC

ATCCAAGTCGGGAGCAGGAGGTATCCAGACGCTGTGTACTTGCACAGAATTGAC

CTCGGTCCTCCCATATCATTGGAGAGGTTGGACGTAGGGACAAATCTGGGGAAT

GCAATTGCTAAGTTGGAGGATGCCAAGGAATTGTTGGAGTCATCGGACCAGATA

TTGAGGAGTATGAAAGGTTTATCGAGCACTAGCATAGTCTACATCCTGATTGCAG

TGTGTCTTGGAGGGTTGATAGGGATCCCCGCTTTAATATGTTGCTGCAGGGGGCG

TTGTAACAAAAAGGGAGAACAAGTTGGTATGTCAAGACCAGGCCTAAAGCCTGA

TCTTACGGGAACATCAAAATCCTATGTAAGGTCGCTCTGATCCTCTACAACTCTT

GAAACACAAATGTCCCACAAGTCTCCTCTTCGTCATCAAGCAACCACCGCACCC

AGCATCAAGCCCACCTGAAATTATCTCCGGCTTCCCTCTGGCCGAACAATATCGG

TAGTTAATTAAAACTTAGGGTGCAAGATCATCGATAATGTCACCACAACGAGAC

CGGATAAATGCCTTCTACAAAGATAACCCCCATCCCAAGGGAAGTAGGATAGTC

ATTAACAGAGAACATCTTATGATTGATAGACCTTATGTTTTGCTGGCTGTTCTGTT

TGTCATGTTTCTGAGCTTGATCGGGTTGCTAGCCATTGCAGGAATTCGACTTCAT

CGGGCAGCCATCTACACCGCAGAGATCCATAAAAGCCTCAGCACCAATCTAGAT

GTAACTAACTCAATCGAGCATCAGGTCAAGGACGTGCTGACACCACTCTTCAAA

ATCATCGGTGATGAAGTGGGCCTGAGGACACCTCAGAGATTCACTGACCTAGTG

AAATTAATCTCTGACAAGATTAAATTCCTTAATCCGGATAGGGAGTACGACTTCA

GAGATCTCACTTGGTGTATCAACCCGCCAGAGAGAATCAAATTGGATTATGATC

AATACTGTGCAGATGTGGCTGCTGAAGAGCTCATGAATGCATTGGTGAACTCAA

CTCTACTGGAGACCAGAACAACCAATCAGTTCCTAGCTGTCTCAAAGGGAAACT

GCTCAGGGCCCACTACAATCAGAGGTCAATTCTCAAACATGTCGCTGTCCCTGTT
```

-continued

```
AGACTTGTATTTAGGTCGAGGTTACAATGTGTCATCTATAGTCACTATGACATCC
CAGGGAATGTATGGGGGAACTTACCTAGTGGAAAAGCCTAATCTGAGCAGCAAA
AGGTCAGAGTTGTCACAACTGAGCATGTACCGAGTGTTTGAAGTAGGTGTTATCA
GAAATCCGGGTTTGGGGGCTCCGGTGTTCCATATGACAAACTATCTTGAGCAACC
AGTCAGTAATGATCTCAGCAACTGTATGGTGGCTTTGGGGGAGCTCAAACTCGC
AGCCCTTTGTCACGGGGAAGATTCTATCACAATTCCCTATCAGGGATCAGGGAA
AGGTGTCAGCTTCCAGCTCGTCAAGCTAGGTGTCTGGAAATCCCCAACCGACAT
GCAATCCTGGGTCCCCTTATCAACGGATGATCCAGTGATAGACAGGCTTTACCTC
TCATCTCACAGAGGTGTTATCGCTGACAACCAAGCAAATGGGCTGTCCCGACA
ACACGAACAGATGACAAGTTGCGAATGGAGACATGCTTCCAACAGGCGTGTAAG
GGTAAAATCCAAGCACTCTGCGAGAATCCCGAGTGGGCACCATTGAAGGATAAC
AGGATTCCTTCATACGGGGTCTTGTCTGTTGATCTGAGTCTGACAGTTGAGCTTA
AAATCAAAATTGCTTCGGGATTCGGGCCATTGATCACACACGGTTCAGGGATGG
ACCTATACAAATCCAACCACAACAATGTGTATTGGCTGACTATCCCGCCAATGA
AGAACCTAGCCTTAGGTGTAATCAACACATTGGAGTGGATACCGAGATTCAAGG
TTAGTCCCTACCTCTTCACTGTCCCAATTAAGGAAGCAGGCGAAGACTGCCATGC
CCCAACATACCTACCTGCGGAGGTGGATGGTGATGTCAAACTCAGTTCCAATCTG
GTGATTCTACCTGGTCAAGATCTCCAATATGTTTTGGCAACCTACGATACTTCCA
GGGTTGAACATGCTGTGGTTTATTACGTTTACAGCCCAAGCCGCTCATTTTCTTAC
TTTTATCCTTTTAGGTTGCCTATAAAGGGGGTCCCCATCGAATTACAAGTGGAAT
GCTTCACATGGGACCAAAAACTCTGGTGCCGTCACTTCTGTGTGCTTGCGGACTC
AGAATCTGGTGGACATATCACTCACTCTGGGATGGTGGGCATGGGAGTCAGCTG
CACAGTCACCCGGGAAGATGGAACCAATCGCAGATAGGGCTGCTAGTGAACCAA
TCACATGATGTCACCCAGACATCAGGCATACCCACTAGTGTGAAATAGACATCA
GAATTAAGAAAAACGTAGGGTCCAAGTGGTTCCCCGTTATGGACTCGCTATCTGT
CAACCAGATCTTATACCCTGAAGTTCACCTAGATAGCCCGATAGTTACCAATAAG
ATAGTAGCCATCCTGGAGTATGCTCGAGTCCCTCACGCTTACAGCCTGGAGGACC
CTACACTGTGTCAGAACATCAAGCACCGCCTAAAAAACGGATTTTCCAACCAAA
TGATTATAAACAATGTGGAAGTTGGGAATGTCATCAAGTCCAAGCTTAGGAGTT
ATCCGGCCCACTCTCATATTCCATATCCAAATTGTAATCAGGATTTATTTAACAT
AGAAGACAAAGAGTCAACGAGGAAGATCCGTGAACTCCTCAAAAAGGGGAATT
CGCTGTACTCCAAAGTCAGTGATAAGGTTTTCCAATGCTTAAGGGACACTAACTC
ACGGCTTGGCCTAGGCTCCGAATTGAGGGAGGACATCAAGGAGAAAGTTATTAA
CTTGGGAGTTTACATGCACAGCTCCCAGTGGTTTGAGCCCTTTCTGTTTTGGTTTA
CAGTCAAGACTGAGATGAGGTCAGTGATTAAATCACAAACCCATACTTGCCATA
GGAGGAGACACACACCTGTATTCTTCACTGGTAGTTCAGTTGAGTTGCTAATCTC
TCGTGACCTTGTTGCTATAATCAGTAAAGAGTCTCAACATGTATATTACCTGACA
TTTGAACTGGTTTTGATGTATTGTGATGTCATAGAGGGGAGGTTAATGACAGAGA
CCGCTATGACTATTGATGCTAGGTATACAGAGCTTCTAGGAAGAGTCAGATACAT
GTGGAAACTGATAGATGGTTTCTTCCCTGCACTCGGGAATCCAACTTATCAAATT
```

```
-continued
GTAGCCATGCTGGAGCCTCTTTCACTTGCTTACCTGCAGCTGAGGGATATAACAG

TAGAACTCAGAGGTGCTTTCCTTAACCACTGCTTTACTGAAATACATGATGTTCT

TGACCAAAACGGGTTTTCTGATGAAGGTACTTATCATGAGTTAACTGAAGCTCTA

GATTACATTTTCATAACTGATGACATACATCTGACAGGGGAGATTTTCTCATTTTT

CAGAAGTTTCGGCCACCCCAGACTTGAAGCAGTAACGGCTGCTGAAAATGTTAG

GAAATACATGAATCAGCCTAAAGTCATTGTGTATGAGACTCTGATGAAAGGTCA

TGCCATATTTTGTGGAATCATAATCAACGGCTATCGTGACAGGCACGGAGGCAG

TTGGCCACCGCTGACCCTCCCCCTGCATGCTGCAGACACAATCCGGAATGCTCAA

GCTTCAGGTGAAGGGTTAACACATGAGCAGTGCGTTGATAACTGGAAATCTTTTG

CTGGAGTGAAATTTGGCTGCTTTATGCCTCTTAGCCTGGATAGTGATCTGACAAT

GTACCTAAAGGACAAGGCACTTGCTGCTCTCCAAAGGGAATGGGATTCAGTTTA

CCCGAAAGAGTTCCTGCGTTACGACCCTCCCAAGGGAACCGGGTCACGGAGGCT

TGTAGATGTTTTCCTTAATGATTCGAGCTTTGACCCATATGATGTGATAATGTATG

TTGTAAGTGGAGCTTACCTCCATGACCCTGAGTTCAACCTGTCTTACAGCCTGAA

AGAAAAGGAGATCAAGGAAACAGGTAGACTTTTTGCTAAAATGACTTACAAAAT

GAGGGCATGCCAAGTGATTGCTGAAAATCTAATCTCAAACGGGATTGGCAAATA

TTTTAAGGACAATGGGATGGCCAAGGATGAGCACGATTTGACTAAGGCACTCCA

CACTCTAGCTGTCTCAGGAGTCCCCAAAGATCTCAAAGAAAGTCACAGGGGGGG

GCCAGTCTTAAAAACCTACTCCCGAAGCCCAGTCCACACAAGTACCAGGAACGT

GAGAGCAGCAAAAGGGTTTATAGGGTTCCCTCAAGTAATTCGGCAGGACCAAGA

CACTGATCATCCGGAGAATATGGAAGCTTACGAGACAGTCAGTGCATTTATCAC

GACTGATCTCAAGAAGTACTGCCTTAATTGGAGATATGAGACCATCAGCTTGTTT

GCACAGAGGCTAAATGAGATTTACGGATTGCCCTCATTTTTCCAGTGGCTGCATA

AGAGGCTTGAGACCTCTGTCCTGTATGTAAGTGACCCTCATTGCCCCCCCGACCT

TGACGCCCATATCCCGTTATATAAAGTCCCCAATGATCAAATCTTCATTAAGTAC

CCTATGGGAGGTATAGAAGGGTATTGTCAGAAGCTGTGGACCATCAGCACCATT

CCCTATCTATACCTGGCTGCTTATGAGAGCGGAGTAAGGATTGCTTCGTTAGTGC

AAGGGGACAATCAGACCATAGCCGTAACAAAAAGGGTACCCAGCACATGGCCC

TACAACCTTAAGAAACGGGAAGCTGCTAGAGTAACTAGAGATTACTTTGTAATT

CTTAGGCAAAGGCTACATGATATTGGCCATCACCTCAAGGCAAATGAGACAATT

GTTTCATCACATTTTTTTGTCTATTCAAAAGGAATATATTATGATGGGCTACTTGT

GTCCCAATCACTCAAGAGCATCGCAAGATGTGTATTCTGGTCAGAGACTATAGTT

GATGAAACAAGGGCAGCATGCAGTAATATTGCTACAACAATGGCTAAAAGCATC

GAGAGAGGTTATGACCGTTACCTTGCATATTCCCTGAACGTCCTAAAAGTGATAC

AGCAAATTCTGATCTCTCTTGGCTTCACAATCAATTCAACCATGACCCGGGATGT

AGTCATACCCCTCCTCACAAACAACGACCTCTTAATAAGGATGGCACTGTTGCCC

GCTCCTATTGGGGGATGAATTATCTGAATATGAGCAGGCTGTTTGTCAGAAACA

TCGGTGATCCAGTAACATCATCAATTGCTGATCTCAAGAGAATGATTCTCGCCTC

ACTAATGCCTGAAGAGACCCTCCATCAGGTAATGACACAACAACCGGGGGACTC

TTCATTCCTAGACTGGGCTAGCGACCCTTACTCAGCAAATCTTGTATGTGTCCAG

AGCATCACTAGACTCCTCAAGAACATAACTGCAAGGTTTGTCCTGATCCATAGTC
```

-continued

```
CAAACCCAATGTTAAAAGGATTATTCCATGATGACAGTAAAGAAGAGGACGAGG

GACTGGCGGCATTCCTCATGGACAGGCATATTATAGTACCTAGGGCAGCTCATG

AAATCCTGGATCATAGTGTCACAGGGGCAAGAGAGTCTATTGCAGGCATGCTGG

ATACCACAAAAGGCTTGATTCGAGCCAGCATGAGGAAGGGGGGTTTAACCTCTC

GAGTGATAACCAGATTGTCCAATTATGACTATGAACAATTCAGAGCAGGGATGG

TGCTATTGACAGGAAGAAAGAGAAATGTCCTCATTGACAAAGAGTCATGTTCAG

TGCAGCTGGCGAGAGCTCTAAGAAGCCATATGTGGGCGAGGCTAGCTCGAGGAC

GGCCTATTTACGGCCTTGAGGTCCCTGATGTACTAGAATCTATGCGAGGCCACCT

TATTCGGCGTCATGAGACATGTGTCATCTGCGAGTGTGGATCAGTCAACTACGGA

TGGTTTTTTGTCCCCTCGGGTTGCCAACTGGATGATATTGACAAGGAAACATCAT

CCTTGAGAGTCCCATATATTGGTTCTACCACTGATGAGAGAACAGACATGAAGCT

TGCCTTCGTAAGAGCCCCAAGTCGATCCTTGCGATCTGCTGTTAGAATAGCAACA

GTGTACTCATGGGCTTACGGTGATGATGATAGCTCTTGGAACGAAGCCTGGTTGT

TGGCTAGGCAAAGGGCCAATGTGAGCCTGGAGGAGCTAAGGGTGATCACTCCCA

TCTCAACTTCGACTAATTTAGCGCATAGGTTGAGGGATCGTAGCACTCAAGTGAA

ATACTCAGGTACATCCCTTGTCCGAGTGGCGAGGTATACCACAATCTCCAACGAC

AATCTCTCATTTGTCATATCAGATAAGAAGGTTGATACTAACTTTATATACCAAC

AAGGAATGCTTCTAGGGTTGGGTGTTTTAGAAACATTGTTTCGACTCGAGAAAGA

TACCGGATCATCTAACACGGTATTACATCTTCACGTCGAAACAGATTGTTGCGTG

ATCCCGATGATAGATCATCCCAGGATACCCAGCTCCCGCAAGCTAGAGCTGAGG

GCAGAGCTATGTACCAACCCATTGATATATGATAATGCACCTTTAATTGACAGAG

ATGCAACAAGGCTATACACCCAGAGCCATAGGAGGCACCTTGTGGAATTTGTTA

CATGGTCCACACCCCAACTATATCACATTTTAGCTAAGTCCACAGCACTATCTAT

GATTGACCTGGTAACAAAATTTGAGAAGGACCATATGAATGAAATTTCAGCTCT

CATAGGGGATGACGATATCAATAGTTTCATAACTGAGTTTCTGCTCATAGAGCCA

AGATTATTCACTATCTACTTGGGCCAGTGTGCGGCCATCAATTGGGCATTTGATG

TACATTATCATAGACCATCAGGGAAATATCAGATGGGTGAGCTGTTGTCATCGTT

CCTTTCTAGAATGAGCAAAGGAGTGTTTAAGGTGCTTGTCAATGCTCTAAGCCAC

CCAAAGATCTACAAGAAATTCTGGCATTGTGGTATTATAGAGCCTATCCATGGTC

CTTCACTTGATGCTCAAAACTTGCACACAACTGTGTGCAACATGGTTTACACATG

CTATATGACCTACCTCGACCTGTTGTTGAATGAAGAGTTAGAAGAGTTCACATTT

CTCTTGTGTGAAAGCGACGAGGATGTAGTACCGGACAGATTCGACAACATCCAG

GCAAAACACTTATGTGTTCTGGCAGATTTGTACTGTCAACCAGGGACCTGCCCAC

CAATTCGAGGTCTAAGACCGGTAGAGAAATGTGCAGTTCTAACCGACCATATCA

AGGCAGAGGCTATGTTATCTCCAGCAGGATCTTCGTGGAACATAAATCCAATTAT

TGTAGACCATTACTCATGCTCCCTGACTTATCTCCGGCGAGGATCGATCAAACAG

ATAAGATTGAGAGTTGATCCAGGATTCATTTTCGACGCCCTCGCTGAGGTAAATG

TCAGTCAGCCAAAGATCGGCAGCAACAACATCTCAAATATGAGCATCAAGGCTT

TCAGACCCCACACGATGATGTTGCAAAATTGCTCAAAGATATCAACACAAGCA

AGCACAATCTTCCCATTTCAGGGGGCAATCTCGCCAATTATGAAATCCATGCTTT
```

-continued

```
CCGCAGAATCGGGTTGAACTCATCTGCTTGCTACAAAGCTGTTGAGATATCAACA
TTAATTAGGAGATGCCTTGAGCCAGGGGAGGACGGCTTGTTCTTGGGTGAGGGA
TCGGGTTCTATGTTGATCACTTATAAGGAGATACTTAAACTAAACAAGTGCTTCT
ATAATAGTGGGGTTTCCGCCAATTCTAGATCTGGTCAAAGGGAATTAGCACCCTA
TCCCTCCGAAGTTGGCCTTGTCGAACACAGAATGGGAGTAGGTAATATTGTCAA
AGTGCTCTTTAACGGGAGGCCCGAAGTCACGTGGGTAGGCAGTGTAGATTGCTT
CAATTTCATAGTTAGTAATATCCCTACCTCTAGTGTGGGGTTTATCCATTCAGATA
TAGAGACCTTGCCTGACAAAGATACTATAGAGAAGCTAGAGGAATTGGCAGCCA
TCTTATCGATGGCTCTGCTCCTGGGCAAAATAGGATCAATACTGGTGATTAAGCT
TATGCCTTTCAGCGGGGATTTTGTTCAGGGATTTATAAGTTATGTAGGGTCTCATT
ATAGAGAAGTGAACCTTGTATACCCTAGATACAGCAACTTCATATCTACTGAATC
TTATTTGGTTATGACAGATCTCAAGGCTAACCGGCTAATGAATCCTGAAAAGATT
AAGCAGCAGATAATTGAATCATCTGTGAGGACTTCACCTGGACTTATAGGTCAC
ATCCTATCCATTAAGCAACTAAGCTGCATACAAGCAATTGTGGGAGACGCAGTT
AGTAGAGGTGATATCAATCCTACTCTGAAAAAACTTACACCTATAGAGCAGGTG
CTGATCAATTGCGGGTTGGCAATTAACGGACCTAAGCTGTGCAAAGAATTGATC
CACCATGATGTTGCCTCAGGGCAAGATGGATTGCTTAATTCTATACTCATCCTCT
ACAGGGAGTTGGCAAGATTCAAAGACAACCAAAGAAGTCAACAAGGGATGTTC
CACGCCTACCCCGTATTGGTAAGTAGCAGGCAACGAGAACTTATATCTAGGATC
ACCCGCAAATTTTGGGGGCACATTCTTCTTTACTCCGGGAACAAAAAGTTGATAA
ATAAGTTTATCCAGAATCTCAAGTCCGGCTATCTGATACTAGACTTACACCAGAA
TATCTTCGTTAAGAATCTATCCAAGTCAGAGAAACAGATTATTATGACGGGGGGT
TTGAAACGTGAGTGGGTTTTTAAGGTAACAGTCAAGGAGACCAAAGAATGGTAT
AAGTTAGTCGGATACAGTGCCCTGATTAAGGACTAATTGGTTGAACTCCGGAAC
CCTAATCCTGCCCTAGGTGGTTAGGCATTATTTGCAATATATTAAAGAAAACTTT
GAAAATACGAAGTTTCTATTCCCAGCTTTGTCTGGTggccggcatAgtcccagcctcctcgctggc
gctggctgggcaacattccgaggggaccgtccccAcggtaatggcgaatgggacgcggccgatccggctgctaacaa
agcccgaaaggaagctgagttggctgctgGcGcTGgctgGgcaataactagcataacccttggggcctctaaacgg
gtcttgaggggttttttgctgaaaggaggaactatatccggatgcGGCCGCGCGCTTGGCGTAATCATGGTCATAGCT
GTTTCCTGTGTGAAATTGTTATCCGCTCACAATTCCACACAACATACGAGCCGGAAGC
ATAAAGTGTAAAGCCTGGGGTGCCTAATGAGTGAGCTAACTCACATTAATTGCG
TTGCGCTCACTGCCCGCTTTCCAGTCGGGAAACCTGTCGTGCCAGCTGCATTAAT
GAATCGGCCAACGCGCGGGGAGAGGCGGTTTGCGTATTGGGCGCTCTTCCGCTT
CCTCGCTCACTGACTCGCTGCGCTCGGTCGTTCGGCTGCGGCGAGCGGTATCAGC
TCACTCAAAGGCGGTAATACGGTTATCCACAGAATCAGGGGATAACGCAGGAAA
GAACATGTGAGCAAAAGGCCAGCAAAAGGCCAGGAACCGTAAAAAGGCCGCGT
TGCTGGCGTTTTTCCATAGGCTCCGCCCCCCTGACGAGCATCACAAAAATCGACG
CTCAAGTCAGAGGTGGCGAAACCCGACAGGACTATAAAGATACCAGGCGTTTCC
CCCTGGAAGCTCCCTCGTGCGCTCTCCTGTTCCGACCCTGCCGCTTACCGGATAC
CTGTCCGCCTTTCTCCCTTCGGGAAGCGTGGCGCTTTCTCATAGCTCACGCTGTA
GGTATCTCAGTTCGGTGTAGGTCGTTCGCTCCAAGCTGGGCTGTGTGCACGAACC
```

```
CCCCGTTCAGCCCGACCGCTGCGCCTTATCCGGTAACTATCGTCTTGAGTCCAAC
CCGGTAAGACACGACTTATCGCCACTGGCAGCAGCCACTGGTAACAGGATTAGC
AGAGCGAGGTATGTAGGCGGTGCTACAGAGTTCTTGAAGTGGTGGCCTAACTAC
GGCTACACTAGAAGGACAGTATTTGGTATCTGCGCTCTGCTGAAGCCAGTTACCT
TCGGAAAAAGAGTTGGTAGCTCTTGATCCGGCAAACAAACCACCGCTGGTAGCG
GTGGTTTTTTGTTTGCAAGCAGCAGATTACGCGCAGAAAAAAAGGATCTCAAG
AAGATCCTTTGATCTTTTCTACGGGGTCTGACGCTCAGTGGAACGAAAACTCACG
TTAAGGGATTTTGGTCATGAGATTATCAAAAAGGATCTTCACCTAGATCCTTTTA
AATTAAAAATGAAGTTTTAAATCAATCTAAAGTATATATGAGTAAACTTGGTCTG
ACAGTTACCAATGCTTAATCAGTGAGGCACCTATCTCAGCGATCTGTCTATTTCG
TTCATCCATAGTTGCCTGACTCCCCGTCGTGTAGATAACTACGATACGGGAGGGC
TTACCATCTGGCCCCAGTGCTGCAATGATACCGCGAGACCCACGCTCACCGGCTC
CAGATTTATCAGCAATAAACCAGCCAGCCGGAAGGGCCGAGCGCAGAAGTGGTC
CTGCAACTTTATCCGCCTCCATCCAGTCTATTAATTGTTGCCGGGAAGCTAGAGT
AAGTAGTTCGCCAGTTAATAGTTTGCGCAACGTTGTTGCCATTGCTACAGGCATC
GTGGTGTCACGCTCGTCGTTTGGTATGGCTTCATTCAGCTCCGGTTCCCAACGAT
CAAGGCGAGTTACATGATCCCCCATGTTGTGCAAAAAAGCGGTTAGCTCCTTCGG
TCCTCCGATCGTTGTCAGAAGTAAGTTGGCCGCAGTGTTATCACTCATGGTTATG
GCAGCACTGCATAATTCTCTTACTGTCATGCCATCCGTAAGATGCTTTTCTGTGAC
TGGTGAGTACTCAACCAAGTCATTCTGAGAATAGTGTATGCGGCGACCGAGTTG
CTCTTGCCCGGCGTCAATACGGGATAATACCGCGCCACATAGCAGAACTTTAAA
AGTGCTCATCATTGGAAAACGTTCTTCGGGGCGAAAACTCTCAAGGATCTTACCG
CTGTTGAGATCCAGTTCGATGTAACCCACTCGTGCACCCAACTGATCTTCAGCAT
CTTTTACTTTCACCAGCGTTTCTGGGTGAGCAAAAACAGGAAGGCAAAATGCCG
CAAAAAAGGGAATAAGGGCGACACGGAAATGTTGAATACTCATACTCTTCCTTT
TTCAATATTATTGAAGCATTTATCAGGGTTATTGTCTCATGAGCGGATACATATTT
GAATGTATTTAGAAAAATAAACAAATAGGGGTTCCGCGCACATTTCCCCGAAAA
GTGCCACCTG.
```

In still another embodiment, the nucleic acid comprises the sequence of SEQ ID NO: 5, shown below:

```
GGACGCGCCCTGTAGCGGCGCATTAAGCGCGGCGGGTGTGGTGGTTACGCGCAG
CGTGACCGCTACACTTGCCAGCGCCCTAGCGCCCGCTCCTTTCGCTTTCTTCCCTT
CCTTTCTCGCCACGTTCGCCGGCTTTCCCCGTCAAGCTCTAAATCGGGGGCTCCC
TTTAGGGTTCCGATTTAGTGCTTTACGGCACCTCGACCCCAAAAAACTTGATTAG
GGTGATGGTTCACGTAGTGGGCCATCGCCCTGATAGACGGTTTTTCGCCCTTTGA
CGTTGGAGTCCACGTTCTTTAATAGTGGACTCTTGTTCCAAACTGGAACAACACT
CAACCCTATCTCGGTCTATTCTTTTGATTTATAAGGGATTTTGCCGATTTCGGCCT
ATTGGTTAAAAAATGAGCTGATTTAACAAAAATTTAACGCGAATTTTAACAAAA
TATTAACGTTTACAATTTCGCGCCATTCGCCATTCAGGCTGCGCAACTGTTGGGA
```

-continued

```
AGGGCGATCGGTGCGGGCCTCTTCGCTATTACGCCAGCTGGCGAAAGGGGGATG

TGCTGCAAGGCGATTAAGTTGGGTAACGCCAGGGTTTTCCCAGTCACGACGTTGT

AAAACGACGGCCAGTGCGCGCCGTTAATACGACTCACTATAGGGAGACCCAAGC

TGGCTAGCTTTGTTTGGTCTGATGAGTCCCGTGAGGACGAAACCCGGCGTACCGG

GTCACCAAACAAAGTTGGGTAAGGATAGTTCAATCAATGATCATCTTCTAGTGCA

CTTAGGATTCAAGATCCTATTATCAGGGACAAGAGCAGGATTAGGGATATCCGA

GATGGCCACACTTTTAAGGAGCTTAGCATTGTTCAAAAGAAACAAGGACAAACC

ACCCATTACATCAGGATCCGGTGGAGCCATCAGAGGAATCAAACACATTATTAT

AGTACCAATCCCTGGAGATTCCTCAATTACCACTCGATCCAGACTTCTGGACCGG

TTGGTGAGGTTAATTGGAAACCCGGATGTGAGCGGGCCCAAACTAACAGGGGCA

CTAATAGGTATATTATCCTTATTTGTGGAGTCTCCAGGTCAATTGATTCAGAGGA

TCACCGATGACCCTGACGTTAGCATAAGGCTGTTAGAGGTTGTCCAGAGTGACC

AGTCACAATCTGGCCTTACCTTCGCATCAAGAGGTACCAACATGGAGGATGAGG

CGGACCAATACTTTTCACATGATGATCCAATTAGTAGTGATCAATCCAGGTTCGG

ATGGTTCGGGAACAAGGAAATCTCAGATATTGAAGTGCAAGACCCTGAGGGATT

CAACATGATTCTGGGTACCATCCTAGCCCAAATTTGGGTCTTGCTCGCAAAGGCG

GTTACGGCCCCAGACACGGCAGCTGATTCGGAGCTAAGAAGGTGGATAAAGTAC

ACCCAACAAAGAAGGGTAGTTGGTGAATTTAGATTGGAGAGAAAATGGTTGGAT

GTGGTGAGGAACAGGATTGCCGAGGACCTCTCCTTACGCCGATTCATGGTCGCTC

TAATCCTGGATATCAAGAGAACACCCGGAAACAAACCCAGGATTGCTGAAATGA

TATGTGACATTGATACATATCGTAGAGGCAGGATTAGCCAGTTTTATCCTGAC

TATTAAGTTTGGGATAGAAACTATGTATCCTGCTCTTGGACTGCATGAATTTGCT

GGTGAGTTATCCACACTTGAGTCCTTGATGAACCTTTACCAGCAAATGGGGGAA

ACTGCACCCTACATGGTAATCCTGGAGAACTCAATTCAGAACAAGTTCAGTGCA

GGATCATACCCTCTGCTCTGGAGCTATGCCATGGGAGTAGGAGTGGAACTTGAA

AACTCCATGGGAGGTTTGAACTTTGGCCGATCTTACTTTGATCCAGCATATTTTA

GATTAGGGCAAGAGATGGTAAGGAGGTCAGCTGGAAAGGTCAGTTCCACATTGG

CATCTGAACTCGGTATCACTGCCGAGGATGCAAGGCTTGTTTCAGAGATTGCAAT

GCATACTACTGAGGACAAGATCAGTAGAGCGGTTGGACCCAGACAAGCCCAAGT

ATCATTTCTACACGGTGATCAAAGTGAGAATGAGCTACCGAGATTGGGGGCAA

GGAAGATAGGAGGGTCAAACAGAGTCGAGGAGAAGCCAGGGAGAGCTACAGAG

AAACCGGGCCCAGCAGAGCAAGTGATGCGAGAGCTGCCCATCTTCCAACCGGCA

CACCCCTAGACATTGACACTGCAACGGAGTCCAGCCAAGATCCGCAGGACAGTC

GAAGGTCAGCTGACGCCCTGCTTAGGCTGCAAGCCATGGCAGGAATCTCGGAAG

AACAAGGCTCAGACACGGACACCCCTATAGTGTACAATGACAGAAATCTTCTAG

ACTAGGTGCGAGAGGCCGAGGGCCAGAACAACATCCGCCTACCATCCATCATTG

TTATAAAAAACTTAGGAACCAGGTCCACACAGCCGCCAGCCCATCAACCATCCA

CTCCCACGATTGGAGCCAATGGCAGAAGAGCAGGCACGCCATGTCAAAAACGG

ACTGGAATGCATCCGGGCTCTCAAGGCCGAGCCCATCGGCTCACTGGCCATCGA

GGAAGCTATGGCAGCATGGTCAGAAATATCAGACAACCCAGGACAGGAGCGAG

CCACCTGCAGGGAAGAGAAGGCAGGCAGTTCGGGTCTCAGCAAACCATGCCTCT
```

-continued

```
CAGCAATTGGATCAACTGAAGGCGGTGCACCTCGCATCCGCGGTCAGGGACCTG

GAGAGAGCGATGACGACGCTGAAACTTTGGGAATCCCCCCAAGAAATCTCCAGG

CATCAAGCACTGGGTTACAGTGTTATTACGTTTATGATCACAGCGGTGAAGCGGT

TAAGGGAATCCAAGATGCTGACTCTATCATGGTTCAATCAGGCCTTGATGGTGAT

AGCACCCTCTCAGGAGGAGACAATGAATCTGAAAACAGCGATGTGGATATTGGC

GAACCTGATACCGAGGGATATGCTATCACTGACCGGGGATCTGCTCCCATCTCTA

TGGGGTTCAGGGCTTCTGATGTTGAAACTGCAGAAGGAGGGGAGATCCACGAGC

TCCTGAGACTCCAATCCAGAGGCAACAACTTTCCGAAGCTTGGGAAAACTCTCA

ATGTTCCTCCGCCCCGGACCCCGGTAGGGCCAGCACTTCCGGGACACCCATTAA

AAAGGGCACAGACGCGAGATTAGCCTCATTTGGAACGGAGATCGCGTCTTTATT

GACAGGTGGTGCAACCCAATGTGCTCGAAAGTCACCCTCGGAACCATCAGGGCC

AGGTGCACCTGCGGGAATGTCCCCGAGTGTGTGAGCAATGCCGCACTGATACA

GGAGTGGACACCCGAATCTGGTACCACAATCTCCCCGAGATCCCAGAATAATGA

AGAAGGGGGAGACTATTATGATGATGAGCTGTTCTCTGATGTCCAAGATATTAA

AACAGCCTTGGCCAAAATACACGAGGATAATCAGAAGATAATCTCCAAGCTAGA

ATCACTGCTGTTATTGAAGGGAGAAGTTGAGTCAATTAAGAAGCAGATCAACAG

GCAAAATATCAGCATATCCACCCTGGAAGGACACCTCTCAAGCATCATGATCGC

CATTCCTGGACTTGGGAAGGATCCCAACGACCCCACTGCAGATGTCGAAATCAA

TCCCGACTTGAAACCCATCATAGGCAGAGATTCAGGCCGAGCACTGGCCGAAGT

TCTCAAGAAACCCGTTGCCAGCCGACAACTCCAAGGAATGACAAATGGACGGAC

CAGTTCCAGAGGACAGCTGCTGAAGGAATTTCAGCTAAAGCCGATCGGGAAAAA

GATGAGCTCAGCCGTCGGGTTTGTTCCTGACACCGGCCCTGCATCACGCAGTGTA

ATCCGCTCCATTATAAAATCCAGCCGGCTAGAGGAGGATCGGAAGCGTTACCTG

ATGACTCTCCTTGATGATATCAAAGGAGCCAATGATCTTGCCAAGTTCCACCAGA

TGCTGATGAAGATAATAATGAAGTAGCTACAGCTCAACTTACCTGCCAACCCCAT

GCCAGTCGACCCACCTAGTACAACCTAAATCCATTATAAAAAACTTAGGAGCAA

AGTGATTGCCTCCCAAGGTCCACAATGACAGAGACCTACGACTTCGACAAGTCG

GCATGGGACATCAAAGGGTCGATCGCTCCGATACAACCCACCACCTACAGTGAT

GGCAGGCTGGTGCCCCAGGTCAGAGTCATAGATCCTGGTCTAGGCGACAGGAAG

GATGAATGCTTTATGTACATGTTTCTGCTGGGGGTTGTTGAGGACAGCGATTCCC

TAGGGCCTCCAATCGGGCGAGCATTTGGGTTCCTGCCCTTAGGTGTTGGCAGATC

CACAGCAAAGCCCGAAAAACTCCTCAAAGAGGCCACTGAGCTTGACATAGTTGT

TAGACGTACAGCAGGGCTCAATGAAAAACTGGTGTTCTACAACAACACCCCACT

AACTCTCCTCACACCTTGGAGAAAGGTCCTAACAACAGGGAGTGTCTTCAACGC

AAACCAAGTGTGCAATGCGGTTAATCTGATACCGCTCGATACCCCGCAGAGGTT

CCGTGTTGTTTATATGAGCATCACCCGTCTTTCGGATAACGGGTATTACACCGTT

CCTAGAAGAATGCTGGAATTCAGATCGGTCAATGCAGTGGCCTTCAACCTGCTG

GTGACCCTTAGGATTGACAAGGCGATAGGCCCTGGGAAGATCATCGACAATACA

GAGCAACTTCCTGAGGCAACATTTATGGTCCACATCGGGAACTTCAGGAGAAAG

AAGAGTGAAGTCTACTCTGCCGATTATTGCAAAATGAAAATCGAAAAGATGGGC
```

-continued

```
CTGGTTTTTGCACTTGGTGGGATAGGGGGCACCAGTCTTCACATTAGAAGCACAG

GCAAAATGAGCAAGACTCTCCATGCACAACTCGGGTTCAAGAAGACCTTATGTT

ACCCGCTGATGGATATCAATGAAGACCTTAATCGATTACTCTGGAGGAGCAGAT

GCAAGATAGTAAGAATCCAGGCAGTTTTGCAGCCATCAGTTCCTCAAGAATTCC

GCATTTACGACGACGTGATCATAAATGATGACCAAGGACTATTCAAAGTTCTGTA

GACCGTAGTGCCCAGCAATGCCCGAAAACGACCCCCCTCACAATGACAGCCAGA

AGGCCCGGACAAAAAAGCCCCCTCCGAAAGACTCCACGGACCAAGCGAGAGGC

CAGCCAGCAGCCGACGGCAAGCGCGAACACCAGGCGGCCCCAGCACAGAACAG

CCCTGACACAAGGCCACCACCAGCCACCCCAATCTGCATCCTCCTCGTGGGACCC

CCGAGGACCAACCCCCAAGGCTGCCCCCGATCCAAACCACCAACCGCATCCCCA

CCACCCCCGGGAAAGAAACCCCCAGCAATTGGAAGGCCCCTCCCCCTCTTCCTC

AACACAAGAACTCCACAACCGAACCGCACAAGCGACCGAGGTGACCCAACCGC

AGGCATCCGACTCCCTAGACAGATCCTCTCTCCCCGGCAAACTAAACAAAACTT

AGGGCCAAGGAACATACACACCCAACAGAACCCAGACCCCGGCCCACGGCGCC

GCGCCCCAACCCCCGACAACCAGAGGGAGCCCCCAACCAATCCCGCCGGCTCC

CCCGGTGCCCACAGGCAGGGACACCAACCCCCGAACAGACCCAGCACCCAACCA

TCGACAATCCAAGACGGGGGGCCCCCCCAAAAAAAGGCCCCCAGGGGCCGAC

AGCCAGCACCGCGAGGAAGCCCACCCACCCCACACACGACCACGGCAACCAAA

CCAGAACCCAGACCACCCTGGGCCACCAGCTCCCAGACTCGGCCATCACCCCGC

AGAAAGGAAAGGCCACAACCCGCGCACCCCAGCCCCGATCCGGCGGGGAGCCA

CCCAACCCGAACCAGCACCCAAGAGCGATCCCCGAAGGACCCCCGAACCGCAA

AGGACATCAGTATCCCACAGCCTCTCCAAGTCCCCCGGTCTCCTCCTCTTCTCGA

AGGGACCAAAAGATCAATCCACCACACCCGACGACACTCAACTCCCCACCCCTA

AAGGAGACACCGGGAATCCCAGAATCAAGACTCATCCAATGTCCATCATGGGTC

TCAAGGTGAACGTCTCTGCCATATTCATGGCAGTACTGTTAACTCTCCAAACACC

CACCGGTCAAATCCATTGGGGCAATCTCTCTAAGATAGGGGTGGTAGGAATAGG

AAGTGCAAGCTACAAAGTTATGACTCGTTCCAGCCATCAATCATTAGTCATAAAA

TTAATGCCCAATATAACTCTCCTCAATAACTGCACGAGGGTAGAGATTGCAGAAT

ACAGGAGACTACTGAGAACAGTTTTGGAACCAATTAGAGATGCACTTAATGCAA

TGACCCAGAATATAAGACCGGTTCAGAGTGTAGCTTCAAGTAGGAGACACAAGA

GATTTGCGGGAGTAGTCCTGGCAGGTGCGGCCCTAGGCGTTGCCACAGCTGCTC

AGATAACAGCCGGCATTGCACTTCACCAGTCCATGCTGAACTCTCAAGCCATCG

ACAATCTGAGAGCGAGCCTGGAAACTACTAATCAGGCAATTGAGACAATCAGAC

AAGCAGGGCAGGAGATGATATTGGCTGTTCAGGGTGTCCAAGACTACATCAATA

ATGAGCTGATACCGTCTATGAACCAACTATCTTGTGATTTAATCGGCCAGAAGCT

CGGGCTCAAATTGCTCAGATACTATACAGAAATCCTGTCATTATTTGGCCCCAGT

TTACGGGACCCCATATCTGCGGAGATATCTATCCAGGCTTTGAGCTATGCGCTTG

GAGGAGACATCAATAAGGTGTTAGAAAAGCTCGGATACAGTGGAGGTGATTTAC

TGGGCATCTTAGAGAGCGGAGGAATAAAGGCCCGGATAACTCACGTCGACACAG

AGTCCTACTTCATTGTCCTCAGTATAGCCTATCCGACGCTGTCCGAGATTAAGGG

GGTGATTGTCCACCGGCTAGAGGGGGTCTCGTACAACATAGGCTCTCAAGAGTG
```

-continued

```
GTATACCACTGTGCCCAAGTATGTTGCAACCCAAGGGTACCTTATCTCGAATTTT

GATGAGTCATCGTGTACTTTCATGCCAGAGGGGACTGTGTGCAGCCAAAATGCCT

TGTACCCGATGAGTCCTCTGCTCCAAGAATGCCTCCGGGGGTACACCAAGTCCTG

TGCTCGTACACTCGTATCCGGGTCTTTTGGGAACCGGTTCATTTTATCACAAGGG

AACCTAATAGCCAATTGTGCATCAATCCTTTGCAAGTGTTACACAACAGGAACG

ATCATTAATCAAGACCCTGACAAGATCCTAACATACATTGCTGCCGATCACTGCC

CGGTAGTCGAGGTGAACGGCGTGACCATCCAAGTCGGGAGCAGGAGGTATCCAG

ACGCTGTGTACTTGCACAGAATTGACCTCGGTCCTCCCATATCATTGGAGAGGTT

GGACGTAGGGACAAATCTGGGGAATGCAATTGCTAAGTTGGAGGATGCCAAGGA

ATTGTTGGAGTCATCGGACCAGATATTGAGGAGTATGAAAGGTTTATCGAGCAC

TAGCATAGTCTACATCCTGATTGCAGTGTGTCTTGGAGGGTTGATAGGGATCCCC

GCTTTAATATGTTGCTGCAGGGGGCGTTGTAACAAAAAGGGAGAACAAGTTGGT

ATGTCAAGACCAGGCCTAAAGCCTGATCTTACGGGAACATCAAAATCCTATGTA

AGGTCGCTCTGATCCTCTACAACTCTTGAAACACAAATGTCCCACAAGTCTCCTC

TTCGTCATCAAGCAACCACCGCACCCAGCATCAAGCCCACCTGAAATTATCTCCG

GCTTCCCTCTGGCCGAACAATATCGGTAGTTAATTAAAACTTAGGGTGCAAGATC

ATCGATAATGTCACCACAACGAGACCGGATAAATGCCTTCTACAAAGATAACCC

CCATCCCAAGGGAAGTAGGATAGTCATTAACAGAGAACATCTTATGATTGATAG

ACCTTATGTTTTGCTGGCTGTTCTGTTTGTCATGTTTCTGAGCTTGATCGGGTTGC

TAGCCATTGCAGGAATTCGACTTCATCGGGCAGCCATCTACACCGCAGAGATCC

ATAAAAGCCTCAGCACCAATCTAGATGTAACTAACTCAATCGAGCATCAGGTCA

AGGACGTGCTGACACCACTCTTCAAAATCATCGGTGATGAAGTGGGCCTGAGGA

CACCTCAGAGATTCACTGACCTAGTGAAATTAATCTCTGACAAGATTAAATTCCT

TAATCCGGATAGGGAGTACGACTTCAGAGATCTCACTTGGTGTATCAACCCGCCA

GAGAGAATCAAATTGGATTATGATCAATACTGTGCAGATGTGGCTGCTGAAGAG

CTCATGAATGCATTGGTGAACTCAACTCTACTGGAGACCAGAACAACCAATCAG

TTCCTAGCTGTCTCAAAGGGAAACTGCTCAGGGCCCACTACAATCAGAGGTCAA

TTCTCAAACATGTCGCTGTCCCTGTTAGACTTGTATTTAGGTCGAGGTTACAATGT

GTCATCTATAGTCACTATGACATCCCAGGGAATGTATGGGGAACTTACCTAGTG

GAAAAGCCTAATCTGAGCAGCAAAAGGTCAGAGTTGTCACAACTGAGCATGTAC

CGAGTGTTTGAAGTAGGTGTTATCAGAAATCCGGGTTTGGGGGCTCCGGTGTTCC

ATATGACAAACTATCTTGAGCAACCAGTCAGTAATGATCTCAGCAACTGTATGGT

GGCTTTGGGGGAGCTCAAACTCGCAGCCCTTTGTCACGGGGAAGATTCTATCACA

ATTCCCTATCAGGGATCAGGGAAAGGTGTCAGCTTCCAGCTCGTCAAGCTAGGT

GTCTGGAAATCCCCAACCGACATGCAATCCTGGGTCCCCTTATCAACGGATGATC

CAGTGATAGACAGGCTTTACCTCTCATCTCACAGAGGTGTTATCGCTGACAACCA

AGCAAAATGGGCTGTCCCGACAACACGAACAGATGACAAGTTGCGAATGGAGA

CATGCTTCCAACAGGCGTGTAAGGGTAAAATCCAAGCACTCTGCGAGAATCCCG

AGTGGGCACCATTGAAGGATAACAGGATTCCTTCATACGGGGTCTTGTCTGTTGA

TCTGAGTCTGACAGTTGAGCTTAAAATCAAAATTGCTTCGGGATTCGGGCCATTG
```

-continued

```
ATCACACACGGTTCAGGGATGGACCTATACAAATCCAACCACAACAATGTGTAT
TGGCTGACTATCCCGCCAATGAAGAACCTAGCCTTAGGTGTAATCAACACATTGG
AGTGGATACCGAGATTCAAGGTTAGTCCCTACCTCTTCACTGTCCCAATTAAGGA
AGCAGGCGAAGACTGCCATGCCCCAACATACCTACCTGCGGAGGTGGATGGTGA
TGTCAAACTCAGTTCCAATCTGGTGATTCTACCTGGTCAAGATCTCCAATATGTTT
TGGCAACCTACGATACTTCCAGGGTTGAACATGCTGTGGTTTATTACGTTTACAG
CCCAAGCCGCTCATTTTCTTACTTTTATCCTTTTAGGTTGCCTATAAAGGGGTCC
CCATCGAATTACAAGTGGAATGCTTCACATGGGACCAAAAACTCTGGTGCCGTC
ACTTCTGTGTGCTTGCGGACTCAGAATCTGGTGGACATATCACTCACTCTGGGAT
GGTGGGCATGGGAGTCAGCTGCACAGTCACCCGGGAAGATGGAACCAATCGCA
GATAGGGCTGCTAGTGAACCAATCACATGATGTCACCCAGACATCAGGCATACC
CACCATCCATCATTGTTATAAAAAACTTAGGAACCAGGTCCACACAGAGTGATA
CGCGTACGCCACCATGTTCGTGTTTCTGGTGCTGCTGCCTCTGGTGAGCTCCCAG
TGCGTGAACCTGACCACAAGGACCCAGCTGCCCCCTGCCTATACCAATTCCTTCA
CACGGGGCGTGTACTATCCCGACAAGGTGTTCCGGAGCAGCGTGCTGCACTCCA
CACAGGATCTGTTTCTGCCTTTCTTTTCTAACGTGACCTGGTTCCACGCCATCCAC
GTGAGCGGCACCAATGGCACAAAGCGGTTCGACAATCCAGTGCTGCCCTTTAAC
GATGGCGTGTACTTCGCCTCCACCGAGAAGTCTAACATCATCAGAGGCTGGATCT
TTGGCACCACACTGGACAGCAAGACACAGTCCCTGCTGATCGTGAACAATGCCA
CCAACGTGGTCATCAAGGTGTGCGAGTTCCAGTTTTGTAATGATCCATTCCTGGG
CGTGTACTATCACAAGAACAATAAGTCTTGGATGGAGAGCGAGTTTCGCGTGTA
TTCCTCTGCCAACAATTGCACATTTGAGTACGTGTCCCAGCCCTTCCTGATGGAC
CTGGAGGGCAAGCAGGGCAATTTCAAGAACCTGAGGGAGTTCGTGTTTAAGAAT
ATCGATGGCTACTTCAAAATCTACTCCAAGCACACCCCAATCAACCTGGTGCGCG
ACCTGCCACAGGGCTTCTCTGCCCTGGAGCCACTGGTGGATCTGCCCATCGGCAT
CAACATCACCCGGTTTCAGACACTGCTGGCCCTGCACAGAAGCTACCTGACACC
AGGCGACAGCTCCTCTGGATGGACCGCAGGAGCAGCAGCCTACTATGTGGGCTA
TCTGCAGCCCAGGACCTTCCTGCTGAAGTACAACGAGAATGGCACCATCACAGA
CGCCGTGGATTGCGCCCTGGATCCCCTGTCTGAGACCAAGTGTACACTGAAGAG
CTTTACCGTGGAGAAGGGCATCTATCAGACAAGCAATTTCAGGGTGCAGCCTAC
CGAGTCCATCGTGCGCTTTCCCAATATCACAAACCTGTGCCCTTTTGGCGAGGTG
TTCAACGCAACCCGCTTCGCCAGCGTGTACGCCTGGAATAGGAAGCGCATCTCC
AACTGCGTGGCCGACTATTCTGTGCTGTACAACAGCGCCTCCTTCTCTACCTTTA
AGTGCTATGGCGTGAGCCCCACAAAGCTGAATGACCTGTGCTTTACCAACGTGTA
CGCCGATTCCTTCGTGATCAGGGGCGACGAGGTGCGCCAGATCGCACCAGGACA
GACAGGCAAGATCGCAGACTACAATTATAAGCTGCCTGACGATTTCACCGGCTG
CGTGATCGCCTGGAACTCTAACAATCTGGATAGCAAAGTGGGCGGCAACTACAA
TTATCTGTACCGGCTGTTTAGAAAGTCTAATCTGAAGCCATTCGAGAGGGACATC
TCCACAGAAATCTACCAGGCCGGCTCTACCCCCTGCAATGGCGTGGAGGGCTTT
AACTGTTATTTCCCTCTGCAGAGCTACGGCTTCCAGCCAACAAACGGCGTGGGCT
ATCAGCCCTACCGCGTGGTGGTGCTGTCTTTTGAGCTGCTGCACGCACCTGCAAC
```

-continued

```
AGTGTGCGGACCAAAGAAGAGCACCAATCTGGTGAAGAACAAGTGCGTGAACTT

CAACTTCAACGGACTGACCGGAACAGGCGTGCTGACCGAGTCCAACAAGAAGTT

CCTGCCTTTTCAGCAGTTCGGCAGGGACATCGCAGATACCACAGACGCCGTGCG

CGACCCTCAGACCCTGGAGATCCTGGACATCACACCATGCTCCTTCGGCGGCGTG

TCTGTGATCACACCAGGCACCAATACAAGCAACCAGGTGGCCGTGCTGTATCAG

GACGTGAATTGTACCGAGGTGCCAGTGGCAATCCACGCAGATCAGCTGACCCCT

ACATGGCGGGTGTACTCTACCGGCAGCAACGTGTTCCAGACAAGAGCCGGATGC

CTGATCGGAGCAGAGCACGTGAACAATAGCTATGAGTGCGACATCCCTATCGGC

GCCGGCATCTGTGCCTCCTACCAGACCCAGACAAACTCCCCAAGGAGAGCACGG

TCTGTGGCCAGCCAGTCCATCATCGCCTATACCATGAGCCTGGGCGCCGAGAATT

CCGTGGCCTACTCCAACAATTCTATCGCCATCCCTACCAACTTCACAATCTCCGT

GACCACAGAGATCCTGCCAGTGAGCATGACCAAGACATCCGTGGACTGCACAAT

GTATATCTGTGGCGATTCCACCGAGTGCTCTAACCTGCTGCTGCAGTACGGCTCT

TTTTGTACCCAGCTGAATAGAGCCCTGACAGGCATCGCCGTGGAGCAGGACAAG

AACACACAGGAGGTGTTCGCCCAGGTGAAGCAAATCTACAAGACCCCACCCATC

AAGGACTTTGGCGGCTTCAACTTCAGCCAGATCCTGCCCGATCCTAGCAAGCCAT

CCAAGCGGTCTTTTATCGAGGACCTGCTGTTCAACAAGGTGACCCTGGCCGATGC

CGGCTTCATCAAGCAGTATGGCGATTGCCTGGGCGACATCGCCGCCAGAGACCT

GATCTGTGCCCAGAAGTTTAATGGCCTGACCGTGCTGCCTCCACTGCTGACAGAT

GAGATGATCGCCCAGTACACATCTGCCCTGCTGGCCGGAACCATCACAAGCGGA

TGGACCTTCGGCGCAGGAGCCGCCCTGCAGATCCCCTTTGCCATGCAGATGGCCT

ATCGGTTCAACGGCATCGGCGTGACCCAGAATGTGCTGTACGAGAACCAGAAGC

TGATCGCCAATCAGTTTAACTCCGCCATCGGCAAGATCCAGGACTCTCTGAGCTC

CACAGCCAGCGCCCTGGGCAAGCTGCAGGATGTGGTGAATCAGAACGCCCAGGC

CCTGAATACCCTGGTGAAGCAGCTGTCTAGCAACTTCGGCGCCATCTCCTCTGTG

CTGAATGACATCCTGAGCCGGCTGGACAAGGTGGAGGCAGAGGTGCAGATCGAC

CGGCTGATCACAGGCAGACTGCAGTCCCTGCAGACCTACGTGACACAGCAGCTG

ATCAGGGCAGCAGAGATCAGGGCCTCTGCCAATCTGGCCGCCACCAAGATGAGC

GAGTGCGTGCTGGGCCAGTCCAAGAGAGTGGACTTTTGTGGCAAGGGCTATCAC

CTGATGAGCTTCCCACAGTCCGCCCCTCACGGAGTGGTGTTTCTGCACGTGACCT

ACGTGCCAGCCCAGGAGAAGAACTTCACCACAGCACCAGCAATCTGCCACGATG

GCAAGGCACACTTTCCTAGGGAGGGCGTGTTCGTGAGCAACGGCACCCACTGGT

TTGTGACACAGCGCAATTTCTACGAGCCACAGATCATCACCACAGACAATACAT

TCGTGTCCGGCAACTGTGACGTGGTCATCGGCATCGTGAACAATACCGTGTATGA

TCCTCTGCAGCCAGAGCTGGACTCTTTTAAGGAGGAGCTGGATAAGTACTTCAAG

AATCACACCAGCCCCGACGTGGATCTGGGCGACATCTCTGGCATCAATGCCAGC

GTGGTGAACATCCAGAAGGAGATCGACAGGCTGAACGAGGTGGCCAAGAATCT

GAACGAGTCCCTGATCGATCTGCAGGAGCTGGGCAAGTATGAGCAGTACATCAA

GTGGCCCTGGTATATCTGGCTGGGCTTCATCGCCGGCCTGATCGCCATCGTGATG

GTGACCATCATGCTGTGCTGTATGACAAGCTGCTGTTCCTGCCTGAAGGGCTGCT
```

-continued

```
GTTCTTGTGGCAGCTGCTGTAAGTTTGATGAGGACGATAGCGAGCCTGTGCTGAA

GGGCGTGAAGCTGCACTACACCTGAGCTAGCGATCGCACTAGTGTGAAATAGAC

ATCAGAATTAAGAAAAACGTAGGGTCCAAGTGGTTCCCCGTTATGGACTCGCTA

TCTGTCAACCAGATCTTATACCCTGAAGTTCACCTAGATAGCCCGATAGTTACCA

ATAAGATAGTAGCCATCCTGGAGTATGCTCGAGTCCCTCACGCTTACAGCCTGGA

GGACCCTACACTGTGTCAGAACATCAAGCACCGCCTAAAAAACGGATTTTCCAA

CCAAATGATTATAAACAATGTGGAAGTTGGGAATGTCATCAAGTCCAAGCTTAG

GAGTTATCCGGCCCACTCTCATATTCCATATCCAAATTGTAATCAGGATTTATTTA

ACATAGAAGACAAAGAGTCAACGAGGAAGATCCGTGAACTCCTCAAAAAGGGG

AATTCGCTGTACTCCAAAGTCAGTGATAAGGTTTTCCAATGCTTAAGGGACACTA

ACTCACGGCTTGGCCTAGGCTCCGAATTGAGGGAGGACATCAAGGAGAAAGTTA

TTAACTTGGGAGTTTACATGCACAGCTCCCAGTGGTTTGAGCCCTTTCTGTTTTGG

TTTACAGTCAAGACTGAGATGAGGTCAGTGATTAAATCACAAACCCATACTTGCC

ATAGGAGGAGACACACACCTGTATTCTTCACTGGTAGTTCAGTTGAGTTGCTAAT

CTCTCGTGACCTTGTTGCTATAATCAGTAAAGAGTCTCAACATGTATATTACCTG

ACATTTGAACTGGTTTTGATGTATTGTGATGTCATAGAGGGGAGGTTAATGACAG

AGACCGCTATGACTATTGATGCTAGGTATACAGAGCTTCTAGGAAGAGTCAGAT

ACATGTGGAAACTGATAGATGGTTTCTTCCCTGCACTCGGGAATCCAACTTATCA

AATTGTAGCCATGCTGGAGCCTCTTTCACTTGCTTACCTGCAGCTGAGGGATATA

ACAGTAGAACTCAGAGGTGCTTTCCTTAACCACTGCTTTACTGAAATACATGATG

TTCTTGACCAAAACGGGTTTTCTGATGAAGGTACTTATCATGAGTTAACTGAAGC

TCTAGATTACATTTTCATAACTGATGACATACATCTGACAGGGGAGATTTTCTCA

TTTTTCAGAAGTTTCGGCCACCCCAGACTTGAAGCAGTAACGGCTGCTGAAAATG

TTAGGAAATACATGAATCAGCCTAAAGTCATTGTGTATGAGACTCTGATGAAAG

GTCATGCCATATTTTGTGGAATCATAATCAACGGCTATCGTGACAGGCACGGAG

GCAGTTGGCCACCGCTGACCCTCCCCCTGCATGCTGCAGACACAATCCGGAATG

CTCAAGCTTCAGGTGAAGGGTTAACACATGAGCAGTGCGTTGATAACTGGAAAT

CTTTTGCTGGAGTGAAATTTGGCTGCTTTATGCCTCTTAGCCTGGATAGTGATCTG

ACAATGTACCTAAAGGACAAGGCACTTGCTGCTCTCCAAAGGGAATGGGATTCA

GTTTACCCGAAAGAGTTCCTGCGTTACGACCCTCCCAAGGGAACCGGGTCACGG

AGGCTTGTAGATGTTTTCCTTAATGATTCGAGCTTTGACCCATATGATGTGATAA

TGTATGTTGTAAGTGGAGCTTACCTCCATGACCCTGAGTTCAACCTGTCTTACAG

CCTGAAAGAAAAGGAGATCAAGGAAACAGGTAGACTTTTTGCTAAAATGACTTA

CAAAATGAGGGCATGCCAAGTGATTGCTGAAAATCTAATCTCAAACGGGATTGG

CAAATATTTTAAGGACAATGGGATGGCCAAGGATGAGCACGATTTGACTAAGGC

ACTCCACACTCTAGCTGTCTCAGGAGTCCCCAAAGATCTCAAAGAAAGTCACAG

GGGGGGGCCAGTCTTAAAAACCTACTCCCGAAGCCCAGTCCACACAAGTACCAG

GAACGTGAGAGCAGCAAAAGGGTTTATAGGGTTCCCTCAAGTAATTCGGCAGGA

CCAAGACACTGATCATCCGGAGAATATGGAAGCTTACGAGACAGTCAGTGCATT

TATCACGACTGATCTCAAGAAGTACTGCCTTAATTGGAGATATGAGACCATCAGC

TTGTTTGCACAGAGGCTAAATGAGATTTACGGATTGCCCTCATTTTTCCAGTGGC
```

```
TGCATAAGAGGCTTGAGACCTCTGTCCTGTATGTAAGTGACCCTCATTGCCCCCC

CGACCTTGACGCCCATATCCCGTTATATAAAGTCCCCAATGATCAAATCTTCATT

AAGTACCCTATGGGAGGTATAGAAGGGTATTGTCAGAAGCTGTGGACCATCAGC

ACCATTCCCTATCTATACCTGGCTGCTTATGAGAGCGGAGTAAGGATTGCTTCGT

TAGTGCAAGGGGACAATCAGACCATAGCCGTAACAAAAAGGGTACCCAGCACA

TGGCCCTACAACCTTAAGAAACGGGAAGCTGCTAGAGTAACTAGAGATTACTTT

GTAATTCTTAGGCAAAGGCTACATGATATTGGCCATCACCTCAAGGCAAATGAG

ACAATTGTTTCATCACATTTTTTTGTCTATTCAAAAGGAATATATTATGATGGGCT

ACTTGTGTCCCAATCACTCAAGAGCATCGCAAGATGTGTATTCTGGTCAGAGACT

ATAGTTGATGAAACAAGGGCAGCATGCAGTAATATTGCTACAACAATGGCTAAA

AGCATCGAGAGAGGTTATGACCGTTACCTTGCATATTCCCTGAACGTCCTAAAAG

TGATACAGCAAATTCTGATCTCTCTTGGCTTCACAATCAATTCAACCATGACCCG

GGATGTAGTCATACCCCTCCTCACAAACAACGACCTCTTAATAAGGATGGCACT

GTTGCCCGCTCCTATTGGGGGATGAATTATCTGAATATGAGCAGGCTGTTTGTC

AGAAACATCGGTGATCCAGTAACATCATCAATTGCTGATCTCAAGAGAATGATT

CTCGCCTCACTAATGCCTGAAGAGACCCTCCATCAGGTAATGACACAACAACCG

GGGGACTCTTCATTCCTAGACTGGGCTAGCGACCCTTACTCAGCAAATCTTGTAT

GTGTCCAGAGCATCACTAGACTCCTCAAGAACATAACTGCAAGGTTTGTCCTGAT

CCATAGTCCAAACCCAATGTTAAAAGGATTATTCCATGATGACAGTAAAGAAGA

GGACGAGGGACTGGCGGCATTCCTCATGGACAGGCATATTATAGTACCTAGGGC

AGCTCATGAAATCCTGGATCATAGTGTCACAGGGGCAAGAGAGTCTATTGCAGG

CATGCTGGATACCACAAAAGGCTTGATTCGAGCCAGCATGAGGAAGGGGGGTTT

AACCTCTCGAGTGATAACCAGATTGTCCAATTATGACTATGAACAATTCAGAGCA

GGGATGGTGCTATTGACAGGAAGAAAGAGAAATGTCCTCATTGACAAAGAGTCA

TGTTCAGTGCAGCTGGCGAGAGCTCTAAGAAGCCATATGTGGGCGAGGCTAGCT

CGAGGACGGCCTATTTACGGCCTTGAGGTCCCTGATGTACTAGAATCTATGCGAG

GCCACCTTATTCGGCGTCATGAGACATGTGTCATCTGCGAGTGTGGATCAGTCAA

CTACGGATGGTTTTTTGTCCCCTCGGGTTGCCAACTGGATGATATTGACAAGGAA

ACATCATCCTTGAGAGTCCCATATATTGGTTCTACCACTGATGAGAGAACAGACA

TGAAGCTTGCCTTCGTAAGAGCCCCAAGTCGATCCTTGCGATCTGCTGTTAGAAT

AGCAACAGTGTACTCATGGGCTTACGGTGATGATGATAGCTCTTGGAACGAAGC

CTGGTTGTTGGCTAGGCAAAGGGCCAATGTGAGCCTGGAGGAGCTAAGGGTGAT

CACTCCCATCTCAACTTCGACTAATTTAGCGCATAGGTTGAGGGATCGTAGCACT

CAAGTGAAATACTCAGGTACATCCCTTGTCCGAGTGGCGAGGTATACCACAATCT

CCAACGACAATCTCTCATTTGTCATATCAGATAAGAAGGTTGATACTAACTTTAT

ATACCAACAAGGAATGCTTCTAGGGTTGGGTGTTTTAGAAACATTGTTTCGACTC

GAGAAAGATACCGGATCATCTAACACGGTATTACATCTTCACGTCGAAACAGAT

TGTTGCGTGATCCCGATGATAGATCATCCCAGGATACCCAGCTCCCGCAAGCTAG

AGCTGAGGGCAGAGCTATGTACCAACCCATTGATATATGATAATGCACCTTTAAT

TGACAGAGATGCAACAAGGCTATACACCCAGAGCCATAGGAGGCACCTTGTGGA
```

-continued

```
ATTTGTTACATGGTCCACACCCCAACTATATCACATTTTAGCTAAGTCCACAGCA

CTATCTATGATTGACCTGGTAACAAAATTTGAGAAGGACCATATGAATGAAATTT

CAGCTCTCATAGGGGATGACGATATCAATAGTTTCATAACTGAGTTTCTGCTCAT

AGAGCCAAGATTATTCACTATCTACTTGGGCCAGTGTGCGGCCATCAATTGGGCA

TTTGATGTACATTATCATAGACCATCAGGGAAATATCAGATGGGTGAGCTGTTGT

CATCGTTCCTTTCTAGAATGAGCAAAGGAGTGTTTAAGGTGCTTGTCAATGCTCT

AAGCCACCCAAAGATCTACAAGAAATTCTGGCATTGTGGTATTATAGAGCCTATC

CATGGTCCTTCACTTGATGCTCAAAACTTGCACACAACTGTGTGCAACATGGTTT

ACACATGCTATATGACCTACCTCGACCTGTTGTTGAATGAAGAGTTAGAAGAGTT

CACATTTCTCTTGTGTGAAAGCGACGAGGATGTAGTACCGGACAGATTCGACAA

CATCCAGGCAAAACACTTATGTGTTCTGGCAGATTTGTACTGTCAACCAGGGACC

TGCCCACCAATTCGAGGTCTAAGACCGGTAGAGAAATGTGCAGTTCTAACCGAC

CATATCAAGGCAGAGGCTATGTTATCTCCAGCAGGATCTTCGTGGAACATAAATC

CAATTATTGTAGACCATTACTCATGCTCCCTGACTTATCTCCGGCGAGGATCGAT

CAAACAGATAAGATTGAGAGTTGATCCAGGATTCATTTTCGACGCCCTCGCTGAG

GTAAATGTCAGTCAGCCAAAGATCGGCAGCAACAACATCTCAAATATGAGCATC

AAGGCTTTCAGACCCCCACACGATGATGTTGCAAAATTGCTCAAAGATATCAAC

ACAAGCAAGCACAATCTTCCCATTTCAGGGGGCAATCTCGCCAATTATGAAATC

CATGCTTTCCGCAGAATCGGGTTGAACTCATCTGCTTGCTACAAAGCTGTTGAGA

TATCAACATTAATTAGGAGATGCCTTGAGCCAGGGGAGGACGGCTTGTTCTTGG

GTGAGGGATCGGGTTCTATGTTGATCACTTATAAGGAGATACTTAAACTAAACA

AGTGCTTCTATAATAGTGGGGTTTCCGCCAATTCTAGATCTGGTCAAAGGGAATT

AGCACCCTATCCCTCCGAAGTTGGCCTTGTCGAACACAGAATGGGAGTAGGTAA

TATTGTCAAAGTGCTCTTTAACGGGAGGCCCGAAGTCACGTGGGTAGGCAGTGT

AGATTGCTTCAATTTCATAGTTAGTAATATCCCTACCTCTAGTGTGGGGTTTATCC

ATTCAGATATAGAGACCTTGCCTGACAAAGATACTATAGAGAAGCTAGAGGAAT

TGGCAGCCATCTTATCGATGGCTCTGCTCCTGGGCAAAATAGGATCAATACTGGT

GATTAAGCTTATGCCTTTCAGCGGGGATTTTGTTCAGGGATTTATAAGTTATGTA

GGGTCTCATTATAGAGAAGTGAACCTTGTATACCCTAGATACAGCAACTTCATAT

CTACTGAATCTTATTTGGTTATGACAGATCTCAAGGCTAACCGGCTAATGAATCC

TGAAAAGATTAAGCAGCAGATAATTGAATCATCTGTGAGGACTTCACCTGGACT

TATAGGTCACATCCTATCCATTAAGCAACTAAGCTGCATACAAGCAATTGTGGGA

GACGCAGTTAGTAGAGGTGATATCAATCCTACTCTGAAAAAACTTACACCTATA

GAGCAGGTGCTGATCAATTGCGGGTTGGCAATTAACGGACCTAAGCTGTGCAAA

GAATTGATCCACCATGATGTTGCCTCAGGGCAAGATGGATTGCTTAATTCTATAC

TCATCCTCTACAGGGAGTTGGCAAGATTCAAAGACAACCAAAGAAGTCAACAAG

GGATGTTCCACGCCTACCCCGTATTGGTAAGTAGCAGGCAACGAGAACTTATATC

TAGGATCACCCGCAAATTTTGGGGGCACATTCTTCTTTACTCCGGGAACAAAAAG

TTGATAAATAAGTTTATCCAGAATCTCAAGTCCGGCTATCTGATACTAGACTTAC

ACCAGAATATCTTCGTTAAGAATCTATCCAAGTCAGAGAAACAGATTATTATGAC

GGGGGGTTTGAAACGTGAGTGGGTTTTTAAGGTAACAGTCAAGGAGACCAAAGA
```

```
ATGGTATAAGTTAGTCGGATACAGTGCCCTGATTAAGGACTAATTGGTTGAACTC

CGGAACCCTAATCCTGCCCTAGGTGGTTAGGCATTATTTGCAATATATTAAAGAA

AACTTTGAAAATACGAAGTTTCTATTCCCAGCTTTGTCTGGTggccggcatAgtcccagcct cctcgctggcgctggctgggcaacattccgaggggaccgtccccAcggtaatggcgaatgggacgcggccgatccggctgctaa caaagcccgaaaggaagctgagttggctgctgGcGcTGgctgGgcaataactagcataacccctttggggcctctaaacgggtct tgagggg ttttttgctgaaaggaggaactatatccggatgcGGCCGCGCGCTTGGCGTAATCATGGTCATA

GCTGTTTCCTGTGTGAAATTGTTATCCGCTCACAATTCCACACAACATACGAGCC

GGAAGCATAAAGTGTAAAGCCTGGGGTGCCTAATGAGTGAGCTAACTCACATTA

ATTGCGTTGCGCTCACTGCCCGCTTTCCAGTCGGGAAACCTGTCGTGCCAGCTGC

ATTAATGAATCGGCCAACGCGCGGGGAGAGGCGGTTTGCGTATTGGGCGCTCTT

CCGCTTCCTCGCTCACTGACTCGCTGCGCTCGGTCGTTCGGCTGCGGCGAGCGGT

ATCAGCTCACTCAAAGGCGGTAATACGGTTATCCACAGAATCAGGGGATAACGC

AGGAAAGAACATGTGAGCAAAAGGCCAGCAAAAGGCCAGGAACCGTAAAAAGG

CCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGC

GTTTCCCCCTGGAAGCTCCCTCGTGCGCTCTCCTGTTCCGACCCTGCCGCTTACCG

GATACCTGTCCGCCTTTCTCCCTTCGGGAAGCGTGGCGCTTTCTCATAGCTCACG

CTGTAGGTATCTCAGTTCGGTGTAGGTCGTTCGCTCCAAGCTGGGCTGTGTGCAC

GAACCCCCCGTTCAGCCCGACCGCTGCGCCTTATCCGGTAACTATCGTCTTGAGT

CCAACCCGGTAAGACACGACTTATCGCCACTGGCAGCAGCCACTGGTAACAGGA

TTAGCAGAGCGAGGTATGTAGGCGGTGCTACAGAGTTCTTGAAGTGGTGGCCTA

ACTACGGCTACACTAGAAGGACAGTATTTGGTATCTGCGCTCTGCTGAAGCCAGT

TACCTTCGGAAAAAGAGTTGGTAGCTCTTGATCCGGCAAACAAACCACCGCTGG

TAGCGGTGGTTTTTTTGTTTGCAAGCAGCAGATTACGCGCAGAAAAAAAGGATCT

CAAGAAGATCCTTTGATCTTTTCTACGGGGTCTGACGCTCAGTGGAACGAAAACT

CACGTTAAGGGATTTTGGTCATGAGATTATCAAAAAGGATCTTCACCTAGATCCT

TTTAAATTAAAAATGAAGTTTTAAATCAATCTAAAGTATATATGAGTAAACTTGG

TCTGACAGTTACCAATGCTTAATCAGTGAGGCACCTATCTCAGCGATCTGTCTAT

TTCGTTCATCCATAGTTGCCTGACTCCCCGTCGTGTAGATAACTACGATACGGGA

GGGCTTACCATCTGGCCCCAGTGCTGCAATGATACCGCGAGACCCACGCTCACC

GGCTCCAGATTTATCAGCAATAAACCAGCCAGCCGGAAGGGCCGAGCGCAGAA

GTGGTCCTGCAACTTTATCCGCCTCCATCCAGTCTATTAATTGTTGCCGGGAAGC

TAGAGTAAGTAGTTCGCCAGTTAATAGTTTGCGCAACGTTGTTGCCATTGCTACA

GGCATCGTGGTGTCACGCTCGTCGTTTGGTATGGCTTCATTCAGCTCCGGTTCCC

AACGATCAAGGCGAGTTACATGATCCCCCATGTTGTGCAAAAAAGCGGTTAGCT

CCTTCGGTCCTCCGATCGTTGTCAGAAGTAAGTTGGCCGCAGTGTTATCACTCAT

GGTTATGGCAGCACTGCATAATTCTCTTACTGTCATGCCATCCGTAAGATGCTTTT

CTGTGACTGGTGAGTACTCAACCAAGTCATTCTGAGAATAGTGTATGCGGCGACC

GAGTTGCTCTTGCCCGGCGTCAATACGGGATAATACCGCGCCACATAGCAGAAC

TTTAAAAGTGCTCATCATTGGAAAACGTTCTTCGGGGCGAAAACTCTCAAGGATC
```

```
TTACCGCTGTTGAGATCCAGTTCGATGTAACCCACTCGTGCACCCAACTGATCTT

CAGCATCTTTTACTTTCACCAGCGTTTCTGGGTGAGCAAAAACAGGAAGGCAAA

ATGCCGCAAAAAAGGGAATAAGGGCGACACGGAAATGTTGAATACTCATACTCT

TCCTTTTTCAATATTATTGAAGCATTTATCAGGGTTATTGTCTCATGAGCGGATAC

ATATTTGAATGTATTTAGAAAAATAAACAAATAGGGGTTCCGCGCACATTTCCCC

GAAAAGTGCCACCTG.
```

In one embodiment, the nucleic acid comprises the sequence of SEQ ID NO: 6, shown below (RABV vector: Coravax V1-China (RABVG-E31)):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAaATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAcatgaaaaaaactaacacccctcccGTACGCCACCATGTTCGTGTTTCTGGTGCTGCT

GCCTCTGGTGAGCTCCCAGTGCGTGAACCTGACCACAAGGACCCAGCTGCCCCC

TGCCTATACCAATTCCTTCACACGGGGCGTGTACTATCCCGACAAGGTGTTCCGG

AGCAGCGTGCTGCACTCCACACAGGATCTGTTTCTGCCTTTCTTTTCTAACGTGAC

CTGGTTCCACGCCATCCACGTGAGCGGCACCAATGGCACAAAGCGGTTCGACAA
```

```
-continued
TCCAGTGCTGCCCTTTAACGATGGCGTGTACTTCGCCTCCACCGAGAAGTCTAAC

ATCATCAGAGGCTGGATCTTTGGCACCACACTGGACAGCAAGACACAGTCCCTG

CTGATCGTGAACAATGCCACCAACGTGGTCATCAAGGTGTGCGAGTTCCAGTTTT

GTAATGATCCATTCCTGGGCGTGTACTATCACAAGAACAATAAGTCTTGGATGGA

GAGCGAGTTTCGCGTGTATTCCTCTGCCAACAATTGCACATTTGAGTACGTGTCC

CAGCCCTTCCTGATGGACCTGGAGGGCAAGCAGGGCAATTTCAAGAACCTGAGG

GAGTTCGTGTTTAAGAATATCGATGGCTACTTCAAAATCTACTCCAAGCACACCC

CAATCAACCTGGTGCGCGACCTGCCACAGGGCTTCTCTGCCCTGGAGCCACTGGT

GGATCTGCCCATCGGCATCAACATCACCCGGTTTCAGACACTGCTGGCCCTGCAC

AGAAGCTACCTGACACCAGGCGACAGCTCCTCTGGATGGACCGCAGGAGCAGCA

GCCTACTATGTGGGCTATCTGCAGCCCAGGACCTTCCTGCTGAAGTACAACGAG

AATGGCACCATCACAGACGCCGTGGATTGCGCCCTGGATCCCCTGTCTGAGACC

AAGTGTACACTGAAGAGCTTTACCGTGGAGAAGGGCATCTATCAGACAAGCAAT

TTCAGGGTGCAGCCTACCGAGTCCATCGTGCGCTTTCCCAATATCACAAACCTGT

GCCCTTTTGGCGAGGTGTTCAACGCAACCCGCTTCGCCAGCGTGTACGCCTGGAA

TAGGAAGCGCATCTCCAACTGCGTGGCCGACTATTCTGTGCTGTACAACAGCGCC

TCCTTCTCTACCTTTAAGTGCTATGGCGTGAGCCCCACAAAGCTGAATGACCTGT

GCTTTACCAACGTGTACGCCGATTCCTTCGTGATCAGGGGCGACGAGGTGCGCC

AGATCGCACCAGGACAGACAGGCAAGATCGCAGACTACAATTATAAGCTGCCTG

ACGATTTCACCGGCTGCGTGATCGCCTGGAACTCTAACAATCTGGATAGCAAAGT

GGGCGGCAACTACAATTATCTGTACCGGCTGTTTAGAAAGTCTAATCTGAAGCCA

TTCGAGAGGGACATCTCCACAGAAATCTACCAGGCCGGCTCTACCCCCTGCAAT

GGCGTGGAgGGCTTTAACTGTTATTTCCCTCTGCAGAgCTACgGCTTCCAGCCAAC

AAACGGCGTGGGCTATCAGCCCTACCGCGTGGTGGTGCTGTCTTTTGAGCTGCTG

CACGCACcTGCAACAGTGTGCGGACCAAAGAAGAGCACCAATCTGGTGAAGAAC

AAGTGCGTGAACTTCAACTTCAACGGACTGACCGGAACAGGCGTGCTGACCGAG

TCCAACAAGAAGTTCCTGCCTTTTCAGCAGTTCGGCAGGGACATCGCAGATACC

ACAGACGCCGTGCGCGACCCTCAGACCCTGGAGATCCTGGACATCACACCATGC

TCCTTCGGCGGCGTGTCTGTGATCACACCAGGCACCAATACAAGCAACCAGGTG

GCCGTGCTGTATCAGGACGTGAATTGTACCGAGGTGCCAGTGGCAATCCACGCA

GATCAGCTGACCCCTACATGGCGGGTGTACTCTACCGGCAGCAACGTGTTCCAG

ACAAGAGCCGGATGCCTGATCGGAGCAGAGCACGTGAACAATAGCTATGAGTGC

GACATCCCTATCGGCGCCGGCATCTGTGCCTCCTACCAGACCCAGACAAACTCCC

CAAGGTCTGTGGGAGATGAGGCCGAAGACTTTGTGGAAGTCCACCTGCCTGATG

TGCATAACCAGGTGTCTGGCGTCGACCTGGGACTGCCAAATTGGGGCAAGTACG

TGCTGCTGAGTGCTGGAGCACTGACTGCCCTGATGCTGATCATTTTCCTGATGAC

CTGCTGTCGGCGCGTGAACAGAAGTGAGCCCACTCAGCACAATCTGCGAGGAAC

CGGGAGAGAAGTGTCAGTCACACCTCAGAGCGGGAAAATCATTAGTAGTTGGGA

ATCACATAAAAGCGGGGGCGAGACCAGGCTGTGAGCTAGCCATGAAAAAAACT

AACACCCCTCCTTTCGAACCATCCCAAACATGAGCAAGATCTTTGTCAATCCTAG

TGCTATTAGAGCCGGTCTGGCCGATCTTGAGATGGCTGAAGAAACTGTTGATCTG
```

```
ATCAATAGAAATATCGAAGACAATCAGGCTCATCTCCAAGGGGAACCCATAGAG

GTGGACAATCTCCCTGAGGATATGGGCGACTTCACCTGGATGATGGAAAATCG

CCCAACCATGGTGAGATAGCCAAGGTGGGAGAAGGCAAGTATCGAGAGGACTTT

CAGATGGATGAAGGAGAGGATCCTAGCTTCCTGTTCCAGTCATACCTGGAAAAT

GTTGGAGTCCAAATAGTCAGACAAATGAGGTCAGGAGAGAGATTTCTCAAGATA

TGGTCACAGACCGTAGAAGAGATTATATCCTATGTCGCGGTCAACTTTCCCAACC

CTCCAGGAAAGTCTTCAGAGGATAAATCAACCCAGACTACTGGCCGAGAGCTCA

AGAAGGAGACAACACCCACTCCTTCTCAGAGAGAAAGCCAATCATCGAAAGCCA

GGATGGCGGCTCAAATTGCTTCTGGCCCTCCAGCCCTTGAATGGTCGGCTACCAA

TGAAGAGGATGATCTATCAGTGGAGGCTGAGATCGCTCACCAGATTGCAGAAAG

TTTCTCCAAAAAATATAAGTTTCCCTCTCGATCCTCAGGGATACTCTTGTATAATT

TTGAGCAATTGAAAATGAACCTTGATGATATAGTTAAAGAGGCAAAAAATGTAC

CAGGTGTGACCCGTTTAGCCCATGACGGGTCCAAACTCCCCCTAAGATGTGTACT

GGGATGGGTCGCTTTGGCCAACTCTAAGAAATTCCAGTTGTTAGTCGAATCCGAC

AAGCTGAGTAAAATCATGCAAGATGACTTGAATCGCTATACATCTTGCTAACCG

AACCTCTCCCCTCAGTCCCTCTAGACAATAAAATCCGAGATGTCCCAAAGTCAAC

ATGAAAAAAACAGGCAACACCACTGATAAAATGAACCTCCTACGTAAGATAGTG

AAAAACCGCAGGGACGAGGACACTCAAAAATCCTCTCCCGCGTCAGCCCCTCTG

GATGACGATGACTTGTGGCTTCCACCCCCTGAATACGTCCCGCTGAAAGAACTTA

CAGGCAAGAAGAACATGAGGAACTTTTGTATCAACGGAAGGGTTAAAGTGTGTA

GCCCGAATGGTTACTCGTTCAGGATCCTGCGGCACATTCTGAAATCATTCGACGA

GATATATTCTGGGAATCATAGGATGATCGGGTTAGTCAAAGTGGTTATTGGACTG

GCTTTGTCAGGATCTCCAGTCCCTGAGGGCCTGAACTGGGTATACAAATTGAGGA

GAACCTTTATCTTCCAGTGGGCTGATTCCAGGGGCCCTCTTGAAGGGGAGGAGTT

GGAATACTCTCAGGAGATCACTTGGGATGATGATACTGAGTTCGTCGGATTGCA

AATAAGAGTGATTGCAAAACAGTGTCATATCCAGGGCAGAGTCTGGTGTATCAA

CATGAACCCGAGAGCATGTCAACTATGGTCTGACATGTCTCTTCAGACACAAAG

GTCCGAAGAGGACAAAGATTCCTCTCTGCTTCTAGAATAATCAGATTATATCCCG

CAAATTTATCACTTGTTTACCTCTGGAGGAGAGAACATATGGGCTCAACTCCAAC

CCTTGGGAGCAATATAACAAAAAACATGTTATGGTGCCATTAAACCGCTGCATTT

CATCAAAGTCAAGTTGATTACCTTTACATTTTGATCCTCTTGGATGTGAAAAAAA

CTATTAACATCCCTCAAAAGAccogggAAAGATGGTTCCTCAGGCTCTCCTGTTTG

TACCCCTTCTGGTTTTTCCATTGTGTTTTGGGAAATTCCCTATTTACACGATACCA

GACAAGCTTGGTCCCTGGAGTCCGATTGACATACATCACCTCAGCTGCCCAAAC

AATTTGGTAGTGGAGGACGAAGGATGCACCAACCTGTCAGGGTTCTCCTACATG

GAACTTAAAGTTGGATACATCTTAGCCATAAAAGTGAACGGGTTCACTTGCACA

GGCGTTGTGACGGAGGCTGAAACCTACACTAACTTCGTTGGTTATGTCACAACCA

CGTTCAAAAGAAAGCATTTCCGCCCAACACCAGATGCATGTAGAGCCGCGTACA

ACTGGAAGATGGCCGGTGACCCCAGATATGAAGAGTCTCTACACAATCCGTACC

CTGACTACCGCTGGCTTCGAACTGTAAAAACCACCAAGGAGTCTCTCGTTATCAT
```

-continued

```
ATCTCCAAGTGTGGCAGATTTGGACCCATATGACAGATCCCTTCACTCGAGGGTC

TTCCCTAGCGGGAAGTGCTCAGGAGTAGCGGTGTCTTCTACCTACTGCTCCACTA

ACCACGATTACACCATTTGGATGCCCGAGAATCCGAGACTAGGGATGTCTTGTG

ACATTTTTACCAATAGTAGAGGGAAGAGAGCATCCAAAGGGAGTGAGACTTGCG

GCTTTGTAGATGAAAGAGGCCTATATAAGTCTTTAAAAGGAGCATGCAAACTCA

AGTTATGTGGAGTTCTAGGACTTAGACTTATGGATGGAACATGGGTCTCGATGCA

AACATCAAATGAAACCAAATGGTGCCCTCCCGATAAGTTGGTGAACCTGCACGA

CTTTCGCTCAGACGAAATTGAGCACCTTGTTGTAGAGGAGTTGGTCAGGAAGAG

AGAGGAGTGTCTGGATGCACTAGAGTCCATCATGACAACCAAGTCAGTGAGTTT

CAGACGTCTCAGTCATTTAAGAAAACTTGTCCCTGGGTTTGGAAAAGCATATACC

ATATTCAACAAGACCTTGATGGAAGCCGATGCTCACTACAAGTCAGTCgagACTT

GGAATGAGATCCTCCCTTCAAAAGGGTGTTTAAGAGTTGGGGGGAGGTGTCATC

CTCATGTGAACGGGGTGTTTTTCAATGGTATAATATTAGGACCTGACGGCAATGT

CTTAATCCCAGAGATGCAATCATCCCTCCTCCAGCAACATATGGAGTTGTTGGAA

TCCTCGGTTATCCCCCTTGTGCACCCCCTGGCAGACCCGTCTACCGTTTTCAAGG

ACGGTGACGAGGCTGAGGATTTTGTTGAAGTTCACCTTCCCGATGTGCACAATCA

GGTCTCAGGAGTTGACTTGGGTCTCCCGAACTGGGGGAAGTATGTATTACTGAGT

GCAGGGGCCCTGACTGCCTTGATGTTGATAATTTTCCTGATGACATGTTGTAGAA

GAGTCAATCGATCAGAACCTACGCAACACAATCTCAGAGGGACAGGGAGGGAG

GTGTCAGTCACTCCCCAAAGCGGGAAGATCATATCTTCATGGGAATCACACAAG

AGTGGGGGTGAGACCAGACTGTAAttaattaaCGTCCTTTCAACGATCCAAGTCcatgaaa aaaactaacacccctcccgtacctagcTTATAAAGTGCTGGGTCATCTAAGCTTTTCAGTCGAGA

AAAAAACATTAGATCAGAAGAACAACTGGCAACACTTCTCAACCTGAGACTTAC

TTCAAGATGCTCGATCCTGGAGAGGTCTATGATGACCCTATTGACCCAATCGAGT

TAGAGGCTGAACCCAGAGGAACCCCCATTGTCCCCAACATCTTGAGGAACTCTG

ACTACAATCTCAACTCTCCTTTGATAGAAGATCCTGCTAGACTAATGTTAGAATG

GTTAAAAACAGGGAATAGACCTTATCGGATGACTCTAACAGACAATTGCTCCAG

GTCTTTCAGAGTTTTGAAAGATTATTTCAAGAAGGTAGATTTGGGTTCTCTCAAG

GTGGGCGGAATGGCTGCACAGTCAATGATTTCTCTCTGGTTATATGGTGCCCACT

CTGAATCCAACAGGAGCCGGAGATGTATAACAGACTTGGCCCATTTCTATTCCAA

GTCGTCCCCATAGAGAAGCTGTTGAATCTCACGCTAGGAAATAGAGGGCTGAG

AATCCCCCCAGAGGGAGTGTTAAGTTGCCTTGAGAGGGTTGATTATGATAATGC

ATTTGGAAGGTATCTTGCCAACACGTATTCCTCTTACTTGTTCTTCCATGTAATCA

CCTTATACATGAACGCCCTAGACTGGGATGAAGAAAAGACCATCCTAGCATTAT

GGAAAGATTTAACCTCAGTGGACATCGGAAGGACTTGGTAAAGTTCAAAGACC

AAATATGGGGACTGCTGATCGTGACAAAGGACTTTGTTTACTCCCAAAGTTCCAA

TTGTCTTTTTGACAGAAACTACACACTTATGCTAAAAGATCTTTTCTTGTCTCGCT

TCAACTCCTTAATGGTCTTGCTCTCTCCCCCAGAGCCCCGATACTCAGATGACTT

GATATCTCAACTATGCCAGCTGTACATTGCTGGGGATCAAGTCTTGTCTATGTGT

GGAAACTCCGGCTATGAAGTCATCAAAATATTGGAGCCATATGTCGTGAATAGT

TTAGTCCAGAGAGCAGAAAAGTTTAGGCCTCTCATTCATTCCTTGGGAGACTTTC
```

-continued

```
CTGTATTTATAAAAGACAAGGTAAGTCAACTTGAAGAGACGTTCGGTCCCTGTGC

AAGAAGGTTCTTTAGGGCTCTGGATCAATTCGACAACATACATGACTTGGTTTTT

GTGTTTGGCTGTTACAGGCATTGGGGGCACCCATATATAGATTATCGAAAGGGTC

TGTCAAAACTATATGATCAGGTTCACCTTAAAAAAATGATAGATAAGTCCTACCA

GGAGTGCTTAGCAAGCGACCTAGCCAGGAGGATCCTTAGATGGGGTTTTGATAA

GTACTCCAAGTGGTATCTGGATTCAAGATTCCTAGCCCGAGACCACCCCTTGACT

CCTTATATCAAAACCCAAACATGGCCACCCAAACATATTGTAGACTTGGTGGGG

GATACATGGCACAAGCTCCCGATCACGCAGATCTTTGAGATTCCTGAATCAATGG

ATCCGTCAGAAATATTGGATGACAAATCACATTCTTTCACCAGAACGAGACTAG

CTTCTTGGCTGTCAGAAAACCGAGGGGGGCCTGTTCCTAGCGAAAAAGTTATTAT

CACGGCCCTGTCTAAGCCGCCTGTCAATCCCCGAGAGTTTCTGAGGTCTATAGAC

CTCGGAGGATTGCCAGATGAAGACTTGATAATTGGCCTCAAGCCAAAGGAACGG

GAATTGAAGATTGAAGGTCGATTCTTTGCTCTAATGTCATGGAATCTAAGATTGT

ATTTTGTCATCACTGAAAAACTCTTGGCCAACTACATCTTGCCACTTTTTGACGCG

CTGACTATGACAGACAACCTGAACAAGGTGTTTAAAAAGCTGATCGACAGGGTC

ACCGGGCAAGGGCTTTTGGACTATTCAAGGGTCACATATGCATTTCACCTGGACT

ATGAAAAGTGGAACAACCATCAAAGATTAGAGTCAACAGAGGATGTATTTTCTG

TCCTAGATCAAGTGTTTGGATTGAAGAGAGTGTTTTCTAGAACACACGAGTTTTT

TCAAAAGGCCTGGATCTATTATTCAGACAGATCAGACCTCATCGGGTTACGGGA

GGATCAAATATACTGCTTAGATGCGTCCAACGGCCCAACCTGTTGGAATGGCCA

GGATGGCGGGCTAGAAGGCTTACGGCAGAAGGGCTGGAGTCTAGTCAGCTTATT

GATGATAGATAGAGAATCTCAAATCAGGAACACAAGAACCAAAATACTAGCTCA

AGGAGACAACCAGGTTTTATGTCCGACATACATGTTGTCGCCAGGGCTATCTCAA

GAGGGGCTCCTCTATGAATTGGAGAGAATATCAAGGAATGCACTTTCGATATAC

AGAGCCGTCGAGGAAGGGGCATCTAAGCTAGGGCTGATCATCAAGAAAGAAGA

GACCATGTGTAGTTATGACTTCCTCATCTATGGAAAAACCCCTTTGTTTAGAGGT

AACATATTGGTGCCTGAGTCCAAAAGATGGGCCAGAGTCTCTTGCGTCTCTAATG

ACCAAATAGTCAACCTCGCCAATATAATGTCGACAGTGTCCACCAATGCGCTAA

CAGTGGCACAACACTCTCAATCTTTGATCAAACCGATGAGGGATTTTCTGCTCAT

GTCAGTACAGGCAGTCTTTCACTACCTGCTATTTAGCCCAATCTTAAAGGGAAGA

GTTTACAAGATTCTGAGCGCTGAAGGGGAGAGCTTTCTCCTAGCCATGTCAAGG

ATAATCTATCTAGATCCTTCTTTGGGAGGGATATCTGGAATGTCCCTCGGAAGAT

TCCATATACGACAGTTCTCAGACCCTGTCTCTGAAGGGTTATCCTTCTGGAGAGA

GATCTGGTTAAGCTCCCAAGAGTCCTGGATTCACGCGTTGTGTCAAGAGGCTGGA

AACCCAGATCTTGGAGAGAACACTCGAGAGCTTCACTCGCCTTCTAGAAGAT

CCGACCACCTTAAATATCAGAGGAGGGGCCAGTCCTACCATTCTACTCAAGGAT

GCAATCAGAAAGGCTTTATATGACGAGGTGGACAAGGTGGAAAATTCAGAGTTT

CGAGAGGCAATCCTGTTGTCCAAGACCCATAGAGATAATTTTATACTCTTCTTAA

TATCTGTTGAGCCTCTGTTTCCTCGATTTCTCAGTGAGCTATTCAGTTCGTCTTTTT

TGGGAATCCCCGAGTCAATCATTGGATTGATACAAAACTCCCGAACGATAAGAA
```

-continued
```
GGCAGTTTAGAAAGAGTCTCTCAAAAACTTTAGAAGAATCCTTCTACAACTCAG

AGATCCACGGGATTAGTCGGATGACCCAGACACCTCAGAGGGTTGGGGGGGTGT

GGCCTTGCTCTTCAGAGAGGGCAGATCTACTTAGGGAGATCTCTTGGGGAAGAA

AAGTGGTAGGCACGACAGTTCCTCACCCTTCTGAGATGTTGGGATTACTTCCCAA

GTCCTCTATTTCTTGCACTTGTGGAGCAACAGGAGGAGGCAATCCTAGAGTTTCT

GTATCAGTACTCCCGTCCTTTGATCAGTCATTTTTTTCACGAGGCCCCCTAAAGG

GATACTTGGGCTCGTCCACCTCTATGTCGACCCAGCTATTCCATGCATGGGAAAA

AGTCACTAATGTTCATGTGGTGAAGAGAGCTCTATCGTTAAAAGAATCTATAAAC

TGGTTCATTACTAGAGATTCCAACTTGGCTCAAGCTCTAATTAGGAACATTATGT

CTCTGACAGGCCCTGATTTCCCTCTAGAGGAGGCCCCTGTCTTCAAAAGGACGGG

GTCAGCCTTGCATAGGTTCAAGTCTGCCAGATACAGCGAAGGAGGGTATTCTTCT

GTCTGCCCGAACCTCCTCTCTCATATTTCTGTTAGTACAGACACCATGTCTGATTT

GACCCAAGACGGGAAGAACTACGATTTCATGTTCCAGCCATTGATGCTTTATGCA

CAGACATGGACATCAGAGCTGGTACAGAGAGACACAAGGCTAAGAGACTCTAC

GTTTCATTGGCACCTCCGATGCAACAGGTGTGTGAGACCCATTGACGACGTGACC

CTGGAGACCTCTCAGATCTTCGAGTTTCCGGATGTGTCGAAAAGAATATCCAGAA

TGGTTTCTGGGGCTGTGCCTCACTTCCAGAGGCTTCCCGATATCCGTCTGAGACC

AGGAGATTTTGAATCTCTAAGCGGTAGAGAAAAGTCTCACCATATCGGATCAGC

TCAGGGGCTCTTATACTCAATCTTAGTGGCAATTCACGACTCAGGATACAATGAT

GGAACCATCTTCCCTGTCAACATATACGGCAAGGTTTCCCCTAGAGACTATTTGA

GAGGGCTCGCAAGGGGAGTATTGATAGGATCCTCGATTTGCTTCTTGACAAGAA

TGACAAATATCAATATTAATAGACCTCTTGAATTGGTCTCAGGGGTAATCTCATA

TATTCTCCTGAGGCTAGATAACCATCCCTCCTTGTACATAATGCTCAGAGAACCG

TCTCTTAGAGGAGAGATATTTTCTATCCCTCAGAAAATCCCCGCCGCTTATCCAA

CCACTATGAAAGAAGGCAACAGATCAATCTTGTGTTATCTCCAACATGTGCTACG

CTATGAGCGAGAGATAATCACGGCGTCTCCAGAGAATGACTGGCTATGGATCTT

TTCAGACTTTAGAAGTGCCAAAATGACGTACCTATCCCTCATTACTTACCAGTCT

CATCTTCTACTCCAGAGGGTTGAGAGAAACCTATCTAAGAGTATGAGAGATAAC

CTGCGACAATTGAGTTCTTTGATGAGGCAGGTGCTGGGCGGGCACGGAGAAGAT

ACCTTAGAGTCAGACGACAACATTCAACGACTGCTAAAAGACTCTTTACGAAGG

ACAAGATGGGTGGATCAAGAGGTGCGCCATGCAGCTAGAACCATGACTGGAGAT

TACAGCCCCAACAAGAAGGTGTCCCGTAAGGTAGGATGTTCAGAATGGGTCTGC

TCTGCTCAACAGGTTGCAGTCTCTACCTCAGCAAACCCGGCCCCTGTCTCGGAGC

TTGACATAAGGGCCCTCTCTAAGAGGTTCCAGAACCCTTTGATCTCGGGCTTGAG

AGTGGTTCAGTGGGCAACCGGTGCTCATTATAAGCTTAAGCCTATTCTAGATGAT

CTCAATGTTTTCCCATCTCTCTGCCTTGTAGTTGGGGACGGGTCAGGGGGATAT

CAAGGGCAGTCCTCAACATGTTTCCAGATGCCAAGCTTGTGTTCAACAGTCTTTT

AGAGGTGAATGACCTGATGGCTTCCGGAACACATCCACTGCCTCCTTCAGCAATC

ATGAGGGGAGGAAATGATATCGTCTCCAGAGTGATAGATCTTGACTCAATCTGG

GAAAAACCGTCCGACTTGAGAAACTTGGCAACCTGGAAATACTTCCAGTCAGTC

CAAAAGCAGGTCAACATGTCCTATGACCTCATTATTTGCGATGCAGAAGTTACTG
```

-continued

```
ACATTGCATCTATCAACCGGATCACCCTGTTAATGTCCGATTTTGCATTGTCTATA

GATGGACCACTCTATTTGGTCTTCAAAACTTATGGGACTATGCTAGTAAATCCAA

ACTACAAGGCTATTCAACACCTGTCAAGAGCGTTCCCCTCGGTCACAGGGTTTAT

CACCCAAGTAACTTCGTCTTTTTCATCTGAGCTCTACCTCCGATTCTCCAAACGA

GGGAAGTTTTTCAGAGATGCTGAGTACTTGACCTCTTCCACCCTTCGAGAAATGA

GCCTTGTGTTATTCAATTGTAGCAGCCCCAAGAGTGAGATGCAGAGAGCTCGTTC

CTTGAACTATCAGGATCTTGTGAGAGGATTTCCTGAAGAAATCATATCAAATCCT

TACAATGAGATGATCATAACTCTGATTGACAGTGATGTAGAATCTTTTCTAGTCC

ACAAGATGGTTGATGATCTTGAGTTACAGAGGGGAACTCTGTCTAAAGTGGCTA

TCATTATAGCCATCATGATAGTTTTCTCCAACAGAGTCTTCAACGTTTCCAAACC

CCTAACTGACCCCTCGTTCTATCCACCGTCTGATCCCAAAATCCTGAGGCACTTC

AACATATGTTGCAGTACTATGATGTATCTATCTACTGCTTTAGGTGACGTCCCTA

GCTTCGCAAGACTTCACGACCTGTATAACAGACCTATAACTTATTACTTCAGAAA

GCAAGTCATTCGAGGGAACGTTTATCTATCTTGGAGTTGGTCCAACGACACCTCA

GTGTTCAAAAGGGTAGCCTGTAATTCTAGCCTGAGTCTGTCATCTCACTGGATCA

GGTTGATTTACAAGATAGTGAAGACTACCAGACTCGTTGGCAGCATCAAGGATC

TATCCAGAGAAGTGGAAAGACACCTTCATAGGTACAACAGGTGGATCACCCTAG

AGGATATCAGATCTAGATCATCCCTACTAGACTACAGTTGCCTGTGAACCGGATA

CTCCTGGAAGCCTGCCCATGCTAAGACTCTTGTGTGATGTATCTTGAAAAAAACA

AGATCCTAAATCTGAACCTTTGGTTGTTTGATTGTTTTTCTCAttttttgttgtttatttgttaagcgt.
```

In another embodiment, the nucleic acid comprises the sequence of SEQ ID NO: 7, shown below (RABV vector: Coravax V1-South Africa (RABVG-E31)):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAaATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT
```

-continued

```
CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAcatgaaaaaaactaacacccctcccGTACGCCACCATGTTCGTGTTTCTGGTGCTGCT

GCCTCTGGTGAGCTCCCAGTGCGTGAACTTCACCACAAGGACCCAGCTGCCCCCT

GCCTATACCAATTCCTTCACACGGGGCGTGTACTATCCCGACAAGGTGTTCCGGA

GCAGCGTGCTGCACTCCACACAGGATCTGTTTCTGCCTTTCTTTTCTAACGTGACC

TGGTTCCACGCCATCCACGTGAGCGGCACCAATGGCACAAAGCGGTTCGCCAAT

CCAGTGCTGCCCTTTAACGATGGCGTGTACTTCGCCTCCACCGAGAAGTCTAACA

TCATCAGAGGCTGGATCTTTGGCACCACACTGGACAGCAAGACACAGTCCCTGC

TGATCGTGAACAATGCCACCAACGTGGTCATCAAGGTGTGCGAGTTCCAGTTTTG

TAATGATCCATTCCTGGGCGTGTACTATCACAAGAACAATAAGTCTTGGATGGAG

AGCGAGTTTCGCGTGTATTCCTCTGCCAACAATTGCACATTTGAGTACGTGTCCC

AGCCCTTCCTGATGGACCTGGAGGGCAAGCAGGGCAATTTCAAGAACCTGAGGG

AGTTCGTGTTTAAGAATATCGATGGCTACTTCAAAATCTACTCCAAGCACACCCC

AATCAACCTGGTGCGCGGCCTGCCACAGGGCTTCTCTGCCCTGGAGCCACTGGTG

GATCTGCCCATCGGCATCAACATCACCCGGTTTCAGACACTGCTGGCCCTGCACA

GAAGCTACCTGACACCAGGCGACAGCTCCTCTGGATGGACCGCAGGAGCAGCAG

CCTACTATGTGGGCTATCTGCAGCCCAGGACCTTCCTGCTGAAGTACAACGAGA

ATGGCACCATCACAGACGCCGTGGATTGCGCCCTGGATCCCCTGTCTGAGACCA

AGTGTACACTGAAGAGCTTTACCGTGGAGAAGGGCATCTATCAGACAAGCAATT

TCAGGGTGCAGCCTACCGAGTCCATCGTGCGCTTTCCCAATATCACAAACCTGTG

CCCTTTTGGCGAGGTGTTCAACGCAACCCGCTTCGCCAGCGTGTACGCCTGGAAT

AGGAAGCGCATCTCCAACTGCGTGGCCGACTATTCTGTGCTGTACAACAGCGCCT

CCTTCTCTACCTTTAAGTGCTATGGCGTGAGCCCCACAAAGCTGAATGACCTGTG

CTTTACCAACGTGTACGCCGATTCCTTCGTGATCAGGGGCGACGAGGTGCGCCA

GATCGCACCAGGACAGACAGGCAATATCGCAGACTACAATTATAAGCTGCCTGA

CGATTTCACCGGCTGCGTGATCGCCTGGAACTCTAACAATCTGGATAGCAAAGTG

GGCGGCAACTACAATTATCTGTACCGGCTGTTTAGAAAGTCTAATCTGAAGCCAT

TCGAGAGGGACATCTCCACAGAAATCTACCAGGCCGGCTCTACCCCCTGCAATG

GCGTGAAGGGCTTTAACTGTTATTTCCCTCTGCAGAGCTACGGCTTCCAGCCAAC

ATATGGCGTGGGCTATCAGCCCTACCGCGTGGTGGTGCTGTCTTTTGAGCTGCTG

CACGCACCTGCAACAGTGTGCGGACCAAAGAAGAGCACCAATCTGGTGAAGAA

CAAGTGCGTGAACTTCAACTTCAACGGACTGACCGGAACAGGCGTGCTGACCGA
```

-continued

```
GTCCAACAAGAAGTTCCTGCCTTTTCAGCAGTTCGGCAGGGACATCGCAGATAC

CACAGACGCCGTGCGCGACCCTCAGACCCTGGAGATCCTGGACATCACACCATG

CTCCTTCGGCGGCGTGTCTGTGATCACACCAGGCACCAATACAAGCAACCAGGT

GGCCGTGCTGTATCAGGGCGTGAATTGTACCGAGGTGCCAGTGGCAATCCACGC

AGATCAGCTGACCCCTACATGGCGGGTGTACTCTACCGGCAGCAACGTGTTCCA

GACAAGAGCCGGATGCCTGATCGGAGCAGAGCACGTGAACAATAGCTATGAGTG

CGACATCCCTATCGGCGCCGGCATCTGTGCCTCCTACCAGACCCAGACAAACTCC

CCaagGTCTGTGGGAGATGAGGCCGAAGACTTTGTGGAAGTCCACCTGCCTGATG

TGCATAACCAGGTGTCTGGCGTCGACCTGGGACTGCCAAATTGGGGCAAGTACG

TGCTGCTGAGTGCTGGAGCACTGACTGCCCTGATGCTGATCATTTTCCTGATGAC

CTGCTGTCGGCGCGTGAACAGAAGTGAGCCCACTCAGCACAATCTGCGAGGAAC

CGGGAGAGAAGTGTCAGTCACACCTCAGAGCGGGAAAATCATTAGTAGTTGGGA

ATCACATAAAAGCGGGGGCGAGACCAGGCTGTGAGCTAGCCATGAAAAAAACT

AACACCCCTCCTTTCGAACCATCCCAAACATGAGCAAGATCTTTGTCAATCCTAG

TGCTATTAGAGCCGGTCTGGCCGATCTTGAGATGGCTGAAGAAACTGTTGATCTG

ATCAATAGAAATATCGAAGACAATCAGGCTCATCTCCAAGGGGAACCCATAGAG

GTGGACAATCTCCCTGAGGATATGGGCGACTTCACCTGGATGATGGAAAATCG

CCCAACCATGGTGAGATAGCCAAGGTGGGAGAAGGCAAGTATCGAGAGGACTTT

CAGATGGATGAAGGAGAGGATCCTAGCTTCCTGTTCCAGTCATACCTGGAAAAT

GTTGGAGTCCAAATAGTCAGACAAATGAGGTCAGGAGAGAGATTTCTCAAGATA

TGGTCACAGACCGTAGAAGAGATTATATCCTATGTCGCGGTCAACTTTCCCAACC

CTCCAGGAAAGTCTTCAGAGGATAAATCAACCCAGACTACTGGCCGAGAGCTCA

AGAAGGAGACAACACCCACTCCTTCTCAGAGAGAAAGCCAATCATCGAAAGCCA

GGATGGCGGCTCAAATTGCTTCTGGCCCTCCAGCCCTTGAATGGTCGGCTACCAA

TGAAGAGGATGATCTATCAGTGGAGGCTGAGATCGCTCACCAGATTGCAGAAAG

TTTCTCCAAAAAATATAAGTTTCCCTCTCGATCCTCAGGGATACTCTTGTATAATT

TTGAGCAATTGAAAATGAACCTTGATGATATAGTTAAAGAGGCAAAAAATGTAC

CAGGTGTGACCCGTTTAGCCCATGACGGGTCCAAACTCCCCCTAAGATGTGTACT

GGGATGGGTCGCTTTGGCCAACTCTAAGAAATTCCAGTTGTTAGTCGAATCCGAC

AAGCTGAGTAAAATCATGCAAGATGACTTGAATCGCTATACATCTTGCTAACCG

AACCTCTCCCCTCAGTCCCTCTAGACAATAAAATCCGAGATGTCCCAAAGTCAAC

ATGAAAAAAACAGGCAACACCACTGATAAAATGAACCTCCTACGTAAGATAGTG

AAAAACCGCAGGGACGAGGACACTCAAAAATCCTCTCCCGCGTCAGCCCCTCTG

GATGACGATGACTTGTGGCTTCCACCCCCTGAATACGTCCCGCTGAAAGAACTTA

CAGGCAAGAAGAACATGAGGAACTTTTGTATCAACGGAAGGGTTAAAGTGTGTA

GCCCGAATGGTTACTCGTTCAGGATCCTGCGGCACATTCTGAAATCATTCGACGA

GATATATTCTGGGAATCATAGGATGATCGGGTTAGTCAAAGTGGTTATTGGACTG

GCTTTGTCAGGATCTCCAGTCCCTGAGGGCCTGAACTGGGTATACAAATTGAGGA

GAACCTTTATCTTCCAGTGGGCTGATTCCAGGGGCCCTCTTGAAGGGGAGGAGTT

GGAATACTCTCAGGAGATCACTTGGGATGATGATACTGAGTTCGTCGGATTGCA

AATAAGAGTGATTGCAAAACAGTGTCATATCCAGGGCAGAGTCTGGTGTATCAA
```

-continued

```
CATGAACCCGAGAGCATGTCAACTATGGTCTGACATGTCTCTTCAGACACAAAG

GTCCGAAGAGGACAAAGATTCCTCTCTGCTTCTAGAATAATCAGATTATATCCCG

CAAATTTATCACTTGTTTACCTCTGGAGGAGAGAACATATGGGCTCAACTCCAAC

CCTTGGGAGCAATATAACAAAAAACATGTTATGGTGCCATTAAACCGCTGCATTT

CATCAAAGTCAAGTTGATTACCTTTACATTTTGATCCTCTTGGATGTGAAAAAAA

CTATTAACATCCCTCAAAAGAcccgggAAAGATGGTTCCTCAGGCTCTCCTGTTTG

TACCCCTTCTGGTTTTTCCATTGTGTTTTGGGAAATTCCCTATTTACACGATACCA

GACAAGCTTGGTCCCTGGAGTCCGATTGACATACATCACCTCAGCTGCCCAAAC

AATTTGGTAGTGGAGGACGAAGGATGCACCAACCTGTCAGGGTTCTCCTACATG

GAACTTAAAGTTGGATACATCTTAGCCATAAAAGTGAACGGGTTCACTTGCACA

GGCGTTGTGACGGAGGCTGAAACCTACACTAACTTCGTTGGTTATGTCACAACCA

CGTTCAAAAGAAAGCATTTCCGCCCAACACCAGATGCATGTAGAGCCGCGTACA

ACTGGAAGATGGCCGGTGACCCCAGATATGAAGAGTCTCTACACAATCCGTACC

CTGACTACCGCTGGCTTCGAACTGTAAAAACCACCAAGGAGTCTCTCGTTATCAT

ATCTCCAAGTGTGGCAGATTTGGACCCATATGACAGATCCCTTCACTCGAGGGTC

TTCCCTAGCGGGAAGTGCTCAGGAGTAGCGGTGTCTTCTACCTACTGCTCCACTA

ACCACGATTACACCATTTGGATGCCCGAGAATCCGAGACTAGGGATGTCTTGTG

ACATTTTTACCAATAGTAGAGGGAAGAGAGCATCCAAAGGGAGTGAGACTTGCG

GCTTTGTAGATGAAAGAGGCCTATATAAGTCTTTAAAAGGAGCATGCAAACTCA

AGTTATGTGGAGTTCTAGGACTTAGACTTATGGATGGAACATGGGTCTCGATGCA

AACATCAAATGAAACCAAATGGTGCCCTCCCGATAAGTTGGTGAACCTGCACGA

CTTTCGCTCAGACGAAATTGAGCACCTTGTTGTAGAGGAGTTGGTCAGGAAGAG

AGAGGAGTGTCTGGATGCACTAGAGTCCATCATGACAACCAAGTCAGTGAGTTT

CAGACGTCTCAGTCATTTAAGAAAACTTGTCCCTGGGTTTGGAAAAGCATATACC

ATATTCAACAAGACCTTGATGGAAGCCGATGCTCACTACAAGTCAGTCgagACTT

GGAATGAGATCCTCCCTTCAAAAGGGTGTTTAAGAGTTGGGGGGAGGTGTCATC

CTCATGTGAACGGGGTGTTTTTCAATGGTATAATATTAGGACCTGACGGCAATGT

CTTAATCCCAGAGATGCAATCATCCCTCCTCCAGCAACATATGGAGTTGTTGGAA

TCCTCGGTTATCCCCCTTGTGCACCCCCTGGCAGACCCGTCTACCGTTTTCAAGG

ACGGTGACGAGGCTGAGGATTTTGTTGAAGTTCACCTTCCCGATGTGCACAATCA

GGTCTCAGGAGTTGACTTGGGTCTCCCGAACTGGGGGAAGTATGTATTACTGAGT

GCAGGGGCCCTGACTGCCTTGATGTTGATAATTTTCCTGATGACATGTTGTAGAA

GAGTCAATCGATCAGAACCTACGCAACACAATCTCAGAGGGACAGGGAGGGAG

GTGTCAGTCACTCCCCAAAGCGGGAAGATCATATCTTCATGGGAATCACACAAG

AGTGGGGGTGAGACCAGACTGTAAttaattaaCGTCCTTTCAACGATCCAAGTCcatgaaa aaaactaacaccccctcccgtacctagcTTATAAAGTGCTGGGTCATCTAAGCTTTTCAGTCGAGA

AAAAAACATTAGATCAGAAGAACAACTGGCAACACTTCTCAACCTGAGACTTAC

TTCAAGATGCTCGATCCTGGAGAGGTCTATGATGACCCTATTGACCCAATCGAGT

TAGAGGCTGAACCCAGAGGAACCCCCATTGTCCCCAACATCTTGAGGAACTCTG

ACTACAATCTCAACTCTCCTTTGATAGAAGATCCTGCTAGACTAATGTTAGAATG
```

-continued

```
GTTAAAAACAGGGAATAGACCTTATCGGATGACTCTAACAGACAATTGCTCCAG

GTCTTTCAGAGTTTTGAAAGATTATTTCAAGAAGGTAGATTTGGGTTCTCTCAAG

GTGGGCGGAATGGCTGCACAGTCAATGATTTCTCTCTGGTTATATGGTGCCCACT

CTGAATCCAACAGGAGCCGGAGATGTATAACAGACTTGGCCCATTTCTATTCCAA

GTCGTCCCCATAGAGAAGCTGTTGAATCTCACGCTAGGAAATAGAGGGCTGAG

AATCCCCCAGAGGGAGTGTTAAGTTGCCTTGAGAGGGTTGATTATGATAATGC

ATTTGGAAGGTATCTTGCCAACACGTATTCCTCTTACTTGTTCTTCCATGTAATCA

CCTTATACATGAACGCCCTAGACTGGGATGAAGAAAAGACCATCCTAGCATTAT

GGAAAGATTTAACCTCAGTGGACATCGGGAAGGACTTGGTAAAGTTCAAAGACC

AAATATGGGACTGCTGATCGTGACAAAGGACTTTGTTTACTCCCAAAGTTCCAA

TTGTCTTTTTGACAGAAACTACACACTTATGCTAAAAGATCTTTTCTTGTCTCGCT

TCAACTCCTTAATGGTCTTGCTCTCTCCCCCAGAGCCCCGATACTCAGATGACTT

GATATCTCAACTATGCCAGCTGTACATTGCTGGGGATCAAGTCTTGTCTATGTGT

GGAAACTCCGGCTATGAAGTCATCAAAATATTGGAGCCATATGTCGTGAATAGT

TTAGTCCAGAGAGCAGAAAAGTTTAGGCCTCTCATTCATTCCTTGGGAGACTTTC

CTGTATTTATAAAGACAAGGTAAGTCAACTTGAAGAGACGTTCGGTCCCTGTGC

AAGAAGGTTCTTTAGGGCTCTGGATCAATTCGACAACATACATGACTTGGTTTTT

GTGTTTGGCTGTTACAGGCATTGGGGGCACCCATATATAGATTATCGAAAGGGTC

TGTCAAAACTATATGATCAGGTTCACCTTAAAAAAATGATAGATAAGTCCTACCA

GGAGTGCTTAGCAAGCGACCTAGCCAGGAGGATCCTTAGATGGGGTTTTGATAA

GTACTCCAAGTGGTATCTGGATTCAAGATTCCTAGCCCGAGACCACCCCTTGACT

CCTTATATCAAAACCCAAACATGGCCACCCAAACATATTGTAGACTTGGTGGGG

GATACATGGCACAAGCTCCCGATCACGCAGATCTTTGAGATTCCTGAATCAATGG

ATCCGTCAGAAATATTGGATGACAAATCACATTCTTTCACCAGAACGAGACTAG

CTTCTTGGCTGTCAGAAAACCGAGGGGGGCCTGTTCCTAGCGAAAAAGTTATTAT

CACGGCCCTGTCTAAGCCGCCTGTCAATCCCCGAGAGTTTCTGAGGTCTATAGAC

CTCGGAGGATTGCCAGATGAAGACTTGATAATTGGCCTCAAGCCAAAGGAACGG

GAATTGAAGATTGAAGGTCGATTCTTTGCTCTAATGTCATGGAATCTAAGATTGT

ATTTTGTCATCACTGAAAAACTCTTGGCCAACTACATCTTGCCACTTTTTGACGCG

CTGACTATGACAGACAACCTGAACAAGGTGTTTAAAAAGCTGATCGACAGGGTC

ACCGGGCAAGGGCTTTTGGACTATTCAAGGGTCACATATGCATTTCACCTGGACT

ATGAAAAGTGGAACAACCATCAAAGATTAGAGTCAACAGAGGATGTATTTTCTG

TCCTAGATCAAGTGTTTGGATTGAAGAGAGTGTTTTCTAGAACACACGAGTTTTT

TCAAAAGGCCTGGATCTATTATTCAGACAGATCAGACCTCATCGGGTTACGGGA

GGATCAAATATACTGCTTAGATGCGTCCAACGGCCCAACCTGTTGGAATGGCCA

GGATGGCGGGCTAGAAGGCTTACGGCAGAAGGGCTGGAGTCTAGTCAGCTTATT

GATGATAGATAGAGAATCTCAAATCAGGAACACAAGAACCAAAATACTAGCTCA

AGGAGACAACCAGGTTTTATGTCCGACATACATGTTGTCGCCAGGGCTATCTCAA

GAGGGGCTCCTCTATGAATTGGAGAGAATATCAAGGAATGCACTTTCGATATAC

AGAGCCGTCGAGGAAGGGGCATCTAAGCTAGGGCTGATCATCAAGAAAGAAGA

GACCATGTGTAGTTATGACTTCCTCATCTATGGAAAAACCCCTTTGTTTAGAGGT
```

```
AACATATTGGTGCCTGAGTCCAAAAGATGGGCCAGAGTCTCTTGCGTCTCTAATG

ACCAAATAGTCAACCTCGCCAATATAATGTCGACAGTGTCCACCAATGCGCTAA

CAGTGGCACAACACTCTCAATCTTTGATCAAACCGATGAGGGATTTTCTGCTCAT

GTCAGTACAGGCAGTCTTTCACTACCTGCTATTTAGCCCAATCTTAAAGGGAAGA

GTTTACAAGATTCTGAGCGCTGAAGGGGAGAGCTTTCTCCTAGCCATGTCAAGG

ATAATCTATCTAGATCCTTCTTTGGGAGGGATATCTGGAATGTCCCTCGGAAGAT

TCCATATACGACAGTTCTCAGACCCTGTCTCTGAAGGGTTATCCTTCTGGAGAGA

GATCTGGTTAAGCTCCCAAGAGTCCTGGATTCACGCGTTGTGTCAAGAGGCTGGA

AACCCAGATCTTGGAGAGAGAACACTCGAGAGCTTCACTCGCCTTCTAGAAGAT

CCGACCACCTTAAATATCAGAGGAGGGGCCAGTCCTACCATTCTACTCAAGGAT

GCAATCAGAAAGGCTTTATATGACGAGGTGGACAAGGTGGAAAATTCAGAGTTT

CGAGAGGCAATCCTGTTGTCCAAGACCCATAGAGATAATTTTATACTCTTCTTAA

TATCTGTTGAGCCTCTGTTTCCTCGATTTCTCAGTGAGCTATTCAGTTCGTCTTTTT

TGGGAATCCCCGAGTCAATCATTGGATTGATACAAAACTCCCGAACGATAAGAA

GGCAGTTTAGAAAGAGTCTCTCAAAAACTTTAGAAGAATCCTTCTACAACTCAG

AGATCCACGGGATTAGTCGGATGACCCAGACACCTCAGAGGGTTGGGGGGGTGT

GGCCTTGCTCTTCAGAGAGGGCAGATCTACTTAGGGAGATCTCTTGGGGAAGAA

AAGTGGTAGGCACGACAGTTCCTCACCCTTCTGAGATGTTGGGATTACTTCCCAA

GTCCTCTATTTCTTGCACTTGTGGAGCAACAGGAGGAGGCAATCCTAGAGTTTCT

GTATCAGTACTCCCGTCCTTTGATCAGTCATTTTTTTCACGAGGCCCCCTAAAGG

GATACTTGGGCTCGTCCACCTCTATGTCGACCCAGCTATTCCATGCATGGGAAAA

AGTCACTAATGTTCATGTGGTGAAGAGAGCTCTATCGTTAAAAGAATCTATAAAC

TGGTTCATTACTAGAGATTCCAACTTGGCTCAAGCTCTAATTAGGAACATTATGT

CTCTGACAGGCCCTGATTTCCCTCTAGAGGAGGCCCCTGTCTTCAAAAGGACGGG

GTCAGCCTTGCATAGGTTCAAGTCTGCCAGATACAGCGAAGGAGGGTATTCTTCT

GTCTGCCCGAACCTCCTCTCTCATATTTCTGTTAGTACAGACACCATGTCTGATTT

GACCCAAGACGGGAAGAACTACGATTTCATGTTCCAGCCATTGATGCTTTATGCA

CAGACATGGACATCAGAGCTGGTACAGAGAGACACAAGGCTAAGAGACTCTAC

GTTTCATTGGCACCTCCGATGCAACAGGTGTGTGAGACCCATTGACGACGTGACC

CTGGAGACCTCTCAGATCTTCGAGTTTCCGGATGTGTCGAAAAGAATATCCAGAA

TGGTTTCTGGGCTGTGCCTCACTTCCAGAGGCTTCCCGATATCCGTCTGAGACC

AGGAGATTTTGAATCTCTAAGCGGTAGAGAAAAGTCTCACCATATCGGATCAGC

TCAGGGCTCTTATACTCAATCTTAGTGGCAATTCACGACTCAGGATACAATGAT

GGAACCATCTTCCCTGTCAACATATACGGCAAGGTTTCCCCTAGAGACTATTTGA

GAGGGCTCGCAAGGGGAGTATTGATAGGATCCTCGATTTGCTTCTTGACAAGAA

TGACAAATATCAATATTAATAGACCTCTTGAATTGGTCTCAGGGGTAATCTCATA

TATTCTCCTGAGGCTAGATAACCATCCCTCCTTGTACATAATGCTCAGAGAACCG

TCTCTTAGAGGAGAGATATTTTCTATCCCTCAGAAAATCCCCGCCGCTTATCCAA

CCACTATGAAAGAAGGCAACAGATCAATCTTGTGTTATCTCCAACATGTGCTACG

CTATGAGCGAGAGATAATCACGGCGTCTCCAGAGAATGACTGGCTATGGATCTT
```

-continued
```
TTCAGACTTTAGAAGTGCCAAAATGACGTACCTATCCCTCATTACTTACCAGTCT

CATCTTCTACTCCAGAGGGTTGAGAGAAACCTATCTAAGAGTATGAGAGATAAC

CTGCGACAATTGAGTTCTTTGATGAGGCAGGTGCTGGGCGGGCACGGAGAAGAT

ACCTTAGAGTCAGACGACAACATTCAACGACTGCTAAAAGACTCTTTACGAAGG

ACAAGATGGGTGGATCAAGAGGTGCGCCATGCAGCTAGAACCATGACTGGAGAT

TACAGCCCCAACAAGAAGGTGTCCCGTAAGGTAGGATGTTCAGAATGGGTCTGC

TCTGCTCAACAGGTTGCAGTCTCTACCTCAGCAAACCCGGCCCCTGTCTCGGAGC

TTGACATAAGGGCCCTCTCTAAGAGGTTCCAGAACCCTTTGATCTCGGGCTTGAG

AGTGGTTCAGTGGGCAACCGGTGCTCATTATAAGCTTAAGCCTATTCTAGATGAT

CTCAATGTTTTCCCATCTCTCTGCCTTGTAGTTGGGGACGGGTCAGGGGGGATAT

CAAGGGCAGTCCTCAACATGTTTCCAGATGCCAAGCTTGTGTTCAACAGTCTTTT

AGAGGTGAATGACCTGATGGCTTCCGGAACACATCCACTGCCTCCTTCAGCAATC

ATGAGGGGAGGAAATGATATCGTCTCCAGAGTGATAGATCTTGACTCAATCTGG

GAAAAACCGTCCGACTTGAGAAACTTGGCAACCTGGAAATACTTCCAGTCAGTC

CAAAAGCAGGTCAACATGTCCTATGACCTCATTATTTGCGATGCAGAAGTTACTG

ACATTGCATCTATCAACCGGATCACCCTGTTAATGTCCGATTTTGCATTGTCTATA

GATGGACCACTCTATTTGGTCTTCAAAACTTATGGGACTATGCTAGTAAATCCAA

ACTACAAGGCTATTCAACACCTGTCAAGAGCGTTCCCCTCGGTCACAGGGTTTAT

CACCCAAGTAACTTCGTCTTTTTCATCTGAGCTCTACCTCCGATTCTCCAAACGA

GGGAAGTTTTTCAGAGATGCTGAGTACTTGACCTCTTCCACCCTTCGAGAAATGA

GCCTTGTGTTATTCAATTGTAGCAGCCCCAAGAGTGAGATGCAGAGAGCTCGTTC

CTTGAACTATCAGGATCTTGTGAGAGGATTTCCTGAAGAAATCATATCAAATCCT

TACAATGAGATGATCATAACTCTGATTGACAGTGATGTAGAATCTTTTCTAGTCC

ACAAGATGGTTGATGATCTTGAGTTACAGAGGGGAACTCTGTCTAAAGTGGCTA

TCATTATAGCCATCATGATAGTTTTCTCCAACAGAGTCTTCAACGTTTCCAAACC

CCTAACTGACCCCTCGTTCTATCCACCGTCTGATCCCAAAATCCTGAGGCACTTC

AACATATGTTGCAGTACTATGATGTATCTATCTACTGCTTTAGGTGACGTCCCTA

GCTTCGCAAGACTTCACGACCTGTATAACAGACCTATAACTTATTACTTCAGAAA

GCAAGTCATTCGAGGGAACGTTTATCTATCTTGGAGTTGGTCCAACGACACCTCA

GTGTTCAAAAGGGTAGCCTGTAATTCTAGCCTGAGTCTGTCATCTCACTGGATCA

GGTTGATTTACAAGATAGTGAAGACTACCAGACTCGTTGGCAGCATCAAGGATC

TATCCAGAGAAGTGGAAAGACACCTTCATAGGTACAACAGGTGGATCACCCTAG

AGGATATCAGATCTAGATCATCCCTACTAGACTACAGTTGCCTGTGAACCGGATA

CTCCTGGAAGCCTGCCCATGCTAAGACTCTTGTGTGATGTATCTTGAAAAAAACA

AGATCCTAAATCTGAACCTTTGGTTGTTTGATTGTTTTTCTCAttttttgttgtttatttgttaagcgt.
```

In some embodiments, the nucleic acid comprises the sequence of SEQ ID NO: 8, shown below (RABV vector: Coravax V2-China (RABVG-E51)):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA
```

```
GGTGGTCTCTTTGAAGCCTGAGATTATCGTGGATCAATATGAGTACAAGTACCCT
GCCATCAAAGATTTGAAAAAGCCCTGTATAACCCTAGGAAAGGCTCCCGATTTA
AATAAAGCATACAAGTCAGTTTTGTCAGGCATGAGCGCCGCCAAACTTAATCCT
GACGATGTATGTTCCTATTTGGCAGCGGCAATGCAGTTTTTTGAGGGGACATGTC
CGGAAGACTGGACCAGCTATGGAATTGTGATTGCACGAAAAGGAGATAAGATCA
CCCCAGGTTCTCTGGTGGAGATAAAACGTACTGATGTAGAAGGGAATTGGGCTC
TGACAGGAGGCATGGAACTGACAAGAGACCCCACTGTCCCTGAGCATGCGTCCT
TAGTCGGTCTTCTCTTGAGTCTGTATAGGTTGAGCAAAATATCCGGGCAAAACAC
TGGTAACTATAAGACAAACATTGCAGACAGGATAGAGCAGATTTTTGAGACAGC
CCCTTTTGTTAAAATCGTGGAACACCATACTCTAATGACAACTCACAAaATGTGT
GCTAATTGGAGTACTATACCAAACTTCAGATTTTTGGCCGGAACCTATGACATGT
TTTTCTCCCGGATTGAGCATCTATATTCAGCAATCAGAGTGGGCACAGTTGTCAC
TGCTTATGAAGACTGTTCAGGACTGGTATCATTTACTGGGTTCATAAAACAAATC
AATCTCACCGCTAGAGAGGCAATACTATATTTCTTCCACAAGAACTTTGAGGAAG
AGATAAGAAGAATGTTTGAGCCAGGGCAGGAGACAGCTGTTCCTCACTCTTATTT
CATCCACTTCCGTTCACTAGGCTTGAGTGGGAAATCTCCTTATTCATCAAATGCT
GTTGGTCACGTGTTCAATCTCATTCACTTTGTAGGATGCTATATGGGTCAAGTCA
GATCCCTAAATGCAACGGTTATTGCTGCATGTGCTCCTCATGAAATGTCTGTTCT
AGGGGGCTATCTGGGAGAGGAATTCTTCGGGAAAGGGACATTTGAAAGAAGATT
CTTCAGAGATGAGAAAGAACTTCAAGAATACGAGGCGGCTGAACTGACAAAGA
CTGACGTAGCACTGGCAGATGATGGAACTGTCAACTCTGACGACGAGGACTACT
TTTCAGGTGAAACCAGAAGTCCGGAGGCTGTTTATACTCGAATCATGATGAATG
GAGGTCGACTAAAGAGATCTCACATACGGAGATATGTCTCAGTCAGTTCCAATC
ATCAAGCCCGTCCAAACTCATTCGCCGAGTTTCTAAACAAGACATATTCGAGTGA
CTCATAAcatgaaaaaaactaacaccccctcccgtacgCCACCATGTTCGTGTTTCTGGTGCTGCTGC
CTCTGGTGAGCTCCCAGTGCGTGAACCTGACCACAAGGACCCAGCTGCCCCCTG
CCTATACCAATTCCTTCACACGGGGCGTGTACTATCCCGACAAGGTGTTCCGGAG
CAGCGTGCTGCACTCCACACAGGATCTGTTTCTGCCTTTCTTTTCTAACGTGACCT
GGTTCCACGCCATCCACGTGAGCGGCACCAATGGCACAAAGCGGTTCGACAATC
CAGTGCTGCCCTTTAACGATGGCGTGTACTTCGCCTCCACCGAGAAGTCTAACAT
CATCAGAGGCTGGATCTTTGGCACCACACTGGACAGCAAGACACAGTCCCTGCT
GATCGTGAACAATGCCACCAACGTGGTCATCAAGGTGTGCGAGTTCCAGTTTTGT
AATGATCCATTCCTGGGCGTGTACTATCACAAGAACAATAAGTCTTGGATGGAG
AGCGAGTTTCGCGTGTATTCCTCTGCCAACAATTGCACATTTGAGTACGTGTCCC
AGCCCTTCCTGATGGACCTGGAGGGCAAGCAGGGCAATTTCAAGAACCTGAGGG
AGTTCGTGTTTAAGAATATCGATGGCTACTTCAAAATCTACTCCAAGCACACCCC
AATCAACCTGGTGCGCGACCTGCCACAGGGCTTCTCTGCCCTGGAGCCACTGGTG
GATCTGCCCATCGGCATCAACATCACCCGGTTTCAGACACTGCTGGCCCTGCACA
GAAGCTACCTGACACCAGGCGACAGCTCCTCTGGATGGACCGCAGGAGCAGCAG
CCTACTATGTGGGCTATCTGCAGCCCAGGACCTTCCTGCTGAAGTACAACGAGA
ATGGCACCATCACAGACGCCGTGGATTGCGCCCTGGATCCCCTGTCTGAGACCA
```

```
AGTGTACACTGAAGAGCTTTACCGTGGAGAAGGGCATCTATCAGACAAGCAATT
TCAGGGTGCAGCCTACCGAGTCCATCGTGCGCTTTCCCAATATCACAAACCTGTG
CCCTTTTGGCGAGGTGTTCAACGCAACCCGCTTCGCCAGCGTGTACGCCTGGAAT
AGGAAGCGCATCTCCAACTGCGTGGCCGACTATTCTGTGCTGTACAACAGCGCCT
CCTTCTCTACCTTTAAGTGCTATGGCGTGAGCCCCACAAAGCTGAATGACCTGTG
CTTTACCAACGTGTACGCCGATTCCTTCGTGATCAGGGGCGACGAGGTGCGCCA
GATCGCACCAGGACAGACAGGCAAGATCGCAGACTACAATTATAAGCTGCCTGA
CGATTTCACCGGCTGCGTGATCGCCTGGAACTCTAACAATCTGGATAGCAAAGTG
GGCGGCAACTACAATTATCTGTACCGGCTGTTTAGAAAGTCTAATCTGAAGCCAT
TCGAGAGGGACATCTCCACAGAAATCTACCAGGCCGGCTCTACCCCCTGCAATG
GCGTGGAGGGCTTTAACTGTTATTTCCCTCTGCAGAGCTACGGCTTCCAGCCAAC
AAACGGCGTGGGCTATCAGCCCTACCGCGTGGTGGTGCTGTCTTTTGAGCTGCTG
CACGCACCTGCAACAGTGTGCGGACCAAAGAAGAGCACCAATCTGGTGAAGAA
CAAGTGCGTGAACTTCAACTTCAACGGACTGACCGGAACAGGCGTGCTGACCGA
GTCCAACAAGAAGTTCCTGCCTTTTCAGCAGTTCGGCAGGGACATCGCAGATAC
CACAGACGCCGTGCGCGACCCTCAGACCCTGGAGATCCTGGACATCACACCATG
CTCCTTCGGCGGCGTGTCTGTGATCACACCAGGCACCAATACAAGCAACCAGGT
GGCCGTGCTGTATcAGGACGTGAATTGTACCGAGGTGCCAGTGGCAATCCACGCA
GATCAGCTGACCCCTACATGGCGGGTGTACTCTACCGGCAGCAACGTGTTCCAG
ACAAGAGCCGGATGCCTGATCGGAGCAGAGCACGTGAACAATAGCTATGAGTGC
GACATCCCTATCGGCGCCGGCATCTGTGCCTCCTACCAGACCCAGACAAACTCCC
CAGAATCAAGCGTGATTCCTCTGGTCCATCCACTGGCAGATCCCTCCACAGTGTT
CAAAGACGGAGATGAGGCCGAAGACTTTGTGGAAGTCCACCTGCCTGATGTGCA
TAACCAGGTGTCTGGCGTCGACCTGGGACTGCCAAATTGGGGCAAGTACGTGCT
GCTGAGTGCTGGAGCACTGACTGCCCTGATGCTGATCATTTTCCTGATGACCTGC
TGTCGGCGCGTGAACAGAAGTGAGCCCACTCAGCACAATCTGCGAGGAACCGGG
AGAGAAGTGTCAGTCACACCTCAGAGCGGGAAAATCATTAGTAGTTGGGAATCA
CATAAAAGCGGGGGCGAGACCAGGCTGTGAgctagcCATGAAAAAAACTAACACCC
CTCCTTTCGAACCATCCCAAACATGAGCAAGATCTTTGTCAATCCTAGTGCTATT
AGAGCCGGTCTGGCCGATCTTGAGATGGCTGAAGAAACTGTTGATCTGATCAAT
AGAAATATCGAAGACAATCAGGCTCATCTCCAAGGGGAACCCATAGAGGTGGAC
AATCTCCCTGAGGATATGGGGCGACTTCACCTGGATGATGGAAAATCGCCCAAC
CATGGTGAGATAGCCAAGGTGGGAGAAGGCAAGTATCGAGAGGACTTTCAGATG
GATGAAGGAGAGGATCCTAGCTTCCTGTTCCAGTCATACCTGGAAAATGTTGGA
GTCCAAATAGTCAGACAAATGAGGTCAGGAGAGAGATTTCTCAAGATATGGTCA
CAGACCGTAGAAGAGATTATATCCTATGTCGCGGTCAACTTTCCCAACCCTCCAG
GAAAGTCTTCAGAGGATAAATCAACCCAGACTACTGGCCGAGAGCTCAAGAAGG
AGACAACACCCACTCCTTCTCAGAGAGAAAGCCAATCATCGAAAGCCAGGATGG
CGGCTCAAATTGCTTCTGGCCCTCCAGCCCTTGAATGGTCGGCTACCAATGAAGA
GGATGATCTATCAGTGGAGGCTGAGATCGCTCACCAGATTGCAGAAAGTTTCTCC
```

-continued

```
AAAAAATATAAGTTTCCCTCTCGATCCTCAGGGATACTCTTGTATAATTTTGAGC
AATTGAAAATGAACCTTGATGATATAGTTAAAGAGGCAAAAAATGTACCAGGTG
TGACCCGTTTAGCCCATGACGGGTCCAAACTCCCCCTAAGATGTGTACTGGGATG
GGTCGCTTTGGCCAACTCTAAGAAATTCCAGTTGTTAGTCGAATCCGACAAGCTG
AGTAAAATCATGCAAGATGACTTGAATCGCTATACATCTTGCTAACCGAACCTCT
CCCCTCAGTCCCTCTAGACAATAAAATCCGAGATGTCCCAAAGTCAACATGAAA
AAAACAGGCAACACCACTGATAAAATGAACCTCCTACGTAAGATAGTGAAAAAC
CGCAGGGACGAGGACACTCAAAAATCCTCTCCCGCGTCAGCCCCTCTGGATGAC
GATGACTTGTGGCTTCCACCCCCTGAATACGTCCCGCTGAAAGAACTTACAGGCA
AGAAGAACATGAGGAACTTTTGTATCAACGGAAGGGTTAAAGTGTGTAGCCCGA
ATGGTTACTCGTTCAGGATCCTGCGGCACATTCTGAAATCATTCGACGAGATATA
TTCTGGGAATCATAGGATGATCGGGTTAGTCAAAGTGGTTATTGGACTGGCTTTG
TCAGGATCTCCAGTCCCTGAGGGCCTGAACTGGGTATACAAATTGAGGAGAACC
TTTATCTTCCAGTGGGCTGATTCCAGGGGCCCTCTTGAAGGGGAGGAGTTGGAAT
ACTCTCAGGAGATCACTTGGGATGATGATACTGAGTTCGTCGGATTGCAAATAA
GAGTGATTGCAAAACAGTGTCATATCCAGGGCAGAGTCTGGTGTATCAACATGA
ACCCGAGAGCATGTCAACTATGGTCTGACATGTCTCTTCAGACACAAAGGTCCG
AAGAGGACAAAGATTCCTCTCTGCTTCTAGAATAATCAGATTATATCCCGCAAAT
TTATCACTTGTTTACCTCTGGAGGAGAGAACATATGGGCTCAACTCCAACCCTTG
GGAGCAATATAACAAAAAACATGTTATGGTGCCATTAAACCGCTGCATTTCATC
AAAGTCAAGTTGATTACCTTTACATTTTGATCCTCTTGGATGTGAAAAAAACTAT
TAACATCCCTCAAAAGACcccgggAAAGATGGTTCCTCAGGCTCTCCTGTTTGTACC
CCTTCTGGTTTTTCCATTGTGTTTTGGGAAATTCCCTATTTACACGATACCAGACA
AGCTTGGTCCCTGGAGTCCGATTGACATACATCACCTCAGCTGCCCAAACAATTT
GGTAGTGGAGGACGAAGGATGCACCAACCTGTCAGGGTTCTCCTACATGGAACT
TAAAGTTGGATACATCTTAGCCATAAAAGTGAACGGGTTCACTTGCACAGGCGTT
GTGACGGAGGCTGAAACCTACACTAACTTCGTTGGTTATGTCACAACCACGTTCA
AAAGAAAGCATTTCCGCCCAACACCAGATGCATGTAGAGCCGCGTACAACTGGA
AGATGGCCGGTGACCCCAGATATGAAGAGTCTCTACACAATCCGTACCCTGACT
ACCGCTGGCTTCGAACTGTAAAAACCACCAAGGAGTCTCTCGTTATCATATCTCC
AAGTGTGGCAGATTTGGACCCATATGACAGATCCCTTCACTCGAGGGTCTTCCCT
AGCGGGAAGTGCTCAGGAGTAGCGGTGTCTTCTACCTACTGCTCCACTAACCAC
GATTACACCATTTGGATGCCCGAGAATCCGAGACTAGGGATGTCTTGTGACATTT
TTACCAATAGTAGAGGGAAGAGAGCATCCAAAGGGAGTGAGACTTGCGGCTTTG
TAGATGAAAGAGGCCTATATAAGTCTTTAAAAGGAGCATGCAAACTCAAGTTAT
GTGGAGTTCTAGGACTTAGACTTATGGATGGAACATGGGTCTCGATGCAAACAT
CAAATGAAACCAAATGGTGCCCTCCCGATAAGTTGGTGAACCTGCACGACTTTC
GCTCAGACGAAATTGAGCACCTTGTTGTAGAGGAGTTGGTCAGGAAGAGAGAGG
AGTGTCTGGATGCACTAGAGTCCATCATGACAACCAAGTCAGTGAGTTTCAGAC
GTCTCAGTCATTTAAGAAAACTTGTCCCTGGGTTTGGAAAAGCATATACCATATT
CAACAAGACCTTGATGGAAGCCGATGCTCACTACAAGTCAGTCgagACTTGGAAT
```

```
GAGATCCTCCCTTCAAAAGGGTGTTTAAGAGTTGGGGGGAGGTGTCATCCTCATG

TGAACGGGGTGTTTTTCAATGGTATAATATTAGGACCTGACGGCAATGTCTTAAT

CCCAGAGATGCAATCATCCCTCCTCCAGCAACATATGGAGTTGTTGGAATCCTCG

GTTATCCCCCTTGTGCACCCCCTGGCAGACCCGTCTACCGTTTTCAAGGACGGTG

ACGAGGCTGAGGATTTTGTTGAAGTTCACCTTCCCGATGTGCACAATCAGGTCTC

AGGAGTTGACTTGGGTCTCCCGAACTGGGGGAAGTATGTATTACTGAGTGCAGG

GGCCCTGACTGCCTTGATGTTGATAATTTTCCTGATGACATGTTGTAGAAGAGTC

AATCGATCAGAACCTACGCAACACAATCTCAGAGGGACAGGGAGGGAGGTGTC

AGTCACTCCCCAAAGCGGGAAGATCATATCTTCATGGGAATCACACAAGAGTGG

GGGTGAGACCAGACTGTAAttaattaaCGTCCTTTCAACGATCCAAGTCcatgaaaaaaactaa caccccctcccgtacctagcTTATAAAGTGCTGGGTCATCTAAGCTTTTCAGTCGAGAAAAA

ACATTAGATCAGAAGAACAACTGGCAACACTTCTCAACCTGAGACTTACTTCAA

GATGCTCGATCCTGGAGAGGTCTATGATGACCCTATTGACCCAATCGAGTTAGAG

GCTGAACCCAGAGGAACCCCCATTGTCCCCAACATCTTGAGGAACTCTGACTAC

AATCTCAACTCTCCTTTGATAGAAGATCCTGCTAGACTAATGTTAGAATGGTTAA

AAACAGGGAATAGACCTTATCGGATGACTCTAACAGACAATTGCTCCAGGTCTTT

CAGAGTTTTGAAAGATTATTTCAAGAAGGTAGATTTGGGTTCTCTCAAGGTGGGC

GGAATGGCTGCACAGTCAATGATTTCTCTCTGGTTATATGGTGCCCACTCTGAAT

CCAACAGGAGCCGGAGATGTATAACAGACTTGGCCCATTTCTATTCCAAGTCGTC

CCCCATAGAGAAGCTGTTGAATCTCACGCTAGGAAATAGAGGGCTGAGAATCCC

CCCAGAGGGAGTGTTAAGTTGCCTTGAGAGGGTTGATTATGATAATGCATTTGGA

AGGTATCTTGCCAACACGTATTCCTCTTACTTGTTCTTCCATGTAATCACCTTATA

CATGAACGCCCTAGACTGGGATGAAGAAAAGACCATCCTAGCATTATGGAAAGA

TTTAACCTCAGTGGACATCGGGAAGGACTTGGTAAAGTTCAAAGACCAAATATG

GGGACTGCTGATCGTGACAAAGGACTTTGTTTACTCCCAAAGTTCCAATTGTCTT

TTTGACAGAAACTACACACTTATGCTAAAAGATCTTTTCTTGTCTCGCTTCAACTC

CTTAATGGTCTTGCTCTCTCCCCCAGAGCCCCGATACTCAGATGACTTGATATCT

CAACTATGCCAGCTGTACATTGCTGGGGATCAAGTCTTGTCTATGTGTGGAAACT

CCGGCTATGAAGTCATCAAAATATTGGAGCCATATGTCGTGAATAGTTTAGTCCA

GAGAGCAGAAAAGTTTAGGCCTCTCATTCATTCCTTGGGAGACTTTCCTGTATTT

ATAAAAGACAAGGTAAGTCAACTTGAAGAGACGTTCGGTCCCTGTGCAAGAAGG

TTCTTTAGGGCTCTGGATCAATTCGACAACATACATGACTTGGTTTTTGTGTTTGG

CTGTTACAGGCATTGGGGGCACCCATATATAGATTATCGAAAGGGTCTGTCAAA

ACTATATGATCAGGTTCACCTTAAAAAAATGATAGATAAGTCCTACCAGGAGTG

CTTAGCAAGCGACCTAGCCAGGAGGATCCTTAGATGGGGTTTTGATAAGTACTCC

AAGTGGTATCTGGATTCAAGATTCCTAGCCCGAGACCACCCCTTGACTCCTTATA

TCAAAACCCAAACATGGCCACCCAAACATATTGTAGACTTGGTGGGGATACAT

GGCACAAGCTCCCGATCACGCAGATCTTTGAGATTCCTGAATCAATGGATCCGTC

AGAAATATTGGATGACAAATCACATTCTTTCACCAGAACGAGACTAGCTTCTTGG

CTGTCAGAAAACCGAGGGGGGCCTGTTCCTAGCGAAAAAGTTATTATCACGGCC
```

-continued

```
CTGTCTAAGCCGCCTGTCAATCCCCGAGAGTTTCTGAGGTCTATAGACCTCGGAG
GATTGCCAGATGAAGACTTGATAATTGGCCTCAAGCCAAAGGAACGGGAATTGA
AGATTGAAGGTCGATTCTTTGCTCTAATGTCATGGAATCTAAGATTGTATTTTGTC
ATCACTGAAAAACTCTTGGCCAACTACATCTTGCCACTTTTTGACGCGCTGACTA
TGACAGACAACCTGAACAAGGTGTTTAAAAAGCTGATCGACAGGGTCACCGGGC
AAGGGCTTTTGGACTATTCAAGGGTCACATATGCATTTCACCTGGACTATGAAAA
GTGGAACAACCATCAAAGATTAGAGTCAACAGAGGATGTATTTTCTGTCCTAGA
TCAAGTGTTTGGATTGAAGAGAGTGTTTTCTAGAACACACGAGTTTTTTCAAAAG
GCCTGGATCTATTATTCAGACAGATCAGACCTCATCGGGTTACGGGAGGATCAA
ATATACTGCTTAGATGCGTCCAACGGCCCAACCTGTTGGAATGGCCAGGATGGC
GGGCTAGAAGGCTTACGGCAGAAGGGCTGGAGTCTAGTCAGCTTATTGATGATA
GATAGAGAATCTCAAATCAGGAACACAAGAACCAAAATACTAGCTCAAGGAGA
CAACCAGGTTTTATGTCCGACATACATGTTGTCGCCAGGGCTATCTCAAGAGGGG
CTCCTCTATGAATTGGAGAGAATATCAAGGAATGCACTTTCGATATACAGAGCC
GTCGAGGAAGGGGCATCTAAGCTAGGGCTGATCATCAAGAAAGAAGAGACCAT
GTGTAGTTATGACTTCCTCATCTATGGAAAAACCCCTTTGTTTAGAGGTAACATA
TTGGTGCCTGAGTCCAAAAGATGGGCCAGAGTCTCTTGCGTCTCTAATGACCAAA
TAGTCAACCTCGCCAATATAATGTCGACAGTGTCCACCAATGCGCTAACAGTGG
CACAACACTCTCAATCTTTGATCAAACCGATGAGGGATTTTCTGCTCATGTCAGT
ACAGGCAGTCTTTCACTACCTGCTATTTAGCCCAATCTTAAAGGGAAGAGTTTAC
AAGATTCTGAGCGCTGAAGGGGAGAGCTTTCTCCTAGCCATGTCAAGGATAATC
TATCTAGATCCTTCTTTGGGAGGGATATCTGGAATGTCCCTCGGAAGATTCCATA
TACGACAGTTCTCAGACCCTGTCTCTGAAGGGTTATCCTTCTGGAGAGAGATCTG
GTTAAGCTCCCAAGAGTCCTGGATTCACGCGTTGTGTCAAGAGGCTGGAAACCC
AGATCTTGGAGAGAGAACACTCGAGAGCTTCACTCGCCTTCTAGAAGATCCGAC
CACCTTAAATATCAGAGGAGGGGCCAGTCCTACCATTCTACTCAAGGATGCAAT
CAGAAAGGCTTTATATGACGAGGTGGACAAGGTGGAAAATTCAGAGTTTCGAGA
GGCAATCCTGTTGTCCAAGACCCATAGAGATAATTTTATACTCTTCTTAATATCT
GTTGAGCCTCTGTTTCCTCGATTTCTCAGTGAGCTATTCAGTTCGTCTTTTTTGGG
AATCCCCGAGTCAATCATTGGATTGATACAAAACTCCCGAACGATAAGAAGGCA
GTTTAGAAAGAGTCTCTCAAAAACTTTAGAAGAATCCTTCTACAACTCAGAGATC
CACGGGATTAGTCGGATGACCCAGACACCTCAGAGGGTTGGGGGGTGTGGCCT
TGCTCTTCAGAGAGGGCAGATCTACTTAGGGAGATCTCTTGGGGAAGAAAAGTG
GTAGGCACGACAGTTCCTCACCCTTCTGAGATGTTGGGATTACTTCCCAAGTCCT
CTATTTCTTGCACTTGTGGAGCAACAGGAGGAGGCAATCCTAGAGTTTCTGTATC
AGTACTCCCGTCCTTTGATCAGTCATTTTTTTCACGAGGCCCCCTAAAGGGATAC
TTGGGCTCGTCCACCTCTATGTCGACCCAGCTATTCCATGCATGGGAAAAAGTCA
CTAATGTTCATGTGGTGAAGAGAGCTCTATCGTTAAAAGAATCTATAAACTGGTT
CATTACTAGAGATTCCAACTTGGCTCAAGCTCTAATTAGGAACATTATGTCTCTG
ACAGGCCCTGATTTCCCTCTAGAGGAGGCCCCTGTCTTCAAAAGGACGGGGTCA
GCCTTGCATAGGTTCAAGTCTGCCAGATACAGCGAAGGAGGGTATTCTTCTGTCT
```

```
GCCCGAACCTCCTCTCTCATATTTCTGTTAGTACAGACACCATGTCTGATTTGACC

CAAGACGGGAAGAACTACGATTTCATGTTCCAGCCATTGATGCTTTATGCACAGA

CATGGACATCAGAGCTGGTACAGAGAGACACAAGGCTAAGAGACTCTACGTTTC

ATTGGCACCTCCGATGCAACAGGTGTGTGAGACCCATTGACGACGTGACCCTGG

AGACCTCTCAGATCTTCGAGTTTCCGGATGTGTCGAAAAGAATATCCAGAATGGT

TTCTGGGGCTGTGCCTCACTTCCAGAGGCTTCCCGATATCCGTCTGAGACCAGGA

GATTTTGAATCTCTAAGCGGTAGAGAAAAGTCTCACCATATCGGATCAGCTCAG

GGGCTCTTATACTCAATCTTAGTGGCAATTCACGACTCAGGATACAATGATGGAA

CCATCTTCCCTGTCAACATATACGGCAAGGTTTCCCCTAGAGACTATTTGAGAGG

GCTCGCAAGGGAGTATTGATAGGATCCTCGATTTGCTTCTTGACAAGAATGACA

AATATCAATATTAATAGACCTCTTGAATTGGTCTCAGGGGTAATCTCATATATTC

TCCTGAGGCTAGATAACCATCCCTCCTTGTACATAATGCTCAGAGAACCGTCTCT

TAGAGGAGAGATATTTTCTATCCCTCAGAAAATCCCCGCCGCTTATCCAACCACT

ATGAAAGAAGGCAACAGATCAATCTTGTGTTATCTCCAACATGTGCTACGCTATG

AGCGAGAGATAATCACGGCGTCTCCAGAGAATGACTGGCTATGGATCTTTTCAG

ACTTTAGAAGTGCCAAAATGACGTACCTATCCCTCATTACTTACCAGTCTCATCT

TCTACTCCAGAGGGTTGAGAGAAACCTATCTAAGAGTATGAGAGATAACCTGCG

ACAATTGAGTTCTTTGATGAGGCAGGTGCTGGGCGGGACGGAGAAGATACCTT

AGAGTCAGACGACAACATTCAACGACTGCTAAAAGACTCTTTACGAAGGACAAG

ATGGGTGGATCAAGAGGTGCGCCATGCAGCTAGAACCATGACTGGAGATTACAG

CCCCAACAAGAAGGTGTCCCGTAAGGTAGGATGTTCAGAATGGGTCTGCTCTGC

TCAACAGGTTGCAGTCTCTACCTCAGCAAACCCGGCCCCTGTCTCGGAGCTTGAC

ATAAGGGCCCTCTCTAAGAGGTTCCAGAACCCTTTGATCTCGGGCTTGAGAGTGG

TTCAGTGGGCAACCGGTGCTCATTATAAGCTTAAGCCTATTCTAGATGATCTCAA

TGTTTTCCCATCTCTCTGCCTTGTAGTTGGGGACGGGTCAGGGGGATATCAAGG

GCAGTCCTCAACATGTTTCCAGATGCCAAGCTTGTGTTCAACAGTCTTTTAGAGG

TGAATGACCTGATGGCTTCCGGAACACATCCACTGCCTCCTTCAGCAATCATGAG

GGGAGGAAATGATATCGTCTCCAGAGTGATAGATCTTGACTCAATCTGGGAAAA

ACCGTCCGACTTGAGAAACTTGGCAACCTGGAAATACTTCCAGTCAGTCCAAAA

GCAGGTCAACATGTCCTATGACCTCATTATTTGCGATGCAGAAGTTACTGACATT

GCATCTATCAACCGGATCACCCTGTTAATGTCCGATTTTGCATTGTCTATAGATG

GACCACTCTATTTGGTCTTCAAAACTTATGGGACTATGCTAGTAAATCCAAACTA

CAAGGCTATTCAACACCTGTCAAGAGCGTTCCCCTCGGTCACAGGGTTTATCACC

CAAGTAACTTCGTCTTTTTCATCTGAGCTCTACCTCCGATTCTCCAAACGAGGGA

AGTTTTTCAGAGATGCTGAGTACTTGACCTCTTCCACCCTTCGAGAAATGAGCCT

TGTGTTATTCAATTGTAGCAGCCCCAAGAGTGAGATGCAGAGAGCTCGTTCCTTG

AACTATCAGGATCTTGTGAGAGGATTTCCTGAAGAAATCATATCAAATCCTTACA

ATGAGATGATCATAACTCTGATTGACAGTGATGTAGAATCTTTTCTAGTCCACAA

GATGGTTGATGATCTTGAGTTACAGAGGGGAACTCTGTCTAAAGTGGCTATCATT

ATAGCCATCATGATAGTTTTCTCCAACAGAGTCTTCAACGTTTCCAAACCCCTAA
```

-continued

```
CTGACCCCTCGTTCTATCCACCGTCTGATCCCAAAATCCTGAGGCACTTCAACAT
ATGTTGCAGTACTATGATGTATCTATCTACTGCTTTAGGTGACGTCCCTAGCTTCG
CAAGACTTCACGACCTGTATAACAGACCTATAACTTATTACTTCAGAAAGCAAGT
CATTCGAGGGAACGTTTATCTATCTTGGAGTTGGTCCAACGACACCTCAGTGTTC
AAAAGGGTAGCCTGTAATTCTAGCCTGAGTCTGTCATCTCACTGGATCAGGTTGA
TTTACAAGATAGTGAAGACTACCAGACTCGTTGGCAGCATCAAGGATCTATCCA
GAGAAGTGGAAAGACACCTTCATAGGTACAACAGGTGGATCACCCTAGAGGATA
TCAGATCTAGATCATCCCTACTAGACTACAGTTGCCTGTGAACCGGATACTCCTG
GAAGCCTGCCCATGCTAAGACTCTTGTGTGATGTATCTTGAAAAAAACAAGATCC
TAAATCTGAACCTTTGGTTGTTTGATTGTTTTTCTCAtttttgttgtttatttgttaagcgt.
```

In other embodiments, the nucleic acid comprises the sequence of SEQ ID NO: 9, shown below (RABV vector: Coravax V2 South Africa (S1-RABVG-E51)):

```
ACGCTTAACAACCAGATCAAAGAAAAAACAGACATTGTCAATTGCAAAGCAAAA
ATGTAACACCCCTACAATGGATGCCGACAAGATTGTATTCAAAGTCAATAATCA
GGTGGTCTCTTTGAAGCCTGAGATTATCGTGGATCAATATGAGTACAAGTACCCT
GCCATCAAAGATTTGAAAAAGCCCTGTATAACCCTAGGAAAGGCTCCCGATTTA
AATAAAGCATACAAGTCAGTTTTGTCAGGCATGAGCGCCGCCAAACTTAATCCT
GACGATGTATGTTCCTATTTGGCAGCGGCAATGCAGTTTTTTGAGGGGACATGTC
CGGAAGACTGGACCAGCTATGGAATTGTGATTGCACGAAAAGGAGATAAGATCA
CCCCAGGTTCTCTGGTGGAGATAAAACGTACTGATGTAGAAGGGAATTGGGCTC
TGACAGGAGGCATGGAACTGACAAGAGACCCCACTGTCCCTGAGCATGCGTCCT
TAGTCGGTCTTCTCTTGAGTCTGTATAGGTTGAGCAAAATATCCGGGCAAAACAC
TGGTAACTATAAGACAAACATTGCAGACAGGATAGAGCAGATTTTTGAGACAGC
CCCTTTTGTTAAAATCGTGGAACACCATACTCTAATGACAACTCACAAaATGTGT
GCTAATTGGAGTACTATACCAAACTTCAGATTTTTGGCCGGAACCTATGACATGT
TTTTCTCCCGGATTGAGCATCTATATTCAGCAATCAGAGTGGGCACAGTTGTCAC
TGCTTATGAAGACTGTTCAGGACTGGTATCATTTACTGGGTTCATAAAACAAATC
AATCTCACCGCTAGAGAGGCAATACTATATTTCTTCCACAAGAACTTTGAGGAAG
AGATAAGAAGAATGTTTGAGCCAGGGCAGGAGACAGCTGTTCCTCACTCTTATTT
CATCCACTTCCGTTCACTAGGCTTGAGTGGGAAATCTCCTTATTCATCAAATGCT
GTTGGTCACGTGTTCAATCTCATTCACTTTGTAGGATGCTATATGGGTCAAGTCA
GATCCCTAAATGCAACGGTTATTGCTGCATGTGCTCCTCATGAAATGTCTGTTCT
AGGGGGCTATCTGGGAGAGGAATTCTTCGGGAAAGGGACATTTGAAAGAAGATT
CTTCAGAGATGAGAAAGAACTTCAAGAATACGAGGCGGCTGAACTGACAAAGA
CTGACGTAGCACTGGCAGATGATGGAACTGTCAACTCTGACGACGAGGACTACT
TTTCAGGTGAAACCAGAAGTCCGGAGGCTGTTTATACTCGAATCATGATGAATG
GAGGTCGACTAAAGAGATCTCACATACGGAGATATGTCTCAGTCAGTTCCAATC
ATCAAGCCCGTCCAAACTCATTCGCCGAGTTTCTAAACAAGACATATTCGAGTGA
CTCATAAcatgaaaaaaactaacaccccctcccgtacgCCACCATGTTCGTGTTTCTGGTGCTGCTGC
```

-continued

```
CTCTGGTGAGCTCCCAGTGCGTGAACTTCACCACAAGGACCCAGCTGCCCCTGC

CTATACCAATTCCTTCACACGGGCGTGTACTATCCCGACAAGGTGTTCCGGAGC

AGCGTGCTGCACTCCACACAGGATCTGTTTCTGCCTTTCTTTTCTAACGTGACCTG

GTTCCACGCCATCCACGTGAGCGGCACCAATGGCACAAAGCGGTTCGCCAATCC

AGTGCTGCCCTTTAACGATGGCGTGTACTTCGCCTCCACCGAGAAGTCTAACATC

ATCAGAGGCTGGATCTTTGGCACCACACTGGACAGCAAGACACAGTCCCTGCTG

ATCGTGAACAATGCCACCAACGTGGTCATCAAGGTGTGCGAGTTCCAGTTTTGTA

ATGATCCATTCCTGGGCGTGTACTATCACAAGAACAATAAGTCTTGGATGGAGA

GCGAGTTTCGCGTGTATTCCTCTGCCAACAATTGCACATTTGAGTACGTGTCCCA

GCCCTTCCTGATGGACCTGGAGGGCAAGCAGGGCAATTTCAAGAACCTGAGGGA

GTTCGTGTTTAAGAATATCGATGGCTACTTCAAAATCTACTCCAAGCACACCCCA

ATCAACCTGGTGCGCGGCCTGCCACAGGGCTTCTCTGCCCTGGAGCCACTGGTGG

ATCTGCCCATCGGCATCAACATCACCCGGTTTCAGACACTGCTGGCCCTGCACAG

AAGCTACCTGACACCAGGCGACAGCTCCTCTGGATGGACCGCAGGAGCAGCAGC

CTACTATGTGGGCTATCTGCAGCCCAGGACCTTCCTGCTGAAGTACAACGAGAAT

GGCACCATCACAGACGCCGTGGATTGCGCCCTGGATCCCCTGTCTGAGACCAAG

TGTACACTGAAGAGCTTTACCGTGGAGAAGGGCATCTATCAGACAAGCAATTTC

AGGGTGCAGCCTACCGAGTCCATCGTGCGCTTTCCCAATATCACAAACCTGTGCC

CTTTTGGCGAGGTGTTCAACGCAACCCGCTTCGCCAGCGTGTACGCCTGGAATAG

GAAGCGCATCTCCAACTGCGTGGCCGACTATTCTGTGCTGTACAACAGCGCCTCC

TTCTCTACCTTTAAGTGCTATGGCGTGAGCCCCACAAAGCTGAATGACCTGTGCT

TTACCAACGTGTACGCCGATTCCTTCGTGATCAGGGGCGACGAGGTGCGCCAGA

TCGCACCAGGACAGACAGGCAATATCGCAGACTACAATTATAAGCTGCCTGACG

ATTTCACCGGCTGCGTGATCGCCTGGAACTCTAACAATCTGGATAGCAAAGTGG

GCGGCAACTACAATTATCTGTACCGGCTGTTTAGAAAGTCTAATCTGAAGCCATT

CGAGAGGGACATCTCCACAGAAATCTACCAGGCCGGCTCTACCCCCTGCAATGG

CGTGAAGGGCTTTAACTGTTATTTCCCTCTGCAGAGCTACGGCTTCCAGCCAACA

TATGGCGTGGGCTATCAGCCCTACCGCGTGGTGGTGCTGTCTTTTGAGCTGCTGC

ACGCACCTGCAACAGTGTGCGGACCAAAGAAGAGCACCAATCTGGTGAAGAAC

AAGTGCGTGAACTTCAACTTCAACGGACTGACCGGAACAGGCGTGCTGACCGAG

TCCAACAAGAAGTTCCTGCCTTTTCAGCAGTTCGGCAGGGACATCGCAGATACC

ACAGACGCCGTGCGCGACCCTCAGACCCTGGAGATCCTGGACATCACACCATGC

TCCTTCGGCGGCGTGTCTGTGATCACACCAGGCACCAATACAAGCAACCAGGTG

GCCGTGCTGTATCAGGGCGTGAATTGTACCGAGGTGCCAGTGGCAATCCACGCA

GATCAGCTGACCCCTACATGGCGGGTGTACTCTACCGGCAGCAACGTGTTCCAG

ACAAGAGCCGGATGCCTGATCGGAGCAGAGCACGTGAACAATAGCTATGAGTGC

GACATCCCTATCGGCGCCGGCATCTGTGCCTCCTACCAGACCCAGACAAACTCCC

CAGAATCAAGCGTGATTCCTCTGGTCCATCCACTGGCAGATCCCTCCACAGTGTT

CAAAGACGGAGATGAGGCCGAAGACTTTGTGGAAGTCCACCTGCCTGATGTGCA

TAACCAGGTGTCTGGCGTCGACCTGGGACTGCCAAATTGGGGCAAGTACGTGCT

GCTGAGTGCTGGAGCACTGACTGCCCTGATGCTGATCATTTTCCTGATGACCTGC
```

```
TGTCGGCGCGTGAACAGAAGTGAGCCCACTCAGCACAATCTGCGAGGAACCGGG

AGAGAAGTGTCAGTCACACCTCAGAGCGGGAAAATCATTAGTAGTTGGGAATCA

CATAAAAGCGGGGGCGAGACCAGGCTGTGAgctagcCATGAAAAAAACTAACACCC

CTCCTTTCGAACCATCCCAAACATGAGCAAGATCTTTGTCAATCCTAGTGCTATT

AGAGCCGGTCTGGCCGATCTTGAGATGGCTGAAGAAACTGTTGATCTGATCAAT

AGAAATATCGAAGACAATCAGGCTCATCTCCAAGGGGAACCCATAGAGGTGGAC

AATCTCCCTGAGGATATGGGGCGACTTCACCTGGATGATGGAAAATCGCCCAAC

CATGGTGAGATAGCCAAGGTGGGAGAAGGCAAGTATCGAGAGGACTTTCAGATG

GATGAAGGAGAGGATCCTAGCTTCCTGTTCCAGTCATACCTGGAAAATGTTGGA

GTCCAAATAGTCAGACAAATGAGGTCAGGAGAGAGATTTCTCAAGATATGGTCA

CAGACCGTAGAAGAGATTATATCCTATGTCGCGGTCAACTTTCCCAACCCTCCAG

GAAAGTCTTCAGAGGATAAATCAACCCAGACTACTGGCCGAGAGCTCAAGAAGG

AGACAACACCCACTCCTTCTCAGAGAGAAAGCCAATCATCGAAAGCCAGGATGG

CGGCTCAAATTGCTTCTGGCCCTCCAGCCCTTGAATGGTCGGCTACCAATGAAGA

GGATGATCTATCAGTGGAGGCTGAGATCGCTCACCAGATTGCAGAAAGTTTCTCC

AAAAAATATAAGTTTCCCTCTCGATCCTCAGGGATACTCTTGTATAATTTTGAGC

AATTGAAAATGAACCTTGATGATATAGTTAAAGAGGCAAAAAATGTACCAGGTG

TGACCCGTTTAGCCCATGACGGGTCCAAACTCCCCCTAAGATGTGTACTGGGATG

GGTCGCTTTGGCCAACTCTAAGAAATTCCAGTTGTTAGTCGAATCCGACAAGCTG

AGTAAAATCATGCAAGATGACTTGAATCGCTATACATCTTGCTAACCGAACCTCT

CCCCTCAGTCCCTCTAGACAATAAAATCCGAGATGTCCCAAAGTCAACATGAAA

AAAACAGGCAACACCACTGATAAAATGAACCTCCTACGTAAGATAGTGAAAAAC

CGCAGGGACGAGGACACTCAAAAATCCTCTCCCGCGTCAGCCCCTCTGGATGAC

GATGACTTGTGGCTTCCACCCCCTGAATACGTCCCGCTGAAAGAACTTACAGGCA

AGAAGAACATGAGGAACTTTTGTATCAACGGAAGGGTTAAAGTGTGTAGCCCGA

ATGGTTACTCGTTCAGGATCCTGCGGCACATTCTGAAATCATTCGACGAGATATA

TTCTGGGAATCATAGGATGATCGGGTTAGTCAAAGTGGTTATTGGACTGGCTTTG

TCAGGATCTCCAGTCCCTGAGGGCCTGAACTGGGTATACAAATTGAGGAGAACC

TTTATCTTCCAGTGGGCTGATTCCAGGGGCCCTCTTGAAGGGGAGGAGTTGGAAT

ACTCTCAGGAGATCACTTGGGATGATGATACTGAGTTCGTCGGATTGCAAATAA

GAGTGATTGCAAAACAGTGTCATATCCAGGGCAGAGTCTGGTGTATCAACATGA

ACCCGAGAGCATGTCAACTATGGTCTGACATGTCTCTTCAGACACAAAGGTCCG

AAGAGGACAAAGATTCCTCTCTGCTTCTAGAATAATCAGATTATATCCCGCAAAT

TTATCACTTGTTTACCTCTGGAGGAGAGAACATATGGGCTCAACTCCAACCCTTG

GGAGCAATATAACAAAAAACATGTTATGGTGCCATTAAACCGCTGCATTTCATC

AAAGTCAAGTTGATTACCTTTACATTTTGATCCTCTTGGATGTGAAAAAACTAT

TAACATCCCTCAAAAGACcccgggAAAGATGGTTCCTCAGGCTCTCCTGTTTGTACC

CCTTCTGGTTTTTCCATTGTGTTTTGGGAAATTCCCTATTTACACGATACCAGACA

AGCTTGGTCCCTGGAGTCCGATTGACATACATCACCTCAGCTGCCCAAACAATTT

GGTAGTGGAGGACGAAGGATGCACCAACCTGTCAGGGTTCTCCTACATGGAACT
```

```
TAAAGTTGGATACATCTTAGCCATAAAAGTGAACGGGTTCACTTGCACAGGCGTT

GTGACGGAGGCTGAAACCTACACTAACTTCGTTGGTTATGTCACAACCACGTTCA

AAAGAAAGCATTTCCGCCCAACACCAGATGCATGTAGAGCCGCGTACAACTGGA

AGATGGCCGGTGACCCCAGATATGAAGAGTCTCTACACAATCCGTACCCTGACT

ACCGCTGGCTTCGAACTGTAAAAACCACCAAGGAGTCTCTCGTTATCATATCTCC

AAGTGTGGCAGATTTGGACCCATATGACAGATCCCTTCACTCGAGGGTCTTCCCT

AGCGGGAAGTGCTCAGGAGTAGCGGTGTCTTCTACCTACTGCTCCACTAACCAC

GATTACACCATTTGGATGCCCGAGAATCCGAGACTAGGGATGTCTTGTGACATTT

TTACCAATAGTAGAGGGAAGAGAGCATCCAAAGGGAGTGAGACTTGCGGCTTTG

TAGATGAAAGAGGCCTATATAAGTCTTTAAAAGGAGCATGCAAACTCAAGTTAT

GTGGAGTTCTAGGACTTAGACTTATGGATGGAACATGGGTCTCGATGCAAACAT

CAAATGAAACCAAATGGTGCCCTCCCGATAAGTTGGTGAACCTGCACGACTTTC

GCTCAGACGAAATTGAGCACCTTGTTGTAGAGGAGTTGGTCAGGAAGAGAGAGG

AGTGTCTGGATGCACTAGAGTCCATCATGACAACCAAGTCAGTGAGTTTCAGAC

GTCTCAGTCATTTAAGAAAACTTGTCCCTGGGTTTGGAAAAGCATATACCATATT

CAACAAGACCTTGATGGAAGCCGATGCTCACTACAAGTCAGTCgagACTTGGAAT

GAGATCCTCCCTTCAAAAGGGTGTTTAAGAGTTGGGGGGAGGTGTCATCCTCATG

TGAACGGGGTGTTTTTCAATGGTATAATATTAGGACCTGACGGCAATGTCTTAAT

CCCAGAGATGCAATCATCCCTCCTCCAGCAACATATGGAGTTGTTGGAATCCTCG

GTTATCCCCCTTGTGCACCCCCTGGCAGACCCGTCTACCGTTTTCAAGGACGGTG

ACGAGGCTGAGGATTTTGTTGAAGTTCACCTTCCCGATGTGCACAATCAGGTCTC

AGGAGTTGACTTGGGTCTCCCGAACTGGGGGAAGTATGTATTACTGAGTGCAGG

GGCCCTGACTGCCTTGATGTTGATAATTTTCCTGATGACATGTTGTAGAAGAGTC

AATCGATCAGAACCTACGCAACACAATCTCAGAGGGACAGGGAGGGAGGTGTC

AGTCACTCCCCAAAGCGGGAAGATCATATCTTCATGGGAATCACACAAGAGTGG

GGGTGAGACCAGACTGTAAttaattaaCGTCCTTTCAACGATCCAAGTCcatgaaaaaaactaa caccctcccgtacctagcTTATAAAGTGCTGGGTCATCTAAGCTTTTCAGTCGAGAAAAAA

ACATTAGATCAGAAGAACAACTGGCAACACTTCTCAACCTGAGACTTACTTCAA

GATGCTCGATCCTGGAGAGGTCTATGATGACCCTATTGACCCAATCGAGTTAGAG

GCTGAACCCAGAGGAACCCCCATTGTCCCCAACATCTTGAGGAACTCTGACTAC

AATCTCAACTCTCCTTTGATAGAAGATCCTGCTAGACTAATGTTAGAATGGTTAA

AAACAGGGAATAGACCTTATCGGATGACTCTAACAGACAATTGCTCCAGGTCTTT

CAGAGTTTTGAAAGATTATTTCAAGAAGGTAGATTTGGGTTCTCTCAAGGTGGGC

GGAATGGCTGCACAGTCAATGATTTCTCTCTGGTTATATGGTGCCCACTCTGAAT

CCAACAGGAGCCGGAGATGTATAACAGACTTGGCCCATTTCTATTCCAAGTCGTC

CCCCATAGAGAAGCTGTTGAATCTCACGCTAGGAAATAGAGGGCTGAGAATCCC

CCCAGAGGGAGTGTTAAGTTGCCTTGAGAGGGTTGATTATGATAATGCATTTGGA

AGGTATCTTGCCAACACGTATTCCTCTTACTTGTTCTTCCATGTAATCACCTTATA

CATGAACGCCCTAGACTGGGATGAAGAAAAGACCATCCTAGCATTATGGAAAGA

TTTAACCTCAGTGGACATCGGGAAGGACTTGGTAAAGTTCAAAGACCAAATATG

GGGACTGCTGATCGTGACAAAGGACTTTGTTTACTCCCAAAGTTCCAATTGTCTT
```

```
TTTGACAGAAACTACACACTTATGCTAAAAGATCTTTTCTTGTCTCGCTTCAACTC
CTTAATGGTCTTGCTCTCTCCCCCAGAGCCCCGATACTCAGATGACTTGATATCT
CAACTATGCCAGCTGTACATTGCTGGGGATCAAGTCTTGTCTATGTGTGGAAACT
CCGGCTATGAAGTCATCAAAATATTGGAGCCATATGTCGTGAATAGTTTAGTCCA
GAGAGCAGAAAAGTTTAGGCCTCTCATTCATTCCTTGGGAGACTTTCCTGTATTT
ATAAAAGACAAGGTAAGTCAACTTGAAGAGACGTTCGGTCCCTGTGCAAGAAGG
TTCTTTAGGGCTCTGGATCAATTCGACAACATACATGACTTGGTTTTTGTGTTTGG
CTGTTACAGGCATTGGGGGCACCCATATATAGATTATCGAAAGGGTCTGTCAAA
ACTATATGATCAGGTTCACCTTAAAAAAATGATAGATAAGTCCTACCAGGAGTG
CTTAGCAAGCGACCTAGCCAGGAGGATCCTTAGATGGGGTTTTGATAAGTACTCC
AAGTGGTATCTGGATTCAAGATTCCTAGCCCGAGACCACCCCTTGACTCCTTATA
TCAAAACCCAAACATGGCCACCCAAACATATTGTAGACTTGGTGGGGATACAT
GGCACAAGCTCCCGATCACGCAGATCTTTGAGATTCCTGAATCAATGGATCCGTC
AGAAATATTGGATGACAAATCACATTCTTTCACCAGAACGAGACTAGCTTCTTGG
CTGTCAGAAAACCGAGGGGGGCCTGTTCCTAGCGAAAAGTTATTATCACGGCC
CTGTCTAAGCCGCCTGTCAATCCCCGAGAGTTTCTGAGGTCTATAGACCTCGGAG
GATTGCCAGATGAAGACTTGATAATTGGCCTCAAGCCAAAGGAACGGGAATTGA
AGATTGAAGGTCGATTCTTTGCTCTAATGTCATGGAATCTAAGATTGTATTTTGTC
ATCACTGAAAAACTCTTGGCCAACTACATCTTGCCACTTTTTGACGCGCTGACTA
TGACAGACAACCTGAACAAGGTGTTTAAAAAGCTGATCGACAGGGTCACCGGGC
AAGGGCTTTTGGACTATTCAAGGGTCACATATGCATTTCACCTGGACTATGAAAA
GTGGAACAACCATCAAAGATTAGAGTCAACAGAGGATGTATTTTCTGTCCTAGA
TCAAGTGTTTGGATTGAAGAGAGTGTTTTCTAGAACACACGAGTTTTTTCAAAAG
GCCTGGATCTATTATTCAGACAGATCAGACCTCATCGGGTTACGGGAGGATCAA
ATATACTGCTTAGATGCGTCCAACGGCCCAACCTGTTGGAATGGCCAGGATGGC
GGGCTAGAAGGCTTACGGCAGAAGGGCTGGAGTCTAGTCAGCTTATTGATGATA
GATAGAGAATCTCAAATCAGGAACACAAGAACCAAAATACTAGCTCAAGGAGA
CAACCAGGTTTTATGTCCGACATACATGTTGTCGCCAGGGCTATCTCAAGAGGGG
CTCCTCTATGAATTGGAGAGAATATCAAGGAATGCACTTTCGATATACAGAGCC
GTCGAGGAAGGGGCATCTAAGCTAGGGCTGATCATCAAGAAAGAAGAGACCAT
GTGTAGTTATGACTTCCTCATCTATGGAAAAACCCCTTTGTTTAGAGGTAACATA
TTGGTGCCTGAGTCCAAAAGATGGGCCAGAGTCTCTTGCGTCTCTAATGACCAAA
TAGTCAACCTCGCCAATATAATGTCGACAGTGTCCACCAATGCGCTAACAGTGG
CACAACACTCTCAATCTTTGATCAAACCGATGAGGGATTTTCTGCTCATGTCAGT
ACAGGCAGTCTTTCACTACCTGCTATTTAGCCCAATCTTAAAGGGAAGAGTTTAC
AAGATTCTGAGCGCTGAAGGGGAGAGCTTTCTCCTAGCCATGTCAAGGATAATC
TATCTAGATCCTTCTTTGGGAGGGATATCTGGAATGTCCCTCGGAAGATTCCATA
TACGACAGTTCTCAGACCCTGTCTCTGAAGGGTTATCCTTCTGGAGAGAGATCTG
GTTAAGCTCCCAAGAGTCCTGGATTCACGCGTTGTGTCAAGAGGCTGGAAACCC
AGATCTTGGAGAGAGAACACTCGAGAGCTTCACTCGCCTTCTAGAAGATCCGAC
```

-continued
```
CACCTTAAATATCAGAGGAGGGGCCAGTCCTACCATTCTACTCAAGGATGCAAT

CAGAAAGGCTTTATATGACGAGGTGGACAAGGTGGAAAATTCAGAGTTTCGAGA

GGCAATCCTGTTGTCCAAGACCCATAGAGATAATTTTATACTCTTCTTAATATCT

GTTGAGCCTCTGTTTCCTCGATTTCTCAGTGAGCTATTCAGTTCGTCTTTTTTGGG

AATCCCCGAGTCAATCATTGGATTGATACAAAACTCCCGAACGATAAGAAGGCA

GTTTAGAAAGAGTCTCTCAAAAACTTTAGAAGAATCCTTCTACAACTCAGAGATC

CACGGGATTAGTCGGATGACCCAGACACCTCAGAGGGTTGGGGGGTGTGGCCT

TGCTCTTCAGAGAGGGCAGATCTACTTAGGGAGATCTCTTGGGGAAGAAAAGTG

GTAGGCACGACAGTTCCTCACCCTTCTGAGATGTTGGGATTACTTCCCAAGTCCT

CTATTTCTTGCACTTGTGGAGCAACAGGAGGAGGCAATCCTAGAGTTTCTGTATC

AGTACTCCCGTCCTTTGATCAGTCATTTTTTTCACGAGGCCCCCTAAAGGGATAC

TTGGGCTCGTCCACCTCTATGTCGACCCAGCTATTCCATGCATGGGAAAAAGTCA

CTAATGTTCATGTGGTGAAGAGAGCTCTATCGTTAAAAGAATCTATAAACTGGTT

CATTACTAGAGATTCCAACTTGGCTCAAGCTCTAATTAGGAACATTATGTCTCTG

ACAGGCCCTGATTTCCCTCTAGAGGAGGCCCCTGTCTTCAAAAGGACGGGGTCA

GCCTTGCATAGGTTCAAGTCTGCCAGATACAGCGAAGGAGGGTATTCTTCTGTCT

GCCCGAACCTCCTCTCTCATATTTCTGTTAGTACAGACACCATGTCTGATTTGACC

CAAGACGGGAAGAACTACGATTTCATGTTCCAGCCATTGATGCTTTATGCACAGA

CATGGACATCAGAGCTGGTACAGAGAGACACAAGGCTAAGAGACTCTACGTTTC

ATTGGCACCTCCGATGCAACAGGTGTGTGAGACCCATTGACGACGTGACCCTGG

AGACCTCTCAGATCTTCGAGTTTCCGGATGTGTCGAAAAGAATATCCAGAATGGT

TTCTGGGGCTGTGCCTCACTTCCAGAGGCTTCCCGATATCCGTCTGAGACCAGGA

GATTTTGAATCTCTAAGCGGTAGAGAAAAGTCTCACCATATCGGATCAGCTCAG

GGGCTCTTATACTCAATCTTAGTGGCAATTCACGACTCAGGATACAATGATGGAA

CCATCTTCCCTGTCAACATATACGGCAAGGTTTCCCCTAGAGACTATTTGAGAGG

GCTCGCAAGGGAGTATTGATAGGATCCTCGATTTGCTTCTTGACAAGAATGACA

AATATCAATATTAATAGACCTCTTGAATTGGTCTCAGGGGTAATCTCATATATTC

TCCTGAGGCTAGATAACCATCCCTCCTTGTACATAATGCTCAGAGAACCGTCTCT

TAGAGGAGAGATATTTTCTATCCCTCAGAAAATCCCCGCCGCTTATCCAACCACT

ATGAAAGAAGGCAACAGATCAATCTTGTGTTATCTCCAACATGTGCTACGCTATG

AGCGAGAGATAATCACGGCGTCTCCAGAGAATGACTGGCTATGGATCTTTTCAG

ACTTTAGAAGTGCCAAAATGACGTACCTATCCCTCATTACTTACCAGTCTCATCT

TCTACTCCAGAGGGTTGAGAGAAACCTATCTAAGAGTATGAGAGATAACCTGCG

ACAATTGAGTTCTTTGATGAGGCAGGTGCTGGGCGGCACGGAGAAGATACCTT

AGAGTCAGACGACAACATTCAACGACTGCTAAAAGACTCTTTACGAAGGACAAG

ATGGGTGGATCAAGAGGTGCGCCATGCAGCTAGAACCATGACTGGAGATTACAG

CCCCAACAAGAAGGTGTCCCGTAAGGTAGGATGTTCAGAATGGGTCTGCTCTGC

TCAACAGGTTGCAGTCTCTACCTCAGCAAACCCGGCCCCTGTCTCGGAGCTTGAC

ATAAGGGCCCTCTCTAAGAGGTTCCAGAACCCTTTGATCTCGGGCTTGAGAGTGG

TTCAGTGGGCAACCGGTGCTCATTATAAGCTTAAGCCTATTCTAGATGATCTCAA

TGTTTTCCCATCTCTCTGCCTTGTAGTTGGGGACGGGTCAGGGGGGATATCAAGG
```

-continued

```
GCAGTCCTCAACATGTTTCCAGATGCCAAGCTTGTGTTCAACAGTCTTTTAGAGG

TGAATGACCTGATGGCTTCCGGAACACATCCACTGCCTCCTTCAGCAATCATGAG

GGGAGGAAATGATATCGTCTCCAGAGTGATAGATCTTGACTCAATCTGGGAAAA

ACCGTCCGACTTGAGAAACTTGGCAACCTGGAAATACTTCCAGTCAGTCCAAAA

GCAGGTCAACATGTCCTATGACCTCATTATTTGCGATGCAGAAGTTACTGACATT

GCATCTATCAACCGGATCACCCTGTTAATGTCCGATTTTGCATTGTCTATAGATG

GACCACTCTATTTGGTCTTCAAAACTTATGGGACTATGCTAGTAAATCCAAACTA

CAAGGCTATTCAACACCTGTCAAGAGCGTTCCCCTCGGTCACAGGGTTTATCACC

CAAGTAACTTCGTCTTTTTCATCTGAGCTCTACCTCCGATTCTCCAAACGAGGGA

AGTTTTTCAGAGATGCTGAGTACTTGACCTCTTCCACCCTTCGAGAAATGAGCCT

TGTGTTATTCAATTGTAGCAGCCCCAAGAGTGAGATGCAGAGAGCTCGTTCCTTG

AACTATCAGGATCTTGTGAGAGGATTTCCTGAAGAAATCATATCAAATCCTTACA

ATGAGATGATCATAACTCTGATTGACAGTGATGTAGAATCTTTTCTAGTCCACAA

GATGGTTGATGATCTTGAGTTACAGAGGGGAACTCTGTCTAAAGTGGCTATCATT

ATAGCCATCATGATAGTTTTCTCCAACAGAGTCTTCAACGTTTCCAAACCCCTAA

CTGACCCCTCGTTCTATCCACCGTCTGATCCCAAAATCCTGAGGCACTTCAACAT

ATGTTGCAGTACTATGATGTATCTATCTACTGCTTTAGGTGACGTCCCTAGCTTCG

CAAGACTTCACGACCTGTATAACAGACCTATAACTTATTACTTCAGAAAGCAAGT

CATTCGAGGGAACGTTTATCTATCTTGGAGTTGGTCCAACGACACCTCAGTGTTC

AAAAGGGTAGCCTGTAATTCTAGCCTGAGTCTGTCATCTCACTGGATCAGGTTGA

TTTACAAGATAGTGAAGACTACCAGACTCGTTGGCAGCATCAAGGATCTATCCA

GAGAAGTGGAAAGACACCTTCATAGGTACAACAGGTGGATCACCCTAGAGGATA

TCAGATCTAGATCATCCCTACTAGACTACAGTTGCCTGTGAACCGGATACTCCTG

GAAGCCTGCCCATGCTAAGACTCTTGTGTGATGTATCTTGAAAAAAACAAGATCC

TAAATCTGAACCTTTGGTTGTTTGATTGTTTTTCTCAttttttgttgtttatttgttaagcgt.
```

In one embodiment, the nucleic acid comprises the sequence of SEQ ID NO: 10, shown below (RABV vector: Coravax V3-China (S1-VSVG-E26)):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAaATGTGT
```

```
GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAcatgaaaaaaactaacacccctcccGTACGCCACCATGTTCGTGTTTCTGGTGCTGCT

GCCTCTGGTGAGCTCCCAGTGCGTGAACCTGACCACAAGGACCCAGCTGCCCCC

TGCCTATACCAATTCCTTCACACGGGGCGTGTACTATCCCGACAAGGTGTTCCGG

AGCAGCGTGCTGCACTCCACACAGGATCTGTTTCTGCCTTTCTTTTCTAACGTGAC

CTGGTTCCACGCCATCCACGTGAGCGGCACCAATGGCACAAAGCGGTTCGACAA

TCCAGTGCTGCCCTTTAACGATGGCGTGTACTTCGCCTCCACCGAGAAGTCTAAC

ATCATCAGAGGCTGGATCTTTGGCACCACACTGGACAGCAAGACACAGTCCCTG

CTGATCGTGAACAATGCCACCAACGTGGTCATCAAGGTGTGCGAGTTCCAGTTTT

GTAATGATCCATTCCTGGGCGTGTACTATCACAAGAACAATAAGTCTTGGATGGA

GAGCGAGTTTCGCGTGTATTCCTCTGCCAACAATTGCACATTTGAGTACGTGTCC

CAGCCCTTCCTGATGGACCTGGAGGGCAAGCAGGGCAATTTCAAGAACCTGAGG

GAGTTCGTGTTTAAGAATATCGATGGCTACTTCAAAATCTACTCCAAGCACACCC

CAATCAACCTGGTGCGCGACCTGCCACAGGGCTTCTCTGCCCTGGAGCCACTGGT

GGATCTGCCCATCGGCATCAACATCACCCGGTTTCAGACACTGCTGGCCCTGCAC

AGAAGCTACCTGACACCAGGCGACAGCTCCTCTGGATGGACCGCAGGAGCAGCA

GCCTACTATGTGGGCTATCTGCAGCCCAGGACCTTCCTGCTGAAGTACAACGAG

AATGGCACCATCACAGACGCCGTGGATTGCGCCCTGGATCCCCTGTCTGAGACC

AAGTGTACACTGAAGAGCTTTACCGTGGAGAAGGGCATCTATCAGACAAGCAAT

TTCAGGGTGCAGCCTACCGAGTCCATCGTGCGCTTTCCCAATATCACAAACCTGT

GCCCTTTTGGCGAGGTGTTCAACGCAACCCGCTTCGCCAGCGTGTACGCCTGGAA

TAGGAAGCGCATCTCCAACTGCGTGGCCGACTATTCTGTGCTGTACAACAGCGCC

TCCTTCTCTACCTTTAAGTGCTATGGCGTGAGCCCCACAAAGCTGAATGACCTGT

GCTTTACCAACGTGTACGCCGATTCCTTCGTGATCAGGGGCGACGAGGTGCGCC

AGATCGCACCAGGACAGACAGGCAAGATCGCAGACTACAATTATAAGCTGCCTG

ACGATTTCACCGGCTGCGTGATCGCCTGGAACTCTAACAATCTGGATAGCAAAGT

GGGCGGCAACTACAATTATCTGTACCGGCTGTTTAGAAAGTCTAATCTGAAGCCA
```

-continued

```
TTCGAGAGGGACATCTCCACAGAAATCTACCAGGCCGGCTCTACCCCCTGCAAT

GGCGTGGAGGGCTTTAACTGTTATTTCCCTCTGCAGAGCTACGGCTTCCAGCCAA

CAAACGGCGTGGGCTATCAGCCCTACCGCGTGGTGGTGCTGTCTTTTGAGCTGCT

GCACGCACCTGCAACAGTGTGCGGACCAAAGAAGAGCACCAATCTGGTGAAGA

ACAAGTGCGTGAACTTCAACTTCAACGGACTGACCGGAACAGGCGTGCTGACCG

AGTCCAACAAGAAGTTCCTGCCTTTTCAGCAGTTCGGCAGGGACATCGCAGATA

CCACAGACGCCGTGCGCGACCCTCAGACCCTGGAGATCCTGGACATCACACCAT

GCTCCTTCGGCGGCGTGTCTGTGATCACACCAGGCACCAATACAAGCAACCAGG

TGGCCGTGCTGTATCAGGACGTGAATTGTACCGAGGTGCCAGTGGCAATCCACG

CAGATCAGCTGACCCCTACATGGCGGGTGTACTCTACCGGCAGCAACGTGTTCC

AGACAAGAGCCGGATGCCTGATCGGAGCAGAGCACGTGAACAATAGCTATGAGT

GCGACATCCCTATCGGCGCCGGCATCTGTGCCTCCTACCAGACCCAGACAAACTC

CCCAAGGTCTGTGGGCGATACAGGCCTGTCCAAGAATCCAATCGAGCTGGTAGA

GGGCTGGTTCAGCAGTTGGAAAAGCTCCATCGCCTCCTTTTTCTTTATCATCGGC

CTGATCATCGGACTGTTCCTGGTGCTCCGCGTGGGTATCCACCTGTGCATCAAGC

TGAAGCACACCAAGAAAAGACAGATTTATACAGACATCGAGATGAACCGCCTGG

GAAAGTGAGCTAGCCATGAAAAAAACTAACACCCCTCCTTTCGAACCATCCCAA

ACATGAGCAAGATCTTTGTCAATCCTAGTGCTATTAGAGCCGGTCTGGCCGATCT

TGAGATGGCTGAAGAAACTGTTGATCTGATCAATAGAAATATCGAAGACAATCA

GGCTCATCTCCAAGGGGAACCCATAGAGGTGGACAATCTCCCTGAGGATATGGG

GCGACTTCACCTGGATGATGGAAAATCGCCCAACCATGGTGAGATAGCCAAGGT

GGGAGAAGGCAAGTATCGAGAGGACTTTCAGATGGATGAAGGAGAGGATCCTA

GCTTCCTGTTCCAGTCATACCTGGAAAATGTTGGAGTCCAAATAGTCAGACAAAT

GAGGTCAGGAGAGAGATTTCTCAAGATATGGTCACAGACCGTAGAAGAGATTAT

ATCCTATGTCGCGGTCAACTTTCCCAACCCTCCAGGAAAGTCTTCAGAGGATAAA

TCAACCCAGACTACTGGCCGAGAGCTCAAGAAGGAGACAACACCCACTCCTTCT

CAGAGAGAAAGCCAATCATCGAAAGCCAGGATGGCGGCTCAAATTGCTTCTGGC

CCTCCAGCCCTTGAATGGTCGGCTACCAATGAAGAGGATGATCTATCAGTGGAG

GCTGAGATCGCTCACCAGATTGCAGAAAGTTTCTCCAAAAAATATAAGTTTCCCT

CTCGATCCTCAGGGATACTCTTGTATAATTTTGAGCAATTGAAAATGAACCTTGA

TGATATAGTTAAAGAGGCAAAAAATGTACCAGGTGTGACCCGTTTAGCCCATGA

CGGGTCCAAACTCCCCCTAAGATGTGTACTGGGATGGGTCGCTTTGGCCAACTCT

AAGAAATTCCAGTTGTTAGTCGAATCCGACAAGCTGAGTAAAATCATGCAAGAT

GACTTGAATCGCTATACATCTTGCTAACCGAACCTCTCCCCTCAGTCCCTCTAGA

CAATAAAATCCGAGATGTCCCAAAGTCAACATGAAAAAAACAGGCAACACCACT

GATAAAATGAACCTCCTACGTAAGATAGTGAAAAACCGCAGGGACGAGGACACT

CAAAAATCCTCTCCCGCGTCAGCCCCTCTGGATGACGATGACTTGTGGCTTCCAC

CCCCTGAATACGTCCCGCTGAAAGAACTTACAGGCAAGAAGAACATGAGGAACT

TTTGTATCAACGGAAGGGTTAAAGTGTGTAGCCCGAATGGTTACTCGTTCAGGAT

CCTGCGGCACATTCTGAAATCATTCGACGAGATATATTCTGGGAATCATAGGATG

ATCGGGTTAGTCAAAGTGGTTATTGGACTGGCTTTGTCAGGATCTCCAGTCCCTG
```

```
AGGGCCTGAACTGGGTATACAAATTGAGGAGAACCTTTATCTTCCAGTGGGCTG
ATTCCAGGGGCCCTCTTGAAGGGGAGGAGTTGGAATACTCTCAGGAGATCACTT
GGGATGATGATACTGAGTTCGTCGGATTGCAAATAAGAGTGATTGCAAAACAGT
GTCATATCCAGGGCAGAGTCTGGTGTATCAACATGAACCCGAGAGCATGTCAAC
TATGGTCTGACATGTCTCTTCAGACACAAAGGTCCGAAGAGGACAAAGATTCCT
CTCTGCTTCTAGAATAATCAGATTATATCCCGCAAATTTATCACTTGTTTACCTCT
GGAGGAGAGAACATATGGGCTCAACTCCAACCCTTGGGAGCAATATAACAAAAA
ACATGTTATGGTGCCATTAAACCGCTGCATTTCATCAAAGTCAAGTTGATTACCT
TTACATTTTGATCCTCTTGGATGTGAAAAAAACTATTAACATCCCTCAAAAGACcc
cgggAAAGATGGTTCCTCAGGCTCTCCTGTTTGTACCCCTTCTGGTTTTTCCATTGT
GTTTTGGGAAATTCCCTATTTACACGATACCAGACAAGCTTGGTCCCTGGAGTCC
GATTGACATACATCACCTCAGCTGCCCAAACAATTTGGTAGTGGAGGACGAAGG
ATGCACCAACCTGTCAGGGTTCTCCTACATGGAACTTAAAGTTGGATACATCTTA
GCCATAAAAGTGAACGGGTTCACTTGCACAGGCGTTGTGACGGAGGCTGAAACC
TACACTAACTTCGTTGGTTATGTCACAACCACGTTCAAAAGAAAGCATTTCCGCC
CAACACCAGATGCATGTAGAGCCGCGTACAACTGGAAGATGGCCGGTGACCCCA
GATATGAAGAGTCTCTACACAATCCGTACCCTGACTACCGCTGGCTTCGAACTGT
AAAAACCACCAAGGAGTCTCTCGTTATCATATCTCCAAGTGTGGCAGATTTGGAC
CCATATGACAGATCCCTTCACTCGAGGGTCTTCCCTAGCGGGAAGTGCTCAGGA
GTAGCGGTGTCTTCTACCTACTGCTCCACTAACCACGATTACACCATTTGGATGC
CCGAGAATCCGAGACTAGGGATGTCTTGTGACATTTTTACCAATAGTAGAGGGA
AGAGAGCATCCAAAGGGAGTGAGACTTGCGGCTTTGTAGATGAAAGAGGCCTAT
ATAAGTCTTTAAAAGGAGCATGCAAACTCAAGTTATGTGGAGTTCTAGGACTTA
GACTTATGGATGGAACATGGGTCTCGATGCAAACATCAAATGAAACCAAATGGT
GCCCTCCCGATAAGTTGGTGAACCTGCACGACTTTCGCTCAGACGAAATTGAGC
ACCTTGTTGTAGAGGAGTTGGTCAGGAAGAGAGAGGAGTGTCTGGATGCACTAG
AGTCCATCATGACAACCAAGTCAGTGAGTTTCAGACGTCTCAGTCATTTAAGAAA
ACTTGTCCCTGGGTTTGGAAAAGCATATACCATATTCAACAAGACCTTGATGGAA
GCCGATGCTCACTACAAGTCAGTCgagACTTGGAATGAGATCCTCCCTTCAAAAG
GGTGTTTAAGAGTTGGGGGGAGGTGTCATCCTCATGTGAACGGGGTGTTTTTCAA
TGGTATAATATTAGGACCTGACGGCAATGTCTTAATCCCAGAGATGCAATCATCC
CTCCTCCAGCAACATATGGAGTTGTTGGAATCCTCGGTTATCCCCCTTGTGCACC
CCCTGGCAGACCCGTCTACCGTTTTCAAGGACGGTGACGAGGCTGAGGATTTTGT
TGAAGTTCACCTTCCCGATGTGCACAATCAGGTCTCAGGAGTTGACTTGGGTCTC
CCGAACTGGGGGAAGTATGTATTACTGAGTGCAGGGGCCCTGACTGCCTTGATG
TTGATAATTTTCCTGATGACATGTTGTAGAAGAGTCAATCGATCAGAACCTACGC
AACACAATCTCAGAGGGACAGGGAGGGAGGTGTCAGTCACTCCCCAAAGCGGG
AAGATCATATCTTCATGGGAATCACACAAGAGTGGGGGTGAGACCAGACTGTAA
ttaattaaCGTCCTTTCAACGATCCAAGTCcatgaaaaaaactaacaccccctcccgtacctagcTTATAAA
GTGCTGGGTCATCTAAGCTTTTCAGTCGAGAAAAAAACATTAGATCAGAAGAAC
```

-continued

```
AACTGGCAACACTTCTCAACCTGAGACTTACTTCAAGATGCTCGATCCTGGAGAG

GTCTATGATGACCCTATTGACCCAATCGAGTTAGAGGCTGAACCCAGAGGAACC

CCCATTGTCCCCAACATCTTGAGGAACTCTGACTACAATCTCAACTCTCCTTTGA

TAGAAGATCCTGCTAGACTAATGTTAGAATGGTTAAAAACAGGGAATAGACCTT

ATCGGATGACTCTAACAGACAATTGCTCCAGGTCTTTCAGAGTTTTGAAAGATTA

TTTCAAGAAGGTAGATTTGGGTTCTCTCAAGGTGGGCGGAATGGCTGCACAGTC

AATGATTTCTCTCTGGTTATATGGTGCCCACTCTGAATCCAACAGGAGCCGGAGA

TGTATAACAGACTTGGCCCATTTCTATTCCAAGTCGTCCCCCATAGAGAAGCTGT

TGAATCTCACGCTAGGAAATAGAGGGCTGAGAATCCCCCCAGAGGGAGTGTTAA

GTTGCCTTGAGAGGGTTGATTATGATAATGCATTTGGAAGGTATCTTGCCAACAC

GTATTCCTCTTACTTGTTCTTCCATGTAATCACCTTATACATGAACGCCCTAGACT

GGGATGAAGAAAAGACCATCCTAGCATTATGGAAAGATTTAACCTCAGTGGACA

TCGGGAAGGACTTGGTAAAGTTCAAAGACCAAATATGGGGACTGCTGATCGTGA

CAAAGGACTTTGTTTACTCCCAAAGTTCCAATTGTCTTTTTGACAGAAACTACAC

ACTTATGCTAAAAGATCTTTTCTTGTCTCGCTTCAACTCCTTAATGGTCTTGCTCT

CTCCCCCAGAGCCCCGATACTCAGATGACTTGATATCTCAACTATGCCAGCTGTA

CATTGCTGGGGATCAAGTCTTGTCTATGTGTGGAAACTCCGGCTATGAAGTCATC

AAAATATTGGAGCCATATGTCGTGAATAGTTTAGTCCAGAGAGCAGAAAAGTTT

AGGCCTCTCATTCATTCCTTGGGAGACTTTCCTGTATTTATAAAAGACAAGGTAA

GTCAACTTGAAGAGACGTTCGGTCCCTGTGCAAGAAGGTTCTTTAGGGCTCTGGA

TCAATTCGACAACATACATGACTTGGTTTTTGTGTTTGGCTGTTACAGGCATTGG

GGGCACCCATATATAGATTATCGAAAGGGTCTGTCAAAACTATATGATCAGGTTC

ACCTTAAAAAAATGATAGATAAGTCCTACCAGGAGTGCTTAGCAAGCGACCTAG

CCAGGAGGATCCTTAGATGGGGTTTTGATAAGTACTCCAAGTGGTATCTGGATTC

AAGATTCCTAGCCCGAGACCACCCCTTGACTCCTTATATCAAAACCCAAACATGG

CCACCCAAACATATTGTAGACTTGGTGGGGATACATGGCACAAGCTCCCGATC

ACGCAGATCTTTGAGATTCCTGAATCAATGGATCCGTCAGAAATATTGGATGACA

AATCACATTCTTTCACCAGAACGAGACTAGCTTCTTGGCTGTCAGAAAACCGAGG

GGGGCCTGTTCCTAGCGAAAAAGTTATTATCACGGCCCTGTCTAAGCCGCCTGTC

AATCCCCGAGAGTTTCTGAGGTCTATAGACCTCGGAGGATTGCCAGATGAAGAC

TTGATAATTGGCCTCAAGCCAAAGGAACGGGAATTGAAGATTGAAGGTCGATTC

TTTGCTCTAATGTCATGGAATCTAAGATTGTATTTTGTCATCACTGAAAAACTCTT

GGCCAACTACATCTTGCCACTTTTTGACGCGCTGACTATGACAGACAACCTGAAC

AAGGTGTTTAAAAAGCTGATCGACAGGGTCACCGGGCAAGGGCTTTTGGACTAT

TCAAGGGTCACATATGCATTTCACCTGGACTATGAAAAGTGGAACAACCATCAA

AGATTAGAGTCAACAGAGGATGTATTTTCTGTCCTAGATCAAGTGTTTGGATTGA

AGAGAGTGTTTTCTAGAACACACGAGTTTTTTCAAAAGGCCTGGATCTATTATTC

AGACAGATCAGACCTCATCGGGTTACGGGAGGATCAAATATACTGCTTAGATGC

GTCCAACGGCCCAACCTGTTGGAATGGCCAGGATGGCGGGCTAGAAGGCTTACG

GCAGAAGGGCTGGAGTCTAGTCAGCTTATTGATGATAGATAGAGAATCTCAAAT

CAGGAACACAAGAACCAAAATACTAGCTCAAGGAGACAACCAGGTTTTATGTCC
```

-continued

```
GACATACATGTTGTCGCCAGGGCTATCTCAAGAGGGGCTCCTCTATGAATTGGAG
AGAATATCAAGGAATGCACTTTCGATATACAGAGCCGTCGAGGAAGGGGCATCT
AAGCTAGGGCTGATCATCAAGAAAGAAGAGACCATGTGTAGTTATGACTTCCTC
ATCTATGGAAAAACCCCTTTGTTTAGAGGTAACATATTGGTGCCTGAGTCCAAAA
GATGGGCCAGAGTCTCTTGCGTCTCTAATGACCAAATAGTCAACCTCGCCAATAT
AATGTCGACAGTGTCCACCAATGCGCTAACAGTGGCACAACACTCTCAATCTTTG
ATCAAACCGATGAGGGATTTTCTGCTCATGTCAGTACAGGCAGTCTTTCACTACC
TGCTATTTAGCCCAATCTTAAAGGGAAGAGTTTACAAGATTCTGAGCGCTGAAG
GGGAGAGCTTTCTCCTAGCCATGTCAAGGATAATCTATCTAGATCCTTCTTTGGG
AGGGATATCTGGAATGTCCCTCGGAAGATTCCATATACGACAGTTCTCAGACCCT
GTCTCTGAAGGGTTATCCTTCTGGAGAGAGATCTGGTTAAGCTCCCAAGAGTCCT
GGATTCACGCGTTGTGTCAAGAGGCTGGAAACCCAGATCTTGGAGAGAGAACAC
TCGAGAGCTTCACTCGCCTTCTAGAAGATCCGACCACCTTAAATATCAGAGGAG
GGGCCAGTCCTACCATTCTACTCAAGGATGCAATCAGAAAGGCTTTATATGACG
AGGTGGACAAGGTGGAAAATTCAGAGTTTCGAGAGGCAATCCTGTTGTCCAAGA
CCCATAGAGATAATTTTATACTCTTCTTAATATCTGTTGAGCCTCTGTTTCCTCGA
TTTCTCAGTGAGCTATTCAGTTCGTCTTTTTGGGAATCCCCGAGTCAATCATTGG
ATTGATACAAAACTCCCGAACGATAAGAAGGCAGTTTAGAAAGAGTCTCTCAAA
AACTTTAGAAGAATCCTTCTACAACTCAGAGATCCACGGGATTAGTCGGATGAC
CCAGACACCTCAGAGGGTTGGGGGGGTGTGGCCTTGCTCTTCAGAGAGGGCAGA
TCTACTTAGGGAGATCTCTTGGGGAAGAAAAGTGGTAGGCACGACAGTTCCTCA
CCCTTCTGAGATGTTGGGATTACTTCCCAAGTCCTCTATTTCTTGCACTTGTGGAG
CAACAGGAGGAGGCAATCCTAGAGTTTCTGTATCAGTACTCCCGTCCTTTGATCA
GTCATTTTTTTCACGAGGCCCCCTAAAGGGATACTTGGGCTCGTCCACCTCTATG
TCGACCCAGCTATTCCATGCATGGGAAAAAGTCACTAATGTTCATGTGGTGAAG
AGAGCTCTATCGTTAAAAGAATCTATAAACTGGTTCATTACTAGAGATTCCAACT
TGGCTCAAGCTCTAATTAGGAACATTATGTCTCTGACAGGCCCTGATTTCCCTCT
AGAGGAGGCCCCTGTCTTCAAAAGGACGGGGTCAGCCTTGCATAGGTTCAAGTC
TGCCAGATACAGCGAAGGAGGGTATTCTTCTGTCTGCCCGAACCTCCTCTCTCAT
ATTTCTGTTAGTACAGACACCATGTCTGATTTGACCCAAGACGGGAAGAACTACG
ATTTCATGTTCCAGCCATTGATGCTTTATGCACAGACATGGACATCAGAGCTGGT
ACAGAGAGACACAAGGCTAAGAGACTCTACGTTTCATTGGCACCTCCGATGCAA
CAGGTGTGTGAGACCCATTGACGACGTGACCCTGGAGACCTCTCAGATCTTCGA
GTTTCCGGATGTGTCGAAAAGAATATCCAGAATGGTTTCTGGGGCTGTGCCTCAC
TTCCAGAGGCTTCCCGATATCCGTCTGAGACCAGGAGATTTTGAATCTCTAAGCG
GTAGAGAAAAGTCTCACCATATCGGATCAGCTCAGGGGCTCTTATACTCAATCTT
AGTGGCAATTCACGACTCAGGATACAATGATGGAACCATCTTCCCTGTCAACATA
TACGGCAAGGTTTCCCCTAGAGACTATTTGAGAGGGCTCGCAAGGGGAGTATTG
ATAGGATCCTCGATTTGCTTCTTGACAAGAATGACAAATATCAATATTAATAGAC
CTCTTGAATTGGTCTCAGGGGTAATCTCATATATTCTCCTGAGGCTAGATAACCA
```

-continued

```
TCCCTCCTTGTACATAATGCTCAGAGAACCGTCTCTTAGAGGAGAGATATTTTCT

ATCCCTCAGAAAATCCCCGCCGCTTATCCAACCACTATGAAAGAAGGCAACAGA

TCAATCTTGTGTTATCTCCAACATGTGCTACGCTATGAGCGAGAGATAATCACGG

CGTCTCCAGAGAATGACTGGCTATGGATCTTTTCAGACTTTAGAAGTGCCAAAAT

GACGTACCTATCCCTCATTACTTACCAGTCTCATCTTCTACTCCAGAGGGTTGAG

AGAAACCTATCTAAGAGTATGAGAGATAACCTGCGACAATTGAGTTCTTTGATG

AGGCAGGTGCTGGGCGGGCACGGAGAAGATACCTTAGAGTCAGACGACAACATT

CAACGACTGCTAAAAGACTCTTTACGAAGGACAAGATGGGTGGATCAAGAGGTG

CGCCATGCAGCTAGAACCATGACTGGAGATTACAGCCCCAACAAGAAGGTGTCC

CGTAAGGTAGGATGTTCAGAATGGGTCTGCTCTGCTCAACAGGTTGCAGTCTCTA

CCTCAGCAAACCCGGCCCCTGTCTCGGAGCTTGACATAAGGGCCCTCTCTAAGA

GGTTCCAGAACCCTTTGATCTCGGGCTTGAGAGTGGTTCAGTGGGCAACCGGTGC

TCATTATAAGCTTAAGCCTATTCTAGATGATCTCAATGTTTTCCCATCTCTCTGCC

TTGTAGTTGGGGACGGGTCAGGGGGGATATCAAGGGCAGTCCTCAACATGTTTC

CAGATGCCAAGCTTGTGTTCAACAGTCTTTTAGAGGTGAATGACCTGATGGCTTC

CGGAACACATCCACTGCCTCCTTCAGCAATCATGAGGGGAGGAAATGATATCGT

CTCCAGAGTGATAGATCTTGACTCAATCTGGGAAAAACCGTCCGACTTGAGAAA

CTTGGCAACCTGGAAATACTTCCAGTCAGTCCAAAAGCAGGTCAACATGTCCTAT

GACCTCATTATTTGCGATGCAGAAGTTACTGACATTGCATCTATCAACCGGATCA

CCCTGTTAATGTCCGATTTTGCATTGTCTATAGATGGACCACTCTATTTGGTCTTC

AAAACTTATGGGACTATGCTAGTAAATCCAAACTACAAGGCTATTCAACACCTGT

CAAGAGCGTTCCCCTCGGTCACAGGGTTTATCACCCAAGTAACTTCGTCTTTTTC

ATCTGAGCTCTACCTCCGATTCTCCAAACGAGGGAAGTTTTTCAGAGATGCTGAG

TACTTGACCTCTTCCACCCTTCGAGAAATGAGCCTTGTGTTATTCAATTGTAGCA

GCCCCAAGAGTGAGATGCAGAGAGCTCGTTCCTTGAACTATCAGGATCTTGTGA

GAGGATTTCCTGAAGAAATCATATCAAATCCTTACAATGAGATGATCATAACTCT

GATTGACAGTGATGTAGAATCTTTTCTAGTCCACAAGATGGTTGATGATCTTGAG

TTACAGAGGGGAACTCTGTCTAAAGTGGCTATCATTATAGCCATCATGATAGTTT

TCTCCAACAGAGTCTTCAACGTTTCCAAACCCCTAACTGACCCCTCGTTCTATCC

ACCGTCTGATCCCAAAATCCTGAGGCACTTCAACATATGTTGCAGTACTATGATG

TATCTATCTACTGCTTTAGGTGACGTCCCTAGCTTCGCAAGACTTCACGACCTGT

ATAACAGACCTATAACTTATTACTTCAGAAAGCAAGTCATTCGAGGGAACGTTTA

TCTATCTTGGAGTTGGTCCAACGACACCTCAGTGTTCAAAAGGGTAGCCTGTAAT

TCTAGCCTGAGTCTGTCATCTCACTGGATCAGGTTGATTTACAAGATAGTGAAGA

CTACCAGACTCGTTGGCAGCATCAAGGATCTATCCAGAGAAGTGGAAAGACACC

TTCATAGGTACAACAGGTGGATCACCCTAGAGGATATCAGATCTAGATCATCCCT

ACTAGACTACAGTTGCCTGTGAACCGGATACTCCTGGAAGCCTGCCCATGCTAA

GACTCTTGTGTGATGTATCTTGAAAAAAACAAGATCCTAAATCTGAACCTTTGGT

TGTTTGATTGTTTTTCTCAttttttgttgtttatttgttaagcgt.
```

In one embodiment, the nucleic acid comprises the sequence of SEQ ID NO: 11, shown below (RABV vector: Coravax V3-South Africa (S1-VSVG-E26)):

ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAaATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAcatgaaaaaaactaacacccctcccGTACGCCACCATGTTCGTGTTTCTGGTGCTGCT

GCCTCTGGTGAGCTCCCAGTGCGTGAACTTCACCACAAGGACCCAGCTGCCCCCT

GCCTATACCAATTCCTTCACACGGGGCGTGTACTATCCCGACAAGGTGTTCCGGA

GCAGCGTGCTGCACTCCACACAGGATCTGTTTCTGCCTTTCTTTTCTAACGTGACC

TGGTTCCACGCCATCCACGTGAGCGGCACCAATGGCACAAAGCGGTTCGCCAAT

CCAGTGCTGCCCTTTAACGATGGCGTGTACTTCGCCTCCACCGAGAAGTCTAACA

TCATCAGAGGCTGGATCTTTGGCACCACACTGGACAGCAAGACACAGTCCCTGC

TGATCGTGAACAATGCCACCAACGTGGTCATCAAGGTGTGCGAGTTCCAGTTTTG

TAATGATCCATTCCTGGGCGTGTACTATCACAAGAACAATAAGTCTTGGATGGAG

AGCGAGTTTCGCGTGTATTCCTCTGCCAACAATTGCACATTTGAGTACGTGTCCC

AGCCCTTCCTGATGGACCTGGAGGGCAAGCAGGGCAATTTCAAGAACCTGAGGG

AGTTCGTGTTTAAGAATATCGATGGCTACTTCAAAATCTACTCCAAGCACACCCC

-continued

```
AATCAACCTGGTGCGCGGCCTGCCACAGGGCTTCTCTGCCCTGGAGCCACTGGTG

GATCTGCCCATCGGCATCAACATCACCCGGTTTCAGACACTGCTGGCCCTGCACA

GAAGCTACCTGACACCAGGCGACAGCTCCTCTGGATGGACCGCAGGAGCAGCAG

CCTACTATGTGGGCTATCTGCAGCCCAGGACCTTCCTGCTGAAGTACAACGAGA

ATGGCACCATCACAGACGCCGTGGATTGCGCCCTGGATCCCCTGTCTGAGACCA

AGTGTACACTGAAGAGCTTTACCGTGGAGAAGGGCATCTATCAGACAAGCAATT

TCAGGGTGCAGCCTACCGAGTCCATCGTGCGCTTTCCCAATATCACAAACCTGTG

CCCTTTTGGCGAGGTGTTCAACGCAACCCGCTTCGCCAGCGTGTACGCCTGGAAT

AGGAAGCGCATCTCCAACTGCGTGGCCGACTATTCTGTGCTGTACAACAGCGCCT

CCTTCTCTACCTTTAAGTGCTATGGCGTGAGCCCCACAAAGCTGAATGACCTGTG

CTTTACCAACGTGTACGCCGATTCCTTCGTGATCAGGGGCGACGAGGTGCGCCA

GATCGCACCAGGACAGACAGGCAATATCGCAGACTACAATTATAAGCTGCCTGA

CGATTTCACCGGCTGCGTGATCGCCTGGAACTCTAACAATCTGGATAGCAAAGTG

GGCGGCAACTACAATTATCTGTACCGGCTGTTTAGAAAGTCTAATCTGAAGCCAT

TCGAGAGGGACATCTCCACAGAAATCTACCAGGCCGGCTCTACCCCCTGCAATG

GCGTGAAGGGCTTTAACTGTTATTTCCCTCTGCAGAGCTACGGCTTCCAGCCAAC

ATATGGCGTGGGCTATCAGCCCTACCGCGTGGTGGTGCTGTCTTTTGAGCTGCTG

CACGCACCTGCAACAGTGTGCGGACCAAAGAAGAGCACCAATCTGGTGAAGAA

CAAGTGCGTGAACTTCAACTTCAACGGACTGACCGGAACAGGCGTGCTGACCGA

GTCCAACAAGAAGTTCCTGCCTTTTCAGCAGTTCGGCAGGGACATCGCAGATAC

CACAGACGCCGTGCGCGACCCTCAGACCCTGGAGATCCTGGACATCACACCATG

CTCCTTCGGCGGCGTGTCTGTGATCACACCAGGCACCAATACAAGCAACCAGGT

GGCCGTGCTGTATCAGGGCGTGAATTGTACCGAGGTGCCAGTGGCAATCCACGC

AGATCAGCTGACCCCTACATGGCGGGTGTACTCTACCGGCAGCAACGTGTTCCA

GACAAGAGCCGGATGCCTGATCGGAGCAGAGCACGTGAACAATAGCTATGAGTG

CGACATCCCTATCGGCGCCGGCATCTGTGCCTCCTACCAGACCCAGACAAACTCC

CCAAGGTCTGTGGGCGATACAGGCCTGTCCAAGAATCCAATCGAGCTGGTAGAG

GGCTGGTTCAGCAGTTGGAAAAGCTCCATCGCCTCCTTTTTCTTTATCATCGGCCT

GATCATCGGACTGTTCCTGGTGCTCCGCGTGGGTATCCACCTGTGCATCAAGCTG

AAGCACACCAAGAAAAGACAGATTTATACAGACATCGAGATGAACCGCCTGGG

AAAGTGAGCTAGCCATGAAAAAAACTAACACCCCTCCTTTCGAACCATCCCAAA

CATGAGCAAGATCTTTGTCAATCCTAGTGCTATTAGAGCCGGTCTGGCCGATCTT

GAGATGGCTGAAGAAACTGTTGATCTGATCAATAGAAATATCGAAGACAATCAG

GCTCATCTCCAAGGGGAACCCATAGAGGTGGACAATCTCCCTGAGGATATGGGG

CGACTTCACCTGGATGATGGAAAATCGCCCAACCATGGTGAGATAGCCAAGGTG

GGAGAAGGCAAGTATCGAGAGGACTTTCAGATGGATGAAGGAGAGGATCCTAG

CTTCCTGTTCCAGTCATACCTGGAAAATGTTGGAGTCCAAATAGTCAGACAAATG

AGGTCAGGAGAGAGATTTCTCAAGATATGGTCACAGACCGTAGAAGAGATTATA

TCCTATGTCGCGGTCAACTTTCCCAACCCTCCAGGAAAGTCTTCAGAGGATAAAT

CAACCCAGACTACTGGCCGAGAGCTCAAGAAGGAGACAACACCCACTCCTTCTC

AGAGAGAAAGCCAATCATCGAAAGCCAGGATGGCGGCTCAAATTGCTTCTGGCC
```

-continued

```
CTCCAGCCCTTGAATGGTCGGCTACCAATGAAGAGGATGATCTATCAGTGGAGG

CTGAGATCGCTCACCAGATTGCAGAAAGTTTCTCCAAAAAATATAAGTTTCCCTC

TCGATCCTCAGGGATACTCTTGTATAATTTTGAGCAATTGAAAATGAACCTTGAT

GATATAGTTAAAGAGGCAAAAAATGTACCAGGTGTGACCCGTTTAGCCCATGAC

GGGTCCAAACTCCCCCTAAGATGTGTACTGGGATGGGTCGCTTTGGCCAACTCTA

AGAAATTCCAGTTGTTAGTCGAATCCGACAAGCTGAGTAAAATCATGCAAGATG

ACTTGAATCGCTATACATCTTGCTAACCGAACCTCTCCCCTCAGTCCCTCTAGAC

AATAAAATCCGAGATGTCCCAAAGTCAACATGAAAAAAACAGGCAACACCACT

GATAAAATGAACCTCCTACGTAAGATAGTGAAAAACCGCAGGGACGAGGACACT

CAAAAATCCTCTCCCGCGTCAGCCCCTCTGGATGACGATGACTTGTGGCTTCCAC

CCCCTGAATACGTCCCGCTGAAAGAACTTACAGGCAAGAAGAACATGAGGAACT

TTTGTATCAACGGAAGGGTTAAAGTGTGTAGCCCGAATGGTTACTCGTTCAGGAT

CCTGCGGCACATTCTGAAATCATTCGACGAGATATATTCTGGGAATCATAGGATG

ATCGGGTTAGTCAAAGTGGTTATTGGACTGGCTTTGTCAGGATCTCCAGTCCCTG

AGGGCCTGAACTGGGTATACAAATTGAGGAGAACCTTTATCTTCCAGTGGGCTG

ATTCCAGGGGCCCTCTTGAAGGGGAGGAGTTGGAATACTCTCAGGAGATCACTT

GGGATGATGATACTGAGTTCGTCGGATTGCAAATAAGAGTGATTGCAAAACAGT

GTCATATCCAGGGCAGAGTCTGGTGTATCAACATGAACCCGAGAGCATGTCAAC

TATGGTCTGACATGTCTCTTCAGACACAAAGGTCCGAAGAGGACAAAGATTCCT

CTCTGCTTCTAGAATAATCAGATTATATCCCGCAAATTTATCACTTGTTTACCTCT

GGAGGAGAGAACATATGGGCTCAACTCCAACCCTTGGGAGCAATATAACAAAA

ACATGTTATGGTGCCATTAAACCGCTGCATTTCATCAAAGTCAAGTTGATTACCT

TTACATTTTGATCCTCTTGGATGTGAAAAAAACTATTAACATCCCTCAAAAGACcc cgggAAAGATGGTTCCTCAGGCTCTCCTGTTTGTACCCCTTCTGGTTTTTCCATTGT

GTTTTGGGAAATTCCCTATTTACACGATACCAGACAAGCTTGGTCCCTGGAGTCC

GATTGACATACATCACCTCAGCTGCCCAAACAATTTGGTAGTGGAGGACGAAGG

ATGCACCAACCTGTCAGGGTTCTCCTACATGGAACTTAAAGTTGGATACATCTTA

GCCATAAAAGTGAACGGGTTCACTTGCACAGGCGTTGTGACGGAGGCTGAAACC

TACACTAACTTCGTTGGTTATGTCACAACCACGTTCAAAAGAAAGCATTTCCGCC

CAACACCAGATGCATGTAGAGCCGCGTACAACTGGAAGATGGCCGGTGACCCCA

GATATGAAGAGTCTCTACACAATCCGTACCCTGACTACCGCTGGCTTCGAACTGT

AAAAACCACCAAGGAGTCTCTCGTTATCATATCTCCAAGTGTGGCAGATTTGGAC

CCATATGACAGATCCCTTCACTCGAGGGTCTTCCCTAGCGGGAAGTGCTCAGGA

GTAGCGGTGTCTTCTACCTACTGCTCCACTAACCACGATTACACCATTTGGATGC

CCGAGAATCCGAGACTAGGGATGTCTTGTGACATTTTTACCAATAGTAGAGGGA

AGAGAGCATCCAAAGGGAGTGAGACTTGCGGCTTTGTAGATGAAAGAGGCCTAT

ATAAGTCTTTAAAAGGAGCATGCAAACTCAAGTTATGTGGAGTTCTAGGACTTA

GACTTATGGATGGAACATGGGTCTCGATGCAAACATCAAATGAAACCAAATGGT

GCCCTCCCGATAAGTTGGTGAACCTGCACGACTTTCGCTCAGACGAAATTGAGC

ACCTTGTTGTAGAGGAGTTGGTCAGGAAGAGAGAGGAGTGTCTGGATGCACTAG
```

```
AGTCCATCATGACAACCAAGTCAGTGAGTTTCAGACGTCTCAGTCATTTAAGAAA

ACTTGTCCCTGGGTTTGGAAAAGCATATACCATATTCAACAAGACCTTGATGGAA

GCCGATGCTCACTACAAGTCAGTCgagACTTGGAATGAGATCCTCCCTTCAAAAG

GGTGTTTAAGAGTTGGGGGAGGTGTCATCCTCATGTGAACGGGGTGTTTTTCAA

TGGTATAATATTAGGACCTGACGGCAATGTCTTAATCCCAGAGATGCAATCATCC

CTCCTCCAGCAACATATGGAGTTGTTGGAATCCTCGGTTATCCCCCTTGTGCACC

CCCTGGCAGACCCGTCTACCGTTTTCAAGGACGGTGACGAGGCTGAGGATTTTGT

TGAAGTTCACCTTCCCGATGTGCACAATCAGGTCTCAGGAGTTGACTTGGGTCTC

CCGAACTGGGGGAAGTATGTATTACTGAGTGCAGGGGCCCTGACTGCCTTGATG

TTGATAATTTTCCTGATGACATGTTGTAGAAGAGTCAATCGATCAGAACCTACGC

AACACAATCTCAGAGGGACAGGGAGGGAGGTGTCAGTCACTCCCCAAAGCGGG

AAGATCATATCTTCATGGGAATCACACAAGAGTGGGGGTGAGACCAGACTGTAA ttaattaaCGTCCTTTCAACGATCCAAGTCcatgaaaaaaactaacacccctcccgtacctagcTTATAAA

GTGCTGGGTCATCTAAGCTTTTCAGTCGAGAAAAAAACATTAGATCAGAAGAAC

AACTGGCAACACTTCTCAACCTGAGACTTACTTCAAGATGCTCGATCCTGGAGAG

GTCTATGATGACCCTATTGACCCAATCGAGTTAGAGGCTGAACCCAGAGGAACC

CCCATTGTCCCCAACATCTTGAGGAACTCTGACTACAATCTCAACTCTCCTTTGA

TAGAAGATCCTGCTAGACTAATGTTAGAATGGTTAAAAACAGGGAATAGACCTT

ATCGGATGACTCTAACAGACAATTGCTCCAGGTCTTTCAGAGTTTTGAAAGATTA

TTTCAAGAAGGTAGATTTGGGTTCTCTCAAGGTGGGCGGAATGGCTGCACAGTC

AATGATTTCTCTCTGGTTATATGGTGCCCACTCTGAATCCAACAGGAGCCGGAGA

TGTATAACAGACTTGGCCCATTTCTATTCCAAGTCGTCCCCCATAGAGAAGCTGT

TGAATCTCACGCTAGGAAATAGAGGGCTGAGAATCCCCCAGAGGGAGTGTTAA

GTTGCCTTGAGAGGGTTGATTATGATAATGCATTTGGAAGGTATCTTGCCAACAC

GTATTCCTCTTACTTGTTCTTCCATGTAATCACCTTATACATGAACGCCCTAGACT

GGGATGAAGAAAAGACCATCCTAGCATTATGGAAAGATTTAACCTCAGTGGACA

TCGGGAAGGACTTGGTAAAGTTCAAAGACCAAATATGGGACTGCTGATCGTGA

CAAAGGACTTTGTTTACTCCCAAAGTTCCAATTGTCTTTTTGACAGAAACTACAC

ACTTATGCTAAAAGATCTTTTCTTGTCTCGCTTCAACTCCTTAATGGTCTTGCTCT

CTCCCCCAGAGCCCCGATACTCAGATGACTTGATATCTCAACTATGCCAGCTGTA

CATTGCTGGGGATCAAGTCTTGTCTATGTGTGGAAACTCCGGCTATGAAGTCATC

AAAATATTGGAGCCATATGTCGTGAATAGTTTAGTCCAGAGAGCAGAAAAGTTT

AGGCCTCTCATTCATTCCTTGGGAGACTTTCCTGTATTTATAAAAGACAAGGTAA

GTCAACTTGAAGAGACGTTCGGTCCCTGTGCAAGAAGGTTCTTTAGGGCTCTGGA

TCAATTCGACAACATACATGACTTGGTTTTTGTGTTTGGCTGTTACAGGCATTGG

GGGCACCCATATATAGATTATCGAAAGGGTCTGTCAAAACTATATGATCAGGTTC

ACCTTAAAAAAATGATAGATAAGTCCTACCAGGAGTGCTTAGCAAGCGACCTAG

CCAGGAGGATCCTTAGATGGGTTTTGATAAGTACTCCAAGTGGTATCTGGATTC

AAGATTCCTAGCCCGAGACCACCCCTTGACTCCTTATATCAAAACCCAAACATGG

CCACCCAAACATATTGTAGACTTGGTGGGGATACATGGCACAAGCTCCCGATC

ACGCAGATCTTTGAGATTCCTGAATCAATGGATCCGTCAGAAATATTGGATGACA
```

-continued

```
AATCACATTCTTTCACCAGAACGAGACTAGCTTCTTGGCTGTCAGAAAACCGAGG

GGGGCCTGTTCCTAGCGAAAAAGTTATTATCACGGCCCTGTCTAAGCCGCCTGTC

AATCCCCGAGAGTTTCTGAGGTCTATAGACCTCGGAGGATTGCCAGATGAAGAC

TTGATAATTGGCCTCAAGCCAAAGGAACGGGAATTGAAGATTGAAGGTCGATTC

TTTGCTCTAATGTCATGGAATCTAAGATTGTATTTTGTCATCACTGAAAAACTCTT

GGCCAACTACATCTTGCCACTTTTTGACGCGCTGACTATGACAGACAACCTGAAC

AAGGTGTTTAAAAAGCTGATCGACAGGGTCACCGGGCAAGGGCTTTTGGACTAT

TCAAGGGTCACATATGCATTTCACCTGGACTATGAAAAGTGGAACAACCATCAA

AGATTAGAGTCAACAGAGGATGTATTTTCTGTCCTAGATCAAGTGTTTGGATTGA

AGAGAGTGTTTTCTAGAACACACGAGTTTTTTCAAAAGGCCTGGATCTATTATTC

AGACAGATCAGACCTCATCGGGTTACGGGAGGATCAAATATACTGCTTAGATGC

GTCCAACGGCCCAACCTGTTGGAATGGCCAGGATGGCGGGCTAGAAGGCTTACG

GCAGAAGGGCTGGAGTCTAGTCAGCTTATTGATGATAGATAGAGAATCTCAAAT

CAGGAACACAAGAACCAAAATACTAGCTCAAGGAGACAACCAGGTTTTATGTCC

GACATACATGTTGTCGCCAGGGCTATCTCAAGAGGGGCTCCTCTATGAATTGGAG

AGAATATCAAGGAATGCACTTTCGATATACAGAGCCGTCGAGGAAGGGGCATCT

AAGCTAGGGCTGATCATCAAGAAAGAAGAGACCATGTGTAGTTATGACTTCCTC

ATCTATGGAAAAACCCCTTTGTTTAGAGGTAACATATTGGTGCCTGAGTCCAAAA

GATGGGCCAGAGTCTCTTGCGTCTCTAATGACCAAATAGTCAACCTCGCCAATAT

AATGTCGACAGTGTCCACCAATGCGCTAACAGTGGCACAACACTCTCAATCTTTG

ATCAAACCGATGAGGGATTTTCTGCTCATGTCAGTACAGGCAGTCTTTCACTACC

TGCTATTTAGCCCAATCTTAAAGGGAAGAGTTTACAAGATTCTGAGCGCTGAAG

GGGAGAGCTTTCTCCTAGCCATGTCAAGGATAATCTATCTAGATCCTTCTTTGGG

AGGGATATCTGGAATGTCCCTCGGAAGATTCCATATACGACAGTTCTCAGACCCT

GTCTCTGAAGGGTTATCCTTCTGGAGAGAGATCTGGTTAAGCTCCCAAGAGTCCT

GGATTCACGCGTTGTGTCAAGAGGCTGGAAACCCAGATCTTGGAGAGAGAACAC

TCGAGAGCTTCACTCGCCTTCTAGAAGATCCGACCACCTTAAATATCAGAGGAG

GGGCCAGTCCTACCATTCTACTCAAGGATGCAATCAGAAAGGCTTTATATGACG

AGGTGGACAAGGTGGAAAATTCAGAGTTTCGAGAGGCAATCCTGTTGTCCAAGA

CCCATAGAGATAATTTTATACTCTTCTTAATATCTGTTGAGCCTCTGTTTCCTCGA

TTTCTCAGTGAGCTATTCAGTTCGTCTTTTTTGGGAATCCCCGAGTCAATCATTGG

ATTGATACAAAACTCCCGAACGATAAGAAGGCAGTTTAGAAAGAGTCTCTCAAA

AACTTTAGAAGAATCCTTCTACAACTCAGAGATCCACGGGATTAGTCGGATGAC

CCAGACACCTCAGAGGGTTGGGGGGTGTGGCCTTGCTCTTCAGAGAGGGCAGA

TCTACTTAGGGAGATCTCTTGGGGAAGAAAAGTGGTAGGCACGACAGTTCCTCA

CCCTTCTGAGATGTTGGGATTACTTCCCAAGTCCTCTATTTCTTGCACTTGTGGAG

CAACAGGAGGAGGCAATCCTAGAGTTTCTGTATCAGTACTCCCGTCCTTTGATCA

GTCATTTTTTTCACGAGGCCCCCTAAAGGGATACTTGGGCTCGTCCACCTCTATG

TCGACCCAGCTATTCCATGCATGGGAAAAAGTCACTAATGTTCATGTGGTGAAG

AGAGCTCTATCGTTAAAAGAATCTATAAACTGGTTCATTACTAGAGATTCCAACT
```

-continued

```
TGGCTCAAGCTCTAATTAGGAACATTATGTCTCTGACAGGCCCTGATTTCCCTCT
AGAGGAGGCCCCTGTCTTCAAAAGGACGGGGTCAGCCTTGCATAGGTTCAAGTC
TGCCAGATACAGCGAAGGAGGGTATTCTTCTGTCTGCCCGAACCTCCTCTCTCAT
ATTTCTGTTAGTACAGACACCATGTCTGATTTGACCCAAGACGGGAAGAACTACG
ATTTCATGTTCCAGCCATTGATGCTTTATGCACAGACATGGACATCAGAGCTGGT
ACAGAGAGACACAAGGCTAAGAGACTCTACGTTTCATTGGCACCTCCGATGCAA
CAGGTGTGTGAGACCCATTGACGACGTGACCCTGGAGACCTCTCAGATCTTCGA
GTTTCCGGATGTGTCGAAAAGAATATCCAGAATGGTTTCTGGGGCTGTGCCTCAC
TTCCAGAGGCTTCCCGATATCCGTCTGAGACCAGGAGATTTTGAATCTCTAAGCG
GTAGAGAAAAGTCTCACCATATCGGATCAGCTCAGGGGCTCTTATACTCAATCTT
AGTGGCAATTCACGACTCAGGATACAATGATGGAACCATCTTCCCTGTCAACATA
TACGGCAAGGTTTCCCCTAGAGACTATTTGAGAGGGCTCGCAAGGGGAGTATTG
ATAGGATCCTCGATTTGCTTCTTGACAAGAATGACAAATATCAATATTAATAGAC
CTCTTGAATTGGTCTCAGGGGTAATCTCATATATTCTCCTGAGGCTAGATAACCA
TCCCTCCTTGTACATAATGCTCAGAGAACCGTCTCTTAGAGGAGAGATATTTTCT
ATCCCTCAGAAAATCCCCGCCGCTTATCCAACCACTATGAAAGAAGGCAACAGA
TCAATCTTGTGTTATCTCCAACATGTGCTACGCTATGAGCGAGAGATAATCACGG
CGTCTCCAGAGAATGACTGGCTATGGATCTTTTCAGACTTTAGAAGTGCCAAAAT
GACGTACCTATCCCTCATTACTTACCAGTCTCATCTTCTACTCCAGAGGGTTGAG
AGAAACCTATCTAAGAGTATGAGAGATAACCTGCGACAATTGAGTTCTTTGATG
AGGCAGGTGCTGGGCGGGCACGGAGAAGATACCTTAGAGTCAGACGACAACATT
CAACGACTGCTAAAAGACTCTTTACGAAGGACAAGATGGGTGGATCAAGAGGTG
CGCCATGCAGCTAGAACCATGACTGGAGATTACAGCCCCAACAAGAAGGTGTCC
CGTAAGGTAGGATGTTCAGAATGGGTCTGCTCTGCTCAACAGGTTGCAGTCTCTA
CCTCAGCAAACCCGGCCCCTGTCTCGGAGCTTGACATAAGGGCCCTCTCTAAGA
GGTTCCAGAACCCTTTGATCTCGGGCTTGAGAGTGGTTCAGTGGGCAACCGGTGC
TCATTATAAGCTTAAGCCTATTCTAGATGATCTCAATGTTTTCCCATCTCTCTGCC
TTGTAGTTGGGGACGGGTCAGGGGGATATCAAGGGCAGTCCTCAACATGTTTC
CAGATGCCAAGCTTGTGTTCAACAGTCTTTTAGAGGTGAATGACCTGATGGCTTC
CGGAACACATCCACTGCCTCCTTCAGCAATCATGAGGGGAGGAAATGATATCGT
CTCCAGAGTGATAGATCTTGACTCAATCTGGGAAAAACCGTCCGACTTGAGAAA
CTTGGCAACCTGGAAATACTTCCAGTCAGTCCAAAAGCAGGTCAACATGTCCTAT
GACCTCATTATTTGCGATGCAGAAGTTACTGACATTGCATCTATCAACCGGATCA
CCCTGTTAATGTCCGATTTTGCATTGTCTATAGATGGACCACTCTATTTGGTCTTC
AAAACTTATGGGACTATGCTAGTAAATCCAAACTACAAGGCTATTCAACACCTGT
CAAGAGCGTTCCCCTCGGTCACAGGGTTTATCACCCAAGTAACTTCGTCTTTTTC
ATCTGAGCTCTACCTCCGATTCTCCAAACGAGGGAAGTTTTTCAGAGATGCTGAG
TACTTGACCTCTTCCACCCTTCGAGAAATGAGCCTTGTGTTATTCAATTGTAGCA
GCCCCAAGAGTGAGATGCAGAGAGCTCGTTCCTTGAACTATCAGGATCTTGTGA
GAGGATTTCCTGAAGAAATCATATCAAATCCTTACAATGAGATGATCATAACTCT
GATTGACAGTGATGTAGAATCTTTTCTAGTCCACAAGATGGTTGATGATCTTGAG
```

-continued

```
TTACAGAGGGGAACTCTGTCTAAAGTGGCTATCATTATAGCCATCATGATAGTTT

TCTCCAACAGAGTCTTCAACGTTTCCAAACCCCTAACTGACCCCTCGTTCTATCC

ACCGTCTGATCCCAAAATCCTGAGGCACTTCAACATATGTTGCAGTACTATGATG

TATCTATCTACTGCTTTAGGTGACGTCCCTAGCTTCGCAAGACTTCACGACCTGT

ATAACAGACCTATAACTTATTACTTCAGAAAGCAAGTCATTCGAGGGAACGTTTA

TCTATCTTGGAGTTGGTCCAACGACACCTCAGTGTTCAAAAGGGTAGCCTGTAAT

TCTAGCCTGAGTCTGTCATCTCACTGGATCAGGTTGATTTACAAGATAGTGAAGA

CTACCAGACTCGTTGGCAGCATCAAGGATCTATCCAGAGAAGTGGAAAGACACC

TTCATAGGTACAACAGGTGGATCACCCTAGAGGATATCAGATCTAGATCATCCCT

ACTAGACTACAGTTGCCTGTGAACCGGATACTCCTGGAAGCCTGCCCATGCTAA

GACTCTTGTGTGATGTATCTTGAAAAAAACAAGATCCTAAATCTGAACCTTTGGT

TGTTTGATTGTTTTTCTCAttttttgttgtttatttgttaagcgt.
```

In one embodiment, the nucleic acid comprises the sequence of SEQ ID NO: 12, shown below (RABV vector: Coravax V4-China (S1-RABVG-T2A-P)):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAaATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC
```

-continued

```
ATCAAGCCCGTCCAAACTCATTCGCCGAGTTTCTAAACAAGACATATTCGAGTGA
CTCATAAcatgaaaaaaactaacacccctcccgtacgGCCACCATGTTCGTGTTTCTGGTGCTGCT
GCCTCTGGTGAGCTCCCAGTGCGTGAACCTGACCACAAGGACCCAGCTGCCCCC
TGCCTATACCAATTCCTTCACACGGGCGTGTACTATCCCGACAAGGTGTTCCGG
AGCAGCGTGCTGCACTCCACACAGGATCTGTTTCTGCCTTTCTTTTCTAACGTGAC
CTGGTTCCACGCCATCCACGTGAGCGGCACCAATGGCACAAAGCGGTTCGACAA
TCCAGTGCTGCCCTTTAACGATGGCGTGTACTTCGCCTCCACCGAGAAGTCTAAC
ATCATCAGAGGCTGGATCTTTGGCACCACACTGGACAGCAAGACACAGTCCCTG
CTGATCGTGAACAATGCCACCAACGTGGTCATCAAGGTGTGCGAGTTCCAGTTTT
GTAATGATCCATTCCTGGGCGTGTACTATCACAAGAACAATAAGTCTTGGATGGA
GAGCGAGTTTCGCGTGTATTCCTCTGCCAACAATTGCACATTTGAGTACGTGTCC
CAGCCCTTCCTGATGGACCTGGAGGGCAAGCAGGGCAATTTCAAGAACCTGAGG
GAGTTCGTGTTTAAGAATATCGATGGCTACTTCAAAATCTACTCCAAGCACACCC
CAATCAACCTGGTGCGCGACCTGCCACAGGGCTTCTCTGCCCTGGAGCCACTGGT
GGATCTGCCCATCGGCATCAACATCACCCGGTTTCAGACACTGCTGGCCCTGCAC
AGAAGCTACCTGACACCAGGCGACAGCTCCTCTGGATGGACCGCAGGAGCAGCA
GCCTACTATGTGGGCTATCTGCAGCCCAGGACCTTCCTGCTGAAGTACAACGAG
AATGGCACCATCACAGACGCCGTGGATTGCGCCCTGGATCCCCTGTCTGAGACC
AAGTGTACACTGAAGAGCTTTACCGTGGAGAAGGGCATCTATCAGACAAGCAAT
TTCAGGGTGCAGCCTACCGAGTCCATCGTGCGCTTTCCCAATATCACAAACCTGT
GCCCTTTTGGCGAGGTGTTCAACGCAACCCGCTTCGCCAGCGTGTACGCCTGGAA
TAGGAAGCGCATCTCCAACTGCGTGGCCGACTATTCTGTGCTGTACAACAGCGCC
TCCTTCTCTACCTTTAAGTGCTATGGCGTGAGCCCCACAAAGCTGAATGACCTGT
GCTTTACCAACGTGTACGCCGATTCCTTCGTGATCAGGGGCGACGAGGTGCGCC
AGATCGCACCAGGACAGACAGGCAAGATCGCAGACTACAATTATAAGCTGCCTG
ACGATTTCACCGGCTGCGTGATCGCCTGGAACTCTAACAATCTGGATAGCAAAGT
GGGCGGCAACTACAATTATCTGTACCGGCTGTTTAGAAAGTCTAATCTGAAGCCA
TTCGAGAGGGACATCTCCACAGAAATCTACCAGGCCGGCTCTACCCCCTGCAAT
GGCGTGGAGGGCTTTAACTGTTATTTCCCTCTGCAGAGCTACGGCTTCCAGCCAA
CAAACGGCGTGGGCTATCAGCCCTACCGCGTGGTGGTGCTGTCTTTTGAGCTGCT
GCACGCACCTGCAACAGTGTGCGGACCAAAGAAGAGCACCAATCTGGTGAAGA
ACAAGTGCGTGAACTTCAACTTCAACGGACTGACCGGAACAGGCGTGCTGACCG
AGTCCAACAAGAAGTTCCTGCCTTTTCAGCAGTTCGGCAGGGACATCGCAGATA
CCACAGACGCCGTGCGCGACCCTCAGACCCTGGAGATCCTGGACATCACACCAT
GCTCCTTCGGCGGCGTGTCTGTGATCACACCAGGCACCAATACAAGCAACCAGG
TGGCCGTGCTGTATCAGGACGTGAATTGTACCGAGGTGCCAGTGGCAATCCACG
CAGATCAGCTGACCCCTACATGGCGGGTGTACTCTACCGGCAGCAACGTGTTCC
AGACAAGAGCCGGATGCCTGATCGGAGCAGAGCACGTGAACAATAGCTATGAGT
GCGACATCCCTATCGGCGCCGGCATCTGTGCCTCCTACCAGACCCAGACAAACTC
CCCAAGGTCTGTGGGAGATGAGGCCGAAGACTTTGTGGAAGTCCACCTGCCTGA
```

-continued

```
TGTGCATAACCAGGTGTCTGGCGTCGACCTGGGACTGCCAAATTGGGGCAAGTA

CGTGCTGCTGAGTGCTGGAGCACTGACTGCCCTGATGCTGATCATTTTCCTGATG

ACCTGCTGTCGGCGCGTGAACAGAAGTGAGCCCACTCAGCACAATCTGCGAGGA

ACCGGGAGAGAAGTGTCAGTCACACCTCAGAGCGGGAAAATCATTAGTAGTTGG

GAATCACATAAAAGCGGGGGCGAGACCAGGCTGggatccggctccggcgagggcaggggaagtct actaacatgcggggacgtggaggaaaatcccggccccATGAGCAAGATCTTTGTCAATCCTAGTGCTA

TTAGAGCCGGTCTGGCCGATCTTGAGATGGCTGAAGAAACTGTTGATCTGATCAA

TAGAAATATCGAAGACAATCAGGCTCATCTCCAAGGGGAACCCATAGAGGTGGA

CAATCTCCCTGAGGATATGGGGCGACTTCACCTGGATGATGGAAAATCGCCCAA

CCATGGTGAGATAGCCAAGGTGGGAGAAGGCAAGTATCGAGAGGACTTTCAGAT

GGATGAAGGAGAGGATCCTAGCTTCCTGTTCCAGTCATACCTGGAAAATGTTGG

AGTCCAAATAGTCAGACAAATGAGGTCAGGAGAGAGATTTCTCAAGATATGGTC

ACAGACCGTAGAAGAGATTATATCCTATGTCGCGGTCAACTTTCCCAACCCTCCA

GGAAAGTCTTCAGAGGATAAATCAACCCAGACTACTGGCCGAGAGCTCAAGAAG

GAGACAACACCCACTCCTTCTCAGAGAGAAAGCCAATCATCGAAAGCCAGGATG

GCGGCTCAAATTGCTTCTGGCCCTCCAGCCCTTGAATGGTCGGCTACCAATGAAG

AGGATGATCTATCAGTGGAGGCTGAGATCGCTCACCAGATTGCAGAAAGTTTCT

CCAAAAAATATAAGTTTCCCTCTCGATCCTCAGGGATACTCTTGTATAATTTTGA

GCAATTGAAAATGAACCTTGATGATATAGTTAAAGAGGCAAAAAATGTACCAGG

TGTGACCCGTTTAGCCCATGACGGGTCCAAACTCCCCCTAAGATGTGTACTGGGA

TGGGTCGCTTTGGCCAACTCTAAGAAATTCCAGTTGTTAGTCGAATCCGACAAGC

TGAGTAAAATCATGCAAGATGACTTGAATCGCTATACATCTTGCTAACCGAACCT

CTCCCCTCAGTCCCTCTAGACAATAAAATCCGAGATGTCCCAAAGTCAACATGA

AAAAAACAGGCAACACCACTGATAAAATGAACCTCCTACGTAAGATAGTGAAAA

ACCGCAGGGACGAGGACACTCAAAAATCCTCTCCCGCGTCAGCCCCTCTGGATG

ACGATGACTTGTGGCTTCCACCCCCTGAATACGTCCCGCTGAAAGAACTTACAGG

CAAGAAGAACATGAGGAACTTTTGTATCAACGGAAGGGTTAAAGTGTGTAGCCC

GAATGGTTACTCGTTCAGGATCCTGCGGCACATTCTGAAATCATTCGACGAGATA

TATTCTGGGAATCATAGGATGATCGGGTTAGTCAAAGTGGTTATTGGACTGGCTT

TGTCAGGATCTCCAGTCCCTGAGGGCCTGAACTGGGTATACAAATTGAGGAGAA

CCTTTATCTTCCAGTGGGCTGATTCCAGGGGCCCTCTTGAAGGGGAGGAGTTGGA

ATACTCTCAGGAGATCACTTGGGATGATGATACTGAGTTCGTCGGATTGCAAATA

AGAGTGATTGCAAAACAGTGTCATATCCAGGGCAGAGTCTGGTGTATCAACATG

AACCCGAGAGCATGTCAACTATGGTCTGACATGTCTCTTCAGACACAAAGGTCC

GAAGAGGACAAAGATTCCTCTCTGCTTCTAGAATAATCAGATTATATCCCGCAAA

TTTATCACTTGTTTACCTCTGGAGGAGAGAACATATGGGCTCAACTCCAACCCTT

GGGAGCAATATAACAAAAAACATGTTATGGTGCCATTAAACCGCTGCATTTCAT

CAAAGTCAAGTTGATTACCTTTACATTTTGATCCTCTTGGATGTGAAAAAAACTA

TTAACATCCCTCAAAAGACCCcggggAAAGATGGTTCCTCAGGCTCTCCTGTTTGTAC

CCCTTCTGGTTTTTCCATTGTGTTTTGGGAAATTCCCTATTTACACGATACCAGAC

AAGCTTGGTCCCTGGAGTCCGATTGACATACATCACCTCAGCTGCCCAAACAATT
```

```
-continued
TGGTAGTGGAGGACGAAGGATGCACCAACCTGTCAGGGTTCTCCTACATGGAAC

TTAAAGTTGGATACATCTTAGCCATAAAAGTGAACGGGTTCACTTGCACAGGCGT

TGTGACGGAGGCTGAAACCTACACTAACTTCGTTGGTTATGTCACAACCACGTTC

AAAAGAAAGCATTTCCGCCCAACACCAGATGCATGTAGAGCCGCGTACAACTGG

AAGATGGCCGGTGACCCCAGATATGAAGAGTCTCTACACAATCCGTACCCTGAC

TACCGCTGGCTTCGAACTGTAAAAACCACCAAGGAGTCTCTCGTTATCATATCTC

CAAGTGTGGCAGATTTGGACCCATATGACAGATCCCTTCACTCGAGGGTCTTCCC

TAGCGGGAAGTGCTCAGGAGTAGCGGTGTCTTCTACCTACTGCTCCACTAACCAC

GATTACACCATTTGGATGCCCGAGAATCCGAGACTAGGGATGTCTTGTGACATTT

TTACCAATAGTAGAGGGAAGAGAGCATCCAAAGGGAGTGAGACTTGCGGCTTTG

TAGATGAAAGAGGCCTATATAAGTCTTTAAAAGGAGCATGCAAACTCAAGTTAT

GTGGAGTTCTAGGACTTAGACTTATGGATGGAACATGGGTCTCGATGCAAACAT

CAAATGAAACCAAATGGTGCCCTCCCGATAAGTTGGTGAACCTGCACGACTTTC

GCTCAGACGAAATTGAGCACCTTGTTGTAGAGGAGTTGGTCAGGAAGAGAGAGG

AGTGTCTGGATGCACTAGAGTCCATCATGACAACCAAGTCAGTGAGTTTCAGAC

GTCTCAGTCATTTAAGAAAACTTGTCCCTGGGTTTGGAAAAGCATATACCATATT

CAACAAGACCTTGATGGAAGCCGATGCTCACTACAAGTCAGTCgagACTTGGAAT

GAGATCCTCCCTTCAAAAGGGTGTTTAAGAGTTGGGGGGAGGTGTCATCCTCATG

TGAACGGGGTGTTTTTCAATGGTATAATATTAGGACCTGACGGCAATGTCTTAAT

CCCAGAGATGCAATCATCCCTCCTCCAGCAACATATGGAGTTGTTGGAATCCTCG

GTTATCCCCCTTGTGCACCCCCTGGCAGACCCGTCTACCGTTTTCAAGGACGGTG

ACGAGGCTGAGGATTTTGTTGAAGTTCACCTTCCCGATGTGCACAATCAGGTCTC

AGGAGTTGACTTGGGTCTCCCGAACTGGGGGAAGTATGTATTACTGAGTGCAGG

GGCCCTGACTGCCTTGATGTTGATAATTTTCCTGATGACATGTTGTAGAAGAGTC

AATCGATCAGAACCTACGCAACACAATCTCAGAGGGACAGGGAGGGAGGTGTC

AGTCACTCCCCAAAGCGGGAAGATCATATCTTCATGGGAATCACACAAGAGTGG

GGGTGAGACCAGACTGTAAttaattaaCGTCCTTTCAACGATCCAAGTCcatgaaaaaaactaa caccccctcccgtacctagcTTATAAAGTGCTGGGTCATCTAAGCTTTTCAGTCGAGAAAAAA

ACATTAGATCAGAAGAACAACTGGCAACACTTCTCAACCTGAGACTTACTTCAA

GATGCTCGATCCTGGAGAGGTCTATGATGACCCTATTGACCCAATCGAGTTAGAG

GCTGAACCCAGAGGAACCCCCATTGTCCCCAACATCTTGAGGAACTCTGACTAC

AATCTCAACTCTCCTTTGATAGAAGATCCTGCTAGACTAATGTTAGAATGGTTAA

AAACAGGGAATAGACCTTATCGGATGACTCTAACAGACAATTGCTCCAGGTCTTT

CAGAGTTTTGAAAGATTATTTCAAGAAGGTAGATTTGGGTTCTCTCAAGGTGGGC

GGAATGGCTGCACAGTCAATGATTTCTCTCTGGTTATATGGTGCCCACTCTGAAT

CCAACAGGAGCCGGAGATGTATAACAGACTTGGCCCATTTCTATTCCAAGTCGTC

CCCCATAGAGAAGCTGTTGAATCTCACGCTAGGAAATAGAGGGCTGAGAATCCC

CCCAGAGGGAGTGTTAAGTTGCCTTGAGAGGGTTGATTATGATAATGCATTTGGA

AGGTATCTTGCCAACACGTATTCCTCTTACTTGTTCTTCCATGTAATCACCTTATA

CATGAACGCCCTAGACTGGGATGAAGAAAAGACCATCCTAGCATTATGGAAAGA
```

-continued

```
TTTAACCTCAGTGGACATCGGGAAGGACTTGGTAAAGTTCAAAGACCAAATATG

GGGACTGCTGATCGTGACAAAGGACTTTGTTTACTCCCAAAGTTCCAATTGTCTT

TTTGACAGAAACTACACACTTATGCTAAAAGATCTTTTCTTGTCTCGCTTCAACTC

CTTAATGGTCTTGCTCTCTCCCCCAGAGCCCCGATACTCAGATGACTTGATATCT

CAACTATGCCAGCTGTACATTGCTGGGGATCAAGTCTTGTCTATGTGTGGAAACT

CCGGCTATGAAGTCATCAAAATATTGGAGCCATATGTCGTGAATAGTTTAGTCCA

GAGAGCAGAAAAGTTTAGGCCTCTCATTCATTCCTTGGGAGACTTTCCTGTATTT

ATAAAAGACAAGGTAAGTCAACTTGAAGAGACGTTCGGTCCCTGTGCAAGAAGG

TTCTTTAGGGCTCTGGATCAATTCGACAACATACATGACTTGGTTTTTGTGTTTGG

CTGTTACAGGCATTGGGGGCACCCATATATAGATTATCGAAAGGGTCTGTCAAA

ACTATATGATCAGGTTCACCTTAAAAAAATGATAGATAAGTCCTACCAGGAGTG

CTTAGCAAGCGACCTAGCCAGGAGGATCCTTAGATGGGGTTTTGATAAGTACTCC

AAGTGGTATCTGGATTCAAGATTCCTAGCCCGAGACCACCCCTTGACTCCTTATA

TCAAAACCCAAACATGGCCACCCAAACATATTGTAGACTTGGTGGGGATACAT

GGCACAAGCTCCCGATCACGCAGATCTTTGAGATTCCTGAATCAATGGATCCGTC

AGAAATATTGGATGACAAATCACATTCTTTCACCAGAACGAGACTAGCTTCTTGG

CTGTCAGAAAACCGAGGGGGGCCTGTTCCTAGCGAAAAAGTTATTATCACGGCC

CTGTCTAAGCCGCCTGTCAATCCCCGAGAGTTTCTGAGGTCTATAGACCTCGGAG

GATTGCCAGATGAAGACTTGATAATTGGCCTCAAGCCAAAGGAACGGGAATTGA

AGATTGAAGGTCGATTCTTTGCTCTAATGTCATGGAATCTAAGATTGTATTTTGTC

ATCACTGAAAAACTCTTGGCCAACTACATCTTGCCACTTTTTGACGCGCTGACTA

TGACAGACAACCTGAACAAGGTGTTTAAAAAGCTGATCGACAGGGTCACCGGGC

AAGGGCTTTTGGACTATTCAAGGGTCACATATGCATTTCACCTGGACTATGAAAA

GTGGAACAACCATCAAAGATTAGAGTCAACAGAGGATGTATTTTCTGTCCTAGA

TCAAGTGTTTGGATTGAAGAGAGTGTTTTCTAGAACACACGAGTTTTTTCAAAAG

GCCTGGATCTATTATTCAGACAGATCAGACCTCATCGGGTTACGGGAGGATCAA

ATATACTGCTTAGATGCGTCCAACGGCCCAACCTGTTGGAATGGCCAGGATGGC

GGGCTAGAAGGCTTACGGCAGAAGGGCTGGAGTCTAGTCAGCTTATTGATGATA

GATAGAGAATCTCAAATCAGGAACACAAGAACCAAAATACTAGCTCAAGGAGA

CAACCAGGTTTTATGTCCGACATACATGTTGTCGCCAGGGCTATCTCAAGAGGGG

CTCCTCTATGAATTGGAGAGAATATCAAGGAATGCACTTTCGATATACAGAGCC

GTCGAGGAAGGGGCATCTAAGCTAGGGCTGATCATCAAGAAAGAAGAGACCAT

GTGTAGTTATGACTTCCTCATCTATGGAAAAACCCCTTTGTTTAGAGGTAACATA

TTGGTGCCTGAGTCCAAAAGATGGGCCAGAGTCTCTTGCGTCTCTAATGACCAAA

TAGTCAACCTCGCCAATATAATGTCGACAGTGTCCACCAATGCGCTAACAGTGG

CACAACACTCTCAATCTTTGATCAAACCGATGAGGGATTTTCTGCTCATGTCAGT

ACAGGCAGTCTTTCACTACCTGCTATTTAGCCCAATCTTAAAGGGAAGAGTTTAC

AAGATTCTGAGCGCTGAAGGGGAGAGCTTTCTCCTAGCCATGTCAAGGATAATC

TATCTAGATCCTTCTTTGGGAGGGATATCTGGAATGTCCCTCGGAAGATTCCATA

TACGACAGTTCTCAGACCCTGTCTCTGAAGGGTTATCCTTCTGGAGAGAGATCTG

GTTAAGCTCCCAAGAGTCCTGGATTCACGCGTTGTGTCAAGAGGCTGGAAACCC
```

-continued

```
AGATCTTGGAGAGAGAACACTCGAGAGCTTCACTCGCCTTCTAGAAGATCCGAC

CACCTTAAATATCAGAGGAGGGGCCAGTCCTACCATTCTACTCAAGGATGCAAT

CAGAAAGGCTTTATATGACGAGGTGGACAAGGTGGAAAATTCAGAGTTTCGAGA

GGCAATCCTGTTGTCCAAGACCCATAGAGATAATTTTATACTCTTCTTAATATCT

GTTGAGCCTCTGTTTCCTCGATTTCTCAGTGAGCTATTCAGTTCGTCTTTTTTGGG

AATCCCCGAGTCAATCATTGGATTGATACAAAACTCCCGAACGATAAGAAGGCA

GTTTAGAAAGAGTCTCTCAAAAACTTTAGAAGAATCCTTCTACAACTCAGAGATC

CACGGGATTAGTCGGATGACCCAGACACCTCAGAGGGTTGGGGGGGTGTGGCCT

TGCTCTTCAGAGAGGGCAGATCTACTTAGGGAGATCTCTTGGGGAAGAAAAGTG

GTAGGCACGACAGTTCCTCACCCTTCTGAGATGTTGGGATTACTTCCCAAGTCCT

CTATTTCTTGCACTTGTGGAGCAACAGGAGGAGGCAATCCTAGAGTTTCTGTATC

AGTACTCCCGTCCTTTGATCAGTCATTTTTTTCACGAGGCCCCCTAAAGGGATAC

TTGGGCTCGTCCACCTCTATGTCGACCCAGCTATTCCATGCATGGGAAAAAGTCA

CTAATGTTCATGTGGTGAAGAGAGCTCTATCGTTAAAAGAATCTATAAACTGGTT

CATTACTAGAGATTCCAACTTGGCTCAAGCTCTAATTAGGAACATTATGTCTCTG

ACAGGCCCTGATTTCCCTCTAGAGGAGGCCCCTGTCTTCAAAAGGACGGGGTCA

GCCTTGCATAGGTTCAAGTCTGCCAGATACAGCGAAGGAGGGTATTCTTCTGTCT

GCCCGAACCTCCTCTCTCATATTTCTGTTAGTACAGACACCATGTCTGATTTGACC

CAAGACGGGAAGAACTACGATTTCATGTTCCAGCCATTGATGCTTTATGCACAGA

CATGGACATCAGAGCTGGTACAGAGAGACACAAGGCTAAGAGACTCTACGTTTC

ATTGGCACCTCCGATGCAACAGGTGTGTGAGACCCATTGACGACGTGACCCTGG

AGACCTCTCAGATCTTCGAGTTTCCGGATGTGTCGAAAAGAATATCCAGAATGGT

TTCTGGGGCTGTGCCTCACTTCCAGAGGCTTCCCGATATCCGTCTGAGACCAGGA

GATTTTGAATCTCTAAGCGGTAGAGAAAAGTCTCACCATATCGGATCAGCTCAG

GGGCTCTTATACTCAATCTTAGTGGCAATTCACGACTCAGGATACAATGATGGAA

CCATCTTCCCTGTCAACATATACGGCAAGGTTTCCCCTAGAGACTATTTGAGAGG

GCTCGCAAGGGGAGTATTGATAGGATCCTCGATTTGCTTCTTGACAAGAATGACA

AATATCAATATTAATAGACCTCTTGAATTGGTCTCAGGGGTAATCTCATATATTC

TCCTGAGGCTAGATAACCATCCCTCCTTGTACATAATGCTCAGAGAACCGTCTCT

TAGAGGAGAGATATTTTCTATCCCTCAGAAAATCCCCGCCGCTTATCCAACCACT

ATGAAAGAAGGCAACAGATCAATCTTGTGTTATCTCCAACATGTGCTACGCTATG

AGCGAGAGATAATCACGGCGTCTCCAGAGAATGACTGGCTATGGATCTTTTCAG

ACTTTAGAAGTGCCAAAATGACGTACCTATCCCTCATTACTTACCAGTCTCATCT

TCTACTCCAGAGGGTTGAGAGAAACCTATCTAAGAGTATGAGAGATAACCTGCG

ACAATTGAGTTCTTTGATGAGGCAGGTGCTGGGCGGGCACGGAGAAGATACCTT

AGAGTCAGACGACAACATTCAACGACTGCTAAAAGACTCTTTACGAAGGACAAG

ATGGGTGGATCAAGAGGTGCGCCATGCAGCTAGAACCATGACTGGAGATTACAG

CCCCAACAAGAAGGTGTCCCGTAAGGTAGGATGTTCAGAATGGGTCTGCTCTGC

TCAACAGGTTGCAGTCTCTACCTCAGCAAACCCGGCCCCTGTCTCGGAGCTTGAC

ATAAGGGCCCTCTCTAAGAGGTTCCAGAACCCTTTGATCTCGGGCTTGAGAGTGG
```

-continued

```
TTCAGTGGGCAACCGGTGCTCATTATAAGCTTAAGCCTATTCTAGATGATCTCAA

TGTTTTCCCATCTCTCTGCCTTGTAGTTGGGGACGGGTCAGGGGGGATATCAAGG

GCAGTCCTCAACATGTTTCCAGATGCCAAGCTTGTGTTCAACAGTCTTTTAGAGG

TGAATGACCTGATGGCTTCCGGAACACATCCACTGCCTCCTTCAGCAATCATGAG

GGGAGGAAATGATATCGTCTCCAGAGTGATAGATCTTGACTCAATCTGGGAAAA

ACCGTCCGACTTGAGAAACTTGGCAACCTGGAAATACTTCCAGTCAGTCCAAAA

GCAGGTCAACATGTCCTATGACCTCATTATTTGCGATGCAGAAGTTACTGACATT

GCATCTATCAACCGGATCACCCTGTTAATGTCCGATTTTGCATTGTCTATAGATG

GACCACTCTATTTGGTCTTCAAAACTTATGGGACTATGCTAGTAAATCCAAACTA

CAAGGCTATTCAACACCTGTCAAGAGCGTTCCCCTCGGTCACAGGGTTTATCACC

CAAGTAACTTCGTCTTTTTCATCTGAGCTCTACCTCCGATTCTCCAAACGAGGGA

AGTTTTTCAGAGATGCTGAGTACTTGACCTCTTCCACCCTTCGAGAAATGAGCCT

TGTGTTATTCAATTGTAGCAGCCCCAAGAGTGAGATGCAGAGAGCTCGTTCCTTG

AACTATCAGGATCTTGTGAGAGGATTTCCTGAAGAAATCATATCAAATCCTTACA

ATGAGATGATCATAACTCTGATTGACAGTGATGTAGAATCTTTTCTAGTCCACAA

GATGGTTGATGATCTTGAGTTACAGAGGGGAACTCTGTCTAAAGTGGCTATCATT

ATAGCCATCATGATAGTTTTCTCCAACAGAGTCTTCAACGTTTCCAAACCCCTAA

CTGACCCCTCGTTCTATCCACCGTCTGATCCCAAAATCCTGAGGCACTTCAACAT

ATGTTGCAGTACTATGATGTATCTATCTACTGCTTTAGGTGACGTCCCTAGCTTCG

CAAGACTTCACGACCTGTATAACAGACCTATAACTTATTACTTCAGAAAGCAAGT

CATTCGAGGGAACGTTTATCTATCTTGGAGTTGGTCCAACGACACCTCAGTGTTC

AAAAGGGTAGCCTGTAATTCTAGCCTGAGTCTGTCATCTCACTGGATCAGGTTGA

TTTACAAGATAGTGAAGACTACCAGACTCGTTGGCAGCATCAAGGATCTATCCA

GAGAAGTGGAAAGACACCTTCATAGGTACAACAGGTGGATCACCCTAGAGGATA

TCAGATCTAGATCATCCCTACTAGACTACAGTTGCCTGTGAACCGGATACTCCTG

GAAGCCTGCCCATGCTAAGACTCTTGTGTGATGTATCTTGAAAAAAACAAGATCC

TAAATCTGAACCTTTGGTTGTTTGATTGTTTTCTCAttttttgttgtttatttgttaagcgt
```

In one embodiment, the nucleic acid comprises the sequence of SEQ ID NO: 13, shown below (RABV vector: Coravax V4 South Africa):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC
```

-continued

```
TGGTAACTATAAGACAAACATTGCAGACAGGATAGAGCAGATTTTTGAGACAGC

CCCTTTTGTTAAAATCGTGGAACACCATACTCTAATGACAACTCACAAaATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAcatgaaaaaaactaacaccccctcccgtacgGCCACCATGTTCGTGTTTCTGGTGCTGCT

GCCTCTGGTGAGCTCCCAGTGCGTGAACTTCACCACAAGGACCCAGCTGCCCCCT

GCCTATACCAATTCCTTCACACGGGGCGTGTACTATCCCGACAAGGTGTTCCGGA

GCAGCGTGCTGCACTCCACACAGGATCTGTTTCTGCCTTTCTTTTCTAACGTGACC

TGGTTCCACGCCATCCACGTGAGCGGCACCAATGGCACAAAGCGGTTCGCCAAT

CCAGTGCTGCCCTTTAACGATGGCGTGTACTTCGCCTCCACCGAGAAGTCTAACA

TCATCAGAGGCTGGATCTTTGGCACCACACTGGACAGCAAGACACAGTCCCTGC

TGATCGTGAACAATGCCACCAACGTGGTCATCAAGGTGTGCGAGTTCCAGTTTTG

TAATGATCCATTCCTGGGCGTGTACTATCACAAGAACAATAAGTCTTGGATGGAG

AGCGAGTTTCGCGTGTATTCCTCTGCCAACAATTGCACATTTGAGTACGTGTCCC

AGCCCTTCCTGATGGACCTGGAGGGCAAGCAGGGCAATTTCAAGAACCTGAGGG

AGTTCGTGTTTAAGAATATCGATGGCTACTTCAAAATCTACTCCAAGCACACCCC

AATCAACCTGGTGCGCGGCCTGCCACAGGGCTTCTCTGCCCTGGAGCCACTGGTG

GATCTGCCCATCGGCATCAACATCACCCGGTTTCAGACACTGCTGGCCCTGCACA

GAAGCTACCTGACACCAGGCGACAGCTCCTCTGGATGGACCGCAGGAGCAGCAG

CCTACTATGTGGGCTATCTGCAGCCCAGGACCTTCCTGCTGAAGTACAACGAGA

ATGGCACCATCACAGACGCCGTGGATTGCGCCCTGGATCCCCTGTCTGAGACCA

AGTGTACACTGAAGAGCTTTACCGTGGAGAAGGGCATCTATCAGACAAGCAATT

TCAGGGTGCAGCCTACCGAGTCCATCGTGCGCTTTCCCAATATCACAAACCTGTG

CCCTTTTGGCGAGGTGTTCAACGCAACCCGCTTCGCCAGCGTGTACGCCTGGAAT

AGGAAGCGCATCTCCAACTGCGTGGCCGACTATTCTGTGCTGTACAACAGCGCCT

CCTTCTCTACCTTTAAGTGCTATGGCGTGAGCCCCACAAAGCTGAATGACCTGTG

CTTTACCAACGTGTACGCCGATTCCTTCGTGATCAGGGGCGACGAGGTGCGCCA

GATCGCACCAGGACAGACAGGCAATATCGCAGACTACAATTATAAGCTGCCTGA

CGATTTCACCGGCTGCGTGATCGCCTGGAACTCTAACAATCTGGATAGCAAAGTG
```

```
GGCGGCAACTACAATTATCTGTACCGGCTGTTTAGAAAGTCTAATCTGAAGCCAT
TCGAGAGGGACATCTCCACAGAAATCTACCAGGCCGGCTCTACCCCCTGCAATG
GCGTGAAGGGCTTTAACTGTTATTTCCCTCTGCAGAGCTACGGCTTCCAGCCAAC
ATATGGCGTGGGCTATCAGCCCTACCGCGTGGTGGTGCTGTCTTTTGAGCTGCTG
CACGCACCTGCAACAGTGTGCGGACCAAAGAAGAGCACCAATCTGGTGAAGAA
CAAGTGCGTGAACTTCAACTTCAACGGACTGACCGGAACAGGCGTGCTGACCGA
GTCCAACAAGAAGTTCCTGCCTTTTCAGCAGTTCGGCAGGGACATCGCAGATAC
CACAGACGCCGTGCGCGACCCTCAGACCCTGGAGATCCTGGACATCACACCATG
CTCCTTCGGCGGCGTGTCTGTGATCACACCAGGCACCAATACAAGCAACCAGGT
GGCCGTGCTGTATCAGGGCGTGAATTGTACCGAGGTGCCAGTGGCAATCCACGC
AGATCAGCTGACCCCTACATGGCGGGTGTACTCTACCGGCAGCAACGTGTTCCA
GACAAGAGCCGGATGCCTGATCGGAGCAGAGCACGTGAACAATAGCTATGAGTG
CGACATCCCTATCGGCGCCGGCATCTGTGCCTCCTACCAGACCCAGACAAACTCC
CCAGAATCAAGCGTGATTCCTCTGGTCCATCCACTGGCAGATCCCTCCACAGTGT
TCAAAGACGGAGATGAGGCCGAAGACTTTGTGGAAGTCCACCTGCCTGATGTGC
ATAACCAGGTGTCTGGCGTCGACCTGGGACTGCCAAATTGGGGCAAGTACGTGC
TGCTGAGTGCTGGAGCACTGACTGCCCTGATGCTGATCATTTTCCTGATGACCTG
CTGTCGGCGCGTGAACAGAAGTGAGCCCACTCAGCACAATCTGCGAGGAACCGG
GAGAGAAGTGTCAGTCACACCTCAGAGCGGGAAAATCATTAGTAGTTGGGAATC
ACATAAAAGCGGGGGCGAGACCAGGCTGggatccggctccggcgagggcaggggaagtctactaacat
gcggggacgtggaggaaaatcccggccccATGAGCAAGATCTTTGTCAATCCTAGTGCTATTAG
AGCCGGTCTGGCCGATCTTGAGATGGCTGAAGAAACTGTTGATCTGATCAATAG
AAATATCGAAGACAATCAGGCTCATCTCCAAGGGGAACCCATAGAGGTGGACAA
TCTCCCTGAGGATATGGGGCGACTTCACCTGGATGATGGAAAATCGCCCAACCA
TGGTGAGATAGCCAAGGTGGGAGAAGGCAAGTATCGAGAGGACTTTCAGATGG
ATGAAGGAGAGGATCCTAGCTTCCTGTTCCAGTCATACCTGGAAAATGTTGGAGT
CCAAATAGTCAGACAAATGAGGTCAGGAGAGAGATTTCTCAAGATATGGTCACA
GACCGTAGAAGAGATTATATCCTATGTCGCGGTCAACTTTCCCAACCCTCCAGGA
AAGTCTTCAGAGGATAAATCAACCCAGACTACTGGCCGAGAGCTCAAGAAGGAG
ACAACACCCACTCCTTCTCAGAGAGAAAGCCAATCATCGAAAGCCAGGATGGCG
GCTCAAATTGCTTCTGGCCCTCCAGCCCTTGAATGGTCGGCTACCAATGAAGAGG
ATGATCTATCAGTGGAGGCTGAGATCGCTCACCAGATTGCAGAAAGTTTCTCCAA
AAAATATAAGTTTCCCTCTCGATCCTCAGGGATACTCTTGTATAATTTTGAGCAA
TTGAAAATGAACCTTGATGATATAGTTAAAGAGGCAAAAAATGTACCAGGTGTG
ACCCGTTTAGCCCATGACGGGTCCAAACTCCCCCTAAGATGTGTACTGGGATGG
GTCGCTTTGGCCAACTCTAAGAAATTCCAGTTGTTAGTCGAATCCGACAAGCTGA
GTAAAATCATGCAAGATGACTTGAATCGCTATACATCTTGCTAACCGAACCTCTC
CCCTCAGTCCCTCTAGACAATAAAATCCGAGATGTCCCAAAGTCAACATGAAAA
AAACAGGCAACACCACTGATAAAATGAACCTCCTACGTAAGATAGTGAAAAACC
GCAGGGACGAGGACACTCAAAAATCCTCTCCCGCGTCAGCCCCTCTGGATGACG
```

-continued
ATGACTTGTGGCTTCCACCCCCTGAATACGTCCCGCTGAAAGAACTTACAGGCAA

GAAGAACATGAGGAACTTTTGTATCAACGGAAGGGTTAAAGTGTGTAGCCCGAA

TGGTTACTCGTTCAGGATCCTGCGGCACATTCTGAAATCATTCGACGAGATATAT

TCTGGGAATCATAGGATGATCGGGTTAGTCAAAGTGGTTATTGGACTGGCTTTGT

CAGGATCTCCAGTCCCTGAGGGCCTGAACTGGGTATACAAATTGAGGAGAACCT

TTATCTTCCAGTGGGCTGATTCCAGGGGCCCTCTTGAAGGGGAGGAGTTGGAATA

CTCTCAGGAGATCACTTGGGATGATGATACTGAGTTCGTCGGATTGCAAATAAG

AGTGATTGCAAAACAGTGTCATATCCAGGGCAGAGTCTGGTGTATCAACATGAA

CCCGAGAGCATGTCAACTATGGTCTGACATGTCTCTTCAGACACAAAGGTCCGA

AGAGGACAAAGATTCCTCTCTGCTTCTAGAATAATCAGATTATATCCCGCAAATT

TATCACTTGTTTACCTCTGGAGGAGAGAACATATGGGCTCAACTCCAACCCTTGG

GAGCAATATAACAAAAAACATGTTATGGTGCCATTAAACCGCTGCATTTCATCA

AAGTCAAGTTGATTACCTTTACATTTTGATCCTCTTGGATGTGAAAAAAACTATT

AACATCCCTCAAAAGACCcccgggAAAGATGGTTCCTCAGGCTCTCCTGTTTGTACC

CCTTCTGGTTTTTCCATTGTGTTTTGGGAAATTCCCTATTTACACGATACCAGACA

AGCTTGGTCCCTGGAGTCCGATTGACATACATCACCTCAGCTGCCCAAACAATTT

GGTAGTGGAGGACGAAGGATGCACCAACCTGTCAGGGTTCTCCTACATGGAACT

TAAAGTTGGATACATCTTAGCCATAAAAGTGAACGGGTTCACTTGCACAGGCGTT

GTGACGGAGGCTGAAACCTACACTAACTTCGTTGGTTATGTCACAACCACGTTCA

AAAGAAAGCATTTCCGCCCAACACCAGATGCATGTAGAGCCGCGTACAACTGGA

AGATGGCCGGTGACCCCAGATATGAAGAGTCTCTACACAATCCGTACCCTGACT

ACCGCTGGCTTCGAACTGTAAAAACCACCAAGGAGTCTCTCGTTATCATATCTCC

AAGTGTGGCAGATTTGGACCCATATGACAGATCCCTTCACTCGAGGGTCTTCCCT

AGCGGGAAGTGCTCAGGAGTAGCGGTGTCTTCTACCTACTGCTCCACTAACCAC

GATTACACCATTTGGATGCCCGAGAATCCGAGACTAGGGATGTCTTGTGACATTT

TTACCAATAGTAGAGGGAAGAGAGCATCCAAAGGGAGTGAGACTTGCGGCTTTG

TAGATGAAAGAGGCCTATATAAGTCTTTAAAAGGAGCATGCAAACTCAAGTTAT

GTGGAGTTCTAGGACTTAGACTTATGGATGGAACATGGGTCTCGATGCAAACAT

CAAATGAAACCAAATGGTGCCCTCCCGATAAGTTGGTGAACCTGCACGACTTTC

GCTCAGACGAAATTGAGCACCTTGTTGTAGAGGAGTTGGTCAGGAAGAGAGAGG

AGTGTCTGGATGCACTAGAGTCCATCATGACAACCAAGTCAGTGAGTTTCAGAC

GTCTCAGTCATTTAAGAAAACTTGTCCCTGGGTTTGGAAAAGCATATACCATATT

CAACAAGACCTTGATGGAAGCCGATGCTCACTACAAGTCAGTCgagACTTGGAAT

GAGATCCTCCCTTCAAAAGGGTGTTTAAGAGTTGGGGGGAGGTGTCATCCTCATG

TGAACGGGGTGTTTTTCAATGGTATAATATTAGGACCTGACGGCAATGTCTTAAT

CCCAGAGATGCAATCATCCCTCCTCCAGCAACATATGGAGTTGTTGGAATCCTCG

GTTATCCCCCTTGTGCACCCCCTGGCAGACCCGTCTACCGTTTTCAAGGACGGTG

ACGAGGCTGAGGATTTTGTTGAAGTTCACCTTCCCGATGTGCACAATCAGGTCTC

AGGAGTTGACTTGGGTCTCCCGAACTGGGGGAAGTATGTATTACTGAGTGCAGG

GGCCCTGACTGCCTTGATGTTGATAATTTTCCTGATGACATGTTGTAGAAGAGTC

AATCGATCAGAACCTACGCAACACAATCTCAGAGGGACAGGGAGGGAGGTGTC

```
AGTCACTCCCCAAAGCGGGAAGATCATATCTTCATGGGAATCACACAAGAGTGG

GGGTGAGACCAGACTGTAAttaattaaCGTCCTTTCAACGATCCAAGTCcatgaaaaaaactaa caccccctcccgtacctagcTTATAAAGTGCTGGGTCATCTAAGCTTTTCAGTCGAGAAAAAA

ACATTAGATCAGAAGAACAACTGGCAACACTTCTCAACCTGAGACTTACTTCAA

GATGCTCGATCCTGGAGAGGTCTATGATGACCCTATTGACCCAATCGAGTTAGAG

GCTGAACCCAGAGGAACCCCCATTGTCCCCAACATCTTGAGGAACTCTGACTAC

AATCTCAACTCTCCTTTGATAGAAGATCCTGCTAGACTAATGTTAGAATGGTTAA

AAACAGGGAATAGACCTTATCGGATGACTCTAACAGACAATTGCTCCAGGTCTTT

CAGAGTTTTGAAAGATTATTTCAAGAAGGTAGATTTGGGTTCTCTCAAGGTGGGC

GGAATGGCTGCACAGTCAATGATTTCTCTCTGGTTATATGGTGCCCACTCTGAAT

CCAACAGGAGCCGGAGATGTATAACAGACTTGGCCCATTTCTATTCCAAGTCGTC

CCCCATAGAGAAGCTGTTGAATCTCACGCTAGGAAATAGAGGGCTGAGAATCCC

CCCAGAGGGAGTGTTAAGTTGCCTTGAGAGGGTTGATTATGATAATGCATTTGGA

AGGTATCTTGCCAACACGTATTCCTCTTACTTGTTCTTCCATGTAATCACCTTATA

CATGAACGCCCTAGACTGGGATGAAGAAAAGACCATCCTAGCATTATGGAAAGA

TTTAACCTCAGTGGACATCGGGAAGGACTTGGTAAAGTTCAAAGACCAAATATG

GGGACTGCTGATCGTGACAAAGGACTTTGTTTACTCCCAAAGTTCCAATTGTCTT

TTTGACAGAAACTACACACTTATGCTAAAAGATCTTTTCTTGTCTCGCTTCAACTC

CTTAATGGTCTTGCTCTCTCCCCCAGAGCCCCGATACTCAGATGACTTGATATCT

CAACTATGCCAGCTGTACATTGCTGGGGATCAAGTCTTGTCTATGTGTGGAAACT

CCGGCTATGAAGTCATCAAAATATTGGAGCCATATGTCGTGAATAGTTTAGTCCA

GAGAGCAGAAAAGTTTAGGCCTCTCATTCATTCCTTGGGAGACTTTCCTGTATTT

ATAAAAGACAAGGTAAGTCAACTTGAAGAGACGTTCGGTCCCTGTGCAAGAAGG

TTCTTTAGGGCTCTGGATCAATTCGACAACATACATGACTTGGTTTTTGTGTTTGG

CTGTTACAGGCATTGGGGGCACCCATATATAGATTATCGAAAGGGTCTGTCAAA

ACTATATGATCAGGTTCACCTTAAAAAAATGATAGATAAGTCCTACCAGGAGTG

CTTAGCAAGCGACCTAGCCAGGAGGATCCTTAGATGGGGTTTTGATAAGTACTCC

AAGTGGTATCTGGATTCAAGATTCCTAGCCCGAGACCACCCCTTGACTCCTTATA

TCAAAACCCAAACATGGCCACCCAAACATATTGTAGACTTGGTGGGGATACAT

GGCACAAGCTCCCGATCACGCAGATCTTTGAGATTCCTGAATCAATGGATCCGTC

AGAAATATTGGATGACAAATCACATTCTTTCACCAGAACGAGACTAGCTTCTTGG

CTGTCAGAAAACCGAGGGGGGCCTGTTCCTAGCGAAAAAGTTATTATCACGGCC

CTGTCTAAGCCGCCTGTCAATCCCCGAGAGTTTCTGAGGTCTATAGACCTCGGAG

GATTGCCAGATGAAGACTTGATAATTGGCCTCAAGCCAAAGGAACGGGAATTGA

AGATTGAAGGTCGATTCTTTGCTCTAATGTCATGGAATCTAAGATTGTATTTTGTC

ATCACTGAAAAACTCTTGGCCAACTACATCTTGCCACTTTTTGACGCGCTGACTA

TGACAGACAACCTGAACAAGGTGTTTAAAAAGCTGATCGACAGGGTCACCGGGC

AAGGGCTTTTGGACTATTCAAGGGTCACATATGCATTTCACCTGGACTATGAAAA

GTGGAACAACCATCAAAGATTAGAGTCAACAGAGGATGTATTTTCTGTCCTAGA

TCAAGTGTTTGGATTGAAGAGAGTGTTTTCTAGAACACACGAGTTTTTTCAAAAG
```

-continued

```
GCCTGGATCTATTATTCAGACAGATCAGACCTCATCGGGTTACGGGAGGATCAA

ATATACTGCTTAGATGCGTCCAACGGCCCAACCTGTTGGAATGGCCAGGATGGC

GGGCTAGAAGGCTTACGGCAGAAGGGCTGGAGTCTAGTCAGCTTATTGATGATA

GATAGAGAATCTCAAATCAGGAACACAAGAACCAAAATACTAGCTCAAGGAGA

CAACCAGGTTTTATGTCCGACATACATGTTGTCGCCAGGGCTATCTCAAGAGGGG

CTCCTCTATGAATTGGAGAGAATATCAAGGAATGCACTTTCGATATACAGAGCC

GTCGAGGAAGGGGCATCTAAGCTAGGGCTGATCATCAAGAAAGAAGAGACCAT

GTGTAGTTATGACTTCCTCATCTATGGAAAAACCCCTTTGTTTAGAGGTAACATA

TTGGTGCCTGAGTCCAAAAGATGGGCCAGAGTCTCTTGCGTCTCTAATGACCAAA

TAGTCAACCTCGCCAATATAATGTCGACAGTGTCCACCAATGCGCTAACAGTGG

CACAACACTCTCAATCTTTGATCAAACCGATGAGGGATTTTCTGCTCATGTCAGT

ACAGGCAGTCTTTCACTACCTGCTATTTAGCCCAATCTTAAAGGGAAGAGTTTAC

AAGATTCTGAGCGCTGAAGGGGAGAGCTTTCTCCTAGCCATGTCAAGGATAATC

TATCTAGATCCTTCTTTGGGAGGGATATCTGGAATGTCCCTCGGAAGATTCCATA

TACGACAGTTCTCAGACCCTGTCTCTGAAGGGTTATCCTTCTGGAGAGAGATCTG

GTTAAGCTCCCAAGAGTCCTGGATTCACGCGTTGTGTCAAGAGGCTGGAAACCC

AGATCTTGGAGAGAGAACACTCGAGAGCTTCACTCGCCTTCTAGAAGATCCGAC

CACCTTAAATATCAGAGGAGGGCCAGTCCTACCATTCTACTCAAGGATGCAAT

CAGAAAGGCTTTATATGACGAGGTGGACAAGGTGGAAAATTCAGAGTTTCGAGA

GGCAATCCTGTTGTCCAAGACCCATAGAGATAATTTTATACTCTTCTTAATATCT

GTTGAGCCTCTGTTTCCTCGATTTCTCAGTGAGCTATTCAGTTCGTCTTTTTTGGG

AATCCCCGAGTCAATCATTGGATTGATACAAAACTCCCGAACGATAAGAAGGCA

GTTTAGAAAGAGTCTCTCAAAAACTTTAGAAGAATCCTTCTACAACTCAGAGATC

CACGGGATTAGTCGGATGACCCAGACACCTCAGAGGGTTGGGGGGGTGTGGCCT

TGCTCTTCAGAGAGGGCAGATCTACTTAGGGAGATCTCTTGGGGAAGAAAAGTG

GTAGGCACGACAGTTCCTCACCCTTCTGAGATGTTGGGATTACTTCCCAAGTCCT

CTATTTCTTGCACTTGTGGAGCAACAGGAGGAGGCAATCCTAGAGTTTCTGTATC

AGTACTCCCGTCCTTTGATCAGTCATTTTTTTCACGAGGCCCCCTAAAGGGATAC

TTGGGCTCGTCCACCTCTATGTCGACCCAGCTATTCCATGCATGGGAAAAAGTCA

CTAATGTTCATGTGGTGAAGAGAGCTCTATCGTTAAAAGAATCTATAAACTGGTT

CATTACTAGAGATTCCAACTTGGCTCAAGCTCTAATTAGGAACATTATGTCTCTG

ACAGGCCCTGATTTCCCTCTAGAGGAGGCCCCTGTCTTCAAAAGGACGGGGTCA

GCCTTGCATAGGTTCAAGTCTGCCAGATACAGCGAAGGAGGGTATTCTTCTGTCT

GCCCGAACCTCCTCTCTCATATTTCTGTTAGTACAGACACCATGTCTGATTTGACC

CAAGACGGGAAGAACTACGATTTCATGTTCCAGCCATTGATGCTTTATGCACAGA

CATGGACATCAGAGCTGGTACAGAGAGACACAAGGCTAAGAGACTCTACGTTTC

ATTGGCACCTCCGATGCAACAGGTGTGTGAGACCCATTGACGACGTGACCCTGG

AGACCTCTCAGATCTTCGAGTTTCCGGATGTGTCGAAAAGAATATCCAGAATGGT

TTCTGGGGCTGTGCCTCACTTCCAGAGGCTTCCCGATATCCGTCTGAGACCAGGA

GATTTTGAATCTCTAAGCGGTAGAGAAAAGTCTCACCATATCGGATCAGCTCAG

GGGCTCTTATACTCAATCTTAGTGGCAATTCACGACTCAGGATACAATGATGGAA
```

-continued

```
CCATCTTCCCTGTCAACATATACGGCAAGGTTTCCCCTAGAGACTATTTGAGAGG
GCTCGCAAGGGGAGTATTGATAGGATCCTCGATTTGCTTCTTGACAAGAATGACA
AATATCAATATTAATAGACCTCTTGAATTGGTCTCAGGGGTAATCTCATATATTC
TCCTGAGGCTAGATAACCATCCCTCCTTGTACATAATGCTCAGAGAACCGTCTCT
TAGAGGAGAGATATTTTCTATCCCTCAGAAAATCCCCGCCGCTTATCCAACCACT
ATGAAAGAAGGCAACAGATCAATCTTGTGTTATCTCCAACATGTGCTACGCTATG
AGCGAGAGATAATCACGGCGTCTCCAGAGAATGACTGGCTATGGATCTTTTCAG
ACTTTAGAAGTGCCAAAATGACGTACCTATCCCTCATTACTTACCAGTCTCATCT
TCTACTCCAGAGGGTTGAGAGAAACCTATCTAAGAGTATGAGAGATAACCTGCG
ACAATTGAGTTCTTTGATGAGGCAGGTGCTGGGCGGGCACGGAGAAGATACCTT
AGAGTCAGACGACAACATTCAACGACTGCTAAAAGACTCTTTACGAAGGACAAG
ATGGGTGGATCAAGAGGTGCGCCATGCAGCTAGAACCATGACTGGAGATTACAG
CCCCAACAAGAAGGTGTCCCGTAAGGTAGGATGTTCAGAATGGGTCTGCTCTGC
TCAACAGGTTGCAGTCTCTACCTCAGCAAACCCGGCCCCTGTCTCGGAGCTTGAC
ATAAGGGCCCTCTCTAAGAGGTTCCAGAACCCTTTGATCTCGGGCTTGAGAGTGG
TTCAGTGGGCAACCGGTGCTCATTATAAGCTTAAGCCTATTCTAGATGATCTCAA
TGTTTTCCCATCTCTCTGCCTTGTAGTTGGGGACGGGTCAGGGGGATATCAAGG
GCAGTCCTCAACATGTTTCCAGATGCCAAGCTTGTGTTCAACAGTCTTTTAGAGG
TGAATGACCTGATGGCTTCCGGAACACATCCACTGCCTCCTTCAGCAATCATGAG
GGGAGGAAATGATATCGTCTCCAGAGTGATAGATCTTGACTCAATCTGGGAAAA
ACCGTCCGACTTGAGAAACTTGGCAACCTGGAAATACTTCCAGTCAGTCCAAAA
GCAGGTCAACATGTCCTATGACCTCATTATTTGCGATGCAGAAGTTACTGACATT
GCATCTATCAACCGGATCACCCTGTTAATGTCCGATTTTGCATTGTCTATAGATG
GACCACTCTATTTGGTCTTCAAAACTTATGGGACTATGCTAGTAAATCCAAACTA
CAAGGCTATTCAACACCTGTCAAGAGCGTTCCCCTCGGTCACAGGGTTTATCACC
CAAGTAACTTCGTCTTTTTCATCTGAGCTCTACCTCCGATTCTCCAAACGAGGGA
AGTTTTTCAGAGATGCTGAGTACTTGACCTCTTCCACCCTTCGAGAAATGAGCCT
TGTGTTATTCAATTGTAGCAGCCCCAAGAGTGAGATGCAGAGAGCTCGTTCCTTG
AACTATCAGGATCTTGTGAGAGGATTTCCTGAAGAAATCATATCAAATCCTTACA
ATGAGATGATCATAACTCTGATTGACAGTGATGTAGAATCTTTTCTAGTCCACAA
GATGGTTGATGATCTTGAGTTACAGAGGGGAACTCTGTCTAAAGTGGCTATCATT
ATAGCCATCATGATAGTTTTCTCCAACAGAGTCTTCAACGTTTCCAAACCCCTAA
CTGACCCCTCGTTCTATCCACCGTCTGATCCCAAAATCCTGAGGCACTTCAACAT
ATGTTGCAGTACTATGATGTATCTATCTACTGCTTTAGGTGACGTCCCTAGCTTCG
CAAGACTTCACGACCTGTATAACAGACCTATAACTTATTACTTCAGAAAGCAAGT
CATTCGAGGGAACGTTTATCTATCTTGGAGTTGGTCCAACGACACCTCAGTGTTC
AAAAGGGTAGCCTGTAATTCTAGCCTGAGTCTGTCATCTCACTGGATCAGGTTGA
TTTACAAGATAGTGAAGACTACCAGACTCGTTGGCAGCATCAAGGATCTATCCA
GAGAAGTGGAAAGACACCTTCATAGGTACAACAGGTGGATCACCCTAGAGGATA
TCAGATCTAGATCATCCCTACTAGACTACAGTTGCCTGTGAACCGGATACTCCTG
```

-continued

```
GAAGCCTGCCCATGCTAAGACTCTTGTGTGATGTATCTTGAAAAAAACAAGATCC

TAAATCTGAACCTTTGGTTGTTTGATTGTTTTTCTCAtttttgttgtttatttgttaagcgt
```

In one embodiment, the nucleic acid comprises the sequence of SEQ ID NO: 14, shown below (RABV vector: Coravax V5 China):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAAATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAGAAGTTGAATAACAAAATGCCGGAAATCTACGGATTGTGTATATCCA

TCATGAAAAAAACTAACACCCCTCCTTTCGAACCATCCCAAACATGAGCAAGAT

CTTTGTCAATCCTAGTGCTATTAGAGCCGGTCTGGCCGATCTTGAGATGGCTGAA

GAAACTGTTGATCTGATCAATAGAAATATCGAAGACAATCAGGCTCATCTCCAA

GGGGAACCCATAGAGGTGGACAATCTCCCTGAGGATATGGGGCGACTTCACCTG

GATGATGGAAAATCGCCCAACCATGGTGAGATAGCCAAGGTGGGAGAAGGCAA

GTATCGAGAGGACTTTCAGATGGATGAAGGAGAGGATCCTAGCTTCCTGTTCCA

GTCATACCTGGAAAATGTTGGAGTCCAAATAGTCAGACAAATGAGGTCAGGAGA

GAGATTTCTCAAGATATGGTCACAGACCGTAGAAGAGATTATATCCTATGTCGCG
```

```
GTCAACTTTCCCAACCCTCCAGGAAAGTCTTCAGAGGATAAATCAACCCAGACT

ACTGGCCGAGAGCTCAAGAAGGAGACAACACCCACTCCTTCTCAGAGAGAAAGC

CAATCATCGAAAGCCAGGATGGCGGCTCAAATTGCTTCTGGCCCTCCAGCCCTTG

AATGGTCGGCTACCAATGAAGAGGATGATCTATCAGTGGAGGCTGAGATCGCTC

ACCAGATTGCAGAAAGTTTCTCCAAAAAATATAAGTTTCCCTCTCGATCCTCAGG

GATACTCTTGTATAATTTTGAGCAATTGAAAATGAACCTTGATGATATAGTTAAA

GAGGCAAAAAATGTACCAGGTGTGACCCGTTTAGCCCATGACGGGTCCAAACTC

CCCCTAAGATGTGTACTGGGATGGGTCGCTTTGGCCAACTCTAAGAAATTCCAGT

TGTTAGTCGAATCCGACAAGCTGAGTAAAATCATGCAAGATGACTTGAATCGCT

ATACATCTTGCTAACCGAACCTCTCCCCTCAGTCCCTCTAGACAATAAAATCCGA

GATGTCCCAAAGTCAACATGAAAAAAACAGGCAACACCACTGATAAAATGAAC

CTCCTACGTAAGATAGTGAAAAACCGCAGGGACGAGGACACTCAAAAATCCTCT

CCCGCGTCAGCCCCTCTGGATGACGATGACTTGTGGCTTCCACCCCCTGAATACG

TCCCGCTGAAAGAACTTACAGGCAAGAAGAACATGAGGAACTTTTGTATCAACG

GAAGGGTTAAAGTGTGTAGCCCGAATGGTTACTCGTTCAGGATCCTGCGGCACA

TTCTGAAATCATTCGACGAGATATATTCTGGGAATCATAGGATGATCGGGTTAGT

CAAAGTGGTTATTGGACTGGCTTTGTCAGGATCTCCAGTCCCTGAGGGCCTGAAC

TGGGTATACAAATTGAGGAGAACCTTTATCTTCCAGTGGGCTGATTCCAGGGGCC

CTCTTGAAGGGGAGGAGTTGGAATACTCTCAGGAGATCACTTGGGATGATGATA

CTGAGTTCGTCGGATTGCAAATAAGAGTGATTGCAAAACAGTGTCATATCCAGG

GCAGAGTCTGGTGTATCAACATGAACCCGAGAGCATGTCAACTATGGTCTGACA

TGTCTCTTCAGACACAAAGGTCCGAAGAGGACAAAGATTCCTCTCTGCTTCTAGA

ATAATCAGATTATATCCCGCAAATTTATCACTTGTTTACCTCTGGAGGAGAGAAC

ATATGGGCTCAACTCCAACCCTTGGGAGCAATATAACAAAAAACATGTTATGGT

GCCATTAAACCGCTGCATTTCATCAAAGTCAAGTTGATTACCTTTACATTTTGATC

CTCTTGGATGTGAAAAAAACTATTAACATCCCTCAAAAGACCCcgggccaccATGTTC

GTGTTTCTGGTGCTGCTGCCTCTGGTGAGCTCCCAGTGCGTGAACCTGACCACAA

GGACCCAGCTGCCCCCTGCCTATACCAATTCCTTCACACGGGGCGTGTACTATCC

CGACAAGGTGTTCCGGAGCAGCGTGCTGCACTCCACACAGGATCTGTTTCTGCCT

TTCTTTTCTAACGTGACCTGGTTCCACGCCATCCACGTGAGCGGCACCAATGGCA

CAAAGCGGTTCGACAATCCAGTGCTGCCCTTTAACGATGGCGTGTACTTCGCCTC

CACCGAGAAGTCTAACATCATCAGAGGCTGGATCTTTGGCACCACACTGGACAG

CAAGACACAGTCCCTGCTGATCGTGAACAATGCCACCAACGTGGTCATCAAGGT

GTGCGAGTTCCAGTTTTGTAATGATCCATTCCTGGGCGTGTACTATCACAAGAAC

AATAAGTCTTGGATGGAGAGCGAGTTTCGCGTGTATTCCTCTGCCAACAATTGCA

CATTTGAGTACGTGTCCCAGCCCTTCCTGATGGACCTGGAGGGCAAGCAGGGCA

ATTTCAAGAACCTGAGGGAGTTCGTGTTTAAGAATATCGATGGCTACTTCAAAAT

CTACTCCAAGCACACCCCAATCAACCTGGTGCGCGACCTGCCACAGGGCTTCTCT

GCCCTGGAGCCACTGGTGGATCTGCCCATCGGCATCAACATCACCCGGTTTCAGA

CACTGCTGGCCCTGCACAGAAGCTACCTGACACCAGGCGACAGCTCCTCTGGAT

GGACCGCAGGAGCAGCAGCCTACTATGTGGGCTATCTGCAGCCCAGGACCTTCC
```

```
TGCTGAAGTACAACGAGAATGGCACCATCACAGACGCCGTGGATTGCGCCCTGG

ATCCCCTGTCTGAGACCAAGTGTACACTGAAGAGCTTTACCGTGGAGAAGGGCA

TCTATCAGACAAGCAATTTCAGGGTGCAGCCTACCGAGTCCATCGTGCGCTTTCC

CAATATCACAAACCTGTGCCCTTTTGGCGAGGTGTTCAACGCAACCCGCTTCGCC

AGCGTGTACGCCTGGAATAGGAAGCGCATCTCCAACTGCGTGGCCGACTATTCT

GTGCTGTACAACAGCGCCTCCTTCTCTACCTTTAAGTGCTATGGCGTGAGCCCCA

CAAAGCTGAATGACCTGTGCTTTACCAACGTGTACGCCGATTCCTTCGTGATCAG

GGGCGACGAGGTGCGCCAGATCGCACCAGGACAGACAGGCAAGATCGCAGACT

ACAATTATAAGCTGCCTGACGATTTCACCGGCTGCGTGATCGCCTGGAACTCTAA

CAATCTGGATAGCAAAGTGGGCGGCAACTACAATTATCTGTACCGGCTGTTTAG

AAAGTCTAATCTGAAGCCATTCGAGAGGGACATCTCCACAGAAATCTACCAGGC

CGGCTCTACCCCCTGCAATGGCGTGGAgGGCTTTAACTGTTATTTCCCTCTGCAGA gCTACgGCTTCCAGCCAACAAACGGCGTGGGCTATCAGCCCTACCGCGTGGTGGT

GCTGTCTTTTGAGCTGCTGCACGCACcTGCAACAGTGTGCGGACCAAAGAAGAGC

ACCAATCTGGTGAAGAACAAGTGCGTGAACTTCAACTTCAACGGACTGACCGGA

ACAGGCGTGCTGACCGAGTCCAACAAGAAGTTCCTGCCTTTTCAGCAGTTCGGC

AGGGACATCGCAGATACCACAGACGCCGTGCGCGACCCTCAGACCCTGGAGATC

CTGGACATCACACCATGCTCCTTCGGCGGCGTGTCTGTGATCACACCAGGCACCA

ATACAAGCAACCAGGTGGCCGTGCTGTATCAGGACGTGAATTGTACCGAGGTGC

CAGTGGCAATCCACGCAGATCAGCTGACCCCTACATGGCGGGTGTACTCTACCG

GCAGCAACGTGTTCCAGACAAGAGCCGGATGCCTGATCGGAGCAGAGCACGTGA

ACAATAGCTATGAGTGCGACATCCCTATCGGCGCCGGCATCTGTGCCTCCTACCA

GACCCAGACAAACTCCCCAAGGTCTgtgggaGATGAGGCCGAAGACTTTGTGGAAG

TCCACCTGCCTGATGTGCATAACCAGGTGTCTGGCGTCGACCTGGGACTGCCAAA

TTGGGGCAAGTACGTGCTGCTGAGTGCTGGAGCACTGACTGCCCTGATGCTGATC

ATTTTCCTGATGACCTGCTGTCGGCGCGTGAACAGAAGTGAGCCCACTCAGCAC

AATCTGCGAGGAACCGGGAGAGAAGTGTCAGTCACACCTCAGAGCGGGAAAAT

CATTAGTAGTTGGGAATCACATAAAAGCGGGGGCGAGACCAGGCTGggatccggctcc ggcgagggcagggGaagtctactaacatgcgGGGACGTGGAGGaaaatcccggccccATGGTTCCTCAGGCTCT

CCTGTTTGTACCCCTTCTGGTTTTTCCATTGTGTTTTGGGAAATTCCCTATTTACAC

GATACCAGACAAGCTTGGTCCCTGGAGTCCGATTGACATACATCACCTCAGCTGC

CCAAACAATTTGGTAGTGGAGGACGAAGGATGCACCAACCTGTCAGGGTTCTCC

TACATGGAACTTAAAGTTGGATACATCTTAGCCATAAAAGTGAACGGGTTCACTT

GCACAGGCGTTGTGACGGAGGCTGAAACCTACACTAACTTCGTTGGTTATGTCAC

AACCACGTTCAAAAGAAAGCATTTCCGCCCAACACCAGATGCATGTAGAGCCGC

GTACAACTGGAAGATGGCCGGTGACCCCAGATATGAAGAGTCTCTACACAATCC

GTACCCTGACTACCGCTGGCTTCGAACTGTAAAAACCACCAAGGAGTCTCTCGTT

ATCATATCTCCAAGTGTGGCAGATTTGGACCCATATGACAGATCCCTTCACTCGA

GGGTCTTCCCTAGCGGGAAGTGCTCAGGAGTAGCGGTGTCTTCTACCTACTGCTC

CACTAACCACGATTACACCATTTGGATGCCCGAGAATCCGAGACTAGGGATGTC
```

-continued

```
TTGTGACATTTTTACCAATAGTAGAGGGAAGAGAGCATCCAAAGGGAGTGAGAC
TTGCGGCTTTGTAGATGAAAGAGGCCTATATAAGTCTTTAAAAGGAGCATGCAA
ACTCAAGTTATGTGGAGTTCTAGGACTTAGACTTATGGATGGAACATGGGTCTCG
ATGCAAACATCAAATGAAACCAAATGGTGCCCTCCCGATAAGTTGGTGAACCTG
CACGACTTTCGCTCAGACGAAATTGAGCACCTTGTTGTAGAGGAGTTGGTCAGG
AAGAGAGAGGAGTGTCTGGATGCACTAGAGTCCATCATGACAACCAAGTCAGTG
AGTTTCAGACGTCTCAGTCATTTAAGAAAACTTGTCCCTGGGTTTGGAAAAGCAT
ATACCATATTCAACAAGACCTTGATGGAAGCCGATGCTCACTACAAGTCAGTCga
gACTTGGAATGAGATCCTCCCTTCAAAAGGGTGTTTAAGAGTTGGGGGGAGGTGT
CATCCTCATGTGAACGGGGTGTTTTTCAATGGTATAATATTAGGACCTGACGGCA
ATGTCTTAATCCCAGAGATGCAATCATCCCTCCTCCAGCAACATATGGAGTTGTT
GGAATCCTCGGTTATCCCCCTTGTGCACCCCCTGGCAGACCCGTCTACCGTTTTC
AAGGACGGTGACGAGGCTGAGGATTTTGTTGAAGTTCACCTTCCCGATGTGCAC
AATCAGGTCTCAGGAGTTGACTTGGGTCTCCCGAACTGGGGGAAGTATGTATTAC
TGAGTGCAGGGGCCCTGACTGCCTTGATGTTGATAATTTTCCTGATGACATGTTG
TAGAAGAGTCAATCGATCAGAACCTACGCAACACAATCTCAGAGGGACAGGGA
GGGAGGTGTCAGTCACTCCCCAAAGCGGGAAGATCATATCTTCATGGGAATCAC
ACAAGAGTGGGGGTGAGACCAGACTGTAAgctagcTTATAAAGTGCTGGGTCATCT
AAGCTTTTCAGTCGAGAAAAAAACATTAGATCAGAAGAACAACTGGCAACACTT
CTCAACCTGAGACTTACTTCAAGATGCTCGATCCTGGAGAGGTCTATGATGACCC
TATTGACCCAATCGAGTTAGAGGCTGAACCCAGAGGAACCCCCATTGTCCCCAA
CATCTTGAGGAACTCTGACTACAATCTCAACTCTCCTTTGATAGAAGATCCTGCT
AGACTAATGTTAGAATGGTTAAAAACAGGGAATAGACCTTATCGGATGACTCTA
ACAGACAATTGCTCCAGGTCTTTCAGAGTTTTGAAAGATTATTTCAAGAAGGTAG
ATTTGGGTTCTCTCAAGGTGGGCGGAATGGCTGCACAGTCAATGATTTCTCTCTG
GTTATATGGTGCCCACTCTGAATCCAACAGGAGCCGGAGATGTATAACAGACTT
GGCCCATTTCTATTCCAAGTCGTCCCCCATAGAGAAGCTGTTGAATCTCACGCTA
GGAAATAGAGGGCTGAGAATCCCCCCAGAGGGAGTGTTAAGTTGCCTTGAGAGG
GTTGATTATGATAATGCATTTGGAAGGTATCTTGCCAACACGTATTCCTCTTACTT
GTTCTTCCATGTAATCACCTTATACATGAACGCCCTAGACTGGGATGAAGAAAG
ACCATCCTAGCATTATGGAAAGATTTAACCTCAGTGGACATCGGGAAGGACTTG
GTAAAGTTCAAAGACCAAATATGGGGACTGCTGATCGTGACAAAGGACTTTGTT
TACTCCCAAAGTTCCAATTGTCTTTTTGACAGAAACTACACACTTATGCTAAAAG
ATCTTTTCTTGTCTCGCTTCAACTCCTTAATGGTCTTGCTCTCTCCCCCAGAGCCC
CGATACTCAGATGACTTGATATCTCAACTATGCCAGCTGTACATTGCTGGGGATC
AAGTCTTGTCTATGTGTGGAAACTCCGGCTATGAAGTCATCAAAATATTGGAGCC
ATATGTCGTGAATAGTTTAGTCCAGAGAGCAGAAAAGTTTAGGCCTCTCATTCAT
TCCTTGGGAGACTTTCCTGTATTTATAAAAGACAAGGTAAGTCAACTTGAAGAGA
CGTTCGGTCCCTGTGCAAGAAGGTTCTTTAGGGCTCTGGATCAATTCGACAACAT
ACATGACTTGGTTTTTGTGTTTGGCTGTTACAGGCATTGGGGGCACCCATATATA
GATTATCGAAAGGGTCTGTCAAAACTATATGATCAGGTTCACCTTAAAAAAATG
```

```
ATAGATAAGTCCTACCAGGAGTGCTTAGCAAGCGACCTAGCCAGGAGGATCCTT

AGATGGGGTTTTGATAAGTACTCCAAGTGGTATCTGGATTCAAGATTCCTAGCCC

GAGACCACCCCTTGACTCCTTATATCAAAACCCAAACATGGCCACCCAAACATA

TTGTAGACTTGGTGGGGATACATGGCACAAGCTCCCGATCACGCAGATCTTTGA

GATTCCTGAATCAATGGATCCGTCAGAAATATTGGATGACAAATCACATTCTTTC

ACCAGAACGAGACTAGCTTCTTGGCTGTCAGAAAACCGAGGGGGCCTGTTCCT

AGCGAAAAGTTATTATCACGGCCCTGTCTAAGCCGCCTGTCAATCCCCGAGAG

TTTCTGAGGTCTATAGACCTCGGAGGATTGCCAGATGAAGACTTGATAATTGGCC

TCAAGCCAAAGGAACGGGAATTGAAGATTGAAGGTCGATTCTTTGCTCTAATGT

CATGGAATCTAAGATTGTATTTTGTCATCACTGAAAAACTCTTGGCCAACTACAT

CTTGCCACTTTTTGACGCGCTGACTATGACAGACAACCTGAACAAGGTGTTTAAA

AAGCTGATCGACAGGGTCACCGGGCAAGGGCTTTTGGACTATTCAAGGGTCACA

TATGCATTTCACCTGGACTATGAAAAGTGGAACAACCATCAAAGATTAGAGTCA

ACAGAGGATGTATTTTCTGTCCTAGATCAAGTGTTTGGATTGAAGAGAGTGTTTT

CTAGAACACACGAGTTTTTTCAAAAGGCCTGGATCTATTATTCAGACAGATCAGA

CCTCATCGGGTTACGGGAGGATCAAATATACTGCTTAGATGCGTCCAACGGCCC

AACCTGTTGGAATGGCCAGGATGGCGGGCTAGAAGGCTTACGGCAGAAGGGCTG

GAGTCTAGTCAGCTTATTGATGATAGATAGAGAATCTCAAATCAGGAACACAAG

AACCAAAATACTAGCTCAAGGAGACAACCAGGTTTTATGTCCGACATACATGTT

GTCGCCAGGGCTATCTCAAGAGGGGCTCCTCTATGAATTGGAGAGAATATCAAG

GAATGCACTTTCGATATACAGAGCCGTCGAGGAAGGGGCATCTAAGCTAGGGCT

GATCATCAAGAAAGAAGAGACCATGTGTAGTTATGACTTCCTCATCTATGGAAA

AACCCCTTTGTTTAGAGGTAACATATTGGTGCCTGAGTCCAAAAGATGGGCCAG

AGTCTCTTGCGTCTCTAATGACCAAATAGTCAACCTCGCCAATATAATGTCGACA

GTGTCCACCAATGCGCTAACAGTGGCACAACACTCTCAATCTTTGATCAAACCGA

TGAGGGATTTTCTGCTCATGTCAGTACAGGCAGTCTTTCACTACCTGCTATTTAGC

CCAATCTTAAAGGGAAGAGTTTACAAGATTCTGAGCGCTGAAGGGGAGAGCTTT

CTCCTAGCCATGTCAAGGATAATCTATCTAGATCCTTCTTTGGGAGGGATATCTG

GAATGTCCCTCGGAAGATTCCATATACGACAGTTCTCAGACCCTGTCTCTGAAGG

GTTATCCTTCTGGAGAGAGATCTGGTTAAGCTCCCAAGAGTCCTGGATTCACGCG

TTGTGTCAAGAGGCTGGAAACCCAGATCTTGGAGAGAGAACACTCGAGAGCTTC

ACTCGCCTTCTAGAAGATCCGACCACCTTAAATATCAGAGGAGGGGCCAGTCCT

ACCATTCTACTCAAGGATGCAATCAGAAAGGCTTTATATGACGAGGTGGACAAG

GTGGAAAATTCAGAGTTTCGAGAGGCAATCCTGTTGTCCAAGACCCATAGAGAT aattttatactcttcttaatatctgttgagcctctgtttcctcgatttctcagtga

GCTATTCAGTTCGTCTTTTTTGGGAATCCCCGAGTCAATCATTGGATTGATACAA

AACTCCCGAACGATAAGAAGGCAGTTTAGAAAGAGTCTCTCAAAAACTTTAGAA

GAATCCTTCTACAACTCAGAGATCCACGGGATTAGTCGGATGACCCAGACACCT

CAGAGGGTTGGGGGGGTGTGGCCTTGCTCTTCAGAGAGGGCAGATCTACTTAGG

GAGATCTCTTGGGGAAGAAAAGTGGTAGGCACGACAGTTCCTCACCCTTCTGAG
```

-continued

```
ATGTTGGGATTACTTCCCAAGTCCTCTATTTCTTGCACTTGTGGAGCAACAGGAG

GAGGCAATCCTAGAGTTTCTGTATCAGTACTCCCGTCCTTTGATCAGTCATTTTTT

TCACGAGGCCCCCTAAAGGGATACTTGGGCTCGTCCACCTCTATGTCGACCCAGC

TATTCCATGCATGGGAAAAAGTCACTAATGTTCATGTGGTGAAGAGAGCTCTATC

GTTAAAAGAATCTATAAACTGGTTCATTACTAGAGATTCCAACTTGGCTCAAGCT

CTAATTAGGAACATTATGTCTCTGACAGGCCCTGATTTCCCTCTAGAGGAGGCCC

CTGTCTTCAAAAGGACGGGGTCAGCCTTGCATAGGTTCAAGTCTGCCAGATACA

GCGAAGGAGGGTATTCTTCTGTCTGCCCGAACCTCCTCTCTCATATTTCTGTTAGT

ACAGACACCATGTCTGATTTGACCCAAGACGGGAAGAACTACGATTTCATGTTCC

AGCCATTGATGCTTTATGCACAGACATGGACATCAGAGCTGGTACAGAGAGACA

CAAGGCTAAGAGACTCTACGTTTCATTGGCACCTCCGATGCAACAGGTGTGTGA

GACCCATTGACGACGTGACCCTGGAGACCTCTCAGATCTTCGAGTTTCCGGATGT

GTCGAAAAGAATATCCAGAATGGTTTCTGGGGCTGTGCCTCACTTCCAGAGGCTT

CCCGATATCCGTCTGAGACCAGGAGATTTTGAATCTCTAAGCGGTAGAGAAAAG

TCTCACCATATCGGATCAGCTCAGGGGCTCTTATACTCAATCTTAGTGGCAATTC

ACGACTCAGGATACAATGATGGAACCATCTTCCCTGTCAACATATACGGCAAGG

TTTCCCCTAGAGACTATTTGAGAGGGCTCGCAAGGGGAGTATTGATAGGATCCTC

GATTTGCTTCTTGACAAGAATGACAAATATCAATATTAATAGACCTCTTGAATTG

GTCTCAGGGGTAATCTCATATATTCTCCTGAGGCTAGATAACCATCCCTCCTTGT

ACATAATGCTCAGAGAACCGTCTCTTAGAGGAGAGATATTTTCTATCCCTCAGAA

AATCCCCGCCGCTTATCCAACCACTATGAAAGAAGGCAACAGATCAATCTTGTG

TTATCTCCAACATGTGCTACGCTATGAGCGAGAGATAATCACGGCGTCTCCAGAG

AATGACTGGCTATGGATCTTTTCAGACTTTAGAAGTGCCAAAATGACGTACCTAT

CCCTCATTACTTACCAGTCTCATCTTCTACTCCAGAGGGTTGAGAGAAACCTATC

TAAGAGTATGAGAGATAACCTGCGACAATTGAGTTCTTTGATGAGGCAGGTGCT

GGGCGGGCACGGAGAAGATACCTTAGAGTCAGACGACAACATTCAACGACTGCT

AAAAGACTCTTTACGAAGGACAAGATGGGTGGATCAAGAGGTGCGCCATGCAGC

TAGAACCATGACTGGAGATTACAGCCCCAACAAGAAGGTGTCCCGTAAGGTAGG

ATGTTCAGAATGGGTCTGCTCTGCTCAACAGGTTGCAGTCTCTACCTCAGCAAAC

CCGGCCCCTGTCTCGGAGCTTGACATAAGGGCCCTCTCTAAGAGGTTCCAGAACC

CTTTGATCTCGGGCTTGAGAGTGGTTCAGTGGGCAACCGGTGCTCATTATAAGCT

TAAGCCTATTCTAGATGATCTCAATGTTTTCCCATCTCTCTGCCTTGTAGTTGGGG

ACGGGTCAGGGGGGATATCAAGGGCAGTCCTCAACATGTTTCCAGATGCCAAGC

TTGTGTTCAACAGTCTTTTAGAGGTGAATGACCTGATGGCTTCCGGAACACATCC

ACTGCCTCCTTCAGCAATCATGAGGGGAGGAAATGATATCGTCTCCAGAGTGAT

AGATCTTGACTCAATCTGGGAAAAACCGTCCGACTTGAGAAACTTGGCAACCTG

GAAATACTTCCAGTCAGTCCAAAAGCAGGTCAACATGTCCTATGACCTCATTATT

TGCGATGCAGAAGTTACTGACATTGCATCTATCAACCGGATCACCCTGTTAATGT

CCGATTTTGCATTGTCTATAGATGGACCACTCTATTTGGTCTTCAAAACTTATGGG

ACTATGCTAGTAAATCCAAACTACAAGGCTATTCAACACCTGTCAAGAGCGTTCC

CCTCGGTCACAGGGTTTATCACCCAAGTAACTTCGTCTTTTTCATCTGAGCTCTAC
```

-continued

```
CTCCGATTCTCCAAACGAGGGAAGTTTTTCAGAGATGCTGAGTACTTGACCTCTT

CCACCCTTCGAGAAATGAGCCTTGTGTTATTCAATTGTAGCAGCCCCAAGAGTGA

GATGCAGAGAGCTCGTTCCTTGAACTATCAGGATCTTGTGAGAGGATTTCCTGAA

GAAATCATATCAAATCCTTACAATGAGATGATCATAACTCTGATTGACAGTGATG

TAGAATCTTTTCTAGTCCACAAGATGGTTGATGATCTTGAGTTACAGAGGGGAAC

TCTGTCTAAAGTGGCTATCATTATAGCCATCATGATAGTTTTCTCCAACAGAGTC

TTCAACGTTTCCAAACCCCTAACTGACCCCTCGTTCTATCCACCGTCTGATCCCA

AAATCCTGAGGCACTTCAACATATGTTGCAGTACTATGATGTATCTATCTACTGC

TTTAGGTGACGTCCCTAGCTTCGCAAGACTTCACGACCTGTATAACAGACCTATA

ACTTATTACTTCAGAAAGCAAGTCATTCGAGGGAACGTTTATCTATCTTGGAGTT

GGTCCAACGACACCTCAGTGTTCAAAAGGGTAGCCTGTAATTCTAGCCTGAGTCT

GTCATCTCACTGGATCAGGTTGATTTACAAGATAGTGAAGACTACCAGACTCGTT

GGCAGCATCAAGGATCTATCCAGAGAAGTGGAAAGACACCTTCATAGGTACAAC

AGGTGGATCACCCTAGAGGATATCAGATCTAGATCATCCCTACTAGACTACAGTT

GCCTGTGAACCGGATACTCCTGGAAGCCTGCCCATGCTAAGACTCTTGTGTGATG

TATCTTGAAAAAAACAAGATCCTAAATCTGAACCTTTGGTTGTTTGATTGTTTTC

TCATTTTGTTGTTTATTTGTTAAGCGT.
```

In one embodiment, the nucleic acid comprises the sequence of SEQ ID NO: 15, shown below (RABV vector: Coravax V5 South Africa):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAAATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT
```

```
AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAGAAGTTGAATAACAAAATGCCGGAAATCTACGGATTGTGTATATCCA

TCATGAAAAAAACTAACACCCCTCCTTTCGAACCATCCCAAACATGAGCAAGAT

CTTTGTCAATCCTAGTGCTATTAGAGCCGGTCTGGCCGATCTTGAGATGGCTGAA

GAAACTGTTGATCTGATCAATAGAAATATCGAAGACAATCAGGCTCATCTCCAA

GGGGAACCCATAGAGGTGGACAATCTCCCTGAGGATATGGGGCGACTTCACCTG

GATGATGGAAAATCGCCCAACCATGGTGAGATAGCCAAGGTGGGAGAAGGCAA

GTATCGAGAGGACTTTCAGATGGATGAAGGAGAGGATCCTAGCTTCCTGTTCCA

GTCATACCTGGAAAATGTTGGAGTCCAAATAGTCAGACAAATGAGGTCAGGAGA

GAGATTTCTCAAGATATGGTCACAGACCGTAGAAGAGATTATATCCTATGTCGCG

GTCAACTTTCCCAACCCTCCAGGAAAGTCTTCAGAGGATAAATCAACCCAGACT

ACTGGCCGAGAGCTCAAGAAGGAGACAACACCCACTCCTTCTCAGAGAGAAAGC

CAATCATCGAAAGCCAGGATGGCGGCTCAAATTGCTTCTGGCCCTCCAGCCCTTG

AATGGTCGGCTACCAATGAAGAGGATGATCTATCAGTGGAGGCTGAGATCGCTC

ACCAGATTGCAGAAAGTTTCTCCAAAAAATATAAGTTTCCCTCTCGATCCTCAGG

GATACTCTTGTATAATTTTGAGCAATTGAAAATGAACCTTGATGATATAGTTAAA

GAGGCAAAAAATGTACCAGGTGTGACCCGTTTAGCCCATGACGGGTCCAAACTC

CCCCTAAGATGTGTACTGGGATGGGTCGCTTTGGCCAACTCTAAGAAATTCCAGT

TGTTAGTCGAATCCGACAAGCTGAGTAAAATCATGCAAGATGACTTGAATCGCT

ATACATCTTGCTAACCGAACCTCTCCCCTCAGTCCCTCTAGACAATAAAATCCGA

GATGTCCCAAAGTCAACATGAAAAAAAACAGGCAACACCACTGATAAAATGAAC

CTCCTACGTAAGATAGTGAAAAACCGCAGGGACGAGGACACTCAAAAATCCTCT

CCCGCGTCAGCCCCTCTGGATGACGATGACTTGTGGCTTCCACCCCCTGAATACG

TCCCGCTGAAAGAACTTACAGGCAAGAAGAACATGAGGAACTTTTGTATCAACG

GAAGGGTTAAAGTGTGTAGCCCGAATGGTTACTCGTTCAGGATCCTGCGGCACA

TTCTGAAATCATTCGACGAGATATATTCTGGGAATCATAGGATGATCGGGTTAGT

CAAAGTGGTTATTGGACTGGCTTTGTCAGGATCTCCAGTCCCTGAGGGCCTGAAC

TGGGTATACAAATTGAGGAGAACCTTTATCTTCCAGTGGGCTGATTCCAGGGGCC

CTCTTGAAGGGGAGGAGTTGGAATACTCTCAGGAGATCACTTGGGATGATGATA

CTGAGTTCGTCGGATTGCAAATAAGAGTGATTGCAAAACAGTGTCATATCCAGG

GCAGAGTCTGGTGTATCAACATGAACCCGAGAGCATGTCAACTATGGTCTGACA

TGTCTCTTCAGACACAAAGGTCCGAAGAGGACAAAGATTCCTCTCTGCTTCTAGA

ATAATCAGATTATATCCCGCAAATTTATCACTTGTTTACCTCTGGAGGAGAGAAC

ATATGGGCTCAACTCCAACCCTTGGGAGCAATATAACAAAAAACATGTTATGGT

GCCATTAAACCGCTGCATTTCATCAAAGTCAAGTTGATTACCTTTACATTTTGATC
```

-continued

```
CTCTTGGATGTGAAAAAAACTATTAACATCCCTCAAAAGACCccgggccaccATGTTC

GTGTTTCTGGTGCTGCTGCCTCTGGTGAGCTCCCAGTGCGTGAACTTCACCACAA

GGACCCAGCTGCCCCCTGCCTATACCAATTCCTTCACACGGGCGTGTACTATCC

CGACAAGGTGTTCCGGAGCAGCGTGCTGCACTCCACACAGGATCTGTTTCTGCCT

TTCTTTTCTAACGTGACCTGGTTCCACGCCATCCACGTGAGCGGCACCAATGGCA

CAAAGCGGTTCGCCAATCCAGTGCTGCCCTTTAACGATGGCGTGTACTTCGCCTC

CACCGAGAAGTCTAACATCATCAGAGGCTGGATCTTTGGCACCACACTGGACAG

CAAGACACAGTCCCTGCTGATCGTGAACAATGCCACCAACGTGGTCATCAAGGT

GTGCGAGTTCCAGTTTTGTAATGATCCATTCCTGGGCGTGTACTATCACAAGAAC

AATAAGTCTTGGATGGAGAGCGAGTTTCGCGTGTATTCCTCTGCCAACAATTGCA

CATTTGAGTACGTGTCCCAGCCCTTCCTGATGGACCTGGAGGGCAAGCAGGGCA

ATTTCAAGAACCTGAGGGAGTTCGTGTTTAAGAATATCGATGGCTACTTCAAAAT

CTACTCCAAGCACACCCCAATCAACCTGGTGCGCGGCCTGCCACAGGGCTTCTCT

GCCCTGGAGCCACTGGTGGATCTGCCCATCGGCATCAACATCACCCGGTTTCAGA

CACTGCTGGCCCTGCACAGAAGCTACCTGACACCAGGCGACAGCTCCTCTGGAT

GGACCGCAGGAGCAGCAGCCTACTATGTGGGCTATCTGCAGCCCAGGACCTTCC

TGCTGAAGTACAACGAGAATGGCACCATCACAGACGCCGTGGATTGCGCCCTGG

ATCCCCTGTCTGAGACCAAGTGTACACTGAAGAGCTTTACCGTGGAGAAGGGCA

TCTATCAGACAAGCAATTTCAGGGTGCAGCCTACCGAGTCCATCGTGCGCTTTCC

CAATATCACAAACCTGTGCCCTTTTGGCGAGGTGTTCAACGCAACCCGCTTCGCC

AGCGTGTACGCCTGGAATAGGAAGCGCATCTCCAACTGCGTGGCCGACTATTCT

GTGCTGTACAACAGCGCCTCCTTCTCTACCTTTAAGTGCTATGGCGTGAGCCCCA

CAAAGCTGAATGACCTGTGCTTTACCAACGTGTACGCCGATTCCTTCGTGATCAG

GGGCGACGAGGTGCGCCAGATCGCACCAGGACAGACAGGCAATATCGCAGACT

ACAATTATAAGCTGCCTGACGATTTCACCGGCTGCGTGATCGCCTGGAACTCTAA

CAATCTGGATAGCAAAGTGGGCGGCAACTACAATTATCTGTACCGGCTGTTTAG

AAAGTCTAATCTGAAGCCATTCGAGAGGGACATCTCCACAGAAATCTACCAGGC

CGGCTCTACCCCCTGCAATGGCGTGAAGGGCTTTAACTGTTATTTCCCTCTGCAG

AGCTACGGCTTCCAGCCAACATATGGCGTGGGCTATCAGCCCTACCGCGTGGTG

GTGCTGTCTTTTGAGCTGCTGCACGCACCTGCAACAGTGTGCGGACCAAAGAAG

AGCACCAATCTGGTGAAGAACAAGTGCGTGAACTTCAACTTCAACGGACTGACC

GGAACAGGCGTGCTGACCGAGTCCAACAAGAAGTTCCTGCCTTTTCAGCAGTTC

GGCAGGGACATCGCAGATACCACAGACGCCGTGCGCGACCCTCAGACCCTGGAG

ATCCTGGACATCACACCATGCTCCTTCGGCGGCGTGTCTGTGATCACACCAGGCA

CCAATACAAGCAACCAGGTGGCCGTGCTGTATCAGGGCGTGAATTGTACCGAGG

TGCCAGTGGCAATCCACGCAGATCAGCTGACCCCTACATGGCGGGTGTACTCTA

CCGGCAGCAACGTGTTCCAGACAAGAGCCGGATGCCTGATCGGAGCAGAGCACG

TGAACAATAGCTATGAGTGCGACATCCCTATCGGCGCCGGCATCTGTGCCTCCTA

CCAGACCCAGACAAACTCCCCAGAATCAAGCGTGATTCCTCTGGTCCATCCACTG

GCAGATCCCTCCACAGTGTTCAAAGACGGAGATGAGGCCGAAGACTTTGTGGAA

GTCCACCTGCCTGATGTGCATAACCAGGTGTCTGGCGTCGACCTGGGACTGCCAA
```

```
ATTGGGGCAAGTACGTGCTGCTGAGTGCTGGAGCACTGACTGCCCTGATGCTGAT

CATTTTCCTGATGACCTGCTGTCGGCGCGTGAACAGAAGTGAGCCCACTCAGCAC

AATCTGCGAGGAACCGGGAGAGAAGTGTCAGTCACACCTCAGAGCGGGAAAAT

CATTAGTAGTTGGGAATCACATAAAAGCGGGGGCGAGACCAGGCTGggatccggctcc ggcgagggcaggggaagtctactaacatgcggggacgtggaggaaaatcccggccccATGGTTCCTCAGGCTCT

CCTGTTTGTACCCCTTCTGGTTTTTCCATTGTGTTTTGGGAAATTCCCTATTTACAC

GATACCAGACAAGCTTGGTCCCTGGAGTCCGATTGACATACATCACCTCAGCTGC

CCAAACAATTTGGTAGTGGAGGACGAAGGATGCACCAACCTGTCAGGGTTCTCC

TACATGGAACTTAAAGTTGGATACATCTTAGCCATAAAAGTGAACGGGTTCACTT

GCACAGGCGTTGTGACGGAGGCTGAAACCTACACTAACTTCGTTGGTTATGTCAC

AACCACGTTCAAAAGAAAGCATTTCCGCCCAACACCAGATGCATGTAGAGCCGC

GTACAACTGGAAGATGGCCGGTGACCCCAGATATGAAGAGTCTCTACACAATCC

GTACCCTGACTACCGCTGGCTTCGAACTGTAAAAACCACCAAGGAGTCTCTCGTT

ATCATATCTCCAAGTGTGGCAGATTTGGACCCATATGACAGATCCCTTCACTCGA

GGGTCTTCCCTAGCGGGAAGTGCTCAGGAGTAGCGGTGTCTTCTACCTACTGCTC

CACTAACCACGATTACACCATTTGGATGCCCGAGAATCCGAGACTAGGGATGTC

TTGTGACATTTTTACCAATAGTAGAGGGAAGAGAGCATCCAAAGGGAGTGAGAC

TTGCGGCTTTGTAGATGAAAGAGGCCTATATAAGTCTTTAAAAGGAGCATGCAA

ACTCAAGTTATGTGGAGTTCTAGGACTTAGACTTATGGATGGAACATGGGTCTCG

ATGCAAACATCAAATGAAACCAAATGGTGCCCTCCCGATAAGTTGGTGAACCTG

CACGACTTTCGCTCAGACGAAATTGAGCACCTTGTTGTAGAGGAGTTGGTCAGG

AAGAGAGAGGAGTGTCTGGATGCACTAGAGTCCATCATGACAACCAAGTCAGTG

AGTTTCAGACGTCTCAGTCATTTAAGAAAACTTGTCCCTGGGTTTGGAAAAGCAT

ATACCATATTCAACAAGACCTTGATGGAAGCCGATGCTCACTACAAGTCAGTCga gACTTGGAATGAGATCCTCCCTTCAAAAGGGTGTTTAAGAGTTGGGGGGAGGTGT

CATCCTCATGTGAACGGGGTGTTTTTCAATGGTATAATATTAGGACCTGACGGCA

ATGTCTTAATCCCAGAGATGCAATCATCCCTCCTCCAGCAACATATGGAGTTGTT

GGAATCCTCGGTTATCCCCCTTGTGCACCCCCTGGCAGACCCGTCTACCGTTTTC

AAGGACGGTGACGAGGCTGAGGATTTTGTTGAAGTTCACCTTCCCGATGTGCAC

AATCAGGTCTCAGGAGTTGACTTGGGTCTCCCGAACTGGGGGAAGTATGTATTAC

TGAGTGCAGGGCCCTGACTGCCTTGATGTTGATAATTTTCCTGATGACATGTTG

TAGAAGAGTCAATCGATCAGAACCTACGCAACACAATCTCAGAGGGACAGGGA

GGGAGGTGTCAGTCACTCCCCAAAGCGGGAAGATCATATCTTCATGGGAATCAC

ACAAGAGTGGGGGTGAGACCAGACTGTAAgctagcTTATAAAGTGCTGGGTCATCT

AAGCTTTTCAGTCGAGAAAAAAACATTAGATCAGAAGAACAACTGGCAACACTT

CTCAACCTGAGACTTACTTCAAGATGCTCGATCCTGGAGAGGTCTATGATGACCC

TATTGACCCAATCGAGTTAGAGGCTGAACCCAGAGGAACCCCCATTGTCCCCAA

CATCTTGAGGAACTCTGACTACAATCTCAACTCTCCTTTGATAGAAGATCCTGCT

AGACTAATGTTAGAATGGTTAAAAACAGGGAATAGACCTTATCGGATGACTCTA

ACAGACAATTGCTCCAGGTCTTTCAGAGTTTTGAAAGATTATTTCAAGAAGGTAG
```

-continued

```
ATTTGGGTTCTCTCAAGGTGGGCGGAATGGCTGCACAGTCAATGATTTCTCTCTG
GTTATATGGTGCCCACTCTGAATCCAACAGGAGCCGGAGATGTATAACAGACTT
GGCCCATTTCTATTCCAAGTCGTCCCCCATAGAGAAGCTGTTGAATCTCACGCTA
GGAAATAGAGGGCTGAGAATCCCCCCAGAGGGAGTGTTAAGTTGCCTTGAGAGG
GTTGATTATGATAATGCATTTGGAAGGTATCTTGCCAACACGTATTCCTCTTACTT
GTTCTTCCATGTAATCACCTTATACATGAACGCCCTAGACTGGGATGAAGAAAAG
ACCATCCTAGCATTATGGAAAGATTTAACCTCAGTGGACATCGGGAAGGACTTG
GTAAAGTTCAAAGACCAAATATGGGGACTGCTGATCGTGACAAAGGACTTTGTT
TACTCCCAAAGTTCCAATTGTCTTTTTGACAGAAACTACACACTTATGCTAAAAG
ATCTTTTCTTGTCTCGCTTCAACTCCTTAATGGTCTTGCTCTCTCCCCCAGAGCCC
CGATACTCAGATGACTTGATATCTCAACTATGCCAGCTGTACATTGCTGGGGATC
AAGTCTTGTCTATGTGTGGAAACTCCGGCTATGAAGTCATCAAAATATTGGAGCC
ATATGTCGTGAATAGTTTAGTCCAGAGAGCAGAAAAGTTTAGGCCTCTCATTCAT
TCCTTGGGAGACTTTCCTGTATTTATAAAAGACAAGGTAAGTCAACTTGAAGAGA
CGTTCGGTCCCTGTGCAAGAAGGTTCTTTAGGGCTCTGGATCAATTCGACAACAT
ACATGACTTGGTTTTTGTGTTTGGCTGTTACAGGCATTGGGGCACCCATATATA
GATTATCGAAAGGGTCTGTCAAAACTATATGATCAGGTTCACCTTAAAAAAATG
ATAGATAAGTCCTACCAGGAGTGCTTAGCAAGCGACCTAGCCAGGAGGATCCTT
AGATGGGTTTTGATAAGTACTCCAAGTGGTATCTGGATTCAAGATTCCTAGCCC
GAGACCACCCCTTGACTCCTTATATCAAAACCCAAACATGGCCACCCAAACATA
TTGTAGACTTGGTGGGGATACATGGCACAAGCTCCCGATCACGCAGATCTTTGA
GATTCCTGAATCAATGGATCCGTCAGAAATATTGGATGACAAATCACATTCTTTC
ACCAGAACGAGACTAGCTTCTTGGCTGTCAGAAAACCGAGGGGGGCCTGTTCCT
AGCGAAAAAGTTATTATCACGGCCCTGTCTAAGCCGCCTGTCAATCCCCGAGAG
TTTCTGAGGTCTATAGACCTCGGAGGATTGCCAGATGAAGACTTGATAATTGGCC
TCAAGCCAAAGGAACGGGAATTGAAGATTGAAGGTCGATTCTTTGCTCTAATGT
CATGGAATCTAAGATTGTATTTTGTCATCACTGAAAAACTCTTGGCCAACTACAT
CTTGCCACTTTTTGACGCGCTGACTATGACAGACAACCTGAACAAGGTGTTTAAA
AAGCTGATCGACAGGGTCACCGGGCAAGGGCTTTTGGACTATTCAAGGGTCACA
TATGCATTTCACCTGGACTATGAAAAGTGGAACAACCATCAAAGATTAGAGTCA
ACAGAGGATGTATTTTCTGTCCTAGATCAAGTGTTTGGATTGAAGAGAGTGTTTT
CTAGAACACACGAGTTTTTTCAAAAGGCCTGGATCTATTATTCAGACAGATCAGA
CCTCATCGGGTTACGGGAGGATCAAATATACTGCTTAGATGCGTCCAACGGCCC
AACCTGTTGGAATGGCCAGGATGGCGGGCTAGAAGGCTTACGGCAGAAGGGCTG
GAGTCTAGTCAGCTTATTGATGATAGATAGAGAATCTCAAATCAGGAACACAAG
AACCAAAATACTAGCTCAAGGAGACAACCAGGTTTTATGTCCGACATACATGTT
GTCGCCAGGGCTATCTCAAGAGGGGCTCCTCTATGAATTGGAGAGAATATCAAG
GAATGCACTTTCGATATACAGAGCCGTCGAGGAAGGGGCATCTAAGCTAGGGCT
GATCATCAAGAAAGAAGAGACCATGTGTAGTTATGACTTCCTCATCTATGGAAA
AACCCCTTTGTTTAGAGGTAACATATTGGTGCCTGAGTCCAAAAGATGGGCCAG
AGTCTCTTGCGTCTCTAATGACCAAATAGTCAACCTCGCCAATATAATGTCGACA
```

```
GTGTCCACCAATGCGCTAACAGTGGCACAACACTCTCAATCTTTGATCAAACCGA

TGAGGGATTTTCTGCTCATGTCAGTACAGGCAGTCTTTCACTACCTGCTATTTAGC

CCAATCTTAAAGGGAAGAGTTTACAAGATTCTGAGCGCTGAAGGGGAGAGCTTT

CTCCTAGCCATGTCAAGGATAATCTATCTAGATCCTTCTTTGGGAGGGATATCTG

GAATGTCCCTCGGAAGATTCCATATACGACAGTTCTCAGACCCTGTCTCTGAAGG

GTTATCCTTCTGGAGAGAGATCTGGTTAAGCTCCCAAGAGTCCTGGATTCACGCG

TTGTGTCAAGAGGCTGGAAACCCAGATCTTGGAGAGAGAACACTCGAGAGCTTC

ACTCGCCTTCTAGAAGATCCGACCACCTTAAATATCAGAGGAGGGGCCAGTCCT

ACCATTCTACTCAAGGATGCAATCAGAAAGGCTTTATATGACGAGGTGGACAAG

GTGGAAAATTCAGAGTTTCGAGAGGCAATCCTGTTGTCCAAGACCCATAGAGAT aatttTATACTCTTCTTAATATCTGTTGAGCCTCTGTTTCCTCGATTTCTCAGTGA

GCTATTCAGTTCGTCTTTTTTGGGAATCCCCGAGTCAATCATTGGATTGATACAA

AACTCCCGAACGATAAGAAGGCAGTTTAGAAAGAGTCTCTCAAAAACTTTAGAA

GAATCCTTCTACAACTCAGAGATCCACGGGATTAGTCGGATGACCCAGACACCT

CAGAGGGTTGGGGGGGTGTGGCCTTGCTCTTCAGAGAGGGCAGATCTACTTAGG

GAGATCTCTTGGGGAAGAAAAGTGGTAGGCACGACAGTTCCTCACCCTTCTGAG

ATGTTGGGATTACTTCCCAAGTCCTCTATTTCTTGCACTTGTGGAGCAACAGGAG

GAGGCAATCCTAGAGTTTCTGTATCAGTACTCCCGTCCTTTGATCAGTCATTTTT

TCACGAGGCCCCCTAAAGGGATACTTGGGCTCGTCCACCTCTATGTCGACCCAGC

TATTCCATGCATGGGAAAAAGTCACTAATGTTCATGTGGTGAAGAGAGCTCTATC

GTTAAAAGAATCTATAAACTGGTTCATTACTAGAGATTCCAACTTGGCTCAAGCT

CTAATTAGGAACATTATGTCTCTGACAGGCCCTGATTTCCCTCTAGAGGAGGCCC

CTGTCTTCAAAAGGACGGGGTCAGCCTTGCATAGGTTCAAGTCTGCCAGATACA

GCGAAGGAGGGTATTCTTCTGTCTGCCCGAACCTCCTCTCTCATATTTCTGTTAGT

ACAGACACCATGTCTGATTTGACCCAAGACGGGAAGAACTACGATTTCATGTTCC

AGCCATTGATGCTTTATGCACAGACATGGACATCAGAGCTGGTACAGAGAGACA

CAAGGCTAAGAGACTCTACGTTTCATTGGCACCTCCGATGCAACAGGTGTGTGA

GACCCATTGACGACGTGACCCTGGAGACCTCTCAGATCTTCGAGTTTCCGGATGT

GTCGAAAAGAATATCCAGAATGGTTTCTGGGGCTGTGCCTCACTTCCAGAGGCTT

CCCGATATCCGTCTGAGACCAGGAGATTTTGAATCTCTAAGCGGTAGAGAAAAG

TCTCACCATATCGGATCAGCTCAGGGGCTCTTATACTCAATCTTAGTGGCAATTC

ACGACTCAGGATACAATGATGGAACCATCTTCCCTGTCAACATATACGGCAAGG

TTTCCCCTAGAGACTATTTGAGAGGGCTCGCAAGGGGAGTATTGATAGGATCCTC

GATTTGCTTCTTGACAAGAATGACAAATATCAATATTAATAGACCTCTTGAATTG

GTCTCAGGGGTAATCTCATATATTCTCCTGAGGCTAGATAACCATCCCTCCTTGT

ACATAATGCTCAGAGAACCGTCTCTTAGAGGAGAGATATTTTCTATCCCTCAGAA

AATCCCCGCCGCTTATCCAACCACTATGAAAGAAGGCAACAGATCAATCTTGTG

TTATCTCCAACATGTGCTACGCTATGAGCGAGAGATAATCACGGCGTCTCCAGAG

AATGACTGGCTATGGATCTTTTCAGACTTTAGAAGTGCCAAAATGACGTACCTAT

CCCTCATTACTTACCAGTCTCATCTTCTACTCCAGAGGGTTGAGAGAAACCTATC
```

-continued

```
TAAGAGTATGAGAGATAACCTGCGACAATTGAGTTCTTTGATGAGGCAGGTGCT

GGGCGGGCACGGAGAAGATACCTTAGAGTCAGACGACAACATTCAACGACTGCT

AAAAGACTCTTTACGAAGGACAAGATGGGTGGATCAAGAGGTGCGCCATGCAGC

TAGAACCATGACTGGAGATTACAGCCCCAACAAGAAGGTGTCCCGTAAGGTAGG

ATGTTCAGAATGGGTCTGCTCTGCTCAACAGGTTGCAGTCTCTACCTCAGCAAAC

CCGGCCCCTGTCTCGGAGCTTGACATAAGGGCCCTCTCTAAGAGGTTCCAGAACC

CTTTGATCTCGGGCTTGAGAGTGGTTCAGTGGGCAACCGGTGCTCATTATAAGCT

TAAGCCTATTCTAGATGATCTCAATGTTTTCCCATCTCTCTGCCTTGTAGTTGGGG

ACGGGTCAGGGGGGATATCAAGGGCAGTCCTCAACATGTTTCCAGATGCCAAGC

TTGTGTTCAACAGTCTTTTAGAGGTGAATGACCTGATGGCTTCCGGAACACATCC

ACTGCCTCCTTCAGCAATCATGAGGGGAGGAAATGATATCGTCTCCAGAGTGAT

AGATCTTGACTCAATCTGGGAAAAACCGTCCGACTTGAGAAACTTGGCAACCTG

GAAATACTTCCAGTCAGTCCAAAAGCAGGTCAACATGTCCTATGACCTCATTATT

TGCGATGCAGAAGTTACTGACATTGCATCTATCAACCGGATCACCCTGTTAATGT

CCGATTTTGCATTGTCTATAGATGGACCACTCTATTTGGTCTTCAAAACTTATGGG

ACTATGCTAGTAAATCCAAACTACAAGGCTATTCAACACCTGTCAAGAGCGTTCC

CCTCGGTCACAGGGTTTATCACCCAAGTAACTTCGTCTTTTTCATCTGAGCTCTAC

CTCCGATTCTCCAAACGAGGGAAGTTTTTCAGAGATGCTGAGTACTTGACCTCTT

CCACCCTTCGAGAAATGAGCCTTGTGTTATTCAATTGTAGCAGCCCCAAGAGTGA

GATGCAGAGAGCTCGTTCCTTGAACTATCAGGATCTTGTGAGAGGATTTCCTGAA

GAAATCATATCAAATCCTTACAATGAGATGATCATAACTCTGATTGACAGTGATG

TAGAATCTTTTCTAGTCCACAAGATGGTTGATGATCTTGAGTTACAGAGGGGAAC

TCTGTCTAAAGTGGCTATCATTATAGCCATCATGATAGTTTTCTCCAACAGAGTC

TTCAACGTTTCCAAACCCCTAACTGACCCCTCGTTCTATCCACCGTCTGATCCCA

AAATCCTGAGGCACTTCAACATATGTTGCAGTACTATGATGTATCTATCTACTGC

TTTAGGTGACGTCCCTAGCTTCGCAAGACTTCACGACCTGTATAACAGACCTATA

ACTTATTACTTCAGAAAGCAAGTCATTCGAGGGAACGTTTATCTATCTTGGAGTT

GGTCCAACGACACCTCAGTGTTCAAAAGGGTAGCCTGTAATTCTAGCCTGAGTCT

GTCATCTCACTGGATCAGGTTGATTTACAAGATAGTGAAGACTACCAGACTCGTT

GGCAGCATCAAGGATCTATCCAGAGAAGTGGAAAGACACCTTCATAGGTACAAC

AGGTGGATCACCCTAGAGGATATCAGATCTAGATCATCCCTACTAGACTACAGTT

GCCTGTGAACCGGATACTCCTGGAAGCCTGCCCATGCTAAGACTCTTGTGTGATG

TATCTTGAAAAAAACAAGATCCTAAATCTGAACCTTTGGTTGTTTGATTGTTTTC

TCATTTTTGTTGTTTATTTGTTAAGCGT.
```

In one embodiment, the nucleic acid comprises the sequence of SEQ ID NO: 16, shown below (RABV vector: Coravax V6 China):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT
```

-continued

```
GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAAATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAGAAGTTGAATAACAAAATGCCGGAAATCTACGGATTGTGTATATCCA

TCATGAAAAAAACTAACACCCCTCCTTTCGAACCATCCCAAACATGAGCAAGAT

CTTTGTCAATCCTAGTGCTATTAGAGCCGGTCTGGCCGATCTTGAGATGGCTGAA

GAAACTGTTGATCTGATCAATAGAAATATCGAAGACAATCAGGCTCATCTCCAA

GGGGAACCCATAGAGGTGGACAATCTCCCTGAGGATATGGGGCGACTTCACCTG

GATGATGGAAAATCGCCCAACCATGGTGAGATAGCCAAGGTGGGAGAAGGCAA

GTATCGAGAGGACTTTCAGATGGATGAAGGAGAGGATCCTAGCTTCCTGTTCCA

GTCATACCTGGAAAATGTTGGAGTCCAAATAGTCAGACAAATGAGGTCAGGAGA

GAGATTTCTCAAGATATGGTCACAGACCGTAGAAGAGATTATATCCTATGTCGCG

GTCAACTTTCCCAACCCTCCAGGAAAGTCTTCAGAGGATAAATCAACCCAGACT

ACTGGCCGAGAGCTCAAGAAGGAGACAACACCCACTCCTTCTCAGAGAGAAAGC

CAATCATCGAAAGCCAGGATGGCGGCTCAAATTGCTTCTGGCCCTCCAGCCCTTG

AATGGTCGGCTACCAATGAAGAGGATGATCTATCAGTGGAGGCTGAGATCGCTC

ACCAGATTGCAGAAAGTTTCTCCAAAAAATATAAGTTTCCCTCTCGATCCTCAGG

GATACTCTTGTATAATTTTGAGCAATTGAAAATGAACCTTGATGATATAGTTAAA

GAGGCAAAAAATGTACCAGGTGTGACCCGTTTAGCCCATGACGGGTCCAAACTC

CCCCTAAGATGTGTACTGGGATGGGTCGCTTTGGCCAACTCTAAGAAATTCCAGT

TGTTAGTCGAATCCGACAAGCTGAGTAAAATCATGCAAGATGACTTGAATCGCT
```

```
ATACATCTTGCTAACCGAACCTCTCCCCTCAGTCCCTCTAGACAATAAAATCCGA
GATGTCCCAAAGTCAACATGAAAAAAACAGGCAACACCACTGATAAAATGAAC
CTCCTACGTAAGATAGTGAAAAACCGCAGGGACGAGGACACTCAAAAATCCTCT
CCCGCGTCAGCCCCTCTGGATGACGATGACTTGTGGCTTCCACCCCCTGAATACG
TCCCGCTGAAAGAACTTACAGGCAAGAAGAACATGAGGAACTTTTGTATCAACG
GAAGGGTTAAAGTGTGTAGCCCGAATGGTTACTCGTTCAGGATCCTGCGGCACA
TTCTGAAATCATTCGACGAGATATATTCTGGGAATCATAGGATGATCGGGTTAGT
CAAAGTGGTTATTGGACTGGCTTTGTCAGGATCTCCAGTCCCTGAGGGCCTGAAC
TGGGTATACAAATTGAGGAGAACCTTTATCTTCCAGTGGGCTGATTCCAGGGGCC
CTCTTGAAGGGGAGGAGTTGGAATACTCTCAGGAGATCACTTGGGATGATGATA
CTGAGTTCGTCGGATTGCAAATAAGAGTGATTGCAAACAGTGTCATATCCAGG
GCAGAGTCTGGTGTATCAACATGAACCCGAGAGCATGTCAACTATGGTCTGACA
TGTCTCTTCAGACACAAAGGTCCGAAGAGGACAAAGATTCCTCTCTGCTTCTAGA
ATAATCAGATTATATCCCGCAAATTTATCACTTGTTTACCTCTGGAGGAGAGAAC
ATATGGGCTCAACTCCAACCCTTGGGAGCAATATAACAAAAAACATGTTATGGT
GCCATTAAACCGCTGCATTTCATCAAAGTCAAGTTGATTACCTTTACATTTTGATC
CTCTTGGATGTGAAAAAAACTATTAACATCCCTCAAAAGACCcgggAAAGATGGT
TCCTCAGGCTCTCCTGTTTGTACCCCTTCTGGTTTTTCCATTGTGTTTTGGGAAATT
CCCTATTTACACGATACCAGACAAGCTTGGTCCCTGGAGTCCGATTGACATACAT
CACCTCAGCTGCCCAAACAATTTGGTAGTGGAGGACGAAGGATGCACCAACCTG
TCAGGGTTCTCCTACATGGAACTTAAAGTTGGATACATCTTAGCCATAAAAGTGA
ACGGGTTCACTTGCACAGGCGTTGTGACGGAGGCTGAAACCTACACTAACTTCGT
TGGTTATGTCACAACCACGTTCAAAAGAAAGCATTTCCGCCCAACACCAGATGC
ATGTAGAGCCGCGTACAACTGGAAGATGGCCGGTGACCCCAGATATGAAGAGTC
TCTACACAATCCGTACCCTGACTACCGCTGGCTTCGAACTGTAAAAACCACCAAG
GAGTCTCTCGTTATCATATCTCCAAGTGTGGCAGATTTGGACCCATATGACAGAT
CCCTTCACTCGAGGGTCTTCCCTAGCGGGAAGTGCTCAGGAGTAGCGGTGTCTTC
TACCTACTGCTCCACTAACCACGATTACACCATTTGGATGCCCGAGAATCCGAGA
CTAGGGATGTCTTGTGACATTTTTACCAATAGTAGAGGGAAGAGAGCATCCAAA
GGGAGTGAGACTTGCGGCTTTGTAGATGAAAGAGGCCTATATAAGTCTTTAAAA
GGAGCATGCAAACTCAAGTTATGTGGAGTTCTAGGACTTAGACTTATGGATGGA
ACATGGGTCTCGATGCAAACATCAAATGAAACCAAATGGTGCCCTCCCGATAAG
TTGGTGAACCTGCACGACTTTCGCTCAGACGAAATTGAGCACCTTGTTGTAGAGG
AGTTGGTCAGGAAGAGAGAGGAGTGTCTGGATGCACTAGAGTCCATCATGACAA
CCAAGTCAGTGAGTTTCAGACGTCTCAGTCATTTAAGAAAACTTGTCCCTGGGTT
TGGAAAAGCATATACCATATTCAACAAGACCTTGATGGAAGCCGATGCTCACTA
CAAGTCAGTCgagACTTGGAATGAGATCCTCCCTTCAAAAGGGTGTTTAAGAGTTG
GGGGAGGTGTCATCCTCATGTGAACGGGGTGTTTTTCAATGGTATAATATTAGG
ACCTGACGGCAATGTCTTAATCCCAGAGATGCAATCATCCCTCCTCCAGCAACAT
ATGGAGTTGTTGGAATCCTCGGTTATCCCCCTTGTGCACCCCCTGGCAGACCCGT
```

```
CTACCGTTTTCAAGGACGGTGACGAGGCTGAGGATTTTGTTGAAGTTCACCTTCC

CGATGTGCACAATCAGGTCTCAGGAGTTGACTTGGGTCTCCCGAACTGGGGGAA

GTATGTATTACTGAGTGCAGGGGCCCTGACTGCCTTGATGTTGATAATTTTCCTG

ATGACATGTTGTAGAAGAGTCAATCGATCAGAACCTACGCAACACAATCTCAGA

GGGACAGGGAGGGAGGTGTCAGTCACTCCCCAAAGCGGGAAGATCATATCTTCA

TGGGAATCACACAAGAGTGGGGGTGAGACCAGACTGTAAttaattaaCGTCCTTTCAA

CGATCCAAGTCcatgaaaaaaactaacacccctcccgtacgaccATGTTCGTGTTTCTGGTGCTGCT

GCCTCTGGTGAGCTCCCAGTGCGTGAACCTGACCACAAGGACCCAGCTGCCCCC

TGCCTATACCAATTCCTTCACACGGGGCGTGTACTATCCCGACAAGGTGTTCCGG

AGCAGCGTGCTGCACTCCACACAGGATCTGTTTCTGCCTTTCTTTTCTAACGTGAC

CTGGTTCCACGCCATCCACGTGAGCGGCACCAATGGCACAAAGCGGTTCGACAA

TCCAGTGCTGCCCTTTAACGATGGCGTGTACTTCGCCTCCACCGAGAAGTCTAAC

ATCATCAGAGGCTGGATCTTTGGCACCACACTGGACAGCAAGACACAGTCCCTG

CTGATCGTGAACAATGCCACCAACGTGGTCATCAAGGTGTGCGAGTTCCAGTTTT

GTAATGATCCATTCCTGGGCGTGTACTATCACAAGAACAATAAGTCTTGGATGGA

GAGCGAGTTTCGCGTGTATTCCTCTGCCAACAATTGCACATTTGAGTACGTGTCC

CAGCCCTTCCTGATGGACCTGGAGGGCAAGCAGGGCAATTTCAAGAACCTGAGG

GAGTTCGTGTTTAAGAATATCGATGGCTACTTCAAAATCTACTCCAAGCACACCC

CAATCAACCTGGTGCGCGACCTGCCACAGGGCTTCTCTGCCCTGGAGCCACTGGT

GGATCTGCCCATCGGCATCAACATCACCCGGTTTCAGACACTGCTGGCCCTGCAC

AGAAGCTACCTGACACCAGGCGACAGCTCCTCTGGATGGACCGCAGGAGCAGCA

GCCTACTATGTGGGCTATCTGCAGCCCAGGACCTTCCTGCTGAAGTACAACGAG

AATGGCACCATCACAGACGCCGTGGATTGCGCCCTGGATCCCCTGTCTGAGACC

AAGTGTACACTGAAGAGCTTTACCGTGGAGAAGGGCATCTATCAGACAAGCAAT

TTCAGGGTGCAGCCTACCGAGTCCATCGTGCGCTTTCCCAATATCACAAACCTGT

GCCCTTTTGGCGAGGTGTTCAACGCAACCCGCTTCGCCAGCGTGTACGCCTGGAA

TAGGAAGCGCATCTCCAACTGCGTGGCCGACTATTCTGTGCTGTACAACAGCGCC

TCCTTCTCTACCTTTAAGTGCTATGGCGTGAGCCCCACAAAGCTGAATGACCTGT

GCTTTACCAACGTGTACGCCGATTCCTTCGTGATCAGGGGCGACGAGGTGCGCC

AGATCGCACCAGGACAGACAGGCAAGATCGCAGACTACAATTATAAGCTGCCTG

ACGATTTCACCGGCTGCGTGATCGCCTGGAACTCTAACAATCTGGATAGCAAAGT

GGGCGGCAACTACAATTATCTGTACCGGCTGTTTAGAAAGTCTAATCTGAAGCCA

TTCGAGAGGGACATCTCCACAGAAATCTACCAGGCCGGCTCTACCCCCTGCAAT

GGCGTGGAgGGCTTTAACTGTTATTTCCCTCTGCAGAgCTACgGCTTCCAGCCAAC

AAACGGCGTGGGCTATCAGCCCTACCGCGTGGTGGTGCTGTCTTTTGAGCTGCTG

CACGCACcTGCAACAGTGTGCGGACCAAAGAAGAGCACCAATCTGGTGAAGAAC

AAGTGCGTGAACTTCAACTTCAACGGACTGACCGGAACAGGCGTGCTGACCGAG

TCCAACAAGAAGTTCCTGCCTTTTCAGCAGTTCGGCAGGGACATCGCAGATACC

ACAGACGCCGTGCGCGACCCTCAGACCCTGGAGATCCTGGACATCACACCATGC

TCCTTCGGCGGCGTGTCTGTGATCACACCAGGCACCAATACAAGCAACCAGGTG

GCCGTGCTGTATCAGGACGTGAATTGTACCGAGGTGCCAGTGGCAATCCACGCA
```

```
GATCAGCTGACCCCTACATGGCGGGTGTACTCTACCGGCAGCAACGTGTTCCAG

ACAAGAGCCGGATGCCTGATCGGAGCAGAGCACGTGAACAATAGCTATGAGTGC

GACATCCCTATCGGCGCCGGCATCTGTGCCTCCTACCAGACCCAGACAAACTCCC

CAAGGTCTGTGGGAGATGAGGCCGAAGACTTTGTGGAAGTCCACCTGCCTGATG

TGCATAACCAGGTGTCTGGCGTCGACCTGGGACTGCCAAATTGGGGCAAGTACG

TGCTGCTGAGTGCTGGAGCACTGACTGCCCTGATGCTGATCATTTTCCTGATGAC

CTGCTGTCGGCGCGTGAACAGAAGTGAGCCCACTCAGCACAATCTGCGAGGAAC

CGGGAGAGAAGTGTCAGTCACACCTCAGAGCGGGAAAATCATTAGTAGTTGGGA

ATCACATAAAAGCGGGGGCGAGACCAGGCTGggatccggctccggcgagggcaggggaagtctact aacatgcggggacgtggaggaaaatcccggccccATGCTCGATCCTGGAGAGGTCTATGATGACCC

TATTGACCCAATCGAGTTAGAGGCTGAACCCAGAGGAACCCCCATTGTCCCCAA

CATCTTGAGGAACTCTGACTACAATCTCAACTCTCCTTTGATAGAAGATCCTGCT

AGACTAATGTTAGAATGGTTAAAAACAGGGAATAGACCTTATCGGATGACTCTA

ACAGACAATTGCTCCAGGTCTTTCAGAGTTTTGAAAGATTATTTCAAGAAGGTAG

ATTTGGGTTCTCTCAAGGTGGGCGGAATGGCTGCACAGTCAATGATTTCTCTCTG

GTTATATGGTGCCCACTCTGAATCCAACAGGAGCCGGAGATGTATAACAGACTT

GGCCCATTTCTATTCCAAGTCGTCCCCCATAGAGAAGCTGTTGAATCTCACGCTA

GGAAATAGAGGGCTGAGAATCCCCCCAGAGGGAGTGTTAAGTTGCCTTGAGAGG

GTTGATTATGATAATGCATTTGGAAGGTATCTTGCCAACACGTATTCCTCTTACTT

GTTCTTCCATGTAATCACCTTATACATGAACGCCCTAGACTGGGATGAAGAAAAG

ACCATCCTAGCATTATGGAAAGATTTAACCTCAGTGGACATCGGGAAGGACTTG

GTAAAGTTCAAAGACCAAATATGGGGACTGCTGATCGTGACAAAGGACTTTGTT

TACTCCCAAAGTTCCAATTGTCTTTTTGACAGAAACTACACACTTATGCTAAAAG

ATCTTTTCTTGTCTCGCTTCAACTCCTTAATGGTCTTGCTCTCTCCCCCAGAGCCC

CGATACTCAGATGACTTGATATCTCAACTATGCCAGCTGTACATTGCTGGGGATC

AAGTCTTGTCTATGTGTGGAAACTCCGGCTATGAAGTCATCAAAATATTGGAGCC

ATATGTCGTGAATAGTTTAGTCCAGAGAGCAGAAAAGTTTAGGCCTCTCATTCAT

TCCTTGGGAGACTTTCCTGTATTTATAAAAGACAAGGTAAGTCAACTTGAAGAGA

CGTTCGGTCCCTGTGCAAGAAGGTTCTTTAGGGCTCTGGATCAATTCGACAACAT

ACATGACTTGGTTTTTGTGTTTGGCTGTTACAGGCATTGGGGGCACCCATATATA

GATTATCGAAAGGGTCTGTCAAAACTATATGATCAGGTTCACCTTAAAAAAATG

ATAGATAAGTCCTACCAGGAGTGCTTAGCAAGCGACCTAGCCAGGAGGATCCTT

AGATGGGTTTTGATAAGTACTCCAAGTGGTATCTGGATTCAAGATTCCTAGCCC

GAGACCACCCCTTGACTCCTTATATCAAAACCCAAACATGGCCACCCAAACATA

TTGTAGACTTGGTGGGGATACATGGCACAAGCTCCCGATCACGCAGATCTTTGA

GATTCCTGAATCAATGGATCCGTCAGAAATATTGGATGACAAATCACATTCTTTC

ACCAGAACGAGACTAGCTTCTTGGCTGTCAGAAAACCGAGGGGGGCCTGTTCCT

AGCGAAAAAGTTATTATCACGGCCCTGTCTAAGCCGCCTGTCAATCCCCGAGAG

TTTCTGAGGTCTATAGACCTCGGAGGATTGCCAGATGAAGACTTGATAATTGGCC

TCAAGCCAAAGGAACGGGAATTGAAGATTGAAGGTCGATTCTTTGCTCTAATGT
```

-continued

```
CATGGAATCTAAGATTGTATTTTGTCATCACTGAAAAACTCTTGGCCAACTACAT
CTTGCCACTTTTTGACGCGCTGACTATGACAGACAACCTGAACAAGGTGTTTAAA
AAGCTGATCGACAGGGTCACCGGGCAAGGGCTTTTGGACTATTCAAGGGTCACA
TATGCATTTCACCTGGACTATGAAAAGTGGAACAACCATCAAAGATTAGAGTCA
ACAGAGGATGTATTTTCTGTCCTAGATCAAGTGTTTGGATTGAAGAGAGTGTTTT
CTAGAACACACGAGTTTTTTCAAAAGGCCTGGATCTATTATTCAGACAGATCAGA
CCTCATCGGGTTACGGGAGGATCAAATATACTGCTTAGATGCGTCCAACGGCCC
AACCTGTTGGAATGGCCAGGATGGCGGGCTAGAAGGCTTACGGCAGAAGGGCTG
GAGTCTAGTCAGCTTATTGATGATAGATAGAGAATCTCAAATCAGGAACACAAG
AACCAAAATACTAGCTCAAGGAGACAACCAGGTTTTATGTCCGACATACATGTT
GTCGCCAGGGCTATCTCAAGAGGGGCTCCTCTATGAATTGGAGAGAATATCAAG
GAATGCACTTTCGATATACAGAGCCGTCGAGGAAGGGGCATCTAAGCTAGGGCT
GATCATCAAGAAAGAAGAGACCATGTGTAGTTATGACTTCCTCATCTATGGAAA
AACCCCTTTGTTTAGAGGTAACATATTGGTGCCTGAGTCCAAAAGATGGGCCAG
AGTCTCTTGCGTCTCTAATGACCAAATAGTCAACCTCGCCAATATAATGTCGACA
GTGTCCACCAATGCGCTAACAGTGGCACAACACTCTCAATCTTTGATCAAACCGA
TGAGGGATTTTCTGCTCATGTCAGTACAGGCAGTCTTTCACTACCTGCTATTTAGC
CCAATCTTAAAGGGAAGAGTTTACAAGATTCTGAGCGCTGAAGGGGAGAGCTTT
CTCCTAGCCATGTCAAGGATAATCTATCTAGATCCTTCTTTGGGAGGGATATCTG
GAATGTCCCTCGGAAGATTCCATATACGACAGTTCTCAGACCCTGTCTCTGAAGG
GTTATCCTTCTGGAGAGAGATCTGGTTAAGCTCCCAAGAGTCCTGGATTCACGCG
TTGTGTCAAGAGGCTGGAAACCCAGATCTTGGAGAGAGAACACTCGAGAGCTTC
ACTCGCCTTCTAGAAGATCCGACCACCTTAAATATCAGAGGAGGGGCCAGTCCT
ACCATTCTACTCAAGGATGCAATCAGAAAGGCTTTATATGACGAGGTGGACAAG
GTGGAAAATTCAGAGTTTCGAGAGGCAATCCTGTTGTCCAAGACCCATAGAGAT
aattttatactcttcttaatatctgttgagcctctgtttcctcgatttctcagtga
GCTATTCAGTTCGTCTTTTTTGGGAATCCCCGAGTCAATCATTGGATTGATACAA
AACTCCCGAACGATAAGAAGGCAGTTTAGAAAGAGTCTCTCAAAAACTTTAGAA
GAATCCTTCTACAACTCAGAGATCCACGGGATTAGTCGGATGACCCAGACACCT
CAGAGGGTTGGGGGGTGTGGCCTTGCTCTTCAGAGAGGGCAGATCTACTTAGG
GAGATCTCTTGGGGAAGAAAAGTGGTAGGCACGACAGTTCCTCACCCTTCTGAG
ATGTTGGGATTACTTCCCAAGTCCTCTATTTCTTGCACTTGTGGAGCAACAGGAG
GAGGCAATCCTAGAGTTTCTGTATCAGTACTCCCGTCCTTTGATCAGTCATTTTTT
TCACGAGGCCCCCTAAAGGGATACTTGGGCTCGTCCACCTCTATGTCGACCCAGC
TATTCCATGCATGGGAAAAAGTCACTAATGTTCATGTGGTGAAGAGAGCTCTATC
GTTAAAAGAATCTATAAACTGGTTCATTACTAGAGATTCCAACTTGGCTCAAGCT
CTAATTAGGAACATTATGTCTCTGACAGGCCCTGATTTCCCTCTAGAGGAGGCCC
CTGTCTTCAAAAGGACGGGGTCAGCCTTGCATAGGTTCAAGTCTGCCAGATACA
GCGAAGGAGGGTATTCTTCTGTCTGCCCGAACCTCCTCTCTCATATTTCTGTTAGT
ACAGACACCATGTCTGATTTGACCCAAGACGGGAAGAACTACGATTTCATGTTCC
AGCCATTGATGCTTTATGCACAGACATGGACATCAGAGCTGGTACAGAGAGACA
```

```
CAAGGCTAAGAGACTCTACGTTTCATTGGCACCTCCGATGCAACAGGTGTGTGA
GACCCATTGACGACGTGACCCTGGAGACCTCTCAGATCTTCGAGTTTCCGGATGT
GTCGAAAAGAATATCCAGAATGGTTTCTGGGGCTGTGCCTCACTTCCAGAGGCTT
CCCGATATCCGTCTGAGACCAGGAGATTTTGAATCTCTAAGCGGTAGAGAAAAG
TCTCACCATATCGGATCAGCTCAGGGGCTCTTATACTCAATCTTAGTGGCAATTC
ACGACTCAGGATACAATGATGGAACCATCTTCCCTGTCAACATATACGGCAAGG
TTTCCCCTAGAGACTATTTGAGAGGGCTCGCAAGGGGAGTATTGATAGGATCCTC
GATTTGCTTCTTGACAAGAATGACAAATATCAATATTAATAGACCTCTTGAATTG
GTCTCAGGGGTAATCTCATATATTCTCCTGAGGCTAGATAACCATCCCTCCTTGT
ACATAATGCTCAGAGAACCGTCTCTTAGAGGAGAGATATTTTCTATCCCTCAGAA
AATCCCCGCCGCTTATCCAACCACTATGAAAGAAGGCAACAGATCAATCTTGTG
TTATCTCCAACATGTGCTACGCTATGAGCGAGAGATAATCACGGCGTCTCCAGAG
AATGACTGGCTATGGATCTTTTCAGACTTTAGAAGTGCCAAAATGACGTACCTAT
CCCTCATTACTTACCAGTCTCATCTTCTACTCCAGAGGGTTGAGAGAAACCTATC
TAAGAGTATGAGAGATAACCTGCGACAATTGAGTTCTTTGATGAGGCAGGTGCT
GGGCGGGCACGGAGAAGATACCTTAGAGTCAGACGACAACATTCAACGACTGCT
AAAAGACTCTTTACGAAGGACAAGATGGGTGGATCAAGAGGTGCGCCATGCAGC
TAGAACCATGACTGGAGATTACAGCCCCAACAAGAAGGTGTCCCGTAAGGTAGG
ATGTTCAGAATGGGTCTGCTCTGCTCAACAGGTTGCAGTCTCTACCTCAGCAAAC
CCGGCCCCTGTCTCGGAGCTTGACATAAGGGCCCTCTCTAAGAGGTTCCAGAACC
CTTTGATCTCGGGCTTGAGAGTGGTTCAGTGGGCAACCGGTGCTCATTATAAGCT
TAAGCCTATTCTAGATGATCTCAATGTTTTCCCATCTCTCTGCCTTGTAGTTGGGG
ACGGGTCAGGGGGGATATCAAGGGCAGTCCTCAACATGTTTCCAGATGCCAAGC
TTGTGTTCAACAGTCTTTTAGAGGTGAATGACCTGATGGCTTCCGGAACACATCC
ACTGCCTCCTTCAGCAATCATGAGGGGAGGAAATGATATCGTCTCCAGAGTGAT
AGATCTTGACTCAATCTGGGAAAAACCGTCCGACTTGAGAAACTTGGCAACCTG
GAAATACTTCCAGTCAGTCCAAAAGCAGGTCAACATGTCCTATGACCTCATTATT
TGCGATGCAGAAGTTACTGACATTGCATCTATCAACCGGATCACCCTGTTAATGT
CCGATTTTGCATTGTCTATAGATGGACCACTCTATTTGGTCTTCAAAACTTATGGG
ACTATGCTAGTAAATCCAAACTACAAGGCTATTCAACACCTGTCAAGAGCGTTCC
CCTCGGTCACAGGGTTTATCACCCAAGTAACTTCGTCTTTTTCATCTGAGCTCTAC
CTCCGATTCTCCAAACGAGGGAAGTTTTTCAGAGATGCTGAGTACTTGACCTCTT
CCACCCTTCGAGAAATGAGCCTTGTGTTATTCAATTGTAGCAGCCCCAAGAGTGA
GATGCAGAGAGCTCGTTCCTTGAACTATCAGGATCTTGTGAGAGGATTTCCTGAA
GAAATCATATCAAATCCTTACAATGAGATGATCATAACTCTGATTGACAGTGATG
TAGAATCTTTTCTAGTCCACAAGATGGTTGATGATCTTGAGTTACAGAGGGGAAC
TCTGTCTAAAGTGGCTATCATTATAGCCATCATGATAGTTTTCTCCAACAGAGTC
TTCAACGTTTCCAAACCCCTAACTGACCCCTCGTTCTATCCACCGTCTGATCCCA
AAATCCTGAGGCACTTCAACATATGTTGCAGTACTATGATGTATCTATCTACTGC
TTTAGGTGACGTCCCTAGCTTCGCAAGACTTCACGACCTGTATAACAGACCTATA
```

-continued

ACTTATTACTTCAGAAAGCAAGTCATTCGAGGGAACGTTTATCTATCTTGGAGTT

GGTCCAACGACACCTCAGTGTTCAAAAGGGTAGCCTGTAATTCTAGCCTGAGTCT

GTCATCTCACTGGATCAGGTTGATTTACAAGATAGTGAAGACTACCAGACTCGTT

GGCAGCATCAAGGATCTATCCAGAGAAGTGGAAAGACACCTTCATAGGTACAAC

AGGTGGATCACCCTAGAGGATATCAGATCTAGATCATCCCTACTAGACTACAGTT

GCCTGTGAACCGGATACTCCTGGAAGCCTGCCCATGCTAAGACTCTTGTGTGATG

TATCTTGAAAAAAACAAGATCCTAAATCTGAACCTTTGGTTGTTTGATTGTTTTC

TCATTTTTGTTGTTTATTTGTTAAGCGT.

In one embodiment, the nucleic acid comprises the sequence of SEQ ID NO: 17, shown below (RABV vector: Coravax V6 South Africa):

ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAAATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAGAAGTTGAATAACAAAATGCCGGAAATCTACGGATTGTGTATATCCA

TCATGAAAAAAACTAACACCCCTCCTTTCGAACCATCCCAAACATGAGCAAGAT

CTTTGTCAATCCTAGTGCTATTAGAGCCGGTCTGGCCGATCTTGAGATGGCTGAA

```
                -continued
GAAACTGTTGATCTGATCAATAGAAATATCGAAGACAATCAGGCTCATCTCCAA

GGGGAACCCATAGAGGTGGACAATCTCCCTGAGGATATGGGGCGACTTCACCTG

GATGATGGAAAATCGCCCAACCATGGTGAGATAGCCAAGGTGGGAGAAGGCAA

GTATCGAGAGGACTTTCAGATGGATGAAGGAGAGGATCCTAGCTTCCTGTTCCA

GTCATACCTGGAAAATGTTGGAGTCCAAATAGTCAGACAAATGAGGTCAGGAGA

GAGATTTCTCAAGATATGGTCACAGACCGTAGAAGAGATTATATCCTATGTCGCG

GTCAACTTTCCCAACCCTCCAGGAAAGTCTTCAGAGGATAAATCAACCCAGACT

ACTGGCCGAGAGCTCAAGAAGGAGACAACACCCACTCCTTCTCAGAGAGAAAGC

CAATCATCGAAAGCCAGGATGGCGGCTCAAATTGCTTCTGGCCCTCCAGCCCTTG

AATGGTCGGCTACCAATGAAGAGGATGATCTATCAGTGGAGGCTGAGATCGCTC

ACCAGATTGCAGAAAGTTTCTCCAAAAAATATAAGTTTCCCTCTCGATCCTCAGG

GATACTCTTGTATAATTTTGAGCAATTGAAAATGAACCTTGATGATATAGTTAAA

GAGGCAAAAAATGTACCAGGTGTGACCCGTTTAGCCCATGACGGGTCCAAACTC

CCCCTAAGATGTGTACTGGGATGGGTCGCTTTGGCCAACTCTAAGAAATTCCAGT

TGTTAGTCGAATCCGACAAGCTGAGTAAAATCATGCAAGATGACTTGAATCGCT

ATACATCTTGCTAACCGAACCTCTCCCCTCAGTCCCTCTAGACAATAAAATCCGA

GATGTCCCAAAGTCAACATGAAAAAAACAGGCAACACCACTGATAAAATGAAC

CTCCTACGTAAGATAGTGAAAAACCGCAGGGACGAGGACACTCAAAAATCCTCT

CCCGCGTCAGCCCCTCTGGATGACGATGACTTGTGGCTTCCACCCCCTGAATACG

TCCCGCTGAAAGAACTTACAGGCAAGAAGAACATGAGGAACTTTTGTATCAACG

GAAGGGTTAAAGTGTGTAGCCCGAATGGTTACTCGTTCAGGATCCTGCGGCACA

TTCTGAAATCATTCGACGAGATATATTCTGGGAATCATAGGATGATCGGGTTAGT

CAAAGTGGTTATTGGACTGGCTTTGTCAGGATCTCCAGTCCCTGAGGGCCTGAAC

TGGGTATACAAATTGAGGAGAACCTTTATCTTCCAGTGGGCTGATTCCAGGGGCC

CTCTTGAAGGGGAGGAGTTGGAATACTCTCAGGAGATCACTTGGGATGATGATA

CTGAGTTCGTCGGATTGCAAATAAGAGTGATTGCAAAACAGTGTCATATCCAGG

GCAGAGTCTGGTGTATCAACATGAACCCGAGAGCATGTCAACTATGGTCTGACA

TGTCTCTTCAGACACAAAGGTCCGAAGAGGACAAAGATTCCTCTCTGCTTCTAGA

ATAATCAGATTATATCCCGCAAATTTATCACTTGTTTACCTCTGGAGGAGAGAAC

ATATGGGCTCAACTCCAACCCTTGGGAGCAATATAACAAAAAACATGTTATGGT

GCCATTAAACCGCTGCATTTCATCAAAGTCAAGTTGATTACCTTTACATTTTGATC

CTCTTGGATGTGAAAAAAACTATTAACATCCCTCAAAAGACCccgggAAAGATGGT

TCCTCAGGCTCTCCTGTTTGTACCCCTTCTGGTTTTTCCATTGTGTTTTGGGAAATT

CCCTATTTACACGATACCAGACAAGCTTGGTCCCTGGAGTCCGATTGACATACAT

CACCTCAGCTGCCCAAACAATTTGGTAGTGGAGGACGAAGGATGCACCAACCTG

TCAGGGTTCTCCTACATGGAACTTAAAGTTGGATACATCTTAGCCATAAAAGTGA

ACGGGTTCACTTGCACAGGCGTTGTGACGGAGGCTGAAACCTACACTAACTTCGT

TGGTTATGTCACAACCACGTTCAAAAGAAAGCATTTCCGCCCAACACCAGATGC

ATGTAGAGCCGCGTACAACTGGAAGATGGCCGGTGACCCCAGATATGAAGAGTC

TCTACACAATCCGTACCCTGACTACCGCTGGCTTCGAACTGTAAAAACCACCAAG

GAGTCTCTCGTTATCATATCTCCAAGTGTGGCAGATTTGGACCCATATGACAGAT
```

```
CCCTTCACTCGAGGGTCTTCCCTAGCGGGAAGTGCTCAGGAGTAGCGGTGTCTTC
TACCTACTGCTCCACTAACCACGATTACACCATTTGGATGCCCGAGAATCCGAGA
CTAGGGATGTCTTGTGACATTTTTACCAATAGTAGAGGGAAGAGAGCATCCAAA
GGGAGTGAGACTTGCGGCTTTGTAGATGAAAGAGGCCTATATAAGTCTTTAAAA
GGAGCATGCAAACTCAAGTTATGTGGAGTTCTAGGACTTAGACTTATGGATGGA
ACATGGGTCTCGATGCAAACATCAAATGAAACCAAATGGTGCCCTCCCGATAAG
TTGGTGAACCTGCACGACTTTCGCTCAGACGAAATTGAGCACCTTGTTGTAGAGG
AGTTGGTCAGGAAGAGAGAGGAGTGTCTGGATGCACTAGAGTCCATCATGACAA
CCAAGTCAGTGAGTTTCAGACGTCTCAGTCATTTAAGAAAACTTGTCCCTGGGTT
TGGAAAAGCATATACCATATTCAACAAGACCTTGATGGAAGCCGATGCTCACTA
CAAGTCAGTCgagACTTGGAATGAGATCCTCCCTTCAAAAGGGTGTTTAAGAGTTG
GGGGGAGGTGTCATCCTCATGTGAACGGGGTGTTTTTCAATGGTATAATATTAGG
ACCTGACGGCAATGTCTTAATCCCAGAGATGCAATCATCCCTCCTCCAGCAACAT
ATGGAGTTGTTGGAATCCTCGGTTATCCCCCTTGTGCACCCCTGGCAGACCCGT
CTACCGTTTTCAAGGACGGTGACGAGGCTGAGGATTTTGTTGAAGTTCACCTTCC
CGATGTGCACAATCAGGTCTCAGGAGTTGACTTGGGTCTCCCGAACTGGGGGAA
GTATGTATTACTGAGTGCAGGGGCCCTGACTGCCTTGATGTTGATAATTTTCCTG
ATGACATGTTGTAGAAGAGTCAATCGATCAGAACCTACGCAACACAATCTCAGA
GGGACAGGGAGGGAGGTGTCAGTCACTCCCCAAAGCGGGAAGATCATATCTTCA
TGGGAATCACACAAGAGTGGGGGTGAGACCAGACTGTAAttaattaaCGTCCTTTCAA
CGATCCAAGTCcatgaaaaaaactaacacccctcccgtacgaccATGTTCGTGTTTCTGGTGCTGCT
GCCTCTGGTGAGCTCCCAGTGCGTGAACTTCACCACAAGGACCCAGCTGCCCCCT
GCCTATACCAATTCCTTCACACGGGGCGTGTACTATCCCGACAAGGTGTTCCGGA
GCAGCGTGCTGCACTCCACACAGGATCTGTTTCTGCCTTTCTTTTCTAACGTGACC
TGGTTCCACGCCATCCACGTGAGCGGCACCAATGGCACAAAGCGGTTCGCCAAT
CCAGTGCTGCCCTTTAACGATGGCGTGTACTTCGCCTCCACCGAGAAGTCTAACA
TCATCAGAGGCTGGATCTTTGGCACCACACTGGACAGCAAGACACAGTCCCTGC
TGATCGTGAACAATGCCACCAACGTGGTCATCAAGGTGTGCGAGTTCCAGTTTTG
TAATGATCCATTCCTGGGCGTGTACTATCACAAGAACAATAAGTCTTGGATGGAG
AGCGAGTTTCGCGTGTATTCCTCTGCCAACAATTGCACATTTGAGTACGTGTCCC
AGCCCTTCCTGATGGACCTGGAGGGCAAGCAGGGCAATTTCAAGAACCTGAGGG
AGTTCGTGTTTAAGAATATCGATGGCTACTTCAAAATCTACTCCAAGCACACCCC
AATCAACCTGGTGCGCGGCCTGCCACAGGGCTTCTCTGCCCTGGAGCCACTGGTG
GATCTGCCCATCGGCATCAACATCACCCGGTTTCAGACACTGCTGGCCCTGCACA
GAAGCTACCTGACACCAGGCGACAGCTCCTCTGGATGGACCGCAGGAGCAGCAG
CCTACTATGTGGGCTATCTGCAGCCCAGGACCTTCCTGCTGAAGTACAACGAGA
ATGGCACCATCACAGACGCCGTGGATTGCGCCCTGGATCCCCTGTCTGAGACCA
AGTGTACACTGAAGAGCTTTACCGTGGAGAAGGGCATCTATCAGACAAGCAATT
TCAGGGTGCAGCCTACCGAGTCCATCGTGCGCTTTCCCAATATCACAAACCTGTG
CCCTTTTGGCGAGGTGTTCAACGCAACCCGCTTCGCCAGCGTGTACGCCTGGAAT
```

```
AGGAAGCGCATCTCCAACTGCGTGGCCGACTATTCTGTGCTGTACAACAGCGCCT

CCTTCTCTACCTTTAAGTGCTATGGCGTGAGCCCCACAAAGCTGAATGACCTGTG

CTTTACCAACGTGTACGCCGATTCCTTCGTGATCAGGGGCGACGAGGTGCGCCA

GATCGCACCAGGACAGACAGGCAATATCGCAGACTACAATTATAAGCTGCCTGA

CGATTTCACCGGCTGCGTGATCGCCTGGAACTCTAACAATCTGGATAGCAAAGTG

GGCGGCAACTACAATTATCTGTACCGGCTGTTTAGAAAGTCTAATCTGAAGCCAT

TCGAGAGGGACATCTCCACAGAAATCTACCAGGCCGGCTCTACCCCCTGCAATG

GCGTGAAGGGCTTTAACTGTTATTTCCCTCTGCAGAGCTACGGCTTCCAGCCAAC

ATATGGCGTGGGCTATCAGCCCTACCGCGTGGTGGTGCTGTCTTTTGAGCTGCTG

CACGCACCTGCAACAGTGTGCGGACCAAAGAAGAGCACCAATCTGGTGAAGAA

CAAGTGCGTGAACTTCAACTTCAACGGACTGACCGGAACAGGCGTGCTGACCGA

GTCCAACAAGAAGTTCCTGCCTTTTCAGCAGTTCGGCAGGGACATCGCAGATAC

CACAGACGCCGTGCGCGACCCTCAGACCCTGGAGATCCTGGACATCACACCATG

CTCCTTCGGCGGCGTGTCTGTGATCACACCAGGCACCAATACAAGCAACCAGGT

GGCCGTGCTGTATCAGGGCGTGAATTGTACCGAGGTGCCAGTGGCAATCCACGC

AGATCAGCTGACCCCTACATGGCGGGTGTACTCTACCGGCAGCAACGTGTTCCA

GACAAGAGCCGGATGCCTGATCGGAGCAGAGCACGTGAACAATAGCTATGAGTG

CGACATCCCTATCGGCGCCGGCATCTGTGCCTCCTACCAGACCCAGACAAACTCC

CCAGAATCAAGCGTGATTCCTCTGGTCCATCCACTGGCAGATCCCTCCACAGTGT

TCAAAGACGGAGATGAGGCCGAAGACTTTGTGGAAGTCCACCTGCCTGATGTGC

ATAACCAGGTGTCTGGCGTCGACCTGGGACTGCCAAATTGGGGCAAGTACGTGC

TGCTGAGTGCTGGAGCACTGACTGCCCTGATGCTGATCATTTTCCTGATGACCTG

CTGTCGGCGCGTGAACAGAAGTGAGCCCACTCAGCACAATCTGCGAGGAACCGG

GAGAGAAGTGTCAGTCACACCTCAGAGCGGGAAAATCATTAGTAGTTGGGAATC

ACATAAAAGCGGGGGCGAGACCAGGCTGggatccggctccggcgagggcaggggaagtctactaacat gcggggacgtggaggaaaatcccggccccATGCTCGATCCTGGAGAGGTCTATGATGACCCTAT

TGACCCAATCGAGTTAGAGGCTGAACCCAGAGGAACCCCCATTGTCCCCAACAT

CTTGAGGAACTCTGACTACAATCTCAACTCTCCTTTGATAGAAGATCCTGCTAGA

CTAATGTTAGAATGGTTAAAAACAGGGAATAGACCTTATCGGATGACTCTAACA

GACAATTGCTCCAGGTCTTTCAGAGTTTTGAAAGATTATTTCAAGAAGGTAGATT

TGGGTTCTCTCAAGGTGGGCGGAATGGCTGCACAGTCAATGATTTCTCTCTGGTT

ATATGGTGCCCACTCTGAATCCAACAGGAGCCGGAGATGTATAACAGACTTGGC

CCATTTCTATTCCAAGTCGTCCCCCATAGAGAAGCTGTTGAATCTCACGCTAGGA

AATAGAGGGCTGAGAATCCCCCCAGAGGGAGTGTTAAGTTGCCTTGAGAGGGTT

GATTATGATAATGCATTTGGAAGGTATCTTGCCAACACGTATTCCTCTTACTTGTT

CTTCCATGTAATCACCTTATACATGAACGCCCTAGACTGGGATGAAGAAAAGAC

CATCCTAGCATTATGGAAAGATTTAACCTCAGTGGACATCGGGAAGGACTTGGT

AAAGTTCAAAGACCAAATATGGGACTGCTGATCGTGACAAAGGACTTTGTTTA

CTCCCAAAGTTCCAATTGTCTTTTTGACAGAAACTACACACTTATGCTAAAAGAT

CTTTTCTTGTCTCGCTTCAACTCCTTAATGGTCTTGCTCTCTCCCCCAGAGCCCCG

ATACTCAGATGACTTGATATCTCAACTATGCCAGCTGTACATTGCTGGGGATCAA
```

-continued

```
GTCTTGTCTATGTGTGGAAACTCCGGCTATGAAGTCATCAAAATATTGGAGCCAT

ATGTCGTGAATAGTTTAGTCCAGAGAGCAGAAAAGTTTAGGCCTCTCATTCATTC

CTTGGGAGACTTTCCTGTATTTATAAAAGACAAGGTAAGTCAACTTGAAGAGAC

GTTCGGTCCCTGTGCAAGAAGGTTCTTTAGGGCTCTGGATCAATTCGACAACATA

CATGACTTGGTTTTTGTGTTTGGCTGTTACAGGCATTGGGGGCACCCATATATAG

ATTATCGAAAGGGTCTGTCAAAACTATATGATCAGGTTCACCTTAAAAAAATGAT

AGATAAGTCCTACCAGGAGTGCTTAGCAAGCGACCTAGCCAGGAGGATCCTTAG

ATGGGGTTTTGATAAGTACTCCAAGTGGTATCTGGATTCAAGATTCCTAGCCCGA

GACCACCCCTTGACTCCTTATATCAAAACCCAAACATGGCCACCCAAACATATTG

TAGACTTGGTGGGGGATACATGGCACAAGCTCCCGATCACGCAGATCTTTGAGA

TTCCTGAATCAATGGATCCGTCAGAAATATTGGATGACAAATCACATTCTTTCAC

CAGAACGAGACTAGCTTCTTGGCTGTCAGAAAACCGAGGGGGCCTGTTCCTAG

CGAAAAAGTTATTATCACGGCCCTGTCTAAGCCGCCTGTCAATCCCCGAGAGTTT

CTGAGGTCTATAGACCTCGGAGGATTGCCAGATGAAGACTTGATAATTGGCCTC

AAGCCAAAGGAACGGGAATTGAAGATTGAAGGTCGATTCTTTGCTCTAATGTCA

TGGAATCTAAGATTGTATTTTGTCATCACTGAAAAACTCTTGGCCAACTACATCT

TGCCACTTTTTGACGCGCTGACTATGACAGACAACCTGAACAAGGTGTTTAAAAA

GCTGATCGACAGGGTCACCGGGCAAGGGCTTTTGGACTATTCAAGGGTCACATA

TGCATTTCACCTGGACTATGAAAAGTGGAACAACCATCAAAGATTAGAGTCAAC

AGAGGATGTATTTTCTGTCCTAGATCAAGTGTTTGGATTGAAGAGAGTGTTTTCT

AGAACACACGAGTTTTTTCAAAAGGCCTGGATCTATTATTCAGACAGATCAGACC

TCATCGGGTTACGGGAGGATCAAATATACTGCTTAGATGCGTCCAACGGCCCAA

CCTGTTGGAATGGCCAGGATGGCGGGCTAGAAGGCTTACGGCAGAAGGGCTGGA

GTCTAGTCAGCTTATTGATGATAGATAGAGAATCTCAAATCAGGAACACAAGAA

CCAAAATACTAGCTCAAGGAGACAACCAGGTTTTATGTCCGACATACATGTTGTC

GCCAGGGCTATCTCAAGAGGGGCTCCTCTATGAATTGGAGAGAATATCAAGGAA

TGCACTTTCGATATACAGAGCCGTCGAGGAAGGGGCATCTAAGCTAGGGCTGAT

CATCAAGAAAGAAGAGACCATGTGTAGTTATGACTTCCTCATCTATGGAAAAAC

CCCTTTGTTTAGAGGTAACATATTGGTGCCTGAGTCCAAAAGATGGGCCAGAGTC

TCTTGCGTCTCTAATGACCAAATAGTCAACCTCGCCAATATAATGTCGACAGTGT

CCACCAATGCGCTAACAGTGGCACAACACTCTCAATCTTTGATCAAACCGATGA

GGGATTTTCTGCTCATGTCAGTACAGGCAGTCTTTCACTACCTGCTATTTAGCCCA

ATCTTAAAGGGAAGAGTTTACAAGATTCTGAGCGCTGAAGGGGAGAGCTTTCTC

CTAGCCATGTCAAGGATAATCTATCTAGATCCTTCTTTGGGAGGGATATCTGGAA

TGTCCCTCGGAAGATTCCATATACGACAGTTCTCAGACCCTGTCTCTGAAGGGTT

ATCCTTCTGGAGAGATCTGGTTAAGCTCCCAAGAGTCCTGGATTCACGCGTTG

TGTCAAGAGGCTGGAAACCCAGATCTTGGAGAGAGAACACTCGAGAGCTTCACT

CGCCTTCTAGAAGATCCGACCACCTTAAATATCAGAGGAGGGGCCAGTCCTACC

ATTCTACTCAAGGATGCAATCAGAAAGGCTTTATATGACGAGGTGGACAAGGTG

GAAAATTCAGAGTTTCGAGAGGCAATCCTGTTGTCCAAGACCCATAGAGATAAT
```

```
-continued
TTTATACTCTTCTTAATATCTGTTGAGCCTCTGTTTCCTCGATTTCTCAGTGAGCT

ATTCAGTTCGTCTTTTTTGGGAATCCCCGAGTCAATCATTGGATTGATACAAAAC

TCCCGAACGATAAGAAGGCAGTTTAGAAAGAGTCTCTCAAAAACTTTAGAAGAA

TCCTTCTACAACTCAGAGATCCACGGGATTAGTCGGATGACCCAGACACCTCAG

AGGGTTGGGGGGTGTGGCCTTGCTCTTCAGAGAGGGCAGATCTACTTAGGGAG

ATCTCTTGGGGAAGAAAAGTGGTAGGCACGACAGTTCCTCACCCTTCTGAGATGT

TGGGATTACTTCCCAAGTCCTCTATTTCTTGCACTTGTGGAGCAACAGGAGGAGG

CAATCCTAGAGTTTCTGTATCAGTACTCCCGTCCTTTGATCAGTCATTTTTTTCAC

GAGGCCCCCTAAAGGGATACTTGGGCTCGTCCACCTCTATGTCGACCCAGCTATT

CCATGCATGGGAAAAGTCACTAATGTTCATGTGGTGAAGAGAGCTCTATCGTT

AAAAGAATCTATAAACTGGTTCATTACTAGAGATTCCAACTTGGCTCAAGCTCTA

ATTAGGAACATTATGTCTCTGACAGGCCCTGATTTCCCTCTAGAGGAGGCCCCTG

TCTTCAAAAGGACGGGGTCAGCCTTGCATAGGTTCAAGTCTGCCAGATACAGCG

AAGGAGGGTATTCTTCTGTCTGCCCGAACCTCCTCTCTCATATTTCTGTTAGTACA

GACACCATGTCTGATTTGACCCAAGACGGGAAGAACTACGATTTCATGTTCCAGC

CATTGATGCTTTATGCACAGACATGGACATCAGAGCTGGTACAGAGAGACACAA

GGCTAAGAGACTCTACGTTTCATTGGCACCTCCGATGCAACAGGTGTGTGAGACC

CATTGACGACGTGACCCTGGAGACCTCTCAGATCTTCGAGTTTCCGGATGTGTCG

AAAAGAATATCCAGAATGGTTTCTGGGGCTGTGCCTCACTTCCAGAGGCTTCCCG

ATATCCGTCTGAGACCAGGAGATTTTGAATCTCTAAGCGGTAGAGAAAAGTCTC

ACCATATCGGATCAGCTCAGGGGCTCTTATACTCAATCTTAGTGGCAATTCACGA

CTCAGGATACAATGATGGAACCATCTTCCCTGTCAACATATACGGCAAGGTTTCC

CCTAGAGACTATTTGAGAGGGCTCGCAAGGGGAGTATTGATAGGATCCTCGATT

TGCTTCTTGACAAGAATGACAAATATCAATATTAATAGACCTCTTGAATTGGTCT

CAGGGGTAATCTCATATATTCTCCTGAGGCTAGATAACCATCCCTCCTTGTACAT

AATGCTCAGAGAACCGTCTCTTAGAGGAGAGATATTTTCTATCCCTCAGAAAATC

CCCGCCGCTTATCCAACCACTATGAAAGAAGGCAACAGATCAATCTTGTGTTATC

TCCAACATGTGCTACGCTATGAGCGAGAGATAATCACGGCGTCTCCAGAGAATG

ACTGGCTATGGATCTTTTCAGACTTTAGAAGTGCCAAAATGACGTACCTATCCCT

CATTACTTACCAGTCTCATCTTCTACTCCAGAGGGTTGAGAGAAACCTATCTAAG

AGTATGAGAGATAACCTGCGACAATTGAGTTCTTTGATGAGGCAGGTGCTGGGC

GGGCACGGAGAAGATACCTTAGAGTCAGACGACAACATTCAACGACTGCTAAAA

G1ACTCTTTACGAAGGACAAGATGGGTGGATCAAGAGGTGCGCCATGCAGCTAGA

ACCATGACTGGAGATTACAGCCCCAACAAGAAGGTGTCCCGTAAGGTAGGATGT

TCAGAATGGGTCTGCTCTGCTCAACAGGTTGCAGTCTCTACCTCAGCAAACCCGG

CCCCTGTCTCGGAGCTTGACATAAGGGCCCTCTCTAAGAGGTTCCAGAACCCTTT

GATCTCGGGCTTGAGAGTGGTTCAGTGGGCAACCGGTGCTCATTATAAGCTTAAG

CCTATTCTAGATGATCTCAATGTTTTCCCATCTCTCTGCCTTGTAGTTGGGGACGG

GTCAGGGGGATATCAAGGGCAGTCCTCAACATGTTTCCAGATGCCAAGCTTGT

GTTCAACAGTCTTTTAGAGGTGAATGACCTGATGGCTTCCGGAACACATCCACTG

CCTCCTTCAGCAATCATGAGGGGAGGAAATGATATCGTCTCCAGAGTGATAGAT
```

-continued

```
CTTGACTCAATCTGGGAAAAACCGTCCGACTTGAGAAACTTGGCAACCTGGAAA

TACTTCCAGTCAGTCCAAAAGCAGGTCAACATGTCCTATGACCTCATTATTTGCG

ATGCAGAAGTTACTGACATTGCATCTATCAACCGGATCACCCTGTTAATGTCCGA

TTTTGCATTGTCTATAGATGGACCACTCTATTTGGTCTTCAAAACTTATGGGACTA

TGCTAGTAAATCCAAACTACAAGGCTATTCAACACCTGTCAAGAGCGTTCCCCTC

GGTCACAGGGTTTATCACCCAAGTAACTTCGTCTTTTTCATCTGAGCTCTACCTCC

GATTCTCCAAACGAGGGAAGTTTTTCAGAGATGCTGAGTACTTGACCTCTTCCAC

CCTTCGAGAAATGAGCCTTGTGTTATTCAATTGTAGCAGCCCCAAGAGTGAGATG

CAGAGAGCTCGTTCCTTGAACTATCAGGATCTTGTGAGAGGATTTCCTGAAGAAA

TCATATCAAATCCTTACAATGAGATGATCATAACTCTGATTGACAGTGATGTAGA

ATCTTTTCTAGTCCACAAGATGGTTGATGATCTTGAGTTACAGAGGGGAACTCTG

TCTAAAGTGGCTATCATTATAGCCATCATGATAGTTTTCTCCAACAGAGTCTTCA

ACGTTTCCAAACCCCTAACTGACCCCTCGTTCTATCCACCGTCTGATCCCAAAAT

CCTGAGGCACTTCAACATATGTTGCAGTACTATGATGTATCTATCTACTGCTTTA

GGTGACGTCCCTAGCTTCGCAAGACTTCACGACCTGTATAACAGACCTATAACTT

ATTACTTCAGAAAGCAAGTCATTCGAGGGAACGTTTATCTATCTTGGAGTTGGTC

CAACGACACCTCAGTGTTCAAAAGGGTAGCCTGTAATTCTAGCCTGAGTCTGTCA

TCTCACTGGATCAGGTTGATTTACAAGATAGTGAAGACTACCAGACTCGTTGGCA

GCATCAAGGATCTATCCAGAGAAGTGGAAAGACACCTTCATAGGTACAACAGGT

GGATCACCCTAGAGGATATCAGATCTAGATCATCCCTACTAGACTACAGTTGCCT

GTGAACCGGATACTCCTGGAAGCCTGCCCATGCTAAGACTCTTGTGTGATGTATC

TTGAAAAAAACAAGATCCTAAATCTGAACCTTTGGTTGTTTGATTGTTTTTCTCAT

TTTTGTTGTTTATTTGTTAAGCGT.
```

In one embodiment, the nucleic acid comprises the sequence of SEQ ID NO: 18, shown below (VSV vector: Convac V1 China):

```
ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC

CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAAATGATCAATGAACAGTTTGAACCTCTTGTGCCAGAAGGT

CGTGACATTTTTGATGTGTGGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC
```

-continued

```
CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

ATATTCTTCCGTCAAAAACCCTGCCTTCCACTTCTGGGGGCAATTGACAGCTCTT

CTGCTCAGATCCACCAGAGCAAGGAATGCCCGACAGCCTGATGACATTGAGTAT

ACATCTCTTACTACAGCAGGTTTGTTGTACGCTTATGCAGTAGGATCCTCTGCCG

ACTTGGCACAACAGTTTTGTGTTGGAGATAACAAATACACTCCAGATGATAGTAC

CGGAGGATTGACGACTAATGCACCGCCACAAGGCAGAGATGTGGTCGAATGGCT

CGGATGGTTTGAAGATCAAAACAGAAAACCGACTCCTGATATGATGCAGTATGC

GAAAAGAGCAGTCATGTCACTGCAAGGCCTAAGAGAAGACAATTGGCAAGT

ATGCTAAGTCAGAATTTGACAAATGACCCTATAATTCTCAGATCACCTATTATAT

ATTATGCTACATATGAAAAAAACTAACAGATATCATGGATAATCTCACAAAAGT

TCGTGAGTATCTCAAGTCCTATTCTCGTCTGGATCAGGCGGTAGGAGAGATAGAT

GAGATCGAAGCACAACGAGCTGAAAAGTCCAATTATGAGTTGTTCCAAGAGGAT

GGAGTGGAAGAGCATACTAAGCCCTCTTATTTTCAGGCAGCAGATGATTCTGAC

ACAGAATCTGAACCAGAAATTGAAGACAATCAAGGTTTGTATGCACCAGATCCA

GAAGCTGAGCAAGTTGAAGGCTTTATACAGGGGCCTTTAGATGACTATGCAGAT

GAGGAAGTGGATGTTGTATTTACTTCGGACTGGAAACAGCCTGAGCTTGAATCTG

ACGAGCATGGAAAGACCTTACGGTTGACATCGCCAGAGGGTTTAAGTGGAGAGC

AGAAATCCCAGTGGCTTTCGACGATTAAAGCAGTCGTGCAAAGTGCCAAATACT

GGAATCTGGCAGAGTGCACATTTGAAGCATCGGGAGAAGGGGTCATTATGAAGG

AGCGCCAGATAACTCCGGATGTATATAAGGTCACTCCAGTGATGAACACACATC

CGTCCCAATCAGAAGCAGTATCAGATGTTTGGTCTCTCTCAAAGACATCCATGAC

TTTCCAACCCAAGAAAGCAAGTCTTCAGCCTCTCACCATATCCTTGGATGAATTG

TTCTCATCTAGAGGAGAGTTCATCTCTGTCGGAGGTGACGGACGAATGTCTCATA

AAGAGGCCATCCTGCTCGGCCTGAGATACAAAAAGTTGTACAATCAGGCGAGAG

TCAAATATTCTCTGTAGACTATGAAAAAAAGTAACAGATATCACGATCTAAGTGT

TATCCCAATCCATTCATCATGAGTTCCTTAAAGAAGATTCTCGGTCTGAAGGGGA

AAGGTAAGAAATCTAAGAAATTAGGGATCGCACCACCCCCTTATGAAGAGGACA

CTAGCATGGAGTATGCTCCGAGCGCTCCAATTGACAAATCCTATTTTGGAGTTGA

CGAGATGGACACCTATGATCCGAATCAATTAAGATATGAGAAATTCTTCTTTACA

GTGAAAATGACGGTTAGATCTAATCGTCCGTTCAGAACATACTCAGATGTGGCA

GCCGCTGTATCCCATTGGGATCACATGTACATCGGAATGGCAGGGAAACGTCCC

TTCTACAAAATCTTGGCTTTTTTGGGTTCTTCTAATCTAAAGGCCACTCCAGCGGT

ATTGGCAGATCAAGGTCAACCAGAGTATCACACTCACTGCGAAGGCAGGGCTTA

TTTGCCACATAGGATGGGGAAGACCCCTCCCATGCTCAATGTACCAGAGCACTTC

AGAAGACCATTCAATATAGGTCTTTACAAGGGAACGATTGAGCTCACAATGACC

ATCTACGATGATGAGTCACTGGAAGCAGCTCCTATGATCTGGGATCATTTCAATT

CTTCCAAATTTTCTGATTTCAGAGAGAAGGCCTTAATGTTTGGCCTGATTGTCGA

GAAAAAGGCATCTGGAGCGTGGGTCCTGGATTCTATCAGCCACTTCAAATGAGC
```

-continued
```
TAGTCTAACTTCTAGCTTCTGAACAATCCCCGGTTTACTCAGTCTCTCCTAATTCC
AGCCTCTCGAACAACTAATATCCTGTCTTTTCTATCCCTATGAAAAAAACTAACA
GAGATCGATCTGTTTACGCGTCACTATGAAGTGCCTTTTGTACTTAGCCTTTTTAT
TCATTGGGGTGAATTGCAAGTTCACCATAGTTTTTCCACACAACCAAAAAGGAA
ACTGGAAAAATGTTCCTTCTAATTACCATTATTGCCCGTCAAGCTCAGATTTAAA
TTGGCATAATGACTTAATAGGCACAGCCATACAAGTCAAAATGCCCAAGAGTCA
CAAGGCTATTCAAGCAGACGGTTGGATGTGTCATGCTTCCAAATGGGTCACTACT
TGTGATTTCCGCTGGTATGGACCGAAGTATATAACACAGTCCATCCGATCCTTCA
CTCCATCTGTAGAACAATGCAAGGAAAGCATTGAACAAACGAAACAAGGAACTT
GGCTGAATCCAGGCTTCCCTCCTCAAAGTTGTGGATATGCAACTGTGACGGATGC
CGAAGCAGTGATTGTCCAGGTGACTCCTCACCATGTGCTGGTTGATGAATACACA
GGAGAATGGGTTGATTCACAGTTCATCAACGGAAAATGCAGCAATTACATATGC
CCCACTGTCCATAACTCTACAACCTGGCATTCTGACTATAAGGTCAAAGGGCTAT
GTGATTCTAACCTCATTTCCATGGACATCACCTTCTTCTCAGAGGACGGAGAGCT
ATCATCCCTGGGAAGGAGGGCACAGGGTTCAGAAGTAACTACTTTGCTTATGA
AACTGGAGGCAAGGCCTGCAAAATGCAATACTGCAAGCATTGGGGAGTCAGACT
CCCATCAGGTGTCTGGTTCGAGATGGCTGATAAGGATCTCTTTGCTGCAGCCAGA
TTCCCTGAATGCCCAGAAGGGTCAAGTATCTCTGCTCCATCTCAGACCTCAGTGG
ATGTAAGTCTAATTCAGGACGTTGAGAGGATCTTGGATTATTCCCTCTGCCAAGA
AACCTGGAGCAAAATCAGAGCGGGTCTTCCAATCTCTCCAGTGGATCTCAGCTAT
CTTGCTCCTAAAAACCCAGGAACCGGTCCTGCTTTCACCATAATCAATGGTACCC
TAAAATACTTTGAGACCAGATACATCAGAGTCGATATTGCTGCTCCAATCCTCTC
AAGAATGGTCGGAATGATCAGTGGAACTACCACAGAAAGGGAACTGTGGGATG
ACTGGGCACCATATGAAGACGTGGAAATTGGACCCAATGGAGTTCTGAGGACCA
GTTCAGGATATAAGTTTCCTTTATACATGATTGGACATGGTATGTTGGACTCCGA
TCTTCATCTTAGCTCAAAGGCTCAGGTGTTCGAACATCCTCACATTCAAGACGCT
GCTTCGCAACTTCCTGATGATGAGAGTTTATTTTTTGGTGATACTGGGCTATCCA
AAAATCCAATCGAGCTTGTAGAAGGTTGGTTCAGTAGTTGGAAAAGCTCTATTGC
CTCTTTTTTCTTTATCATAGGGTTAATCATTGGACTATTCTTGGTTCTCCGAGTTG
GTATCCATCTTTGCATTAAATTAAAGCACACCAAGAAAAGACAGATTTATACAG
ACATAGAGATGAACCGACTTGGAAAGTAACTCAAATCCTGCTAGGTATGAAAAA
AACTAACaGATATCACGCTCGAGCGTACGCCACCATGTTCGTGTTTCTGGTGCTG
CTGCCTCTGGTGAGCTCCCAGTGCGTGAACCTGACCACAAGGACCCAGCTGCCC
CCTGCCTATACCAATTCCTTCACACGGGGCGTGTACTATCCCGACAAGGTGTTCC
GGAGCAGCGTGCTGCACTCCACACAGGATCTGTTTCTGCCTTTCTTTTCTAACGT
GACCTGGTTCCACGCCATCCACGTGAGCGGCACCAATGGCACAAAGCGGTTCGA
CAATCCAGTGCTGCCCTTTAACGATGGCGTGTACTTCGCCTCCACCGAGAAGTCT
AACATCATCAGAGGCTGGATCTTTGGCACCACACTGGACAGCAAGACACAGTCC
CTGCTGATCGTGAACAATGCCACCAACGTGGTCATCAAGGTGTGCGAGTTCCAGT
TTTGTAATGATCCATTCCTGGGCGTGTACTATCACAAGAACAATAAGTCTTGGAT
GGAGAGCGAGTTTCGCGTGTATTCCTCTGCCAACAATTGCACATTTGAGTACGTG
```

-continued

```
TCCCAGCCCTTCCTGATGGACCTGGAGGGCAAGCAGGGCAATTTCAAGAACCTG

AGGGAGTTCGTGTTTAAGAATATCGATGGCTACTTCAAAATCTACTCCAAGCACA

CCCCAATCAACCTGGTGCGCGACCTGCCACAGGGCTTCTCTGCCCTGGAGCCACT

GGTGGATCTGCCCATCGGCATCAACATCACCCGGTTTCAGACACTGCTGGCCCTG

CACAGAAGCTACCTGACACCAGGCGACAGCTCCTCTGGATGGACCGCAGGAGCA

GCAGCCTACTATGTGGGCTATCTGCAGCCCAGGACCTTCCTGCTGAAGTACAACG

AGAATGGCACCATCACAGACGCCGTGGATTGCGCCCTGGATCCCCTGTCTGAGA

CCAAGTGTACACTGAAGAGCTTTACCGTGGAGAAGGGCATCTATCAGACAAGCA

ATTTCAGGGTGCAGCCTACCGAGTCCATCGTGCGCTTTCCCAATATCACAAACCT

GTGCCCTTTTGGCGAGGTGTTCAACGCAACCCGCTTCGCCAGCGTGTACGCCTGG

AATAGGAAGCGCATCTCCAACTGCGTGGCCGACTATTCTGTGCTGTACAACAGC

GCCTCCTTCTCTACCTTTAAGTGCTATGGCGTGAGCCCCACAAAGCTGAATGACC

TGTGCTTTACCAACGTGTACGCCGATTCCTTCGTGATCAGGGGCGACGAGGTGCG

CCAGATCGCACCAGGACAGACAGGCAAGATCGCAGACTACAATTATAAGCTGCC

TGACGATTTCACCGGCTGCGTGATCGCCTGGAACTCTAACAATCTGGATAGCAAA

GTGGGCGGCAACTACAATTATCTGTACCGGCTGTTTAGAAAGTCTAATCTGAAGC

CATTCGAGAGGGACATCTCCACAGAAATCTACCAGGCCGGCTCTACCCCCTGCA

ATGGCGTGGAGGGCTTTAACTGTTATTTCCCTCTGCAGAGCTACGGCTTCCAGCC

AACAAACGGCGTGGGCTATCAGCCCTACCGCGTGGTGGTGCTGTCTTTTGAGCTG

CTGCACGCACCTGCAACAGTGTGCGGACCAAAGAAGAGCACCAATCTGGTGAAG

AACAAGTGCGTGAACTTCAACTTCAACGGACTGACCGGAACAGGCGTGCTGACC

GAGTCCAACAAGAAGTTCCTGCCTTTTCAGCAGTTCGGCAGGGACATCGCAGAT

ACCACAGACGCCGTGCGCGACCCTCAGACCCTGGAGATCCTGGACATCACACCA

TGCTCCTTCGGCGGCGTGTCTGTGATCACACCAGGCACCAATACAAGCAACCAG

GTGGCCGTGCTGTATCAGGACGTGAATTGTACCGAGGTGCCAGTGGCAATCCAC

GCAGATCAGCTGACCCCTACATGGCGGGTGTACTCTACCGGCAGCAACGTGTTC

CAGACAAGAGCCGGATGCCTGATCGGAGCAGAGCACGTGAACAATAGCTATGA

GTGCGACATCCCTATCGGCGCCGGCATCTGTGCCTCCTACCAGACCCAGACAAA

CTCCCCAAGGTCTGTGGGCGATACAGGCCTGTCCAAGAATCCAATCGAGCTGGT

AGAGGGCTGGTTCAGCAGTTGGAAAAGCTCCATCGCCTCCTTTTTCTTTATCATC

GGCCTGATCATCGGACTGTTCCTGGTGCTCCGCGTGGGTATCCACCTGTGCATCA

AGCTGAAGCACACCAAGAAAAGACAGATTTATACAGACATCGAGATGAACCGC

CTGGGAAAGTGAGCTAGCCAGATTCTTCATGTTTGGACCAAATCAACTTGTGATA

CCATGCTCAAAGAGGCCTCAATTATATTTGAGTTTTTAATTTTTATGAAAAAAAC

TAACAGCAATCATGGAAGTCCACGATTTTGAGACCGACGAGTTCAATGATTTCA

ATGAAGATGACTATGCCACAAGAGAATTCCTGAATCCCGATGAGCGCATGACGT

ACTTGAATCATGCTGATTACAATTTGAATTCTCCTCTAATTAGTGATGATATTGAC

AATTTGATCAGGAAATTCAATTCTCTTCCGATTCCCTCGATGTGGGATAGTAAGA

ACTGGGATGGAGTTCTTGAGATGTTAACATCATGTCAAGCCAATCCCATCTCAAC

ATCTCAGATGCATAAATGGATGGGAAGTTGGTTAATGTCTGATAATCATGATGCC
```

-continued

```
AGTCAAGGGTATAGTTTTTTACATGAAGTGGACAAAGAGGCAGAAATAACATTT

GACGTGGTGGAGACCTTCATCCGCGGCTGGGGCAACAAACCAATTGAATACATC

AAAAAGGAAAGATGGACTGACTCATTCAAAATTCTCGCTTATTTGTGTCAAAGT

TTTTGGACTTACACAAGTTGACATTAATCTTAAATGCTGTCTCTGAGGTGGAATT

GCTCAACTTGGCGAGGACTTTCAAAGGCAAAGTCAGAAGAAGTTCTCATGGAAC

GAACATATGCAGGATTAGGGTTCCCAGCTTGGGTCCTACTTTTATTTCAGAAGGA

TGGGCTTACTTCAAGAAACTTGATATTCTAATGGACCGAAACTTTCTGTTAATGG

TCAAAGATGTGATTATAGGGAGGATGCAAACGGTGCTATCCATGGTATGTAGAA

TAGACAACCTGTTCTCAGAGCAAGACATCTTCTCCCTTCTAAATATCTACAGAAT

TGGAGATAAAATTGTGGAGAGGCAGGGAAATTTTTCTTATGACTTGATTAAAAT

GGTGGAACCGATATGCAACTTGAAGCTGATGAAATTAGCAAGAGAATCAAGGCC

TTTAGTCCCACAATTCCCTCATTTTGAAAATCATATCAAGACTTCTGTTGATGAA

GGGGCAAAAATTGACCGAGGTATAAGATTCCTCCATGATCAGATAATGAGTGTG

AAAACAGTGGATCTCACACTGGTGATTTATGGATCGTTCAGACATTGGGGTCATC

CTTTTATAGATTATTACACTGGACTAGAAAAATTACATTCCCAAGTAACCATGAA

GAAAGATATTGATGTGTCATATGCAAAAGCACTTGCAAGTGATTTAGCTCGGATT

GTTCTATTTCAACAGTTCAATGATCATAAAAAGTGGTTCGTGAATGGAGACTTGC

TCCCTCATGATCATCCCTTTAAAAGTCATGTTAAAGAAAATACATGGCCCACAGC

TGCTCAAGTTCAAGATTTTGGAGATAAATGGCATGAACTTCCGCTGATTAAATGT

TTTGAAATACCCGACTTACTAGACCCATCGATAATATACTCTGACAAAAGTCATT

CAATGAATAGGTCAGAGGTGTTGAAACATGTCCGAATGAATCCGAACACTCCTA

TCCCTAGTAAAAAGGTGTTGCAGACTATGTTGGACACAAAGGCTACCAATTGGA

AAGAATTTCTTAAAGAGATTGATGAGAAGGGCTTAGATGATGATGATCTAATTA

TTGGTCTTAAAGGAAAGGAGAGGGAACTGAAGTTGGCAGGTAGATTTTTCTCCC

TAATGTCTTGGAAATTGCGAGAATACTTTGTAATTACCGAATATTTGATAAAGAC

TCATTTCGTCCCTATGTTTAAAGGCCTGACAATGGCGGACGATCTAACTGCAGTC

ATTAAAAAGATGTTAGATTCCTCATCCGGCCAAGGATTGAAGTCATATGAGGCA

ATTTGCATAGCCAATCACATTGATTACGAAAAATGGAATAACCACCAAAGGAAG

TTATCAAACGGCCCAGTGTTCCGAGTTATGGGCCAGTTCTTAGGTTATCCATCCT

TAATCGAGAGAACTCATGAATTTTTTGAGAAAAGTCTTATATACTACAATGGAAG

ACCAGACTTGATGCGTGTTCACAACAACACACTGATCAATTCAACCTCCCAACG

AGTTTGTTGGCAAGGACAAGAGGGTGGACTGGAAGGTCTACGGCAAAAAGGAT

GGACTATCCTCAATCTACTGGTTATTCAAAGAGAGGCTAAAATCAGAAACACTG

CTGTCAAAGTCTTGGCACAAGGTGATAATCAAGTTATTTGCACACAGTATAAAAC

GAAGAAATCGAGAAACGTTGTAGAATTACAGGGTGCTCTCAATCAAATGGTTTC

TAATAATGAGAAAATTATGACTGCAATCAAAATAGGGACAGGGAAGTTAGGACT

TTTGATAAATGACGATGAGACTATGCAATCTGCAGATTACTTGAATTATGGAAAA

ATACCGATTTTCCGTGGAGTGATTAGAGGGTTAGAGACCAAGAGATGGTCACGA

GTGACTTGTGTCACCAATGACCAAATACCCACTTGTGCTAATATAATGAGCTCAG

TTTCCACAAATGCTCTCACCGTAGCTCATTTTGCTGAGAACCCAATCAATGCCAT

GATACAGTACAATTATTTTGGGACATTTGCTAGACTCTTGTTGATGATGCATGAT
```

-continued

```
CCTGCTCTTCGTCAATCATTGTATGAAGTTCAAGATAAGATACCGGGCTTGCACA

GTTCTACTTTCAAATACGCCATGTTGTATTTGGACCCTTCCATTGGAGGAGTGTC

GGGCATGTCTTTGTCCAGGTTTTTGATTAGAGCCTTCCCAGATCCCGTAACAGAA

AGTCTCTCATTCTGGAGATTCATCCATGTACATGCTCGAAGTGAGCATCTGAAGG

AGATGAGTGCAGTATTTGGAAACCCCGAGATAGCCAAGTTTCGAATAACTCACA

TAGACAAGCTAGTAGAAGATCCAACCTCTCTGAACATCGCTATGGGAATGAGTC

CAGCGAACTTGTTAAAGACTGAGGTTAAAAAATGCTTAATCGAATCAAGACAAA

CCATCAGGAACCAGGTGATTAAGGATGCAACCATATATTTGTATCATGAAGAGG

ATCGGCTCAGAAGTTTCTTATGGTCAATAAATCCTCTGTTCCCTAGATTTTTAAGT

GAATTCAAATCAGGCACTTTTTTGGGAGTCGCAGACGGGCTCATCAGTCTATTTC

AAAATTCTCGTACTATTCGGAACTCCTTTAAGAAAAAGTATCATAGGGAATTGGA

TGATTTGATTGTGAGGAGTGAGGTATCCTCTTTGACACATTTAGGGAAACTTCAT

TTGAGAAGGGGATCATGTAAAATGTGGACATGTTCAGCTACTCATGCTGACACA

TTAAGATACAAATCCTGGGGCCGTACAGTTATTGGGACAACTGTACCCCATCCAT

TAGAAATGTTGGGTCCACAACATCGAAAAGAGACTCCTTGTGCACCATGTAACA

CATCAGGGTTCAATTATGTTTCTGTGCATTGTCCAGACGGGATCCATGACGTCTT

TAGTTCACGGGACCATTGCCTGCTTATCTAGGGTCTAAAACATCTGAATCTACA

TCTATTTTGCAGCCTTGGGAAAGGGAAAGCAAAGTCCCACTGATTAAAAGAGCT

ACACGTCTTAGAGATGCTATCTCTTGGTTTGTTGAACCCGACTCTAAACTAGCAA

TGACTATACTTTCTAACATCCACTCTTTAACAGGCGAAGAATGGACCAAAAGGC

AGCATGGGTTCAAAAGAACAGGGTCTGCCCTTCATAGGTTTTCGACATCTCGGAT

GAGCCATGGTGGGTTCGCATCTCAGAGCACTGCAGCATTGACCAGGTTGATGGC

AACTACAGACACCATGAGGGATCTGGGAGATCAGAATTTCGACTTTTTATTCCAA

GCAACGTTGCTCTATGCTCAAATTACCACCACTGTTGCAAGAGACGGATGGATCA

CCAGTTGTACAGATCATTATCATATTGCCTGTAAGTCCTGTTTGAGACCCATAGA

AGAGATCACCCTGGACTCAAGTATGGACTACACGCCCCCAGATGTATCCCATGT

GCTGAAGACATGGAGGAATGGGGAAGGTTCGTGGGGACAAGAGATAAAACAGA

TCTATCCTTTAGAAGGGAATTGGAAGAATTTAGCACCTGCTGAGCAATCCTATCA

AGTCGGCAGATGTATAGGTTTTCTATATGGAGACTTGGCGTATAGAAAATCTACT

CATGCCGAGGACAGTTCTCTATTTCCTCTATCTATACAAGGTCGTATTAGAGGTC

GAGGTTTCTTAAAAGGGTTGCTAGACGGATTAATGAGAGCAAGTTGCTGCCAAG

TAATACACCGGAGAAGTCTGGCTCATTTGAAGAGGCCGGCCAACGCAGTGTACG

GAGGTTTGATTTACTTGATTGATAAATTGAGTGTATCACCTCCATTCCTTTCTCTT

ACTAGATCAGGACCTATTAGAGACGAATTAGAAACGATTCCCCACAAGATCCCA

ACCTCCTATCCGACAAGCAACCGTGATATGGGGGTGATTGTCAGAAATTACTTCA

AATACCAATGCCGTCTAATTGAAAAGGGAAAATACAGATCACATTATTCACAAT

TATGGTTATTCTCGAGATGTCTTATCCATAGACTTCATTGGACCATTCTCTATTTCC

ACCACCCTCTTGCAAATCCTATACAAGCCATTTTTATCTGGGAAAGATAAGAATG

AGTTGAGAGAGCTGGCAAATCTTTCTTCATTGCTAAGATCAGGAGAGGGGTGGG

AAGACATACATGTGAAATTCTTCACCAAGGACATATTATTGTGTCCAGAGGAAA
```

-continued
```
TCAGACATGCTTGCAAGTTCGGGATTGCTAAGGATAATAATAAAGACATGAGCT
ATCCCCCTTGGGGAAGGGAATCCAGAGGGACAATTACAACAATCCCTGTTTATT
ATACGACCACCCCTTACCCAAAGATGCTAGAGATGCCTCCAAGAATCCAAATC
CCCTGCTGTCCGGAATCAGGTTGGGCCAATTACCAACTGGCGCTCATTATAAAT
TCGGAGTATATTACATGGAATGGGAATCCATTACAGGGACTTCTTGAGTTGTGGA
GACGGCTCCGGAGGGATGACTGCTGCATTACTACGAGAAAATGTGCATAGCAGA
GGAATATTCAATAGTCTGTTAGAATTATCAGGGTCAGTCATGCGAGGCGCCTCTC
CTGAGCCCCCAGTGCCCTAGAAACTTTAGGAGGAGATAAATCGAGATGTGTAA
ATGGTGAAACATGTTGGGAATATCCATCTGACTTATGTGACCCAAGGACTTGGG
ACTATTTCCTCCGACTCAAAGCAGGCTTGGGGCTTCAAATTGATTTAATTGTAAT
GGATATGGAAGTTCGGGATTCTTCTACTAGCCTGAAAATTGAGACGAATGTTAG
AAATTATGTGCACCGGATTTTGGATGAGCAAGGAGTTTTAATCTACAAGACTTAT
GGAACATATATTTGTGAGAGCGAAAAGAATGCAGTAACAATCCTTGGTCCCATG
TTCAAGACGGTCGACTTAGTTCAAACAGAATTTAGTAGTTCTCAAACGTCTGAAG
TATATATGGTATGTAAAGGTTTGAAGAAATTAATCGATGAACCCAATCCCGATTG
GTCTTCCATCAATGAATCCTGGAAAAACCTGTACGCATTCCAGTCATCAGAACAG
GAATTTGCCAGAGCAAAGAAGGTTAGTACATACTTTACCTTGACAGGTATTCCCT
CCCAATTCATTCCTGATCCTTTTGTAAACATTGAGACTATGCTACAAATATTCGG
AGTACCCACGGGTGTGTCTCATGCGGCTGCCTTAAAATCATCTGATAGACCTGCA
GATTTATTGACCATTAGCCTTTTTTATATGGCGATTATATCGTATTATAACATCAA
TCATATCAGAGTAGGACCGATACCTCCGAACCCCCCATCAGATGGAATTGCACA
AAATGTGGGGATCGCTATAACTGGTATAAGCTTTTGGCTGAGTTTGATGGAGAA
AGACATTCCACTATATCAACAGTGTTTAGCAGTTATCCAGCAATCATTCCCGATT
AGGTGGGAGGCTGTTTCAGTAAAAGGAGGATACAAGCAGAAGTGGAGTACTAG
AGGTGATGGGCTCCCAAAAGATACCCGAACTTCAGACTCCTTGGCCCCAATCGG
GAACTGGATCAGATCTCTGGAATTGGTCCGAAACCAAGTTCGTCTAAATCCATTC
AATGAGATCTTGTTCAATCAGCTATGTCGTACAGTGGATAATCATTTGAAATGGT
CAAATTTGCGAAGAAACACAGGAATGATTGAATGGATCAATAGACGAATTTCAA
AAGAAGACCGGTCTATACTGATGTTGAAGAGTGACCTACACGAGGAAAACTCTT
GGAGAGATTAAAAAATCATGAGGAGACTCCAAACTTTAAGTATGAAAAAAACTT
TGATCCTTAAGACCCTCTTGTGGTTTTTATTTTTTATCTGGTTTTGTGGTCTTCGT.
```

In another embodiment, the nucleic acid comprises the sequence of SEQ ID NO: 19, shown below (VSV vector: Convac V1 South Africa):

```
ACGAAGACAAACAAACCATTATTATCATTAAAAGGCTCAGGAGAAACTTTAACA
GTAATCAAAATGTCTGTTACAGTCAAGAGAATCATTGACAACACAGTCATAGTTC
CAAAACTTCCTGCAAATGAGGATCCAGTGGAATACCCGGCAGATTACTTCAGAA
AATCAAAGGAGATTCCTCTTTACATCAATACTACAAAAAGTTTGTCAGATCTAAG
AGGATATGTCTACCAAGGCCTCAAATCCGGAAATGTATCAATCATACATGTCAA
CAGCTACTTGTATGGAGCATTAAAGGACATCCGGGGTAAGTTGGATAAAGATTG
```

-continued
GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAAATGATCAATGAACAGTTTGAACCTCTTGTGCCAGAAGGT

CGTGACATTTTTGATGTGTGGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

ATATTCTTCCGTCAAAAACCCTGCCTTCCACTTCTGGGGGCAATTGACAGCTCTT

CTGCTCAGATCCACCAGAGCAAGGAATGCCCGACAGCCTGATGACATTGAGTAT

ACATCTCTTACTACAGCAGGTTTGTTGTACGCTTATGCAGTAGGATCCTCTGCCG

ACTTGGCACAACAGTTTTGTGTTGGAGATAACAAATACACTCCAGATGATAGTAC

CGGAGGATTGACGACTAATGCACCGCCACAAGGCAGAGATGTGGTCGAATGGCT

CGGATGGTTTGAAGATCAAAACAGAAAACCGACTCCTGATATGATGCAGTATGC

GAAAAGAGCAGTCATGTCACTGCAAGGCCTAAGAGAAGACAATTGGCAAGT

ATGCTAAGTCAGAATTTGACAAATGACCCTATAATTCTCAGATCACCTATTATAT

ATTATGCTACATATGAAAAAAACTAACAGATATCATGGATAATCTCACAAAAGT

TCGTGAGTATCTCAAGTCCTATTCTCGTCTGGATCAGGCGGTAGGAGAGATAGAT

GAGATCGAAGCACAACGAGCTGAAAAGTCCAATTATGAGTTGTTCCAAGAGGAT

GGAGTGGAAGAGCATACTAAGCCCTCTTATTTTCAGGCAGCAGATGATTCTGAC

ACAGAATCTGAACCAGAAATTGAAGACAATCAAGGTTTGTATGCACCAGATCCA

GAAGCTGAGCAAGTTGAAGGCTTTATACAGGGGCCTTTAGATGACTATGCAGAT

GAGGAAGTGGATGTTGTATTTACTTCGGACTGGAAACAGCCTGAGCTTGAATCTG

ACGAGCATGGAAAGACCTTACGGTTGACATCGCCAGAGGGTTTAAGTGGAGAGC

AGAAATCCCAGTGGCTTTCGACGATTAAAGCAGTCGTGCAAAGTGCCAAATACT

GGAATCTGGCAGAGTGCACATTTGAAGCATCGGGAGAAGGGGTCATTATGAAGG

AGCGCCAGATAACTCCGGATGTATATAAGGTCACTCCAGTGATGAACACACATC

CGTCCCAATCAGAAGCAGTATCAGATGTTTGGTCTCTCTCAAAGACATCCATGAC

TTTCCAACCCAAGAAAGCAAGTCTTCAGCCTCTCACCATATCCTTGGATGAATTG

TTCTCATCTAGAGGAGAGTTCATCTCTGTCGGAGGTGACGGACGAATGTCTCATA

AAGAGGCCATCCTGCTCGGCCTGAGATACAAAAAGTTGTACAATCAGGCGAGAG

TCAAATATTCTCTGTAGACTATGAAAAAAAGTAACAGATATCACGATCTAAGTGT

TATCCCAATCCATTCATCATGAGTTCCTTAAAGAAGATTCTCGGTCTGAAGGGGA

AAGGTAAGAAATCTAAGAAATTAGGGATCGCACCACCCCCTTATGAAGAGGACA

CTAGCATGGAGTATGCTCCGAGCGCTCCAATTGACAAATCCTATTTTGGAGTTGA

CGAGATGGACACCTATGATCCGAATCAATTAAGATATGAGAAATTCTTCTTTACA

GTGAAAATGACGGTTAGATCTAATCGTCCGTTCAGAACATACTCAGATGTGGCA

GCCGCTGTATCCCATTGGGATCACATGTACATCGGAATGGCAGGGAAACGTCCC

-continued

```
TTCTACAAAATCTTGGCTTTTTTGGGTTCTTCTAATCTAAAGGCCACTCCAGCGGT

ATTGGCAGATCAAGGTCAACCAGAGTATCACACTCACTGCGAAGGCAGGGCTTA

TTTGCCACATAGGATGGGGAAGACCCCTCCCATGCTCAATGTACCAGAGCACTTC

AGAAGACCATTCAATATAGGTCTTTACAAGGGAACGATTGAGCTCACAATGACC

ATCTACGATGATGAGTCACTGGAAGCAGCTCCTATGATCTGGGATCATTTCAATT

CTTCCAAATTTTCTGATTTCAGAGAGAAGGCCTTAATGTTTGGCCTGATTGTCGA

GAAAAAGGCATCTGGAGCGTGGGTCCTGGATTCTATCAGCCACTTCAAATGAGC

TAGTCTAACTTCTAGCTTCTGAACAATCCCCGGTTTACTCAGTCTCTCCTAATTCC

AGCCTCTCGAACAACTAATATCCTGTCTTTTCTATCCCTATGAAAAAAACTAACA

GAGATCGATCTGTTTACGCGTCACTATGAAGTGCCTTTTGTACTTAGCCTTTTTAT

TCATTGGGGTGAATTGCAAGTTCACCATAGTTTTTCCACACAACCAAAAAGGAA

ACTGGAAAAATGTTCCTTCTAATTACCATTATTGCCCGTCAAGCTCAGATTTAAA

TTGGCATAATGACTTAATAGGCACAGCCATACAAGTCAAAATGCCCAAGAGTCA

CAAGGCTATTCAAGCAGACGGTTGGATGTGTCATGCTTCCAAATGGGTCACTACT

TGTGATTTCCGCTGGTATGGACCGAAGTATATAACACAGTCCATCCGATCCTTCA

CTCCATCTGTAGAACAATGCAAGGAAAGCATTGAACAAACGAAACAAGGAACTT

GGCTGAATCCAGGCTTCCCTCCTCAAAGTTGTGGATATGCAACTGTGACGGATGC

CGAAGCAGTGATTGTCCAGGTGACTCCTCACCATGTGCTGGTTGATGAATACACA

GGAGAATGGGTTGATTCACAGTTCATCAACGGAAAATGCAGCAATTACATATGC

CCCACTGTCCATAACTCTACAACCTGGCATTCTGACTATAAGGTCAAAGGGCTAT

GTGATTCTAACCTCATTTCCATGGACATCACCTTCTTCTCAGAGGACGGAGAGCT

ATCATCCCTGGGAAAGGAGGGCACAGGGTTCAGAAGTAACTACTTTGCTTATGA

AACTGGAGGCAAGGCCTGCAAAATGCAATACTGCAAGCATTGGGGAGTCAGACT

CCCATCAGGTGTCTGGTTCGAGATGGCTGATAAGGATCTCTTTGCTGCAGCCAGA

TTCCCTGAATGCCCAGAAGGGTCAAGTATCTCTGCTCCATCTCAGACCTCAGTGG

ATGTAAGTCTAATTCAGGACGTTGAGAGGATCTTGGATTATTCCCTCTGCCAAGA

AACCTGGAGCAAAATCAGAGCGGGTCTTCCAATCTCTCCAGTGGATCTCAGCTAT

CTTGCTCCTAAAAACCCAGGAACCGGTCCTGCTTTCACCATAATCAATGGTACCC

TAAAATACTTTGAGACCAGATACATCAGAGTCGATATTGCTGCTCCAATCCTCTC

AAGAATGGTCGGAATGATCAGTGGAACTACCACAGAAAGGGAACTGTGGGATG

ACTGGGCACCATATGAAGACGTGGAAATTGGACCCAATGGAGTTCTGAGGACCA

GTTCAGGATATAAGTTTCCTTTATACATGATTGGACATGGTATGTTGGACTCCGA

TCTTCATCTTAGCTCAAAGGCTCAGGTGTTCGAACATCCTCACATTCAAGACGCT

GCTTCGCAACTTCCTGATGATGAGAGTTTATTTTTTGGTGATACTGGGCTATCCA

AAAATCCAATCGAGCTTGTAGAAGGTTGGTTCAGTAGTTGGAAAAGCTCTATTGC

CTCTTTTTTCTTTATCATAGGGTTAATCATTGGACTATTCTTGGTTCTCCGAGTTG

GTATCCATCTTTGCATTAAATTAAAGCACACCAAGAAAAGACAGATTTATACAG

ACATAGAGATGAACCGACTTGGAAAGTAACTCAAATCCTGCTAGGTATGAAAAA

AACTAACaGATATCACGCTCGAGCCACCATGTTCGTGTTTCTGGTGCTGCTGCCTC

TGGTGAGCTCCCAGTGCGTGAACTTCACCACAAGGACCCAGCTGCCCCCTGCCTA
```

-continued

```
TACCAATTCCTTCACACGGGGCGTGTACTATCCCGACAAGGTGTTCCGGAGCAGC

GTGCTGCACTCCACACAGGATCTGTTTCTGCCTTTCTTTTCTAACGTGACCTGGTT

CCACGCCATCCACGTGAGCGGCACCAATGGCACAAAGCGGTTCGCCAATCCAGT

GCTGCCCTTTAACGATGGCGTGTACTTCGCCTCCACCGAGAAGTCTAACATCATC

AGAGGCTGGATCTTTGGCACCACACTGGACAGCAAGACACAGTCCCTGCTGATC

GTGAACAATGCCACCAACGTGGTCATCAAGGTGTGCGAGTTCCAGTTTTGTAATG

ATCCATTCCTGGGCGTGTACTATCACAAGAACAATAAGTCTTGGATGGAGAGCG

AGTTTCGCGTGTATTCCTCTGCCAACAATTGCACATTTGAGTACGTGTCCCAGCC

CTTCCTGATGGACCTGGAGGGCAAGCAGGGCAATTTCAAGAACCTGAGGGAGTT

CGTGTTTAAGAATATCGATGGCTACTTCAAAATCTACTCCAAGCACACCCCAATC

AACCTGGTGCGCGGCCTGCCACAGGGCTTCTCTGCCCTGGAGCCACTGGTGGATC

TGCCCATCGGCATCAACATCACCCGGTTTCAGACACTGCTGGCCCTGCACAGAA

GCTACCTGACACCAGGCGACAGCTCCTCTGGATGGACCGCAGGAGCAGCAGCCT

ACTATGTGGGCTATCTGCAGCCCAGGACCTTCCTGCTGAAGTACAACGAGAATG

GCACCATCACAGACGCCGTGGATTGCGCCCTGGATCCCCTGTCTGAGACCAAGT

GTACACTGAAGAGCTTTACCGTGGAGAAGGGCATCTATCAGACAAGCAATTTCA

GGGTGCAGCCTACCGAGTCCATCGTGCGCTTTCCCAATATCACAAACCTGTGCCC

TTTTGGCGAGGTGTTCAACGCAACCCGCTTCGCCAGCGTGTACGCCTGGAATAGG

AAGCGCATCTCCAACTGCGTGGCCGACTATTCTGTGCTGTACAACAGCGCCTCCT

TCTCTACCTTTAAGTGCTATGGCGTGAGCCCCACAAAGCTGAATGACCTGTGCTT

TACCAACGTGTACGCCGATTCCTTCGTGATCAGGGGCGACGAGGTGCGCCAGAT

CGCACCAGGACAGACAGGCAATATCGCAGACTACAATTATAAGCTGCCTGACGA

TTTCACCGGCTGCGTGATCGCCTGGAACTCTAACAATCTGGATAGCAAAGTGGGC

GGCAACTACAATTATCTGTACCGGCTGTTTAGAAAGTCTAATCTGAAGCCATTCG

AGAGGGACATCTCCACAGAAATCTACCAGGCCGGCTCTACCCCCTGCAATGGCG

TGAAGGGCTTTAACTGTTATTTCCCTCTGCAGAGCTACGGCTTCCAGCCAACATA

TGGCGTGGGCTATCAGCCCTACCGCGTGGTGGTGCTGTCTTTTGAGCTGCTGCAC

GCACCTGCAACAGTGTGCGGACCAAAGAAGAGCACCAATCTGGTGAAGAACAA

GTGCGTGAACTTCAACTTCAACGGACTGACCGGAACAGGCGTGCTGACCGAGTC

CAACAAGAAGTTCCTGCCTTTTCAGCAGTTCGGCAGGGACATCGCAGATACCAC

AGACGCCGTGCGCGACCCTCAGACCCTGGAGATCCTGGACATCACACCATGCTC

CTTCGGCGGCGTGTCTGTGATCACACCAGGCACCAATACAAGCAACCAGGTGGC

CGTGCTGTATCAGGGCGTGAATTGTACCGAGGTGCCAGTGGCAATCCACGCAGA

TCAGCTGACCCCTACATGGCGGGTGTACTCTACCGGCAGCAACGTGTTCCAGAC

AAGAGCCGGATGCCTGATCGGAGCAGAGCACGTGAACAATAGCTATGAGTGCGA

CATCCCTATCGGCGCCGGCATCTGTGCCTCCTACCAGACCCAGACAAACTCCCCA

AGGTCTGTGGGCGATACAGGCCTGTCCAAGAATCCAATCGAGCTGGTAGAGGGC

TGGTTCAGCAGTTGGAAAAGCTCCATCGCCTCCTTTTTCTTTATCATCGGCCTGAT

CATCGGACTGTTCCTGGTGCTCCGCGTGGGTATCCACCTGTGCATCAAGCTGAAG

CACACCAAGAAAAGACAGATTTATACAGACATCGAGATGAACCGCCTGGGAAA

GTGAGCTAGCCAGATTCTTCATGTTTGGACCAAATCAACTTGTGATACCATGCTC
```

-continued

```
AAAGAGGCCTCAATTATATTTGAGTTTTTAATTTTTATGAAAAAAACTAACAGCA

ATCATGGAAGTCCACGATTTTGAGACCGACGAGTTCAATGATTTCAATGAAGAT

GACTATGCCACAAGAGAATTCCTGAATCCCGATGAGCGCATGACGTACTTGAAT

CATGCTGATTACAATTTGAATTCTCCTCTAATTAGTGATGATATTGACAATTTGAT

CAGGAAATTCAATTCTCTTCCGATTCCCTCGATGTGGGATAGTAAGAACTGGGAT

GGAGTTCTTGAGATGTTAACATCATGTCAAGCCAATCCCATCTCAACATCTCAGA

TGCATAAATGGATGGGAAGTTGGTTAATGTCTGATAATCATGATGCCAGTCAAG

GGTATAGTTTTTTACATGAAGTGGACAAAGAGGCAGAAATAACATTTGACGTGG

TGGAGACCTTCATCCGCGGCTGGGGCAACAAACCAATTGAATACATCAAAAAGG

AAAGATGGACTGACTCATTCAAAATTCTCGCTTATTTGTGTCAAAAGTTTTTGGA

CTTACACAAGTTGACATTAATCTTAAATGCTGTCTCTGAGGTGGAATTGCTCAAC

TTGGCGAGGACTTTCAAAGGCAAAGTCAGAAGAAGTTCTCATGGAACGAACATA

TGCAGGATTAGGGTTCCCAGCTTGGGTCCTACTTTTATTTCAGAAGGATGGGCTT

ACTTCAAGAAACTTGATATTCTAATGGACCGAAACTTTCTGTTAATGGTCAAAGA

TGTGATTATAGGGAGGATGCAAACGGTGCTATCCATGGTATGTAGAATAGACAA

CCTGTTCTCAGAGCAAGACATCTTCTCCCTTCTAAATATCTACAGAATTGGAGAT

AAAATTGTGGAGAGGCAGGGAAATTTTTCTTATGACTTGATTAAAATGGTGGAA

CCGATATGCAACTTGAAGCTGATGAAATTAGCAAGAGAATCAAGGCCTTTAGTC

CCACAATTCCCTCATTTTGAAAATCATATCAAGACTTCTGTTGATGAAGGGGCAA

AAATTGACCGAGGTATAAGATTCCTCCATGATCAGATAATGAGTGTGAAAACAG

TGGATCTCACACTGGTGATTTATGGATCGTTCAGACATTGGGGTCATCCTTTTAT

AGATTATTACACTGGACTAGAAAAATTACATTCCCAAGTAACCATGAAGAAAGA

TATTGATGTGTCATATGCAAAAGCACTTGCAAGTGATTTAGCTCGGATTGTTCTA

TTTCAACAGTTCAATGATCATAAAAAGTGGTTCGTGAATGGAGACTTGCTCCCTC

ATGATCATCCCTTTAAAAGTCATGTTAAAGAAAATACATGGCCCACAGCTGCTCA

AGTTCAAGATTTTGGAGATAAATGGCATGAACTTCCGCTGATTAAATGTTTTGAA

ATACCCGACTTACTAGACCCATCGATAATATACTCTGACAAAAGTCATTCAATGA

ATAGGTCAGAGGTGTTGAAACATGTCCGAATGAATCCGAACACTCCTATCCCTA

GTAAAAAGGTGTTGCAGACTATGTTGGACACAAAGGCTACCAATTGGAAAGAAT

TTCTTAAAGAGATTGATGAGAAGGGCTTAGATGATGATGATCTAATTATTGGTCT

TAAAGGAAAGGAGAGGGAACTGAAGTTGGCAGGTAGATTTTTCTCCCTAATGTC

TTGGAAATTGCGAGAATACTTTGTAATTACCGAATATTTGATAAAGACTCATTTC

GTCCCTATGTTAAAGGCCTGACAATGGCGGACGATCTAACTGCAGTCATTAAAA

AGATGTTAGATTCCTCATCCGGCCAAGGATTGAAGTCATATGAGGCAATTTGCAT

AGCCAATCACATTGATTACGAAAAATGGAATAACCACCAAAGGAAGTTATCAAA

CGGCCCAGTGTTCCGAGTTATGGGCCAGTTCTTAGGTTATCCATCCTTAATCGAG

AGAACTCATGAATTTTTTGAGAAAAGTCTTATATACTACAATGGAAGACCAGACT

TGATGCGTGTTCACAACAACACACTGATCAATTCAACCTCCCAACGAGTTTGTTG

GCAAGGACAAGAGGGTGGACTGGAAGGTCTACGGCAAAAAGGATGGACTATCC

TCAATCTACTGGTTATTCAAAGAGAGGCTAAAATCAGAAACACTGCTGTCAAAG
```

-continued

```
TCTTGGCACAAGGTGATAATCAAGTTATTTGCACACAGTATAAAACGAAGAAAT

CGAGAAACGTTGTAGAATTACAGGGTGCTCTCAATCAAATGGTTTCTAATAATGA

GAAAATTATGACTGCAATCAAAATAGGGACAGGGAAGTTAGGACTTTTGATAAA

TGACGATGAGACTATGCAATCTGCAGATTACTTGAATTATGGAAAAATACCGATT

TTCCGTGGAGTGATTAGAGGGTTAGAGACCAAGAGATGGTCACGAGTGACTTGT

GTCACCAATGACCAAATACCCACTTGTGCTAATATAATGAGCTCAGTTTCCACAA

ATGCTCTCACCGTAGCTCATTTTGCTGAGAACCCAATCAATGCCATGATACAGTA

CAATTATTTTGGGACATTTGCTAGACTCTTGTTGATGATGCATGATCCTGCTCTTC

GTCAATCATTGTATGAAGTTCAAGATAAGATACCGGGCTTGCACAGTTCTACTTT

CAAATACGCCATGTTGTATTTGGACCCTTCCATTGGAGGAGTGTCGGGCATGTCT

TTGTCCAGGTTTTTGATTAGAGCCTTCCCAGATCCCGTAACAGAAAGTCTCTCAT

TCTGGAGATTCATCCATGTACATGCTCGAAGTGAGCATCTGAAGGAGATGAGTG

CAGTATTTGGAAACCCCGAGATAGCCAAGTTTCGAATAACTCACATAGACAAGC

TAGTAGAAGATCCAACCTCTCTGAACATCGCTATGGGAATGAGTCCAGCGAACT

TGTTAAAGACTGAGGTTAAAAAATGCTTAATCGAATCAAGACAAACCATCAGGA

ACCAGGTGATTAAGGATGCAACCATATATTTGTATCATGAAGAGGATCGGCTCA

GAAGTTTCTTATGGTCAATAAATCCTCTGTTCCCTAGATTTTTAAGTGAATTCAAA

TCAGGCACTTTTTTGGGAGTCGCAGACGGGCTCATCAGTCTATTTCAAAATTCTC

GTACTATTCGGAACTCCTTTAAGAAAAAGTATCATAGGGAATTGGATGATTTGAT

TGTGAGGAGTGAGGTATCCTCTTTGACACATTTAGGGAAACTTCATTTGAGAAGG

GGATCATGTAAAATGTGGACATGTTCAGCTACTCATGCTGACACATTAAGATACA

AATCCTGGGGCCGTACAGTTATTGGGACAACTGTACCCCATCCATTAGAAATGTT

GGGTCCACAACATCGAAAAGAGACTCCTTGTGCACCATGTAACACATCAGGGTT

CAATTATGTTTCTGTGCATTGTCCAGACGGGATCCATGACGTCTTTAGTTCACGG

GGACCATTGCCTGCTTATCTAGGGTCTAAAACATCTGAATCTACATCTATTTTGC

AGCCTTGGGAAAGGGAAAGCAAAGTCCCACTGATTAAAAGAGCTACACGTCTTA

GAGATGCTATCTCTTGGTTTGTTGAACCCGACTCTAAACTAGCAATGACTATACT

TTCTAACATCCACTCTTTAACAGGCGAAGAATGGACCAAAAGGCAGCATGGGTT

CAAAAGAACAGGGTCTGCCCTTCATAGGTTTTCGACATCTCGGATGAGCCATGGT

GGGTTCGCATCTCAGAGCACTGCAGCATTGACCAGGTTGATGGCAACTACAGAC

ACCATGAGGGATCTGGGAGATCAGAATTTCGACTTTTTATTCCAAGCAACGTTGC

TCTATGCTCAAATTACCACCACTGTTGCAAGAGACGGATGGATCACCAGTTGTAC

AGATCATTATCATATTGCCTGTAAGTCCTGTTTGAGACCCATAGAAGAGATCACC

CTGGACTCAAGTATGGACTACACGCCCCCAGATGTATCCCATGTGCTGAAGACA

TGGAGGAATGGGGAAGGTTCGTGGGACAAGAGATAAAACAGATCTATCCTTTA

GAAGGGAATTGGAAGAATTTAGCACCTGCTGAGCAATCCTATCAAGTCGGCAGA

TGTATAGGTTTTCTATATGGAGACTTGGCGTATAGAAAATCTACTCATGCCGAGG

ACAGTTCTCTATTTCCTCTATCTATACAAGGTCGTATTAGAGGTCGAGGTTTCTTA

AAAGGGTTGCTAGACGGATTAATGAGAGCAAGTTGCTGCCAAGTAATACACCGG

AGAAGTCTGGCTCATTTGAAGAGGCCGGCCAACGCAGTGTACGGAGGTTTGATT

TACTTGATTGATAAATTGAGTGTATCACCTCCATTCCTTTCTCTTACTAGATCAGG
```

-continued

```
ACCTATTAGAGACGAATTAGAAACGATTCCCCACAAGATCCCAACCTCCTATCC

GACAAGCAACCGTGATATGGGGGTGATTGTCAGAAATTACTTCAAATACCAATG

CCGTCTAATTGAAAAGGGAAAATACAGATCACATTATTCACAATTATGGTTATTC

TCAGATGTCTTATCCATAGACTTCATTGGACCATTCTCTATTTCCACCACCCTCTT

GCAAATCCTATACAAGCCATTTTTATCTGGGAAAGATAAGAATGAGTTGAGAGA

GCTGGCAAATCTTTCTTCATTGCTAAGATCAGGAGAGGGGTGGGAAGACATACA

TGTGAAATTCTTCACCAAGGACATATTATTGTGTCCAGAGGAAATCAGACATGCT

TGCAAGTTCGGGATTGCTAAGGATAATAATAAAGACATGAGCTATCCCCCTTGG

GGAAGGGAATCCAGAGGGACAATTACAACAATCCCTGTTTATTATACGACCACC

CCTTACCCAAAGATGCTAGAGATGCCTCCAAGAATCCAAAATCCCCTGCTGTCCG

GAATCAGGTTGGGCCAATTACCAACTGGCGCTCATTATAAAATTCGGAGTATATT

ACATGGAATGGGAATCCATTACAGGGACTTCTTGAGTTGTGGAGACGGCTCCGG

AGGGATGACTGCTGCATTACTACGAGAAAATGTGCATAGCAGAGGAATATTCAA

TAGTCTGTTAGAATTATCAGGGTCAGTCATGCGAGGCGCCTCTCCTGAGCCCCCC

AGTGCCCTAGAAACTTTAGGAGGAGATAAATCGAGATGTGTAAATGGTGAAACA

TGTTGGGAATATCCATCTGACTTATGTGACCCAAGGACTTGGGACTATTTCCTCC

GACTCAAAGCAGGCTTGGGGCTTCAAATTGATTTAATTGTAATGGATATGGAAGT

TCGGGATTCTTCTACTAGCCTGAAAATTGAGACGAATGTTAGAAATTATGTGCAC

CGGATTTTGGATGAGCAAGGAGTTTTAATCTACAAGACTTATGGAACATATATTT

GTGAGAGCGAAAAGAATGCAGTAACAATCCTTGGTCCCATGTTCAAGACGGTCG

ACTTAGTTCAAACAGAATTTAGTAGTTCTCAAACGTCTGAAGTATATATGGTATG

TAAAGGTTTGAAGAAATTAATCGATGAACCCAATCCCGATTGGTCTTCCATCAAT

GAATCCTGGAAAAACCTGTACGCATTCCAGTCATCAGAACAGGAATTTGCCAGA

GCAAAGAAGGTTAGTACATACTTTACCTTGACAGGTATTCCCTCCCAATTCATTC

CTGATCCTTTTGTAAACATTGAGACTATGCTACAAATATTCGGAGTACCCACGGG

TGTGTCTCATGCGGCTGCCTTAAAATCATCTGATAGACCTGCAGATTTATTGACC

ATTAGCCTTTTTTATATGGCGATTATATCGTATTATAACATCAATCATATCAGAGT

AGGACCGATACCTCCGAACCCCCCATCAGATGGAATTGCACAAAATGTGGGGAT

CGCTATAACTGGTATAAGCTTTTGGCTGAGTTTGATGGAGAAAGACATTCCACTA

TATCAACAGTGTTTAGCAGTTATCCAGCAATCATTCCCGATTAGGTGGGAGGCTG

TTTCAGTAAAAGGAGGATACAAGCAGAAGTGGAGTACTAGAGGTGATGGGCTCC

CAAAAGATACCCGAACTTCAGACTCCTTGGCCCCAATCGGGAACTGGATCAGAT

CTCTGGAATTGGTCCGAAACCAAGTTCGTCTAAATCCATTCAATGAGATCTTGTT

CAATCAGCTATGTCGTACAGTGGATAATCATTTGAAATGGTCAAATTTGCGAAGA

AACACAGGAATGATTGAATGGATCAATAGACGAATTTCAAAAGAAGACCGGTCT

ATACTGATGTTGAAGAGTGACCTACACGAGGAAAACTCTTGGAGAGATTAAAAA

ATCATGAGGAGACTCCAAACTTTAAGTATGAAAAAAACTTTGATCCTTAAGACC

CTCTTGTGGTTTTTATTTTTTATCTGGTTTTGTGGTCTTCGT.
```

In some embodiments, the nucleic acid comprises the sequence of SEQ ID NO: 20, shown below (VSV vector: Convac V2 China):

ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC

CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAATGATCAATGAACAGTTTGAACCTCTTGTGCCAGAAGGT

CGTGACATTTTTGATGTGTGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

ATATTCTTCCGTCAAAAACCCTGCCTTCCACTTCTGGGGGCAATTGACAGCTCTT

CTGCTCAGATCCACCAGAGCAAGGAATGCCCGACAGCCTGATGACATTGAGTAT

ACATCTCTTACTACAGCAGGTTTGTTGTACGCTTATGCAGTAGGATCCTCTGCCG

ACTTGGCACAACAGTTTTGTGTTGGAGATAACAAATACACTCCAGATGATAGTAC

CGGAGGATTGACGACTAATGCACCGCCACAAGGCAGAGATGTGGTCGAATGGCT

CGGATGGTTTGAAGATCAAAACAGAAAACCGACTCCTGATATGATGCAGTATGC

GAAAAGAGCAGTCATGTCACTGCAAGGCCTAAGAGAGAAGACAATTGGCAAGT

ATGCTAAGTCAGAATTTGACAAATGACCCTATAATTCTCAGATCACCTATTATAT

ATTATGCTACATATGAAAAAAACTAACAGATATCATGGATAATCTCACAAAAGT

TCGTGAGTATCTCAAGTCCTATTCTCGTCTGGATCAGGCGGTAGGAGAGATAGAT

GAGATCGAAGCACAACGAGCTGAAAAGTCCAATTATGAGTTGTTCCAAGAGGAT

GGAGTGGAAGAGCATACTAAGCCCTCTTATTTTCAGGCAGCAGATGATTCTGAC

ACAGAATCTGAACCAGAAATTGAAGACAATCAAGGTTTGTATGCACCAGATCCA

GAAGCTGAGCAAGTTGAAGGCTTTATACAGGGGCCTTTAGATGACTATGCAGAT

GAGGAAGTGGATGTTGTATTTACTTCGGACTGGAAACAGCCTGAGCTTGAATCTG

ACGAGCATGGAAAGACCTTACGGTTGACATCGCCAGAGGGTTTAAGTGGAGAGC

AGAAATCCCAGTGGCTTTCGACGATTAAAGCAGTCGTGCAAAGTGCCAAATACT

GGAATCTGGCAGAGTGCACATTTGAAGCATCGGGAGAAGGGGTCATTATGAAGG

AGCGCCAGATAACTCCGGATGTATATAAGGTCACTCCAGTGATGAACACACATC

CGTCCCAATCAGAAGCAGTATCAGATGTTTGGTCTCTCTCAAAGACATCCATGAC

TTTCCAACCCAAGAAAGCAAGTCTTCAGCCTCTCACCATATCCTTGGATGAATTG

-continued
```
TTCTCATCTAGAGGAGAGTTCATCTCTGTCGGAGGTGACGGACGAATGTCTCATA

AAGAGGCCATCCTGCTCGGCCTGAGATACAAAAAGTTGTACAATCAGGCGAGAG

TCAAATATTCTCTGTAGACTATGAAAAAAAGTAACAGATATCACGATCTAAGTGT

TATCCCAATCCATTCATCATGAGTTCCTTAAAGAAGATTCTCGGTCTGAAGGGGA

AAGGTAAGAAATCTAAGAAATTAGGGATCGCACCACCCCCTTATGAAGAGGACA

CTAGCATGGAGTATGCTCCGAGCGCTCCAATTGACAAATCCTATTTTGGAGTTGA

CGAGATGGACACCTATGATCCGAATCAATTAAGATATGAGAAATTCTTCTTTACA

GTGAAAATGACGGTTAGATCTAATCGTCCGTTCAGAACATACTCAGATGTGGCA

GCCGCTGTATCCCATTGGGATCACATGTACATCGGAATGGCAGGGAAACGTCCC

TTCTACAAAATCTTGGCTTTTTTGGGTTCTTCTAATCTAAAGGCCACTCCAGCGGT

ATTGGCAGATCAAGGTCAACCAGAGTATCACACTCACTGCGAAGGCAGGGCTTA

TTTGCCACATAGGATGGGAAGACCCCTCCCATGCTCAATGTACCAGAGCACTTC

AGAAGACCATTCAATATAGGTCTTTACAAGGGAACGATTGAGCTCACAATGACC

ATCTACGATGATGAGTCACTGGAAGCAGCTCCTATGATCTGGGATCATTTCAATT

CTTCCAAATTTTCTGATTTCAGAGAGAAGGCCTTAATGTTTGGCCTGATTGTCGA

GAAAAAGGCATCTGGAGCGTGGGTCCTGGATTCTATCAGCCACTTCAAATGAGC

TAGTCTAACTTCTAGCTTCTGAACAATCCCCGGTTTACTCAGTCTCTCCTAATTCC

AGCCTCTCGAACAACTAATATCCTGTCTTTTCTATCCCTATGAAAAAAACTAACA

GAGATCGATCTGTTTACGCGTCACTATGAAGTGCCTTTTGTACTTAGCCTTTTTAT

TCATTGGGGTGAATTGCAAGTTCACCATAGTTTTTCCACACAACCAAAAAGGAA

ACTGGAAAAATGTTCCTTCTAATTACCATTATTGCCCGTCAAGCTCAGATTTAAA

TTGGCATAATGACTTAATAGGCACAGCCATACAAGTCAAAATGCCCAAGAGTCA

CAAGGCTATTCAAGCAGACGGTTGGATGTGTCATGCTTCCAAATGGGTCACTACT

TGTGATTTCCGCTGGTATGGACCGAAGTATATAACACAGTCCATCCGATCCTTCA

CTCCATCTGTAGAACAATGCAAGGAAAGCATTGAACAAACGAAACAAGGAACTT

GGCTGAATCCAGGCTTCCCTCCTCAAAGTTGTGGATATGCAACTGTGACGGATGC

CGAAGCAGTGATTGTCCAGGTGACTCCTCACCATGTGCTGGTTGATGAATACACA

GGAGAATGGGTTGATTCACAGTTCATCAACGGAAAATGCAGCAATTACATATGC

CCCACTGTCCATAACTCTACAACCTGGCATTCTGACTATAAGGTCAAAGGGCTAT

GTGATTCTAACCTCATTTCCATGGACATCACCTTCTTCTCAGAGGACGGAGAGCT

ATCATCCCTGGGAAAGGAGGGCACAGGGTTCAGAAGTAACTACTTTGCTTATGA

AACTGGAGGCAAGGCCTGCAAAATGCAATACTGCAAGCATTGGGGAGTCAGACT

CCCATCAGGTGTCTGGTTCGAGATGGCTGATAAGGATCTCTTTGCTGCAGCCAGA

TTCCCTGAATGCCCAGAAGGGTCAAGTATCTCTGCTCCATCTCAGACCTCAGTGG

ATGTAAGTCTAATTCAGGACGTTGAGAGGATCTTGGATTATTCCCTCTGCCAAGA

AACCTGGAGCAAAATCAGAGCGGGTCTTCCAATCTCTCCAGTGGATCTCAGCTAT

CTTGCTCCTAAAAACCCAGGAACCGGTCCTGCTTTCACCATAATCAATGGTACCC

TAAAATACTTTGAGACCAGATACATCAGAGTCGATATTGCTGCTCCAATCCTCTC

AAGAATGGTCGGAATGATCAGTGGAACTACCACAGAAAGGGAACTGTGGGATG

ACTGGGCACCATATGAAGACGTGGAAATTGGACCCAATGGAGTTCTGAGGACCA

GTTCAGGATATAAGTTTCCTTTATACATGATTGGACATGGTATGTTGGACTCCGA
```

-continued

```
TCTTCATCTTAGCTCAAAGGCTCAGGTGTTCGAACATCCTCACATTCAAGACGCT
GCTTCGCAACTTCCTGATGATGAGAGTTTATTTTTTGGTGATACTGGGCTATCCA
AAAATCCAATCGAGCTTGTAGAAGGTTGGTTCAGTAGTTGGAAAAGCTCTATTGC
CTCTTTTTTCTTTATCATAGGGTTAATCATTGGACTATTCTTGGTTCTCCGAGTTG
GTATCCATCTTTGCATTAAATTAAAGCACACCAAGAAAAGACAGATTTATACAG
ACATAGAGATGAACCGACTTGGAAAGTAACTCAAATCCTGCTAGGTATGAAAAA
AACTAACaGATATCACGCTCGAGCGTACGCCACCATGTTCGTGTTTCTGGTGCTG
CTGCCTCTGGTGAGCTCCCAGTGCGTGAACCTGACCACAAGGACCCAGCTGCCC
CCTGCCTATACCAATTCCTTCACACGGGGCGTGTACTATCCCGACAAGGTGTTCC
GGAGCAGCGTGCTGCACTCCACACAGGATCTGTTTCTGCCTTTCTTTTCTAACGT
GACCTGGTTCCACGCCATCCACGTGAGCGGCACCAATGGCACAAAGCGGTTCGA
CAATCCAGTGCTGCCCTTTAACGATGGCGTGTACTTCGCCTCCACCGAGAAGTCT
AACATCATCAGAGGCTGGATCTTTGGCACCACACTGGACAGCAAGACACAGTCC
CTGCTGATCGTGAACAATGCCACCAACGTGGTCATCAAGGTGTGCGAGTTCCAGT
TTTGTAATGATCCATTCCTGGGCGTGTACTATCACAAGAACAATAAGTCTTGGAT
GGAGAGCGAGTTTCGCGTGTATTCCTCTGCCAACAATTGCACATTTGAGTACGTG
TCCCAGCCCTTCCTGATGGACCTGGAGGGCAAGCAGGGCAATTTCAAGAACCTG
AGGGAGTTCGTGTTTAAGAATATCGATGGCTACTTCAAAATCTACTCCAAGCACA
CCCCAATCAACCTGGTGCGCGACCTGCCACAGGGCTTCTCTGCCCTGGAGCCACT
GGTGGATCTGCCCATCGGCATCAACATCACCCGGTTTCAGACACTGCTGGCCCTG
CACAGAAGCTACCTGACACCAGGCGACAGCTCCTCTGGATGGACCGCAGGAGCA
GCAGCCTACTATGTGGGCTATCTGCAGCCCAGGACCTTCCTGCTGAAGTACAACG
AGAATGGCACCATCACAGACGCCGTGGATTGCGCCCTGGATCCCCTGTCTGAGA
CCAAGTGTACACTGAAGAGCTTTACCGTGGAGAAGGGCATCTATCAGACAAGCA
ATTTCAGGGTGCAGCCTACCGAGTCCATCGTGCGCTTTCCCAATATCACAAACCT
GTGCCCTTTTGGCGAGGTGTTCAACGCAACCCGCTTCGCCAGCGTGTACGCCTGG
AATAGGAAGCGCATCTCCAACTGCGTGGCCGACTATTCTGTGCTGTACAACAGC
GCCTCCTTCTCTACCTTTAAGTGCTATGGCGTGAGCCCCACAAAGCTGAATGACC
TGTGCTTTACCAACGTGTACGCCGATTCCTTCGTGATCAGGGGCGACGAGGTGCG
CCAGATCGCACCAGGACAGACAGGCAAGATCGCAGACTACAATTATAAGCTGCC
TGACGATTTCACCGGCTGCGTGATCGCCTGGAACTCTAACAATCTGGATAGCAAA
GTGGGCGGCAACTACAATTATCTGTACCGGCTGTTTAGAAAGTCTAATCTGAAGC
CATTCGAGAGGGACATCTCCACAGAAATCTACCAGGCCGGCTCTACCCCCTGCA
ATGGCGTGGAGGGCTTTAACTGTTATTTCCCTCTGCAGAGCTACGGCTTCCAGCC
AACAAACGGCGTGGGCTATCAGCCCTACCGCGTGGTGGTGCTGTCTTTTGAGCTG
CTGCACGCACCTGCAACAGTGTGCGGACCAAAGAAGAGCACCAATCTGGTGAAG
AACAAGTGCGTGAACTTCAACTTCAACGGACTGACCGGAACAGGCGTGCTGACC
GAGTCCAACAAGAAGTTCCTGCCTTTTCAGCAGTTCGGCAGGGACATCGCAGAT
ACCACAGACGCCGTGCGCGACCCTCAGACCCTGGAGATCCTGGACATCACACCA
TGCTCCTTCGGCGGCGTGTCTGTGATCACACCAGGCACCAATACAAGCAACCAG
```

-continued
```
GTGGCCGTGCTGTATCAGGACGTGAATTGTACCGAGGTGCCAGTGGCAATCCAC
GCAGATCAGCTGACCCCTACATGGCGGGTGTACTCTACCGGCAGCAACGTGTTC
CAGACAAGAGCCGGATGCCTGATCGGAGCAGAGCACGTGAACAATAGCTATGA
GTGCGACATCCCTATCGGCGCCGGCATCTGTGCCTCCTACCAGACCCAGACAAA
CTCCCCAAGGTCTGTGGGAGATGAGGCCGAAGACTTTGTGGAAGTCCACCTGCC
TGATGTGCATAACCAGGTGTCTGGCGTCGACCTGGGACTGCCAAATTGGGGCAA
GTACGTGCTGCTGAGTGCTGGAGCACTGACTGCCCTGATGCTGATCATTTTCCTG
ATGACCTGCTGTCGGCGCGTGAACAGAAGTGAGCCCACTCAGCACAATCTGCGA
GGAACCGGGAGAGAAGTGTCAGTCACACCTCAGAGCGGGAAAATCATTAGTAGT
TGGGAATCACATAAAAGCGGGGGCGAGACCAGGCTGTGAGCTAGCCAGATTCTT
CATGTTTGGACCAAATCAACTTGTGATACCATGCTCAAAGAGGCCTCAATTATAT
TTGAGTTTTTAATTTTTATGAAAAAAACTAACAGCAATCATGGAAGTCCACGATT
TTGAGACCGACGAGTTCAATGATTTCAATGAAGATGACTATGCCACAAGAGAAT
TCCTGAATCCCGATGAGCGCATGACGTACTTGAATCATGCTGATTACAATTTGAA
TTCTCCTCTAATTAGTGATGATATTGACAATTTGATCAGGAAATTCAATTCTCTTC
CGATTCCCTCGATGTGGGATAGTAAGAACTGGGATGGAGTTCTTGAGATGTTAAC
ATCATGTCAAGCCAATCCCATCTCAACATCTCAGATGCATAAATGGATGGGAAG
TTGGTTAATGTCTGATAATCATGATGCCAGTCAAGGGTATAGTTTTTTACATGAA
GTGGACAAAGAGGCAGAAATAACATTTGACGTGGTGGAGACCTTCATCCGCGGC
TGGGGCAACAAACCAATTGAATACATCAAAAAGGAAAGATGGACTGACTCATTC
AAAATTCTCGCTTATTTGTGTCAAAAGTTTTTGGACTTACACAAGTTGACATTAA
TCTTAAATGCTGTCTCTGAGGTGGAATTGCTCAACTTGGCGAGGACTTTCAAAGG
CAAAGTCAGAAGAAGTTCTCATGGAACGAACATATGCAGGATTAGGGTTCCCAG
CTTGGGTCCTACTTTTATTTCAGAAGGATGGGCTTACTTCAAGAAACTTGATATT
CTAATGGACCGAAACTTTCTGTTAATGGTCAAAGATGTGATTATAGGGAGGATG
CAAACGGTGCTATCCATGGTATGTAGAATAGACAACCTGTTCTCAGAGCAAGAC
ATCTTCTCCCTTCTAAATATCTACAGAATTGGAGATAAAATTGTGGAGAGGCAGG
GAAATTTTTCTTATGACTTGATTAAAATGGTGGAACCGATATGCAACTTGAAGCT
GATGAAATTAGCAAGAGAATCAAGGCCTTTAGTCCCACAATTCCCTCATTTTGAA
AATCATATCAAGACTTCTGTTGATGAAGGGGCAAAAATTGACCGAGGTATAAGA
TTCCTCCATGATCAGATAATGAGTGTGAAAACAGTGGATCTCACACTGGTGATTT
ATGGATCGTTCAGACATTGGGGTCATCCTTTTATAGATTATTACACTGGACTAGA
AAAATTACATTCCCAAGTAACCATGAAGAAAGATATTGATGTGTCATATGCAAA
AGCACTTGCAAGTGATTTAGCTCGGATTGTTCTATTTCAACAGTTCAATGATCAT
AAAAAGTGGTTCGTGAATGGAGACTTGCTCCCTCATGATCATCCCTTTAAAAGTC
ATGTTAAAGAAAATACATGGCCCACAGCTGCTCAAGTTCAAGATTTTGGAGATA
AATGGCATGAACTTCCGCTGATTAAATGTTTTGAAATACCCGACTTACTAGACCC
ATCGATAATATACTCTGACAAAAGTCATTCAATGAATAGGTCAGAGGTGTTGAA
ACATGTCCGAATGAATCCGAACACTCCTATCCCTAGTAAAAAGGTGTTGCAGACT
ATGTTGGACACAAAGGCTACCAATTGGAAAGAATTTCTTAAAGAGATTGATGAG
AAGGGCTTAGATGATGATGATCTAATTATTGGTCTTAAAGGAAAGGAGAGGGAA
```

```
CTGAAGTTGGCAGGTAGATTTTTCTCCCTAATGTCTTGGAAATTGCGAGAATACT

TTGTAATTACCGAATATTTGATAAAGACTCATTTCGTCCCTATGTTTAAAGGCCT

GACAATGGCGGACGATCTAACTGCAGTCATTAAAAAGATGTTAGATTCCTCATCC

GGCCAAGGATTGAAGTCATATGAGGCAATTTGCATAGCCAATCACATTGATTAC

GAAAAATGGAATAACCACCAAAGGAAGTTATCAAACGGCCCAGTGTTCCGAGTT

ATGGGCCAGTTCTTAGGTTATCCATCCTTAATCGAGAGAACTCATGAATTTTTG

AGAAAAGTCTTATATACTACAATGGAAGACCAGACTTGATGCGTGTTCACAACA

ACACACTGATCAATTCAACCTCCCAACGAGTTTGTTGGCAAGGACAAGAGGGTG

GACTGGAAGGTCTACGGCAAAAAGGATGGACTATCCTCAATCTACTGGTTATTC

AAAGAGAGGCTAAAATCAGAAACACTGCTGTCAAAGTCTTGGCACAAGGTGATA

ATCAAGTTATTTGCACACAGTATAAAACGAAGAAATCGAGAAACGTTGTAGAAT

TACAGGGTGCTCTCAATCAAATGGTTTCTAATAATGAGAAAATTATGACTGCAAT

CAAAATAGGGACAGGGAAGTTAGGACTTTTGATAAATGACGATGAGACTATGCA

ATCTGCAGATTACTTGAATTATGGAAAAATACCGATTTTCCGTGGAGTGATTAGA

GGGTTAGAGACCAAGAGATGGTCACGAGTGACTTGTGTCACCAATGACCAAATA

CCCACTTGTGCTAATATAATGAGCTCAGTTTCCACAAATGCTCTCACCGTAGCTC

ATTTTGCTGAGAACCCAATCAATGCCATGATACAGTACAATTATTTTGGGACATT

TGCTAGACTCTTGTTGATGATGCATGATCCTGCTCTTCGTCAATCATTGTATGAAG

TTCAAGATAAGATACCGGGCTTGCACAGTTCTACTTTCAAATACGCCATGTTGTA

TTTGGACCCTTCCATTGGAGGAGTGTCGGGCATGTCTTTGTCCAGGTTTTTGATTA

GAGCCTTCCCAGATCCCGTAACAGAAAGTCTCTCATTCTGGAGATTCATCCATGT

ACATGCTCGAAGTGAGCATCTGAAGGAGATGAGTGCAGTATTTGGAAACCCCGA

GATAGCCAAGTTTCGAATAACTCACATAGACAAGCTAGTAGAAGATCCAACCTC

TCTGAACATCGCTATGGGAATGAGTCCAGCGAACTTGTTAAAGACTGAGGTTAA

AAAATGCTTAATCGAATCAAGACAAACCATCAGGAACCAGGTGATTAAGGATGC

AACCATATATTTGTATCATGAAGAGGATCGGCTCAGAAGTTTCTTATGGTCAATA

AATCCTCTGTTCCCTAGATTTTTAAGTGAATTCAAATCAGGCACTTTTTTGGGAGT

CGCAGACGGGCTCATCAGTCTATTTCAAAATTCTCGTACTATTCGGAACTCCTTT

AAGAAAAAGTATCATAGGGAATTGGATGATTTGATTGTGAGGAGTGAGGTATCC

TCTTTGACACATTTAGGGAAACTTCATTTGAGAAGGGGATCATGTAAAATGTGGA

CATGTTCAGCTACTCATGCTGACACATTAAGATACAAATCCTGGGGCCGTACAGT

TATTGGGACAACTGTACCCCATCCATTAGAAATGTTGGGTCCACAACATCGAAA

AGAGACTCCTTGTGCACCATGTAACACATCAGGGTTCAATTATGTTTCTGTGCAT

TGTCCAGACGGGATCCATGACGTCTTTAGTTCACGGGACCATTGCCTGCTTATC

TAGGGTCTAAAACATCTGAATCTACATCTATTTTGCAGCCTTGGGAAAGGGAAA

GCAAAGTCCCACTGATTAAAAGAGCTACACGTCTTAGAGATGCTATCTCTTGGTT

TGTTGAACCCGACTCTAAACTAGCAATGACTATACTTTCTAACATCCACTCTTTA

ACAGGCGAAGAATGGACCAAAAGGCAGCATGGGTTCAAAAGAACAGGGTCTGC

CCTTCATAGGTTTTCGACATCTCGGATGAGCCATGGTGGGTTCGCATCTCAGAGC

ACTGCAGCATTGACCAGGTTGATGGCAACTACAGACACCATGAGGGATCTGGGA
```

-continued
GATCAGAATTTCGACTTTTTATTCCAAGCAACGTTGCTCTATGCTCAAATTACCA

CCACTGTTGCAAGAGACGGATGGATCACCAGTTGTACAGATCATTATCATATTGC

CTGTAAGTCCTGTTTGAGACCCATAGAAGAGATCACCCTGGACTCAAGTATGGA

CTACACGCCCCCAGATGTATCCCATGTGCTGAAGACATGGAGGAATGGGGAAGG

TTCGTGGGACAAGAGATAAAACAGATCTATCCTTTAGAAGGGAATTGGAAGAA

TTTAGCACCTGCTGAGCAATCCTATCAAGTCGGCAGATGTATAGGTTTTCTATAT

GGAGACTTGGCGTATAGAAAATCTACTCATGCCGAGGACAGTTCTCTATTTCCTC

TATCTATACAAGGTCGTATTAGAGGTCGAGGTTTCTTAAAAGGGTTGCTAGACGG

ATTAATGAGAGCAAGTTGCTGCCAAGTAATACACCGGAGAAGTCTGGCTCATTT

GAAGAGGCCGGCCAACGCAGTGTACGGAGGTTTGATTTACTTGATTGATAAATT

GAGTGTATCACCTCCATTCCTTTCTCTTACTAGATCAGGACCTATTAGAGACGAA

TTAGAAACGATTCCCCACAAGATCCCAACCTCCTATCCGACAAGCAACCGTGAT

ATGGGGTGATTGTCAGAAATTACTTCAAATACCAATGCCGTCTAATTGAAAAG

GGAAAATACAGATCACATTATTCACAATTATGGTTATTCTCAGATGTCTTATCCA

TAGACTTCATTGGACCATTCTCTATTTCCACCACCCTCTTGCAAATCCTATACAAG

CCATTTTTATCTGGGAAAGATAAGAATGAGTTGAGAGAGCTGGCAAATCTTTCTT

CATTGCTAAGATCAGGAGAGGGGTGGGAAGACATACATGTGAAATTCTTCACCA

AGGACATATTATTGTGTCCAGAGGAAATCAGACATGCTTGCAAGTTCGGGATTG

CTAAGGATAATAATAAAGACATGAGCTATCCCCCTTGGGGAAGGGAATCCAGAG

GGACAATTACAACAATCCCTGTTTATTATACGACCACCCCTTACCCAAAGATGCT

AGAGATGCCTCCAAGAATCCAAATCCCCTGCTGTCCGGAATCAGGTTGGGCCA

ATTACCAACTGGCGCTCATTATAAAATTCGGAGTATATTACATGGAATGGGAATC

CATTACAGGGACTTCTTGAGTTGTGGAGACGGCTCCGGAGGGATGACTGCTGCA

TTACTACGAGAAAATGTGCATAGCAGAGGAATATTCAATAGTCTGTTAGAATTAT

CAGGGTCAGTCATGCGAGGCGCCTCTCCTGAGCCCCCCAGTGCCCTAGAAACTTT

AGGAGGAGATAAATCGAGATGTGTAAATGGTGAAACATGTTGGGAATATCCATC

TGACTTATGTGACCCAAGGACTTGGGACTATTTCCTCCGACTCAAAGCAGGCTTG

GGGCTTCAAATTGATTTAATTGTAATGGATATGGAAGTTCGGGATTCTTCTACTA

GCCTGAAAATTGAGACGAATGTTAGAAATTATGTGCACCGGATTTTGGATGAGC

AAGGAGTTTTAATCTACAAGACTTATGGAACATATATTTGTGAGAGCGAAAAGA

ATGCAGTAACAATCCTTGGTCCCATGTTCAAGACGGTCGACTTAGTTCAAACAGA

ATTTAGTAGTTCTCAAACGTCTGAAGTATATATGGTATGTAAAGGTTTGAAGAAA

TTAATCGATGAACCCAATCCCGATTGGTCTTCCATCAATGAATCCTGGAAAAACC

TGTACGCATTCCAGTCATCAGAACAGGAATTTGCCAGAGCAAAGAAGGTTAGTA

CATACTTTACCTTGACAGGTATTCCCTCCCAATTCATTCCTGATCCTTTTGTAAAC

ATTGAGACTATGCTACAAATATTCGGAGTACCCACGGGTGTGTCTCATGCGGCTG

CCTTAAAATCATCTGATAGACCTGCAGATTTATTGACCATTAGCCTTTTTTATATG

GCGATTATATCGTATTATAACATCAATCATATCAGAGTAGGACCGATACCTCCGA

ACCCCCCATCAGATGGAATTGCACAAAATGTGGGGATCGCTATAACTGGTATAA

GCTTTTGGCTGAGTTTGATGGAGAAAGACATTCCACTATATCAACAGTGTTTAGC

AGTTATCCAGCAATCATTCCCGATTAGGTGGGAGGCTGTTTCAGTAAAAGGAGG

-continued

ATACAAGCAGAAGTGGAGTACTAGAGGTGATGGGCTCCCAAAAGATACCCGAAC

TTCAGACTCCTTGGCCCCAATCGGGAACTGGATCAGATCTCTGGAATTGGTCCGA

AACCAAGTTCGTCTAAATCCATTCAATGAGATCTTGTTCAATCAGCTATGTCGTA

CAGTGGATAATCATTTGAAATGGTCAAATTTGCGAAGAAACACAGGAATGATTG

AATGGATCAATAGACGAATTTCAAAAGAAGACCGGTCTATACTGATGTTGAAGA

GTGACCTACACGAGGAAAACTCTTGGAGAGATTAAAAAATCATGAGGAGACTCC

AAACTTTAAGTATGAAAAAAACTTTGATCCTTAAGACCCTCTTGTGGTTTTTATTT

TTTATCTGGTTTTGTGGTCTTCGT.

In other embodiments, the nucleic acid comprises the sequence of SEQ ID NO: 21, shown below (VSV vector: Convac V2 South Africa):

ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC

CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAATGATCAATGAACAGTTTGAACCTCTTGTGCCAGAAGGT

CGTGACATTTTTGATGTGTGGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

ATATTCTTCCGTCAAAAACCCTGCCTTCCACTTCTGGGGGCAATTGACAGCTCTT

CTGCTCAGATCCACCAGAGCAAGGAATGCCCGACAGCCTGATGACATTGAGTAT

ACATCTCTTACTACAGCAGGTTTGTTGTACGCTTATGCAGTAGGATCCTCTGCCG

ACTTGGCACAACAGTTTTGTGTTGGAGATAACAAATACACTCCAGATGATAGTAC

CGGAGGATTGACGACTAATGCACCGCCACAAGGCAGAGATGTGGTCGAATGGCT

CGGATGGTTTGAAGATCAAAACAGAAAACCGACTCCTGATATGATGCAGTATGC

GAAAAGAGCAGTCATGTCACTGCAAGGCCTAAGAGAGAAGACAATTGGCAAGT

ATGCTAAGTCAGAATTTGACAAATGACCCTATAATTCTCAGATCACCTATTATAT

ATTATGCTACATATGAAAAAAACTAACAGATATCATGGATAATCTCACAAAAGT

TCGTGAGTATCTCAAGTCCTATTCTCGTCTGGATCAGGCGGTAGGAGAGATAGAT

GAGATCGAAGCACAACGAGCTGAAAAGTCCAATTATGAGTTGTTCCAAGAGGAT

GGAGTGGAAGAGCATACTAAGCCCTCTTATTTTCAGGCAGCAGATGATTCTGAC

-continued

```
ACAGAATCTGAACCAGAAATTGAAGACAATCAAGGTTTGTATGCACCAGATCCA

GAAGCTGAGCAAGTTGAAGGCTTTATACAGGGGCCTTTAGATGACTATGCAGAT

GAGGAAGTGGATGTTGTATTTACTTCGGACTGGAAACAGCCTGAGCTTGAATCTG

ACGAGCATGGAAAGACCTTACGGTTGACATCGCCAGAGGGTTTAAGTGGAGAGC

AGAAATCCCAGTGGCTTTCGACGATTAAAGCAGTCGTGCAAAGTGCCAAATACT

GGAATCTGGCAGAGTGCACATTTGAAGCATCGGGAGAAGGGGTCATTATGAAGG

AGCGCCAGATAACTCCGGATGTATATAAGGTCACTCCAGTGATGAACACACATC

CGTCCCAATCAGAAGCAGTATCAGATGTTTGGTCTCTCTCAAAGACATCCATGAC

TTTCCAACCCAAGAAAGCAAGTCTTCAGCCTCTCACCATATCCTTGGATGAATTG

TTCTCATCTAGAGGAGAGTTCATCTCTGTCGGAGGTGACGGACGAATGTCTCATA

AAGAGGCCATCCTGCTCGGCCTGAGATACAAAAAGTTGTACAATCAGGCGAGAG

TCAAATATTCTCTGTAGACTATGAAAAAAAGTAACAGATATCACGATCTAAGTGT

TATCCCAATCCATTCATCATGAGTTCCTTAAAGAAGATTCTCGGTCTGAAGGGGA

AAGGTAAGAAATCTAAGAAATTAGGGATCGCACCACCCCCTTATGAAGAGGACA

CTAGCATGGAGTATGCTCCGAGCGCTCCAATTGACAAATCCTATTTTGGAGTTGA

CGAGATGGACACCTATGATCCGAATCAATTAAGATATGAGAAATTCTTCTTTACA

GTGAAAATGACGGTTAGATCTAATCGTCCGTTCAGAACATACTCAGATGTGGCA

GCCGCTGTATCCCATTGGGATCACATGTACATCGGAATGGCAGGGAAACGTCCC

TTCTACAAAATCTTGGCTTTTTTGGGTTCTTCTAATCTAAAGGCCACTCCAGCGGT

ATTGGCAGATCAAGGTCAACCAGAGTATCACACTCACTGCGAAGGCAGGGCTTA

TTTGCCACATAGGATGGGGAAGACCCCTCCCATGCTCAATGTACCAGAGCACTTC

AGAAGACCATTCAATATAGGTCTTTACAAGGGAACGATTGAGCTCACAATGACC

ATCTACGATGATGAGTCACTGGAAGCAGCTCCTATGATCTGGGATCATTTCAATT

CTTCCAAATTTTCTGATTTCAGAGAGAAGGCCTTAATGTTTGGCCTGATTGTCGA

GAAAAAGGCATCTGGAGCGTGGGTCCTGGATTCTATCAGCCACTTCAAATGAGC

TAGTCTAACTTCTAGCTTCTGAACAATCCCCGGTTTACTCAGTCTCTCCTAATTCC

AGCCTCTCGAACAACTAATATCCTGTCTTTTCTATCCCTATGAAAAAAACTAACA

GAGATCGATCTGTTTACGCGTCACTATGAAGTGCCTTTTGTACTTAGCCTTTTTAT

TCATTGGGGTGAATTGCAAGTTCACCATAGTTTTTCCACACAACCAAAAGGAA

ACTGGAAAAATGTTCCTTCTAATTACCATTATTGCCCGTCAAGCTCAGATTTAAA

TTGGCATAATGACTTAATAGGCACAGCCATACAAGTCAAAATGCCCAAGAGTCA

CAAGGCTATTCAAGCAGACGGTTGGATGTGTCATGCTTCCAAATGGGTCACTACT

TGTGATTTCCGCTGGTATGGACCGAAGTATATAACACAGTCCATCCGATCCTTCA

CTCCATCTGTAGAACAATGCAAGGAAAGCATTGAACAAACGAAACAAGGAACTT

GGCTGAATCCAGGCTTCCCTCCTCAAAGTTGTGGATATGCAACTGTGACGGATGC

CGAAGCAGTGATTGTCCAGGTGACTCCTCACCATGTGCTGGTTGATGAATACACA

GGAGAATGGGTTGATTCACAGTTCATCAACGGAAAATGCAGCAATTACATATGC

CCCACTGTCCATAACTCTACAACCTGGCATTCTGACTATAAGGTCAAAGGGCTAT

GTGATTCTAACCTCATTTCCATGGACATCACCTTCTTCTCAGAGGACGGAGAGCT

ATCATCCCTGGGAAAGGAGGGCACAGGGTTCAGAAGTAACTACTTTGCTTATGA
```

-continued

```
AACTGGAGGCAAGGCCTGCAAAATGCAATACTGCAAGCATTGGGGAGTCAGACT
CCCATCAGGTGTCTGGTTCGAGATGGCTGATAAGGATCTCTTTGCTGCAGCCAGA
TTCCCTGAATGCCCAGAAGGGTCAAGTATCTCTGCTCCATCTCAGACCTCAGTGG
ATGTAAGTCTAATTCAGGACGTTGAGAGGATCTTGGATTATTCCCTCTGCCAAGA
AACCTGGAGCAAAATCAGAGCGGGTCTTCCAATCTCTCCAGTGGATCTCAGCTAT
CTTGCTCCTAAAAACCCAGGAACCGGTCCTGCTTTCACCATAATCAATGGTACCC
TAAAATACTTTGAGACCAGATACATCAGAGTCGATATTGCTGCTCCAATCCTCTC
AAGAATGGTCGGAATGATCAGTGGAACTACCACAGAAAGGGAACTGTGGGATG
ACTGGGCACCATATGAAGACGTGGAAATTGGACCCAATGGAGTTCTGAGGACCA
GTTCAGGATATAAGTTTCCTTTATACATGATTGGACATGGTATGTTGGACTCCGA
TCTTCATCTTAGCTCAAAGGCTCAGGTGTTCGAACATCCTCACATTCAAGACGCT
GCTTCGCAACTTCCTGATGATGAGAGTTTATTTTTTGGTGATACTGGGCTATCCA
AAAATCCAATCGAGCTTGTAGAAGGTTGGTTCAGTAGTTGGAAAAGCTCTATTGC
CTCTTTTTCTTTATCATAGGGTTAATCATTGGACTATTCTTGGTTCTCCGAGTTG
GTATCCATCTTTGCATTAAATTAAAGCACACCAAGAAAAGACAGATTTATACAG
ACATAGAGATGAACCGACTTGGAAAGTAACTCAAATCCTGCTAGGTATGAAAAA
AACTAACaGATATCACGCTCGAGCGTACGCCACCATGTTCGTGTTTCTGGTGCTG
CTGCCTCTGGTGAGCTCCCAGTGCGTGAACTTCACCACAAGGACCCAGCTGCCCC
CTGCCTATACCAATTCCTTCACACGGGGCGTGTACTATCCCGACAAGGTGTTCCG
GAGCAGCGTGCTGCACTCCACACAGGATCTGTTTCTGCCTTTCTTTTCTAACGTG
ACCTGGTTCCACGCCATCCACGTGAGCGGCACCAATGGCACAAAGCGGTTCGCC
AATCCAGTGCTGCCCTTTAACGATGGCGTGTACTTCGCCTCCACCGAGAAGTCTA
ACATCATCAGAGGCTGGATCTTTGGCACCACACTGGACAGCAAGACACAGTCCC
TGCTGATCGTGAACAATGCCACCAACGTGGTCATCAAGGTGTGCGAGTTCCAGTT
TTGTAATGATCCATTCCTGGGCGTGTACTATCACAAGAACAATAAGTCTTGGATG
GAGAGCGAGTTTCGCGTGTATTCCTCTGCCAACAATTGCACATTTGAGTACGTGT
CCCAGCCCTTCCTGATGGACCTGGAGGGCAAGCAGGGCAATTTCAAGAACCTGA
GGGAGTTCGTGTTTAAGAATATCGATGGCTACTTCAAAATCTACTCCAAGCACAC
CCCAATCAACCTGGTGCGCGGCCTGCCACAGGGCTTCTCTGCCCTGGAGCCACTG
GTGGATCTGCCCATCGGCATCAACATCACCCGGTTTCAGACACTGCTGGCCCTGC
ACAGAAGCTACCTGACACCAGGCGACAGCTCCTCTGGATGGACCGCAGGAGCAG
CAGCCTACTATGTGGGCTATCTGCAGCCCAGGACCTTCCTGCTGAAGTACAACGA
GAATGGCACCATCACAGACGCCGTGGATTGCGCCCTGGATCCCCTGTCTGAGAC
CAAGTGTACACTGAAGAGCTTTACCGTGGAGAAGGGCATCTATCAGACAAGCAA
TTTCAGGGTGCAGCCTACCGAGTCCATCGTGCGCTTTCCCAATATCACAAACCTG
TGCCCTTTTGGCGAGGTGTTCAACGCAACCCGCTTCGCCAGCGTGTACGCCTGGA
ATAGGAAGCGCATCTCCAACTGCGTGGCCGACTATTCTGTGCTGTACAACAGCG
CCTCCTTCTCTACCTTTAAGTGCTATGGCGTGAGCCCCACAAAGCTGAATGACCT
GTGCTTTACCAACGTGTACGCCGATTCCTTCGTGATCAGGGGCGACGAGGTGCGC
CAGATCGCACCAGGACAGACAGGCAATATCGCAGACTACAATTATAAGCTGCCT
GACGATTTCACCGGCTGCGTGATCGCCTGGAACTCTAACAATCTGGATAGCAAA
```

-continued

```
GTGGGCGGCAACTACAATTATCTGTACCGGCTGTTTAGAAAGTCTAATCTGAAGC
CATTCGAGAGGGACATCTCCACAGAAATCTACCAGGCCGGCTCTACCCCCTGCA
ATGGCGTGAAGGGCTTTAACTGTTATTTCCCTCTGCAGAGCTACGGCTTCCAGCC
AACATATGGCGTGGGCTATCAGCCCTACCGCGTGGTGGTGCTGTCTTTTGAGCTG
CTGCACGCACCTGCAACAGTGTGCGGACCAAAGAAGAGCACCAATCTGGTGAAG
AACAAGTGCGTGAACTTCAACTTCAACGGACTGACCGGAACAGGCGTGCTGACC
GAGTCCAACAAGAAGTTCCTGCCTTTTCAGCAGTTCGGCAGGGACATCGCAGAT
ACCACAGACGCCGTGCGCGACCCTCAGACCCTGGAGATCCTGGACATCACACCA
TGCTCCTTCGGCGGCGTGTCTGTGATCACACCAGGCACCAATACAAGCAACCAG
GTGGCCGTGCTGTATCAGGGCGTGAATTGTACCGAGGTGCCAGTGGCAATCCAC
GCAGATCAGCTGACCCCTACATGGCGGGTGTACTCTACCGGCAGCAACGTGTTC
CAGACAAGAGCCGGATGCCTGATCGGAGCAGAGCACGTGAACAATAGCTATGA
GTGCGACATCCCTATCGGCGCCGGCATCTGTGCCTCCTACCAGACCCAGACAAA
CTCCCCAGAATCAAGCGTGATTCCTCTGGTCCATCCACTGGCAGATCCCTCCACA
GTGTTCAAAGACGGAGATGAGGCCGAAGACTTTGTGGAAGTCCACCTGCCTGAT
GTGCATAACCAGGTGTCTGGCGTCGACCTGGGACTGCCAAATTGGGGCAAGTAC
GTGCTGCTGAGTGCTGGAGCACTGACTGCCCTGATGCTGATCATTTTCCTGATGA
CCTGCTGTCGGCGCGTGAACAGAAGTGAGCCCACTCAGCACAATCTGCGAGGAA
CCGGGAGAGAAGTGTCAGTCACACCTCAGAGCGGGAAAATCATTAGTAGTTGGG
AATCACATAAAAGCGGGGGCGAGACCAGGCTGTGAGCTAGCCAGATTCTTCATG
TTTGGACCAAATCAACTTGTGATACCATGCTCAAAGAGGCCTCAATTATATTTGA
GTTTTTAATTTTTATGAAAAAAAACTAACAGCAATCATGGAAGTCCACGATTTTGA
GACCGACGAGTTCAATGATTTCAATGAAGATGACTATGCCACAAGAGAATTCCT
GAATCCCGATGAGCGCATGACGTACTTGAATCATGCTGATTACAATTTGAATTCT
CCTCTAATTAGTGATGATATTGACAATTTGATCAGGAAATTCAATTCTCTTCCGA
TTCCCTCGATGTGGGATAGTAAGAACTGGGATGGAGTTCTTGAGATGTTAACATC
ATGTCAAGCCAATCCCATCTCAACATCTCAGATGCATAAATGGATGGGAAGTTG
GTTAATGTCTGATAATCATGATGCCAGTCAAGGGTATAGTTTTTTACATGAAGTG
GACAAAGAGGCAGAAATAACATTTGACGTGGTGGAGACCTTCATCCGCGGCTGG
GGCAACAAACCAATTGAATACATCAAAAAGGAAAGATGGACTGACTCATTCAAA
ATTCTCGCTTATTTGTGTCAAAAGTTTTTGGACTTACACAAGTTGACATTAATCTT
AAATGCTGTCTCTGAGGTGGAATTGCTCAACTTGGCGAGGACTTTCAAAGGCAA
AGTCAGAAGAAGTTCTCATGGAACGAACATATGCAGGATTAGGGTTCCCAGCTT
GGGTCCTACTTTTATTTCAGAAGGATGGGCTTACTTCAAGAAACTTGATATTCTA
ATGGACCGAAACTTTCTGTTAATGGTCAAAGATGTGATTATAGGGAGGATGCAA
ACGGTGCTATCCATGGTATGTAGAATAGACAACCTGTTCTCAGAGCAAGACATCT
TCTCCCTTCTAAATATCTACAGAATTGGAGATAAAATTGTGGAGAGGCAGGGAA
ATTTTTCTTATGACTTGATTAAAATGGTGGAACCGATATGCAACTTGAAGCTGAT
GAAATTAGCAAGAGAATCAAGGCCTTTAGTCCCACAATTCCCTCATTTTGAAAAT
CATATCAAGACTTCTGTTGATGAAGGGGCAAAAATTGACCGAGGTATAAGATTC
```

-continued

```
CTCCATGATCAGATAATGAGTGTGAAAACAGTGGATCTCACACTGGTGATTTATG

GATCGTTCAGACATTGGGGTCATCCTTTTATAGATTATTACACTGGACTAGAAAA

ATTACATTCCCAAGTAACCATGAAGAAAGATATTGATGTGTCATATGCAAAAGC

ACTTGCAAGTGATTTAGCTCGGATTGTTCTATTTCAACAGTTCAATGATCATAAA

AAGTGGTTCGTGAATGGAGACTTGCTCCCTCATGATCATCCCTTTAAAGTCATG

TTAAAGAAAATACATGGCCCACAGCTGCTCAAGTTCAAGATTTTGGAGATAAAT

GGCATGAACTTCCGCTGATTAAATGTTTTGAAATACCCGACTTACTAGACCCATC

GATAATATACTCTGACAAAAGTCATTCAATGAATAGGTCAGAGGTGTTGAAACA

TGTCCGAATGAATCCGAACACTCCTATCCCTAGTAAAAGGTGTTGCAGACTATG

TTGGACACAAAGGCTACCAATTGGAAAGAATTTCTTAAAGAGATTGATGAGAAG

GGCTTAGATGATGATGATCTAATTATTGGTCTTAAAGGAAAGGAGAGGGAACTG

AAGTTGGCAGGTAGATTTTTCTCCCTAATGTCTTGGAAATTGCGAGAATACTTTG

TAATTACCGAATATTTGATAAAGACTCATTTCGTCCCTATGTTTAAAGGCCTGAC

AATGGCGGACGATCTAACTGCAGTCATTAAAAAGATGTTAGATTCCTCATCCGGC

CAAGGATTGAAGTCATATGAGGCAATTTGCATAGCCAATCACATTGATTACGAA

AAATGGAATAACCACCAAAGGAAGTTATCAAACGGCCCAGTGTTCCGAGTTATG

GGCCAGTTCTTAGGTTATCCATCCTTAATCGAGAGAACTCATGAATTTTTTGAGA

AAAGTCTTATATACTACAATGGAAGACCAGACTTGATGCGTGTTCACAACAACA

CACTGATCAATTCAACCTCCCAACGAGTTTGTTGGCAAGGACAAGAGGGTGGAC

TGGAAGGTCTACGGCAAAAAGGATGGACTATCCTCAATCTACTGGTTATTCAAA

GAGAGGCTAAAATCAGAAACACTGCTGTCAAAGTCTTGGCACAAGGTGATAATC

AAGTTATTTGCACACAGTATAAAACGAAGAAATCGAGAAACGTTGTAGAATTAC

AGGGTGCTCTCAATCAAATGGTTTCTAATAATGAGAAAATTATGACTGCAATCAA

AATAGGGACAGGGAAGTTAGGACTTTTGATAAATGACGATGAGACTATGCAATC

TGCAGATTACTTGAATTATGGAAAAATACCGATTTTCCGTGGAGTGATTAGAGGG

TTAGAGACCAAGAGATGGTCACGAGTGACTTGTGTCACCAATGACCAAATACCC

ACTTGTGCTAATATAATGAGCTCAGTTTCCACAAATGCTCTCACCGTAGCTCATT

TTGCTGAGAACCCAATCAATGCCATGATACAGTACAATTATTTTGGGACATTTGC

TAGACTCTTGTTGATGATGCATGATCCTGCTCTTCGTCAATCATTGTATGAAGTTC

AAGATAAGATACCGGGCTTGCACAGTTCTACTTTCAAATACGCCATGTTGTATTT

GGACCCTTCCATTGGAGGAGTGTCGGGCATGTCTTTGTCCAGGTTTTTGATTAGA

GCCTTCCCAGATCCCGTAACAGAAAGTCTCTCATTCTGGAGATTCATCCATGTAC

ATGCTCGAAGTGAGCATCTGAAGGAGATGAGTGCAGTATTTGGAAACCCCGAGA

TAGCCAAGTTTCGAATAACTCACATAGACAAGCTAGTAGAAGATCCAACCTCTCT

GAACATCGCTATGGGAATGAGTCCAGCGAACTTGTTAAAGACTGAGGTTAAAAA

ATGCTTAATCGAATCAAGACAAACCATCAGGAACCAGGTGATTAAGGATGCAAC

CATATATTTGTATCATGAAGAGGATCGGCTCAGAAGTTTCTTATGGTCAATAAAT

CCTCTGTTCCCTAGATTTTTAAGTGAATTCAAATCAGGCACTTTTTTGGGAGTCGC

AGACGGGCTCATCAGTCTATTTCAAAATTCTCGTACTATTCGGAACTCCTTTAAG

AAAAAGTATCATAGGGAATTGGATGATTTGATTGTGAGGAGTGAGGTATCCTCTT

TGACACATTTAGGGAAACTTCATTTGAGAAGGGGATCATGTAAAATGTGGACAT
```

-continued

```
GTTCAGCTACTCATGCTGACACATTAAGATACAAATCCTGGGGCCGTACAGTTAT
TGGGACAACTGTACCCCATCCATTAGAAATGTTGGGTCCACAACATCGAAAAGA
GACTCCTTGTGCACCATGTAACACATCAGGGTTCAATTATGTTTCTGTGCATTGTC
CAGACGGGATCCATGACGTCTTTAGTTCACGGGGACCATTGCCTGCTTATCTAGG
GTCTAAAACATCTGAATCTACATCTATTTTGCAGCCTTGGGAAAGGGAAAGCAA
AGTCCCACTGATTAAAAGAGCTACACGTCTTAGAGATGCTATCTCTTGGTTTGTT
GAACCCGACTCTAAACTAGCAATGACTATACTTTCTAACATCCACTCTTTAACAG
GCGAAGAATGGACCAAAAGGCAGCATGGGTTCAAAAGAACAGGGTCTGCCCTTC
ATAGGTTTTCGACATCTCGGATGAGCCATGGTGGGTTCGCATCTCAGAGCACTGC
AGCATTGACCAGGTTGATGGCAACTACAGACACCATGAGGGATCTGGGAGATCA
GAATTTCGACTTTTTATTCCAAGCAACGTTGCTCTATGCTCAAATTACCACCACTG
TTGCAAGAGACGGATGGATCACCAGTTGTACAGATCATTATCATATTGCCTGTAA
GTCCTGTTTGAGACCCATAGAAGAGATCACCCTGGACTCAAGTATGGACTACAC
GCCCCCAGATGTATCCCATGTGCTGAAGACATGGAGGAATGGGGAAGGTTCGTG
GGGACAAGAGATAAAACAGATCTATCCTTTAGAAGGGAATTGGAAGAATTTAGC
ACCTGCTGAGCAATCCTATCAAGTCGGCAGATGTATAGGTTTTCTATATGGAGAC
TTGGCGTATAGAAAATCTACTCATGCCGAGGACAGTTCTCTATTTCCTCTATCTAT
ACAAGGTCGTATTAGAGGTCGAGGTTTCTTAAAAGGGTTGCTAGACGGATTAAT
GAGAGCAAGTTGCTGCCAAGTAATACACCGGAGAAGTCTGGCTCATTTGAAGAG
GCCGGCCAACGCAGTGTACGGAGGTTTGATTTACTTGATTGATAAATTGAGTGTA
TCACCTCCATTCCTTTCTCTTACTAGATCAGGACCTATTAGAGACGAATTAGAAA
CGATTCCCCACAAGATCCCAACCTCCTATCCGACAAGCAACCGTGATATGGGGG
TGATTGTCAGAAATTACTTCAAATACCAATGCCGTCTAATTGAAAAGGGAAAAT
ACAGATCACATTATTCACAATTATGGTTATTCTCAGATGTCTTATCCATAGACTTC
ATTGGACCATTCTCTATTTCCACCACCCTCTTGCAAATCCTATACAAGCCATTTTT
ATCTGGGAAAGATAAGAATGAGTTGAGAGAGCTGGCAAATCTTTCTTCATTGCT
AAGATCAGGAGAGGGGTGGGAAGACATACATGTGAAATTCTTCACCAAGGACAT
ATTATTGTGTCCAGAGGAAATCAGACATGCTTGCAAGTTCGGGATTGCTAAGGAT
AATAATAAAGACATGAGCTATCCCCCTTGGGGAAGGGAATCCAGAGGGACAATT
ACAACAATCCCTGTTTATTATACGACCACCCCTTACCCAAAGATGCTAGAGATGC
CTCCAAGAATCCAAAATCCCCTGCTGTCCGGAATCAGGTTGGGCCAATTACCAA
CTGGCGCTCATTATAAAATTCGGAGTATATTACATGGAATGGGAATCCATTACAG
GGACTTCTTGAGTTGTGGAGACGGCTCCGGAGGGATGACTGCTGCATTACTACG
AGAAAATGTGCATAGCAGAGGAATATTCAATAGTCTGTTAGAATTATCAGGGTC
AGTCATGCGAGGCGCCTCTCCTGAGCCCCCAGTGCCCTAGAAACTTTAGGAGG
AGATAAATCGAGATGTGTAAATGGTGAAACATGTTGGGAATATCCATCTGACTT
ATGTGACCCAAGGACTTGGGACTATTTCCTCCGACTCAAAGCAGGCTTGGGGCTT
CAAATTGATTTAATTGTAATGGATATGGAAGTTCGGGATTCTTCTACTAGCCTGA
AAATTGAGACGAATGTTAGAAATTATGTGCACCGGATTTTGGATGAGCAAGGAG
TTTTAATCTACAAGACTTATGGAACATATATTTGTGAGAGCGAAAAGAATGCAGT
```

-continued

AACAATCCTTGGTCCCATGTTCAAGACGGTCGACTTAGTTCAAACAGAATTTAGT

AGTTCTCAAACGTCTGAAGTATATATGGTATGTAAAGGTTTGAAGAAATTAATCG

ATGAACCCAATCCCGATTGGTCTTCCATCAATGAATCCTGGAAAAACCTGTACGC

ATTCCAGTCATCAGAACAGGAATTTGCCAGAGCAAAGAAGGTTAGTACATACTT

TACCTTGACAGGTATTCCCTCCCAATTCATTCCTGATCCTTTTGTAAACATTGAGA

CTATGCTACAAATATTCGGAGTACCCACGGGTGTGTCTCATGCGGCTGCCTTAAA

ATCATCTGATAGACCTGCAGATTTATTGACCATTAGCCTTTTTTATATGGCGATTA

TATCGTATTATAACATCAATCATATCAGAGTAGGACCGATACCTCCGAACCCCCC

ATCAGATGGAATTGCACAAAATGTGGGGATCGCTATAACTGGTATAAGCTTTTG

GCTGAGTTTGATGGAGAAAGACATTCCACTATATCAACAGTGTTTAGCAGTTATC

CAGCAATCATTCCCGATTAGGTGGGAGGCTGTTTCAGTAAAAGGAGGATACAAG

CAGAAGTGGAGTACTAGAGGTGATGGGCTCCCAAAAGATACCCGAACTTCAGAC

TCCTTGGCCCCAATCGGGAACTGGATCAGATCTCTGGAATTGGTCCGAAACCAA

GTTCGTCTAAATCCATTCAATGAGATCTTGTTCAATCAGCTATGTCGTACAGTGG

ATAATCATTTGAAATGGTCAAATTTGCGAAGAAACACAGGAATGATTGAATGGA

TCAATAGACGAATTTCAAAAGAAGACCGGTCTATACTGATGTTGAAGAGTGACC

TACACGAGGAAAACTCTTGGAGAGATTAAAAAATCATGAGGAGACTCCAAACTT

TAAGTATGAAAAAAACTTTGATCCTTAAGACCCTCTTGTGGTTTTTATTTTTATC

TGGTTTTGTGGTCTTCGT.

In one embodiment, the nucleic acid comprises the sequence of SEQ ID NO: 22, shown below (VSV vector: Convac V3 China):

ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC

CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAAATGATCAATGAACAGTTTGAACCTCTTGTGCCAGAAGGT

CGTGACATTTTTGATGTGTGGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

ATATTCTTCCGTCAAAAACCCTGCCTTCCACTTCTGGGGGCAATTGACAGCTCTT

-continued

```
CTGCTCAGATCCACCAGAGCAAGGAATGCCCGACAGCCTGATGACATTGAGTAT

ACATCTCTTACTACAGCAGGTTTGTTGTACGCTTATGCAGTAGGATCCTCTGCCG

ACTTGGCACAACAGTTTTGTGTTGGAGATAACAAATACACTCCAGATGATAGTAC

CGGAGGATTGACGACTAATGCACCGCCACAAGGCAGAGATGTGGTCGAATGGCT

CGGATGGTTTGAAGATCAAAACAGAAAACCGACTCCTGATATGATGCAGTATGC

GAAAAGAGCAGTCATGTCACTGCAAGGCCTAAGAGAGAAGACAATTGGCAAGT

ATGCTAAGTCAGAATTTGACAAATGACCCTATAATTCTCAGATCACCTATTATAT

ATTATGCTACATATGAAAAAAACTAACAGATATCATGGATAATCTCACAAAAGT

TCGTGAGTATCTCAAGTCCTATTCTCGTCTGGATCAGGCGGTAGGAGAGATAGAT

GAGATCGAAGCACAACGAGCTGAAAAGTCCAATTATGAGTTGTTCCAAGAGGAT

GGAGTGGAAGAGCATACTAAGCCCTCTTATTTTCAGGCAGCAGATGATTCTGAC

ACAGAATCTGAACCAGAAATTGAAGACAATCAAGGTTTGTATGCACCAGATCCA

GAAGCTGAGCAAGTTGAAGGCTTTATACAGGGGCCTTTAGATGACTATGCAGAT

GAGGAAGTGGATGTTGTATTTACTTCGGACTGGAAACAGCCTGAGCTTGAATCTG

ACGAGCATGGAAAGACCTTACGGTTGACATCGCCAGAGGGTTTAAGTGGAGAGC

AGAAATCCCAGTGGCTTTCGACGATTAAAGCAGTCGTGCAAAGTGCCAAATACT

GGAATCTGGCAGAGTGCACATTTGAAGCATCGGGAGAAGGGGTCATTATGAAGG

AGCGCCAGATAACTCCGGATGTATATAAGGTCACTCCAGTGATGAACACACATC

CGTCCCAATCAGAAGCAGTATCAGATGTTTGGTCTCTCAAAGACATCCATGAC

TTTCCAACCCAAGAAAGCAAGTCTTCAGCCTCTCACCATATCCTTGGATGAATTG

TTCTCATCTAGAGGAGAGTTCATCTCTGTCGGAGGTGACGGACGAATGTCTCATA

AAGAGGCCATCCTGCTCGGCCTGAGATACAAAAAGTTGTACAATCAGGCGAGAG

TCAAATATTCTCTGTAGACTATGAAAAAAAGTAACAGATATCACGATCTAAGTGT

TATCCCAATCCATTCATCATGAGTTCCTTAAAGAAGATTCTCGGTCTGAAGGGGA

AAGGTAAGAAATCTAAGAAATTAGGGATCGCACCACCCCCTTATGAAGAGGACA

CTAGCATGGAGTATGCTCCGAGCGCTCCAATTGACAAATCCTATTTTGGAGTTGA

CGAGATGGACACCTATGATCCGAATCAATTAAGATATGAGAAATTCTTCTTTACA

GTGAAAATGACGGTTAGATCTAATCGTCCGTTCAGAACATACTCAGATGTGGCA

GCCGCTGTATCCCATTGGGATCACATGTACATCGGAATGGCAGGGAAACGTCCC

TTCTACAAAATCTTGGCTTTTTTGGGTTCTTCTAATCTAAAGGCCACTCCAGCGGT

ATTGGCAGATCAAGGTCAACCAGAGTATCACACTCACTGCGAAGGCAGGGCTTA

TTTGCCACATAGGATGGGGAAGACCCCTCCCATGCTCAATGTACCAGAGCACTTC

AGAAGACCATTCAATATAGGTCTTTACAAGGGAACGATTGAGCTCACAATGACC

ATCTACGATGATGAGTCACTGGAAGCAGCTCCTATGATCTGGGATCATTTCAATT

CTTCCAAATTTTCTGATTTCAGAGAGAAGGCCTTAATGTTTGGCCTGATTGTCGA

GAAAAAGGCATCTGGAGCGTGGGTCCTGGATTCTATCAGCCACTTCAAATGAGC

TAGTCTAACTTCTAGCTTCTGAACAATCCCCGGTTTACTCAGTCTCTCCTAATTCC

AGCCTCTCGAACAACTAATATCCTGTCTTTTCTATCCCTATGAAAAAAACTAACA

GAGATCGATCTGTTTACGCGTCACTATGAAGTGCCTTTTGTACTTAGCCTTTTTAT

TCATTGGGGTGAATTGCAAGTTCACCATAGTTTTTCCACACAACCAAAAAGGAA

ACTGGAAAAATGTTCCTTCTAATTACCATTATTGCCCGTCAAGCTCAGATTTAAA
```

```
TTGGCATAATGACTTAATAGGCACAGCCATACAAGTCAAAATGCCCAAGAGTCA

CAAGGCTATTCAAGCAGACGGTTGGATGTGTCATGCTTCCAAATGGGTCACTACT

TGTGATTTCCGCTGGTATGGACCGAAGTATATAACACAGTCCATCCGATCCTTCA

CTCCATCTGTAGAACAATGCAAGGAAAGCATTGAACAAACGAAACAAGGAACTT

GGCTGAATCCAGGCTTCCCTCCTCAAAGTTGTGGATATGCAACTGTGACGGATGC

CGAAGCAGTGATTGTCCAGGTGACTCCTCACCATGTGCTGGTTGATGAATACACA

GGAGAATGGGTTGATTCACAGTTCATCAACGGAAAATGCAGCAATTACATATGC

CCCACTGTCCATAACTCTACAACCTGGCATTCTGACTATAAGGTCAAAGGGCTAT

GTGATTCTAACCTCATTTCCATGGACATCACCTTCTTCTCAGAGGACGGAGAGCT

ATCATCCCTGGGAAAGGAGGGCACAGGGTTCAGAAGTAACTACTTTGCTTATGA

AACTGGAGGCAAGGCCTGCAAAATGCAATACTGCAAGCATTGGGGAGTCAGACT

CCCATCAGGTGTCTGGTTCGAGATGGCTGATAAGGATCTCTTTGCTGCAGCCAGA

TTCCCTGAATGCCCAGAAGGGTCAAGTATCTCTGCTCCATCTCAGACCTCAGTGG

ATGTAAGTCTAATTCAGGACGTTGAGAGGATCTTGGATTATTCCCTCTGCCAAGA

AACCTGGAGCAAAATCAGAGCGGGTCTTCCAATCTCTCCAGTGGATCTCAGCTAT

CTTGCTCCTAAAAACCCAGGAACCGGTCCTGCTTTCACCATAATCAATGGTACCC

TAAAATACTTTGAGACCAGATACATCAGAGTCGATATTGCTGCTCCAATCCTCTC

AAGAATGGTCGGAATGATCAGTGGAACTACCACAGAAAGGGAACTGTGGGATG

ACTGGGCACCATATGAAGACGTGGAAATTGGACCCAATGGAGTTCTGAGGACCA

GTTCAGGATATAAGTTTCCTTTATACATGATTGGACATGGTATGTTGGACTCCGA

TCTTCATCTTAGCTCAAAGGCTCAGGTGTTCGAACATCCTCACATTCAAGACGCT

GCTTCGCAACTTCCTGATGATGAGAGTTTATTTTTTGGTGATACTGGGCTATCCA

AAAATCCAATCGAGCTTGTAGAAGGTTGGTTCAGTAGTTGGAAAAGCTCTATTGC

CTCTTTTTTCTTTATCATAGGGTTAATCATTGGACTATTCTTGGTTCTCCGAGTTG

GTATCCATCTTTGCATTAAATTAAAGCACACCAAGAAAAGACAGATTTATACAG

ACATAGAGATGAACCGACTTGGAAAGTAACTCAAATCCTGCTAGGTATGAAAAA

AACTAACaGATATCACGCtcgagGCCACCATGTTCGTGTTTCTGGTGCTGCTGCCTCT

GGTGAGCTCCCAGTGCGTGAACCTGACCACAAGGACCCAGCTGCCCCCTGCCTA

TACCAATTCCTTCACACGGGGCGTGTACTATCCCGACAAGGTGTTCCGGAGCAGC

GTGCTGCACTCCACACAGGATCTGTTTCTGCCTTTCTTTTCTAACGTGACCTGGTT

CCACGCCATCCACGTGAGCGGCACCAATGGCACAAAGCGGTTCGACAATCCAGT

GCTGCCCTTTAACGATGGCGTGTACTTCGCCTCCACCGAGAAGTCTAACATCATC

AGAGGCTGGATCTTTGGCACCACACTGGACAGCAAGACACAGTCCCTGCTGATC

GTGAACAATGCCACCAACGTGGTCATCAAGGTGTGCGAGTTCCAGTTTTGTAATG

ATCCATTCCTGGGCGTGTACTATCACAAGAACAATAAGTCTTGGATGGAGAGCG

AGTTTCGCGTGTATTCCTCTGCCAACAATTGCACATTTGAGTACGTGTCCCAGCC

CTTCCTGATGGACCTGGAGGGCAAGCAGGGCAATTTCAAGAACCTGAGGGAGTT

CGTGTTTAAGAATATCGATGGCTACTTCAAAATCTACTCCAAGCACACCCCAATC

AACCTGGTGCGCGACCTGCCACAGGGCTTCTCTGCCCTGGAGCCACTGGTGGATC

TGCCCATCGGCATCAACATCACCCGGTTTCAGACACTGCTGGCCCTGCACAGAA
```

-continued

```
GCTACCTGACACCAGGCGACAGCTCCTCTGGATGGACCGCAGGAGCAGCAGCCT

ACTATGTGGGCTATCTGCAGCCCAGGACCTTCCTGCTGAAGTACAACGAGAATG

GCACCATCACAGACGCCGTGGATTGCGCCCTGGATCCCCTGTCTGAGACCAAGT

GTACACTGAAGAGCTTTACCGTGGAGAAGGGCATCTATCAGACAAGCAATTTCA

GGGTGCAGCCTACCGAGTCCATCGTGCGCTTTCCCAATATCACAAACCTGTGCCC

TTTTGGCGAGGTGTTCAACGCAACCCGCTTCGCCAGCGTGTACGCCTGGAATAGG

AAGCGCATCTCCAACTGCGTGGCCGACTATTCTGTGCTGTACAACAGCGCCTCCT

TCTCTACCTTTAAGTGCTATGGCGTGAGCCCCACAAAGCTGAATGACCTGTGCTT

TACCAACGTGTACGCCGATTCCTTCGTGATCAGGGGCGACGAGGTGCGCCAGAT

CGCACCAGGACAGACAGGCAAGATCGCAGACTACAATTATAAGCTGCCTGACGA

TTTCACCGGCTGCGTGATCGCCTGGAACTCTAACAATCTGGATAGCAAAGTGGGC

GGCAACTACAATTATCTGTACCGGCTGTTTAGAAAGTCTAATCTGAAGCCATTCG

AGAGGGACATCTCCACAGAAATCTACCAGGCCGGCTCTACCCCCTGCAATGGCG

TGGAGGGCTTTAACTGTTATTTCCCTCTGCAGAGCTACGGCTTCCAGCCAACAAA

CGGCGTGGGCTATCAGCCCTACCGCGTGGTGGTGCTGTCTTTTGAGCTGCTGCAC

GCACCTGCAACAGTGTGCGGACCAAAGAAGAGCACCAATCTGGTGAAGAACAA

GTGCGTGAACTTCAACTTCAACGGACTGACCGGAACAGGCGTGCTGACCGAGTC

CAACAAGAAGTTCCTGCCTTTTCAGCAGTTCGGCAGGGACATCGCAGATACCAC

AGACGCCGTGCGCGACCCTCAGACCCTGGAGATCCTGGACATCACACCATGCTC

CTTCGGCGGCGTGTCTGTGATCACACCAGGCACCAATACAAGCAACCAGGTGGC

CGTGCTGTATCAGGACGTGAATTGTACCGAGGTGCCAGTGGCAATCCACGCAGA

TCAGCTGACCCCTACATGGCGGGTGTACTCTACCGGCAGCAACGTGTTCCAGAC

AAGAGCCGGATGCCTGATCGGAGCAGAGCACGTGAACAATAGCTATGAGTGCGA

CATCCCTATCGGCGCCGGCATCTGTGCCTCCTACCAGACCCAGACAAACTCCCCA

AGGTCTGGATCCGGCTACATCCCCGAGGCCCCCAGAGACGGCCAGGCCTACGTG

CGGAAGGACGGCGAGTGGGTACTGctcagcaccttcctgggcAGCAGTTGGAAAAGCTCCA

TCGCCTCCTTTTTCTTTATCATCGGCCTGATCATCGGACTGTTCCTGGTGCTCCGC

GTGGGTATCCACCTGTGCATCAAGCTGAAGCACACCAAGAAAAGACAGATTTAT

ACAGACATCGAGATGAACCGACTTGGAAAGTAAGCTAGCCAGATTCTTCATGTT

TGGACCAAATCAACTTGTGATACCATGCTCAAAGAGGCCTCAATTATATTTGAGT

TTTTAATTTTTATGAAAAAAACTAACAGCAATCATGGAAGTCCACGATTTTGAGA

CCGACGAGTTCAATGATTTCAATGAAGATGACTATGCCACAAGAGAATTCCTGA

ATCCCGATGAGCGCATGACGTACTTGAATCATGCTGATTACAATTTGAATTCTCC

TCTAATTAGTGATGATATTGACAATTTGATCAGGAAATTCAATTCTCTTCCGATTC

CCTCGATGTGGGATAGTAAGAACTGGGATGGAGTTCTTGAGATGTTAACATCAT

GTCAAGCCAATCCCATCTCAACATCTCAGATGCATAAATGGATGGGAAGTTGGTT

AATGTCTGATAATCATGATGCCAGTCAAGGGTATAGTTTTTTACATGAAGTGGAC

AAAGAGGCAGAAATAACATTTGACGTGGTGGAGACCTTCATCCGCGGCTGGGC

AACAAACCAATTGAATACATCAAAAAGGAAAGATGGACTGACTCATTCAAAATT

CTCGCTTATTTGTGTCAAAAGTTTTTGGACTTACACAAGTTGACATTAATCTTAAA

TGCTGTCTCTGAGGTGGAATTGCTCAACTTGGCGAGGACTTTCAAAGGCAAAGTC
```

-continued

```
AGAAGAAGTTCTCATGGAACGAACATATGCAGGATTAGGGTTCCCAGCTTGGGT

CCTACTTTTATTTCAGAAGGATGGGCTTACTTCAAGAAACTTGATATTCTAATGG

ACCGAAACTTTCTGTTAATGGTCAAAGATGTGATTATAGGGAGGATGCAAACGG

TGCTATCCATGGTATGTAGAATAGACAACCTGTTCTCAGAGCAAGACATCTTCTC

CCTTCTAAATATCTACAGAATTGGAGATAAAATTGTGGAGAGGCAGGGAAATTT

TTCTTATGACTTGATTAAAATGGTGGAACCGATATGCAACTTGAAGCTGATGAAA

TTAGCAAGAGAATCAAGGCCTTTAGTCCCACAATTCCCTCATTTTGAAAATCATA

TCAAGACTTCTGTTGATGAAGGGGCAAAAATTGACCGAGGTATAAGATTCCTCC

ATGATCAGATAATGAGTGTGAAAACAGTGGATCTCACACTGGTGATTTATGGAT

CGTTCAGACATTGGGGTCATCCTTTTATAGATTATTACACTGGACTAGAAAAATT

ACATTCCCAAGTAACCATGAAGAAAGATATTGATGTGTCATATGCAAAAGCACT

TGCAAGTGATTTAGCTCGGATTGTTCTATTTCAACAGTTCAATGATCATAAAAAG

TGGTTCGTGAATGGAGACTTGCTCCCTCATGATCATCCCTTTAAAAGTCATGTTA

AAGAAAATACATGGCCCACAGCTGCTCAAGTTCAAGATTTTGGAGATAAATGGC

ATGAACTTCCGCTGATTAAATGTTTTGAAATACCCGACTTACTAGACCCATCGAT

AATATACTCTGACAAAAGTCATTCAATGAATAGGTCAGAGGTGTTGAAACATGT

CCGAATGAATCCGAACACTCCTATCCCTAGTAAAAAGGTGTTGCAGACTATGTTG

GACACAAAGGCTACCAATTGGAAAGAATTTCTTAAAGAGATTGATGAGAAGGGC

TTAGATGATGATGATCTAATTATTGGTCTTAAAGGAAAGGAGAGGGAACTGAAG

TTGGCAGGTAGATTTTTCTCCCTAATGTCTTGGAAATTGCGAGAATACTTTGTAA

TTACCGAATATTTGATAAAGACTCATTTCGTCCCTATGTTTAAAGGCCTGACAAT

GGCGGACGATCTAACTGCAGTCATTAAAAAGATGTTAGATTCCTCATCCGGCCA

AGGATTGAAGTCATATGAGGCAATTTGCATAGCCAATCACATTGATTACGAAAA

ATGGAATAACCACCAAAGGAAGTTATCAAACGGCCCAGTGTTCCGAGTTATGGG

CCAGTTCTTAGGTTATCCATCCTTAATCGAGAGAACTCATGAATTTTTTGAGAAA

AGTCTTATATACTACAATGGAAGACCAGACTTGATGCGTGTTCACAACAACACA

CTGATCAATTCAACCTCCCAACGAGTTTGTTGGCAAGGACAAGAGGGTGGACTG

GAAGGTCTACGGCAAAAAGGATGGACTATCCTCAATCTACTGGTTATTCAAAGA

GAGGCTAAAATCAGAAACACTGCTGTCAAAGTCTTGGCACAAGGTGATAATCAA

GTTATTTGCACACAGTATAAAACGAAGAAATCGAGAAACGTTGTAGAATTACAG

GGTGCTCTCAATCAAATGGTTTCTAATAATGAGAAAATTATGACTGCAATCAAAA

TAGGGACAGGGAAGTTAGGACTTTTGATAAATGACGATGAGACTATGCAATCTG

CAGATTACTTGAATTATGGAAAAATACCGATTTTCCGTGGAGTGATTAGAGGGTT

AGAGACCAAGAGATGGTCACGAGTGACTTGTGTCACCAATGACCAAATACCCAC

TTGTGCTAATATAATGAGCTCAGTTTCCACAAATGCTCTCACCGTAGCTCATTTTG

CTGAGAACCCAATCAATGCCATGATACAGTACAATTATTTTGGGACATTTGCTAG

ACTCTTGTTGATGATGCATGATCCTGCTCTTCGTCAATCATTGTATGAAGTTCAAG

ATAAGATACCGGGCTTGCACAGTTCTACTTTCAAATACGCCATGTTGTATTTGGA

CCCTTCCATTGGAGGAGTGTCGGGCATGTCTTTGTCCAGGTTTTTGATTAGAGCC

TTCCCAGATCCCGTAACAGAAAGTCTCTCATTCTGGAGATTCATCCATGTACATG
```

-continued
```
CTCGAAGTGAGCATCTGAAGGAGATGAGTGCAGTATTTGGAAACCCCGAGATAG

CCAAGTTTCGAATAACTCACATAGACAAGCTAGTAGAAGATCCAACCTCTCTGA

ACATCGCTATGGGAATGAGTCCAGCGAACTTGTTAAAGACTGAGGTTAAAAAT

GCTTAATCGAATCAAGACAAACCATCAGGAACCAGGTGATTAAGGATGCAACCA

TATATTTGTATCATGAAGAGGATCGGCTCAGAAGTTTCTTATGGTCAATAAATCC

TCTGTTCCCTAGATTTTTAAGTGAATTCAAATCAGGCACTTTTTTGGGAGTCGCA

GACGGGCTCATCAGTCTATTTCAAAATTCTCGTACTATTCGGAACTCCTTTAAGA

AAAAGTATCATAGGGAATTGGATGATTTGATTGTGAGGAGTGAGGTATCCTCTTT

GACACATTTAGGGAAACTTCATTTGAGAAGGGGATCATGTAAAATGTGGACATG

TTCAGCTACTCATGCTGACACATTAAGATACAAATCCTGGGGCCGTACAGTTATT

GGGACAACTGTACCCCATCCATTAGAAATGTTGGGTCCACAACATCGAAAAGAG

ACTCCTTGTGCACCATGTAACACATCAGGGTTCAATTATGTTTCTGTGCATTGTCC

AGACGGGATCCATGACGTCTTTAGTTCACGGGACCATTGCCTGCTTATCTAGGG

TCTAAAACATCTGAATCTACATCTATTTTGCAGCCTTGGGAAAGGGAAAGCAAA

GTCCCACTGATTAAAAGAGCTACACGTCTTAGAGATGCTATCTCTTGGTTTGTTG

AACCCGACTCTAAACTAGCAATGACTATACTTTCTAACATCCACTCTTTAACAGG

CGAAGAATGGACCAAAAGGCAGCATGGGTTCAAAAGAACAGGGTCTGCCCTTCA

TAGGTTTTCGACATCTCGGATGAGCCATGGTGGGTTCGCATCTCAGAGCACTGCA

GCATTGACCAGGTTGATGGCAACTACAGACACCATGAGGGATCTGGGAGATCAG

AATTTCGACTTTTTATTCCAAGCAACGTTGCTCTATGCTCAAATTACCACCACTGT

TGCAAGAGACGGATGGATCACCAGTTGTACAGATCATTATCATATTGCCTGTAAG

TCCTGTTTGAGACCCATAGAAGAGATCACCCTGGACTCAAGTATGGACTACACG

CCCCCAGATGTATCCCATGTGCTGAAGACATGGAGGAATGGGGAAGGTTCGTGG

GGACAAGAGATAAAACAGATCTATCCTTTAGAAGGGAATTGGAAGAATTTAGCA

CCTGCTGAGCAATCCTATCAAGTCGGCAGATGTATAGGTTTTCTATATGGAGACT

TGGCGTATAGAAAATCTACTCATGCCGAGGACAGTTCTCTATTTCCTCTATCTAT

ACAAGGTCGTATTAGAGGTCGAGGTTTCTTAAAAGGGTTGCTAGACGGATTAAT

GAGAGCAAGTTGCTGCCAAGTAATACACCGGAGAAGTCTGGCTCATTTGAAGAG

GCCGGCCAACGCAGTGTACGGAGGTTTGATTTACTTGATTGATAAATTGAGTGTA

TCACCTCCATTCCTTTCTCTTACTAGATCAGGACCTATTAGAGACGAATTAGAAA

CGATTCCCCACAAGATCCCAACCTCCTATCCGACAAGCAACCGTGATATGGGGG

TGATTGTCAGAAATTACTTCAAATACCAATGCCGTCTAATTGAAAAGGGAAAAT

ACAGATCACATTATTCACAATTATGGTTATTCTCAGATGTCTTATCCATAGACTTC

ATTGGACCATTCTCTATTTCCACCACCCTCTTGCAAATCCTATACAAGCCATTTTT

ATCTGGGAAAGATAAGAATGAGTTGAGAGAGCTGGCAAATCTTTCTTCATTGCT

AAGATCAGGAGAGGGTGGGAAGACATACATGTGAAATTCTTCACCAAGGACAT

ATTATTGTGTCCAGAGGAAATCAGACATGCTTGCAAGTTCGGGATTGCTAAGGAT

AATAATAAAGACATGAGCTATCCCCCTTGGGGAAGGGAATCCAGAGGGACAATT

ACAACAATCCCTGTTTATTATACGACCACCCCTTACCCAAAGATGCTAGAGATGC

CTCCAAGAATCCAAAATCCCCTGCTGTCCGGAATCAGGTTGGGCCAATTACCAA

CTGGCGCTCATTATAAAATTCGGAGTATATTACATGGAATGGGAATCCATTACAG
```

-continued

```
GGACTTCTTGAGTTGTGGAGACGGCTCCGGAGGGATGACTGCTGCATTACTACG

AGAAAATGTGCATAGCAGAGGAATATTCAATAGTCTGTTAGAATTATCAGGGTC

AGTCATGCGAGGCGCCTCTCCTGAGCCCCCAGTGCCCTAGAAACTTTAGGAGG

AGATAAATCGAGATGTGTAAATGGTGAAACATGTTGGGAATATCCATCTGACTT

ATGTGACCCAAGGACTTGGGACTATTTCCTCCGACTCAAAGCAGGCTTGGGCTT

CAAATTGATTTAATTGTAATGGATATGGAAGTTCGGGATTCTTCTACTAGCCTGA

AAATTGAGACGAATGTTAGAAATTATGTGCACCGGATTTTGGATGAGCAAGGAG

TTTTAATCTACAAGACTTATGGAACATATATTTGTGAGAGCGAAAAGAATGCAGT

AACAATCCTTGGTCCCATGTTCAAGACGGTCGACTTAGTTCAAACAGAATTTAGT

AGTTCTCAAACGTCTGAAGTATATATGGTATGTAAAGGTTTGAAGAAATTAATCG

ATGAACCCAATCCCGATTGGTCTTCCATCAATGAATCCTGGAAAAACCTGTACGC

ATTCCAGTCATCAGAACAGGAATTTGCCAGAGCAAAGAAGGTTAGTACATACTT

TACCTTGACAGGTATTCCCTCCCAATTCATTCCTGATCCTTTTGTAAACATTGAGA

CTATGCTACAAATATTCGGAGTACCCACGGGTGTGTCTCATGCGGCTGCCTTAAA

ATCATCTGATAGACCTGCAGATTTATTGACCATTAGCCTTTTTTATATGGCGATTA

TATCGTATTATAACATCAATCATATCAGAGTAGGACCGATACCTCCGAACCCCCC

ATCAGATGGAATTGCACAAAATGTGGGGATCGCTATAACTGGTATAAGCTTTTG

GCTGAGTTTGATGGAGAAAGACATTCCACTATATCAACAGTGTTTAGCAGTTATC

CAGCAATCATTCCCGATTAGGTGGGAGGCTGTTTCAGTAAAAGGAGGATACAAG

CAGAAGTGGAGTACTAGAGGTGATGGGCTCCCAAAAGATACCCGAACTTCAGAC

TCCTTGGCCCCAATCGGGAACTGGATCAGATCTCTGGAATTGGTCCGAAACCAA

GTTCGTCTAAATCCATTCAATGAGATCTTGTTCAATCAGCTATGTCGTACAGTGG

ATAATCATTTGAAATGGTCAAATTTGCGAAGAAACACAGGAATGATTGAATGGA

TCAATAGACGAATTTCAAAAGAAGACCGGTCTATACTGATGTTGAAGAGTGACC

TACACGAGGAAAACTCTTGGAGAGATTAAAAAATCATGAGGAGACTCCAAACTT

TAAGTATGAAAAAAACTTTGATCCTTAAGACCCTCTTGTGGTTTTTATTTTTATC

TGGTTTTGTGGTCTTCGT.
```

In another embodiment, the nucleic acid comprises the sequence of SEQ ID NO: 23, shown below (VSV vector: Convac V3 South Africa):

```
ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC

CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG
```

-continued

```
ACAAATCAATGCAAAATGATCAATGAACAGTTTGAACCTCTTGTGCCAGAAGGT
CGTGACATTTTTGATGTGTGGGGAAATGACAGTAATTACACAAAAATTGTCGCTG
CAGTGGACATGTTCTTCCACATGTTCAAAAAACATGAATGTGCCTCGTTCAGATA
CGGAACTATTGTTTCCAGATTCAAAGATTGTGCTGCATTGGCAACATTTGGACAC
CTCTGCAAAATAACCGGAATGTCTACAGAAGATGTAACGACCTGGATCTTGAAC
CGAGAAGTTGCAGATGAAATGGTCCAAATGATGCTTCCAGGCCAAGAAATTGAC
AAGGCCGATTCATACATGCCTTATTTGATCGACTTTGGATTGTCTTCTAAGTCTCC
ATATTCTTCCGTCAAAAACCCTGCCTTCCACTTCTGGGGGCAATTGACAGCTCTT
CTGCTCAGATCCACCAGAGCAAGGAATGCCCGACAGCCTGATGACATTGAGTAT
ACATCTCTTACTACAGCAGGTTTGTTGTACGCTTATGCAGTAGGATCCTCTGCCG
ACTTGGCACAACAGTTTTGTGTTGGAGATAACAAATACACTCCAGATGATAGTAC
CGGAGGATTGACGACTAATGCACCGCCACAAGGCAGAGATGTGGTCGAATGGCT
CGGATGGTTTGAAGATCAAAACAGAAAACCGACTCCTGATATGATGCAGTATGC
GAAAAGAGCAGTCATGTCACTGCAAGGCCTAAGAGAGAAGACAATTGGCAAGT
ATGCTAAGTCAGAATTTGACAAATGACCCTATAATTCTCAGATCACCTATTATAT
ATTATGCTACATATGAAAAAAACTAACAGATATCATGGATAATCTCACAAAAGT
TCGTGAGTATCTCAAGTCCTATTCTCGTCTGGATCAGGCGGTAGGAGAGATAGAT
GAGATCGAAGCACAACGAGCTGAAAAGTCCAATTATGAGTTGTTCCAAGAGGAT
GGAGTGGAAGAGCATACTAAGCCCTCTTATTTTCAGGCAGCAGATGATTCTGAC
ACAGAATCTGAACCAGAAATTGAAGACAATCAAGGTTTGTATGCACCAGATCCA
GAAGCTGAGCAAGTTGAAGGCTTTATACAGGGGCCTTTAGATGACTATGCAGAT
GAGGAAGTGGATGTTGTATTTACTTCGGACTGGAAACAGCCTGAGCTTGAATCTG
ACGAGCATGGAAAGACCTTACGGTTGACATCGCCAGAGGGTTTAAGTGGAGAGC
AGAAATCCCAGTGGCTTTCGACGATTAAAGCAGTCGTGCAAAGTGCCAAATACT
GGAATCTGGCAGAGTGCACATTTGAAGCATCGGGAGAAGGGGTCATTATGAAGG
AGCGCCAGATAACTCCGGATGTATATAAGGTCACTCCAGTGATGAACACACATC
CGTCCCAATCAGAAGCAGTATCAGATGTTTGGTCTCTCTCAAAGACATCCATGAC
TTTCCAACCCAAGAAAGCAAGTCTTCAGCCTCTCACCATATCCTTGGATGAATTG
TTCTCATCTAGAGGAGAGTTCATCTCTGTCGGAGGTGACGGACGAATGTCTCATA
AAGAGGCCATCCTGCTCGGCCTGAGATACAAAAAGTTGTACAATCAGGCGAGAG
TCAAATATTCTCTGTAGACTATGAAAAAAAGTAACAGATATCACGATCTAAGTGT
TATCCCAATCCATTCATCATGAGTTCCTTAAAGAAGATTCTCGGTCTGAAGGGGA
AAGGTAAGAAATCTAAGAAATTAGGGATCGCACCACCCCCTTATGAAGAGGACA
CTAGCATGGAGTATGCTCCGAGCGCTCCAATTGACAAATCCTATTTTGGAGTTGA
CGAGATGGACACCTATGATCCGAATCAATTAAGATATGAGAAATTCTTCTTTACA
GTGAAAATGACGGTTAGATCTAATCGTCCGTTCAGAACATACTCAGATGTGGCA
GCCGCTGTATCCCATTGGGATCACATGTACATCGGAATGGCAGGGAAACGTCCC
TTCTACAAAATCTTGGCTTTTTTGGGTTCTTCTAATCTAAAGGCCACTCCAGCGGT
ATTGGCAGATCAAGGTCAACCAGAGTATCACACTCACTGCGAAGGCAGGGCTTA
TTTGCCACATAGGATGGGGAAGACCCCTCCCATGCTCAATGTACCAGAGCACTTC
```

-continued

```
AGAAGACCATTCAATATAGGTCTTTACAAGGGAACGATTGAGCTCACAATGACC
ATCTACGATGATGAGTCACTGGAAGCAGCTCCTATGATCTGGGATCATTTCAATT
CTTCCAAATTTTCTGATTTCAGAGAGAAGGCCTTAATGTTTGGCCTGATTGTCGA
GAAAAAGGCATCTGGAGCGTGGGTCCTGGATTCTATCAGCCACTTCAAATGAGC
TAGTCTAACTTCTAGCTTCTGAACAATCCCCGGTTTACTCAGTCTCTCCTAATTCC
AGCCTCTCGAACAACTAATATCCTGTCTTTTCTATCCCTATGAAAAAAACTAACA
GAGATCGATCTGTTTACGCGTCACTATGAAGTGCCTTTTGTACTTAGCCTTTTTAT
TCATTGGGGTGAATTGCAAGTTCACCATAGTTTTTCCACACAACCAAAAAGGAA
ACTGGAAAAATGTTCCTTCTAATTACCATTATTGCCCGTCAAGCTCAGATTTAAA
TTGGCATAATGACTTAATAGGCACAGCCATACAAGTCAAAATGCCCAAGAGTCA
CAAGGCTATTCAAGCAGACGGTTGGATGTGTCATGCTTCCAAATGGGTCACTACT
TGTGATTTCCGCTGGTATGGACCGAAGTATATAACACAGTCCATCCGATCCTTCA
CTCCATCTGTAGAACAATGCAAGGAAAGCATTGAACAAACGAAACAAGGAACTT
GGCTGAATCCAGGCTTCCCTCCTCAAAGTTGTGGATATGCAACTGTGACGGATGC
CGAAGCAGTGATTGTCCAGGTGACTCCTCACCATGTGCTGGTTGATGAATACACA
GGAGAATGGGTTGATTCACAGTTCATCAACGGAAAATGCAGCAATTACATATGC
CCCACTGTCCATAACTCTACAACCTGGCATTCTGACTATAAGGTCAAAGGGCTAT
GTGATTCTAACCTCATTTCCATGGACATCACCTTCTTCTCAGAGGACGGAGAGCT
ATCATCCCTGGGAAAGGAGGGCACAGGGTTCAGAAGTAACTACTTTGCTTATGA
AACTGGAGGCAAGGCCTGCAAAATGCAATACTGCAAGCATTGGGGAGTCAGACT
CCCATCAGGTGTCTGGTTCGAGATGGCTGATAAGGATCTCTTTGCTGCAGCCAGA
TTCCCTGAATGCCCAGAAGGGTCAAGTATCTCTGCTCCATCTCAGACCTCAGTGG
ATGTAAGTCTAATTCAGGACGTTGAGAGGATCTTGGATTATTCCCTCTGCCAAGA
AACCTGGAGCAAAATCAGAGCGGGTCTTCCAATCTCTCCAGTGGATCTCAGCTAT
CTTGCTCCTAAAAACCCAGGAACCGGTCCTGCTTTCACCATAATCAATGGTACCC
TAAAATACTTTGAGACCAGATACATCAGAGTCGATATTGCTGCTCCAATCCTCTC
AAGAATGGTCGGAATGATCAGTGGAACTACCACAGAAAGGGAACTGTGGGATG
ACTGGGCACCATATGAAGACGTGGAAATTGGACCCAATGGAGTTCTGAGGACCA
GTTCAGGATATAAGTTTCCTTTATACATGATTGGACATGGTATGTTGGACTCCGA
TCTTCATCTTAGCTCAAAGGCTCAGGTGTTCGAACATCCTCACATTCAAGACGCT
GCTTCGCAACTTCCTGATGATGAGAGTTTATTTTTTGGTGATACTGGGCTATCCA
AAAATCCAATCGAGCTTGTAGAAGGTTGGTTCAGTAGTTGGAAAAGCTCTATTGC
CTCTTTTTTCTTTATCATAGGGTTAATCATTGGACTATTCTTGGTTCTCCGAGTTG
GTATCCATCTTTGCATTAAATTAAAGCACACCAAGAAAAGACAGATTTATACAG
ACATAGAGATGAACCGACTTGGAAAGTAACTCAAATCCTGCTAGGTATGAAAAA
AACTAACaGATATCACGCtcgagGCCACCATGTTCGTGTTTCTGGTGCTGCTGCCTCT
GGTGAGCTCCCAGTGCGTGAACTTCACCACAAGGACCCAGCTGCCCCCTGCCTAT
ACCAATTCCTTCACACGGGGCGTGTACTATCCCGACAAGGTGTTCCGGAGCAGC
GTGCTGCACTCCACACAGGATCTGTTTCTGCCTTTCTTTTCTAACGTGACCTGGTT
CCACGCCATCCACGTGAGCGGCACCAATGGCACAAAGCGGTTCGCCAATCCAGT
GCTGCCCTTTAACGATGGCGTGTACTTCGCCTCCACCGAGAAGTCTAACATCATC
```

-continued

```
AGAGGCTGGATCTTTGGCACCACACTGGACAGCAAGACACAGTCCCTGCTGATC

GTGAACAATGCCACCAACGTGGTCATCAAGGTGTGCGAGTTCCAGTTTTGTAATG

ATCCATTCCTGGGCGTGTACTATCACAAGAACAATAAGTCTTGGATGGAGAGCG

AGTTTCGCGTGTATTCCTCTGCCAACAATTGCACATTTGAGTACGTGTCCCAGCC

CTTCCTGATGGACCTGGAGGGCAAGCAGGGCAATTTCAAGAACCTGAGGGAGTT

CGTGTTTAAGAATATCGATGGCTACTTCAAAATCTACTCCAAGCACACCCCAATC

AACCTGGTGCGCGGCCTGCCACAGGGCTTCTCTGCCCTGGAGCCACTGGTGGATC

TGCCCATCGGCATCAACATCACCCGGTTTCAGACACTGCTGGCCCTGCACAGAA

GCTACCTGACACCAGGCGACAGCTCCTCTGGATGGACCGCAGGAGCAGCAGCCT

ACTATGTGGGCTATCTGCAGCCCAGGACCTTCCTGCTGAAGTACAACGAGAATG

GCACCATCACAGACGCCGTGGATTGCGCCCTGGATCCCCTGTCTGAGACCAAGT

GTACACTGAAGAGCTTTACCGTGGAGAAGGGCATCTATCAGACAAGCAATTTCA

GGGTGCAGCCTACCGAGTCCATCGTGCGCTTTCCCAATATCACAAACCTGTGCCC

TTTTGGCGAGGTGTTCAACGCAACCCGCTTCGCCAGCGTGTACGCCTGGAATAGG

AAGCGCATCTCCAACTGCGTGGCCGACTATTCTGTGCTGTACAACAGCGCCTCCT

TCTCTACCTTTAAGTGCTATGGCGTGAGCCCCACAAAGCTGAATGACCTGTGCTT

TACCAACGTGTACGCCGATTCCTTCGTGATCAGGGGCGACGAGGTGCGCCAGAT

CGCACCAGGACAGACAGGCAATATCGCAGACTACAATTATAAGCTGCCTGACGA

TTTCACCGGCTGCGTGATCGCCTGGAACTCTAACAATCTGGATAGCAAAGTGGGC

GGCAACTACAATTATCTGTACCGGCTGTTTAGAAAGTCTAATCTGAAGCCATTCG

AGAGGGACATCTCCACAGAAATCTACCAGGCCGGCTCTACCCCCTGCAATGGCG

TGAAGGGCTTTAACTGTTATTTCCCTCTGCAGAGCTACGGCTTCCAGCCAACATA

TGGCGTGGGCTATCAGCCCTACCGCGTGGTGGTGCTGTCTTTTGAGCTGCTGCAC

GCACCTGCAACAGTGTGCGGACCAAAGAAGAGCACCAATCTGGTGAAGAACAA

GTGCGTGAACTTCAACTTCAACGGACTGACCGGAACAGGCGTGCTGACCGAGTC

CAACAAGAAGTTCCTGCCTTTTCAGCAGTTCGGCAGGGACATCGCAGATACCAC

AGACGCCGTGCGCGACCCTCAGACCCTGGAGATCCTGGACATCACACCATGCTC

CTTCGGCGGCGTGTCTGTGATCACACCAGGCACCAATACAAGCAACCAGGTGGC

CGTGCTGTATCAGGGCGTGAATTGTACCGAGGTGCCAGTGGCAATCCACGCAGA

TCAGCTGACCCCTACATGGCGGGTGTACTCTACCGGCAGCAACGTGTTCCAGAC

AAGAGCCGGATGCCTGATCGGAGCAGAGCACGTGAACAATAGCTATGAGTGCGA

CATCCCTATCGGCGCCGGCATCTGTGCCTCCTACCAGACCCAGACAAACTCCCCA

AGGGGATCCGGCTACATCCCCGAGGCCCCCAGAGACGGCCAGGCCTACGTGCGG

AAGGACGGCGAGTGGGTACTGctcagcaccttcctgggcAGCAGTTGGAAAAGCTCCATCG

CCTCCTTTTTCTTTATCATCGGCCTGATCATCGGACTGTTCCTGGTGCTCCGCGTG

GGTATCCACCTGTGCATCAAGCTGAAGCACACCAAGAAAAGACAGATTTATACA

GACATCGAGATGAACCGACTTGGAAAGTAAGCTAGCCAGATTCTTCATGTTTGG

ACCAAATCAACTTGTGATACCATGCTCAAAGAGGCCTCAATTATATTTGAGTTTT

TAATTTTTATGAAAAAAACTAACAGCAATCATGGAAGTCCACGATTTTGAGACC

GACGAGTTCAATGATTTCAATGAAGATGACTATGCCACAAGAGAATTCCTGAAT
```

-continued

```
CCCGATGAGCGCATGACGTACTTGAATCATGCTGATTACAATTTGAATTCTCCTC
TAATTAGTGATGATATTGACAATTTGATCAGGAAATTCAATTCTCTTCCGATTCC
CTCGATGTGGGATAGTAAGAACTGGGATGGAGTTCTTGAGATGTTAACATCATGT
CAAGCCAATCCCATCTCAACATCTCAGATGCATAAATGGATGGGAAGTTGGTTA
ATGTCTGATAATCATGATGCCAGTCAAGGGTATAGTTTTTTACATGAAGTGGACA
AAGAGGCAGAAATAACATTTGACGTGGTGGAGACCTTCATCCGCGGCTGGGGCA
ACAAACCAATTGAATACATCAAAAAGGAAAGATGGACTGACTCATTCAAAATTC
TCGCTTATTTGTGTCAAAAGTTTTTGGACTTACACAAGTTGACATTAATCTTAAAT
GCTGTCTCTGAGGTGGAATTGCTCAACTTGGCGAGGACTTTCAAAGGCAAAGTC
AGAAGAAGTTCTCATGGAACGAACATATGCAGGATTAGGGTTCCCAGCTTGGGT
CCTACTTTTATTTCAGAAGGATGGGCTTACTTCAAGAAACTTGATATTCTAATGG
ACCGAAACTTTCTGTTAATGGTCAAAGATGTGATTATAGGGAGGATGCAAACGG
TGCTATCCATGGTATGTAGAATAGACAACCTGTTCTCAGAGCAAGACATCTTCTC
CCTTCTAAATATCTACAGAATTGGAGATAAAATTGTGGAGAGGCAGGGAAATTT
TTCTTATGACTTGATTAAAATGGTGGAACCGATATGCAACTTGAAGCTGATGAAA
TTAGCAAGAGAATCAAGGCCTTTAGTCCCACAATTCCCTCATTTTGAAAATCATA
TCAAGACTTCTGTTGATGAAGGGGCAAAAATTGACCGAGGTATAAGATTCCTCC
ATGATCAGATAATGAGTGTGAAAACAGTGGATCTCACACTGGTGATTTATGGAT
CGTTCAGACATTGGGGTCATCCTTTTATAGATTATTACACTGGACTAGAAAAATT
ACATTCCCAAGTAACCATGAAGAAAGATATTGATGTGTCATATGCAAAAGCACT
TGCAAGTGATTTAGCTCGGATTGTTCTATTTCAACAGTTCAATGATCATAAAAAG
TGGTTCGTGAATGGAGACTTGCTCCCTCATGATCATCCCTTTAAAAGTCATGTTA
AAGAAAATACATGGCCCACAGCTGCTCAAGTTCAAGATTTTGGAGATAAATGGC
ATGAACTTCCGCTGATTAAATGTTTTGAAATACCCGACTTACTAGACCCATCGAT
AATATACTCTGACAAAAGTCATTCAATGAATAGGTCAGAGGTGTTGAAACATGT
CCGAATGAATCCGAACACTCCTATCCCTAGTAAAAAGGTGTTGCAGACTATGTTG
GACACAAAGGCTACCAATTGGAAAGAATTTCTTAAAGAGATTGATGAGAAGGGC
TTAGATGATGATGATCTAATTATTGGTCTTAAAGGAAAGGAGAGGGAACTGAAG
TTGGCAGGTAGATTTTTCTCCCTAATGTCTTGGAAATTGCGAGAATACTTTGTAA
TTACCGAATATTTGATAAAGACTCATTTCGTCCCTATGTTTAAAGGCCTGACAAT
GGCGGACGATCTAACTGCAGTCATTAAAAAGATGTTAGATTCCTCATCCGGCCA
AGGATTGAAGTCATATGAGGCAATTTGCATAGCCAATCACATTGATTACGAAAA
ATGGAATAACCACCAAAGGAAGTTATCAAACGGCCCAGTGTTCCGAGTTATGGG
CCAGTTCTTAGGTTATCCATCCTTAATCGAGAGAACTCATGAATTTTTTGAGAAA
AGTCTTATATACTACAATGGAAGACCAGACTTGATGCGTGTTCACAACAACACA
CTGATCAATTCAACCTCCCAACGAGTTTGTTGGCAAGGACAAGAGGGTGGACTG
GAAGGTCTACGGCAAAAAGGATGGACTATCCTCAATCTACTGGTTATTCAAAGA
GAGGCTAAAATCAGAAACACTGCTGTCAAAGTCTTGGCACAAGGTGATAATCAA
GTTATTTGCACACAGTATAAAACGAAGAAATCGAGAAACGTTGTAGAATTACAG
GGTGCTCTCAATCAAATGGTTTCTAATAATGAGAAAATTATGACTGCAATCAAAA
TAGGGACAGGGAAGTTAGGACTTTTGATAAATGACGATGAGACTATGCAATCTG
```

```
CAGATTACTTGAATTATGGAAAAATACCGATTTTCCGTGGAGTGATTAGAGGGTT

AGAGACCAAGAGATGGTCACGAGTGACTTGTGTCACCAATGACCAAATACCCAC

TTGTGCTAATATAATGAGCTCAGTTTCCACAAATGCTCTCACCGTAGCTCATTTTG

CTGAGAACCCAATCAATGCCATGATACAGTACAATTATTTTGGGACATTTGCTAG

ACTCTTGTTGATGATGCATGATCCTGCTCTTCGTCAATCATTGTATGAAGTTCAAG

ATAAGATACCGGGCTTGCACAGTTCTACTTTCAAATACGCCATGTTGTATTTGGA

CCCTTCCATTGGAGGAGTGTCGGGCATGTCTTTGTCCAGGTTTTTGATTAGAGCC

TTCCCAGATCCCGTAACAGAAAGTCTCTCATTCTGGAGATTCATCCATGTACATG

CTCGAAGTGAGCATCTGAAGGAGATGAGTGCAGTATTTGGAAACCCCGAGATAG

CCAAGTTTCGAATAACTCACATAGACAAGCTAGTAGAAGATCCAACCTCTCTGA

ACATCGCTATGGGAATGAGTCCAGCGAACTTGTTAAAGACTGAGGTTAAAAAT

GCTTAATCGAATCAAGACAAACCATCAGGAACCAGGTGATTAAGGATGCAACCA

TATATTTGTATCATGAAGAGGATCGGCTCAGAAGTTTCTTATGGTCAATAAATCC

TCTGTTCCCTAGATTTTTAAGTGAATTCAAATCAGGCACTTTTTTGGGAGTCGCA

GACGGGCTCATCAGTCTATTTCAAAATTCTCGTACTATTCGGAACTCCTTTAAGA

AAAAGTATCATAGGGAATTGGATGATTTGATTGTGAGGAGTGAGGTATCCTCTTT

GACACATTTAGGGAAACTTCATTTGAGAAGGGGATCATGTAAAATGTGGACATG

TTCAGCTACTCATGCTGACACATTAAGATACAAATCCTGGGGCCGTACAGTTATT

GGGACAACTGTACCCCATCCATTAGAAATGTTGGGTCCACAACATCGAAAAGAG

ACTCCTTGTGCACCATGTAACACATCAGGGTTCAATTATGTTTCTGTGCATTGTCC

AGACGGGATCCATGACGTCTTTAGTTCACGGGACCATTGCCTGCTTATCTAGGG

TCTAAAACATCTGAATCTACATCTATTTTGCAGCCTTGGGAAAGGGAAAGCAAA

GTCCCACTGATTAAAAGAGCTACACGTCTTAGAGATGCTATCTCTTGGTTTGTTG

AACCCGACTCTAAACTAGCAATGACTATACTTTCTAACATCCACTCTTTAACAGG

CGAAGAATGGACCAAAAGGCAGCATGGGTTCAAAAGAACAGGGTCTGCCCTTCA

TAGGTTTTCGACATCTCGGATGAGCCATGGTGGGTTCGCATCTCAGAGCACTGCA

GCATTGACCAGGTTGATGGCAACTACAGACACCATGAGGGATCTGGGAGATCAG

AATTTCGACTTTTTATTCCAAGCAACGTTGCTCTATGCTCAAATTACCACCACTGT

TGCAAGAGACGGATGGATCACCAGTTGTACAGATCATTATCATATTGCCTGTAAG

TCCTGTTTGAGACCCATAGAAGAGATCACCCTGGACTCAAGTATGGACTACACG

CCCCCAGATGTATCCCATGTGCTGAAGACATGGAGGAATGGGGAAGGTTCGTGG

GGACAAGAGATAAAACAGATCTATCCTTTAGAAGGGAATTGGAAGAATTTAGCA

CCTGCTGAGCAATCCTATCAAGTCGGCAGATGTATAGGTTTTCTATATGGAGACT

TGGCGTATAGAAAATCTACTCATGCCGAGGACAGTTCTCTATTTCCTCTATCTAT

ACAAGGTCGTATTAGAGGTCGAGGTTTCTTAAAAGGGTTGCTAGACGGATTAAT

GAGAGCAAGTTGCTGCCAAGTAATACACCGGAGAAGTCTGGCTCATTTGAAGAG

GCCGGCCAACGCAGTGTACGGAGGTTTGATTTACTTGATTGATAAATTGAGTGTA

TCACCTCCATTCCTTTCTCTTACTAGATCAGGACCTATTAGAGACGAATTAGAAA

CGATTCCCCACAAGATCCCAACCTCCTATCCGACAAGCAACCGTGATATGGGGG

TGATTGTCAGAAATTACTTCAAATACCAATGCCGTCTAATTGAAAAGGGAAAAT
```

-continued

```
ACAGATCACATTATTCACAATTATGGTTATTCTCAGATGTCTTATCCATAGACTTC

ATTGGACCATTCTCTATTTCCACCACCCTCTTGCAAATCCTATACAAGCCATTTTT

ATCTGGGAAAGATAAGAATGAGTTGAGAGAGCTGGCAAATCTTTCTTCATTGCT

AAGATCAGGAGAGGGGTGGGAAGACATACATGTGAAATTCTTCACCAAGGACAT

ATTATTGTGTCCAGAGGAAATCAGACATGCTTGCAAGTTCGGGATTGCTAAGGAT

AATAATAAAGACATGAGCTATCCCCCTTGGGGAAGGGAATCCAGAGGGACAATT

ACAACAATCCCTGTTTATTATACGACCACCCCTTACCCAAAGATGCTAGAGATGC

CTCCAAGAATCCAAAATCCCCTGCTGTCCGGAATCAGGTTGGGCCAATTACCAA

CTGGCGCTCATTATAAAATTCGGAGTATATTACATGGAATGGGAATCCATTACAG

GGACTTCTTGAGTTGTGGAGACGGCTCCGGAGGGATGACTGCTGCATTACTACG

AGAAAATGTGCATAGCAGAGGAATATTCAATAGTCTGTTAGAATTATCAGGGTC

AGTCATGCGAGGCGCCTCTCCTGAGCCCCCCAGTGCCCTAGAAACTTTAGGAGG

AGATAAATCGAGATGTGTAAATGGTGAAACATGTTGGGAATATCCATCTGACTT

ATGTGACCCAAGGACTTGGGACTATTTCCTCCGACTCAAAGCAGGCTTGGGCTT

CAAATTGATTTAATTGTAATGGATATGGAAGTTCGGGATTCTTCTACTAGCCTGA

AAATTGAGACGAATGTTAGAAATTATGTGCACCGGATTTTGGATGAGCAAGGAG

TTTTAATCTACAAGACTTATGGAACATATATTTGTGAGAGCGAAAAGAATGCAGT

AACAATCCTTGGTCCCATGTTCAAGACGGTCGACTTAGTTCAAACAGAATTTAGT

AGTTCTCAAACGTCTGAAGTATATATGGTATGTAAAGGTTTGAAGAAATTAATCG

ATGAACCCAATCCCGATTGGTCTTCCATCAATGAATCCTGGAAAAACCTGTACGC

ATTCCAGTCATCAGAACAGGAATTTGCCAGAGCAAAGAAGGTTAGTACATACTT

TACCTTGACAGGTATTCCCTCCCAATTCATTCCTGATCCTTTTGTAAACATTGAGA

CTATGCTACAAATATTCGGAGTACCCACGGGTGTGTCTCATGCGGCTGCCTTAAA

ATCATCTGATAGACCTGCAGATTTATTGACCATTAGCCTTTTTTATATGGCGATTA

TATCGTATTATAACATCAATCATATCAGAGTAGGACCGATACCTCCGAACCCCCC

ATCAGATGGAATTGCACAAAATGTGGGGATCGCTATAACTGGTATAAGCTTTTG

GCTGAGTTTGATGGAGAAAGACATTCCACTATATCAACAGTGTTTAGCAGTTATC

CAGCAATCATTCCCGATTAGGTGGGAGGCTGTTTCAGTAAAAGGAGGATACAAG

CAGAAGTGGAGTACTAGAGGTGATGGGCTCCCAAAAGATACCCGAACTTCAGAC

TCCTTGGCCCCAATCGGGAACTGGATCAGATCTCTGGAATTGGTCCGAAACCAA

GTTCGTCTAAATCCATTCAATGAGATCTTGTTCAATCAGCTATGTCGTACAGTGG

ATAATCATTTGAAATGGTCAAATTTGCGAAGAAACACAGGAATGATTGAATGGA

TCAATAGACGAATTTCAAAAGAAGACCGGTCTATACTGATGTTGAAGAGTGACC

TACACGAGGAAAACTCTTGGAGAGATTAAAAAATCATGAGGAGACTCCAAACTT

TAAGTATGAAAAAACTTTGATCCTTAAGACCCTCTTGTGGTTTTATTTTTATC

TGGTTTTGTGGTCTTCGT.
```

In some embodiments, the nucleic acid comprises the sequence of SEQ ID NO: 24, shown below (VSV vector: Convac V4 China):

ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC

CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAATGATCAATGAACAGTTTGAACCTCTTGTGCCAGAAGGT

CGTGACATTTTTGATGTGTGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

ATATTCTTCCGTCAAAAACCCTGCCTTCCACTTCTGGGGGCAATTGACAGCTCTT

CTGCTCAGATCCACCAGAGCAAGGAATGCCCGACAGCCTGATGACATTGAGTAT

ACATCTCTTACTACAGCAGGTTTGTTGTACGCTTATGCAGTAGGATCCTCTGCCG

ACTTGGCACAACAGTTTTGTGTTGGAGATAACAAATACACTCCAGATGATAGTAC

CGGAGGATTGACGACTAATGCACCGCCACAAGGCAGAGATGTGGTCGAATGGCT

CGGATGGTTTGAAGATCAAAACAGAAAACCGACTCCTGATATGATGCAGTATGC

GAAAAGAGCAGTCATGTCACTGCAAGGCCTAAGAGAGAAGACAATTGGCAAGT

ATGCTAAGTCAGAATTTGACAAATGACCCTATAATTCTCAGATCACCTATTATAT

ATTATGCTACATATGAAAAAAACTAACAGATATCATGGATAATCTCACAAAAGT

TCGTGAGTATCTCAAGTCCTATTCTCGTCTGGATCAGGCGGTAGGAGAGATAGAT

GAGATCGAAGCACAACGAGCTGAAAAGTCCAATTATGAGTTGTTCCAAGAGGAT

GGAGTGGAAGAGCATACTAAGCCCTCTTATTTTCAGGCAGCAGATGATTCTGAC

ACAGAATCTGAACCAGAAATTGAAGACAATCAAGGTTTGTATGCACCAGATCCA

GAAGCTGAGCAAGTTGAAGGCTTTATACAGGGGCCTTTAGATGACTATGCAGAT

GAGGAAGTGGATGTTGTATTTACTTCGGACTGGAAACAGCCTGAGCTTGAATCTG

ACGAGCATGGAAAGACCTTACGGTTGACATCGCCAGAGGGTTTAAGTGGAGAGC

AGAAATCCCAGTGGCTTTCGACGATTAAAGCAGTCGTGCAAAGTGCCAAATACT

GGAATCTGGCAGAGTGCACATTTGAAGCATCGGGAGAAGGGGTCATTATGAAGG

AGCGCCAGATAACTCCGGATGTATATAAGGTCACTCCAGTGATGAACACACATC

CGTCCCAATCAGAAGCAGTATCAGATGTTTGGTCTCTCAAAGACATCCATGAC

TTTCCAACCCAAGAAAGCAAGTCTTCAGCCTCTCACCATATCCTTGGATGAATTG

-continued

```
TTCTCATCTAGAGGAGAGTTCATCTCTGTCGGAGGTGACGGACGAATGTCTCATA

AAGAGGCCATCCTGCTCGGCCTGAGATACAAAAAGTTGTACAATCAGGCGAGAG

TCAAATATTCTCTGTAGACTATGAAAAAAAGTAACAGATATCACGATCTAAGTGT

TATCCCAATCCATTCATCATGAGTTCCTTAAAGAAGATTCTCGGTCTGAAGGGGA

AAGGTAAGAAATCTAAGAAATTAGGGATCGCACCACCCCCTTATGAAGAGGACA

CTAGCATGGAGTATGCTCCGAGCGCTCCAATTGACAAATCCTATTTTGGAGTTGA

CGAGATGGACACCTATGATCCGAATCAATTAAGATATGAGAAATTCTTCTTTACA

GTGAAAATGACGGTTAGATCTAATCGTCCGTTCAGAACATACTCAGATGTGGCA

GCCGCTGTATCCCATTGGGATCACATGTACATCGGAATGGCAGGGAAACGTCCC

TTCTACAAAATCTTGGCTTTTTTGGGTTCTTCTAATCTAAAGGCCACTCCAGCGGT

ATTGGCAGATCAAGGTCAACCAGAGTATCACACTCACTGCGAAGGCAGGGCTTA

TTTGCCACATAGGATGGGGAAGACCCCTCCCATGCTCAATGTACCAGAGCACTTC

AGAAGACCATTCAATATAGGTCTTTACAAGGGAACGATTGAGCTCACAATGACC

ATCTACGATGATGAGTCACTGGAAGCAGCTCCTATGATCTGGGATCATTTCAATT

CTTCCAAATTTTCTGATTTCAGAGAGAAGGCCTTAATGTTTGGCCTGATTGTCGA

GAAAAAGGCATCTGGAGCGTGGGTCCTGGATTCTATCAGCCACTTCAAATGAGC

TAGTCTAACTTCTAGCTTCTGAACAATCCCCGGTTTACTCAGTCTCTCCTAATTCC

AGCCTCTCGAACAACTAATATCCTGTCTTTTCTATCCCTATGAAAAAAACTAACA

GAGATCGATCTGTTTACGCGTGCCACCATGTTCGTGTTTCTGGTGCTGCTGCCTCT

GGTGAGCTCCCAGTGCGTGAACCTGACCACAAGGACCCAGCTGCCCCCTGCCTA

TACCAATTCCTTCACACGGGGCGTGTACTATCCCGACAAGGTGTTCCGGAGCAGC

GTGCTGCACTCCACACAGGATCTGTTTCTGCCTTTCTTTTCTAACGTGACCTGGTT

CCACGCCATCCACGTGAGCGGCACCAATGGCACAAAGCGGTTCGACAATCCAGT

GCTGCCCTTTAACGATGGCGTGTACTTCGCCTCCACCGAGAAGTCTAACATCATC

AGAGGCTGGATCTTTGGCACCACACTGGACAGCAAGACACAGTCCCTGCTGATC

GTGAACAATGCCACCAACGTGGTCATCAAGGTGTGCGAGTTCCAGTTTTGTAATG

ATCCATTCCTGGGCGTGTACTATCACAAGAACAATAAGTCTTGGATGGAGAGCG

AGTTTCGCGTGTATTCCTCTGCCAACAATTGCACATTTGAGTACGTGTCCCAGCC

CTTCCTGATGGACCTGGAGGGCAAGCAGGGCAATTTCAAGAACCTGAGGGAGTT

CGTGTTTAAGAATATCGATGGCTACTTCAAAATCTACTCCAAGCACACCCCAATC

AACCTGGTGCGCGACCTGCCACAGGGCTTCTCTGCCCTGGAGCCACTGGTGGATC

TGCCCATCGGCATCAACATCACCCGGTTTCAGACACTGCTGGCCCTGCACAGAA

GCTACCTGACACCAGGCGACAGCTCCTCTGGATGGACCGCAGGAGCAGCAGCCT

ACTATGTGGGCTATCTGCAGCCCAGGACCTTCCTGCTGAAGTACAACGAGAATG

GCACCATCACAGACGCCGTGGATTGCGCCCTGGATCCCCGTCTGAGACCAAGT

GTACACTGAAGAGCTTTACCGTGGAGAAGGGCATCTATCAGACAAGCAATTTCA

GGGTGCAGCCTACCGAGTCCATCGTGCGCTTTCCCAATATCACAAACCTGTGCCC

TTTTGGCGAGGTGTTCAACGCAACCCGCTTCGCCAGCGTGTACGCCTGGAATAGG

AAGCGCATCTCCAACTGCGTGGCCGACTATTCTGTGCTGTACAACAGCGCCTCCT

TCTCTACCTTTAAGTGCTATGGCGTGAGCCCCACAAAGCTGAATGACCTGTGCTT

TACCAACGTGTACGCCGATTCCTTCGTGATCAGGGGCGACGAGGTGCGCCAGAT
```

-continued

```
CGCACCAGGACAGACAGGCAAGATCGCAGACTACAATTATAAGCTGCCTGACGA
TTTCACCGGCTGCGTGATCGCCTGGAACTCTAACAATCTGGATAGCAAAGTGGGC
GGCAACTACAATTATCTGTACCGGCTGTTTAGAAAGTCTAATCTGAAGCCATTCG
AGAGGGACATCTCCACAGAAATCTACCAGGCCGGCTCTACCCCCTGCAATGGCG
TGGAGGGCTTTAACTGTTATTTCCCTCTGCAGAGCTACGGCTTCCAGCCAACAAA
CGGCGTGGGCTATCAGCCCTACCGCGTGGTGGTGCTGTCTTTTGAGCTGCTGCAC
GCACCTGCAACAGTGTGCGGACCAAAGAAGAGCACCAATCTGGTGAAGAACAA
GTGCGTGAACTTCAACTTCAACGGACTGACCGGAACAGGCGTGCTGACCGAGTC
CAACAAGAAGTTCCTGCCTTTTCAGCAGTTCGGCAGGGACATCGCAGATACCAC
AGACGCCGTGCGCGACCCTCAGACCCTGGAGATCCTGGACATCACACCATGCTC
CTTCGGCGGCGTGTCTGTGATCACACCAGGCACCAATACAAGCAACCAGGTGGC
CGTGCTGTATCAGGACGTGAATTGTACCGAGGTGCCAGTGGCAATCCACGCAGA
TCAGCTGACCCCTACATGGCGGGTGTACTCTACCGGCAGCAACGTGTTCCAGAC
AAGAGCCGGATGCCTGATCGGAGCAGAGCACGTGAACAATAGCTATGAGTGCGA
CATCCCTATCGGCGCCGGCATCTGTGCCTCCTACCAGACCCAGACAAACTCCCCA
AGGTCTGTGGGCGATACAGGCCTGTCCAAGAATCCAATCGAGCTGGTAGAGGGC
TGGTTCAGCAGTTGGAAAAGCTCCATCGCCTCCTTTTTCTTTATCATCGGCCTGAT
CATCGGACTGTTCCTGGTGCTCCGCGTGGGTATCCACCTGTGCATCAAGCTGAAG
CACACCAAGAAAAGACAGATTTATACAGACATCGAGATGAACCGCCTGGGAAA
GggatccggctccggcgagggcaggggaagtctactaacatgcggggacgtggaggaaaatcccggccccATGAAGTG
CCTTTTGTACTTAGCCTTTTTATTCATTGGGGTGAATTGCAAGTTCACCATAGTTT
TTCCACACAACCAAAAAGGAAACTGGAAAAATGTTCCTTCTAATTACCATTATTG
CCCGTCAAGCTCAGATTTAAATTGGCATAATGACTTAATAGGCACAGCCATACA
AGTCAAAATGCCCAAGAGTCACAAGGCTATTCAAGCAGACGGTTGGATGTGTCA
TGCTTCCAAATGGGTCACTACTTGTGATTTCCGCTGGTATGGACCGAAGTATATA
ACACAGTCCATCCGATCCTTCACTCCATCTGTAGAACAATGCAAGGAAAGCATT
GAACAAACGAAACAAGGAACTTGGCTGAATCCAGGCTTCCCTCCTCAAAGTTGT
GGATATGCAACTGTGACGGATGCCGAAGCAGTGATTGTCCAGGTGACTCCTCAC
CATGTGCTGGTTGATGAATACACAGGAGAATGGGTTGATTCACAGTTCATCAAC
GGAAAATGCAGCAATTACATATGCCCCACTGTCCATAACTCTACAACCTGGCATT
CTGACTATAAGGTCAAAGGGCTATGTGATTCTAACCTCATTTCCATGGACATCAC
CTTCTTCTCAGAGGACGGAGAGCTATCATCCCTGGGAAAGGAGGGCACAGGGTT
CAGAAGTAACTACTTTGCTTATGAAACTGGAGGCAAGGCCTGCAAAATGCAATA
CTGCAAGCATTGGGGAGTCAGACTCCCATCAGGTGTCTGGTTCGAGATGGCTGAT
AAGGATCTCTTTGCTGCAGCCAGATTCCCTGAATGCCCAGAAGGGTCAAGTATCT
CTGCTCCATCTCAGACCTCAGTGGATGTAAGTCTAATTCAGGACGTTGAGAGGAT
CTTGGATTATTCCCTCTGCCAAGAAACCTGGAGCAAAATCAGAGCGGGTCTTCCA
ATCTCTCCAGTGGATCTCAGCTATCTTGCTCCTAAAAACCCAGGAACCGGTCCTG
CTTTCACCATAATCAATGGTACCCTAAAATACTTTGAGACCAGATACATCAGAGT
CGATATTGCTGCTCCAATCCTCTCAAGAATGGTCGGAATGATCAGTGGAACTACC
```

-continued
```
ACAGAAAGGGAACTGTGGGATGACTGGGCACCATATGAAGACGTGGAAATTGG

ACCCAATGGAGTTCTGAGGACCAGTTCAGGATATAAGTTTCCTTTATACATGATT

GGACATGGTATGTTGGACTCCGATCTTCATCTTAGCTCAAAGGCTCAGGTGTTCG

AACATCCTCACATTCAAGACGCTGCTTCGCAACTTCCTGATGATGAGAGTTTATT

TTTTGGTGATACTGGGCTATCCAAAAATCCAATCGAGCTTGTAGAAGGTTGGTTC

AGTAGTTGGAAAAGCTCTATTGCCTCTTTTTTCTTTATCATAGGGTTAATCATTGG

ACTATTCTTGGTTCTCCGAGTTGGTATCCATCTTTGCATTAAATTAAAGCACACCA

AGAAAAGACAGATTTATACAGACATAGAGATGAACCGACTTGGAAAGTAAgCTA

GCCAGATTCTTCATGTTTGGACCAAATCAACTTGTGATACCATGCTCAAAGAGGC

CTCAATTATATTTGAGTTTTTAATTTTTATGAAAAAAACTAACAGCAATCATGGA

AGTCCACGATTTTGAGACCGACGAGTTCAATGATTTCAATGAAGATGACTATGCC

ACAAGAGAATTCCTGAATCCCGATGAGCGCATGACGTACTTGAATCATGCTGATT

ACAATTTGAATTCTCCTCTAATTAGTGATGATATTGACAATTTGATCAGGAAATT

CAATTCTCTTCCGATTCCCTCGATGTGGGATAGTAAGAACTGGGATGGAGTTCTT

GAGATGTTAACATCATGTCAAGCCAATCCCATCTCAACATCTCAGATGCATAAAT

GGATGGGAAGTTGGTTAATGTCTGATAATCATGATGCCAGTCAAGGGTATAGTTT

TTTACATGAAGTGGACAAAGAGGCAGAAATAACATTTGACGTGGTGGAGACCTT

CATCCGCGGCTGGGGCAACAAACCAATTGAATACATCAAAAAGGAAAGATGGA

CTGACTCATTCAAAATTCTCGCTTATTTGTGTCAAAAGTTTTTGGACTTACACAAG

TTGACATTAATCTTAAATGCTGTCTCTGAGGTGGAATTGCTCAACTTGGCGAGGA

CTTTCAAAGGCAAAGTCAGAAGAAGTTCTCATGGAACGAACATATGCAGGATTA

GGGTTCCCAGCTTGGGTCCTACTTTTATTTCAGAAGGATGGGCTTACTTCAAGAA

ACTTGATATTCTAATGGACCGAAACTTTCTGTTAATGGTCAAAGATGTGATTATA

GGGAGGATGCAAACGGTGCTATCCATGGTATGTAGAATAGACAACCTGTTCTCA

GAGCAAGACATCTTCTCCCTTCTAAATATCTACAGAATTGGAGATAAAATTGTGG

AGAGGCAGGGAAATTTTTCTTATGACTTGATTAAAATGGTGGAACCGATATGCA

ACTTGAAGCTGATGAAATTAGCAAGAGAATCAAGGCCTTTAGTCCCACAATTCC

CTCATTTTGAAAATCATATCAAGACTTCTGTTGATGAAGGGGCAAAAATTGACCG

AGGTATAAGATTCCTCCATGATCAGATAATGAGTGTGAAAACAGTGGATCTCAC

ACTGGTGATTTATGGATCGTTCAGACATTGGGGTCATCCTTTTATAGATTATTAC

ACTGGACTAGAAAAATTACATTCCCAAGTAACCATGAAGAAAGATATTGATGTG

TCATATGCAAAAGCACTTGCAAGTGATTTAGCTCGGATTGTTCTATTTCAACAGT

TCAATGATCATAAAAAGTGGTTCGTGAATGGAGACTTGCTCCCTCATGATCATCC

CTTTAAAAGTCATGTTAAAGAAAATACATGGCCCACAGCTGCTCAAGTTCAAGA

TTTTGGAGATAAATGGCATGAACTTCCGCTGATTAAATGTTTTGAAATACCCGAC

TTACTAGACCCATCGATAATATACTCTGACAAAAGTCATTCAATGAATAGGTCAG

AGGTGTTGAAACATGTCCGAATGAATCCGAACACTCCTATCCCTAGTAAAAAGG

TGTTGCAGACTATGTTGGACACAAAGGCTACCAATTGGAAAGAATTTCTTAAAG

AGATTGATGAGAAGGGCTTAGATGATGATGATCTAATTATTGGTCTTAAAGGAA

AGGAGAGGGAACTGAAGTTGGCAGGTAGATTTTTCTCCCTAATGTCTTGGAAATT

GCGAGAATACTTTGTAATTACCGAATATTTGATAAAGACTCATTTCGTCCCTATG
```

-continued

```
TTTAAAGGCCTGACAATGGCGGACGATCTAACTGCAGTCATTAAAAAGATGTTA
GATTCCTCATCCGGCCAAGGATTGAAGTCATATGAGGCAATTTGCATAGCCAATC
ACATTGATTACGAAAAATGGAATAACCACCAAAGGAAGTTATCAAACGGCCCAG
TGTTCCGAGTTATGGGCCAGTTCTTAGGTTATCCATCCTTAATCGAGAGAACTCA
TGAATTTTTTGAGAAAAGTCTTATATACTACAATGGAAGACCAGACTTGATGCGT
GTTCACAACAACACACTGATCAATTCAACCTCCCAACGAGTTTGTTGGCAAGGA
CAAGAGGGTGGACTGGAAGGTCTACGGCAAAAGGATGGACTATCCTCAATCTA
CTGGTTATTCAAAGAGAGGCTAAAATCAGAAACACTGCTGTCAAAGTCTTGGCA
CAAGGTGATAATCAAGTTATTTGCACACAGTATAAAACGAAGAAATCGAGAAAC
GTTGTAGAATTACAGGGTGCTCTCAATCAAATGGTTTCTAATAATGAGAAAATTA
TGACTGCAATCAAAATAGGGACAGGGAAGTTAGGACTTTTGATAAATGACGATG
AGACTATGCAATCTGCAGATTACTTGAATTATGGAAAAATACCGATTTTCCGTGG
AGTGATTAGAGGGTTAGAGACCAAGAGATGGTCACGAGTGACTTGTGTCACCAA
TGACCAAATACCCACTTGTGCTAATATAATGAGCTCAGTTTCCACAAATGCTCTC
ACCGTAGCTCATTTTGCTGAGAACCCAATCAATGCCATGATACAGTACAATTATT
TTGGGACATTTGCTAGACTCTTGTTGATGATGCATGATCCTGCTCTTCGTCAATCA
TTGTATGAAGTTCAAGATAAGATACCGGGCTTGCACAGTTCTACTTTCAAATACG
CCATGTTGTATTTGGACCCTTCCATTGGAGGAGTGTCGGGCATGTCTTTGTCCAG
GTTTTTGATTAGAGCCTTCCCAGATCCCGTAACAGAAAGTCTCTCATTCTGGAGA
TTCATCCATGTACATGCTCGAAGTGAGCATCTGAAGGAGATGAGTGCAGTATTTG
GAAACCCCGAGATAGCCAAGTTTCGAATAACTCACATAGACAAGCTAGTAGAAG
ATCCAACCTCTCTGAACATCGCTATGGGAATGAGTCCAGCGAACTTGTTAAAGAC
TGAGGTTAAAAAATGCTTAATCGAATCAAGACAAACCATCAGGAACCAGGTGAT
TAAGGATGCAACCATATATTTGTATCATGAAGAGGATCGGCTCAGAAGTTTCTTA
TGGTCAATAAATCCTCTGTTCCCTAGATTTTTAAGTGAATTCAAATCAGGCACTTT
TTTGGGAGTCGCAGACGGGCTCATCAGTCTATTTCAAAATTCTCGTACTATTCGG
AACTCCTTTAAGAAAAAGTATCATAGGGAATTGGATGATTTGATTGTGAGGAGT
GAGGTATCCTCTTTGACACATTTAGGGAAACTTCATTTGAGAAGGGGATCATGTA
AAATGTGGACATGTTCAGCTACTCATGCTGACACATTAAGATACAAATCCTGGG
GCCGTACAGTTATTGGGACAACTGTACCCCATCCATTAGAAATGTTGGGTCCACA
ACATCGAAAAGAGACTCCTTGTGCACCATGTAACACATCAGGGTTCAATTATGTT
TCTGTGCATTGTCCAGACGGGATCCATGACGTCTTTAGTTCACGGGACCATTGC
CTGCTTATCTAGGGTCTAAAACATCTGAATCTACATCTATTTTGCAGCCTTGGGA
AAGGGAAAGCAAAGTCCCACTGATTAAAAGAGCTACACGTCTTAGAGATGCTAT
CTCTTGGTTTGTTGAACCCGACTCTAAACTAGCAATGACTATACTTTCTAACATCC
ACTCTTTAACAGGCGAAGAATGGACCAAAAGGCAGCATGGGTTCAAAAGAACA
GGGTCTGCCCTTCATAGGTTTTCGACATCTCGGATGAGCCATGGTGGGTTCGCAT
CTCAGAGCACTGCAGCATTGACCAGGTTGATGGCAACTACAGACACCATGAGGG
ATCTGGGAGATCAGAATTTCGACTTTTTATTCCAAGCAACGTTGCTCTATGCTCA
AATTACCACCACTGTTGCAAGAGACGGATGGATCACCAGTTGTACAGATCATTAT
```

-continued
```
CATATTGCCTGTAAGTCCTGTTTGAGACCCATAGAAGAGATCACCCTGGACTCAA

GTATGGACTACACGCCCCCAGATGTATCCCATGTGCTGAAGACATGGAGGAATG

GGGAAGGTTCGTGGGGACAAGAGATAAAACAGATCTATCCTTTAGAAGGGAATT

GGAAGAATTTAGCACCTGCTGAGCAATCCTATCAAGTCGGCAGATGTATAGGTTT

TCTATATGGAGACTTGGCGTATAGAAAATCTACTCATGCCGAGGACAGTTCTCTA

TTTCCTCTATCTATACAAGGTCGTATTAGAGGTCGAGGTTTCTTAAAAGGGTTGC

TAGACGGATTAATGAGAGCAAGTTGCTGCCAAGTAATACACCGGAGAAGTCTGG

CTCATTTGAAGAGGCCGGCCAACGCAGTGTACGGAGGTTTGATTTACTTGATTGA

TAAATTGAGTGTATCACCTCCATTCCTTTCTCTTACTAGATCAGGACCTATTAGAG

ACGAATTAGAAACGATTCCCCACAAGATCCCAACCTCCTATCCGACAAGCAACC

GTGATATGGGGGTGATTGTCAGAAATTACTTCAAATACCAATGCCGTCTAATTGA

AAAGGGAAAATACAGATCACATTATTCACAATTATGGTTATTCTCAGATGTCTTA

TCCATAGACTTCATTGGACCATTCTCTATTTCCACCACCCTCTTGCAAATCCTATA

CAAGCCATTTTTATCTGGGAAAGATAAGAATGAGTTGAGAGAGCTGGCAAATCT

TTCTTCATTGCTAAGATCAGGAGAGGGGTGGGAAGACATACATGTGAAATTCTTC

ACCAAGGACATATTATTGTGTCCAGAGGAAATCAGACATGCTTGCAAGTTCGGG

ATTGCTAAGGATAATAATAAAGACATGAGCTATCCCCCTTGGGGAAGGGAATCC

AGAGGGACAATTACAACAATCCCTGTTTATTATACGACCACCCCTTACCCAAAG

ATGCTAGAGATGCCTCCAAGAATCCAAATCCCCTGCTGTCCGGAATCAGGTTG

GGCCAATTACCAACTGGCGCTCATTATAAAATTCGGAGTATATTACATGGAATGG

GAATCCATTACAGGGACTTCTTGAGTTGTGGAGACGGCTCCGGAGGGATGACTG

CTGCATTACTACGAGAAAATGTGCATAGCAGAGGAATATTCAATAGTCTGTTAG

AATTATCAGGGTCAGTCATGCGAGGCGCCTCTCCTGAGCCCCCCAGTGCCCTAGA

AACTTTAGGAGGAGATAAATCGAGATGTGTAAATGGTGAAACATGTTGGGAATA

TCCATCTGACTTATGTGACCCAAGGACTTGGGACTATTTCCTCCGACTCAAAGCA

GGCTTGGGGCTTCAAATTGATTTAATTGTAATGGATATGGAAGTTCGGGATTCTT

CTACTAGCCTGAAAATTGAGACGAATGTTAGAAATTATGTGCACCGGATTTTGGA

TGAGCAAGGAGTTTTAATCTACAAGACTTATGGAACATATATTTGTGAGAGCGA

AAAGAATGCAGTAACAATCCTTGGTCCCATGTTCAAGACGGTCGACTTAGTTCAA

ACAGAATTTAGTAGTTCTCAAACGTCTGAAGTATATATGGTATGTAAAGGTTTGA

AGAAATTAATCGATGAACCCAATCCCGATTGGTCTTCCATCAATGAATCCTGGAA

AAACCTGTACGCATTCCAGTCATCAGAACAGGAATTTGCCAGAGCAAAGAAGGT

TAGTACATACTTTACCTTGACAGGTATTCCCTCCCAATTCATTCCTGATCCTTTTG

TAAACATTGAGACTATGCTACAAATATTCGGAGTACCCACGGGTGTGTCTCATGC

GGCTGCCTTAAAATCATCTGATAGACCTGCAGATTTATTGACCATTAGCCTTTTTT

ATATGGCGATTATATCGTATTATAACATCAATCATATCAGAGTAGGACCGATACC

TCCGAACCCCCCATCAGATGGAATTGCACAAAATGTGGGGATCGCTATAACTGG

TATAAGCTTTTGGCTGAGTTTGATGGAGAAAGACATTCCACTATATCAACAGTGT

TTAGCAGTTATCCAGCAATCATTCCCGATTAGGTGGGAGGCTGTTTCAGTAAAAG

GAGGATACAAGCAGAAGTGGAGTACTAGAGGTGATGGGCTCCCAAAAGATACC

CGAACTTCAGACTCCTTGGCCCCAATCGGGAACTGGATCAGATCTCTGGAATTGG
```

-continued

```
TCCGAAACCAAGTTCGTCTAAATCCATTCAATGAGATCTTGTTCAATCAGCTATG

TCGTACAGTGGATAATCATTTGAAATGGTCAAATTTGCGAAGAAACACAGGAAT

GATTGAATGGATCAATAGACGAATTTCAAAAGAAGACCGGTCTATACTGATGTT

GAAGAGTGACCTACACGAGGAAAACTCTTGGAGAGATTAAAAAATCATGAGGA

GACTCCAAACTTTAAGTATGAAAAAAACTTTGATCCTTAAGACCCTCTTGTGGTT

TTTATTTTTATCTGGTTTTGTGGTCTTCGT.
```

In other embodiments, the nucleic acid comprises the sequence of SEQ ID NO: 25, shown below (VSV vector: Convac V4 South Africa):

```
ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC

CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAAATGATCAATGAACAGTTTGAACCTCTTGTGCCAGAAGGT

CGTGACATTTTTGATGTGTGGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

ATATTCTTCCGTCAAAAACCCTGCCTTCCACTTCTGGGGGCAATTGACAGCTCTT

CTGCTCAGATCCACCAGAGCAAGGAATGCCCGACAGCCTGATGACATTGAGTAT

ACATCTCTTACTACAGCAGGTTTGTTGTACGCTTATGCAGTAGGATCCTCTGCCG

ACTTGGCACAACAGTTTTGTGTTGGAGATAACAAATACACTCCAGATGATAGTAC

CGGAGGATTGACGACTAATGCACCGCCACAAGGCAGAGATGTGGTCGAATGGCT

CGGATGGTTTGAAGATCAAAACAGAAAACCGACTCCTGATATGATGCAGTATGC

GAAAAGAGCAGTCATGTCACTGCAAGGCCTAAGAGAAGACAATTGGCAAGT

ATGCTAAGTCAGAATTTGACAAATGACCCTATAATTCTCAGATCACCTATTATAT

ATTATGCTACATATGAAAAAAACTAACAGATATCATGGATAATCTCACAAAAGT

TCGTGAGTATCTCAAGTCCTATTCTCGTCTGGATCAGGCGGTAGGAGAGATAGAT

GAGATCGAAGCACAACGAGCTGAAAAGTCCAATTATGAGTTGTTCCAAGAGGAT

GGAGTGGAAGAGCATACTAAGCCCTCTTATTTTCAGGCAGCAGATGATTCTGAC

ACAGAATCTGAACCAGAAATTGAAGACAATCAAGGTTTGTATGCACCAGATCCA

GAAGCTGAGCAAGTTGAAGGCTTTATACAGGGGCCTTTAGATGACTATGCAGAT
```

```
GAGGAAGTGGATGTTGTATTTACTTCGGACTGGAAACAGCCTGAGCTTGAATCTG

ACGAGCATGGAAAGACCTTACGGTTGACATCGCCAGAGGGTTTAAGTGGAGAGC

AGAAATCCCAGTGGCTTTCGACGATTAAAGCAGTCGTGCAAAGTGCCAAATACT

GGAATCTGGCAGAGTGCACATTTGAAGCATCGGGAGAAGGGGTCATTATGAAGG

AGCGCCAGATAACTCCGGATGTATATAAGGTCACTCCAGTGATGAACACACATC

CGTCCCAATCAGAAGCAGTATCAGATGTTTGGTCTCTCTCAAAGACATCCATGAC

TTTCCAACCCAAGAAAGCAAGTCTTCAGCCTCTCACCATATCCTTGGATGAATTG

TTCTCATCTAGAGGAGAGTTCATCTCTGTCGGAGGTGACGGACGAATGTCTCATA

AAGAGGCCATCCTGCTCGGCCTGAGATACAAAAAGTTGTACAATCAGGCGAGAG

TCAAATATTCTCTGTAGACTATGAAAAAAAGTAACAGATATCACGATCTAAGTGT

TATCCCAATCCATTCATCATGAGTTCCTTAAAGAAGATTCTCGGTCTGAAGGGGA

AAGGTAAGAAATCTAAGAAATTAGGGATCGCACCACCCCCTTATGAAGAGGACA

CTAGCATGGAGTATGCTCCGAGCGCTCCAATTGACAAATCCTATTTTGGAGTTGA

CGAGATGGACACCTATGATCCGAATCAATTAAGATATGAGAAATTCTTCTTTACA

GTGAAAATGACGGTTAGATCTAATCGTCCGTTCAGAACATACTCAGATGTGGCA

GCCGCTGTATCCCATTGGGATCACATGTACATCGGAATGGCAGGGAAACGTCCC

TTCTACAAAATCTTGGCTTTTTTGGGTTCTTCTAATCTAAAGGCCACTCCAGCGGT

ATTGGCAGATCAAGGTCAACCAGAGTATCACACTCACTGCGAAGGCAGGGCTTA

TTTGCCACATAGGATGGGGAAGACCCCTCCCATGCTCAATGTACCAGAGCACTTC

AGAAGACCATTCAATATAGGTCTTTACAAGGGAACGATTGAGCTCACAATGACC

ATCTACGATGATGAGTCACTGGAAGCAGCTCCTATGATCTGGGATCATTTCAATT

CTTCCAAATTTTCTGATTTCAGAGAGAAGGCCTTAATGTTTGGCCTGATTGTCGA

GAAAAAGGCATCTGGAGCGTGGGTCCTGGATTCTATCAGCCACTTCAAATGAGC

TAGTCTAACTTCTAGCTTCTGAACAATCCCCGGTTTACTCAGTCTCTCCTAATTCC

AGCCTCTCGAACAACTAATATCCTGTCTTTTCTATCCCTATGAAAAAAACTAACA

GAGATCGATCTGTTTACGCGTGCCACCATGTTCGTGTTTCTGGTGCTGCTGCCTCT

GGTGAGCTCCCAGTGCGTGAACTTCACCACAAGGACCCAGCTGCCCCCTGCCTAT

ACCAATTCCTTCACACGGGGCGTGTACTATCCCGACAAGGTGTTCCGGAGCAGC

GTGCTGCACTCCACACAGGATCTGTTTCTGCCTTTCTTTTCTAACGTGACCTGGTT

CCACGCCATCCACGTGAGCGGCACCAATGGCACAAAGCGGTTCGCCAATCCAGT

GCTGCCCTTTAACGATGGCGTGTACTTCGCCTCCACCGAGAAGTCTAACATCATC

AGAGGCTGGATCTTTGGCACCACACTGGACAGCAAGACACAGTCCCTGCTGATC

GTGAACAATGCCACCAACGTGGTCATCAAGGTGTGCGAGTTCCAGTTTTGTAATG

ATCCATTCCTGGGCGTGTACTATCACAAGAACAATAAGTCTTGGATGGAGAGCG

AGTTTCGCGTGTATTCCTCTGCCAACAATTGCACATTTGAGTACGTGTCCCAGCC

CTTCCTGATGGACCTGGAGGGCAAGCAGGGCAATTTCAAGAACCTGAGGGAGTT

CGTGTTTAAGAATATCGATGGCTACTTCAAAATCTACTCCAAGCACACCCCAATC

AACCTGGTGCGCGGCCTGCCACAGGGCTTCTCTGCCCTGGAGCCACTGGTGGATC

TGCCCATCGGCATCAACATCACCCGGTTTCAGACACTGCTGGCCCTGCACAGAA

GCTACCTGACACCAGGCGACAGCTCCTCTGGATGGACCGCAGGAGCAGCAGCCT
```

-continued

```
ACTATGTGGGCTATCTGCAGCCCAGGACCTTCCTGCTGAAGTACAACGAGAATG
GCACCATCACAGACGCCGTGGATTGCGCCCTGGATCCCCTGTCTGAGACCAAGT
GTACACTGAAGAGCTTTACCGTGGAGAAGGGCATCTATCAGACAAGCAATTTCA
GGGTGCAGCCTACCGAGTCCATCGTGCGCTTTCCCAATATCACAAACCTGTGCCC
TTTTGGCGAGGTGTTCAACGCAACCCGCTTCGCCAGCGTGTACGCCTGGAATAGG
AAGCGCATCTCCAACTGCGTGGCCGACTATTCTGTGCTGTACAACAGCGCCTCCT
TCTCTACCTTTAAGTGCTATGGCGTGAGCCCCACAAAGCTGAATGACCTGTGCTT
TACCAACGTGTACGCCGATTCCTTCGTGATCAGGGGCGACGAGGTGCGCCAGAT
CGCACCAGGACAGACAGGCAATATCGCAGACTACAATTATAAGCTGCCTGACGA
TTTCACCGGCTGCGTGATCGCCTGGAACTCTAACAATCTGGATAGCAAAGTGGGC
GGCAACTACAATTATCTGTACCGGCTGTTTAGAAAGTCTAATCTGAAGCCATTCG
AGAGGGACATCTCCACAGAAATCTACCAGGCCGGCTCTACCCCCTGCAATGGCG
TGAAGGGCTTTAACTGTTATTTCCCTCTGCAGAGCTACGGCTTCCAGCCAACATA
TGGCGTGGGCTATCAGCCCTACCGCGTGGTGGTGCTGTCTTTTGAGCTGCTGCAC
GCACCTGCAACAGTGTGCGGACCAAAGAAGAGCACCAATCTGGTGAAGAACAA
GTGCGTGAACTTCAACTTCAACGGACTGACCGGAACAGGCGTGCTGACCGAGTC
CAACAAGAAGTTCCTGCCTTTTCAGCAGTTCGGCAGGGACATCGCAGATACCAC
AGACGCCGTGCGCGACCCTCAGACCCTGGAGATCCTGGACATCACACCATGCTC
CTTCGGCGGCGTGTCTGTGATCACACCAGGCACCAATACAAGCAACCAGGTGGC
CGTGCTGTATCAGGGCGTGAATTGTACCGAGGTGCCAGTGGCAATCCACGCAGA
TCAGCTGACCCCTACATGGCGGGTGTACTCTACCGGCAGCAACGTGTTCCAGAC
AAGAGCCGGATGCCTGATCGGAGCAGAGCACGTGAACAATAGCTATGAGTGCGA
CATCCCTATCGGCGCCGGCATCTGTGCCTCCTACCAGACCCAGACAAACTCCCCA
AGGTCTGTGGGCGATACAGGCCTGTCCAAGAATCCAATCGAGCTGGTAGAGGGC
TGGTTCAGCAGTTGGAAAAGCTCCATCGCCTCCTTTTTCTTTATCATCGGCCTGAT
CATCGGACTGTTCCTGGTGCTCCGCGTGGGTATCCACCTGTGCATCAAGCTGAAG
CACACCAAGAAAAGACAGATTTATACAGACATCGAGATGAACCGCCTGGGAAA
GggatccggctccggcgagggcaggggaagtctactaacatgcgggggacgtggaggaaaatcccggccccATGAAGTG
CCTTTTGTACTTAGCCTTTTTATTCATTGGGGTGAATTGCAAGTTCACCATAGTTT
TTCCACACAACCAAAAAGGAAACTGGAAAAATGTTCCTTCTAATTACCATTATTG
CCCGTCAAGCTCAGATTTAAATTGGCATAATGACTTAATAGGCACAGCCATACA
AGTCAAAATGCCCAAGAGTCACAAGGCTATTCAAGCAGACGGTTGGATGTGTCA
TGCTTCCAAATGGGTCACTACTTGTGATTTCCGCTGGTATGGACCGAAGTATATA
ACACAGTCCATCCGATCCTTCACTCCATCTGTAGAACAATGCAAGGAAAGCATT
GAACAAACGAAACAAGGAACTTGGCTGAATCCAGGCTTCCCTCCTCAAAGTTGT
GGATATGCAACTGTGACGGATGCCGAAGCAGTGATTGTCCAGGTGACTCCTCAC
CATGTGCTGGTTGATGAATACACAGGAGAATGGGTTGATTCACAGTTCATCAAC
GGAAAATGCAGCAATTACATATGCCCCACTGTCCATAACTCTACAACCTGGCATT
CTGACTATAAGGTCAAAGGGCTATGTGATTCTAACCTCATTTCCATGGACATCAC
CTTCTTCTCAGAGGACGGAGAGCTATCATCCCTGGGAAAGGAGGGCACAGGGTT
CAGAAGTAACTACTTTGCTTATGAAACTGGAGGCAAGGCCTGCAAAATGCAATA
```

-continued

```
CTGCAAGCATTGGGGAGTCAGACTCCCATCAGGTGTCTGGTTCGAGATGGCTGAT
AAGGATCTCTTTGCTGCAGCCAGATTCCCTGAATGCCCAGAAGGGTCAAGTATCT
CTGCTCCATCTCAGACCTCAGTGGATGTAAGTCTAATTCAGGACGTTGAGAGGAT
CTTGGATTATTCCCTCTGCCAAGAAACCTGGAGCAAAATCAGAGCGGGTCTTCCA
ATCTCTCCAGTGGATCTCAGCTATCTTGCTCCTAAAAACCCAGGAACCGGTCCTG
CTTTCACCATAATCAATGGTACCCTAAAATACTTTGAGACCAGATACATCAGAGT
CGATATTGCTGCTCCAATCCTCTCAAGAATGGTCGGAATGATCAGTGGAACTACC
ACAGAAAGGGAACTGTGGGATGACTGGGCACCATATGAAGACGTGGAAATTGG
ACCCAATGGAGTTCTGAGGACCAGTTCAGGATATAAGTTTCCTTTATACATGATT
GGACATGGTATGTTGGACTCCGATCTTCATCTTAGCTCAAAGGCTCAGGTGTTCG
AACATCCTCACATTCAAGACGCTGCTTCGCAACTTCCTGATGATGAGAGTTTATT
TTTTGGTGATACTGGGCTATCCAAAAATCCAATCGAGCTTGTAGAAGGTTGGTTC
AGTAGTTGGAAAAGCTCTATTGCCTCTTTTTTCTTTATCATAGGGTTAATCATTGG
ACTATTCTTGGTTCTCCGAGTTGGTATCCATCTTTGCATTAAATTAAAGCACACCA
AGAAAAGACAGATTTATACAGACATAGAGATGAACCGACTTGGAAAGTAAgCTA
GCCAGATTCTTCATGTTTGGACCAAATCAACTTGTGATACCATGCTCAAAGAGGC
CTCAATTATATTTGAGTTTTTAATTTTTATGAAAAAAACTAACAGCAATCATGGA
AGTCCACGATTTTGAGACCGACGAGTTCAATGATTTCAATGAAGATGACTATGCC
ACAAGAGAATTCCTGAATCCCGATGAGCGCATGACGTACTTGAATCATGCTGATT
ACAATTTGAATTCTCCTCTAATTAGTGATGATATTGACAATTTGATCAGGAAATT
CAATTCTCTTCCGATTCCCTCGATGTGGGATAGTAAGAACTGGGATGGAGTTCTT
GAGATGTTAACATCATGTCAAGCCAATCCCATCTCAACATCTCAGATGCATAAAT
GGATGGGAAGTTGGTTAATGTCTGATAATCATGATGCCAGTCAAGGGTATAGTTT
TTTACATGAAGTGGACAAAGAGGCAGAAATAACATTTGACGTGGTGGAGACCTT
CATCCGCGGCTGGGCAACAAACCAATTGAATACATCAAAAAGGAAAGATGGA
CTGACTCATTCAAAATTCTCGCTTATTTGTGTCAAAAGTTTTTGGACTTACACAAG
TTGACATTAATCTTAAATGCTGTCTCTGAGGTGGAATTGCTCAACTTGGCGAGGA
CTTTCAAAGGCAAAGTCAGAAGAAGTTCTCATGGAACGAACATATGCAGGATTA
GGGTTCCCAGCTTGGGTCCTACTTTTATTTCAGAAGGATGGGCTTACTTCAAGAA
ACTTGATATTCTAATGGACCGAAACTTTCTGTTAATGGTCAAAGATGTGATTATA
GGGAGGATGCAAACGGTGCTATCCATGGTATGTAGAATAGACAACCTGTTCTCA
GAGCAAGACATCTTCTCCCTTCTAAATATCTACAGAATTGGAGATAAAATTGTGG
AGAGGCAGGGAAATTTTTCTTATGACTTGATTAAAATGGTGGAACCGATATGCA
ACTTGAAGCTGATGAAATTAGCAAGAGAATCAAGGCCTTTAGTCCCACAATTCC
CTCATTTTGAAAATCATATCAAGACTTCTGTTGATGAAGGGGCAAAAATTGACCG
AGGTATAAGATTCCTCCATGATCAGATAATGAGTGTGAAAACAGTGGATCTCAC
ACTGGTGATTTATGGATCGTTCAGACATTGGGGTCATCCTTTTATAGATTATTAC
ACTGGACTAGAAAAATTACATTCCCAAGTAACCATGAAGAAAGATATTGATGTG
TCATATGCAAAAGCACTTGCAAGTGATTTAGCTCGGATTGTTCTATTTCAACAGT
TCAATGATCATAAAAAGTGGTTCGTGAATGGAGACTTGCTCCCTCATGATCATCC
```

-continued

```
CTTTAAAAGTCATGTTAAAGAAAATACATGGCCCACAGCTGCTCAAGTTCAAGA

TTTTGGAGATAAATGGCATGAACTTCCGCTGATTAAATGTTTTGAAATACCCGAC

TTACTAGACCCATCGATAATATACTCTGACAAAAGTCATTCAATGAATAGGTCAG

AGGTGTTGAAACATGTCCGAATGAATCCGAACACTCCTATCCCTAGTAAAAAGG

TGTTGCAGACTATGTTGGACACAAAGGCTACCAATTGGAAAGAATTTCTTAAAG

AGATTGATGAGAAGGGCTTAGATGATGATGATCTAATTATTGGTCTTAAAGGAA

AGGAGAGGGAACTGAAGTTGGCAGGTAGATTTTTCTCCCTAATGTCTTGGAAATT

GCGAGAATACTTTGTAATTACCGAATATTTGATAAAGACTCATTTCGTCCCTATG

TTTAAAGGCCTGACAATGGCGGACGATCTAACTGCAGTCATTAAAAAGATGTTA

GATTCCTCATCCGGCCAAGGATTGAAGTCATATGAGGCAATTTGCATAGCCAATC

ACATTGATTACGAAAAATGGAATAACCACCAAAGGAAGTTATCAAACGGCCCAG

TGTTCCGAGTTATGGGCCAGTTCTTAGGTTATCCATCCTTAATCGAGAGAACTCA

TGAATTTTTTGAGAAAAGTCTTATATACTACAATGGAAGACCAGACTTGATGCGT

GTTCACAACAACACACTGATCAATTCAACCTCCCAACGAGTTTGTTGGCAAGGA

CAAGAGGGTGGACTGGAAGGTCTACGGCAAAAAGGATGGACTATCCTCAATCTA

CTGGTTATTCAAAGAGAGGCTAAAATCAGAAACACTGCTGTCAAAGTCTTGGCA

CAAGGTGATAATCAAGTTATTTGCACACAGTATAAAACGAAGAAATCGAGAAAC

GTTGTAGAATTACAGGGTGCTCTCAATCAAATGGTTTCTAATAATGAGAAAATTA

TGACTGCAATCAAAATAGGGACAGGGAAGTTAGGACTTTTGATAAATGACGATG

AGACTATGCAATCTGCAGATTACTTGAATTATGGAAAAATACCGATTTTCCGTGG

AGTGATTAGAGGGTTAGAGACCAAGAGATGGTCACGAGTGACTTGTGTCACCAA

TGACCAAATACCCACTTGTGCTAATATAATGAGCTCAGTTTCCACAAATGCTCTC

ACCGTAGCTCATTTTGCTGAGAACCCAATCAATGCCATGATACAGTACAATTATT

TTGGGACATTTGCTAGACTCTTGTTGATGATGCATGATCCTGCTCTTCGTCAATCA

TTGTATGAAGTTCAAGATAAGATACCGGGCTTGCACAGTTCTACTTTCAAATACG

CCATGTTGTATTTGGACCCTTCCATTGGAGGAGTGTCGGGCATGTCTTTGTCCAG

GTTTTTGATTAGAGCCTTCCCAGATCCCGTAACAGAAAGTCTCTCATTCTGGAGA

TTCATCCATGTACATGCTCGAAGTGAGCATCTGAAGGAGATGAGTGCAGTATTTG

GAAACCCCGAGATAGCCAAGTTTCGAATAACTCACATAGACAAGCTAGTAGAAG

ATCCAACCTCTCTGAACATCGCTATGGGAATGAGTCCAGCGAACTTGTTAAAGAC

TGAGGTTAAAAAATGCTTAATCGAATCAAGACAAACCATCAGGAACCAGGTGAT

TAAGGATGCAACCATATATTTGTATCATGAAGAGGATCGGCTCAGAAGTTTCTTA

TGGTCAATAAATCCTCTGTTCCCTAGATTTTTAAGTGAATTCAAATCAGGCACTTT

TTTGGGAGTCGCAGACGGGCTCATCAGTCTATTTCAAAATTCTCGTACTATTCGG

AACTCCTTTAAGAAAAAGTATCATAGGGAATTGGATGATTTGATTGTGAGGAGT

GAGGTATCCTCTTTGACACATTTAGGGAAACTTCATTTGAGAAGGGGATCATGTA

AAATGTGGACATGTTCAGCTACTCATGCTGACACATTAAGATACAAATCCTGGG

GCCGTACAGTTATTGGGACAACTGTACCCCATCCATTAGAAATGTTGGGTCCACA

ACATCGAAAAGAGACTCCTTGTGCACCATGTAACACATCAGGGTTCAATTATGTT

TCTGTGCATTGTCCAGACGGGATCCATGACGTCTTTAGTTCACGGGACCATTGC

CTGCTTATCTAGGGTCTAAAACATCTGAATCTACATCTATTTTGCAGCCTTGGGA
```

-continued

```
AAGGGAAAGCAAAGTCCCACTGATTAAAAGAGCTACACGTCTTAGAGATGCTAT

CTCTTGGTTTGTTGAACCCGACTCTAAACTAGCAATGACTATACTTTCTAACATCC

ACTCTTTAACAGGCGAAGAATGGACCAAAAGGCAGCATGGGTTCAAAAGAACA

GGGTCTGCCCTTCATAGGTTTTCGACATCTCGGATGAGCCATGGTGGGTTCGCAT

CTCAGAGCACTGCAGCATTGACCAGGTTGATGGCAACTACAGACACCATGAGGG

ATCTGGGAGATCAGAATTTCGACTTTTTATTCCAAGCAACGTTGCTCTATGCTCA

AATTACCACCACTGTTGCAAGAGACGGATGGATCACCAGTTGTACAGATCATTAT

CATATTGCCTGTAAGTCCTGTTTGAGACCCATAGAAGAGATCACCCTGGACTCAA

GTATGGACTACACGCCCCCAGATGTATCCCATGTGCTGAAGACATGGAGGAATG

GGGAAGGTTCGTGGGGACAAGAGATAAAACAGATCTATCCTTTAGAAGGGAATT

GGAAGAATTTAGCACCTGCTGAGCAATCCTATCAAGTCGGCAGATGTATAGGTTT

TCTATATGGAGACTTGGCGTATAGAAAATCTACTCATGCCGAGGACAGTTCTCTA

TTTCCTCTATCTATACAAGGTCGTATTAGAGGTCGAGGTTTCTTAAAAGGGTTGC

TAGACGGATTAATGAGAGCAAGTTGCTGCCAAGTAATACACCGGAGAAGTCTGG

CTCATTTGAAGAGGCCGGCCAACGCAGTGTACGGAGGTTTGATTTACTTGATTGA

TAAATTGAGTGTATCACCTCCATTCCTTTCTCTTACTAGATCAGGACCTATTAGAG

ACGAATTAGAAACGATTCCCCACAAGATCCCAACCTCCTATCCGACAAGCAACC

GTGATATGGGGGTGATTGTCAGAAATTACTTCAAATACCAATGCCGTCTAATTGA

AAAGGGAAAATACAGATCACATTATTCACAATTATGGTTATTCTCAGATGTCTTA

TCCATAGACTTCATTGGACCATTCTCTATTTCCACCACCCTCTTGCAAATCCTATA

CAAGCCATTTTTATCTGGGAAAGATAAGAATGAGTTGAGAGAGCTGGCAAATCT

TTCTTCATTGCTAAGATCAGGAGAGGGGTGGGAAGACATACATGTGAAATTCTTC

ACCAAGGACATATTATTGTGTCCAGAGGAAATCAGACATGCTTGCAAGTTCGGG

ATTGCTAAGGATAATAATAAAGACATGAGCTATCCCCCTTGGGGAAGGGAATCC

AGAGGGACAATTACAACAATCCCTGTTTATTATACGACCACCCCTTACCCAAAG

ATGCTAGAGATGCCTCCAAGAATCCAAAATCCCCTGCTGTCCGGAATCAGGTTG

GGCCAATTACCAACTGGCGCTCATTATAAAATTCGGAGTATATTACATGGAATGG

GAATCCATTACAGGGACTTCTTGAGTTGTGGAGACGGCTCCGGAGGGATGACTG

CTGCATTACTACGAGAAAATGTGCATAGCAGAGGAATATTCAATAGTCTGTTAG

AATTATCAGGGTCAGTCATGCGAGGCGCCTCTCCTGAGCCCCCCAGTGCCCTAGA

AACTTTAGGAGGAGATAAATCGAGATGTGTAAATGGTGAAACATGTTGGGAATA

TCCATCTGACTTATGTGACCCAAGGACTTGGGACTATTTCCTCCGACTCAAAGCA

GGCTTGGGGCTTCAAATTGATTTAATTGTAATGGATATGGAAGTTCGGGATTCTT

CTACTAGCCTGAAAATTGAGACGAATGTTAGAAATTATGTGCACCGGATTTTGGA

TGAGCAAGGAGTTTTAATCTACAAGACTTATGGAACATATATTTGTGAGAGCGA

AAAGAATGCAGTAACAATCCTTGGTCCCATGTTCAAGACGGTCGACTTAGTTCAA

ACAGAATTTAGTAGTTCTCAAACGTCTGAAGTATATATGGTATGTAAAGGTTTGA

AGAAATTAATCGATGAACCCAATCCCGATTGGTCTTCCATCAATGAATCCTGGAA

AAACCTGTACGCATTCCAGTCATCAGAACAGGAATTTGCCAGAGCAAAGAAGGT

TAGTACATACTTTACCTTGACAGGTATTCCCTCCCAATTCATTCCTGATCCTTTTG
```

-continued

```
TAAACATTGAGACTATGCTACAAATATTCGGAGTACCCACGGGTGTGTCTCATGC

GGCTGCCTTAAAATCATCTGATAGACCTGCAGATTTATTGACCATTAGCCTTTTT

ATATGGCGATTATATCGTATTATAACATCAATCATATCAGAGTAGGACCGATACC

TCCGAACCCCCCATCAGATGGAATTGCACAAAATGTGGGGATCGCTATAACTGG

TATAAGCTTTTGGCTGAGTTTGATGGAGAAAGACATTCCACTATATCAACAGTGT

TTAGCAGTTATCCAGCAATCATTCCCGATTAGGTGGGAGGCTGTTTCAGTAAAAG

GAGGATACAAGCAGAAGTGGAGTACTAGAGGTGATGGGCTCCCAAAAGATACC

CGAACTTCAGACTCCTTGGCCCCAATCGGGAACTGGATCAGATCTCTGGAATTGG

TCCGAAACCAAGTTCGTCTAAATCCATTCAATGAGATCTTGTTCAATCAGCTATG

TCGTACAGTGGATAATCATTTGAAATGGTCAAATTTGCGAAGAAACACAGGAAT

GATTGAATGGATCAATAGACGAATTTCAAAAGAAGACCGGTCTATACTGATGTT

GAAGAGTGACCTACACGAGGAAAACTCTTGGAGAGATTAAAAAATCATGAGGA

GACTCCAAACTTTAAGTATGAAAAAAACTTTGATCCTTAAGACCCTCTTGTGGTT

TTTATTTTTATCTGGTTTTGTGGTCTTCGT.
```

In one embodiment, the nucleic acid comprises the sequence of SEQ ID NO: 26, shown below (VSV vector: Convac V5 China):

```
ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC

CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAATGATCAATGAACAGTTTGAACCTCTTGTGCCAGAAGGT

CGTGACATTTTTGATGTGTGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

ATATTCTTCCGTCAAAAACCCTGCCTTCCACTTCTGGGGGCAATTGACAGCTCTT

CTGCTCAGATCCACCAGAGCAAGGAATGCCCGACAGCCTGATGACATTGAGTAT

ACATCTCTTACTACAGCAGGTTTGTTGTACGCTTATGCAGTAGGATCCTCTGCCG

ACTTGGCACAACAGTTTTGTGTTGGAGATAACAAATACACTCCAGATGATAGTAC

CGGAGGATTGACGACTAATGCACCGCCACAAGGCAGAGATGTGGTCGAATGGCT

CGGATGGTTTGAAGATCAAAACAGAAAACCGACTCCTGATATGATGCAGTATGC
```

-continued

```
GAAAAGAGCAGTCATGTCACTGCAAGGCCTAAGAGAGAAGACAATTGGCAAGT

ATGCTAAGTCAGAATTTGACAAATGACCCTATAATTCTCAGATCACCTATTATAT

ATTATGCTACATATGAAAAAAACTAACAGATATCATGGATAATCTCACAAAAGT

TCGTGAGTATCTCAAGTCCTATTCTCGTCTGGATCAGGCGGTAGGAGAGATAGAT

GAGATCGAAGCACAACGAGCTGAAAAGTCCAATTATGAGTTGTTCCAAGAGGAT

GGAGTGGAAGAGCATACTAAGCCCTCTTATTTTCAGGCAGCAGATGATTCTGAC

ACAGAATCTGAACCAGAAATTGAAGACAATCAAGGTTTGTATGCACCAGATCCA

GAAGCTGAGCAAGTTGAAGGCTTTATACAGGGGCCTTTAGATGACTATGCAGAT

GAGGAAGTGGATGTTGTATTTACTTCGGACTGGAAACAGCCTGAGCTTGAATCTG

ACGAGCATGGAAAGACCTTACGGTTGACATCGCCAGAGGGTTTAAGTGGAGAGC

AGAAATCCCAGTGGCTTTCGACGATTAAAGCAGTCGTGCAAAGTGCCAAATACT

GGAATCTGGCAGAGTGCACATTTGAAGCATCGGGAGAAGGGGTCATTATGAAGG

AGCGCCAGATAACTCCGGATGTATATAAGGTCACTCCAGTGATGAACACACATC

CGTCCCAATCAGAAGCAGTATCAGATGTTTGGTCTCTCAAAGACATCCATGAC

TTTCCAACCCAAGAAAGCAAGTCTTCAGCCTCTCACCATATCCTTGGATGAATTG

TTCTCATCTAGAGGAGAGTTCATCTCTGTCGGAGGTGACGGACGAATGTCTCATA

AAGAGGCCATCCTGCTCGGCCTGAGATACAAAAAGTTGTACAATCAGGCGAGAG

TCAAATATTCTCTGTAGACTATGAAAAAAAGTAACAGATATCACGATCTAAGTGT

TATCCCAATCCATTCATCATGAGTTCCTTAAAGAAGATTCTCGGTCTGAAGGGGA

AAGGTAAGAAATCTAAGAAATTAGGGATCGCACCACCCCCTTATGAAGAGGACA

CTAGCATGGAGTATGCTCCGAGCGCTCCAATTGACAAATCCTATTTTGGAGTTGA

CGAGATGGACACCTATGATCCGAATCAATTAAGATATGAGAAATTCTTCTTTACA

GTGAAAATGACGGTTAGATCTAATCGTCCGTTCAGAACATACTCAGATGTGGCA

GCCGCTGTATCCCATTGGGATCACATGTACATCGGAATGGCAGGGAAACGTCCC

TTCTACAAAATCTTGGCTTTTTTGGGTTCTTCTAATCTAAAGGCCACTCCAGCGGT

ATTGGCAGATCAAGGTCAACCAGAGTATCACACTCACTGCGAAGGCAGGGCTTA

TTTGCCACATAGGATGGGGAAGACCCCTCCCATGCTCAATGTACCAGAGCACTTC

AGAAGACCATTCAATATAGGTCTTTACAAGGGAACGATTGAGCTCACAATGACC

ATCTACGATGATGAGTCACTGGAAGCAGCTCCTATGATCTGGGATCATTTCAATT

CTTCCAAATTTTCTGATTTCAGAGAGAAGGCCTTAATGTTTGGCCTGATTGTCGA

GAAAAAGGCATCTGGAGCGTGGGTCCTGGATTCTATCAGCCACTTCAAATGAGC

TAGTCTAACTTCTAGCTTCTGAACAATCCCCGGTTTACTCAGTCTCTCCTAATTCC

AGCCTCTCGAACAACTAATATCCTGTCTTTTCTATCCCTATGAAAAAAACTAACA

GAGATCGATCTGTTTACGCGTCACTATGAAGTGCCTTTTGTACTTAGCCTTTTTAT

TCATTGGGGTGAATTGCAAGTTCACCATAGTTTTTCCACACAACCAAAAAGGAA

ACTGGAAAAATGTTCCTTCTAATTACCATTATTGCCCGTCAAGCTCAGATTTAAA

TTGGCATAATGACTTAATAGGCACAGCCATACAAGTCAAAATGCCCAAGAGTCA

CAAGGCTATTCAAGCAGACGGTTGGATGTGTCATGCTTCCAAATGGGTCACTACT

TGTGATTTCCGCTGGTATGGACCGAAGTATATAACACAGTCCATCCGATCCTTCA

CTCCATCTGTAGAACAATGCAAGGAAAGCATTGAACAAACGAAACAAGGAACTT

GGCTGAATCCAGGCTTCCCTCCTCAAAGTTGTGGATATGCAACTGTGACGGATGC
```

```
CGAAGCAGTGATTGTCCAGGTGACTCCTCACCATGTGCTGGTTGATGAATACACA

GGAGAATGGGTTGATTCACAGTTCATCAACGGAAAATGCAGCAATTACATATGC

CCCACTGTCCATAACTCTACAACCTGGCATTCTGACTATAAGGTCAAAGGGCTAT

GTGATTCTAACCTCATTTCCATGGACATCACCTTCTTCTCAGAGGACGGAGAGCT

ATCATCCCTGGGAAGGAGGGCACAGGGTTCAGAAGTAACTACTTTGCTTATGA

AACTGGAGGCAAGGCCTGCAAAATGCAATACTGCAAGCATTGGGGAGTCAGACT

CCCATCAGGTGTCTGGTTCGAGATGGCTGATAAGGATCTCTTTGCTGCAGCCAGA

TTCCCTGAATGCCCAGAAGGGTCAAGTATCTCTGCTCCATCTCAGACCTCAGTGG

ATGTAAGTCTAATTCAGGACGTTGAGAGGATCTTGGATTATTCCCTCTGCCAAGA

AACCTGGAGCAAAATCAGAGCGGGTCTTCCAATCTCTCCAGTGGATCTCAGCTAT

CTTGCTCCTAAAAACCCAGGAACCGGTCCTGCTTTCACCATAATCAATGGTACCC

TAAAATACTTTGAGACCAGATACATCAGAGTCGATATTGCTGCTCCAATCCTCTC

AAGAATGGTCGGAATGATCAGTGGAACTACCACAGAAAGGGAACTGTGGGATG

ACTGGGCACCATATGAAGACGTGGAAATTGGACCCAATGGAGTTCTGAGGACCA

GTTCAGGATATAAGTTTCCTTTATACATGATTGGACATGGTATGTTGGACTCCGA

TCTTCATCTTAGCTCAAAGGCTCAGGTGTTCGAACATCCTCACATTCAAGACGCT

GCTTCGCAACTTCCTGATGATGAGAGTTTATTTTTTGGTGATACTGGGCTATCCA

AAAATCCAATCGAGCTTGTAGAAGGTTGGTTCAGTAGTTGGAAAAGCTCTATTGC

CTCTTTTTTCTTTATCATAGGGTTAATCATTGGACTATTCTTGGTTCTCCGAGTTG

GTATCCATCTTTGCATTAAATTAAAGCACACCAAGAAAAGACAGATTTATACAG

ACATAGAGATGAACCGACTTGGAAAGTAACTCAAATCCTGCTAGGTATGAAAAA

AACTAACaGATATCACGCtcgagGCCACCATGAAGTGCCTGTTGTACTTAGCCTTCC

TGTTCATCGGGGTGAATTGCCGCTTTCCCAATATCACAAACCTGTGCCCTTTTGG

CGAGGTGTTCAACGCAACCCGCTTCGCCAGCGTGTACGCCTGGAATAGGAAGCG

CATCTCCAACTGCGTGGCCGACTATTCTGTGCTGTACAACAGCGCCTCCTTCTCT

ACCTTTAAGTGCTATGGCGTGAGCCCCACAAAGCTGAATGACCTGTGCTTTACCA

ACGTGTACGCCGATTCCTTCGTGATCAGGGGCGACGAGGTGCGCCAGATCGCAC

CAGGACAGACAGGCAAGATCGCAGACTACAATTATAAGCTGCCTGACGATTTCA

CCGGCTGCGTGATCGCCTGGAACTCTAACAATCTGGATAGCAAAGTGGGCGGCA

ACTACAATTATCTGTACCGGCTGTTTAGAAAGTCTAATCTGAAGCCATTCGAGAG

GGACATCTCCACAGAAATCTACCAGGCCGGCTCTACCCCCTGCAATGGCGTGGA

GGGCTTTAACTGTTATTTCCCTCTGCAGAGCTACGGCTTCCAGCCAACAAACGGC

GTGGGCTATCAGCCCTACCGCGTGGTGGTGCTGTCTTTTGAGCTGCTGCACGCAC

CTGCAACAGTGTGCGGACCAAAGAAGAGCACCAATCTGGTGAAGAACAAGTGC

GTGAACTTCAAcggCTCTGGATCCGGCTACATCCCCGAGGCCCCCAGAGACGGCC

AGGCCTACGTGCGGAAGGACGGCGAGTGGGTACTGctcagcaccttcctgggcAGCAGTTG

GAAAAGCTCCATCGCCTCCTTTTTCTTTATCATCGGCCTGATCATCGGACTGTTCC

TGGTGCTCCGCGTGGGTATCCACCTGTGCATCAAGCTGAAGCACACCAAGAAAA

GACAGATTTATACAGACATCGAGATGAACCGACTTGGAAAGTAAGCTAGCCAGA

TTCTTCATGTTTGGACCAAATCAACTTGTGATACCATGCTCAAAGAGGCCTCAAT
```

-continued

```
TATATTTGAGTTTTTAATTTTTATGAAAAAAACTAACAGCAATCATGGAAGTCCA

CGATTTTGAGACCGACGAGTTCAATGATTTCAATGAAGATGACTATGCCACAAG

AGAATTCCTGAATCCCGATGAGCGCATGACGTACTTGAATCATGCTGATTACAAT

TTGAATTCTCCTCTAATTAGTGATGATATTGACAATTTGATCAGGAAATTCAATT

CTCTTCCGATTCCCTCGATGTGGGATAGTAAGAACTGGGATGGAGTTCTTGAGAT

GTTAACATCATGTCAAGCCAATCCCATCTCAACATCTCAGATGCATAAATGGATG

GGAAGTTGGTTAATGTCTGATAATCATGATGCCAGTCAAGGGTATAGTTTTTTAC

ATGAAGTGGACAAAGAGGCAGAAATAACATTTGACGTGGTGGAGACCTTCATCC

GCGGCTGGGGCAACAAACCAATTGAATACATCAAAAAGGAAAGATGGACTGAC

TCATTCAAAATTCTCGCTTATTTGTGTCAAAAGTTTTTGGACTTACACAAGTTGAC

ATTAATCTTAAATGCTGTCTCTGAGGTGGAATTGCTCAACTTGGCGAGGACTTTC

AAAGGCAAAGTCAGAAGAAGTTCTCATGGAACGAACATATGCAGGATTAGGGTT

CCCAGCTTGGGTCCTACTTTTATTTCAGAAGGATGGGCTTACTTCAAGAAACTTG

ATATTCTAATGGACCGAAACTTTCTGTTAATGGTCAAAGATGTGATTATAGGGAG

GATGCAAACGGTGCTATCCATGGTATGTAGAATAGACAACCTGTTCTCAGAGCA

AGACATCTTCTCCCTTCTAAATATCTACAGAATTGGAGATAAAATTGTGGAGAGG

CAGGGAAATTTTTCTTATGACTTGATTAAAATGGTGGAACCGATATGCAACTTGA

AGCTGATGAAATTAGCAAGAGAATCAAGGCCTTTAGTCCCACAATTCCCTCATTT

TGAAAATCATATCAAGACTTCTGTTGATGAAGGGGCAAAAATTGACCGAGGTAT

AAGATTCCTCCATGATCAGATAATGAGTGTGAAAACAGTGGATCTCACACTGGT

GATTTATGGATCGTTCAGACATTGGGTCATCCTTTTATAGATTATTACACTGGA

CTAGAAAAATTACATTCCCAAGTAACCATGAAGAAAGATATTGATGTGTCATAT

GCAAAAGCACTTGCAAGTGATTTAGCTCGGATTGTTCTATTTCAACAGTTCAATG

ATCATAAAAAGTGGTTCGTGAATGGAGACTTGCTCCCTCATGATCATCCCTTTAA

AAGTCATGTTAAAGAAAATACATGGCCCACAGCTGCTCAAGTTCAAGATTTTGG

AGATAAATGGCATGAACTTCCGCTGATTAAATGTTTTGAAATACCCGACTTACTA

GACCCATCGATAATATACTCTGACAAAAGTCATTCAATGAATAGGTCAGAGGTG

TTGAAACATGTCCGAATGAATCCGAACACTCCTATCCCTAGTAAAAAGGTGTTGC

AGACTATGTTGGACACAAAGGCTACCAATTGGAAAGAATTTCTTAAAGAGATTG

ATGAGAAGGGCTTAGATGATGATGATCTAATTATTGGTCTTAAAGGAAAGGAGA

GGGAACTGAAGTTGGCAGGTAGATTTTTCTCCCTAATGTCTTGGAAATTGCGAGA

ATACTTTGTAATTACCGAATATTTGATAAAGACTCATTTCGTCCCTATGTTTAAAG

GCCTGACAATGGCGGACGATCTAACTGCAGTCATTAAAAAGATGTTAGATTCCTC

ATCCGGCCAAGGATTGAAGTCATATGAGGCAATTTGCATAGCCAATCACATTGA

TTACGAAAAATGGAATAACCACCAAAGGAAGTTATCAAACGGCCCAGTGTTCCG

AGTTATGGGCCAGTTCTTAGGTTATCCATCCTTAATCGAGAGAACTCATGAATTT

TTTGAGAAAAGTCTTATATACTACAATGGAAGACCAGACTTGATGCGTGTTCACA

ACAACACACTGATCAATTCAACCTCCCAACGAGTTTGTTGGCAAGGACAAGAGG

GTGGACTGGAAGGTCTACGGCAAAAAGGATGGACTATCCTCAATCTACTGGTTA

TTCAAAGAGAGGCTAAAATCAGAAACACTGCTGTCAAAGTCTTGGCACAAGGTG

ATAATCAAGTTATTTGCACACAGTATAAAACGAAGAAATCGAGAAACGTTGTAG
```

-continued

```
AATTACAGGGTGCTCTCAATCAAATGGTTTCTAATAATGAGAAAATTATGACTGC
AATCAAAATAGGGACAGGGAAGTTAGGACTTTTGATAAATGACGATGAGACTAT
GCAATCTGCAGATTACTTGAATTATGGAAAAATACCGATTTTCCGTGGAGTGATT
AGAGGGTTAGAGACCAAGAGATGGTCACGAGTGACTTGTGTCACCAATGACCAA
ATACCCACTTGTGCTAATATAATGAGCTCAGTTTCCACAAATGCTCTCACCGTAG
CTCATTTTGCTGAGAACCCAATCAATGCCATGATACAGTACAATTATTTTGGGAC
ATTTGCTAGACTCTTGTTGATGATGCATGATCCTGCTCTTCGTCAATCATTGTATG
AAGTTCAAGATAAGATACCGGGCTTGCACAGTTCTACTTTCAAATACGCCATGTT
GTATTTGGACCCTTCCATTGGAGGAGTGTCGGGCATGTCTTTGTCCAGGTTTTTG
ATTAGAGCCTTCCCAGATCCCGTAACAGAAAGTCTCTCATTCTGGAGATTCATCC
ATGTACATGCTCGAAGTGAGCATCTGAAGGAGATGAGTGCAGTATTTGGAAACC
CCGAGATAGCCAAGTTTCGAATAACTCACATAGACAAGCTAGTAGAAGATCCAA
CCTCTCTGAACATCGCTATGGGAATGAGTCCAGCGAACTTGTTAAAGACTGAGGT
TAAAAAATGCTTAATCGAATCAAGACAAACCATCAGGAACCAGGTGATTAAGGA
TGCAACCATATATTTGTATCATGAAGAGGATCGGCTCAGAAGTTTCTTATGGTCA
ATAAATCCTCTGTTCCCTAGATTTTTAAGTGAATTCAAATCAGGCACTTTTTTGGG
AGTCGCAGACGGGCTCATCAGTCTATTTCAAAATTCTCGTACTATTCGGAACTCC
TTTAAGAAAAAGTATCATAGGGAATTGGATGATTTGATTGTGAGGAGTGAGGTA
TCCTCTTTGACACATTTAGGGAAACTTCATTTGAGAAGGGGATCATGTAAAATGT
GGACATGTTCAGCTACTCATGCTGACACATTAAGATACAAATCCTGGGGCCGTAC
AGTTATTGGGACAACTGTACCCCATCCATTAGAAATGTTGGGTCCACAACATCGA
AAAGAGACTCCTTGTGCACCATGTAACACATCAGGGTTCAATTATGTTTCTGTGC
ATTGTCCAGACGGGATCCATGACGTCTTTAGTTCACGGGACCATTGCCTGCTTA
TCTAGGGTCTAAAACATCTGAATCTACATCTATTTTGCAGCCTTGGGAAAGGGAA
AGCAAAGTCCCACTGATTAAAAGAGCTACACGTCTTAGAGATGCTATCTCTTGGT
TTGTTGAACCCGACTCTAAACTAGCAATGACTATACTTTCTAACATCCACTCTTTA
ACAGGCGAAGAATGGACCAAAAGGCAGCATGGGTTCAAAAGAACAGGGTCTGC
CCTTCATAGGTTTTCGACATCTCGGATGAGCCATGGTGGGTTCGCATCTCAGAGC
ACTGCAGCATTGACCAGGTTGATGGCAACTACAGACACCATGAGGGATCTGGGA
GATCAGAATTTCGACTTTTTATTCCAAGCAACGTTGCTCTATGCTCAAATTACCA
CCACTGTTGCAAGAGACGGATGGATCACCAGTTGTACAGATCATTATCATATTGC
CTGTAAGTCCTGTTTGAGACCCATAGAAGAGATCACCCTGGACTCAAGTATGGA
CTACACGCCCCCAGATGTATCCCATGTGCTGAAGACATGGAGGAATGGGGAAGG
TTCGTGGGACAAGAGATAAAACAGATCTATCCTTTAGAAGGGAATTGGAAGAA
TTTAGCACCTGCTGAGCAATCCTATCAAGTCGGCAGATGTATAGGTTTTCTATAT
GGAGACTTGGCGTATAGAAAATCTACTCATGCCGAGGACAGTTCTCTATTTCCTC
TATCTATACAAGGTCGTATTAGAGGTCGAGGTTTCTTAAAAGGGTTGCTAGACGG
ATTAATGAGAGCAAGTTGCTGCCAAGTAATACACCGGAGAAGTCTGGCTCATTT
GAAGAGGCCGGCCAACGCAGTGTACGGAGGTTTGATTTACTTGATTGATAAATT
GAGTGTATCACCTCCATTCCTTTCTCTTACTAGATCAGGACCTATTAGAGACGAA
```

-continued

```
TTAGAAACGATTCCCCACAAGATCCCAACCTCCTATCCGACAAGCAACCGTGAT

ATGGGGGTGATTGTCAGAAATTACTTCAAATACCAATGCCGTCTAATTGAAAAG

GGAAAATACAGATCACATTATTCACAATTATGGTTATTCTCAGATGTCTTATCCA

TAGACTTCATTGGACCATTCTCTATTTCCACCACCCTCTTGCAAATCCTATACAAG

CCATTTTTATCTGGGAAAGATAAGAATGAGTTGAGAGAGCTGGCAAATCTTTCTT

CATTGCTAAGATCAGGAGAGGGGTGGGAAGACATACATGTGAAATTCTTCACCA

AGGACATATTATTGTGTCCAGAGGAAATCAGACATGCTTGCAAGTTCGGGATTG

CTAAGGATAATAATAAAGACATGAGCTATCCCCCTTGGGGAAGGGAATCCAGAG

GGACAATTACAACAATCCCTGTTTATTATACGACCACCCCTTACCCAAAGATGCT

AGAGATGCCTCCAAGAATCCAAAATCCCCTGCTGTCCGGAATCAGGTTGGGCCA

ATTACCAACTGGCGCTCATTATAAAATTCGGAGTATATTACATGGAATGGGAATC

CATTACAGGGACTTCTTGAGTTGTGGAGACGGCTCCGGAGGGATGACTGCTGCA

TTACTACGAGAAAATGTGCATAGCAGAGGAATATTCAATAGTCTGTTAGAATTAT

CAGGGTCAGTCATGCGAGGCGCCTCTCCTGAGCCCCCCAGTGCCCTAGAAACTTT

AGGAGGAGATAAATCGAGATGTGTAAATGGTGAAACATGTTGGGAATATCCATC

TGACTTATGTGACCCAAGGACTTGGGACTATTTCCTCCGACTCAAAGCAGGCTTG

GGGCTTCAAATTGATTTAATTGTAATGGATATGGAAGTTCGGGATTCTTCTACTA

GCCTGAAAATTGAGACGAATGTTAGAAATTATGTGCACCGGATTTTGGATGAGC

AAGGAGTTTTAATCTACAAGACTTATGGAACATATATTTGTGAGAGCGAAAAGA

ATGCAGTAACAATCCTTGGTCCCATGTTCAAGACGGTCGACTTAGTTCAAACAGA

ATTTAGTAGTTCTCAAACGTCTGAAGTATATATGGTATGTAAAGGTTTGAAGAAA

TTAATCGATGAACCCAATCCCGATTGGTCTTCCATCAATGAATCCTGGAAAAACC

TGTACGCATTCCAGTCATCAGAACAGGAATTTGCCAGAGCAAAGAAGGTTAGTA

CATACTTTACCTTGACAGGTATTCCCTCCCAATTCATTCCTGATCCTTTTGTAAAC

ATTGAGACTATGCTACAAATATTCGGAGTACCCACGGGTGTGTCTCATGCGGCTG

CCTTAAAATCATCTGATAGACCTGCAGATTTATTGACCATTAGCCTTTTTTATATG

GCGATTATATCGTATTATAACATCAATCATATCAGAGTAGGACCGATACCTCCGA

ACCCCCCATCAGATGGAATTGCACAAAATGTGGGGATCGCTATAACTGGTATAA

GCTTTTGGCTGAGTTTGATGGAGAAAGACATTCCACTATATCAACAGTGTTTAGC

AGTTATCCAGCAATCATTCCCGATTAGGTGGGAGGCTGTTTCAGTAAAAGGAGG

ATACAAGCAGAAGTGGAGTACTAGAGGTGATGGGCTCCAAAAGATACCCGAAC

TTCAGACTCCTTGGCCCCAATCGGGAACTGGATCAGATCTCTGGAATTGGTCCGA

AACCAAGTTCGTCTAAATCCATTCAATGAGATCTTGTTCAATCAGCTATGTCGTA

CAGTGGATAATCATTTGAAATGGTCAAATTTGCGAAGAAACACAGGAATGATTG

AATGGATCAATAGACGAATTTCAAAAGAAGACCGGTCTATACTGATGTTGAAGA

GTGACCTACACGAGGAAAACTCTTGGAGAGATTAAAAAATCATGAGGAGACTCC

AAACTTTAAGTATGAAAAAAACTTTGATCCTTAAGACCCTCTTGTGGTTTTATTT

TTTATCTGGTTTTGTGGTCTTCGT.
```

In other embodiments, the nucleic acid comprises the sequence of SEQ ID NO: 27, shown below (VSV vector: Convac V5 South Africa):

```
ACGAAGACAAACAAACCATTATTATCATTAAAAGGCTCAGGAGAAACTTTAACA
GTAATCAAAATGTCTGTTACAGTCAAGAGAATCATTGACAACACAGTCATAGTTC
CAAAACTTCCTGCAAATGAGGATCCAGTGGAATACCCGGCAGATTACTTCAGAA
AATCAAAGGAGATTCCTCTTTACATCAATACTACAAAAAGTTTGTCAGATCTAAG
AGGATATGTCTACCAAGGCCTCAAATCCGGAAATGTATCAATCATACATGTCAA
CAGCTACTTGTATGGAGCATTAAAGGACATCCGGGGTAAGTTGGATAAAGATTG
GTCAAGTTTCGGAATAAACATCGGGAAAGCAGGGGATACAATCGGAATATTTGA
CCTTGTATCCTTGAAAGCCCTGGACGGCGTACTTCCAGATGGAGTATCGGATGCT
TCCAGAACCAGCGCAGATGACAAATGGTTGCCTTTGTATCTACTTGGCTTATACA
GAGTGGGCAGAACACAAATGCCTGAATACAGAAAAAAGCTCATGGATGGGCTG
ACAAATCAATGCAAATGATCAATGAACAGTTTGAACCTCTTGTGCCAGAAGGT
CGTGACATTTTTGATGTGTGGGAAATGACAGTAATTACACAAAAATTGTCGCTG
CAGTGGACATGTTCTTCCACATGTTCAAAAAACATGAATGTGCCTCGTTCAGATA
CGGAACTATTGTTTCCAGATTCAAAGATTGTGCTGCATTGGCAACATTTGGACAC
CTCTGCAAAATAACCGGAATGTCTACAGAAGATGTAACGACCTGGATCTTGAAC
CGAGAAGTTGCAGATGAAATGGTCCAAATGATGCTTCCAGGCCAAGAAATTGAC
AAGGCCGATTCATACATGCCTTATTTGATCGACTTTGGATTGTCTTCTAAGTCTCC
ATATTCTTCCGTCAAAAACCCTGCCTTCCACTTCTGGGGCAATTGACAGCTCTT
CTGCTCAGATCCACCAGAGCAAGGAATGCCCGACAGCCTGATGACATTGAGTAT
ACATCTCTTACTACAGCAGGTTTGTTGTACGCTTATGCAGTAGGATCCTCTGCCG
ACTTGGCACAACAGTTTTGTGTTGGAGATAACAAATACACTCCAGATGATAGTAC
CGGAGGATTGACGACTAATGCACCGCCACAAGGCAGAGATGTGGTCGAATGGCT
CGGATGGTTTGAAGATCAAAACAGAAAACCGACTCCTGATATGATGCAGTATGC
GAAAAGAGCAGTCATGTCACTGCAAGGCCTAAGAGAGAAGACAATTGGCAAGT
ATGCTAAGTCAGAATTTGACAAATGACCCTATAATTCTCAGATCACCTATTATAT
ATTATGCTACATATGAAAAAAACTAACAGATATCATGGATAATCTCACAAAAGT
TCGTGAGTATCTCAAGTCCTATTCTCGTCTGGATCAGGCGGTAGGAGAGATAGAT
GAGATCGAAGCACAACGAGCTGAAAAGTCCAATTATGAGTTGTTCCAAGAGGAT
GGAGTGGAAGAGCATACTAAGCCCTCTTATTTTCAGGCAGCAGATGATTCTGAC
ACAGAATCTGAACCAGAAATTGAAGACAATCAAGGTTTGTATGCACCAGATCCA
GAAGCTGAGCAAGTTGAAGGCTTTATACAGGGGCCTTTAGATGACTATGCAGAT
GAGGAAGTGGATGTTGTATTTACTTCGGACTGGAAACAGCCTGAGCTTGAATCTG
ACGAGCATGGAAAGACCTTACGGTTGACATCGCCAGAGGGTTTAAGTGGAGAGC
AGAAATCCCAGTGGCTTTCGACGATTAAAGCAGTCGTGCAAAGTGCCAAATACT
GGAATCTGGCAGAGTGCACATTTGAAGCATCGGGAGAAGGGGTCATTATGAAGG
AGCGCCAGATAACTCCGGATGTATATAAGGTCACTCCAGTGATGAACACACATC
CGTCCCAATCAGAAGCAGTATCAGATGTTTGGTCTCTCTCAAAGACATCCATGAC
TTTCCAACCCAAGAAAGCAAGTCTTCAGCCTCTCACCATATCCTTGGATGAATTG
```

-continued
```
TTCTCATCTAGAGGAGAGTTCATCTCTGTCGGAGGTGACGGACGAATGTCTCATA

AAGAGGCCATCCTGCTCGGCCTGAGATACAAAAAGTTGTACAATCAGGCGAGAG

TCAAATATTCTCTGTAGACTATGAAAAAAAGTAACAGATATCACGATCTAAGTGT

TATCCCAATCCATTCATCATGAGTTCCTTAAAGAAGATTCTCGGTCTGAAGGGGA

AAGGTAAGAAATCTAAGAAATTAGGGATCGCACCACCCCCTTATGAAGAGGACA

CTAGCATGGAGTATGCTCCGAGCGCTCCAATTGACAAATCCTATTTTGGAGTTGA

CGAGATGGACACCTATGATCCGAATCAATTAAGATATGAGAAATTCTTCTTTACA

GTGAAAATGACGGTTAGATCTAATCGTCCGTTCAGAACATACTCAGATGTGGCA

GCCGCTGTATCCCATTGGGATCACATGTACATCGGAATGGCAGGGAAACGTCCC

TTCTACAAAATCTTGGCTTTTTTGGGTTCTTCTAATCTAAAGGCCACTCCAGCGGT

ATTGGCAGATCAAGGTCAACCAGAGTATCACACTCACTGCGAAGGCAGGGCTTA

TTTGCCACATAGGATGGGGAAGACCCCTCCCATGCTCAATGTACCAGAGCACTTC

AGAAGACCATTCAATATAGGTCTTTACAAGGGAACGATTGAGCTCACAATGACC

ATCTACGATGATGAGTCACTGGAAGCAGCTCCTATGATCTGGGATCATTTCAATT

CTTCCAAATTTTCTGATTTCAGAGAGAAGGCCTTAATGTTTGGCCTGATTGTCGA

GAAAAAGGCATCTGGAGCGTGGGTCCTGGATTCTATCAGCCACTTCAAATGAGC

TAGTCTAACTTCTAGCTTCTGAACAATCCCCGGTTTACTCAGTCTCTCCTAATTCC

AGCCTCTCGAACAACTAATATCCTGTCTTTTCTATCCCTATGAAAAAAACTAACA

GAGATCGATCTGTTTACGCGTCACTATGAAGTGCCTTTTGTACTTAGCCTTTTTAT

TCATTGGGGTGAATTGCAAGTTCACCATAGTTTTTCCACACAACCAAAAAGGAA

ACTGGAAAAATGTTCCTTCTAATTACCATTATTGCCCGTCAAGCTCAGATTTAAA

TTGGCATAATGACTTAATAGGCACAGCCATACAAGTCAAAATGCCCAAGAGTCA

CAAGGCTATTCAAGCAGACGGTTGGATGTGTCATGCTTCCAAATGGGTCACTACT

TGTGATTTCCGCTGGTATGGACCGAAGTATATAACACAGTCCATCCGATCCTTCA

CTCCATCTGTAGAACAATGCAAGGAAAGCATTGAACAAACGAAACAAGGAACTT

GGCTGAATCCAGGCTTCCCTCCTCAAAGTTGTGGATATGCAACTGTGACGGATGC

CGAAGCAGTGATTGTCCAGGTGACTCCTCACCATGTGCTGGTTGATGAATACACA

GGAGAATGGGTTGATTCACAGTTCATCAACGGAAAATGCAGCAATTACATATGC

CCCACTGTCCATAACTCTACAACCTGGCATTCTGACTATAAGGTCAAAGGGCTAT

GTGATTCTAACCTCATTTCCATGGACATCACCTTCTTCTCAGAGGACGGAGAGCT

ATCATCCCTGGGAAAGGAGGGCACAGGGTTCAGAAGTAACTACTTTGCTTATGA

AACTGGAGGCAAGGCCTGCAAAATGCAATACTGCAAGCATTGGGGAGTCAGACT

CCCATCAGGTGTCTGGTTCGAGATGGCTGATAAGGATCTCTTTGCTGCAGCCAGA

TTCCCTGAATGCCCAGAAGGGTCAAGTATCTCTGCTCCATCTCAGACCTCAGTGG

ATGTAAGTCTAATTCAGGACGTTGAGAGGATCTTGGATTATTCCCTCTGCCAAGA

AACCTGGAGCAAAATCAGAGCGGGTCTTCCAATCTCTCCAGTGGATCTCAGCTAT

CTTGCTCCTAAAAACCCAGGAACCGGTCCTGCTTTCACCATAATCAATGGTACCC

TAAAATACTTTGAGACCAGATACATCAGAGTCGATATTGCTGCTCCAATCCTCTC

AAGAATGGTCGGAATGATCAGTGGAACTACCACAGAAAGGGAACTGTGGGATG

ACTGGGCACCATATGAAGACGTGGAAATTGGACCCAATGGAGTTCTGAGGACCA

GTTCAGGATATAAGTTTCCTTTATACATGATTGGACATGGTATGTTGGACTCCGA
```

-continued

```
TCTTCATCTTAGCTCAAAGGCTCAGGTGTTCGAACATCCTCACATTCAAGACGCT

GCTTCGCAACTTCCTGATGATGAGAGTTTATTTTTTGGTGATACTGGGCTATCCA

AAAATCCAATCGAGCTTGTAGAAGGTTGGTTCAGTAGTTGGAAAAGCTCTATTGC

CTCTTTTTTCTTTATCATAGGGTTAATCATTGGACTATTCTTGGTTCTCCGAGTTG

GTATCCATCTTTGCATTAAATTAAAGCACACCAAGAAAAGACAGATTTATACAG

ACATAGAGATGAACCGACTTGGAAAGTAACTCAAATCCTGCTAGGTATGAAAAA

AACTAACaGATATCACGCtcgagGCCACCATGAAGTGCCTGTTGTACTTAGCCTTCC

TGTTCATCGGGGTGAATTGCCGCTTTCCCAATATCACAAACCTGTGCCCTTTTGG

CGAGGTGTTCAACGCAACCCGCTTCGCCAGCGTGTACGCCTGGAATAGGAAGCG

CATCTCCAACTGCGTGGCCGACTATTCTGTGCTGTACAACAGCGCCTCCTTCTCT

ACCTTTAAGTGCTATGGCGTGAGCCCCACAAAGCTGAATGACCTGTGCTTTACCA

ACGTGTACGCCGATTCCTTCGTGATCAGGGGCGACGAGGTGCGCCAGATCGCAC

CAGGACAGACAGGCAATATCGCAGACTACAATTATAAGCTGCCTGACGATTTCA

CCCGGCTGCGTGATCGCCTGGAACTCTAACAATCTGGATAGCAAAGTGGGCGGCA

ACTACAATTATCTGTACCGGCTGTTTAGAAAGTCTAATCTGAAGCCATTCGAGAG

GGACATCTCCACAGAAATCTACCAGGCCGGCTCTACCCCCTGCAATGGCGTGAA

GGGCTTTAACTGTTATTTCCCTCTGCAGAGCTACGGCTTCCAGCCAACATATGGC

GTGGGCTATCAGCCCTACCGCGTGGTGGTGCTGTCTTTTGAGCTGCTGCACGCAC

CTGCAACAGTGTGCGGACCAAAGAAGAGCACCAATCTGGTGAAGAACAAGTGC

GTGAACTTCAAcggCTCTGGATCCGGCTACATCCCCGAGGCCCCCAGAGACGGCC

AGGCCTACGTGCGGAAGGACGGCGAGTGGGTACTGctcagcaccttcctgggcAGCAGTTG

GAAAAGCTCCATCGCCTCCTTTTTCTTTATCATCGGCCTGATCATCGGACTGTTCC

TGGTGCTCCGCGTGGGTATCCACCTGTGCATCAAGCTGAAGCACACCAAGAAAA

GACAGATTTATACAGACATCGAGATGAACCGACTTGGAAAGTAAGCTAGCCAGA

TTCTTCATGTTTGGACCAAATCAACTTGTGATACCATGCTCAAAGAGGCCTCAAT

TATATTTGAGTTTTTAATTTTTATGAAAAAAACTAACAGCAATCATGGAAGTCCA

CGATTTTGAGACCGACGAGTTCAATGATTTCAATGAAGATGACTATGCCACAAG

AGAATTCCTGAATCCCGATGAGCGCATGACGTACTTGAATCATGCTGATTACAAT

TTGAATTCTCCTCTAATTAGTGATGATATTGACAATTTGATCAGGAAATTCAATT

CTCTTCCGATTCCCTCGATGTGGGATAGTAAGAACTGGGATGGAGTTCTTGAGAT

GTTAACATCATGTCAAGCCAATCCCATCTCAACATCTCAGATGCATAAATGGATG

GGAAGTTGGTTAATGTCTGATAATCATGATGCCAGTCAAGGGTATAGTTTTTTAC

ATGAAGTGGACAAAGAGGCAGAAATAACATTTGACGTGGTGGAGACCTTCATCC

GCGGCTGGGGCAACAAACCAATTGAATACATCAAAAAGGAAAGATGGACTGAC

TCATTCAAAATTCTCGCTTATTTGTGTCAAAAGTTTTTGGACTTACACAAGTTGAC

ATTAATCTTAAATGCTGTCTCTGAGGTGGAATTGCTCAACTTGGCGAGGACTTTC

AAAGGCAAAGTCAGAAGAAGTTCTCATGGAACGAACATATGCAGGATTAGGGTT

CCCAGCTTGGGTCCTACTTTTATTTCAGAAGGATGGGCTTACTTCAAGAAACTTG

ATATTCTAATGGACCGAAACTTTCTGTTAATGGTCAAAGATGTGATTATAGGGAG

GATGCAAACGGTGCTATCCATGGTATGTAGAATAGACAACCTGTTCTCAGAGCA
```

-continued
AGACATCTTCTCCCTTCTAAATATCTACAGAATTGGAGATAAAATTGTGGAGAGG

CAGGGAAATTTTTCTTATGACTTGATTAAAATGGTGGAACCGATATGCAACTTGA

AGCTGATGAAATTAGCAAGAGAATCAAGGCCTTTAGTCCCACAATTCCCTCATTT

TGAAAATCATATCAAGACTTCTGTTGATGAAGGGGCAAAAATTGACCGAGGTAT

AAGATTCCTCCATGATCAGATAATGAGTGTGAAAACAGTGGATCTCACACTGGT

GATTTATGGATCGTTCAGACATTGGGGTCATCCTTTTATAGATTATTACACTGGA

CTAGAAAAATTACATTCCCAAGTAACCATGAAGAAAGATATTGATGTGTCATAT

GCAAAAGCACTTGCAAGTGATTTAGCTCGGATTGTTCTATTTCAACAGTTCAATG

ATCATAAAAAGTGGTTCGTGAATGGAGACTTGCTCCCTCATGATCATCCCTTTAA

AAGTCATGTTAAAGAAAATACATGGCCCACAGCTGCTCAAGTTCAAGATTTTGG

AGATAAATGGCATGAACTTCCGCTGATTAAATGTTTTGAAATACCCGACTTACTA

GACCCATCGATAATATACTCTGACAAAAGTCATTCAATGAATAGGTCAGAGGTG

TTGAAACATGTCCGAATGAATCCGAACACTCCTATCCCTAGTAAAAAGGTGTTGC

AGACTATGTTGGACACAAAGGCTACCAATTGGAAAGAATTTCTTAAAGAGATTG

ATGAGAAGGGCTTAGATGATGATGATCTAATTATTGGTCTTAAAGGAAAGGAGA

GGGAACTGAAGTTGGCAGGTAGATTTTTCTCCCTAATGTCTTGGAAATTGCGAGA

ATACTTTGTAATTACCGAATATTTGATAAAGACTCATTTCGTCCCTATGTTTAAAG

GCCTGACAATGGCGGACGATCTAACTGCAGTCATTAAAAAGATGTTAGATTCCTC

ATCCGGCCAAGGATTGAAGTCATATGAGGCAATTTGCATAGCCAATCACATTGA

TTACGAAAAATGGAATAACCACCAAAGGAAGTTATCAAACGGCCCAGTGTTCCG

AGTTATGGGCCAGTTCTTAGGTTATCCATCCTTAATCGAGAGAACTCATGAATTT

TTTGAGAAAAGTCTTATATACTACAATGGAAGACCAGACTTGATGCGTGTTCACA

ACAACACACTGATCAATTCAACCTCCCAACGAGTTTGTTGGCAAGGACAAGAGG

GTGGACTGGAAGGTCTACGGCAAAAAGGATGGACTATCCTCAATCTACTGGTTA

TTCAAAGAGAGGCTAAAATCAGAAACACTGCTGTCAAAGTCTTGGCACAAGGTG

ATAATCAAGTTATTTGCACACAGTATAAAACGAAGAAATCGAGAAACGTTGTAG

AATTACAGGGTGCTCTCAATCAAATGGTTTCTAATAATGAGAAAATTATGACTGC

AATCAAAATAGGGACAGGGAAGTTAGGACTTTTGATAAATGACGATGAGACTAT

GCAATCTGCAGATTACTTGAATTATGGAAAAATACCGATTTTCCGTGGAGTGATT

AGAGGGTTAGAGACCAAGAGATGGTCACGAGTGACTTGTGTCACCAATGACCAA

ATACCCACTTGTGCTAATATAATGAGCTCAGTTTCCACAAATGCTCTCACCGTAG

CTCATTTTGCTGAGAACCCAATCAATGCCATGATACAGTACAATTATTTTGGGAC

ATTTGCTAGACTCTTGTTGATGATGCATGATCCTGCTCTTCGTCAATCATTGTATG

AAGTTCAAGATAAGATACCGGGCTTGCACAGTTCTACTTTCAAATACGCCATGTT

GTATTTGGACCCTTCCATTGGAGGAGTGTCGGGCATGTCTTTGTCCAGGTTTTTG

ATTAGAGCCTTCCCAGATCCCGTAACAGAAAGTCTCTCATTCTGGAGATTCATCC

ATGTACATGCTCGAAGTGAGCATCTGAAGGAGATGAGTGCAGTATTTGGAAACC

CCGAGATAGCCAAGTTTCGAATAACTCACATAGACAAGCTAGTAGAAGATCCAA

CCTCTCTGAACATCGCTATGGGAATGAGTCCAGCGAACTTGTTAAAGACTGAGGT

TAAAAAATGCTTAATCGAATCAAGACAAACCATCAGGAACCAGGTGATTAAGGA

TGCAACCATATATTTGTATCATGAAGAGGATCGGCTCAGAAGTTTCTTATGGTCA

```
ATAAATCCTCTGTTCCCTAGATTTTTAAGTGAATTCAAATCAGGCACTTTTTTGGG

AGTCGCAGACGGGCTCATCAGTCTATTTCAAAATTCTCGTACTATTCGGAACTCC

TTTAAGAAAAAGTATCATAGGGAATTGGATGATTTGATTGTGAGGAGTGAGGTA

TCCTCTTTGACACATTTAGGGAAACTTCATTTGAGAAGGGGATCATGTAAAATGT

GGACATGTTCAGCTACTCATGCTGACACATTAAGATACAAATCCTGGGGCCGTAC

AGTTATTGGGACAACTGTACCCCATCCATTAGAAATGTTGGGTCCACAACATCGA

AAAGAGACTCCTTGTGCACCATGTAACACATCAGGGTTCAATTATGTTTCTGTGC

ATTGTCCAGACGGGATCCATGACGTCTTTAGTTCACGGGACCATTGCCTGCTTA

TCTAGGGTCTAAAACATCTGAATCTACATCTATTTTGCAGCCTTGGGAAAGGGAA

AGCAAAGTCCCACTGATTAAAAGAGCTACACGTCTTAGAGATGCTATCTCTTGGT

TTGTTGAACCCGACTCTAAACTAGCAATGACTATACTTTCTAACATCCACTCTTTA

ACAGGCGAAGAATGGACCAAAAGGCAGCATGGGTTCAAAAGAACAGGGTCTGC

CCTTCATAGGTTTTCGACATCTCGGATGAGCCATGGTGGGTTCGCATCTCAGAGC

ACTGCAGCATTGACCAGGTTGATGGCAACTACAGACACCATGAGGGATCTGGGA

GATCAGAATTTCGACTTTTTATTCCAAGCAACGTTGCTCTATGCTCAAATTACCA

CCACTGTTGCAAGAGACGGATGGATCACCAGTTGTACAGATCATTATCATATTGC

CTGTAAGTCCTGTTTGAGACCCATAGAAGAGATCACCCTGGACTCAAGTATGGA

CTACACGCCCCCAGATGTATCCCATGTGCTGAAGACATGGAGGAATGGGGAAGG

TTCGTGGGACAAGAGATAAAACAGATCTATCCTTTAGAAGGGAATTGGAAGAA

TTTAGCACCTGCTGAGCAATCCTATCAAGTCGGCAGATGTATAGGTTTTCTATAT

GGAGACTTGGCGTATAGAAAATCTACTCATGCCGAGGACAGTTCTCTATTTCCTC

TATCTATACAAGGTCGTATTAGAGGTCGAGGTTTCTTAAAAGGGTTGCTAGACGG

ATTAATGAGAGCAAGTTGCTGCCAAGTAATACACCGGAGAAGTCTGGCTCATTT

GAAGAGGCCGGCCAACGCAGTGTACGGAGGTTTGATTTACTTGATTGATAAATT

GAGTGTATCACCTCCATTCCTTTCTCTTACTAGATCAGGACCTATTAGAGACGAA

TTAGAAACGATTCCCCACAAGATCCCAACCTCCTATCCGACAAGCAACCGTGAT

ATGGGGGTGATTGTCAGAAATTACTTCAAATACCAATGCCGTCTAATTGAAAAG

GGAAAATACAGATCACATTATTCACAATTATGGTTATTCTCAGATGTCTTATCCA

TAGACTTCATTGGACCATTCTCTATTTCCACCACCCTCTTGCAAATCCTATACAAG

CCATTTTTATCTGGGAAAGATAAGAATGAGTTGAGAGAGCTGGCAAATCTTTCTT

CATTGCTAAGATCAGGAGAGGGGTGGGAAGACATACATGTGAAATTCTTCACCA

AGGACATATTATTGTGTCCAGAGGAAATCAGACATGCTTGCAAGTTCGGGATTG

CTAAGGATAATAATAAAGACATGAGCTATCCCCCTTGGGGAAGGGAATCCAGAG

GGACAATTACAACAATCCCTGTTTATTATACGACCACCCCTTACCCAAAGATGCT

AGAGATGCCTCCAAGAATCCAAAATCCCCTGCTGTCCGGAATCAGGTTGGGCCA

ATTACCAACTGGCGCTCATTATAAAATTCGGAGTATATTACATGGAATGGGAATC

CATTACAGGGACTTCTTGAGTTGTGGAGACGGCTCCGGAGGGATGACTGCTGCA

TTACTACGAGAAAATGTGCATAGCAGAGGAATATTCAATAGTCTGTTAGAATTAT

CAGGGTCAGTCATGCGAGGCGCCTCTCCTGAGCCCCCCAGTGCCCTAGAAACTTT

AGGAGGAGATAAATCGAGATGTGTAAATGGTGAAACATGTTGGGAATATCCATC
```

```
-continued
TGACTTATGTGACCCAAGGACTTGGGACTATTTCCTCCGACTCAAAGCAGGCTTG

GGGCTTCAAATTGATTTAATTGTAATGGATATGGAAGTTCGGGATTCTTCTACTA

GCCTGAAAATTGAGACGAATGTTAGAAATTATGTGCACCGGATTTTGGATGAGC

AAGGAGTTTTAATCTACAAGACTTATGGAACATATATTTGTGAGAGCGAAAAGA

ATGCAGTAACAATCCTTGGTCCCATGTTCAAGACGGTCGACTTAGTTCAAACAGA

ATTTAGTAGTTCTCAAACGTCTGAAGTATATATGGTATGTAAAGGTTTGAAGAAA

TTAATCGATGAACCCAATCCCGATTGGTCTTCCATCAATGAATCCTGGAAAAACC

TGTACGCATTCCAGTCATCAGAACAGGAATTTGCCAGAGCAAAGAAGGTTAGTA

CATACTTTACCTTGACAGGTATTCCCTCCCAATTCATTCCTGATCCTTTTGTAAAC

ATTGAGACTATGCTACAAATATTCGGAGTACCCACGGGTGTGTCTCATGCGGCTG

CCTTAAAATCATCTGATAGACCTGCAGATTTATTGACCATTAGCCTTTTTTATATG

GCGATTATATCGTATTATAACATCAATCATATCAGAGTAGGACCGATACCTCCGA

ACCCCCCATCAGATGGAATTGCACAAAATGTGGGGATCGCTATAACTGGTATAA

GCTTTTGGCTGAGTTTGATGGAGAAAGACATTCCACTATATCAACAGTGTTTAGC

AGTTATCCAGCAATCATTCCCGATTAGGTGGGAGGCTGTTTCAGTAAAAGGAGG

ATACAAGCAGAAGTGGAGTACTAGAGGTGATGGGCTCCCAAAAGATACCCGAAC

TTCAGACTCCTTGGCCCCAATCGGGAACTGGATCAGATCTCTGGAATTGGTCCGA

AACCAAGTTCGTCTAAATCCATTCAATGAGATCTTGTTCAATCAGCTATGTCGTA

CAGTGGATAATCATTTGAAATGGTCAAATTTGCGAAGAAACACAGGAATGATTG

AATGGATCAATAGACGAATTTCAAAAGAAGACCGGTCTATACTGATGTTGAAGA

GTGACCTACACGAGGAAAACTCTTGGAGAGATTAAAAAATCATGAGGAGACTCC

AAACTTTAAGTATGAAAAAAACTTTGATCCTTAAGACCCTCTTGTGGTTTTTATTT

TTTATCTGGTTTTGTGGTCTTCGT.
```

In another aspect, the invention provides an isolated nucleic acid encoding a recombinant fusion protein comprising (a) a glycoprotein (G) of a virus or a portion thereof, and (b) a SARS-CoV-2 spike protein (S) or a portion thereof. In some embodiments, the virus is a rhabdovirus. In some embodiments, the virus is a rabies virus or a vesicular stomatitis virus (VSV). In a particular embodiment, the virus is a rabies virus.

In one embodiment, the portion of the SARS-CoV-2 spike protein (S) is a receptor binding site of the SARS-CoV-2 spike protein (S). In another embodiment, the portion of the SARS-CoV-2 spike protein (S) is the S1 domain. In another embodiment, the portion of the SARS-CoV-2 spike protein (S) is the N-terminal 750 amino acids of the SARS-CoV-2 spike protein (S).

In some embodiments, the glycoprotein (G) comprises a mutation substituting arginine with glutamic acid at position 333. In some embodiments, the portion of glycoprotein (G) comprises an ectodomain, a cytoplasmic domain, and a transmembrane domain. In some embodiments, the portion of the glycoprotein (G) comprises 31 amino acids of the ectodomain. In some embodiments, the glycoprotein (G) comprises 31 amino acids of the ectodomain and the full-length cytoplasmic domain.

In some embodiments, the sequence encoding the SARS-CoV-2 spike protein (S) or portion thereof is codon-optimized for expression in a human cell. In some embodiments, the sequence encoding the SARS-CoV-2 spike protein (S) or portion thereof fused to a glycoprotein (G) or portion thereof is codon-optimized for expression in a human cell.

Figure 18:
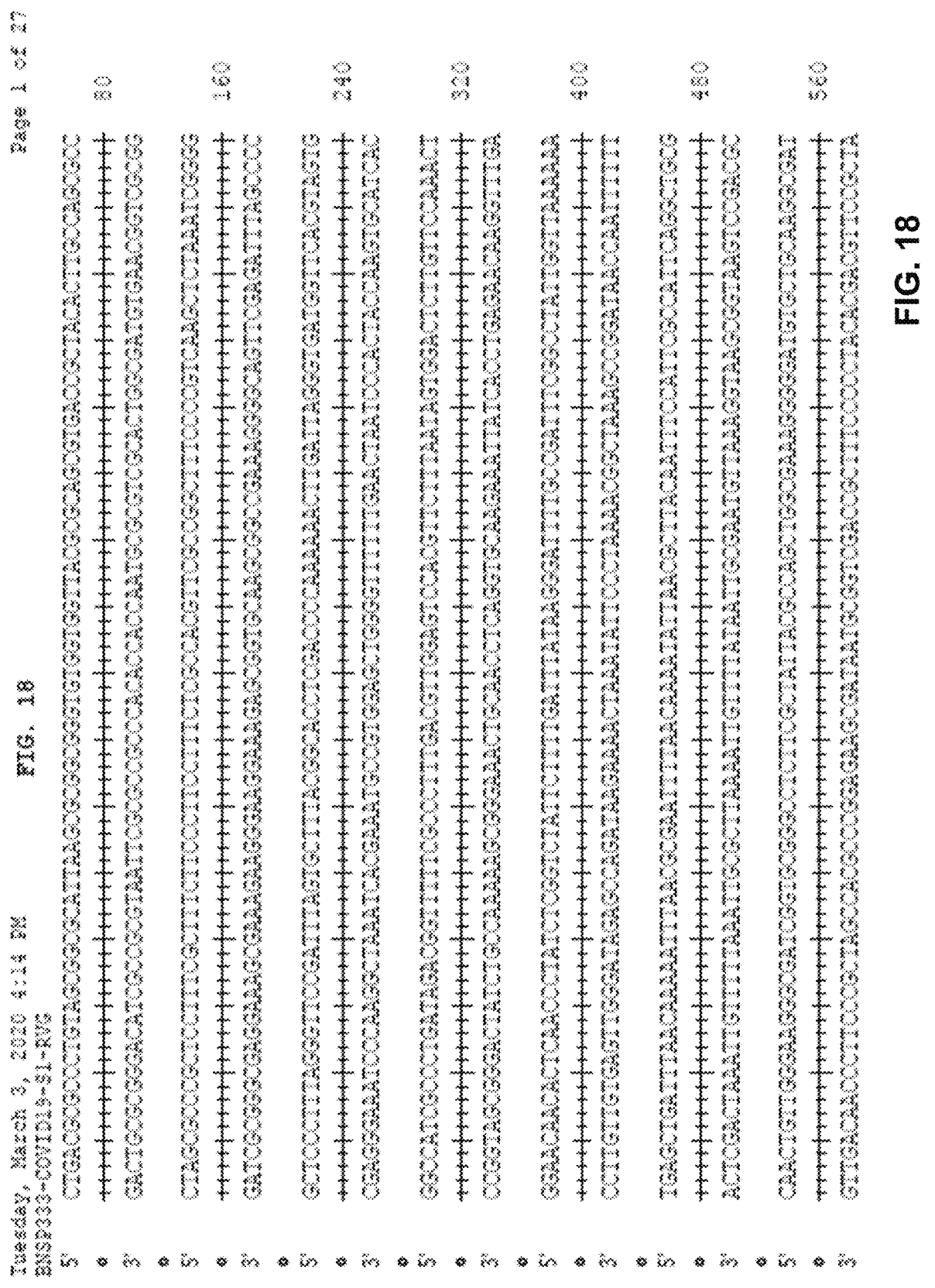
Figure 18:
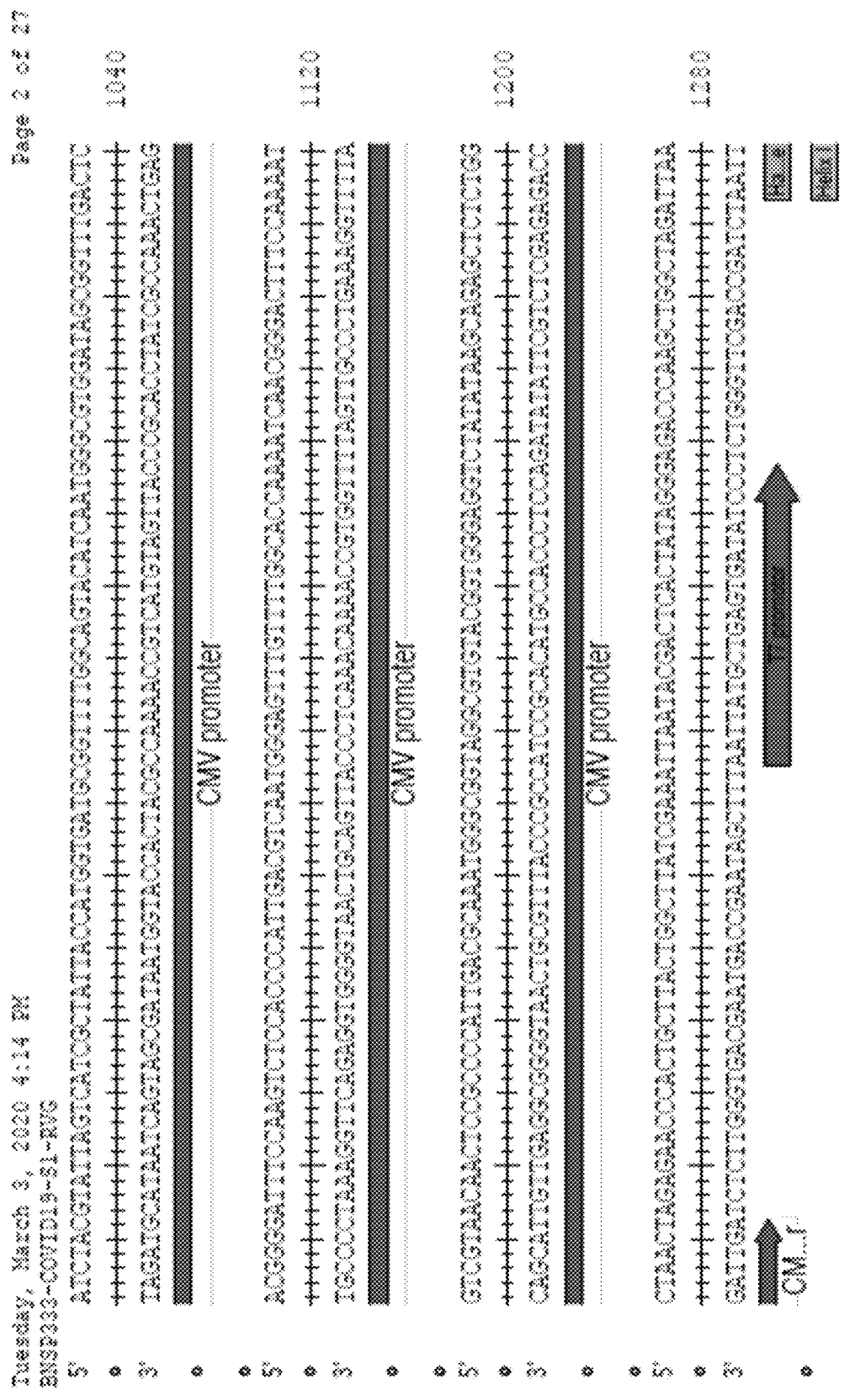
Figure 18:
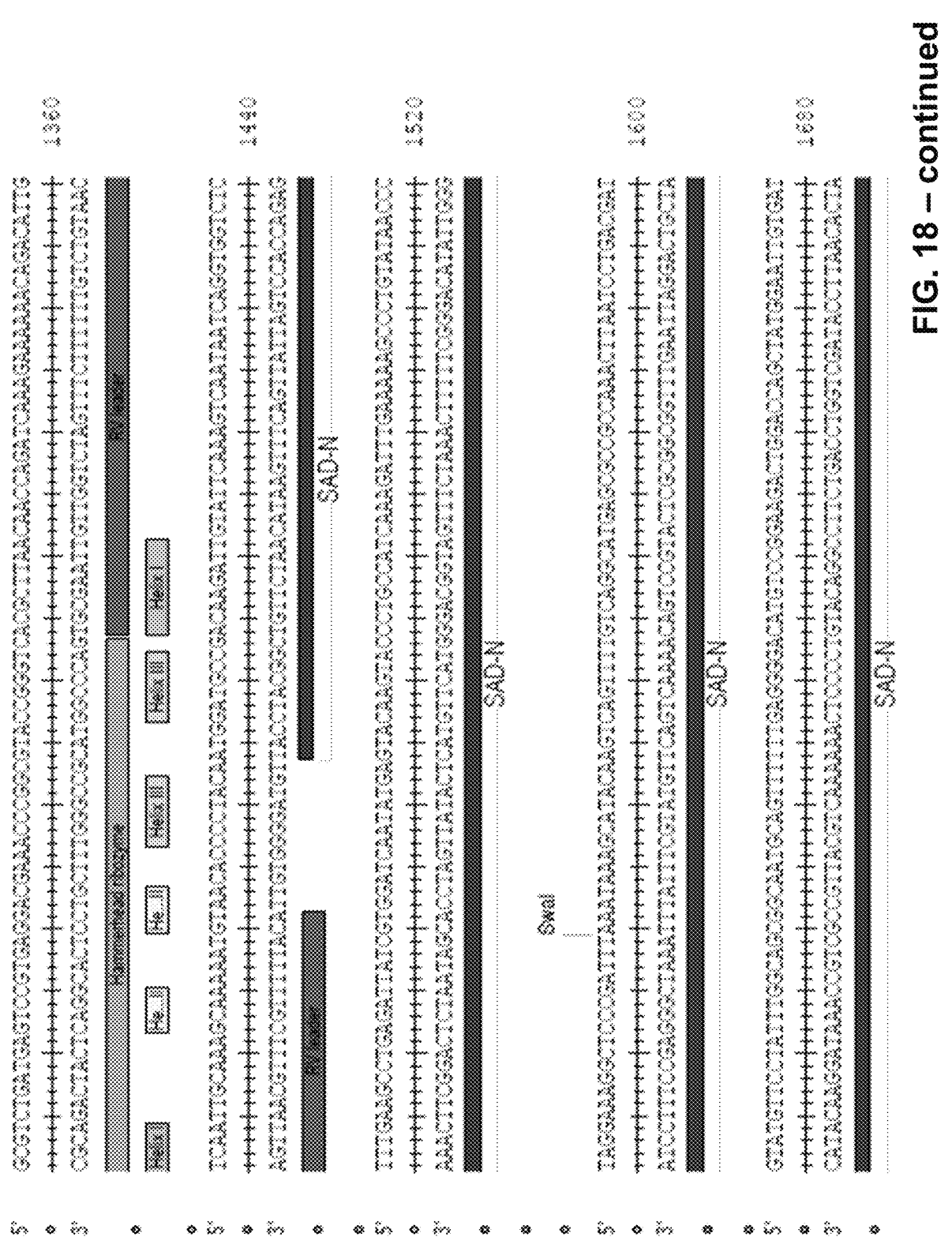
Figure 18:
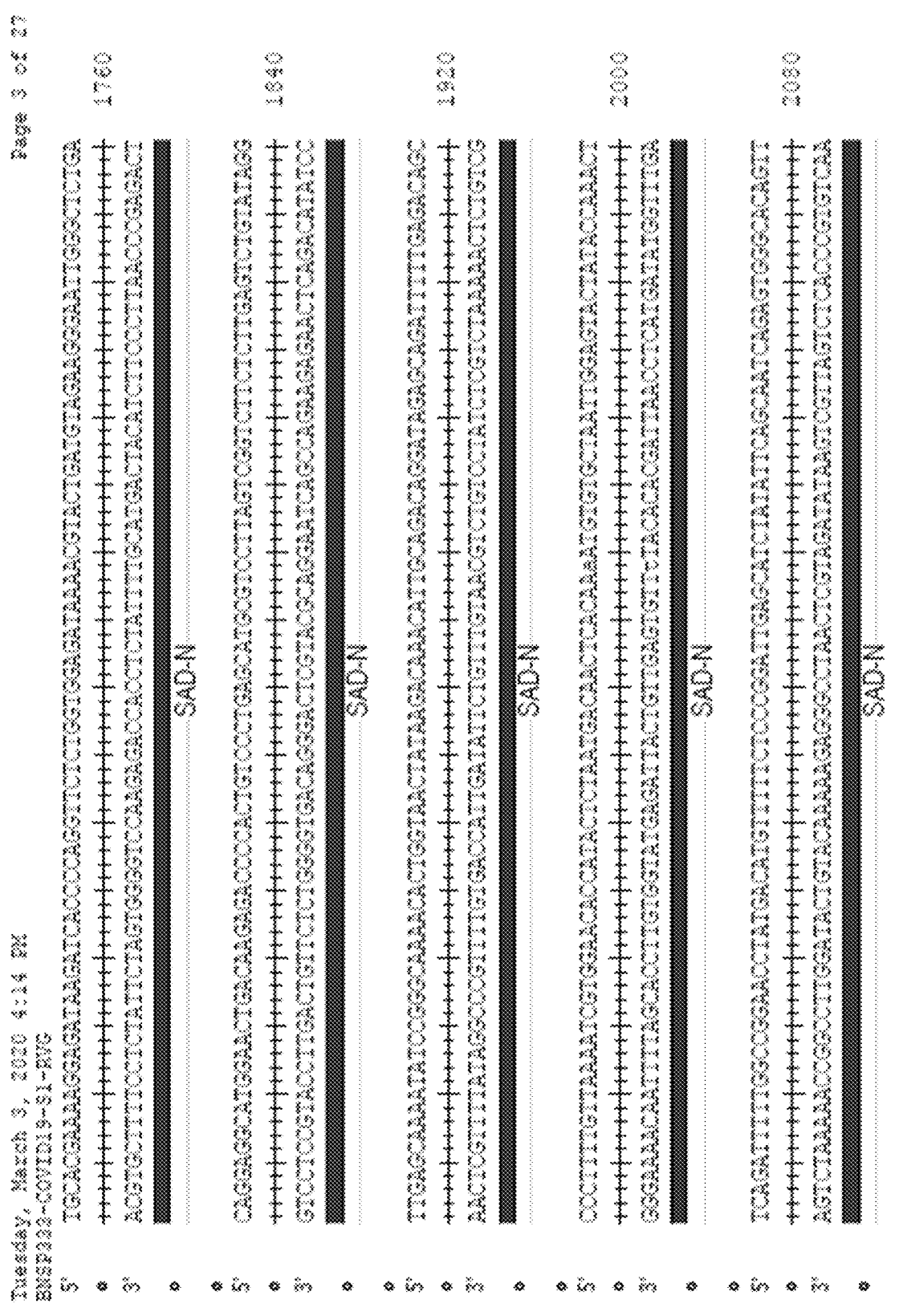
Figure 18:
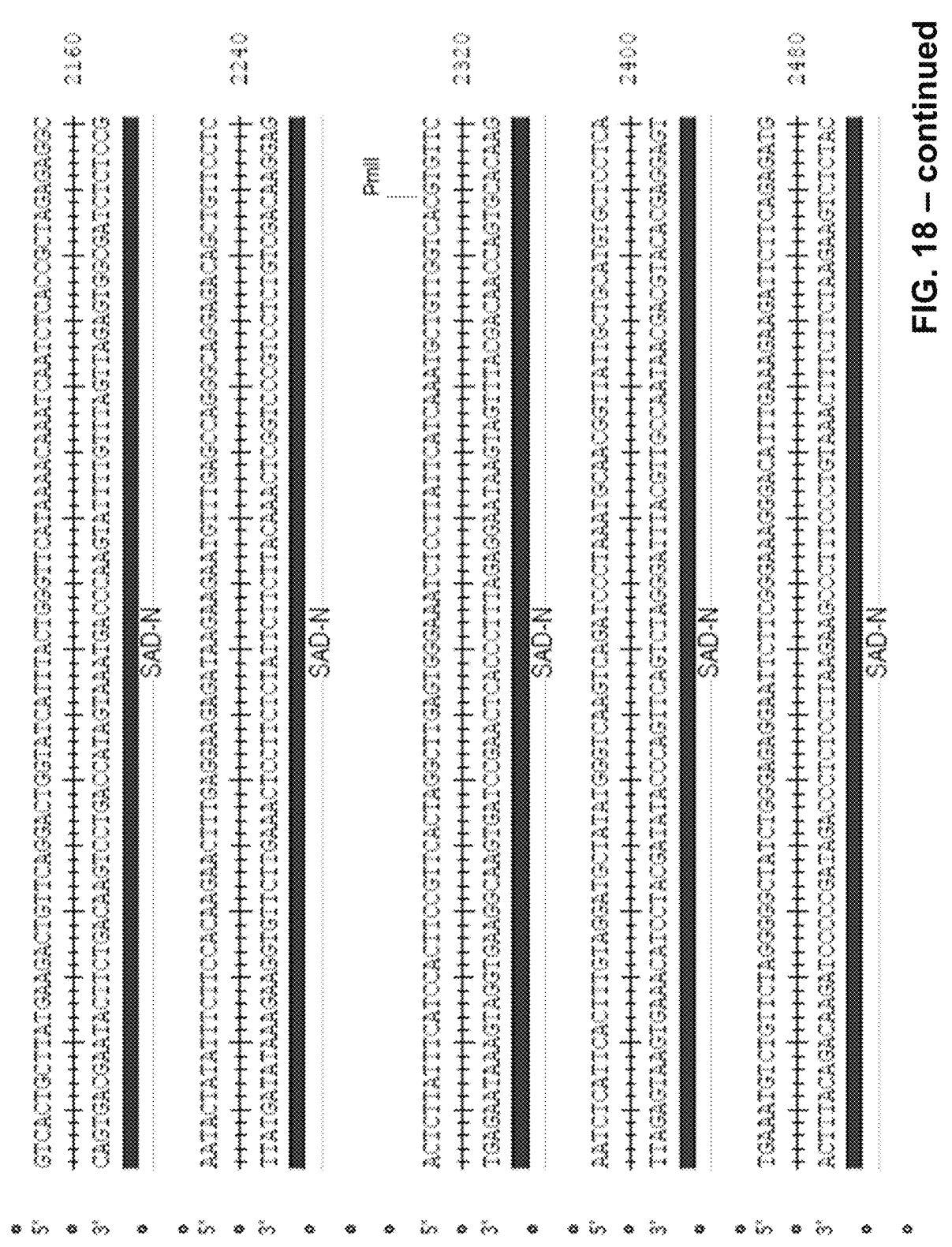
Figure 18:
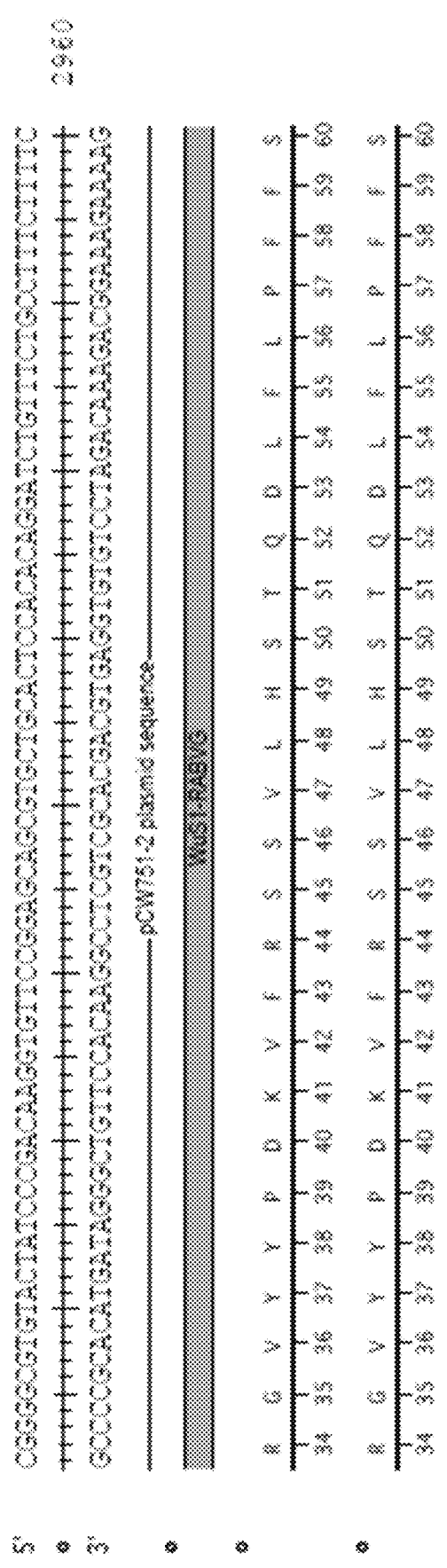
Figure 18:
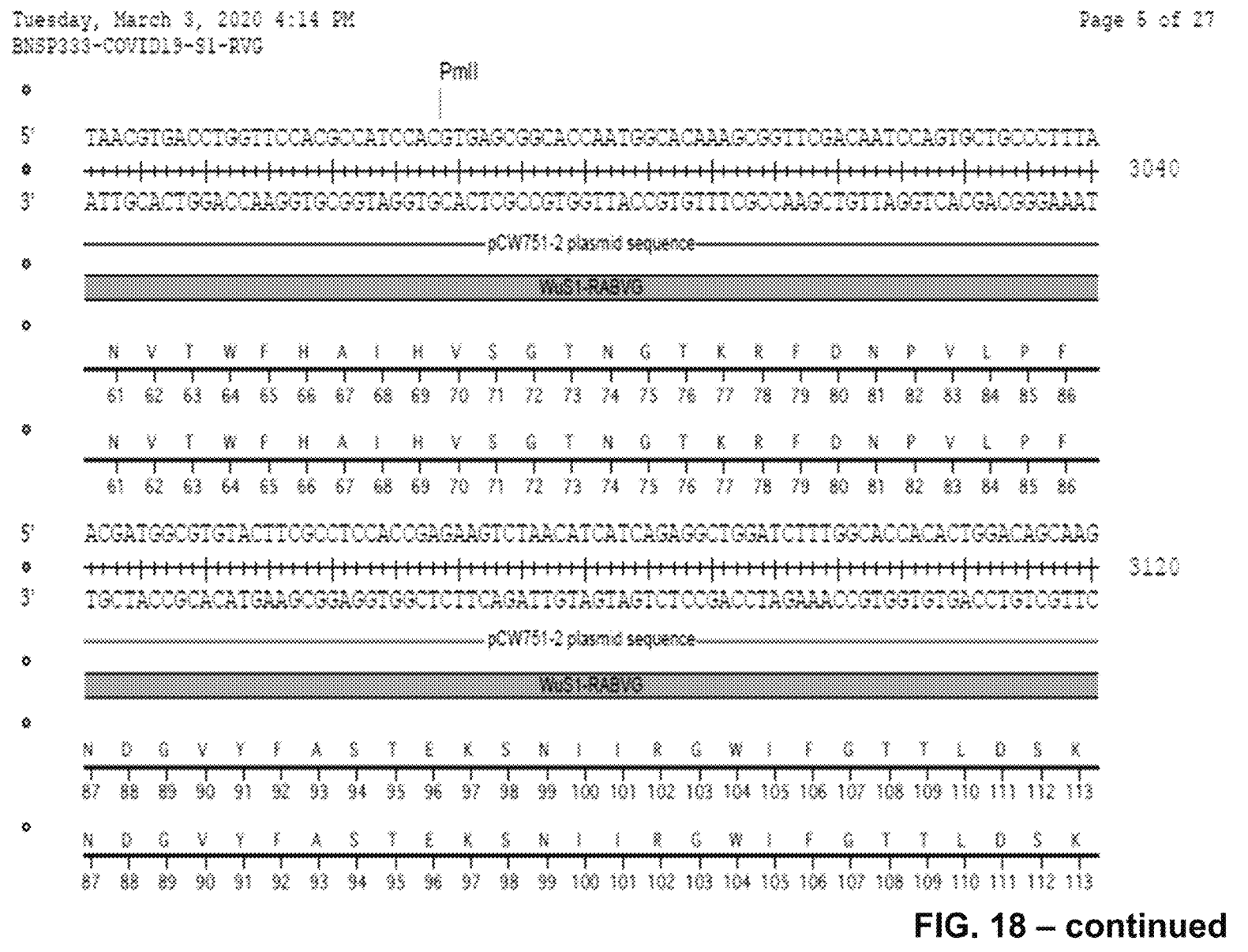
Figure 18:
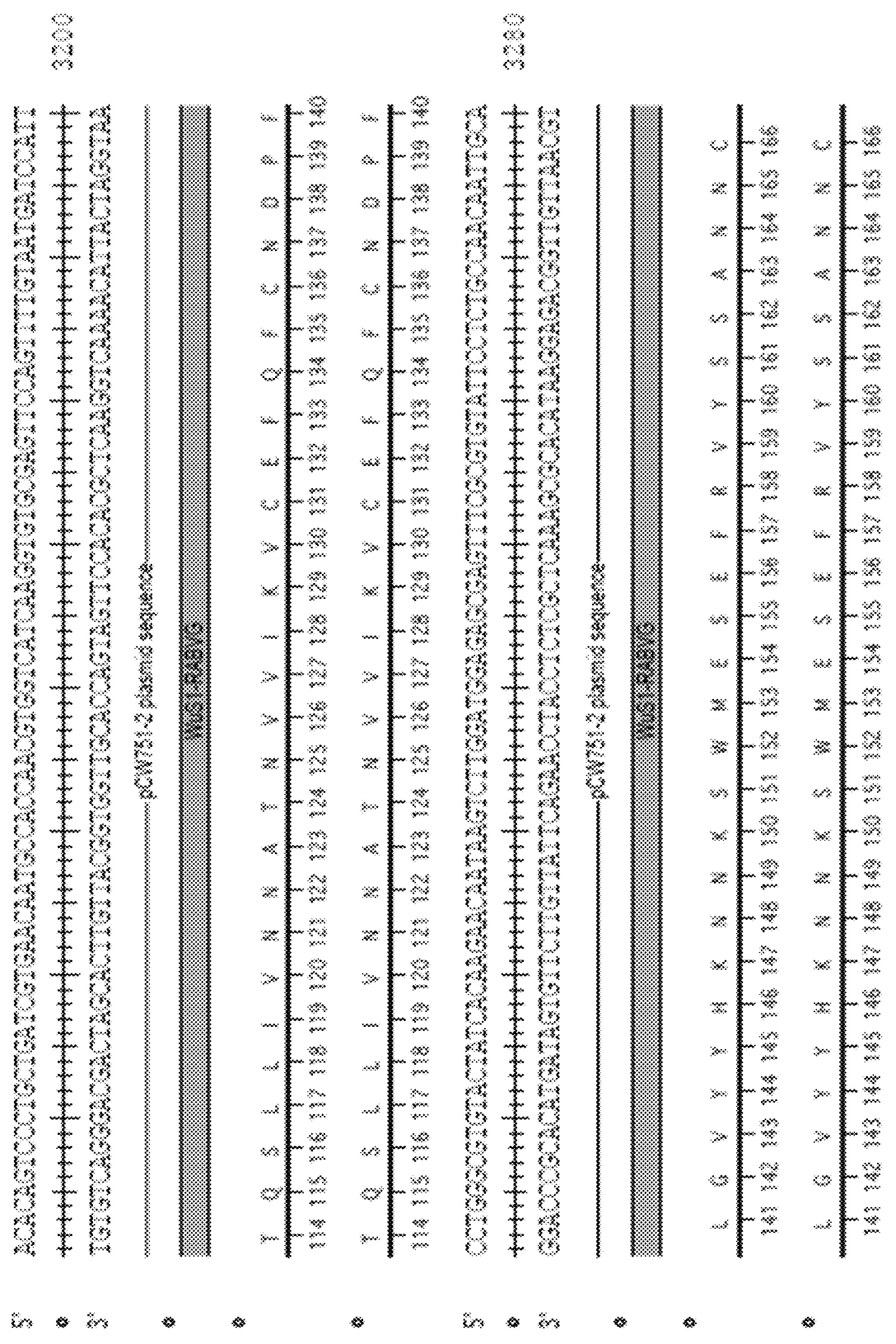
Figure 18:
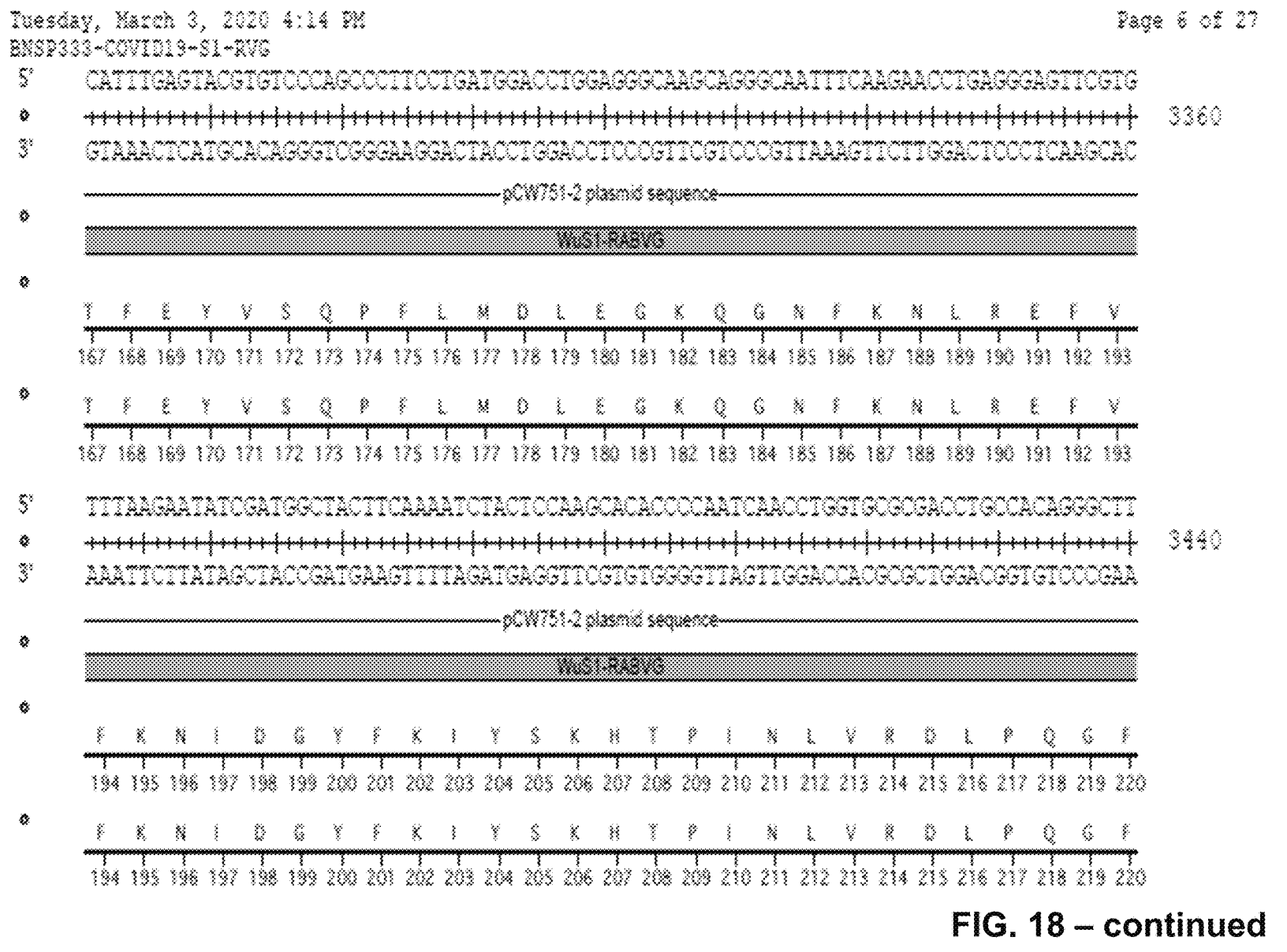
Figure 18:
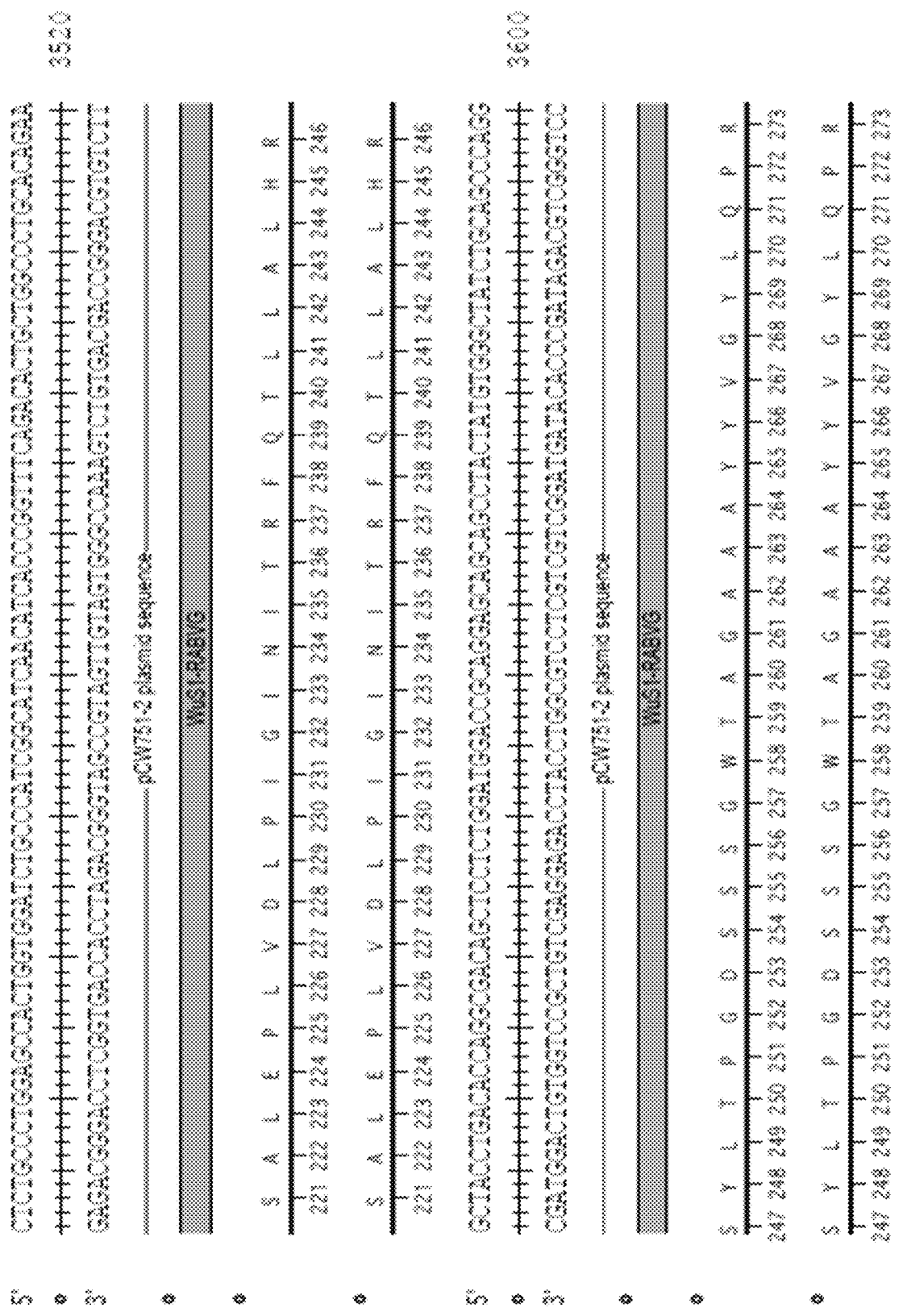
Figure 18:
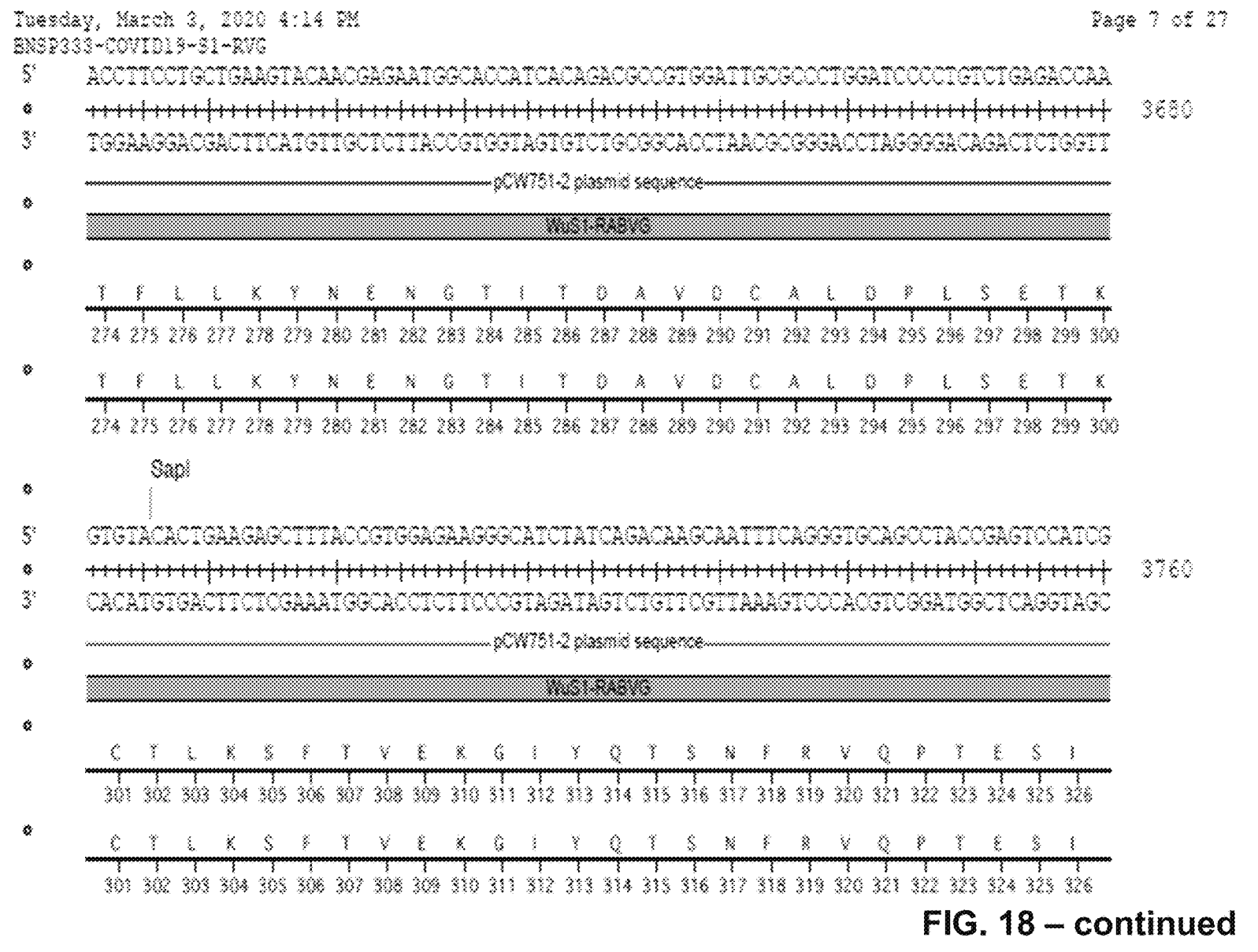
Figure 18:
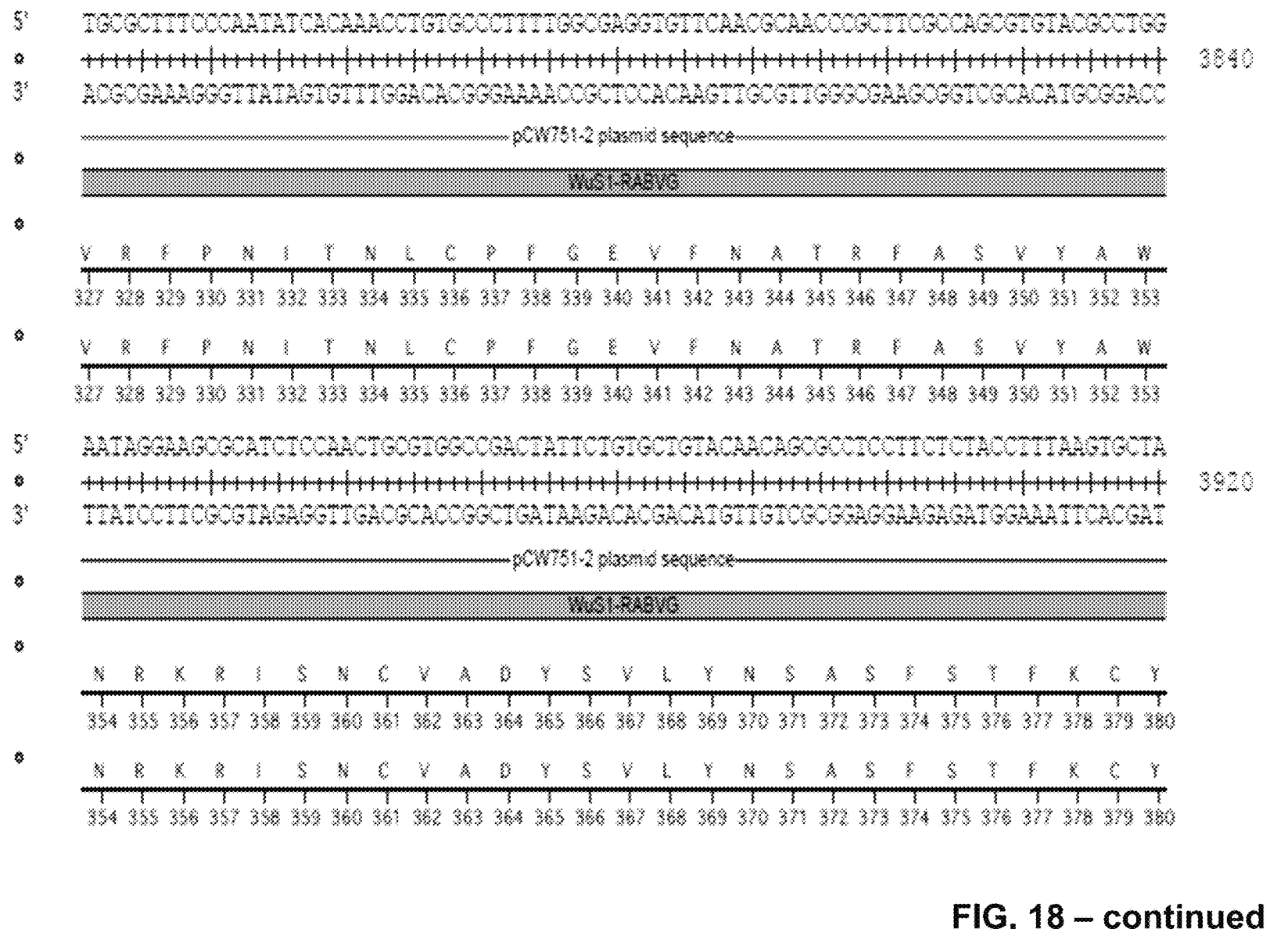
Figure 18:
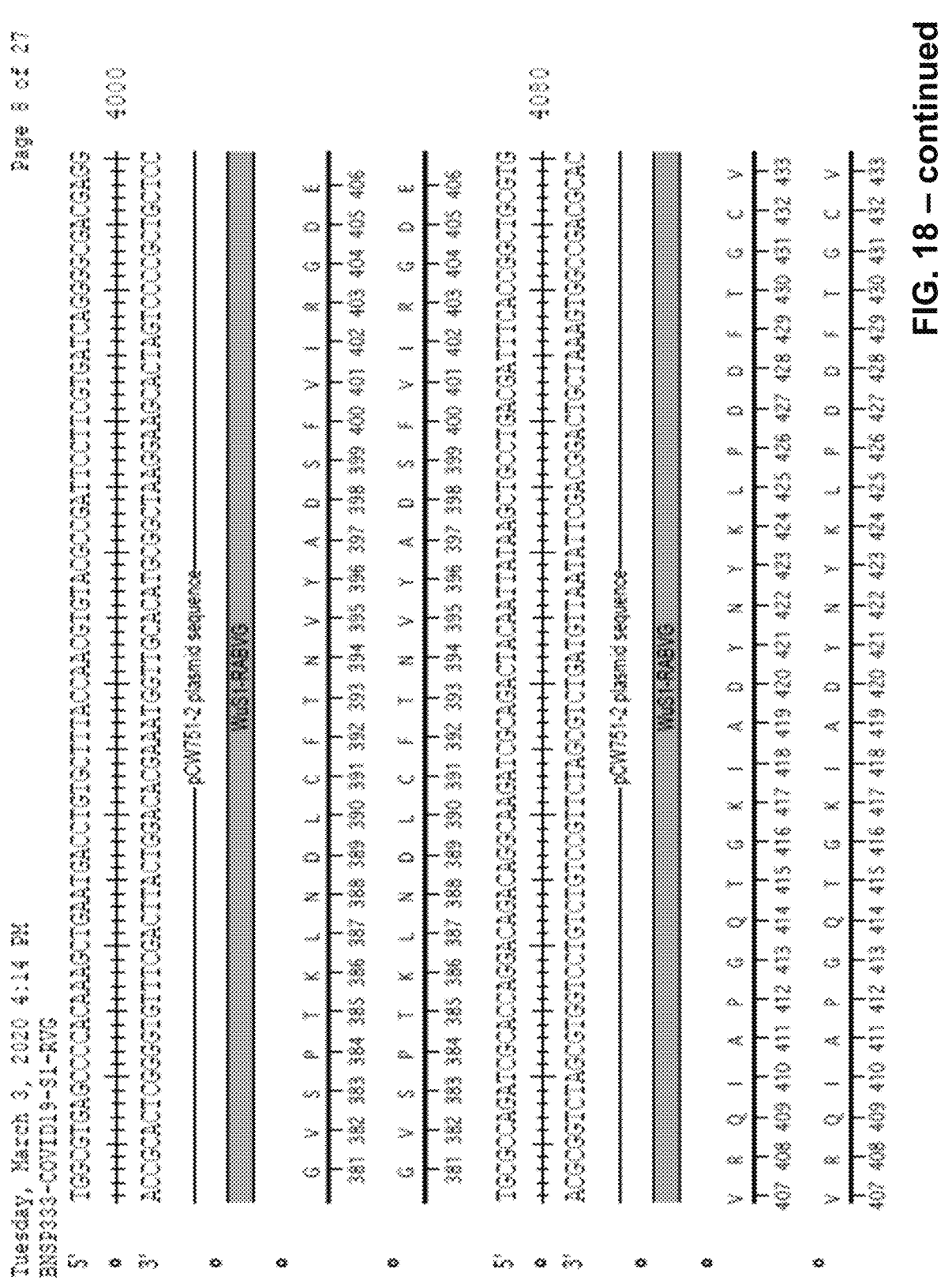
Figure 18:
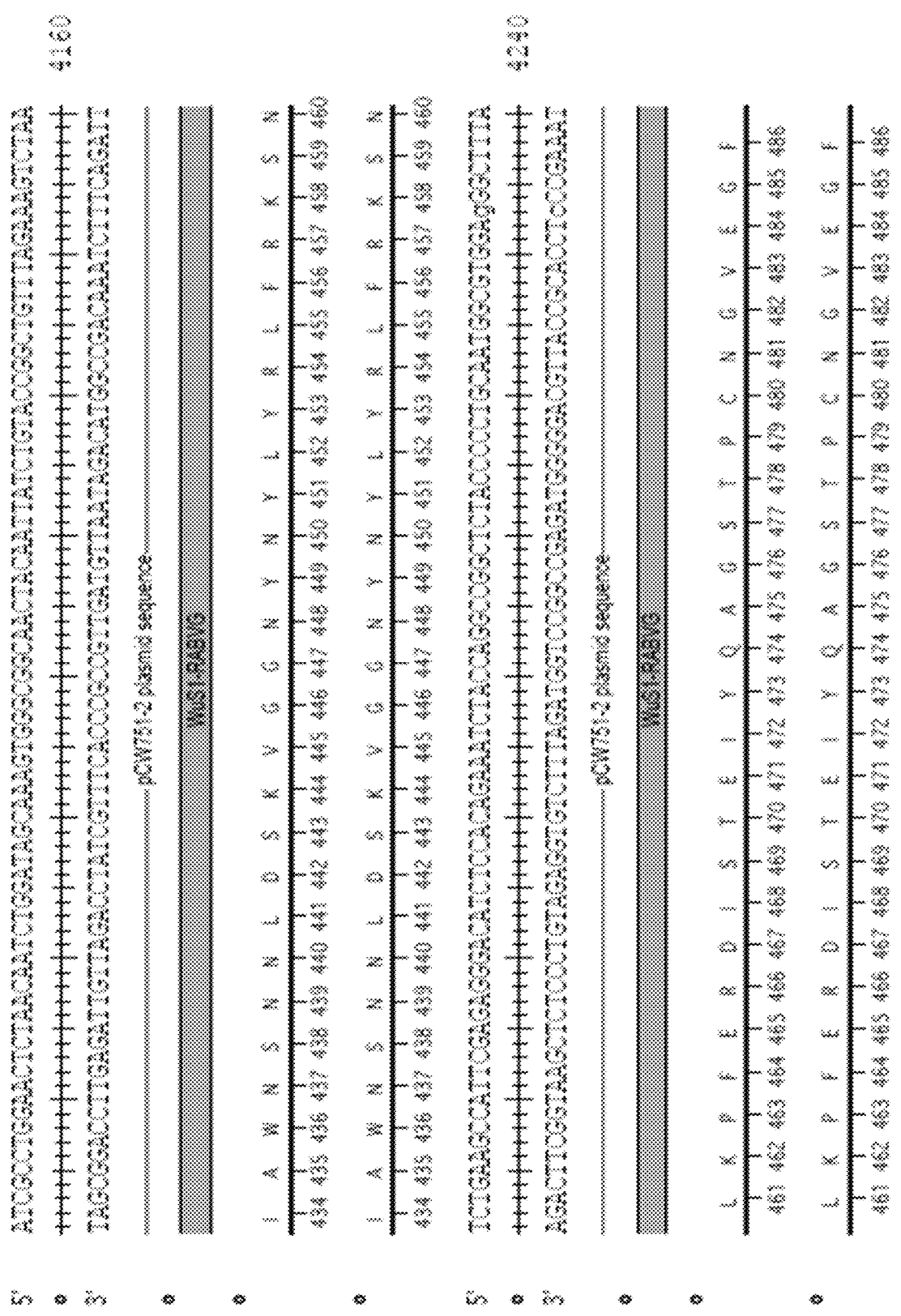
Figure 18:
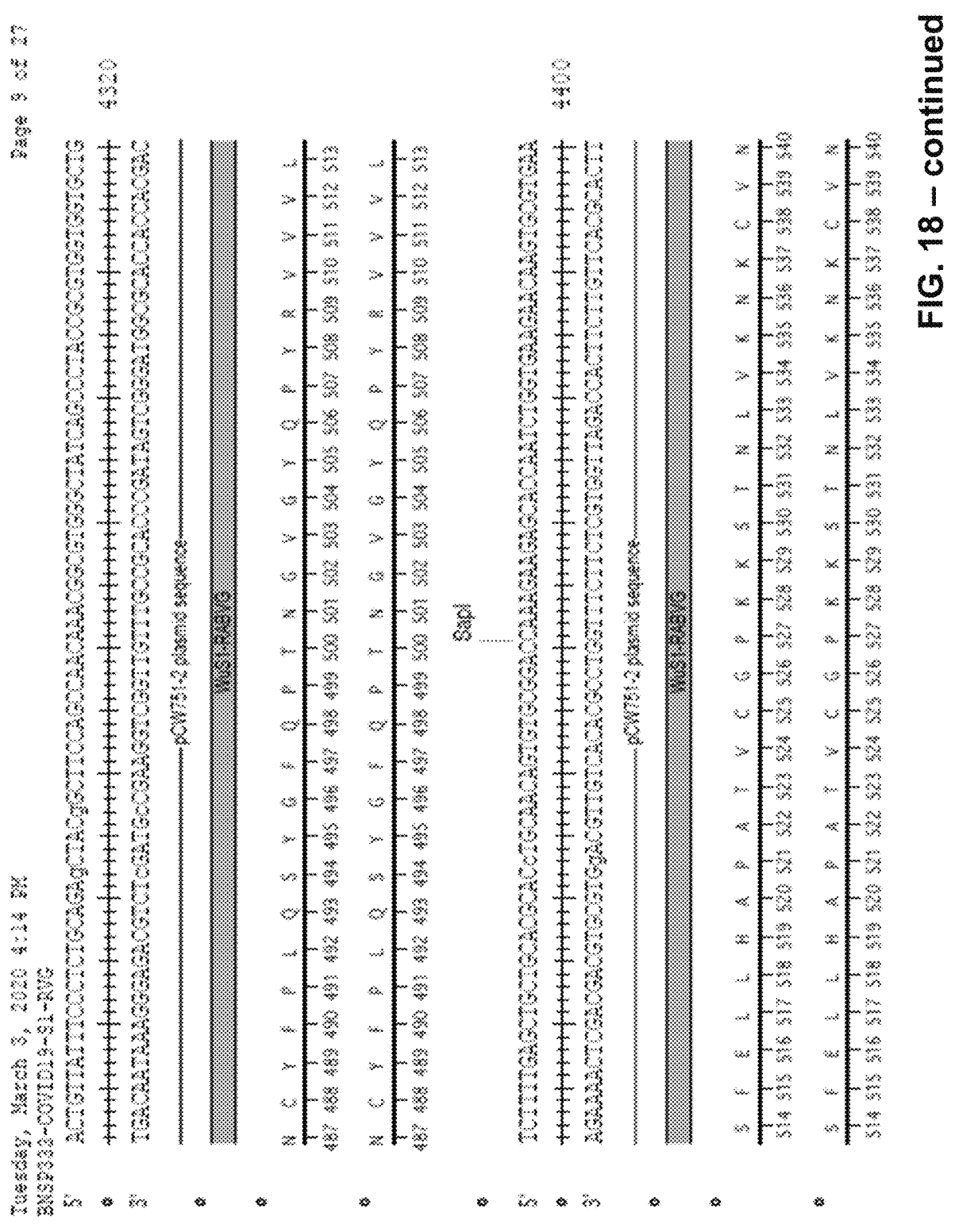
Figure 18:
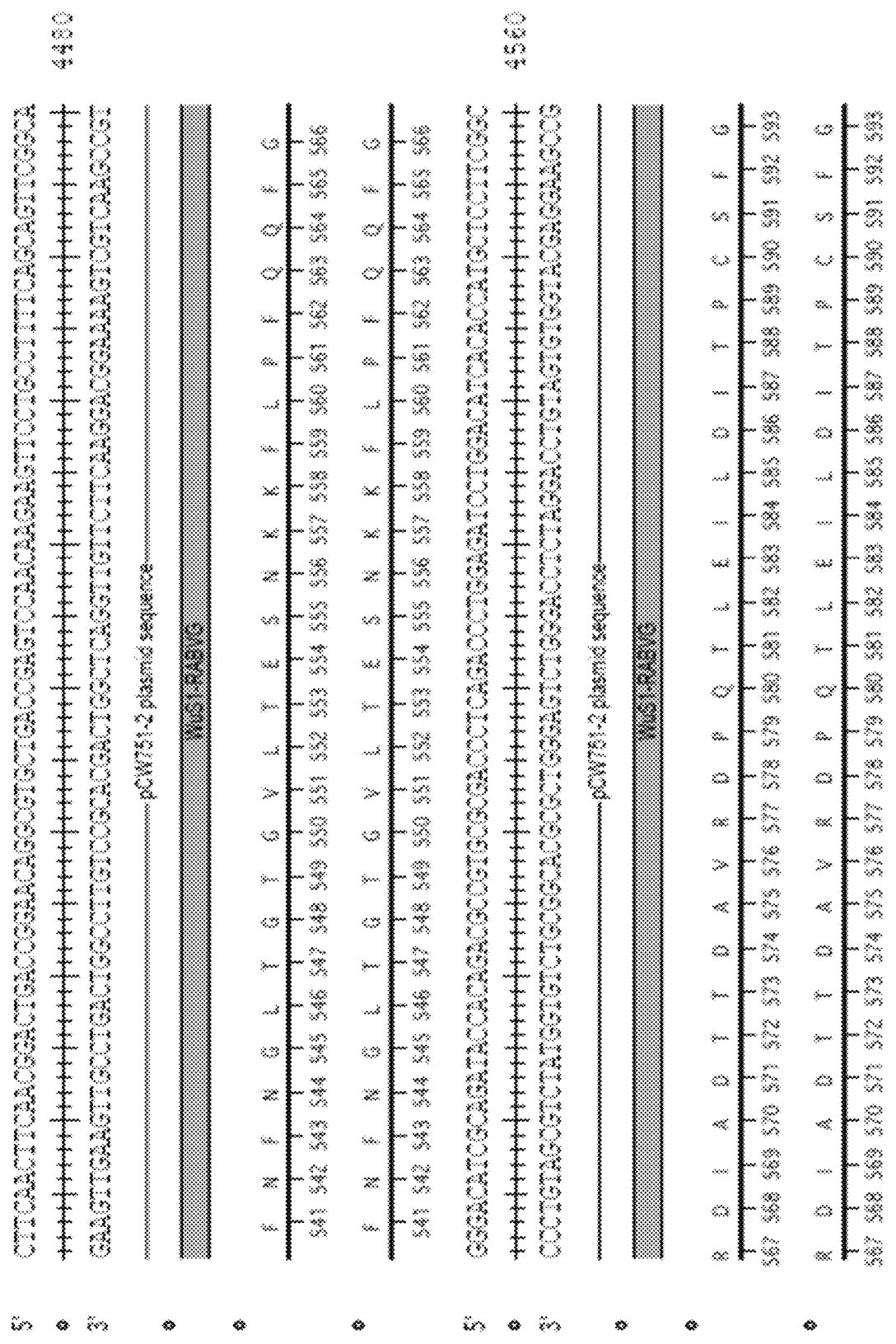
Figure 18:
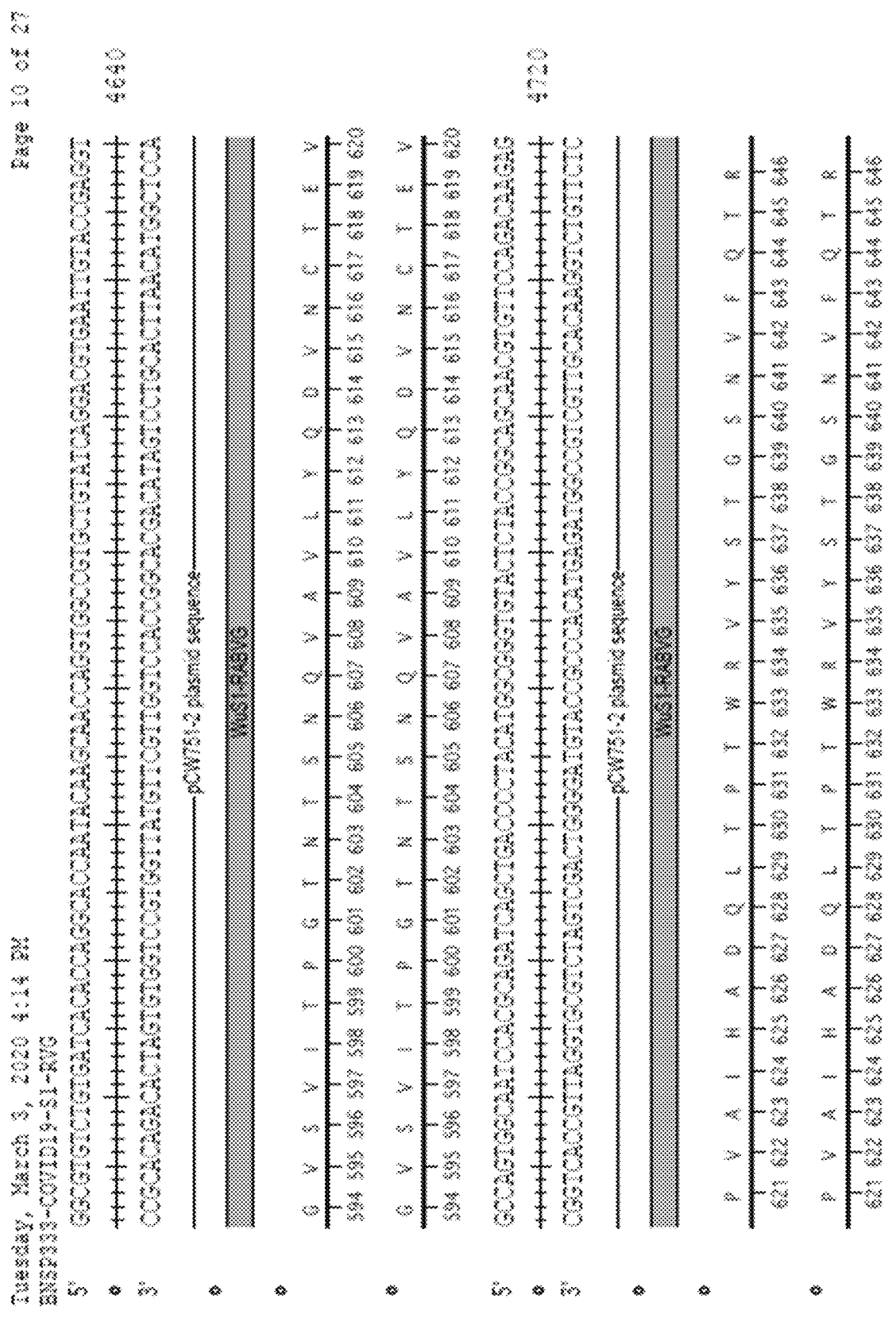
Figure 18:
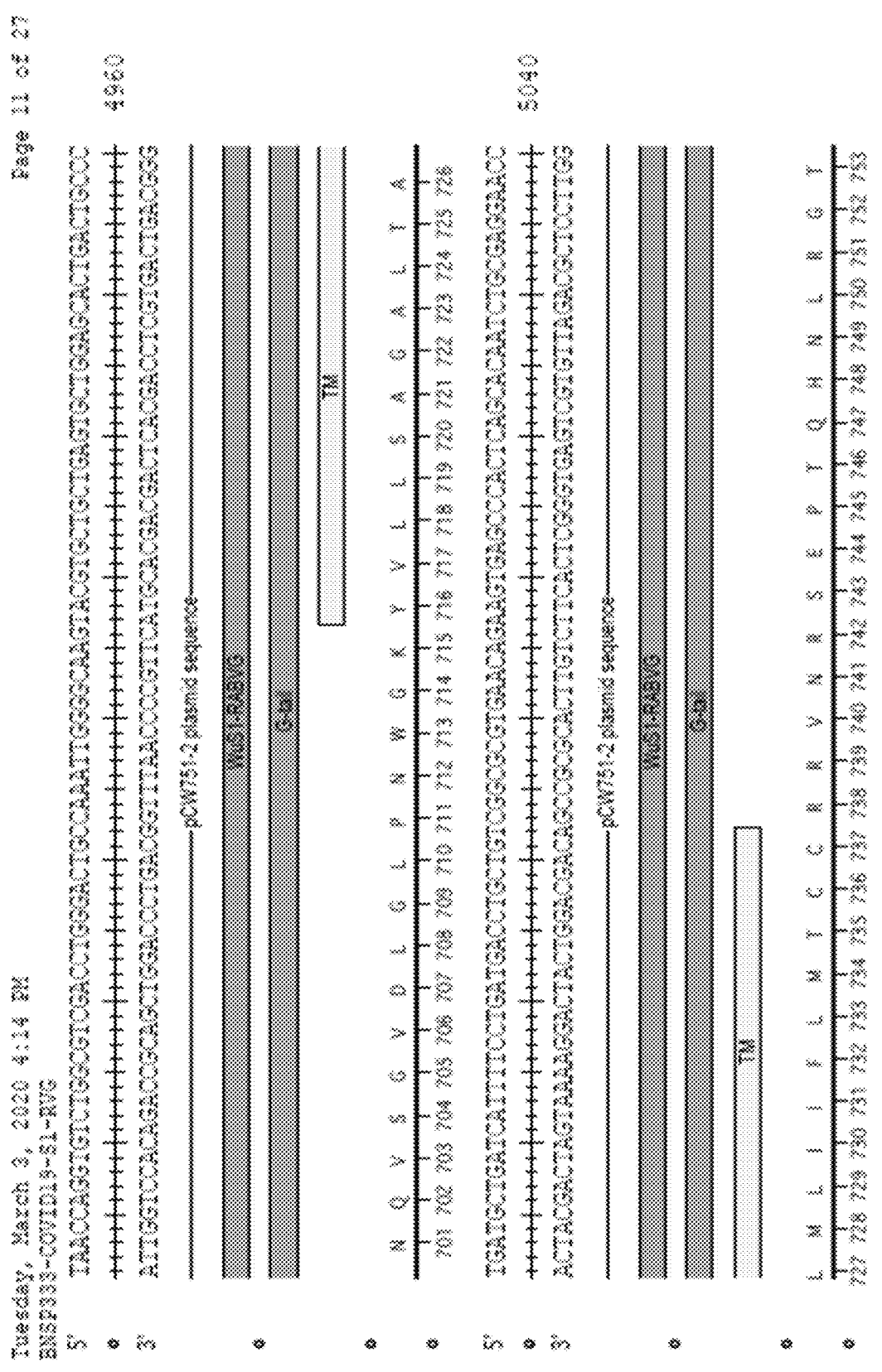
Figure 18:
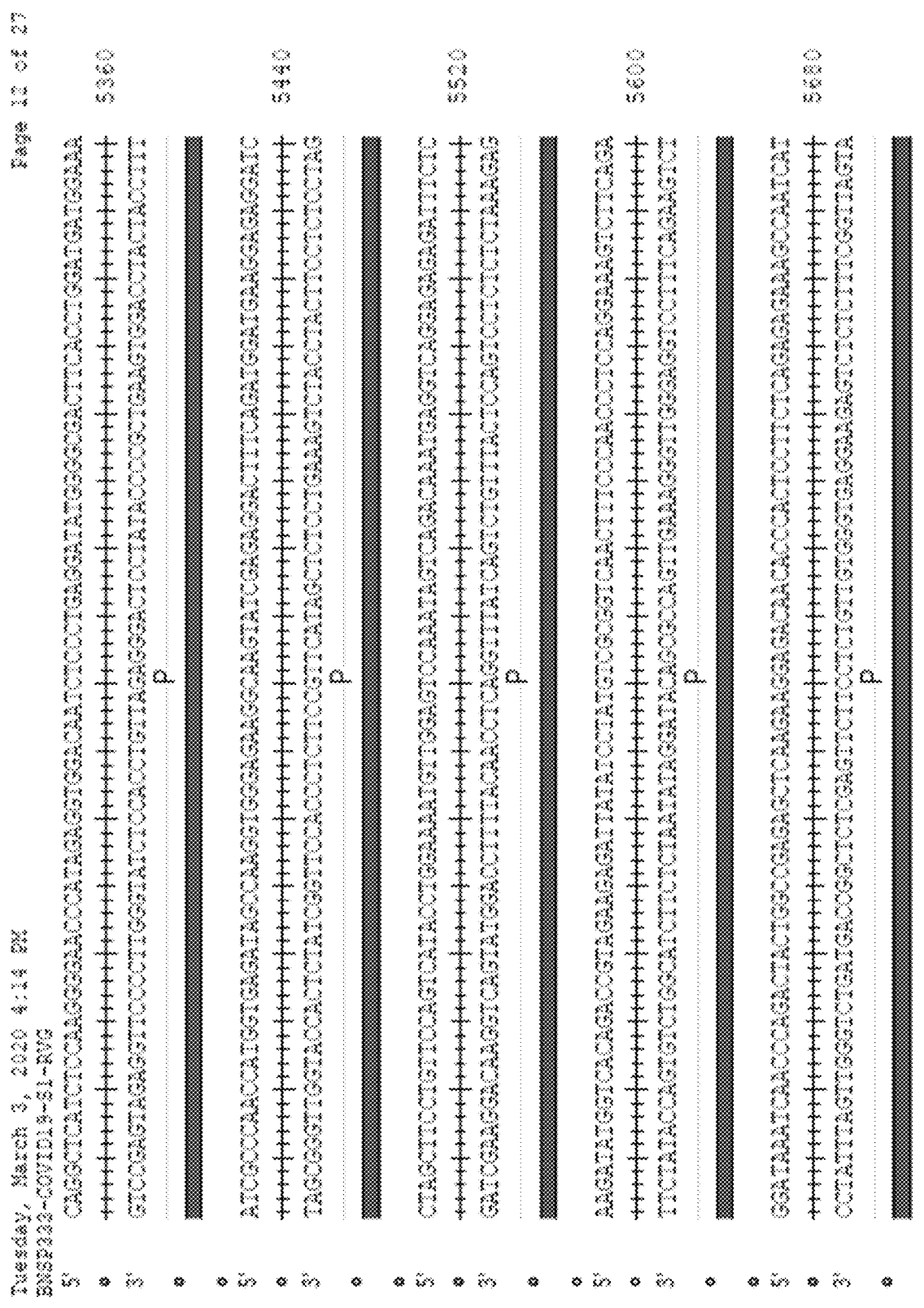
Figure 18:
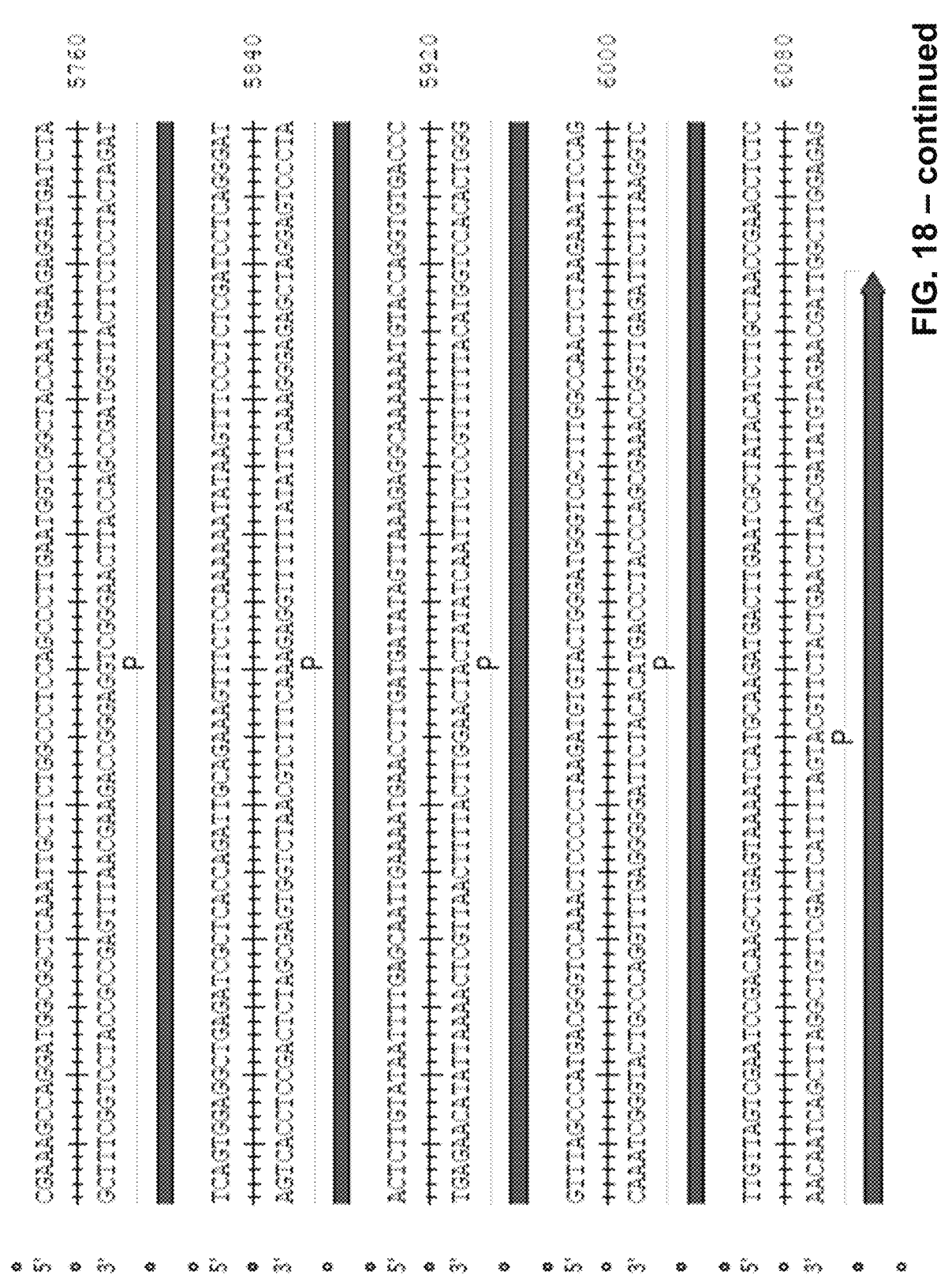
Figure 18:
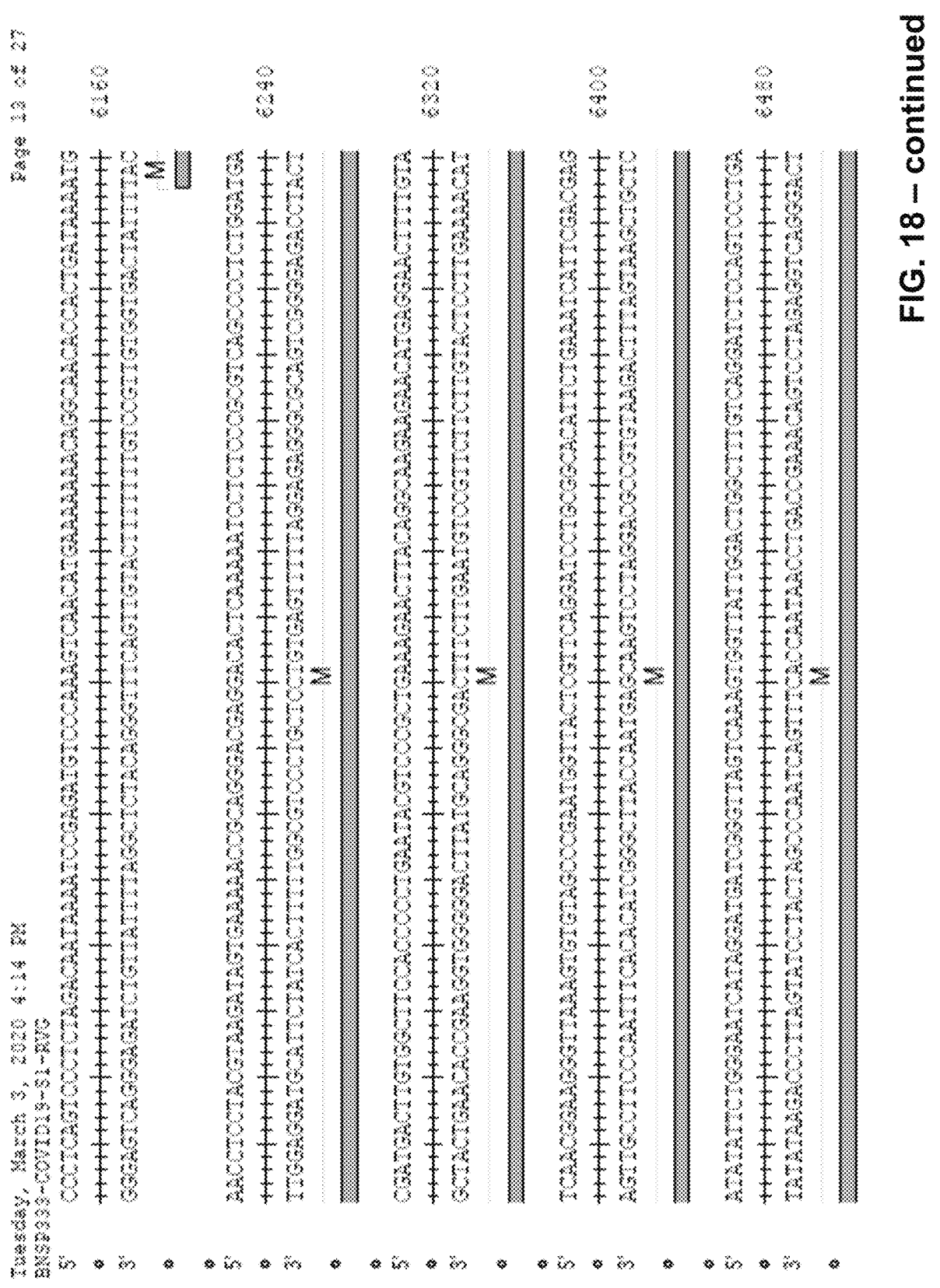
Figure 18:
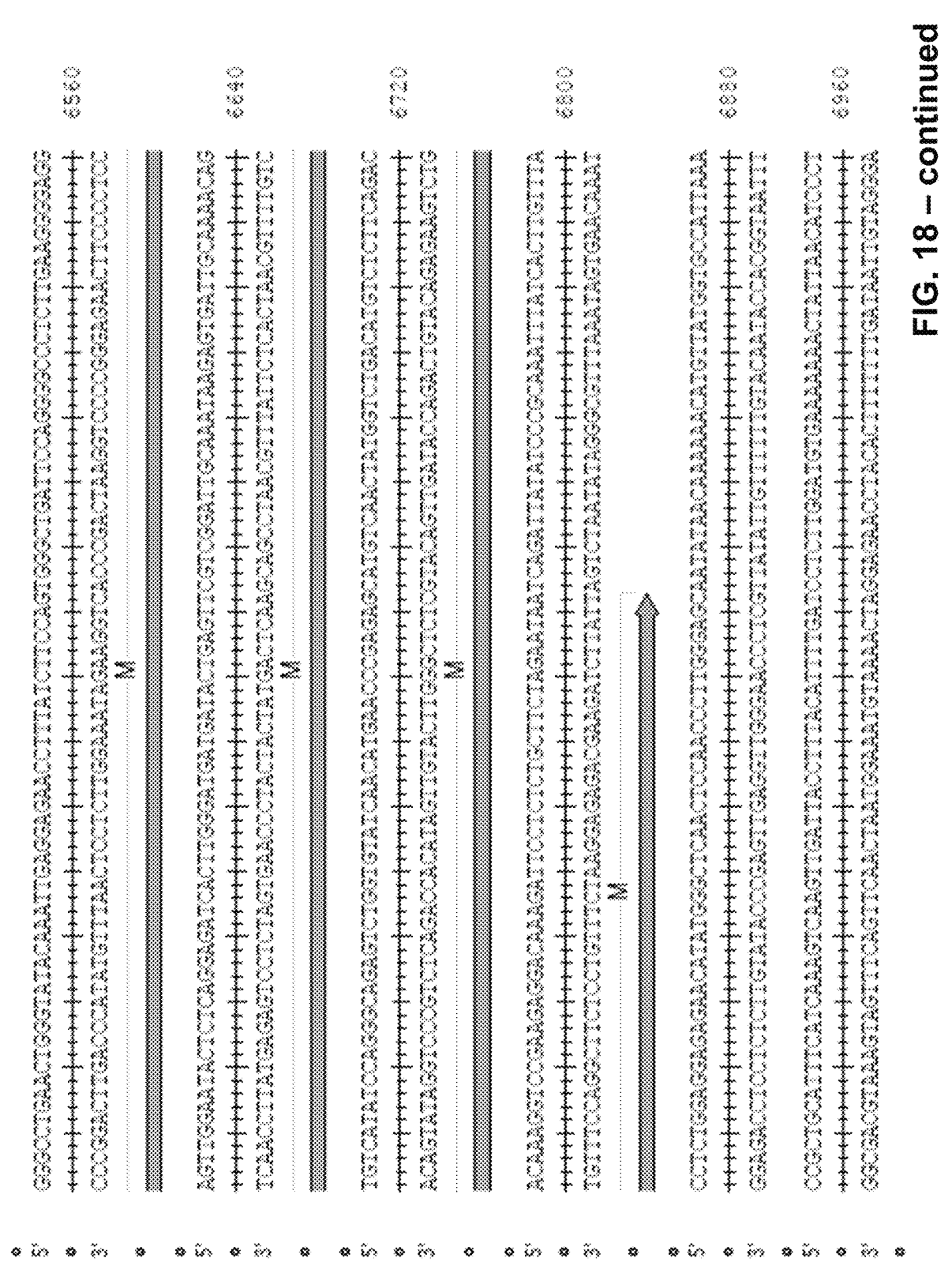
Figure 18:
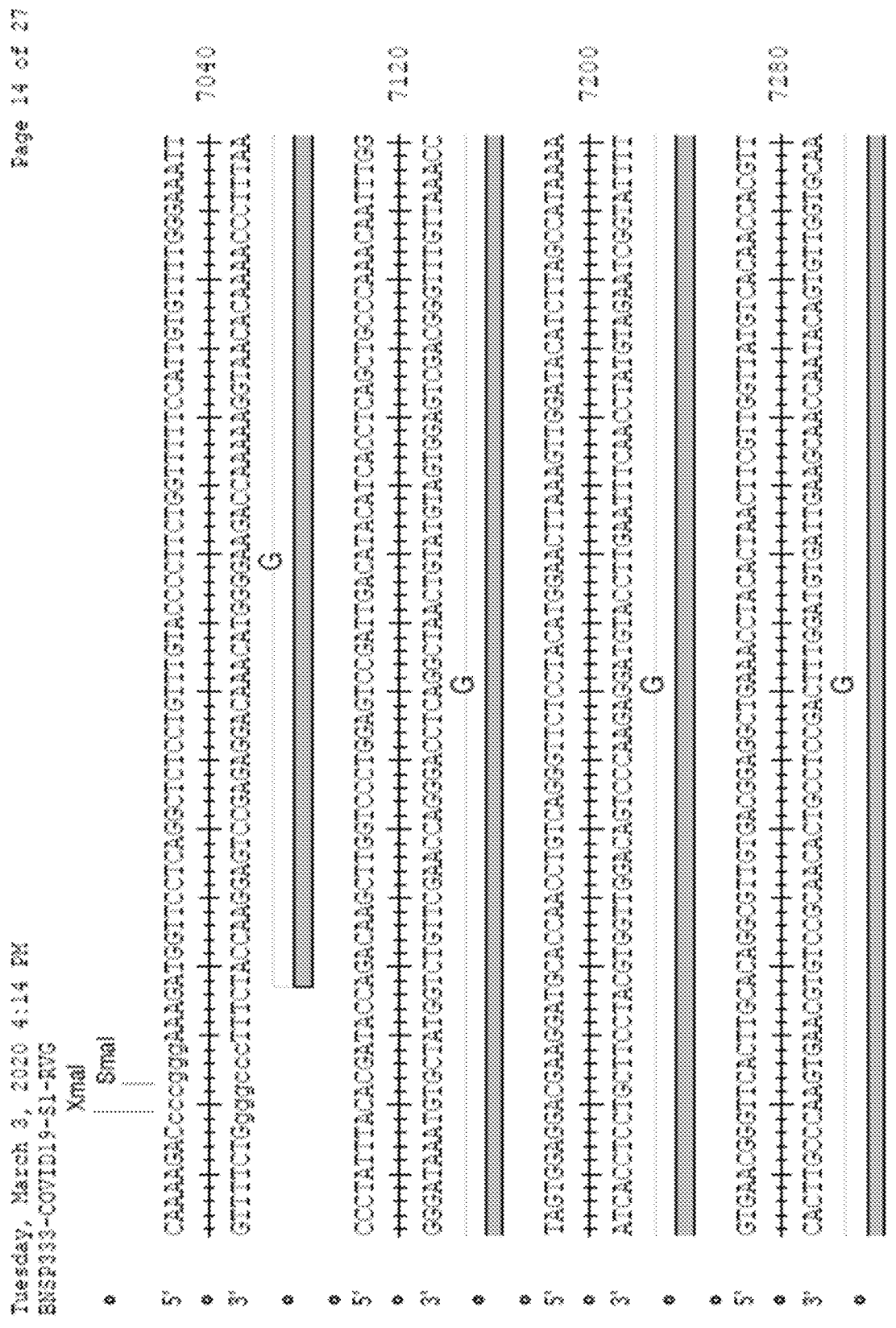
Figure 18:
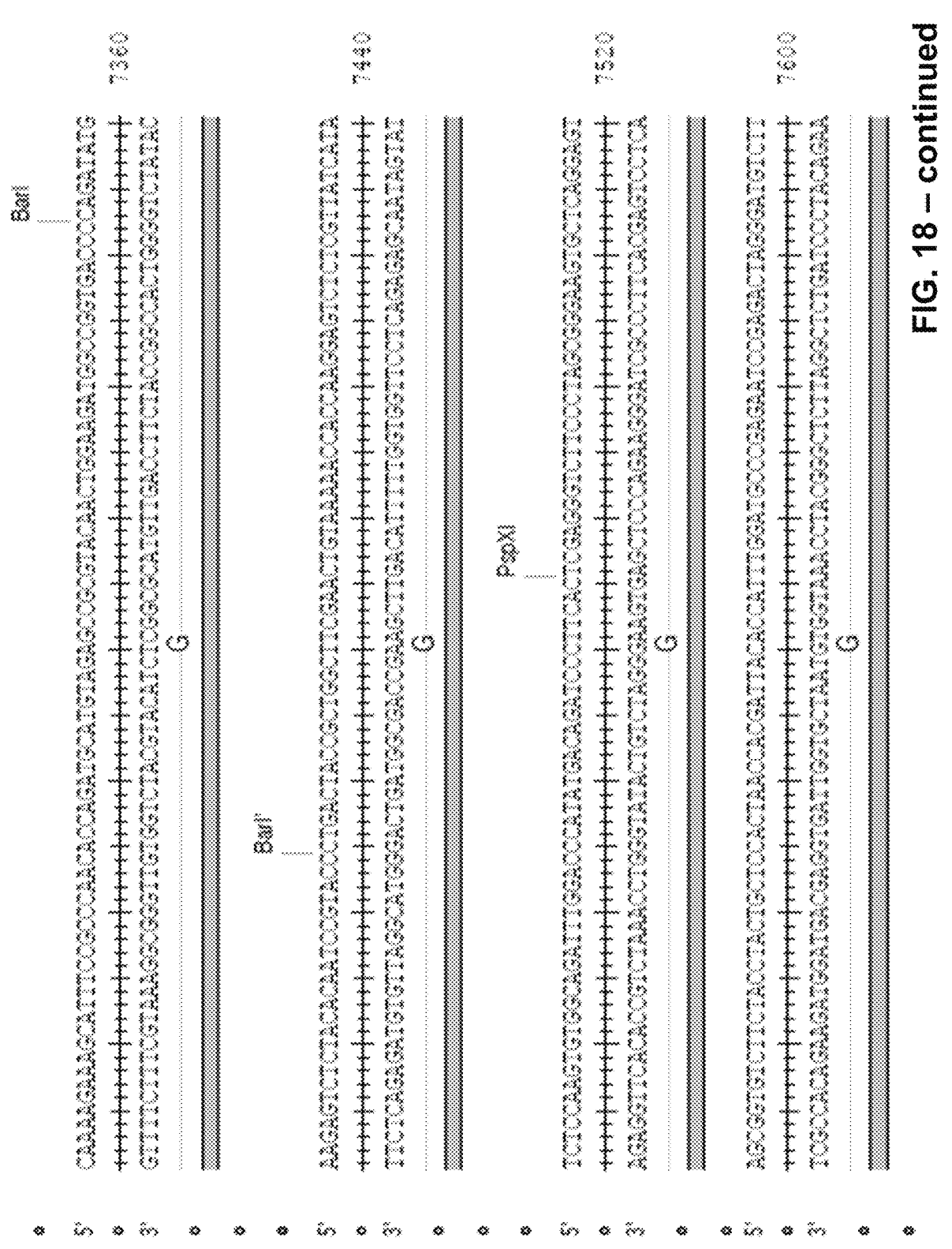
Figure 18:
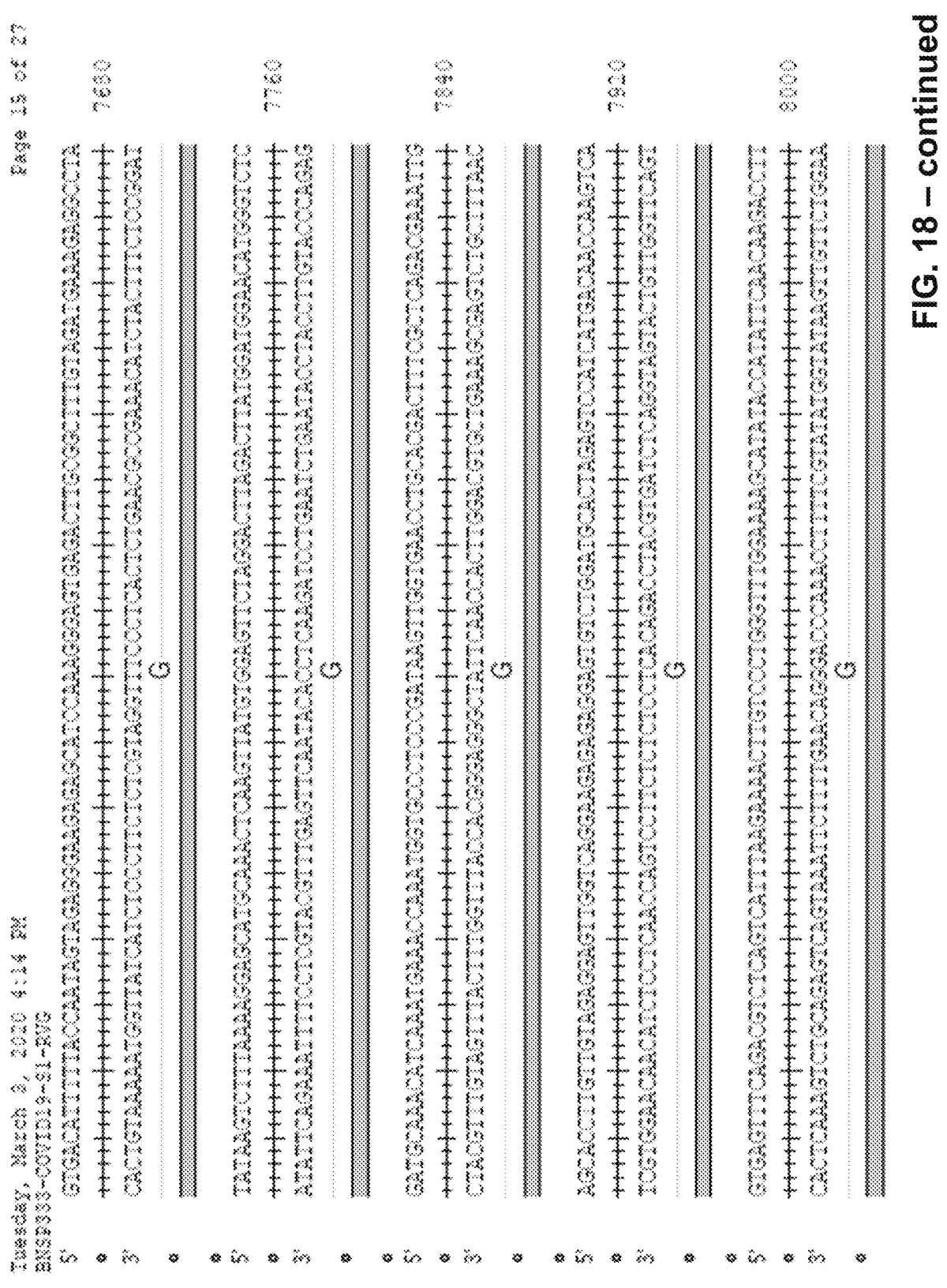
Figure 18:
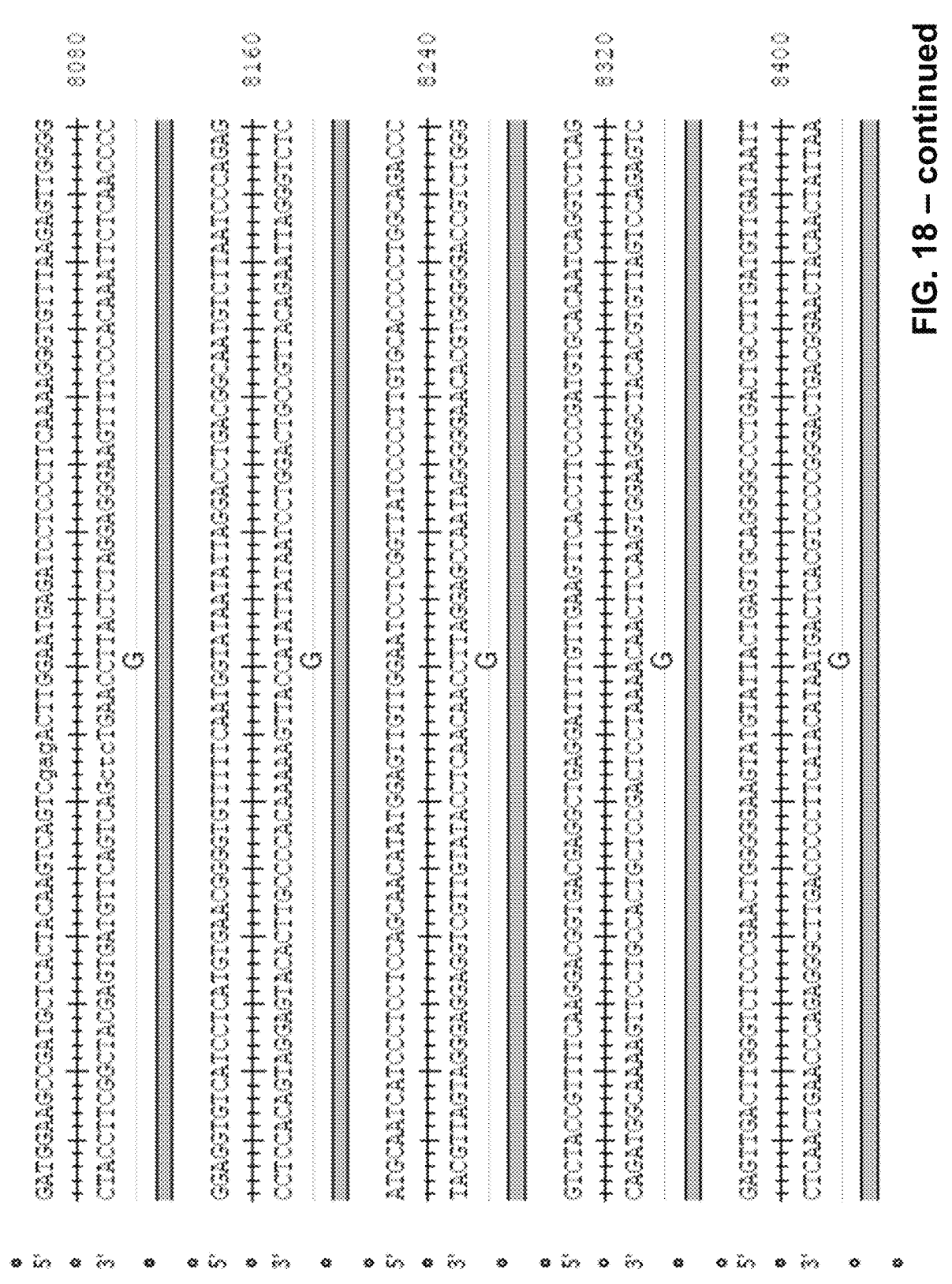
Figure 18:
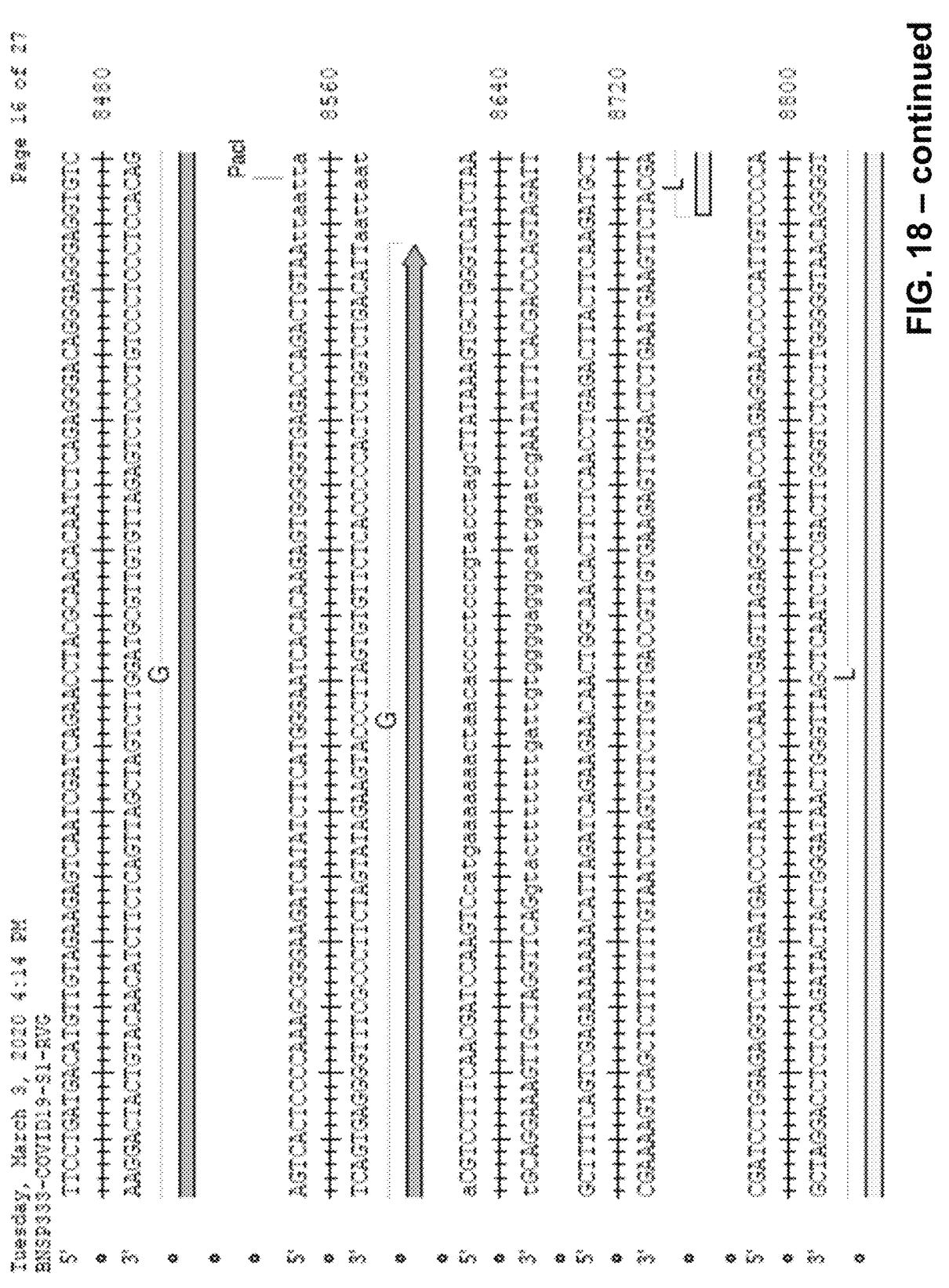
Figure 18:
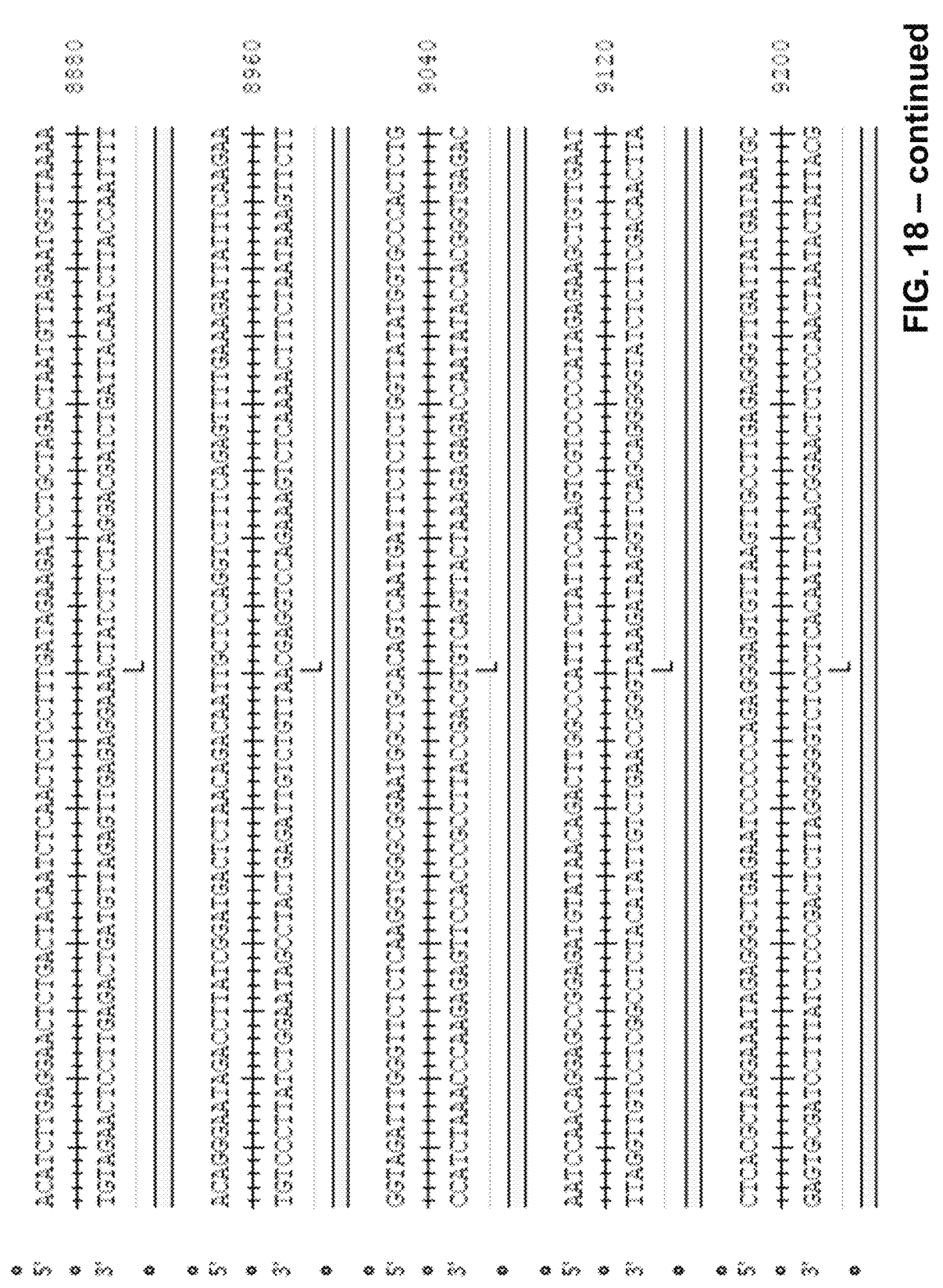
Figure 18:
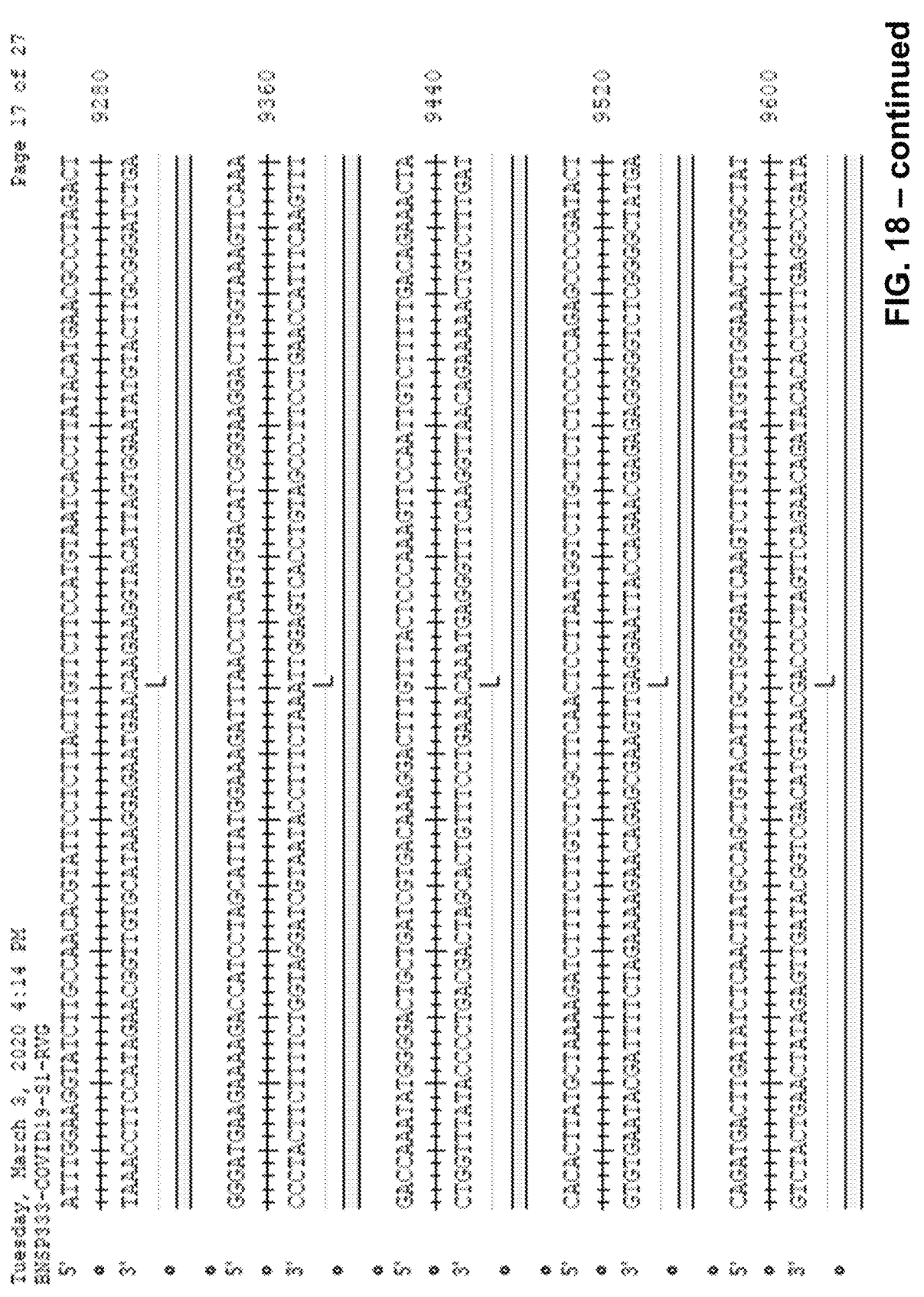
Figure 18:
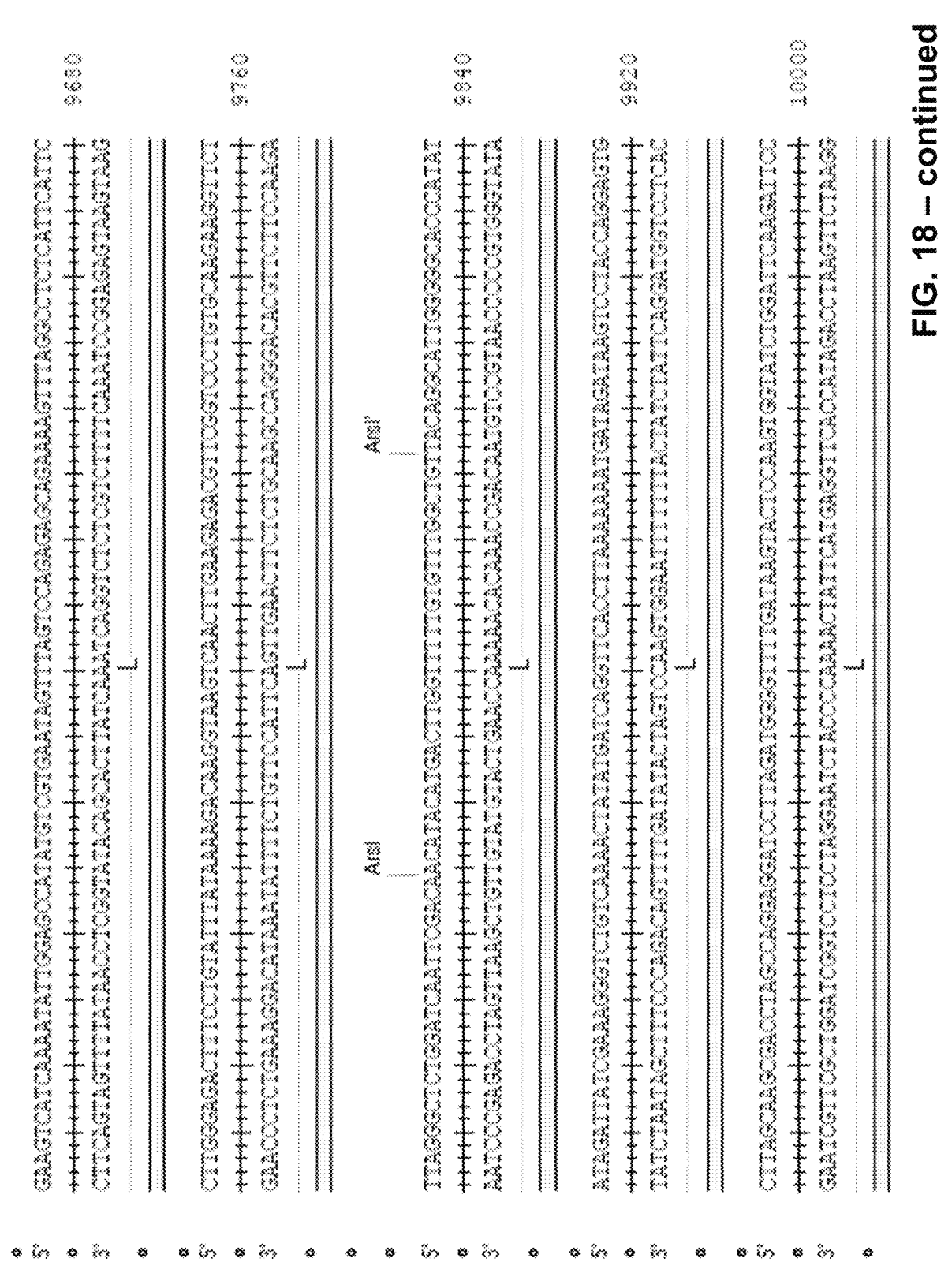
Figure 18:
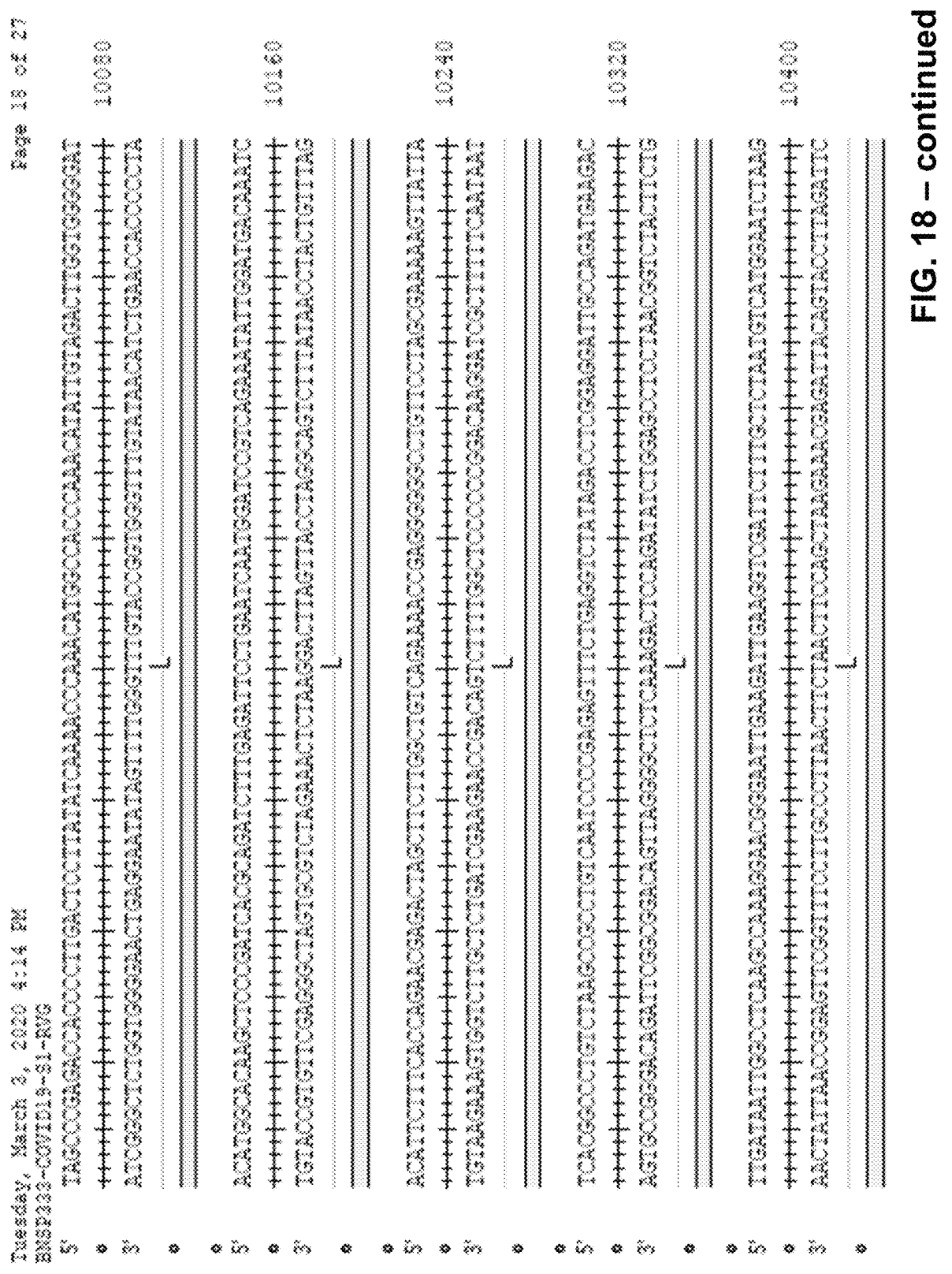
Figure 18:
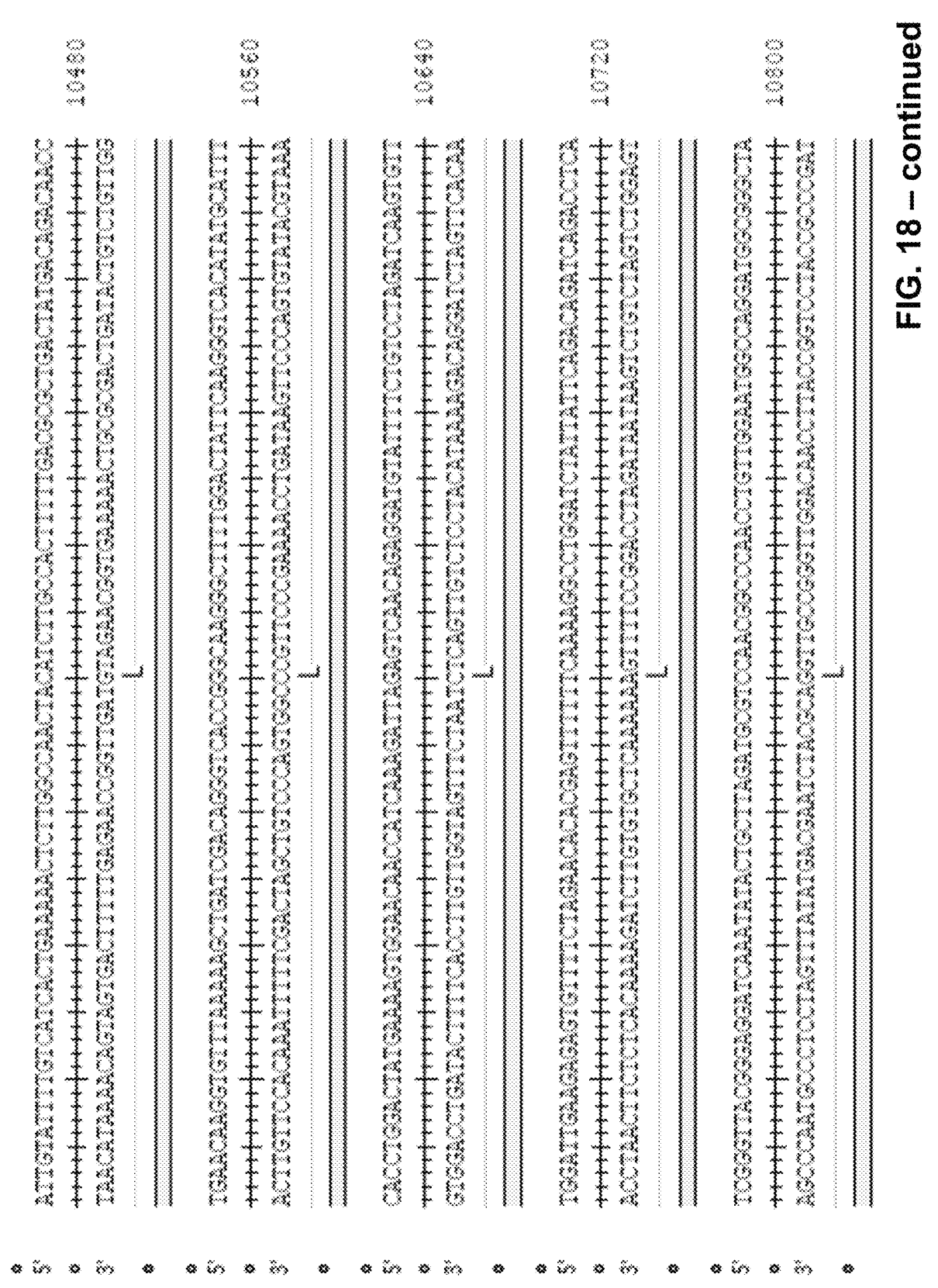
Figure 18:
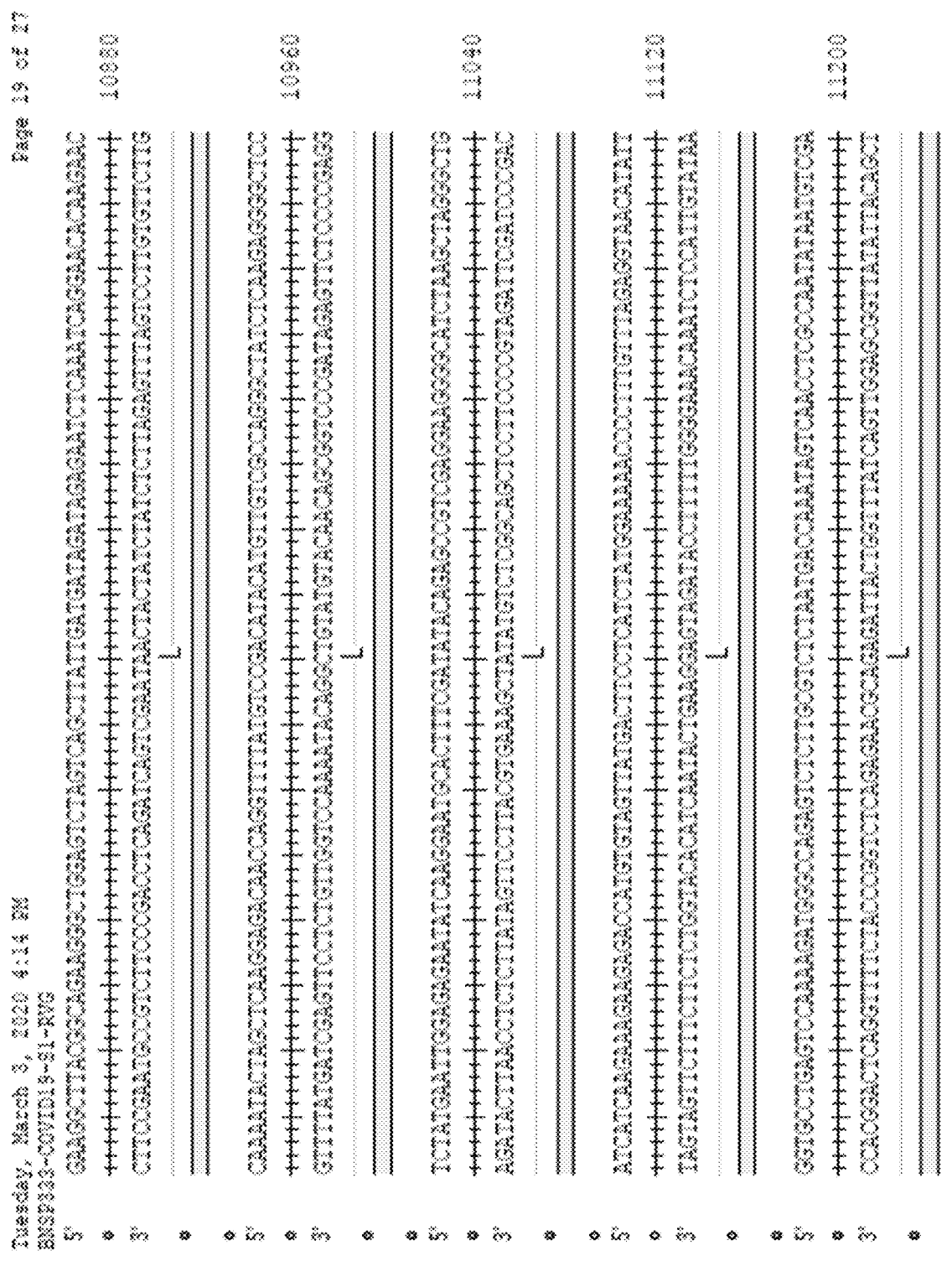
Figure 18:
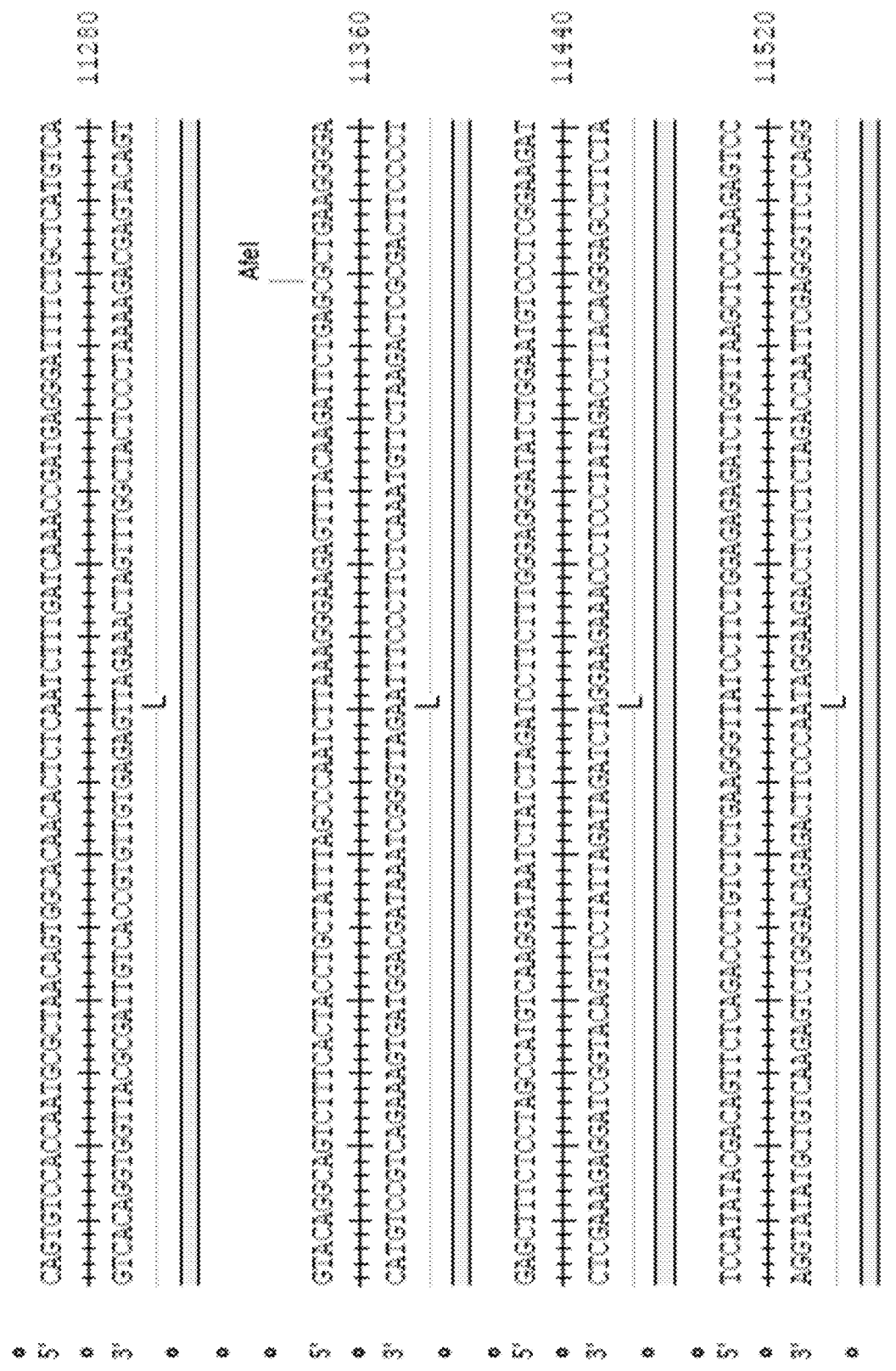
Figure 18:
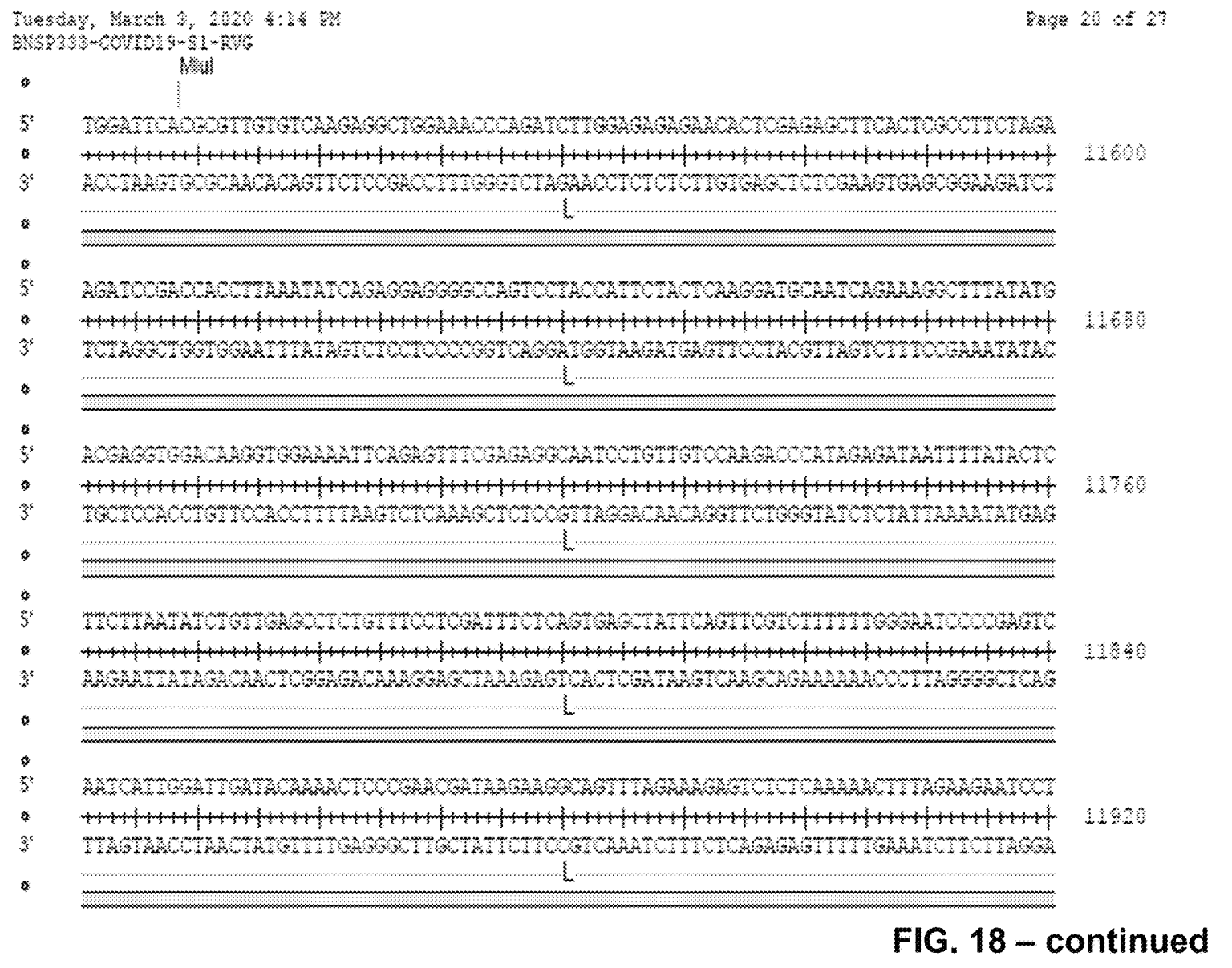
Figure 18:
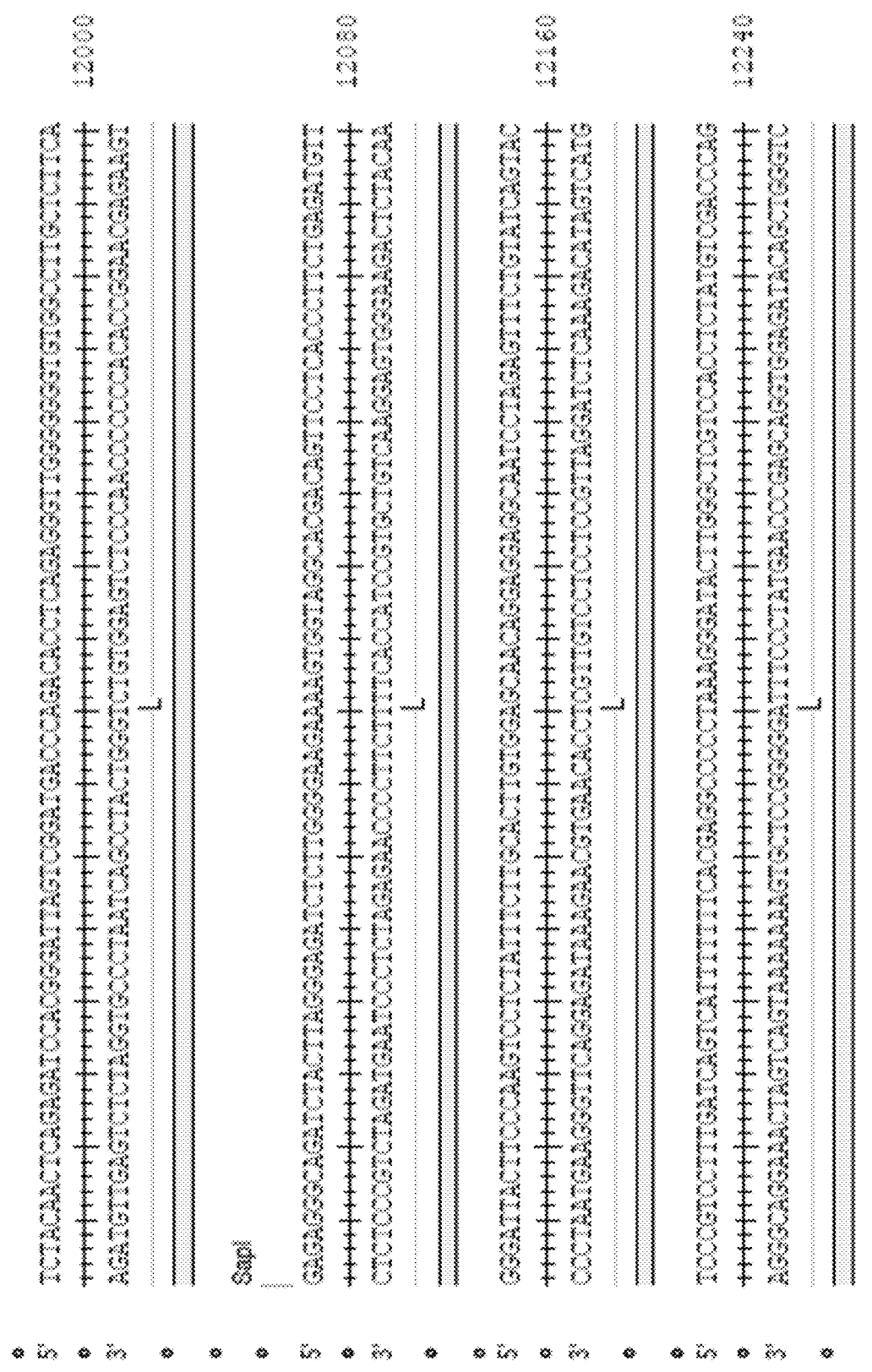
Figure 18:
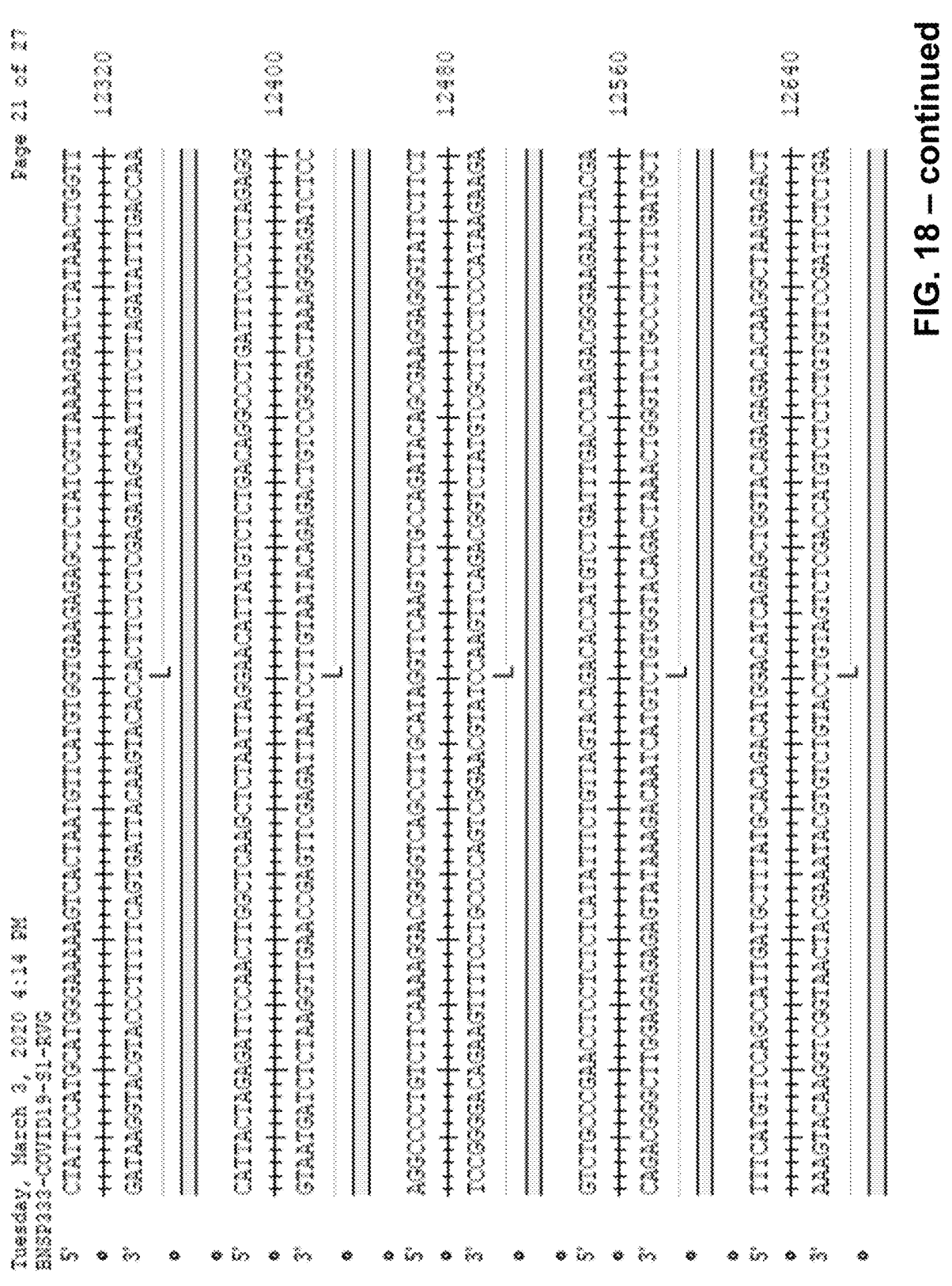
Figure 18:
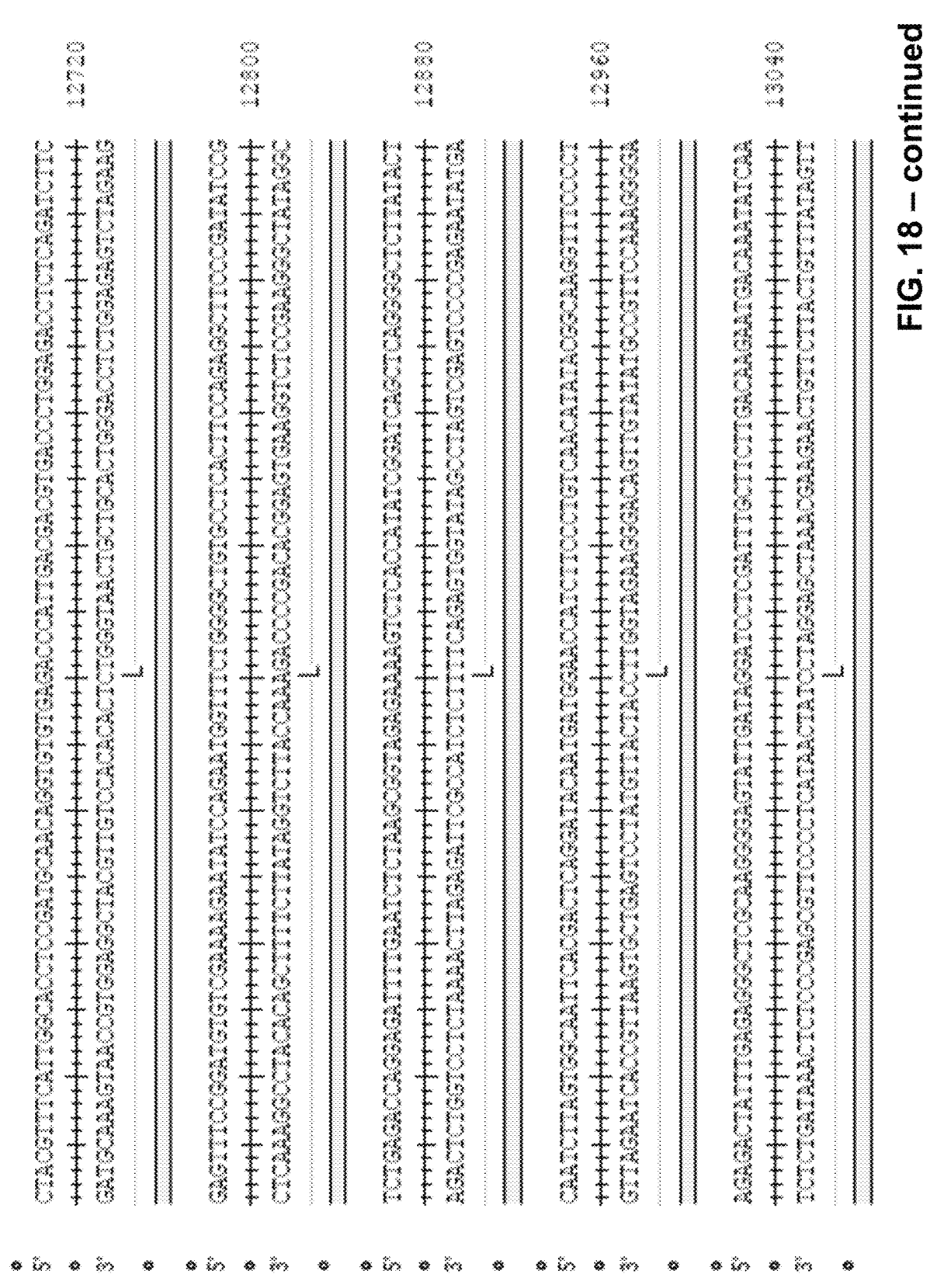
Figure 18:
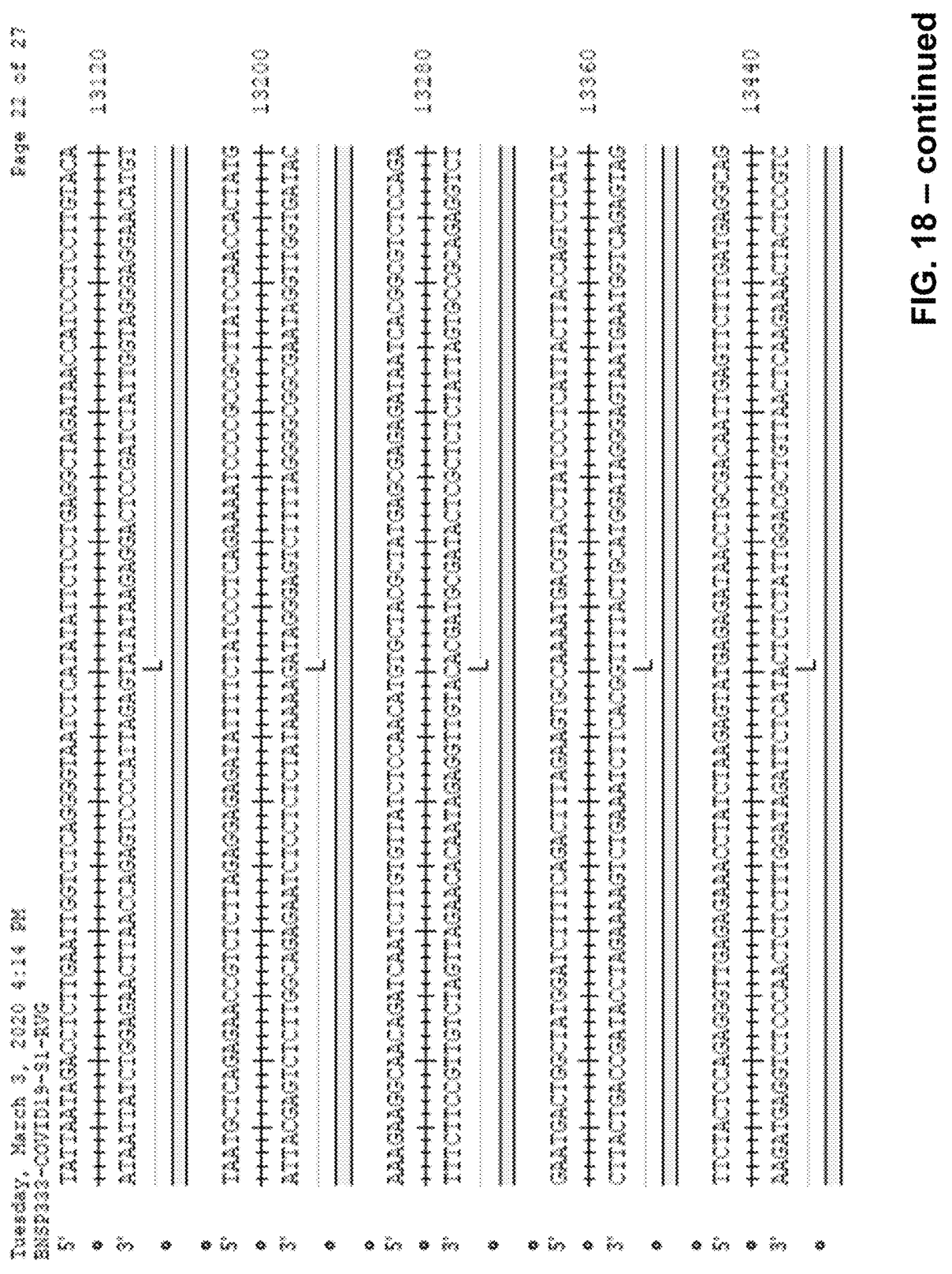
Figure 18:
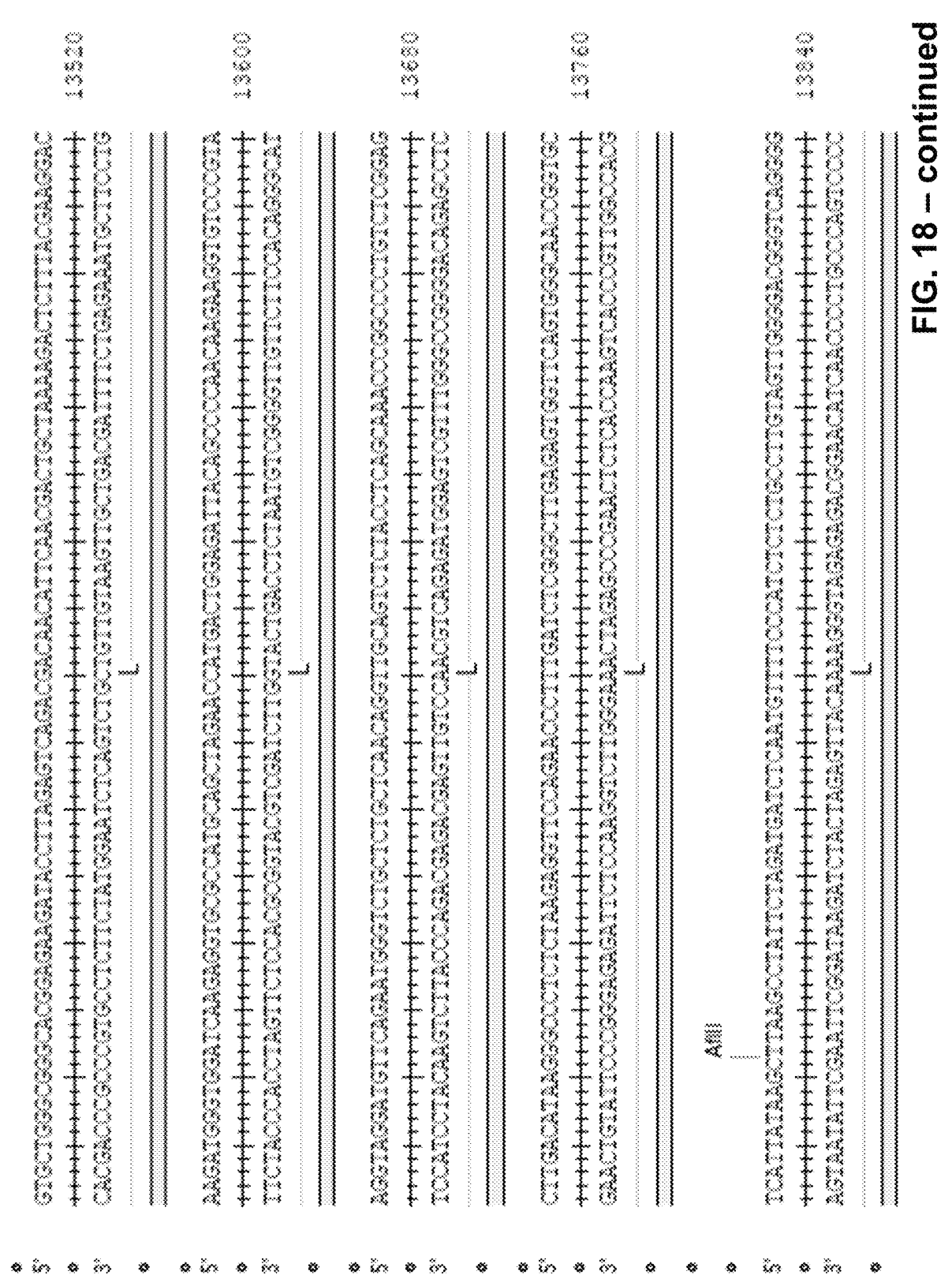
Figure 18:
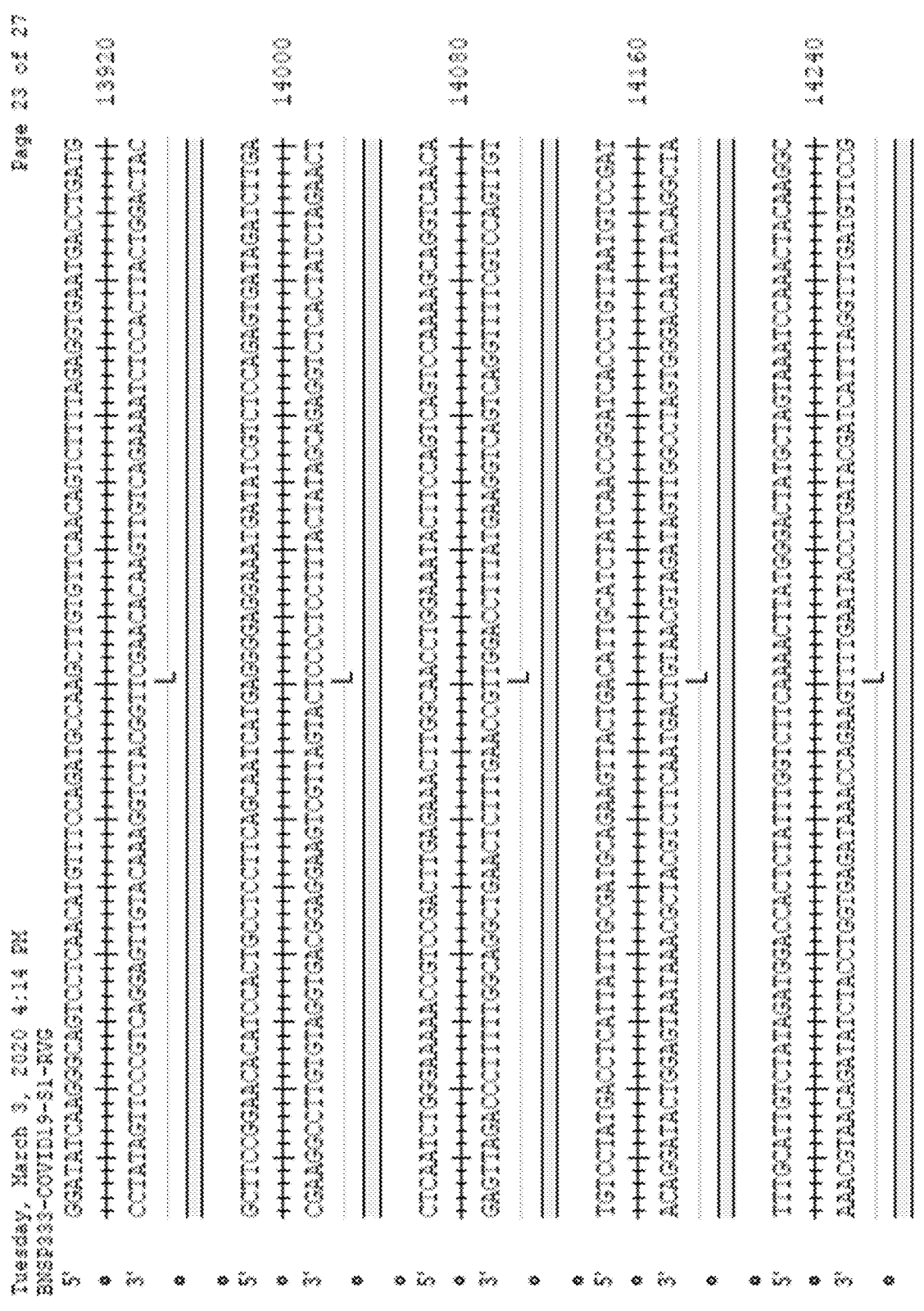
Figure 18:
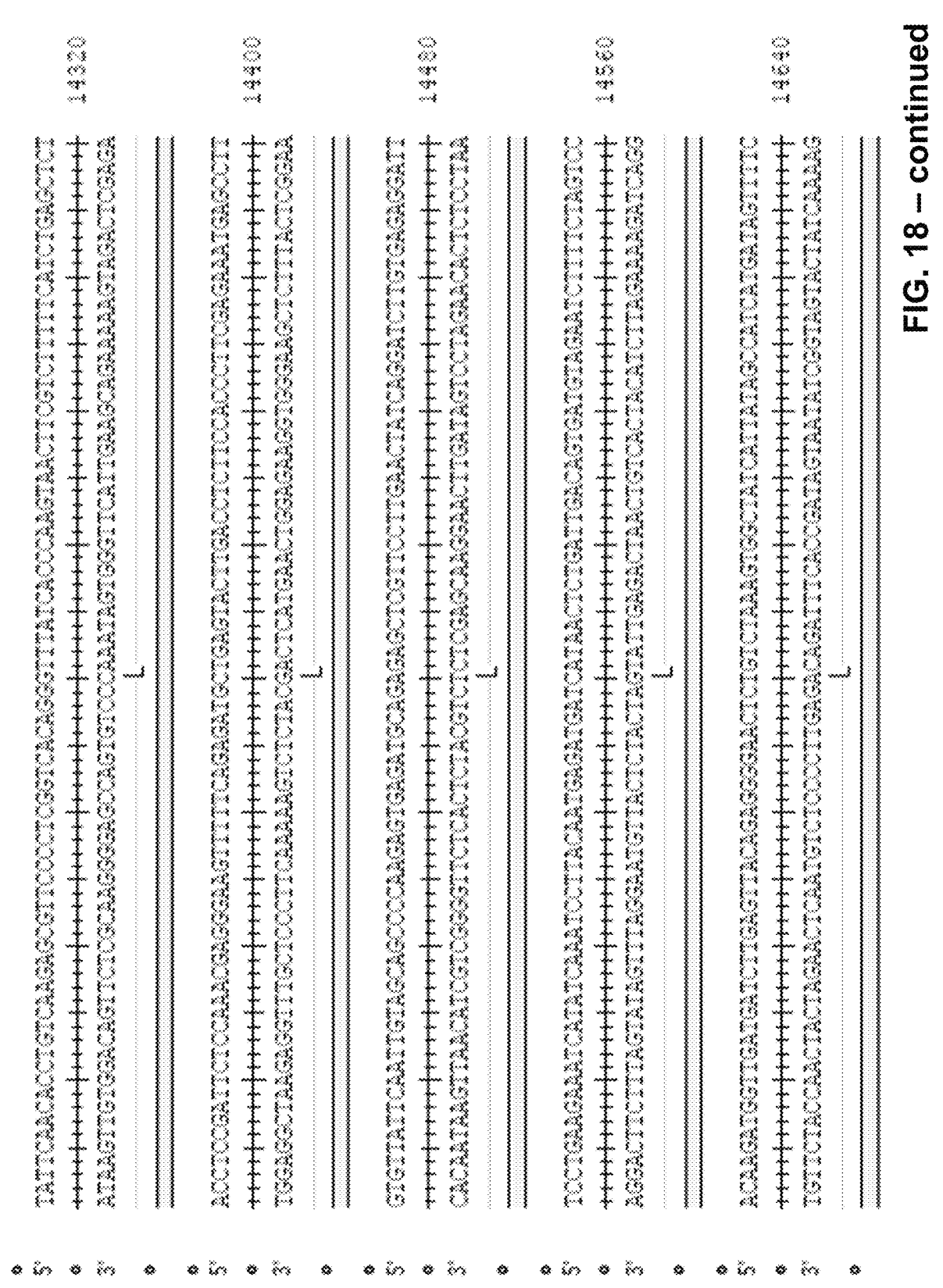
Figure 18:
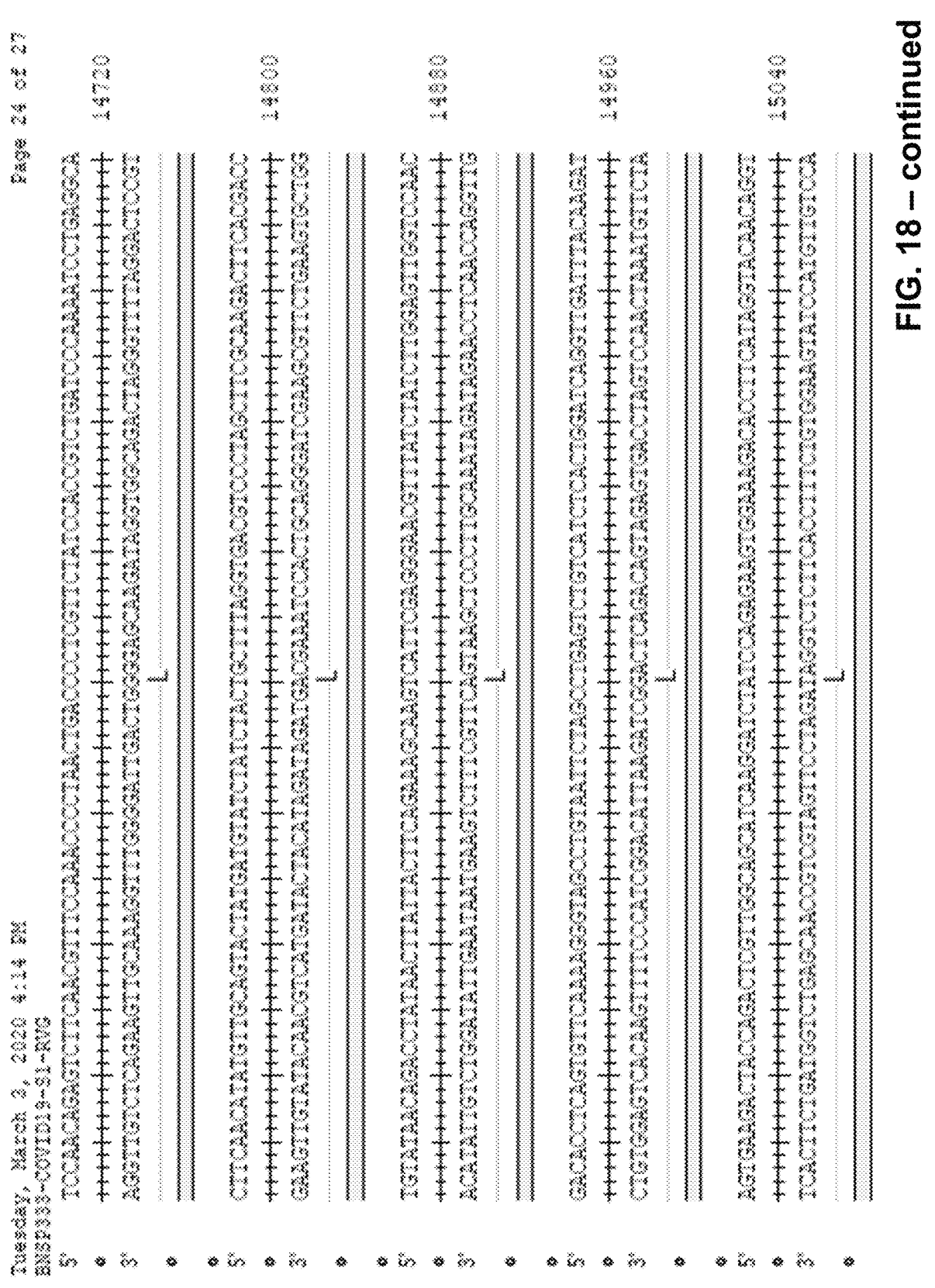
Figure 18:
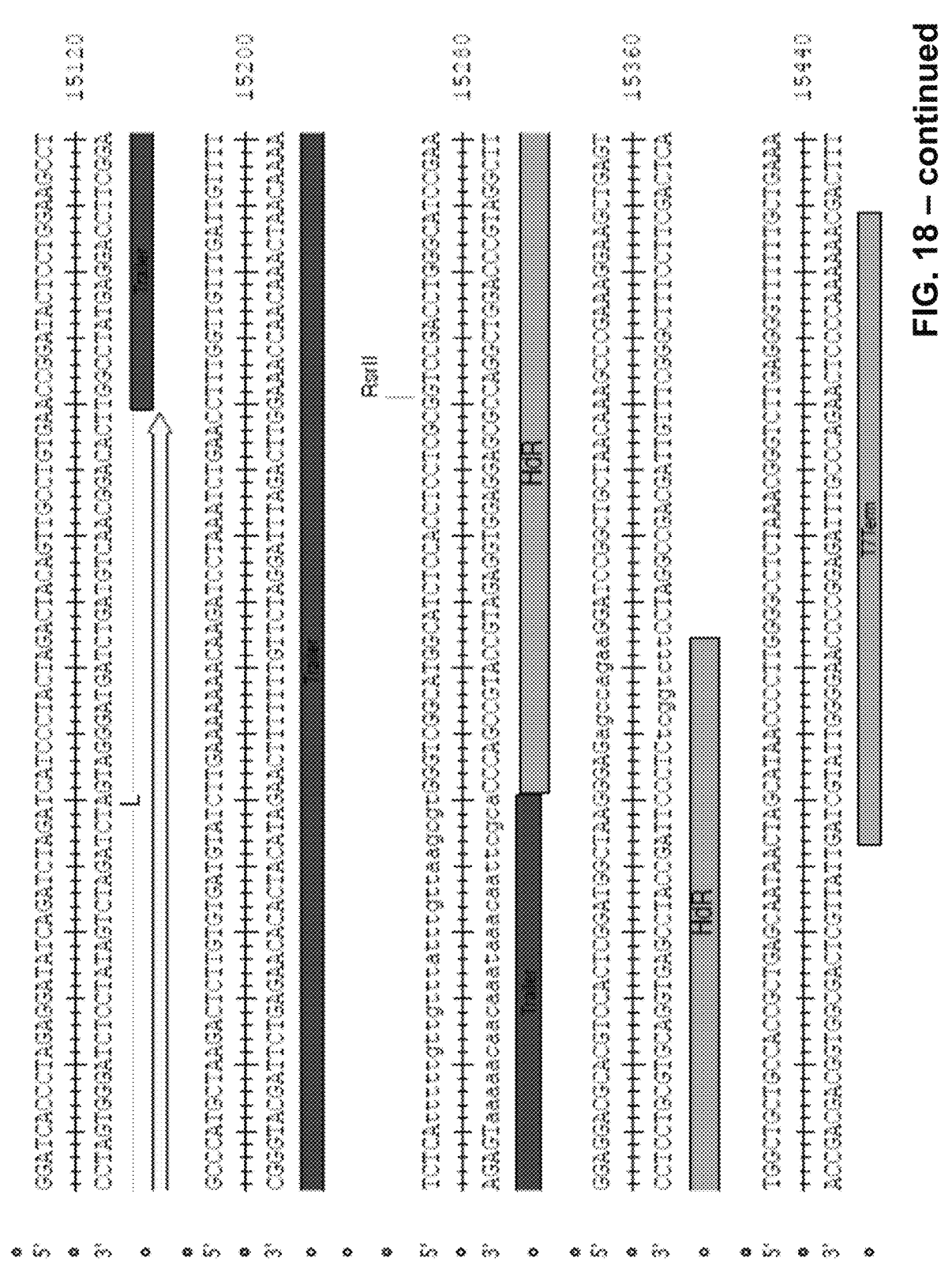
Figure 18:
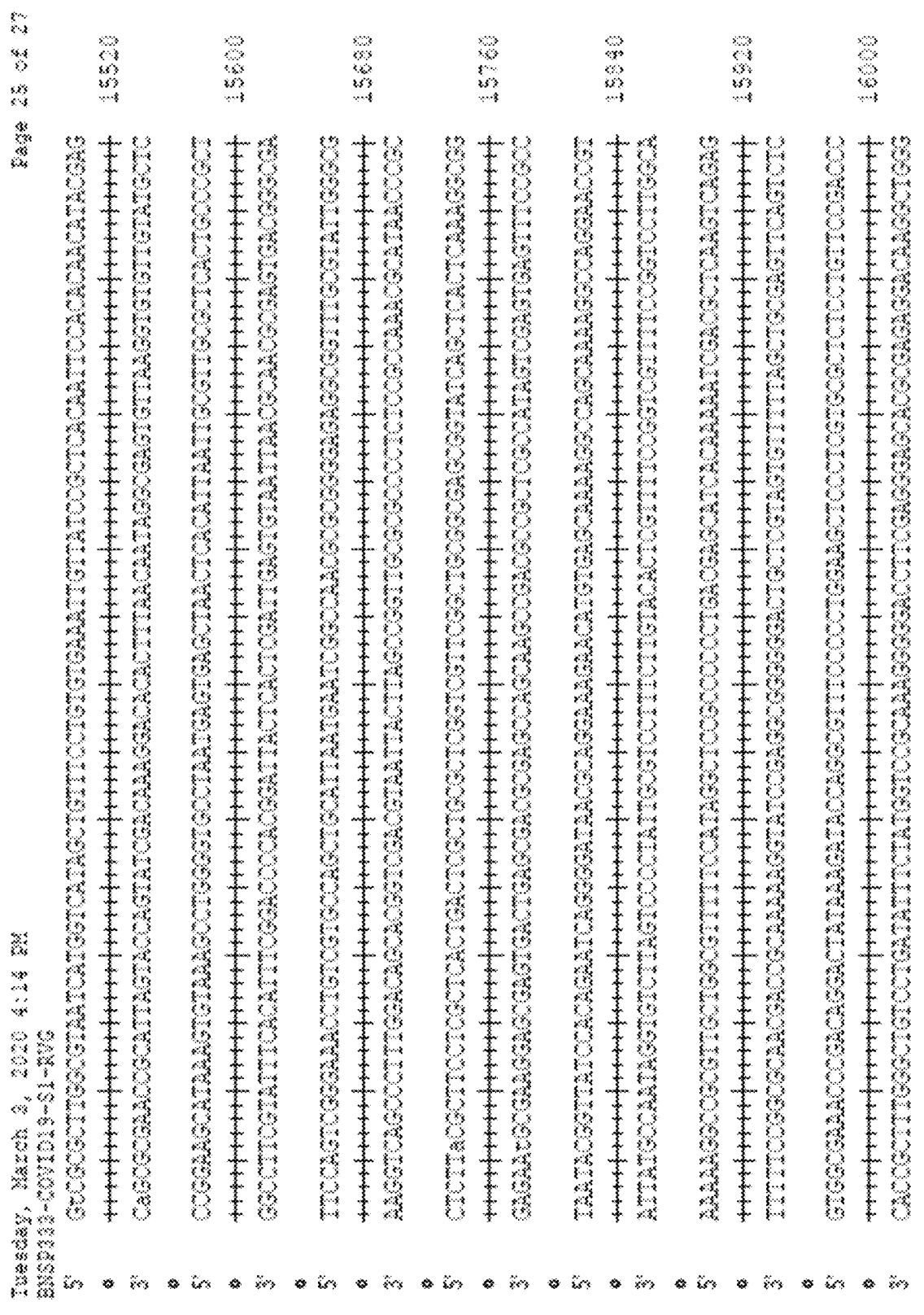
Figure 18:
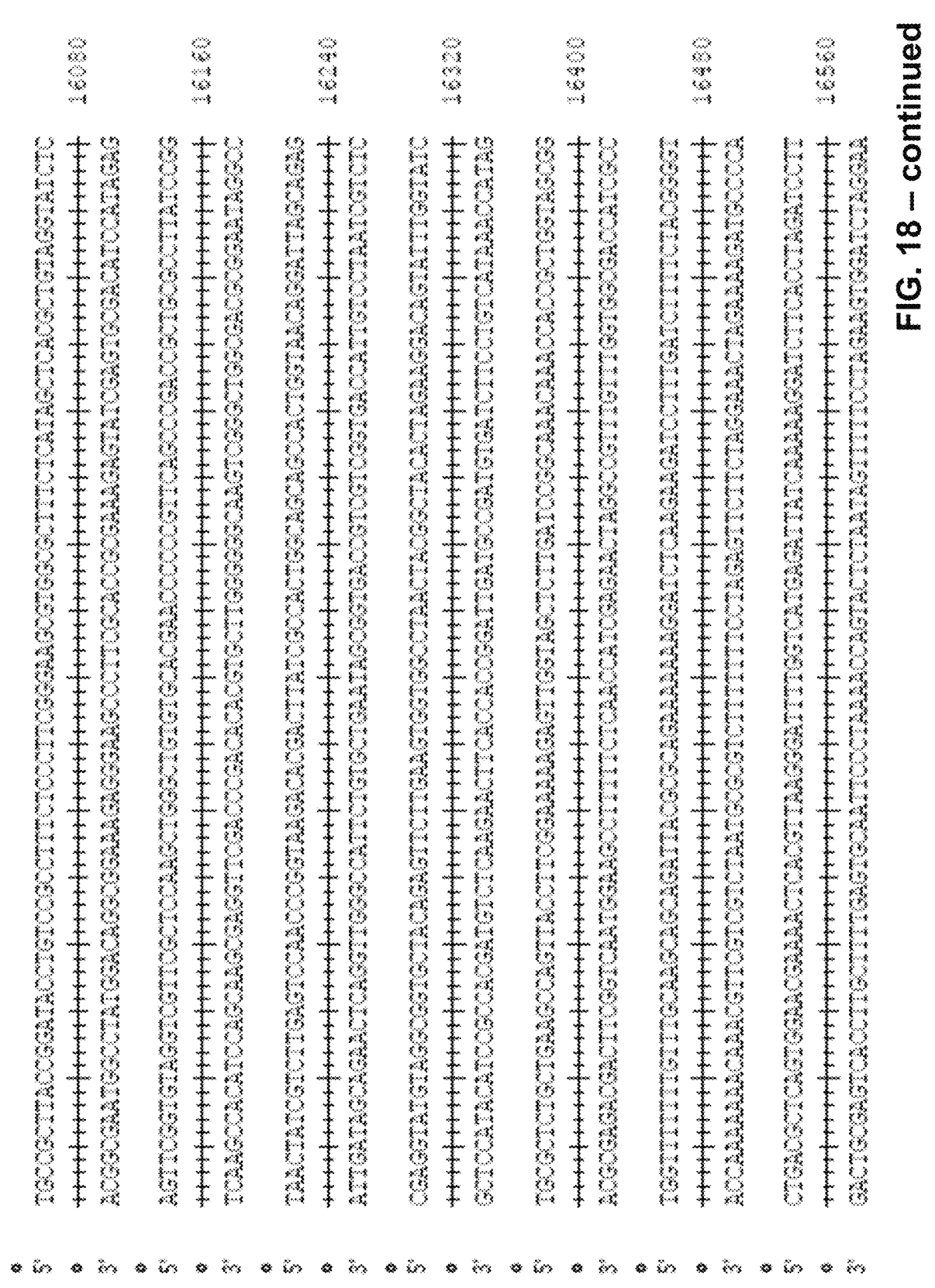
Figure 18:
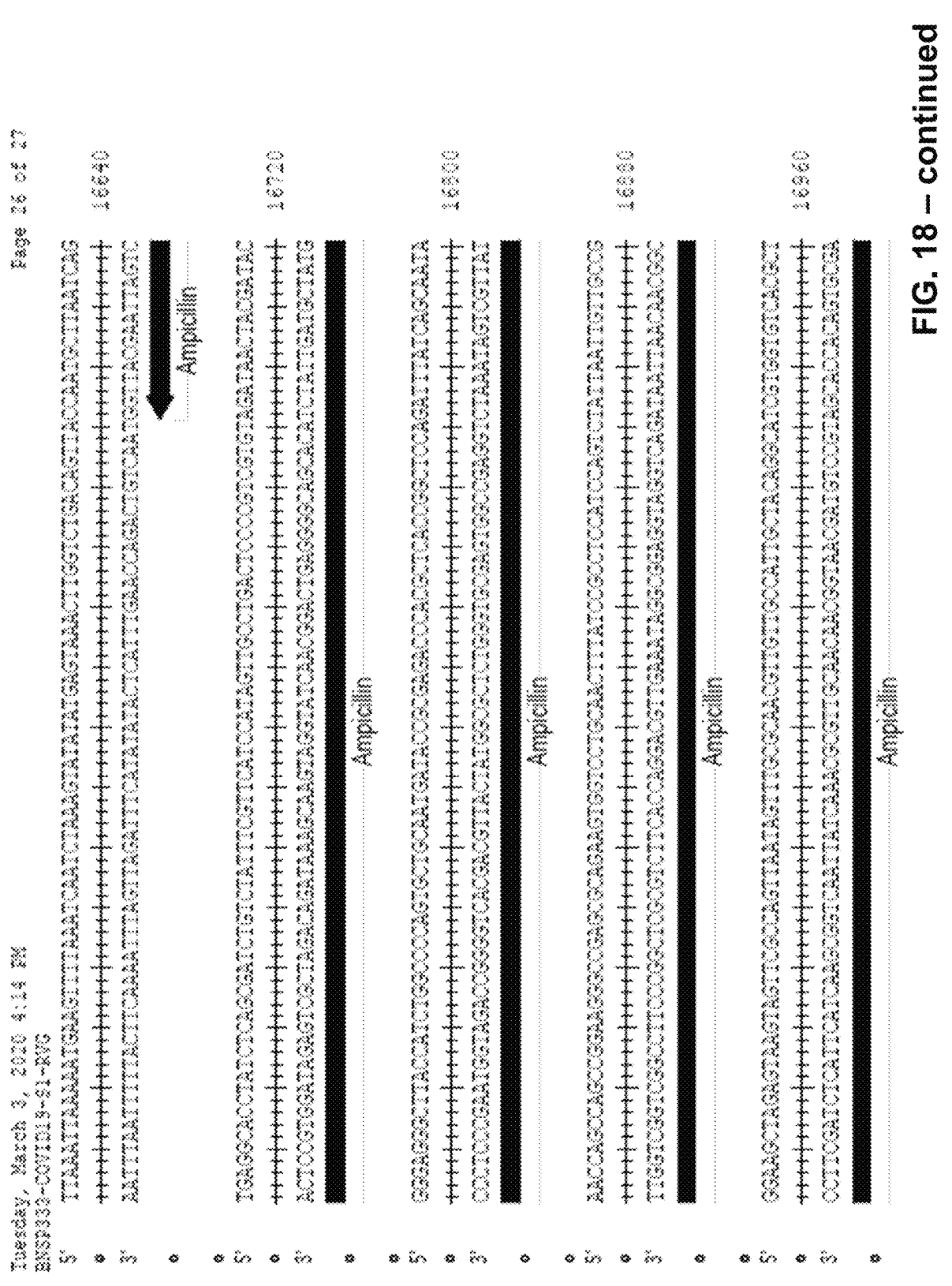
Figure 18:
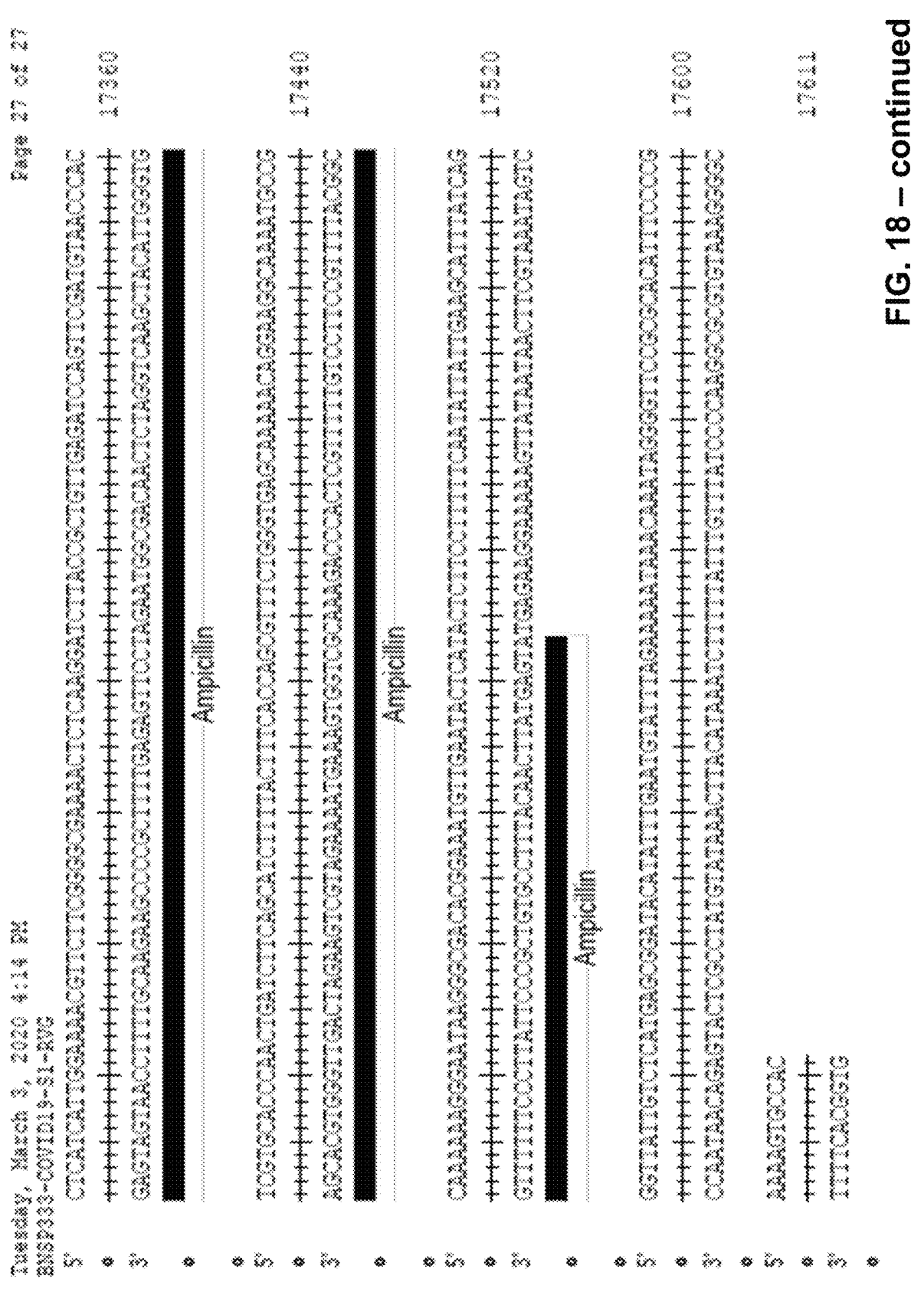

In some embodiments, the recombinant fusion protein comprises the sequence of the S1 domain of the SARS-CoV-2 spike protein (S) fused to a rabies glycoprotein (G) or portion thereof, shown as element "WuS1-RABVG" in "BNSP333-COVID19-S1-RVG" in FIG. 18.

Figure 17:
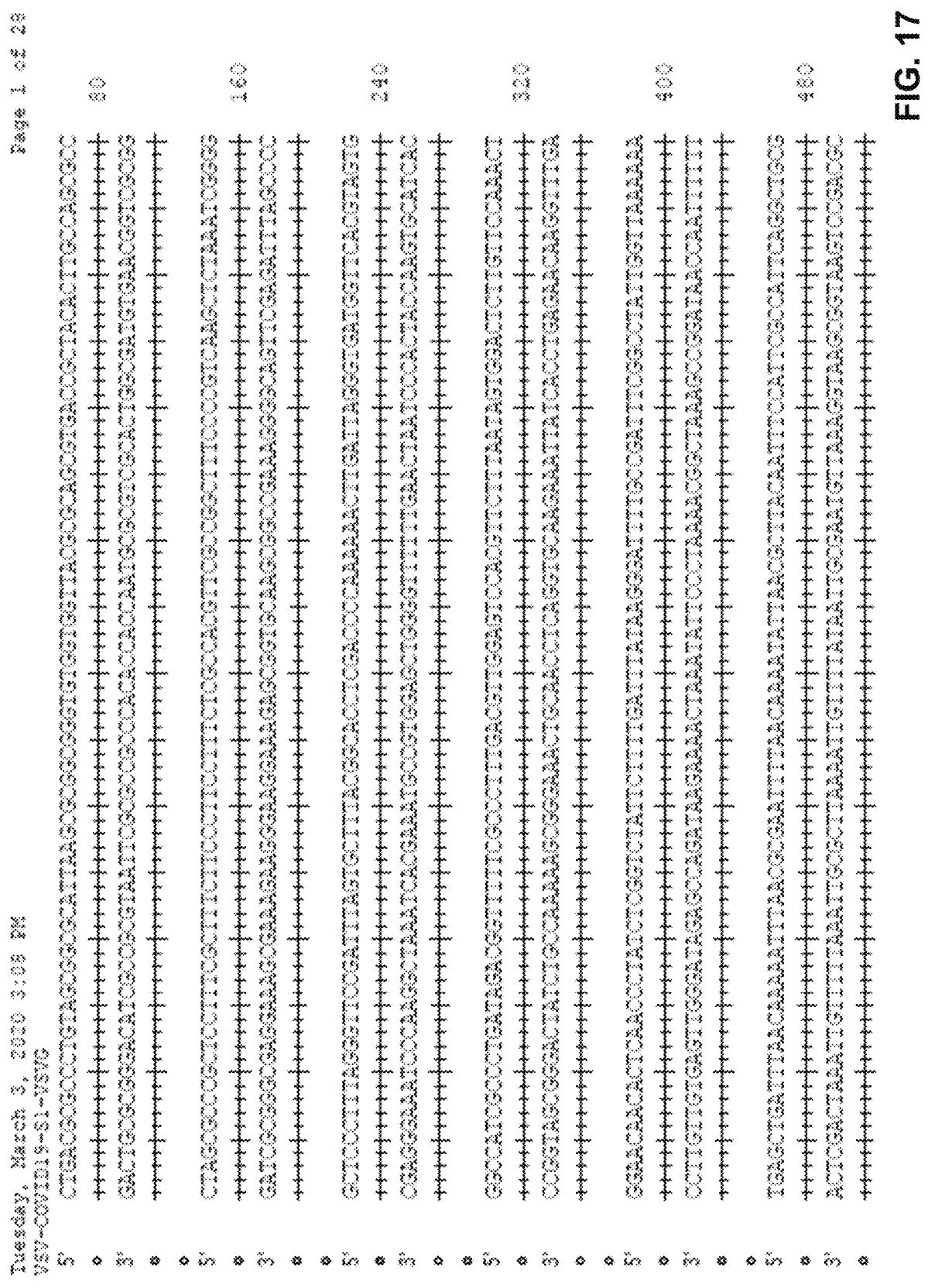
Figure 17:
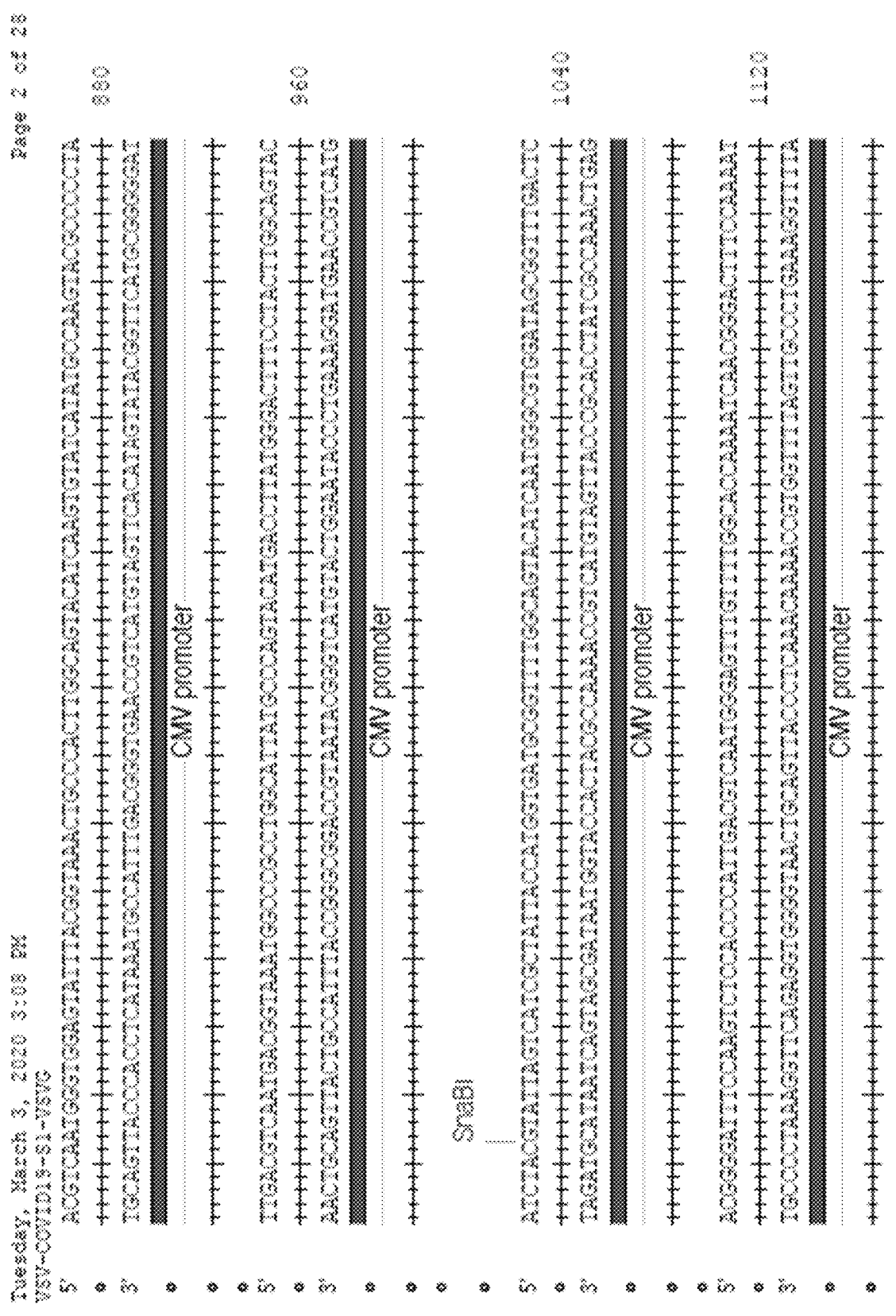
Figure 17:
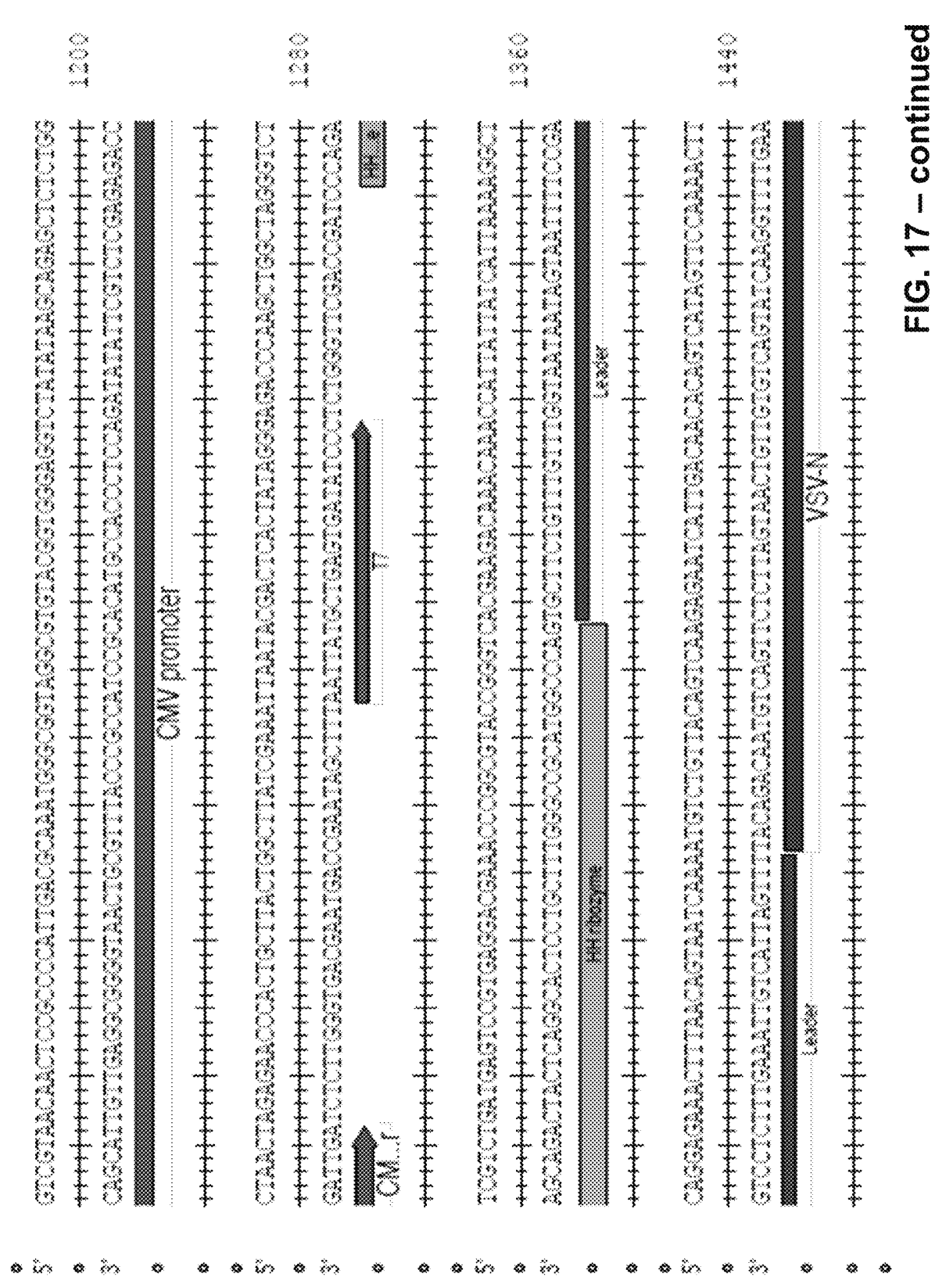
Figure 17:
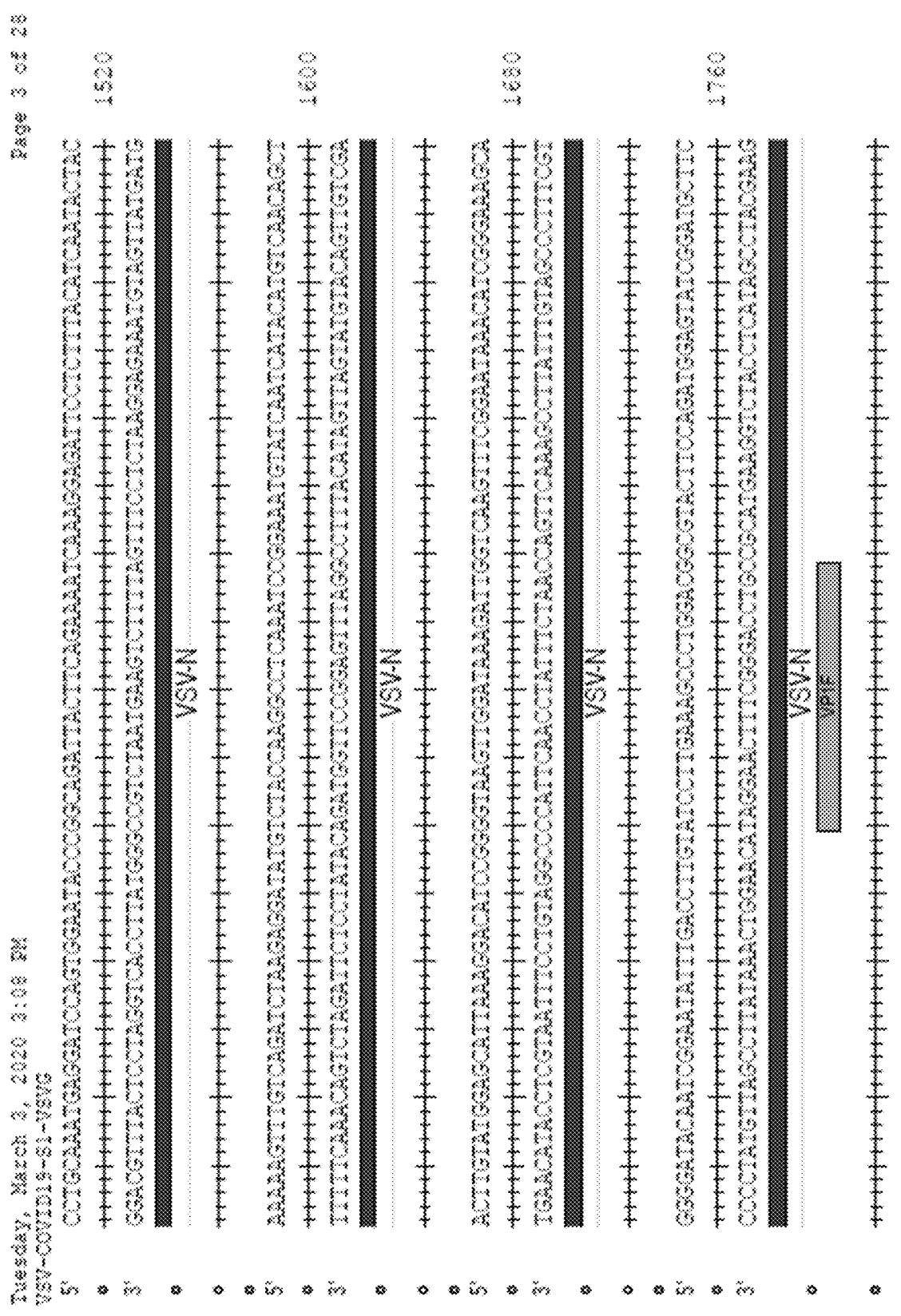
Figure 17:
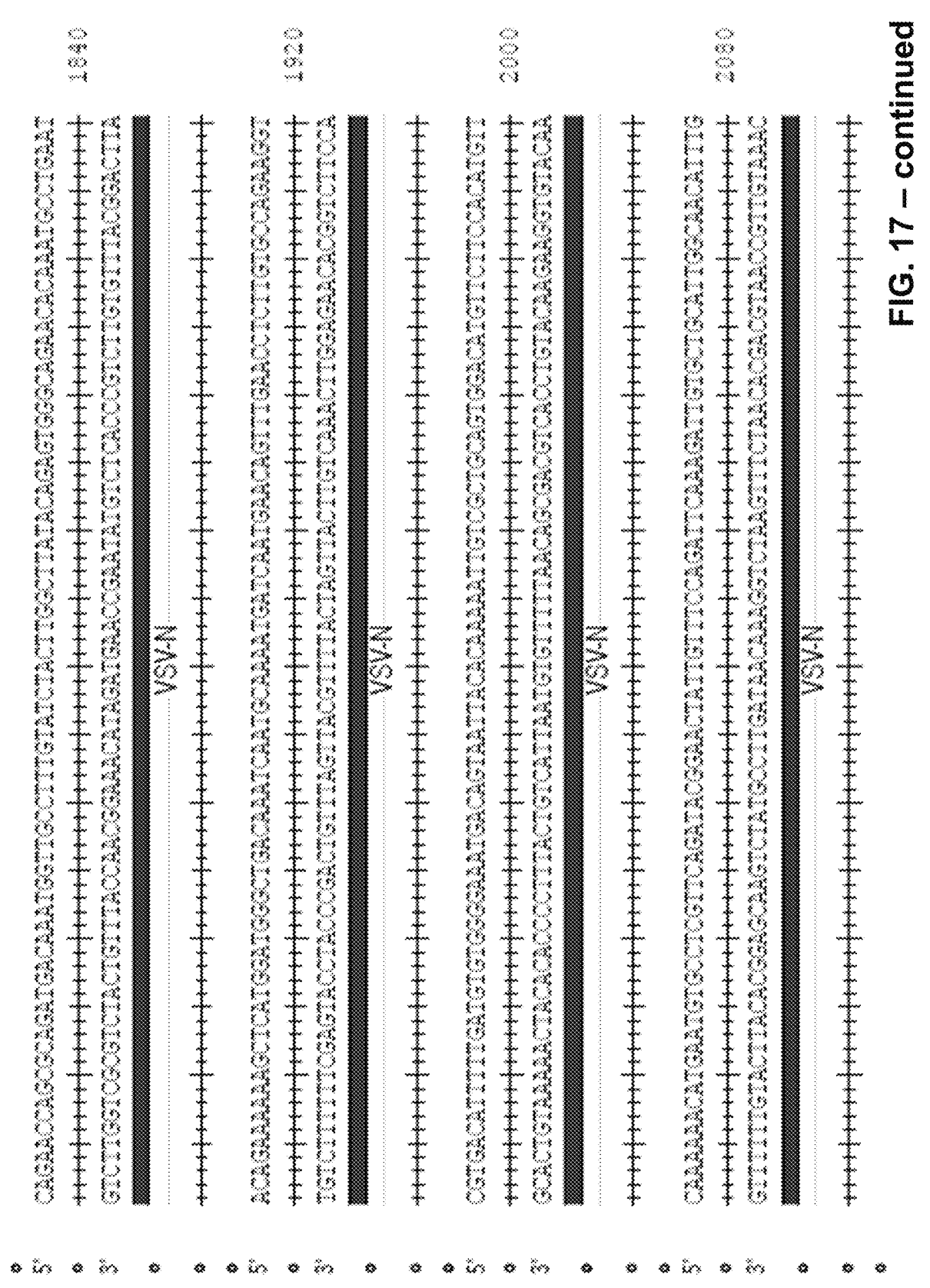
Figure 17:
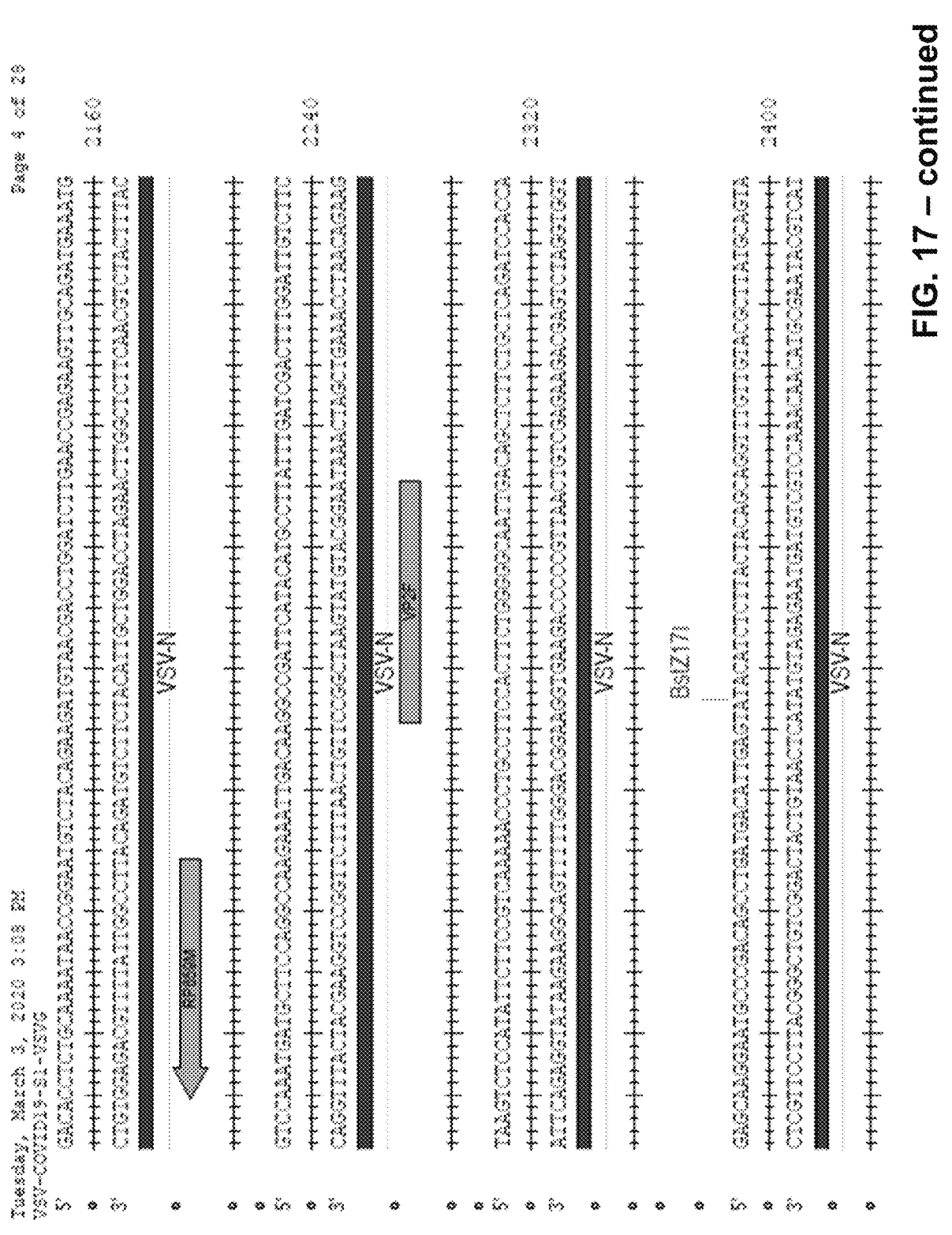
Figure 17:
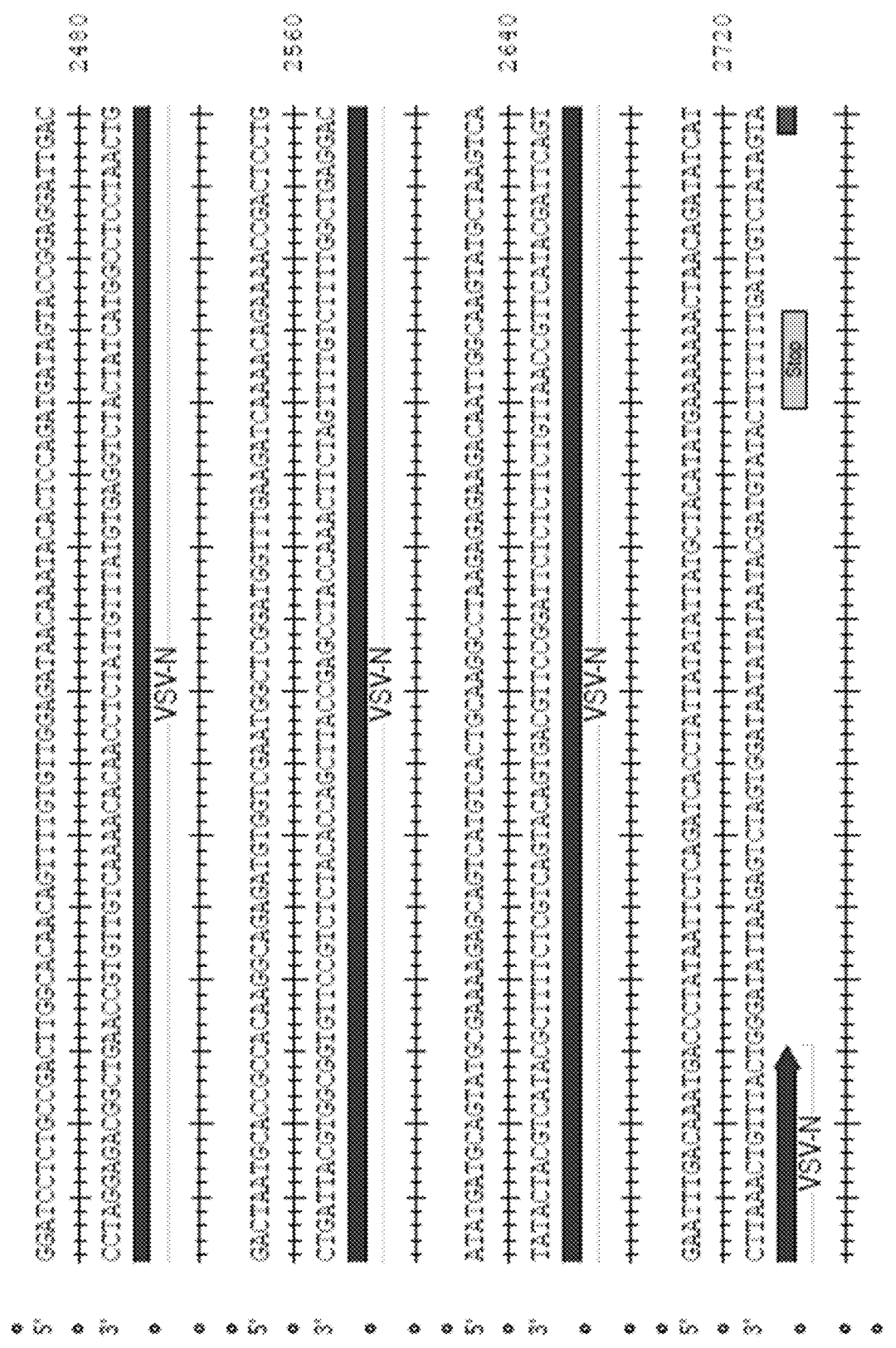
Figure 17:
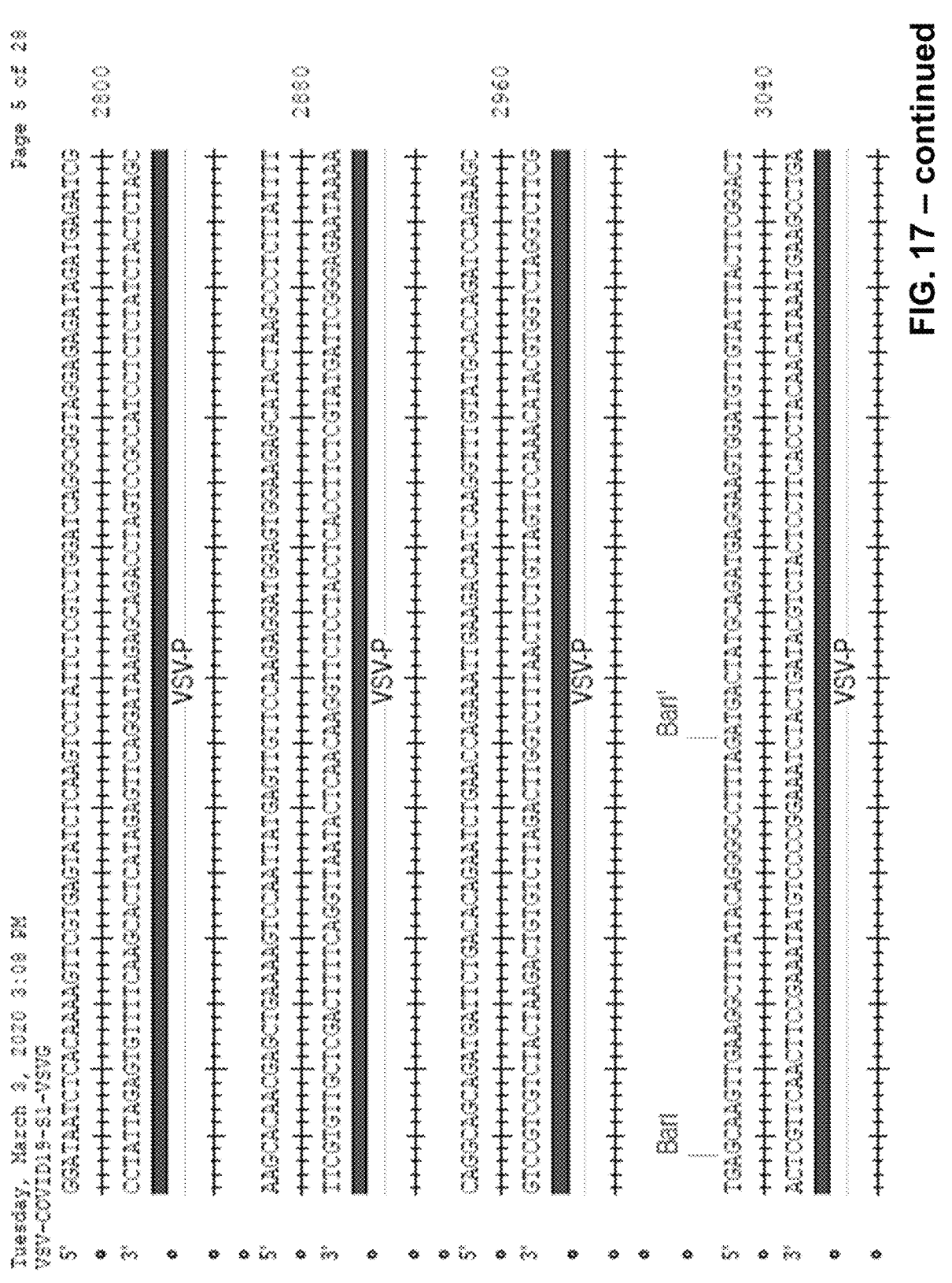
Figure 17:
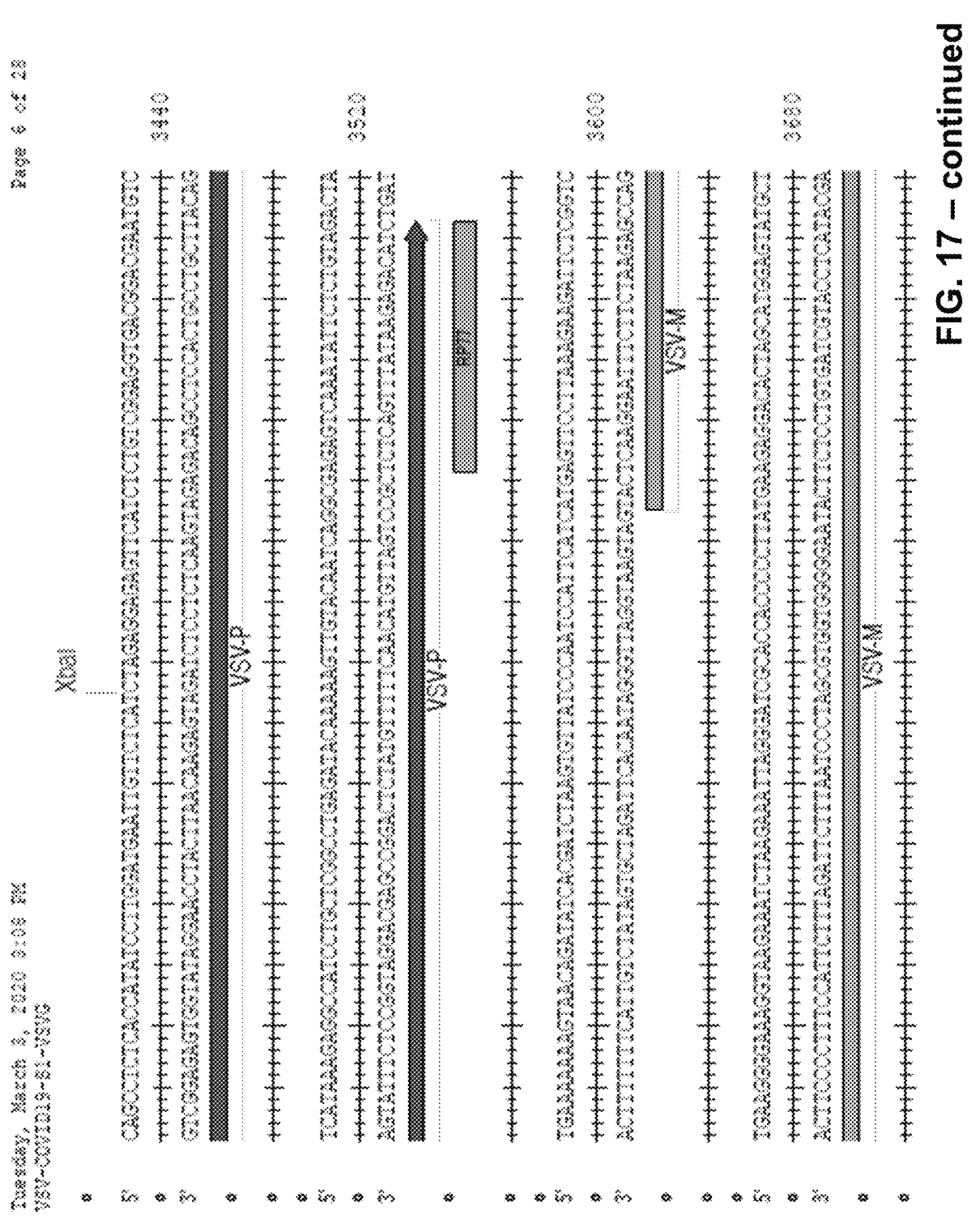
Figure 17:
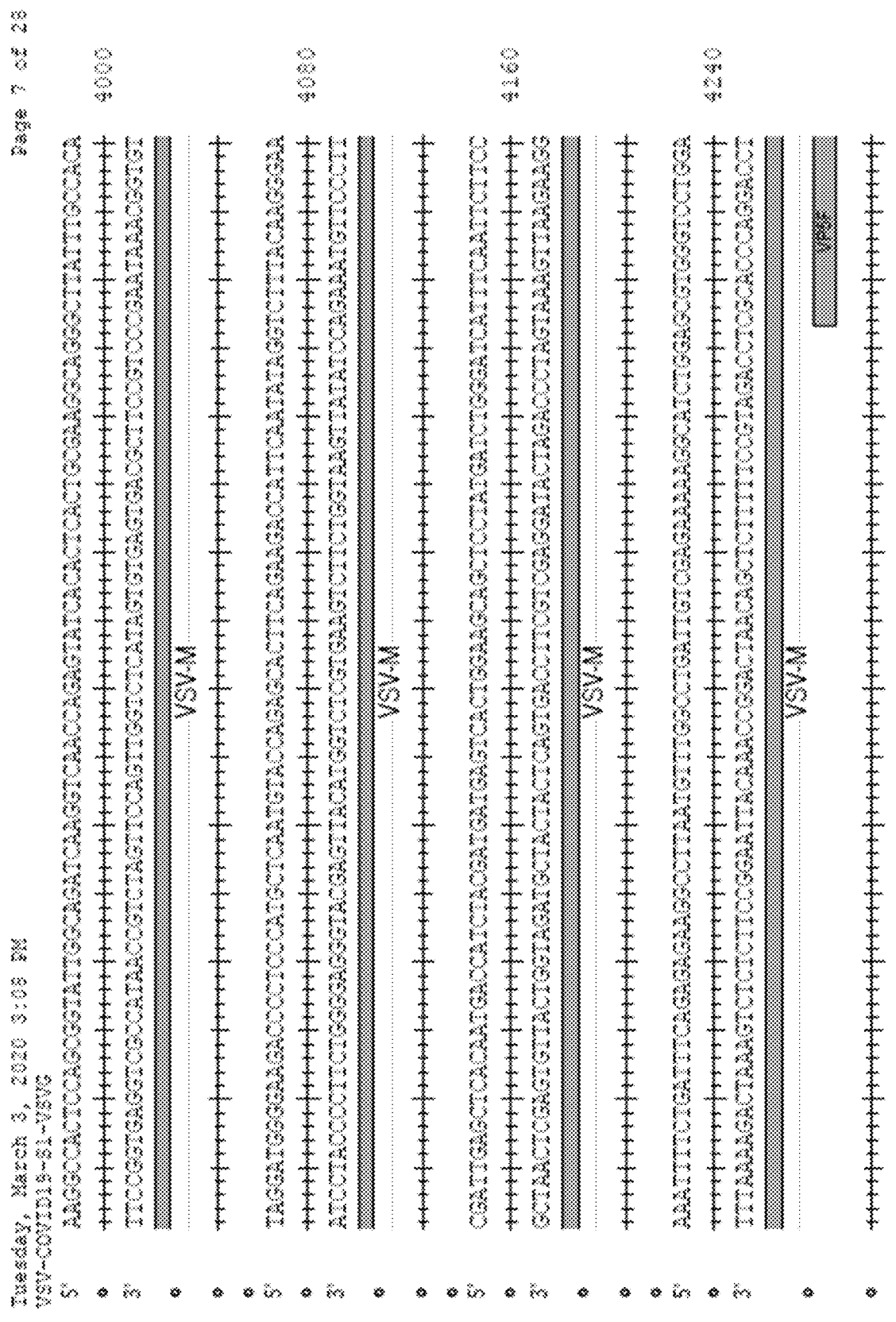
Figure 17:
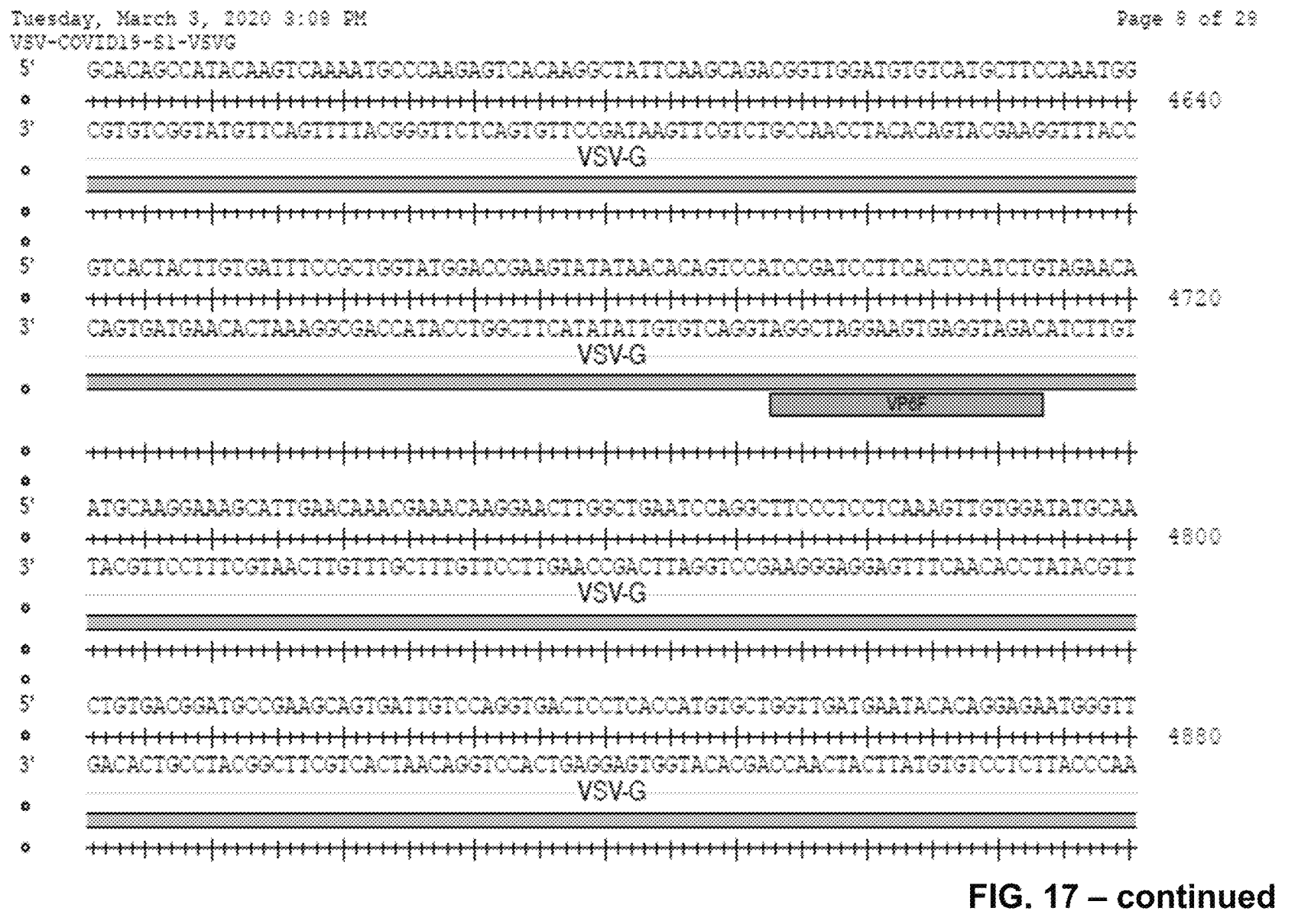
Figure 17:
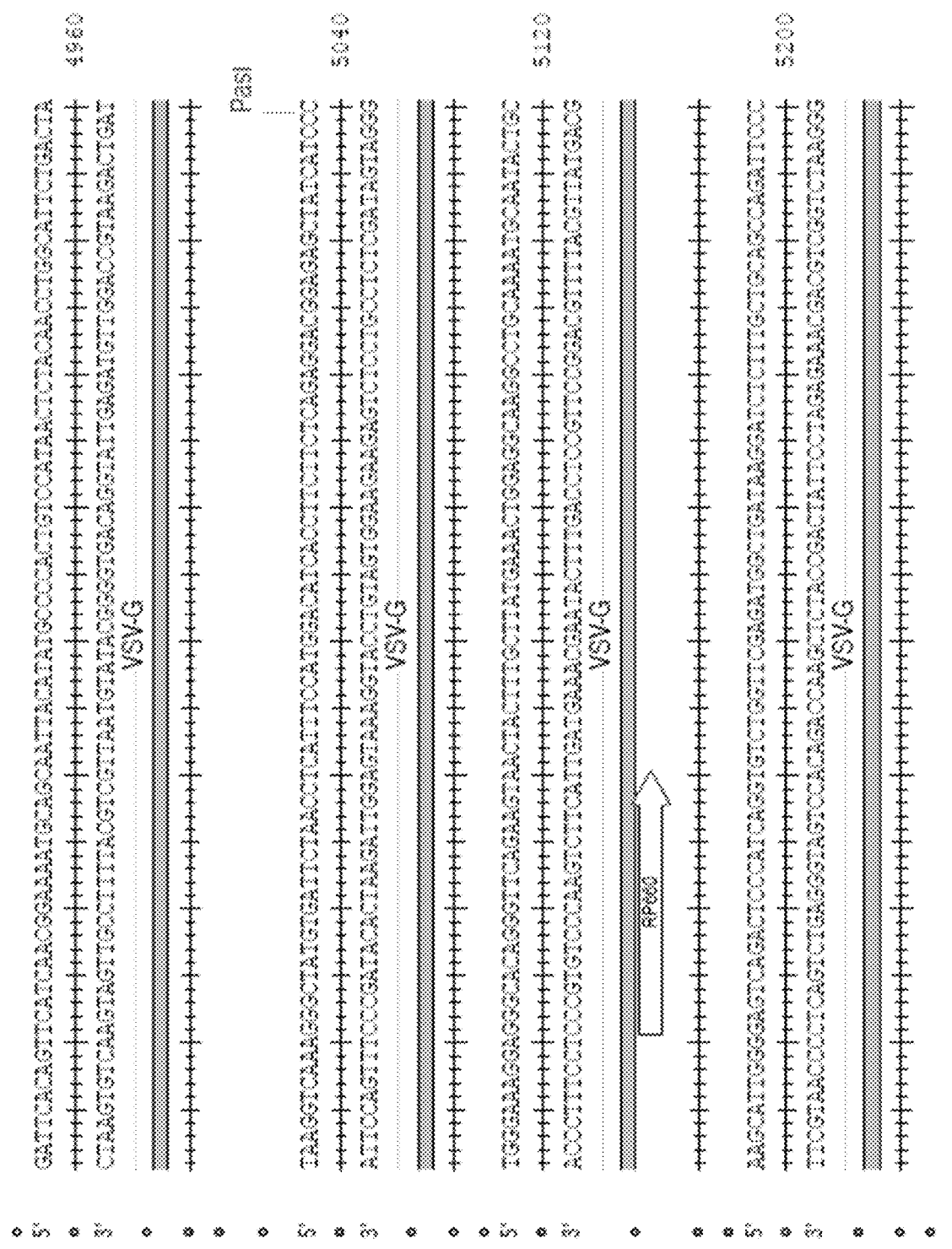
Figure 17:
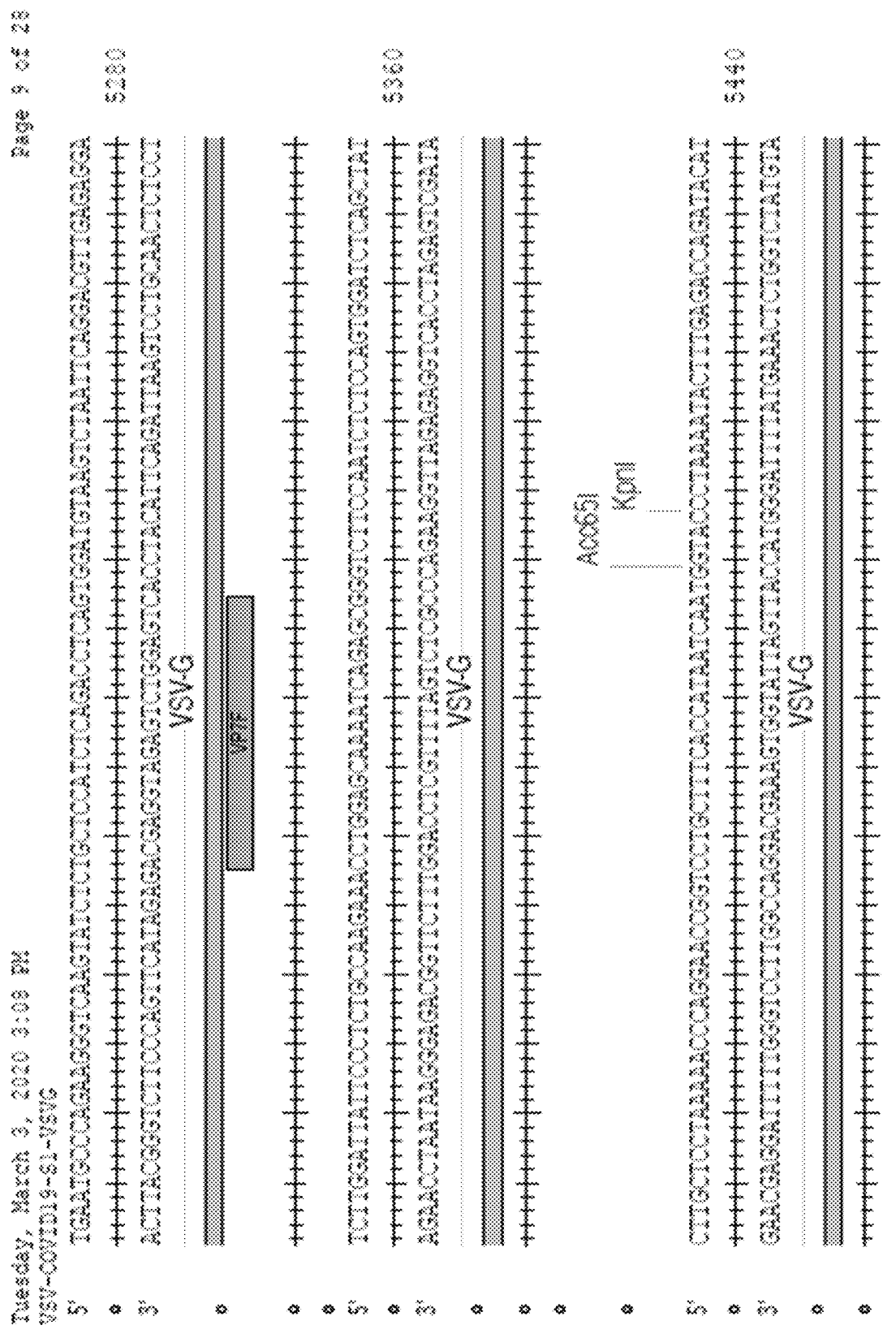
Figure 17:
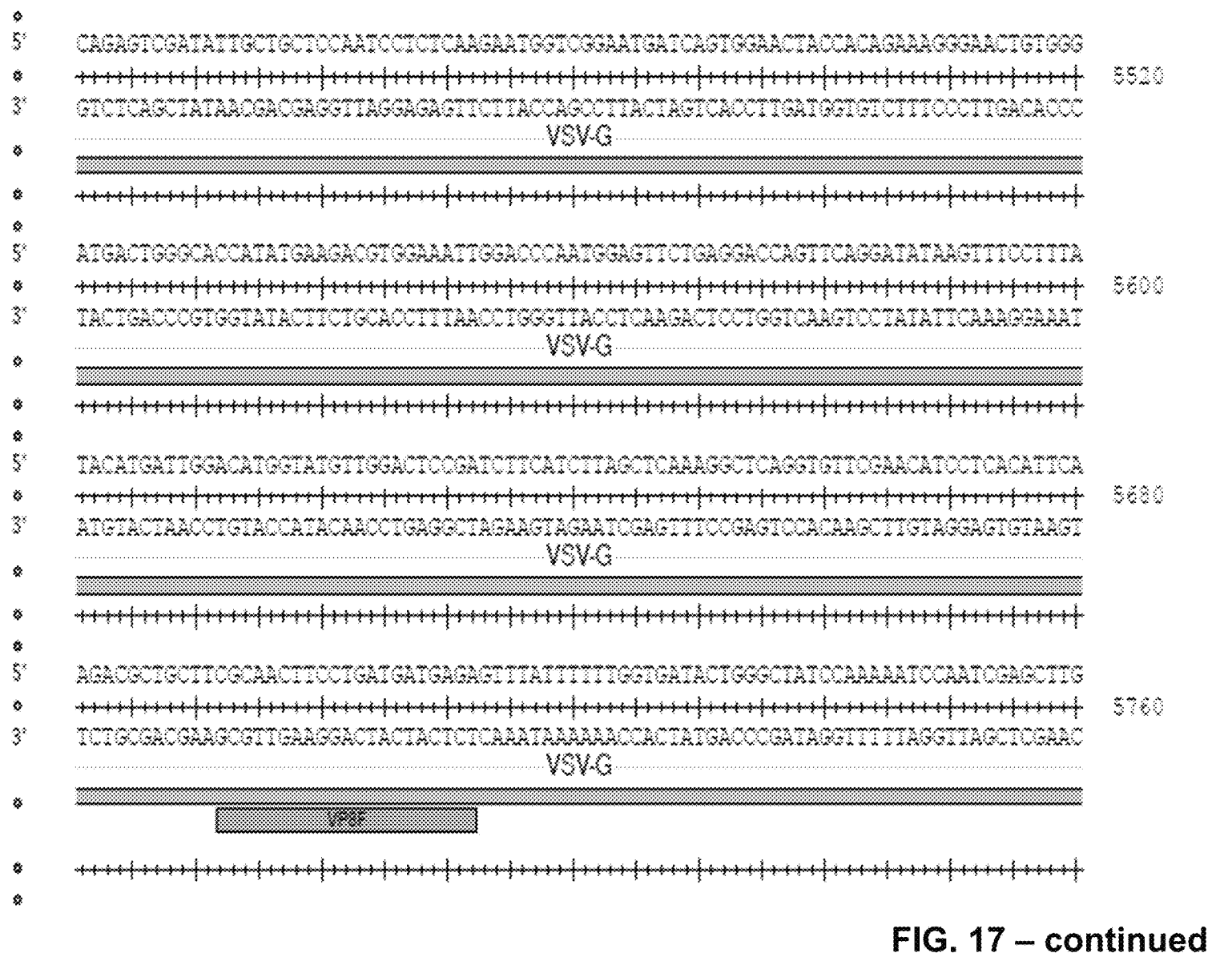
Figure 17:
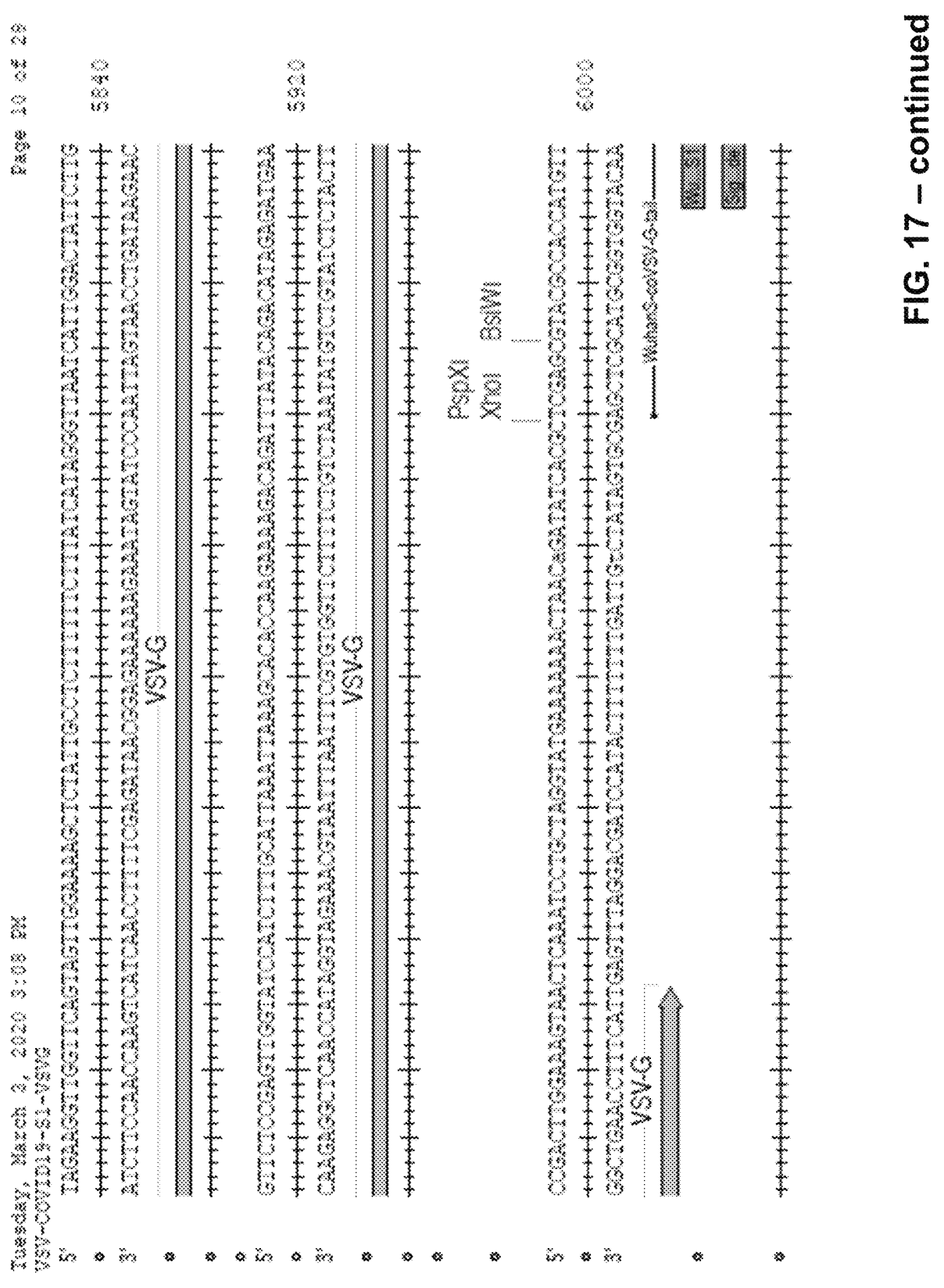
Figure 17:
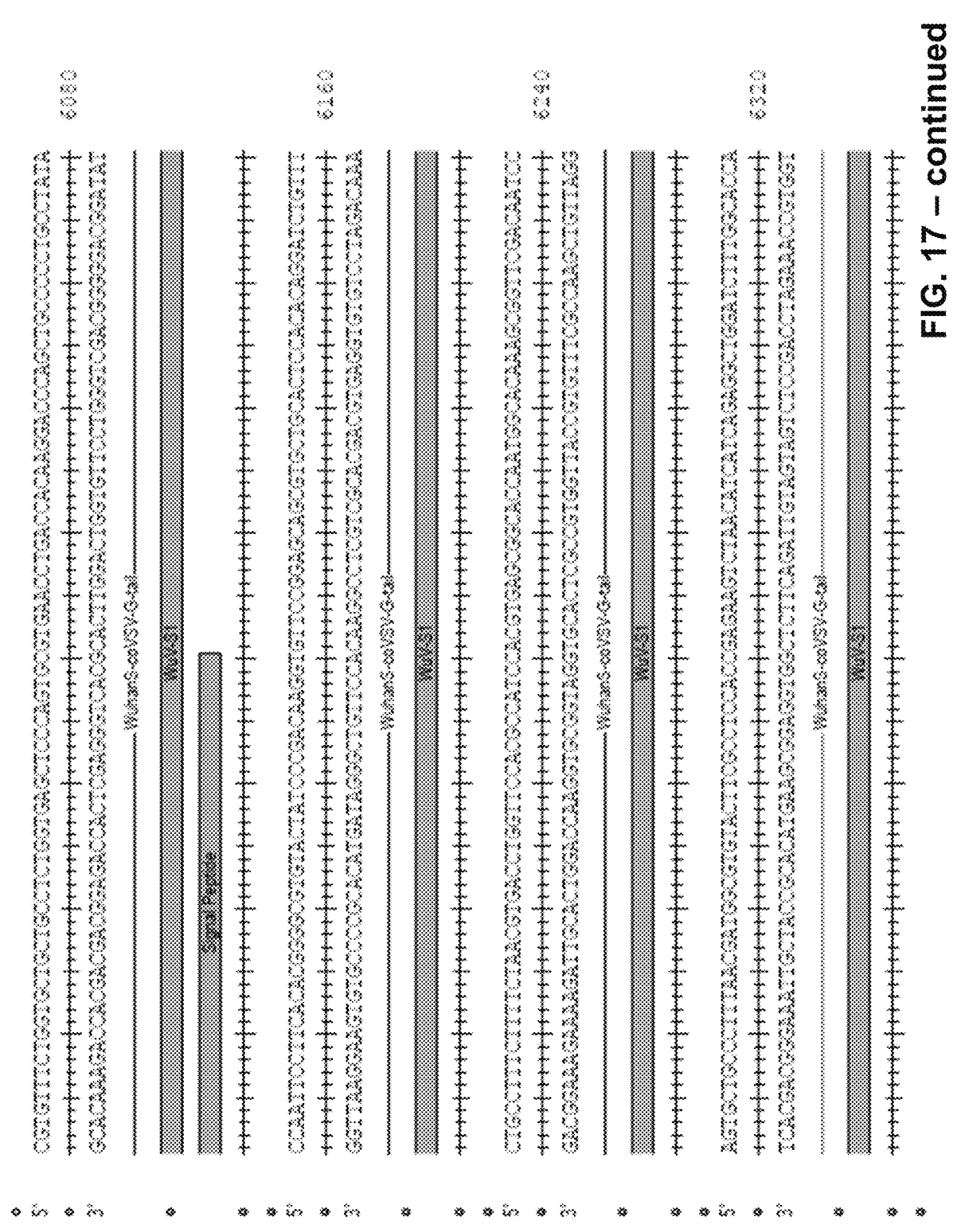
Figure 17:
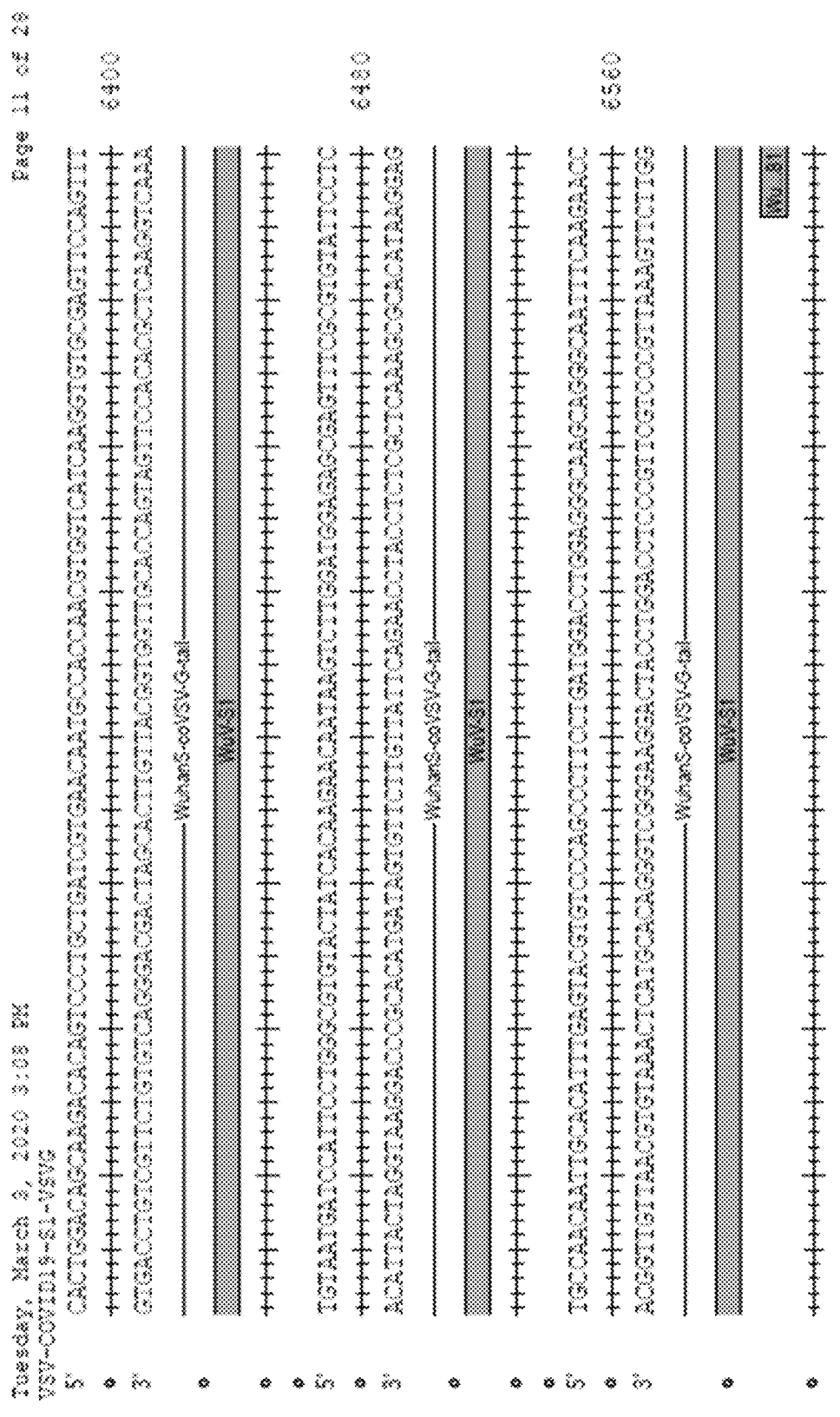
Figure 17:
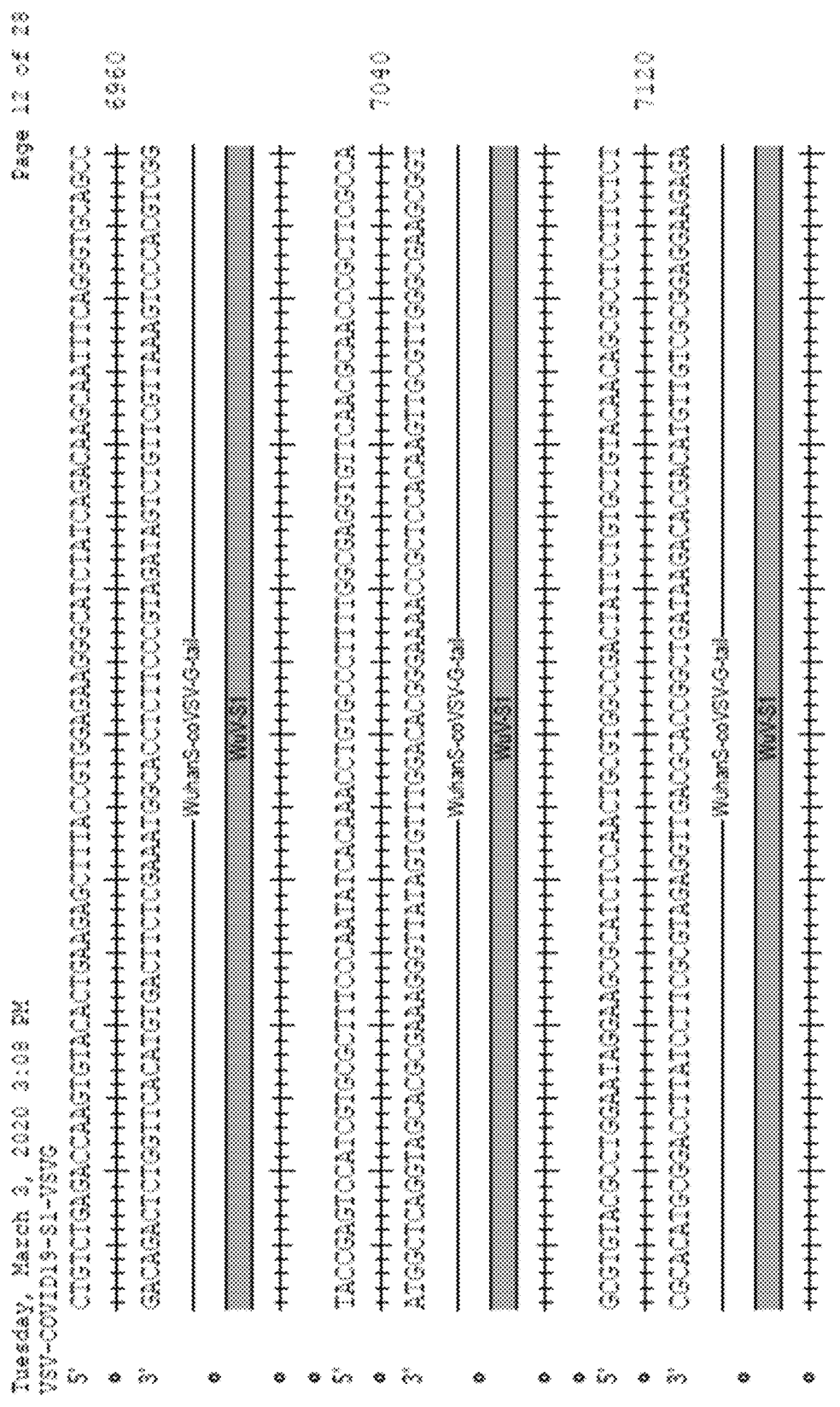
Figure 17:
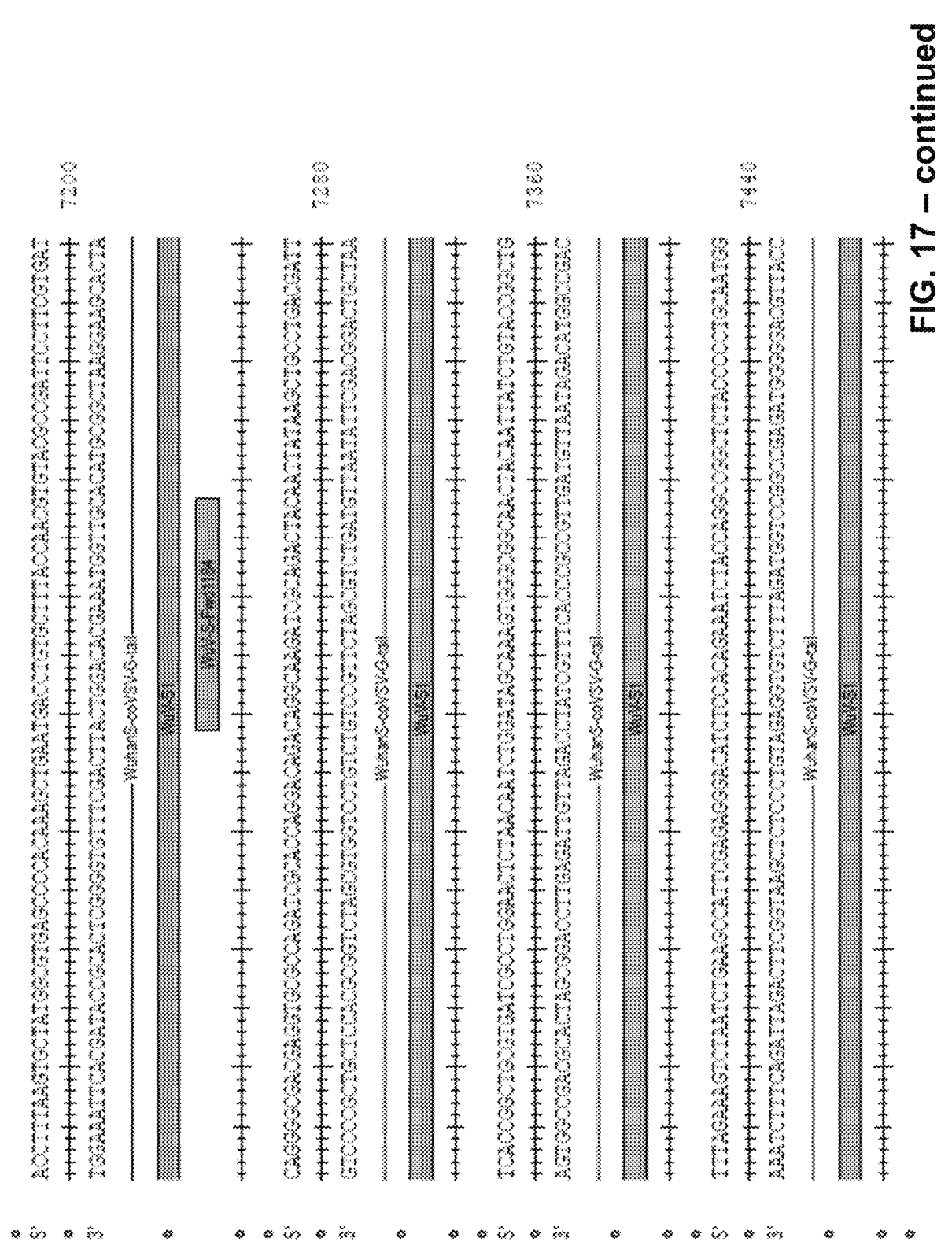
Figure 17:
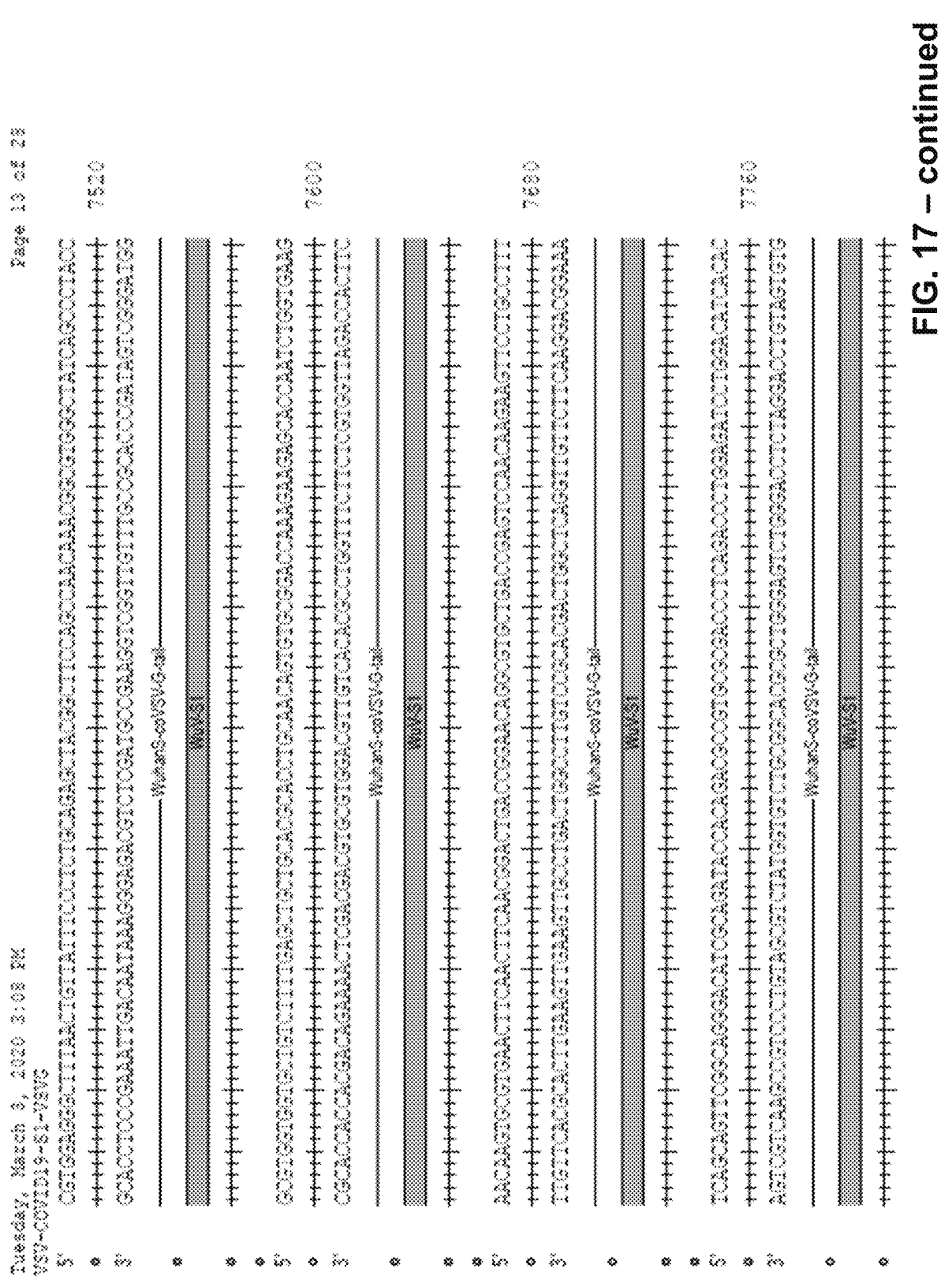
Figure 17:
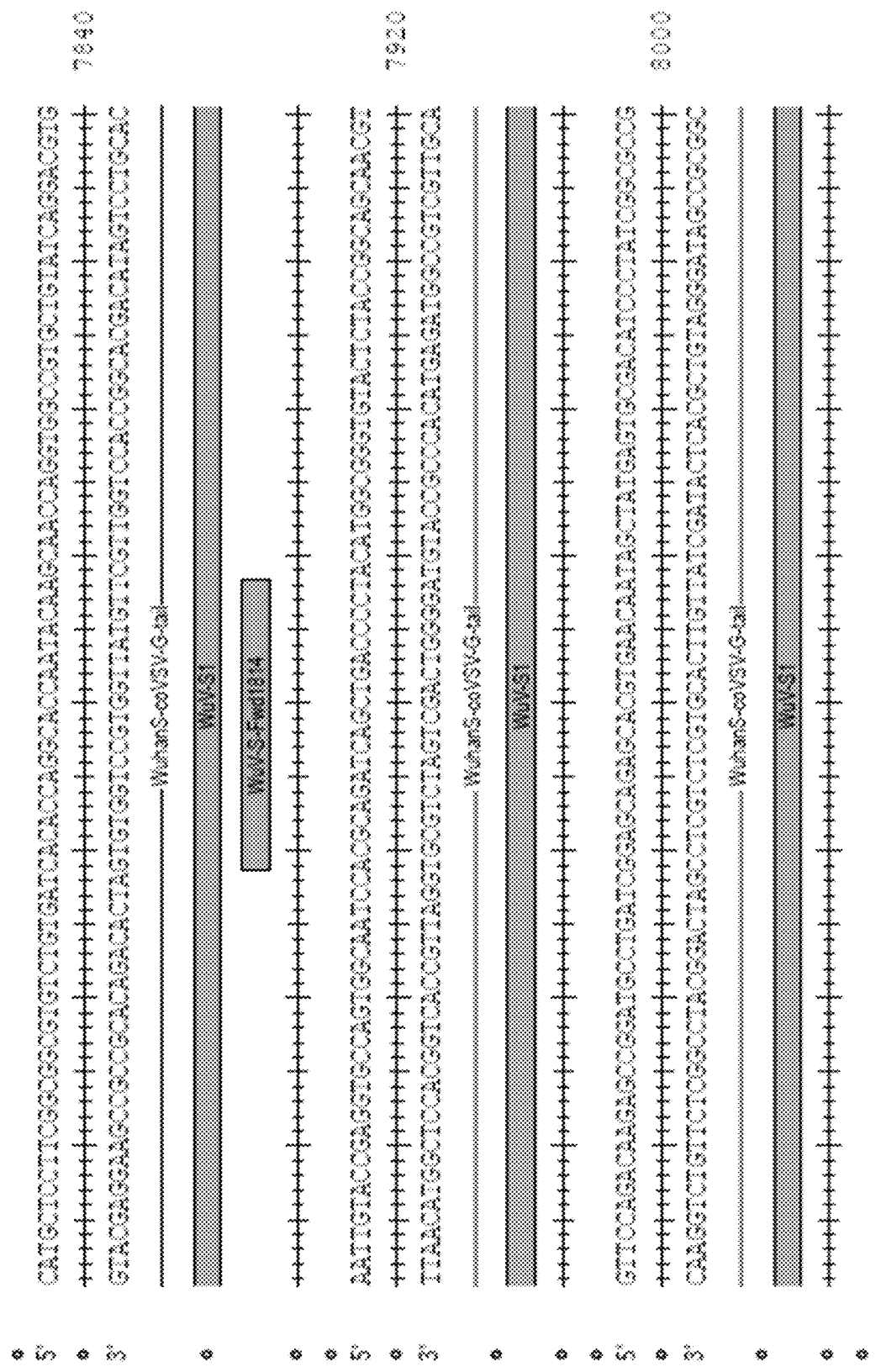
Figure 17:
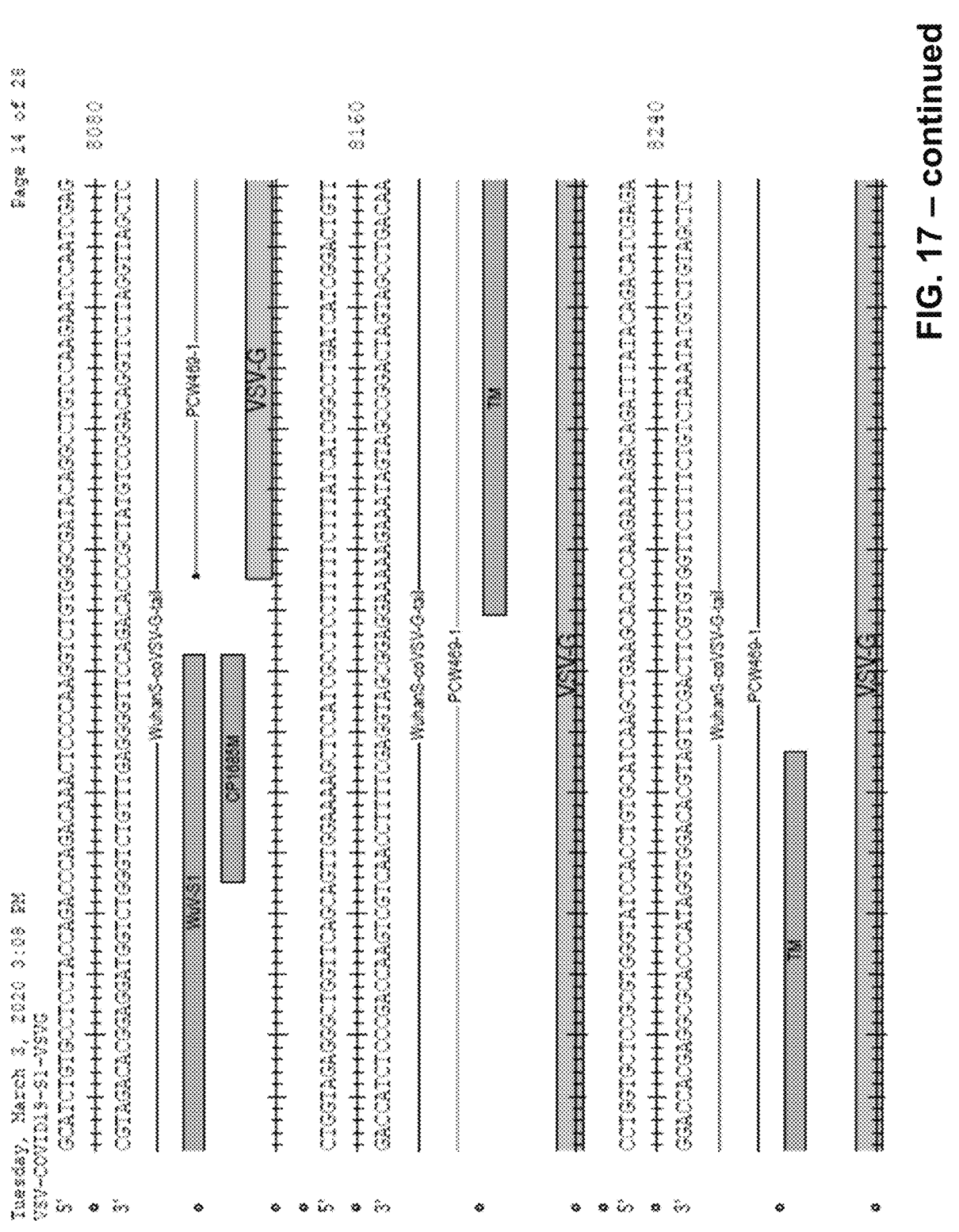
Figure 17:
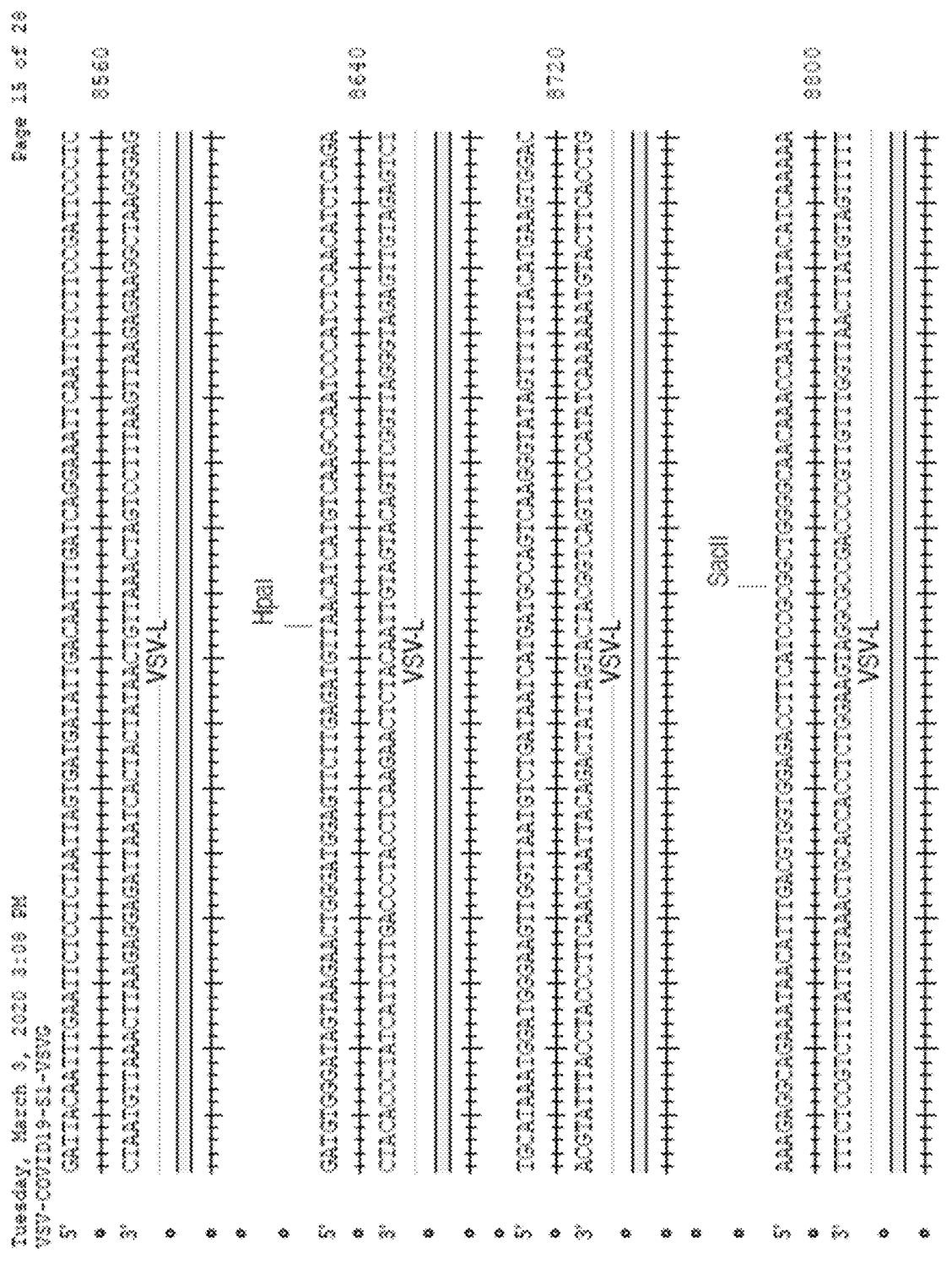
Figure 17:
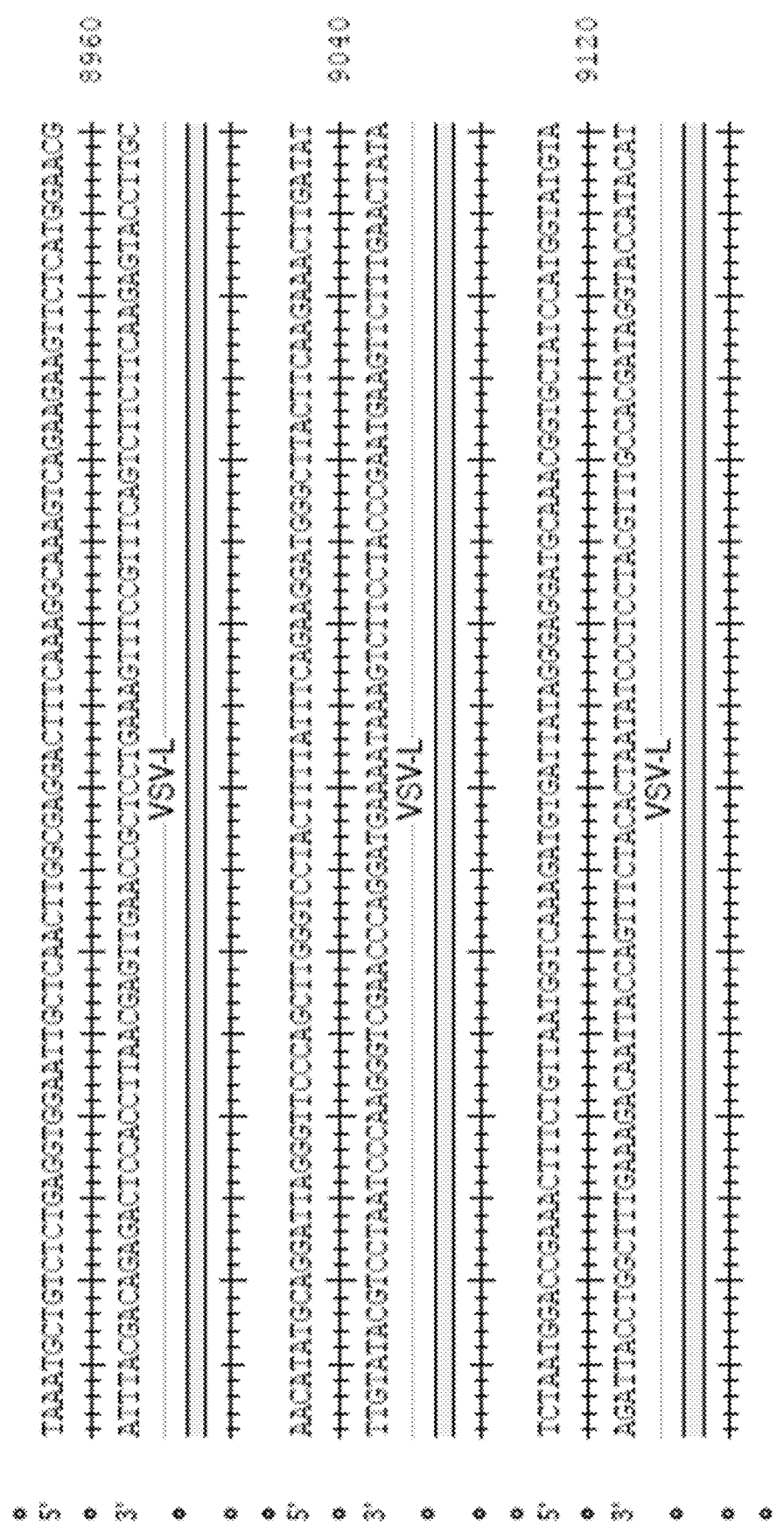
Figure 17:
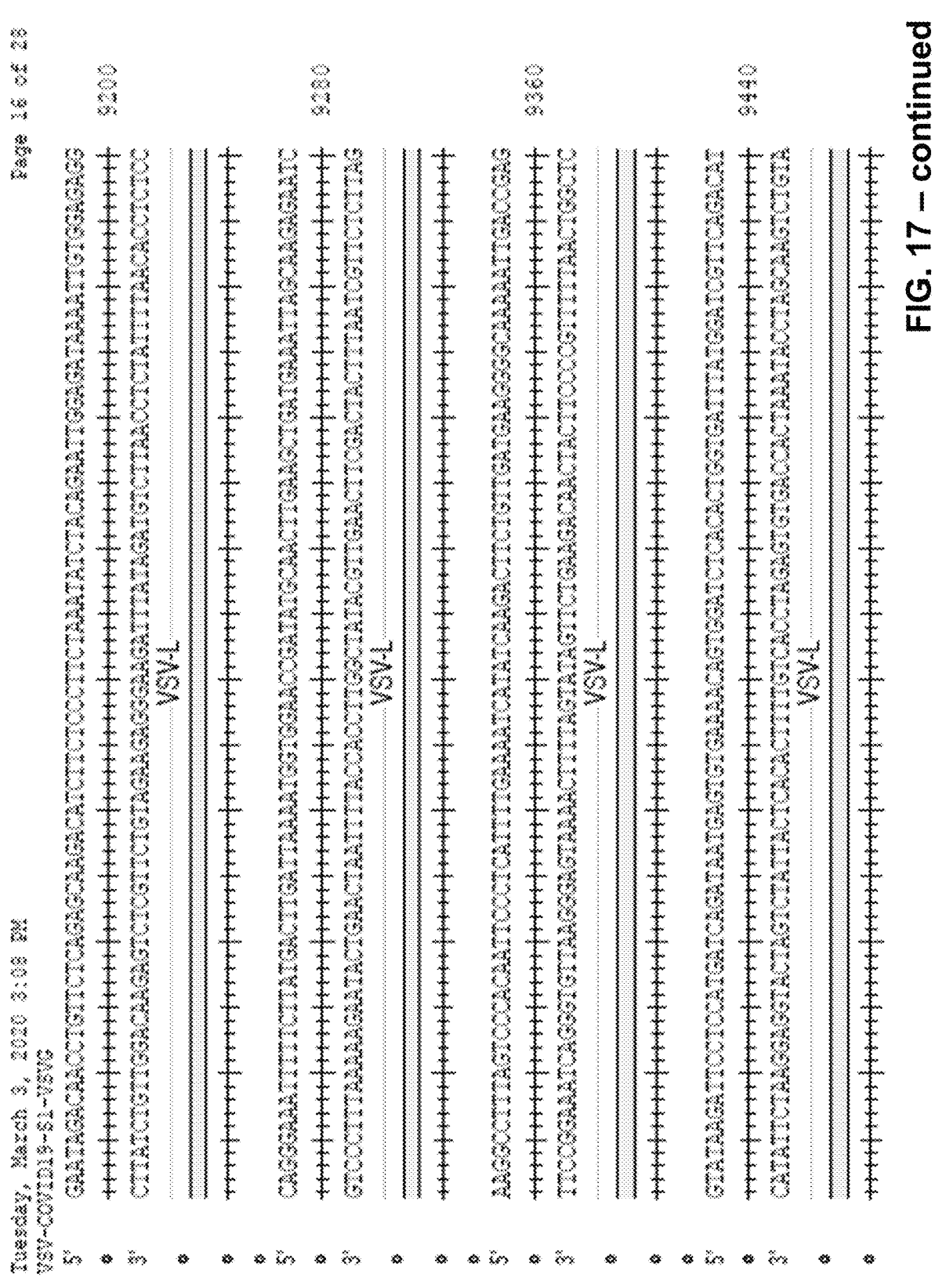
Figure 17:
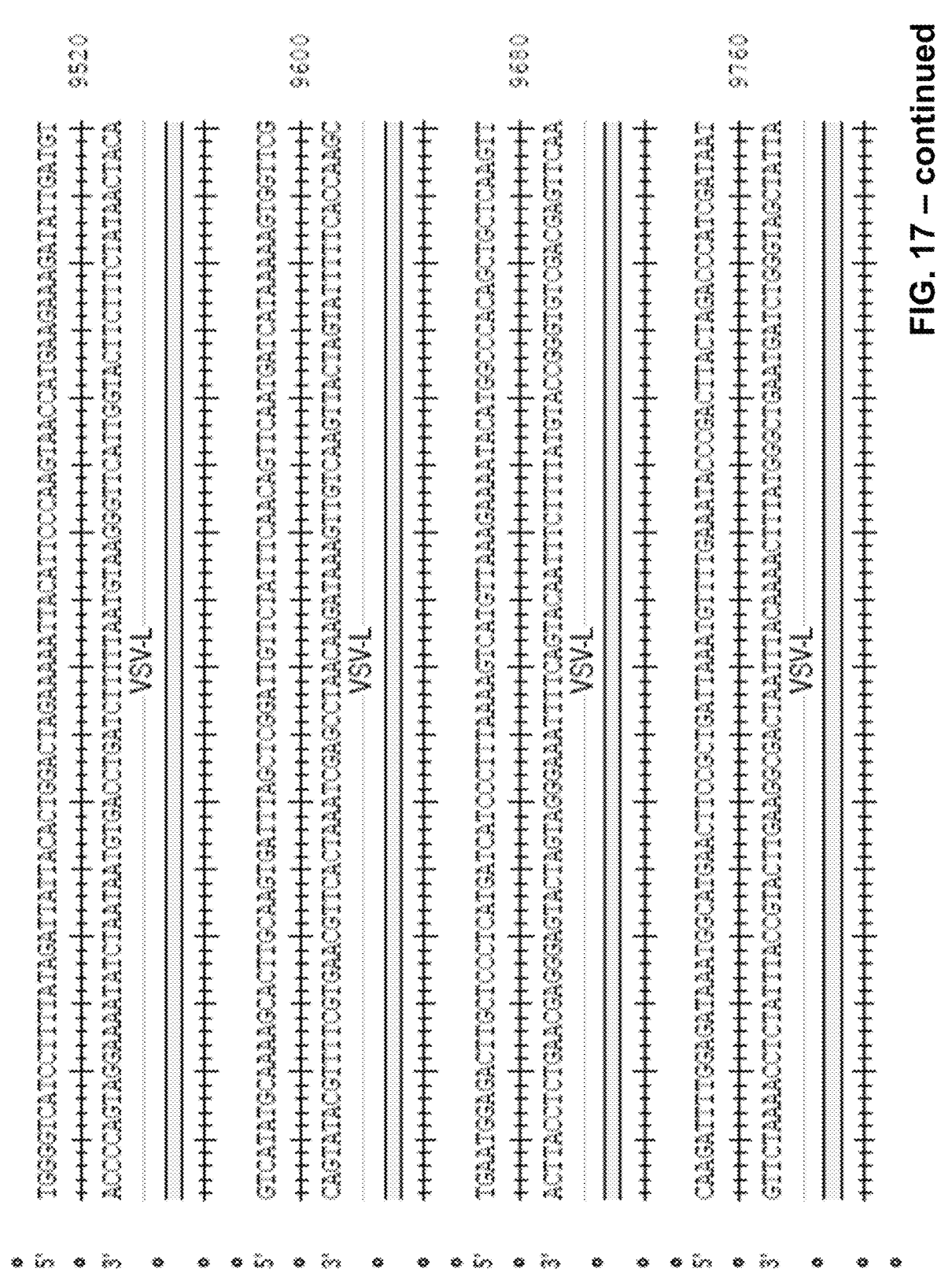
Figure 17:
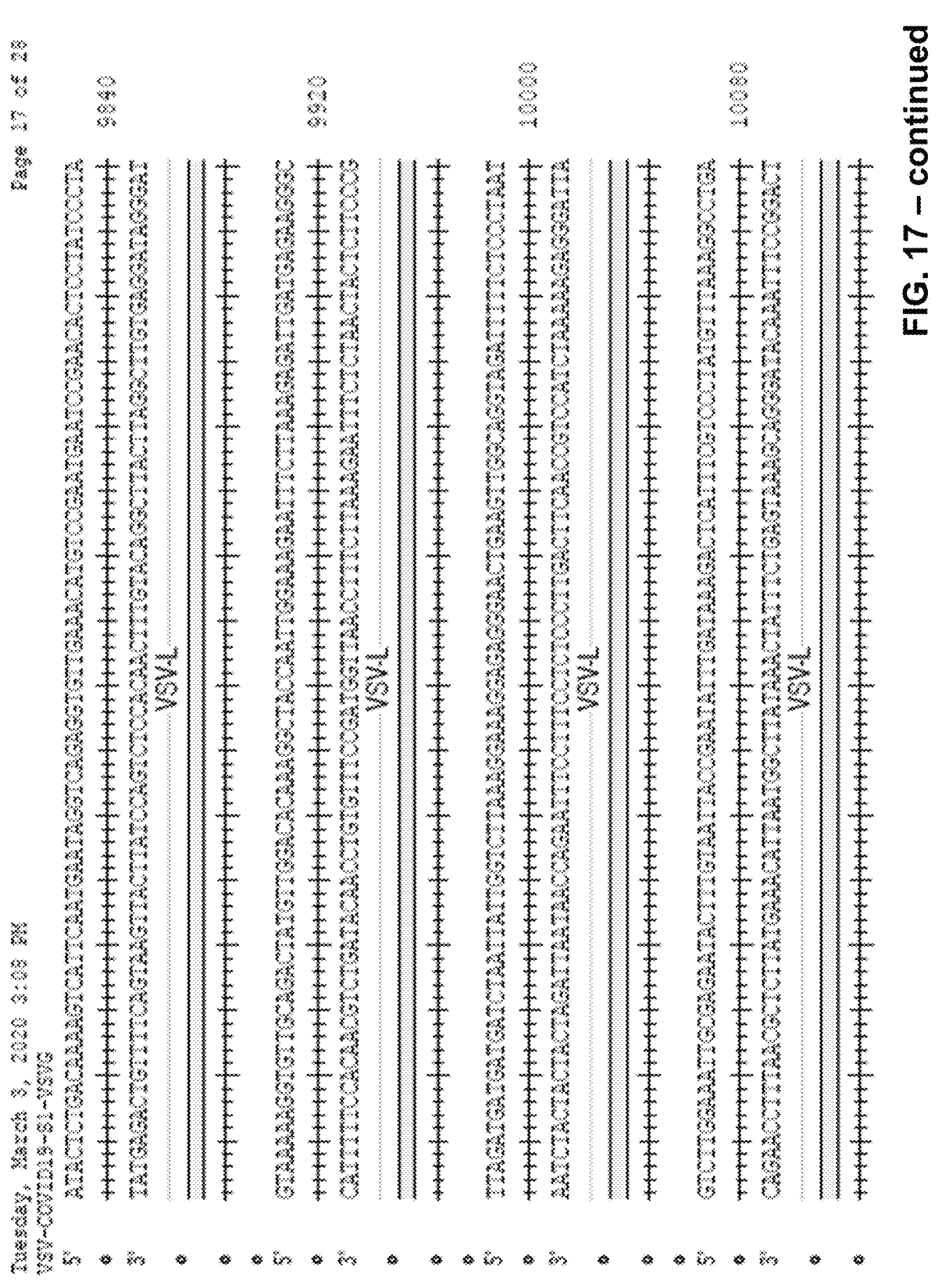
Figure 17:
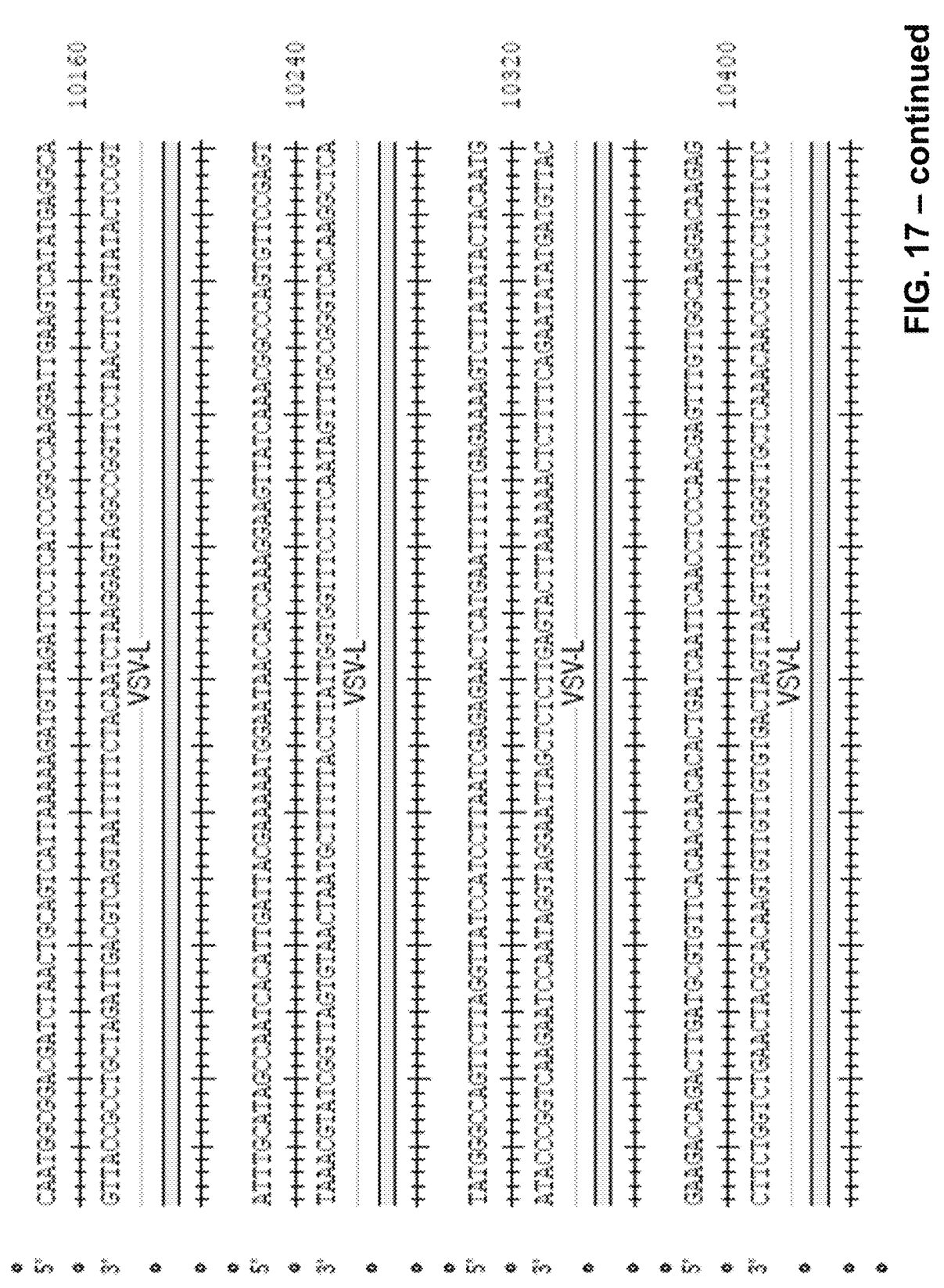
Figure 17:
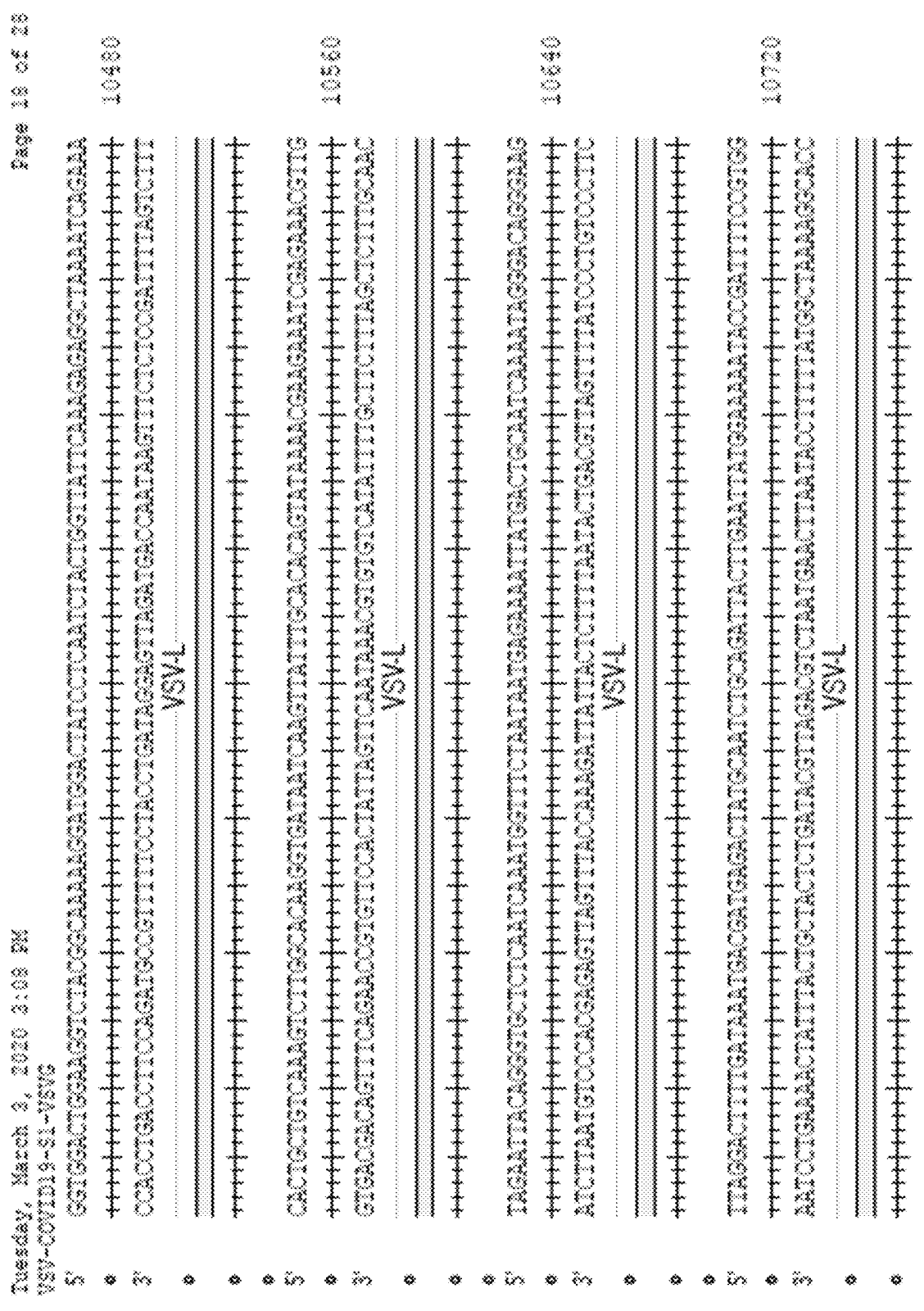
Figure 17:
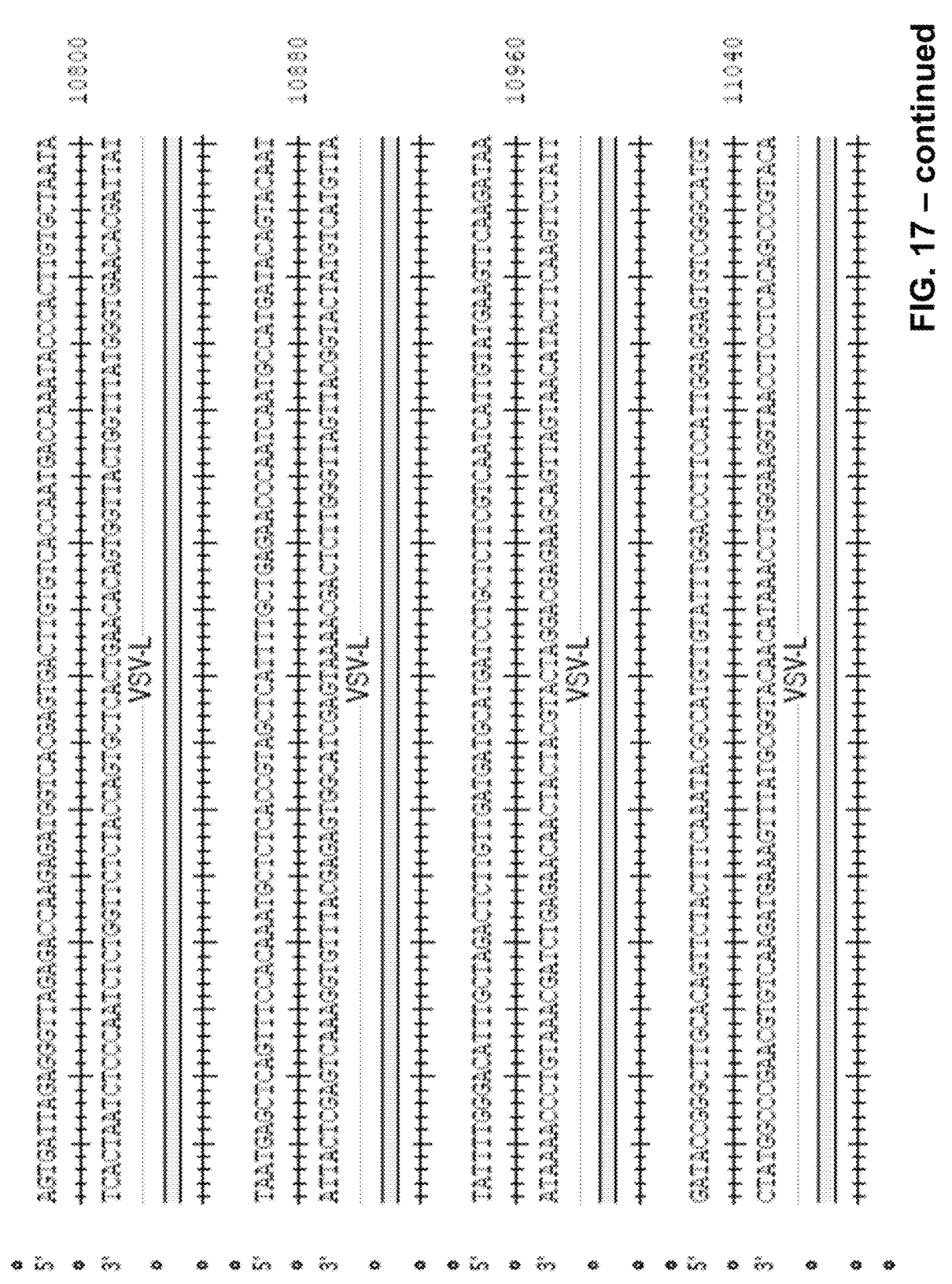
Figure 17:
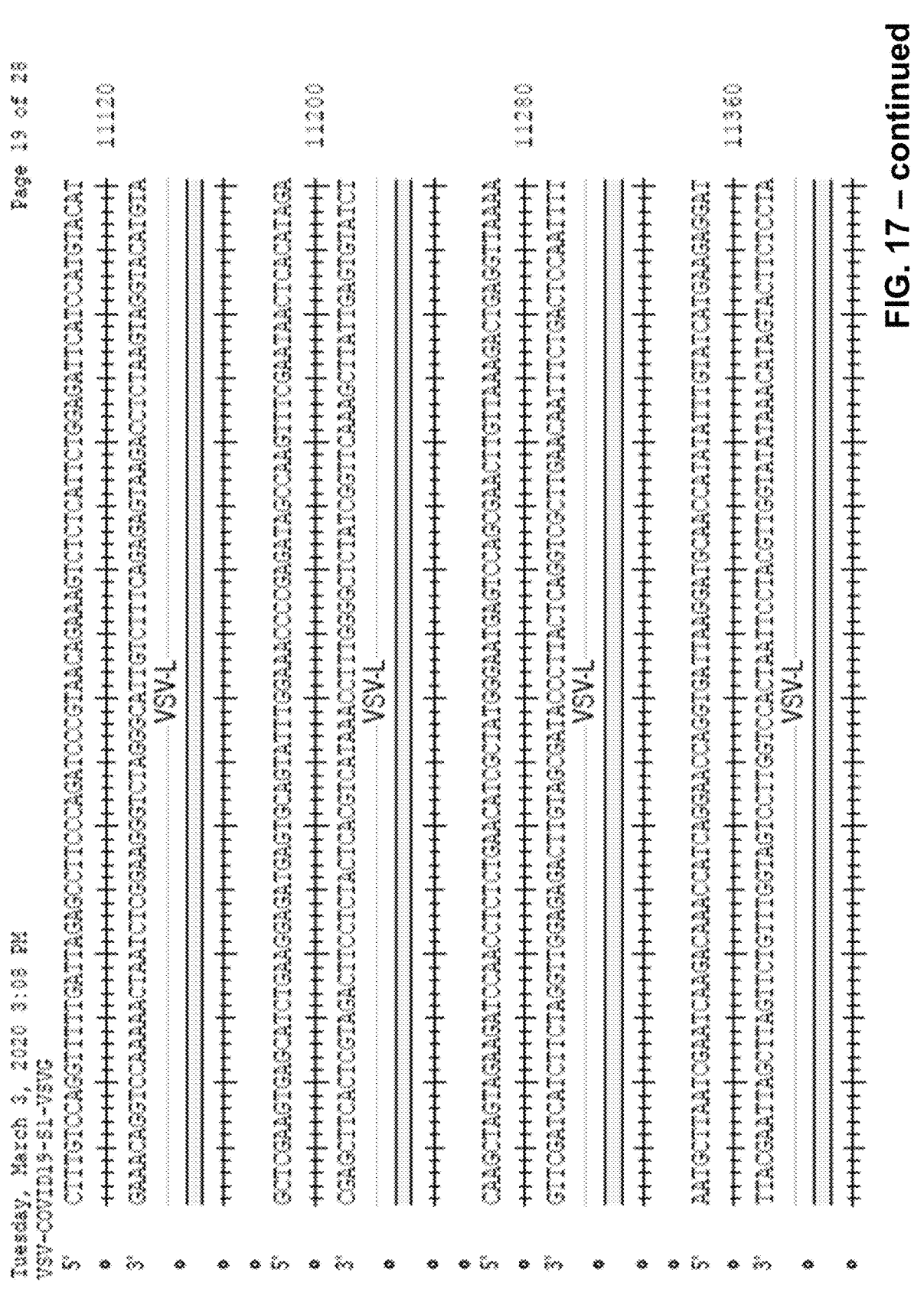
Figure 17:
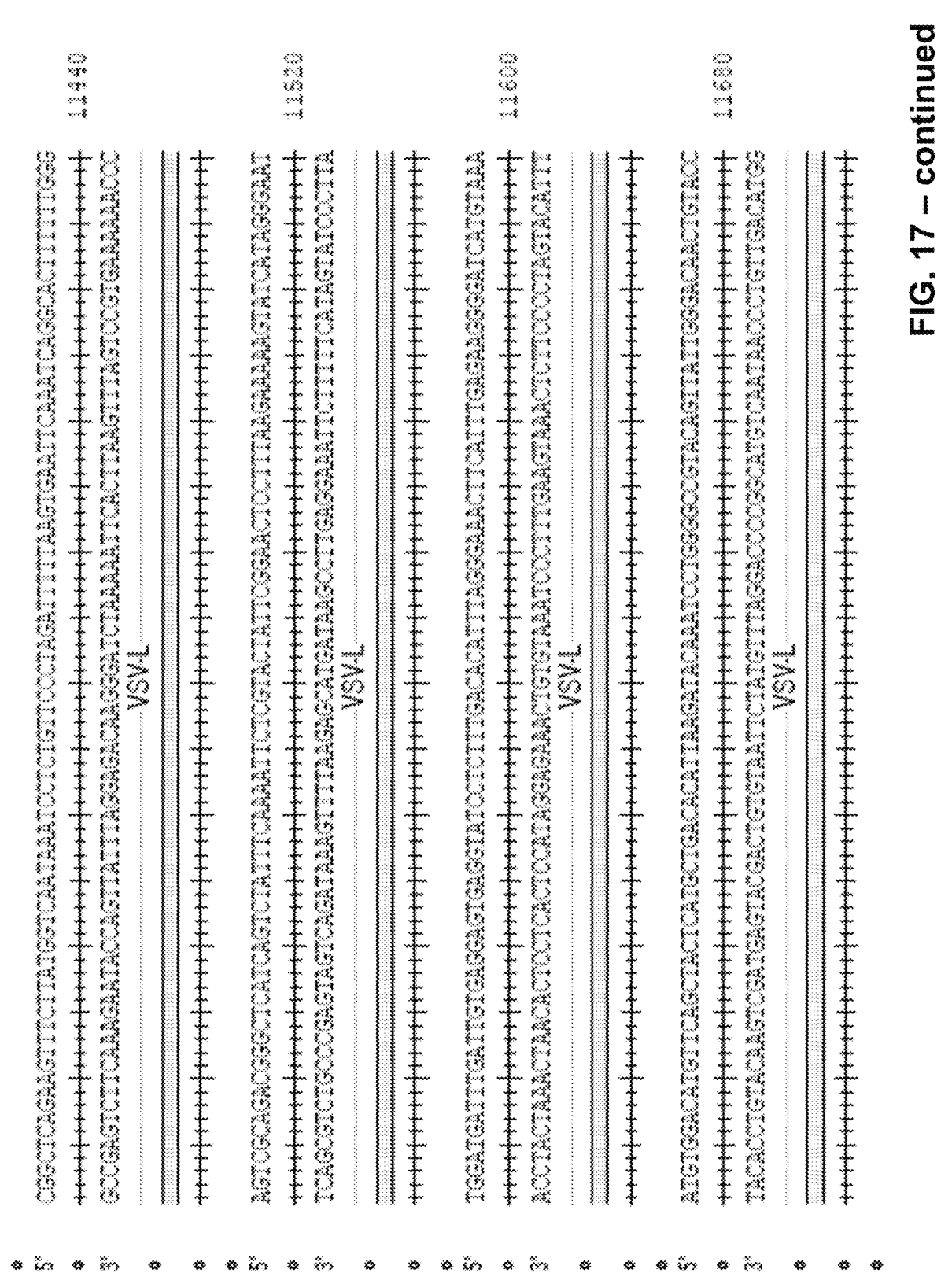
Figure 17:
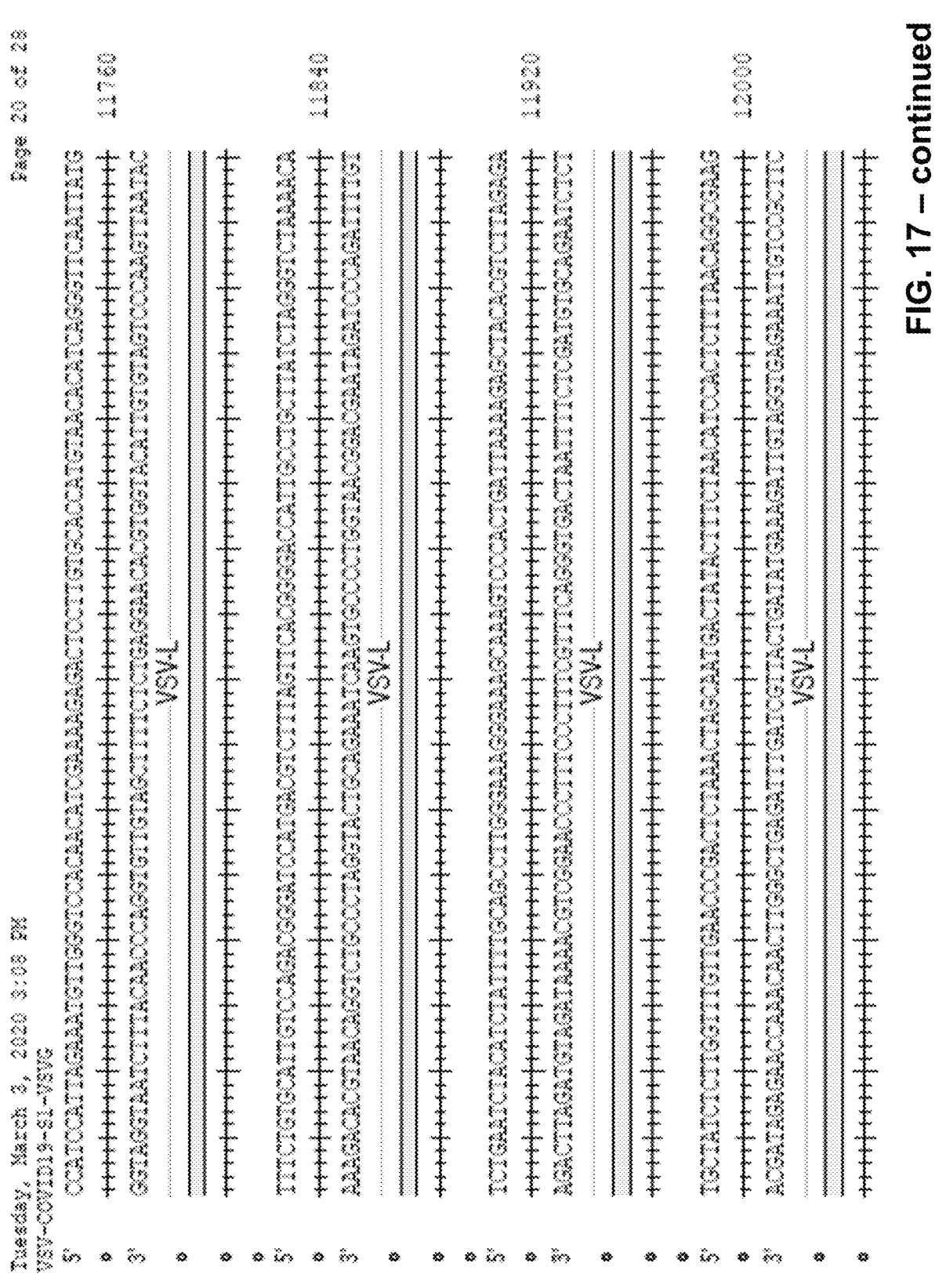
Figure 17:
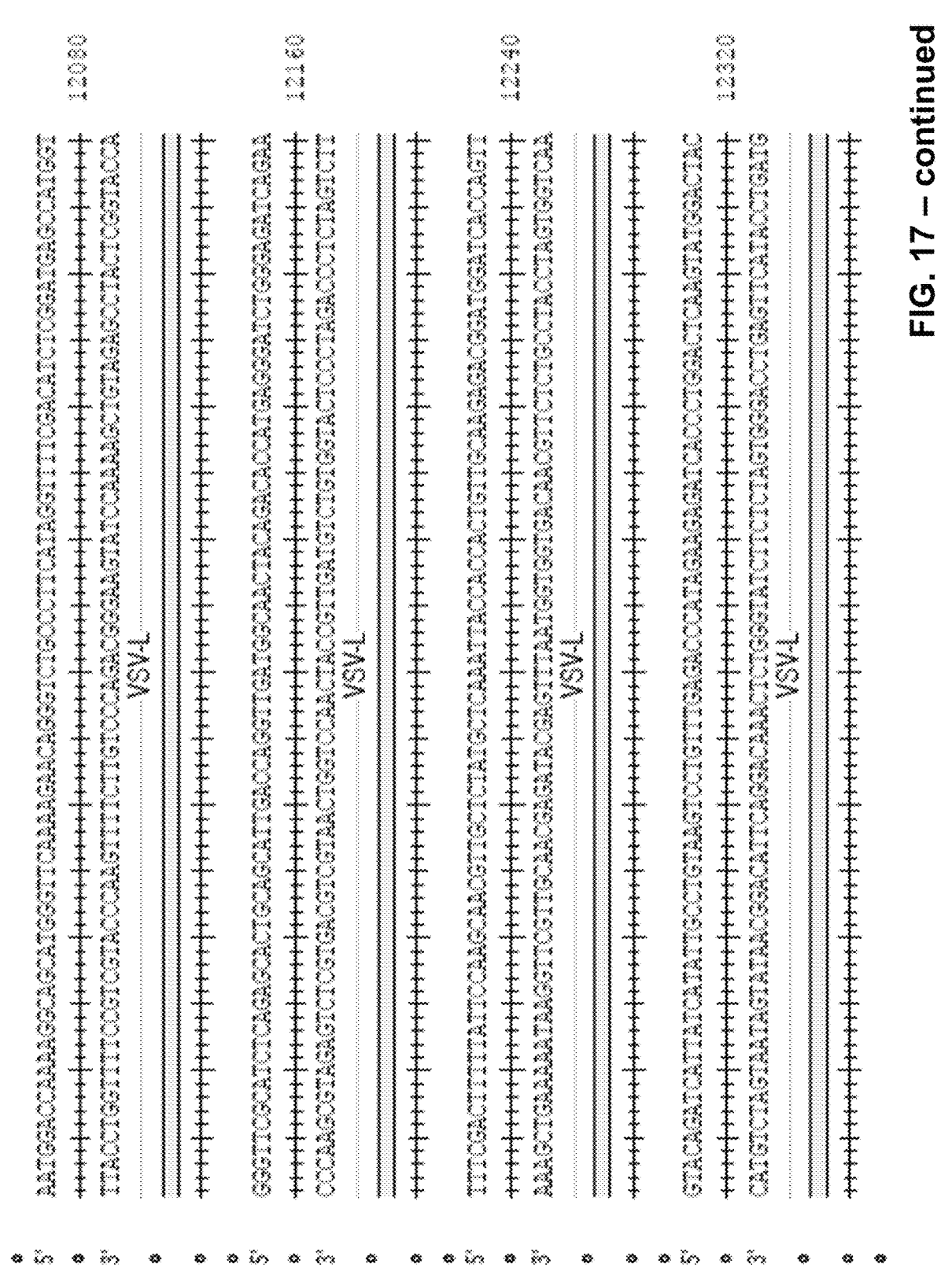
Figure 17:
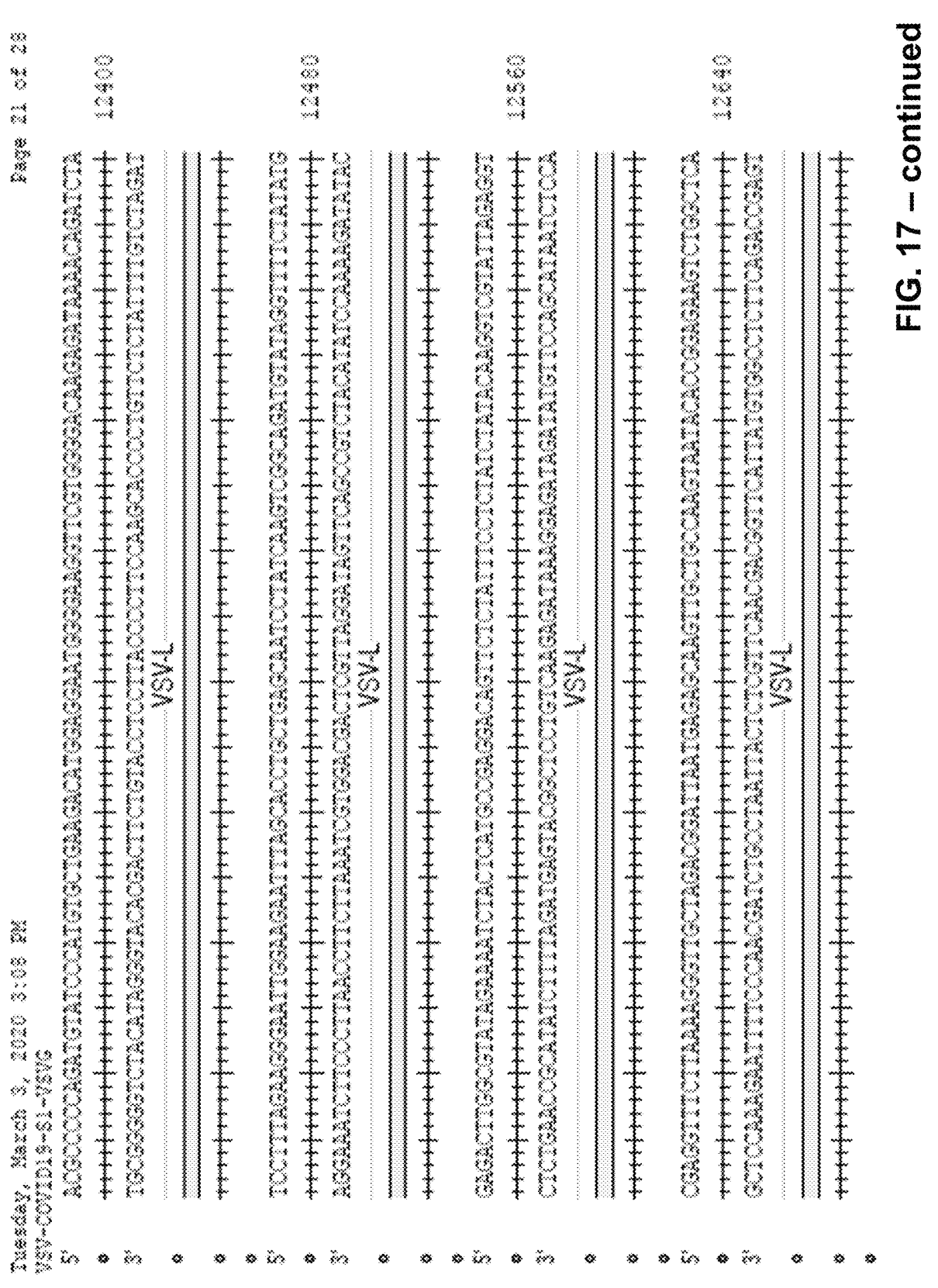
Figure 17:
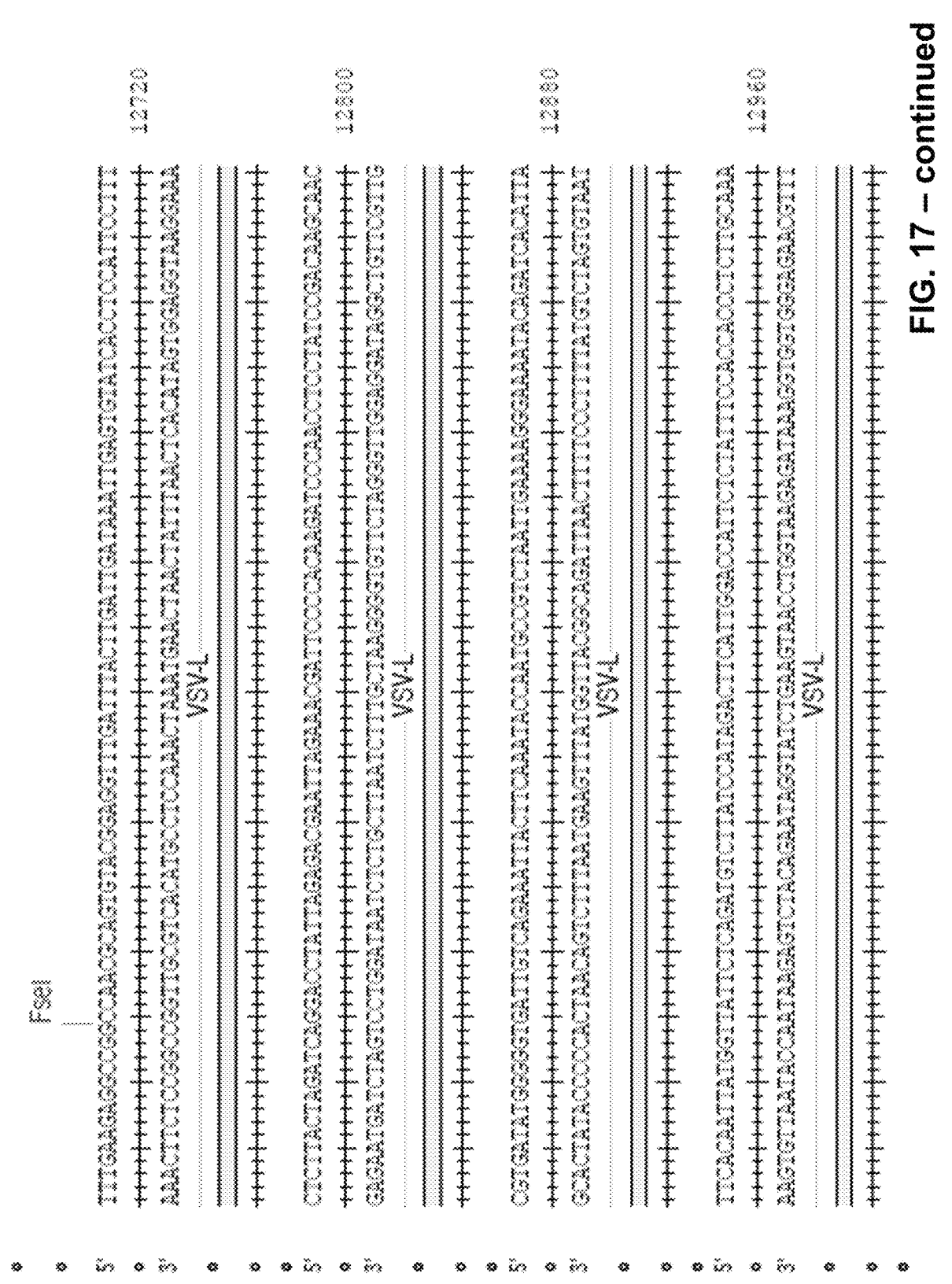
Figure 17:
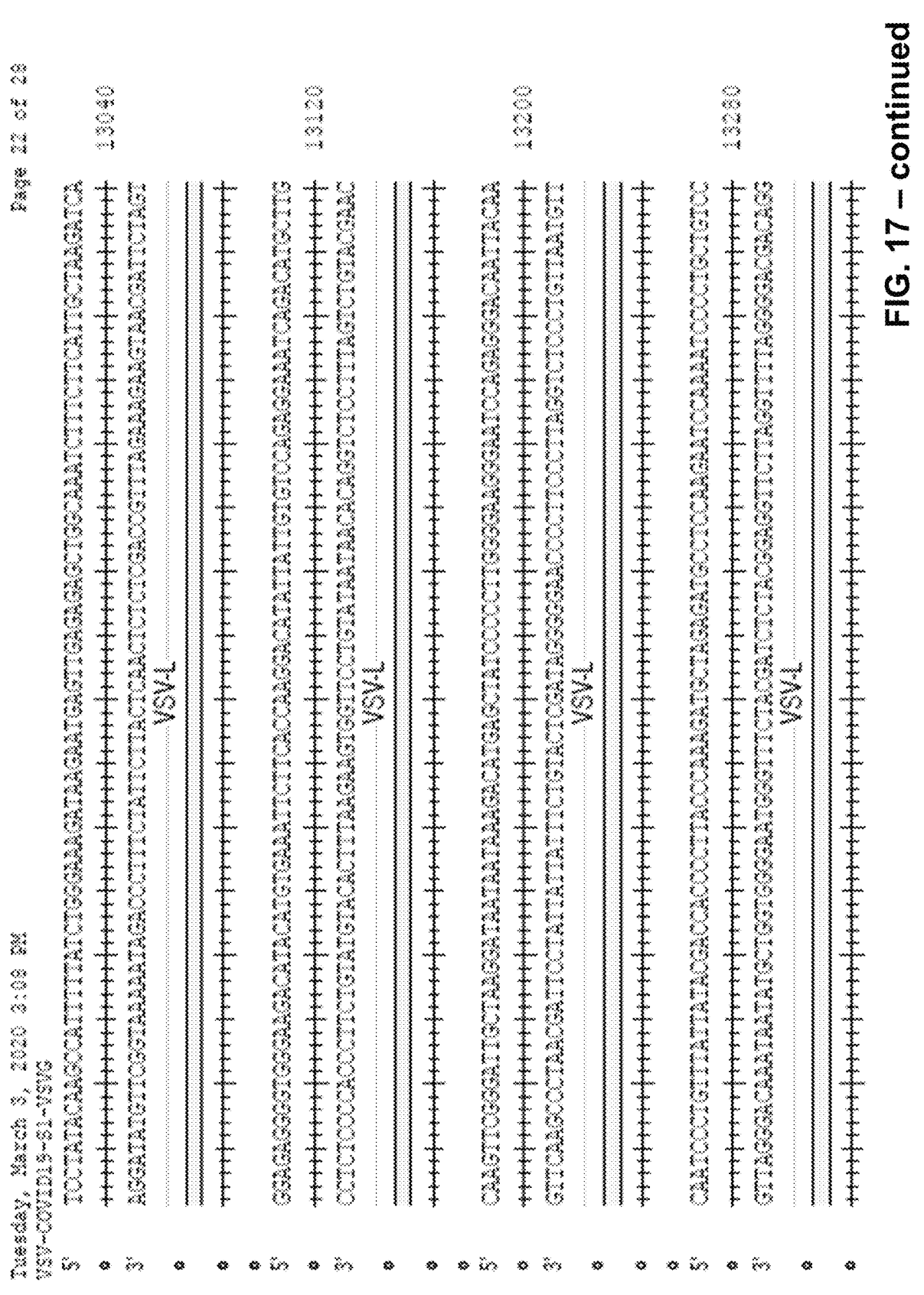
Figure 17:
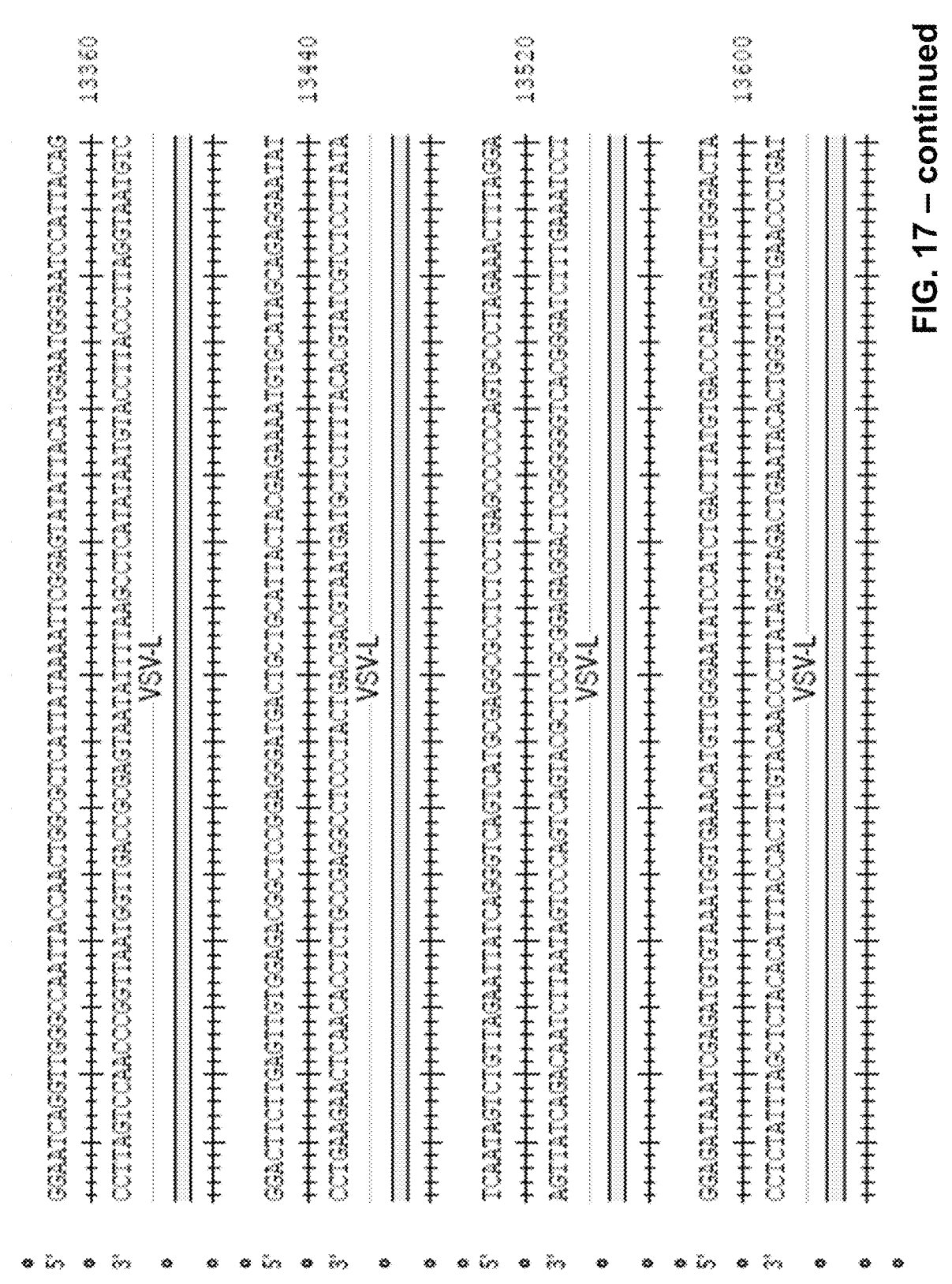
Figure 17:
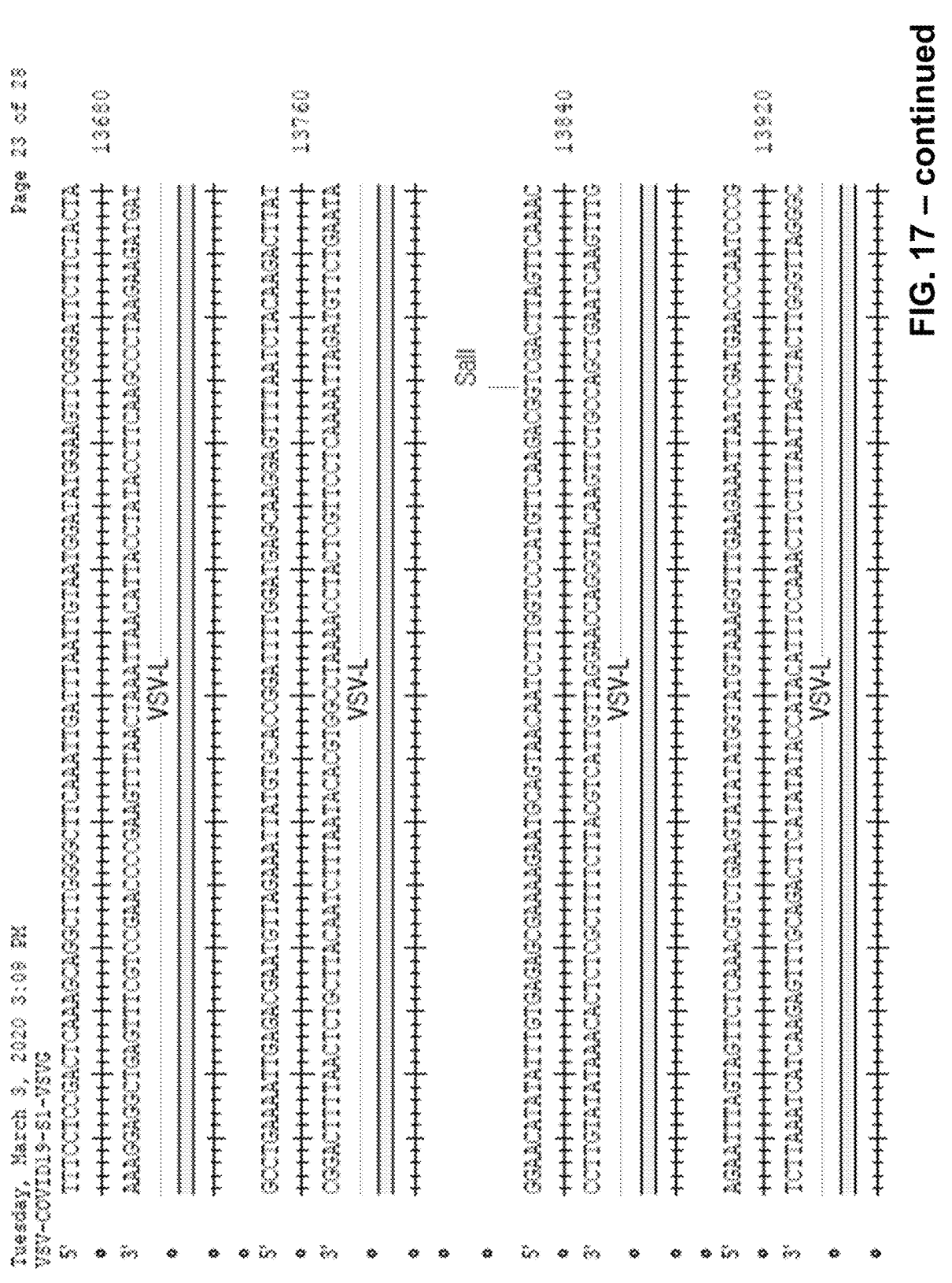
Figure 17:
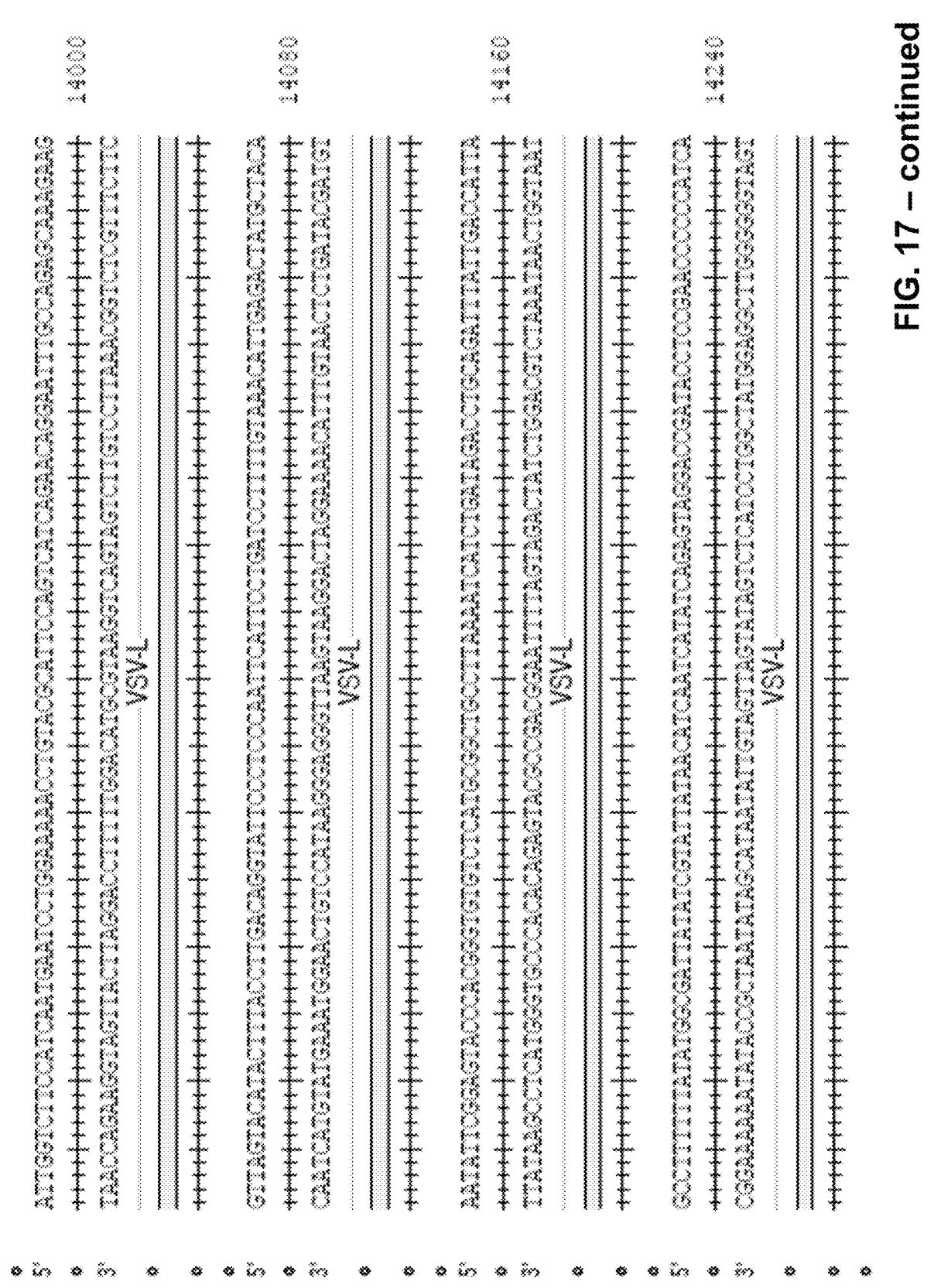
Figure 17:
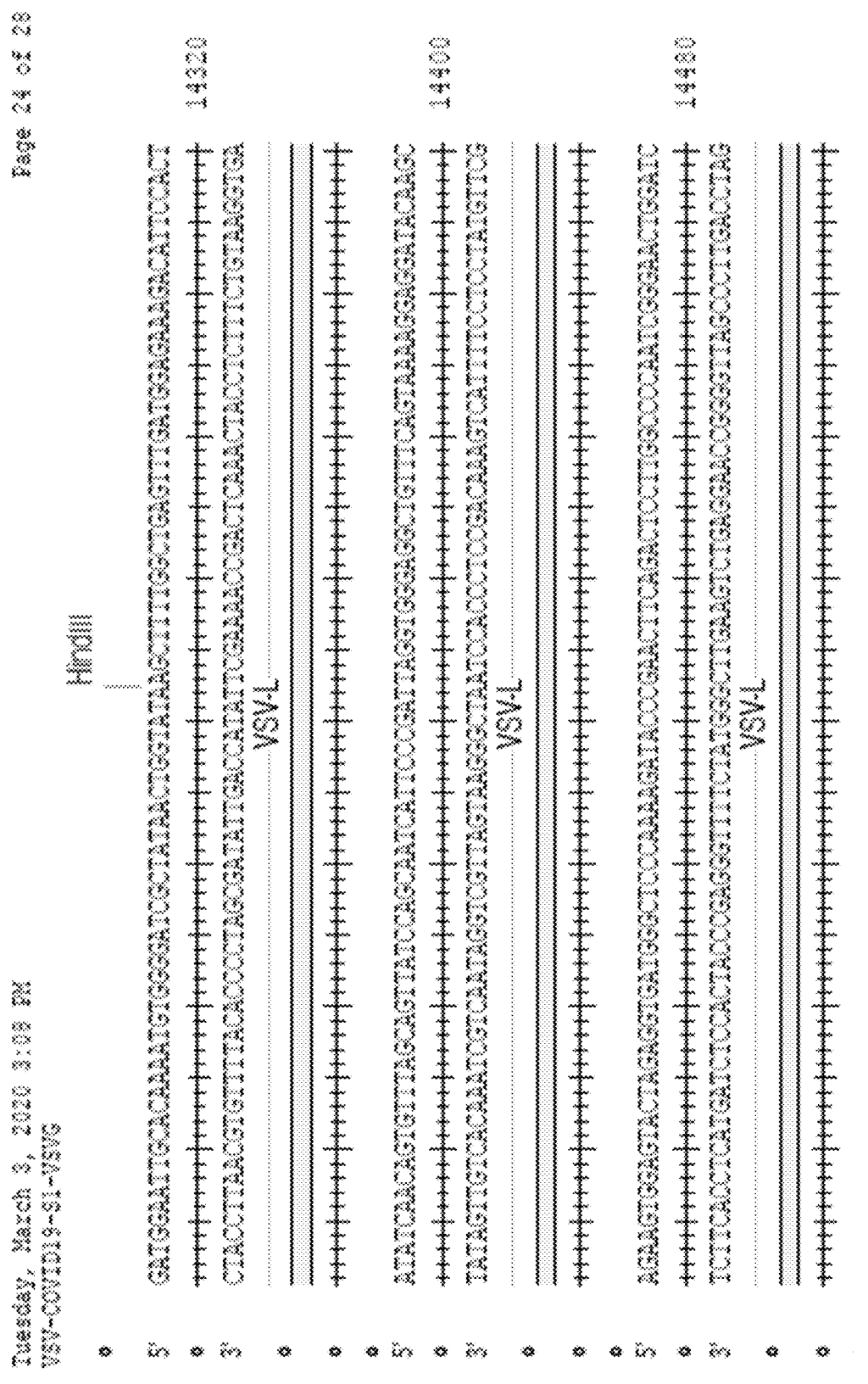
Figure 17:
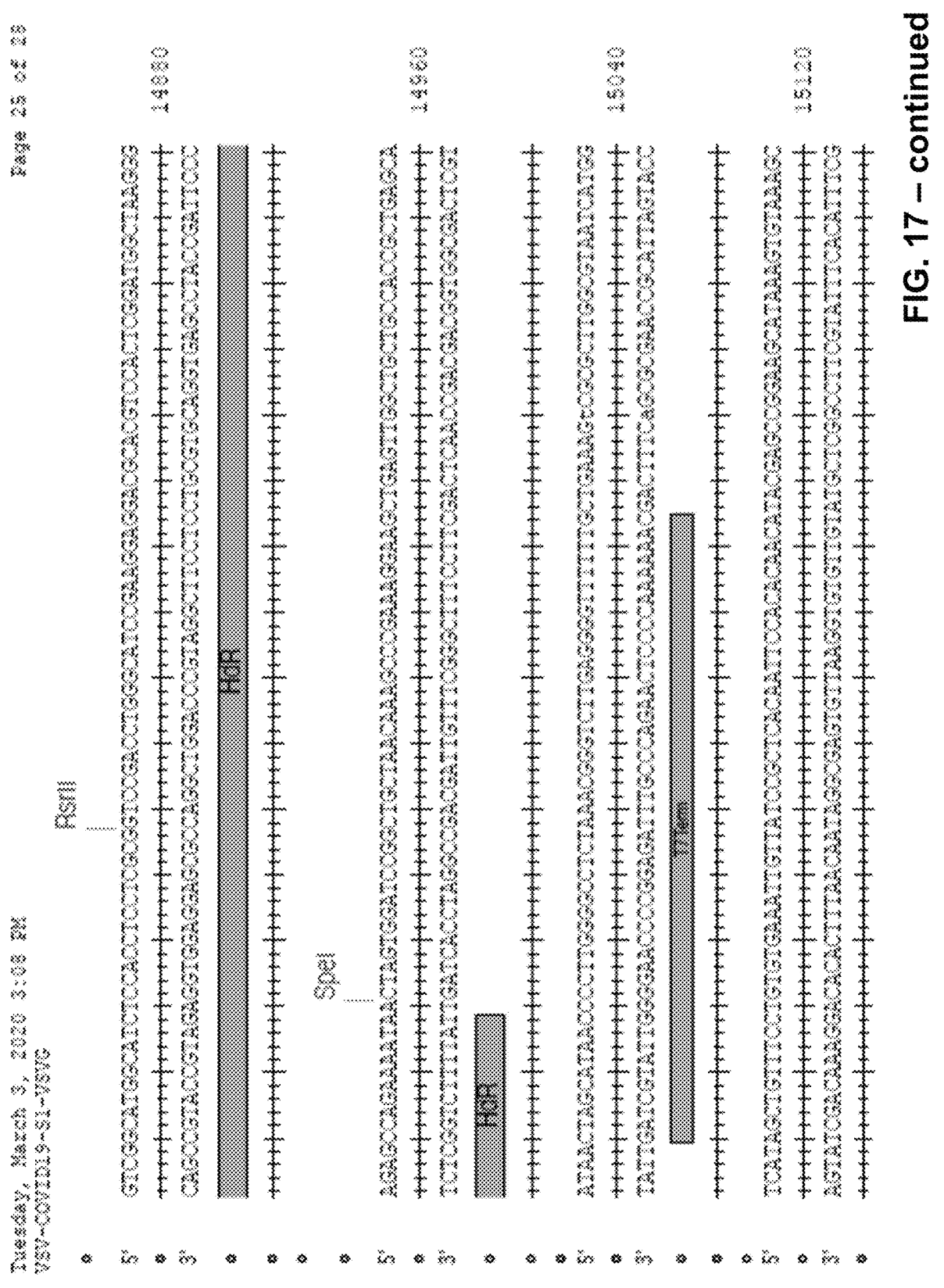
Figure 17:
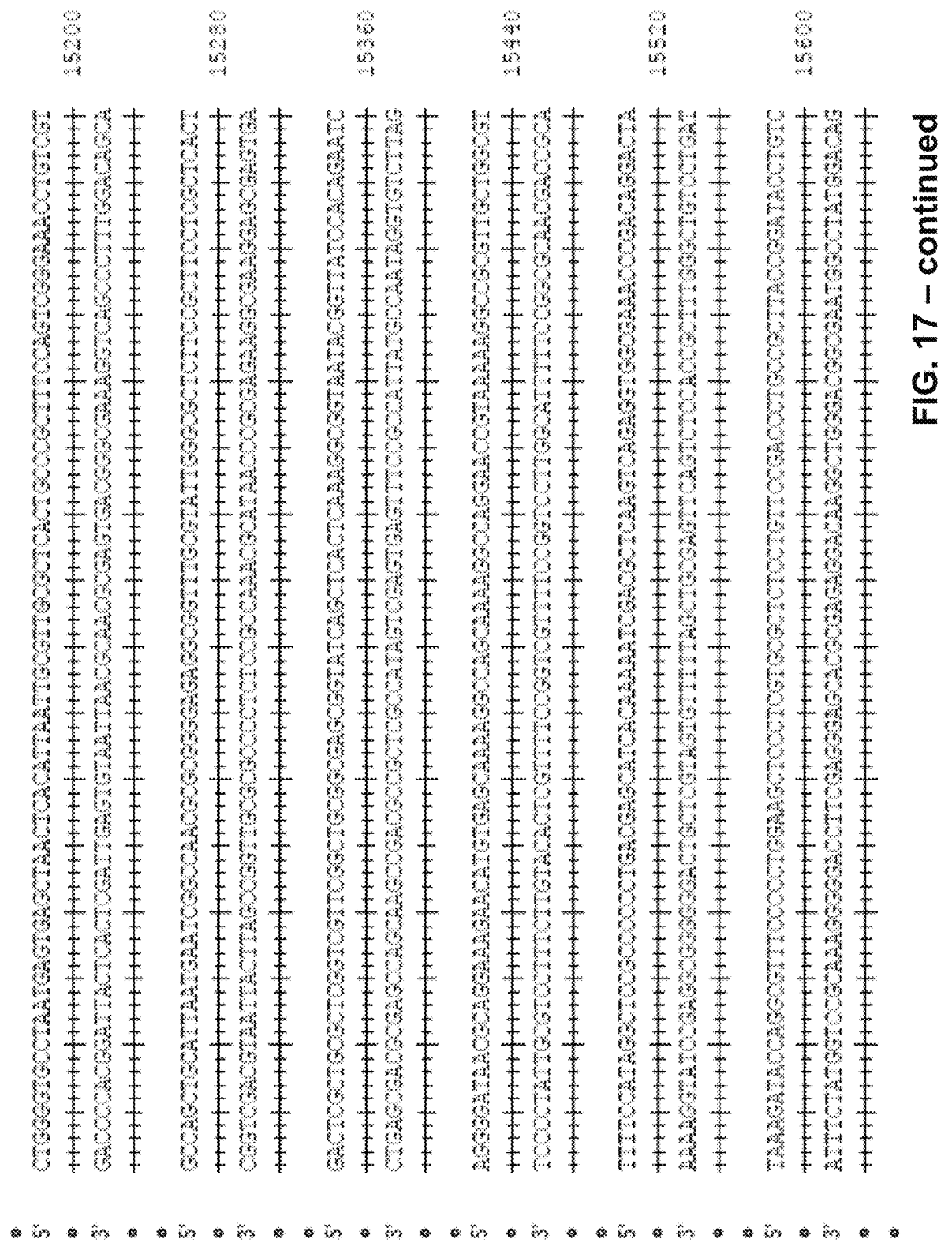
Figure 17:
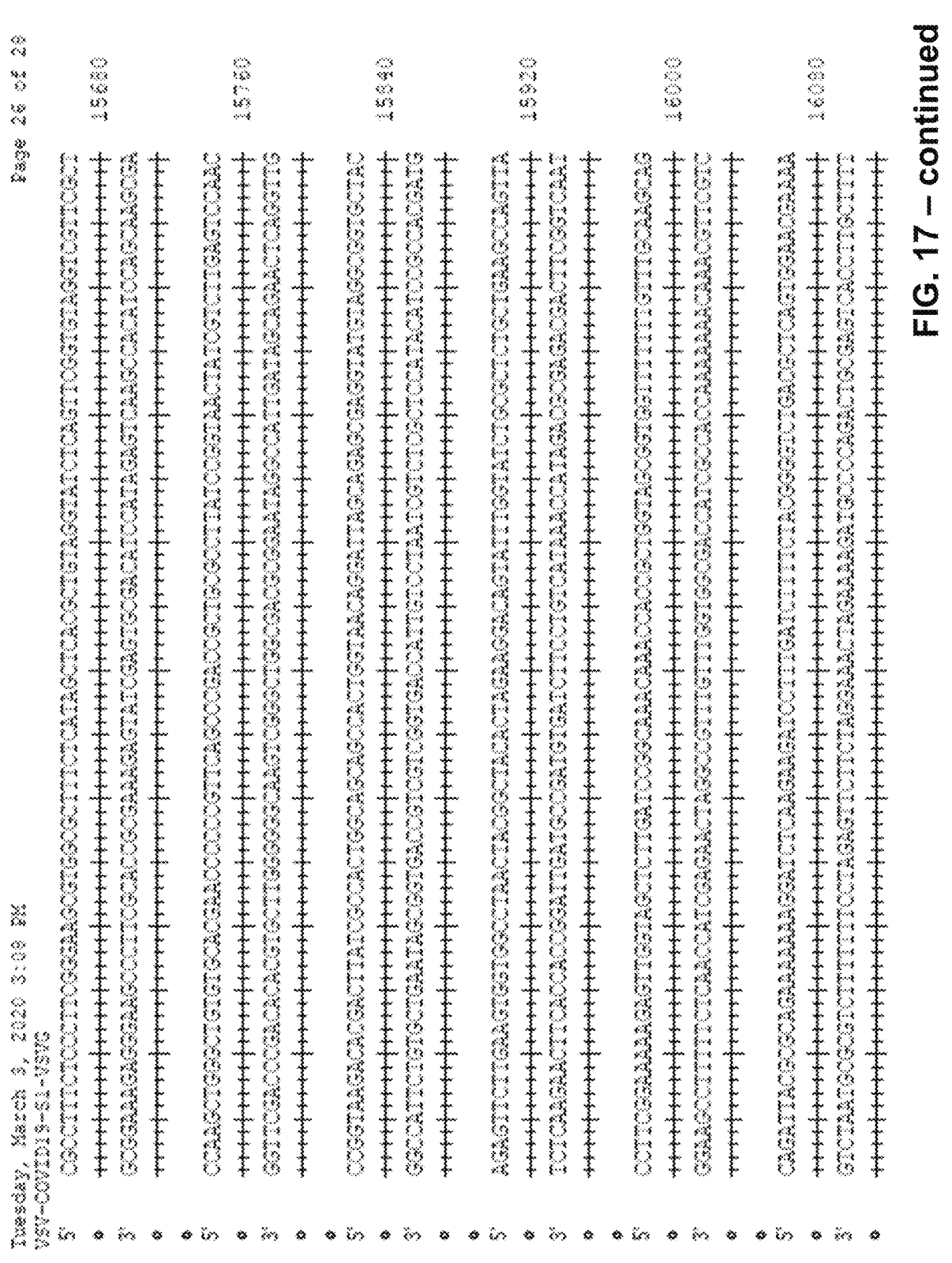
Figure 17:
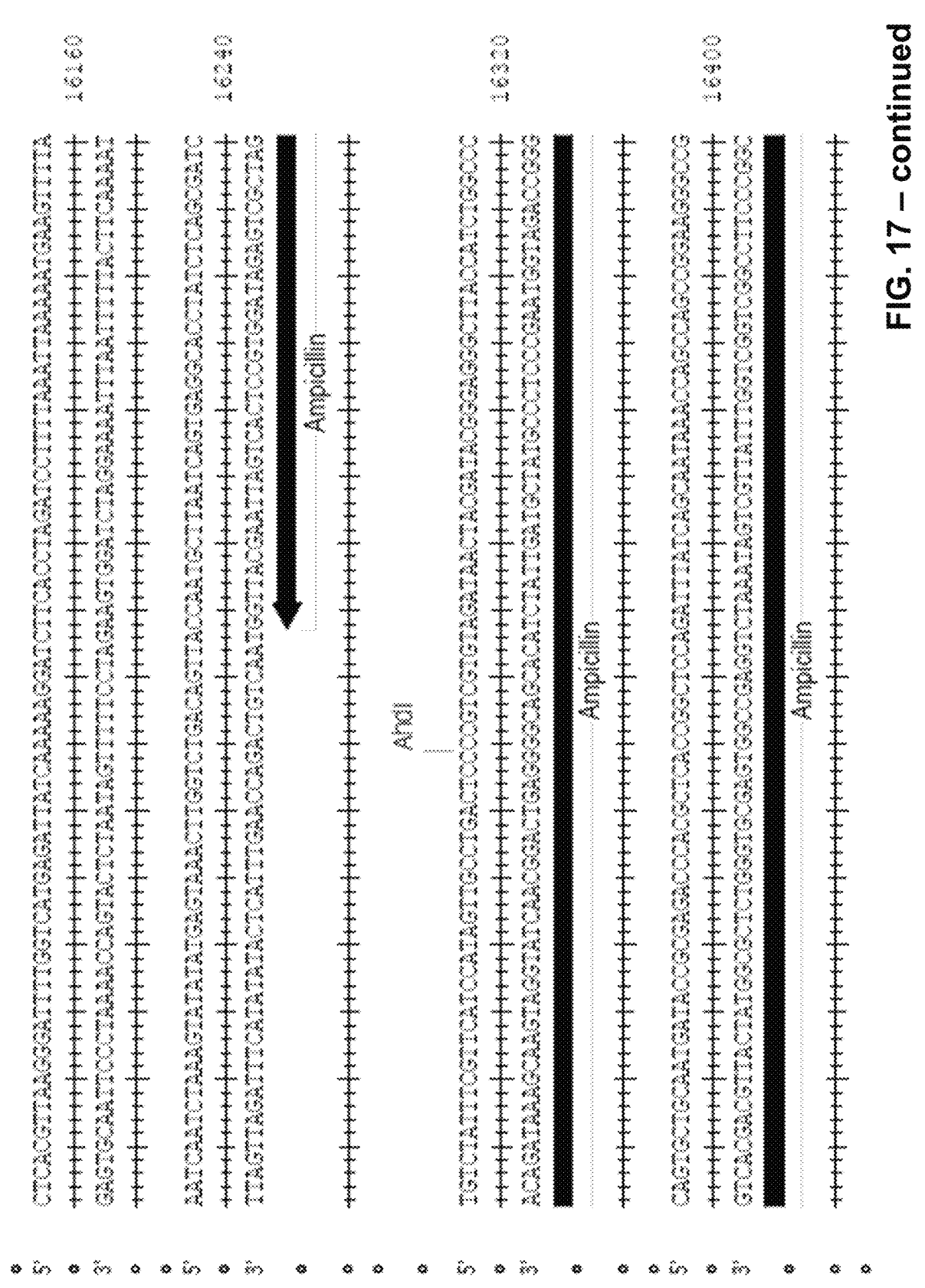
Figure 17:
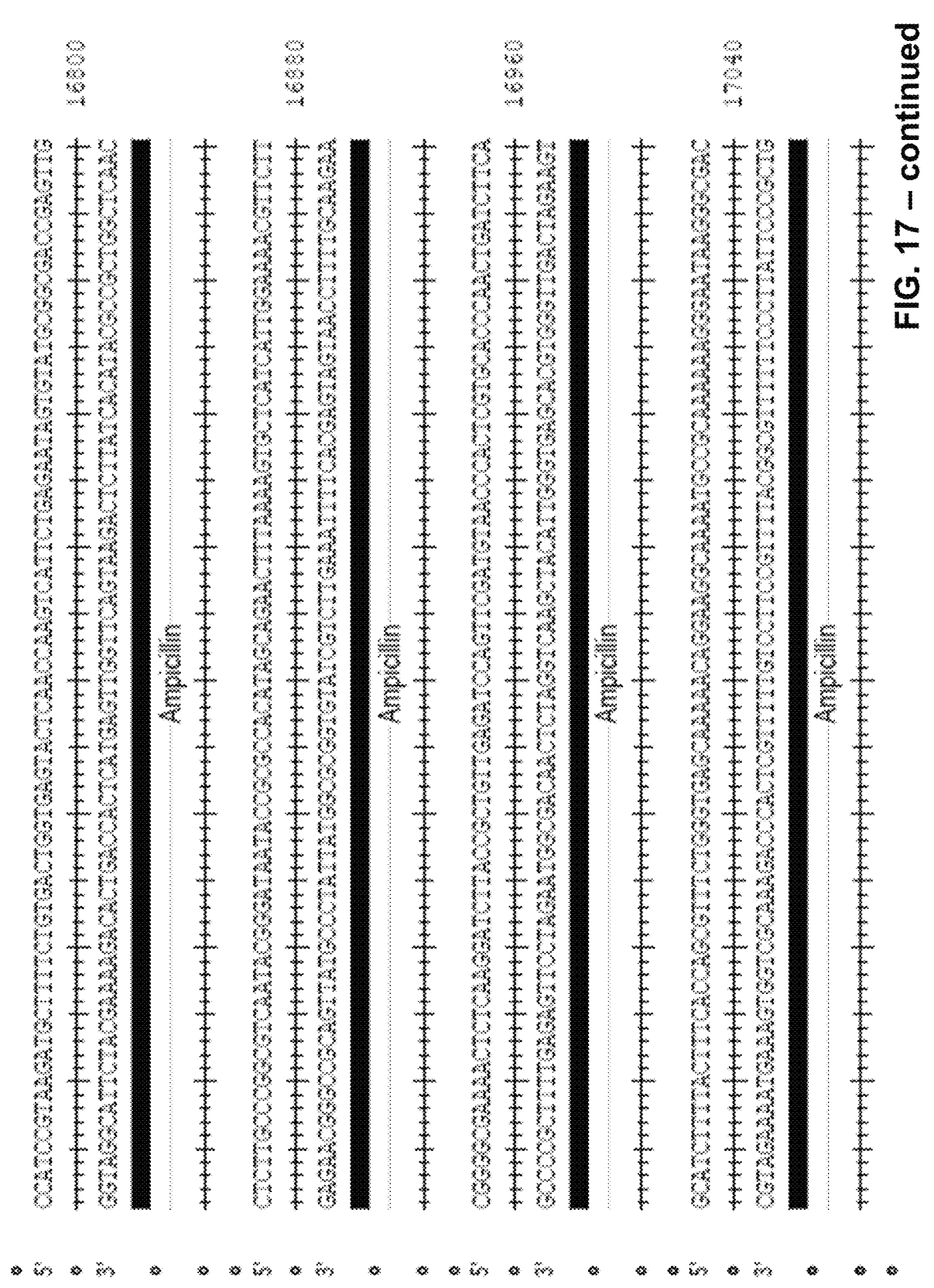
Figure 17:
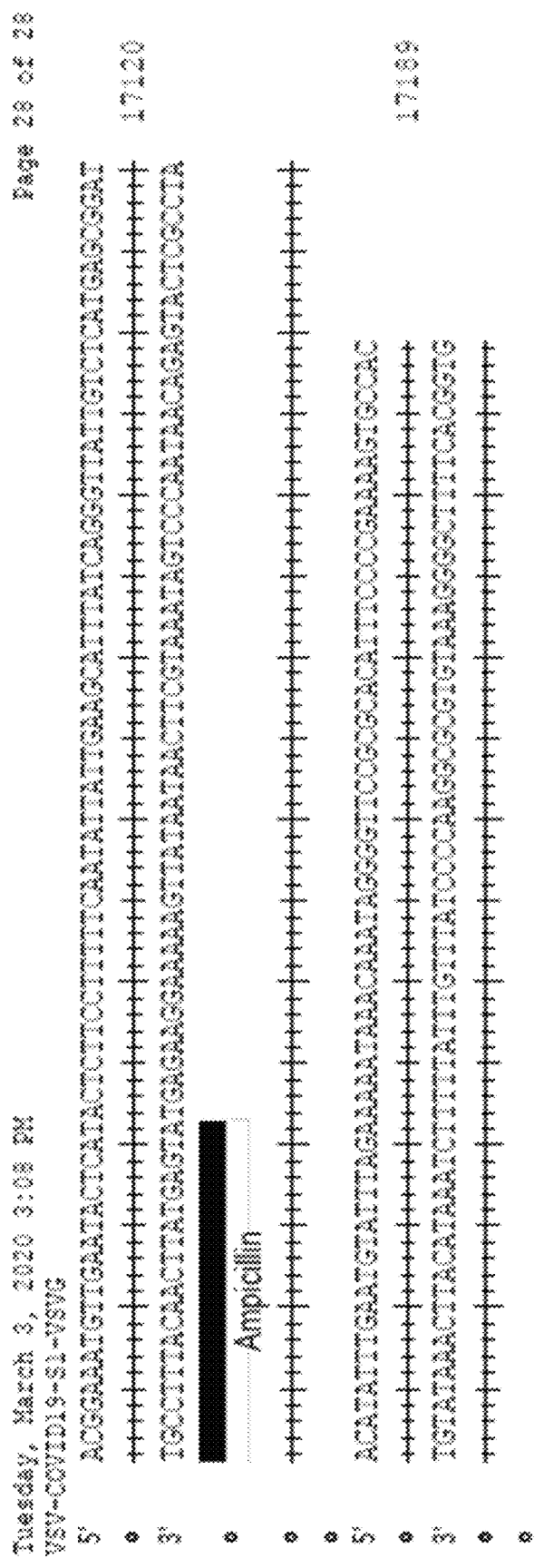

In some embodiments, the recombinant fusion protein comprises the sequence of the S1 domain of the SARS-CoV-2 spike protein (S) fused to a VSV glycoprotein (G) or portion thereof, shown as element "WuhanS-coVSV-G-tail" in "VSV-COVID19-S1-VSVG" in FIG. 17.

In other aspects, the present invention provides nucleic acid molecules having double-stranded, single-stranded, and/or combinations of double- and single-stranded regions as well as full or partial complements of any of the sequences of the present disclosure.

In some aspects, the present disclosure provides the following sequences, or complements thereof:

| SEQ ID NO: | Sequence |
|---|---|
| 34 | ATGTGCT...GCGATTA AT...TA |
| 35 | TGTGCTG...ATTAAG TGT...AAG |

| SEQ ID NO: | Sequence |
|---|---|
| 36 | GTTTTCCCAGTCACGAC |
| 37 | AAAcgacgGcCagtgGaattCCGTTAATACGACTCACTATAGG AAA...GG |
| 38 | ggtTGCGCGCCGTT...GACTCACTATAGG ggtT...AGG |
| 39 | gaGagCgcgcatCGaaaTTAATACGACTCACTATA ga...TA |
| 40 | GagacGTaCGCGtaaT...ACGACTCACTATAGGG Gaga...GGG |
| 41 | TAATAC...ATAGGG TAAT...GGG |
| 42 | gtGtcgtctcgCgcgtgcggCcgcGCTAGCCAGCTTGGGTCTCCCT |
| 43 | gtGtCGTctCt...GGGTAAGGATA<br>gtGtCGTctCtG...GGGTAAGGATA |
| 44 | gtGtgGTctCtG...AGGATAGTTCA<br>gtGtgGTctCtGGTC...GGTAAGGATAGTTCA |
| 45 | gAgaaGGTTTgAgaacgcgTctcGGTACGCCGGGTTT |
| 46 | tgTCaCGGATATCCATCCTGCTCTTGTCCtgTCC |
| 47 | cAgtccaccGgtgTCaCGGATATCCCTAATCCTGCT |
| 48 | GGATTAGGGATATCCGAGATGGCCACACTT |
| 49 | AAGTGTGGCCATCTCGGATATCCCTAATCCTGCTCT |
| 50 | TGGCCACACTTTTAAGGAGCT |
| 51 | CCACCGGATCCTGATGTAAT |
| 52 | CTGGCCTTACCTTCGCATCA |
| 53 | AGGATTAGCCAGTTTTATCCTGACT |
| 54 | AGAAGCCAG...GAGCTACA |
| 55 | gt...A gtgtGcgatcgcgtGCgagaGGCCAGAACAACA |
| 56 | gTGtacGcgtTCc...GCCAGAACAACA<br>gTGtacGcgtTCcTgacG...gagaGGCCAGAACAACA |
| 57 | GTGtGcGgccgctaTaGcgTAAGTTTTTTATAACAATGGTGtGcG gccgctaTaGcgatcTCCTAAGTTTTTTATAACAATG |
| 58 | GtgTGcgGccgTTATAACAATGGtgTGcgGccgctataaCgcgtT TCCTAAGTTTTTTATAACAATG |
| 59 | gtGtgcgGccgctaTaAcGTAAGTTTTTTATAACAATGgtTgtgcg GccgctaTaAcGcGtTTCCTAAGTTTTTTATAACAATG |
| 60 | GACAACCCAGGACAGGAGC |
| 61 | ACTCTCAATGTTCCTCCGCC |
| 62 | GCCATTCCTGGACTTGGGAA |
| 63 | gtgtgcGGccgcAGGTTGTACTAGGTGGGTC |
| 64 | AGTGATTGCCTCCCAAGGTC |
| 65 | TGAG...TTCG TGAGC...TTTCG |
| 66 | tcTCTGTAGACCGTAGTGCCCA |
| 67 | CAACCCCCGACAACCAGAG |
| 68 | CACCCCTAAAGGAGACACCG |
| 69 | gtgtgAa...TCTCAA<br>gtgtgAagacttcatg...CATCATGGGTCTCAA |
| 70 | GAGCGAGC...AAACTACT |
| 71 | CCCAAGTATGTTGCAACCCA |
| 72 | TCGAGCACTAGCATAGTCTACA |
| 73 | gTGTtctaGATCAGAGCGACCTTACATAGGA |
| 74 | GtgtcgtctctATGTCACCACAACGAGACCG Gtg...CG |
| 75 | CTTGATCGGGTTGCTAGCCA |
| 76 | CCAGGGAATGTATGGGGGAA |
| 77 | ATGCTTCCAACAGGCGTGTA |
| 78 | GTTGCCTATAAAGGGGGTCCC |
| 79 | GGGGTCC...AATTACA GG...CA |
| 80 | gtgttCCATCTTgtgttCtagaCTATATTGGTTCCATCTT |
| 81 | gcagAgaCgcgtctTTTTTTATAACAATGgcagAgaCgcgtcTTT TATAACAATG |
| 82 | gcTataaCgcgtatcTTTTTTATAACAATGgcTataaCgcgtaTT TTATAACAATG |
| 83 | TATCACTCTGTGTTTTATAACAATGTATCACTCTGTTTTATAAC AATG |
| 84 | GTATGCTCGAGTCCCTCACG |
| 85 | TCTCTCGTGACCTTGTTGCT |
| 86 | ACGGCTGCTGAAAATGTTAGG |
| 87 | AGTTCA...AGCCT AGTTC...GCCT |
| 88 | AGGCTTGAGACCTCTGTCCT |
| 89 | ATGAAACAAGGGCAGCATGC |
| 90 | AGAAGAGGACGAGGGACTGG |
| 91 | CGGGTT...ATGAT CGGG...TGAT |
| 92 | TTGTTGCGTGATCCCGATGA |
| 93 | TCAATGCTCTAAGCCACCCA |
| 94 | TCGGCAGCAACAACATCTCA |
| 95 | CCCTACCTCTAGTGTGGGGT |
| 96 | ACGGACCTAAGCTGTGCAAA |
| 97 | CTcgcgAt...ATCCTGCC<br>CTcgcgAtcGcCTAATTG...CGGAACCCTAATCCTGCC |
| 98 | GCCCTAGGTGGTTAGGCATTA |
| 99 | CctTaCCCAaCTTTGTtTGGTGGCCGGCATAGTCCCAGCCT |
| 100 | TCAGCAAAAAACCCCTCA |
| 101 | GgttGcgCGCATCCGGATATAGTTCCTCCTTTGgTT |
| 102 | gaccatgattAcGCcaGCGGCCGCATCCGGATAT |
| 103 | AGCGGATAACAATTTCACACAGGA |
| 104 | TATTACCGCCTTTGAGTGAGCTGA |

-continued

| SEQ ID NO: | Sequence |
|---|---|
| 105 | CTTTTTACGGTTCCTGGCCT |
| 106 | ACATTTCCCCGAAAAGTGC |

Pharmaceutical Compositions and Formulations.

The vaccine of the invention may be formulated as a pharmaceutical composition. In some embodiments, the vaccine contains a live virus. In some embodiments, the vaccine contains deactivated viral particles. In some embodiments, the virus is a recombinant virus encoded by any one of the nucleic acid constructs as described herein.

Such a pharmaceutical composition may be in a form suitable for administration to a subject (i.e. mammal), or the pharmaceutical composition may further comprise one or more pharmaceutically acceptable carriers, one or more additional ingredients, or some combination of these. The various components of the pharmaceutical composition may be present in the form of a physiologically acceptable salt, such as in combination with a physiologically acceptable cation or anion, as is well known in the art.

In one embodiment, the pharmaceutical compositions useful for practicing the method of the invention may comprise an adjuvant. Non-limiting examples of suitable adjuvants are Freund's complete adjuvant, Freund's incomplete adjuvant, Quil A, Detox, ISCOMs or squalene. In one embodiment, the adjuvant is an ADVAX™ adjuvant. In another embodiment, the adjuvant comprises Sepivac SWE™ adjuvant. In another embodiment, the adjuvant is monophosphoryl Lipid A (MPLA) (PHAD®) in squalene. In one embodiment, the adjuvant is MPLA 3D(6-acyl) PHAD® in 2% squalene. In one embodiment, the adjuvant increases or induces a Th-1 type immune response. The pharmaceutical composition or vaccine composition can comprise any one or more of the adjuvants described herein.

In some embodiments, the adjuvant comprises inulin e.g., delta inulin (e.g., delta inulin manufactured under current Good Manufacturing Practices is referred to in the art as Advax).

In one embodiment, the adjuvant comprises a delta inulin polysaccharide formulated with the TLR9 agonist (e.g., CpG oligodeoxynucleotides (CpG ODN)). In some embodiments, the adjuvant is Advax-SM™ (Vaxine Pty Ltd, Bedford Park, Australia).

In some embodiments, the adjuvant comprises a mixture of an oil component and a surfactant component.

In one embodiment, the composition may be an oil/surfactant dispersion or an oil/surfactant solution.

In other embodiments, the adjuvant comprises an emulsion e.g., an oil in water (o/w) emulsion.

In one embodiment, the composition includes an oil component which is formed from one or more oil(s).

In another embodiment, the oil(s) and the surfactant(s) in the composition are metabolizable (biodegradable) and biocompatible.

In some embodiments, the composition further comprises component(s) in addition to the oil and surfactant components.

In other embodiments, the proportions of the oil component and the surfactant component can vary. In some embodiments, an oil-in-water emulsion comprises oil droplets (e.g., submicron oil droplets as determined by e.g., dynamic light scattering (DLS)) when mixed with a volume of an aqueous material (e.g., water). In other embodiments, the oil droplets have an average diameter of less than about 300 nm when mixed with a volume of an aqueous material (e.g., water), illustratively, about 50 to about 290 nm, about 60 to about 280 nm, about 70 to about 270 nm, about 80 to about 260 nm, about 90 to about 250 nm, about 100 to about 240 nm, about 110 to about 230 nm, about 120 to about 220 nm, about 130 to about 210 nm, and about 140 to about 200 nm. In some embodiments, the oil droplets have an average diameter of about 160 nm (e.g., 160±10 nm), about 155 nm (e.g., 155±10 nm), about 142 nm (e.g., 142±5 nm), about 120 nm (e.g., 120±40 nm), or about 100 nm (e.g., 10±20 nm). In some embodiments, the oil droplets have an average diameter of about 142 nm (e.g., 142±5 nm).

In one embodiment, the total oil component is about 50% to about 90% by volume of the adjuvant composition. In another embodiment, the total oil component is no more than about 50%, no more than about 55%, no more than about 60%, no more than about 65%, no more than about 70%, no more than about 75%, no more than about 80%, no more than about 85%, or no more than about 90% by volume of the adjuvant composition.

In some embodiments, the oil comprises a terpenoid (e.g., a branched, unsaturated terpenoid).

In one embodiment, the oil comprises squalene.

In another embodiment, the oil comprises a saturated analog to squalene. In one embodiment, saturated analog to squalene is squalane.

In one embodiment, the adjuvant comprises a squalene oil in water emulsion. In another embodiment, the squalene in water emulsion comprises one or more non-ionic surfactants and/or other oils and/or stabilizers.

In other embodiments, the adjuvant comprises about 7 mgs to about 13 mgs, about 8 mgs to about 12 mgs, about 8 mgs to about 11 mgs, about 9 mgs to about 10 mgs, about 9.5 mgs to about 9.75 mgs of squalene (e.g., (mgs of squalene per 0.25 ml) or in 0.5 ml vaccine dose)). In one embodiment, the adjuvant comprises about 8.6 mgs, 9.75 mgs, 10.75 mgs, or 12.5 mgs of squalene.

In another embodiment, the adjuvant is a squalene in water emulsion comprising about 7 to about 13 mgs of squalene (e.g., (mgs of squalene per 0.25 ml) or in 0.5 ml vaccine dose)), illustratively, about 7 to about 13 mgs, about 8 to about 12 mgs, about 8 to about 11 mgs, about 9 to about 10 mgs, about 9.5 to about 9.75 mgs of squalene (e.g., (mgs per 0.25 ml) or in 0.5 ml vaccine dose)). In one embodiment, the adjuvant is a squalene in water emulsion comprising about 9.75 mgs of squalene (e.g., (mgs of squalene per 0.25 ml) or in 0.5 ml vaccine dose)).

In other embodiments, the oil component comprises one or more tocopherols (e.g., a, (3, y, 6, £, tocopherol). In one embodiment, the tocopherol is D-α-tocopherol and/or DL-α-tocopherol. In another embodiment, the α-tocopherol is DL-α-tocopherol. In other embodiments, the oil component of the adjuvant is an oil combination comprising squalene and a tocopherol (e.g. DL-α-tocopherol).

In some embodiments, the surfactant component comprises an ionic, a non-ionic, or a zwitterionic surfactant, and any combination thereof. In one embodiment, the surfactant component comprises only non-ionic surfactant(s).

Examples of surfactants include, but are not limited to, the polyoxyethylene sorbitan esters surfactants (e.g., Tweens, polysorbates, such as, e.g., polysorbate 80 (e.g., Tween™ 80), copolymers of ethylene oxide, propylene oxide, butylene oxide), sorbitan esters (e.g., sorbitan trioleate (e.g., Span™ 85), sorbitan monolaurate), and polyoxyethylene lauryl ether (e.g., Emulgen 104P), octoxynols (e.g., Triton X-100, IGEPAL CA-630/NP-40), phospholipids (e.g., lecithin), and Brij surfactants (e.g., polyoxyl 4 lauryl ether (Brij 30)).

In some embodiments, the surfactant in the composition (% by volume of the oil/surfactant composition) is no more than about: 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, or 10%.

In one embodiment, the surfactant component consists of a mixture of polysorbate 80 (e.g., Tween™ 80) and sorbitan trioleate (e.g., Span™ 85). In another embodiment, the surfactant component consists of a mixture of polysorbate 80 (e.g., Tween™ 80) and sorbitan trioleate (e.g., Span™ 85) in a volume ratio having more sorbitan trioleate (e.g., Span™ 85) than polysorbate 80 (e.g., Tween™ 80). In some embodiments, the surfactant component consists of a mixture of polysorbate 80 (e.g., Tween™ 80) and sorbitan trioleate (e.g., Span™ 85) in a volume ratio that achieves a HLB of about 8. In some embodiments, the surfactant component consists of a mixture (e.g., (mgs of squalene per 0.25 ml) or in 0.5 ml vaccine dose)) of about 1.175 mgs polysorbate 80 (e.g., Tween™ 80) and about 1.175 mgs sorbitan trioleate (e.g., Span™ 85).

In other embodiments, the aqueous component (e.g., water) further comprises one or more components e.g. solutes/salts/buffers. In one embodiment, the salts (e.g., sodium salts) form a pH buffer (e.g. citrate, phosphate). In another embodiments, one or more buffers include, but are not limited to, a citrate buffer, phosphate buffer (e.g., phosphate buffered saline, ammonium phosphate), a Tris buffer, a borate buffer, a succinate buffer, or a histidine buffer. In some embodiment, a buffered aqueous component comprises about 1 to about 20 mM of total buffer.

In other embodiments, the pH of the aqueous component is buffered at about pH 5.5 to about pH 8.0, illustratively, about pH 6.1 to about pH 7.9, about pH 6.2 to about pH 7.8, about pH 6.3 to about pH 7.7, about pH 6.4 to about pH 7.6, about pH 6.5 to about pH 7.5, about pH 6.6 to about pH 7.4, about pH 6.7 to about pH 7.3, about pH 6.8 to about pH 7.2, and about pH 6.9 to about pH 7.1. In one embodiment, the pH of the aqueous component is buffered at about pH: 5.7, 6.0, 6.5, 6.8, or 7.2. In another embodiment, the pH of the aqueous component is buffered at about pH 6.0 to about pH 6.5. In other embodiments, the buffer is 10 mM citrate buffer with a pH of about 6.5.

In other embodiments, the adjuvant is a squalene in water emulsion comprising (e.g., (mgs of squalene per 0.25 ml) or in 0.5 ml vaccine dose)) about 9.75 mgs squalene, 1.175 mgs polysorbate 80 (e.g., Tween™ 80), 1.175 mgs sorbitan trioleate (e.g., Span™ 85), citrate buffer, and a pH of about 6.5.

In some embodiments, an adjuvant of the present disclosure is co-formulated or co-administered with the vaccine.

In other embodiments, an adjuvant of the present disclosure is not co-formulated or co-administered with the vaccine.

Pharmaceutical compositions that are useful in the methods of the invention may be suitably developed for inhalation, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations.

The route(s) of administration is readily apparent to the skilled artisan and depends upon any number of factors including the type and severity of the disease being treated, the type and age of the veterinary or human patient being treated, and the like.

Although the descriptions of pharmaceutical compositions provided herein are principally directed to pharmaceutical compositions suitable for ethical administration to humans, it is understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

The composition of the invention may comprise a preservative from about 0.005% to 2.0% by total weight of the composition. The preservative is used to prevent spoilage in the case of exposure to contaminants in the environment.

Administration/Dosing

The regimen of administration of the compositions of the present invention may affect what constitutes an effective amount. For example, the vaccines, polypeptides, and/or the nucleic acids of the invention may be administered to the subject (i.e. mammal) in a single dose, in several divided dosages, as well as staggered dosages may be administered daily or sequentially, or the dose may be continuously infused, or may be a bolus injection. Further, the dosages may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to treat the disease in the subject. An effective amount of the composition necessary to achieve the intended result will vary and will depend on factors such as the disease to be treated or prevented, the age, sex, weight, condition, general health and prior medical history of the subject being treated, and like factors well-known in the medical arts. In particular embodiments, it is especially advantageous to formulate the composition in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the composition and the heterologous protein to be expressed, and the particular therapeutic effect to be achieved.

In some embodiments, the vaccine administered may be in an amount that will depend e.g., on the subject to be treated, the capacity of the subject's immune system to develop the desired immune response, and/or the degree of protection desired.

In other embodiments, the administration of the vaccines of the present invention can be in accordance with any suitable vaccination schedule, e.g., day 0, one month, four months, and twelve months from day 0. In other embodiments, the vaccines described herein may also be given in a single dose schedule, or a multiple dose schedule in which a primary course of vaccination may be with 1-10 separate doses, followed by other doses given at subsequent time intervals required to maintain and/or reinforce the immune response, for example, at 1-4 months for a second dose, and if needed, a subsequent dose(s) after several months. In some embodiment, other examples of suitable immunization schedules include, but are not limited to: (i) 0, 1 month and 6 months, (ii) 0, 7 days and 1 month, (iii) 0 and 1 month, (iv) 0 and 6 months, (v) 0, 1 month and 2 months, or other schedules sufficient to elicit the desired immune responses expected to confer protective immunity, and/or reduce disease symptoms, or reduce severity of disease.

In one embodiment, the administration of the vaccines of the present can be in accordance with any suitable vaccination schedule and/or dosage(s) effective to produce an antigen-specific immune response. In some embodiments, an antigen-specific immune response comprises a B and/or T cell response. In other embodiments, the antigen-specific immune response comprises administration of a single dose (no booster dose). In some embodiments, a second (booster) dose of the vaccine may be administered. In other embodiments, additional doses may be administered.

In some embodiments, the administration of the vaccines of the present can be in accordance with any suitable vaccination schedule and/or dosage(s) effective such that the subjects exhibit a seroconversion rate of at least 60%, at least 70%, at least 80%, at least 85%, at least 90%, or at least 95% following the first dose or the second (booster) dose of the vaccine.

In other embodiments, the administration of the vaccines of the present can be in accordance with any suitable vaccination schedule and/or dosage(s) effective to produce an antigen-specific immune response in the subject, wherein the anti-antigen antibody titer produced in the subject is increased by at least 1 log relative to a control.

In some embodiments, the control is an anti-antigen antibody titer produced in a subject who has not been administered a vaccine of the present disclosure. In other embodiments, the control is a titer produced in a subject that has been administered a live attenuated or inactivated vaccine; a recombinant or purified protein vaccine; or a virus-like particle vaccine.

In one embodiment, the titer produced in the subject is increased by 1-3 log relative to the control. In another embodiment, the titer produced in a subject is increased at least 2 times relative to the control. In other embodiments, the titer produced in the subject is increased at least 3, 4, 5, 10 or more times relative to the control. In one embodiment, the titer produced in the subject is increased at least 10 times relative to a control. In another embodiment, the titer produced in the subject is increased 2-10 times relative to a control.

In some embodiments, the vaccine of the present disclosure is administered to a subject in an effective amount (e.g., an amount effective to induce an immune response). In some embodiments, the effective amount is a dose equivalent to an at least 2-fold, at least 4-fold, at least 10-fold, at least 100-fold, at least 1000-fold reduction in the standard of care dose of a recombinant protein vaccine, wherein the anti-antigen antibody titer produced in the subject is equivalent to an anti-antigen antibody titer produced in a control subject administered the standard of care dose of a recombinant protein vaccine, a purified protein vaccine, a live attenuated vaccine, an inactivated vaccine, or a VLP vaccine. In some embodiments, the effective amount is a dose equivalent to 2-1000-fold reduction in the standard of care dose of a recombinant protein vaccine, a purified protein vaccine, a live attenuated vaccine, an inactivated vaccine, or a VLP vaccine.

In other embodiments, the effective amount of the vaccine administered comprises a total dose of about 0.1 µg to about 1000 µg of the vaccine or active ingredient (e.g., VLP, virion, viral vector, antigen, or nucleic acid molecule), illustratively, about 1 µg to about 900 µg, about 5 µg to about 700 µg, about 10 µg to about 500 µg, about 15 µg to about 300 µg, about 20 µg to about 200 µg, and about 25 µg to about 100 µg, In some embodiments, the effective amount is a total dose of about 25 µg, about 50 µg, or about 100 µg. In other embodiments, the effective amount is a total dose of not less than (NLT) about 1 µg, about 5 µg, about 10 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, or about 100 µg. In other embodiments, the effective amount is a total dose of about 0.1 µg to about 10 µg.

In some embodiments, doses of the vaccine are based on quantification of DNase-resistant particles (DRPs). In one embodiment, DRPs are equivalent to encapsidated vector genomes. In some embodiments, the subject receives at least one dose (e.g., a first dose at time zero) of the vaccine of about $10^5$ to $10^{20}$ about DRPs, illustratively, about $10^6$ to $10^{18}$, about $10^7$ to $10^{17}$, about $10^8$ to $10^{16}$, about $10^9$ to $10^{15}$, about $10^{10}$ to $10^{14}$, and about $10^{11}$ to $10^{13}$ DRPs. In other embodiments, the subject receives at least one dose (e.g., a first does at time zero) of at least about $10^5$, at least about $10^6$, at least about $10^7$, at least about $10^8$, at least about $10^9$, at least about $10^{10}$, at least about $10^{11}$, at least about $10^{12}$, at least about $10^{13}$, at least about $10^{14}$, at least about $10^{15}$, at least about $10^{16}$, at least about $10^{17}$, at least about $10^{18}$, at least about $10^{19}$, or at least about $10^{20}$ DRPs.

In some embodiments, the effective amount is a dose administered to the subject a total of one, two, three, four, five, or more times.

In some embodiments, the efficacy or effectiveness of a vaccine of the present disclosure is equal to or greater than about 60%. Vaccine efficacy or effectiveness may be assessed using e.g., standard analyses and protocols known in the art. In one embodiment, the efficacy or effectiveness of the vaccine is at least about 60%, at least about 65%, at least about 70%, at least about 75%, at least about 80%, at least about 85%, or at least about 90%.

In some embodiments, the vaccine immunizes the subject against a coronavirus (e.g., SARS-CoV-2 virus) for up to 6 months, 1 year or 2 years. In some embodiments, the vaccine immunizes the subject against a coronavirus (e.g., SARS-CoV-2 virus) for at least about 6 months, at least about 1 year, at least about 2 years, at least about 3 years, at least about 4 years, or about 5 years to about 10 years, or more.

Routes of Administration

One skilled in the art will recognize that although more than one route can be used for administration, a particular route can provide a more immediate and more effective reaction than another route. Routes of administration of any of the compositions of the invention include inhalation, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, electroporation and topical administration.

Kits

In some embodiments a kit is provided for treating, preventing, or ameliorating an a given disease, disorder or condition, or a symptom thereof, as described herein wherein the kit comprises: a) a compound or compositions as described herein; and optionally b) an additional agent or therapy as described herein. The kit can further include instructions or a label for using the kit to treat, prevent, or ameliorate the disease, disorder or condition. In yet other embodiments, the invention extends to kits assays for a given disease, disorder or condition, or a symptom thereof, as described herein. Such kits may, for example, contain the reagents from PCR or other nucleic acid hybridization technology (microarrays) or reagents for immunologically based detection techniques (e.g., ELISpot, ELISA).

Methods of Treatment

In one aspect, the invention includes a method of generating an immune response against a SARS-CoV-2 virus in a subject in need thereof. In another aspect, a method of vaccinating a subject against a SARS-CoV-2 virus is provided. In yet another aspect, a method of providing immunity against a SARS-CoV-2 virus in a subject is provided. In still another aspect, a method of treating and/or preventing a disease or disorder associated with SARS-CoV-2 virus in a subject in need thereof. In some embodiments, the method comprises administering to the subject an effective amount of a recombinant virus as described herein. In some embodiments, the method comprises administering to the subject an effective amount of a vaccine described herein.

In some embodiments, the disease or disorder associated with the SARS-CoV-2 virus is a respiratory disease. In some embodiments, the disease or disorder associated with the SARS-CoV-2 virus is coronavirus disease. In some embodiments, the disease or disorder associated with the SARS-CoV-2 virus is COVID-19.

Pharmaceutical compositions comprising the vaccine of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The administration of the vaccine of the invention may be carried out in any convenient manner known to those of skill in the art. The vaccine of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally.

Subjects to which administration of the pharmaceutical compositions of the invention is contemplated include, but are not limited to, humans and other primates, mammals, and birds, including commercially relevant mammals and birds such as cattle, pigs, horses, sheep, chicken, ducks, cats, dogs, and ferrets.

In some embodiments, the subject is a domesticated animal. In some embodiments, the subject is a domestic pet. In some embodiments, the animal is a captive animal, e.g., an animal maintained in an exhibit or in a zoological park. In some embodiments, the animal is livestock. In some embodiments, the subject is an animal susceptible to infection with SARS-CoV-2 and can be a reservoir for the SARS-CoV-2 virus. In some embodiments, the subject is a feline. In some other embodiments, the subject is a canine. In some embodiments, the subject is a member of the Mustelidae family, such as a weasel, polecat, stoat, marten, mink, badger, otter, or ferret. In some embodiments, the subject is a cat. In some other embodiments, the subject is a dog. In some embodiments, the subject is a ferret.

In one aspect, a method of preventing SARS-CoV-2 infection or providing immunity to SARS-CoV-2 in a subject is provided, the method comprising administering to a subject a SARS-CoV-2 vaccine described herein, wherein the subject is a domestic pet selected from a cat, a dog, and a ferret. In particular, felines and ferrets have been identified as a potential host for SARS-CoV-2 (J. Shi et al., *Science* 10.1126/science.abb7015 (2020)). Cats are one of the most favored pets of the USA's citizens. In the United States, one in three households owns a pet cat, with an average of 2.2 cats per cat-owning household. However, pet cats are only a part of the total cat population in the country, which is estimated to be around 76.5 million.

Currently, rabies vaccination is recommended for cats, dogs, and ferrets. CDC guidelines recommend that all dogs, cats, and ferrets should be vaccinated and revaccinated against rabies according to product label directions (www.cdc.gov/rabies/specific_groups/veterinarians/vaccination.html). If a previously vaccinated animal is overdue for a booster, it should be revaccinated. Immediately following the booster, the animal is considered currently vaccinated and should be placed on a vaccination schedule according to the labeled duration of the vaccine used.

The existing RABV vaccine for cats, dogs, or ferrets can be replaced with a rabies virus-based SARS-CoV-2 vaccine to induce protection from both diseases. Thus, in one aspect, a method of providing immunity to rabies and a SARS-CoV-2 associated disease in a subject is provided, wherein the subject is a cat, dog, or ferret. The method includes the step of administering to the subject a vaccine comprising a rabies virus-based SARS-CoV-2 vaccine. In another aspect, a vaccine for cats, dogs, or ferrets is provided, the vaccine comprising a rabies virus-based SARS-CoV-2 vaccine. In some embodiments, the vaccine comprises a recombinant rabies virus comprising a SARS-CoV-2 spike protein (S) or a portion thereof. In some embodiments, the vaccine comprises a recombinant rabies virus comprising a fusion of (a) a glycoprotein (G) of a virus or a portion thereof, and (b) a SARS-CoV-2 spike protein (S) or a portion thereof. In some embodiments, the vaccine comprises an inactivated virus. In particular embodiments, the vaccine comprises an adjuvant. In some embodiments, the vaccine is formulated for administration to a cat. In some other embodiments, the vaccine is formulated for administration to a dog. In still other embodiments, the vaccine is formulated for administration to a ferret.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Green, M. R. & Sambrook, J., Cold Spring Harbor Laboratory Press, 2012); "Oligonucleotide Synthesis, a practical approach" (Paselk R. A., edited by Gait, M. J., IRL Press, Oxford, 1984); "Culture of Animal Cells: A Manual of Basic Technique and Specialized Applications, Sixth Edition" (Freshney, R. I., John Wiley & Sons, Inc., 2010); "Methods in Enzymology" (Vol. 152, Guide to Molecular Cloning Techniques, Berger and Kimmel, Eds., San Diego: Academic Press, Inc., 1987); "Handbook of Experimental Immunology" (Herzenberg L. A., Weir, D. M., Blackwell, C., Wiley, 1997); "Gene Transfer Vectors for Mammalian Cells" (Miller and Calos, eds., Cold Spring Harbor Laboratory, Cold Spring Harbor, 1987); "Short Protocols in Molecular Biology" (Ausubel, F. M., et al., ed., John Wiley & Sons, 2002); "Polymerase Chain Reaction: Principles, Applications and Troubleshooting" (Babar, M. E., publisher VDM Verlag Dr. Müller, 2011); "Current Protocols in Immunology" (Colligan, J. E., et al., ed., Greene Pub. Associates and Wiley-Interscience, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

Example 1

RABV, VSV, and MV Expressing Covid S or Covid-S1

The materials and methods employed in Examples 1-5 are now described.
Generation of RABV-, VSV-, and MV-Based Vaccines Against COVID-19

The SARS-CoV-2 spike protein (S) was used in generating the vaccines against COVID-19 described herein. SARS-CoV-2 causes Covid-19. The S1 domain (receptor binding site of the S protein) was incorporated into the Genome of rabies virus (RABV) and vesicular stomatitis virus (VSV). For both constructs part of their native G protein was used to promote the incorporation of the S1 domain. The full-length SARS-CoV-2 S was found to interfere with viral growth (VSV or RABV G) making it almost impossible to produce the vaccine; thus the S1 domain was used instead.

Three measles virus (MV)-based vaccine expressing full-length SARS-CoV-2 spike protein (S) were also prepared. These three viruses express the SARS-CoV-2 spike protein (S) from position 2, 3, or 6 of the genome. Previous research indicates that for measles virus the position a foreign gene is expressed is important for MV replication and immunogenicity of the trans-gene. However this depends on the antigen, so three different viruses were prepared.
Testing of RABV-, VSV-, and MV-Based Vaccines Against COVID-19 in Animals In the next phase, the vaccines are tested in animals. The receptor for both viruses is believed to be ACE 2. The model that will be used is a hamster or mice (transgenic expressing ACE2 or wildtype infected with an Adenovirus expressing ACE2).

Both live and killed viruses are tested. After immunization mice or hamster are challenged with the SARS-CoV-2 (Covid-19).

Immunological Parameters of the 2019-nCoV Vaccine.
The parameters of the induced humoral and cellular immune responses will be studied after i.m. inoculation of mice (including 2019-nCoV challenge), and non-human primate (NHP) (immunogenicity). ELISA and virus neutralization assays (VNA) will be utilized to analyze the humoral immune response. These assays are developed for mice and NHP and, based on the limited space, only briefly described below. Previous experience will be used in the development of such assays especially in the field of coronaviruses
ELISA Assay for Detection of 2019-nCoV S1 and Vector RABV G-Specific Humoral Responses.

Preparation of highly purified antigens against 2019-nCoV S1 or RABV G. Purification of the HA-tagged soluble protein from the supernatant of transfected 293T cells is carried out as described previously for MERS-CoV (17). Purified proteins can be prepared in the mg range sufficient for large numbers of assay plates. Approximately 10-20 mg of purified RABV G is produced on a regular basis in the Schnell laboratory.

To determine antibody responses to the 2019-nCoV S or RABV G, an indirect ELISA will be developed utilizing purified S1 or G protein (26) and unpublished. Sera from vaccinated mice or NHP will be used at different dilutions to determine the EC50 over time. Serum IgM and IgG antibodies (total IgM, IgG, IgG1, IgG2 for NHP, IgG2c and IgG1 for B6) to each vaccine antigen will be measured by a qualified ELISA that is well established in the Thomas Jefferson University (TJU) laboratories. Prior to performing the ELISA assays, we will qualify the assay for each vaccine antigen. Our ELISA platform will be standardized to measure serum IgG specific for the vaccine antigens by characterizing assay variability, determining the limit of quantitation, defining the positive and negative quality control ranges, and defining assay acceptance criteria. TJU has substantial experience in qualifying and performing ELISA assays using this platform and plan to use it for future clinical studies as well. Assays will be transferred for the human clinical samples to a contractor via IQVIA.

Virus Neutralization assays (VNA) for RABV are well established in the TJU laboratory (12, 27, 28) for mouse, monkey, and human sera. Use of an internal WHO standard, allows determining the international unit (I.U.) achieved by the immunization. The presence of 0.5 I.U or more in the sera is considered a correlate of protection from rabies. VNA for MERS-CoV are established at the University of Maryland in the Frieman lab. Dr. Frieman has a virus sample from CDC from the Washington St patient. He is also recreating multiple strains using his infectious clone and synthesizing full genomes.
Cellular Responses Most likely, humoral responses are the key for protection based on previous studies of coronaviruses but as a research part, frequencies and cytokine expression profiles of vaccine antigen-specific T cells will be measured in splenocytes or cryopreserved NHP PBMCs using a qualified 13-color ICS assay. In order to assess potential for durable antibody responses, antigen specific $IgG^+$ ELISPOT analysis will be performed to detect antibody-secreting plasma cells in the bone marrow 28 days post-boost immunization.

The results of the experiments are now described.
RABV, VSV, and MV Expressing Covid S or Covid-S1

VSV expressing codon-optimized Covid-S1, RABV expressing codon-optimized Covid-S1, and MV expressing codon-optimized Covid-S from positions 2, 3, and 6 of the genome were generated (FIGS. 1-5; FIGS. 17-21).

Figure 6:
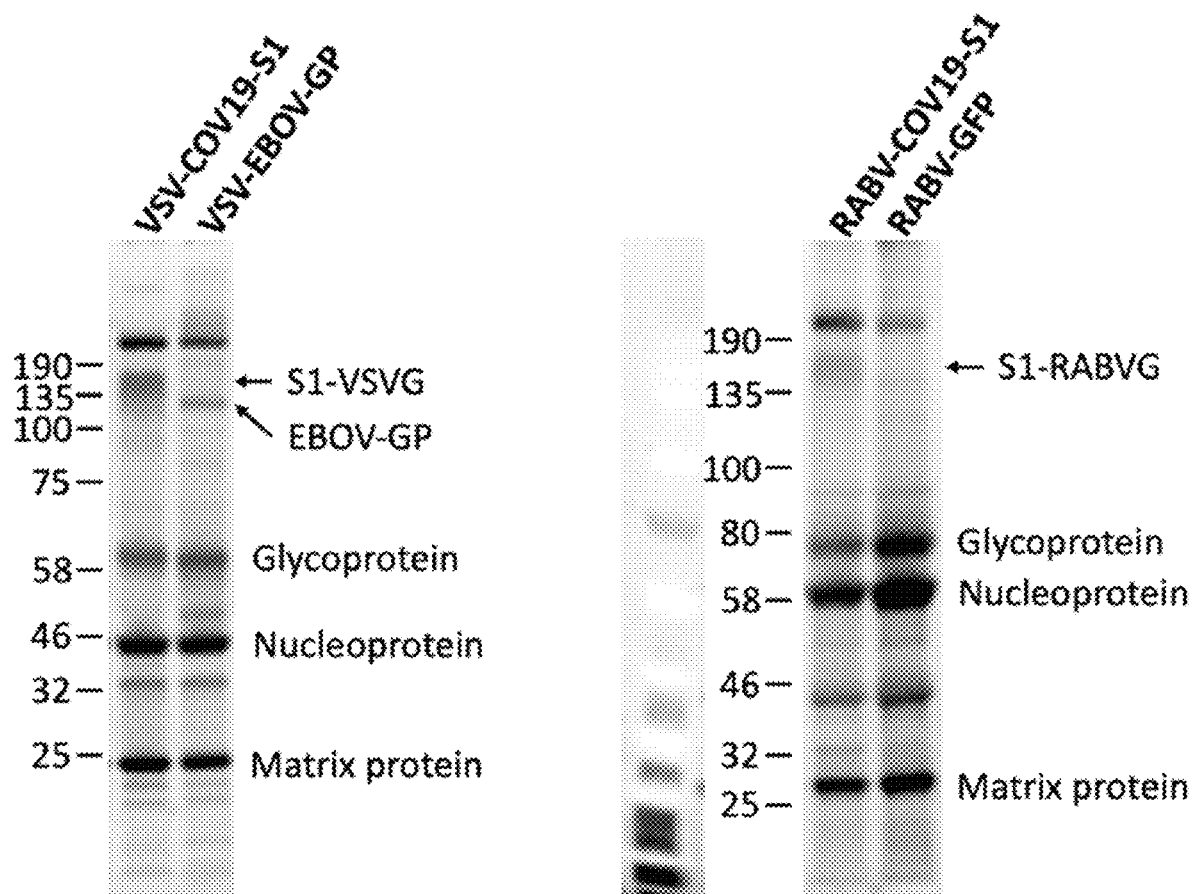
FIG. 6: Characterization of RABV (RABV-COV19-S1) and VSV (VSV-COV19-S1) expressing a chimeric S1-G fusion protein. SDS-PAGE analysis of purified virions after sucrose gradient purification. Letters indicate the positions of the VSV or RABV L, G, N, P, and M proteins. Numbers to the left indicate the sizes of the molecular mass standards. The Covid-19 S1 protein is indicated. The controls show VSV and RABV virions.

FIG. 6 shows characterization of RABV (RABV-COV19-S1) and VSV (VSV-COV19-S1) expressing a chimeric S1-G fusion protein. SDS-PAGE analysis of purified virions after sucrose gradient purification. Letters indicate the positions of the VSV or RABV L, G, N, P, and M proteins. Numbers to the left indicate the sizes of the molecular mass standards. The Covid-19 S1 protein is indicated. The controls show VSV and RABV virions.

Example 2

A Rabies Vaccine Based Bivalent Vaccine Against 2019-nCoV

Technologies developed for MERS-CoV and SARS-CoV can be transferred to the 2019-nCov. Most vaccine design has focused on the major immunodominant antigen, the Spike (S) protein located on the surface of the virion, which serves as the ligand for the MERS-CoV receptor dipeptidyl peptidase 4 (DPP4, also known as CD26) (1). Similar to MERS-CoV S 2019-nCoV S is a transmembrane glycoprotein that is likely cleaved by the furin protease into S1 and S2 domains as MERS-CoV S (2). Without intending to be bound by theory, it is believed that, as for other coronaviruses such as MERS-CoV, virus neutralizing antibodies (VNA), which are produced in response to infection or vaccination with MERS-CoV S, will neutralize virus infection in vitro and protect lungs from infection in mouse models of disease (3-6).

Described herein is a Rhabdovirus-based vaccine that offers a combination of features that could prove desirable for an effective 2019-nCoV vaccine. Rhabdovirus-vectored vaccine candidates have been developed for several human pathogens (7). More recently both RABV and VSV have been successfully utilized as Ebola virus (EBOV) vaccines and both approaches are either close to clinical trials (RABV) or have already completed phase 2 clinical trials (VSV) (8, 9). Chemically inactivated RABV vaccines are widely used and safe for humans; approximately 100 million doses of inactivated RABV vaccines are administered to humans every year, demonstrating an excellent safety profile (10). Both live and chemically inactivated RABV vaccines are shown to be safe for animals. In a proof of concept study both live-attenuated as well as inactivated RABV-EBOV have been utilized successfully against EBOV and this vaccine enters a phase 1 clinical trial in 2020. (11-14). Construction of an attenuated RABV 2019-CoV based on the well-characterized MERS-CoV vaccine (FIGS. 12 and 15)).

Figure 12:
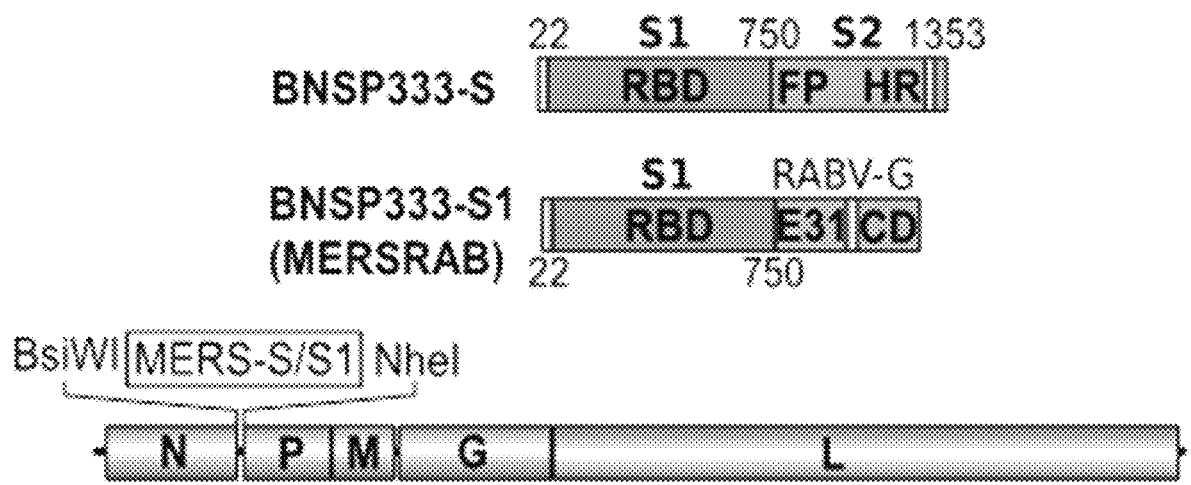
FIG. 12: Schematic illustration of the 2019-nCoV vaccine constructs used in this study. Spike protein cDNA is inserted between the N and P genes of the SAD-B19-derived RABV virus vaccine vector BNSP333. The BNSP333-S1-G construct expresses a chimeric protein that contains the entire S1 domain fused to the C-terminal part of the RABV G glycoprotein (amino acids 428-524), which encompasses the entire cytoplasmic domain (CD), the transmembrane domain (TM), plus 31 amino acids of the ectodomain (E31) of RABV G. Different structural elements of the spike protein are indicated in the full length construct: signal peptide (SP), receptor-binding domain (RBD), fusion peptide (FP), heptad repeat regions 1 and 2 (HR1 and HR2), transmembrane domain (TM), and cytoplasmic domain (CD).

The nucleotide sequence encoding 2019-nCoV S1 protein was inserted into the cBNSP333 vector (FIG. 12; FIG. 18 "BNSP333-COVID19-S1-RVG"). 2019-nCoV S is a glycoprotein anchored in the membrane of the 2019-nCoV virions that projects from the surface of the virus to act as a ligand to susceptible cells, and is therefore a major immunogen. The BNSP333 vaccine vector utilized is derived from the attenuated RABV strain SAD-B19 (16). Several modifications were introduced into the parent strain to increase safety and maximize expression of foreign genes. It was previously shown that foreign genes can be stably introduced into this vector (14, 17-20). Moreover, it was shown that expression of foreign antigens from a position between the RABV N and P gene, as well as codon optimization for human cells of the target gene, results in the highest expression level of the foreign antigen (14). Additionally, replacing the arginine with glutamic acid at position 333 (333R→333E) within the RABV glycoprotein (G) further reduces the pathogenicity of the already highly attenuated vector (19). This improved vector was successfully used to generate candidate vaccines against several emerging zoonotic viral diseases like EBOV and Henipaviruses (14, 21). However, expression of full length CoV S was found to inhibit expression of RABV G protein and reduces viral titers dramatically. However, expression of S1 fused to the C-terminal part of RABV G resulted in strong incorporation of RABV G-MERS-CoV-S1 fusion protein. The RABV G-2019-nCoV-S1 vaccine is similar to the MERS-CoV 331-S1=MERSRAB) expressing the N-terminal 750 aa of 2019-nCoV S fused to a truncated RABV glycoprotein, which comprises 31 aa of the ectodomain (ED) of RABV G and the complete CD and the transmembrane domain of RABV G to allow chimeric glycoprotein incorporation into RABV virions. The chimeric 2019-nCoV S1/RABV G protein utilizes the original 2019-CoV ER translocation sequence (SS) and is generated by PCR of codon optimized cDNA fragments (FIG. 12).

All the following results are presented from previous studies with the MERS construct (MERSRAB). For MERSRAB, infectious virus was recovered. The new virus expressing the S1 fragment grew to similar titers of roughly 108 FFU/mL as the control virus BNSP333 on Vero cells, which are approved for human vaccine production. The BNSP333 RABV expressing the S1 was entitled MERSRAB and the animal efficacy studies listed below resulted from this constructs. The RABV-based MERSRAB vaccine proved efficacious in three different animal models: mice transduced with an Ad5 virus expressing human hDPP4 (the receptor for MERS-CoV), CRISPR-CASc mice expressing human hDPP4 and Alpacas (camelid).

MERSRAB is immunogenic in mice and protects against challenge with MERS-CoV. To analyze the immunogenicity of the MERSRAB (FIG. 12 and FIG. 13), we immunized 4 groups of BALB/c mice (5 mice per group) with 10 µg of the control virus FILORAB1 (Ebola virus vaccine, group1), 10 µg of MERSRAB (groups 2 and 3), or PBS (group 4) at day 0, 7, and 21 post-inoculations. We followed the immune response against RABV G and MERS-CoV S by antigen-specific ELISAs. The antigen-specific IgG responses increased over time and after each immunization; they reached high antibody levels against both RABV G and MERS-CoV S after the third inoculations. MERS-CoV-S specific immune responses were only detected in groups 2 and 3, but RABV G specific IgG was detected in groups 1-3. None of the animals of group 4, which were mock immunized, demonstrated immune responses against RABV G or MERS-CoV S protein, confirming the specificity of the ELISAs assays. Whereas the RABV G-specific ELISA titers are known to predict protection against RABV challenge (22-24), the protective abilities of the MERS-CoV S-directed antibodies are unknown. Therefore VNA was performed against MERS-CoV of sera on day 35 of the immunized mice of all four groups. Low levels of MERS-CoV neutralizing antibodies were detected in the sera of mice from group 1 (FILORAB1) or mock (PBS) immunized mice (group 4), but the sera of mice immunized with MERSRAB (group 2 and 3) neutralized MERS-CoV at serum dilutions between 1:1280 and 1:5120. This demonstrates a high level of anti-MERS-CoV neutralizing antibody produced in the BNSP333-S1 vaccinated mice.

Figure 13:
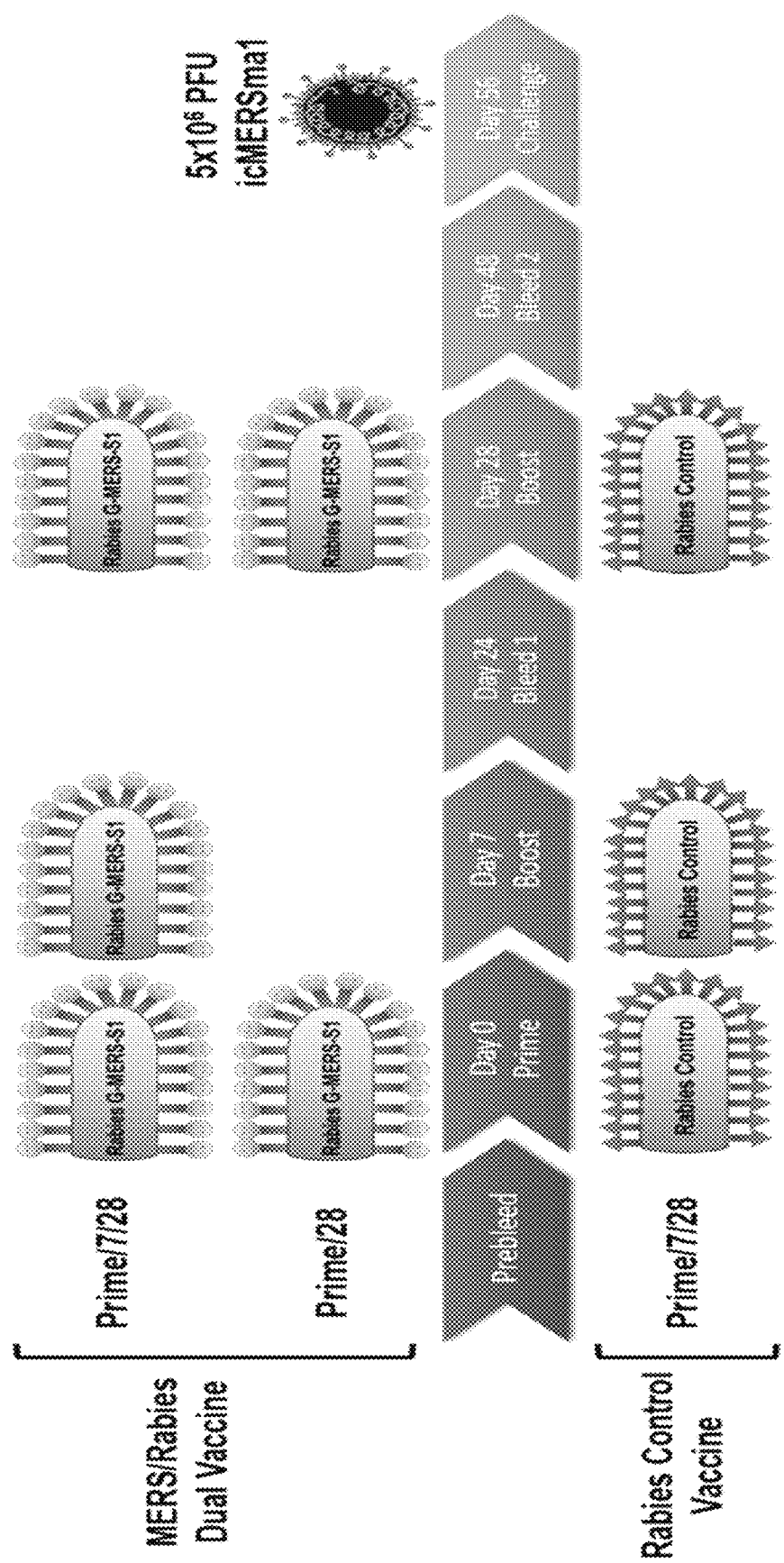
FIG. 13: Schematic illustration of the MERSRAB immunization schedule and challenge with MERS-CoV. Two and three immunization were analyzed with the deactivated vaccine.

Efficacy testing of the RABV-MERS vaccine was performed using the adenovirus-hDPP4 transduced mouse model (25). All four groups of mice were transduced, and after five days, mice in groups 1, 2, and 4 were challenged intranasally (IN) with MERS-CoV at $1\times10^5$ pfu/mouse (strain Jordan-n3/2012). Four days after the challenge, the mice were euthanized, and their lungs were dissected, homogenized, and assayed for viral load by qRT-PCR and a viral plaque assay. For BNSP333-S1 immunized mice, both genomic and mRNA were reduced to background levels similar to those found in mice not transduced by the Ad5-expressing hDPP4. Moreover, the immunization with BNSP333-S1 reduced the viral load in the lungs to a level below detection of the assay. In the next step the RABV based vaccine MERSRAB was tested in the CRISPR-CAS generated transgenic mouse model (mice expressing human hDPP4). Transgenic mice in groups of 10 mice were immunized with 10 µg of the control virus FILORAB (Empty vector, group Rabies control vaccine), 10 µg of MERSRAB (MERS/Rabies dual vaccine), at day 0, 7, and 28 or only at day 0 and 28 (FIG. 13). The immune response against RABV G and MERS-CoV S was followed by antigen-specific ELISAs. The antigen-specific IgG responses increased over time and after each immunization; they reached high antibody levels against both RABV G and MERS-CoV S after the second or third immunization. MERS-CoV-S specific immune responses were only detected in groups 1 and 2 (MERS-Rabies), but RABV G specific IgG was detected in all three groups.

Whereas the RABV G-specific ELISA titers are known to predict protection against RABV challenge (22-24), the protective abilities of the MERS-CoV S-directed antibodies are not well characterized. The transgenic mice were therefore challenged with pathogenic MERS-CoV at day 56. As shown in FIG. 14A all immunized mice survived the infection whereas 40% of the mock immunized animals succumbed to the infection. As shown all mice, which received one or two inoculation with the MERSRAB were protected from weight-loss completely. Moreover, immunization did reduce viral loads to undetectable levels (FIGS. 14A-14C) whereas the MERS-CoV replicated to very high levels in empty vector immunized animals (FIG. 14C). This can also be seen in FIG. 15. Two or three inoculations with MERSRAB protect animals from viral replication in the lung and MERS-CoV antigen in lungs of immunized mice is detected at day three after challenge, no antigen is detected at day six. In contrast, the lung tissue of animal immunized with the vector only, large amount of tissue damage and viral antigen can be detected at both time points consistent with the viral load shown in FIGS. 14A-14C.

Figure 15:
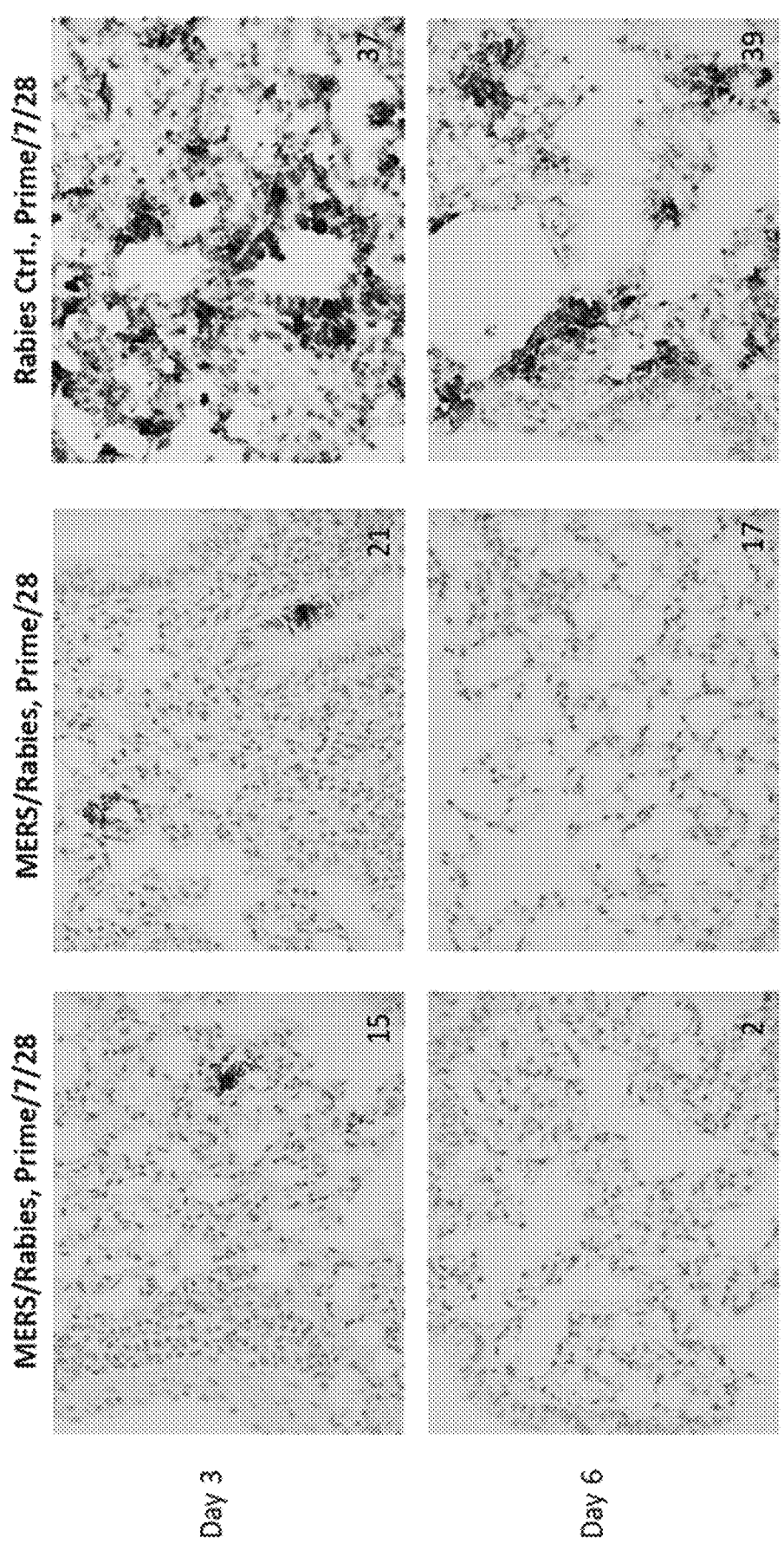
FIG. 15: Two or three inoculation with MERSRAB protect animals from viral replication in the lung. The figure shows that only small amounts of MERS-CoV antigen is detected in lungs of immunized mice at day three after challenge, and no antigen is detected at day six. In contrast, in the lung tissue of animal immunized with the rabies virus vector only large amount of tissue damage and viral antigen can be detected at both time points consistent with the viral load shown in FIG. 14.
Figure 16A:
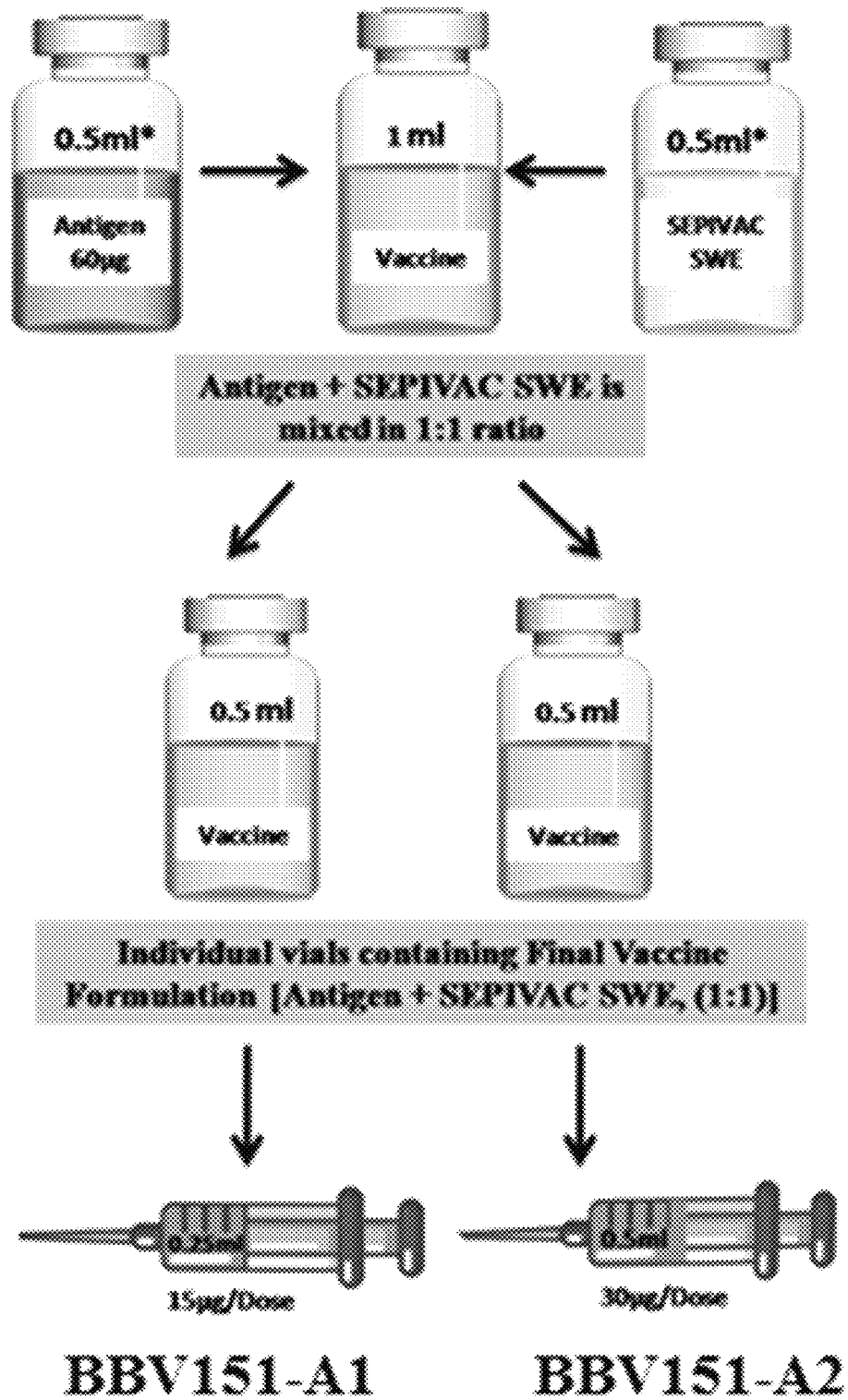

Lastly, to determine the potential of preventing transmission from host species to humans, the next study tested if the MERSRAB vaccine was efficacious in Camelids. In brief, a group of five Alpacas were immunized with 107 foci forming units (ffu) of live MERSRAB i.m., or intranasally or immunized i.m. with 100 µg or 300 µg of the inactivated MERSRAB vaccine. After 56 days the animals were challenged with MERS-CoV intranasally and nasal swabs were taken over time to analyse viral shedding. No disease was detected after immunization with either the live or the killed MERSRAB vaccine. As shown in FIG. 15, two inoculations with 100 or 300 µg resulted in almost complete suppression of viral shedding from the infected animals.

Inactivated RABV has a 30-year long history as an efficient and safe vaccine. Taken together, the results presented above clearly indicate that a vaccine based on deactivated RABV particles is a strong candidate against 2019-nCoV infection.

Furthermore, the use of an adjuvant might allow clinical benefit after just one vaccination. Appropriate adjuvant selection is likely be critical to design of a safe and effective nCoV vaccine. Notably, vaccine-enhanced eosinophilic lung disease was seen to be exacerbated when SARS vaccines were formulated with aluminium salt adjuvants whereas it was completely prevented when the same SARS vaccines were formulated with Advax-SM adjuvant, which is a formulation of polysaccharide particles combined with a potent TLR9 agonist. The addition of Advax to a broad range of vaccines results in significant benefits including enhanced protection associated with higher antibody titers, increased B cell receptor affinity maturation, IgG subtype diversification, enhanced memory CD4 and CD8 T cell responses and antigen dose sparing. Advax adjuvant have been shown to provide protective immunity with a single dose in neonatal pups. A particular advantage of Advax adjuvants is that they have already been shown to be safe and well tolerated in human clinical trials in combination with many different antigens thereby facilitating rapid translation of successful vaccines from preclinical studies to human trials.

Adjuvants increase the immunity of vaccines and can also change the antibody isotype. It was previously shown for a rabies virus platform that the addition of MPLA in squalene (PHAD®) increased both the total humoral responses as well as the Th1/TH2 bias. For most viral vaccines, it has been shown that a TH1-bias is beneficial. It has been demonstrated a TH1 bias is necessary for robust protection against EBOV by the FILORAB1 vaccine. For the 2019-nCoV vaccine, the MPLA 3D(6-acyl)PHAD® in 2% Squalene can be used as well as an adjuvant with the potential to increase immunity and induce TH1 responses (e.g., CpG-Oligodeoxynucleotide).

Example 3

Preclinical Studies

The following describes preclinical studies to test the 2019-nCoV vaccine:

1) Most critical is the ability to test efficacy in animal models (small animal and NHP), which will be performed in parallel to the proposed Phase 1 clinical trial to evaluate safety and immunogenicity and potential adverse effects such as enhancement of infection after vaccination. Because 2019-nCoV and the SARS-CoV seem to utilize the same receptor the human ACE2 transgenic mice may be a suitable model for 2019-nCoV, however evaluation of this model has not been characterized and experiments to confirm the model are in the planning stages. NHP animal modelling is expected to start in mid-March 2020. Cynomolgus monkeys, African Green monkeys, common marmosets, and rhesus monkeys will be evaluated for disease development following intratracheal, small-particle aerosol, or large-particle aerosol. The IRF-Frederick has experience with MERS, ebola virus, nipah virus and cowpox aerosol models. The unique positron emission tomography with computed tomography (PET/CT will be incorporated into the animal model to measure disease progression since the nonhuman primate model is expected to be sublethal. CT has been used previously to demonstrate vaccine efficacy and to complement small molecule countermeasure efficacy tests (www.ncbi.nlm.nih.gov/pubmed/26218507 and www.ncbi.nlm.nih.gov/pmc/articles/PMC5640857/).

CT has also been used to evaluated a MERS monoclonal antibody in the rhesus monkey model of MERS and to evaluate disease progression in the common marmoset model of MERS (www.ncbi.nlm.nih.gov/pubmed/26828465 and www.ncbi.nlm.nih.gov/pubmed/26342468)

2) Characterization of the 2019-nCoV vaccine by biochemical and virological assay at TJU 3) Recovery of the vaccine at BBIL under GLP 4) Establish VNA against the 2019-nCoV strain. Establish pseudotype VNA assay for BSL2

5) ELISA for 2019-nCoV S—similar to the previously developed ELISA for MERS-CoV S.

6) Formulation of the vaccine and adjuvant.

Example 4

Clinical Studies

The following describes clinical studies to test the 2019-nCoV vaccine:

Based on the information from preclinical studies, efficacy in animal models will be performed in parallel to the proposed Phase 1 clinical trial to evaluate safety and immunogenicity in human subjects. Of note, our previous discussion (pre-IND) with the FDA for a similar killed rabies-virus based vaccine against EBOV was agreed not to require a toxicity study based on the safety history of deactivated rabies vaccines applied to more than 100 million people. The phase 1 study, if successful, would be followed by a Phase 2 clinical trial to increase the upper end of the age spectrum (since older persons have most severe 2019 nCoV disease) and to expand the cohort size to obtain statistically valid data related to the immune response.

Target populations: Healthy U.S. adults 18 through 55 years of age, inclusive.

Clinical Trial Design: Phase 1 Clinical Trial.

The Phase 1 trial is a randomized, observer-blinded, dose-escalation study to evaluate the safety, reactogenicity, and immunogenicity of the inactivated rabies virus (RABV) based 2019-nCoV vaccine candidates (RABV-nCoV). The clinical trial will be performed at a single site at the University of Maryland, Baltimore, in healthy adults 18 through 55 years of age. Enrolment will proceed in a staged fashion. We will being with 8 subjects in cohort 1. If no pausing rules are met by day 8 following the first dose of vaccine, then cohort 2 can begin immediately after full enrolment of Cohort 1, with no pausing. Cohorts 3 and 4 will proceed simultaneously after review of day 8 data in cohort 2 (assuming no halting rules are met. Importantly, we will include a single dose arm with adjuvant that will commence simultaneously with the 100 ug group (so groups 3 and 4 will be enrolled together after safety data available from all of group 2 through day 8). The study consists of four cohorts totaling 64 subjects (2 rabies vaccine controls and 14 investigational vaccines in each cohort). All study injections will be administered by the intramuscular (IM) route. Treatment assignments are outlined in Table 1.

TABLE 1

Treatment Assignment for the Phase I Ranging Safety Study of the nCoVRAB Vaccine

| Cohort | Sample size | Vaccine | Dose | Timing |
|---|---|---|---|---|
| 1 | 14 | nCoVRAB | 25 μg | Days 0 and 28 |
| 2 | 14 | nCoVRAB | 50 μg | Days 0 and 28 |
| 3 | 14 | nCoVRAB | 100 μg | Days 0 and 28 |
| 4 | 14 | nCoVRAB and adjuvant AdVax ® | 50 μg | Days 0 - single dose |
| Control | 8 (2 in each cohort above) | RabAvert © (Rabies Vaccine) | — | Days 0 and 28 (According to label) |

Primary Objective: To assess the safety and tolerability of a 2-dose schedule of the unadjuvanted nCoVRAB and a 1-dose schedule of the adjuvanted vaccine candidates delivered IM at 0 and 28 days.

Secondary Objective: To evaluate the immunogenicity of the nCoVRAB vaccine candidates delivered IM at 0 and 28 days (or day 0 for adjuvanted) at escalating dose levels at Days 0, 28, 56, 120 (with primary measure at day 56 for unadjuvanted and day 28 for adjuvanted).

Primary Endpoints: The number and percentage of study participants who experience any study injection-associated adverse events, solicited systemic events, or serious adverse events at the following time points:

- Solicited events for 7 days after each study injection.
- Unsolicited events through 28 days after the last study injection (Day 56).
- Serious adverse events (SAEs) for 56 days and at Days 56 and 120 and 365 per a scripted interview.
- Number of participants with early discontinuation of study injections and reason for discontinuation.

Secondary Endpoints: Immunogenicity as measured by ELISA to 2019-nCoV and rabies GP.

- nCoV S1- and nCoV S1 and RABV G specific serum IgG ELISA titers per time point through Day 120: geometric mean antibody titers (GMT) and percentage of subjects seroconverting (4-fold rise over baseline).
- nCoV and rabies neutralizing antibody titers through Day 120: GMT and percentage of subjects seroconverting (4-fold rise over baseline); for rabies, percentage of subjects with titers >0.5 IU/ml (correlate of protection).

Exploratory (future studies)

- Antigen-specific serum IgM, IgA and IgG subclasses (selected time-points).
- T cell responses (Th1, Th2 and Th17 cytokines and chemokines post vaccination).
- B cell responses (magnitude of antigen-specific plasmablasts and memory B cells post vaccination).
- IgG avidity.

Phase 2 Clinical Trial

This clinical trial is proposed as a Phase 2, randomized, observer-blinded, single antigen level study to evaluate the safety and immunogenicity of a two Dose Rabies-Vectored nCoVRAB Vaccine (or a one dose adjuvanted regimen). Given the demographics of the current NCoV outbreak, we will expand the upper age to 70 years. Volunteers will be assessed before the injection and days 1, 3, 7, 14, and 28 after the vaccine for safety, reactogenicity, and immunogenicity. The clinical trial will be performed in healthy adults meeting all inclusion criteria and no exclusion criteria at 2 sites in the US—Baltimore, Md. and one additional site. total of 200 adults will be consecutively enrolled into groups, stratified by age. All study injections will be administered by the intramuscular (IM) route. Treatment assignments are outlined in Table 2 below.

TABLE 2

Treatment Assignment for the First Dose Ranging Safety Study of the nCoVRAB Vaccine*

| Group | Number of Participants | Study Injections | Antigen Dose* | Dosing Schedule |
|---|---|---|---|---|
| 1 | 180 | nCoVRAB, Liquid | x μg determined in phase 1) | Days 0 and 28 Or one inoculation |
| 2 | 20 | RabAvert | TBD | Days 0 and 28 |

*The overall antigen dose, the relative concentration of the antigen component used for this study will depend upon the outcome of the Phase 1 clinical trial.

Primary Objective: To assess the safety and tolerability of a leading nCoVRAB vaccine candidates delivered IM at 0 and 28 days.

Secondary Objective: To evaluate the immunogenicity of the nCoVRAB vaccine candidates delivered IM at 0 and 28 Days 7, 14, 28, 35, 42, 56, 90, 120, 180, and 365.

Primary Endpoints: The number and percentage of study participants who experience any study injection-associated adverse events or serious adverse events at the following time point:

Solicited events for 7 days after each study injection.

Unsolicited events through 28 days after the last study injection (Day 56).

Serious adverse events (SAEs) for 56 days and at Days 56 and 120 and 365 per a scripted interview.

Number of participants with early discontinuation of study injections and reason for discontinuation.

Secondary Endpoints/Exploratory endpoints see above (Phase 1 Clinical Trial.)

Example 5

Manufacturing

In the setting of the public health emergency of 2019 Novel Coronavirus (2019-nCoV or SARS-CoV-2), considerations for the development of a 2019-nCoV vaccine must balance manufacturing speed and technical feasibility with clinical safety and immunogenicity considerations. Ultimately, the manufacturing must be scalable, and the delivery simple in order to reach the maximum number of people in the shortest period of time. A collaborator, Bharat Biotech Ltd (BBIL) is a large vaccine manufacturer with the ability to scale production of such a vaccine to millions of doses rapidly. Relying on an existing technology to maximize feasibility and speed of development is the best approach to achieving this goal.

BBIL experience in positioning licensed vaccines for International supplies is summarized in the table below.

Experience in Manufacture and Scale-Up/Infrastructures and Facilities

BBIL has several facilities for the manufacturing of Viral, Bacterial and recombinant Drug Substance. BBIL is the largest viral vaccine manufacturer in India. For the manufacturing of viral vaccines, it possesses expertise in the utilization of Vero, MDCK cell lines and platforms like Cell factories, Micro carriers and fermenters. There are 5 viral bulk manufacturing facilities including a pilot plant, these facilities have capabilities ranging from 50 L to 1000 L fermentation and purification by TFF, Gel permeation and Affinity chromatography. These automated facilities can produce up to 500 million doses of vaccines.

BBIL also has capabilities of manufacturing recombinant and bacterial drug substances and these are manufactured in 6 facilities including one pilot plant, BBIL expertise ranges from usage of recombinant E. coli, Yeast, Toxins producing bacteria such as, Diphtheria, tetanus and Whole cell bacteria viz pertussis and Cholera. These organisms are processed from 50 L to 1500 L fermenters and subsequent purifications are carried out using either Ion Exchange, Gel permeation chromatography's.

For Drug Product, all bulk product is either filled in vials, PFS or BFS ranging from 0.5 ML to 25 ml capacities in filling machine having capacity from 50-300 vials per min. Keeping in view, of the various products manufactured and also the products to be manufactured in future, BBIL has a Developmental QC Lab, which in involved in the development and validation of different assays and a Strong QC department for routine batch testing and release of all vaccines and biotherapeutics.

Manufacturing capacity: Approximately, 500 million doses of vaccines and 4 million units of Bio-therapeutics are manufactured per year. About 20-30% of the vaccines are supplied to GAVI countries.

With a strong QC department, BBIL manufacture, test and release following vaccines and biotherapeutics. Apart from the facilities available at BBIL, in case of Emergency situation, higher manufacturing capacities of 5,000 L, at BSL3/Ag+ facility is available at BIOVET, Bengaluru.

Example 6

CORAVAX (rDNA-BBV151)

To evaluate the reactogenicity and safety of BBV151 (inactivated rabies vector platform Corona Virus) vaccine administered via the intramuscular route, a dose escalation study of an intramuscular inactivated rabies vector platform Corona Virus Vaccine (rDNA-BBV151) in healthy volunteers will be performed.

CORAVAX (rDNA-BBV151) is an adjuvanted rabies vectored Corona virus vaccine, that express the S1 domain of the SARSCoV-2 spike (S) protein fused to part of the N terminal domain of the RABV glycoprotein (G) and is incorporated in RABV particles. CORAVAX (rDNA-BBV151) vaccine has two presentations.

TABLE 1

| Coronavirus Vaccine (rDNA) - BBVI51 composition | | |
|---|---|---|
| Dosage form: | Liquid (Injection for Intramuscular route) | |
| Composition: | Each dose of 0.5 ml contains | |
| I | Active ingredient | Quantity |
| | Coronavirus Vaccine (rDNA) BBVI51 | NLT 15 (or) 30 mcg |
| | Inactive ingredients | |
| | 2-Phenoxyethanol (2-PE) - I.P. | 2.5 mg |
| | Phosphate Buffered Saline | Qs to 0.25 mL |
| II | Adjuvant | |
| | SEPIVAC SWE - Oil in water (O/W) emulsion* | 0.25 ml |

PRESENTATION 1 (BBV151-A)—Ingredients I and II will be provided as two separate vials (each 0.5 mL) and these two vials (A and B) will be mixed at the time of administration. The final reconstituted 1.0 mL volume is equivalent to 2 doses. BBV151-A presentation has two vaccine formulations with a variation in the dosage strength of active ingredient (Figure XA):
BBV151-A1: BBV151-A1 formulation has 15 mcg of the active ingredient.
BBV151-A2: BBV151-A2 formulation has 30 mcg of the active ingredient.
PRESENTATION 2 (BBV151-B): Ingredients I and II will be mixed together, before itself and will be provided as a single vial (0.5 mL dose volume). BBV151-B presentation has only one formulation (Figure XB):
BBV151-B: BBV151-B formulation has 30 mcg of the active ingredient.

The study is designed to evaluate the safety, reactogenicity, and immunogenicity of four groups of healthy volunteers who receive either vaccine or placebo.
Group 1 (BBV151-A1): In this group, 15 participants will be recruited and administered with BBV151-A1 vaccine formulation on day 0 and day 28 via intramuscular route.
Group 2 (BBV151-A2): In this group, 15 participants will be recruited and administered with BBV151-A2 vaccine formulation on day 0 and day 28 via intramuscular route.
Group 3 (BBV151-B): In this group, 15 participants will be recruited and administered with BBV151-B vaccine formulation on day 0 via intramuscular route.

Data will be un-blinded to the third-party bio-statistician and an interim analysis will be performed at day 42 for Immunogenicity and Safety. nAb titer of the COVID-19 virus will be assessed by the MNT/PRNT assay and evaluate the immunogenicity in terms of GMT of vaccine comparison with the placebo group. Serum samples will be assessed for nAb. Binding antibody titer against spike protein of SARS-CoV-2 virus will be assessed for serum samples by using ELISA. Cell Mediated Immunity will be assessed from the subset of the study population.

The GMT will be calculated for neutralization titers in each vaccine group (one dose and two doses) separately. A two-sided 95% confidence interval (CI) for the GMT will be calculated from a 95% CI for the mean of $\log_{10}$-transformed titer, using a normal approximation for the distribution of $\log_{10}$ (titer). The ratio of GMTs in the two vaccine groups (GMT with two doses/GMT with one dose) and the corresponding 95% CI will also be presented. The two-sided 95% CI for the GMT ratio will be calculated from a 95% CI for the difference in means of $\log_{10}$ (titer). The two vaccine groups will be compared using a two-sided two-sample t-test on the means of $\log_0$-transformed titers, at the 5% significance level.

To evaluate the humoral immune responses of BBV151, GMT and four-fold seroconversion rate (SCR) of neutralizing antibodies (NAb's) by MNT/PRNT assays across the three groups, from baseline to days 28±2, 42±2, 90±7 and 180±7, will be performed.

To compare the humoral responses between single dose group and double dose group, GMT and four-fold seroconversion rate (SCR) of neutralizing antibodies (NAb's) by MNT/PRNT assays across the three groups, from baseline to days 28+2, 42±2, 90±7 and 180±7.

To evaluate the immune responses against spike protein of SARS-CoV-2 virus and Rabies vector, GMT and four-fold seroconversion rate of binding antibodies (bAb's) IgA and IgG against spike protein across the three groups, from baseline to days 28+2, 42±2, 90±7 and 180±7, will be determined. Immune response (binding/or neutralization) to the vector will be assessed by ELISA from baseline to days 28+2, 42±2, 90±7 and 180±7.

To evaluate the safety of the vaccine in terms of assessing adverse event of special interest (AESI), the occurrence of AESI will be monitored and documented throughout the study duration.

REFERENCES

1. Raj V S, Mou H, Smits S L, Dekkers D H, Muller M A, Dijkman R, Muth D, Demmers J A, Zaki A, Fouchier R A, Thiel V, Drosten C, Rottier P J, Osterhaus A D, Bosch B J, Haagmans B L. Dipeptidyl peptidase 4 is a functional receptor for the emerging human coronavirus-EMC. Nature. 2013; 495(7440):251-4. doi: 10.1038/nature12005. PubMed PMID: 23486063
2. Burkard C, Verheije M H, Wicht O, van Kasteren S I, van Kuppeveld F J, Haagmans B L, Pelkmans L, Rottier P J, Bosch B J, de Haan C A. Coronavirus cell entry occurs through the endo-/lysosomal pathway in a proteolysis-dependent manner. PLoS pathogens. 2014; 10(11): e1004502. doi: 10.1371/journal.ppat.1004502. PubMed PMID: 25375324; PMCID: PMC422306
3. Volz A, Kupke A, Song F, Jany S, Fux R, Shams-Eldin H, Schmidt J, Becker C, Eickmann M, Becker S, Sutter G. Protective Efficacy of Recombinant Modified Vaccinia Virus Ankara Delivering Middle East Respiratory Syndrome Coronavirus Spike Glycoprotein. J Virol. 2015; 89(16):8651-6. doi: 10.1128/JVI.00614-15. PubMed PMID: 26018172; PMCID: PMC4524222
4. Ma C, Wang L, Tao X, Zhang N, Yang Y, Tseng C T, Li F, Zhou Y, Jiang S, Du L. Searching for an ideal vaccine candidate among different MERS coronavirus receptor-binding fragments—the importance of immunofocusing in subunit vaccine design. Vaccine. 2014; 32(46):6170-6. doi: 10.1016/j.vaccine.2014.08.086. PubMed PMID: 25240756; PMCID: PMC4194190
5. Hudacek A W, Al-Saleem F H, Willet M, Eisemann T, Mattis J A, Simpson L L, Schnell M J. Recombinant rabies virus particles presenting botulinum neurotoxin antigens elicit a protective humoral response in vivo. Molecular therapy Methods & clinical development. 2014; 1:14046. doi: 10.1038/mtm.2014.46. PubMed PMID: 26015984; PMCID: 4362357
6. Muthumani K, Falzarano D, Reuschel E L, Tingey C, Flingai S, Villarreal D O, Wise M, Patel A, Izmirly A, Aljuaid A, Seliga A M, Soule G, Morrow M, Kraynyak K A, Khan A S, Scott D P, Feldmann F, LaCasse R, Meade-White K, Okumura A, Ugen K E, Sardesai N Y, Kim J J, Kobinger G, Feldmann H, Weiner D B. A synthetic consensus anti-spike protein DNA vaccine induces protective immunity against Middle East respiratory syndrome coronavirus in nonhuman primates. Sci Transl Med. 2015; 7(301):301ra132. doi: 10.1126/scitranslmed.aac7462. PubMed PMID: 26290414; PMCID: PMC4573558
7. Pfaller C K, Cattaneo R, Schnell M J. Reverse genetics of Mononegavirales: How they work, new vaccines, and new cancer therapeutics. Virology. 2015; 479-480:331-44. doi: 10.1016/j.virol.2015.01.029. PubMed PMID: 25702088; PMCID: 4557643
8. Willet M, Kurup D, Papaneri A, Wirblich C, Hooper J W, Kwilas S A, Keshwara R, Hudacek A, Beilfuss S, Rudolph G, Pommerening E, Vos A, Neubert A, Jahrling P, Blaney J E, Johnson R F, Schnell M J. Preclinical Development of Inactivated Rabies Virus-Based Polyvalent Vaccine Against Rabies and Filoviruses. J Infect Dis. 2015; 212 Suppl 2:S414-24. doi: 10.1093/infdis/jiv251. PubMed PMID: 26063224; PMCID: 4564550
9. Huttner A, Dayer J A, Yerly S, Combescure C, Auderset F, Desmeules J, Eickmann M, Finckh A, Goncalves A R, Hooper J W, Kaya G, Krahling V, Kwilas S, Lemaitre B, Matthey A, Silvera P, Becker S, Fast P E, Moorthy V, Kieny M P, Kaiser L, Siegrist C A, Consortium V S-E. The effect of dose on the safety and immunogenicity of the VSV Ebola candidate vaccine: a randomised double-blind, placebo-controlled phase 1/2 trial. Lancet Infect Dis. 2015; 15(10):1156-66. doi: 10.1016/S1473-3099(15) 00154-1. PubMed PMID: 26248510
10. WHO. Rabies, Fact Sheet #99. 2015.
11. Blaney J E, Marzi A, Willet M, Papaneri A B, Wirblich C, Feldmann F, Holbrook M, Jahrling P, Feldmann H, Schnell M J. Antibody quality and protection from lethal Ebola virus challenge in nonhuman primates immunized with rabies virus based bivalent vaccine. PLoS pathogens. 2013; 9(5):e1003389. doi: 10.1371/journal.ppat.1003389. PubMed PMID: 23737747; PMCID: 3667758.
12. Blaney J E, Wirblich C, Papaneri A B, Johnson R F, Myers C J, Juelich T L, Holbrook M R, Freiberg A N, Bernbaum J G, Jahrling P B, Paragas J, Schnell M J. Inactivated or live-attenuated bivalent vaccines that confer protection against rabies and Ebola viruses. J Virol. 2011; 85(20):10605-16. Epub 2011/08/19. doi: 10.1128/ JVI.00558-11. PubMed PMID: 21849459; PMCID: 3187516.
13. Blaney J E, Wirblich C, Papaneri A B, Johnson R F, Myers C J, Juelich T L, Holbrook M R, Freiberg A N, Bernbaum J G, Jahrling P B, Paragas J, Schnell M J. Inactivated or live-attenuated bivalent vaccines that confer protection against rabies and Ebola viruses. J Virol. 2011; 85(20):10605-16. Epub 2011/08/19. doi: 10.1128/ JVI.00558-11. PubMed PMID: 21849459; PMCID: 3187516.
14. Willet M, Kurup D, Papaneri A, Wirblich C, Hooper J W, Kwilas S A, Keshwara R, Hudacek A, Beilfuss S, Rudolph G, Pommerening E, Vos A, Neubert A, Jahrling P, Blaney J E, Johnson R F, Schnell M J. Preclinical Development of Inactivated Rabies Virus-Based Polyvalent Vaccine Against Rabies and Filoviruses. J Infect Dis. 2015. doi: 10.1093/infdis/jiv251. PubMed PMID: 26063224
15. Wirblich C, Coleman C M, Kurup D, Abraham T S, Bernbaum J G, Jahrling P B, Hensley L E, Johnson R F, Frieman M B, Schnell M J. One-Health: a Safe, Efficient, Dual-Use Vaccine for Humans and Animals against Middle East Respiratory Syndrome Coronavirus and Rabies Virus. Journal of virology. 2017; 91(2). Epub 2016/11/04. doi: 10.1128/JVI.02040-16. PubMed PMID: 27807241; PMCID: PMC5215356
16. Conzelmann K K, Cox J H, Schneider L G, Thiel H J. Molecular cloning and complete nucleotide sequence of the attenuated rabies virus SAD B19. Virology. 1990; 175(2):485-99. PubMed PMID: 2139267
17. Kurup D, Wirblich C, Feldmann H, Marzi A, Schnell M J. Rhabdoviral-Based Vaccine Platforms against Henipaviruses. J Virol. 2014. doi: 10.1128/JVI.02308-14. PubMed PMID: 25320306
18. Hudacek A W, Al-Saleem F H, Willet M, Eisemann T, Mattis J A, Simpson L L, Schnell M J. Recombinant rabies virus particles presenting botulinum neurotoxin antigens elicit a protective humoral response in vivo. Molecular Therapy—Methods & Clinical Development. 2014; 1
19. McGettigan J P, Pomerantz R J, Siler C A, McKenna P M, Foley H D, Dietzschold B, Schnell M J. Second-generation rabies virus-based vaccine vectors expressing human immunodeficiency virus type 1 gag have greatly reduced pathogenicity but are highly immunogenic. J Virol. 2003; 77(1):237-44. Epub 2002/12/13. PubMed PMID: 12477829; PMCID: 140592.
20. McGettigan J P, Naper K, Orenstein J, Koser M, McKenna P M, Schnell M J. Functional human immunodeficiency virus type 1 (HIV-1) Gag-Pol or HIV-1 Gag-Pol and env expressed from a single rhabdovirus-based vaccine vector genome. J Virol. 2003; 77(20):10889-99. Epub 2003/09/27. PubMed PMID: 14512539; PMCID: 224996
21. Kurup D, Wirblich C, Feldmann H, Marzi A, Schnell M J. Rhabdovirus-based vaccine platforms against henipaviruses. J Virol. 2015; 89(1):144-54. doi: 10.1128/JVI.02308-14. PubMed PMID: 25320306; PMCID: 4301098
22. Servat A, Feyssaguet M, Blanchard I, Morize J L, Schereffer J L, Boue F, Cliquet F. A quantitative indirect ELISA to monitor the effectiveness of rabies vaccination in domestic and wild carnivores. J Immunol Methods. 2007; 318(1-2):1-10. doi: 10.1016/j.jim.2006.07.026. PubMed PMID: 17166510
23. Wasniewski M, Cliquet F. Evaluation of ELISA for detection of rabies antibodies in domestic carnivores. J Virol Methods. 2012; 179(1):166-75. doi: 10.1016/j.jviromet.2011.10.019. PubMed PMID: 22080853
24. Wasniewski M, Guiot A L, Schereffer J L, Tribout L, Mahar K, Cliquet F. Evaluation of an ELISA to detect rabies antibodies in orally vaccinated foxes and raccoon dogs sampled in the field. J Virol Methods. 2013; 187(2): 264-70. doi: 10.1016/j.jviromet.2012.11.022. PubMed PMID: 23201293
25. Zhao J, Li K, Wohlford-Lenane C, Agnihothram S S, Fett C, Gale M J, Jr., Baric R S, Enjuanes L, Gallagher T, McCray P B, Jr., Perlman S. Rapid generation of a mouse model for Middle East respiratory syndrome. Proc Natl Acad Sci USA. 2014; 111(13):4970-5. Epub 2014/03/07. doi: 10.1073/pnas.1323279111. PubMed PMID: 24599590; PMCID: 3977243
26. Blaney J E, Wirblich C, Papaneri A B, Johnson R F, Myers C J, Juelich T L, Holbrook M R, Freiberg A N, Bernbaum J G, Jahrling P B, Paragas J, Schnell M J. Inactivated or Live-Attenuated Bivalent Vaccines that Confer Protection against Rabies and Ebola Viruses. PLoS Pathog, under review. 2011
27. Johnson R F, Kurup D, Hagen K R, Fisher C, Keshwara R, Papaneri A, Perry D L, Cooper K, Jahrling P B, Wang J T, Ter Meulen J, Wirblich C, Schnell M J. An Inactivated Rabies Virus-Based Ebola Vaccine, FILORAB1, Adjuvanted With Glucopyranosyl Lipid A in Stable Emulsion Confers Complete Protection in Nonhuman Primate Challenge Models. The Journal of infectious diseases. 2016; 214(suppl 3):S342-S54. doi: 10.1093/infdis/jiw231. PubMed PMID: 27456709; PMCID: PMC5050469
28. Papaneri A B, Wirblich C, Marissen W E, Schnell M J. Alanine scanning of the rabies virus glycoprotein antigenic site III using recombinant rabies virus: implication for post-exposure treatment. Vaccine. 2013; 31(49):5897-902. Epub 2013/10/15. doi: 10.1016/j.vaccine.2013.09.038. PubMed PMID: 24120673
29. Bhandari N, Rongsen-Chandola T, Bavdekar A, John J, Antony K, Taneja S, Goyal N, Kawade A, Kang G, Rathore S S, Juvekar S, Muliyil J, Arya A, Shaikh H, Abraham V, Vrati S, Proschan M, Kohberger R, Thiry G, Glass R, Greenberg H B, Curlin G, Mohan K, Harshavardhan G V J A, Prasad S, Rao T S, Boslego J, Bhan M K, Group IRV. Efficacy of a monovalent human-bovine (116E) rotavirus vaccine in Indian children in the second year of life. Vaccine. 2014; 32 Suppl 1:A110-6. doi: 10.1016/j.vaccine.2014.04.079. PubMed PMID: 25091663; PMCID: 25091663
30. Bhandari N, Rongsen-Chandola T, Bavdekar A, John J, Antony K, Taneja S, Goyal N, Kawade A, Kang G, Rathore S S, Juvekar S, Muliyil J, Arya A, Shaikh H, Abraham V, Vrati S, Proschan M, Kohberger R, Thiry G, Glass R, Greenberg H B, Curlin G, Mohan K, Harshavardhan G V, Prasad S, Rao T S, Boslego J, Bhan M K. Efficacy of a monovalent human-bovine (116E) rotavirus vaccine in Indian infants: a randomised, double-blind, placebo-controlled trial. Lancet. 2014; 383(9935):2136-43. Epub 2014/03/19. doi: 10.1016/s0140-6736(13) 62630-6. PubMed PMID: 24629994; PMCID: PMC4532697
31. Bhandari N, Sharma P, Taneja S, Kumar T, Rongsen-Chandola T, Appaiahgari M B, Mishra A, Singh S, Vrati S. A dose-escalation safety and immunogenicity study of live attenuated oral rotavirus vaccine 116E in infants: a randomized, double-blind, placebo-controlled trial. J Infect Dis. 2009; 200(3):421-9. Epub 2009/06/24. doi: 10.1086/600104. PubMed PMID: 19545211
32. Bhandari N, Sharma P, Glass R I, Ray P, Greenberg H, Taneja S, Saksena M, Rao C D, Gentsch J R, Parashar U, Maldonado Y, Ward R L, Bhan M K. Safety and immunogenicity of two live attenuated human rotavirus vaccine candidates, 116E and I321, in infants: results of a randomised controlled trial. Vaccine. 2006; 24(31-32):5817-23. Epub 2006/06/01. doi: 10.1016/j.vaccine.2006.05.001. PubMed PMID: 16735085
33. Mohan V K, Varanasi V, Singh A, Pasetti M F, Levine M M, Venkatesan R, Ella K M. Safety and immunogenicity of a Vi polysaccharide-tetanus toxoid conjugate vaccine (Typbar-TCV) in healthy infants, children, and adults in typhoid endemic areas: a multicenter, 2-cohort, open-label, double-blind, randomized controlled phase 3 study. Clinical infectious diseases: an official publication of the Infectious Diseases Society of America. 2015; 61(3):393-402. Epub 2015/04/15. doi: 10.1093/cid/civ295. PubMed PMID: 25870324
34. Shakya M, Colin-Jones R, Theiss-Nyland K, Voysey M, Pant D, Smith N, Liu X, Tonks S, Mazur O, Farooq Y G, Clarke J, Hill J, Adhikari A, Dongol S, Karkey A, Bajracharya B, Kelly S, Gurung M, Baker S, Neuzil K M, Shrestha S, Basnyat B, Pollard A J. Phase 3 Efficacy Analysis of a Typhoid Conjugate Vaccine Trial in Nepal. New England Journal of Medicine. 2019; 381(23):2209-18. doi: 10.1056/NEJMoa1905047
35. Voysey M, Pollard A J. Seroefficacy of Vi Polysaccharide-Tetanus Toxoid Typhoid Conjugate Vaccine (Typbar TCV). Clinical Infectious Diseases. 2018; 67(1):18-24. doi: 10.1093/cid/cix1145
36. Jin C, Gibani M M, Moore M, Juel H B, Jones E, Meiring J, Harris V, Gardner J, Nebykova A, Kerridge S A, Hill J, Thomaides-Brears H, Blohmke C J, Yu L-M, Angus B, Pollard A J. Efficacy and immunogenicity of a Vi-tetanus toxoid conjugate vaccine in the prevention of typhoid fever using a controlled human infection model of Salmonella typhi: a randomised controlled, phase 2b trial. The Lancet. 2017; 390(10111):2472-80. doi: doi.org/10.1016/S0140-6736(17)32149-9
37. Vadrevu K M, Potula V, Khalatkar V, Mahantshetty N S, Shah A, Ella R. Persistence of Immune Responses With an Inactivated Japanese Encephalitis Single-Dose Vaccine, JENVAC and Interchangeability With a Live-Attenuated Vaccine. The Journal of Infectious Diseases. 2019. doi: 10.1093/infdis/jiz672
38. Singh A, Mitra M, Sampath G, Venugopal P, Rao J V, Krishnamurthy B, Gupta M K, Sri Krishna S, Sudhakar B, Rao N B, Kaushik Y, Gopinathan K, Hegde N R, Gore M M, Krishna Mohan V, Ella K M. A Japanese Encephalitis Vaccine From India Induces Durable and Cross-protective Immunity Against Temporally and Spatially Wide-ranging Global Field Strains. The Journal of Infectious Diseases. 2015; 212(5):715-25. doi: 10.1093/infdis/jiv023

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated nucleic acid encoding a recombinant virus comprising a SARS-CoV-2 spike protein (S) or a portion thereof, wherein the virus is a rabies virus, a vesicular stomatitis virus (VSV), or a measles virus, and wherein the portion of the SARS-CoV-2 spike protein (S) comprises a receptor binding site of the SARS-CoV-2 spike protein (S).

2. The isolated nucleic acid of claim 1, wherein the virus is a rhabdovirus.

3. The isolated nucleic acid of claim 1, wherein the portion of the SARS-CoV-2 spike protein (S) is a S1 domain.

4. The isolated nucleic acid of claim 1, wherein the nucleic acid comprises (a) a sequence encoding at least a portion of the genome of a measles virus and (b) a sequence encoding the SARS-CoV-2 spike protein (S) or the portion thereof.

5. The isolated nucleic acid of claim 4, wherein the sequence encoding the SARS-CoV-2 spike protein (S) or portion thereof is inserted into positions 2, 3, or 6 of the genome of the measles virus.

6. The isolated nucleic acid of claim 1, wherein the nucleic acid comprises (a) a sequence encoding at least a portion of the genome of a rabies virus and (b) a sequence encoding the SARS-CoV-2 spike protein (S) or the portion thereof.

7. The isolated nucleic acid of claim 6, wherein the at least a portion of the genome of the rabies virus comprises an N gene and a P gene, and the sequence encoding the SARS-CoV-2 spike protein (S) or portion thereof is inserted into a position between the N gene and P gene.

8. The isolated nucleic acid of claim 1, wherein the nucleic acid comprises (a) a sequence encoding at least a portion of the genome of a vesicular stomatitis virus (VSV), and (b) a sequence encoding the SARS-CoV-2 spike protein (S) or the portion thereof.

9. The isolated nucleic acid of claim 1, wherein the protein comprising a SARS-CoV-2 spike protein (S) or a portion thereof is a fusion protein comprising a glycoprotein (G) or a portion thereof and the SARS-CoV-2 spike protein (S) or the portion thereof.

10. The isolated nucleic acid of claim 9, wherein the fusion protein comprises a glycoprotein (G) or portion thereof fused to the S1 domain of a SARS-CoV-2 spike protein (S).

11. The isolated nucleic acid of claim 1, wherein the nucleic acid comprises the sequence set forth in any one of SEQ ID NOs: 1-27.

12. The isolated nucleic acid of claim 11, wherein the nucleic acid comprises the sequence set forth in SEQ ID NO: 2.

13. The isolated nucleic acid of claim 1, wherein the SARS-CoV-2 spike protein (S) comprises the sequence of SEQ ID NO: 28; or a sequence comprising at least 98%, but not 100%, sequence identity to the sequence of SEQ ID NO: 28.

14. A vector comprising the nucleic acid of claim 1.

15. A vaccine comprising the isolated nucleic acid of claim 1, and a pharmaceutically acceptable carrier.

16. The vaccine of claim 15, further comprising an adjuvant.

17. The vaccine of claim 16, wherein the adjuvant is MPLA 3D(6-acyl) in 2% squalene.

18. A method of generating an immune response against a SARS-CoV-2 virus in a subject in need thereof, the method comprising administering to the subject an effective amount of the vaccine of claim 15.

19. A method of vaccinating a subject against a SARS-CoV-2 virus, the method comprising administering to the subject an effective amount of the vaccine of claim 15.

20. A method of treating and/or preventing a disease or disorder associated with a SARS-CoV-2 virus in a subject in need thereof, the method comprising administering to the subject an effective amount of the vaccine of claim 15.

* * * * *

SEQUENCE LISTING

```
Sequence total quantity: 106
SEQ ID NO: 1            moltype = DNA   length = 17189
FEATURE                 Location/Qualifiers
misc_feature            1..17189
                        note = VSV-COVID19-S1-VSVG
source                  1..17189
                        mol_type = other DNA
                        organism = synthetic construct
SEQUENCE: 1
ctgacgcgcc ctgtagcggc gcattaagcg cggcgggtgt ggtggttacg cgcagcgtga    60
ccgctacact tgccagcgcc ctagcgcccg ctcctttcgc tttcttccct tcctttctcg   120
ccacgttcgc cggctttccc cgtcaagctc taaatcgggg gctcccttta gggttccgat   180
ttagtgcttt acggcacctc gacccaaaa aacttgatta gggtgatggt tcacgtagtg    240
ggccatcgcc ctgatagacg gtttttcgcc ctttgacgtt ggagtccacg ttctttaata   300
gtggactctt gttccaaact ggaacaacac tcaaccctat ctcggtctat tcttttgatt   360
tataagggat tttgccgatt tcggcctatt ggttaaaaaa tgagctgatt taacaaaaat   420
ttaacgcgaa ttttaacaaa atattaacgc ttacaatttc cattcgccat tcaggctgcg   480
caactgttgg gaagggcgat cggtgcgggc ctcttcgcta ttacgccagc tggcgaaagg   540
gggatgtgct gcaaggcgat taagttgggt aacgccaggg ttttcccagt cacgacgttg   600
taaaacgacg gccagtgagc gcgccctagt tattaatagt aatcaattac ggggtcatta   660
gttcatagcc catatatgga gttccgcgtt acataactta cggtaaatgg cccgcctggc   720
tgaccgccca acgaccccg cccattgacg tcaataatga cgtatgttcc catagtaacg   780
ccaataggga ctttccattg acgtcaatgg gtggagtatt tacggtaaac tgcccacttg   840
gcagtacatc aagtgtatca tatgccaagt acgccccca ttgacgtcaa tgacggtaaa   900
tggcccgcct ggcattatgc ccagtacatg accttatggg actttcctac ttggcagtac   960
atctacgtat tagtcatcgc tattaccatg gtgatgcggt tttggcagta catcaatggg  1020
cgtggatagc ggtttgactc acggggattt ccaagtctcc accccattga cgtcaatggg  1080
agtttgtttt ggcaccaaaa tcaacgggac tttccaaaat gtcgtaacaa ctccgcccca  1140
ttgacgcaaa tgggcggtag gcgtgtacgg tgggaggtct atataagcag agctctctgg  1200
ctaactagag aacccactgc ttactggctt atcgaaatta atacgactca ctataggag  1260
acccaagctg gctagggtct tcgtctgatg agtccgtgag gacgaaaccc ggcgtaccgg  1320
gtcacgaaga caaacaaacc attattatca ttaaaaggct caggagaaac tttaacagta  1380
atcaaaatgt ctgttacagt caagagaatc attgacaaca cagtcatagt tccaaaactt  1440
cctgcaaatg aggatccagt ggaatacccg gcagattact tcagaaaatc aaaggagatt  1500
cctctttaca tcaatactac aaaaagtttg tcagatctaa gaggatatgt ctaccaaggc  1560
ctcaaatccg gaaatgtatc aatcatacat gtcaacagct acttgtatgg agcattaaag  1620
gacatccggg gtaagttgga taaagattgg tcaagtttcg gaataaacat cgggaaagca  1680
ggggatacaa tcggaatatt tgaccttgta tccttgaaag ccctggacgg cgtacttcca  1740
gatggagtat cggatgcttc cagaaccagc gcagatgaca aatggttgcc tttgtatcta  1800
cttggcttat acagagtggg cagaacacaa atgcctgaat acagaaaaaa gctcatggat  1860
gggctgacaa atcaatgcaa aatgatcaat gaacagtttg aacctcttgt gccagaaggt  1920
cgtgacattt ttgatgtgtg gggaaatgac agtaattaca caaaaattgt cgctgcagtg  1980
```

```
gacatgttct tccacatgtt caaaaaacat gaatgtgcct cgttcagata cggaactatt    2040
gtttccagat tcaaagattg tgctgcattg gcaacatttg gacacctctg caaaataacc    2100
ggaatgtcta cagaagatgt aacgacctgg atcttgaacc gagaagttgc agatgaaatg    2160
gtccaaatga tgcttccagg ccaagaaatt gacaaggccg attcatacat gccttatttg    2220
atcgactttg gattgtcttc taagtctcca tattcttcag tcaaaaacct tgccttccac    2280
ttctgggggc aattgacagc tcttctgctc agatccacca gagcaaggaa tgcccgacag    2340
cctgatgaca ttgagtatac atctcttact acagcaggtt tgttgtacgc ttatgcagta    2400
ggatcctctg ccgacttggc acaacagttt tgtgttggag ataacaaata cactccagat    2460
gatagtaccg gaggattgac gactaatgca ccgccacaag gcagagatgt ggtcgaatgg    2520
ctcggatggt ttgaagatca aaacagaaaa ccgactcctg atatgatgca gtatgcgaaa    2580
agagcagtca tgtcactgca aggcctaaga gagaagacaa ttggcaagta tgctaagtca    2640
gaatttgaca aatgacccta taattctcag atcacctatt atatattatg ctacatatga    2700
aaaaaactaa cagatatcat ggataatctc acaaaagttc gtgagtatct caagtcctat    2760
tctcgtctgg atcaggcggt aggagagata gatgagatcg aagcacaacg agctgaaaag    2820
tccaattatg agttgttcca agaggatgga gtggaagagc atactaagcc ctcttatttt    2880
caggcagcag atgattctga cacagaatct gaaccagaaa ttgaagacaa tcaaggtttg    2940
tatgcaccag atccagaagc tgagcaagtt gaaggcttta tacaggggcc tttagatgac    3000
tatgcagatg aggaagtgga tgtttgtattt acttcggact ggaaacagcc tgagcttgaa    3060
tctgacgagc atggaaagac cttacggttg acatcgccag agggtttaag tggagagcag    3120
aaatcccagt ggctttcgac gattaaagca gtcgtgcaaa gtgccaaata ctggaatctg    3180
gcagagtgca catttgaagc atcgggagaa ggggtcatta tgaaggagcg ccagataact    3240
ccggatgtat ataaggtcac tccagtgatg aacacacatc cgtcccaatc agaagcagta    3300
tcagatgttt ggtctctctc aaagacatcc atgactttcc aacccaagaa agcaagtctt    3360
cagcctctca ccatatcctt ggatgaattg ttctcatcta gaggagagtt catctctgtc    3420
ggaggtgacg gacgaatgtc tcataaagag gccatcctgc tcggcctgag atacaaaaag    3480
ttgtacaatc aggcgagagt caaatattct ctgtagacta tgaaaaaaag taacagatat    3540
cacgatctaa gtgttatccc aatccattca tcatgagttc cttaaagaag attctcggtc    3600
tgaagggaa aggtaagaaa tctaagaaat tagggatcgc accacccct tatgaagagg       3660
acactagcat ggagtatgct ccgagcgctc caattgacaa atcctatttt ggagttgacg    3720
agatggacac ctatgatccg aatcaattaa gatatgaaa attcttcttt acagtgaaaa     3780
tgacggttag atctaatcgt ccgttcagaa catactcaga tgtggcagcc gctgtatccc    3840
attgggatca catgtacatc ggaatggcag ggaaacgtcc cttctacaaa atcttggctt    3900
ttttgggttc ttctaatcta aaggccactc cagcggtatt ggcagatcaa ggtcaaccag    3960
agtatcacac tcactgcgaa ggcagggctt atttgccaca taggatgggg aagaccccctc  4020
ccatgctcaa tgtaccagag cacttcagaa gaccattcaa tataggtctt tacaagggaa    4080
cgattgagct cacaatgacc atctacgatg atgagtcact ggaagcagct cctatgatct    4140
gggatcattt caattcttcc aaattttctg atttcagaga gaaggcctta atgtttggcc    4200
tgattgtcga gaaaaaggca tctggagcgt gggtcctgga ttctatcagc cacttcaaat    4260
gagctagtct aacttctagc ttctgaacaa tccccggttt actcagtctc tcctaattcc    4320
agcctctcga caactaata tcctgtcttt tctatcccta tgaaaaaaac taacagagat     4380
cgatctgttt acgcgtcact atgaagtgcc ttttgtactt agccttttta ttcattgggg    4440
tgaattgcaa gttcaccata gttttccac acaaccaaaa aggaaactgg aaaaatgttc      4500
cttctaatta ccattattgc ccgtcaagct cagatttcaa ttggcataat gacttaatag    4560
gcacagccat acaagtcaaa atgcccaaga gtcacaaggc tattcaagca gacggttgga    4620
tgtgtcatgc ttccaaatgg gtcactacttt gtgatttccg ctggtatgga ccgaagtata    4680
taacacagtc catccgatcc ttcactccat ctgtagaaca atgcaaggaa agcattgaac    4740
aaacgaaaca aggaacttgg ctgaatccag gcttccctcc tcaaagttgt ggatatgcaa    4800
ctgtgacgga tgccgaagca gtgattgtcc aggtgactcc tcaccatgtg ctggttgatg    4860
aatacacagg agaatgggtt gattcacagt tcatcaacgg aaaatgcagc aattacatat    4920
gccccactgt ccataactct acaacctggc attctgacta taaggtcaaa gggctatgtg    4980
attctaacct catttccatg gacatcaccot tcttctcaga ggacggagag ctatcatccc   5040
tgggaaagga gggcacaggg ttcagaagta actactttgc ttatgaaact ggaggcaagg    5100
cctgcaaaat gcaatactgc aagcattggg gagtcagact cccatcaggt gtctggttcg    5160
agatggctga taaggatctc tttgctgcag ccagattccc tgaatgccca aagggtcaa     5220
gtatctctgc tccatctgg acctcagtgg atgtaagtct aattcaggac gttgagagga    5280
tcttggatta ttccctctgc caagaaacct ggagcaaaat cagagcgggt cttccaatct    5340
ctccagtgga tctcagctat cttgctccta aaacccagg aaccggtcct gctttcacca    5400
taatcaatga taccctaaaa tactttgaga ccagatacat cagagtcgat attgctgctc    5460
caatcctctc aagaatggtc ggaatgatca gtggaactac cacagaaagg gaactgtggg    5520
atgactgggc accatatgaa gacgtgaaa ttggacccaa tggagttctg aggaccagtt     5580
caggatataa gtttccttta tacatgattg gacatggtat gttggactcc gatcttcatc    5640
ttagctcaaa ggctcaggtg ttcgaacatc ctcacattca agacgctgct tcgcaacttc    5700
ctgatgatga gagtttattt tttggtgata ctgggctatc caaaaatcca atcgagcttg    5760
tagaaggttg gttcagtagt tggaaaagct ctattgcctc tttttttctt atcatgaggt    5820
taatcattgg actattcttg gttctccgag ttggtatcca tctttgcatt aaattaaagc    5880
acaccaagaa aagacagatt tatacagaca tagagatgaa ccgacttgga aagtaactca    5940
aatcctgcta ggtatgaaaa aaactaacag atatcacgct cgagcgtacg ccaccatgtt    6000
cgtgtttctg gtgctgctgc ctctggtgag ctcccagtgt gtgaacctga ccacaaggac    6060
ccagctgccc cctgcctata ccaattcctt cacacgtggc gtgtactatc ccgacaaggt    6120
gttccggagc agcgtgctgc actccacaca ggatctgttt ctgccttttct tttctaacgt    6180
gacctggttc cacgccatcc acgtgagcgg caccaatggc acaaagcggt tcgacaatcc    6240
agtgctgccc tttaacgatg gcgtgtactt cgcctccacc gagaagtcta acatcatcag    6300
aggctggatc tttggcacca cactggacag caagacacag tccctgctga tcgtgaacaa    6360
cgccaccaac gtggtcatca aggtgtgcga gttccagttt tgtaatgatc cattcctggg    6420
cgtgtactat cacaagaaca ataagtcttg gatggagagc gagtttcgcg tgtattcctc    6480
tgccaacaat tgcacatttg agtacgtgtc ccagccttc ctgatggacc tggagggcaa     6540
gcagggcaat ttcaagaacc tgagggagtt cgtgtttaag aatatcgatg gctacttcaa    6600
aatctactcc aagcacaccc caatcaacct ggtgcgcgca ctgccacagg gcttctctgc    6660
cctggagcca ctggtggatc tgcccatcgg catcaacatc acccggttc agacactgct     6720
```

```
ggccctgcac agaagctacc tgacaccagg cgacagctcc tctggatgga ccgcaggagc   6780
agcagcctac tatgtgggct atctgcagcc caggaccttc ctgctgaagt acaacgagaa   6840
tggcaccatc acagacgccg tggattgcgc cctggatccc ctgtctgaga ccaagtgtac   6900
actgaagagc tttaccgtgg agaagggcat ctatcagaca agcaatttca gggtgcagcc   6960
taccgagtcc atcgtgcgct ttcccaatat cacaaacctg tgcccttttg gcgaggtgtt   7020
caacgcaacc cgcttcgcca gcgtgtacgc ctggaatagg aagcgcatct ccaactgcgt   7080
ggccgactat tctgtgctgt acaacagcgc ctccttctct acctttaagt gctatggcgt   7140
gagccccaca aagctgaatg acctgtgctt taccaacgtg tacgccgatt ccttcgtgat   7200
caggggcgac gaggtgcgcc agatcgcacc aggacagaca ggcaagatcg cagactacaa   7260
ttataagctg cctgacgatt tcaccggctg cgtgatcgcc tggaactcta acaatctgga   7320
tagcaaagtg ggcggcaact acaattatct gtaccggctg tttagaaagt ctaatctgaa   7380
gccattcgag agggacatct ccacagaaat ctaccaggcc ggctctaccc cctgcaatgg   7440
cgtggagggc tttaactgtt attccctct gcagagctac ggcttccagc caacaaacgg   7500
cgtgggctat cagcccacc gcgtggtggt gctgtctttt gagctgctgc acgcacctgc   7560
aacagtgtgc ggaccaaaga agagcaccaa tctggtgaag aacaagtgcg tgaacttcaa   7620
cttcaacgga ctgaccggaa caggcgtgct gaccgagtcc aacaagaagt tcctgccttt   7680
tcagcagttc ggcagggaca tcgcagatac acagacgcc gtgcgcgacc ctcagaccct   7740
ggagatcctg gacatcacac catgctcctt cggcggcgtg tctgtgatca caccaggcac   7800
caatacaagc aaccaggtgg ccgtgctgta tcaggacgtg aattgtaccg aggtgccagt   7860
ggcaatccac gcagatcagc tgaccccac atggcgggtg tactctaccg gcagcaacgt   7920
gttccagaca agagccggat gcctgatcgg agcagagcac gtgaacaata gctatgagtg   7980
cgacatccct atcggcgcgg gcatctgtgc ctccctaccag acccagacaa actccccag   8040
gtctgtgggc gatacaggcc tgtccaagaa tccaatcgag ctggtagagg gctggttcag   8100
cagttggaaa agctccatcg cctcctttt ctttatcatc ggcctgatca tcggactgtt   8160
cctggtgctc cgcgtgggta tccacctgtg catcaagctg aagcacacca agaaaagaca   8220
gattataca gacatcgaga tgaaccgcct gggaaagtga gctagccaga ttcttcatgt   8280
ttggaccaaa tcaacttgtg ataccatgct caaagaggcc tcaattatat ttgagttttt   8340
aattttttatg aaaaaaacta acagcaatca tggaagtcca cgatttttgag accgacgagt   8400
tcaatgatt caatgaagat gactatgcca caagagaatt cctgaatccc gatgagcgca   8460
tgacgtactt gaatcatgct gattacaatt tgaattctcc tctaattagt gatgatattg   8520
acaatttgat caggaaattc aattctcttc cgattcctc gatgtgggat agtaagaact   8580
gggatggagt tcttgagatg ttaacatcat gtcaagccaa tcccatctca acatctcaga   8640
tgcataaatg gatgggaagt tggttaatgt ctgataatca tgatgccagt caagggtata   8700
gtttttaca tgaagtggac aaagaggcag aaataacatt tgacgtggtg gagaccttca   8760
tccgcggctg gggcaacaaa ccaattgaat acatcaaaaa ggaaagatgg actgactcat   8820
tcaaaattct cgcttatttg tgtcaaaagt ttttggactt acacaagttg acattaatct   8880
taaatgctgt ctctgaggtg gaattgctca acttggcgag gacttcaaa ggcaaagtca   8940
gaagaagttc tcatggaacg aacatatgca ggattagggt tccagcttg ggtcctactt   9000
ttattcaga aggatgggct tacttcaaga aacttgatat tctaatggac cgaaacttc   9060
tgttaatggt caaagatgtg attataggga ggatgcaaac ggtgcatcc atggtatgta   9120
gaatagacaa cctgttctca gagcaagaca tcttctccct tctaaatatc tacagaattg   9180
gagataaaat tgtggagagg cagggaaatt tttcttatga cttgattaaa atggtggaac   9240
cgatatgcaa cttgaagctg atgaaattag caagagaatc aaggccttta gtcccacaat   9300
tccctcattt tgaaaatcat atcaagactc ctgttgatga aggggcaaaa attgaccgag   9360
gtataagatt cctccatgat cagataatga gtgtgaaaac agtggatctc acactggtga   9420
tttatggatc gttcagacat tggggtcatc cttttataga ttattacact ggactagaaa   9480
aattcattc ccaagtaacc atgaagaaag atattgatgt gtcatatgca aaagcacttg   9540
caagtgattt agctcggatt gttctatttc aacagttcaa tgatcataaa aagtggttcg   9600
tgaatggaga cttgctccct catgatcatc ccttttaaaag tcatgttaaa gaaaatacat   9660
ggcccacagc tgctcaagtt caagattttg gagataaatg gcatgaactt ccgctgatta   9720
aatgttttga aataccgac ttactagacc catcgataat atactctgac aaaagtcatt   9780
caatgaatag gtcagaggtg ttgaaacatg tccgaatgaa tccgaacact cctatcccta   9840
gtaaaaaggt gttgcagact atgttggaca caaaggctac caattggaaa gaatttctta   9900
aagagattga tgagaagggc ttagatgatg atgatctaat tattggtctt aaaggaaagg   9960
agagggaact gaagttggca ggtagatttt tctccctaat gtcttggaaa ttgcgagaat  10020
actttgtaat taccgaatat ttgataaaga ctcatttcgt ccctatgttt aaaggcctga  10080
caatggcgga cgatctaact gcagtcatta aaaagatgtt agattcctca tccggccaag  10140
gattgaagtc atatgaggca atttgcatag ccaatcacat tgattacgaa aaatggaata  10200
accaccaaag gaagttatca aacgaccag tgttccgagt tatgggccag ttcttaggtt  10260
atccatcctt aatcgagaga actcatgaat tttttgagaa aagtcttata tactacaatg  10320
gaagaccaga cttgatgcgt gttcacaaca acacactgat caattcaacc tcccaacgag  10380
tttgttggca aggacaagag ggtggactgg aaggtctacg gcaaaaagga tggactatcc  10440
tcaatctact ggttattcaa agagaggcta aaatcagaaa cactgctgtc aaagtcttgg  10500
cacaaggtga taatcaagtt attttgcacac agtataaaac gaagaaatcg agaaacgttg  10560
tagaattaca gggtgctctc aatcaaatgg tttctaataa tgagaaaatt atgactgcaa  10620
tcaaaatagg gacagggaag ttaggacttt tgataaatga cgatgagact atgcaatctg  10680
cagattactt gaattatgga aaaataccga ttttcgtgg agtgattaga gggttagaga  10740
ccaagagata gtcacgagtg acttgtgtca ccaatgacca aatacccact tgtgctaata  10800
taatgagctc agtttccaca aatgctctca ccgtagctca ttttgctgag aacccaatca  10860
atgccatgat acagtacaat tattttggga catttgctag actcttgttg atgatgcatg  10920
atcctgctct tcgtcaatca ttgtatgaag ttcaagataa gataccgggc ttgcacagtt  10980
ctactttcaa atacgccatg ttgtatttgg accttccat ggaggagtg tcgggcatgt  11040
cttgtccag gttttgatt agagccttcc cagatcccgt aacagaaagt ctctcattct  11100
ggagattcat ccatgtacat gctcgaagtg agcatctgga ggagatgagt gcagtatttg  11160
gaaaccccga gatagccaag tttcgaataa ctcacataga caagctagta gaagatccaa  11220
cctctctgaa catcgctatg ggaatgagtc cagcgaactt gttaaagact gaggttaaaa  11280
aatgcttaat cgaatcaaga caaaccatca ggaaccaggt gattaaggat gcaaccatat  11340
attttgtatca tgaagaggat cggctcagaa gtttcttatg tcaataaaat cctctgttcc  11400
ctagattttt aagtgaattc aaatcaggca ctttttttggg agtcgcagac gggctcatca  11460
```

```
gtctatttca aaattctcgt actattcgga actcctttaa gaaaaagtat catagggaat  11520
tggatgattt gattgtgagg agtgaggtat cctctttgac acatttaggg aaacttcatt  11580
tgagaagggg atcatgtaaa atgtggacat gttcagctac tcatgctgac acattaagat  11640
acaaatcctg gggccgtaca gttattggga caactgtacc ccatccatta gaatgttgg   11700
gtccacaaca tcgaaaagag actccttgtg caccatgtaa cacatcaggg ttcaattatg  11760
tttctgtgca ttgtccagac gggatccatg acgtctttag ttcacgggga ccattgcctg  11820
cttatctagg gtctaaaaca tctgaatcta catctatttt gcagccttgg gaagggaaa   11880
gcaaagtccc actgattaaa agagctacac gtcttagaga tgctatctct tggtttgttg  11940
aacccgactc taaactagca atgactatac tttctaacat ccactcttta acaggcgaag  12000
aatggaccaa aaggcagcat gggttcaaaa gaacagggtc tgcccttcat aggttttcga  12060
catctcggat gagccatggt gggttcgcat ctcagagcac tgcagcattg accaggttga  12120
tggcaactac agacaccatg agggatctgg agatcagaa tttcgacttt ttattccaag   12180
caacgttgct ctatgctcaa attaccacca ctgttgcaag agacggatgg atcaccagtt  12240
gtacagatca ttatcatatt gcctgtaagt cctgtttaga acccatagaa gagatcaccc  12300
tggactcaag tatggactac acgccccag atgtatccca tgtgctgaag acatggagga   12360
atggggaagg ttcgtgggga caagagataa aacagatcta tcctttagaa gggaattgga  12420
agaatttagc acctgctgag caatcctatc aagtcggcag atgtataggt tttctatatg  12480
gagacttggc gtatagaaaa tctactcatg ccgaggacag ttctctattt cctctatcta  12540
tacaaggtcg tattagaggt cgaggtttct taaaagggtt gctagacgga ttaatgagag  12600
caagttgctg ccaagtaata caccggagaa gtctggctca tttgaagagg ccggccaacg  12660
cagtgtacgg aggtttgatt tacttgattg ataaattgag tgtatcacct ccattccttt  12720
ctcttactag atcaggacct attagagacg aattagaaac gattccccac aagatcccaa  12780
cctcctatcc gacaagcaac cgtgatatgg gggtgattgt cagaaattac ttcaaatacc  12840
aatgccgtct aattgaaaag ggaaaataca gatcacatta ttcacaatta tggttattct  12900
cagatgtctt atccatagac ttcattggac cattctctat ttccaccacc ctcttgcaaa  12960
tcctatacaa gccatttta tctgggaaag ataagaatga gttgagagag ctggcaaatc   13020
tttcttcatt gctaagatca ggagagggggt gggaagacat acatgtgaaa ttcttcacca  13080
aggacatatt attgtgtcca gaggaaatca gacatgcttg caagttcggg attgctaagg  13140
ataataataa agacatgagc tatccccctt ggggaaggga atccagaggg acaattacaa  13200
caatccctgt ttattatacg accaccccctt acccaaagat gctagagatg cctccaagaa  13260
tccaaaatcc cctgctgtcc ggaatcaggt tgggccaatt accaactggc gctcattata  13320
aaattcggag tatattacat ggaatgggaa tccattacag ggacttcttg agttgtggag  13380
acggctccgg agggatgact gctgcattac tacgagaaaa tgtgcatagc agaggaatat  13440
tcaatagtct gttagaatta tcagggtcag tcatgcgagg cgcctctcct gagccccca   13500
gtgccctaga aactttagga ggagataaat cgagatgtgt aaatggtgaa acatgttggg  13560
aatatccatc tgacttatgt gacccaagga cttgggacta tttcctccga ctcaaagcag  13620
gcttggggct tcaaattgat ttaattgtaa tggatatgga agttcgggat tcttctacta  13680
gcctgaaaat tgagacgaat gttagaaatt atgtgcaccg gattttggat gagcaaggag  13740
ttttaatcta caagcttat ggaacatata tttgtgaagg cgaaaagaat gcagtaacaa   13800
tccttggtcc catgttcaag acggtcgact tagttcaaac agaatttagt agttctcaaa  13860
cgtctgaagt atatatggta tgtaaaggtt tgaagaaatt aatcgatgaa cccaatcccg  13920
attggtcttc catcaatgaa tcctggaaaa acctgtacgc attccagtca tcagaacagg  13980
aatttgccag agcaaagaag gttagtacat actttaccct gacaggtatt ccctcccaat  14040
tcattcctga tccttttgta aacattgaga ctatgctaca aatattcgga gtacccacgg  14100
gtgtgtctca tgcggctgcc ttaaaatcat ctgatagacc tgcagattta ttgaccatta  14160
gccttttta tatggcgatt atatcgtatt ataacatcaa tcatatcaga gtaggaccga   14220
tacctccgaa ccccccatca gatggaattg cacaaaatgt gggatcgct ataactggta   14280
taagcttttg gctgagtttg atggagaaag acattccact atatcaacag tgtttagcag  14340
ttatccagca atcattcccg attaggtggg aggctgtttc agtaaaagga ggatacaagc  14400
agaagtggag tactagaggt gatgggctcc caaagataac cgaacttca gactccttgg   14460
ccccaatcgg gaactggatc agatctctgg aattggtccg aaaccaagtt cgtctcaaaa  14520
cattcaatga gatcttgttc aatcagctat gtcgtacagt ggataatcat ttgaaatggt  14580
caaatttgcg aagaaacaca ggaatgattg aatggatcaa tagacgaatt tcaaaagaag  14640
accggtctat actgatgttg aagagtgacc tacacgagga aaactcttgg agagattaaa  14700
aaatcatgag agactccaa actttaagta tgaaaaaaac tttgatcctt aagaccctct   14760
tgtggtttt attttttatc tggttttgtg gtcttcgtgg gtcggcatgg catctccacc  14820
tcctcgcggt ccgacctggg catccgaagg aggacgcacg tccactcgga tggctaaggg  14880
agagccagaa aataactagt ggatccggct gctaacaaag cccgaaagga agctgagttg  14940
gctgctgcca ccgctgagca ataactagca taaccccttg gggcctctaa acgggtcttg  15000
agggggtttt tgctgaaagt cgcgcttggc gtaatcatgg tcatagctgt ttcctgtgtg  15060
aaattgttat ccgctcacaa ttccacacaa catacgagcc ggaagcataa agtgtaaagc  15120
ctggggtgcc taatgagtga gctaactcac attaattgcg ttgcgctcac tgcccgcttt  15180
ccagtcggga aacctgtcgt gccagctgca ttaatgaatc ggccaacgcg cggggagagg  15240
cggtttgcgt attgggcgct cttccgcttc ctcgctcact gactcgctgc gctcggtcgt  15300
tcggctgcgg cgagcggtat cagctcactc aaaggcggta atacggttat ccacagaatc  15360
aggggataac gcaggaaaga acatgtgagc aaaaggccag caaaaggcca ggaaccgtaa  15420
aaaggccgcg ttgctggcgt ttttccatag gctccgcccc cctgacgagc atcacaaaaa  15480
tcgacgctca agtcagaggt ggcgaaaccc gacaggacta taaagatacc aggcgtttcc  15540
ccctggaagc tccctcgtgc gctctcctgt tccgaccctg ccgcttaccg gatacctgtc  15600
cgcctttctc ccttcgggaa gcgtggcgct ttctcatagc tcacgctgta ggtatctcag  15660
ttcggtgtag gtcgttcgct ccaagctggg ctgtgtgcac gaaccccccg ttcagcccga  15720
ccgctgcgcc ttatccggta actatcgtct tgagtccaac ccggtaagac acgacttatc  15780
gccactggca gcagccactg gtaacaggat tagcagagcg aggtatgtag gcggtgctac  15840
agagttcttg aagtggtggc ctaactacgg ctacactaga agaacagtat ttggtatctg  15900
cgctctgctg aagccagtta ccttcggaaa aagagttggt agctcttgat ccggcaaaca  15960
aaccaccgct ggtagcggtg gtttttttgt ttgcaagcag cagattacgc gcagaaaaaa  16020
aggatctcaa gaagatcctt tgatcttttc tacgggtct gacgctcagt ggaacgaaaa   16080
ctcacgttaa gggattttgg tcatgagatt atcaaaaagg atcttcacct agatcctttt  16140
aaattaaaaa tgaagtttta aatcaatcta agtatatat gagtaaactt ggtctgacag   16200
```

```
ttaccaatgc ttaatcagtg aggcacctat ctcagcgatc tgtctatttc gttcatccat  16260
agttgcctga ctccccgtcg tgtagataac tacgatacgg gagggcttac catctggccc  16320
cagtgctgca atgataccgc gagacccacg ctcaccggct ccagatttat cagcaataaa  16380
ccagccagcc ggaagggccg agcgcagaag tggtcctgca actttatccg cctccatcca  16440
gtctattaat tgttgccggg aagctagagt aagtagttcg ccagttaata gtttgcgcaa  16500
cgttgttgcc attgctacag gcatcgtggt gtcacgctcg tcgtttggta tggcttcatt  16560
cagctccggt tcccaacgat caaggcgagt tacatgatcc cccatgttgt gcaaaaaagc  16620
ggttagctcc ttcggtcctc cgatcgttgt cagaagtaag ttggccgcag tgttatcact  16680
catggttatg gcagcactgc ataattctct tactgtcatg ccatccgtaa gatgcttttc  16740
tgtgactggt gagtactcaa ccaagtcatt ctgagaatag tgtatgcggc gaccgagttg  16800
ctcttgcccg gcgtcaatac gggataatac cgcgccacat agcagaactt taaaagtgct  16860
catcattgga aaacgttctt cggggcgaaa actctcaagg atcttaccgc tgttgagatc  16920
cagttcgatg taacccactc gtgcacccaa ctgatcttca gcatctttta ctttcaccag  16980
cgtttctggg tgagcaaaaa caggaaggca aaatgccgca aaaaagggaa taagggcgac  17040
acggaaatgt tgaatactca tactcttcct ttttcaatat tattgaagca tttatcaggg  17100
ttattgtctc atgagcggat acatatttga atgtatttag aaaaataaac aaataggggt  17160
tccgcgcaca tttccccgaa aagtgccac                                    17189

SEQ ID NO: 2           moltype = DNA  length = 17611
FEATURE                Location/Qualifiers
misc_feature           1..17611
                       note = BNSP333-COVID19-S1-RVG
source                 1..17611
                       mol_type = other DNA
                       organism = synthetic construct
SEQUENCE: 2
ctgacgcgcc ctgtagcggc gcattaagcg cggcgggtgt ggtggttacg cgcagcgtga  60
ccgctacact tgccagcgcc ctagcgcccg ctcctttcgc tttcttccct tcctttctcg  120
ccacgttcgc cggctttccc cgtcaagctc taaatcgggg gctcccttta gggttccgat  180
ttagtgcttt acggcacctc gaccccaaaa aacttgatta gggtgatggt tcacgtagtg  240
ggccatcgcc ctgatagacg gtttttcgcc ctttgacgtt ggagtccacg ttctttaata  300
gtggactctt gttccaaact ggaacaacac tcaaccctat ctcggtctat tcttttgatt  360
tataagggat tttgccgatt tcggcctatt ggttaaaaaa tgagctgatt taacaaaaat  420
ttaacgcgaa ttttaacaaa atattaacgc ttacaatttc cattcgccat tcaggctgcg  480
caactgttgg gaagggcgat cggtgcgggc ctcttcgcta ttacgccagc tggcgaaagg  540
gggatgtgct gcaaggcgat taagttgggt aacgccaggg ttttcccagt cacgacgttg  600
taaaacgacg gccagtgagc gcgccctagt tattaatagt aatcaattac ggggtcatta  660
gttcatagcc catatatgga gttccgcgtt acataactta cggtaaatgg cccgcctggc  720
tgaccgccca acgacccccg cccattgacg tcaataatga cgtatgttcc catagtaacg  780
ccaataggga ctttccattg acgtcaatgg gtggagtatt tacggtaaac tgcccacttg  840
gcagtacatc aagtgtatca tatgccaagt acgcccccta ttgacgtcaa tgacggtaaa  900
tggcccgcct ggcattatgc ccagtacatg accttatggg actttcctac ttggcagtac  960
atctacgtat tagtcatcgc tattaccatg gtgatgcggt tttggcagta catcaatggg  1020
cgtggatagc ggtttgactc acggggattt ccaagtctcc accccattga cgtcaatggg  1080
agtttgtttt ggcaccaaaa tcaacgggac tttccaaaat gtcgtaacaa ctccgcccca  1140
ttgacgcaaa tgggcggtag gcgtgtacgg tgggaggtct atataagcag agctctctgg  1200
ctaactagag aacccactgc ttactggctt atcgaaatta atacgactca ctatagggag  1260
acccaagctg gctagattaa gcgtctgatg agtccgtgag gacgaaaccc ggcgtaccgg  1320
gtcacgctta acaaccagat caaagaaaaa acagacattg tcaattgcaa agcaaaaatg  1380
taacacccct acaatggatg ccgacaagat tgtattcaaa gtcaataatc aggtggtctc  1440
tttgaagcct gagattatcg tggatcaata tgagtacaag taccctgcca tcaaagattt  1500
gaaaaagccc tgtataaccc taggaaaggc tcccgattta aataaagcat acaagtcagt  1560
tttgtcaggc atgagcgccg ccaaacttaa tcctgacgat gtatgttcct atttggcagc  1620
ggcaatgcag tttttgagg ggcatgtcc ggaagactgg accagctatg gaattgtgat  1680
tgcacgaaaa ggagataaga tcaccccagg ttctctggtg gagataaaac gtactgatgt  1740
agaagggaat tgggctctga caggaggcat ggaactgaca agagacccca ctgtccctga  1800
gcatgcgtcc ttagtcggtc ttctcttgag tctgtatagg ttgagcaaaa tatccgggca  1860
aaacactggt aactataaga caaacattgc agacaggata gagcagattt ttgagacagc  1920
ccctttgtt aaaatcgtgg aacaccatac tctaatgaca actcacaaaa tgtgtgctaa  1980
ttggagtact ataccaaact tcagattttt ggccggaacc tatgacatgt ttttctcccg  2040
gattgagcat ctatattcag caatcagagt gggcacagtt gtcactgctt atgaagactg  2100
ttcaggactg gtatcattta ctgggttcat aaaacaaatc aatctcaccg ctagagaggc  2160
aatactatat ttcttccaca agaactttga ggaagagata agaagaatgt ttgagccagg  2220
gcaggagaca gctgttcctc actcttattt catccacttc cgttcactag gcttgagtgg  2280
gaaatctcct tattcatcaa atgctgttgg tcacgtgttc aatctcattc actttgtagg  2340
atgctatatg ggtcaagtca gatccctaaa tgcaacggtt attgctgcat gtgctcctca  2400
tgaaatgtct gttctagggg gctatctggg agaggaattc ttcgggaaag ggacatttga  2460
aagaagattc ttcagagatg agaaagaact tcaagaatac gaggcggctg aactgacaaa  2520
gactgacgta gcactggcag atgatggaac tgtcaactct gacgacgagg actacttttc  2580
aggtgaaacc agaagtccgg aggctgttta tactcgaatc atgatgaatg gaggtcgact  2640
aaagagatct cacatacgga gatatgtctc agtcagttcc aatcatcaag cccgtccaaa  2700
ctcattcgcc gagtttctaa acaagacata ttcgagtgac tcataacatg aaaaaaacta  2760
acacccctcc cgtacgccac catgttcgtg tttctggtgc tgctgcctct ggtgagctcc  2820
cagtgcgtga acctgaccac aaggacccag ctgccccctg cctataccaa ttccttcaca  2880
cggggcgtgt actatcccga caaggtgttc cggagcagcg tgctgcactc cacacaggat  2940
ctgtttctgc ctttctttc taacgtgacc tggttccacg ccatccacgt gagcggcacc  3000
aatggcacaa agcggttcga caatccagtg ctgcccttta acgatggcgt gtacttcgcc  3060
tccaccgaga agtctaacat catcagaggc tggatctttg gcaccacact ggacagcaag  3120
acacagtccc tgctgatcgt gaacaatgcc accaacgtgg tcatcaaggt gtgcgagttc  3180
```

```
cagttttgta atgatccatt cctgggcgtg tactatcaca agaacaataa gtcttggatg   3240
gagagcgagt ttcgcgtgta ttcctctgcc aacaattgca catttgagta cgtgtcccag   3300
cccttcctga tggacctgga gggcaagcag ggcaatttca agaacctgag ggagttcgtg   3360
tttaagaata tcgatggcta cttcaaaatc tactccaagc acaccccaat caacctggtg   3420
cgcgacctgc cacagggctt ctctgccctg gagccactgg tggatctgcc catcggcatc   3480
aacatcaccc ggtttcagac actgctggcc ctgcacagaa gctacctgac accaggcgac   3540
agctcctctg gatggaccgc aggagcagca gcctactatg tgggctatct gcagcccagg   3600
accttcctgc tgaagtacaa cgagaatggc accatcacag acgccgtgga ttgcgccctg   3660
gatccctgt ctgagaccaa gtgtacactg aagagcttta ccgtggagaa gggcatctat   3720
cagacaagca atttcagggt gcagcctacc gagtccatcg tgcgctttcc caatatcaca   3780
aacctgtgcc cttttggcga ggtgttcaac gcaacccgct cgccagcgt gtacgctgg    3840
aataggaagc gcatctccaa ctgcgtggcc gactattctg tgctgtacaa cagcgcctcc   3900
ttctctacct ttaagtgcta tggcgtgagc cccacaaagc tgaatgacct gtgctttacc   3960
aacgtgtacg ccgattcctt cgtgatcagg ggcgacgagg tcgccagat cgcaccagga    4020
cagacaggca agatcgcaga ctacaattat aagctgcctg acgatttcac cggctgcgtg   4080
atcgcctgga actctaacaa tctggatagc aaagtgggcg gcaactacaa ttatctgtac   4140
cggctgtttta gaaagtctaa tctgaagcca ttcgagaggg acatctccac agaaatctac   4200
caggccggct ctaccccctg caatggcgtg gagggcttta actgttattt ccctctgcag   4260
agctacggct tccagccaac aaacggcgtg ggctatcagc cctaccgcgt ggtggtgctg   4320
tcttttgagc tgctgcacgc acctgcaaca gtgtgcggac caagaagag caccaatctg    4380
gtgaagaaca agtgcgtgaa cttcaacttc aacgactga ccggaacagg cgtgctgacc    4440
gagtccaaca agaagttcct gccttttcag cagttcggca ggacatcgcc agataccaca   4500
gacgccgtgc gcgaccctca gaccctggag atcctggaca tcacaccatg ctccttcggc   4560
ggcgtgtctg tgatcacacc aggcaccaat acaagcaacc aggtggccgt gctgtatcag   4620
gacgtgaatt gtaccgaggt gccagtggca atccacgcag atcagctgac ccctacatgg   4680
cgggtgtact ctaccggcag caacgtgttc cagacaagg ccggatgcct gatcggagca    4740
gagcacgtga acaatagcta tgagtgcgca atccctatcg gcgccggcat ctgtgcctcc   4800
taccagaccc agacaaactc cccaaggtct gtgggagatg aggccgaaga ctttgtggaa   4860
gtccacctgc ctgatgtgca taaccaggtg tctggcgtcg acctgggact gccaaattgg   4920
ggcaagtacg tgctgctgag tgctgctgca ctgactgccc tgatgctgat cattttcctg   4980
atgacctgct gtcggcgcgt gaacagaagt gagcccactc agcacaatct gcgaggaacc   5040
gggagagaag tgtcagtcac acctcagagc gggaaaatca ttagtagttg ggaatcacat   5100
aaaagcgggg gcgagaccag gctgtgagct agccatgaaa aaaactaaca cccctccttt   5160
cgaaccatcc caaacatgag caagatcttt gtcaatccta gtgctattag agccggtctg   5220
gccgatcttg agatggctga agaaactgtt gatctgatca atagaaatat cgaagacaat   5280
caggctcatc tccaagggga acccatagag gtggacaatc tccctgagga tatggggcga   5340
cttcacctgg atgatggaaa atcgcccaac catggtgaga tagccaaggt gggagaaggc   5400
aagtatcgag aggactttca gatggatgaa ggagaggatc ctagcttcct gttccagtca   5460
tacctggaaa atgttggagt ccaaaatagtc agacaaatga ggtcaggaga gagatttctc   5520
aagatatggt cacagaccgt agaagagatt atatcctatg tcgcggtcaa cttttcccaac   5580
cctccaggaa agtcttcaga ggataaaatca acccagacta ctggccgaga gctcaagaag   5640
gagacaacac ccactcctcc tcagagagaa agccaatcat cgaaagccag gatggcggct   5700
caaattgctt ctggccctcc agcccttgaa tggtcggcta ccaatgaaga ggatgatctca   5760
tcagtggagg ctgagatcgc tcaccagatt gcagaaagtt tctccaaaaa atataagttt   5820
ccctctcgat cctcagggat acttctgtat aattttgagc aattgaaaat gaaccttgat   5880
gatatagtta aagaggcaaa aaatgtacca ggtgtgaccc gtttagccca tgacgggtcc   5940
aaactccccc taagatgtgt actgggatgg gtcgcttttg ccaactctaa gaaattccag   6000
ttgttagtcg aatccgacaa gctgagtaaa atcatgcaag atgacttgaa tcgctataca   6060
tcttgctaac cgaacctctc ccctcagtcc ctctagacaa taaaatccga gatgtcccaa   6120
agtcaacatg aaaaaaacag gcaacaccac tgataaaatg aacctcctac gtaagatagt   6180
gaaaaaccgc agggacgagg acactcaaaa atcctctccc gcgtcagccc ctctggatga   6240
cgatgacttg tggcttccac cccctgaata cgtcccgctg aaagaactta caggcaagaa   6300
gaacatgagg aacttttgta tcaacgaagg ggttaaagtg tgtagccga atggttactc   6360
gttcaggatc ctgcggcaca ttctgaaatc attcgacgag atatattctg ggaatcatag   6420
gatgatcggg ttagtcaaag tggttattgg actggctttg tcaggatctc cagtccctga   6480
gggcctgaac tgggtataca aattgaggag aacctttatc ttccagtggg ctgattccaa   6540
gggccctctt gaaggggagg agttggaata ctctcaggag atcacttggg atgatgatac   6600
tgagttcgtc ggattgcaaa taagagtgat tgcaaaacag tgtcatatcc agggcagagt   6660
ctggtgtatc aacatgaacc cgagagcatg tcaactatgg tctgacatgt ctcttcagac   6720
acaaaggtcc gaagaggaca aagattcctc tctgcttcta gaataatcag attatatccc   6780
gcaaatttat cacttgttta cctctggagg agagaacata tgggctcaac tccaaccctt   6840
gggagcaata taacaaaaaa catgttatgg tgccattaaa ccgctgcatt tcatcaaagt   6900
caagttgatt acctttacat tttgatcctc ttggatgtga aaaaaactat taacatccct   6960
caaaagaccc cgggaaagat ggttcctcag gctctcctgt ttgtaccct tctggttttt   7020
ccattgtgtt ttgggaaatt ccctatttac acgataccag acaagcttgg tccctggagt   7080
ccgattgaca tacatcacct cagctgccca acaatttgg tagtggagga cgaaggatgc    7140
accaacctgt cagggttctc ctacatggaa cttaaagttg gatacatctt agccataaaa   7200
gtgaacgggt tcacttgcac aggcgttgtg acggaggctg aaacctacac taacttcgtt   7260
ggttatgtca caaccacgtt caaaagaag catttcggct caacaccaga tgcatgtaga   7320
gccgcgtaca actggaagat ggccggtgac cccagatatg aagagtctct acacaatccg   7380
taccctgact accgctggct tcgaactgta aaaaccacca aggagtctct cgttatcata   7440
tctccaagtg tggcagattt ggacccatat gacagatccc ttcactcgag ggtcttccct   7500
agcgggaagt gctcaggagt agcggtgtct tctacctact gctccactaa ccacgattac   7560
accatttgga tgcccgagaa tccgagacta gggatgtagt gtgacatttt taccaatagt   7620
agagggaaga gagcatccaa agggagtgag acttgcggct ttgtagatga aagaggccta   7680
tataagtctt taaaggagc atgcaaactc aagttatgtg gagttctagg acttagactt   7740
atggatggaa catgggtctc gatgcaaaca tcaaatgaaa ccaaatggtg ccctcccgat   7800
aagttggtga acctgcacga ctttcgctca gacgaaattg agcaccttgt tgtagaggag   7860
ttggtcagga agagagagga gtgtctggat gcactagagt ccatcatgac aaccaagtca   7920
```

```
gtgagtttca gacgtctcag tcatttaaga aaacttgtcc ctgggtttgg aaaagcatat    7980
accatattca acaagacctt gatggaagcc gatgctcact acaagtcagt cgagacttgg    8040
aatgagatcc tcccttcaaa agggtgttta agagttgggg ggaggtgtca tcctcatgtg    8100
aacgggtgt ttttcaatgg tataatatta ggacctgacg gcaatgtctt aatcccagag    8160
atgcaatcat ccctcctcca gcaacatatg gagttgttga aatcctcggt tatccccctt    8220
gtgcaccccc tggcagaccc gtctaccgtt ttcaaggacg gtgacgaggc tgaggatttt    8280
gttgaagttc accttcccga tgtgcacaat caggtctcag gagttgactt gggtctcccg    8340
aactgggga agtatgtatt actgagtgca ggggccctga ctgccttgat gttgataatt    8400
ttcctgatga catgttgtag aagagtcaat cgatcagaac ctacgcaaca caatctcaga    8460
gggacaggga gggaggtgtc agtcactccc caaagcggga agatcatatc ttcatgggaa    8520
tcacacaaga gtggggtga gaccagactg taattaatta acgtcctttc aacgatccaa    8580
gtccatgaaa aaaactaaca cccctcccgt acctagctta taaagtgctg ggtcatctaa    8640
gcttttcagt cgagaaaaaa acattagatc agaagaacaa ctggcaacac ttctcaacct    8700
gagacttact tcaagatgct cgatcctgga gaggtctatg atgaccctat tgacccaatc    8760
gagttagagg ctgaacccag aggaaccccc attgtcccca acatcttgag gaactctgac    8820
tacaatctca actctccttt gatagaagat cctgctagac taatgttaga atggttaaaa    8880
acagggaata gaccttatcg gatgactcta acagacaatt gctccaggtc tttcagagtt    8940
ttgaaagatt atttcaagaa ggtagatttg ggttctctca aggtgggcgg aatgctgca    9000
cagtcaatga tttctctctg gttatatggt gcccactctg aatccaacag gagccggaga    9060
tgtataacag acttggccca tttctattcc aagtcgtccc ccatagagaa gctgttgaat    9120
ctcacgctag gaaatagagg gctgagaatc cccccagagg gagtgttaag ttgccttgag    9180
aggggttgatt atgataatgc attttggaagg tatcttgtca acacgtattc ctcttacttg    9240
ttcttccatg taatcacctt atacatgaac gccctagact gggatgaaga aaagaccatc    9300
ctagcattat ggaaagattt aacctcagtg gacatcggga aggacttggt aaagttcaaa    9360
gaccaaatat ggggactgct gatcgtgaca aaggactttg tttactccca aagttccaat    9420
tgtcttttttg acagaaacta cacacttatg ctaaaagatc ttttcttgtc tcgcttcaac    9480
tccttaatgg tcttgctctc tcccccagag ccccgatact cagatgactt gatatctcaa    9540
ctatgccagc tgtacattgc tggggatcaa gtcttgtcta tgtgtggaaa ctccggctat    9600
gaagtcatca aaatattgga gccatatgtc gtgaatagtt tagtccagag agcagaaaag    9660
tttaggcctc tcattcattc cttgggagac tttcctgtat ttataaaaga caaggtaagt    9720
caacttgaag agacgttcgg tccctgtgca agaaggttct ttagggctct ggatcaattc    9780
gacaacatac atgactggt ttttgtgttt ggctgttaca ggcattgggg gcacccatat    9840
atagattatc gaaagggtct gtcaaaacta tatgatcagg ttcaccttaa aaaaatgata    9900
gataagtcct accaggagtg cttagcaagc gacctagcca ggaggatcct tagatggggt    9960
tttgataagt actccaagtg gtatctggat tcaagattcc tagcccgaga ccaccccttg   10020
actccttata tcaaaaccca aacatggcca cccaaacata ttgtagactt ggtggggat   10080
acatggcaca agctcccgat cacgcagatc tttgagattc ctgaatcaat ggatccgtca   10140
gaaatattgg atgacaaatc acattctttc accagaacga gactagcttc ttggctgtca   10200
gaaaaccgag gggggcctgt tcctagcgaa aagttatta tcacggccct gtctaagccg   10260
cctgtcaatc cccgagagtt tctgaggtct atagaccteg gaggattgcc agatgaagac   10320
ttgataattg gcctcaagcc aaaggaacgg gaattgaaga ttgaaggtcg atttctttgct   10380
ctaatgtcat ggaatctaag attgtattt gtcatcactg aaaaactctt ggccaactac   10440
atcttgccac tttttgacgc gctgactatg acagcaacc tgaacaaggt gtttaaaaag   10500
ctgatcgaca gggtcaccgg gcaaggcctt ttggactatt caagggtcac atatgcattt   10560
cacctgact atgaaaagtg gaacaaccat caaagattag agtcaacaga ggatgtattt   10620
tctgtcctag atcaagtgtt tggattgaag agagtgtttt ctagaacaca cgagtttttt   10680
caaaaggcct ggatctatta ttcagacaga tcagacctca tcgggttacg ggaggatcaa   10740
atatactgct tagatgcgtc caacggccca acctgttgga atggccagga tggcgggcta   10800
gaaggcttac ggcagaaggg ctggagtcta gtcagcttat tgatgataga tagagaatct   10860
caaatcagga acacaagaac caaaatacta gctcaaggag acaaccaggt tttatgtccg   10920
acatacatgt tgtcgccagg gctatctcaa gaggggctcc tctatgaatt ggagagaata   10980
tcaaggaatg cactttcgat atacagagcc gtcgaggaag gggcatctaa gctagggctg   11040
atcatcaaga aagaagagac catgtgtagt tatgacttcc tcatctatgg aaaaaccccct   11100
ttgtttagag gtaacatatt ggtgcctgag tccaaaagat gggccagagt ctcttgcgtc   11160
tctaatgacc aaatagtcaa cctcgccaat ataatgctga cagtgtccac caatgcgcta   11220
acagtggcac aacactctca atctttgatc aaaccgatga gggattttct gctcatgtca   11280
gtacaggcag tctttcacta cctgctattt agcccaatct aaagggaag agtttacaag   11340
attctgagcg ctgaagggga gagctttctc ctagccatgt caaggataat ctatctagat   11400
ccttcttttgg gagggatatc tggaatgtcc ctcggaagat tccatatacg acagttctca   11460
gaccctgtct ctgaagggt atccttctgg agagaatct ggttaagctc caagagtcc   11520
tggattcacg cgttgtgtca agaggctgga aacccagatc ttggagagag aacactcgag   11580
agcttcactc gccttctaga agatccgacc accttaaata tcagaggagg ggccagtcct   11640
accattctac tcaaggatgc aatcagaaag gcttatatg acgaggtgga caaggtggaa   11700
aattcagagt ttcgagaggc aatcctgttg tccaagaccc atagagataa ttttatactc   11760
ttcttaatat ctgttgagcc tctgtttcct cgatttctca gtgagctatt cagttcgtct   11820
tttttgggaa tccccgagtc aatcattgga ttgatacaaa actcccgaac gataagaagg   11880
cagtttagaa agagtctctc aaaaactta gaagaatcct tctacaactc agagatccac   11940
gggattagtc ggatgaccca gacacctcag agggttgggg gggtgtggcc ttgctcttca   12000
gagagggcag atctacttag ggagatctct tgggaagaa aagtggtagg cacgacagtt   12060
cctcacccttt ctgagatgtt gggattactt cccaagtcct ctatttcttg cacttgtgga   12120
gcaacaggag gaggcaatcc tagagttct gtatcagtac tcccgtcctt tgatcagtca   12180
ttttttcac gaggccccct aaagggatac ttgggctcgt ccacctctat gtcgacccag   12240
ctattccatg catgggaaaa agtcactaat gttcatgtgg tgaagagagc tctatcgtta   12300
aaagaatcta taaactggtt cattactaga gattccaatc tggctcaagc tctaattagg   12360
aacattatgt ctctgacagg ccctgatttc cctctagagg aggcccctgt cttcaaaagg   12420
acggggtcag ccttgcatag gttcaagtct gccagataca gcgaaggagg gtattcttct   12480
gtctgcccga acctcctctc tcatatttct gttagtacag acaccatgtc tgatttgacc   12540
caagacggga agaactacga tttcatgttc cagccattga tgcttatgc acagacatgg   12600
acatcagagc tggtacagag agacacaagg ctaagagact ctacgtttca ttggcacctc   12660
```

```
cgatgcaaca ggtgtgtgag acccattgac gacgtgaccc tggagacctc tcagatcttc   12720
gagtttccgg atgtgtcgaa aagaatatcc agaatggttt ctgggctgt gcctcacttc    12780
cagaggcttc ccgatatccg tctgagacca ggagattttg aatctctaag cggtagagaa   12840
aagtctcacc atatcggatc agctcagggg ctcttatact caatcttagt ggcaattcac   12900
gactcaggat acaatgatgg aaccatcttc cctgtcaaca tatacggcaa ggtttcccct   12960
agagactatt tgagagggct cgcaagggga gtattgatag gatcctcgat ttgcttcttg   13020
acaagaatga caaatatcaa tattaataga cctcttgaat tggtctcagg ggtaatctca   13080
tatattctcc tgaggctaga taaccatccc tccttgtaca taatgctcag agaaccgtct   13140
cttagaggag agatattttc tatccctcag aaaatccccg ccgcttatcc aaccactatg   13200
aaagaaggca acagatcaat cttgtgttat ctccaacatg tgctacgcta tgagcgagag   13260
ataatcacgg cgtctccaga gaatgactgg ctatggatct tttcagactt tagaagtgcc   13320
aaaatgacgt acctatccct cattacttac cagtctcatc ttctactcca gagggttgag   13380
agaaacctat ctaagagtat gagagataac ctgcgacaat tgagttcttt gatgaggcag   13440
gtgctgggcg ggcacggaga agataccttg agtcagacg acaacattca acgactgcta   13500
aaagactctt tacgaaggac aagatggggt gatcaagagg tgcgccatgc agctagaacc   13560
atgactggag attacagccc caacaagaag gtgtcccgta aggtaggatg ttcagaatgg   13620
gtctgctctg ctcaacaggt tgcagtctct acctcagcaa accggcccc tgtctcggag    13680
cttgacataa gggccctctc taaggagttc cagaacccct tgatctcggg cttgagagtg   13740
gttcagtggg caaccggtgc tcattataag cttaagccta ttctagatga tctcaatgtt   13800
ttcccatctc tctgccttgt agttggggac gggtcagggg ggatatcaag ggcagtcctc   13860
aacatgtttc cagatgccaa gcttgtgttc aacagtcttt tagaggtgaa tgacctgatg   13920
gcttccggaa cacatccact gcctccttca gcaatcatga tgatatcgtc                13980
tccagagtga tagatcttga ctcaatctgg gaaaaaccgt ccgacttgag aaacttggca   14040
acctggaaat acttccagtc agtccaaaag caggtcaaca tgtcctatga cctcattatt   14100
tgcgatgcag aagttactga cattgcatct atcaaccgga tcaccctgtt aatgtccgat   14160
tttgcattgt ctatagatgg ccactctat ttggtcttca aaacttatgg gactatgcta   14220
gtaaatccaa actacaaggc tattcaacac ctgtcaagag cgttcccctc ggtcacaggg   14280
tttatcaccc aagtaacttc gtcttttttca tctgagctct acctccgatt ctccaaacga   14340
gggaagtttt tcagagatgc tgagtacttg acctcttcca cccttcgaga aatgagcctt   14400
gtgttattca attgtagcag ccccaagagt gagatgcaga gagctcgttc cttgaactat   14460
caggatcttg tgagaggatt tcctgaagaa atcatatcaa atccttacaa tgagatgatc   14520
ataactctga ttgacagtga tgtagaatct tttctagtcc acaagatggt tgatgatctt   14580
gagttacaga ggggaactct gtctaaagtg gctatcatta tagccatcat gatagttttc   14640
tccaacagag tcttcaacgt ttccaaaccc ctaactgacc cctcgttcta tccaccgtct   14700
gatcccaaaa tcctgaggca cttcaacata tgttgcagta ctatgatgta tctatctact   14760
gctttaggtg acgtccctag cttcgcaaga cttcacgacc tgtataacag acctataact   14820
tattacttca gaaagcaagt cattcgaggg aacgtttatc tatcttggag ttggtccaac   14880
gacacctcag tgttcaaaag ggtagcctgt aattctagcc tgagtctgtc atctcactgg   14940
atcaggttga tttacaagat agtgaagact accagactcg ttggcagcat caaggatca   15000
tccagagaag tggaaagaca ccttcatagg tacaacaggg ggatcaccct agaggatatc   15060
agatctagat catccctact agactacagt tgcctgtgaa ccggatactc ctggaagcct   15120
gcccatgcta agactcttgt gtgatgtatc ttgaaaaaaa caagatccta aatctgaacc   15180
tttggttgtt tgattgtttt tctcattttt gttgtttatt tgttaagcgt gggtcggcat   15240
ggcatctcca cctcctcgcg gtccgacctg ggcatccgaa ggaggacgca cgtccactcg   15300
gatggctaag ggagagccag aaggatccgg ctgctaacaa agcccgaaag gaagctgagt   15360
tggctgctgc caccgctgag caataactag cataaccct tggggcctct aaacgggtct    15420
tgagggtttt tttgctgaaa gtcgcgcttg gcgtaatcat ggtcatagct gtttcctgtg   15480
tgaaattgtt atccgctcac aattccacac aacatacgag ccggaagcat aaagtgtaaa   15540
gcctggggtg cctaatgagt gagctaactc acattaattg cgttgcgctc actgcccgct   15600
ttccagtcgg gaaacctgtc gtgccagctg cattaatgaa tcggccaacg cgcgggggaga   15660
ggcggtttgc gtattgggcg ctcttacgct tcctcgctca ctgactcgct gcgctcgtca   15720
gttcggctgc ggcgagcggt atcagctcac tcaaaggcgg taatacggtt atccacagaa   15780
tcaggggata acgcaggaaa gaacatgtga gcaaaaggcc agcaaaaggc caggaaccgt   15840
aaaaaggccg cgttgctggc gtttttccat aggctccgcc cccctgacga gcatcacaaa   15900
aatcgacgct caagtcagag gtggcgaaac ccgacaggac tataaagata ccaggcgttt   15960
ccccctggaa gctccctcgt gcgctctcct gttccgaccc tgccgcttac cggatacctg   16020
tccgcctttc tcccttcggg aagcgtggcg ctttctcata gctcacgctg taggtatctc   16080
agttcggtgt aggtcgttcg ctccaagctg ggctgtgtgc acgaaccccc cgttcagccc   16140
gaccgctgcg ccttatccgg taactatcgt cttgagtcca acccggtaag acacgactta   16200
tcgccactgg cagcagccac tggtaacagg attagcagag cgaggtatgt aggcggtgct   16260
acagagttct tgaagtggtg gcctaactac ggctacacta aaggacagt atttggtatc    16320
tgcgctctgc tgaagccagt taccttcgga aaaagagttg gtagctcttg atccggcaaa   16380
caaaccaccg ctggtagcgg tggtttttt gtttgcaagc agcagattac gcgcagaaaa   16440
aaaggatctc aagaagatcc tttgatcttt tctacggggt ctgacgctca gtggaacgaa   16500
aactcacgtt aagggatttt ggtcatgaga ttatcaaaaa ggatcttcac ctagatcctt   16560
ttaaattaaa aatgaagttt taaatcaatc taaagtatat atgagtaaac ttggtctgac   16620
agttaccaat gcttaatcag tgaggcacct atctcagcga tctgtctatt tcgttcatcc   16680
atagttgcct gactccccgt cgtgtagata actacgatac gggagggctt accatctggc   16740
cccagtgctg caatgatacc gcgagaccca cgctcaccgg ctccagattt atcagcaata   16800
aaccagccag ccggaagggc cgagcgcaga agtggtcctg caactttatc cgcctccatc   16860
cagtctatta attgttgccg ggaagctaga gtaagtagtt cgccagttaa tagtttgcgc   16920
aacgttgttg ccattgctac aggcatcgtg gtgtcacgct cgtcgtttgg tatggcttca   16980
ttcagctccg gttcccaacg atcaaggcga gttacatgat ccccccatgtt gtgcaaaaaa   17040
gcggttagct ccttcggtcc tccgatcgtt gtcagaagta agttggccgc agtgttatca   17100
ctcatggtta tggcagcact gcataattct cttactgtca tgccatccgt aagatgcttt   17160
tctgtgactg gtgagtactc aaccaagtca ttctgagaat agtgtatgcg gcgaccgagt   17220
tgctcttgcc cggcgtcaat acgggataat accgcgccac atagcagaac tttaaaagtg   17280
ctcatcattg gaaaacgttc ttcggggcga aaactctcaa ggatcttacc gctgttgaga   17340
tccagttcga tgtaacccac tcgtgcaccc aactgatctt cagcatcttt tactttcacc   17400
```

```
agcgtttctg ggtgagcaaa acaggaagg caaaatgccg caaaaaaggg aataagggcg    17460
acacggaaat gttgaatact catactcttc cttttttcaat attattgaag catttatcag   17520
ggttattgtc tcatgagcgg atacatattt gaatgtattt agaaaaataa acaaataggg    17580
gttccgcgca catttccccg aaaagtgcca c                                   17611

SEQ ID NO: 3           moltype = DNA  length = 22946
FEATURE                Location/Qualifiers
misc_feature           1..22946
                       note = MV-coWuhan-S Position 2
source                 1..22946
                       mol_type = other DNA
                       organism = synthetic construct
SEQUENCE: 3
ggacgcgccc tgtagcggcg cattaagcgc ggcgggtgtg gtggttacgc gcagcgtgac    60
cgctacactt gccagcgccc tagcgcccgc tcctttcgct ttcttccctt cctttctcgc   120
cacgttcgcc ggctttcccc gtcaagctct aaatcggggg ctccctttag ggttccgatt   180
tagtgcttta cggcacctcg accccaaaaa acttgattag ggtgatggtt cacgtagtgg   240
gccatcgccc tgatagacgg ttttcgccc tttgacgttg gagtccacgt tctttaatag    300
tggactcttg ttccaaactg gaacaacact caacccctatc tcggtctatt cttttgattt   360
ataagggatt tgccgatttt cggcctattg gttaaaaaat gagctgattt aacaaaaatt    420
taacgcgaat tttaacaaaa tattaacgtt tacaatttcg cgccattcgc cattcaggct    480
gcgcaactgt tgggaagggc gatcggtgcg ggcctcttcg ctattacgcc agctggcgaa    540
aggggggatgt gctgcaaggc gattaagttg ggtaacgcca gggttttccc agtcacgacg    600
ttgtaaaacg acggccagtg cgcgccgtta atacgactca ctatagggag acccaagctg    660
gctagctttg tttggtctga tgagtcccgt gaggacgaaa cccggcgtac cgggtcacca    720
aacaagttg ggtaaggata gttcaatcaa tgatcatctt ctagtgcact taggattcaa     780
gatcctatta tcaggacaa gagcaggatt agggatatcc gagatggcca cacttttaag     840
gagcttagca ttgttcaaaa gaacaagga caaaccaccc attacatcag gatccggtgg     900
agccatcaga ggaatcaaac acattattat agtaccaatc cctggagatt cctcaattac    960
cactcgatcc agacttctgg accggttggt gaggttaatt ggaaacccgg atgtgagcgg   1020
gcccaaacta acaggggcac taataggtat attatcctta tttgtggagt ctccaggtca   1080
attgattcag aggatcaccg atgaccctga cgttagcata aggctgttag aggttgtcca   1140
gagtgaccag tcacaatctg gccttacctt cgcatcaaga ggtaccaaca tggaggatga   1200
ggcggaccaa tacttttcac atgatgatcc aattagtagt gatcaatcca ggttcggatg   1260
gttcgggaac aaggaaatct cagatattga agtgcaagac cctgagggat tcaacatgat   1320
tctgggtacc atcctagccc aaatttgggc cttgctcgca aaggcggtta cggcccaga    1380
cacggcagct gattcggagc taagaaggtg ataaagtac acccaacaaa gaagggtagt    1440
tggtgaattt agattggaga gaaaatggtt ggatgtggtg aggaacagga ttgccggagga   1500
cctctcctta cgccgattca tggtcgctct aatcctggat atcaagagaa caccggaaa    1560
caaacccagg attgctgaaa tgatatgtga cattgataca tatatcgtag aggcaggatt    1620
agccagtttt atcctgacta ttaagtttgg gatagaaact atgtatcctg ctcttggact   1680
gcatgaattt gctggtgagt tatccacact tgagtccttg atgaacctt accagcaaat     1740
ggggaaact gcaccctaca tggtaatcct ggagaactca attcagaaca agttcagtgc    1800
aggatcatac cctctgctct ggagctatgc catgggagta ggagtggaac ttgaaaactc   1860
catgggaggt ttgaactttg gccgatctta ctttgatcca gcatattta gattagggca    1920
agagatggta aggaggtcag ctggaaaggt cagttccaca ttggcatctg aactcggtat    1980
cactgccgag gatgcaaggc ttgtttcaga gattgcaatg catactactg aggacaagat    2040
cagtagagcg gttggacccca gacaagccca agtatcattt ctacacgtg atcaaagtga    2100
gaatgagcta ccgagattgg ggggcaagga agataggagg gtcaaacaga gtcgaggaga   2160
agccaggag agctacagag aaaccgggcc cagcagagca agtgatgcga gagctgccca    2220
tcttccaacc ggcacacccc tagacattga cactgcaacg gagtccagcc aagatccgca   2280
ggacagtcga aggtcagctg acgccctgct taggctgcaa gccatggcag gaatctcgga    2340
agaacaaggc tcagacacgg acaccccctat agtgtacaat gacagaaatc ttctagacta   2400
ggtgcgagag gccgagggcc agaacaacat ccgcctacca tccatcattg ttataaaaaa   2460
cttaggaacc aggtccacac agagtgatac gcgtacgcca ccatgttcgt gtttctggtg    2520
ctgctgcctc tggtgagctc ccagtgcgtg aacctgacca aaggaccca gctgcccct    2580
gcctatacca attccttcac acgggcgtt tactatcccg acaaggtgtt ccggagcagc    2640
gtgctgcact ccacacagga tctgtttctg ccttttcttt ctaacgtgac ctggttccac    2700
gccatccacg tgagcggcac caatggcaca aagcggttca acaatccagt gctgcccttt    2760
aacgatggcg tgtacttcgc ctccaccgag aagtctaaca tcatcagagg ctggatcttt    2820
ggcaccacc tggacagcaa gacacagtcc ctgctgatcg tgaacaatgc caccaacgtg    2880
gtcatcaagg tgtgcgagtt ccagtttttgt aatgatccat tcctgggcgt gtactatcac   2940
aagaacaata agtcttggat ggagagcgag tttcgcgtgt attcctctgc caacaattgc    3000
acatttgagt acgtgtccca gcccttcctg atggacctgg agggcaagca gggcaatttc    3060
aagaacctga gggagttcgt gtttaagaat atcgatggc acttcaaaat ctactccaag    3120
cacaccccaa tcaacctggt gcgcgacctg ccacaggct ctctctgccct ggagccactg    3180
gtggatctgc catcggcat caacatcacc cggtttcaga cactgctggc cctgcacaga    3240
agctacctga caccaggcga cagctcctct ggatggaccg caggagcagc agcctactat    3300
gtgggctatc tgcagcccag gaccttcctg ctgaagtaca acgagaatgg caccatcaca    3360
gacgccgtgg attgcgccct ggatcccctg tctgagacca gtgtacact gaagagcttt    3420
accgtgagaa agggcatcta tcagacaagc aatttcaggg tgcagcctac cgagtccatc    3480
gtgcgctttc caatatcac aaacctgtgc ccttttggcg aggtgttcaa cgcaaccgc    3540
ttcgccagcg tgtacgcctg gaataggaag cgcatctcca actgcgtggc cgactattct    3600
gtgctgtaca acagcgcctc cttctctacc tttaagtgct atggcgtgtc ccccacaaag    3660
ctgaatgacc tgtgctttac caacgtgtac gccgattcc tcgtgatcag ggcgacgag    3720
gtgcgccaga tcgcaccagg acagacaggg aagatcgcag actacaatta taagctgcct    3780
gacgatttca ccggctgcgt gatcgcctgg aactctaaca atctggatag caaagtgggc    3840
ggcaactaca attatctgta ccggctgttt agaaagtcta atctgaagcc attcgagagg    3900
gacatctcca cagaaatcta ccaggccggc tctacccccct gcaatggcgt ggagggcttt    3960
```

```
aactgttatt tccctctgca gagctacggc ttccagccaa caaacggcgt gggctatcag    4020
ccctaccgcg tggtggtgct gtcttttgag ctgctgcacg cacctgcaac agtgtgcgga    4080
ccaaagaaga gcaccaatct ggtgaagaac aagtgcgtga acttcaactt caacggactg    4140
accggaacag gcgtgctgac cgagtccaac aagaagttcc tgccttttca gcagttcggc    4200
agggacatcg cagataccac agacgccgtg cgcgaccctc agaccctgga gatcctggac    4260
atcacaccat gctccttcgg cggcgtgtct gtgatcacac caggcaccaa tacaagcaac    4320
caggtggccg tgctgtatca ggacgtgaat tgtaccgagg tgccagtggc aatccacgca    4380
gatcagctga cccctacatg gcgggtgtac tctaccggca gcaacgtgtt ccagacaaga    4440
gccggatgcc tgatcggagc agagcacgtg aacaatagct atgagtgcga catccctatc    4500
ggcgccggca tctgtgcctc ctaccagacc cagacaaact ccccaaggag agcacggtct    4560
gtggccagcc agtccatcat cgcctatacc atgagcctgg gcgccgagaa ttccgtggcc    4620
tactccaaca attctatcgc catccctacc aacttcacaa tctccgtgac cacagagatc    4680
ctgccagtga gcatgaccaa gacatccgtg gactgcacaa tgtatatctg tggcgattcc    4740
accgagtgct ctaacctgct gctgcagtac ggctcttttt gtacccagct gaatagagcc    4800
ctgacaggca tcgccgtgga gcaggacaag aacacacagg aggtgttcgc ccaggtgaag    4860
caaatctaca agaccccacc catcaaggac tttggcggct tcaacttcag ccagatcctg    4920
cccgatccta gcaagccatc caagcggtct tttatcgagg acctgctgtt caacaaggtg    4980
accctggccg atgccggctt catcaagcag tatggcgatt gcctgggcga catcgccgcc    5040
agagacctga tctgtgccca gaagtttaat ggcctgaccg tgctgcctcc actgctgaca    5100
gatgagatga tcgcccagta cacatctgcc ctgctggccg gaaccatcac aagcggatgg    5160
accttcggcg caggagccgc cctgcagatc ccctttgcca tgcagatggc ctatcggttc    5220
aacggcatcg gcgtgaccca gaatgtgctg tacgagaacc agaagctgat cgccaatcag    5280
tttaactccg ccatcggcaa gatccaggac tctctgagct ccacagccag cgccctgggc    5340
aagctgcagg atgtggtgaa tcagaacgcc caggccctga ataccctggt gaagcagctg    5400
tctagcaact tcggcgccat ctcctctgtg ctgaatgaca tcctgagccg gctggacaag    5460
gtggaggcag aggtgcagat cgaccggctg atcacaggca gactgcagtc cctgcagacc    5520
tacgtgacac agcagctgat cagggcagca gagatcaggg cctctgccaa tctggccgga    5580
accaagatga gcgagtgcgt gctgggccag tccaagagag tggactttg tggcaagggc    5640
tatcacctga tgagcttccc acagtccgcc cctcacggag tggtgtttct gcacgtgacc    5700
tacgtgccag cccaggagaa gaacttcacc acagcaccag caatctgcca tgatggcaag    5760
gcacactttc ctaggaggg cgtgttcgtg agcaacggca cccactggtt tgtgacacag    5820
cgcaatttct acgagccaca gatcatcacc acagacaata cattcgtgtc cggcaactgt    5880
gacgtggtca tcggcatcgt gaacaatacc gtgtatgatc tctgcagcc agagctggac    5940
tcttttaagg aggagctgga taagtactc aagaatcaca cagcccga cgtggatctg    6000
ggcgacatct ctggcatcaa tgccagcgtg gtgaacatcc agaaggagt cgacaggctg    6060
aacgaggtgg ccaagaatct gaacgagtcc ctgatcgatc tgcaggagct gggcaagtat    6120
gagcagtaca tcaagtggcc ctggtatatc tggctgggct tcatcgccgg cctgatcgcc    6180
atcgtgatgg tgaccatcat gctgtgctgt atgacaagct gctgttcctg cctgaagggc    6240
tgctgttctt gtggcagctg ctgtaagttt gatgaggacg actctgagcc tgtgctgaag    6300
ggcgtgaagc tgcactacac ctgatagcta gcgatcgcgt gcgagaggcc agaacaacat    6360
ccgcctacca tccatcattg ttataaaaaa cttaggaacc aggtccacac agccgccagc    6420
ccatcaacca tccactccca cgattggagc caatggcaga agagcaggca cgccatgtca    6480
aaaacggact ggaatgcatc cgggctctca aggccgagcc catcggctca ctggccatcg    6540
aggaagctat ggcagcatgg tcagaaatat cagacaaccc aggacaggag cgagccacct    6600
gcagggaaga gaaggcaggc agttcgggtc tcagcaaacc atgcctctca gcaattggat    6660
caactgaagg cggtgcacct cgcatccgcg gtcagggacc tggagagagc gatgacgacg    6720
ctgaaacttt gggaatcccc caagaaatc tccaggcatc aagcactggg ttacagtgtt    6780
attacgttta tgatcacagc ggtgaagcgg ttaagggaat ccaagatgct gactctatca    6840
tggttcaatc aggccttgat ggtgatagca ccctctcagg aggagacaat gaatctgaaa    6900
acagcgatgg ggatattggc gaacctgata ccgagggata tgctatcact gaccggggat    6960
ctgctcccat ctctatgggg ttcagggctt ctgatgttga aactgcagaa ggaggggaaa    7020
tccacgagct cctgagactc caatccagag gcaacaactt tccgaagctt gggaaaactc    7080
tcaatgttcc tcccgccccg gaccccggta gggccagcac ttcgggaca cccattaaaa    7140
agggcacaga cgcgagatta gcctcatttg aacggagat cgcgtctta ttgacaggtg    7200
gtgcaaccca atgtgctcga aagtcaccct cggaaccatc agggccaggt gcacctgcgg    7260
ggaatgtccc cgagtgtgtg agcaatgccg cactgataca ggagtggaca cccgaatctg    7320
gtaccacaat ctccccgaga tcccagaata tgaagaagg gggagactat tatgatgatg    7380
agctgttctc tgatgtccaa gatattaaaa cagccttggc caaaatacac gaggataatc    7440
agaagataat ctccaagcta gaatcactgc tgttattgaa gggagaagtt gagtcaatta    7500
agaagcagat caacaggcaa aatatcagca tatccaccct ggaaggacac ctctcaagca    7560
tcatgatcgc cattcctgga cttgggaagg atcccaacga ccccactgca gatgtcgaaa    7620
tcaatcccga cttgaaaccc atcataggca gagattcagg ccgagcactg gccgaagttc    7680
tcaagaaacc cgttgccagc cgacaactcc aaggaatgac aaatgacgg accagttcca    7740
gaggacagct gctgaaggaa tttcagctaa agccgatcga gaaaaagatg agctcagccg    7800
tcgggtttgt tcctgacacc ggccctgcat cacgcagtgt aatccgctcc attataaat    7860
ccagccggct agaggaggat cggaagcgtt acctgatgac tctccttgat gatatcaaag    7920
gagccaatga tcttgccaag ttccaccaga tgctgatgaa gataataatg aagtagctac    7980
agctcaactt acctgccaac cccatgccag tcgacccacc tagtacaacc taaatccatt    8040
ataaaaaact taggagcaaa gtgattgcct cccaaggtcc acaatgacag agacctacga    8100
cttcgacaag tcggcatggg acatcaaagg gtcgatcgtc ccgatacaac ccaccaccta    8160
cagtgatggc aggctggtgc cccaggtcag agtcatagat cctggtctag cgacaggaa    8220
ggatgaatgc tttatgtaca tgtttctgct ggggtgtt gaggacagcg attccctagg    8280
gcctccaatc gggcagcat ttgggttcct gcccttaggg gttggcagat ccacagcaaa    8340
gcccgaaaaa ctcctcaaag aggcactga gcttgacata gttgttagac gtacagcagg    8400
gctcaatgaa aaactggtgt ctacaacaa caccccacta actctcctca cccttggag    8460
aaaggtccta acaacaggga gtgtcttcaa cgcaaaccaa gtgtcaatg cggttaatct    8520
gataccgctc gatacccgc agaggttccg tgttgtttat atgagcatca cccgtctttc    8580
ggataacggg tattacaccg ttcctagaag aatgctggaa ttcagatcgg tcaatgcagt    8640
ggcctttcaac ctgctggtga cccttaggat tgacaaggcg ataggccctg ggaagatcat    8700
```

```
cgacaataca gagcaacttc ctgaggcaac atttatggtc cacatcggga acttcaggag   8760
aaagaagagt gaagtctact ctgccgatta ttgcaaaatg aaaatcgaaa agatgggcct   8820
ggttttttgca cttggtggga tagggggcac cagtcttcac attagaagca caggcaaaat  8880
gagcaagact ctccatgcac aactcgggtt caagaagacc ttatgttacc cgctgatgga   8940
tatcaatgaa gaccttaatc gattactctg gaggagcaga tgcaagatag taagaatcca   9000
ggcagttttg cagccatcag ttcctcaaga attccgcatt tacgacgacg tgatcataaa   9060
tgatgaccaa ggactattca aagttctgta gaccgtagtg cccagcaatg cccgaaaacg   9120
acccccctca caatgacagc cagaaggccc ggacaaaaaa gcccctccg aaagactcca    9180
cggaccaagc gagaggccag ccagcagccg acggcaagcg cgaacaccag gcggcccac    9240
cacagaacag ccctgacaca aggccaccac cagccacccc aatctgcatc ctcctcgtgg   9300
gaccccccgag gaccaacccc caaggctgcc cccgatccaa accaccaacc gcatcccac    9360
cacccccggg aaagaaaccc ccagcaattg aaggcccct ccccctcttc ctcaacacaa    9420
gaactccaca accgaaccgc acaagcgacc gaggtgaccc aaccgcaggc atccgactcc    9480
ctagacagat cctctctccc cggcaaacta aacaaaactt agggccaagg aacatacaca    9540
cccaacagaa cccagacccc ggccacggc gccgcgcccc caaccccga caaccagagg      9600
gagcccccaa ccaatcccgc cggctccccc ggtgccaca ggcagggaca ccaacccccg      9660
aacagaccca gcacccaacc atcgacaatc caagacgggg gggcccccccc aaaaaaaggc   9720
ccccaggggc cgacagccag caccgcgagg aagcccaccc accccacaca cgaccacggc   9780
aaccaaacca gaaccagac caccctgggc caccagctcc cagactcggc catcacccccg    9840
cagaaaggaa aggccacaac ccgcgcaccc cagcccgat ccggcgggga gccacccaac     9900
ccgaaccagc acccaagagc gatccccgaa ggaccccga accgcaaagg acatcagtat    9960
cccacgcct ctccaagtcc cccggtctcc tcctcttctc gaagggacca aaagatcaat    10020
ccaccacacc cgacgacact caactcccca cccctaaagg agacaccggg aatcccagaa   10080
tcaagactca tccaatgtcc atcatgggtc tcaaggtgaa cgtctctgcc atattcatgg   10140
cagtactgtt aactctccaa acaccaccg gtcaaatcca ttggggcaat ctctctaaga   10200
taggggtggt aggaatagga agtgcaagct acaaagttat gactcgttcc agccatcaat   10260
cattagtcat aaaattaatg cccaatataa ctctcctcaa taactcacg agggtagaga   10320
ttgcagaata caggagacta ctgagaacag ttttggaacc aattagagat gcacttaatg   10380
caatgaccca gaatataaga ccggttcaga gtgtagcttc aagtaggaga cacaagagat   10440
ttgcgggagt agtcctggca ggtgcggccc taggcgttgc cacagctgcc cagataacag   10500
ccggcattgc acttcaccag tccatgctga actctcaagc catcgacaat ctgagagcga   10560
gcctggaaac tactaatcag gcaattgaga caatcagaca agcagggcag gagatgatat   10620
tggctgttca gggtgtccaa gactacatca ataatgagct gataccgtct atgaaccaac   10680
tatcttgtga tttaatcggc cagaagctcg ggctcaaatt gctcgatac tatacagaaa    10740
tcctgtcatt atttggcccc agtttacggg accccatatc tgccgagata tctatccagg   10800
ctttgagcta tgcgcttgga ggagacatca ataaggtgtt agaaaagctc ggatacagtg   10860
gaggtgattc actgggcatc ttagagagcg gaggaataaa ggcccggata actcacgtcg   10920
acacagagtc ctacttcatt gtcctcagta tagcctatcc gacgctgtcc gagattaagg   10980
gggtgattgt ccaccggcta gaggggggtct cgtacaacat aggctctcaa gagtggtata   11040
ccactgtgcc caagtatgtt gcaacccaag ggtaccttat ctcgaatttt gatgagtcat   11100
cgtgtactt catgccagag gggactgtgt gcagccaaaa tgccttgtac ccgatgagtc    11160
ctctgctcca agaatgcctc cgggggtaca ccaagtcctg tgctcgtaca ctcgtatccg   11220
ggtcttttgg gaaccggttc attttatcac aagggaacct aatagccaat tgtgcatcaa   11280
tcctttgcaa gtgttacaca acaggaacga tcattaatca agaccctgac aagatcctaa   11340
catacattgc tgccgatcac tgcccggtag tcgaggtgaa cggcgtgacc atccaagtcg   11400
ggagcaggag gtatccagac gctgtgtact tgcacagaat tgacctcggt cctcccatat   11460
cattggaggg gttggacgta gggacaaatc tgggagatgc aattgctaag ttgaaggatg   11520
ccaaggaatt gttggagtca tcggaccaga tattgaggag tatgaaaggt ttatcgagca   11580
ctagcatagt ctacatcctg attgcagtgt gtcttggagg gttgatagg atccccgctt    11640
taatatgttg ctgcaggggg cgttgtaaca aaaagggaga acaagttggt atgtcaagac   11700
caggcctaaa gcctgatctt acgggaacat caaaatccta tgtaaggtcg ctctgatcct   11760
ctacaactct tgaaacacaa atgtcccaca agtctcctct tcgtcatcaa gcaaccaccg   11820
cacccagcat caagcccacc tgaaattatc tccggcttcc ctctggccga acaatatcgg   11880
tagttaatta aaacttaggg tgcaagatca tcgataatgt caccacaacg agaccggata   11940
aatgccttct acaaagataa ccccccatccc aagggaagta ggatagtcat taacagagaa   12000
catcttatga ttgatagacc ttatgttttg ctggctgttc tgtttgtcat gtttctgagc   12060
ttgatcgggt tgctagccat tgcaggaatt cgacttcatc gggcagccat ctacaccgca   12120
gagatccata aaagcctcag caccaatcta gatgtaacta actcaatcga gcatcaggtc   12180
aaggacgtgc tgacaccact cttcaaaatc atcggtgatg aagtgggcct gaggacacct   12240
cagagattca ctgacctagt gaaattaatc tctgacaaga ttaaattcct taatccggat   12300
agggagtacg acttcagaga tctcacttgg tgtatcaacc cgccagagag aatcaaattg   12360
gattatgatc aatactgtgc agatgtggct gctgaagagc tcatgaatgc attggtgaac   12420
tcaactctac tggagaccag aacaaccaat cagttcctag ctgtctcaaa gggaaactgc   12480
tcagggccca ctacaatcag aggtcaattc tcaaacatgt cgctgtcct gttagactttg   12540
tatttaggtc gaggttacaa tgtgtcatct atagtcacta tgacatccca gggaatgtat   12600
gggggaactt acctagtgga aaagcctaat ctgagcagca aaaggtcaga gttgtcacaa   12660
ctgagcatgt accgagtgtt tgaagtaggt gttatcagaa atccgggttt gggggctccg   12720
gtgttccata tgcaaaacta tcttgagcaa ccagtcagta atgatctcag caactgtatg   12780
gtgcttttgg gggagctcaa actcgtagcc cttttgtcacg gggaagattc tatcacaatt   12840
ccctatcagg gatcagggaa aggtgtcagc ttccagctcg tcaagctagg tgtctggaaa   12900
tccccaaccg acatgcaatc ctgggtcccc ttatcaacgg atgatccagt gatagacagg   12960
cttttacctct catctcacag aggtgttatc gctgacaacc aagcaaaatg gctgtcccg    13020
acaacacgaa cagatgacaa gttgcgaatg gagacatgct tccaacaggc gtgtaagggt    13080
aaaatccaag cactctgcga gaatcccgag tgggcaccat tgaaggataa caggattcct    13140
tcatacgggg tcttgtctgt tgatctgagt ctgacagttg agcttaaaat caaaattgct    13200
tcgggattcg ggccattgat cacacacggt tcagggatgg acctatacaa atccaaccac    13260
aacaatgtgt attggctgac tatcccgcca atgaagaacc tagccttagg tgtaatcaac    13320
acattggagt ggatccgag attcaaggtt agtccctacc tcttcactgt cccaattaag    13380
gaagcaggcg aagactgcca tgccccaaca tacctacctg cggaggtgga tggtgatgtc    13440
```

```
aaactcagtt ccaatctggt gattctacct ggtcaagatc tccaatatgt tttggcaacc   13500
tacgatactt ccagggttga acatgctgtg gtttattacg tttacagccc aagccgctca   13560
ttttcttact tttatccttt taggttgcct ataaaggggg tccccatcga attacaagtg   13620
gaatgcttca catgggacca aaaactctgg tgccgtcact tctgtgtgct tgcggactca   13680
gaatctggtg gacatatcac tcactctggg atggtgggca tgggagtcag ctgcacagtc   13740
acccgggaag atggaaccaa tcgcagatag ggctgctagt gaaccaatca catgatgtca   13800
cccagacatc aggcataccc actagtgtga aatagacatc agaattaaga aaaacgtagg   13860
gtccaagtgg ttccccgtta tggactcgct atctgtcaac cagatcttat accctgaagt   13920
tcacctagat agcccgatag ttaccaataa gatagtagcc atcctggagt atgctcgagt   13980
ccctcacgct tacagcctgg aggaccctac actgtgtcag aacatcaagc accgcctaaa   14040
aaacggattt tccaaccaaa tgattataaa caatgtggaa gttgggaatg tcatcaagtc   14100
caagcttagg agttatccgg cccactctca tattccatat ccaaattgta atcaggattt   14160
atttaacata gaagacaaag agtcaacgag gaagatccgt gaactcctca aaaagggaa   14220
ttcgctgtac tccaaagtca gtgataaggt tttccaatgc ttaagggaca ctaactcacg   14280
gcttggccta ggctccgaat tgagggagga catcaaggag aaagttatta acttgggagt   14340
ttacatgcac agctcccagt ggtttgagcc cttttctgttt tggtttacag tcaagactga   14400
gatgaggtca gtgattaaat cacaaaccca tacttgccat aggaggagac acacacctgt   14460
attcttcact ggtagttcag ttgagttgct aatctctcgt gaccttgttg ctataatcag   14520
taaagagtct caacatgtat attacctgac atttgaactg gttttgatgt attgtgatgt   14580
catagagggg aggttaatga cagagaccgc tatgactatt gatgctaggt atacagagct   14640
tctaggaaga gtcagataca tgtggaaact gatagatggt ttcttccctg cactcggaa   14700
tccaacttat caaattgtag ccatgctgga gcctcttca cttgcttact tgcagctgaa   14760
ggatataaca gtagaactca gaggtgcttt ccttaaccac tgctttactg aaatacatga   14820
tgttcttgac caaacgggt tttctgatga aggtacttat catgagttaa ctgaagctct   14880
agattacatt ttcataactg atgacataca tctgacaggg gagattttct cattttcag   14940
aagttttcggc cacccccagac ttgaagcagt aacggctcgt gaaaatgtta ggaaatacat   15000
gaatcagcct aaagtcattg tgtatgagac tctgatgaaa ggtcatgcca tattttgtgg   15060
aatcataatc aacggctatc gtgacaggca cggaggcagt tggccaccgc tgaccctccc   15120
cctgcatgct gcagacacaa tccggaatgc tcaagcttca ggtgaagggt taacacatga   15180
gcagtgcgtt gataactgga aatcttttgc tggagtgaaa tttggctgct ttatgcctct   15240
tagcctggat agtgatctga caatgtacct aaaggacaag gcacttgctg ctctccaaag   15300
ggaatgggat tcagtttacc cgaaagagtt cctgcgttac gaccctccca agggaaccgg   15360
gtcacggagg cttgtagatg ttttccttaa tgattcgagc tttgacccat atgatgtgat   15420
aatgtatgtt gtaagtggag cttacctcca tgaccctgag ttcaacctgt cttacagcct   15480
gaaagaaaag gagatcaagg aaacaggtag actttttgct aaaatgactt acaaaatgac   15540
ggcatgccaa gtgattgctg aaaatctaat ctcaaacggg atttggcaat attttaagga   15600
caatgggatg gccaaggatg agcacgattt gactaaggca ctccacactc tagctgtctc   15660
aggagtcccc aaagatctca aagaagtca caggggggg ccagtcttaa aaacctactc   15720
ccgaagccca gtccacacaa gtaccaggaa cgtgagagca gcaaagggt ttatagggtt   15780
cccctcaagta attcggcagg accaagacac tgatcatccg gagaatatgg aagcttacga   15840
gacagtcagt gcatttatca cgactgatct caagaagtac tgccttaatt ggagatatga   15900
gaccatcagc ttgtttgcac agaggctaaa tgagatttac ggattgccct catttttcca   15960
gtggctgcat aagaggcttg agacctctgt cctgtatgta agtgaccctc attgccccc   16020
cgaccttgac gcccatatcc cgttatataa agtccccaat gatcaaatct tcattaagta   16080
ccctatggga ggtatagaag ggtattgtca gaagctgtgg accatcagca ccattcccta   16140
tctatacctg gctgcttatg agagcggagt aaggattgct tcgttagtgc aaggggacaa   16200
tcagaccata gccgtaacaa aaagggtacc cagcacatgg ccctacaacc ttaagaaacg   16260
ggaagctgct agagtaacta gagattactt tgtaattctt aggcaaaggc tacatgatat   16320
tggccatcac ctcaaggcaa atgagacaat tgtttcatca catttttttg tctattcaaa   16380
aggaatatat tatgatgggc tacttgtgtc ccaatcactc aagagcatcg caagatgtgt   16440
attctggtca gagactatag ttgatgaaac aagggcagca tgcagtaata ttgctacaac   16500
aatggctaaa agcatcgaga gaggttatga ccgttacctt gcatattccc tgaacgtcct   16560
aaaagtgata cagcaaattc tgatctctct tggcttcaca atcaattcaa ccatgacccg   16620
ggatgtagtc ataccctcc tcacaaacaa cgacctctta ataaggatgg cactgttgcc   16680
cgctcctatt gggggatga attatctgaa tatgagcagg ctgttttgtca gaaacatcgg   16740
tgatccagta acatcatcaa ttgctgatct caagagaatg attctcgcct cactaatgcc   16800
tgaagagacc ctccatcagg taatgacaca acaaccgggg gactcttcat tcctagactg   16860
ggctagcgac ccttactcag caaatcttgt atgtgtccag agcatcacta gactcctcaa   16920
gaacataact gcaaggtttg tcctgatcca tagtccaaac ccaatgttaa aaggattatt   16980
ccatgatgac agtaaagaag aggacgaggg actggcggca ttcctcatgg acaggcatat   17040
tatagtacct agggcagctc atgaaatcct ggatcatagt gtcacagggg caagagagtc   17100
tattgcaggc atgctggata ccacaaaagg cttgattcga gccagcatga ggaagggggg   17160
tttaacctct cgagtgataa ccagattgtc caattatgac tatgaacaat tcagagcagg   17220
gatgtgtcta ttgacaggaa gaaagagaaa tgtcctcatt gacaaagat catgttcagt   17280
gcagctggcg agagtctaa gaagccatat gtgggcgagg ctagctcgag gacggcctat   17340
ttacggcctt gaggtccctg atgtactaga atctatgcga ggccaccta tcggcgtca   17400
tgagacatgt gtcatctgcg agtgtggatc agtcaactac ggatggtttt ttgtcccctc   17460
gggttgccaa ctggatgata ttgacaagga aacatcatcc ttgagagtcc catatattgg   17520
ttctaccact gatgagagaa cagacatgaa gcttgccttc taagagccc caagtcgatc   17580
cttgcgatct gctgttagaa tagcaacagt gtactcatgg gcttacggtg atgatgatag   17640
ctcttggaac gaagcctggt tgttggctag gcaaaggggcc aatgtgagcc tggaggagct   17700
aaggggtgatc actcccatct caacttcgac taattagcg cataggttga gggatcgtag   17760
cactcaagtg aaatactcag gtacatccct tgtccgagtg gcgaggtata ccacaatctc   17820
caacgacaat ctctcattttg tcatatcaga taagaaggct gatactaact ttatataccca   17880
acaaggaatg cttctagggt tgggtgtttt agaaacattg tttcgactcg agaaagatac   17940
cggatcatct aacacggtat tacatcttca cgtcgaaca gattgttgcg tgatcccgat   18000
gatagatcat cccaggatac ccagctcccg caagctagag ctgagggcag agctatgtac   18060
caacccattg atatatgata atgcaccttt aattgacaga gatgcaacaa ggctatacac   18120
ccagagccat aggaggcacc ttgtggaatt tgttacatgg tccacacccc aactatatca   18180
```

```
catttagct aagtccacag cactatctat gattgacctg gtaacaaaat ttgagaagga    18240
ccatatgaat gaaatttcag ctctcatagg ggatgacgat atcaatagtt tcataactga    18300
gtttctgctc atagagccaa gattattcac tatctacttg ggccagtgtg cggccatcaa    18360
ttgggcattt gatgtacatt atcatagacc atcaggaaaa tatcagatgg gtgagctgtt    18420
gtcatcgttc cttctagaa tgagcaaagg agtgtttaag gtgcttgtca atgctctaag    18480
ccacccaaag atctacaaga aattctggca ttgtggtatt atagagccta tccatggtcc    18540
ttcacttgat gctcaaaact tgcacacaac tgtgtgcaac atggtttaca catgctatat    18600
gacctacctc gacctgttgt tgaatgaaga gttagaagag ttcacatttc tcttgtgtga    18660
aagcgacgag gatgtagtac cggacagatt cgacaacatc caggcaaaac acttatgtgt    18720
tctggcagat ttgtactgtc aaccaggac ctgcccacca attcgaggtc taagaccgat    18780
agagaaatgt gcagttctaa ccgaccatat caaggcagag gctatgttat ctccagcagg    18840
atcttcgtgg aacataaatc caattattgt agaccattac tcatgctccc tgacttatct    18900
ccggcgagga tcgatcaaac agataagatt gagagttgat ccaggattca ttttcgacgc    18960
cctcgctgag gtaaatgtca gtcagccaaa gatcggcagc aacaacatct caaatatgag    19020
catcaaggct ttcagacccc cacacgatga tgttgcaaaa ttgctcaaag atatcaacac    19080
aagcaagcac aatcttccca tttcaggggg caatctcgcc aattatgaaa tccatgcttt    19140
ccgcagaatc gggttgaact catctgcttg ctacaaagct gttgagatat caacattaat    19200
taggagatgc cttgagccag ggaggacgg ctttgttcttg ggtgagggat cgggttctat    19260
gttgatcact tataaggaga tacttaaact aaacaagtgc ttctataata gtggggttc    19320
cgccaattct agatctggtc aaagggaatt agcaccctat ccctccgaag ttggccttgt    19380
cgaacacaga atgggagtag gtaatattgt caaagtgctc tttaacggga ggcccgaagt    19440
cacgtgggta ggcagtgtag attgcttcaa tttcatagtt agtaatatcc ctacctctag    19500
tgtggggttt atccattcag atatagagac cttgcctgac aaagatacta tagagaagct    19560
agaggaattg gcagccatct tatcgatggc tctgctcctg ggcaaaatag gatcaatact    19620
ggtgattaag cttatgcctt tcagcgggga ttttgttcag ggatttataa gttatgtagg    19680
gtctcattat agagaagtga accttgtata ccctagatac agcaacttca tatctactga    19740
atcttatttg gttatgacag atctcaaggc taaccggcta atgaatcctg aaaagattaa    19800
gcagcagata attgaatcat ctgtgaggac ttcacctgga cttataggtc acatcctatc    19860
cattaagcaa ctaagctgca tacaagcaat tgtgggagac gcagttagta gaggtgatat    19920
caatcctact ctgaaaaaac ttacacctat agagcaggtg agcaatt gcgggttggc    19980
aattaacgga cctaagctgt gcaaagaatt gatccaccat gatgttgcct cagggcaaga    20040
tggattgctt aattctatac tcatcctcta caggagttg gcaagattca aagcaaccca    20100
aagaagtcaa caagggatgt tccacgccta ccccgtattg gtaagtagca ggcaacgaga    20160
acttatatct aggatcaccc gcaaattttg ggggcacatt cttctttact ccgggaacaa    20220
aaagttgata aataagttta tccgaatctc caagtccggc tatctgatac tagacttaca    20280
ccagaatatc ttcgttaaga atctatccaa gtcagagaaa cagattatta tgacgggggg    20340
tttgaaacgt gagtgggttt taaggtaac agtcaaggag accaaagaat ggtataagtt    20400
agtcggatac agtgccctga ttaaggacta attggttgaa ctccggaacc ctaatcctgc    20460
cctaggtggt taggcattat ttgcaatata ttaaagaaat cttttgaaaat acgaagttc    20520
tattcccagc tttgtctggt ggccggcata gtcccagcct cctcgctggc gctggctggg    20580
caacattccg aggggaccgt ccccacggta atggcgaatg ggacgcggcc gatccggctg    20640
ctaacaaagc ccgaaaggaa gctgagttgg ctgctggcgc tggctgggca ataactagca    20700
taaccccttg gggcctctaa acgggtcttg aggggtttt tgctgaaagg aggaactata    20760
tccggatgcg gccgcgcgct tggcgtaatc atggtcatag ctgtttcctg tgtgaaattg    20820
ttatccgctc acaattccac acaacatacg agccggaagc ataaagtgta aagcctgggg    20880
tgcctaatga gtgagctaac tcacattaat tgcgttgcgc tcactgcccg ctttccagtc    20940
gggaaacctg tcgtgccagc tgcattaatg aatcggccaa cgcgcgggga gaggcggttt    21000
gcgtattggg cgctcttccg cttcctcgct cactgactcg ctgcgctcgg tcgttcggct    21060
gcggcgagcg gtatcagctc actcaaaggc ggtaatacgg ttatccacag aatcaggga    21120
taacgcagga aagaacatgt gagcaaaagg ccagcaaaag gccaggaacc gtaaaaaggc    21180
cgcgttgctg gcgtttttcc ataggctccg ccccctgac gagcatcaca aaaatcgacg    21240
ctcaagtcag aggtggcgaa acccgacagg actataaaga taccaggcgt ttccccctgg    21300
aagctccctc gtgcgctctc ctgttccgac cctgccgctt accggatacc tgtccgcctt    21360
tctcccttcg ggaagcgtgg cgcttctca tagctcacgc tgtaggtatc tcagttcggt    21420
gtaggtcgtt cgctccaagc tgggctgtgt gcacgaaccc cccgttcagc ccgaccgctg    21480
cgccttatcc ggtaactatc gtcttgagtc caacccggta agacacgact tatcgccact    21540
ggcagcagcc actggtaaca ggattagcag agcgaggtat gtaggcggtg ctacagagtt    21600
cttgaagtgg tggcctaact acggctacac tagaaggaca gtatttggta tctgcgctct    21660
gctgaagcca gttaccttcg gaaaaagagt tggtagctct tgatccggca aacaaaccac    21720
cgctggtagc ggtggtttt tgtttgcaa gcagcagatt acgcgcagaa aaaaaggatc    21780
tcaagaagat cctttgatct tttctacggg gtctgacgct cagtggaacg aaaactcacg    21840
ttaagggatt ttggtcatga gattatcaaa aaggatcttc acctagatcc ttttaaatta    21900
aaaatgaagt tttaaatcaa tctaaagtat atatgagtaa acttggtctg acagttacca    21960
atgcttaatc agtgaggcac ctatctcagc gatctgtcta tttcgttcat ccatagttgc    22020
ctgactcccc gtcgtgtaga taactacgat acgggagggc ttaccatctg gccccagtgc    22080
tgcaatgata ccgcgagacc cacgctcacc ggctccagat ttatcagcaa taaaccagcc    22140
agccggaagg gccgagcgca gaagtggtcc tgcaacttta tccgcctcca tccagtctat    22200
taattgttgc cgggaagcta gagtaagtag ttcgccagtt aatagtttgc gcaacgttgt    22260
tgccattgct acaggcatcg tggtgtcacg ctcgtcgttt ggtatggctt cattcagctc    22320
cggttcccaa cgatcaaggc gagttacatg atccccatg ttgtgcaaaa aagcggttag    22380
ctccttcggt cctccgatcg ttgtcagaag taagttggcc gcagtgttat cactcatggt    22440
tatggcagca ctgcataatt ctcttactgt catgccatcc gtaagatgct tttctgtgac    22500
tggtgagtac tcaaccaagt cattctgaga atagtgtatg cggcgaccga gttgctcttg    22560
cccggcgtca acatgcggata ataccgcgcc acatagcaga actttaaaag tgctcatcat    22620
tggaaaacgt tcttcgggc gaaaactctc aaggatctta ccgctgttga gatccagttc    22680
gatgtaaccc actcgtgcac ccaactgatc ttcagcatct tttacttca ccagcgtttc    22740
tgggtgagca aaaacaggaa ggcaaaatgc cgcaaaaaag gaataaggg cgacacggaa    22800
atgttgaata ctcatactct tcctttttca atattattga agcatttatc agggttattg    22860
tctcatgagc ggatacatat ttgaatgtat ttagaaaaat aaacaaatag gggttccgcg    22920
```

```
cacatttccc cgaaaagtgc cacctg                                             22946

SEQ ID NO: 4            moltype = DNA  length = 22916
FEATURE                 Location/Qualifiers
misc_feature            1..22916
                        note = MV Wu S in position 3
source                  1..22916
                        mol_type = other DNA
                        organism = synthetic construct
SEQUENCE: 4
ggacgcgccc tgtagcggcg cattaagcgc ggcgggtgtg gtggttacgc gcagcgtgac   60
cgctacactt gccagcgccc tagcgcccgc tcctttcgct ttcttccctt cctttctcgc  120
cacgttcgcc ggctttcccc gtcaagctct aaatcggggg ctcccttttag ggttccgatt  180
tagtgcttta cggcacctcg accccaaaaa acttgattag ggtgatggtt cacgtagtgg  240
gccatcgccc tgatagacgg ttttttcgcc tttgacgttg gagtccacgt tctttaatag  300
tggactcttg ttccaaactg gaacaacact caaccctatc tcggtctatt cttttgattt  360
ataagggatt ttgccgattt cggcctattg gttaaaaaat gagctgattt aacaaaaatt  420
taacgcgaat tttaacaaaa tattaacgtt tacaatttcg cgccattcgc cattcaggct  480
gcgcaactgt tgggaagggc gatcggtgcg ggcctcttcg ctattacgcc agctggcgaa  540
agggggatgt gctgcaaggc gattaagttg ggtaacgcca gggttttccc agtcacgacg  600
ttgtaaaacg acggccagtg cgcgccgtta atacgactca ctataggag cccaagctg   660
gctagcttg tttggtctga tgagtcccgt gaggacgaaa cccgcgtac cgggtcacca  720
aacaaagttg ggtaaggata gttcaatcaa tgatcatctt ctagtgcact taggattcaa  780
gatcctatta tcaggacaa gagcaggatt agggatatcc gagatggcca cactttaag  840
gagcttagca ttgttcaaaa gaaacaagga caaaccaccc attacatcag gatccggtgg  900
agccatcaga ggaatcaaac acattattat agtaccatcc cctggagatt cctcaattac  960
cactcgatcc agacttctgg accggttggt gaggttaatt ggaaaccggg atgtgagcgg  1020
gcccaaacta acaggggcac taataggtat attatccttta tttgtggagt ctccaggtca  1080
attgattcag aggatcaccg atgaccctga cgttagcata aggctgttag aggttgtcca  1140
gagtgaccag tcacaatctg gccttacctt cgcatcaaga ggtaccaaca tggaggatga  1200
ggcggaccaa tactttttcac atgatgatcc aattagtagt gatcaatcca ggttcggatg  1260
gttcgggaac aaggaaatct cagatattga agtgcaagac cctgagggat tcaacatgat  1320
tctgggtacc atcctagccc aaatttgggt cttgctcgca aaggcggtta cggccccaga  1380
cacggcagct gattcggagc taagaaggtg gataaagtac acccaacaa gaagggtagt  1440
tggtgaattt agattggaga gaaaatggtt ggatgtggtg aggaacagga ttgccgagga  1500
cctctcctta cgccgattca tggtcgctct aatcctggat atcaagaaa cacccggaaa  1560
caaacccagg attgctgaaa tgatatgtga cattgataca tatatcgtag aggcaggatt  1620
agccagtttt atcctgacta ttaagtttgg gatagaaact atgtatcctg ctcttggact  1680
gcatgaattt gctggtgagt tatccacact tgagtccttg atgaacctttt accagcaaat  1740
gggggaaact gcaccctaca tggtaatcct ggagaactca attcagaaca gttcagtgc  1800
aggatcatac cctctgctct ggagctatgc catgggagta ggagtggaac ttgaaaactc  1860
catgggaggt ttgaactttg ccgatcttac ctttgatcca gcatattta gattagggca  1920
agagatggta aggaggtcag ctggaaaggt cagttccaca ttggcatctg aactcggtta  1980
cactgccgag gatgcaaggc ttgtttcaga gattgcaatg catactactg aggacaagat  2040
cagtagagcg gttggaccca gacaagccca agtatcattt ctacacggtg atcaaagtga  2100
gaatgagcta ccgagattgg gggcaagga agataggagg tcaaacaga gtcgaggaga  2160
agccgggag agctacagag aaaccgggcc cagcagagca agtgatgcga gagctgccca  2220
tcttccaacc ggcacacccc tagacattga cactgcaacg gagtccagcc aagatccgca  2280
ggacagtcga aggtcagctg acgccctgct aggctgcaa gccatggcag gaatccggga  2340
agaacaaggc tcagacacgg acaccccctat agtgtacaat gacagaaatc ttctagacta  2400
ggtgcgagag gccgagggcc agaacaacat ccgcctacca tccatcattg ttataaaaaa  2460
cttaggaacc aggtccacac agccgccagc ccatcaacca tccactccca cgattggagc  2520
caatggcaga agagcaggca cgccatgtca aaaacggact ggaatgcatc cgggctctca  2580
aggccgagcc catcggctca ctggccatcg aggaagctat ggcagcatgg tcagaaatat  2640
cagacaccc aggacaggac cgaaccacct gcagggagga gaaggcaggc agttcgggtc  2700
tcagcaaacc atgccctcta gcaattggat caactgaagg cggtgcacct cgcatccgcg  2760
gtcagggacc tggagagagc gatgacgacg ctgaaacttt gggaatcccc ccaagaaatc  2820
tccaggcatc aagcactggg ttacagtgtt attacgttta tgatcacagc ggtgaagcgg  2880
ttaagggaat ccaagatgct gactctatca tggttcaatc aggccttttgat ggtgatagca  2940
ccctctcagg aggagacaat gaatctgaaa acagcgatgt ggatattggc gaacctgata  3000
ccgagggata tgctatcact gaccggggat ctgctcccat ctctatgggg ttcagggctt  3060
ctgatgttga aactgcagaa ggaggggaga tccacgagct cctgagactc caatccagag  3120
gcaacaactt tccgaagctt gggaaaactc tcaatgttcc tccgccccg gaccccggta  3180
gggccagcac ttccgggaca cccattaaaa agggcacaga ggctgcattg cgcctcattg  3240
gaacggagat cgcgtcttta ttgacaggtg gtgcaaccca atgtgctcga aagtcaccct  3300
cggaaccatc agggccaggt gcacctgcgg ggaatgtccc cgagtgtgtg agcaatgccg  3360
cactgatacc ggagtggaca cccgaatctg taccacaat ctcccgaga tcccagaata  3420
atgaagaagg gggagactat tatgatgatg agctgttctc tgatgtccaa gatattaaaa  3480
cagccttggc caaaatacac gaggataatc agaagataat ctccaagcta gaatcactga  3540
tgttattgaa gggagaagtt gagtcaatta agaagcagat caacaggcaa atatcagca  3600
tatccacccct ggaaggacac ctctcaagca tcatgatcgc cattcctgga cttgggaagg  3660
atcccaacga ccccactgca gatgtcgaaa tcaatcccga cttgaaaccc atcataggca  3720
gagattcagg ccgagcactg gccgaagttc tcaagaaaaac cgttgccagc cgacaactcc  3780
aaggaatgac aaacagtgacg accagttcca gaaggtgaagga gctgaaggaa tttcagctaa  3840
agccgatcgg gaaaaagatg agctcagccg tcgggtttgt tcctgacacc ggccctgcat  3900
cacgcagtgt aatccgctcc attataaaat ccagccggct agaggaggat cggaagcgtt  3960
acctgatgac tctccttgat gatatcaaag gagccaatga tcttgccaag ttccaccaga  4020
tgctgatgaa gataataatg aagtagctac agctcaactt acctgccaac ccatgccag  4080
tcgatcatcc atcattgtta taaaaaactt aggaaccagg tccacacaga gtgatacgcg  4140
```

-continued

```
tacgccacca tgttcgtgtt tctggtgctg ctgcctctgg tgagctccca gtgcgtgaac  4200
ctgaccacaa ggacccagct gcccctgcc tataccaatt ccttcacacg ggcgtgtac    4260
tatcccgaca aggtgttccg gagcagcgtg ctgcactcca cacaggatct gtttctgcct  4320
ttcttttcta acgtgacctg gttccacgcc atccacgtga gcggcaccaa tggcacaaag  4380
cggttcgaca atccagtgct gcccttaac gatggcgtg acttcgcctc caccgagaag    4440
tctaacatca tcagaggctg gatctttggc accacactgg acagcaagac acagtccctg  4500
ctgatcgtga acaatgccac caacgtggtc atcaaggtgt gcgagttcca gttttgtaat  4560
gatccattcc tgggcgtgta ctatcacaag aacaataagt cttggatgga gagcgagttt  4620
cgcgtgtatt cctctgccaa caattgcaca tttgagtacg tgtcccagcc cttcctgatg  4680
gacctggagg gcaagcaggg caatttcaag aacctgaggg agttcgtgtt taagaatatc  4740
gatggctact tcaaaatcta ctccaagcac accccaatca acctggtgcg cgacctgcca  4800
cagggcttct ctgccctgga gccactgtg gatctgccca tcggcatcaa catcacccgg    4860
tttcagacac tgctggccct gcacagaagc tacctgacac aggcgacag ctcctctgga    4920
tggaccgcag gagcagcagc ctactatgtg ggctatctgc agccaggac cttcctgctg    4980
aagtacaacg agaatggcac catcacagac gccgtggatt gcgccctgga tccctgtct    5040
gagaccaagt gtacactgaa gagctttacc gtggagaagg gcatctatca gacaagcaat  5100
ttcagggtgc agcctaccga gtccatcgtg cgctttccca atatcacaaa cctgtgccct  5160
tttggcgagg tgttcaacgc aacccgcttc gccagcgtgt acgcctggaa taggaagcgc  5220
atctccaact gcgtggccga ctattctgtg ctgtacaaca gcgcctcctt ctctaccttt  5280
aagtgctatg gcgtgagccc cacaaagctg aatgacctgt gctttaccaa cgtgtacgcc  5340
gattcctcg tgatcagggg cgacgaggtg cgccagatcg caccaggaca gacaggcaag    5400
atcgcagact acaattataa gctgcctgac gatttcacgg gctgcgtgat cgcctggaac  5460
tctaacaatc tggatagcaa agtgggcggc aactacaatt atctgtaccg gctgtttaga  5520
aagtctaatc tgaagccatt cgagagggac atctccacag aaatctacca ggccggctct  5580
acccctgca atgcgtgga gggctttaac tgttatttcc ctctgcagag ctacggcttc    5640
cagccaacaa acggcgtggg ctatcagccc taccgctgg tggtgctgtc ttttgagctg    5700
ctgcacgcac ctgcaacagt gtgcggacca aagaagagca ccaatctggt gaagaacaag  5760
tgcgtgaact tcaacttcaa cggactgacc ggaacaggcg tgctgaccga gtccaacaag  5820
aagttcctgc cttttcagca gttcggcagg gacatcgcag ataccacaga cgccgtgcgc  5880
gaccctcaga ccctggagat cctggacata acaccatgct ccttcggcgg cgtgtctgtg  5940
atcacaccag gcaccaatac aagcaaccag gtgccgtgc tgtatcagga cgtgaattga    6000
accgaggtgc cagtggcaat ccacgcagat cagctgaccc ctacatgcg ggtgtactct    6060
accggcagca acgtgttcca gacaagagcc ggatgcctga tcggagcaga gcacgtgaac  6120
aatagctatg agtgcgacat ccctatcggc gccggctct gtgcctccta ccagacccca    6180
acaaactccc caaggagagc acggtctgtg gccagccagt ccatcatcgc ctataccatg  6240
agcctgggcg ccgagaattc cgtggcctac tccaacaatt ctatcgccat ccctaccaac  6300
ttcacaatct ccgtgaccac agagatcctg ccagtgagca tgaccaagac atccgtggac  6360
tgcacaatgt atatctgtgg cgattccacc gagtgctcta acctgctgct gcagtacggc  6420
tcttttgta cccagctgaa tagagccctg acaggcatcg ccgtggagca ggacaagaac  6480
acacaggagg tgttcgccca ggtgaagcaa atctacaaga ccccacccat caaggacttt  6540
ggcggcttca acttcagcca gatcctgcc gatcctagca agccatccaa gcggtctttt    6600
atcgaggacc tgctgttcaa caaggtgacc ctggccgatg ccggcttcat caagcagtat  6660
ggcgattgcc tgggcgacat cgccgccaga gacctgatct gtgcccagaa gtttaatggc  6720
ctgaccgtgc tgcctccact gctgacagat gagatgatcg cccagtacac atctgccctg  6780
ctggccggaa ccatcacaag cggatggacc ttcggcgcag gagccgccct gcagatcccc  6840
tttgccatgc agatggccta tcggttcaac ggcatcggcg tgacccagaa tgtgctgtac  6900
gagaaccaga agctgatcgc caatcagttt aactccgca tcggcaagat ccaggactct    6960
ctgagctcca cagccagcgc cctgggcaag ctgcaggatg tggtgaatca gaacgcccag  7020
gccctgaata ccctggtgaa gcagctgtct agcaacttcg cgccatctc ctctgtgctg    7080
aatgacatcc tgagccggct ggacaaggtg gaggcagagg tgcagatcga ccggctgatc  7140
acaggcagac tgcagtccct gcagacctac gtgacacaag agctgatcag ggcagcagga  7200
atcagggcct ctgccaatct ggccgccacc aagatgagcg agtgcgtgct gggccagtcc  7260
aagagagtgg acttttgtgg caagggctat cacctgatga gcttcccaca gtccgcccct  7320
cacgagtgg tgtttctgca cgtgacctac gtgccagccc aggagaagaa cttcaccaca  7380
gcaccagcaa tctgccacga tggcaaggca cactttccta gggagggcgt gttcgtgagc  7440
aacggcaccc actggtttgt gacacagcgc aatttctacg agccacagat catccaccac  7500
gacaatacat tcgtgtccgg caactgtgac gtggtcatcg gcatcgtgaa caataccgtg  7560
tatgatcctc tgcagccaga gctggactct tttaaggagg agctggataa gtacttcaag  7620
aatcacacca gccccgacgt ggatctctg gacatcaatg cccagcgtgg tg            7680
aacatccaga aggagatcga caggctgaac gaggtggcca agaatctgaa cgagtccctg  7740
atcgatctgc aggagctggg caagtatgag cagtacatca gtggccctg gtatatctgg    7800
ctgggcttca tcgccggcct gatcgccatc gtgatggtga ccatcatgct gtgctgtatg  7860
acaagctgct gttcctgcct gaaggctgc tgttcttgtg gcagctgctg taagtttgat    7920
gaggacgata gcgagcctgt gctgaagggc gtgaagctgc actacacctg atagctagcg  7980
atcgccacc tagtacaacc taaatccatt ataaaaaact taggagcaaa gtgattgcct    8040
cccaaggtcc acaatgacag agacctacga cttgacaag tcggcatggg acatcaaagg    8100
gtcgatcgct ccgatacaac ccaccaccta cagtgatggc aggctggtgc ccaggtcag    8160
agtcatagat cctggtctag gcgacaggaa ggatgaatgc tttatgtaca tgtttctgct  8220
gggggttgtt gaggacgacg attccctagg gcctccaatc gggcgagcat ttgggttcct  8280
gcccttaggt gttggcagat ccacagcaaa gcccgaaaaa ctcctcaaag aggccactga  8340
gcttgacata gttgttagac gtacagcagg gctcaatgaa aaactggtgt ctacaaacaa  8400
cacccccacta actctcctca caccttggag aaaggtccta caacaggga gtgtcttcaa    8460
cgcaaaccaa gtgtgcaatg cggttaatct gatccgctc gatacccgc agaggttccg    8520
tgtttttat atgagcatca cccgtctttc ggataacgag tattacaccg ttcctagaag    8580
aatgctggaa ttcagatcgg tcaatgcagt ggccttcaac ctgctggtga cccttaggat  8640
tgacaaggcg ataggcctg ggaagatcat cgacaataca gagcaacttc ctgaggcaac    8700
atttatggtc cacatcggga acttcaggag aaagaagagt gaagtctact ctgccgatta  8760
ttgcaaaatg aaaatcgaaa agatgggcct ggttttgca cttggtggga tagggggcac    8820
cagtcttcac attagaagca caggcaaaat gagcaagact ctccatgcac aactcgggtt  8880
```

```
caagaagacc ttatgttacc cgctgatgga tatcaatgaa gaccttaatc gattactctg   8940
gaggagcaga tgcaagatag taagaatcca ggcagttttg cagccatcag ttcctcaaga   9000
attccgcatt tacgacgacg tgatcataaa tgatgaccaa ggactattca aagttctgta   9060
gaccgtagtg cccagcaatg cccgaaaacg accccccctca caatgacagc cagaaggccc   9120
ggacaaaaaa gcccccctccg aaagactcca cggaccaagc gagaggccag ccagcagccg   9180
acggcaagcg cgaacaccag gcggcccccag cacagaacag ccctgacaca aggccaccac   9240
cagccacccc aatctgcatc ctcctcgtgg gaccccgag gaccaacccc caaggctgcc   9300
cccgatccaa accaccaacc gcatcccac caccccggg aaagaaaccc ccagcaattg   9360
gaaggcccct cccctcttc ctcaaacacaa gaactccaca accgacgc acaagcgacc   9420
gaggtgaccc aaccgcaggc atccgactcc ctagacagat cctctctccc cggcaaacta   9480
aacaaaactt agggcaagg aacatacaca cccaacagaa cccagacccc ggcccacggc   9540
gccgcgcccc caaccccga caaccagagg gagccccaa ccaatcccgc cggctccccc   9600
ggtgcccaca ggcagggaca ccaacccccg aacagaccca gcaccaacc atcgacaatc   9660
caagacgggg gggccccccc aaaaaaaggc ccccaggggc cgcagccga caccgcgagg   9720
aagcccaccc accccacaca cgaccacggc aaccaaacca gaaccccagac caccctgggc   9780
caccagctcc cagactcggc catcaccccg cagaaggaa aggccacaac ccgcgcacc   9840
cagcccgat ccggcgggga gccacccaac ccgaaccagc cccaagagc gatccccgaa   9900
ggacccccga accgcaaagg acatcagtat cccacagct ctccaagtcc cccggtctcc   9960
tcctcttctc gaagggacca aaagatcaat ccaccacacc cgacgacact caactccccca  10020
cccctaaagg agacaccggg aatcccagaa tcaagactca tccaatgtcc atcatgggtc  10080
tcaaggtgaa cgtctctgcc atattcatgg cagtactgtt aactctccaa acacccaccg  10140
gtcaaatcca ttgggcaat ctctctaaga tagggtggt aggaataggga agtgcaagct  10200
acaaagttat gactcgttcc agccatcaat cattagtcat aaaattaatg cccaatataa  10260
ctctcctcaa taactgcacg agggtagaga ttgcagaata caggagacta ctgagaacag  10320
tttttggaacc aattagagat gcacttaatg caatgaccca gaatataaga ccggttcaga  10380
gtgtagcttc aagtaggaga cacaagagat ttgcgggagt agtcctggca ggtgcggccc  10440
taggcgttgc cacagctgct cagataacag ccggcattgc acttcaccag tccatgctga  10500
actctcaagc catcgacaat ctgagagcga gcctggaaac tactaatcag gcaattgaga  10560
caatcagaca agcagggcag gagatgatat tggctgttca gggtgtccaa gactacatca  10620
ataatgagct gatccgtctc atgaaccaac tatcttgtga tttaatcggc cagaagctcg  10680
ggctcaaatt gctcagatac tatacagaaa tcctgtcatt atttggcccc agtttacggg  10740
accccatatc tgcggagata tctatccagg ctttgagcta tgcgcttgga ggagacatca  10800
ataaggtgtt agaaaagctc ggatacagtg gaggtgattt actgggcatc ttagagagcg  10860
gaggaataaa ggcccggata actcacgtcg acacagagtc ctacttcatt gtcctcagta  10920
tagcctatcc gacgctgtcc gagattaagg gggtgattgt ccaccggcta gagggggtct  10980
cgtacaacat aggctctcaa gagtggtata ccactgtgcc caagtatgtt gcaacccaag  11040
ggtaccttat ctcgaatttt gatgagtcat cgtgtacttt catgccagag gggactgtgt  11100
gcagccaaaa tgccttgtac ccgatgagtc ctctgctcca agaatgcctc cggggtaca  11160
ccaagtcctg tgctcgtaca ctcgtatccg ggtctttgg gaaccggttc attttatcac  11220
aagggaacct aatagccaat tgtgcatcaa tcctttgcaa gtgttacaca acaggaacga  11280
tcattaatca agaccctgac aagatcctaa catacattgc tgccgatcac tgcccggtag  11340
tcgaggtgaa cggcgtgacc atccaagtcg ggagcaggag gtatccagac gctgtgtact  11400
tgcacagaat tgacctcggt cctcccatat cattggaagg ttggacgta gggacaaatc  11460
tggggaatgc aattgctaag ttggaggatg ccaaggaatt gttggagtca tcggaccaga  11520
tattgaggag tatgaaaggt ttatcgagca ctagcatagt ctacatcctg attgcagtgt  11580
gtcttggagg gttgatagg atccccgctt taatatgttg ctgcaggggg cgttgtaaca  11640
aaaagggaga acaagttggt atgtcaagac caggcctaaa gcctgatctt acgggaacat  11700
caaaatccta tgtaaggtcg ctctgatcct ctacaactct tgaaacacaa atgtcccaca  11760
agtctcctct tcgtcatcaa gcaaccaccg caccagcat caagcccacc tgaaattatc  11820
tccggcttcc ctctggccga acaatatcgg tagttaatta aaacttaggg tgcaagatca  11880
tcgataatgt caccacaacg agaccggata aatgccttct acaaagataa ccccccatccc  11940
aagggaagta ggatagtcat taacagaaa catcttatga ttgatagacc ttatgttttg  12000
ctggctgttc tgttttgtcat gtttctgagc ttgatcgggt tgctagccat tgcaggaatt  12060
cgacttcatc gggcagccat ctacaccgca gagatccata aaagcctcag caccaatcta  12120
gatgtaacta actcaatcga gcatcaggtc aaggacgtgc tgacaccact cttcaaaatc  12180
atcggtgatg aagtgggcct gaggacacct cagagattca ctgacctagt gaaattaatc  12240
tctgacaaga ttaaattcct taatccggat agggagtacg acttcagaga tctcacttgg  12300
tgtatcaacc cgcagagag aatcaaattg gattatgatc aatactgtgc agatgtggct  12360
gctgaagagc tcatgaatgc attggtgaac tcaactctac tggagaccag aacaaccaat  12420
cagttcctag ctgtctcaaa gggaaactgc tcagggccca ctacaatcag aggtcaattc  12480
tcaaacatgt cgctgtccct gttagacttg tatttaggtc gaggttacaa tgtgtcatct  12540
atagtcacta tgacatccca gggaatgtat gggggaactt acctagtgga aaagcctaat  12600
ctgagcagca aaaggtcaga gttgtcacaa ctgagcatgt accgagtgtt tgaagtaggt  12660
gttatcagaa atccgggttt gggggctccg gtgttccata tgacaaacta tcttgagcaa  12720
ccagtcagta atgatctcag caactgtatg gtggctttgg gggagctcaa actcgcagcc  12780
ctttgtcacg gggaagattc tatcacaatt ccctatcagg gatcagggaa aggtgtcagc  12840
ttccagctcg tcaagctagg tgtctggaaa tccccaaccg acatgcaatc ctgggtcccc  12900
ttatcaacgg atgatccagt gatagacagg ctttacctct catctcacag aggtgttatc  12960
gctgacaacc aagcaaaatg ggctgtcccg acaacacgaa cagatgacaa gttcgaatg  13020
gagacatgct tccaacaggc gtgtaaggggt aaaatccaag cactctgcga gaatcccgag  13080
tgggcaccat tgaaggataa caggattcct tcatacgggg tcttgtcgt tgatctgagt  13140
ctgacagtta agcttaaaat caaaattgct tcgggattcg ggccattgat cacacacggt  13200
tcagggatgg acctatacaa atccaaccac aacaatgtgt attggctgac tatccgccca  13260
atgaagaacc tagccttagg tgtaatcaac atcattggagt gataccgag attcaaggtt  13320
agtcctacc tcttcactgt cccaattaag gaagcaggcg aagactgcca tgccccaaca  13380
tacctacctg cggaggtgga tggtgatgtc aaactcagtt ccaatctggt gattctacct  13440
ggtcaagatc tccaatatgt tttggcaacc tacgatactt ccagggttga acatgctgtg  13500
gtttattacg tttacagccc aagccgctca ttttctttact tttatccttt taggttgcct  13560
ataaaggggg tccccatcga attacaagtg gaatgcttca catgggacca aaaactctgg  13620
```

```
tgccgtcact tctgtgtgct tgcggactca gaatctggtg gacatatcac tcactctggg    13680
atggtgggca tgggagtcag ctgcacagtc acccgggaag atggaaccaa tcgcagatag    13740
ggctgctagt gaaccaatca catgatgtca cccagacatc aggcataccc actagtgtga    13800
aatagacatc agaattaaga aaaacgtagg gtccaagtgg ttccccgtta tggactcgct    13860
atctgtcaac cagatcttat accctgaagt tcacctagat agccgatag ttaccaataa     13920
gatagtagcc atcctggagt atgctcgagt ccctcacgct tacagcctgg aggaccctac    13980
actgtgtcag aacatcaagc accgcctaaa aaacggattt tccaaccaaa tgattataaa    14040
caatgtggaa gttgggaatg tcatcaagtc caagcttagg agttatccgg cccactctca    14100
tattccatat ccaaattgta atcaggattt atttaacata gaagacaaag agtcaacgag    14160
gaagatccgt gaactcctca aaaagggaa ttcgctgtac tccaaagtca gtgataaggt     14220
tttccaatgc ttaagggaca ctaactcacg gcttggccta ggctccgaat tgagggagga    14280
catcaaggag aaagttatta acttgggagt ttacatgcac agctcccagt ggtttgagcc    14340
ctttctgttt tggtttacag tcaagactga gatgaggtca gtgattaaat cacaaaccca    14400
tacttgccat aggaggagac acacacctgt attcttcact ggtagttcag ttgagttgct    14460
aatctctcgt gaccttgttg ctataatcag taaagagtct caacatgtat attacctgac    14520
atttgaactg gttttgatgt attgtgatgt catagagggg aggttaatga cagagaccgc    14580
tatgactatt gatgctaggt atacagagct tctaggaaga gtcagataca tgtggaaact    14640
gatagatggt ttcttccctg cactcgggaa tccaacttat caaattgtag ccatgctgga    14700
gcctctttca cttgcttacc tgcagctgag ggatataaca gtagaactca gaggtgcttt    14760
ccttaaccac tgctttactg aaatacatga tgttcttgac caaaacgggg tttctgatga    14820
aggtacttat catgagttaa ctgaagctct agattacatt ttcataactg atgacataca    14880
tctgacaggg gagattttct cattttcag aagtttcggc caccccagac ttgaagcagt     14940
aacggctgct gaaaatgtta ggaaatacat gaatcagcct aaagtcattg tgtatgagac    15000
tctgatgaaa ggtcatgcca tattttgtgg aatcataatc aacggctatc gtgacaggca    15060
cggaggcagt tggccaccgc tgaccctccc cctgcatgct gcagacacaa tccggaatgc    15120
tcaagcttca ggtgaaggt taacacatga gcagtgcatt gataactgga aatctttgc     15180
tggagtgaaa tttggctgct ttatgcctct tagcctggat agtgatctga caatgtacct    15240
aaaggacaag gcacttgctg ctctccaaag ggaatgggat tcagtttacc cgaaagagtt    15300
cctgcgttac gaccctccca agggaaccgg gtcacggagg cttgtagatg tttccttaa    15360
tgattcgagc tttgacccat atgatgtgat aatgtatgtt gtaagtggaa cttacctcca    15420
tgaccctgag ttcaacctgt cttacagcct gaaagaaaag gagatcaagg aaacaggtag    15480
acttttgct aaaatgactt acaaaatgag ggcatgccaa gtgattgctg aaaatctaat     15540
ctcaaacggg attggcaaat attttaagga caatgggatg gccaaggatg agcacgattt    15600
gactaaggca ctccacactc tagctgtctc aggagtcccc aaagatctca aagaaagtca    15660
caggggggg ccagtcttaa aaacctactc ccgaagccca gtccacacaa gtaccaggaa     15720
cgtgagagca gcaaaagggt ttatagggtt ccctcaagta attcggcagg accaagacac    15780
tgatcatccg gagaatatgg aagcttacga cacagtcagt gcatttatca cgactgatct    15840
caagaagtac tgccttaatt ggagatatga gaccatcagc ttgtttgcac agaggctaaa    15900
tgagatttac ggattgccct cattttcca gtggctgact aagaggcttg agacctctgt    15960
cctgtatgta agtgaccctc attgccccc cgaccttgac gcccatatcc cgttatataa     16020
agtcccaat gatcaaatct tcattaagta ccctatggga ggtatagaag ggtattgtca    16080
gaagctgtgg accatcagca ccattcccta tctataccctg gctgcttatg agagcggagt  16140
aaggctgct tcgttagtgc aaggggacaa tcagaccata gccgtaacaa aaagggtacc    16200
cagcacatgg ccctacaacc ttaagaaacg ggaagctgct agagtaacta gagattactt    16260
tgtaattctt aggcaaaggc tacatgatat tggccatcac ctcaaggcaa atgagacaat    16320
tgtttcatca cattttttg tctattcaaa aggaatatat tatgatgggc tacttgtgtc     16380
ccaatcactc aagagcatcg caagatgtgt attctggtca gagactatag ttgatgaaac    16440
aagggcagca tgcagtaata ttgctacaac aatggctaaa agcatcgaga gaggttatga    16500
ccgttacctt gcatattccc tgaacgtcct aaaagtgata cagcaaaattc tgatctctct   16560
tggcttcaca atcaattcaa ccatgacccg ggatgtagtc ataccctcc tcacaaacaa    16620
cgacctctta ataaggatgg cactgttgcc cgctcctcat gggggatga attatctgaa     16680
tatgagcagg ctgtttgtca gaaacatcgg tgatccagta acatcatcaa ttgctgatct    16740
caagagaatg attctcgcct cactaatgcc tgaagagacc ctccatcagg taatgacaca    16800
acaaccgggg gactcttcat tcctagactg gctagcgac ccttactcag caaatcttgt     16860
atgtgtccag agcatcacta gactcctcaa gaacataact gcaaggtttg tcctgatcca    16920
tagtccaaac ccaatgttaa aaggattatt ccatgatgac agtaaagaag aggacgaggg    16980
actggcggca ttcctcatgg acaggcatat tatagtacct agggcagctc atgaaatcct    17040
ggatcatagt gtcacagggg caagagagtc tattgcaggc atgctggata ccacaaaagg    17100
cttgattcga gccagcatga gggaaggggg tttaaccctct cgagtgataa ccagattgtc    17160
caattatgac tatgaacaat tcagagcagg atggttgcta ttgacaggaa gaaagagaaa    17220
tgtcctcatt gacaaagagt catgttcagt gcagctggcg agagctctaa gaagccatat    17280
gtgggcgagg ctagctcgag gacggccat ttacggcctt gaggtccctg atgtactaga     17340
atctatgcga ggccaccta ttcggcgtca tgagacatgt gtcatctgcg agtgtggatc     17400
agtcaactac ggatggttt ttgtccccctc gggttgccaa ctggatgata ttgacaagga    17460
aacatcatcc ttgagagtcc catatattgg ttctaccact gatgagagaa cagacatgaa    17520
gcttgccttc gtaagagccc caagtcgatc cttgcgatct gctgttagaa tagcaacagt    17580
gtactcatgg gcttacggtg atgatgatag ctcttggaac gaagcctggt tgttggctag    17640
gcaaagggcc aatgtgagcc tggaggagct aagggtgatc actcccatct caacttcgac    17700
taatttagcg cataggtgga gggatcgtag cactcaagtg aaatactcag gtacatcctt    17760
tgtccgagtg gcgaggtata ccacaatctc caacgacaat ctctcatttg tcatatcaga    17820
taagaaggtt gatactaact ttatataccca acaaggaatg cttctagggt tgggtgtttt    17880
agaaacattg tttcgactcg agaaagatac cggatcatct aacacggtat tacatcttca    17940
cgtcgaaaca gattgttgcg tgatcccgat gatagatcat cccaggatac ccagctcccg    18000
caagctagag ctgagggcag agctatgtac caacccattg atatatgata atgcaccttt    18060
aattgacaga gatgcaacaa ggctatacac ccagagccat aggaggcacc ttgtggaatt    18120
tgttacatgg tccacacccc aactatatca cattttagct aagtcacag cactatctat     18180
gattgacctg gtaacaaaat ttgagaagga ccatatgaat gaaatttcag ctctcatagg    18240
ggatgacgat atcaatagtt tcataactga gtttctgctc atagagccaa gattattcac    18300
tatctacttg ggccagtgtg cggccatcaa ttgggcatt tgatgtacatt atcatagacc     18360
```

```
atcagggaaa tatcagatgg gtgagctgtt gtcatcgttc ctttctagaa tgagcaaagg   18420
agtgtttaag gtgcttgtca atgctctaag ccacccaaag atctacaaga aattctggca   18480
ttgtggtatt atagagccta tccatggtcc ttcacttgat gctcaaaact tgcacacaac   18540
tgtgtgcaac atggtttaca catgctatat gacctacctc gacctgttgt tgaatgaaga   18600
gttagaagag ttcacatttc tcttgtgtga aagcgacgag gatgtagtac cggacagatt   18660
cgacaacatc caggcaaaac acttatgtgt tctggcagat ttgtactgtc aaccagggac   18720
ctgcccacca attcgaggtc taagaccggt agagaaatgt gcagttctaa ccgaccatat   18780
caaggcagag gctatgttat ctccagcagg atcttcgtgg aacataaatc caattattgt   18840
agaccattac tcatgctccc tgacttatct ccggcgagga tcgatcaaac agataagatt   18900
gagagttgat ccaggattca ttttcgacgc cctcgctgag gtaaatgtca gtcagccaaa   18960
gatcggcagc aacaacatct caaatatgag catcaaggct ttcagacccc cacacgatga   19020
tgttgcaaaa ttgctcaaag atatcaacac aagcaagcac aatcttccca tttcaggggg   19080
caatctcgcc aattatgaaa tccatgcttt ccgcagaatc gggttgaact catctgcttg   19140
ctacaaagct gttgagatat caacattaat taggagatgc cttgagccag gggaggacgg   19200
cttgttcttg ggtgagggat cgggttctat gttgatcact tataaggaga tacttaaact   19260
aaacaagtgc ttctataata gtggggtttc cgccaattct agatctggtc aaagggaatt   19320
agcaccctat ccctccgaag ttggccttgt cgaacacaga atgggagtag gtaatattgt   19380
caaagtgctc tttaacggga ggcccgaagt cacgtgggta ggcagtgtag attgcttcaa   19440
tttcatagtt agtaatatcc ctacctctag tgtggggttt atccattcag atatagagac   19500
cttgcctgac aaagatacta tagagaagct agaggaattg gcagccatct tatcgatggc   19560
tctgctcctg ggcaaaatag gatcaatact ggtgattaag cttatgcctt tcagcgggga   19620
ttttgttcag ggattttataa gttatgtagg gtctcattat agagaagtga accttgtata   19680
ccctagatac agcaacttca tatctactga atcttatttg gttatgacag atctcaaggc   19740
taaccggcta atgaatcctg aaaagattaa gcagcagata attgaatcat ctgtgaggac   19800
ttcacctgga cttataggtc acatcctatc cattaagcaa ctaagctgca tacaagcaat   19860
tgtggagac gcagttagta gaggtgatat caatcctact ctgaaaaaac ttacacctat   19920
agagcaggtg ctgatcaatt gcgggttggc aattaacgga cctaagctgt gcaaagaatt   19980
gatccaccat gatgttgcct cagggcaaga tggattgctt aattctatac tcatcctcta   20040
cagggagttg gcaagattca aagacaacca aagaagtcaa caagggatgt tccacgccta   20100
ccccgtattg gtaagtagca ggcaacgaga acttatatct aggatcaccc gcaaattttg   20160
ggggcacatt cttctttact ccgggaacaa aaagttgata aataagttta tccagaatct   20220
caagtccggc tatctgatac tagacttaca ccagaatatc ttcgttaaga atctatccaa   20280
gtcagagaaa cagattatta tgacgggggg tttgaaacgt gagtgggttt ttaaggtaac   20340
agtcaaggag accaaagaat ggtataagtt agtcggatac agtgccctga ttaaggacta   20400
attggttgaa ctccggaacc ctaatcctgc ctaggtggt taggcattat ttgcaatata   20460
ttaaagaaaa ctttgaaaat acgaagtttc tattcccagc tttgtctggt ggccggcata   20520
gtcccagcct cctcgctggc gctggctggg caacattccg aggggaccgt ccccacggta   20580
atggcgaatg ggacgcggcc gatccggctg ctaacaaagc ccgaaaggaa gctgagttgg   20640
ctgctggcgc tggctgggca ataactagca taaccccttg gggcctctaa acgggtcttg   20700
agggggttttt tgctgaaagg aggaactata tccggatgcg gccgcgcgct tggcgtaatc   20760
atggtcatag ctgtttcctg tgtgaaattg ttatccgctc acaattccac acaacatacg   20820
agccggaagc ataaagtgta aagcctgggg tgcctaatga gtgagctaac tcacattaat   20880
tgcgttgcgc tcactgcccg ctttccagtc gggaaacctg tcgtgccagc tgcattaatg   20940
aatcggccaa cgcgcgggga gaggcggttt gcgtattggg cgctcttccg cttcctcgct   21000
cactgactcg ctgcgctcgg tcgttcggct gcggcgagcg gtatcagctc actcaaaggc   21060
ggtaatacgg ttatccacag aatcagggga taacgcagga agaacatgt gagcaaaagg   21120
ccagcaaaag gccaggaacc gtaaaaaggc cgcgttgctg gcgtttttcc ataggctccg   21180
cccccctgac gagcatcaca aaaatcgacg ctcaagtcag aggtggcgaa acccgacagg   21240
actataaaga taccaggcgt ttccccctgg aagctccctc gtgcgctctc ctgttccgac   21300
cctgccgctt accggatacc tgtccgcctt tctcccttcg ggaagcgtgg cgctttctca   21360
tagctcacgc tgtaggtatc tcagttcggt gtaggtcgtt cgctccaagc tgggctgtgt   21420
gcacgaaccc cccgttcagc ccgaccgctg cgccttatcc ggtaactatc gtcttgagtc   21480
caacccggta agacacgact tatcgccact ggcagcagcc actggtaaca ggattagcag   21540
agcgaggtat gtaggcggtg ctacagagtt cttgaagtgg tggcctaact acggctacac   21600
tagaaggaca gtatttggta tctgcgctct gctgaagcca gttaccttcg gaaaaagagt   21660
tggtagctct tgatccggca aacaaaccac cgctggtagc ggtggttttt tgtttgcaa   21720
gcagcagatt acgcgcagaa aaaaaggatc tcaagaagat cctttgatct tttctacggg   21780
gtctgacgct cagtggaacg aaaactcacg ttaagggatt ttggtcatga gattatcaaa   21840
aaggatcttc acctagatcc ttttaaatta aaaatgaagt tttaaatcaa tctaaagtat   21900
atatgagtaa acttggtctg acagttacca atgcttaatc agtgaggcac ctatctcagc   21960
gatctgtcta tttcgttcat ccatagttgc ctgactcccc gtcgtgtaga taactacgat   22020
acgggagggc ttaccatctg gccccagtgc tgcaatgata ccgcgagacc cacgctcacc   22080
ggctccagat ttatcagcaa taaaccagcc agccggaagg gccgagcgca gaagtggtcc   22140
tgcaacttta tccgcctcca tccagtctat taattgttgc cgggaagcta gagtaagtag   22200
ttcgccagtt aatagtttgc gcaacgttgt tgccattgct acaggcatcg tggtgtcacg   22260
ctcgtcgttt ggtatggctt cattcagctc cggttcccaa cgatcaaggc gagttacatg   22320
atcccccatg ttgtgcaaaa aagcggttag ctccttcggt cctccgatcg ttgtcagaag   22380
taagttggcc gcagtgttat cactcatggt tatggcagca ctgcataatt ctcttactgt   22440
catgccatcc gtaagatgct tttctgtgac tggtgagtac tcaaccaagt cattctgaga   22500
atagtgtatg cggcgaccga gttgctcttg cccggcgtca atacgggata taccgcgcc   22560
acatagcaga actttaaaag tgctcatcat tggaaaacgt tcttcggggc gaaaactctc   22620
aaggatctta ccgctgttga tccagttc gatgtaaccc actcgtgcac ccaactgatc   22680
ttcagcatct tttactttca ccagcgtttc tgggtgagca aaaacaggaa ggcaaaatgc   22740
cgcaaaaaag ggaataaggg cgacacgaaa atgttgaata ctcatactct tcctttttca   22800
atattattga agcattttatc agggttattg tctcatgagc ggatacatat ttgaatgtat   22860
ttagaaaaat aaacaaatag ggggttccgcg cacatttccc cgaaaagtgc cacctg       22916
SEQ ID NO: 5      moltype = DNA   length = 22916
FEATURE           Location/Qualifiers
```

```
misc_feature        1..22916
                    note = MV WuhanCoV S in position 6
source              1..22916
                    mol_type = other DNA
                    organism = synthetic construct
SEQUENCE: 5
ggacgcgccc tgtagcggcg cattaagcgc ggcgggtgtg gtggttacgc gcagcgtgac    60
cgctacactt gccagcgccc tagcgcccgc tcctttcgct ttcttccctt cctttctcgc   120
cacgttcgcc ggctttcccc gtcaagctct aaatcggggg ctcccttag ggttccgatt    180
tagtgcttta cggcacctcg accccaaaaa acttgattag ggtgatggtt cacgtagtgg   240
gccatcgccc tgatagacgg ttttttcgcc tttgacgttg gagtccacgt tctttaatag   300
tggactcttg ttccaaactg gaacaacact caaccctatc tcggtctatt cttttgattt   360
ataagggatt ttgccgattt cggcctattg gttaaaaaat gagctgattt aacaaaaatt   420
taacgcgaat tttaacaaaa tattaacgtt tacaatttcg cgcattcgc cattcaggct    480
gcgcaactgt tgggaagggc gatcggtgcg ggcctcttcg ctattacgcc agctggcgaa   540
agggggatgt gctgcaaggc gattaagttg gtaacgcca gggttttccc agtcacgacg    600
ttgtaaaacg acggccagtg cgcgccgtta atacgactca ctatagggag acccaagctg   660
gctagctttg tttggtctga tgagtcccgt gaggacgaaa cccgcgtac cgggtcacca    720
aacaaagttg ggtaaggata gttcaatcaa tgatcatctt ctagtgcact taggattcaa   780
gatcctatta tcaggacaa gagcaggatt agggatatcc gagatggcca cacttttaag    840
gagcttagca ttgttcaaaa gaaacaagga caaaccaccc attacatcag gatccggtgg   900
agccatcaga ggaatcaaac acattattat agtacccatt cctggagatt cctcaattac   960
cactcgatcc agacttctgg accggttggt gaggttaatt ggaaaccgg atgtgagcgg   1020
gcccaaacta cacggggcac taataggtat attatcctta tttgtggagt ctccaggtca   1080
attgattcag aggatcaccg atgaccctga cgttagcata aggctgttag aggttgtcca   1140
gagtgaccag tcacaatctg gccttacctt cgcatcaaga gtaccaaca tggaggatga    1200
ggcggaccaa tacttttcac atgatgatcc aattagtagt gatcaatcca ggttcggatg   1260
gttcgggaac aaggaaatct cagatattga agtgcaagac cctgagggat tcaacatgat   1320
tctgggtacc atcctagccc aaatttgggt cttgctcgca aaggcggtta cggcccaga    1380
cacggcagct gattcggagc taagaaggtg gataaagtac acccaacaaa gaagggtagt   1440
tggtgaattt agattggaga gaaatggtt ggatgtggtg aggaacagga ttgccgagga    1500
cctctcctta cgccgattca tggtcgctct aatcctggat atcaagagaa cacccggaaa   1560
caaacccagg attgctgaaa tgatatgtga cattgataca tatatcgtag aggcaggatt   1620
agccagtttt atcctgacta ttaagtttgg gatagaaact atgtatcctg ctcttggact   1680
gcatgaattt gctggtgagt tatccacact tgagtccttg atgaaccttt accagcaaat   1740
gggggaaact gcaccctaca tggtaatcct ggagaactca attcagaaca gttcagtgc    1800
aggatcatac cctctgctct ggagctatgc catgggagta ggagtggaac ttgaaaactc   1860
catgggaggt ttgaactttg ccgatctta ctttgatcca gcatatttta gattaggca    1920
agagatggta aggaggtcag ctggaaaggt cagttccaca ttggcatctg aactcggtat   1980
cactgccgag gatgcaaggc ttgtttcaga gattgcaatg catactactg aggacaagat   2040
cagtagagcg gttggaccca gacaagccca agtatcattt ctacgcgtg atcaaagtga    2100
gaatgagcta ccgagattgg ggggcaagga agataggagg gtcaaacaga gtcgaggaga   2160
agccgggag agctacagag aaaccggggcc cagcagacag agtgatgcga gagctgccca   2220
tcttccaacc ggcacacccc tagacattga cactgcaacg gagtccagcc aagatccgca   2280
ggacagtcga aggtcagctg acgccctgct taggctgcaa gccatggcag gaatctcgga   2340
agaacaaggc tcagacacgg acacccctat agtgtacaat gacagaaatc ttctagacta   2400
ggtgcgagag gccgagggcc agaacaacat ccgcctacca tccatcattg ttataaaaa    2460
cttaggaacc aggtccacac agccgccagc ccatcaacca tccactccca cgattggagc   2520
caatggcaga agagcaggca cgccatgtca aaaacggact ggaatgcatc cgggctctca   2580
aggccgagcc catcggctca ctggccatcg aggaagctat ggcagcatgg tcagaaatat   2640
cagacaaccc aggacaggag cgagccacct gcagggagaa gaaggcaggc agttcagtc    2700
tcagcaaacc atgcctctca gcaattggat caactgaagg cggtgcacct cgcatccgcg   2760
gtcagggacc tggagagagc gatgacgacg ctgaaacttt gggaatcccc caagaaatc    2820
tccaggcatc aagcactggg ttacagtgtt ttacgtttta tgatcacagc ggtgaagcgg   2880
ttaagggaat ccaagatgct gactctatca tggttcaatc aggcctttga ggtgatagca   2940
ccctctcagg aggagacaat gaatctgaaa acagcgatgt ggatattggc gaacctgata   3000
ccgagggata tgctatcact gaccggggat ctgctcccat ctctatgggg ttcagggctt   3060
ctgatgttga aactgcagaa ggaggggaga tccacgagct cctgagactc caatccagag   3120
gcaacaactt tccgaagctt gggaaaactc tcaatgttcc tccgccccg gaccccggta    3180
gggccagcac ttccgggaca cccattaaaa agggcacaga cgcgagatta gcctcatttg   3240
gaacggagat cgcgtcttta ttgacaggtg gtgcaaccca atgtgctcga aagtcaccct   3300
cggaaccatc agggccaggt gcacctgcgg gaatgtccc cgagtgtgtg agcaatgccg   3360
cactgataca ggagtggaca cccgaatctg gtaccacaat ctccccgaga tcccagaata   3420
atgaagaagg gggagactat tatgatgatg agctgttctc tgatgtccaa gatattaaaa   3480
cagccttggc caaatacac gaggataatc agaagtataat ctccaagcta aatcactgc    3540
tgttattgaa gggagaagtt agtcaattag agaagcagat caaacagcaa aatatcagca   3600
tatccaccct ggaaggacac ctctcaagca tcatgatcgc cattcctgga cttgggaagg   3660
atcccaacga ccccactgca gatgtcgaaa tcaatcccga cttgaaaccc atcataggca   3720
gagattcagg ccgagcactg gccgaagttc tcaagaaacc cgttgccagc cgacaactcg   3780
aaggaatgac aaatgacgg accagttcca gaggacagct gctgaaggaa tttcagctaa   3840
agccgatcgg gaaaaagatg agctcagccg tcgggtttgt tcctgacacc ggccctgcat   3900
cacgcagtgt aatccgctcc attataaaat ccagccggct agaggaggat cggaagcgtt   3960
acctgatgac tctccttgat gatatcaaag agccaatga tcttgccaag ttccaccaga   4020
tgctgatgaa gataataatg aagtagctac agctcaactc agctgccaac cccatgccaa   4080
tcgacccacc tagtacaaac caaatcattt ataaaaaact taggagcaaa gtgattgcct   4140
cccaaggtcc acaatgacag agacctacga cttcgacaag tcggcatggg acatcaaagg   4200
gtcgatcgct ccgatacaac ccaccaccta cagtgatggc aggctggtgc cccaggtcag   4260
agtcatagat cctggtctag cgacaggaa ggatgaatgc tttatgtaca tgtttctgct    4320
gggggttgtt gaggacagcg attccctagg gcctccaatc gggcgagcat ttgggttcct   4380
```

```
gcccttaggt gttggcagat ccacagcaaa gcccgaaaaa ctcctcaaag aggccactga   4440
gcttgacata gttgttagac gtacagcagg gctcaatgaa aaactggtgt tctacaacaa   4500
caccccacta actctcctca caccttggag aaaggtccta acaacaggga gtgtcttcaa   4560
cgcaaaccaa gtgtgcaatg cggttaatct gataccgctc gataccccgc agaggttccg   4620
tgttgtttat atgagcatca cccgtctttc ggataacgat tattacaccg ttcctagaag   4680
aatgctggaa ttcagatcgg tcaatgcagt ggccttcaac ctgctggtga cccttaggat   4740
tgacaaggcg ataggccctg ggaagatcat cgacaataca gagcaacttc ctgaggcaac   4800
atttatggtc cacatcggga acttcaggag aagaagagt gaagtctact ctgccgatta   4860
ttgcaaaatg aaaatcgaaa agatgggcct ggttttttgca cttggtggga taggggcac   4920
cagtcttcac attagaagca caggcaaaat gagcaagact ctccatgcac aactcgggtt   4980
caagaagacc ttatgttacc cgctgatgga tatcaatgaa gaccttaatc gattactctg   5040
gaggagcaga tgcaagatag taagaatcca ggcagttttg cagccatcag ttcctcaaga   5100
attccgcatt tacgacgacg tgatcataaa tgatgaccaa ggactattca aagttctgta   5160
gaccgtagtg cccagcaatg cccgaaaacg accccccctca caatgacagc cagaaggccc   5220
ggacaaaaaa gcccctccg aaagactcca cggaccaagc gagaggccag ccagcagccg   5280
acggcaagcg cgaacaccag gcggcccag cacagaacag ccctgacaca aggccaccac   5340
cagccacccc aatctgcatc ctcctcgtgg gacccccgag gaccaacccc caaggctgcc   5400
cccgatccaa accaccaacc gcatcccaac caccccccggg aaagaaaccc ccagcaattg   5460
gaaggcccct cccctctttc ctcaacacaa gaactccaca accgaaccgc acaagcgacc   5520
gaggtgaccc aaccgcaggc atccgactcc ctagacagat cctctctccc cggcaaaacta   5580
aacaaaacttt agggccaagg aacatacaca cccaacagaa cccagacccc ggcccacggc   5640
gccgcgcccc caaccccga caaccagagg gagccccaa ccaatcccgc cggctcccca   5700
ggtgccccaca ggcagggaca ccaaccccccg aacagaccca gcaccccaacc atcgacaatc   5760
caagacgggg gggccccccc aaaaaaaggc ccccagggggc cgacagccag caccgcgagg   5820
aagccccaccc accccacaca cgaccacggc aaccaaacca gaacccagac cacccctgggc   5880
caccagctcc cagactcggc catcaccccg cagaaaggaa aggccacaac ccgcgcaccc   5940
cagccccgat ccggcgggga gccacccaac ccgaaccagc acccaagagc gatccccgaa   6000
ggaccccgga accgcaaagg acatcagtat cccacagcct ctccaagtcc cccggtctcc   6060
tcctcttctc gaagggacca aaagatcaat ccaccacacc cgacgacact caactcccca   6120
cccctaaagg agacacgggg aatcccagaa tcaagactca tccaatgtcc atcatgggtc   6180
tcaaggtgaa cgtctctgcc atattcatgg cagtactgtt aactctccaa acacccaccg   6240
gtcaaatcca ttgggcaat ctctctaaga taggggtggt aggaatagga agtgcaagct   6300
acaaagttat gactcgttcc agccatcaat cattagtcat aaaattaatg cccaatataa   6360
ctctcctcaa taactgcacg agggtagaga ttgcagaata caggagacta ctgagaacag   6420
ttttggaacc aattagagat gcacttaatg caatgaccca gaatataaga ccggttcaga   6480
gtgtagcttc aagtaggaga cacaagagat ttgcgggagt agtcctggca ggtgcggccc   6540
taggcgttgc cacagctgct cagataacag ccggcattgc acttcaccag tccatgctga   6600
actctcaagc catcgacaat ctgagagcga gcctggaaac tactaatcag gcaattgaga   6660
caatcagaca agcagggcag gagatgatat tggctgttca gggtgtccaa gactacatca   6720
ataatgagct gataccgtct atgaaccaac tatcttgtga tttaatcggc cagaagctcg   6780
ggctcaaatt gctcagatac tatacagaaa tcctgtcatt atttggcccc agtttacggg   6840
accccatatc tgcggagata tctatccagg cttttgagcta tgcgcttgga ggagacatca   6900
ataaggtgtt agaaaagctc ggatacagtg gaggtgattt actggcatc ttagagacgg   6960
gaggaataaa ggcccggata actcacgtcg acacagagtc ctacttcatt gtcctcagta   7020
tagcctatcc gacgctgtcc gagattaagg gggtgattgt ccaccggcta gagggggtct   7080
cgtacaacat aggctctcaa gagtggtata ccactgtgcc caagtatgtt gcaacccaag   7140
ggtaccttat ctcgaatttt gatgagtcat cgtgtacttt catgccagag gggactgtgt   7200
gcagccaaaa tgccttgtac ccgatgagtc ctctgctcca agaatgcctc cggggggtaca   7260
ccaagtcctg tgctcgtaca ctcgtatccg ggtcttttgg gaaccggttc attttatcac   7320
aagggaacct aatagccaat tgtgcatcaa tcctttgcaa gtgttacaca acaggaacga   7380
tcattaatca agaccctgac aagatcctca catcattgc tgccgatcac tgcccggtag   7440
tcgaggtgaa cggcgtgacc atccaagtcg ggagcaggag gtatccagac gctgtgtact   7500
tgcacagaat tgacctcggt cctcccatat cattggagag gttggacgta gggacaaatc   7560
tggggaatgc aattgctaag ttgaggatg ccaaggaatt gttggagtca tcggaccaga   7620
tattgaggag tatgaaaggt ttatcgagca ctagcatatt ctacatcctg attgcagtgt   7680
gtcttggagg gttgatagg atccccgctt taatatgttg ctgcaggggg cgttgtaaca   7740
aaaagggaga acaagttggt atgtcaagac caggcctaaa gcctgatctt acgggaacat   7800
caaaatccta tgtaaggtcg ctctgatcct ctacaactct tgaaacacaa atgtcccaca   7860
agtctcctct tcgtcatcaa gcaaccaccg cacccagcat caagcccacc tgaaattatc   7920
tccggcttcc ctctggccga acaatatcgg tagttaatta aaacttaggg tgcaagatca   7980
tcgataatgt caccaaacg agaccggata aatgccttct acaaagataa cccccatccc   8040
aagggaagta ggatagtcat taacagagaa catcttatga ttgatagacc ttatgttttg   8100
ctggctgttc tgtttgtcat gtttctgagc ttgatcgggt tgctagccat tgcaggaatt   8160
cgacttcatc gggcagcata ctacaccgca gagatccata aaagcctcag caccaattca   8220
gatgtaacta actcaatcga gcatcaggtc aaggacgtgc tgacaccact cttcaaaatc   8280
atcggtgatg aagtgggcct gaggacacct cagagattca ctgaccctagt gaaattaatc   8340
tctgacaaga ttaaattcct taatccggat agggagtacg acttcagaga tctcacttgg   8400
tgtatcaacc cgccagagag aatcaaattg gattatgatc aatctgtgc agatgtggct   8460
gctgaagagc tcatgaatgc attggtgaac tcaactctac tggagaccag aacaaccaat   8520
cagttcctag ctgtctcaaa gggaaactgc tcagggccca ctacaatcag aggtcaattc   8580
tcaaacatgt cgctgtccct gttagacttg tatttaggtc gaggttacaa tgtgtcatct   8640
atagtcacta tgacatccca gggaatgtat ggggaactt acctagtgga aaagcctaat   8700
ctgagcagca aaggtcaga gttgtcacaa ctgagcatgt accgagtgtt tgaagtaggt   8760
gttatcgaaa atcggggttt gggggctccg gtgttccata tgacaaacta tcttgagcaa   8820
ccagtcagta atgatctcag caactgtatg gtgcctttgg gggagctcaa actcgcagcc   8880
ctttgtcacg gggaagattc tatcacaatt ccctatcagg gatcagggaa aggtgtcagc   8940
ttccagctcg tcaagctagg tgtctggaaa tccccaaccg acatgcaatc ctgggtcccc   9000
ttatcaacgg atgatccagt gatagacagg ctttacctct catctcacag aggtgttatc   9060
gctgacaacc aagcaaaatg ggctgtcccg acaacacgaa cagatgacaa gttgcgaatg   9120
```

```
gagacatgct tccaacaggc gtgtaagggg aaaatccaag cactctgcga gaatcccgag   9180
tgggcaccat tgaaggataa caggattcct tcatacgggg tcttgtctgt tgatctgagt   9240
ctgacagttg agcttaaaat caaaattgct tcgggattcg ggccattgat cacacacggt   9300
tcagggatgg acctatacaa atccaaccac aacaatgtgt attggctgac tatcccgcca   9360
atgaagaacc tagcctttagg tgtaatcaac acattggagt ggataccgag attcaaggtt   9420
agtccctacc tcttcactgt cccaattaag gaagcaggcg aagactgcca tgccccaaca   9480
tacctacctg cggaggtgga tggtgatgtc aaactcagtt ccaatctggt gattctacct   9540
ggtcaagatc tccaatatgt tttggcaacc tacgatactt ccagggttga acatgctgtg   9600
gtttattacg tttacagccc aagccgctca ttttcttact tttatccttt taggttgcct   9660
ataaagggg tccccatcga attacaagtg gaatgcttca catgggacca aaaactctgg   9720
tgccgtcact tctgtgtgct tgcggactca gaatctggtg gacatatcac tcactctggg   9780
atggtgggca tgggagtcag ctgcacagtc acccgggaag atggaaccaa tcgcagatag   9840
ggctgctagt gaaccaatca catgatgtca cccagacatc aggcataccc accatccatc   9900
attgttataa aaaacttagg aaccaggtcc acacagagtg atacgcgtac gccaccaGtg   9960
tcgtgtttct ggtgctgctg cctctggtga gctcccagtg cgtgaacctg accacaagga  10020
cccagctgcc ccctgcctat accaattcct tcacacgggg cgtgtactat cccgacaagg  10080
tgttccggag cagcgtgctg cactccacac aggatctgtt tctgccttc tttctaacg    10140
tgacctggtt ccacgccatc cacgtgagcg gcaccaatgg cacaaagcgg ttcgacaatc  10200
cagtgctgcc ctttaacgat ggcgtgtact tcgcctccac cgagaagtct aacatcatca  10260
gaggctggat ctttggcacc acactggaca gcaagacaca gtccctgctg atcgtgaaca  10320
atgccaccaa cgtggtcatc aaggtgtgcg agttccagtt ttgtaatgat ccattcctgg  10380
gcgtgtacta tcacaagaac aataagtctt ggatggagag agttttcgc gtgtattcct   10440
ctgccaacaa ttgcacattt gagtacgtgt cccagcccTt cctgatgcac ctggagggca  10500
agcagggcaa tttcaagaac ctgagggagt tcgtgtttaa gaatatcgat ggctacttca  10560
aaatctactc caagcacacc ccaatcaacc tggtgcgcga cctgccacag ggcttctctg  10620
ccctgagccc actggtggat ctgcccatcg gcatcaacat caccggtttt cagacactgc  10680
tggccctgca cagaagctac ctgacaccag gcgacagctc ctctggatgg accgcaggag  10740
cagcagccta ctatgtgggc tatctgcagc ccaggacctt cctgctgaag tacaacgaga  10800
atggcaccat cacagacgcc gtggattgcg ccctggatcc cctgtctgag accaagtgta  10860
cactgaagag ctttaccgtg gagaagggca tctatcagac aagcaatttc agggtgcagc  10920
ctaccgagtc catcgtgcgc tttcccaata tcacaaacct gtgccctttt ggcgaggtgt  10980
tcaacgcaac ccgcttcgcc agcgtgtacg cctggaatag gaagcgcatc tccaactgcg  11040
tggccgacta ttctgtgctg tacaacagcg cctccttctc tacctttaag tgctatggcg  11100
tgagccccac aaagctgaat gacctgtgct ttaccaacgt gtacgccgat tccttcgtga  11160
tcagggggca cgaggtgcgc cagatcgcac caggacagca aggcaagatc gcagactaca  11220
attataagct gcctgacgat ttcaccggct gcgtgatcgc ctggaactct aacaatctgg  11280
atagcaaagt gggcggcaac tacaattatc tgtaccggct gtttagaaag tctaatctga  11340
agccattcga gagggacatc tccacagaaa tctaccaggc cggctctacc ccctgcaatg  11400
gcgtggaggg ctttaactgt tatttccctc tgcagagcta cggcttccag ccaacaaacg  11460
gcgtgggcta tcagccctac cgcgtggtgg tgctgtcttt tgagctgctg cacgcacctg  11520
caacagtgtg cggaccaaag aagagcacca atctggtgaa gaacaagtgc gtgaacttca  11580
acttcaacgg actgaccgga acaggcgtgc tgaccgagtc caacaagaag ttcctgcctt  11640
ttcagcagtt cggcagggac atcgcagata ccacagacgc cgtgcgcgac cctcagaccc  11700
tggagatcct ggacatcaca ccatgctcct tcggcggcgt gtctgtgatc acaccaggca  11760
ccaatacaag caaccaggtg gccgtgctgt atcaggacgt gaattgtacc gaggtgccag  11820
tggcaatcca cgcagatcag ctgacccta catggcgggt gtactctacc ggcagcaacg  11880
tgttccagac aagagccgga tgcctgatcg gagcagagca cgtgaacaat agctatgagt  11940
gcgacatccc tatcgcgcc ggcatctgtg cctcctacca gacccagaca aactcccccaa  12000
ggagagcacg gtctgtggcc agccagtcca tcatcgccta ccatgagc ctgggcgccg    12060
agaattccgt ggcctactcc aacaattcta tcgccatccc taccaacttc acaatctccg  12120
tgaccacaga gatcctgcca gtgagcatga ccaagacatc cgtggactgc acaatgtata  12180
tctgtggcga ttccaccgag tgctctaacc tgctgctgca gtacggctct ttttgtaccc  12240
agctgaatag agccctgaca ggcatcgccg tggagcagga caagaacaca caggaggtgt  12300
tcgcccaggt gaagcaaatc tacaagaccc cacccatcaa ggactttggc ggcttcaact  12360
tcagccagat cctgcccgat cctagcaagc catccaagcg gtcttttatc gaggacctgc  12420
tgttcaacaa ggtgaccctg gccgatgccg gcttcatcaa gcagtatgcc gattgcctgc  12480
gcgacatcgc cgccagagac ctgatctgtg cccagaagtt taatggctg accgtgctgc   12540
ctccactgct gacagatgag atgatcgccc agtacacatc tgccctgctg gccggaacca  12600
tcacaagcgg atggaccttc ggcgcaggag ccgcctgca gatcccctt gccatgcaga    12660
tggcctatcg gttcaacggc atcggcgtga cccagaatgt gctgtacgag aaccagaagc  12720
tgatcgccaa tcagtttaac tccgccatcg gcaagatcca ggactctctg agctccacag  12780
ccagcgccct gggcaagctg caggatgtgg tgaatcagaa cgcccaggcc tgaatacccc  12840
tggtgaagca gctgtctagc aacttcggcg ccatctcctc tgtgctgaat gacatcctga  12900
gccggctgga caaggtggag cagaggtgc agatcgaccg agcagactgc 12960
agtccctgca gacctacgtg acacagcagc tgatcagggc agcagagatc agggcctctg  13020
ccaatctggc cgccaccaag atgagcgagt gcgtgctggg ccagtccaag agagtggact  13080
tttgtggcaa gggctatcac ctgatgagct tcccacagtc cgcccctcac ggagtggtgt  13140
ttctgcacgt gacctacgtg ccagcccagg agaagaacct caccacagca ccagcaatct  13200
gccacgatgg caaggcacac tttcctaggg agggcgtgtt cgtgagcaac ggcacccact  13260
ggtttgtgac acagcgcaat ttctacgagc cacagatcat caccacagac aatacattcg  13320
tgtccggcaa ctgtgacgtg gtcatcggca tcgtgaacaa taccgtgtat gatcctctgc  13380
agccagagct ggactctttt aaggaggagc tggataagta cttcaagaat cacaccagcc  13440
ccgacgtgga tctgggcgac atctctggca tcaatgccag cgtggtgaac atccagaagg  13500
agatcgacag gctgaacgag gtggccaaga atctgaacga gtccctgatc gatctgcagg  13560
agctgggcaa gtatgagcag tacatcaagt ggccctggta tatctggctg ggcttcatcg  13620
ccggcctgat cgccatcgtg atggtgacca tcatgctgtg ctgtatgaca agctgctgtt  13680
cctgcctgaa gggctgctgt tcttgtggca gctgctgtaa gtttgatgag gacgatagcg  13740
agcctgtgct gaagggcgtg aagctgcact acacctgagc tagcgatcgc actagtgtga  13800
aatagacatc agaattaaga aaaacgtagg gtccaagtgg ttccccgtta tggactcgct  13860
```

```
atctgtcaac cagatcttat accctgaagt tcacctagat agcccgatag ttaccaataa   13920
gatagtagcc atcctggagt atgctcgagt ccctcacgct tacagcctgg aggaccctac   13980
actgtgtcag aacatcaagc accgcctaaa aaacggattt tccaaccaaa tgattataaa   14040
caatgtggaa gttgggaatg tcatcaagtc caagcttagg agttatccgg cccactctca   14100
tattccatat ccaaattgta atcaggattt atttaacata gaagacaaag agtcaacgag   14160
gaagatccgt gaactcctca aaagggggaa ttcgctgtac tccaaagtca gtgataaggt   14220
tttcaaatgc ttaagggaca ctaactcacg gcttggccta ggctccgaat tgagggagga   14280
catcaaggag aaagttatta acttgggagt ttacatgcac agctcccagt ggtttgagcc   14340
ctttctgttt tggtttacag tcaagactga gatgaggtca gtgattaaat cacaaaccca   14400
tacttgccat aggaggagac acacacctgt attcttcact ggtagttcag ttgagttgct   14460
aatctctcgt gaccttgttg ctataatcag taaagagtct caacatgtat attacctgac   14520
atttgaactg gttttgatgt attgtgatgt catagagggg aggttaatga cagagaccgc   14580
tatgactatt gatgctaggt atacagagct tctaggaaga gtcagataca tgtggaaact   14640
gatagatggt ttcttccctg cactcgggaa tccaacttat caaattgtag ccatgctgga   14700
gcctctttca cttgcttacc tgcagctgag ggatataaca gtagaactca gaggtgcttt   14760
ccttaaccac tgctttactg aaatacatga tgttcttgac caaaacgggt ttctgatga   14820
aggtacttat catgagttaa ctgaagctct agattacatt tcataactg atgacataca   14880
tctgacaggg gagattttct cattttttcag aagtttcggc cacccccagac ttgaagcagt   14940
aacggctgct gaaaatgtta ggaaatacat gaatcagcct aaagtcattg tgtatgagac   15000
tctgatgaaa ggtcatgcca tattttgtgg aatcataatc aacggctatc gtgacaggca   15060
cggaggcagt tggccaccgc tgaccctccc cctgcatgct gcagacacaa tccggaatgc   15120
tcaagcttca ggtgaagggt taacacatga gcagtgcgtt gataactgga aatctttgc   15180
tggagtgaaa tttggctgct ttatgcctct tagcctggat agtgatctga caatgtacct   15240
aaaggacaag gcacttgctg ctctccaaag ggaatgggat tcagtttacc cgaaagagtt   15300
cctgcgttac gaccctccca agggaaccgg gtcacggagg cttgtagatg ttttccttaa   15360
tgattcgaag tttgacccat atgatgtgat aatgtatgtt gtaagtggag cttacctcca   15420
tgaccctgag ttcaacctgt cttacagcct gaaagaaaag gagatcaagg aaacaggtag   15480
acttttttgct aaaatgactt acaaaatgag ggcatgccaa gtgattgctg aaaatctaat   15540
ctcaaacggg attggcaaat attttaagga caatgggatg gccaaggatg agcacgattt   15600
gactaaggca ctccacactc tagctgtctc aggagtcccc aaagatctca aagaaagtca   15660
caggggggg ccagtcttaa aaacctactc ccgaagccca gtccacacaa gtaccaggaa   15720
cgtgagagca gcaaaagggt ttataggggtt ccctcaagta attcggcagg accaagacac   15780
tgatcatccg gagaatatgg aagcttacga gacagtcagt gcatttatca cgactgatct   15840
caagaagtac tgccttaatt ggagatatga gaccatcagc ttgtttgcac agaggctaaa   15900
tgagatttac ggattgccct cattttttcca gtggctgcat aagaggcttg agacctctgt   15960
cctgtatgta agtgaccctc attgcccccc cgaccttgac gcccatatcc cgttatataa   16020
agtcccccaat gatcaaatct tcattaagta ccctatggga ggtatagaag ggtattgtca   16080
gaagctgtgg accatcagca ccattcccta tctataacctg gctgcttatg agagcggagt   16140
aaggatgct tcgttagtgc aagggggacaa tcagaccata gccgtaacaa aaagggtacc   16200
cagcacatgg ccctacaacc ttaagaaacg ggaagctgct agagtaacta gagattactt   16260
tgtaattctt aggcaaaggc tacatgatat tggccatcac ctcaaggcaa atgagacaat   16320
tgtttcatca catttttttg tctattcaaa aggaatatat tatgatgggc tacttgtgtc   16380
ccaatcactc aagagcatcg caagatgtgt attctgctga agactatag ttgatgaaac   16440
aagggcagca tgcagtaata ttgctacaac aatggctaaa agcatcgaga gaggttatga   16500
ccgttacctt gcatattccc tgaacgtcct aaaaagtgata cagcaaattc tgatctctct   16560
tggcttcaca atcaattcaa ccatgacccg ggatgtagtc ataccctcc tcacaaacaa   16620
cgacctctta ataaggatgg cactgttgcc cgctcctatt ggggggatga attatctgaa   16680
tatgagcagg ctgtttgtca gaaacatcgg tgatccagta acatcatcaa ttgctgatct   16740
caagagaatg attctcgcct cactaatgcc tgaagagacc ctccatcagg taatgacaca   16800
acaaccgggg gactcttcat tcctagactg ggctagcgac ccttactcag caaatcttgt   16860
atgtgtccag agcatcacta gactcctcaa gaacataact gcaaggtttg tcctgatcca   16920
tagtccaaac ccaatgttaa aaggattatt ccatgatgac agtaaagaag aggacgaggg   16980
actggcggca ttcctcatgg acaggcatat tatagtacct agggcagctc atgaaatcct   17040
ggatcatagt gtcacagggg caagagagtc tattgcaggc atgctggata ccacaaaagg   17100
cttgattcga gccagcatga ggaaggggg tttaacctct cgagtgataa ccagattgtc   17160
caattatgac tatgaacaat tcagagcagg gatggtgcta ttgacaggaa gaaagagaaa   17220
tgtcctcatt gacaaagagt catgttcagt gcagctggcg agagctctaa gaagccatat   17280
gtgggcgagg ctagctcgag gacggcctat ttacggcctt gaggtccctg atgtactaga   17340
atctatgcga ggccacctta ttcggcgtca tgagacatgt gtcatctgcg agtgtggatca   17400
agtcaactac ggatggtttt tgtcccctc gggttgccaa ctggatgata ttgacaagga   17460
aacatcatcc ttgagagtcc catatattgg ttctaccact gatgagagaa cagacatgaa   17520
gcttgccttc gtaagagccc caagtcgatc cttgcgatct gctgttagaa tagcaacagt   17580
gtactcatgg gcttacggtg atgatgatag ctcttggaac gaagcctggt tgttggctag   17640
gcaaaaggcc aatgtgagcc tggaggagct aagggtgatc actcccatct caacttcgac   17700
taatttagcg cataggttga gggatcgtag cactcaagtg aaatactcag gtacatccct   17760
tgtccgagtg gcgaggtata ccacaatctc caacgacaat ctctcatttg tcatatcaga   17820
taagaaggtt gatactaact ttatataccca acaaggaatg cttctagggt tgggtgtttt   17880
agaacattg tttcgactcg agaaagatac cggatcatct aacacggtat tacatcttca   17940
cgtcgaaaca gattgttgcg tgatcccgat gatagatcca cccaggatga ccagctcccg   18000
caagctagag ctgagggcag agctatgtac caacccattg atatatgata atgcacccttt   18060
aattgacaga gatgcaacaa ggctatacac ccagagccat aggaggcacc ttgtggaatt   18120
tgttacatgg tccacacccc aactatatca catttttagct aagtcacag cactatctat   18180
gattgacctg gtaacaaaat tgagaagga ccatatgaat gaaatttcag ctctcatagg   18240
ggatgacgat atcaatagtt tcatcaactga gttttctgct aatagccaa gattattcac   18300
tatctacttg ggccagtgtg cggccatcaa ttgggcattt gatgtacatt atcatagacc   18360
atcagggaaa tatcagatgg gtgagctgtt gtcatcgttc ctttctagaa tgagcaaagg   18420
agtgtttaag gtgcttgtca atgctctaag ccacccaaag atctacaaga aattctggca   18480
ttgtggtatt atagagccta tccatggtcc ttcacttgat gctcaaaact gcacacaac   18540
tgtgtgcaac atggttttaca catgctatat gacctacctc gacctgttgt tgaatgaaga   18600
```

```
gttagaagag ttcacatttc tcttgtgtga aagcgacgag gatgtagtac cggacagatt    18660
cgacaacatc caggcaaaac acttatgtgt tctggcagat ttgtactgtc aaccagggac    18720
ctgcccacca attcgaggtc taagaccggt agagaaatgt gcagttctaa ccgaccatat    18780
caaggcagag gctatgttat ctccagcagg atcttcgtgg aacataaatc caattattgt    18840
agaccattac tcatgctccc tgacttatct ccggcgaagg tcgatcaaac agataagatt    18900
gagagttgat ccaggattca tttttcgacgc cctcgctgag gtaaatgtca gtcagccaaa    18960
gatcggcagc aacaacatct caaatatgag catcaaggct ttcagacccc cacacgatga    19020
tgttgcaaaa ttgctcaaag atatcaacac aagcaagcac aatcttccca tttcaggggg    19080
caatctcgcc aattatgaaa tccatgcttt ccgcagaatc gggttgaact catctgcttg    19140
ctacaaagct gttgagatat caacattaat taggagatgc cttgagccag gggaggacgg    19200
cttgttcttg ggtgagggat cgggttctat gttgatcact tataaggaga tacttaaact    19260
aaacaagtgc ttctataata gtggggtttc cgccaattct agatctggtc aaagggaatt    19320
agcaccctat ccctccgaag ttggccttgt cgaacacaga atgggagtag gtaatattgt    19380
caaagtgctc tttaacggga ggcccgaagt cacgtgggta ggcagtgtga attgcttcaa    19440
tttcatagtt agtaatatcc ctacctctag tgtggggttt atccattcag atatagagac    19500
cttgcctgac aaagatacta tagagaagct agaggaattg gcagccatct tatcgatggc    19560
tctgctcctg ggcaaaatag gatcaatact ggtgattaag cttatgcctt tcagcgggga    19620
ttttgttcag ggatttataa gttatgtagg gtctcattat agagaagtga accttgtata    19680
ccctagatac agcaacttca tatctactga atcttatttg gttatgacag atctcaaggc    19740
taaccggcta atgaatcctg aaaagattaa gcagcagata attgaatcat ctgtgaggac    19800
ttcacctgga cttataggtc acatcctatc cattaagcaa ctaagctgca tacaagcaat    19860
tgtggagac gcagttagta gaggtgatat caatcctact ctgaaaaaac ttacacctat    19920
agagcaggtg ctgatcaatt gcgggttggc aattaacgga cctaagctgt gcaaagaatt    19980
gatccaccat gatgttgcct cagggcaaga tggattgctt aattctatac tcatcctcta    20040
cagggagttg gcaagattca aagacaacca aagaagtcaa caagggatgt tccacgccta    20100
ccccgtattg gtaagtagca ggcaacgaga acttatatct aggatcaccc gcaaattttg    20160
ggggcacatt cttctttact ccgggaacaa aaagttgata aataagttta tccagaatct    20220
caagtccggc tatctgatac tagacttaca ccagaatatc ttcgttaaga atctatccaa    20280
gtcagagaaa cagattatta tgacgggggg tttgaaacgt gagtgggttt ttaaggtaac    20340
agtcaaggag accaaagaat ggtataagtt agtcggatac agtgccctga ttaaggacta    20400
attggttgaa ctccggaacc ctaatcctgc cctaggtggt taggcattat ttgcaatata    20460
ttaaagaaaa ctttgaaaat acgaagtttc tattcccagc tttgtctggt ggccggcata    20520
gtcccagcct cctcgctggc gctggctggg caacattccg aggggaccgt ccccacggta    20580
atggcgaatg ggacgcggcc gatccggctg ctaacaaagc ccgaaaggaa gctgagttgg    20640
ctgctggcgc tggctggca ataactagca taacccttg gggcctctaa acgggtcttg    20700
agggtttt tgctgaaagg aggaactata tccggatgcg gccgcgcgct tggcgtaatc    20760
atggtcatag ctgtttcctg tgtgaaattg ttatccgctc acaattccac acaacatacg    20820
agccggaagc ataaagtgta aagcctgggg tgcctaatga gtgagctaac tcacattaat    20880
tgcgttgcgc tcactgcccg ctttccagtc gggaaacctg tcgtgccagc tgcattaatg    20940
aatcggccaa cgcgcgggga gaggcggttt gcgtattggg cgctcttccg cttcctcgct    21000
cactgactcg ctgcgctcgg tcgttcggct gcggcgagcg gtatcagctc actcaaaggc    21060
ggtaatacgg ttatccacag aatcagggga taacgcagga agaacatgt gagcaaaagg    21120
ccagcaaaag gccaggaacc gtaaaaaggc cgcgttgctg gcgtttttcc ataggctccg    21180
cccccctgac gagcatcaca aaaatcgacg ctcaagtcag aggtggcgaa acccgacagg    21240
actataaaga taccaggcgt ttccccctgg aagctccctc gtgcgctctc ctgttccgac    21300
cctgccgctt accggatacc tgtccgcctt tctcccttcg ggaagcgtgg cgctttctca    21360
tagctcacgc tgtaggtatc tcagttcggt gtaggtcgtt cgctccaagc tgggctgtgt    21420
gcacgaaccc cccgttcagc ccgaccgctg cgccttatcc ggtaactatc gtcttgagtc    21480
caacccggta agacacgact tatcgccact ggcagcagcc actggtaaca ggattagcag    21540
agcgaggtat gtaggcggtg ctacagagtt cttgaagtgg tggcctaact acggctacac    21600
tagaaggaca gtatttggta tctgcgctct gctgaagcca gttaccttcg gaaaaagagt    21660
tggtagctct tgatccggca aacaaaccac cgctggtagc ggtggttttt tgtttgcaa    21720
gcagcagatt acgcgcagaa aaaaaggatc tcaagaagat cctttgatct tttctacggg    21780
gtctgacgct cagtggaacg aaaactcacg ttaagggatt ttggtcatga gattatcaaa    21840
aaggatcttc acctagatcc ttttaaatta aaaatgaagt tttaaatcaa tctaaagtat    21900
atatgagtaa acttggtctg acagttacca atgcttaatc agtgaggcac ctatctcagc    21960
gatctgtcta tttcgttcat ccatagttgc ctgactcccc gtcgtgtaga taactacgat    22020
acgggagggc ttaccatctg gccccagtgc tgcaatgata ccgcgagacc cacgctcacc    22080
ggctccagat ttatcagcaa taaaccagcc agccggaagg gccgagcgca gaagtggtcc    22140
tgcaacttta tccgcctcca tccagtctat taattgttgc cgggaagcta gagtaagtag    22200
ttcgccagtt aatagtttgc gcaacgttgt tgccattgct acaggcatcg tggtgtcacg    22260
ctcgtcgttt ggtatggctt cattcagctc cggttcccaa cgatcaaggc gagttacatg    22320
atccccccatg ttgtgcaaaa aagcggttag ctccttcggt cctccgatcg ttgtcagaag    22380
taagttggcc gcagtgttat cactcatggt tatggcagca ctgcataatt ctcttactgt    22440
catgccatcc gtaagatgct tttctgtgac tggtgagtac tcaaccaagt cattctgaga    22500
atagtgtatg cggcgaccga gttgctcttg cccggcgtca atacgggata taccgcgcc    22560
acatagcaga actttaaaag tgctcatcat tggaaaacgt tcttcggggc gaaaactctc    22620
aaggatctta ccgctgttga gatccagttc gatgtaacc actcgtgcac ccaactgatc    22680
ttcagcatct tttactttca ccagcgtttc tgggtgagca aaaacaggaa ggcaaaatgc    22740
cgcaaaaaag gaataagggc gacacggaaa tgttgaatac tcatactct tcctttttca    22800
atattattga agcatttatc agggttattg tctcatgagc ggatacatat ttgaatgtat    22860
ttagaaaaat aaacaaatag gggttccgcg cacatttccc cgaaaagtgc cacctg        22916

SEQ ID NO: 6          moltype = DNA  length = 13907
FEATURE               Location/Qualifiers
misc_feature          1..13907
                      note = RABV vector: Coravax V1-China (RABVG-E31)
source                1..13907
                      mol_type = other DNA
```

-continued organism = synthetic construct
SEQUENCE: 6

```
acgcttaaca accagatcaa agaaaaaaca gacattgtca attgcaaagc aaaaatgtaa    60
cacccctaca atggatgccg acaagattgt attcaaagtc aataatcagg tggtctcttt   120
gaagcctgag attatcgtgg atcaaatatga gtacaagtac cctgccatca aagatttgaa   180
aaagccctgt ataaccctag gaaaggctcc cgatttaaat aaagcataca agtcagtttt   240
gtcaggcatg agcgccgcca aacttaatcc tgacgatgta tgttcctatt tggcagcggc   300
aatgcagttt tttgagggga catgtccgga agactggacc agctatgaa ttgtgattgc   360
acgaaaagga gataagatca ccccaggttc tctggtggag ataaaacgta ctgatgtaga   420
agggaattgg gctctgacag gaggcatgga actgacaaga gaccccactg tccctgagca   480
tgcgtcctta gtcggtcttc tcttgagtct gtataggttg agcaaaatat ccgggcaaaa   540
cactggtaac tataagacaa acattgcaga caggatagag cagattttg agacagcccc   600
tttttgttaaa atcgtggaac accatactct aatgacaact cacaaatgt gtgctaattg   660
gagtactata ccaaacttca gattttggc cggaacctat gacatgtttt tctcccggat   720
tgagcatcta tattcagcaa tcagagtggg cacagttgtc actgcttatg aagactgttc   780
aggactggta tcatttactg ggttcataaa acaaatcaat ctcaccgcta gagaggcaat   840
actatattc ttccacaaga actttgagga agagataaga agaatgtttg agccagggca   900
ggagacagct gttcctcact cttatttcat ccacttccgt tcactaggct tgagtgggaa   960
atctccttat tcatcaaatg ctgttggtca cgtgttcaat ctcattcact ttgtaggatg  1020
ctatatgggg caagtcagat ccctaaatgc aacggttatt gctgcatgtg ctcctcatga  1080
aatgtctgtt ctaggggct atctgggaga ggaattcttc gggaaaggga catttgaaag  1140
aagattcttc agagatgaga aagaacttca agaatacgag gcggctgaac tgacaaagac  1200
tgacgtagca ctggcagatg atggaactgt caactctgac gacgaggact acttttcagg  1260
tgaaaccaga agtccggagg ctgttttatac tcgaatcatg atgaatggag gtcgactaaa  1320
gagatctcac atacggagat atgtctcagt cagttccaat catcaagccc gtccaaactc  1380
attcgccgag tttctaaaca agacatattc gagtgactca taacatgaaa aaaactaaca  1440
cccctcccgt acgccaccat gttcgtgttt ctggtgctgc tgcctctggt gagctcccag  1500
tgcgtgaacc tgaccacaag gacccagctg cccctgcct ataccaattc cttcacacgg  1560
ggcgtgtact atcccgacaa ggtgttccgg agcagcgtgc tgcactccac acaggatctg  1620
tttctgcctt tctttttctaa cgtgacctgg ttccacgcca tccacgtgga cggcaccaat  1680
ggcacaaagc ggttcgacaa tccagtgctg cccctttaacg atggcgtgta cttcgcctcc  1740
accgagaagt ctaacatcat cagaggctgg atctttggca ccacactgga cagcaagaca  1800
cagtccctgc tgatcgtgaa caatgccacc aacgtggtca tcaaggtgtg cgagttccag  1860
ttttgtaatg atccattcct gggcgtgtac tatcacaaga acaataagtc ttggatggag  1920
agcgagtttc gcgtgtattc ctctgccaac aatttgcacat ttgagtacgt gtcccagccc  1980
ttcctgatgg acctggaggg caagcagggc aatttcaaga acctgagga gttcgtgttt  2040
aagaatatcg atggctactt caaaatctac tccaagcaca cccccaatcaa cctggtgcgc  2100
gacctgccac agggcttctc tgccctggag ccactggtgg atctgcccat cggcatcaac  2160
atcacccggt ttcagacact gctgccctg cacagaagct acctgacacc aggcgacagc  2220
tcctctggat ggaccgcagg agcagcagcc tactatgtgg gctatctgca gcccaggacc  2280
ttcctgctga gtacaacga gaatggcacc atcacagacg ccgtggattg cgccctggat  2340
cccctgtctg agaccaagtg tacactgaag agctttaccg tggagaaggg catctatcag  2400
acaagcaatt tcagggtgca gcctaccgag tccatcgtgc gcttcccaa tatcacaaac  2460
ctgtgccctt ttggcgaggt gttcaacgca acccgcttcg ccagcgtgta cgcctggaat  2520
aggaagcgca tctccaactg cgtggccgac tattctgtgc tgtacaacag cgcctccttc  2580
tctaccttta agtgctatgg cgtgagcccc acaaagctga tgacctgtg ctttaccaac  2640
gtgtaccgcg attccttcgt gatcaggggc gacgaggtgc gccagatcgc accaggacag  2700
acaggcaaga tcgcagacta caattataag ctgcctgacg atttcaccgg ctgcgtgatc  2760
gcctggaact ctaacaatct ggatagcaaa gtgggcggca actacaatta tctgtaccgg  2820
ctgtttagaa agtctaatct gaagccattc gagagggaca tctccacaga aatctaccag  2880
gccggctcta cccctgcaa tggcgtggag ggctttaact gttatttccc tctgcagagc  2940
tacggcttcc agccaacaaa cggcgtgggc tatcagccct accgcgtggt ggtgctgtct  3000
tttgagctgc tgcacgcacc tgcaacagtg tgcggaccaa agaagagcac caatctggtg  3060
aagaacaagt gcgtgaactt caacttcaac ggactgaccg gaacaggcgt gctgaccgag  3120
tccaacaaga agttcctgcc ttttcagcag ttcggcagga catcgcaga taccacagac  3180
gccgtgcgcg accctcagac cctggagatc ctggacatca ccatgctc cttcggcggc  3240
gtgtctgtga tcacaccagg caccaataca agcaaccagg tggccgtgct gtatcaggac  3300
gtgaattgta ccgaggtgcc agtggcaatc cacgcagatc agctgacccc tacatggcgg  3360
gtgtactcta ccggcagcaa cgtgttccag acaagagccg gatgcctgat cggagcagag  3420
cacgtgaaca atagctatga gtgcgacatc cctatcggcg ccggcatctg tgcctcctac  3480
cagacccaga caaactcccc aaggtctgtg ggagatgagg ccgaagactt tgtggaagtc  3540
cacctgcctg atgtgcataa ccaggtgtct ggcgtcgacc tgggactgcc aaattggggc  3600
aagtacgtgc tgctgagtgc tggagcactg actgccctga tgctgatcat tttcctgatg  3660
acctgctgtc ggcgcgtgaa cagaagtgag cccactcagc acaatctgcg aggaaccagg  3720
agagaagtgt cagtcacacc tcagagcggg aaaatcatta gtagtgggga atcacataaa  3780
agcgggggcg agaccaggct gtgagctagc catgaaaaaa actaacaccc ctcctttcga  3840
accatcccaa acatgagcaa gatctttgtc aatcctagtg ctattagagc cggtctggcc  3900
gatcttgaga tggctgaaga aactgttgat ctgatcaata gaaatatcga agacaatcag  3960
gctcatctcc aaggggaacc catagaggtg gacaatctcc ctgaggatat ggggcgactt  4020
cacctggatg atggaaaatc gcccaaccat ggtgagatag ccaaggtggg agaaggcaag  4080
tatcgagagg acttcagat ggatgaagga gaggatccta gcttcctgtt ccagtcatac  4140
ctggaaaatg ttggagtcca atagtcaga caaatgaggt caggagagag atttctcaag  4200
atatggtcac agaccgtaga agagattata tcctatgtcg cggtcaactt tccaaccct  4260
ccaggaaagt cttcagagga taaatcaacc cagactactg caagactggg aaagaaggag  4320
acaacaccca ctccttctca gagagaaagc caatcatcga aagccaggat ggcggctcaa  4380
attgcttctg gccctccagc ccttgaatgg tcggctacca atgaagagga tgatctatca  4440
gtggaggctg agatcgctca ccagattgca gaaagttttct ccaaaaata taagtttccc  4500
tctcgatcct cagggatact cttgtataat tttgagcaat tgaaaatgaa ccttgatgat  4560
atagttaaag aggcaaaaaa tgtaccaggt gtgacccgtt tagcccatga cgggtccaaa  4620
```

```
ctcccccctaa gatgtgtact gggatgggtc gctttggcca actctaagaa attccagttg   4680
ttagtcgaat ccgacaagct gagtaaaatc atgcaagatg acttgaatcg ctatacatct   4740
tgctaaccga acctctcccc tcagtccctc tagacaataa aatccgagat gtcccaaagt   4800
caacatgaaa aaaacaggca acaccactga taaaatgaac ctcctacgta agatagtgaa   4860
aaaccgcagg gacgaggaca ctcaaaaatc ctctcccgcg tcagcccctc tggatgacga   4920
tgacttgtgg cttccacccc ctgaatacgt cccgctgaaa gaacttacag gcaagaagaa   4980
catgaggaac ttttgtatca acggaagggt taaagtgtgt agcccgaatg gttactcgtt   5040
caggatcctg cggcacattc tgaaatcatt cgacgagata tattctggga atcataggat   5100
gatcgggtta gtcaaagtgg ttattggact ggctttgtca ggatctccag tccctgaggg   5160
cctgaactgg gtatacaaat tgaggagaac ctttatcttc cagtgggctg attccagggg   5220
ccctcttgaa ggggaggagt tggaatactc tcaggagatc acttgggatg atgatactga   5280
gttcgtcgga ttgcaaataa gagtgattgc aaaacagtgt catatccagg gcagagtctg   5340
gtgtatcaac atgaacccga gagcatgtca actatggtct gacatgtctc ttcgacaca    5400
aaggtccgaa gaggacaaag attcctctct gcttctagaa taatcagatt atatcccgca   5460
aatttatcac ttgttttacct ctggaggaga gaacatatgg gctcaactcc aacccttggg  5520
agcaatataa caaaaaacat gttatggtgc cattaaaccg ctgcatttca tcaaagtcaa   5580
gttgattacc tttacatttt gatcctcttg gatgtgaaaa aaactattaa catccctcaa   5640
aagaccccgg gaaagatggt tcctcaggct ctcctgtttg taccccttct ggttttcca   5700
ttgtgttttg ggaaattccc tatttacacg ataccagaca agcttggtcc ctggagtccg   5760
attgacatac atcacctcag ctgcccaaac aatttggtag tggaggacga aggatgcacc   5820
aacctgtcag ggttctccta catggaactt aaagttggat acatcttagc cataaaagtg   5880
aacgggttca cttgcacagg cgttgtgacg gaggctgaaa cctacactaa cttcgttggt   5940
tatgtcacaa ccacgttcaa aagaaagcat ttccgcccaa caccagatgc atgtagagcc   6000
gcgtacaact ggaagatggc cggtgacccc agatatgaag agtctctaca caatccgtac   6060
cctgactacc gctggcttcg aactgtaaaa accaccaagg agtctctcgt tatcatatct   6120
ccaagtctgtg cagatttgga cccatatgac agatcccttc actcgagggt cttccctagc  6180
gggaagtgct caggagtagc ggtgtcttct acctactgct ccactaacca cgattacacc   6240
atttggatgc ccgagaatcc gagactaggg atgtcttgtg acatttttac caatagtaga   6300
gggaagagag catccaaagg gagtgagact tgcggctttg tagatgaaag aggcctatat   6360
aagtctttaa aaggagcatg caaactcaag ttatgtggga ttctaggact tagacttatg   6420
gatgaaacat gggtctcgat gcaaacatca aatgaaacca aatggtgccc tcccgataag   6480
ttggtgaacc tgcacgactt tcgctcagac gaaattgagc accttgttgt agaggagttg   6540
gtcaggaaga gagaggagtg tctggatgca ctagagtcca tcatgacaac caagtcagtg   6600
agtttcagac gtctcagtca tttaagaaaa cttgtccctg ggtttggaaa agcatatacc   6660
atattcaaca agaccttgat ggaagccgat gctcactaca agtcagtcga gacttggaat   6720
gagatcctcc cttcaaaagg gtgtttaaga gttggggggga ggtgtcatcc tcatgtgaac   6780
ggggtgtttt tcaatggtat aatattagga cctgacggca atgtcttaat cccagagatg   6840
caatcatccc tcctccagca acatatggag ttgttggaat cctcggttat ccccccttgtg  6900
caccccctgg cagaccgtc taccgttttc aaggacggtg acgaggctga ggattttgtt    6960
gaagttcacc ttcccgatgt gcacaatcag gtctcaggag ttgacttggg tctcccgaac   7020
tgggggaagt atgtattact gagtgcaggg gccctgactg ccttgatgtt gataattttc   7080
ctgatgcatt gttgtagaag agtcaatcga tcagaaccta cgcaacacaa tctcagaggg   7140
acagggaggg aggtgtcagt cactcccaa agcgggaaga tcatatcttc atgggaatca   7200
cacaagagtg ggggtgagac cagactgtaa ttaattaacg tcctttcaac gatccaagtc   7260
catgaaaaaa actaacaccc ctcccgtacc tagcttataa agtgctgggt catctaagct   7320
tttcagtcga gaaaaaaaca ttagatcaga agaacaactg gcaacacttc tcaacctgag   7380
acttacttca agatgctcga tcctggaagg gtctatgatg aaccctattga cccaatcgag   7440
ttagaggctg aacccagagg aacccccatt gtccccaaca tcttgaggaa ctctgactac   7500
aatctcaact ctcctttgat agaagatcct gctagactaa tgttagaatg gttaaaaaca   7560
gggaatagac cttatcggat gactctaaca gacaattgct ccaggtcttt cagagttttg   7620
aaagattatt tcaagaaggt agatttgggt tctctcaaga tgggcggaan ggctgacag    7680
tcaatgattt ctctctggtt atatggtgcc cactctgaat ccaacaggag ccggagatgt   7740
ataacagact tggcccattt ctattccaag tcgtcccccca tagagaagct gttgaatctc   7800
acgctaggaa atagagggct gagaatcccc cagagggag tgttaagttg ccttgagagg    7860
gttgattatg ataatgcatt tggaaggtat cttgccaaca cgtattcctc ttacttgttc   7920
ttccatgtaa tcaccttata catgaacgcc ctagactggg atgaagaaaa gaccatccta   7980
gcattatgga aagatttaac ctcagtggac atcgggaagg acttggtaaa gttcaaagac   8040
caaatatggg gactgctgat cgtgacaaag gactttgttt actcccaaag ttccaattgt   8100
cttttgaca gaaactacac acttatgcta aaagatcttt tcttgtctcg cttcaactcc   8160
ttaatggtct tgctctctcc cccagagccc cgatactcag atgacttgat atctcaacta   8220
tgccagctgt acattgctgg ggatcaagtc ttgtctatgt gtggaaactc cggctatgaa   8280
gtcatcaaaa tattggagcc atatgtcgtg aatagtttag tccagagagc agaaaagttt   8340
aggcctctca ttcattcctt gggagacttt cctgtatta taaagacaa ggtaagtcaa    8400
cttgaagaga cgttcggtcc ctgtgcaaga aggttcctga gggctctgga tcaattcgaa   8460
aacatacatg acttggtttt tgtgtttggc tgttacaggc attggggggca cccatatata   8520
gattatcgaa agggtctgtc aaaactatat gatcaggttc accttaaaaa aatgatagat   8580
aagtcctacc aggagtgctt agcaagcgac ctagccagga ggatcctaag atgggggttt   8640
gataagtact ccaagtggta tctggattca agattcctag cccgagacca cccccttgact  8700
ccttatatca aaaccccaaac atggccaccc aaacatattg tagacttggt ggggggatca   8760
tggcacaagc tcccgatcac gcagatcttt gagattcctg aatcaatgga tccgtcagaa   8820
atattggatg acaaatcaca ttcttttcacc agaacgagac tagcttcttg gctgtcagaa   8880
aaccgagggg ggcctgttcc tagcgaaaaa gttattatca cggccctgtc taagccgcct   8940
gtcaatcccc gagagtttct gaggtctata gacctcggag gattgccaga tgaagacttg   9000
ataattggcc tcaagccaaa ggaacggaa ttgaagattg aaggtcgatt ctttgctcta   9060
atgtcatgga atcaagatt gtattttgtc atcactgaaa aactcttggc caactacatc   9120
ttgccacttt ttgacgcgct gactatgaca gacaacctga acaaggtgtt taaaaagctg   9180
atcgacaggg tcaccgggca agggcttttg gactattcaa gggtcacata tgcatttcac   9240
ctggactatg aaaagtggaa caaccatcaa agattagagt caacagagga tgtatttctc   9300
gtcctagatc aagtgtttgg attgaagaga gtgttttcta gaacacacga gttttttcaa   9360
```

```
aaggcctgga tctattattc agacagatca gacctcatcg ggttacggga ggatcaaata  9420
tactgcttag atgcgtccaa cggcccaacc tgttggaatg gccaggatgg cgggctagaa  9480
ggcttacggc agaagggctg gagtctagtc agcttattga tgatagatag agaatctcaa  9540
atcaggaaca caagaaccaa aatactagct caaggagaca accaggtttt atgtccgaca  9600
tacatgttgt cgccagggct atctcaagag gggctcctct atgaattgga gagaatatca  9660
aggaatgcac tttcgatata cagagccgtc gaggaagggg catctaagct agggctgatc  9720
atcaagaaag aagagaccat gtgtagttat gacttcctca tctatggaaa aacccctttg  9780
tttagaggta acatattggt gcctgagtcc aaaagatggg ccagagtctc ttgcgtctct  9840
aatgaccaaa tagtcaacct cgccaatata atgtcgacag tgtccaccaa tgcgctaaca  9900
gtggcacaac actctcaatc tttgatcaaa ccgatgaggg attttctgct catgtcagta  9960
caggcagtct ttcactacct gctatttagc ccaatcttaa agggaagagt ttacaagatt 10020
ctgagcgctg aaggggagag ctttctccta gccatgtcaa ggataatcta tctagatcct 10080
tctttgggag ggatatctgg aatgtccctc ggaagattcc atatacgaca gttctcagac 10140
cctgtctctg aagggttatc cttctggaga gagatctgat taagctccca agagtcctgg 10200
attcacgcgt tgtgtcaaga ggctggaaac ccagatcttg gagagagaac actcgagagc 10260
ttcactcgcc ttctagaaga tccgaccacc ttaaatatca gaggaggggc cagtcctacc 10320
attctactca aggatgcaat cagaaaggct ttatatgacg aggtggacaa ggtggaaaat 10380
tcagagtttc gagaggcaat cctgttgtcc aagacccata gagtaattt tatactcttc 10440
ttaatatctg ttgagcctct gtttcctcga tttctcagtg agctattcag ttcgtctttt 10500
ttgggaatcc ccgagtcaat cattggattg atacaaaact cccgaacgat aagaaggcag 10560
tttagaaaga gtctctcaaa aactttagaa gaatccttct acaactcaga gatccacggg 10620
attagtcgga tgacccagac acctcagagg gttgggggg tgtggccttg ctcttcagag 10680
agggcagatc tacttaggga gatctcttgg ggaagaaaag tggtaggcac gacagttcct 10740
cacccttctg agatgttggg attacttccc aagtcctcta tttcttgcac ttgtggagca 10800
acaggaggag gcaatcctag agtttctgta tcagtactcc cgtcctttga tcagtcattt 10860
ttttcacgag gccccctaaa gggatacttg ggctcgtcca cctctatgtc gacccagcta 10920
ttccatgcat gggaaaaagt cactaatgtt catgtggtga agagagctct atcgttaaaa 10980
gaatctataa actggttcat tactagagat tccaacttgg ctcaagctct aattaggaac 11040
attatgtctc tgacaggccc tgatttccct ctagaggagg ccctgtctt caaaaggacg 11100
gggtcagcct tgcataggtt caagtctgcc agatacagcg aaggaggta ttcttctgtg 11160
tgcccgaacc tcctctctca tatttctgtt agtacagaca ccatgtctga tttgacccaa 11220
gacgggaaga actacgattt catgttccag ccattgatgc tttatgcaca gacatggaca 11280
tcagagctgg tacagagaga cacaaggcta agagactcta cgtttcattg gcacctccga 11340
tgcaacaggt gtgtgagacc cattgacgac gtgacctgg agacctctca gatcttcgag 11400
tttccggatg tgtcgaaaag aatatccaga atggtttctg gggctgtgcc tcacttccag 11460
aggcttcccg atatccgtct gagaccagga gattttgaat ctctaagcgg tagagaaaag 11520
tctcaccata tcggatcagc tcaggggctc ttatactcaa tcttagtggc aattcacgac 11580
tcaggataca atgatggaac catcttccct gtcaacatat acggcaaggt ttcccctaga 11640
gactatttga gagggctcgc aaggggagta ttgataggat cctcgatttg cttcttgaca 11700
agaatgacaa atatcaatat taatagacct cttgaattgg tctcaggggt aatctcatat 11760
attctcctga ggctagataa ccatccctcc ttgtacataa tgctcagaga accgtctctt 11820
agaggagaga tattttctat ccctcagaaa atccccgccg cttatccaac cactatgaaa 11880
gaaggcaaca gatcaatctt gtgttatctc caacatgtc tacgctatga gcgagagata 11940
atcacggcgt ctccagagaa tgactggcta tggatctttt cagactttag aagtgccaaa 12000
atgacgtacc tatccctcat tacttaccag tctcatcttc tactccagag ggttgagaga 12060
aacctatcta agagtatgag agataacctg cgacaattga gttctttgat gaggcaggtg 12120
ctgggcgggc acgagaaga taccttagag tcagacgaca acattcaacg actgctaaaa 12180
gactctttac gaaggacaag atgggtggat caagaggtgc gccatgcagc tagaaccatg 12240
actggagatt acagccccaa caagaaggtg tcccgtaagg taggatgttc agaatgggtc 12300
tgctctgctc aacaggttgc agtctctacc tcagcaaacc cggcccctgt ctcggagctt 12360
gacataaggg ccctctctaa gaggttccag aacccttga tctcgggctt gagagtggtt 12420
cagtgggcaa ccggtgctca ttataagctt aagcctattc tagatgatct caatgttttc 12480
ccatctctct gccttgtagt tggggacggg tcagggggga tatcaagggc agtcctcaac 12540
atgtttccag atgccaagct tgtgttcaac agtcttttag aggtgaatga cctgatggct 12600
tccggaacac atccactgcc tccttcagca atcatgaggg gaggaaatga tatcgtctcc 12660
agagtgatag atcttgactc aatctgggaa aaaccgtccg acttgagaaa cttggcaacc 12720
tggaaatact tccagtcagt ccaaaagcag gtcaacatgt cctatgacct cattatttgc 12780
gatgcagaag ttactgacat tgcatctatc aaccggatca ccctgttaat gtccgatttt 12840
gcattgtcta tagatggacc actctatttg gtcttcaaaa cttatgggac tatgctagta 12900
aatccaaact acaaggctat tcaacacctg tcaagagcgt tcccctcggt cacagggttt 12960
atcacccaag taacttcgtc tttttcatct gagctctacc tccgattctc caaacgaggg 13020
aagttttca gagatgctga gtacttgacc tcttccaccc ttgagaaat gagccttgtg 13080
ttattcaatt gtagcagccc caagagtgag atgcagagag ctcgttcctt gaactatcag 13140
gatcttgtga gaggatttcc tgaagaaatc atatcaaatc cttacaatga gatgatcata 13200
actctgattg acagtgatgt agaatctttt ctagtccaca agatggttga tgatcttgag 13260
ttacagaggg gaactctgtc taaagtggct atcattatag ccatcatgat agttttctcc 13320
aacagagtct tcaacgtttc caaacccta actgaccct cgttctatcc accgtctgat 13380
cccaaaatcc tgaggcactt caacatatgt tgcagtacta tgatgtatct atctactgct 13440
ttaggtgacg tccctagctt cgcaagactt cacgacctgt ataacagacc tataacttat 13500
tacttcagaa agcaagtcat tcgagggaac gtttatcat cttggagttg gtccaacgac 13560
acctcagtgt tcaaaagggg agcctgtaat tctagcctga gtctgtcatc tcactggatc 13620
aggttgattt acaagatagt gaagactacc agactcgttg gcagcatcaa ggatctatcc 13680
agagaagtgg aaagacacct tcataggtac aacaggtgga tcaccctaga ggatatcaga 13740
tctagatcat ccctactaga ctacttgc tgtgaaccg gaagcctgcc 13800
catgctaaga ctcttgtgtg atgtatcttg aaaaaaacaa gatccctaaat ctgaacctt 13860
ggttgtttga ttgttttct catttttgtt gtttattttgt taagcgt           13907

SEQ ID NO: 7       moltype = DNA   length = 13907
FEATURE            Location/Qualifiers
```

```
misc_feature      1..13907
                  note = RABV vector: Coravax V1-South Africa (RABVG-E31)
source            1..13907
                  mol_type = other DNA
                  organism = synthetic construct
SEQUENCE: 7
acgcttaaca accagatcaa agaaaaaaca gacattgtca attgcaaagc aaaaatgtaa    60
caccccctaca atggatgccg acaagattgt attcaaagtc aataatcagg tggtctcttt   120
gaagcctgag attatcgtgg atcaaatatga gtacaagtac cctgccatca aagatttgaa   180
aaagccctgt ataaccctag gaaaggctcc cgatttaaat aaagcataca agtcagtttt   240
gtcaggcatg agcgccgcca aacttaatcc tgacgatgta tgttcctatt tggcagcggc   300
aatgcagttt tttgagggga catgtccgga agactggacc agctatggaa ttgtgattgc   360
acgaaaagga gataagatca ccccaggttc tctggtggga ataaaacgta ctgatgtaga   420
agggaattgg gctctgacag gaggcatgga actgacaaga gaccccactg tccctgacca   480
tgcgtcctta gtcggtcttc tcttgagtct gtataggttg agcaaaatat ccgggcaaaa   540
cactggtaac tataagacaa acattgcaga caggatagag cagattttg agacagcccc   600
ttttgttaaa atcgtggaac accatactct aatgacaact cacaaaatgt gtgctaattg   660
gagtactata ccaaacttca gatttttggc cggaacctat gacatgtttt tctccccggat   720
tgagcatcta tattcagcaa tcagagtggg cacagttgtc actgcttatg aagactgttc   780
aggactggta tcatttactg ggttcataaa acaaatcaat ctcaccgcta gagaggcaat   840
actatatttc ttccacaaga actttgagga agagataaga agaatgtttg agccagggca   900
ggagacagct gttcctcact cttatttcat ccacttcctg tcactaggct tgagtgggaa   960
atctccttat tcatcaaatg ctgttggtca cgtgttcaat ctcattcact tgtaggatg   1020
ctatatgggt caagtcagat ccctaaatgc aacggttatt gctgcatgtg ctcctcatga  1080
aatgtctgtt ctagggggct atctgggaga ggaattcttc gggaaaggga catttgaaag  1140
aagattcttc agagatgaga aagaacttca agaaatacga gcggctgaac tgacaaagac  1200
tgacgtagca ctggcagatg atggaactgt caactctgac gacgaggact acttttcagg  1260
tgaaaccaga agtccggagg ctgtttttatac tcgaatcatg atgaatggag tcgactaaa  1320
gagatctcac atacggagat atgtctcagt cagttccaat catcaagccc gtccaaactc  1380
attcgccgag tttctaaaca agacatattc gagtgactca taacatgaaa aaaactaaca  1440
cccctcccgt acgccaccat gttcgtgttt ctggtgctgc tgcctctggt gagctcccga  1500
tgcgtgaact tcaccacaag gacccagctg cccctgcct ataccaattc ttcacacgg   1560
ggcgtgtact atcccgacaa ggtgttccgg agcagcgtgc tgcactccac acaggatctg  1620
tttctgcctt tcttttctaa cgtgacctgg ttccacgcca tccacgtgag cggcaccaat  1680
ggcacaaagc ggttcgccaa tccagtgctg ccctttaacg atggcgtgta cttcgcctcc  1740
accgagaagt ctaacatcat cagaggctgg atctttggca ccactggag cagcaagaca  1800
cagtccctgc tgatcgtgaa caatgccacc aacgtggtca tcaaggtgtg cgagttccag  1860
ttttgtaatg atccattcct gggcgtgtac tatcacaaga acaataagtc ttggatggag  1920
agcgagtttc gcgtgtattc ctctgccaac aattgcacat ttgaatacgt gtcccagccc  1980
ttcctgatgg acctggaggg caagcagggc aatttcaaga acctgaggga gttcgtgttt  2040
aagaatatcg atggctactt caaaatctac tccaagcaca cccccaatcaa cctggtgcgc  2100
ggcctgccac agggcttctc tgccctggag ccactggtgg atctgcccat cggcatcaac  2160
atcacccggt ttcagacact gctggccctg cacagatct acctgacacc aggcgacagc  2220
tcctctggat ggaccgcagg agcagcagcc tactatgtgg gctatctgca gcccaggacc  2280
ttcctgctga agtacaacga gaatggcacc atcacagacg ccgtggattg cgccctggat  2340
cccctgtctg agaccaagtg tacactgaag agctttaccg tggagaaggg catctatcag  2400
acaagcaatt tcagggtgca gcctaccgag tccatcgtgc gcttcccaa tatcacaaac  2460
ctgtgccctt ttggcgaggt gttcaacgca cccgcttcg ccagcgtgta cgcctggaat  2520
aggaagcgca tctccaactg cgtggccgac tattctgtgc tgtacaacag cgcctccttc  2580
tctaccttta gtgctatgg cgtgagcccc acaaagctga atgacctgtg ctttaccaac  2640
gtgtacgccg attccttcgt gatcaggggc gacgaggtgc gccagatcgc accaggacag  2700
acaggcaata tcgcagacta caattataag ctgcctgacg atttcaccgg ctgcgtgatc  2760
gcctggaact ctaacaatct ggatagcaaa gtgggcggca actacaatta tctgtaccgg  2820
ctgttagaa agtctaatct gaagccattc gagagggaca tctccacaga aatctaccag  2880
gccggctcta cccctgcaa tggcgtgaag ggctttaact gttattcccc tctgcagagc  2940
tacggcttcc agccaacata tggcgtgggc tatcagccct accgcgtggt ggtgctgtct  3000
tttgagctgc tgcacgcacc tgcaacagtg tgcggaccaa agaagagcac caatctggtg  3060
aagaacaagt gcgtgaactt caacttcaac ggactgaccg gaacaggcgt gctgaccgag  3120
tccaacaaga agttcctgcc ttttcagcag ttcggcaggg acatcgcaga taccacagac  3180
gccgtgcgcg accctcagac cctggagatc ctggacatca ccatgctc cttcggcgcc  3240
gtgtctgtga tcacaccagg caccaataca agcaaccagg tggccgtgct gtatcaggc  3300
gtgaattgta ccgaggtgcc agtggcaatc cacgcagatc agctgacccc tacatgcggg  3360
gtgtactcta ccggcagcaa cgtgttccag acaagagccg gatgcctgat cggagcagag  3420
cacgtgaaca tagctatga gtgcgacatc ccctatcgc ccggcatctg tgcctcctac  3480
cagacccaga caaactcccc aaggtctgtg gagatgagg ccgaagactt tgtggaagtc  3540
cacctgcctg atgtgcataa ccaggtgtct ggcgtcgacc tgggactgcc aaatgggc   3600
aagtacgtgc tgctgagtgc tggagcactg actgccctga tgctgatcat ttttcctgatg  3660
acctgctgtc ggcgcgtgaa cagaagtgag cccactcagc acaatgtgcg aggaaccggg  3720
agagaagtgt cagtcacacc tcagagcggg aaaatcatta tagttgggga atcacataaa  3780
agcgggggcg agaccaggct gtgagctagc catgaaaaaa actaacaccc ctcctttcga  3840
accatcccaa acatgagcaa gatctttgtc aatcctagtg ctattagagc cggtctggcc  3900
gatcttgaga tggctgaaga aactgttgat ctgatcaata gaaatatcga agacaatcag  3960
gctcatctcc aaggggaacc catagaggtg acaatctcc ctgaggatat ggggcgactt  4020
cacctggctg atggaaaatc gcccaaccat gtgagatag ccaaggtggg agaaggcaag  4080
tatcgagagg actttcagat ggatgaagga gaggatccta gcttcctgtt ccagtcatac  4140
ctggaaaatg ttggagtcca aatagtcaga caaatgaggt caggagagag atttctcaag  4200
atatggtcac agaccgtaga agagattata tcctatgtcg cggtcaactt tcccaaccct  4260
ccaggaaagt cttcagagga taatcaacc cagactactg gccgagagct caagaaggag  4320
acaacaccca ctccttctca gagagaaagc caatcatcga aagccaggat ggcggctcaa  4380
```

```
attgcttctg gccctccagc ccttgaatgg tcggctacca atgaagagga tgatctatca 4440
gtggaggctg agatcgctca ccagattgca gaaagtttct ccaaaaaata taagtttccc 4500
tctcgatcct cagggatact cttgtataat tttgagcaat tgaaaatgaa ccttgatgat 4560
atagttaaag aggcaaaaaa tgtaccaggt gtgacccgtt tagcccatga cgggtccaaa 4620
ctccccctaa gatgtgtact gggatgggtc gctttggcca actctaagaa attccagttg 4680
ttagtcgaat ccgacaagct gagtaaaatc atgcaagatg acttgaatcg ctatacatct 4740
tgctaaccga acctctcccc tcagtccctc tagacaataa aatccgagat gtcccaaagt 4800
caacatgaaa aaaacaggca acaccactga taaaatgaac ctcctacgta agatagtgaa 4860
aaaccgcagg gacgaggaca ctcaaaaatc tctcccgcg tcagcccctc tggatgacga 4920
tgacttgtgg cttccacccc ctgaatacgt cccgctgaaa gaacttacag gcaagaagaa 4980
catgaggaac ttttgtatca acggaagggt taaagtgtgt agcccgaatg gttactcgtt 5040
caggatcctg cggcacattc tgaaatcatt cgacgagata tattctggga atcataggat 5100
gatcgggtta gtcaaagtgg ttattggact ggctttgtca ggatctccag tccctgaggg 5160
cctgaactgg gtatacaaat tgaggagaac ctttatcttc cagtgggctg attccagggg 5220
ccctcttgaa gggaggagt tggaatactc tcaggagatc acttgggatg atgatactga 5280
gttcgtcgga ttgcaaataa gagtgattgc aaaacagtgt catatccagg gcagagtctg 5340
gtgtatcaac atgaacccga gagcatgtca actatggtct gacatgtctc ttcagacaca 5400
aaggtccgaa gaggacaaag attcctctct gcttctagaa taatcagatt atatcccgca 5460
aatttatcac ttgtttacct ctggaggaga gaacatatgg gctcaactcc aacccttggg 5520
agcaatataa caaaaaacat gttatggtgc cattaaaccg ctgcatttca tcaaagtcaa 5580
gttgattacc tttacatttt gatcctcttg gatgtgaaaa aaactattaa catccctcaa 5640
aagaccccgg gaaagatggt tcctcaggct ctcctgtttg taccccttct ggttttcca 5700
ttgtgttttg ggaaattccc tatttacacg ataccagaca agcttggtcc ctggagtccg 5760
attgacatac atcacctcag ctgcccaaac aatttggtag tggaggacga aggatgcacc 5820
aacctgtcag ggttctccta catggaactt aaagttggat acatcttagc cataaaagtg 5880
aacgggttca cttgcacagg cgttgtgacg gaggctgaaa cctacactaa cttcgttggt 5940
tatgtcacaa ccacgttcaa aagaaagcat ttccgcccaa caccagatgc atgtagagcc 6000
gcgtacaact ggaagatggc cggtgacccc agatatgaag agtctctaca caatccgtac 6060
cctgactacc gctggcttcg aactgtaaaa accaccaagg agtctctcgt tatcatatct 6120
ccaagtgtgg cagatttgga cccatatgac agatcccttc actcgagggt cttccctagc 6180
gggaagtgct caggagtagc ggtgtcttct acctactgct ccactaacca cgattacacc 6240
atttggatgc ccgagaatcc gagactaggg atgtcttgtg acattttac caatagtaga 6300
gggaagagag catccaaagg gagtgagact tgcggctttg tagatgaaag aggcctatat 6360
aagtctttaa aaggagcatg caaactcaag ttatgtggag ttctaggact tagacttatg 6420
gatggaacat gggtctcgat gcaaacatca aatgaaacca aatggtgccc tcccgataag 6480
ttggtgaacc tgcacgactt tcgctcagac gaaattgagc accttgttgt agaggagttg 6540
gtcaggaaga gagaggagtg tctggatgca ctagagtcca tcatgacaac caagtcagtg 6600
agtttcagac gtcctagtca tttaagaaaa acttgtccctg ggtttggaaa agcatatacc 6660
atattcaaca agaccttgat ggaagccgat gctcactaca agtcagtcga gacttggaat 6720
gagatcctcc cttcaaaagg gtgtttaaga gttggggga ggtgtcatcc tcatgtgaac 6780
gggtgtttt tcaatggtat aatattagga cctgacggca atgtcttaat cccagagatg 6840
caatcatccc tcctccagca acatatggag ttgttggaat cctcggttat cccccttgtg 6900
cacccctgg cagacccgtc taccgttttc aaggacggtg acgaggctga ggattttgtt 6960
gaagttcacc ttcccgatgt gcacaatcag gtctcaggag ttgacttggg tctcccgaac 7020
tgggggaagt atgtattact gagtgcaggg gccctgactg ccttgatgtt gataattttc 7080
ctgatgacat gttgtagaag agtcaatcga tcagaaccta cgcaacacaa tctcagaggg 7140
acagggaggg aggtgtcagt cactccccaa agcgggaaga tcatatcttc atgggaatca 7200
cacaagagtg ggggtgagac cagactgtaa ttaattaacg tccttcaac gatccaagtc 7260
catgaaaaaa actaacaccc ctcccgtacc tagcttataa agtgctgggt catctaagct 7320
tttcagtcga gaaaaaaaca ttagatcaga agaacaactg gcaacacttc tcaacctgag 7380
acttacttca agatgctcga tcctggaagg gtctatgatg accctattga cccaatcgag 7440
ttagaggctg aacccagagg aaccccccatt gtccccaaca tcttgaggaa ctctgactac 7500
aatctcaact ctcctttgat agaagatcct gctagactaa tgttagaatg gttaaaaaca 7560
gggaatagac cttatcggat gactctaaca gacaattgct ccaggtcttt cagagttttg 7620
aaagattatt tcaagaaggt agatttgggt tctctcaagg tgggcggaam ggctgcacag 7680
tcaatgattt ctctctggtt atatggtgcc cactctgaat ccaacaggag ccggagatgt 7740
ataacagact ggcccatttt ctattccaag tcgtccccca tagagaagct gttgaatctc 7800
acgctaggaa atagagggct gagaatcccc ccagagggag tgttaagttg ccttgagagg 7860
gttgattatg ataatgcatt tggaaggtat cttgccaaca cgtattcctc ttacttgttc 7920
ttccatgtaa tcaccttata catgaacgcc ctagactggg atgaagaaaa gaccatccta 7980
gcattatgga aagatttaac ctcagtggac atcgggaagg acttggtaaa gttcaaagac 8040
caaatatggg gactgctgat cgtgacaaag gactttgttt actcccaaag ttccaattgt 8100
cttttttgaca gaaactacac acttatgcta aaagatcttt tcttgtctcg cttcaactta 8160
ttaatggtct tgctctctcc cccagagccc cgatactcag atgacttgat atctcaacta 8220
tgccagctgt acattgctgg ggatcaagtc ttgtctatgt gtggaaactc cggctatgaa 8280
gtcatcaaaa tattggagcc atatgtcgtg aatagtttag tccagagagc agaaaagttt 8340
aggcctctca ttcattcctt gggagacttt cctgtattta taaaagacaa ggtaagtcaa 8400
cttgaagaga cgttcggtcc ctgtgtcaaga aggtctttta gggctctgga tcaattcgac 8460
aacatacatg acttggtttt tgtgtttggc tgttacaggc attggggca cccatatata 8520
gattatcgaa agggtctgtc aaaactatat gatcaggttc accttaaaaa aatgatagat 8580
aagtcctacc aggagtgctt agcaagcgac ctagccagga ggatccttag atgggttttt 8640
gataagtact ccagtggta tctggattca agattcctag cccgagacca ccccttgact 8700
ccttatatca aaacccaaac atggccaccc aaacatattg tagacttggt gggggataca 8760
tggcacagc tcccgatcac gcagatcttt gagattccgg aatcaatgga tccgtcagaa 8820
atattggatg acaaatcaca ttctttcacc agaacgagac tagcttcttg gctgtcagaa 8880
aaccgagggg ggcctgttcc tagcgaaaaa gttattatca cggccctgtc taagccgcct 8940
gtcaatcccc gagagtttct gaggtctata gacctcggag gattgccaga tgaagacttg 9000
ataattggcc tcaagccaaa ggaacgggaa ttgaagattg aaggtcgatt ctttgctcta 9060
atgtcatgga atctaagatt gtattttgtc atcactgaaa aactcttggc caactacatc 9120
```

```
ttgccacttt ttgacgcgct gactatgaca gacaacctga acaaggtgtt taaaaagctg   9180
atcgacaggg tcaccgggca agggcttttg gactattcaa gggtcacata tgcatttcac   9240
ctggactatg aaaagtggaa caaccatcaa agattagagt caacagagga tgtattttct   9300
gtcctagatc aagtgtttgg attgaagaga gtgtttttcta gaacacacga gttttttcaa   9360
aaggcctgga tctattattc agacagatca gacctcatcg ggttacgggg ggatcaaata   9420
tactgcttag atgcgtccaa cggcccaacc tgttggaatg gccaggatgg cgggctagaa   9480
ggcttacggc agaagggctg gagtctagtc agctattga tgatagatag agaatctcaa   9540
atcaggaaca caagaaccaa aatactagct caaggagaca accaggtttt atgtccgaca   9600
tacatgttgt cgccagggct atctcaagag gggctcctct atgaattgga gagaatatca   9660
aggaatgcac tttcgatata cagagccgtc gaggaagggg catctaagct agggctgatc   9720
atcaagaaag aagagaccat gtgtagttat gacttcctca tctatggaaa aaccccctttg   9780
tttagaggta acatattggt gcctgagtcc aaaagatggg ccagagtctc ttgcgtctct   9840
aatgaccaaa tagtcaacct cgccaatata atgtcgacag tgtccaccaa tgcgctaaca   9900
gtggcacaac actctcaatc tttgatcaaa ccgatgaggg attttctgct catgtcagta   9960
caggcagtct ttcactacct gctatttagc ccaatcttaa agggaagagt ttacaagatt  10020
ctgagcgctg aaggggagag cttttctcct a gccatgtcaa ggataatcta tctagatcct  10080
tctttgggag ggatatctgg aatgtccctc ggaagattcc atatacgaca gttctcagac  10140
cctgtctctg aagggttatc cttctggaga gagatctgat taagctccca agagtcctgg  10200
attcacgcgt tgtgtcaaga ggctggaaac ccagatcttg gagagagaac actcgagagc  10260
ttcactcgcc ttctagaaga tccgaccacc ttaaatatca gaggaggggc cagtcctacc  10320
attctactca aggatgcaat cagaaaggct ttatatgacg aggtggacaa ggtggaaaat  10380
tcagagtttc gagaggcaat cctgttgtcc aagacccata gagataattt tatactcttc  10440
ttaatatctg ttgagcctct gtttcctcga tttctcagtg agctattcag ttcgtctttt  10500
ttgggaatcc ccgagtcaat cattggattg atacaaaact cccgaacgat aagaaggcag  10560
tttagaaaga gtctctcaaa aactttagaa gaatccttct acaactcaga gatccacggg  10620
attagtcgga tgacccagac acctcagagg gttgggggggg tgtggccttg ctcttcagag  10680
agggcagatc tactagggga gatctcttgg ggaagaaaag tggtaggcac gacagttcct  10740
cacccttctg agatgttggg attacttccc aagtcctcta tttcttgcac ttgtggagca  10800
acaggaggag gcaatcctag agtttctgta tcagtactcc cgtcctttga tcagtcattt  10860
ttttcacgag gccccctaaa gggatacttg ggctcgtcca cctctatgtc gacccagcta  10920
ttccatgcat gggaaaaagt cactaatgtt catgtggtga agagagctct atcgttaaaa  10980
gaatctataa actggttcat tactagagat tccaacttgg ctcaagctct aattaggaac  11040
attatgtctc tgacaggccc tgatttccct ctagaggagg ccctgtcttc aaaaggacg  11100
gggtcagcct tgcataggtt caagtctgcc agatacagcg aaggagggta ttcttctgtc  11160
tgcccgaacc tcctctctca tatttctgtt agtacagaca ccatgtctga tttgacccaa  11220
gacgggaaga actacgattt catgttccag ccattgatgc tttatgcaca gacatggaca  11280
tcagagctgg tacagagaga cacaaggcta agagactcta cgtttcattg gcacctccga  11340
tgcaacaggt gtgtgagacc cattgacgac gtgacccctgg agacctctca gatcttcgag  11400
tttccggatg tgtcgaaaag aatatccaga atggtttctg gggctgtgcc tcacttccag  11460
aggcttcccg atatccgtct gagaccagga gattttgaat ctctaagcgg tagagaaaag  11520
tctcaccata tcggatcagc tcaggggctc ttatactcaa tcttagtggc aattcacgac  11580
tcaggataca atgatggaac catcttccct gtcaacatat acggcaaggt ttcccctaga  11640
gactatttga gagggctcgc aagggagta ttgataggat ttcgatttg cttcttgaca  11700
agaatgacaa atatcaatat taatagacct cttgaattgg tctcaggggt aatctctat  11760
attctcctga ggctagataa ccatccctcc ttgtacataa tgctcagaga accgtctctt  11820
agaggagaga tattttctat ccctcagaaa atccccgccg cttatccaac cactatgaaa  11880
gaaggcaaca gatcaatctt gtgttatctc caacatgtgc tacgctatga gcgagagata  11940
atcacggcgt ctccagagaa tgactggcta tggatctttt cagactttag aagtgccaaa  12000
atgacgtacc tatccctcat tacttaccag tctcatcttc tactccagag ggttgagaga  12060
aacctatcta agagtatgag agataacctg cgacaattga gttctttgat gaggcaggtg  12120
ctgggcgggc acgagaaga taccttagag tcagacgaca acattcaacg actgctaaaa  12180
gactctttac gaaggacaag atgggtggat caagaggtgc gccatgcagc tagaaccatg  12240
actggagatt acagccccaa caagaaggtg tcccgtaagg taggatgttc agaatgggtc  12300
tgctctgctc aacaggttgc agtctctacc tcagcaaacc cggcccctgt ctcggagctt  12360
gacataaggg ccctctctaa gaggttccag aaccctttga tctcgggctt gagagtggtt  12420
cagtgggcaa ccgtgctca ttataagctt aagcctattc tagatgatct caatgttttc  12480
ccatctctct gccttgtagt tggggacggg tcagggggga tatcaagggc agtcctcaac  12540
atgtttccag atgccaagct tgtgttcaac agtcttttag aggtaatga cctgatggct  12600
tccggaacac atccactgcc tccttcagca atcatgaggg gaggaaatga tatcgtctcc  12660
agagtgatag atcttgactc aatctgggaa aaaccgtccg acttgagaaa cttggcaac  12720
tggaaatact tccagtcagt ccaaaagcag gtcaacatgt cctatgacct cattatttgc  12780
gatgcagaag ttactgacat tgcatctatc aaccggatca ccctgttaat gtccgatttt  12840
gcattgtcta tagatggacc actctatttg gtcttcaaaa cttatgggac tatgctagta  12900
aatccaaact caaggctat tcaacacctg tcaagagct cacagggttt  12960
atcacccaag taacttcgtc tttttcatct gagctctacc tccgattctc aaacgaggg  13020
aagtttttca gagatgctga gtacttgacc tcttccaccc ttcgagaaat gagccttgtg  13080
ttattcaatt gtagcagccc caagagtgag atgcagagag ctcgttcctt gaactatcag  13140
gatcttgtga gaggatttcc tgaagaaatc atatcaaatc cttacaatga gatgatcata  13200
actctgattg acagtgatgt agaatctttt ctagtccaca gatggtga tgatcttgag  13260
ttacagaggg gaactctgtc taaagtggct atcattatag ccatcatgat agttttctcc  13320
aacagagtct tcaacgtttc caaacccca actgaccct cgttcatacc accgtctgat  13380
cccaaaatcc tgaggcactt caacatatgt tgcagtacta tgatgtatct atctactgct  13440
ttaggtacg tccctagctt cgcaagactt cacgacctgt ataacagacc tataaacttat  13500
tacttcagaa gcaagtcat tcgaggggaac gtttatctat cttggaggttg gtccaacgac  13560
acctcagtgt tcaaaagggt agcctgtaat tctagcctga gtctgtcatc tcactgatc  13620
aggttgatttt acaagatagt gaagactacc agactcgttg gcagcatcaa ggatctatcc  13680
agagaagtgg aaagacacct tcataggtac aacaggtgga tcaccctaga ggatatcaga  13740
tctagatcat ccctactaga ctacagttgc ctgtgaaccg gatactcctg gaagcctgcc  13800
catgctaaga ctcttgtgtg atgtatcttg aaaaaaacaa gatcctaaat ctgaacctttt  13860
```

| SEQ ID NO: 8 | moltype = DNA   length = 13958 |
|---|---|
| FEATURE | Location/Qualifiers |
| misc_feature | 1..13958 |
| | note = RABV vector: Coravax V2-China (RABVG-E51) |
| source | 1..13958 |
| | mol_type = other DNA |
| | organism = synthetic construct |

SEQUENCE: 8

```
acgcttaaca accagatcaa agaaaaaaca gacattgtca attgcaaagc aaaaatgtaa    60
caccccctaca atggatgccg acaagattgt attcaaagtc aataatcagg tggtctcttt   120
gaagcctgag attatcgtgg atcaatatga gtacaagtac cctgccatca aagatttgaa   180
aaagccctgt ataaccctag gaaaggctcc cgatttaaat aaagcataca agtcagtttt   240
gtcaggcatg agcgccgcca aacttaatcc tgacgatgta tgttcctatt ggcagcggc    300
aatgcagttt tttgagggga catgtccgga agactggacc agctatgaa ttgtgattgc    360
acgaaaagga gataagatca ccccaggttc tctggtggga ataaaacgta ctgatgtaga   420
agggaattgg gctctgacag gaggcatgga actgacaaga gaccccactg tccctgagca   480
tgcgtcctta gtcggtcttc tcttgagtct gtataggttg agcaaaatat ccgggcaaaa   540
cactggtaac tataagacaa acattgcaga caggatagag cagattttg agacagcccc   600
ttttgttaaa atcgtggaac accatactct aatgacaact cacaaaatgt gtgctaattg   660
gagtactata ccaaacttca gatttttggc cggaacctat gacatgtttt tctcccggat   720
tgagcatcta tattcagcaa tcagagtggg cacagttgtc actgcttatg aagactgttc   780
aggactggta tcatttactg ggttcataaa acaaatcaat ctcaccgcta gagaggcaat   840
actatatttc ttccacaaga actttgagga agagataaga agaatgtttg agccagggca   900
ggagacagct gttcctcact cttattctat ccacttcgtg tcactaggct tgagtgggaa   960
atctccttat tcatcaaatg ctgttggtca cgtgttcaat ctcattcact tgtaggatg   1020
ctatatgggt caagtcagat ccctaaatgc aacggttatt gctgcatgtg ctcctcatga  1080
aatgtctgtt ctaggggct atctgggaga ggaattcttc gggaaggga catttgaaag  1140
aagattcttc agagatgaga aagaacttca agaatacgag gcggctgaac tgacaaagac  1200
tgacgtagca ctggcagatg atggaactgt caactctgac gacgaggact acttttcagg  1260
tgaaaccaga agtccggagg ctgtttatac tcgaatcatg atgaatggag tcgactaaa   1320
gagatctcac atacggagat atgtctcagt cagttccaat catcaagccc gtccaaactc  1380
attcgccgag tttctaaaca agacatattc gagtgactca taacatgaaa aaaactaaca  1440
cccctcccgt acgccaccat gttcgtgttt ctggtgctgc tgcctctggt gagctcccag  1500
tgcgtgaacc tgaccacaag gacccagctg ccccctgcct ataccaattc cttcacacgg  1560
ggcgtgtact atcccgacaa ggtgttccgg agcagcgtgc tgcactccac acaggatctg  1620
tttctgcctt tctttctaa cgtgacctgg ttccacgcca tccacgtgag cggcaccaat  1680
ggcacaaagc ggttcgacaa tccagtgctg ccctttaacg atggcgtgta cttcgcctcc  1740
accgagaagt ctaacatcat cagaggctgg atctttggca ccacactgga cagcaagaca  1800
cagtccctgc tgatcgtgaa caatgccacc aacgtggtca tcaaggtgtg cgagttccag  1860
ttttgtaatg atccattcct gggcgtgtac tatcacaaga caataagtc ttggatggag  1920
agcgagtttc gcgtgtattc ctctgccaac aattgcacat ttgagtacgt gtcccagccc  1980
ttcctgatgg acctggaggg caagcagggc aatttcaaga acctgaggga gttcgtgttt  2040
aagaatatcg atggctactt caaaatctac tccaagcaca cccaatcaa cctggtgcgc  2100
gacctgccaa agggcttctc tgccctggag ccactggtgg atctgcccat cggcatcaac  2160
atcacccggt ttcagacact gctggcctg cacagaagct acctgaccc aggcgacagc  2220
tcctctggat ggaccgcagg agcagcagcc tactatgtgg gctatctgca gccaggacc   2280
ttcctgctga gtacaacga aatggcacc atcacagacg ccgtggattg cgccctggat  2340
cccctgtctg agaccaagtg tacactgaag agctttaccg tggagaaggg catctatcag  2400
acaagcaatt tcagggtgca gcctaccgag tccatcgtgc gctttccaa tatcacaaac  2460
ctgtgccctt tggcgaggt gttcaacgca acccgcttcg ccagcgtgta cgcctggaat  2520
aggaagcgca tctccaactg cgtggccgac tattctgtgc tgtacaacag cgcctccttc  2580
tctaccttta gtgctatgg cgtgagcccc acaaagctga atgacctgtg ctttaccaac  2640
gtgtacgccg attccttcgt gatcaggggc gacgaggtgc gccagatcgc accaggacag  2700
acaggcaaga tcgcagacta caattataag ctgcctgacg atttcaccgg ctgcgtgatc  2760
gcctggaact ctaacaatct ggatagcaaa gtgggcggca actacaatta tctgtaccgg  2820
ctgtttagaa agtctaatct gaagccattc gagagggaca tctccacaga aatctaccag  2880
gccggctcta cccccctgca atggcgtgag ggctttaact gttattttcc tctgcagagc  2940
tacggcttcc agccaacaaa cggcgtgggc tatcagccct accgcgtggt ggtgctgtct  3000
tttgagctgc tgcacgcacc tgcaacagtg tgcggaccaa agaagagcac caatctggtg  3060
aagaacaagt gcgtgaactt caacttcaac ggactgaccg gaacaggcgt gctgaccgag  3120
tccaacaaga gttcctgcc ttttcagcag ttcggcaggg acatcgcaga taccacagac  3180
gccgtgcgcg accctcagac cctggagatc ctggacatca ccatgctc cttcggcgac  3240
gtgtctgtga tcacaccagg caccaataca agcaaccagg tggccgtgct gtatcaggac  3300
gtgaattgta ccgaggtgcc agtggcaatc cacgcagatc agctgacccc tacatggcgg  3360
gtgtactcta ccggcagcaa cgtgttccag acaagagccg gatgcctgat cggagcagag  3420
cacgtgaaca tagctatga gtgcgacatc cctatcggcg ccggcatctg tgcctctac   3480
cagacccaca caaactcccc agaatcaag gtgattcctc tggtcatca actgcagat   3540
cccctccacag tgttcaaaga cggagatgag gccgaagact tgtgtaagt ccacctgcct  3600
gatgtgcata accaggtgtc tggcgtcgac ctgggactgc aaattgggg caagtacgtg  3660
ctgctgagtg ctggagcact gactgcctg atgctgatca ttttcctgat gcctgctgt   3720
cggcgcgtga acagaagtga gcccactcag cacaatctgc gaggaaccgg gagagaagtg  3780
tcagtcgaca ctcagagcgg gaaatcatt agtagttgga aatcacataa aagcggggc   3840
gagaccaggc tgtgagctag ccatgaaaaa aactaacacc cctcctttcg aaccatccca  3900
aacatgagca agatctttgt caatcctagt gctattagag ccggtctggc cgatcttgag  3960
atggctgaag aaactgttga tctgatcaat agaaatatcg aagacaatca ggctcatctc  4020
caaggggaac ccatagaggt ggacaatctc cctgaggata tggggcgact tcacctggat  4080
gatggaaaat cgcccaacca tggtgagata gccaaggtgg gagaaggcaa gtatcgagag  4140
```

```
gactttcaga tggatgaagg agaggatcct agcttcctgt tccagtcata cctggaaaat  4200
gttggagtcc aaatagtcag acaaatgagg tcaggagaga gatttctcaa gatatggtca  4260
cagaccgtag aagagattat atcctatgtc gcggtcaact ttcccaaccc tccaggaaag  4320
tcttcagagg ataaatcaac ccagactact ggccgagagc tcaagaagga gacaacaccc  4380
actccttctc agagagaaag ccaatcatcg aaagccgata tggcggctca aattgcttct  4440
ggccctccag cccttgaatg gtcggctacc aatgaagagg atgatctatc agtggaggct  4500
gagatcgctc accagattgc agaaagtttc tccaaaaaat ataagtttcc ctctcgatcc  4560
tcagggatac tcttgtataa ttttgagcaa ttgaaaatga accttgatga tatagttaaa  4620
gaggcaaaaa atgtaccagg tgtgacccgt ttagcccatg acgggtccaa actcccccta  4680
agatgtgtac tgggatgggt cgcttttggc aactctaaga aattccagtt gttagtcgaa  4740
tccgacaagc tgagtaaaat catgcaagat gacttgaatc gctatacatc ttgctaaccg  4800
aacctctccc ctcagtccct ctagacaata aaatccgaga tgtcccaaag tcaacatgaa  4860
aaaaacaggc aacaccactg ataaatgaa cctcctacgt aagatagtga aaaaccgcag  4920
ggacgaggac actcaaaaat cctctcccgc gtcagccct ctggatgacg atgacttgtg  4980
gcttccaccc cctgaatacg tcccgctgaa agaacttaca ggcaagaaga acatgaggaa  5040
cttttgtatc aacggaaggg ttaaagtgtg tagcccgaat ggttactcgt tcaggatcct  5100
gcggcacatt ctgaaatcat tcgacgagat atattctggg aatcatagga tgatcgggtt  5160
agtcaaagtg gttattggac tggctttgtc aggatctcca gtccctgagg gcctgaactg  5220
ggtatacaaa ttgaggagaa cctttatctt ccagtgggct gattccaggg gccctcttga  5280
aggggaggag ttggaatact ctcaggagat cacttgggat gatgatactg agttcgtcgg  5340
attgcaaata agagtgattg caaaacagtg tcatatccag ggcagagtct ggtgtatcaa  5400
catgaacccg agagcatgtc aactatggtc tgacatgtct cttcagacac aaaggtccga  5460
agaggacaaa gattcctctc tgcttctaga ataatcagat tatatcccgc aaatttatca  5520
cttgtttacc tctgcaggag agaacatatg ggctcaactc caacccttgg gagcaatata  5580
acaaaaaaca tgttatggtg ccattaaacc gctgcatttc atcaaagtca agttgattac  5640
ctttacattt tgatcctctt ggatgtgaaa aaaactatta acatccctca aaagaccccg  5700
ggaaagatgg ttcctcaggc tctcctgttt gtaccccttc tggttttcc attgtgtttt  5760
gggaaattcc ctatttacac gataccagac aagcttggtc cctggagtcc gattgacata  5820
catcacctca gctgcccaaa caatttggta gtggaggacg aaggatgcac caacctgtca  5880
gggttctcct acatgaaact taaagttgga tacatcttag ccataaaagt gaacgggttc  5940
acttgcacag gcgttgtgac ggaggctgaa acctacacta acttcgttgg ttatgtcaca  6000
accacgttca aaagaaagca tttccgccca acaccagatg catgtagagc cgcgtacaac  6060
tggaagatgg ccggtgaccc cagatatgaa gagtctctac acaatccgta ccctgactac  6120
cgctggcttc gaactgtaaa aaccaccaag gagtctctcg ttatcatatc tccaagtgtg  6180
gcagatttgg acccatatga cagatcccctt cactcgaggg tcttccctag cgggaagtgc  6240
tcaggagtag cggtgtcttc tacctactgc tccactaacc acgattacac catttggatg  6300
cccgagaatc cgagactagg gatgtcttgt gacattttta ccaatagtag agggaagaga  6360
gcatccaaag ggagtgagac ttgcggcttt gtagatgaaa gaggcctata taagtcttta  6420
aaaggagcat gcaaactcaa gttatgtgga gttctaggac ttagacttat ggatgaaaca  6480
tgggtctcga tgcaaacatc aaatgaaacc aaatggtgcc ctcccgataa gttggtgaac  6540
ctgcacgact ttcgctcaga cgaaattgag caccttgttg tagaggagtt ggtcaggaag  6600
agagaggagt gtctggatgc actagagtcc atcatgacaa ccaagtcagt gagtttcaga  6660
cgtctcagtc atttaagaaa actgtccct gggtttggaa agcatatac catattcaac  6720
aagaccttga tggaagccga tgctcactac aagtcagtcg agacttgaa tgagatcctc  6780
ccttcaaaag ggtgttttaag agttgggggg aggtgtcatc ctcatgtgaa cggggtgttt  6840
ttcaatggta taatattagg acctgacggc aatgtcttaa tcccagagat gcaatcatcc  6900
ctcctccagc aacatatgga gttgttggaa tcctcggtta cccccttgt gcacccctg  6960
gcagacccgt ctaccgtttt caaggacggt gacgaggctg aggattttgt tgaagttcac  7020
cttcccgatg tgcacaatca ggtctcagga gttgacttgg gtctcccgaa ctgggggaag  7080
tatgtattac tgagtgcagg ggccctgact gccttgatgt tgataatttt cctgatgaca  7140
tgttgtagaa gagtcaatcg atcagaacct acgcaacaca atctcagagg gacagggagg  7200
gaggtgtcag tcactcccca aagcgggaag atcatatctt catgggaatc acacaagagt  7260
ggggggtgaga ccagactgta attaattaac gtccttttcaa cgatccaagt ccatgaaaaa  7320
aactaacacc cctcccgtac ctagcttata aagtgctggg tcatctaagc ttttcagtcg  7380
agaaaaaaac attagatcag aagaacactt ggcaacactt ctcaacctga gacttacttc  7440
aagatgctcg atcctggaga ggtctatgat gaccctattg accccaatcga gttagaggct  7500
gaacccagag gaacccccat tgtccccaac atcttgagga actctgacta caatctcaac  7560
tctccttga tagaagatcc tgctagacta atgttagaat ggttaaaaac agggaataga  7620
ccttatcgga tgactctaac agacaattgc tccaggtcct tcaggttttt gaaagattat  7680
ttcaagaagg tagatttggg ttctctcaag gtgggcggaa tggctgcaca gtcaatgatt  7740
tctctctggt tatatggtgc ccactctgaa tccaacagga gccggagatg taaacagac  7800
ttggcccatt tctattccaa gtcgtcccc atagagaagc tgttgaatct cacgctagga  7860
aatagagggc tgagaatccc cccagaggga gtgttaagtt gccttgagag ggttgattat  7920
gataatgcat ttggaaggta tcttgccaac acgtatctgt cttacttgtt cttccatgta  7980
atcaccttat acatgaacgc cctagactgg gatgaagaaa agaccatcct agcattatgg  8040
aaagatttaa cctcagtgga catcgggaag gacttggtaa agtcaaaga ccaaatatgg  8100
ggactgctga tcgtgacaaa ggactttgtt tactcccaaa gttccaattg tcttttgac  8160
agaaactaca cacttatgct aaaagatctt ttcttgtctc gcttcaactc cttaagtggtc  8220
ttgctctctc cccagagcc ccgatactca gatgacttga tatctcaact atgccagctg  8280
tacattgctg gggatcaagt cttgtctatg tgtggaaact ccggctatga agtcatcaaa  8340
atattggagc catatgtcgt gaatagtttta gtccagagag cagaaaagtt taggcctctc  8400
attcattcct tgggagactt tcctgtattt ataaaagaca aggtaagtca acttgaagag  8460
acgttcggtc cctgtgcaag aaggttcttt agggctctgg atcaattcga caacatacat  8520
gactggtttt ttgtgtttgg ctgttacagg cattggggc acccatatat agattatgca  8580
aagggtctgt caaaactata tgatcaggtt cacttaaaaa aatgataga taagtcctac  8640
cagggagtgct tagcaagcga cctagccagg aggatcctta tgggggtttt tgataagtac  8700
tccaagtggt atctggattc aagattccta gcccgagacc accccttgac tccttatatc  8760
aaaacccaaa catggccacc caaacatatt gtagacttgg tggggataac atggcacaag  8820
ctcccgatca cgcagatctt tgagattcct gaatcaatgg atccgtcaga aatattggat  8880
```

```
gacaaatcac attctttcac cagaacgaga ctagcttctt ggctgtcaga aaaccgaggg   8940
gggcctgttc ctagcgaaaa agttattatc acggccctgt ctaagccgcc tgtcaatccc   9000
cgagagtttc tgaggtctat agacctcgga ggattgccag atgaagactt gataattggc   9060
ctcaagccaa aggaacggga attgaagatt gaaggtcgat tctttgctct aatgtcatgg   9120
aatctaagat tgtattttgt catcactgaa aaactcttgg ccaactacat cttgccactt   9180
tttgacgcgc tgactatgac agacaacctg aacaaggtgt ttaaaaagct gatcgacagg   9240
gtcaccgggc aagggctttt ggactattca agggtcacat atgcatttca cctggactat   9300
gaaaagtgga acaaccatca aagattagag tcaacagagg atgtattttc tgtcctagat   9360
caagtgtttg gattgaagag agtgttttct agaacacacg agttttttca aaaggcctag   9420
atctattatt cagacagatc agacctcatc gggttacgag aggatcaaat atactgctta   9480
gatgcgtcca acggcccaac ctgttggaat ggccaggatg gcgggctaga aggcttacgg   9540
cagaagggct ggagtctagt cagcttattg atgatagata gagaatctca aatcaggaac   9600
acaagaacca aaatactagc tcaaggagac aaccaggttt tatgtccgac atacatgttg   9660
tcgccagggc tatctcaaga ggggctcctc tatgaattgg agagaatatc aaggaatgca   9720
cttttcgatat acagagccgt cgaggaaggg gcatctaagc tagggctgat catcaagaaa   9780
gaagagacca tgtgtagtta tgacttcctc atctatggaa aaacccctttt gtttagaggt   9840
aacatattgg tgcctgagtc caaaagatgg gccagagtc cttgcgtctc taatgaccaa   9900
atagtcaacc tcgccaatat aatgtcgaca gtgtccacca atgcgctaac agtggcaaa   9960
cactctcaat ctttgatcaa accgatgagg gattttctgc tcatgtcagt acaggcagtc  10020
tttcactacc tgctatttag cccaatctta aagggaagag tttacaagat tctgagcgct  10080
gaaggggaga gctttctcct agccatgtca aggataatct atctagatcc ttctttggga  10140
gggatatctg gaatgtccct cggaagattc catatacgac agttctcaga ccctgtctct  10200
gaagggttat cctctgtgag agagatctgg ttaagctccc aagagtcctg gattcacgcg  10260
ttgtgtcaag aggctggaaa cccagatctt ggagagagaa cactcgagag cttcactcgc  10320
cttctagaag atccgaccac cttaaatatc agaggagggg ccagtcctac cattctactc  10380
aaggatgcaa tcagaaaggc tttatatgac gaggtgacag aggtgaaaa ttcagagttt  10440
cgagaggcaa tcctgttgtc caagacccat agagataatt ttatactctt cttaatatct  10500
gttgagcctc tgtttcctcg atttctcagt gagctattca gttcgtcttt tttgggaatc  10560
cccgagtcaa tcattggatt gatacaaaac tcccgaacga taagaaggca gtttagaaag  10620
agtctctcaa aaactttaga agaatccttc tacaactcag agatccacgg gattagtcgg  10680
atgacccaga cacctcagag ggttgggggg gtgtggcctt gctcttcaga gagggcagat  10740
ctacttaggg agatctcttg gggaagaaaa gtggtaggca cgacagttcc tcacccttct  10800
gagatgttgg gattacttcc caagtcctct atttcttgca cttgtggagc aacaggagga  10860
ggcaatccta cgtgtttctgt atcagtactc ccgtcctttg atcagtcatt tttttcacga  10920
ggcccctaa agggatactt gggctcgtcc acctctatgt cgacccagct attccatgca  10980
tgggaaaaag tcactaatgt tcatgtggtg aagagagctc tatcgttaaa agaatctata  11040
aactggttca ttactagaga ttccaacttg gctcaagctc taattaggaa cattatgtct  11100
ctgacaggcc ctgatttccc tctagaggag gcccctgtct tcaaaaggac ggggtcagcc  11160
ttgcataggt tcaagtctgc cagatacagc gaaggagggt attcttctgt ctgcccgaac  11220
ctcctctctc atatttctgt tagtacagac accatgtctg atttgaccca agacgggaag  11280
aactacgatt tcatgttcca gccattgatg ctttatgcac agacatggac atcagagctg  11340
gtacagagag acacaaggct aagagactct acgtttcatt ggcacctccg atgcaacagg  11400
tgtgtgagac ccattgacga cgtgaccctg gagacctctc agatcttcga gtttccggat  11460
gtgtcgaaaa gaatatccag aatgggtttct ggggctgtgc ctcacttcca gaggcttccc  11520
gatatccgtc tgagaccagg agattttgaa tctctaagcg gtagagaaaa gtctcaccat  11580
atcggatcag ctcaggggct cttatactca atcttagtgg caattcacga ctcaggatac  11640
aatgatgaa ccatcttccc tgtcaacata tacggcaagg tttcccctag agactatttg  11700
agagggctcg caaggggagt attgatagga tcctcgattt gcttcttgac aagaatgaca  11760
aatatcaata ttaatagacc tcttgaattg gtctcagggg taatctcata tattctcctg  11820
aggctagata ccatccctc cttgtacata atgctcagag aaccgtctct tagaggagag  11880
atattttcta tccctcagaa aatccccgcc gcttatccaa ccactatgaa agaaggcaac  11940
agatcaatct tgtgttatct ccaacatgtg ctacgctatg agcgagagat aatcacggcg  12000
tctccagaga atgactggct atggatcttt tcagacttta gaagtgccaa aatgacgtac  12060
ctatccctca ttacttacca gtctcatctt ctactccaga gggttgagag aaacctatct  12120
aagagtatga gagataaacct gcgacaattg agttctttga tgaggcaggt gctgggcggg  12180
cacggagaag ataccttaga gtcagacgac aacattcaac gactgctaaa agactcttta  12240
cgaaggacaa gatgggtgga tcaagaggtg cgccatgcag ctagaaccat gactggagat  12300
tacagccca acaagaaggt gtcccgtaag gtaggatgtt cagaatgggt ctgctctgct  12360
caacaggttg cagtctctac ctcagcaaac ccggccctg tctcggagct tgacataagg  12420
gccctctcta agaggttcca gaacccttg atctcgggct tgagagtggt tcagtgggca  12480
accggtgctc attataagct taagcctatt ctagatgatc tcaatgtttt cccatctctc  12540
tgccttgtag ttggggacgg gtcaggggga atatcaaggg cagtcctcaa catgtttcca  12600
gatgccaagc ttgtgttcaa cagtcttta gaggtgaatg acctgatggc ttccggaaca  12660
catccactgc ctccttcagc aatcatgagg ggaggaaata atatcgtctc cagagtgata  12720
gatcttgact caatctggga aaaaccgtcc gacttgaaga acttggcaac ctggaaatac  12780
ttccagtcag tccaaaagca ggtcaacatg tcctatgacc tcattatttg cgatgcagaa  12840
gttactgaca ttgcatctat caaccggatc accctgttaa tgtccgattt tgcattgtct  12900
atagatggac cactctattt ggtcttcaaa acttatggga ctatgctagt aaatccaaac  12960
tacaaggcta ttcaacacct gtcaagagcg ttccctctgg tcacaggtt tatcacccaa  13020
gtaacttcgt ctttttcatc tgagctctac ctccgattct ccaaacgagg gaagtttttc  13080
agagatgctg agtacttgac ctcttccacc cttgagaaa tgagccttgt gttattcaat  13140
tgtagcagcc ccaagagtga gatgcagaga gctcgttcct tgaactatca ggatcttgtg  13200
agaggattc ctgaagaaat catatcaaat ccttacaatg atgatcat aactctgatt  13260
gacagtgatg tagaatcttt tctagtccac aagatggttg atgatcttga gttacagagg  13320
ggaactctgt ctaaagtggc tatcattata gccatcatga tagttttctc caacagagtc  13380
ttcaacgttt ccaaacccct aactgacccc tcgttctatc caccgtctga tcccaaaatc  13440
ctgaggcact tcaacatatg ttgcagtact atgatgtatc tatctactgc tttaggtgac  13500
gtccctagct tcgcaagact tcacgacctg tataacagac ctaaacttta ttacttcaga  13560
aagcaagtca ttcgagggaa cgtttatcta tcttggagtt ggtccaacga cacctcagtg  13620
```

```
ttcaaaaggg tagcctgtaa ttctagcctg agtctgtcat ctcactggat caggttgatt   13680
tacaagatag tgaagactac cagactcgtt ggcagcatca aggatctatc cagagaagtg   13740
gaaagacacc ttcataggta caacaggtgg atcaccctag aggatatcag atctagatca   13800
tccctactag actacagttg cctgtgaacc ggatactcct ggaagcctgc ccatgctaag   13860
actcttgtgt gatgtatctt gaaaaaaaca agatcctaaa tctgaacctt tggttgtttg   13920
attgtttttc tcattttttgt tgtttatttg ttaagcgt                          13958

SEQ ID NO: 9            moltype = DNA   length = 13958
FEATURE                 Location/Qualifiers
misc_feature            1..13958
                        note = RABV vector: Coravax V2 South Africa (S1-RABVG-E51)
source                  1..13958
                        mol_type = other DNA
                        organism = synthetic construct
SEQUENCE: 9
acgcttaaca accagatcaa agaaaaaaca gacattgtca attgcaaagc aaaaatgtaa     60
caccccctaca atggatgccg acaagattgt attcaaagtc aataatcagg tggtctcttt   120
gaagcctgag attatcgtgg atcaaatatga gtacaagtac cctgccatca aagatttgaa   180
aaagccctgt ataaccctag gaaaggctcc cgatttaaat aaagcataca agtcagtttt   240
gtcaggcatg agcgccgcca aacttaatcc tgacgatgta tgttcctatt tggcagcggc   300
aatgcagttt tttgagggga catgtccgga agactggacc agctatggaa ttgtgattgc   360
acgaaaagga gataagatca cccaggttc tctggtggga ataaaacgta ctgatgtaga   420
agggaattgg gctctgacag gaggcatgga actgacaaga gacccccactg tccctgagca   480
tgcgtcctta gtcggtcttc tcttgagtct gtataggttg agcaaatata ccgggcaaaa   540
cactggtaac tataagacaa acattgcaga caggatagag cagattttttg agacagcccc   600
ttttgttaaa atcgtggaac accatactct aatgcaaact cacaaaagtg tgctaattg    660
gagtactata ccaaacttca gattttttggc cggaacctat gacatgttttt ctcccggat   720
tgagcatcta tattcagcaa tcagagtggg cacagttgtc actgcttatg aagactgttc   780
aggactggta tcatttactg ggttcataaa acaaatcaat ctcaccgcta gagaggcaat   840
actatatttc ttccacaaga actttgagga agagtaaga agaatgtttg agcagggca   900
ggagacagct gttcctcact cttatttcat ccacttccgt tcactaggct tgagtgggaa   960
atctccttat tcatcaaatg ctgttggtca cgtgttcaat ctcattcact ttgtaggatg  1020
ctatatgggt caagtcagat ccctaaatgc aacggttatt gctgcatgtg ctcctcatga  1080
aatgtctgtt ctaggggggct atctgggaga ggaattcttc gggaaaggga catttgaaag  1140
aagattcttc agagatgaga gaaacttca agaatacgag gcggctgaac tgacaaagac  1200
tgacgtagca ctggcagatg atggaactgt caactctgac gacgaggact acttttcagg  1260
tgaaaccaga agtccggagg ctgtttatac tcgaatcatg atgaatggag tcgactaaa   1320
gagatctcac atacggagat atgtctcagt cagttccaat catcaagccc gtccaaactc  1380
attcgccgag tttctaaaca agacatattc gagtgactca taacatgaaa aaaactaaca  1440
cccctcccgt acgccaccat gttcgtgttt ctggtgctgc tgcctctggt gagctcccag  1500
tgcgtgaact tcaccacaag gaccccagctg ccccctgcct ataccaattc cttcacacgg  1560
ggcgtgtact atcccgacaa ggtgttccgg agcagcgtgc tgcactccac acaggatctg  1620
tttctgcctt tcttttctaa cgtgacctgg ttccacgcca tccacgtgag cggcaccaat  1680
ggcacaaagc ggttcgccaa tccagtgctg cccttttaacg atggcgtgta cttcgcctcc  1740
accgagaagt ctaacatcat cagaggctgg atctttggca ccacactgga cagcaagaca  1800
cagtccctgc tgatcgtgaa caatgccacc aacgtggtca tcaaggtgtg cgagttccag  1860
ttttgtaatg atccattcct gggcgtgtac atcacaagaa acaataagt ttggatggag  1920
agcgagtttc gcgtgtattc ctctgccaac aattgcacat tgagtacgt gtcccagccc  1980
ttcctgatgg acctggaggg caagcaggc aatttcaaga acctgagggg gttcgtgttt  2040
aagaatatcg atggctactt caaaatctac tccaagcaca ccccaatcaa cctggtgcgc  2100
ggcctgccac agggcttctc tgccctggag ccactggtga tctgcccat cggcatcaac  2160
atcacccggt tcagacact gctggccctg cacagaagct acctgacacc aggcgacagc  2220
tcctctggat ggaccgcagg agcagcagcc tactatgtgg gctatctgca gcccaggacc  2280
ttcctgctga gtacaacga gaatggcacc atcacagacg ccgtggattg cgccctggat  2340
ccctgtctg agaccaagtg tacactgaag agctttccgt ggagaaggg catctatcag  2400
acaagcaatt tcagggtgca gcctaccgag tccatcgtgc gctttccaa tatcacaaac  2460
ctgtgcccctt ttggcgaggt gttcaacgca cccgcttcg ccagcgtgta cgcctggaat  2520
aggaagcgca ctccaactg cgtggccgac tattctgtgc tgtacaacag cgcctccttc  2580
tctaccttta agtgctatgg cgtgagcccc acaaagctga atgacctgtg ctttaccaac  2640
gtgtacgccg attccttcgt gatcagggc gacgaggtgc gccagatcgc accaggacag  2700
acaggcaata tcgcagacta caattataag ctgcctgacg atttcaccgg ctgcgtgatc  2760
gcctggaact ctaacaatct ggatagcaaa gtgggcggca actacaatta tctgtaccgg  2820
ctgtttagaa agtctaatct gaagccattc gagagggaca tctccacaga aatctaccag  2880
gccggctcta ccccctgcaa tggcgtgaag ggctttaact gttatttccc tctgcagagc  2940
tacggcttcc agccaacata tggcgtgggc tatcagccct accgcgtggt ggtgctgtct  3000
tttgagctgc tgcacgcacc tgcaacagtg tgcggaccaa agaagagcac caatctggtg  3060
aagaacaagt gcgtgaactt caacttcaac ggactgaccg gaacaggcgt gctgaccgag  3120
tccaacaaga agttcctgcc ttttcagcag ttcggcaggg acatcgcaga taccacagac  3180
gccgtgcgcg accctcagac cctggagatc ctggacatca ccccatgctc cttcggcgac  3240
gtgtctgtga tcaccccagg caccaataca agcaaccagg tggccgtgct gtatcagggc  3300
gtgaattgta ccgaggtgcc agtggcaatc cacgcagatc agctgacccc tacatggcgg  3360
gtgtactcta ccggcagcaa cgtgttccag acaagagccg gatgcctgat cggagcagag  3420
cacgtgaaca atagctatga gtcgacatc cctatcggcg ccggcatctg tgcctcctac  3480
cagacccaga caactccct agaatcaagc gtgattcctc ttggccatcc actggcagat  3540
cccctccacag tgttcaaaga cggagatgag gccgaagact ttgtggaagt ccacctgcct  3600
gatgtgcata accaggtgtc tggcgtcgac ctgggactgc caaattgggg caagtacgtg  3660
ctgctgagtg ctggagcact gactgccctg atgctgatca ttttcctgat gacctgctgt  3720
cggcgcgtga acagaagtga gccccactcag cacaatctgc gaggaaccgg gagagaagtg  3780
tcagtcacac ctcagagcgg gaaaatcatt agtagttggg aatcacataa aagcggggc  3840
```

```
gagaccaggc tgtgagctag ccatgaaaaa aactaacacc cctcctttcg aaccatccca 3900
aacatgagca agatctttgt caatcctagt gctattagag ccggtctggc cgatcttgag 3960
atggctgaag aaactgttga tctgatcaat agaaatatcg aagacaatca ggctcatctc 4020
caaggggaac ccatagaggt ggacaatctc cctgaggata tggggcgact tcacctggat 4080
gatggaaaat cgcccaacca tggtgagata gccaaggtgg gagaaggcaa gtatcgagag 4140
gactttcaga tggatgaagg agaggatcct agcttcctgt tccagtcata cctggaaaat 4200
gttggagtcc aaatagtcag acaaatgagg tcaggagaga gatttctcaa gatatggtca 4260
cagaccgtag aagagattat atcctatgtc gcggtcaact ttcccaaccc tccaggaaag 4320
tcttcagagg ataaatcaac ccagactact ggccgagagc tcaagaagga gacaacaccc 4380
actccttctc agagagaaag ccaatcatcg aaagccagga tggcggctca aattgcttct 4440
ggccctccag cccttgaatg gtcggctacc aatgaagagg atgatctatc agtgagggct 4500
gagatcgctc accagattgc agaaagtttc tccaaaaaat ataagtttcc ctctcgatcc 4560
tcagggatac tcttgtataa ttttgagcaa ttgaaaatga accttgatga tatagttaaa 4620
gaggcaaaaa atgtaccagg tgtgacccgt ttagcccatg acgggtccaa actccccta  4680
agatgtgtac tgggatgggt cgctttggcc aactctaaga aattccagtt gttagtcgaa 4740
tccgacaagc tgagtaaaat catgcaagat gacttgaatc gctatacatc ttgctaaccg 4800
aacctctccc ctcagtccct ctagacaata aaatccgaga tgtcccaaag tcaacatgaa 4860
aaaaacaggc aacaccactg ataaaatgaa cctcctacgt aagatagtga aaaaccgcag 4920
ggacgaggac actcaaaaat cctctcccgc gtcagcccct ctggatgacg atgacttgtg 4980
gcttccaccc cctgaatacg tcccgctgaa agaacttaca ggcaagaaga acatgaggaa 5040
cttttgtatc aacggaaggg ttaaagtgtg tagcccgaat ggttactcgt tcaggatcct 5100
gcggcacatt ctgaaatcat tcgacgagat atattctgag aatcatagga tgatcgggtt 5160
agtcaaagtg gttattggac tggctttgtc aggatctcca gtccctgagg gcctgaactg 5220
ggtatacaaa ttgaggagaa cctttatctt ccagtgggct gattcaggg  gccctcttga 5280
aggggaggag ttggaatact ctcaggagat cacttgggat gatgatactg agttcgtcgg 5340
attgcaaata agagtgattg caaaacagtg tcatatccag ggcagagtct ggtgtatcaa 5400
catgaacccg agagcatgtc aactatggtc tgacatgtct cttcagacac aaaggtccga 5460
agaggacaaa gattcctctc tgcttctaga ataatcagat tatatcccgc aaatttatca 5520
cttgtttacc tctggaggag agaacatatg ggctcaactc caaccttgg  gagcaatata 5580
acaaaaaaca tgttatggtg ccattaaacc gctgcatttc atcaaagtca agttgattac 5640
ctttacattt tgatcctctt ggatgtgaaa aaaactatta acatccctca aaagaccccg 5700
ggaaagatgt tcctcaggc  tctcctgttt gtacccttc  tggttttcc  attgtgtttt 5760
gggaaattcc ctatttacac gataccagac aagcttggtc cctggagtcc gattgacata 5820
catcacctca gctgcccaaa caatttggta gtggaggacg aaggatgcac caacctgtca 5880
gggttctcct acatggaact taaagttgga tacatcttag ccataaaagt gaacgggttc 5940
acttgcacag gcgttgtgac ggaggctgaa acctacacta acttcgttgg ttatgtcaca 6000
accacgttca aaagaaagca tttccgccca acaccagatg catgtagagc cgcgtacaac 6060
tggaagatgg ccggtgaccc cagatatgaa gagtctctac acaatccgta ccctgactac 6120
cgctggcttc gaactgtaaa aaccaccaag gagtctctcg ttatcatatc tccaagtgtg 6180
gcagatttgg acccatatga cagatcccct cactcgaggg tcttccctag cgggaagtgc 6240
tcaggagtag cggtgtcttc tacctactgc tccactaacc acgattacac catttggatg 6300
cccgagaatc cgagactagg gatgtcttgt gacattttta ccaatagtag agggaagaga 6360
gcatccaaag ggagtgagac ttgcggcttt gtagatgaag gaggcctata taagtcttta 6420
aaaggagcat gcaaactcaa gttatgtgga gttctaggac ttagacttat ggatggaaca 6480
tgggtctcga tgcaaacatc aaatgaaacc aaatggtgcc ctcccgataa gttggtgaac 6540
ctgcacgact ttcgctcaga cgaaattgag caccttgttg tagaggagtt ggtcaggaag 6600
agagaggagt gtctggatgc actagagtcc atcatgacaa ccaagtcagt ggttttcaga 6660
cgtctcagtc atttaagaaa acttgtccct gggtttggaa aagcatatac catattcaac 6720
aagaccttga tggaagccga tgctcactac aagtcagtcg agacttggaa tgagatcctc 6780
ccttcaaaag ggtgtttaag agttgggggg aggtgtcatc ctcatgtgaa cggggtgttt 6840
ttcaatggta taatattagg acctgacggc aatgtcttaa tcccagagat gcaatcatcc 6900
ctcctccagc aacatatgga gttgttggaa tcctcggtta tccccttgt  gcaccccctg 6960
gcagaccgt  ctaccgtttt caaggacggt gacgaggctg aggatttgt  tgaagttcac 7020
cttcccgatg tgcacaatca ggtctcagga gttgacttgg gtctcccgaa ctggggaag  7080
tatgtattac tgagtgcagg ggccctgact gccttgttgt tgataattt  cctgatgaca 7140
tgttgtagaa gagtcaatcg atcagaacct acgcaacaca atctcagagg gacagggagg 7200
gaggtgtcag tcactcccca aagcgggaag atcatatctt catgggaatc acacaagagt 7260
gggggtgaga ccagactgta attaattaac gtcctttcaa cgatccaagt ccatgaaaaa 7320
aactaacacc cctcccgtac ctagcttata aagtgctggg tcatctaagc tttttcagtcg 7380
agaaaaaac  attagatcag aagaacaact ggcaacactt ctcaacctga gacttacttc 7440
aagatgctcg atcctggaga ggtctatgat gaccctattg acccaatcga gttagaggct 7500
gaacccagag aaccccccat tgtccccaac atcttgagga actctgacta caatctcaac 7560
tctccttga  tagaagatcc tgctagacta atgttagaat ggttaaaaac agggaataga 7620
ccttatcgga tgactctaa  agacaattgc tccaggtctt tcagagtttt gaaagattat 7680
ttcaagaagg tagatttggg ttctctcaag gtgggcggaa tggctgcaca gtcaatgatt 7740
tctctctggt tatatggtgc ccactctgaa tccaacagga gccggagatg tataacagac 7800
ttggcccatt tctattccaa gtcgtccccc atagagaagc tgttgaatct cacgctagga 7860
aatagagggc tgagaatccc cccagaggga gtgttaagt  gccttgagag ggttgattat 7920
gataatgcat ttggaaggta tcttgccaac acgttaccgg cttacttgtt cttccatgta 7980
atcaccttat acatgaacgc cctagactgg gatgaagaaa agaccatcct agcattatgg 8040
aaagatttaa cctcagtgga catcgggaag gacttggtaa agttcaaaga ccaaatatgg 8100
ggactgctga tcgtgacaaa ggactttgtt tactcccaaa gttccaattg tcttttgac  8160
agaaactaca cacttatgct aaaagatctt ttcttgtctc gcttcaactc cttaatggtc 8220
ttgctctctc ccccagagcc ccgatactca gatgacttga tatctcaact atgccagctg 8280
tacattgctg gggatcaagt cttgtctatg tgtggaaact ccggctatga agtcatcaaa 8340
atattggagc catatgtcgt gaatagttta gtccagagag cagaaaagtt taggcctctc 8400
attcattcct tgggagactt tcctgtattt ataaaagaca aggtaagtca acttgaagag 8460
acgttcggtc cctgtgcaag aaggttcttt agggctctgg atcaattcga caacatacat 8520
gacttggttt ttgtgtttgg ctgttacagg cattggggc  acccatatat agattatcga 8580
```

```
aagggtctgt caaaactata tgatcaggtt caccttaaaa aaatgataga taagtcctac   8640
caggagtgct tagcaagcga cctagccagg aggatcctta gatggggttt tgataagtac   8700
tccaagtggt atctggattc aagattccta gcccgagacc accccttgac tccttatatc   8760
aaaacccaaa catggccacc caaacatatt gtagacttgg tggggatac  atggcacaag   8820
ctcccgatca cgcagatctt tgagattcct gaatcaatgg atccgtcaga aatattggat   8880
gacaaatcac attctttcac cagaacgaga ctagcttctt ggctgtcaga aaaccgaggg   8940
gggcctgttc ctagccgaaaa agttattatc acggccctgt ctaagccgcc tgtcaatccc   9000
cgagagtttc tgaggtctat agacctcgga ggattgccag atgaagactt gataattggc   9060
ctcaagccaa aggaacggga attgaagatt gaaggtcgat tctttgctct aatgtcatgg   9120
aatctaagat tgtatttttgt catcactgaa aaactcttgg ccaactacat cttgccactt   9180
tttgacgcgc tgactatgac agacaacctg aacaaggtgt ttaaaaagct gatcgacagg   9240
gtcaccgggc aagggctttt ggactattca agggtcacat atgcatttca cctgactat   9300
gaaaagtgga acaaccatca aagattagag tcaacagagg atgtatttc  tgtcctagat   9360
caagtgtttg gattgaagag agtgtttctt agaacacatc agttttttca aaaggcctgg   9420
atctattatt cagacagatc agacctcatc gggttacggg aggatcaaat atactgctta   9480
gatgcgtcca acgcccaac  ctgttggaat ggccaggatg gcgggctaga aggcttacgg   9540
cagaagggct ggagtctagt cagcttattg atgatagata gagaatctca aatcaggaac   9600
acaagaacca aaatactagc tcaaggaaga aaccaggttt tatgtccgac atacatgttg   9660
tcgccagggc tatctcaaga ggggctcctc tatgaattgg agagaatatc aaggaatgca   9720
cttccgatat acagagccgt cgaggaaggg gcatctaagc tagggctgat catcaagaaa   9780
gaagagacca tgtgtagtta tgacttcctc atctatggaa aaaccccttt gtttagaggt   9840
aacatattgg tgcctgagtc caaaaagatgg gccagagtct cttgcgtctc taatgaccaa   9900
atagtcaacc tcgccaatat aatgtcgaca gtgtccacca atgcgctaac agtggcacaa   9960
cactctcaat ctttgatcaa accgatgagg gattttctgc tcatgtcagt acaggcagtc  10020
tttcactacc tgctatttag cccaatctta aaggaaagag tttacaagat tctgagcgct  10080
gaagggagag gcttttctcct agccatgtca aggataatct atctagatcc ttctttggga  10140
gggatatctg gaatgtccct cggaagattc catatacgac agttctcaga ccctgtctct  10200
gaagggttat ccttctggag agagatctgg ttaagctccc aagagtcctg gattcacgcg  10260
ttgtgtcaag aggctggaaa cccagatctt ggagagagaa cactcgagag cttcactcgc  10320
cttctagaag atccgaccac cttaaatatc agaggagggg ccagtcctac cattctactc  10380
aaggatgcaa tcagaaaggc tttatatgac gaggtggaca aggtggaaaa ttcagagttt  10440
cgagaggcaa tcctgttgtc caagacccat agagataatt ttatactctt cttaatatct  10500
gttgagcctc tgtttcctcg atttctcagt gagctattca gttcgtcttt tttgggaatc  10560
cccgagtcaa tcattggatt gatacaaaac tcccgaacga taagaaggca gtttagaaag  10620
agtctctcaa aaacttttaga agaatccttc tacaactcag agatccacgg gattagtcgg  10680
atgacccaga cacctcagag ggttgggggg gtgtggcctt gctcttcaga gagggcagat  10740
ctacttaggg agatctcttg gggaagaaaa gtggtaggca cgacagttcc tcacccttct  10800
gagatgttgg gattacttcc caagtcctct atttcttgca cttgtggagc aacaggagga  10860
ggcaatccta gagttttctgt atcagtactc ccgtccttct tcagtcatt tttttcacga  10920
ggccccctaa agggatactt gggctcgtcc acctctatgt cgacccagct attccatgca  10980
tgggaaaaag tcactaatgt tcatgtggtg aagagagctc tatcgttaaa agaatctata  11040
aactggttca ttactagaga ttccaacttg gctcaagctc taattaggaa cattatgtct  11100
ctgacaggcc ctgatttccc tctagacgag gccccctgtc tcaaaaggac ggggtcagcc  11160
ttgcataggt tcaagtctgc cagatacagc gaaggagggt attcttctgt ctgcccgaac  11220
ctcctctctc atattctgt  tagtacagac accatgtctg atttgaccca agacgggaag  11280
aactacgatt tcatgttcca gccattgatg ctttatgcac agacatggac atcagagctg  11340
gtacagagag acacaaggct aagagactct acgtttcatt ggcacctccg atgcaacagg  11400
tgtgtgagac ccattgacga cgtgaccctg gagacctctc agatcttcga gtttccggat  11460
gtgtcgaaaa gaatatccag aatggtttct ggggctgtgc ctcacttcca gaggcttccc  11520
gatatccgtc tgagaccagg agatttttgaa tctctaagcg gtagagaaaa gtctcaccat  11580
atcggatcag ctcaggggct cttatactca atcttagttg caattcacga ctccaggatac  11640
aatgatggaa ccatcttccc tgtcaacata tacggcaagg tttccccctag agactatttg  11700
agagggctcg caaggggagt attgatagga tcctcgattt gcttcttgac aagaatgaca  11760
aatatcaata ttaatagacc tcttgaattg gtctcagggg taatctcata tattctcctg  11820
aggctagata accatcctc  cttgtacata atgctcagag aaccgtctct tagaggagag  11880
atattttcta tccctcagaa aatccccgcc gcttatccaa ccactatgaa agaaggcaac  11940
agatcaatct tgtgttatct ccaacatgtg ctacgctatg agcgagagat aatcacggcg  12000
tctccagaga atgactggct atggatcttt tcagactta  gaagtgccaa aatgacgtac  12060
ctatccctca ttacttacca gtctcatctt ctactccaga gggttgagag aaacctatct  12120
aagagtatga gagataacct gcgacaattg agttctttga tgaggcaggt gctgggcggg  12180
cacggagaag ataccttaga gtcagacgac aacattcaac gactgctaaa agactcttta  12240
cgaaggacaa gatgggtgga tcaagaggtg cgccatgcag ctagaaccat gactggagat  12300
tacagccccca acaagaaggt gtcccgtaag gtaggatgtt cagaatgggt ctgctctgct  12360
caacaggtta cagtcctac  ctcagcaaac ccggccccg  tctcggagct tgacataagg  12420
gccctctcta agaggttcca gaaccctttg atctcgggct tgagagtggt tcagtgggca  12480
accggtgctc attataagct taagcctatt ctagatgatc tcaatgtttt cccatctctc  12540
tgccttgtag ttggggacgg gtcagggggg atatcaaggg cagtcctcaa catgtttcca  12600
gatgccaagc ttgtgttcaa cagtcttttta gaggtgaatg acctgatggc ttccggaaca  12660
catctcactgc ctccttcagc aatcatgagg ggaggaaatg atatcgttca cagagtgata  12720
gatcttgact caatctggga aaaaccgtcc gacttgagaa acttggcaac ctggaaatac  12780
ttccagtcag tccaaaagca ggtcaacatg tcctatgacc tcattatttg cgatgcagaa  12840
gttactgaca ttgcatctat caaccggatc acctgttaa  tgtccgattt tgcattgtct  12900
atagatggac cactctattt ggtcttcaaa acttatggga ctatgctagt aaatccaaac  12960
tacaaggcta ttcaacacct gtcaaggcg  ttccctcgg  tcacaggstt tatcacccaa  13020
gtaacttcgt cttttttcatc tgagctctac ctccgattct ccaaacgagg gaagttttc   13080
agagatgctg agtacttgac ctcttccacc cttgagaaa  tgagccttgt gttattcaat  13140
tgtagcagcc ccaagagtga gatgcagaga gctcgttcct tgaactatca ggatcttgtg  13200
agaggatttc ctgaagaaat catatcaaat ccttacaatg atgatgatcat aactctgatt  13260
gacagtgatg tagaatcttt tctagtccac aagatggttg atgatcttga gttacagagg  13320
```

```
ggaactctgt ctaaagtggc tatcattata gccatcatga tagttttctc caacagagtc  13380
ttcaacgttt ccaaacccct aactgacccc tcgttctatc caccgtctga tcccaaaatc  13440
ctgaggcact tcaacatatg ttgcagtact atgatgtatc tatctactgc tttaggtgac  13500
gtccctagct tcgcaagact tcacgacctg tataacagac ctataactta ttacttcaga  13560
aagcaagtca ttcgagggaa cgtttatcta tcttggagtt ggtccaacga cacctcagtg  13620
ttcaaaaggg tagcctgtaa ttctagcctg agtctgtcat ctcactggat caggttgatt  13680
tacaagatag tgaagactac cagactcgtt ggcagcatca aggatctatc cagagaagtg  13740
gaaagacacc ttcataggta caacaggtgg atcaccctag aggatatcag atctagatca  13800
tccctactag actacagttg cctgtgaacc ggatactcct ggaagcctgc ccatgctaag  13860
actcttgtgt gatgtatctt gaaaaaaaca agatcctaaa tctgaaccct tggttgtttg  13920
attgttttc tcattttgt tgtttatttg ttaagcgt                             13958
```

```
SEQ ID NO: 10           moltype = DNA  length = 13826
FEATURE                 Location/Qualifiers
misc_feature            1..13826
                        note = RABV vector: Coravax V3-China (S1-VSVG-E26)
source                  1..13826
                        mol_type = other DNA
                        organism = synthetic construct SEQUENCE: 10
acgcttaaca accagatcaa agaaaaaaca gacattgtca attgcaaagc aaaaatgtaa   60
caccctaca atggatgccg acaagattgt attcaaagtc aataatcagg tggtctcttt    120
gaagcctgag attatcgtgg atcaatatga gtacaagtac cctgccatca agatttgaa    180
aaagccctgt ataaccctag gaaaggctcc cgatttaaat aaagcataca agtcagtttt   240
gtcaggcatg agcgccgcca aacttaatcc tgacgatgta tgttcctatt tggcagcggc   300
aatgcagttt tttgagggga catgtccgga agactgagca agctatggaa ttgtgattgc   360
acgaaaagga gataagatca ccccaggttc tctggtggag ataaaacgta ctgatgtaga   420
agggaattgg gctctgacag gaggcatgga actgacaaga accccactg tccctgagca    480
tgcgtcctta gtcggtcttc tcttgagtct gtataggttg agcaaaatat ccgggcaaaa   540
cactggtaac tataagacaa acattgcaga caggatagaa cagattttttg agacagcccc  600
ttttgttaaa atcgtggaac accatactct aatgacaact cacaaaatgt gtgctaattg   660
gagtactata ccaaacttca gatttttggc cggaacctat gacatgtttt tctcccggat   720
tgagcatcta tattcagcaa tcagagtggg cacagttgtc actgcttatg aagactgttc   780
aggactggta tcatttactg ggttcataaa acaaatcaat ctcaccgcta gagaggcaat   840
actatatttc ttccacaaga acttgagga agagataaga agaatgtttg agccagggca   900
ggagacagct gttcctcact ctttatttcat ccacttccgt tcactaggct tgagtgggaa  960
atctccttat tcatcaaatg ctgttggtca cgtgttcaat ctcattcact ttgtaggatg  1020
ctatatgggt caagtcagat ccctaaatgc aacggttatt gctgcatgtg ctcctcatga  1080
aatgtctgtt ctaggggct atctgggaga ggaattcttc gggaaaggga catttgaaag  1140
aagattcttc agagatgaga aagaacttca agaatacgag gcggctgaac tgacaaagac  1200
tgacgtagca ctggcagatg atggaactgt caactctgac gacgaggact acttttcagg  1260
tgaaaccaga agtccggagg ctgtttatac tcgaatcatg atgaatggag tcgactaaa   1320
gagatcttcac atacggagat atgtctcagt cagttccaat catcaagccc gtccaaactc  1380
attcgccgag tttctaaaca agacatattc gagtgactca taacatgaaa aaaactaaca  1440
cccctcccgt acgccaccat gttcgtgttt ctggtgctgc tgcctctggt gagctcccag  1500
tgcgtgaacc tgaccacaag gacccagctg ccccctgcct ataccaattc cttcacacgg  1560
ggcgtgtact atcccgacaa ggtgttccgg agcagcgtgc tgcactccac acaggatctg  1620
tttctgcctt tcttttctaa cgtgacctgg ttccacgcca tccacgtgag cggcaccaat  1680
ggcacaaagc ggttcgacaa tccagtgctg ccctttaacg atggcgtgta cttcgcctcc  1740
accgagaagt ctaacatcat cagaggctgg atctttggca ccacactgga cagcaagaca  1800
cagtccctgc tgatcgtgaa caatgccacc aacgtggtca tcaaggtgtg cgagttccag  1860
ttttgtaatg atccattcct gggcgtgtac tatcacaaga caataagtc ttggatggag   1920
agcgagtttc gcgtgtattc ctctgccaac aatggcacat ttgagtacgt gtcccagccc  1980
ttcctgatgg acctggaggg caagcagggc aatttcaaga acctgaggga gttcgtgttt  2040
aagaatatcg atggctactt caaaatctac tccaagcaca ccccaatcaa cctggtgcgc  2100
gacctgccac agggcttctc tgccctggag ccactggtgg atctgcccat cggcatcaac  2160
atcacccggt tcagacact gctggcccct cacagaagct acctgacacc aggcgacagc  2220
tcctctggat ggaccgcagg agcagcagcc tactatgtgg gctatctgca gcccaggacc  2280
ttcctgctga gtacaacga gaatggcacc atcacagacg ccgtggattg cgccctggat  2340
ccccctgtctg agaccaagtg tacactgaag agctttaccg tggagaaggg catctatcag  2400
acaagcaatt tcagggtgca gcctaccgag tccatcgtgc gctttcccaa tatcacaaac  2460
ctgtgccctt ttggcgaggt gttcaacgca cccgcttcg ccagcgtgta cgcctggaat  2520
aggaagcgca ctctccaactg cgtggccgac tattctgtgc tgtacaacag cgcctccttc  2580
tctaccttta agtgctatgg cgtgagcccc acaaagctga atgacctgtg ctttaccaac  2640
gtgtacgccg attccttcgt gatcaggggc gacgaggtgc gccagatcgc accagacag   2700
acaggcaaga tcgcagacta caattataag ctgcctgacg atttcaccgg ctgcgtgatc  2760
gcctggaact ctaacaatct ggatagcaaa gtgggcggca actacaatta tctgtaccgg  2820
ctgtttagaa agtctaatct gaagccattc gagagggaca tctccacaga aatctaccag  2880
gccggctcta cccccctgca tggcgtggag ggctttaact gttattttcc tctgcagagc  2940
tacggcttcc agccaacaaa cggcgtgggc tatcagccct accgcgtggt ggtgctgtct  3000
tttgagctgc tgcacgcacc tgcaacagtg tgcggaccaa agaagagcac caatctggtg  3060
aagaacaagt gcgtgaactt caacttcaac ggactgaccg gaacaggcgt gctgaccgag  3120
tccaacaaga gttcctgcc ttttcagcag ttcggcaggg acatcgcaga taccacagac  3180
gccgtgagca ccctcagac cctggagatc tggacataca accatcgctc cttcggccc   3240
gtgtctgtga tcacaccagg caccaataca agcaaccagg tggccgtgct gtatcaggac  3300
gtgaattgta ccgaggtgcc agtggcaatc cacgcagatc agctgacccc tacatggcgg  3360
gtgtactcta ccggcagcaa cgtgttccag acaagagccg gatgcctgat cggagcagag  3420
cacgtgaaca atagctatga gtcgacatcc ctatcggcg ccggcatctg tgcctcctac  3480
cagacccaga caaactcccc aaggtctgtg ggcgatacag gcctgtccaa gaatccaatc  3540
```

```
gagctggtag agggctggtt cagcagttgg aaaagctcca tcgcctcctt tttctttatc  3600
atcggcctga tcatcggact gttcctggtg ctccgcgtgg gtatccacct gtgcatcaag  3660
ctgaagcaca ccaagaaaag acagatttat acagacatcg agatgaaccg cctgggaaag  3720
tgagctagcc atgaaaaaaa ctaacacccc tcctttcgaa ccatcccaaa catgagcaag  3780
atctttgtca atcctagtgc tattagagcc ggtctggccg atcttgagat ggctgaagaa  3840
actgttgatc tgatcaatag aaatatcgaa gacaatcagg ctcatctcca agggaaccc   3900
atagaggtgg acaatctccc tgaggatatg gggcgacttc acctggatga tggaaaatcg  3960
cccaaccatg tgagatagc caaggtggga gaaggcaagt atcgagagga cttcagatg    4020
gatgaaggag aggatcctag cttcctgttc cagtcatacc tggaaaatgt tggagtccaa  4080
atagtcagac aaatgaggtc aggagagaga tttctcaaga tatggtcaca gaccgtagaa  4140
gagattatat cctatgtcgc ggtcaacttt cccaaccctc caggaaagtc ttcagaggat  4200
aaatcaaccc agactactgg ccgagagctc aagaaggaga caaacccac tccttctcag   4260
agagaaagcc aatcatcgaa agccaggatg gcggctcaaa ttgcttctgg ccctccagcc  4320
cttgaatggt cggctaccaa tgaagaggat gatctatcag tggaggctga gatcgctcac  4380
cagattgcag aaagtttctc caaaaaatat aagtttccct ctcgatcctc agggatactc  4440
ttgtataatt tgagcaatt gaaaatgaac cttgatgata tagttaaaga ggcaaaaaat   4500
gtaccaggtg tgacccgttt agcccatgac gggtccaaac tcccctaag atgtgtactg    4560
ggatgggtcg cttttggcca ctctaagaaa ttccagttgt tagtcgaatc cgacaagctg  4620
agtaaaatca tgcaagatga cttgaatcgc tatacatctt gctaaccgaa cctctcccct  4680
cagtccctct agacaataaa atccgagatg tcccaaagtc aacatgaaaa aaacaggcaa  4740
caccactgat aaaatgaacc tcctacgtaa gatagtgaaa accgcaggg acgaggacac    4800
tcaaaaatcc tctcccgcgt cagccctct ggatgacgat gacttgtgc ttccaccccc    4860
tgaatacgtc ccgctgaaag aacttacagg caagaagaac atgaggaact tttgtatcaa  4920
cggaagggtt aaagtgtgta gcccgaatgg ttactcgttc aggatcctgc ggcacattct  4980
gaaatcattc gacgagatat attctgggaa tcataggatg atcgggttag tcaaagtggt  5040
tattggactg gcttttgtcag gatctccagt ccctgaggc ctgaactggg tatacaaatt   5100
gaggagaacc tttatcttcc agtgggctga ttccaggggc cctcttgaag gggaggagtt  5160
ggaatactct caggagatca cttgggatga tgatactgga ttcgtcggat tgcaaataag  5220
agtgattgca aacagtgtc atatccaggg cagagtctgg tgtatcaaca tgaacccgag   5280
agcatgtcaa ctatggtctg acatgtctct tcagacacaa aggtccgaag aggacaaaga  5340
ttcctctctg cttctagaat aatcagatta tatcccgcaa atttatcact tgtttacctc  5400
tggaggagag aacatatggg ctcaactcca acccttggga gcaatataac aaaaaacatg  5460
ttatggtgcc attaaaccgc tgcatttcat caaagtcaag ttgattacct ttacattttg  5520
atcctcttgg atgtgaaaaa aactattaac atccctcaaa agaccccggg aaagatggtt  5580
cctcaggctc tcctgtttgt acccccttctg gttttccat tgtgttttgg gaaattccct   5640
atttacacga taccagacaa gcttggtccc tggagtccga ttgacataca tcacctcagc  5700
tgcccaaaca atttggtagt ggaggacgaa ggatgcacca acctgtcagg ttctcctac   5760
atggaactta aagttggata catcttagcc ataaaagtga acgggttcac ttgcacaggc  5820
gttgtgacgg aggctgaaac ctacactaac ttcgttggtt atgtcacaac cacgttcaaa  5880
agaaaagcatt tccgcccaac accagatgca tgtagagccg cgtacaactg gaagatggcc  5940
ggtgacccca gatatgaaga gtctctacac aatccgtacc ctgactaccg ctggcttcga  6000
actgtaaaaa ccaccaagga gtctctcgtt atcatatctc caagtgtggc agatttggac  6060
ccatatgaca gatcccttca ctcgagggtc ttccctaggg ggaagtgctc aggagtagcg  6120
gtgtcttcta cctactgctc cactaaccac gattacacca tttggatgcc cgagaatccg  6180
agactaggga tgtcttgtga catttttacc aatagtagag ggaagagagc atccaaaggg  6240
agtgagactt gcggctttgt agatgaaaga ggcctatata agtctttaaa aggagcatgc  6300
aaactcaagt tatgtggagt tctaggactt agacttatgg atggaacatg ggtctcgatg  6360
caaacatcaa atgaaaccaa atggtgccct cccgataagt tggtgaacct gcacgacttt  6420
cgctcagacg aaattgagca ccttgttgta gaggagttgg tcaggaagag agaggagtgt  6480
ctggatgcac tagagtccat catgacaacc aagtcagtga gtttcagacg tctcagtcat  6540
ttaagaaaac ttgtccctgg gtttggaaaa gcatatacca tattcaacaa gaccttgatg  6600
gaagccgatg ctcactacaa gtcagtcgag acttggaatg agatcctccc ttcaaagggg  6660
tgtttaagag ttgggggggag gtgtcatcct catgtgaacg gggtgttttt caatggtata  6720
atattaggac ctgacggcaa tgtcttaatc ccagagatgc aatcatccct cctccagcaa  6780
catatggagt tgtgaaatc ctcggttatc cccttgtgc accccctggc agacccgtct    6840
accgtttttca aggacggtga cgaggctgag gattttgttg aagttcacct tcccgatgtg  6900
cacaatcagg tctcaggagt tgacttgggt ctcccgaact ggggaagta tgtattactg    6960
agtgcagggg ccctgactgc cttgatgttg ataattttcc tgatgacatg ttgtagaaga  7020
gtcaatcgat cagaacctac gcaacacaat ctcagaggga cagaggga ggtgtcagtc     7080
actccccaaa gcgggaagat catatcttca tgggaatcac acaagagtgg gggtgagacc  7140
agactgtaat taattaacgt cctttcaacg atccaagtcc atgaaaaaaa ctaacacccc  7200
tcccgtacct agcttataaa gtgctgggtc atctaagctt ttcagtcgag aaaaaaacat  7260
tagatcagaa gaacaactgg caacacttct caacctgaga cttacttcaa gatgctcgat  7320
cctggaagga tctatgatga ccctattgac ccaatcgagt tagaggctga accagagga    7380
accccccattg tccccaacat cttgaggaac tctgactaca atctcaactc tccttttgata  7440
gaagatcctg ctagactaat gttagaatgg ttaaaaacag ggataagacc ttatcggatg  7500
actctaacag acaattgctc caggtctttc agagttttga agattatttt caagaaggta  7560
gattttgggtt ctctcaaggt gggcggaatg gctgcacagt caatgattc tctctggtta  7620
tatggtgccc actctgaatc caacaggagc cggagatta taacagactt ggcccatttc  7680
tattccaagt cgtcccccat agagaagctg ttgaatctca cgctaggaaa tagagggctg  7740
agaatccccc cagagggagt gttaagttgc cttgagaggg ttgattatga taatgcattt  7800
ggaaggtatc ttgccaacac gtattcctct tacttgttct tccatgtaat caccttatac  7860
atgaacgccc tagactggga tgaagaaaag accatcctag cattatgaa agatttaacc  7920
tcagtggaca tcgggaagga cttggtaaag ttcaaagacc aaatatgggg actgctgatc  7980
gtgacaaagg actttgttta ctcccaaagt tccaattgtc tttttgacag aaactacaca  8040
cttatgctaa aagatctttt cttgtctcgc ttcaactcct taatggtctt gctctctccc  8100
ccagagcccc gatactcaga tgacttgata tctcaactat gccagctgta cattgctggg  8160
gatcaagtct tgtctatgtg tggaaactcc ggctatgaag tcatcaaaat attggagcca  8220
tatgtcgtga atagtttagt ccagagagca gaaaagttta ggcctctcat tcattccttg  8280
```

```
ggagactttc ctgtatttat aaaagacaag gtaagtcaac ttgaagagac gttcggtccc   8340
tgtgcaagaa ggttctttag ggctctggat caattcgaca acatacatga cttggttttt   8400
gtgtttggct gttacaggca ttgggggcac ccatatatag attatcgaaa gggtctgtca   8460
aaactatatg atcaggttca ccttaaaaaa atgatagata agtcctacca ggagtgctta   8520
gcaagcgacc tagccaggag gatccttaga tggggttttg ataagtactc caagtggtat   8580
ctggattcaa gattcctagc ccgagaccac cccttgactc cttatatcaa aacccaaaca   8640
tggccaccca aacatattgt agactggtg ggggatacat ggcacaagct cccgatcacg   8700
cagatctttg agattcctga atcaatggat ccgtcagaaa tattgatga caaatcacat    8760
tctttcacca gaacgagact agcttcttgg ctgtcagaaa accgagggg gcctgttcct    8820
agcgaaaaag ttattatcac ggccctgtct aagccgcctg tcaatcccg agagtttctg    8880
aggtctatag acctcggagg attgccagat gaagacttga taattggcct caagccaaag   8940
gaacgggaat tgaagattga aggtcgattc tttgctctaa tgtcatggaa tctaagattg   9000
tattttgtca tcactgaaaa actcttggcc aactacatct tgccacttt tgacgcgctg    9060
actatgacag acaacctgaa caaggtgttt aaaaagctga tcgacagggt cacccgggcaa  9120
gggcttttgg actattcaag ggtcacatat gcatttcacc tggactatga aaagtggaac   9180
aaccatcaaa gattagagtc aacagaggat gtattttctg tcctagatca agtgtttgga   9240
ttgaagagag tgttttctag aacacacgag ttttttcaaa aggcctggat ctattattca   9300
gacagatcag acctcatcgg gttacaggag gatcaaatat actgcttaga tgcgtccaac   9360
ggcccaacct gttggaatgg ccaggatggc gggctagaag gcttacggca gaagggctgg   9420
agtctagtca gcttattgat gatagataga gaatctcaaa tcaggaacac aagaaccaaa   9480
atactagctc aaggagacaa ccaggtttta tgtccgacat acatgttgtc gccagggcta   9540
tctcaagagg ggctcctcta tgaattggag agaatatcaa ggaatgcact ttcgatatac   9600
agagccgtcg aggaagggggc atctaagcta gggctgatca tcaagaaaga agagaccatg  9660
tgtagttatg acttcctcat ctatggaaaa accccttttgt ttagaggtaa catattggtg  9720
cctgagtcca aaagatgggc cagagtctct tgcgtctcta atgaccaaat agtcaacctc   9780
gccaatataa tgtcgacagt gtccaccaat gcgctaacag tggcacaaca ctctcaatct   9840
ttgatcaaac cgatgaggga ttttctgctc atgtcagtac aggcagtctt tcactacctg   9900
ctatttagcc caatcttaaa gggaagagtt tacaagattc tgagcgctga aggggagagc   9960
tttctcctag ccatgtcaag gataatctat ctagatcctt ctttgggagg gatatctgga  10020
atgtccctcg gaagattcca tatacgacag ttctcagacc ctgtctctga agggttatcc  10080
ttctggagag agatctggtt aagctcccaa gagtcctgga ttcacgcgtt gtgtcaagag  10140
gctgaaaacc cagatcttgg agagagaaca ctcgagagct tcactcgcct tctagaagat  10200
ccgaccacct taaatatcag aggaggggcc agtcctacca ttctactcaa ggatgcaatc  10260
agaaaggctt tatatgacga ggtggacaag gtggaaaatt cagagtttcg agaggcaatc  10320
ctgttgtcca agaccatag agataattt atactcttct taatatctgt tgagcctctg   10380
tttcctcgat ttctcagtga gctattcagt tcgtctttt tgggaatccc cgagtcaatc   10440
attggattga tacaaaactc ccgaacgata agaaggcagt ttagaaagag tctctcaaaa   10500
actttagaag aatccttcta caactcagag atccacggga ttagtcggat gacccagaca   10560
cctcagaggg tgggggggt gtggccttgc tcttcagaga gggcagatct acttagggag   10620
atctcttggg gaagaaaagt ggtaggcacg acagttcctc acccttctga gatgttggga   10680
ttacttccca gtcctctat ttcttgcact tgtggagcaa caggaggagg caatcctaga    10740
gtttctgtat cagtactccc gtcctttgat cagtcatttt tttcacgagg cccctaaag    10800
ggatacttgg gctcgtccac ctctatgtcg acccagctat tccatgcatg gcgaaaagtc   10860
actaatgttc atgtggtgaa gagagctcta tcgttaaaag aatctatata ctggttcatt   10920
actagagatt ccaacttggc tcaagctcta attaggaaca ttatgtctct gacaggccct   10980
gatttccctc tagaggaggc ccctgtcttc aaaaggacgg ggtcagcctt gcataggttc   11040
aagtctgcca gatacagcga aggagggtat tcttctgtct gcccgaacct cctctctcat   11100
atttctgtta gtacagacac catgtctgat ttgacccaag acgggaagaa ctacgatttc   11160
atgttccagc cattgatgct ttatgcacag acatggacat cagagctggt acagagagac   11220
acaaggctaa gagactctac gtttcattgg caactccgat gcaacaggtg tgtgagaccc   11280
attgacgacg tgaccctgga gacctctcag atcttcgagt ttccggatgt gtcgaaaaga   11340
atatccagaa tggtttctgg ggctgtgcct cacttccaga ggcttccgga tatccgtctg   11400
agaccaggag atttttgaatc tctaagcggt agagaaaagt ctcaccatat cggatcagct  11460
caggggctct tatactcaat cttagtggca attcacgact caggatacaa tgatggaacc  11520
atcttccctg tcaacatata cggcaaggtt tcccctagag actatttgag agggctcgca  11580
aggggagtat tgataggatc ctcgatttgc ttcttgacaa gaatgacaaa tatcaatatt  11640
aatagacctc ttgaattggt ctcaggggta atctcatata ttctcctgag gctagataac  11700
catccctcct tgtacataat gctcagaaa ccgtctctta gaggagagat attttctatc   11760
cctcagaaaa tccccgccgc ttatccaacc actatgaaag aaggcaacag atcaatcttg  11820
tgttatctcc aacatgtgct acgctatgag cgagagataa tcacggcgtc tccagagaat  11880
gactggctat ggatcttttc agactttaga agtgccaaaa tgacgtacct atccctcatt  11940
acttaccagt ctcatcttct actccagagg gttgagagaa acctatctaa gagtatgaga  12000
gataacctgc gacaattgag ttctttgatg aggcaggtgc tgggcgggca cggagaagat  12060
accttagagt cagacgacaa cattcaacga ctgcaaaag actcttttacg aaggacaaga  12120
tgggtggatc aagaggtgcg ccatgcagct agaaccatga ctggagatta cagccccaac  12180
aagaaggtgt cccgtaaggt aggatgttca gaatgggtct gctctgctca acaggttgca  12240
gtctctacct cagcaaaccc ggcccctgtc tcggagcttg acataagggc cctctctaag  12300
aggttccaga acccttttgat ctcgggcttg agagtggttc agtgggcaac cggtgctcat  12360
tataagctta agcctattct agatgatctc aatgttttcc catctctctg ccttgtagtt  12420
ggggacgggt caggggggat atcaagggca gtcctcaaca tgtttccaga tgccaagctt  12480
gtgttcaaca gtcttttaga ggtgaatgac ctgatggctt ccgaacaca tccactgcct  12540
ccttcagcaa tcatgagggg aggaaatgat atcgtctcca gagtgataga tcttgactca  12600
atctgggaaa aaccgtccga cttgagaaac ttggcaacct ggaaatactt ccagtcagtc  12660
caaaaggtta tcaacatgtc ctatgacctc attatttgcg atgcagagt tactgacatt  12720
gcatctatca accggatcac cctgttaatg tccgattttg cattgtctat agatgaacca  12780
ctctatttgg tcttcaaaac ttatgggact atgctagtaa atccaaacta caaggctatt  12840
caacacctgt caagagcgtt cccctcggtc acaggttta tcacccaagt aacttcgtct  12900
ttttcatctg agctctacct ccgattctcc aaacgaggga gtttttcag agatgctgag  12960
tacttgacct cttccaccct tcgagaaatg agccttgtgt tattcaattg tagcagcccc  13020
```

```
aagagtgaga tgcagagagc tcgttccttg aactatcagg atcttgtgag aggatttcct   13080
gaagaaatca tatcaaatcc ttacaatgag atgatcataa ctctgattga cagtgatgta   13140
gaatcttttc tagtccacaa gatggttgat gatcttgagt tacagagggg aactctgtct   13200
aaagtggcta tcattatagc catcatgata gttttctcca acagagtctt caacgtttcc   13260
aaaccccta a ctgacccctc gttctatcca ccgtctgatc ccaaaatcgc gaggcacttc   13320
aacatatgtt gcagtactat gatgtatcta tctactgctt taggtgacgt ccctagcttc   13380
gcaagacttc acgacctgta taacagacct ataacttatt acttcagaaa gcaagtcatt   13440
cgagggaacg tttatctatc ttggagttgg tccaacgaca cctcagtgtt caaaagggta   13500
gcctgtaatt ctagcctgag tctgtcatct cactggatca ggttgattta caagatagtg   13560
aagactacca gactcgttgg cagcatcaag gatctatcca gagaagtgga aagacacctt   13620
cataggtaca acaggtggat caccctagag gatatcagat ctagatcatc cctactagac   13680
tacagttgcc tgtgaaccgg atactcctgg aagcctgccc atgctaagac tcttgtgtga   13740
tgtatcttga aaaaaacaag atcctaaatc tgaacctttg gttgtttgat tgttttctc   13800
attttttgttg tttatttgtt aagcgt                                       13826

SEQ ID NO: 11           moltype = DNA  length = 13826
FEATURE                 Location/Qualifiers
misc_feature            1..13826
                        note = RABV vector: Coravax V3-South Africa (S1-VSVG-E26)
source                  1..13826
                        mol_type = other DNA
                        organism = synthetic construct
SEQUENCE: 11
acgcttaaca accagatcaa agaaaaaaca gacattgtca attgcaaagc aaaaatgtaa     60
cacccctaca atggatgccg acaagattgt attcaaagtc aataatcagg tggtctcttg    120
gaagcctgag attatcgtgg atcaaatatga gtacaagtac cctgccatca aagatttgaa    180
aaagccctgt ataaccctag gaaaggctcc cgatttaaat aaagcataca agtcagtttt    240
gtcaggcatg agcgccgcca aacttaatcc tgacgatgta tgttcctatt tggcagcggc    300
aatgcagttt tttgagggga catgtccgga agactggacc agctatgaa ttgtgattgc    360
acgaaaagga gataagatca ccccaggttc tctggtgaga ataaaacgta ctgatgtaga    420
agggaattgg gctctgacag gaggcatgga actgacaaga gacccccactg tccctgagca    480
tgcgtcctta gtcggtcttc tcttgagtct gtataggttg agcaaaatat ccgggcaaaa    540
cactggtaac tataagacaa acattgcaga caggatagag cagattttg agacagcccc    600
ttttgttaaa atcgtggaac accatactct aatgacaact cacaaaatgt gtgctaattg    660
gagtactata ccaaacttca gatttttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatattc ttccacaaga actttgagga agagtaaaga agaatgtttg agcagggca      900
ggagacagct gttcctcact cttatttcat ccacttccgt tcactaggct tgagtgggaa    960
atctccttat tcatcaaatg ctgttggtca cgtgttcaat ctcattcact ttgtaggatg   1020
ctatatgggt caagtcagat ccctaaatgc aacggttatt gctgcatgtg ctcctcatga   1080
aatgtctgtt ctagggggct atctgggaga ggaattcttc gggaaaggga catttgaaag   1140
aagattcttc agagatgaga aagaacttca agaatacgag gcggctgaac tgacaaagac   1200
tgacgtagca ctggcagatg atggaactgt caactctgac gacgaggact acttttcagg   1260
tgaaaccaga agtccggagg ctgttttatac tcgaatcatg atgaatggag gtcgactaaa   1320
gagatctcac atacggagat atgtctcagt cagttccaat catcaagccc gtccaaactc   1380
attcgccgag tttctaaaca agacatattc gagtgactca taacatgaaa aaaactaaca   1440
ccctcccgt acgccaccat gttcgtgttt ctggtgctgc tgcctctggt gagctcccag   1500
tgcgtgaact tcaccacaag gacccagctg cccctgcct ataccaattc cttcacacgg   1560
ggcgtgtact atcccgacaa ggtgttccgg agcagcgtgc tgcactccac acaggatctg   1620
tttctgcctt tcttttctaa cgtgacctgg ttccacgcca tccacgtgag cggcaccaat   1680
ggcacaaagc ggttcgccaa tccagtgctg cccctttaacg atggcgtgta cttcgcctcc   1740
accgagaagt ctaacatcat cagaggctgg atctttggca ccacactgga cagcaagaca   1800
cagtccctgc tgatcgtgaa caatgccacc aacgtggtca tcaaggtgtg cgagttccag   1860
ttttgtaatg atccatttct gggcgtgtac tatcacaaga acaataagtc ttggatggag   1920
agcgagtttc gcgtgtattc ctctgccaac aattgcacat tgagtacgt gtcccagccc   1980
ttcctgatgg acctggaggg caagcagggc aatttcaaga acctgagggga gttcgtgttt   2040
aagaatatcg atggctactt caaaatctac tccaagcaca cccaatcaa cctggtgcgc   2100
ggcctgccac agggcttctc tgccctggag ccactggtgg atctgcccat cggcatcaac   2160
atcacccggt tcagacact gctggccctg cacagaagct acctgacacc aggcgacagc   2220
tcctctggat ggaccgcagg agcagcagcc tactatgtgg gctatctgca gcccaggacc   2280
ttcctgctga gtacaacga gaatggcacc atcacagacg ccgtggattg cgccctggat   2340
cccctgtctg agaccaagtg tacactgaag agctttaccg tggagaaggg catctatcag   2400
acaagcaatt tcagggtgca gcctaccgag tccatcgtgc gctttcccaa tatcacaaac   2460
ctgtgccctt ttggcgaggt gttcaacgca accgcttcg ccagcgtgta cgcctggaat   2520
aggaagcgca tctccaactg cgtggccgac tattctgtgc tgtacaacag cgcctccttc   2580
tctaccttta gtgctatgg cgtgagcccc acaaagctga atgacctgtg ctttaccaac   2640
gtgtacgccg attccttcgt gatcagggc gacgaggtgc gccagatcgc accaggacag   2700
acaggcaata tcgcagacta caattataag ctgcctgacg atttcaccgg ctgcgtgatc   2760
gcctggaact ctaacaatct ggatagcaaa gtgggcggca actacaatta tctgtaccgg   2820
ctgtttagaa agtctaatct gaagccattc gagagggaca tctccacaga aatctaccag   2880
gccggctcta ccccctgcaa tggcgtgaag ggctttaact gttatttccc tctgcagagc   2940
tacggcttcc agccaacata tggcgtgggc tatcagccct accgcgtggt ggtgctgtct   3000
tttgagctgc tgcacgcacc tgcaacagtg tgcggaccaa agaagagcac caatctggtg   3060
aagaacaagt gcgtgaactt caacttcaac ggactgaccg gaacaggcgt gctgaccgag   3120
tccaacaaga gttcctgcc ttttcagcag ttcggcaggg acatcgcaga taccacagac   3180
gccgtgcgcg acactcagac cctggagatc ctggacatca ccatgctc cttcggcggc   3240
gtgtctgtga tcacaccagg caccaataca agcaaccagg tggccgtgct gtatcagggc   3300
gtgaattgta ccgaggtgcc agtggcaatc cacgcagatc agctgacccc tacatggcgg   3360
```

```
gtgtactcta ccggcagcaa cgtgttccag acaagagccg gatgcctgat cggagcagag    3420
cacgtgaaca atagctatga gtgcgacatc cctatcggcg ccggcatctg tgcctcctac    3480
cagacccaga caaactcccc aaggtctgtg ggcgatacag gcctgtccaa gaatccaatc    3540
gagctggtag agggctggtt cagcagttgg aaaagctcca tcgcctcctt tttctttatc    3600
atcggcctga tcatcggact gttcctggtg ctccgcgtgg gtatccacct gtgcatcaag    3660
ctgaagcaca ccaagaaaag acagatttat acagacatcg agatgaaccg cctgggaaag    3720
tgagctagcc atgaaaaaaa ctaacacccc tcctttcgaa ccatcccaaa catgagcaag    3780
atctttgtca atcctagtgc tattagagcc ggtctggccg atcttgagat ggctgaagaa    3840
actgttgatc tgatcaatag aaatatcgaa gacaatcagg ctcatctcca agggaaccc    3900
atagaggtgg acaatctccc tgaggatatg gggcgacttc acctggatga tggaaaatcg    3960
cccaaccatg gtgagatagc caaggtggga gaaggcaagt atcgagagga ctttcagatg    4020
gatgaaggag aggatcctag cttcctgttc cagtcatacc tggaaaatgt tggagtccaa    4080
atagtcagac aaatgaggtc aggagagaga tttctcaaga tatggtcaca gaccgtagaa    4140
gagattatat cctatgtcgc ggtcaacttt cccaaccctc caggaaagtc ttcagaggat    4200
aaatcaaccc agactactgg ccgagagctc aagaaggaga caacacccac tccttctcag    4260
agagaaagcc aatcatcgaa agccaggatg gcggctcaaa ttgcttctgg ccctccagcc    4320
cttgaatggt cggctaccaa tgaagaggat gatctatcag tggaggctga gatcgctcac    4380
cagattgcag aaagtttctc caaaaaatat aagtttccct ctcgatcctc agggatactc    4440
ttgtataatt ttgagcaatt gaaaatgaac cttgatgata tagttaaaga ggcaaaaaat    4500
gtaccaggtg tgacccgttt agcccatgac gggtccaaac tcccccctaag atgtgtactg    4560
ggatgggtcg ctttggccaa ctctaagaaa ttccagttgt tagtcgaatc cgacaagctg    4620
agtaaaatca tgcaagatga cttgaatcgc tatacatctt gctaaccgaa cctctcccct    4680
cagtccctct agacaataaa atccgagatg tcccaaagtc aacatgaaaa aaacaggcaa    4740
caccactgat aaaatgaacc tcctacgtaa gatagtgaaa aaccgcaggg acgaggacac    4800
tcaaaaatcc tctcccgcgt cagcccctct ggatgacgat gacttgtggc ttccacccc    4860
tgaatacgtc ccgctgaaag aacttacagg caagaagaac atgaggaact tttgtatcaa    4920
cggaagggtt aaagtgtgta gcccgaatgg ttactcgttc aggatcctgc ggcacattct    4980
gaaatcattc gacgagatat attctgggaa tcataggatg atcgggttag tcaaagtggt    5040
tattggactg gctttgtcag gatctccagt ccctgagggc ctgaactggg tatacaaatt    5100
gaggagaacc tttatcttcc agtgggctga ttccagggga cctcttgaag gggaggagtt    5160
ggaatactct caggagatca cttgggatga tgatactgag ttcgtcggat tgcaaataag    5220
agtgattgca aaacagtgtc atatccaggg cagagtctgg tgtatcaaca tgaacccgag    5280
agcatgtcaa ctatggtctg acatgtctct tcagacacaa aggtccgaag aggacaaaga    5340
ttcctctctg cttctagaat aatcagatta tatcccgcaa atttatcact tgtttacctc    5400
tggaggagag aacatatggg ctcaactcca acccttggga gcaatataac aaaaaacatg    5460
ttatggtgcc attaaaccgc tgcatttcat caaagtcaag ttgattacct ttacattttg    5520
atcctcttgg atgtgaaaaa aactattaac atccctcaaa agaccccggg aaagatggtt    5580
cctcaggctc tcctgtttgt accccttctg gttttttccat tgtgtttttgg gaaattccct    5640
atttacacga taccagacaa gcttggtccc tggagtccga ttgacataca tcacctcagc    5700
tgcccaaaca atttggtagt ggaggacgaa ggatgcacca acctgtcagg gttctcctac    5760
atggaactta aagttggata catcttagcc ataaaagtga acgggttcac ttgcacaggc    5820
gttgtgacgg aggctgaaac ctacactaac ttcgttggtt atgtcacaac cacgttcaaa    5880
agaaagcatt tccgcccaac accagatgca tgtagagccg cgtcaactg gaagatgcct    5940
ggtgaccccca gatatgaaga gtctctacac aatccgtacc ctgactaccg ctggcttcga    6000
actgtaaaaa ccaccaagga gtctctcgtt atcatatctc caagtgtggc agatttggac    6060
ccatatgaca gatcccttca ctcgagggtc ttccctagcg ggaagtgctc aggagtagcc    6120
gtgtcttcta cctactgctc cactaaccac gattacacca tttggatgcc cgagaatccg    6180
agactaggga tgtcttgtga catttttacc aatagtagag ggaagagagc atccaaaggg    6240
agtgagactt gcggctttgt agatgaaaga ggcctatata agtctttaaa aggagcatgc    6300
aaactcaagt tatgtggagt tctaggactt agacttatgg atggaacatg ggtctcgatg    6360
caaacatcaa atgaaaccaa atggtgccct cccgataagt tggtgaacct gcacgacttc    6420
cgctcagacg aaattgagca ccttgttgta gaggagttgg tcaggaagag agaggagtgt    6480
ctggatgcac tagagtccat catgacaacc aagtcagtga gtttcagacg tctcagtcat    6540
ttaagaaaac ttgtccctgg gtttggaaaa gcatatacca tattcaacaa gaccttgatg    6600
gaagccgatg ctcactacaa gtcagtcgag acttggaagg agatcctcc ttcaaagggg    6660
tgtttaagag ttgggggggag gtgtcatcct catgtgaacg gggtgttttt caatggtata    6720
atattaggac ctgacggcaa tgtcttaatc ccagagatgc aatcatccct cctccagcaa    6780
catatgagt tgttggaatc ctcggttatc ccccttgtgc accccctggc agacccgtct    6840
accgttttca aggacggtga cgaggctgag gattttgttg aagttcacct tccccgatgtg    6900
cacaatcagg tctcaggagt tgacttgggt ctcccgaact ggggaagta tgtattactg    6960
agtcaggggg ccctgactgc cttgatgttg ataatttttcc tgatgacatg ttgtagaaga    7020
gtcaatcgat cagaacctac gcaacacaat ctcagaggga cagggaggga ggtgtcagtc    7080
actccccaaa gcgggaagat catatcttca tgggaatcac acaagagtgg gggtgagacc    7140
agactgtaat taattaacgt cctttcaacg atccaagtcc atgaaaaaaa ctaacaccc    7200
tcccgtacct agcttataaa gtgctgggtc atctaagctt ttcagtcgag aaaaaaacat    7260
tagatcagaa gaacaactgg caacacttct caacctgaga cttacttcaa gatgctcgat    7320
cctggagagg tctatgatga cccctattgac ccaatcgagt tagaggctga acccagagga    7380
accccattg tccccaacat cttgaggaac tctgactaca atctcaactc tccttttgata    7440
gaagatcctg ctagactaat gttagaatgg ttaaaacag ggaatagacc ttatcggatg    7500
actctaacag acaattgctc caggtctttc agagttttga aagattattt caagaaggta    7560
gatttggtt ctctcaaggt gggcggaatg gctgcacagt caatgatttc tctctggtta    7620
tatggtgccc actctgaatc caacaggagc cggagatgta taacagactt ggcccatttc    7680
tattccaagt cgtcccccat agagaagctg ttgaatctca cgctaggaaa tagagggctg    7740
agaatccctc cagagggagt gttaagttgc ctggagggg ttgattatga taatgcattt    7800
ggaaggtatc ttgccaacac gtattcctct tacttgttct tccatgtaat caccttatac    7860
atgaacgccc tagactggga tgaagaaaag accatcctag cattatgaa agatttaacc    7920
tcagtggaca tcgggaagga cttggtaaag ttcaaagacc aaatatgggg actgctgatc    7980
gtgacaaagg actttgttta ctcccaaagt tccaattgtc ttttttgacag aaactacaca    8040
cttatgctaa aagatctttt cttgtctcgc ttcaactcct taatggtctt gctctctccc    8100
```

```
ccagagcccc gatactcaga tgacttgata tctcaactat gccagctgta cattgctggg   8160
gatcaagtct tgtctatgtg tggaaactcc ggctatgaag tcatcaaaat attggagcca   8220
tatgtcgtga atagtttagt ccagagagca gaaaagttta ggcctctcat tcattccttg   8280
ggagactttc ctgtatttat aaaagacaag gtaagtcaac ttgaagagac gttcggtccc   8340
tgtgcaagaa ggttctttag ggctctggat caattcgaca acatacatga cttggttttt   8400
gtgtttggct gttacaggca ttgggggcac ccatatatag attatcgaaa gggtctgtca   8460
aaactatatg atcaggttca ccttaaaaaa atgatagata agtcctacca ggagtgctta   8520
gcaagcgacc tagccaggag gatccttaga tggggttttg ataagtactc caagtggtat   8580
ctggattcaa gattcctagc ccgagaccac cccttgactc cttatatcaa aacccaaaca   8640
tggccaccca aacatattgt agacttggtg ggggatacat ggcacaagct cccgatcacg   8700
cagatctttg agattcctga atcaatggat ccgtcagaaa tattggatga caatcacat   8760
tctttcacca gaacgagact agcttcttgg ctgtcagaaa accgaggggg gcctgttcct   8820
agcgaaaaag ttattatcac ggcctgtct aagccgcctg tcaatcccg agagtttctg    8880
aggtctatag acctcggagg attgccagat gaagacttga taattggcct caagccaaag   8940
gaacgggaat tgaagattga aggtcgattc tttgctctaa tgtcatggaa tctaagattg   9000
tattttgtca tcactgaaaa actcttggcc aactacatct tgccactttt tgacgcgctg   9060
actatgcacg acaacctgaa caaggtgttt aaaaagctga tcgacagggt caccgggcaa   9120
gggcttttgg actattcaag ggtcacatat gcatttcacc tggactatga aaagtggaac   9180
aaccatcaaa gattagagtc aacagaggat gtatttttctg tcctagatca agtgtttgga   9240
ttgaagagag tgttttctag aacacacgag ttttttcaaa aggcctggat ctattattca   9300
gacagatcag acctcatcgg gttacgggag gatcaaatat actgcttaga tgcgtccaac   9360
ggcccaacct gttggaatgg ccaggatggc gggctagaaa gcttacggca gaagggctgg   9420
agtctagtca gcttattgat gatagataga gaatctcaaa tcaggaacac aagaaccaaa   9480
atactagctc aaggagacaa ccaggtttta tgtccgacat acatgttgtc gccagggcta   9540
tctcaagagg ggctcctcta tgaattggag agaatatcaa ggaatgcact ttcgatatac   9600
agagccgtcg aggaaggggc atctaagcta gggctgatca tcaagaaaga agagaccatg   9660
tgtagttatg acttcctcat ctatggaaaa acccctttgt ttagaggtaa catattggtg   9720
cctgagtcca aaagatgggc cagagtctct tgcgtctcta atgaccaaat agtcaacctc   9780
gccaatataa tgtcgacagt gtccaccaat gcgctaacag tggcacaaca ctctcaatct   9840
ttgatcaaac cgatgaggga ttttctgctc atgtcagtac aggcagtctt tcactacctg   9900
ctatttagcc caatcttaaa gggaagagtt tacaagattc tgagcgctga aggggagagc   9960
tttctcctag ccatgtcaag gataatctat ctagatcctt ctttgggagg gatatctgga  10020
atgtccctcg gaagattcca tatacgacag ttctcagacc ctgtctctga agggttatcc  10080
ttctggagag agatctggtt aagctcccaa gagtcctgga ttcacgcgtt gtgtcaagag 10140
gctgaaaacc cagatcttgg agagagaaca ctcgagagct tcactcgcct tctagaagat  10200
ccgaccacct taaatatcag aggaggggcc agtcctacca ttctactcaa ggatgcaatc  10260
agaaaggctt tatatgacga ggtggacaag gtggaaaatt cagagtttcg agaggcaatc  10320
ctgttgtcca agaccatag agataatttt atactcttct taatatcgt tgagcctctg  10380
tttcctcgat ttctcagtga gctattcagt tcgtcttttt tgggaatccc cagtcaatc  10440
attggattga tacaaaactc ccgaacgata agaaggcagt ttagaaagag tctctcaaaa  10500
actttagaag aatccttcta caactcagag atccacggga ttagtcggat gacccagaca  10560
cctcagaggg ttgggggggt gtggccttgc tcttcagaga gggcagatct acttaggagg  10620
atctcttggg gaagaaaagt ggtaggcacg acagttcctc acccttctga gatgttggga  10680
ttacttccca agtcctctat ttcttgcact tgtggagcaa caggaggagg caatcctaga  10740
gtttctgtat cagtactccc gtcctttgat cagtcatttt tttcacgagg cccccctaaag 10800
ggatacttgg gctcgtccac ctctatgtcg acccagctat tccatgcatg ggaaaaagtc  10860
actaatgttc atgtggtgaa gagagctcta tcgttaaaag aatctataaa ctggttcatt  10920
actagagatt ccaacttggc tcaagctcta attaggaaca ttatgtctct gacaggccct  10980
gatttccctc tagaggaggc ccctgtcttc aaaaggacgg ggtcagcctt gcataggttc  11040
aagtctgcca gatacagcga aggagggtat tcttctgtct gcccgaacct cctctctcat  11100
atttcgttta gtacagacac catgtctgat ttgacccaag acgggaagaa ctacgatttc  11160
atgttccagc cattgatgct ttatgcacag acatggacat cagagctggt acagagagac  11220
acaaggctaa gagactctac gttcattgg cacctccgat gcaacaggtg tgtgagaccc  11280
attgacgacg tgaccctgga gacctctcag atcttcgagt ttccggatgt gtcgaaaaga  11340
atatccagaa tggttctcgg ggctgtgcct cacttccaga ggcttcccga tatccgtctg  11400
agaccaggag attttgaatc tctaagcggt agagaaaagt ctcaccatat cggatcagct  11460
caggggctct tatactcaat cttagtggca attcacgact caggatacaa tgatggaacc  11520
atcttccctg tcaacatata cggcaaggtt tcccctagag actatttgag aggctcgca  11580
agggagtat tgataggatc ctcgatttgc ttcttgacaa gaatgacaaa tatcaatatt  11640
aatagacctc ttgaattggt ctcagggta atctcatata ttctcctgag gctagataac  11700
catccctcct tgtacataat gctcagagaa ccgtctctta gaggagagat attttctatc  11760
cctcagaaaa tccccgccgc ttatccaacc actatgaaag aaggcaacag atcaatcttg  11820
tgttatctcc aacatgtgct acgctatgag cgagagataa tcacgcgtc tccagagaat  11880
gactggctat ggatcttttc agactttaga atgccaaaa tgacgtacct atccctcatt  11940
acttaccagt ctcatcttct actccagagg gttgagagaa acctatctaa gagtatgaga  12000
gataacctgc gacaattgag ttctttgatg aggcaggtgc tgggcgggca cggagaagat  12060
accttagagt cagacgacaa cattcaacga ctgctaaaag actcttacg aaggacaaga  12120
tgggtggatc aagaggtgcg ccatgcagct agaaccatga ctggagatta cagccccac  12180
aagaaggtgt cccgtaaggt aggatgttca gatgtcct gctgctca acaggttgca  12240
gtctctacct cagcaaaccc ggcccctgtc tcggagcttg acataagggc cctctctaag  12300
aggttccaga acccttgat ctcgggcttg agagtggttc agtgggcaac cggtgctcat  12360
tataagctta agcctattct agatgatctc aatgttttcc catctctctg ccttgtagtt  12420
ggggacgggt caggggggat atcaagggca gtcctcaaca tgtttccaga tgccaagctt  12480
gtgttcaaca gtcttttaga ggtgaatgac ctgatggcct gggaaaccaa tccactgcct  12540
ccttcagcaa tcatgagggg aggaaatgat atcgtctcca gagtgataga tcttgactca  12600
atctgggaaa aaccgtccga cttgagaaac ttggcaacct ggaatactt ccagtcagtc  12660
caaaagcagg tcaacatgtc ctatgacctc attatttgcg atgcagaagt tactgacatt  12720
gcatctatca accggatcac cctgttaatg tccgattttt cattgtctat agatggacca  12780
ctctatttgg tcttcaaaac ttatgggact atgctagtaa atccaaacta caaggctatt  12840
```

```
caacacctgt caagagcgtt cccctcggtc acagggttta tcacccaagt aacttcgtct  12900
ttttcatctg agctctacct ccgattctcc aaacgaggga agtttttcag agatgctgag  12960
tacttgacct cttccaccct tcgagaaatg agccttgtgt tattcaattg tagcagcccc  13020
aagagtgaga tgcagagagc tcgttccttg aactatcagg atcttgtgag aggatttcct  13080
gaagaaatca tatcaaatcc ttacaatgag atgatcaag ctctgattga cagtgatgta  13140
gaatcttttc tagtccacaa gatggttgat gatcttgagt tacagagggg aactctgtct  13200
aaagtggcta tcattatagc catcatgata gtttttctcca acagagtctt caacgtttcc  13260
aaaccccta ctgacccctc gttctatcca ccgtctgatc ccaaaatcct gaggcacttc  13320
aacatatgtt gcagtactat gatgtatcta tctactgctt taggtgacgt ccctagcttc  13380
gcaagacttc acgacctgta taacagacct ataacttatt acttcagaaa gcaagtcatt  13440
cgagggaacg tttatctatc ttggagttgg tccaacgaca cctcagtgtt caaaagggta  13500
gcctgtaatt ctagcctgag tctgtcatct cactggatca ggttgattta caagatagtg  13560
aagactacca gactcgttgg cagcatcaag gatctatcca gagaagtgga aagacacctt  13620
cataggtaca acaggtggat caccctagag gatatcagat ctagatcatc cctactagac  13680
tacagttgcc tgtgaaccgg atactcctgg aagcctgccc atgctaagac tcttgtgtga  13740
tgtatcttga aaaaaacaag atcctaaatc tgaacctttg gttgtttgat tgttttttctc  13800
attttttgttg tttatttgtt aagcgt                                      13826

SEQ ID NO: 12           moltype = DNA  length = 13926
FEATURE                 Location/Qualifiers
misc_feature            1..13926
                        note = RABV vector: Coravax V4-China (S1-RABVG-T2A-P)
source                  1..13926
                        mol_type = other DNA
                        organism = synthetic construct
SEQUENCE: 12
acgcttaaca accagatcaa agaaaaaaca gacattgtca attgcaaagc aaaaatgtaa  60
caccccctaca atggatgccg acaagattgt attcaaagtc aataatcagg tggtctcttt  120
gaagcctgag attatcgtgg atcaatatga gtacaagtac cctgccatca agatttgaa  180
aaagcccctgt ataaccctag gaaaggctcc cgatttaaat aaagcataca agtcagtttt  240
gtcaggcatg agcgccgcca aacttaatcc tgacgatgta tgttcctatt tggcagcggc  300
aatgcagttt tttgaggga catgtccgga agactggacc agctatgaag ttgtgattgc  360
acgaaaagga gataagatca ccccaggttc tctggtggag ataaaacgta ctgatgtaga  420
agggaattgg gctctgacag gaggcatgga actgacaaga gaccccactg tccctgagca  480
tgcgtcctta gtcggtcttc tcttgagtct gtataggttg agcaaaatat ccgggcaaaa  540
cactggtaac tataagacaa acattgcaga caggatagag cagattttttg agacagcccc  600
ttttgttaaa atcgtggaac accatactct aatgacaact cacaaaatgt gtgctaattg  660
gagtactaca ccaaacttca gatttttggc cggaaccctat gacatgtttt tctcccggat  720
tgagcatcta tattcagcaa tcagagtggg cacagttgtc actgcttatg aagactgttc  780
aggactggta tcatttactg ggttcataaa acaaatcaat ctcaccgcta gagaggcaat  840
actatatttc ttccacaaga actttgagga agagataaga agaatgtttg agccagggca  900
ggagacagct gttcctcact cttatttcat ccacttccgt tcactaggct tgagtgggaa  960
atctccttat tcatcaaatg ctgttggtca cgtgttcaat ctcatccact ttgtaggatg  1020
ctatatgggt caagtcagat ccctaaatgc aacggttatt gctgcatgtg ctcctcatga  1080
aatgtctgtt ctagggggct atctgggaga ggaattcttc gggaaaggga catttgaaag  1140
aagattcttc agagatgaga agaacttcca agaatacgag cgcggctgaac tgacaaagac  1200
tgacgtagca ctggcagatg atggaactgt caactctgac gacgaggact actttttcagg  1260
tgaaaccaga agtccggagg ctgtttatac tcgaatcatg atgaatggag tcgactaaa  1320
gagatctcac atacggagat atgtctcagt cagttccaat catcaagccc gtccaaactc  1380
attcgccgag tttctaaaca agacatattc gagtgactca taacatgaaa aaaactaaca  1440
cccctccccgt acggccacca tgttcgtgtt tctggtgctg ctgcctctgg tgagctccca  1500
gtgcgtgaac ctgaccacaa ggacccagct gccccctgcc tataccaatt ccttcacacg  1560
gggcgtgtac tatcccgaca aggtgttccg gagcagcgtg ctgcactcca cacaggatct  1620
gtttctgcct ttcttttcta acgtgacctg gttccacgcc atcacgtga gcggcaccaa  1680
tggcacaaag cggttcgaca atccgtatgc gccctttaac gatggcgtgt acttcgcctc  1740
caccgagaag tctaacatca tcagaggctg gatctttggc accacactgg acagcaagac  1800
acagtccctg ctgatcgtga caatgccac caacgtggtc atcaaggtgt gcgagttcca  1860
gttttgtaat gatccattcc tgggcgtgta ctatcacaag aacaataagt cttggatgga  1920
gagcgagttt cgcgtgtatt cctctgccaa caattgcaca tttgagtacg tgtcccagcc  1980
cttcctgatg gacctggagg gcaagcaggg caatttcaag aacctgaggg agttcgtgtt  2040
taagaatatc gatggctact caaaatcta ctccaagcac accccaatca acctggtgcg  2100
cgacctgcca cagggcttct ctgccctgga gccactggtg gatctgccca tcggcatcaa  2160
catcacccgg tttcagacac tgctggccct gcacagaagc tacctgacac aggcgacag  2220
ctcctctgga tggaccgcag gagcagcagc tactatatg ggctatctgc agccagagc  2280
cttcctgctg aagtacaacg agaatggcac catcacagac gccgtggatt gcgccctgga  2340
tcccctgtct gagaccaagt gtacactgaa gagcttacc gtgagaagg gcatctatca  2400
gacaagcaat ttcagggtgc agcctaccga gtccatcgtg cgctttccca atatcacaaa  2460
cctgtgccct tttggcgagg tgttcaacgc aacccgcttc gccagcgtgt acgcctggaa  2520
taggaagcgc atctccaact gcgtcgccga ctattctgtg ctgtacaaca gcgcctcctt  2580
ctctaccttt aagtgctatg gcgtgagccc cacaaagctg aatgacctgt gctttaccaa  2640
cgtgtacgcc gattccttcg tgatcagggg cgacgaggtg cgccagatcg caccaggaca  2700
gacaggcaag atcgcagact acaattataa gctgcctgac gatttccacg gctgcgtgat  2760
cgcctggaac tctaacaatc tggatagcaa agtgggcggc aactacaatt atctgtaccg  2820
gctgtttaga aagtcaatc tgaagccatt cgagagggac atctccacag aaatctacca  2880
ggccggctct accccctgca atggcgtgga gggctttaac tgttatttcc ctctgcagag  2940
ctacggcttc cagccaacaa acggcgtggg ctatcagccc taccgcgtgg tggtgctgtc  3000
ttttgagctg ctgcacgcac ctgcaacagt gtgcggacca aagaagagca ccaatctggt  3060
gaagaacaag tgcgtgaact tcaacttcaa cggactgacc ggaacaggcg tgctgaccga  3120
gtccaacaag aagttcctgc cttttcagca gttcggcagg gacatcgcag ataccacaga  3180
```

```
cgccgtgcgc gaccctcaga ccctggagat cctggacatc acaccatgct ccttcggcgg   3240
cgtgtctgtg atcacaccag gcaccaatac aagcaaccag gtggccgtgc tgtatcagga   3300
cgtgaattgt accgaggtgc cagtggcaat ccacgcagat cagctgaccc ctacatggcg   3360
ggtgtactct accggcagca acgtgttcca gacaagagcc ggatgcctga tcggagcaga   3420
gcacgtgaac aatagctatg agtgcgacat ccctatcgc gccggcatct gtgcctccta   3480
ccagacccag acaaactccc caaggtctgt gggagatgag gccgaagact ttgtggaagt   3540
ccacctgcct gatgtgcata accaggtgtc tggcgtcgac ctgggactgc caaattgggg   3600
caagtacgtg ctgctgagtg ctggagcact gactgccctg atgctgatca ttttcctgat   3660
gacctgctgt cggcgcgtga acagaagtga gcccactcag cacaatctgc gaggaaccgg   3720
gagagaagtg tcagtcacac ctcagagcgg gaaaatcatt agtagttggg aatcacataa   3780
aagcggggc gagaccaggc tgggatccgg ctccggcgag ggcaggggaa gtctactaac   3840
atgcggggac gtgaggaaaa atcccggccc catgagcaag atctttgtca atcctagtgc   3900
tattagagcc ggtctggccg atcttgagat ggctgaagaa actgttgatc tgatcaatag   3960
aaatatcgaa gacaatcagg ctcatctcca agggaaccc atagaggtgg acaatctccc   4020
tgaggatatg gggcgacttc acctggatga tggaaaatcg cccaaccatg gtgagatagc   4080
caaggtggga gaaggcaagt atcgagagga cttcagatg gatgaaggag aggatcctag   4140
cttcctgttc cagtcatacc tggaaaatgt tggagtccaa atagtcagac aaatgaggtc   4200
aggagagaga tttctcaaga tatggtcaca gaccgtagaa gagattatat cctatgtcgc   4260
ggtcaacttt cccaaccctc caggaaagtc ttcagaggat aaatcaaccc agactactgg   4320
ccgagagctc aagaaggaga caacacccac tccttctcag agagaaagcc aatcatcgaa   4380
agccaggatg gcggctcaaa ttgcttctgg ccctccagcc cttgaatggt cggctaccaa   4440
tgaagaggat gatctatcag tggaggctga gatcgctcac cagattgcag aaagtttctc   4500
caaaaaaatat aagtttccct ctcgatcctc agggatactc ttgtataatt ttgagcaatt   4560
gaaaatgaac cttgatgata tagttaaaga ggcaaaaaat gtaccaggtg tgacccgttt   4620
agcccatgac gggtccaaac tcccctaag atgtgtactg gatggtcg ctttggccaa   4680
ctctaagaaa ttccagttgt tagtgaatc cgacaagctg agtaaaatca tgcaagatga   4740
cttgaatcgc tatacatctt gctaaccgaa cctctcccct cagtccctct agacaataaa   4800
atccgagatg tcccaaagtc aacatgaaaa aaacaggcaa caccactgat aaaatgaacc   4860
tcctacgtaa gatagtgaaa aaccgcaggg acgaggcac tcaaaaatcc tctcccgcgt   4920
cagccectct ggatgacgat gacttgtggc ttccaccccc tgaatacgtc ccgctgaaag   4980
aacttacagg caagaagaac atgaggaact tttgtatcaa cggaagggtt aaagtgtgta   5040
gcccgaatgg ttactcgttc aggatcctgc ggcacattct gaaatcattc gacgagatat   5100
attctgggaa tcataggatg atcggtttag tcaaagtggt tattggactg gctttgtcag   5160
gatctccagt ccctgagggc ctgaactggg tatacaaatt gaggagaacc tttatcttcc   5220
agtgggactg ttccaggggc cctcttgaag gggaggagtt ggaatactct caggagatca   5280
cttgggatga tgatactgag ttcgtcggat tgcaataag agtgattgca aaacagtgtc   5340
atatccaggg cagagtctgg tgtatcaaca tgaaccccgag agcatgtcaa ctatggtctg   5400
acatgtctct tcagacacaa aggtccgaag aggacaaaga ttcctctctg cttctagaat   5460
aatcagatta tatcccgcaa atttatcact tgtttacctc tggaggagag aacatatggg   5520
ctcaactcca acccttggga gcaatataac aaaaaacatg ttatggtgcc attaaaccgc   5580
tgcatttcat caaagtcaag ttgattacct ttacattttg atcctcttgg atgtgaaaaa   5640
aactattaac atccctcaaa agaccccggg aaagatggtt cctcaggctc tcctgttttgt   5700
accccttctg gttttttccat tgtgttttgg gaaattccat atttacacga taccagacaa   5760
gcttggtccc tggagtccga ttgacataca tcacctcagc tgcccaaaca atttggtagt   5820
ggaggacgaa ggatgcacca acctgtcagg gttctcctac atggaactta agttggata   5880
catcttagcc ataaaagtga acgggttcac ttgcacaggc gttgtgacgg aggctgaaac   5940
ctacactaca ttcgttggtt atgtcacaac cacgttcaaa agaaagcatt tccgccaat   6000
accagatgca tgtagagccg cgtacaactg gaagatggcc ggtgacccca gatatgaaga   6060
gtctctacac aatccgtacc ctgactaccg ctggcttcga actgtaaaaa ccaccaagga   6120
gtctctcgtt atcatactc caagtgtggc agatttggac ccatatgaca gatcccttca   6180
ctcgagggtc ttccctagcg ggaagtgctc aggagtagcg gtgtcttcta cctactgctc   6240
cactaaccac gattacacca tttggaatgcc cgagaatccg agactagga tgtcttgtga   6300
cattttacc aatagtagag ggaagagagc atccaaaggg agtgagactt gcggcttgtg   6360
agatgaaaga ggcctatata agtctttaaa aggagcatgc aaactcaagt tatgtggagt   6420
tctaggactt agacttatgg atggaacatg ggtctcgatg caaacatcaa atgaaaccaa   6480
atggtgccct cccgataagt tggtgaacct gcacgacttt cgctcagacg aaattgagca   6540
ccttgttgta gaggagttgg tcaggaagag aggagtgt ctggatgcac tagagtccat   6600
catgacaacc aagtcagtga gtttcagacg tctcagtcat ttaagaaaac ttgtccctgg   6660
gtttggaaaa gcatatacca tattcaacaa gacctgatg gaagccgatg ctcactacaa   6720
gtcagtcgag acttgaatg agatcctccc ttcaaaaggg tgtttaagag ttggggggag   6780
gtgtcatcct catgtgaacg gggtgttttt caatggtata atattaggac ctgacggcaa   6840
tgtcttaatc ccagagatgc aatcatccct cctccagcaa catatggagt tgttggaatc   6900
ctcggttatc cccccttgtgc acccctggc agaccgtct accgttttca aggacggtga   6960
cgaggctgag gatttttgtga aagttcaccct tcccgatgtg cacaatcagg tctcaggagt   7020
tgacttgggt ctcccgaact gggggaagta tgtattactg agtgcagggg ccctgactgc   7080
cttgatgttg ataattttcc tgatgacatg ttgtagaaga gtcaatcgat cagaacctac   7140
gcaacacaat ctcagaggga cagggaggga ggtgtcagtc actccccaaa gcggaagat   7200
catatcttca tgggaatcac acaagagtgg gggtgagacc agactgtaat taattaacgt   7260
cctttcaacg atccaagtcc atgaaaaaa ctaacacccc tcccgtacct agcttataaa   7320
gtgctgggtc atctaagctt ttcagtcgag aaaaaaacat tagatcagaa gaacaactgg   7380
caacacttct caacctgaga cttacttcaa gatgctcgat cctggagagg tctatgatga   7440
ccctattgac ccaatcgagt tagaggctga acccagagga acccccattg tccccaacat   7500
cttgaggaac tctgactaca atctcaactc cctttgata agatcctg ctagactaat   7560
gttagaatgt ttaaaaacag ggaatagacc ttatcggatg actctaacag acaattgctc   7620
caggtctttc agagttttga aagattattt caagaaggta gatttgggtt ctctcaaggt   7680
gggcggaatg gctgcacagt caatgattc tctctggtta tatggtgccc actctgaatc   7740
caacaggagc cggagatgta taacagactt ggcccatttc tattccaagt cgtccccat   7800
agagaagctg ttgaatctca cgctaggaaa tagagggctg agaatccccc cagagggagt   7860
gttaagttgc cttgagaggg ttgattatga taatgcattt ggaaggtatc ttgccaacac   7920
```

```
gtattcctct tacttgttct tccatgtaat caccttatac atgaacgccc tagactggga   7980
tgaagaaaag accatcctag cattatggaa agatttaacc tcagtggaca tcggaagga    8040
cttggtaaag ttcaaagacc aaatatgggg actgctgatc gtgacaaagg actttgttta   8100
ctcccaaagt tccaattgtc tttttgacag aaactacaca cttatgctaa aagatctttt   8160
cttgtctcgc ttcaactcct taatggtctt gctctctccc ccagagcccc gatactcaga   8220
tgacttgata tctcaactat gccagctgta cattgctggg gatcaagtct tgtctatgtg   8280
tggaaactcc ggctatgaag tcatcaaaat attggagcca tatgtcgtga atagtttagt   8340
ccagagagca gaaaagttta ggcctctcat tcattccttg ggagactttc ctgtatttat   8400
aaaagacaag gtaagtcaac ttgaagagac gttcggtccc tgtgcaagaa ggttctttag   8460
ggctctggat caattcgaca acatacatga cttggttttt gtgtttggct gttacaggca   8520
ttgggggcac ccatatatag attatcgaaa gggtctgtca aaactatatg atcaggttca   8580
ccttaaaaaa atgatagata agtcctacca ggagtgctta gcaagcgacc tagccaggag   8640
gatccttaga tggggttttg ataagtactc caagtgtat ctggattcaa gattcctagc    8700
ccgagaccac cccttgactc cttatatcaa aacccaaaca tggccaccca aacatatgt    8760
agacttggtg ggggatacat ggcacaagct cccgatcacg cagatctttg agattcctag   8820
atcaatggat ccgtcagaaa tattggatga caaatcacat tctttcacca gaacgagact   8880
agcttcttgg ctgtcagaaa accgaggggg gcctgttcct agcgaaaaag ttattatcac   8940
ggccctgtct aagccgcctg tcaatccccg agagttttctg aggtctatag acctcggagg  9000
attgccagat gaagacttga taattggcct caagccaaag gaacgggaat tgaagattga   9060
aggtcgattc tttgctctaa tgtcatggaa tctaagattg tattttgtca tcactgaaaa   9120
actcttggcc aactacatct tgccactttt tgacgcgctg actatgacag acaacctgaa   9180
caaggtgttt aaaaagctga tcgacaggtt caccgggcaa gggcttttgg actattcaag   9240
ggtcacatat gcatttcacc tggactatga aaagtggaac aaccatcaaa gattagagtc   9300
aacagaggat gtattttctg tcctagatca agtgttgga ttgaagagag tgttttctag    9360
aacacacgag ttttttcaaa aggcctggat ctattattca gacagatcag acctcatcgg   9420
gttacgggag gatcaaatat actgcttaga tgcgtccaac ggcccaacct gttggaatgg   9480
ccaggatggc gggctagaag gcttacggca gaagggctgg agtctagtca gcttattgat   9540
gatagataga gaatctcaaa tcaggaacac aagaaccaaa atactagctc aaggagacaa   9600
ccaggttta tgtccgacat acatgttgtc gccagggcta tctcaagagg ggctcctcta    9660
tgaattggag agaatatcaa ggaatgcact ttcgatatac agagccgtcg aggaagggc    9720
atctaagcta gggctgatca tcaagaaaga agagaccatg tgtagttatg acttcctcat   9780
ctatggaaaa acccctttgt ttagaggtaa catattggtg cctgagtcca aaagatgggc   9840
cagagtctct tgcgtctcta atgaccaaat agtcaacctc gccaatataa tgtcgacagt   9900
gtccaccaat gcgctaacag tggcacaca ctctcaatct ttgatcaaac cgatagaggga   9960
ttttctgctc atgtcagtac aggcagtctt tcactacctg ctatttagcc caatcttaaa   10020
gggaagagtt tacaagattc tgagcgctga aggggagagc tttctcctag ccatgtcaag   10080
gataatctat ctagatcctt ctttgggagg gatatctgga atgtccctcg gaagattcca   10140
tatacgacag ttctcagacc ctgtctctga agggttatcc ttctggagag agatctggtt   10200
aagctcccaa gagtcctgga ttcacgcgtt gtgtcaagag gctgaaaacc cagatcttgg   10260
agagagaaca ctcgagagct tcactcgcct tctagaagat ccgaccacct taaatatcag   10320
aggagggcc agtcctacca ttctactcaa ggatgcaatc agaaaggctt tatatgacga    10380
ggtggacaag gtggaaaatt cagagtttcg agaggcaatc ctgttgtcca agacccatag   10440
agataaatttt atactcttct taatatctgt tgagcctcgt tttcctcgat ttctcagtga   10500
gctattcagt tcgtctttttt tgggaatccc cgagtcaatc attggattga tacaaaactc   10560
ccgaacgata agaaggcagt ttagaaagag tctctcaaaa actttagaag aatccttcta   10620
caactcagag atccacggga ttagtcggat gacccagaca cctcagaggg ttgggggggt   10680
gtggccttgc tcttcagaga gggcagatct acttagggag atctcttggg gaagaaagt    10740
ggtaggcacg acagttcctc acccttctga gatgttggga ttacttccca agtcctctat   10800
ttcttgcact tgtggagcaa caggaggagg caatcctaga gttctgtat cagtactccc    10860
gtcctttgat cagtcatttt tttcacgagg cccctaaag ggatacttgg gctcgtccac    10920
ctctatgtcg acccagctat tccatgcatg ggaaaagtc actaatgttc atgtggtgaa   10980
gagagctcta tcgttaaaag aatctataaa ctggttcatt actagagatt ccaacttggc   11040
tcaagctcta attaggaaca ttatgtctct gacaggccct gatttccctc tagaggaggc   11100
ccctgtcttc aaaaggacgg ggtcagcctt gcataggttc aagtctgcca gatacagcga   11160
aggagggtat tcttctgtct gcccgaacct cctctctcat atttctgtta gtacagacac   11220
catgtctgat ttgacccaag acgggaagaa ctacgatttc atgttccagc cattgatgct   11280
ttatgcacag acatggacat cagagctggt acagagagac acaaggctaa gagactctac   11340
gtttcattgg caacctcgat gcaacaggtg tgtgagaccc attgacgacg tgaccctgga   11400
gacctctcag atcttcgagt ttccggatgt gtcgaaaaga atatccagaa tggtttctgg   11460
ggctgtgcct cacttccaga ggcttcccga tatccgtctg agaccaggag attttgaatc   11520
tctaagcggt agagaaaagt ctcaccatat cggatcagct caggggtctc tatactcaat   11580
cttagtggca attcacgact caggatacaa tgatggaacc atcttccctg tcaacatata   11640
cggcaaggtt tcccctagag actatttgag agggctcgca aggggagtat tgataggatc   11700
ctcgatttgc ttcttgacaa gaatgacaaa tatcaatatt aatagacctc ttgaattggt   11760
ctcaggggta atctcatata ttctcctgag gctagataac catccctcct tgtacataat   11820
gctcagagaa ccgtctctta gaggagagat attttctatc cctcagaaaa tccccgccgc   11880
ttatccaacc actatgaaag aaggcaacag atcaatcttg tgttatctcc aacatgtgct   11940
acgctatgag cgagagataa tcacggcgtc tccagagaat gactggctag gatcttttc    12000
agactttaga agtgccaaaa tcaccgtacct acttaccagt ctcatcttct   12060
actccagagg gttgagagaa acctatctaa gagtatgaga gataacctgc gacaattgag   12120
ttctttgatg aggcaggtgc tggcgggca cggagaagat accttagagt cagacgacaa    12180
cattcaacga ctgctaaaag actctttacg aggacaaga tgggtggatc aagaggtgcg    12240
ccatgcagct agaaccatga ctggagatta cagccccaac aagaaggtgt cccgtaaggt   12300
aggatgttca gaatgggtct gctctgctca acaggttgca gtctctacct cagcaaaccc   12360
ggccctgtc tcggagcttg acataagggc cctctctaag aggttccaga acctttgat    12420
ctcgggcttg agagtggttc agtgggcaac cggtgctcat tataagctta agcctattct   12480
agatgatctc aatgtttttcc catctctctg ccttgtagtt ggggacgggt caggggggat   12540
atcaaggca gtcctcaaca tgtttccaga tgccaagctt gtgttcaaca gtcttttaga   12600
ggtgaatgac ctgatggctt ccggaacaca tccactgcct ccttcagcaa tcatgagggg   12660
```

```
aggaaatgat atcgtctcca gagtgataga tcttgactca atctgggaaa aaccgtccga 12720
cttgagaaac ttggcaacct ggaaatactt ccagtcagtc caaaagcagg tcaacatgtc 12780
ctatgacctc attatttgcg atgcagaagt tactgacatt gcatctatca accggatcac 12840
cctgttaatg tccgattttg cattgtctat agatggacca ctctatttgg tcttcaaaac 12900
ttatgggact atgctagtaa atccaaacta caaggctatt caacacctgt caagagcgtt 12960
cccctcggtc acagggttta tcacccaagt aacttcgtct ttttcatctg agctctacct 13020
ccgattctcc aaacgaggga agttttcag agatgctgag tacttgacct cttccaccct 13080
tcgagaaatg agccttgtgt tattcaattg tagcagcccc aagagtgaga tgcagagagc 13140
tcgttccttg aactatcagg atcttgtgag aggatttcct gaagaaatca tatcaaatcc 13200
ttacaatgag atgatcataa ctctgattga cagtgatgta gaatcttttc tagtccacaa 13260
gatggttgat gatcttgagt tacagagggg aactctgtct aaagtggcta tcattatagc 13320
catcatgata gttttctcca acagagtctt caacgtttcc aaaccctaa ctgacccctc 13380
gttctatcca ccgtctgatc ccaaaatcct gaggcacttc aacatatgtt gcagtactat 13440
gatgtatcta tctactgctt taggtgacgt ccctagcttc gcaagacttc acgacctgta 13500
taacagacct ataacttatt acttcagaaa gcaagtcatt cgagggaacg tttatctatc 13560
ttggagttgg tccaacgaca cctcagtgtt caaaagggta gcctgtaatt ctagcctgag 13620
tctgtcatct cactggatca ggttgattta caagatagtg aagactacca gactcgttgg 13680
cagcatcaag gatctatcca gagaagtgga aagcaccctt cataggtaca acaggtggat 13740
caccctagag gatatcagat ctagatcatc cctactagac tacagttgcc tgtgaaccga 13800
atactcctgg aagcctgccc atgctaagac tcttgtgtga tgtatcttga aaaaaacaag 13860
atcctaaatc tgaacctttg gttgtttgat tgttttctc attttgttg ttatttgtt 13920
aagcgt                                                          13926
```

SEQ ID NO: 13        moltype = DNA   length = 13977
FEATURE              Location/Qualifiers
misc_feature         1..13977
                     note = RABV vector: Coravax V4 South Africa
source               1..13977
                     mol_type = other DNA
                     organism = synthetic construct
SEQUENCE: 13

```
acgcttaaca accagatcaa agaaaaaaca gacattgtca attgcaaagc aaaaatgtaa   60
cacccctaca atggatgccg acaagattgt attcaaagtc aataatcagg tggtctcttt  120
gaagcctgag attatcgtgg atcaaatatga gtacaagtac tgtgccatca aagatttgaa  180
aaagccctgt ataacctag gaaaggctcc cgatttaaat aaagcataca agtcagtttt  240
gtcaggcatg agcgccgcca aacttaatcc tgacgatgta tgttcctatt ggcagcggc   300
aatgcagttt tttgagggga catgtccgga agactggacc agctatgaa ttgtgattgc   360
acgaaaagga gataagatca ccccaggttc tctggtggag ataaaacgta ctgatgtaga   420
agggaattgg gctctgacag gaggcatgga actgacaaga gaccccactg tccctgacaa   480
tgcgtcctta gtcggtcttc tcttgagtct gtataggttg agcaaaatat ccgggcaaaa   540
cactggtaac tataagacaa acattgcaga caggatagaca cagatttttg agacagcccc   600
ttttgttaaa atcgtggaac accatactct aatgacaact cacaaaatgt gtgctaattg   660
gagtactata ccaaacttca gattttttggc cggaacctat gacatgtttt tctcccggat   720
tgagcatcta tattcagcaa tcagagtggg cacagttgtc actgcttatg aagactgttc   780
aggactggta tcatttactg ggttcataaa acaaatcaat ctcaccgcta gagaggcaat   840
actatatttc ttccacaaga actttgagga agagataaga agaatgtttg agccagggca   900
ggagacagct gttcctcact ctttattcat ccacttccgtg tcactaggct tgagtgggaa   960
atctccttat tcatcaaatg ctgttggtca cgtgttcaat ctcattcact tgtaggatg  1020
ctatatgggt caagtcagat ccctaaatgc aacggttatt gctgcatgtg ctcctcatga  1080
aatgtctgtt ctagggggct atctggagaga ggaattcttc gggaagggca catttgaaag  1140
aagttcttc agagatgaga aagaacttca agaatacgag cggcctgaac tgacaaagac  1200
tgacgtagca ctggcagatg atggaactgt caactctgac gacgaggact acttttcagg  1260
tgaaaccaga agtccggagg ctgttttatac tcgaatcatg atgaatggag tcgactaaa  1320
gagatctcac atacggagat atgtctcagt cagttccaat catcaagccc gtccaaactc  1380
attcgccgag ttttcaaaca agacatattc gagtgactca taacatgaaa aaaactaaca  1440
cccctcccgt acggccacca tgttcgtgtt tctggtgctg ctgcctctgg tgagctccca  1500
gtgcgtgaac ttcaccacaa ggaccagct gccccctgcc tataccaatt ccttcacacg  1560
gggcgtgtac tatcccgaca aggtgttccg gagcagcgtg ctgcactcca cacaggatct  1620
gtttctgcct ttcttttcta acgtgacctg gttccacgcc atcacgtga gcggcaccaa  1680
tggcacaaag cggttcgcca atcagtgct gccctttaac gatggcgtgt acttcgcctc  1740
caccgagaag tctaacatca tcagaggctg gatcttggc accacactgg acagcaagac  1800
acagtccctg ctgatcgtga caatgccac caacgtggtc atcaaggtgt gcgagttcca  1860
gttttgtaat gatccattcc tgggcgtgta ctatcacaag aacaataagt cttggatgga  1920
gagcgagttt cgcgtgtatt cctctgccaa caattgcaca tttgagtacg tgtcccagcc  1980
cttcctgatg gacctggagg gcaagcaggg caatttcaag aacctgaggg agttcgtgtt  2040
taagaatatc gatggctact tcaaaatcta ctccaagcac accccaatca acctggtgcg  2100
cggcctgcca cagggcttct ctgccctgga gccactggtg gatctgccca tcggcatcaa  2160
catcacccgg tttcagacac tgctggccct gcacagaagc tacctgacac caggcgacag  2220
ctcctctgga tggaccgcag gagcagcagc ctactatgtg ggctatctgc agcccaggac  2280
cttcctgctg aagtacaacg agaatggcac catcacagac gccgtggatt gcgccctgga  2340
tccccctgtct gagaccaagt gtacactgaa gagcttacc gtgagaagg catctatca  2400
gacaagcaat ttcagggtgc agcctaccga gtccatcgtg cgctttccca atatcacaaa  2460
cctgtgccct tttggcgagg tgttcaacgc aacccgcttc gccagcgtgt acgcctggaa  2520
taggaagcga atctccaact gctgtcggcga ctattctgg ctgtacaaca aggtgggat  2580
ctctacctt aagtgctatg gcgtgagccc cacaaagctg aatgacctgt gctttaccaa  2640
cgtgtacgcc gattccttcg tgatcagggg cgacgaggtg cgccagatcg caccaggaca  2700
gacaggcaat atcgcagact acaattataa gctgcctgac gatttcaccg gctgcgtgat  2760
cgcctggaac tctaacaatc tggatagcaa agtgggcggc aactacaatt atctgtaccg  2820
gctgtttaga aagtctaatc tgaagccatt cgagagggac atctccacag aaatctacca  2880
```

```
ggccggctct accccctgca atggcgtgaa gggctttaac tgttatttcc ctctgcagag  2940
ctacggcttc cagccaacat atggcgtggg ctatcagccc taccgcgtgg tggtgctgtc  3000
ttttgagctg ctgcacgcac ctgcaacagt gtgcggacca agaagagca  ccaatctggt  3060
gaagaacaag tgcgtgaact tcaacttcaa cggactgacc ggaacaggcg tgctgaccga  3120
gtccaacaag aagttcctgc cttttcagca gttcggcagg gacatcgcag ataccacaga  3180
cgccgtgcgc gaccctcaga ccctggagat cctggacatc acaccatgct ccttcggcgg  3240
cgtgtctgtg atcacaccag gcaccaatac aagcaaccag gtggccgtgc tgtatcaggg  3300
cgtgaattgt accgaggtgc cagtggcaat ccacgcagat cagctgaccc ctacatggcg  3360
ggtgtactct accggcagca acgtgttcca gacaagagcc ggatgcctga tcggagcaga  3420
gcacgtgaac aatagctatg agtgcgacat ccctatcggc gccggcatct gtgcctccta  3480
ccagacccag acaaactccc cagaatcaag cgtgattcct ctggtccatc cactggcaga  3540
tccctccaca gtgttcaaag acggagatga ggccgaagac tttgtggaag tccacctgcc  3600
tgatgtgcat aaccaggtgt ctggcgtcga cctgggactg ccaaattggg gcaagtacgt  3660
gctgctgagt gctggagcac tgactgccct gatgctgatc attttcctga tgacctgctg  3720
tcggcgcgtg aacagaagtg agcccactca gcacaatctg cgaggaaccg ggagagaagt  3780
gtcagtcaca cctcagagcg ggaaaatcat tagtagttgg gaatcacata aaagcggggg  3840
cgagaccagg ctgggatccg gctccggcga gggcagggga agtctactaa catgcgggga  3900
cgtggaggaa aatcccggcc ccatgagcaa gatctttgtc aatcctagtg ctattagagc  3960
cggtctggcc gatcttgaga tggctgaaga aactgttgat ctgatcaata gaaatatcga  4020
agacaatcag gctcatctcc aaggggaacc catagaggtg gacaatctcc ctgaggatat  4080
ggggcgactt cacctggatg atggaaaatc gcccaaccat ggtgagatag ccaaggtggg  4140
agaaggcaag tatcgaggag actttcagat ggatgaagga gaggatccta gcttcctgtt  4200
ccagtcatac ctggaaaatg ttggagtcca aatagtcaga caaatgaggt caggagagag  4260
atttctcaag atatggtcac agaccgtaga agagattata tcctatgtcg cggtcaactt  4320
tcccaacccc ccaggaaagt cttcagagga taaatcaacc cagactactg gccgagagct  4380
caagaaggag acaacaccca ctccttctca gagagaaagc caatcatcga aagccaggat  4440
ggcggctcaa attgcttctg gccctccagc ccttgaatgg tcggctacca atgaagagga  4500
tgatctatca gtggaggctg agatcgctca ccagattgca gaaagtttct ccaaaaaata  4560
taagtttccc tctcgatcct cagggatact cttgtataat tttgagcaat gaaaatgaa   4620
ccttgatgat atagttaaag aggcaaaaaa tgtaccaggt gtgacccgtt tagcccatga  4680
cgggtccaaa ctcccctaa  gatgtgtact gggatgggtc gctttggcca actctaagaa   4740
attccagttg ttagtcgaat ccgacaagct gagtaaaatc atgcaagatg acttgaatcg  4800
ctatacatct tgctaaccga acctctcccc tcagtccctc tagacaataa aatccgagat  4860
gtcccaaagt caacatgaaa aaaacaggca acaccactga taaaatgaac ctcctacgta  4920
agatagtgaa aaaccgcagg gacgaggaca ctcaaaaatc ctctcccgcg tcagccctc   4980
tggatgacga tgacttgtgg cttccacccc ctgaatacgt cccgctgaaa gaacttacag  5040
gcaagaagaa catgaggaac ttttgtatca acggaagggt taaagtgtgt agcccgaatg  5100
gttactcgtt caggatcctg cggcacattc tgaaatcatt cgacgagata tattctggga  5160
atcatagat gatcgggtta gtcaaagtgg ttattggact ggctttgtca ggatctccga  5220
tccctgaggg cctgaactgg gtatacaaat tgaggagaac cttatcttc  cagtgggctg  5280
attccagggg ccctcttgaa ggggaggagt tggaatactc caggagatc acttgggatg  5340
atgatactga gttcgtcgga ttgcaaataa gagtgattgc aaaacagtgt catatccagg  5400
gcagagtctg gtgtatcaac atgaacccga gagcatgtca actatggtct gacatgtctc  5460
ttcagacaca aagtccgaa  gaggacaaag attcctctct gcttctagaa taatcagatt  5520
atatcccgca aatttatcac ttgtttaccct ctggaggaga gaacatatgg gctcaactcc  5580
aacccttggg agcaatataa caaaaaacat gttatggtgc cattaaaccg ctgcatttca  5640
tcaaagtcaa gttgattacc tttacatttt gatcctcttg gatgtgaaaa aaactattaa  5700
catccctcaa aagaccccgg gaaagatggt tcctcaggct ctcctgtttg tacccttct   5760
ggtttttcca ttgtgttttg ggaaattccc tatttacacg ataccagaca agcttggtcc  5820
ctggagtccg attgacatac atcacctcag ctgcccaaac aatttggtag tggaggacga  5880
aggatgcacc aacctgtcag ggttctccta catggaactt aaagttggat acatcttagc  5940
cataaaagtg aacgggttca cttgcacagg cgttgtgacg gaggctgaaa cctacactaa  6000
cttcgttggt tatgtcacaa ccacgttcaa aagaaagcat ttccgcccaa caccagatgc  6060
atgtagagcc gcgtacaact ggaagatggc cggtgacccc agatatgaag agtctctaca  6120
caatccgtac cctgactacc gctggctggt aactgtaaaa accaccaagg agtctctcgt  6180
tatcatatct ccaagtgtgg cagatttgga cccatgtgac agatcccttc actcgagggt  6240
cttccctagc gggaagtgct caggagtagc ggtgtcttct acctactgct ccactaacca  6300
cgattacacc atttggatgc ccgagaatcc gagactaggg atgtcttgtg acatttttac  6360
caatagtaga gggaagagag catccaaagg gagtgaactg tgcggctttg tagatgaaag  6420
aggcctatat aagtctttaa aaggagcatg caaactcaag ttatgtggag ttctaggact  6480
tagacttatg gatggaacat gggtctcgat gcaaacatca aatgaaacca aatggtgccc  6540
tcccgataag ttggtgaacc tgcacgactt cgctcagac  gaaattgagc accttgttgt  6600
agaggagttg gtcaggaaga gagaggagtg tctggatgca ctagagtcca tcatgacaac  6660
caagtcagtg agtttcagac gtctcagtca tttaagaaaa cttgtccctg ggtttggaaa  6720
agcatatacc atattcaaca gaccttgat ggaagccgat gctcactaca agtcagtcga  6780
gacttggaat gagatcctcc cttcaaaagg gtgtttaaga gttgggggga ggtgtcatcc  6840
tcatgtgaac gggggtgttt tcaatggtat aatattagga cctgacggca atgtcttaat  6900
cccagagatg caatcatccc tcctccagca acatatggag ttgttggaat cctcggttat  6960
ccccttgtg cacccctgg  cagacccgtc taccgttttc aaggacggtg acgaggctga  7020
ggatttgtt gaagttcacc ttcccgatgt gcacaatcag gtctcaggag ttgacttggg   7080
tctcccgaac tggggggaagt atgtattact gagtgcaggg gccctgactg ccttgatgtt  7140
gataattttc ctgatgacat gttgtagaag agtcaatcga tcagaaccta cgcaacacaa  7200
tctcagaggg acagggaggg aggtgtcagt cactccccaa agcgggaaga tcatatcttc  7260
atgggaatca cacaagagtg gggtgagac cagactgtaa ttaattaacg tccttcaac   7320
gatccaagtc catgaaaaaa actaacaccc ctcccgtacc tagcttataa agtgctgggt  7380
catctaagct tttcagtcga gaaaaaaaca ttagatcaga gaacaactg  gcaacacttc  7440
tcaacctgag acttacttca agatgctcga tcctggagag gtctatgatg acctattga   7500
cccaatcgag ttagaggctg aacccagagg aaccccatt  gtcccaaaca tcttgaggaa  7560
ctctgactac aatctcaact ctccctttga agaagatcct gctagactaa tgttagaatg  7620
```

```
gttaaaaaca gggaatagac cttatcggat gactctaaca gacaattgct ccaggtctttt  7680
cagagttttg aaagattatt tcaagaaggt agatttgggt tctctcaagg tgggcgaat    7740
ggctgcacag tcaatgattt ctctctggtt atatggtgcc cactctgaat ccaacaggag   7800
ccggagatgt ataacagact tggcccattt ctattccaag tcgtccccca tagagaagct   7860
gttgaatctc acgctaggaa atagaggact gagaatcccc ccagagggag tgttaagttg   7920
ccttgagagg gttgattatg ataatgcatt tggaaggtat cttgccaaca cgtattcctc   7980
ttacttgttc ttccatgtaa tcaccttata catgaacgcc ctagactggg atgaagaaaa   8040
gaccatccta gcattatgga aagatttaac ctcagtggac atcgggaagg acttggtaaa   8100
gttcaaagac caaatatggg gactgctgat cgtgacaaag gactttgttt actcccaaag   8160
ttccaattgt ctttttgaca gaaactacac acttatgcta aaagatcttt tcttgtctcg   8220
cttcaactcc ttaatggtct tgctctctcc cccagagccc cgatactcag atgacttgat   8280
atctcaacta tgccagctgt acattgctgg ggatcaagtc ttgtctatgt gtggaaactc   8340
cggctatgaa gtcatcaaaa tattggagcc atatgtcgtg aatagtttag tccagagagc   8400
agaaaagttt aggcctctca ttcattcctt gggagacttt cctgtattta taaaagacaa   8460
ggtaagtcaa cttgaagaga cgttcggtcc ctgtgcaaga aggttcttta gggctctgga   8520
tcaattcgac aacatacatg acttggtttt tgtgtttggc tgttacaggc attgggggca   8580
cccatatata gattatcgaa agggtctgtc aaaactatat gatcaggttc accttaaaaa   8640
aatgatagat aagtcctacc aggagtgctt agcaagcgac ctagccagga ggatccttag   8700
atggggtttt gataagtact ccaagtggta tctggattca agattcctag cccgagacca   8760
cccccttgact cctatatca aaacccaaac atggccaccc aaacatattg tagacttggt   8820
gggggataca tggcacaagc tcccgatcac gcagatcttt gagattcctg aatcaatgga   8880
tccgtcagaa atattggatg acaaatcaca ttctttcaca gaaacgagac tagcttcttg   8940
gctgtcagaa aaccgagggg ggcctgttcc tagcgaaaaa gttattatca cggccctgtc   9000
taagccgcct gtcaatcccc gagagtttct gaggtctata gacctcggag gattgccaga   9060
tgaagacttg ataattggcc tcaagccaaa ggaacgggaa ttgaagattg aaggtcgatt   9120
ctttgctcta atgtcatgga atcttaagatt gtatttgtc atcactgaaa aactcttggc   9180
caactacatc ttgccacttt ttgacgcgct gactatgaca gacaacctga caaggtgtt   9240
taaaaagctg atcgacaggg tcaccgggca agggcttttg gactattcaa gggtcacata   9300
tgcatttcac ctgactatg aaaagtgaa caaccatcaa agattagagt caacagagga   9360
tgtattttct gtcctagatc aagtgtttgg attgaagaga gtgttttcta gaacacacga   9420
gtttttttcaa aaggcctgga tctattattc agacagatca gacctcatcg ggttacggga   9480
ggatcaaata tactgcttag atgcgtccaa cggcccaacc tgttggaatg gccaggatgg   9540
cgggctagaa ggcttacggc agaagggctg gagtctagtc agcttattga tgatagatag   9600
agaatctcaa atcaggaaca caagaaccaa aatactagct caaggagaca accaggtttt   9660
atgtccgaca tacatgttgt cgccagggct atctcaagag gggctcctct atgaattgga   9720
gagaatatca aggaatgcac tttcgatata cagagccgtc gaggaagggg catctaagct   9780
agggctgatc atcaagaaag aagagaccat gtgtagttat gacttcctca tctatgggaaa  9840
aacccctttg tttagaggta acatattggt gcctgagtcc aaaagatggg ccagagtctc   9900
ttgcgtctct aatgaccaaa tagtcaacct cgccaatata atgtcgacag tgtccaccaa   9960
tgcgctaaca gtggcacaac actctcaatc tttgatcaaa ccgatgaggg attttctgct   10020
catgtcagta caggcagtct ttcactacct gctatttagc ccaatcttaa agggaagagt   10080
ttacaagatt ctgagcgctg aagggagag cttctctcca gccatgtcaa ggataatcta   10140
tctagatcct tctttgggag ggatatctgg aatgtccctc ggaagattcc atatacgaca   10200
gttctcagac cctgtctctg aagggttatc cttctggaga gagatctggt taagctccca   10260
agagtcctgg attcacgcgt tgtgtcaaga ggctggaaac ccagatcttg agagagaac    10320
actcgagagc ttcactcgcc ttctagaaga tccgaccacc ttaaatatca gaggaggggc   10380
cagtcctacc attctactca aggatgcaat cagaaaggct ttatatgacg aggtggacaa   10440
ggtgaaaat tcagagtttc gagaggcaat cctgttgtcc aagacccata gagataattt    10500
tatactcttc ttaatatctg ttgagcctct gtttcctcga tttctcagtg agctattcag   10560
ttcgtctttt ttgggaatcc ccgagtcaat cattggattg atacaaaact cccgaacgat   10620
aagaaggcag tttagaaaga gtctctcaaa aactttagaa gaatccttct acaactcaga   10680
gatccacggg attagtcgga tgacccagac acctcagagg gttgggggg tgtggccttg    10740
ctcttcagag agggcagatc tacttaggga gatctcttgg ggaagaaaag tggtaggcac   10800
gacagttcct caccctctg agatgttggg attacttccc aagtcctcta tttcttgcac   10860
ttgtgagca acaggaggag gcaatcctag agttctgta tcagtactcc cgtcctttga    10920
tcagtcattt ttttcacgag gcccctaaa gggatacttg ggctcgtcca cctctatgtc    10980
gacccagcta ttccatgcat gggaaaaagt cactaatgtt catgtggtga agagagctct   11040
atcgttaaaa gaatctataa actggttcat tactagagat tccaacttgg ctcaagctct   11100
aattaggaac attatgtctc tgacaggccc tgatttccct ctagaggagg ccctgtctt    11160
caaaaggacg gggtcagcct tgcataggtt caagtctgcc agatacagcg aaggagggta   11220
ttcttctgtc tgcccgaacc tcctctctca tatttctgtt agtacagaca ccatgtctga   11280
tttgacccaa gacgggaaga actacgattt catgttccag ccattgatgc tttatgcaca   11340
gacatggaca tcagagctgg tacagagaga cacaaggcta agagactcta cgtttcattg   11400
gcacctccga tgcaacaggt gtgtgagacc cattgacgac gtgaccctgg agacctctca   11460
gatcttcgag tttccggatg tgtcgaaaag aatatccaga atgtttctg gggctgtgcc    11520
tcacttccag aggcttcccg atatccgtct gagaccagga gattttgaat ctctaagcgg   11580
tagagaaaag tctcaccata tcggatcagc tcaggggctc ttatactcaa tcttagtggc   11640
aattcacgac tcaggataca atgatggaac catcttccct gtcaacatat acggcaaggt   11700
ttccctaga gactatttga gagggctcgc aaggggagta ttgataggat cctcgatttg   11760
cttcttgaca agaatgacaa atatcaatat taatagacct cttgaattgg tctcaggggt   11820
aatctcatat attctcctga ggctagataa ccatccctcc ttgtacataa tgctcagaga   11880
accgtctctt agaggagaga tatttctat cctcagaaa atccccgccg cttatccaac    11940
cactatgaaa gaaggcaaca gatcaatctt gtgttatctc caacatgtgc tacgctatga   12000
gcgagagata tcacgcgt ctccagagaa tgactggtca tggatcttt cagactttag      12060
aagtgccaaa atgacgtacc tatccctcat tacttaccag tctcatcttc tactccagag   12120
ggttgagaga aacctatcta agagtatgag agataacctg cgacaattga gttcttgat    12180
gaggcaggtg ctgggcgggc acggagaaga taccttagag tcagacgaca acattcaacg   12240
actgctaaaa gactctttac gaaggacaag atgggtggat caagaggtgc gccatgcagc   12300
tagaaccatg actggagatt acagcccaa caagaaggtg tcccgtaagg taggatgttc    12360
```

```
agaatgggtc tgctctgctc aacaggttgc agtctctacc tcagcaaacc cggcccctgt    12420
ctcggagctt gacataaggg ccctctctaa gaggttccag aacccttgga tctcgggctt    12480
gagagtggtt cagtgggcaa ccggtgctca ttataagctt aagccattc tagatgatct    12540
caatgttttc ccatctctct gccttgtagt tgggacggg tcaggggga tatcaagggc     12600
agtcctcaac atgtttccag atgccaagct tgtgttcaac agtcttttag aggtgaatga    12660
cctgatggct tccggaacac atccactgcc tccttcagca atcatgaggg gaggaaatga    12720
tatcgtctcc agagtgatag atcttgactc aatctgggaa aaaccgtccg acttgagaaa    12780
cttggcaacc tggaaatact tccagtcagt ccaaaagcag gtcaacatgt cctatgacct    12840
cattatttgc gatgcagaag ttactgacat tgcatctatc aaccggatca ccctgttaat    12900
gtccgatttt gcattgtcta tagatggacc actctatttg gtcttcaaaa cttatgggac    12960
tatgctagta aatccaaact acaaggctat tcaacacctg tcaagagcgt tccctcggt    13020
cacagggttt atcacccaag taacttcgtc ttttcatct gagctctacc tccgattctc    13080
caaacgaggg aagttttca gagatgctga gtacttgacc tcttccaccc ttcgagaaat    13140
gagccttgtg ttattcaatt gtagcagccc caagagtgag atgcagagag ctcgttcctt    13200
gaactatcag gatcttgtga gaggatttcc tgaagaaatc atatcaaatc cttacaatga    13260
gatgatcata actctgattg acagtgatgt agaatctttt ctagtccaca agatggttga    13320
tgatcttgag ttacagaggg gaactctgtc taaagtggct atcattatag ccatcatgat    13380
agttttctcc aacagagtct tcaacgtttc caaacccta actgacccct cgttctatcc    13440
accgtctgat cccaaaatcc tgaggcactt caacatatgt tgcagtacta tgatgtatct    13500
atctactgct ttaggtgacg tccctagctt cgcaagactt cacgacctgt ataacagacc    13560
tataactat tacttcagaa agcaagtcat tcgagggaac gtttatctat cttggagttg    13620
gtccaacgac acctcagtgt tcaaaagggt agcctgttga tctagcctga gtctgtcatc    13680
tcactggatc aggttgattt acaagatagt gaagactacc agactcgttg gcagcatcaa    13740
ggatctatcc agagaagtgg aaagacacct tcataggtac aacaggtgga tcaccctaga    13800
ggatatcaga tctagatcat ccctactaga ctacagttgc ctgtgaaccg gatactcctg    13860
gaagcctgcc catgctaaga ctcttgtgtg atgtatcttg aaaaaaacaa gatcctaaat    13920
ctgaacctt ggttgtttga ttgttttct cattttgtt gtttatttgt taagcgt        13977

SEQ ID NO: 14         moltype = DNA  length = 13923
FEATURE               Location/Qualifiers
misc_feature          1..13923
                      note = RABV vector: Coravax V5 China
source                1..13923
                      mol_type = other DNA
                      organism = synthetic construct
SEQUENCE: 14
acgcttaaca accagatcaa agaaaaaaca gacattgtca attgcaaagc aaaaatgtaa    60
cacccctaca atggatgccg acaagattgt attcaaagtc aataatcagg tggtctcttt    120
gaagcctgag attatcgtgg atcaatatga gtacaagtac cctgccatca aagatttgaa    180
aaagccctgt ataaccctag gaaaggctcc cgatttaaat aaagcataca agtcagtttt    240
gtcaggcatg agcgccgcca aacttaatcc tgacgatgta tgttcctatt ggcagcggc    300
aatgcagttt tttgagggga catgtccgga agactggacc agctatggaa ttgtgattgc    360
acgaaaagga gataagatca ccccaggttc tctggtgagt ataaaacgta ctgatgtaga    420
agggaattgg gctctgacag gaggcatgga actgacaaga gaccccactg tccctgagca    480
tgcgtcctta gtcggtcttc tcttgagtct gtataggttg agcaaaatat ccgggcaaaa    540
cactggtaac tataagacaa acattgcaga caggatagag cagatttttg agacagcccc    600
ttttgttaaa atcgtggaac accatactct aatgacaact cacaaaatgt gtgctaattg    660
gagtactata ccaaacttca gattttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatattc ttccacaaga actttgagga agagtaaga agaatgtttg agccagggca    900
ggagacagct gttcctcact cttatttcat ccacttccgt tcactaggct tgagtgggaa    960
atctccttat tcatcaaatg ctgttggtca cgtgttcaat ctcattcact ttgtaggatg    1020
ctatatgggt caagtcagat ccctaaatgc aacggttatt gctgcatgtg ctcctcatga    1080
aatgtctgtt ctaggggct atctgggaga ggaattcttc gggaaaggga catttgaaag    1140
aagattcttc agagatgaga agaacttca gaatacgag gcggctgaac tgacaaagac    1200
tgacgtagca ctgcagatg atggaactgt caactctgac gacgaggact acttttcagg    1260
tgaaaccaga agtccggagg ctgttttatac tcgaatcatg atgaatggag tcgactaaa    1320
gagatctcac atacggagat atgtctcagt cagttccaat catcaagccc gtccaaactc    1380
attcgccgag tttctaaaca agacatattc gagtgactca taagaagttg aataacaaaa    1440
tgccggaaat ctacggattg tgtatatcca tcatgaaaaa aactaacacc cctccttcg    1500
aaccatccca aacatgagca agatctttgt caatcctagt gctattagag ccggtctggc    1560
cgatcttgag atggctgaag aaactgttga tctgatcaat agaaatatcg aagacaatca    1620
ggctcatctc caaggggaac catagaggt ggacaatctc cctggagata tggggcaaat    1680
tcacctggat gatggaaaat cgcccaacca tggtgagata gccaaggtgg agaaggcaa    1740
gtatcgagag gactttcaga tggatgaagg agaggatcct agcttcctgt tccagtcata    1800
cctggaaaat gttggagtcc aaatagtcag acaaatgagg tcaggagaga gatttctcaa    1860
gatatggtca cagaccgtag aagagattat atcctatgtc gcggtcaact ttcccaaccc    1920
tccaggaaag tcttcagagg ataaatcaac ccagactact gacgagagc tcaagaagga    1980
gacaacaccc actccttctc agagagaaag ccaatcatcg aaagccagga tggcggctca    2040
aattgcttct ggccctccag cccttgaatg gtcggctacc aatgaagagg atgatctatc    2100
agtggaggct gagatcgctc accagattgc agaaagtttc tccaaaaaat ataagtttcc    2160
ctctcgatcc tcagggatac tcttgtataa ttttgagcaa ttgaaaatga accttgatga    2220
tatagttaaa gaggcaaaa atgtaccagg tgtgacccgt ttagccccag acgggtcaa    2280
actccccta agatgtgtac tgggatgggt cgctttggcc aactctaaga aattccagtt    2340
gttagtcgaa tccgacaagc tgagtaaaat catgcaagat gacttgaatc gctatacatc    2400
ttgctaaccg aacctctccc ctcagtccct ctagacaata aaatccgaga tgtcccaaag    2460
tcaacatgaa aaaacaggc aacaccctg ataaaatgaa cctcctacgt aagatagtga    2520
aaaaccgcag ggacgaggac actcaaaaat cctctccgg gtcagcccct ctggatgacg    2580
```

```
atgacttgtg gcttccaccc cctgaatacg tcccgctgaa agaacttaca ggcaagaaga    2640
acatgaggaa cttttgtatc aacgaagggt ttaaagtgtg tagcccgaat ggttactcgt    2700
tcaggatcct gcggcacatt ctgaaatcat tcgacgagat atattctggg aatcatagga    2760
tgatcgggtt agtcaaagtg gttattggac tggctttgtc aggatctcca gtccctgagg    2820
gcctgaactg ggtatacaaa ttgaggagaa cctttatctt ccagtgggct gattccaggg    2880
gccctcttga aggggaggag ttggaatact ctcaggagat cacttgggat gatgatactg    2940
agttcgtcgg attgcaaata agagtgattg caaaacagtg tcatatccag ggcagagtct    3000
ggtgtatcaa catgaacccg agagcatgtc aactatggtc tgacatgtct cttcagacac    3060
aaaggtccga agaggacaaa gattcctctc tgcttctaga ataatcagat tatatcccgc    3120
aaatttatca cttgtttacc tctgaggag agaacatatg ggctcaactc caacccttgg    3180
gagcaatata acaaaaaaca tgttatggtg ccattaaacc gctgcatttc atcaaagtca    3240
agttgattac ctttacatt tgatcctctt ggatgtgaaa aaaactatta acatccctca    3300
aaagaccccg ggccaccatg ttcgtgtttc tggtgctgct gcctctggtg agctcccagt    3360
gcgtgaacct gaccacaagg acccagctgc cccctgccta taccaattcc ttcacacggg    3420
gcgtgtacta tcccgacaag gtgttccgga gcagcgtggt gcactccaca caggatctgt    3480
ttctgccttt cttttctaac gtgacctggt tccacgccat ccacgtgagc ggcaccaatg    3540
gcacaaagcg gttcgacaat ccagtgctgc cctttaacga tggcgtgtac ttcgcctcca    3600
ccgagaagtc taacatcatc agaggctgga tcttttggca cacactggac agcaagacac    3660
agtccctgct gatcgtgaac aatgccacca acgtggtcat caaggtgtgc gagttccagt    3720
tttgtaatga tccattcctg ggcgtgtact atcacaagaa caataagtct tggatggaga    3780
gcgagtttcg cgtgtattcc tctgccaaca attgcacatt tgagtacgtg tcccagccct    3840
tcctgatgga cctggagggc aagcagggca atttcaagaa cctgagggag ttcgtgttta    3900
agaatatcga tggctacttc aaaatctact ccaagcacac cccaatcaac ctggtgcgcg    3960
acctgccaca gggcttctct gccctggagc cactggtgga tctgcccatc ggcatcaaca    4020
tcacccggtt tcagacactg ctggccctgc acagaagcta cctgacacca ggcgacagct    4080
cctctgatgg gaccgcagga gcagcagcct actatgtgcg ctatctgcag cccaggacct    4140
tcctgctgaa gtacaacgag aatggcacca tcacagacgc cgtggattgc gccctggatc    4200
ccctgtctga gaccaagtgt acactgaaga gctttaccgt ggagaagggc atctatcaga    4260
caagcaattt cagggtgcag cctaccgagt ccatcgtgcg ctttcccaat atcacaaacc    4320
tgtgccctt tggcgaggtg ttcaacgcaa cccgcttcgc cagcgtgtac gcctggaata    4380
ggaagcgcat ctccaactgc gtggccgact attctgtgct gtacaacagc gcctccttct    4440
ctacctttaa gtgctatggc gtgagcccca caaagctgaa tgacctgtgc tttaccaacg    4500
tgtacgccga ttccttcgtg atcaggggcg acgaggtgcg ccagatcgca ccaggacaga    4560
caggcaagat cgcagactac aattataagc tgcctgacga tttcaccggc tgcgtgatcg    4620
cctgaactc taacaatctg gatagcaaag tgggcggcaa ctacaattat ctgtaccggc    4680
tgtttagaaa gtctaatctg aagccattgc agagggacat ctccacagaa atctaccagg    4740
ccggctctac cccctgcaat ggcgtggagg ctttaactg ttatttccct ctgcagagct    4800
acggcttcca gccaacaaac ggcgtgggct atcagcccta ccgcgtggtg gtgctgtctt    4860
ttgagctgct gcacgcacct gcaacagtgt gcggaccaaa gaagagcacc aatctggtga    4920
agaacaagtg cgtgaacttc aacttcaacg gactgaccgg aacaggcgtg ctgaccgagt    4980
ccaacaagaa gttcctgcct tttcagcagt tcggcaggga catcgcagat accacagacg    5040
ccgtgcgcga ccctcagacc ctggagatcc tggacatcac accatgctcc ttcggcggcg    5100
tgtctgtgat cacaccaggc accaatacaa gcaaccaggt ggccgtgctg tatcaggacg    5160
tgaattgtac cgaggtgcca gtggcaatcc acgcagatca gctgacccct acatggcggg    5220
tgtactctac cggcagcaac gtgttccaga caagagccgg atgcctgatc ggagcagagc    5280
acgtgaacaa tagctatgag tgcgacatcc ctatcggcgc cggcatctgt gcctcctacc    5340
agacccagac aaactcccca aggtctgtgg gagatgagac cgaagacttt gtggaagtcc    5400
acctgcctga tgtgcataac caggtgtctg gcgtcgacct gggactgcca aattgggca    5460
agtacgtgct gctgagtgct ggagcactga ctgcccgat gctgatcatt ttcctgatga    5520
cctgctgtcg gcgcgtgaac agaagtgagc ccactcagca caatctgcga ggaaccggga    5580
gagaagtgtc agtcacacct cagagcggga aaatcattag tagttgggaa tcacataaaa    5640
gcggggggcga gaccaggctg ggatccggct ccggcgaggg caggggaagt ctactaacat    5700
gcggggacgt ggaggaaaat cccggcccca tggttcctca ggctctcctg tttgtacccc    5760
ttctggtttt tccattgtgt tttgggaaat tccctatta cacgatacca gacaagcttg    5820
gtccctggag tccgattgac atacatcacc tcagctgccc aaacaatttg gtagtggagg    5880
acgaaggatg caccaacctg tcagggttct cctacatgga acttaaagtt ggatacatct    5940
tagccataaa agtgaacggg ttcacttgca caggcgttgt gacggaggct gaaacctaca    6000
ctaacttcgt tggttatgtc acaaccacgt tcaaaagaaa gcatttccgc caacaccag    6060
atgcatgtag agccgcgtac aactggaaga tggccggtga ccccagatat gaagagtctc    6120
tacacaatcc gtaccctgac taccgctggc ttcgaactgt aaaaaccacc aaggagtctc    6180
tcgttatcat atctccaagt gtggcagatt tggacccata tgacagatcc cttcactcga    6240
gggtcttccc tagcgggaag tgctcaggag tagcggtgtc ttctacctac tgctccacta    6300
accacgatta caccatttgg atgcccgaga tccgagact agggatgtct tgtgacattt    6360
ttaccaatag tagagggaag agagcatcca aagggagtga gacttgccgc tttgtagatg    6420
aaagaggcct atataagtct ttaaaaggag catgcaaact caagttatgt ggagttctag    6480
gacttagact tatggatgga acatgggtct cgatgcaaac atcaaatgaa accaaatggt    6540
gccctcccga taagttggtg aacctgcacg actttcgctc agacgaaatt gagcaccttg    6600
ttgtagagga gttggtcagg aagagagagg agtgtctgga tgcactagag tccatcatga    6660
caaccaagtc agtgagtttc agacgtctca gtcatttaag aaaacttgtc cctgggttg    6720
gaaaagcata taccatattc aacaagacct tgatggaagc cgatgctcac tacaagtcag    6780
tcgagacttg gaatgagatc ctcccttcaa aagggtgttt aagagttggg ggaggtgtc    6840
atcctcatgt gaacgggtgt ttttcaatg gtataatatt aggacctgac ggcaatgtct    6900
taatcccaga gatgcaatca tccctcctcc agcaacatat ggagttgttg gaatcctcgg    6960
ttatccccct tgtgcacccc ctggcagacc cgtcaaccgt tttcaaggac ggtgacgagg    7020
ctgaggattt tgttgaagtt caccttcccg atgtgcacaa tcaggtctca ggagtgactg    7080
tgggtctccc gaactggggg aagtatgtat tactgagtgc aggggccctg actgccttga    7140
tgttgataat tttcctgatg acatgttgta agaagagtca atcgatcagaa cctacgcaac    7200
acaatctcag agggacaggg agggaggtgt cagtcactcc ccaaagcggg aagatcatat    7260
cttcatggga atcacacaag agtgggggtg agaccagact gtaagctagc ttataaagtg    7320
```

```
ctgggtcatc taagcttttc agtcgagaaa aaaacattag atcagaagaa caactggcaa  7380
cacttctcaa cctgagactt acttcaagat gctcgatcct ggagaggtct atgatgaccc  7440
tattgaccca atcgagttag aggctgaacc cagaggaacc cccattgtcc caacatctt   7500
gaggaactct gactacaatc tcaactctcc tttgatagaa gatcctgcta gactaatgtt  7560
agaatggtta aaaacaggga atagaccta tcggatgact ctaacagaca attgctccag  7620
gtctttcaga gtttttgaaag attatttcaa gaaggtagat ttgggttctc tcaaggtggg  7680
cggaatggct gcacagtcaa tgatttctct ctggttatat ggtgcccact ctgaatccaa  7740
caggagccgg agatgtataa cagacttggc ccatttctat tccaagtcgt cccccataga  7800
gaagctgttg aatctcacgc taggaaatag agggctgaga atcccccag agggagtgtt   7860
aagttgcctt gagagggttg attatgataa tgcattggga aggtatcttg ccaacacgta  7920
ttcctcttac ttgttcttcc atgtaatcac cttatacatg aacgccctag actgggatga  7980
agaaaagacc atcctagcat tatggaaaga tttaacctca gtggacatcg ggaaggactt  8040
ggtaaagttc aaagaccaaa tatggggact gctgatcgtg acaaaggact ttgtttactc  8100
ccaaagttcc aattgtcttt ttgacagaaa ctacacactt atgctaaaag atcttttctt  8160
gtctcgcttc aactccttaa tggtcttgct ctctccccca gagccccgat actcagatga  8220
cttgatatct caactatgcc agctgtacat tgctggggat caagtcttgt ctatgtgtgg  8280
aaactccggc tatgaagtca tcaaaatatt ggagccatat gtcgtgaata gtttagtcca  8340
gagagcagaa aagtttaggc ctctccattca ttccttggga gactttccctg tatttataaa  8400
agacaaggta agtcaacttg aagagacgtt cggtccctgt gcaagaaggt tctttagggc  8460
tctggatcaa ttcgacaaca tacatgactt ggttttttgtg tttggctgtt acaggcattg  8520
ggggcaccca tatatagatt atcgaaaggg tctgtcaaaa ctatatgatc aggttcacct  8580
taaaaaaatg atagataagt cctaccagga gtgcttagca agcgaccctag ccaggaggat  8640
ccttagatgg ggttttgata agtactccaa gtggtatctg gattcaagat tcctagcccg  8700
agaccacccc ttgactcctt atatcaaaac ccaaacatgg ccaccaaac atattgtaga   8760
cttggtgggg gatacatggc acaagctccc gatcacgcag atctttgaga ttcctgaatc  8820
aatggatccg tcagaaatat tggatgcaa atcacattct ttcaccagaa cgagactagc   8880
ttcttggctg tcagaaaacc gagggggggcc tgttcctagc gaaaaagtta ttatcacggc  8940
cctgtctaag ccgcctgtca atccccgaga gttctgaggg tctatagacc tcggaggatt  9000
gccagatgaa gacttgataa ttggcctcaa gccaaaggaa cgggaattga agattgaagg  9060
tcgattctt gctctaatgt catggaatct aagattgtat tttgtcatca ctgaaaact    9120
cttggccaac tacatcttgc cacttttga cgcgctgact atgacagaca acctgaacaa  9180
ggtgtttaaaa aagctgatcg acagggtcac cgggcaaggg cttttggact attcaagggt  9240
cacatatgca tttcacctgg actatgaaaa gtggaacaac catcaaagat tagagtcaac  9300
agaggatgta ttttctgtcc tagatcaagt gttttggattg aagagagtgt tttctagaac  9360
acacgagttt tttcaaaagg cctggatcta ttattcagac agatcagacc tcatcgggtt  9420
acgggaggat caaatatact gcttagatgc gtccaacggc ccaacctgtt ggaatggcca  9480
ggatggcggg ctagaaggct tacgcagaaa gggctggagt ctagtcagct tattgatgat  9540
agatagaaa tctcaaatca ggaacacaag aaccaaaata ctagctcaag gagacaacca   9600
ggttttatgt ccgacataca tgttgtcgcc agggctatct caagaggggc tcctctatga  9660
attggagaga atatcaagga atgcactttc gatatacaga gccgtcgagg aaggggcatc  9720
taagctaggg ctgatcatca agaaagaaga gaccatgtgt agttatgact tcctcatcta  9780
tggaaaaacc ccttttgttta gaggtaacat attggtgcct gagtccaaaa gatgggccag  9840
agtctcttgc gtctctaatg accaaatagt caacctcgcc aatataatgt cacagtgtc   9900
caccaatgcg ctaacagtgg cacaacactc tcaatctttg atcaaaccga tgagggattt  9960
tctgctcatg tcagtacagg cagtctttca ctacctgcta tttagcccaa tcttaaaggg  10020
aagagtttac aagattctga gcgctgaagg ggagagcttt ctcctagcca tgtcaaggat  10080
aatctatcta gatccttctt tgggagggat atctggaatg tccctcggaa gattccatat  10140
acgacagttc tcagaccctg tctctgaagg gttatccttc tggagagaga tctggttaag  10200
ctcccaagag tcctgattc acgcgttgtg tcaagaggct ggaacccag atcttggaga   10260
gagaacactc gagagcttca ctcgccttct agaagatccg accaccttaa atatcagagg  10320
aggggccagt cctaccattc tactcaagga tgcaatcaga aaggctttat attgacgagt  10380
ggacaaggtg gaaaattcag agtttcgaga ggcaatcctg ttgtccaaga cccatagaga  10440
taattttata ctcttcttaa tatctgttga gcctctgttt cctcgattc tcagtgagct   10500
attcagttcg tcttttttgg gaatcccga gtcaatcatt ggattgatac aaaactcccg   10560
aacgataaga aggcagttta gaaagagtct ctcaaaaact ttagaagaat ccttctacaa  10620
ctcagagatc cacgggatta gtcggatgac ccagacacct cagagggttg gggggtgtg   10680
gccttgctct tcagagaggg cagatctact tagggagatc tcttggggaa gaaaagtggt  10740
aggcacgaca gttcctcacc cttctgagat gttgggatta cttcccaagt cctctatttc  10800
ttgcacttgt ggagcaacag gaggaggcaa tcctagagtt tctgtatcga tactcccgtc  10860
ctttgatcag tcattttttt cacgaggccc cctaaaggga tacttgggct cgtccacctc  10920
tatgtcgacc cagctattcc atgcatggga aaaagtcact aatgttcatg tggtgaagag  10980
agctctatcg ttaaaagaat ctataaactg gttcattact agagattcca acttggctca  11040
agctctaatt aggaacatta tgtctctgac aggccctgat ttccctctag aggaggcccc  11100
tgtcttcaaa aggacggggt cagccttgca taggttcaag tctgccagat acagcgaagg  11160
agggtattct tctgtctgcc cgaacctcct ctctcatatt tctgttagta cagacaccat  11220
gtctgatttg acccaagacg ggaagaacta cgatttcatg ttccagccat tgatgctta   11280
tgcacagaca tggacatcag agctggtaca gagagacaca aggctaagag actctacgtt  11340
tcattggcac ctccgatgca acaggccatt gagacccatt gacgacgtga ccctggagac  11400
ctctcagatc ttcgagtttc tcggatgtgc gaaaagaata tccagaatgg tttctgggtc  11460
tgtgcctcac ttccagaggc ttcccgatat ccgtctgaga ccaggagatt ttgaatctct  11520
aagcggtaga gaaaagtctc accatatcgg atcagctcag ggctcttat actcaatctt   11580
agtggcaatt cacgactcag gatacaatga tggaaccatc ttccctgtca acatatacg    11640
caaggttttcc cctagagact atttgagagg gctcgcaagg ggagtattga taggatcctc  11700
gatttgcttc ttgacaagaa tgacaaatat caatattaat agacctcttg aattgatctc  11760
aggggtaatc tcatatattc tcctgaggct agataaccat ccctccttgt acataatgct  11820
cagagaaccg tctcttagag gagagatatt ttctatccct cagaaaatcc ccgccgctta  11880
tccaccact atgaaagaag gcaacagatc aatcttgtgt tatctccaac atgtgctacg   11940
ctatgagcga gagataatca cggcgtctcc agagaatgac tggctatgga tctttttcaga  12000
cttagaagt gccaaaatga cgtacctatc cctcattact taccagtctc atcttctact    12060
```

-continued

```
ccagagggtt gagagaaacc tatctaagag tatgagagat aacctgcgac aattgagttc    12120
tttgatgagg caggtgctgg gcgggcacgg agaagatacc ttagagtcag acgacaacat    12180
tcaacgactg ctaaaagact ctttacgaag gacaagatgg gtggatcaag aggtgcgcca    12240
tgcagctaga accatgactg gagattacag ccccaacaag aaggtgtccc gtaaggtagg    12300
atgttcagaa tgggtctgct ctgctcaaca ggttgcagtc tctacctcag caaacccggc    12360
ccctgtctcg gagcttgaca taagggcccc ctctaagagg ttccagaacc ctttgatctc    12420
gggcttgaga gtggttcagt gggcaaccgg tgctcattat aagcttaagc ctattctaga    12480
tgatctcaat gttttcccat ctctctgcct tgtagttggg gacgggtcag gggggatatc    12540
aagggcagtc ctcaacatgt ttccagatgc caagcttgtg ttcaacagtc ttttagaggt    12600
gaatgacctg atggcttccg gaacacatcc actgcctcct tcagcaatca tgaggggagg    12660
aaatgatatc gtctccagag tgatagatct tgactcaatc tgggaaaaac cgtccgactt    12720
gagaaacttg gcaacctgga aatacttcca gtcagtccaa aagcaggtca acatgtccta    12780
tgacctcatt atttgcgatg cagaagttac tgacattgca tctatcaacc ggatcaccct    12840
gttaatgtcc gattttgcat tgtctataga tggaccactc tatttggtct tcaaaactta    12900
tgggactatg ctagtaaatc caaactacaa ggctattcaa cacctgtcaa gagcgttccc    12960
ctcggtcaca gggtttatca cccaagtaac ttcgtctttt tcatctgagc tctacctccg    13020
attctccaaa cgagggaagt ttttcagaga tgctgagtac ttgacctctt ccaccccttcg    13080
agaaatgagc cttgtgttat tcaattgtag cagccccaag agtgagatgc agagagctcg    13140
ttccttgaac tatcaggatc ttgtgagagg atttcctgaa gaaatcatat caaatccttga   13200
caatgagatg atcataactc tgattgacag tgatgtagaa tcttttctag tccacaagat    13260
ggttgatgat cttgagttac agaggggaac tctgtctaaa gtggctatca ttatagccat    13320
catgatagtt ttctccaaca gagtcttcaa cgtttccaaa cccctaactg accctcgtt    13380
ctatccaccg tctgatccca aaatcctgag gcacttcaac atatgttgca gtactatgat    13440
gtatctatct actgctttag gtgacgtccc tagcttcgca agacttcacg acctgtataa    13500
cagacctata acttattact tcagaaagca agtcattcga gggaacgttt atctatcttg    13560
gagttggtcc aacgacacct cagtgttcaa aagggtgtcc tgtaattcta gcctgagtct    13620
gtcatctcac tggatcaggt tgatttacaa gatagtgaag actaccagac tcgttggcag    13680
catcaaggat ctatccagag aagtggaaag acaccttcat aggtacaaca ggtggatcac    13740
cctagaggat atcagatcta gatcatccct actagactac agttgcctgt gaaccggata    13800
ctcctggaag cctgcccatg ctaagactct tgtgtgatgt atcttgaaaa aaacaagatc    13860
ctaaatctga acctttggtt gtttgattgt ttttctcatt tttgttgttt atttgttaag    13920
cgt                                                                  13923
SEQ ID NO: 15         moltype = DNA  length = 13974
FEATURE               Location/Qualifiers
misc_feature          1..13974
                      note = RABV vector: Coravax V5 South Africa
source                1..13974
                      mol_type = other DNA
                      organism = synthetic construct
SEQUENCE: 15
acgcttaaca accagatcaa agaaaaaaca gacattgtca attgcaaagc aaaaatgtaa      60
caccctaca atggatgccg acaagattgt attcaaagtc tggtctcttt                 120
gaagcctgag attatcgtgg atcaatatga gtacaagtac cctgccatca aagatttgaa    180
aaagccctgt ataaccctag gaaaggctcc cgatttaaat aaagcataca agtcagtttt    240
gtcaggcatg agcgccgcca aacttaatcc tgacgatgta tgttcctatt tggcagcggc    300
aatgcagttt tttgagggga catgtccgga agactgacc agctatggaa ttgtgattgc    360
acgaaaagga gataagatca ccccaggttc tctggtggag ataaaacgta ctgatgtaga    420
agggaattgg gctctgacag gaggcatgga actgacaaga gaccccactg tccctgagca    480
tgcgtcctta gtcggtcttc tcttgagtct gtataggttg agcaaaatat ccgggcaaaa    540
cactggtaac tataagacaa acattgcaga caggataga cagattttg agacagcccc    600
ttttgttaaa atcgtggaac accatactct aatgacaact cacaaaatgt gtgctaattg    660
gagtactata ccaaacttca gattttttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatattc ttccacaaga acttgagga agagataaga gaatgtttg agccagggca    900
ggagacagct gttcctcact cttatttcat ccacttccgt tcactaggct tgagtgggaa    960
atctccttat tcatcaaatg ctgttggtca cgtgttcaat ctcattcact tgtaggatg    1020
ctatatgggt caagtcagat ccctaaatgc aacggttatt gctgcatgtg ctcctcatga    1080
aatgtctgtt ctagggggct atctgggaca ggaattcttc gggaaaggga catttgaaag    1140
aagattcttc agagatgaga aagaacttca agaatacgag gcggctgaac tgacaaagac    1200
tgacgtagca ctggcagatg atggaactgt caactctgac gacgaggact acttttcagg    1260
tgaaaccaga agtccggagg ctgttttatac tcgaatcatg atgaatggag gtcgactaaa    1320
gagatctcac atacggaagt atgtctcagt cagttccaat catcaagccc gtccaaactc    1380
attcgccgag tttctaaaca agacatattc gagtgactca taagaagttg aataacaaa    1440
tgccggaaat ctacggattg tgtatatcca tcatgaaaaa aactaacacc cctcctttcg    1500
aaccatccca aacatgagca agatcttgt caatcctagt gctattagag ccggtctggc    1560
cgatcttgag atggctgaag aaactgttga tctgatcaat agaaatatcg aagacaatca    1620
ggctcatctc caaggggaac catagaggt ggacaatctc cctgaggata tgggggcgact    1680
tcacctggat gatggaaaat cgcccaacca tggtgagata gccaaggtgg agaaggcaa    1740
gtatcgagag gactttcaga tggatgaagg agaggatcct agcttcctgt tccagtcata    1800
cctggaaaat gttggagtcc aaatagtcag acaaatgagg tcaggagaga gatttctcaa    1860
gatatggtca cagaccgtag aagagattat atcctatgtc gcggtcaact ttcccaaccc    1920
tccaggaaag tcttcagagg ataaatcaac ccagactact ggcgagagc tcaagaagga    1980
gacaacaccc actccttctc agagagaaag ccaatcatcg aaagccagga tggcggctca    2040
aattgcttct ggccctccag cccttgaatg gtcggctacc aatgaagagg atgatctatc    2100
agtggaggct gagatcgctc accagattgc agaaagttc tccaaaaat ataagtttcc    2160
ctctcgatcc tcagggatac tcttgtataa ttttgagcaa ttgaaaatga accttgatga    2220
tatagttaaa gaggcaaaaa atgtaccagg tgtgacccgt ttagcccatg acgggtccaa    2280
```

```
actcccccta agatgtgtac tgggatgggt cgctttggcc aactctaaga aattccagtt  2340
gttagtcgaa tccgacaagc tgagtaaaat catgcaagat gacttgaatc gctatacatc  2400
ttgctaaccg aacctctccc ctcagtccct ctagacaata aaatccgaga tgtcccaaag  2460
tcaacatgaa aaaacaggc aacaccactg ataaaatgaa cctcctacgt aagatagtga  2520
aaaaccgcag ggacgaggac actcaaaaat cctctcccgc gtcagcccct ctggatgacg  2580
atgacttgtg gcttccaccc cctgaatacg tcccgctgaa agaacttaca ggcaagaaga  2640
acatgaggaa cttttgtatc aacggaaggg ttaaagtgtg tagcccgaat ggttactcgt  2700
tcaggatcct gcggcacatt ctgaaatcat tcgacgagat atattctggg aatcatagga  2760
tgatcgggtt agtcaaagtg gttattggac tggctttgtc aggatctcca gtccctgagg  2820
gcctgaactg ggtatacaaa ttgaggagaa cctttatctt ccagtgggct gattccagtg  2880
gccctcttga agggaggag ttggaatact ctcaggagat cacttgggat gatgatactg  2940
agttcgtcgg attgcaaata agagtgattg caaaacagtg tcatatccag ggcagagtct  3000
ggtgtatcaa catgaacccg agagcatgtc aactatggtc tgacatgtct cttcagacac  3060
aaaggtccga agaggacaaa gattcctctc tgcttctaga ataatcagat tatatcccgc  3120
aaatttatca cttgtttacc tctggaggag agaacatatg ggctcaactc caaccttgg  3180
gagcaatata acaaaaaaca tgttatggtg ccattaaacc gctgcatttc atcaaagtca  3240
agttgattac ctttacattt tgatcctctt ggatgtgaaa aaactatta acatccctca  3300
aaagaccccg ggccaccatg ttcgtgtttc tggtgctgct gcctctggtg agctcccagt  3360
gcgtgaactt caccacaagg acccagctgc ccctgcccta taccaattcc ttcacacggg  3420
gcgtgtacta tcccgacaag gtgttccgga gcagcgtgct gcactccaca caggatctgt  3480
ttctgccttt cttttctaac gtgacctggt tccacgccat ccacgtgagc ggcaccaatg  3540
gcacaaagcg gttcgccaat ccagtcgtgc cctttaacgg tgccgtgtac ttcgcctcca  3600
ccgagaagtc taacatcatc agaggctgga tcttttggcac cacactggac agcaagacac  3660
agtccctgct gatcgtgaac aatgccacca acgtggtcat caaggtgtgc gagttccagt  3720
tttgtaatga tccattcctg ggcgtgtact atcacaagaa caataagtct tggatggaga  3780
gcgagtttcg cgtgtattcc tctgccaaca attgcacatt tgaatacgtg tcccagccgt  3840
tcctgatgga cctggagggc aagcagggca atttcaagaa cctgagggag ttcgtgttta  3900
agaatatcga tggctacttc aaaatctact ccaagcacac cccaatcaac ctggtgcgcg  3960
gcctgccaca gggcttctct gccctggagc cactggtgga tctgcccatc ggcatcaaca  4020
tcacccggtt tcagacactg ctggccctgc acagaagcta cctgacacca ggcgacagct  4080
cctctggatg gaccgcagga gcagcagcct actatgtggg ctatctgcag cccaggacct  4140
tcctgctgaa gtacaacgag aatggcacca tcacagacgc cgtggattgc gccctggatc  4200
ccctgtctga gaccaagtgt acactgaaga gcttaccgt ggagaagggc atctatcaga  4260
caagcaattt cagggtgcag cctaccgagt ccatcgtgcg ctttcccaat atcacaaacc  4320
tgtgcccttt tggcgaggtg ttcaacgcaa cccgcttcgc cagcgtgtac gcctggaata  4380
ggaagcgcat ctccaactgc gtggccgact attctgtgct gtacaacagc gcctccttct  4440
ctacctttaa gtgctatggc gtgagcccca caaagctgaa tgacctgtgc tttaccaacg  4500
tgtacgccga ttccttcgtg atcaggggcg acgaggtgcg ccagatcgca ccaggacaga  4560
caggcaatat cgcagactac aattataagc tgcctgacga tttcaccggc tgcgtgatcg  4620
cctggaactc taacaatctg gatagcaaag tgggcggcaa ctacaattat ctgtaccggc  4680
tgtttagaaa gtctaatctg aagccattcg agaggacat ctccacagaa atctaccagg  4740
ccggctctac ccccctgcaat ggcgtgaagg ctttaactg ttatttccct ctgcagagct  4800
acggcttcca gccaacatat ggcgtgggct atcagcctcc cgcggtggtg gtgctgtctt  4860
ttgagctgct gcacgcacct gcaacagtgt gcggaccaaa gaagagcacc aatctggtga  4920
agaacaagtg cgtgaacttc aacttcaacg gactgaccgg aacaggcgtg ctgaccgagt  4980
ccaacaagaa gttcctgcct tttcagcagt tcggcaggga catcgcagat accacagacg  5040
ccgtcgcgca ccctcagacc ctggagatcc tggacatcac accatgctcc ttcggcggcg  5100
tgtctgtgat cacaccaggc accaatacaa gcaaccaggt ggccgtgctg tatcagggcg  5160
tgaattgtac cgaggtgcca gtggcaatcc acgcagatca gctgacccct acatggcggg  5220
tgtactctac cggcagcaac gtgttccaga caagagccgg atgcctgatc ggagcagagc  5280
acgtgaacaa tagctatgag tgcgacatcc ctatcggcgc cggcatctgt gcctcctacc  5340
agacccagac aaaactcccca gaatcaagcg tgattcctct ggtccatcca ctggcagatc  5400
cctccacagt gttcaaagac ggagatgagg ccgaagactt tgtggaagtc cacctgcctg  5460
atgtgcataa ccaggtgtct ggcgtcgacc tgggactgcc aaattggggc aagtacgtgc  5520
tgctgagtgc tggagcactg actgccctga gctgtgatcat tttcctgatg acctgctgtc  5580
ggcgcgtgaa cagaagtgag cccactcagc acaatctgcg aggaaccggg agagaagtgt  5640
cagtcacacc tcagagcggg aaaatcatta gtagttggga atcacataaa agcggggcg  5700
agaccaggct gggatccggc tccggcgagg caggggaag tctactaaca tgcggggacg  5760
tggaggaaaa tccggcccc atggttcctc aggctctcct gtttgtaccc cttctggttt  5820
ttccattgtg ttttgggaaa ttccctattt acacgatacc agacaagctt ggtccctgga  5880
gtccgattga catacatcac ctcagctgcc aaacaatttt ggtagtggag gacgaaggat  5940
gcaccaacct gtcagggttc tcctacatgg aacttaaagt tggatacatc ttagccataa  6000
aagtgaacgg gttcacttgc acaggcgttg tgacggaggc tgaaacctac actaacttcg  6060
ttggttatgt cacaaccacg ttcaaaagaa agcatttccc ccaacacca gatgcatgta  6120
gagccgcgta caactggaag atggccggtg accccagata tgaagagtct ctacacaatc  6180
cgtaccctga ctaccgctgg cttcgaactg taaaaaccac caaggagtct ctcgttatca  6240
tatctccaag tgtggcagat ttggacccat atgacagatc ccttcactcg agggtcttcc  6300
ctagcgggaa gtgctcagga gtagcggtgt cttctaccta ctgctccact aaccacgatt  6360
acaccatttg gatgcccgag aatccggac tagggatctc ttgtgacatt tttaccaata  6420
gtagagggaa gagagcatcc aaagggagtg agacttgcgg cttttgtagat gaaagaggcc  6480
tatataagtc tttaaaagga gcatgcaaac tcaagttatg tggagttcta ggacttagac  6540
ttatggatgg aacatgggtc tcgatgcaaa catcaatga aaccaaatgg tgccctcccg  6600
ataagttggt gaacctgcac gactttgcgt cagacgaaat tgagcacctt gttgtagagg  6660
agttggtcag gaagagagag gagtgtctgg atgccagtga gtccatcatg acaaccaagt  6720
cagtgagttt cagacgtctc agtcatttaa gaaaacttgt ccctgggttt ggaaaagcat  6780
ataccatatt caacaagacc ttgatggaag ccgatgctca ctacaagtca gtcgagactt  6840
ggaatgagat cctccctca aaagggtgtt aagagttgg ggaggtgt catcctcatg  6900
tgaacggggt gtttttcaat ggtataatat taggacctga cggcaatgtc ttaatcccag  6960
agatgcaatc atccctcctc cagcaacata tggagttgtt ggaatcctcg ttatccccc  7020
```

```
ttgtgcaccc cctggcagac ccgtctaccg ttttcaagga cggtgacgag gctgaggatt  7080
ttgttgaagt tcaccttccc gatgtgcaca atcaggtctc aggagttgac ttgggtctcc  7140
cgaactgggg gaagtatgta ttactgagtg caggggccct gactgccttg atgttgataa  7200
ttttcctgat gacatgttgt agaagagtca atcgatcaga acctacgcaa cacaatctca  7260
gagggacagg gagggaggtg tcagtcactc cccaaagcgg gaagatcata tcttcatggg  7320
aatcacacaa gagtggggt gagaccagac tgtaagctag cttataaagt gctgggtcat  7380
ctaagctttt cagtcgagaa aaaaacatta gatcagaaga acaactggca acacttctca  7440
acctgagact tacttcaaga tgctcgatcc tggagaggtc tatgatgacc ctattgaccc  7500
aatcgagtta gaggctgaac ccagaggaac ccccattgtc cccaacatct tgaggaactc  7560
tgactacaat ctcaactctc ctttgataga agatcctgct agactaatgt tagaatggtt  7620
aaaaacaggg aatagacctt atcggatgac tctaacagac aattgctcca ggtctttcag  7680
agttttgaaa gattatttca agaaggtaga tttgggttct ctcaaggtgg gcggaatggc  7740
tgcacagtca atgatttctc tctggttata tggtgcccac tctgaatcca acaggagccg  7800
gagatgtata acagacttgg cccatttcta ttccaagtcg tccccatag agaagctgtt  7860
gaatctcacg ctaggaaata gagggctgag aatccccca gagggagtgt taagttgcct  7920
tgagagggtt gattatgata atgcatttgg aaggtatctt gccaacacgt attcctctta  7980
cttgttcttc catgtaatca cctttatacat gaacgcccta gactgggatg aagaaaagac  8040
catcctagca ttatggaaag attaacctc agtggacatc gggaaggact tggtaaagtt  8100
caaagaccaa atatggggac tgctgatcgt gacaaaggac tttgtttact cccaaagttc  8160
caattgtctt tttgacagaa actacacact tatgctaaaa gatcttttct tgtctcgctt  8220
caactcctta atggtcttgc tctctccccc agagccccga tactcagatg acttgatatc  8280
tcaactatgc cagctgtaca ttgctgggga tcaagtcttg tctatgtgtg gaaactccgg  8340
ctatgaagtc atcaaaatat tggagccata tgtcgtgaat agtttagtcc agagagcaga  8400
aaagtttagg cctctcattc attccttggg agactttcct gtatttataa aagacaaggt  8460
aagtcaactt gaagagacgt tcggtccctg tgcaagaagg ttctttaggg ctctggatca  8520
attcgacaac atacatgact tggttttgt gtttggcttg tacaggcatt ggggggcaccc  8580
atatatagat tatcgaaagg gtctgtcaaa actatatgat caggttcacc ttaaaaaaat  8640
gatagataag tcctaccagg agtgcttagc aagcgaccta gccaggagga tccttagatg  8700
gggttttgat aagtactcca agtggtatct ggattcaaga ttcctagccc gagaccaccc  8760
cttgactcct tatatcaaaa cccaaacatg gccacccaaa catattgtag acttggtggg  8820
ggatacatgg cacaagctcc cgatcacgca gatctttgag attcctgaat caatggatcc  8880
gtcagaaata ttgatgacaa atcacattc tttcaccaga acgagactag cttcttggct  8940
gtcagaaaac cgagggggc ctgttcctag cgaaaaagtt attatcacgg ccctgtctaa  9000
gccgctgtc aatccccgag agtttctgag gtctatagac ctcggaggat tgccagatga  9060
agacttgata attggcctca agccaaagga acgggaattg aagattgaag gtcgattctt  9120
tgctctaatg tcatggaatc taagattgta ttttgtcatc actgaaaaac tcttggccaa  9180
ctacatcttg ccacttttg acgcgctgac tatgacagac aacctgaaca aggtgtttaa  9240
aaaagctgatc gacagggtca ccgggcaagg gcttttggac tattcaaggg tcacatatgc  9300
atttcacctg gactatgaaa agtggaacaa ccatcaacga ttagagtcaa cagaggattg  9360
attttctgtc ctagatcaag tgtttggatt gaagagagtg ttttctagaa cacacgagtt  9420
ttttcaaaag gcctggatct attattcaga cagatcagac ctcatcgggt tacgggagga  9480
tcaaatatac tgcttagatg cgtccaacgg cccaacctgt tggaatggcc aggatggcgg  9540
gctagaaggc ttacggcaga agggctggag tctagtcagc ttattgatga tagatagaga  9600
atctcaaatc aggaacacaa gaaccaaaat actagctcaa ggagacaacc aggttttatg  9660
tccgacatac atgttgtcgc cagggctatc tcaagagggg ctcctctatg aattggagag  9720
aatatcaagg aatgcacttt cgatatacag agccgtcgag gaaggggcat ctaagctagg  9780
gctgatcatc aagaaagaag agaccatgtg tagttatgac ttcctcatct atggaaaaac  9840
ccctttgttt agaggtaaca tattggtgcc tgagtccaaa agatgggcca gagtctcttg  9900
cgtctctaat gaccaaatag tcaacctcgc caatataatg tcgacagtgt ccaccaatgc  9960
gctaacagtg gcacaacact ctcaatcttt gatcaaaccg atgagggatt ttctgctcat  10020
gtcagtacag gcagtctttc actacctgct atttagccca atcttaaagg gaagagttta  10080
caagattctg agcgctgaag gggagagctt tctcctagcc atgtcaagga taatctatct  10140
agatccttct ttgggaggga tatctggaat gtccctcgga agattccata tacgacagtt  10200
ctcagaccct gtctctgaag ggttatcctt ctggagagag atctggttaa gctcccaaga  10260
gtcctggatt cacgcgttgt gtcaaggagc tggaaaccca gatcttggag agagaacact  10320
cgagagcttc actcgccttc tagaagatcc gaccaccta aatatcagag gagggccag  10380
tcctaccatt ctactcaagg atgcaatcag aaaggcttta tatgacgagg tggacaaggt  10440
ggaaaattca gagtttcgag aggcaatcct gttgtccaag acccatagag ataatttat  10500
actcttctta atatctgttg agcctctgtt tcctcgattt ctcagtgagc tattcagttc  10560
gtctttttg ggaatcccccg agtcaatcat tggattgata caaaactccc gaacgataag  10620
aaggcagttt agaaagagtc tctcaaaaac tttagaagaa tccttctaca actcagagat  10680
ccacgggatt agtcggatga cccagacacc tcagagggtt ggggggtgt ggccttgctc  10740
ttcagagagg gcagatctac ttaggagat ctcttgggga agaaaagtgg taggcacgac  10800
agttcctcac ccttctgaga tgttgggatt acttcccaag tcctctattt cttgcacttg  10860
tggagcaaca ggaggaggca atcctagagt ttctgtatca gtactcccgt cctttgatca  10920
gtcatttttt tcacgaggcc ccctaaaggg atacttgggc tcgtccacct ctatgtcgac  10980
ccagctattc catgcatggg aaaaagtcac taatgttcat gtggtgaaga gagctctatc  11040
gttaaaagaa tctatacact ggttcattac tagagattcc aacttggctc aagctctaat  11100
taggaacatt atgtctctga caggccctga tttccctcta gaggagccc ctgtcttcaa  11160
aaggacgggg tcagccttgc ataggttcaa gtctgccaga tacagcgaag gagggtattc  11220
ttctgtctgc ccgaacctcc tctctcatat ttctgttagt acagacacca tgtctgattt  11280
gacccaagac gggaagaact acgatttcat gttccagcca ttgatgcttt atgcacagac  11340
atggacatca gagctggtac agagagacac aaggctaaga gactctacgt ttcattggca  11400
cctccgatcc aacaggtgtg tgagcccat tgacgacggg acgctgaaga cctctcagat  11460
cttcgagttt ccggatgtgt cgaaagaat atccagaatg gtttctgggg ctgtgcctca  11520
cttcagagg cttcccgata tccgtctgag accaggagat tttgaatctc taagcggtag  11580
agaaaagtct caccatatcg gatcagctca ggggctctta tactcaatct tagtggcaat  11640
tcacgactca ggatacaatg atggaaccat cttccctgtc aacatatacg gcaaggtttc  11700
ccctagagac tatttgagag ggctcgcaag gggagtattg ataggatcct cgatttgctt  11760
```

```
cttgacaaga atgacaaata tcaatattaa tagacctctt gaattggtct caggggtaat  11820
ctcatatatt ctcctgaggc tagataacca tccctccttg tacataatgc tcagagaacc  11880
gtctcttaga ggagagatat tttctatccc tcagaaaatc cccgccgctt atccaaccac  11940
tatgaaagaa ggcaacagat caatcttgtg ttatctccaa catgtgctac gctatgagcg  12000
agagataatc acggcgtctc cagagaatga ctggctatgg atcttttcag actttagaag  12060
tgccaaaatg acgtacctat ccctcattac ttaccagtct catcttctac tccagagggt  12120
tgagagaaac ctatctaaga gtatgagaga taacctgcga caattgagtt ctttgatgag  12180
gcaggtgctg ggcgggcacg gagaagatac cttagagtca gacgacaaca ttcaacgact  12240
gctaaaagac tctttacgaa ggacaagatg ggtggatcaa gaggtgcgcc atgcagctag  12300
aaccatgact ggagattaca gccccaacaa gaaggtgtcc cgtaaggtag gatgttcaga  12360
atgggtctgc tctgctcaac aggttgcagt ctctacctca gcaaacccgg cccctgtctc  12420
ggagcttgac ataagggccc tctctaagag gttccagaac cctttgatct cgggcttgag  12480
agtggttcag tgggcaaccg gtgctcatta taagcttaag cctattctag atgatctcaa  12540
tgttttccca tctctctgcc ttgtagttgg ggacgggtca gggggggatat caagggcagt  12600
cctcaacatg tttccagatg ccaagcttgt gttcaacagt cttttagagg tgaatgacct  12660
gatggcttcc ggaacacatc cactgcctcc ttcagcaatc atgaggggag gaaatgatat  12720
cgtctccaga gtgatagatc ttgactcaat ctgggaaaaa ccgtccgact tgagaaactt  12780
ggcaacctgg aaatacttcc agtcagtcca aaagcaggtc aacatgtcct atgacctcat  12840
tatttgcgat gcagaagtta ctgacattgc atctatcaac cggatcaccc tgttaatgtc  12900
cgattttgca ttgtctatag atggaccact ctatttggtc ttcaaaactt atgggactat  12960
gctagtaaat ccaaactaca aggctattca acacctgtca agagcgttcc cctcggtcac  13020
agggtttatc acccaagtaa cttcgtcttt ttcatctgag ctctacctcc gattctccaa  13080
acgagggaag tttttcagag atgctgagta cttgacctct tccacccttc gagaaatgag  13140
ccttgtgtta ttcaattgta gcagccccaa gagtgagatg cagagagctc gttccttgaa  13200
ctatcaggat cttgtgagag gatttcctga agaaatcata tcaaatcctt acaatgagat  13260
gatcataact ctgattgaca gtgatgtaga atcttttcta gtccacaaga tggttgatga  13320
tcttgagtta cagaggggaa ctctgtctaa agtggctatc attatagcca tcatgatagt  13380
tttctccaac agagtcttca acgtttccaa acccctaact gacccctcgt tctatccacc  13440
gtctgatccc aaaatcctga ggcacttcaa catatgttgc agtactatga tgtatctatc  13500
tactgcttta ggtgacgtcc ctagcttcgc aagacttcac gacctgtata acagacctat  13560
aacttattac ttcagaaagc aagtcattcg agggaacgtt tatctatctt ggagttggtc  13620
caacgacacc tcagtgttca aaagggtagc ctgtaattct agcctgagtc tgtcatctca  13680
ctggatcagg ttgatttaca agatagtgaa gactaccaga ctcgttggca gcatcaagga  13740
tctatccaga gaagtggaaa gacaccttca taggtacaac aggtggatca ccctagagga  13800
tatcagatct agatcatccc tactagacta cagttgcctg tgaaccggat actcctggaa  13860
gcctgcccat gctaagactc ttgtgtgatg tatcttgaaa aaaacaagat cctaaatctg  13920
aacctttggt tgtttgattg tttttctcat tttgttgtt tatttgttaa gcgt        13974
```

```
SEQ ID NO: 16          moltype = DNA  length = 13881
FEATURE                Location/Qualifiers
misc_feature           1..13881
                       note = RABV vector: Coravax V6 China
source                 1..13881
                       mol_type = other DNA
                       organism = synthetic construct
SEQUENCE: 16
acgcttaaca accagatcaa agaaaaaaca gacattgtca attgcaaagc aaaaatgtaa  60
cacccctaca atggatgccg acaagattgt attcaaagtc aataatcagg tggtctcttt  120
gaagcctgag attatcgtgg atcaatatga gtacaagtac cctgccatca aagatttgaa  180
aaagccctgt ataaccctag gaaaggctcc cgatttaaat aaagcataca agtcagtttt  240
gtcaggcatg agcgccgcca aacttaatcc tgacgatgta tgttcctatt tggcagcggc  300
aatgcagttt tttgagggga catgtccgga agactggacc agctatggaa ttgtgattgc  360
acgaaaagga gataagatca ccccaggttc tctggtggag ataaaacgta ctgatgtaga  420
agggaattgg gctctgacag gaggcatgga actgacaaga gaccccactg tccctgagca  480
tgcgtcctta gtcggtcttc tcttgagtct gtataggttg agcaaaatat ccgggcaaaa  540
cactggtaac tataagacaa acattgcaga caggatagag cagatttttg agacagcccc  600
ttttgttaaa atcgtggaac accatactct aatgacaact cacaaaatgt gtgctaattg  660
gagtactata ccaaacttca gatttttggc cggaacctat gacatgtttt tctcccggat  720
tgagcatcta tattcagcaa tcagagtggg cacagttgtc actgcttatg aagactgttc  780
aggactggta tcatttactg ggttcataaa acaaatcaat ctcaccgcta gagaggcaat  840
actatatttc ttccacaaga actttgagga agagataaga agaatgtttg agccagggca  900
ggagacagct gttcctcact cttatttcat ccacttccgt tcactaggct tgagtgggaa  960
atctccttat tcatcaaatg ctgttggtca cgtgttcaat ctcattcact ttgtaggatg  1020
ctatatgggt caagtcagat ccctaaatgc aacggttatt gctgcatgtg ctcctcatga  1080
aatgtctgtt ctagggggct atctgggaga ggaattcttc gggaaaggga catttgaaag  1140
aagattcttc agagatgaga aagaacttca agaatacgag gcggctgaac tgacaaagac  1200
tgacgtagca ctggcagatg atggaactgt caactctgac gacgaggact acttttcagg  1260
tgaaaccaga agtccggagg ctgtttatac tcgaatcatg atgaatggag gtcgactaaa  1320
gagatctcac atacggagat atgtctcagt cagttccaat catcaagccc gtccaaactc  1380
attcgccgag tttctaaaca agacatattc gagtgactca taagaagttg aataacaaaa  1440
tgccggaaat ctacggattg tgtatatcca tcatgaaaaa aactaacacc cctcctttcg  1500
aaccatccca aacatgagca agatctttgt caatcctagt gctattagag ccggtctggc  1560
cgatcttgag atggctgaag aaactgttga tctgatcaat agaaatatcg aagacaatca  1620
ggctcatctc caaggggaac ccatagaggt ggacaatctc cctgaggata tggggcgact  1680
tcacctggat gatggaaaat cgcccaacca tggtgagata gccaaggtgg gagaaggcaa  1740
gtatcgagag gactttcaga tggatgaagg agaggatcct agcttcctgt tccagtcata  1800
cctggaaaat gttggagtcc aaatagtcag acaaatgagg tcaggagaga gatttctcaa  1860
gatatggtca cagaccgtag aagagattat atcctatgtc gcggtcaact ttcccaaccc  1920
tccaggaaag tcttcagagg ataaatcaac ccagactact ggccgagagc tcaagaagga  1980
```

```
gacaacaccc actccttctc agagagaaag ccaatcatcg aaagccagga tggcggctca    2040
aattgcttct ggccctccag cccttgaatg gtcggctacc aatgaagagg atgatctatc    2100
agtggaggct gagatcgctc accagattgc agaaagtttc tccaaaaaat ataagtttcc    2160
ctctcgatct tcaggatact tcttgtataa ttttgagcaa ttgaaaatga accttgatga    2220
tatagttaaa gaggcaaaaa atgtaccagg tgtgacccgt ttagcccatg acgggtccaa    2280
actccccta agatgtgtac tgggatgggt cgctttggcc aactctaaga aattccagtt    2340
gttagtcgaa tccgacaagc tgagtaaaat catgcaagat gacttgaatc gctatacatc    2400
ttgctaaccg aacctctccc ctcagtccct ctagacaata aaatccgaga tgtcccaaag    2460
tcaacatgaa aaaaacaggc aacaccactg ataaaatgaa cctcctacgt aagatagtga    2520
aaaaccgcag ggacgaggac actcaaaaat cctctcccgc gtcagcccct ctggatgacg    2580
atgacttgtg gcttccaccc cctgaatacg tcccgctgaa agaacttaca ggcaagaaga    2640
acatgaggaa cttttgtatc aacggaaggg ttaaagtgtg tagcccgaat ggttactcgt    2700
tcaggatcct gcggcacatt ctgaaatcat tcgacgagat atattctggg aatcatagga    2760
tgatcgggtt agtcaaagtg gttattggac tggctttgtc aggatctcca gtccctgagg    2820
gcctgaactg ggtatacaaa ttgaggagaa cctttatctt ccagtgggct gattccaggg    2880
gccctcttga aggggaggag ttggaatact ctcaggagat cacttgggat gatgatactg    2940
agttcgtcgg attgcaaata agagtgattg caaaacagtg tcatatccag ggcagagtct    3000
ggtgtatcaa catgaacccg agagcatgtc aactatggtc tacatgtct cttcagacac    3060
aaaggtccga agaggacaaa gattcctctc tgcttctaga ataatcagat tatatcccgc    3120
aaatttatca cttgtttacc tctggaggag agaacatatg ggctcaactc caaccctttgg   3180
gagcaatata acaaaaaaca tgttatggtg ccattaaacc gctgcattc atcaaagtca    3240
agttgattac ctttacattt tgatcctctt ggatgtgaaa aaaactatta acatccctca    3300
aaagaccccg ggaagatgg ttcctcaggc tctcctgttt gtaccccttc tggttttttcc   3360
attgtgtttt gggaaattcc ctatttacac gataccagac aagcttggtc cctggagtcc    3420
gattgacata catcacctca gctgcccaaa caatttggta gtggaggacg aaggatgcac    3480
caacctgtca gggttctcct acatggaact taaagttgga tacatcttag ccataaaagt    3540
gaacgggttc acttgcacag gcgttgtgac ggaggctgaa acctacacta acttcgttgg    3600
ttatgtcaca accacgttca aaagaaagca tttccgccca acaccagatg catgtagagc    3660
cgcgtacaac tggaagatgg ccggtgaccc cagatatgaa gagtctctac acaatccgta    3720
ccctgactac cgctggcttc gaactgtaaa aaccaccaag gagtcctctcg ttatcatatc    3780
tccaagtgtg gcagatttgg acccatatga cagatccctt cactcgaggg tcttccctag    3840
cgggaagtgc tcaggagtag cggtgtcttc tacctactgc tccactaacc acgattacac    3900
catttggatg cccgagaatc cgagactagg gatgtcttgt gacatttta ccaatagtag     3960
agggaagaga gcatccaaag ggagtgagac ttgcggcttt gtagatgaaa gaggcctata    4020
taagtcttta aaaggagcat gcaaactcaa gttatgtgga gttctaggac ttagacttat    4080
ggatggaaca tgggtctcga tgcaaacatc aaatgaaacc aaatggtgcc ctcccgataa    4140
gttggtgaac ctgcacgact ttcgctcaga cgaaattgag caccttgttg tagaggagtt    4200
ggtcaggaag agagaggagt gtctggatgc actagagtcc atcatgacaa ccaagtcagt    4260
gagtttcaga cgtctcagtc atttaagaaa acttgtccct gggtttggaa aagcatatac    4320
catattcaac aagaccttga tggaagccga tgctcactac aagtcagtcg agacttggaa    4380
tgagatcctc ccttcaaaag ggtgtttaag agttggggg aggtgtcatc ctcatgtgaa     4440
cggggtgttt ttcaatggta taatattagg acctgacggg aatgtcttaa tcccagagat    4500
gcaatcatcc ctcctccagc aacatatgga gttgttggaa tcctcggtta tcccccttgg    4560
gcaccccctg gcagaccccg ctaccgtttt caaggacggt gacgaggctg aggattttgt    4620
tgaagttcac cttcccgatg tgcacaatca ggtctcagga gttgacttgg gtctcccgaa    4680
ctggggggaag tatgtattac tgagtgcagg ggccctgact gccttgatgt tgataatttt    4740
cctgatgca tgttgtagaa gagtcaatcg atcagaacct acgcaacaca atctcagagg    4800
gacagggagg gaggtgtcag tcactcccca aagcgggaag atcatatctt catgggaatc    4860
acacaagagt gggggtgaga ccagactgta attaattaac gtcctttcaa cgatccaagt    4920
ccatgaaaaa aactaacacc cctcccgtac gaccatgttc gtgtttctgg tgctgctgcc    4980
tctggtgagc tcccagtgcg tgaacctgac cacaaggacc cagctgcccc ctgcctatac    5040
caattccttc acacggggcg tgtactatcc cgacaaggtg ttccggagca gcgtgctgca    5100
ctccacacag gatctgtttc tgcctttctt ttctaacgtg acctggttcc acgccatcca    5160
cgtgagcggc accaatggca caaagcggtt cgacaatcca gtgctgccct taacgatgg    5220
cgtgtacttc gcctccaccg agaagtctaa catcatcaga ggctggatct ttggcaccac    5280
actggacagc aagacacagt ccctgctgat cgtgaacaat gccaccaacg tggtcatcaa    5340
ggtgtgcgag ttccagtttt gtaatgatcc attcctgggc gtgtactatc acaagaacaa    5400
taagtcttgg atggagagcg agtttcgcgt gtattcctct gccaacaatt gcacatttga    5460
gtacgtgtcc cagcccttcc tgatggacct ggagggcaag cagggcaatt tcaagaacct    5520
gagggagttc gtgtttaaga atatcgatgg ctacttcaaa atctactcca agcacacccc    5580
aatcaacctg gtgcgcgacc tgccacaggg ctttctctgcc ctggagccac tggtggatct    5640
gcccatcggc atcaacatca cccggtttca gacactgctg gccctgcaca gaagctacct    5700
gacaccaggc gacagctcct ctggatggac cgcaggagca gcagcctact atgtgggcta    5760
tctgcagccc aggaccttcc tgctgaagta caacgagaat ggcaccatca cagacgccgt    5820
ggattgcgcc ctggatcccc tgtctgagac caagtgtaca ctgaagagct ttaccgtgga    5880
gaagggcatc tatcagacaa gcaatttcag ggtgcagcct accgagtcca tcgtgcgctt    5940
tcccaatatc acaaacctgt gccctttgg cgaggtgttc aacgcaaccc gcttcgccag    6000
cgtgtacgcc tggaataggga agcgcatctc caactgcgtg gccgactatt ctgtgctgta    6060
caacagcgcc tccttctcta cctttaagtg ctatggagtgt ccccacaaa agctgaatga    6120
cctgtgcttt accaacgtgt acgccgattc cttcgtgatc aggggcgacg aggtgcgcca    6180
gatcgcacca ggacagacag gcaagatcgc agactacaat tataagctgc ctgacgattt    6240
caccggctgc gtgatcgcct ggaactctaa caatctggat agcaaagtgg gcggcaacta    6300
caattatctg taccggctgt ttagaaagtc taatctgaag ccattcgaga gggacatctc    6360
cacagaaatc taccaggccg gctctacccc gtgcaatggg gttgagggct ttaactgtta    6420
tttccctctg cagagctacg gcttccagcc aacaaacggc gtgggctatc agccctaccg    6480
cgtggtggtg ctgtctttg agctgctgca cgcacctgca cagtgtgcg gaccaaagaa    6540
gagcaccaat ctggtgaaga acaagtgcgt gaacttcaac ttcaacggac tgaccggaac    6600
aggcgtgctg accgagtcca acaagaagtt cctgcctttt cagcagttcg gcagggacat    6660
cgcagatacc acagacgccg tgcgcgaccc tcagaccctg gagatcctgg acatcacacc    6720
```

```
atgctccttc ggcggcgtgt ctgtgatcac accaggcacc aatacaagca accaggtggc   6780
cgtgctgtat caggacgtga attgtaccga ggtgccagtg gcaatccacg cagatcagct   6840
gaccoctaca tggcgggtgt actctaccgg cagcaacgtg ttccagacaa gagccggatg   6900
cctgatcgga gcagagcacg tgaacaatag ctatgagtgc gacatcccta tcggcgccgg   6960
catctgtgcc tcctaccaga cccagacaaa ctccccaagg tctgtgggag atgaggccga   7020
agactttgtg gaagtccacc tgcctgatgt gcataaccag gtgtctggcg tcgacctggg   7080
actgccaaat tggggcaagt acgtgctgct gagtgctgga gcactgactg ccctgatgct   7140
gatcattttc ctgatgacct gctgtcggcg cgtgaacaga agtgagccca ctcagcacaa   7200
tctgcgagga accgggagag aagtgtcagt cacacctcag agcgggaaaa tcattagtag   7260
ttgggaatca cataaaagcg ggggcgagac caggctggga tccggctccg gcgagggcag   7320
gggaagtcta ctaacatgcg gggacgtgga ggaaaatccc ggcccatgc tcgatcctgg   7380
agaggtctat gatgacccta ttgacccaat cgagttagag gctgaaccca gaggaacccc   7440
cattgtcccc aacatcttga ggaactctga ctacaatctc aactctcctt tgatagaaga   7500
tcctgctaga ctaatgttag aatggttaaa aacagggaat agaccttatc ggatgactct   7560
aacagacaat tgctccaggt cttttcagagt tttgaaagat tatttcaaga aggtagattt   7620
gggttctctc aaggtgggcg gaatggctgc acagtcaatg attttctctct ggttatatgg   7680
tgcccactct gaatccaaca ggagccggag atgtataaca gacttggccc atttctattc   7740
caagtcgtcc cccatagaga agctgttgaa tctcacgcta ggaaatagag ggctgagaat   7800
cccccagag ggagtgttaa gttgccttga gagggttgat tatgataatg catttggaag   7860
gtatcttgcc aacacgtatt cctcttactt gttcttccat gtaatcacct tatacatgaa   7920
cgccctagac tgggatgaag aaaagaccat cctagcatta tggaaagatt taacctcagt   7980
ggacatcggg aaggacttgg taagttcaa agaccaaata tgggactgc tgatcgtgac   8040
aaaggacttt gtttactccc aaagttccaa ttgtcttttt gacagaaact acacacttat   8100
gctaaaagat cttttcttgt ctcgcttcaa ctccttaatg gtcttgctct ctccccccaga  8160
gccccgatac tcagatgact tgatatctca actatgccag ctgtacattg ctggggatca   8220
agtcttgtct atgtgtggaa actccggcta tgaagtcatc aaaatattgg agccatatgt   8280
cgtgaatagt ttagtccaga gagcagaaaa gtttaggcct ctcattcatt ccttgggaga   8340
ctttcctgta tttataaaag acaaggtaag tcaacttgaa gagacgttcg gtccctgtgc   8400
aagaaggttc tttagggctc tggatcaatt cgacaacata catgacttgg tttttgtgtt   8460
tggctgttac aggcattggg ggcacccata tagattat cgaaagggtc tgtcaaaact   8520
atatgatcag gttcacctta aaaaaatgat agataagtcc taccaggagt gcttagcaag   8580
cgacctagcc aggaggatcc ttagatgggg ttttgataag tactccaagt ggtatctgga   8640
ttcaagattc ctagcccgag accaccccctt gactccttat atcaaaaccc aaacatggcc   8700
acccaaacat atttgtagact tggtggggga tacatgccaa aagtcccga tcacgcagat   8760
ctttgagatt cctgaatcaa tggatccgtc agaaatattg gatgacaaat cacattcttt   8820
caccagaacg agactagctt cttggctgtc agaaaaccga gggggcctg ttcctagcga   8880
aaaagttatt atcacggccc tgtctaagcc gcctgtcaat ccccgagagt ttctgaggtc   8940
tatagacctc ggaggattgc cagatgaaga cttgataatt ggcctagc caaaggaacg   9000
ggaattgaag attgaaggtc gattctttgc tctaatgtca tggaatctaa gattgtattt   9060
tgtcatcact gaaaaactct tggccaacta catcttgcca cttttgacg cgctgactat   9120
gacagacaac ctgaacaagg tgtttaaaaa gctgatcgac agggtcaccg ggcaagggct   9180
tttgactat tcaagggtca catatgcatt tcacctggca tatgaaaagt ggaacaacca   9240
tcaaagatta gagtcaacag aggatgtatt ttctgtccta atcaagtgt ttggattgaa   9300
gagagtgttt tctagaacac acgagttttt tcaaaaggcc tggatctatt attcagacag   9360
atcagacctc atcgggttac gggaggatca aatatactgc ttagatgcgt ccaacggccc   9420
aacctgttgg aatggccagg atggcgggct agaaggctta cggcagaagg gctggagtct   9480
agtcagctta ttgatgatag atagagaatc tcaaatcagg aacacaagaa ccaaaatact   9540
agctcaagga gacaaccagg ttttatgtcc gacatacatg ttgtcgccag ggctatctca   9600
agaggggctc ctctatgaat tggagagaat atcaaggaat gcactttcga tatacagagc   9660
cgtcgaggaa ggggcatcta agctagggct gatcatcaag aaagaagaga ccatgtgtag   9720
ttatgactc ctcatctatg gaaaaacccc tttgtttaga ggtaacatat tggtgcctga   9780
gtccaaaaga tgggcagag tctcttgcgt ctctaatgac caaatagtca acctcgccaa   9840
tataatgtcg acagtgtcca ccaatgcgct aacagtggca caacactctc aatctttgat   9900
caaaccgatg agggattttc tgctcatgtc agtacaggca gtctttcact acctgctatt   9960
tagcccaatc ttaaagggaa gagtttacaa gattctgagc gctgaaggga agagctttct  10020
cctagccatg tcaaggataa tctatctaga tccttcttg ggagggatat ctggaatgtc  10080
cctcggaaga ttccatatac gacagttctc agacccgtc tctgaagggt atccttctg  10140
gagagagatc tggttaagct cccaagagtc ctggattcac gcgttgtgtc aagaggctgg  10200
aaacccagat cttggagaga gaacactcga gagcttcact cgccttctag aagatccgca  10260
caccttaaat atcagaggag gggccagtcc taccattcta ctcaaggatg caatcagaaa  10320
ggctttatat gacgaggtgg acaaggtgga aaattcagag tttcgagagg caatcctgtt  10380
gtccaagacc catagagata atttttatact cttcttaata tctgttgagc ctctgttcc  10440
tcgatttctc agtgagctat tcagttcgtc tttttttggga atcccgagt caatcattgg  10500
attgatacaa aactcccgaa cgataagaag gcagtttaga aagagtctct caaaaacttt  10560
agaagaatcc ttctcaaact cagagatcca cgggattagt cggatgaccc agacacctca  10620
gagggttggg gggtgtggc cttgctcttc agagagggca gatctactta gggagatctc  10680
ttggggaaga aaagtggtag gcacgacagt tcctcaccct tctgagatgt tgggattact  10740
tcccaagtcc tctatttctt gcacttgtgg agcaacagga ggaggcaatc ctagagtttc  10800
tgtatcagta ctcccgtcct ttgatcagtc attttttca gaggccccc taaagggata  10860
cttgggctcg tccacctcta tgtcgaccca gctattccat gcatgggaaa agtcactaa  10920
tgttcatgtg gtgaagagag ctctatcgtt aaaagaatct ataaactggt tcattactag  10980
agattccaac ttggctcaag ctctaattag gaacattatg tctctgacag gccctgtttt  11040
ccctctagag gaggcccctg tcttcaaaag gacggggtca gccttgcata ggttcaagtc  11100
tgccagatac agcgaaggag ggtattcttc tgtctgccca aacctcctct ctcatatttc  11160
tgttagtaca gacaccatgt ctgatttgac ccaagacggg aagaactacg atttcatgtt  11220
ccagccattg atgcttatg cacagacatg gacatcagag ctggtacaga gagacacaag  11280
gctaagagac tctacgtttc attggcacct ccgatgcaac aggtgtgtga cacccattga  11340
cgacgtgacc ctggagacct ctcagatctt cgagtttccg gatgtgtcga aagaatatc  11400
cagaatggtt tctggggctg tgcctcactt ccagaggctt cccgatatcc gtctgagacc  11460
```

-continued

```
aggagatttt gaatctctaa gcggtagaga aaagtctcac catatcggat cagctcaggg    11520
gctcttatac tcaatcttag tggcaattca cgactcagga tacaatgatg gaaccatctt    11580
ccctgtcaac atatacggca aggtttcccc tagagactat ttgagagggc tcgcaagggg    11640
agtattgata ggatcctcga tttgcttctt gacaagaatg acaaatatca atattaatag    11700
acctcttgaa ttggtctcag gggtaatctc atatattctc ctgaggctag ataaccatcc    11760
ctccttgtac ataatgctca gagaaccgtc tcttagagga gagatatttt ctatccctca    11820
gaaaatcccc gccgcttatc caaccactat gaaagaaggc aacagatcaa tcttgtgtta    11880
tctccaacat gtgctacgct atgagcgaga gataatcacg cgctctccag agaatgactg    11940
gctatggatc ttttcagact ttagaagtgc caaaatgacg tacctatccc tcattactta    12000
ccagtctcat cttctactcc agagggttga gagaaaccta tctaagagta tgagagataa    12060
cctgcgacaa ttgagttctt tgatgaggca ggtgctgggc gggcacggag aagatacctt    12120
agagtcagac gacaacattc aacgactgct aaaagactct ttacgaagga caagatgggt    12180
ggatcaagag gtgcgccatg cagctagaac catgactgga gattacagcc ccaacaagaa    12240
ggtgtcccgt aaggtaggat gttcagaatg ggtctgctct gctcaacagg ttgcagtctc    12300
tacctcagca aacccggccc ctgtctcgga gcttgacata agggccctct ctaagaggtt    12360
ccagaaccct ttgatctcgg gcttgagagt ggttcagtgg gcaaccggtg ctcattataa    12420
gcttaagcct attctagatg atctcaatgt ttttcccatct ctctgccttg tagttgggga    12480
cgggtcaggg gggatatcaa gggcagtcct caacatgttt ccagatgcca agcttgtgtt    12540
caacagtctt ttagaggtga atgacctgat ggcttccgga acacatccac tgcctccttc    12600
agcaatcatg aggggaggaa atgatatcgt ctccagagtg atagatcttg actcaatctg    12660
ggaaaaaccg tccgacttga gaaacttggc aacctgaaaa tacttccagt cagtccaaaa    12720
gcaggtcaac atgtcctatg acctcattat ttgcgatgca gaagttactg acattgcatc    12780
tatcaaccgg atcaccctgt taatgtccga ttttgcattg tctatagatg gaccactcta    12840
tttggtcttc aaaacttatg ggactatgct agtaaatcca aactacaagg ctattcaaca    12900
cctgtcaaga gcgttcccct cggtcacagg gtttatcacc caagtaactt cgtcttttc     12960
atctgagctc tacctccgat tctccaaacg agggaagttt ttcagagatg ctgagtactt    13020
gacctcttcc acccttcgag aaatgagcct tgtgttattc aattgtagca gcccccaagg    13080
tgagatgcag agagctcgtt ccttgaacta tcaggatctt gtgagaggat ttcctgaaga    13140
aatcatatca aatccttaca atgagatgat cataactctg attgacagtg atgtagaatc    13200
ttttctagtc cacaagatgg ttgatgatct tgagttacga aggggaactc tgtctaaagt    13260
ggctatcatt atagccatca tgatagtttt ctccaacaga gtcttcaacg tttccaaacc    13320
cctaactgac ccctcgttct atccaccgtc tgatcccaaa atcctgaggc acttcaacat    13380
atgttgcagt actatgatgt atctatctac tgctttaggt gacgtcccta gcttcgcaag    13440
acttcacgac ctgtataaca gacctataac ttattacttc agaaagcaag tcattcgagg    13500
gaacgtttat ctatcttgga gttggtccaa cgacacctca gtgttcaaaa gggtagcctg    13560
taattctagc ctgagtctgt catctcactg gatcaggttg atttacaaga tagtgaagac    13620
taccagactc gttggcagca tcaaggatct atccagagaa gtggaaagac accttcatag    13680
gtacaacagg tggatcaccc tagaggatat cagatctaga tcatccctac tagactacag    13740
ttgcctgtga accggatact cctggaagcc tgccatgct aagactcttg tgtgatgtat      13800
cttgaaaaaa acaagatcct aaatctgaac cttttggttgt ttgattgttt ttctcatttt    13860
tgttgtttat ttgttaagcg t                                              13881
```

| SEQ ID NO: 17 | moltype = DNA length = 13932 |
| --- | --- |
| FEATURE | Location/Qualifiers |
| misc_feature | 1..13932 |
| | note = RABV vector: Coravax V6 South Africa |
| source | 1..13932 |
| | mol_type = other DNA |
| | organism = synthetic construct |

SEQUENCE: 17

```
acgcttaaca accagatcaa agaaaaaaca gacattgtca attgcaaagc aaaaatgtaa      60
caccccctaca atggatgccg acaagattgt attcaaagtc aataatcagg tggtctcttt    120
gaagcctgag attatcgtgg atcaaatga gtacaagtac cctgccatca aagatttgaa     180
aaagccctgt ataaccctag gaaaggctcc cgatttaaat aaagcataca agtcagtttt    240
gtcaggcatg agcgccgcca aacttaatcc tgacgatgta tgttcctatt tggcagcggc    300
aatgcagttt tttgagggga catgtccgga agactggacc agctatgaa ttgtgattgc     360
acgaaaagga gataagatca ccccaggttc tctggtggag ataaaacgta ctgatgtaga    420
agggaattgg gctctgacag gaggcatgga actgacaaga gaccccactg tccctgagca    480
tgcgtcctta gtcggtcttc tcttgagtct gtataggttg agcaaaaatat ccgggcaaaa   540
cactggtaac tataagacaa acattgcaga caggatagag cagatttttg agacagcccc    600
ttttgttaaa atcgtggaac accatactct aatgacaact cacaaaatgt gtgctaattg    660
gagtactata ccaaacttca gattttttggc cggaacctat gacatgttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga agagataaga agaatgtttg agccagggca    900
ggagacagct gttcctcact cttatttcat ccacttccgt tcactaggct tgagtgggaa    960
atctcgcttat tcatcaaatg ctgttggtca cgtgttcaat ctcattcact tgtaggatg    1020
ctatatgggt caagtcagat ccctaaatgc aacggttatt gctgcatgtg ctcctcatga    1080
aatgtctgtt ctaggggggct atctgggaga ggaattcttc gggaaaggga cattgaaag    1140
aagattcttc agagatgaga aagaacttca agaatacgag gcggctgaac tgacaaagac    1200
tgacgtagca ctgcagatg atggaactgt caactctgac gacgaggact acttttcagg    1260
tgaaaccaga agtccggagg ctgttttatac tcgaatcatg atgaatggag tcgactaaa    1320
gagatctcac atacggagat atgtctcagt cagttccaat catcaagccc gtccaaactc    1380
attcgccgag tttctaaaca agacatattc gagtgactca taagaagttg aataacaaaa    1440
tgccggaaat ctacggattg tgtatatcca tcatgaaaaa aactaacacc ctcctttcg     1500
aaccatccca aacatgagca agatctttgt caatcctagt gctattagag ccggtctggc    1560
cgatcttgag atggctgaag aaactgttga tctgatcaat agaaatatcg aagacaatca    1620
ggctcatctc caagggaac ccatagaggt ggacaatctc cctgaggata tggggcgact    1680
tcacctggat gatggaaaat cgcccaacca tggtgagata gccaaggtgg agaagggcaa    1740
```

```
gtatcgagag gactttcaga tggatgaagg agaggatcct agcttcctgt tccagtcata  1800
cctggaaaat gttggagtcc aaatagtcag acaaatgagg tcaggagaga gatttctcaa  1860
gatatggtca cagaccgtag aagagattat atcctatgtc gcggtcaact ttcccaaccc  1920
tccaggaaag tcttcagagg ataaatcaac ccagactact ggccgagagc tcaagaagga  1980
gacaacaccc actccttctc agagagaaag ccaatcatcg aaagccagga tggcggctca  2040
aattgcttct ggccctccag cccttgaatg gtcggctacc aatgaagagg atgatctatc  2100
agtggaggct gagatcgctc accagattgc agaaagtttc tccaaaaaat ataagtttcc  2160
ctctcgatcc tcaggatac  tcttgtataa ttttgagcaa ttgaaaatga accttgatga  2220
tatagttaaa gaggcaaaaa atgtaccagg tgtgaccgt  ttagcccatg acgggtccaa  2280
actccccta  agatgtgtac tgggatgggt cgctttggcc aactctaaga aattccagtt  2340
gttagtcgaa tccgacaagc tgagtaaaat catgcaagat gacttgaatc gctatacatc  2400
ttgctaaccg aacctctccc ctcagtccct ctagacaata aaatccgaga tgtcccaaag  2460
tcaacatgaa aaaacaggc  aacaccactg ataaaatgaa cctcctacgt aagatagtga  2520
aaaaccgcag ggacgaggac actcaaaaat cctctcccgc gtcagcccct ctggatgacg  2580
atgacttgtg gcttccaccc cctgaatacg tcccgctgaa agaacttaca ggcaagaaga  2640
acatgaggaa cttttgtatc aacggaaggg ttaaagtgtg tagcccgaat ggttactcgt  2700
tcaggatcct gcggcacatt ctgaaatcat tcgacgagat atattctggg aatcatagga  2760
tgatcgggtt agtcaaagtg gttattggac tggctttgtc aggatctcca tcccctgagg  2820
gcctgaactg gtatacaaaa ttgaggagaa cctttatctt ccagtgggct gattccaggg  2880
gccctcttga agggaggag  ttggaatact ctcaggagat cacttgggat gatgatactg  2940
agttcgtcgg attgcaaata agagtgattg caaaacagtg tcatatccag ggcagagtct  3000
ggtgtatcaa catgaacccg agagcatgtc aactatggtc tgacatgtct cttcagacac  3060
aaaggtccga agaggacaaa gattcctctc tgcttctaga ataatcagat tatatcccgc  3120
aaatttatca cttgtttacc tctggaggag agaacatatg ggctcaactc caaccctgg   3180
gagcaatata acaaaaaaca tgttatgtg  ccattaaacc gctgcatttc atcaaagtca  3240
agttgattac ctttacattt tgatcctctt ggatgtgaaa aaactatta  acatccctca  3300
aaagaccccg ggaaagatgg ttcctcaggc tctcctgttt gtaccccttc tggttttttcc 3360
attgtgtttt gggaaattcc ctatttacac gataccagac aagcttggtc cctggagtcc  3420
gattgacata catcacctca gctgcccaaa caatttggta gtggaggacg aaggatgcac  3480
caacctgtca gggttctcct acatggaact taaagttgga tacatcttag ccataaaagt  3540
gaacgggttc acttgcacag gcgttgtgac ggaggctgaa acctacacta acttcgttga  3600
ttatgtcaca accacgttca aaagaaagca tttccgccca acaccagatg catgtagagc  3660
cgcgtacaac tggaagatgg ccggtgaccc cagatatgaa gagtctctac acaatccgta  3720
ccctgactac cgctggcttc gaactgtaaa aaccaccaag gagtcctctcg ttatcatatc  3780
tccaagtgtg gcagatttgg acccatatga cagatcccct cactcgaggg tcttccctag  3840
cgggaagtgc tcaggagtag cggtgtcttc tacctactgc tccactaacc acgattacac  3900
catttggatg cccgagaatc cgagactagg gatgtcttgt gacatttttta ccaatagtag  3960
agggaagaga gcatccaaag ggagtgagac ttgcggcttt gtagatgaaa gaggcctata  4020
taagtcttta aaaggagcat gcaaactcaa gttatgtgga gttctaggac ttagacttat  4080
ggatggaaca tgggtctcga tgcaaacatc aaatgaaacc aaatggtgcc ctcccgataa  4140
gttggtgaac ctgcacgact ttcgctcaga cgaaattgag caccttgttg tagaggagtt  4200
ggtcaggaag agagaggagt gtctggatgc actagagtcc atcatgacaa ccaagtcagt  4260
gagtttcaga cgtctcagtc atttaagaaa acttgtccct gggtttggaa aagcatatac  4320
catattcaac aagaccttga tggaagccga tgctcactac aagtcagtcg agacttggaa  4380
tgagatcctc ccttcaaaag ggtgtttaag agttgggggg aggtgtcatc ctcatgtgaa  4440
cggggtgttt ttcaatggta taatattagg acctgacggc aatgtcttaa tcccagagat  4500
gcaatcatcc ctcctccagc aacatatgga gttgttggaa tcctcggtta tccccctttgt 4560
gcaccccctg gcagaccgt  ctaccgttttt caaggacggt gacgaggctg aggattttgt  4620
tgaagttcac cttcccgatg tgcacaatca ggtctcagga gttgacttgg gtctcccgaa  4680
ctggggggaag tatgtattac tgagtgcagg ggccctgact gccttgatgt tgataatttt  4740
cctgatgaca tgttgtagaa gagtcaatcg atcagaacct acgcaacaca atctcagagg  4800
gacagggagg gaggtgtcag tcactcccca aagcgggaag atcatatctt catgggaatc  4860
acacaagagt gggggtgaga ccagactgta attaattaac gtccttttcaa cgatccaagt  4920
ccatgaaaaa aactaacacc cctcccgtac gaccatgttc gtgtttctgg tgctgctgcc  4980
tctggtgagc tcccagtgcg tgaacttcac cacaaggacc cagctgcccc ctgcctatac  5040
caattccttc acacggggcg tgtactatcc cgacaaggtg ttccggagca gcgtgctgca  5100
ctccacacag gatctgtttc tgcctttctt ttctaacgtg acctggttcc acgccatcca  5160
cgtgagcggc accaatggca caaagcggtt cgccaatcca gtgctgccct taacgatgg   5220
cgtgtacttc gcctccaccg agaagtctaa catcatcaga ggctggatct ttggcaccat  5280
actggacagc aagacacagt ccctgctgat cgtgaacaat gccaccaacg tggtcatcaa  5340
ggtgtgcgag ttccagtttt gtaatgatcc attcctgggc gtgtactatc acaagaacaa  5400
taagtcttgg atggagagcg agtttcgcgt gtattcctct gccaacaatt gcacatttga  5460
gtacgtgtcc cagcccttcc tgatggacct ggagggcaag cagggcaatt tcaagaacct  5520
gagggagttc gtgtttaaga atatcgatgg ctacttcaaa atctactcca agcacacacc  5580
aatcaacctg gtgcgcggcc tgccacaggg cttctctgcc ctggagccac tggtggatct  5640
gcccatcggc atcaacatca cccgtttca  gacactgctg gccctgcaca aagctacct   5700
gacaccaggc gacagctcct ctggatggac cgcaggagca gcagcctact atgtgggcta  5760
tctgcagccc aggaccttcc tgctgaagta caacgagaat ggcaccatca cagacgcgt   5820
ggattgcgcc ctggatcccc tgtctgagac caagtgtaca ctgaagagct ttaccgtgga  5880
gaagggcatc tatcagacaa gcaatttcag ggtgcagcct accgagtcca tcgtgcgctt  5940
tcccaatatc acaaacctgt gcccttttgg cgaggtgttc aacgcaaccc gcttcgccag  6000
cgtgtacgcc tggaataggg agcgcatctc caactgcgtg gccgactatt ctgtgctgta  6060
caacagcgcc tccttctcta ccttttaagtg ctatggcgta gccccacaa  agctgaatga  6120
cctgtgcttt accaacgtgt acgccgattc cttcgtgatc aggggcgacg aggtgcgcca  6180
gatcgcacca ggacagacag gcaatatcgc agactacaat tataagctgc ctgacgattt  6240
caccggctgc gtgatcgcct ggaactctaa caatctggat agcaaagtgg gcggcaacta  6300
caattatctg taccggctgt ttagaaagtc taatctgaag ccattcgaga gggacatctc  6360
cacagaaatc taccaggccg gctctacccc ctgcaatggc gtgaagggct ttaactgtta  6420
tttccctctg cagagctacg gcttccagcc aacatatggc gtgggctatc agccctaccg  6480
```

```
cgtggtggtg ctgtcttttg agctgctgca cgcacctgca acagtgtgcg gaccaaagaa 6540
gagcaccaat ctggtgaaga acaagtgcgt gaacttcaac ttcaacggac tgaccggaac 6600
aggcgtgctg accgagtcca acaagaagtt cctgcctttt cagcagttcg gcagggacat 6660
cgcagatacc acagacgccg tgcgcgaccc tcagaccctg gagatcctgg acatcacacc 6720
atgctccttc ggcggcgtgt ctgtgatcac accaggcacc aatacaagca accaggtggc 6780
cgtgctgtat cagggcgtga attgtaccga ggtgccagtg gcaatccacg cagatcagct 6840
gaccccctaca tggcgggtgt actctaccgg cagcaacgtg ttccagacaa gagccggatg 6900
cctgatcgga gcagagcacg tgaacaatag ctatgagtgc gacatcccta tcggcgccgg 6960
catctgtgcc tcctaccaga cccagacaaa ctccccagaa tcaagcgtga ttcctctgag 7020
ccatccactg gcagatccct ccacagtgtt caaagacgga gatgaggccg aagactttgt 7080
ggaagtccac ctgcctgatg tgcataacca ggtgtctggc gtcgacctgg gactgccaaa 7140
ttggggcaag tacgtgctgc tgagtgctgg agcactgact gccctgatgc tgatcatttt 7200
cctgatgacc tgctgtcggc gcgtgaacag aagtgagccc actcagcaca atctgcgagg 7260
aaccgggaga gaagtgtcag tcacacctca gagcgggaaa atcattagta gttgggaatc 7320
acataaaagc gggggcgaga ccaggctggg atccggctcc ggcgagggca ggggaagtct 7380
actaacatgc ggggacgtgg aggaaaatcc cggcccatg ctcgatcctg gagaggtcta 7440
tgatgaccct attgacccaa tcgagttaga ggctgaaccc agaggaaccc ccattgtccc 7500
caacatcttg aggaactctg actacaatct caactctcct ttgatagaag atcctgctag 7560
actaatgtta gaatggttaa aaacaggaa tagaccttat cggatgactc taacagacaa 7620
ttgctccagg tctttcagag ttttgaaaga ttatttcaag aaggtagatt tgggttctct 7680
caaggtgggc ggaatggctg cacagtcaat gatttctctc tggttatatg gtgcccactc 7740
tgaatccaac aggagccgga gatgtataac agacttgacc catttctatt ccaagtcgtc 7800
ccccatagag aagctgttga atctcacgct aggaaataga gggctgagaa tcccccaga 7860
gggagtgtta agttgccttg agagggttga ttatgataat gcatttggaa ggtatcttgc 7920
caacacgtat tcctcttact tgttcttcca tgtaatcacc ttatacatga acgccctaga 7980
ctgggatgaa gaaaagacca tcctagcatt atggaaagat taacctgag tggacatcgg 8040
gaaggacttg gtaaagttca aagaccaaat atggggactg ctgatcgtga caaaggactt 8100
tgtttactcc caaagttcca attgtctttt tgacagaaac tacacactta tgctaaaaga 8160
tcttttcttg tctcgcttca actccttaat ggtcttgctc tctccccag agccccgata 8220
ctcagatgac ttgatatctc aactatgcca gctgtacatt gctggggatc aagtcttgtc 8280
tatgtgtgga aactccggct atgaagtcat caaaatattg gagccatatg tcgtgaataag 8340
tttagtccag agagcagaaa agtttaggcc tctcattcat tccttgggag actttcctgt 8400
attttataaaaa gacaaggtaa gtcaacttga agagacgttc ggtccctgtg caagaaggtt 8460
ctttagggct ctggatcaat tcgacaacat acatgacttg gtttttgtgt ttggctgtta 8520
caggcattgg gggcacccat atatagatta tcgaaagggt ctgtcaaaac tatatgatca 8580
ggttcacctt aaaaaaatga tagataagtc ctaccaggag tgcttagcaa gcgacctagc 8640
caggaggatc cttagatggg gttttgataa gtactccaag tggtatctgg attcaagatt 8700
cctagcccga gaccacccct tgactcctta tatcaaaacc caaacatggc cacccaaaca 8760
tattgtagac ttggtggggg atacatggca caagctcccg atcacgcaga tctttgagat 8820
tcctgaatca atggatccgt cagaaatatt ggatgacaaa tcacattctt tcaccagaac 8880
gagactagct tcttggctgt cagaaaaccg aggggggcct gttcctagcg aaaaagttat 8940
tatcacggcc ctgtctaagc cgcctgtcaa tccccgagag tttctgaggt ctatagacct 9000
cggaggattg ccagatgaag acttgataat tggcctcaag ccaaaggaac gggaattgaa 9060
gattgaaggt cgattcttg ctctaatgtc atggaatcta agattgtatt ttgtcatcac 9120
tgaaaaactc ttggccaact acatcttgcc acttttttgac gcgctgacta tgacagacaa 9180
cctgaacaag gtgtttaaaa agctgatcga cagggtcacc gggcaaggc ttttggacta 9240
ttcaaggtc acatatgcat ttcacctgga ctatgaaaag tggaacaacc atcaaagatt 9300
agagtcaaca gaggatgtat tttctgtcct agatcaagtg tttggattga agagagtgtt 9360
ttctagaaca cacgagtttt ttcaaaaggc ctggatctat tattcagaca gatcagacct 9420
catcgggtta cgggaggatc aaatatactg cttagatgcg tccaacgcc caacctgttg 9480
gaatggcag gatgcgggc tagaaggctt acggcagaag ggctggagtc tagtcagctt 9540
attgatgata gatagagaat ctcaaatcag gaacacaaga accaaaatac tagctcaagg 9600
agacaaccag gttttatgtc cgacatacat gttgtcgcca gggctatctc aagaggggct 9660
cctctatgaa ttggagagaa tatcaaggaa tgcactttcg atatacagag ccgtcgagga 9720
aggggcatct aagctagggc tgatcatcaa gaagaagag accatgtgta gttatgactt 9780
cctcatctat ggaaaaaccc ctttgtttag aggtaacata ttggtgcctg agtccaaaag 9840
atgggcaga gtctcttgcg tctctaatga ccaaatagtc aacctcgcca ataatgtc 9900
gacagtgtcc accaatgcgc taacagtggc acaacactct caatctttga tcaaaccgat 9960
gagggatttt ctgctcatgt cagtacaggc agtctttcac tacctgctat ttagcccaat 10020
cttaaaggga agagtttaca agattctgac cgctgaaggg gagagctttc tcctagccat 10080
gtcaaggata atctatctag atccttcttt gggagggata tctggaatgt ccctcggaag 10140
attccatata cgacagttct cagaccctgt ctctgaaggg ttatccttct ggagagagat 10200
ctggttaagc tcccaagagt cctggattca cgcgttgtgt caagaggctg aaacccaga 10260
tcttggagag agaacactcg agagcttcac tcgccttcca ccacctaaa 10320
tatcagagga ggggccagtc ctaccattct actcaaggat gcaatcagaa aggctttata 10380
tgacgaggtg gacaaggtgg aaaattcaga gtttcgagag gcaatcctgt tgtccaagac 10440
ccatagagat aattttatac tcttcttaat atctgttgag cctctgtttc ctcgatttct 10500
cagtgagcta ttcagttcgt cttttttggg aatcccgag tcaatcattg gattgataca 10560
aaactcccga acgataagaa gctttag aaagagtcc tcaaaaactt tagaagaatc 10620
cttctacaac tcagagatcc acgggattag tcggatgacc cagacacctc agagggttgg 10680
gggggtgtgg ccttgctctt cagagagggc agatctactt agggagatct cttggggaag 10740
aaaagtggta ggcacgacag ttcctcaccc ttctgagatg ttgggattac ttccaagtc 10800
ctctatttct tgcacttgtg gagcaacagg aggaggcaat cctagagtttt ctgtatcagt 10860
actcccgtcc tttgatcagt cattttttttc acgaggcccc ctaaagggat acttgggctc 10920
gtccacctct atgtcgaccc agctattcca tgcatgggaa aaagtcacta atgttcatgt 10980
ggtgaagaga gctctatcgt taaaagaatc tataaactgg ttcattacta gagattccaa 11040
cttggctcaa gctctaatta ggaacattat gtctctgaca ggccctgatt tccctctaga 11100
ggaggcccct gtcttcaaaa ggacggggtc agccttgcat aggttcaagt ctgccagata 11160
cagcgaagga gggtattctt ctgtctgccc gaacctcctc tctcatattt ctgttagtac 11220
```

```
agacaccatg tctgatttga cccaagacgg gaagaactac gatttcatgt tccagccatt  11280
gatgctttat gcacagacat ggacatcaga gctggtacag agagacacaa ggctaagaga  11340
ctctacgttt cattggcacc tccgatgcaa caggtgtgtg agacccattg acgacgtgac  11400
cctggagacc tctcagatct tcgagtttcc ggatgtgtcg aaaagaatat ccagaatggt  11460
ttctggggct gtgcctcact tccagaggct tcccgatatc cgtctgagac caggagattt  11520
tgaatctcta agcggtagag aaaagtctca ccatatcgga tcagctcagg ggctcttata  11580
ctcaatctta gtggcaattc acgactcagg atacaatgat ggaaccatct tccctgtcaa  11640
catatacggc aaggtttccc ctagagacta tttgagaggg ctcgcaaggg gagtattgat  11700
aggatcctcg atttgcttct tgacaagaat gacaaatatc aatattaata gacctcttga  11760
attggtctca ggggtaatct catatattct cctgaggcta gataaccatc cctccttgta  11820
cataatgctc agagaaccgt ctcttagagg agagatattt tctatccctc agaaaatccc  11880
cgccgcttat ccaaccacta tgaaagaagg caacagatca atcttgtgtt atctccaaca  11940
tgtgctacgc tatgagcgag agataatcac ggcgtctcca gagaatgact ggctatggat  12000
cttttcagac tttagaagtg ccaaaatgac gtacctatcc ctcattactt accagtctca  12060
tcttctactc cagagggttg agagaaacct atctaagagt atgagagata acctgcgaca  12120
attgagttct ttgatgaggc aggtgctggg cgggcacgga gaagatacct tagagtcaga  12180
cgacaacatt caacgactgc taaaagactc tttacgaagg acaagatggg tggatcaaga  12240
ggtgcgccat gcagctagaa ccatgactgg agattacagc cccaacaaga aggtgtcccg  12300
taaggtagga tgttcagaat gggtctgctc tgctcaacag gttgcagtct ctacctcagc  12360
aaacccggcc cctgtctcgg agcttgacat aagggccctc tctaagaggt tccagaaccc  12420
tttgatctcg ggcttgagag tggttcagtg ggcaaccggt gctcattata agcttaagcc  12480
tattctagat gatctcaatg ttttcccatc tctctgcctt gtagttgggg acgggtcagg  12540
ggggatatca agggcagtcc tcaacatgtt tccagatgcc aagcttgtgt tcaacagtct  12600
tttagaggtg aatgacctga tggcttccgg aacacatcca ctgcctcctt cagcaatcat  12660
gaggggagga aatgatatcg tctccagagt gatagatctt gactcaatct gggaaaaacc  12720
gtccgacttg agaaacttgg caacctggaa atacttccag tcagtccaaa agcaggtcaa  12780
catgtcctat gacctcatta tttgcgatgc agaagttact gacattgcat ctatcaaccg  12840
gatcaccctg ttaatgtccg attttgcatt gtctatagat ggaccactct atttggtctt  12900
caaaacttat gggactatgc tagtaaatcc aaactacaag gctattcaac acctgtcaag  12960
agcgttcccc tcggtcacag ggtttatcac ccaagtaact tcgtcttttt catctgagct  13020
ctacctccga ttctccaaac gagggaagtt tttcagagat gctgagagtact tgacctcttc  13080
caccccttcga gaaatgagcc ttgtgttatt caattgtagc agccccaaga gtgagatgca  13140
gagagctcgt tccttgaact atcaggatct tgtgagagga tttcctgaag aaatcatatc  13200
aaatccttac aatgagatga tcataactct gattgacagt gatgtagaat cttttctagt  13260
ccacaagatg gttgatgatc ttgagttaca gaggggaact ctgtctaaag tggctatcat  13320
tatagccatc atgatagttt tctccaacag agtcttcaac gtttccaaac ccctaactga  13380
cccctcgttc tatccaccgt ctgatcccaa aatcctgagg cacttcaaca tatgttgcag  13440
tactatgatg tatctatcta ctgctttagg tgacgtccct agcttcgcaa gacttcacga  13500
cctgtataac agacctataa cttattactt cagaaagcaa gtcattcgag ggaacgttta  13560
tctatcttgg agttggtcca acgacacctc agtgttcaaa agggtagcct gtaattctag  13620
cctgagtctg tcatctcact ggatcaggtt gatttacaag atagtgaaga ctaccagact  13680
cgttggcagc atcaaggatc tatccagaga agtggaaaga caccttcata ggtacaacag  13740
gtggatcacc ctagaggata tcagatctag atcatcccta ctagactaca gttgcctgtg  13800
aaccggatac tcctggaagc ctgcccatgc taagactctt gtgtgatgta tcttgaaaaa  13860
aacaagatcc taaatctgaa cctttggttg tttgattgtt tttctcattt ttgttgttta  13920
tttgttaagc gt                                                        13932
```

```
SEQ ID NO: 18           moltype = DNA  length = 13475
FEATURE                 Location/Qualifiers
misc_feature            1..13475
                        note = VSV vector: Convac V1 China
source                  1..13475
                        mol_type = other DNA
                        organism = synthetic construct
SEQUENCE: 18
acgaagacaa acaaaccatt attatcatta aaaggctcag gagaaacttt aacagtaatc  60
aaaatgtctg ttacagtcaa gagaatcatt gacaacacag tcatagttcc aaaacttcct  120
gcaaatgagg atccagtgga atacccggca gattacttca gaaaatcaaa ggagattcct  180
ctttacatca atactacaaa aagtttgtca gatctaagag gatatgtcta ccaaggcctc  240
aaatccggaa atgtatcaat catacatgtc aacagctact tgtatggagc attaaaggac  300
atccggggta agttggataa agattggtca agtttcggaa taaacatcgg gaaagcaggg  360
gatacaatcg gaatatttga ccttgtatcc ttgaaagccc tggacggcgt acttccagat  420
ggagtatcgg atgcttccag aaccagcgca gatgacaaat ggttgccttt gtatctactt  480
ggcttataca gagtgggcag aacacaaatg cctgaataca gaaaaaagct catggatggg  540
ctgacaaatc aatgcaaaat gatcaatgaa cagtttgaac ctcttgtgcc agaaggtcgt  600
gacatttttg atgtgtgggg aaatgacagt aattacacaa aaattgtcgc tgcagtggac  660
atgttcttcc acatgttcaa aaaacatgaa tgtgcctcgt tcagatacgg aactattgtt  720
tccagattca aagattgtgc tgcattggca acatttggac acctctgcaa aataaccgga  780
atgtctacag aagatgtaac gacctggatc ttgaaccgag aagttgcaga tgaaatggtc  840
caaatgatgc ttccaggcca agaaattgac aaggccgatt catacatgcc ttatttgatc  900
gactttggat tgtcttctaa gtctccatat tcttccgtca aaaaccctgc cttccacttc  960
tgggggcaat tgacagctct tctgctcaga tccaccagag caaggaatgc ccgacagcct  1020
gatgacattg agtatacatc tcttactaca gcaggtttgt tgtacgctta tgcagtagga  1080
tcctctgccg acttggcaca acagttttgt gttggagata acaaatacac tccagatgat  1140
agtaccggag gattgacgac taatgcaccg ccacaaggca gagatgtggt cgaatggctc  1200
ggatggtttg aagatcaaaa cagaaaaccg actcctgata tgatgcagta tgcgaaaaga  1260
gcagtcatgt cactgcaagg cctaagagag aagacaattg gcaagtatgc taagtcagaa  1320
tttgacaaat gaccctataa ttctcagatc acctattata tattatgcta catatgaaaa  1380
aaactaacag atatcatgga taatctcaca aaagttcgtg agtatctcaa gtcctattct  1440
```

```
cgtctggatc aggcggtagg agagatagat gagatcgaag cacaacgagc tgaaaagtcc   1500
aattatgagt tgttccaaga ggatggagtg gaagagcata ctaagccctc ttattttcag   1560
gcagcagatg attctgacac agaatctgaa ccagaaattg aagacaatca aggtttgtat   1620
gcaccagatc cagaagctga gcaagttgaa ggctttatac aggggccttt agatgactat   1680
gcagatgagg aagtggatgt tgtatttact tcggactgga aacagcctga gcttgaatct   1740
gacgagcatg gaaagacctt acggttgaca tcgccagagg gtttaagtgg agagcagaaa   1800
tcccagtggc tttcgacgat taaagcagtc gtgcaaagtg ccaaatactg gaatctggca   1860
gagtgcacat ttgaagcatc gggagaaggg gtcattatga aggagcgcca gataactccg   1920
gatgtatata aggtcactcc agtgatgaac acacatccgt cccaatcaga agcagtatca   1980
gatgtttggt ctctctcaaa gacatccatg actttccaac ccaagaaagc aagtcttcag   2040
cctctcacca tatccttgga tgaattgttc tcatctagag gagagttcat ctctgtcgga   2100
ggtgacggac gaatgtctca taagaggcc atcctgctcg gcctgagata caaaaagttg   2160
tacaatcagg cgagagtcaa atattctctg tagactatga aaaaagtaa cagatatcac   2220
gatctaagtg ttatcccaat ccattcatca tgagttcctt aaagaagatt ctcggtctga   2280
aggggaaagg taagaaatct aagaaattag ggatcgcacc accccttat gaagaggaca   2340
ctagcatgga gtatgctccg agcgctccaa ttgacaaatc ctattttgga gttgacgaga   2400
tggacaccta tgatccgaat caattaagat atgagaaatt cttctttaca gtgaaaatga   2460
cggttagatc taatcgtccg ttcagaacat actcagatgt ggcagccgct gtatcccatt   2520
gggatcacat gtacatcgga atggcaggga aacgtccctt ctacaaaatc ttggcttttt   2580
tgggttcttc taatctaaag gccactccag cggtattggc agatcaaggt caaccagagt   2640
atcacactca ctgcgaaggc agggcttatt tgccacatag gatggggaag acccctccca   2700
tgctcaatgt accagagcac ttcagaagac cattcaatat aggtctttac aagggaacga   2760
ttgagctcac aatgaccatc tacgatgatg agtcactgga agcagctcct atgatctggg   2820
atcatttcaa ttcttccaaa ttttctgatt tcagagagaa ggcttaatg tttggcctga   2880
ttgtcgagaa aaaggcatct ggagcgtggg tcctggattc tatcagccac ttcaaatgag   2940
ctagtctaac ttctagcttc tgaacaatcc ccggttcact cagtctctcc taattccagc   3000
ctctcgaaca actaatatcc tgtctttct atccctatga aaaaaactaa cagagatcga   3060
tctgtttacg cgtcactatg aagtgccttt tgtacttagc cttttattc attgggtga   3120
attgcaagtt caccatagtt tttccacaca accaaaaagg aaactggaaa aatgttcctt   3180
ctaattacca ttattgcccg tcaagctcag atttaaattg gcataatgac ttaataggca   3240
cagccataca agtcaaaatg cccaagagtc acaaggctat tcaagcagac ggttggatgt   3300
gtcatgcttc caaatgggtc actacttgtg atttccgctg gtatggaccg aagtatataa   3360
cacagtccat ccgatccttc actccatctg tagaacaatg caaggaaagc attgaacaaa   3420
cgaaacaagg aacttggctg aatccaggct tccctcctca aagttgtgga tatgcaactg   3480
tgacggatgc cgaagcagtg attgtccagg tgactcctca ccatgtgctg gttgatgaat   3540
acacaggaga atgggttgat tcacagttca tcaacggaaa atgcagcaat tacatatgcc   3600
ccactgtcca taactctaca acctggcatt ctgactataa ggtcaaaggg ctatgtgatt   3660
ctaacctcat ttccatggac atcaccttct tctcagagga cggagagcta tcatccctgg   3720
gaaaggaggg cacagggttc agaagtaact actttgctta tgaactgga ggcaaggcct   3780
gcaaaatgca atactgcaag cattgggga g tcagactccc atcaggtgtc tggttcgaga   3840
tggctgataa ggatctcttt gctgcagcca gattccctga atgcccagaa gggtcaagta   3900
tctctgctcc atctcagacc tcagtggatg taagtctaat tcaggacgtt gagaggatct   3960
tggattattc cctctgccaa gaaacctgga gcaaaatgag gcgggtctt ccaatctctc   4020
cagtggatct cagctatctt gctcctaaaa acccaggaac cggtcctgct ttcaccataa   4080
tcaatggtac cctaaaatac tttgagacca gatacatcag agtcgatatt gctgctccaa   4140
tcctctcaag aatggtcgga atgatcagtg aactaccac agaaagggaa ctgtgggatg   4200
actgggcacc atatgaagac gtggaaattg gacccaatgg agttctgagg accagttcag   4260
gatataagtt tccttatac atgattggac atggtatgtt ggactccgat cttcatctta   4320
gctcaaaggc tcaggtgttc gaacatcctc acattcaaga cgctgcttcg caacttcctg   4380
atgatgagag tttattttt ggtgatactg ggctatccaa aaatccaatc gagcttgtag   4440
aaggttggtt cagtagttgg aaaagctcta ttgcctctt tttctttatc atagggttaa   4500
tcattggact attcttggtt ctccgagttg gtatccatct ttgcattaaa ttaaagcaca   4560
ccaagaaaag acagatttat acagacatag agatgaaccg acttggaaag taactcaaat   4620
cctgctaggt atgaaaaaa ctaacagata tcacgctcga gcgtacgcca ccatgttcgt   4680
gtttctggtg ctgctgcctc tggtgagctc ccagtgcgtg aacctgacca agggaccca   4740
gctgcccct gcctataca attccttcac acggggcgtg tactatcccg acaaggtgtt   4800
ccggagcagc gtgctgcact ccacacagga tctgtttctg ccttctttt ctaacgtgac   4860
ctggttccac gccatccacg tgagcggcac caatggcaca aagcggttcg acaatccagt   4920
gctgcccttt aacgatggcg tgtacttcgc ctccaccgaa aagtctaaca tcatcagagg   4980
ctggatcttt ggcaccacac tggacagcaa gacacagtcc ctgctgatcg tgaacaatgc   5040
caccaacgtg gtcatcaagg tgtgcgagtt ccagtttgt aatgatccat tcctgggcgt   5100
gtactatcac aagaacaata gtcttggat ggagagcgag tttcgcgtgt attcctctgc   5160
caacaattgc acatttgagt acgtgtccca gcccttcctg atggacctgg agggcaagca   5220
gggcaatttc aagaacctga gggagttcgt gtttaaaaat atcgatggct acttcaagat   5280
ctactccaag cacaccccaa tcaacctggt gcgcgacctg ccacaggget ctctgccct   5340
ggagccactg tgtgatctgc ccatcggcat caacatcacc cggttcagaa cactgctggc   5400
cctgcacaga agctacctga caccaggcga cagctcctct ggatgaccg caggagcagc   5460
agcctactat gtgggctatc tgcagccag gaccttcctg ctgaagtaca acgaatgga   5520
caccatcaca gacgccgtgg attgcgccct ggatcctg tctgagacca gtgtacact   5580
gaagagcttt accgtggaga agggcatcta tcagacaagc aatttcaggg tgcagcctac   5640
cgagtccatc gtgcgcttc caatatcac aaacctgtgc cctttggcg aggtgttcaa   5700
cgcaacccgc ttcgccagcg tgtacgcctg gaataggaag cgcatctcca actgcgtggc   5760
cgactattct gtgctgtaca acagcgcctc cttctctacc tttaagtgct atggcgtgag   5820
ccccacaaag ctgaatgacc tgtgctttac caacgtgtac gccgattct tcgtgatcag   5880
gggcgacgag gtgcgccaga tcgcaccagg acagacaggc aagatcgcag actacaatta   5940
taagctgcct gacgatttca ccggctgcgt gatcgcctgg aactctaaca atctggatag   6000
caaagtgggc ggcaactaca attatctgta ccggctgttt agaaagtcta atctgaagcc   6060
attcgagagg gacatctcca cagaaatcta ccaggccgg tctaccccct gcaatggcgt   6120
ggagggcttt aactgttatt tccctctgca gagctacggc ttcagccaa caaacggcgt   6180
```

```
gggctatcag ccctaccgcg tggtggtgct gtcttttgag ctgctgcacg cacctgcaac   6240
agtgtgcgga ccaaagaaga gcaccaatct ggtgaagaac aagtgcgtga acttcaactt   6300
caacggactg accggaacag gcgtgctgac cgagtccaac aagaagttcc tgccttttca   6360
gcagttcggc agggacatcg cagataccac agacgccgtg cgcgaccctc agaccctgga   6420
gatcctggac atcacaccat gctccttcgg cggcgtgtct gtgatcacac caggcaccaa   6480
tacaagcaac caggtggccg tgctgtatca ggacgtgaat tgtaccgagg tgccagtggc   6540
aatccacgca gatcagctga cccctacatg gcgggtgtac tctaccggca gcaacgtgtt   6600
ccagacaaga gccggatgcc tgatcggagc agagcacgtg aacaatagct atgagtgcga   6660
catccctatc ggcgccggca tctgtgcctc ctaccagacc cagacaaact cccaaggtgc   6720
tgtgggcgat acaggcctgt ccaagaatcc aatcgagctg gtagagggct ggttcagcag   6780
ttggaaaagc tccatcgcct cctttttctt tatcatcggc ctgatcatcg gactgttcct   6840
ggtgctccgc gtgggtatcc acctgtgcat caagctgaag cacaccaaga aaagacagat   6900
ttatacagac atcgagatga accgcctggg aaagtgagct agccagattc ttcatgtttg   6960
gaccaaatca acttgtgata ccatgctcaa agaggcctca attatatttg agttttttaat   7020
ttttatgaaa aaaactaaca gcaatcatgg aagtccacga ttttgagacc gacgagttca   7080
atgatttcaa tgaagatgac tatgccacaa gagaattcct gaatcccgat gagcgcatga   7140
cgtacttgaa tcatgctgat tacaaattga attctcctct aattagtgat gatattgaca   7200
atttgatcag gaaattcaat tctcttccga ttccctcgat gtgggatagt aagaactggg   7260
atggagttct tgagatgtta acatcatgtc aagccaatcc catctcaaca tctcagatgc   7320
ataaaatggat gggaagttgg ttaatgtctg ataatcatga tgccagtcaa gggtatagtt   7380
ttttacatga agtggacaaa gaggcagaaa taacatttga cgtggtggag accttcatcc   7440
gcggctgggg caacaaacca attgaataca tcaaaaagga aagatgact gactcattca   7500
aaattctcgc ttatttgtgt caaaagtttt tggacttaca caagttgaca ttaatcttaa   7560
atgctgtctc tgaggtggaa ttgctcaact ggcgaggac tttcaaaggc aaagtcagaa   7620
gaagttctca tggaacgaac atatgcagga ttagggttcc cagcttgggt cctactttta   7680
tttcagaagg atgggcttac ttcaagaaac ttgatatct aatggaccga aactttctgt   7740
taatggtcaa agatgtgatt atagggagga tgcaaacggt gctatccatg gtatgtagaa   7800
tagcaacct gttctcagag caagacatct tctcccttct aaatatctac agaattggag   7860
ataaaattgt ggagaggcag ggaaattttt cttatgactt gattaaaatg gtggaaccga   7920
tatgcaaatct gaagctgatg aaattagcaa gagaatcaag gcctttagtc ccacaattcc   7980
ctcattttga aaatcatatc aagacttctg ttgatgaagg ggcaaaaatt gaccgaggta   8040
taagattcct ccatgatcag ataatgagtg tgaaaacagt ggatctcaca ctggtgattt   8100
atggatcgtt cagacattgg ggtcatcctt ttatagatta ttacactgga ctagaaaaat   8160
tacattccca agtaaccatg aagaaagata ttgatgtgtc atatgcaaaa gcacttgcaa   8220
gtgatttagc tcggattgtt ctatttcaac agttcaatga tcataaaaag tggttcgtga   8280
atggagactt gctccctcat gatcatccct taaaagtca tgttaaagaa atacatggc   8340
ccacagctgc tcaagttcaa gattttggag ataaatggca tgaacttccg ctgattaaat   8400
gttttgaaat acccgactta ctagaccat cgataatata tctctgacaaa agtcattcaa   8460
tgaataggtc agaggtgttg aaacatgtcc gaatgaatcc gaacactcct atccctagta   8520
aaaaggtgtt gcagactatg ttggacacaa aggctaccaa ttggaaagaa tttcttaaag   8580
agattgatga aagggcttaa gatgatgatg atctaattat tggtcttaaa ggaaaggaga   8640
gggaactgaa gttggcaggt agattttct ccctaatgtc ttggaaattg cgagaatact   8700
ttgtaattac cgaatatttg ataaagactc atttcgttcct tatgttttaa ggcctgacaa   8760
tggcggacga tctaactgca gtcattaaaa agatgttaga ttcctcatcc ggccaaggat   8820
tgaagtcata tgaggcaatt tgcatagcca atcacattga ttacgaaaaa tggaataacc   8880
accaaaggaa gttatcaaac ggcccagtgt tccgagttat gggccagttc ttaggttatc   8940
catccttaat cgagagaact catgaatttt ttgagaaaga tcttatatac tacaatggaa   9000
gaccagactt gatgcgtgtt cacaacaaca cactgatcaa ttcaacctcc caacgagttt   9060
gttggcaagg acaagagggt ggactggaag gtctacggca aaaaggatgg actatcctca   9120
atctactggt tattcaaaga gaggctaaaa tcagaaacac tgctgtcaaa gtcttggcac   9180
aaggtgataa tcaagttatt tgcacacagt ataaaacgaa gaaatcgaga aacgttgtag   9240
aattacaggg tgctctcaat caaatgtttt ctaataatga gaaaattatg actgcaatca   9300
aaataggac agggaagtta ggacttttga taaatgacga tgagactatg caatctgcag   9360
attacttgaa ttatgaaaa ataccgattt tccgtggagt gattagaggg ttagagacca   9420
agagatggtc acgagtgact tgtgtcacca atgaccaaat acccacttgt gctaatataa   9480
tgagctcagt ttccacaaat gctctcaccg tagctcattt tgctgagaac ccaatcaatg   9540
ccatgataca gtacaattat tttgggacat tgctagact cttgttgatg atgcatgatc   9600
ctgctcttcg tcaatcattg tatgaagttc aagataagat accgggcttg cacagttcta   9660
ctttcaaata cgccatgttg tatttggacc cttcattgg aggagtgtcg ggcatgtctt   9720
tgtccaggtt tttgattaga gccttccag atcccgtaac agaaagttc tcattctgga   9780
gattcatcca tgtacatgct cgaagtgagc atctcaagga gatgagtgca gtatttggaa   9840
accccgagat agccaagttt cgaataactc acatagacaa gctagtagaa gatccaacct   9900
ctctgaacat cgctatggga atgagtccag cgaacttgtt aaagactgag gttaaaaaat   9960
gcttaatcga atcaagacaa accatcagga accaggtgat taaggatgca accatatatt  10020
tgtatcatga agaggatcgg ctcagaagtt tcttatggtc aataaatcct ctgttcccta  10080
gattttaag tgaattcaaa tcaggcactt ttttgggagt cgcagacggg ctcatcagtc  10140
tatttcaaaa ttctcgtact attcggaact cctttaagaa aaagtatcat agggaattgg  10200
atgatttgat tgtgaggagt gaggtatcct cttttgacaa tttagggaaa cttcatttga  10260
gaagggatc atgtaaaatg tggacatgtt cagctactca tgctgacaca ttaaggtaca  10320
aatcctgggg ccgtcagtt attgggacaa ctgtaccca tccattagaa atgttgggtc  10380
cacaacatcg aaaagagact ccttgtgcac catgtaacac atcagggttc aattatgttt  10440
ctgtgcattg tccagacggg atccatgacg tctttagttc acgggaccat tgcctgcttt  10500
atctagggtc taaaacatct gaatctacat ctatttttgca gccttgggaa agggaaagca  10560
aagtcccact gattaaaaga gctcacgtct tagagatgtc atctcttgg ttgttgaac  10620
ccgactctaa actagcaatg actatactttt ctaacatcca ctcttttaaca ggcgaagaat  10680
ggaccaaaag gcagcatggg ttcaaaagaa cagggtctgc ccttcatagg tttttcgcat  10740
ctcggatgag ccatggtggg ttcgcatctc agagcactgc agcattgacc aggttgatgg  10800
caactacaga caccatgagg gatctgggag atcagaattt cgacttttta ttccaagcaa  10860
cgttgctcta tgctcaaatt accaccactg ttgcaagaga cggatggatc accagttgta  10920
```

-continued

```
cagatcatta tcatattgcc tgtaagtcct gtttgagacc catagaagag atcaccctgg  10980
actcaagtat ggactacacg cccccagatg tatcccatgt gctgaagaca tggaggaatg  11040
gggaaggttc gtggggacaa gagataaaac agatctatcc tttagaaggg aattggaaga  11100
atttagcacc tgctgagcaa tcctatcaag tcggcagatg tataggtttt ctatatggag  11160
acttggcgta tagaaaatct actcatgccg aggacagttc tctatttcct ctatctatac  11220
aaggtcgtat tagaggtcga ggtttcttaa aagggttgct agacggatta atgagagcaa  11280
gttgctgcca agtaatacac cggagaagtc tggctcattt gaagaggccg gccaacgcag  11340
tgtacggagg tttgatttac ttgattgata aattgagtgt atcacctcca ttcctttctc  11400
ttactagatc aggacctatt agagacgaat tagaaacgat tccccacaag atcccaacct  11460
cctatccgac aagcaaccgt gatatggggg tgattgtcag aaattacttc aaataccaat  11520
gccgtctaat tgaaaaggga aaatacagat cacattattc acaattatgg ttattctcag  11580
atgtcttatc catagacttc attggaccat tctctatttc cacccccctc ttgcaaatcc  11640
tatacaagcc atttttatct gggaaagata agaatgagtt gagagagctg gcaaatcttt  11700
cttcattgct aagatcagga gaggggtggg aagacataca tgtgaaattc ttcaccaagg  11760
acatattatt gtgtccagag gaaatcgagc atgcttgcaa gttcgggatt gctaaggata  11820
ataattaaga catgagctat cccccttggg aagggaatcc agagggaca attcaaacaa  11880
tccctgttta ttatacgacc accccttacc caaagatgct agagatgcct ccaagaatcc  11940
aaaatcccct gctgtccgga acaggttgg gccaattacc aactgcgct cattataaaa  12000
ttcggagtat attacatgga atgggaatcc attacaggga cttcttgagt tgtggagacg  12060
gctccggagg gatgactgct gcattactac gagaaaatgt gcatagcaga ggaattca  12120
atagtctgtt agaattatca gggtcagtca tgcgaggcgc ctctcctgag cccccagtg  12180
ccctagaaac tttaggagga gataaatcga gatgtgtaaa tggtgaaaca tgttgggaat  12240
atccatctga cttatgtgac caaggactt gggactattt cctccgactc aaagcaggct  12300
tggggcttca aattgattta attgtaatgg atatggaagt tcgggattct tctactagcc  12360
tgaaaattga gacgaatgtt agaaattatg tgcaccggat tttggatgag caaggagttt  12420
taatctacaa gacttatgga acatatattt gtgagagcga aaagaatgca gtaacaatcc  12480
ttggtcccat gttcaagacg gtcgacttag ttcaaacaga atttagtagt tctcaaacgt  12540
ctgaagtata tatggtatgt aaaggtttga agaaattaat cgatgaaccc aatcccgatt  12600
ggtcttccat caatgaatcc tggaaaaaacc tgtacgcatt ccagtcatca gaacaggaat  12660
ttgccagagc aaaagaggtt agtacatact ttaccttgac aggtattccc tcccaattca  12720
ttcctgatcc ttttgtaaac attgagacta tgctacaaat attcggagta cccacgggtg  12780
tgtctcatgc ggctgcctta aaatcatctg atagacctgc agatttattg accattagcc  12840
ttttttatat ggcgattata tcgtattata acatcaatca tatcagagta ggaccgatac  12900
ctccgaaccc cccatcagat ggaattgcac aaaatgtggg gatcgctata actggtataa  12960
gcttttggct gagtttgatg gagaaagaca ttccactata tcaacagtgt ttagcagtta  13020
tccagcaatc attcccgatt aggtgggagg ctgtttcagt aaaaggagga tacaagcaga  13080
agtggagtac tagaggtgat gggctcccaa aagatacccg aacttcagac tccttggccc  13140
caatcgggaa ctggatcaga tctctggaat tggtccgaaa ccaagttcgt ctaaatccat  13200
tcaatgagat cttgttcaat cagctatgtc gtacagtgga taatcatttg aaatggtcaa  13260
atttgcgaag aaacacagga atgattgaat ggatcaatag acgaatttca aaagaagacc  13320
ggtctatact gatgttgaag agtgacctac acgaggaaaa ctcttggaga gattaaaaaa  13380
tcatgaggag actccaaact ttaagtatga aaaaacttt gatccttaag accctcttgt  13440
ggttttattt ttttatctgg ttttgtggtc ttcgt  13475
```

```
SEQ ID NO: 19          moltype = DNA   length = 13469
FEATURE                Location/Qualifiers
misc_feature           1..13469
                       note = VSV vector: Convac V1 South Africa
source                 1..13469
                       mol_type = other DNA
                       organism = synthetic construct
SEQUENCE: 19
acgaagacaa acaaaccatt attatcatta aaaggctcag gagaaacttt aacagtaatc    60
aaaatgtctg ttacagtcaa gagaatcatt gacaacacag tcatagttcc aaaacttcct   120
gcaaatgagg atccagtgga ataccccggca gattacttca gaaaatcaaga ggagattcct   180
ctttacatca atactacaaa aagtttgtca gatctaagag gatatgtcta ccaaggcctc   240
aaatccggaa atgtatcaat catacatgtc aacagctact tgtatggagc attaaaggac   300
atccggggta agttggataa agattggtca agtttcggaa taaacatcgg gaaagcaggg   360
gatacaatcg gaatatttga ccttgtatcc ttgaaagccc tggacggcgt acttccagat   420
ggagtatcgg atgcttccag aaccagcgca gatgacaaat ggttgccttt gtatctactt   480
ggcttataca gagtgggcag aacacaaatg cctgaataca gaaaaaagct catggatggg   540
ctgacaaatc aatgcaaaat gatcaatgaa cagtttgaac ctcttgtgcc agaaggtcgt   600
gacattttg atgtgtgggg aaatgacagt aattacacaa aaattgtcgc tgcagtggac   660
atgttcttcc acatgttcaa aaaacatgaa tgtgcctcgt tcagatacgg aactattgtt   720
tccagattca aagattgtgc tgcattggca acatttggac acctctgcaa ataaccgga   780
atgtctacag aagatgtaac gacctggatc ttgaaccgag aagttgcaga tgaaatggtc   840
caaatgatgc ttcagccca gaaaattgac aaggccgatt catacatgcc ttatttgatc   900
gactttggat tgtcttctaa tctcccatat tcttccgtca aaaaccatgc cttccacttc   960
tgggggcaat tgacagctct tctgctcaga tccaccagag caaggaatgc ccgacagcct  1020
gatgacattg agtatacatc tcttactaca gcaggtttgt tgtacgctta tgcagtagga  1080
tcctctgccg acttggcaca acagtttttgt gttggagata caaatacac tccagatgat  1140
agtaccggag gattgacgac taatgcaccg ccacaaggca gagatgtggt cgaatggctc  1200
ggatggtttg aagatcaaaa cagaaaaccg actcctgata tgatgcagta tgcgaaaaga  1260
gcagtcatgt cactgcaagg cctaagagag aagacaattg caagtatgc taagtcagaa  1320
tttgacaaat gacccctataa ttctcagatc acctattata tattatgcta catatgaaaa  1380
aaactaacag atatcatgga taatctcaca aagttcgtg agtatctcaa gtccattctt  1440
cgtctggatc aggcggtagg agagatagat gagatcgaag cacaacgagc tgaaaagtcc  1500
aattatgagt tgttccaaga ggatggagtg gaagagcata ctaagccctc ttattttcag  1560
gcagcagatg attctgacac agaatctgaa ccagaaattg aagacaatca aggttttgtat  1620
```

```
gcaccagatc cagaagctga gcaagttgaa ggctttatac aggggccttt agatgactat   1680
gcagatgagg aagtggatgt tgtatttact tcggactgga aacagcctga gcttgaatct   1740
gacgagcatg gaaagacctt acggttgaca tcgccagagg gtttaagtgg agagcagaaa   1800
tcccagtggc tttcgacgat taaagcagtc gtgcaaagtg ccaaatactg gaatctggca   1860
gagtgcacat ttgaagcatc gggagaaggg gtcattatga aggagcgcca gataactccg   1920
gatgtatata aggtcactcc agtgatgaac acacatccgt cccaatcaga agcagtatca   1980
gatgtttggt ctctctcaaa gacatccatg actttccaac ccaagaaagc aagtcttcag   2040
cctctcacca tatccttgga tgaattgttc tcatctagag gagagttcat ctctgtcgga   2100
ggtgacggac gaatgtctca taaagaggcc atcctgctcg gcctgagata caaaaagttg   2160
tacaatcagg cgagagtcaa atattctctg tagactatga aaaaaagtaa cagatatcac   2220
gatctaagtg ttatcccaat ccattcatca tgagttcctt aaagaagatt ctcggtctga   2280
aggggaaagg taagaaatct aagaaattag ggatcgcacc accccttat gaagaggaca    2340
ctagcatgga gtatgctccg agcgctccaa ttgacaaatc ctattttgga gttgacgaga   2400
tggacaccta tgatccgaat caattaagat atgagaaatt cttctttaca gtgaaaatga   2460
cggttagatc taatcgtccg ttcagaacat actcagatgt ggcagccgct gtatcccatt   2520
gggatcacat gtacatcgga atggcaggga acgtcccttc tacaaaatct tggcttttt    2580
tgggttcttc taatctaaag gccactccag cggtattggc agatcaaggt caaccagagt   2640
atcacactca ctgcgaaggc agggcttatt gccacatag gatggggaag accctccaa    2700
tgctcaatgt accagagcac ttcagaagac cattcaatat aggtctttac aagggaacga   2760
ttgagctcac aatgaccatc tacgatgatg agtcactgga agcagctcct atgatctggg   2820
atcatttcaa ttcttccaaa ttttctgatt tcagagagaa ggccttaatg tttggcctga   2880
ttgtcgagaa aaaggcatct ggagcgtggg tcctggattc tatcagccac ttcaaatgag   2940
ctagtctaac ttctagcttc tgaacaatcc ccggttact cagtctctcc taattccagc     3000
ctctcgaaca actaatatcc tgtcttttct atccctatga aaaaaactaa cagagatcga   3060
tctgtttacg cgtcactatg aagtgccttt tgtacttagc cttttattc attggggtga    3120
attgcaagtt caccataagg ttttccacaca accaaaaagg aaactggaaa aatgttcctt   3180
ctaattacca ttattgcccg tcaagctcag atttaaattg gcataatgac ttaataggca   3240
cagccataca agtcaaaatg cccaagagtc acaaggctat tcaagcagac ggttggatgt   3300
gtcatgcttc caaatgggtc actacttgtg atttccgctg gtatggaccg aagtatataa   3360
cacagtccat ccgatccttc actccatctg tagaacagtc caaggaaagc attgaacaaa   3420
cgaaacaagg aacttggctg aatccaggct tccctcctca aagttgtgga tatgcaactg   3480
tgacggatgc cgaagcagtg attgtccagg tgactcctca ccatgtgctg gttgatgaat   3540
acacaggaga atgggttgat tcacagttca tcaacgaaaa atgcagcaat tacatatgcc   3600
ccactgtcca taactctaca acctggcatt ctgactataa ggtcaaaggg ctatgtgatt   3660
ctaacctcat ttccatggac atcaccttct tctcgagaga cggagagcta tcatccctgg   3720
gaaaggaggg cacagggttc agaagtaact actttgctta tgaaactgga ggcaaggcct   3780
gcaaaatgca atactgcaag cattgggag tcagactccc atcaggtgtc tggttcgaga    3840
tggctgataa ggatctcttt gctgcagcca gattccctga atgcccagaa gggtcaagta   3900
tctctgctcc atctcagacc tcagtggatg taagtcaat tcaggacgtt gagaggatct    3960
tggattattc cctctgccaa gaaacctgga gcaaaatcag agcgggtctt ccaatctctc   4020
cagtggatct cagctatctt gctcctaaaa acccaggaac cggtcctgct ttcaccataa   4080
tcaatggtac cctaaaatac tttgagacca gatacatcag agtcgatatt gctgctccaa   4140
tcctctcaag aatggtcgga agaatcagtg gaactaccac agaaagggaa ctgtgggatg   4200
actgggcacc atatgaagac gtggaaattg gacccaatgg agttctgagg accagttcag   4260
gatataagtt tccttatac atgattggac atggtatgtt ggactccgat cttcatctta   4320
gctcaaaggc tcaggtgttc gaacatcctc acattcaaga cgctgcttcg caacttcctg   4380
atgatgagag tttatttttt ggtgatactg ggctatccaa aaatccaatc gagcttgtag   4440
aaggttggtt cagtagttgg aaaagctcta ttgcctcttt tttctttatc ataggttaa    4500
tcattggact attcttggtt ctccgagttg gtatccatct ttgcattaaa ttaaagcaca   4560
ccaagaaaag acagatttat acagacatag agatgaaccg acttggaaag taactcaaat   4620
cctgctaggt atgaaaaaaa ctaacagata tcacgctagg gccaccatgt tcgtgttct     4680
ggtgctgctg cctctggtga gctcccagtg cgtgaacttc accacaagga cccagctgcc   4740
ccctgcctat accaattcct tcacacgggg cgtgtactat cccgacaagg tgttccggag   4800
cagcgtgctg cactccacac aggatctgtt tctgcctttc ttttctaacg tgacctggtt   4860
ccacgccatc cacgtgagcg gcaccaatgg cacaaagcgg ttcgccaatc cagtcgtgcc   4920
ctttaacgat ggcgtgtact cgcctccac cgagaagtct aacatcatca gaggctggat   4980
ctttggcacc acactggaca gcaagacaca gtccctgctg atcgtgaaca atgccaccaa   5040
cgtggtcatc aaggtgtgcg agttccagtt ttgtaatgat ccattcctgg gcgtgtacta   5100
tcacaagaac aataagtctt ggatggagag cgagtttcgc gtgtattcct ctgccaacaa   5160
ttgcacattt gagtacgtgt cccagccctt cctgatggac ctggagggca agcagggcaa   5220
tttcaagaac ctgagggagt tcgtgtttaa gaatatcgat ggctacttca aaatctactc   5280
caagcacacc ccaatcaacc tggtgcgcgg cctgccacag gcttctctg ccctggagcc    5340
actggtggat ctgcccatcg gcatcaacat cacccggttt cagacactgc tggccctgca   5400
cagaagctac ctgacaccag gcgacagctc ctctggatgg accgcaggag ccagccgcta   5460
ctatgtgggc tatctgcagc caggaccttt cctgctgaag tacaacgaga tggcaccatt   5520
cacagacgcc gtggattgcg ccctggatcc cctgtctgag accaagtgta cactgaagag   5580
ctttaccgtg gagaagggca tctatcagac aagcaatttc agggtgcagc ctaccgagtc   5640
catcgtcgcg tttcccaata tcacaaacct gtgcccttt ggcgaggtgt tcaacgcaac    5700
ccgcttcgcc agcgtgtacg cctggaatag gaagcgcatc tccaactgcg tggccgacta   5760
ttctgtgctg tacaacagcg cctccttctc taccttaaag tgctatggcg tgagccccac   5820
aaaagctgaat gacctgtgct ttaccaacgt gtacgccgat tccttcgtga tcaggggcga   5880
cgaggtgcgc cagatcgcac aggacagac aggcaatatc gcagactaca attataagct   5940
gcctgacgat ttcaccggct gcgtgatcgc ctggaactct aacaatctgg atagcaaagt   6000
gggcggcaac tacaattatc tgtaccggct gttagaaag tctaatctga agccattcga    6060
gagggacatc tccacagaaa tctaccaggc cggctctacc ccctgcaatg gcgtgaaggg   6120
ctttaactgt tatttccctc tgcagagcta cggcttccag ccaacatatg gcgtgggcta   6180
tcagccctac cgcgtggtgg tgctgtcttt tgagctgctg cacgcacctg caacagtgtg   6240
cggaccaaag aagagcacca atctggtgaa gaacaagtgc gtgaacttca acttcaacgg   6300
actgaccgga acaggcgtgc tgaccgagtc caacaagaag ttcctgcctt tcagcagtt    6360
```

-continued

```
cggcagggac atcgcagata ccacagacgc cgtgcgcgac cctcagaccc tggagatcct  6420
ggacatcaca ccatgctcct tcggcggcgt gtctgtgatc acaccaggca ccaatacaag  6480
caaccaggtg gccgtgctgt atcagggcgt gaattgtacc gaggtgccag tgcaatcca   6540
cgcagatcag ctgacccta catggcgggt gtactctacc ggcagcaacg tgttccagac   6600
aagagccgga tgcctgatcg gagcagagca cgtgaacaat agctatgagt gcgcatccc   6660
tatcggcgcc ggcatctgtg cctcctacca gacccagaca aactcccaa ggtctgtggg   6720
cgatacaggc ctgtccaaga atccaatcga gctggtagag ggctggttca gcagttggaa  6780
aagctccatc gcctccttt tctttatcat cggcctgatc atcggactgt tcctggtgct   6840
ccgcgtgggt atccacctgt gcatcaagct gaagcacacc aagaaaagac agatttatac   6900
agacatcgag atgaaccgcc tgggaaagtg agctagccag attcttcatg tttggaccaa   6960
atcaacttgt gataccatgc tcaaagaggc ctcaattata tttgagtttt taatttttat   7020
gaaaaaaact aacagcaatc atggaagtcc acgatttga gaccgacgag ttcaatgatt   7080
tcaatgaaga tgactatgcc acaagagaat tcctgaatcc cgatgagcgc atgacgtact   7140
tgaatcatgc tgattacaat ttgaattctc ctctaattag tgatgatatt gacaatttga   7200
tcaggaaatt caattctctt ccgattccct cgatgtggga tagtaagaac tgggatggag   7260
ttcttggagat gttaacatca tgtcaagcca atcccatctc aacatctcag atgcataaat   7320
ggatgggaag ttggttaatg tctgataatc atgatgccag tcaagggtat agttttttac   7380
atgaagtgga caaagaggca gaaataacat ttgacgtggt ggagaccttc atccgcggct   7440
ggggcaacaa accaattgaa tacatcaaaa aggaaagatg gactgactca ttcaaaattc   7500
tcgcttattt gtgtcaaaag ttttttggact tacacaagtt gacattaatc ttaaatgctg   7560
tctctgaggt ggaattgctc aacttggcga ggactttcaa aggcaaagtc agaagaagtt   7620
ctcatggaac gaacatatgc aggattaggg ttcccagctc gggtcctact ttatttcag    7680
aaggatgggc ttacttcaag aaacttgata ttctaatgaa ccgaaacttt ctgttaatgc   7740
tcaaagatgt gattataggg aggatgcaaa cggtgctatc catggtatgt agaatagaca   7800
acctgttctc agagcaagac atcttctccc ttctaaatat ctacagaatt ggagataaaa   7860
ttgtggagag gcagggaaat ttttcttatg acttgattaa aatggtggaa ccgatatgca   7920
acttgaagct gatgaaatta gcaagagaat caaggccttt agtcccacaa ttccctcatt   7980
ttgaaaatca tatcaagact tctgttgatg aaggggcaaa aattgaccga ggtataagat   8040
tcctccatga tcagataatg agtgtgaaaa cagtggatct cacactggtg atttatggat   8100
cgttcagaca ttgggtcat ccttttatag attattacac tggactagaa aaattacatt    8160
cccaagtaac catgaagaaa gatattgatg tgtcatatgc aaagcactt gcaagtgatt    8220
tagctcggat tgttcatttt caacagttca atgatcataa aaagtggttc gtgaatggag   8280
acttgctccc tcatgatcat cccttttaaa gtcatgttaa agaaaataca tggcccacag   8340
ctgctcaagt tcaagatttt ggagataaat ggcatgaact tccgctgatt aaatgttttg   8400
aaatacccga cttactagac ccatcgataa tatactctga caaagtcat tcaatgaata    8460
ggtcagaggt gttgaaacat gtccgaatga atccgaacac tcctatccct agtaaaaagg   8520
tgttgcagac tatgttggac acaaaggcta ccaattggaa agaatttctt aaagagattg   8580
atgagaaggg cttagatgat gatgatcaa ttattggtct taaaggaaag gagagggaac   8640
tgaagttggc aggtagattt ttctccctaa tgtcttggaa attgcgagaa tactttgtaa   8700
ttaccgaata tttgataaag actcatttcg tcccctatgt taaaggcctg acaatggcgg   8760
acgatctaac tgcagtcatt aaaaagatgt tagattcctc atccggccaa ggattgaagt   8820
catatgaggc aatttgcata gccaatcaca ttgattacga aaaatggaat aaccaccaaa   8880
ggaagttatc aaacgcccca gtgttccgag ttatgggcca gttcttaggt tatccatcct   8940
taatcgagag aactcatgaa ttttttgaga aaagtcttat atactacaat ggaagaccag   9000
acttgatgcg tgttcacaac aacacactga tcaattcaac ctcccaacga gtttgttggc   9060
aaggacaaga gggtggactg gaaggtctac ggcaaaaagg atggactatc ctcaatctac   9120
tggttattca aagagaggct aaaatcagaa acactgctgt caaagtcttg gcacaaggtg   9180
ataatcaagt tatttgcaca cagtataaaa cgaagaaatc gagaaacgtt gtagaattac   9240
agggtgctct caatcaaatg gtttctaata atgagaaaat tatgactgca atcaaaatag   9300
ggacaggaa gttaggactt ttgataaatg acgatgagac tatgcaatct gcagattact   9360
tgaattatgg aaaaataccg attttccgtg gagtgattag agggttagag accaagagat   9420
ggtcacgagt gacttgtgtc accaatgacc aaatacccac ttgtgctaat ataatgagct   9480
cagtttccac aaatgctctc accgtagctc attttgctga aacccaatc aatgccatga   9540
tacagtacaa ttattttggg acatttgcta gactcttgtt gatgatgcat gatcctgctc   9600
ttcgtcaatc atttgtatga gttcaagata agataccgag cttgcacagt tctactttca   9660
aatacgccat gttgtatttg gacccttcca ttggaggagt gtcgggcatg tctttgtcca   9720
ggttttttgat tagagccttc ccagatcccg taacagaaag tctctcattc tggagattca   9780
tccatgtaca tgctcgaagt gagcatctga aggagatgag tgcagtattt ggaaaccccg   9840
agatagccaa gtttcgaata actcacatag acaagctagt agaagatcca acctctctga   9900
acatcgctat gggaatgagt ccagcgaact tgttaaagac tgaggttaaa aaatgcttaa   9960
tcgaatcaag acaaaccatc aggaaccagg tgattaagga tgcaaccata tatttgtatc  10020
atgaagagga tcggctcaga agtttcttat ggtcaataaa tcctctgttc cctagatttt  10080
taagtgaatt caaatcaggc acttttttgg gagtcgcaga cgggctcatc agtctatttc  10140
aaaattctcg tactattcgg aactccttta agaaaagta tcatagggaa ttggatgatt   10200
tgattgtgag gagtgaggta tcctcttga cacatttagg gaaacttcat ttgaaggg     10260
gatcatgtaa aatgtggaca tgttcagcta ctcatgctga cacattaaga tacaaatcct  10320
ggggccgtac agttattggg acaactgtac cccatccatt agaaatgttg ggtccacaac  10380
atcgaaaaga gactccttgt gcaccatgta acacatcagg gttcaattat gtttctgtgc  10440
attgtccaga cgggatccat gacgtcttta gttcacgggg accattgcct gcttatctag  10500
ggtctaaaac atctgaatct acatctatt tgcagccttg ggaaagggaa agcaaagtcc   10560
cactgattaa aagagctaca cgtcttagag atgctatctc ttggtttgtt gaacccgact  10620
ctaaactagc aatgactata ctttctaaca tccactcttt aacaggcgaa gaatggacca  10680
aaaggcagca tgggttcaaa agaacagggt ctgcccttca taggtttcg acatctcgga  10740
tgagccatgt tgggttcgca tctcagagca ctgcagcat gaccaggttg atggcaacta  10800
cagacaccat gagggatctg ggagatcaga atttcgactt tttattccaa gcaacgttgc  10860
tctatgctca aattaccacc actgttgcaa gagacggatg gatcaccagt tgtacagatc  10920
attatcatat tgcctgtaag tcctgtttga gacccataga agagatcacc ctggactcaa  10980
gtatggacta cacgccccca gatgtatccc atgtgctgaa gacatggagg aatgggaag   11040
gttcgtgggg acaagagata aaacagatct atcctttaga agggaattgg aagaattag   11100
```

```
cacctgctga gcaatcctat caagtcggca gatgtatagg ttttctatat ggagacttgg   11160
cgtatagaaa atctactcat gccgaggaca gttctctatt tcctctatct atacaaggtc   11220
gtattagagg tcgaggtttc ttaaaagggt tgctagacgg attaatgaga gcaagttgct   11280
gccaagtaat acaccggaga agtctggctc atttgaagag gccggccaac gcagtgtacg   11340
gaggtttgat ttacttgatt gataaattga gtgtatcacc tccattcctt tctcttacta   11400
gatcaggacc tattagagac gaattagaaa cgattcccca caagatccca acctcctatc   11460
cgacaagcaa ccgtgatatg ggggtgattg tcagaaatta cttcaaatac caatgccgtc   11520
taattgaaaa gggaaaatac agatcacatt attcacaatt atggttattc tcagatgtct   11580
tatccataga cttcattgga ccattctcta tttccaccac cctcttgcaa atcctataca   11640
agccattttt atctgggaaa gataagaatg agttgagaga gctggcaaat ctttcttcat   11700
tgctaagatc aggagagggg tgggaagaca tacatgtgaa attcttcacc aaggacatat   11760
tattgtgtcc agaggaaatc agacatgctt gcaagttcgg gattgctaag gataataata   11820
aagacatgag ctatcccoct tggggaaggg aatccgagg acaattaca acaatccctg   11880
tttattatac gaccaccoct tacccaaaga tgctagagat gcctccaaga atccaaaatc   11940
ccctgctgtc cggaatcagg ttgggccaat taccaactgg cgctcattat aaaattcgga   12000
gtatattaca tggaatggga atccattaca gggacttctt gagttgtgga gacggctccg   12060
gagggatgac tgctgcatta ctacgagaaa atgtgcatag cagaggaata ttcaatagtc   12120
tgttagaatt atcagggtca gtcatgcgag gcgcctctcc tgagcccccc agtgccctag   12180
aaactttagg aggagataaa tcgagatgtg taaatggtga aacatgttgg gaatatccat   12240
ctgacttatg tgacccaagg acttgggact atttcctccg actcaaagca ggcttggggc   12300
ttcaaattga tttaattgta atggatatgg aagttcggga ttcttctact agcctgaaaa   12360
ttgagacgaa tgttagaaat tatgtgcacc ggatttgaa tgagcaagga gttttaatct   12420
acaagactta tggaacatat atttgtgaga gcgaaaagaa tgcagtaaca atccttggtc   12480
ccatgttcaa gacggtcgac ttagttcaaa cagaatttag tagttctcaa acgtctgaag   12540
tatatatggt atgtaaggt ttgaagaaat taatcgatga acccaatccc gattggtctt   12600
ccatcaatga atcctggaaa aacctgtacg cattccgatc atcagaacag gaatttgcca   12660
gagcaaagaa ggttagtaca tactttaccct tgacaggtat tccctcccaa ttcattcctg   12720
atccttttgt aaacattgag actatgctac aaatattcgg agtacccacg ggtgtgtctc   12780
atgcggctgc cttaaaatca tctgatagac ctgcagattt attgaccatt agccttttttt   12840
atatggcgat tatatcgtat tataacatca atcatatcag agtaggaccg atacctccga   12900
accccccatc agatggaatt gcacaaaatg tggggatcgc tataactggt ataagctttt   12960
ggctgagttt gatggagaaa gacattccac tatatcaaca gtgtttagca gttatcccagc   13020
aatcattccc gattaggtgg gaggctgttt cagtaaaagg aggatacaag cagaagtgga   13080
gtactagagg tgatgggctc ccaaaagata cccgaacttc agactccttg gccccaatcg   13140
ggaactggat cagatctctg gaattggtcc gaaaccaagt tcgtctaaat ccattcaatg   13200
agatcttgtt caatcagcta tgtcgtacag tggataatca tttgaaatgg tcaaatttgc   13260
gaagaaacac aggaatgatt gaatggatca atagacgaat ttcaaaagaa gaccggtcta   13320
tactgatgtt gaagagtgac ctacacgagg aaaaactctt gagagattaa aaaatcatga   13380
ggagactcca aactttaagt atgaaaaaaa ctttgatcct taagaccctc ttgtggtttt   13440
tatttttttat ctggttttgt ggtcttcgt                                    13469

SEQ ID NO: 20          moltype = DNA   length = 13556
FEATURE                Location/Qualifiers
misc_feature           1..13556
                       note = VSV vector: Convac V2 China
source                 1..13556
                       mol_type = other DNA
                       organism = synthetic construct
SEQUENCE: 20
acgaagacaa acaaaccatt attatcatta aaaggctcag gagaaacttt aacagtaatc     60
aaaatgtctg ttacagtcaa gagaatcatt gacaacacag tcatagttcc aaaacttcct    120
gcaaatgagg atccagtgga ataccccgca gattacttca gaaaatcaaa ggagattcct    180
ctttacatca atactacaaa aagtttgtca gatctaagag gatatgtcta ccaaggcctc    240
aaatccggaa atgtatcaat catacatgtc aacagctact gtatggagc attaaaggac    300
atccgggta agttggataa agattggtca agtttcggaa taaacatggt gaaagcaggg    360
gatacaatcg gaatatttga ccttgtatcc ttgaaagccc tggacggcgt acttccagat    420
ggagtatcgg atgcttccag aaccagcgca gatgacaaat ggttgccttt gtatctactt    480
ggcttataca gagtgggcag aacacaaatg cctgaataca gaaaaagct catggatggg    540
ctgacaaatc aatgcaaaat gatcaatgaa cagtttgaac ctcttgtgc agaaggtcgt    600
gacattttg atgtgtgggg aaatgacagt aattacacaa aaattgtcgc tgcagtgaca    660
atgttcttcc acatgttcaa aaaacatgaa tgtgcctcgt tcagatacgg aactattgtt    720
tccagattca aagattgtgc tgcattggca acatttggac acctgcaa ataaccgga    780
atgtctacag aagatgtaac gacctggatc ttgaaccgag aagttgcaga tgaatggtc    840
caaatgatgc ttccaggcca agaaattgac aaggccgatt catcatgcc ttatttgatc    900
gactttggat tgtcttctaa gtctccatat tcttccgtca aaaaccctgc cttccacttc    960
tgggggcaat tgcagctcat tctgctcaga tccaccagag caaggaatgc ccgacagcct   1020
gatgacattt agtatacatc tcttactaca gcaggtttgt tgtacgctta tgcagtagga   1080
tcctctgccg acttggcaca acagttttgt gttggagata acaaatacac tccagatgat   1140
agtaccggag gattgacgac taatgcaccg ccacaaggca gagatgtggt cgaatggctc   1200
ggatggttg aagatcaaaa cagaaaaccg actcctgata tgatgcagta tgcgaaaaga   1260
gcagtcatgt cactgcaagg cctaagagag aagacaattg caagtatgc taagtcagaa   1320
tttgacaaat gaccctataa ttctcagatc acctattata tattatgcta catatgaaaa   1380
aaactaacag atatcatgga taatctcaca aaagttcgtg agtatctcaa gtcctattct   1440
cgtctggatc aggcggtagg agagatagat cacaacgagc tgaaagtcc                 1500
aattatgagt tgttccaaga ggatggagtg gaagagcata ctaagcctc ttattttcag   1560
gcagcagatg attctgacac agaatctgaa ccagaaattg aagacaatca aggtttgtat    1620
gcaccagatc cagaagctga gcaagttgaa ggctttatac aggggcctttt agatgactat   1680
gcagatgagg aagtggatgt tgtattact tcggactgga acagcctga gcttgaatct   1740
gacgagcatg gaaagacctt acggttgaca tcgccagagg gtttaagtgg agagcagaaa    1800
```

```
tcccagtggc tttcgacgat taaagcagtc gtgcaaagtg ccaaatactg gaatctggca    1860
gagtgcacat ttgaagcatc gggagaaggg gtcattatga aggagcgcca gataactccg    1920
gatgtatata aggtcactcc agtgatgaac acacatccgt cccaatcaga agcagtatca    1980
gatgtttggt ctctctcaaa gacatccatg actttccaac ccaagaaagc aagtcttcag    2040
cctctcacca tatccttgga tgaattgttc tcatctagag gagagtttcat ctctgtcgga    2100
ggtgacggac gaatgtctca taaagaggcc atcctgctcg gcctgagata caaaaagttg    2160
tacaatcagg cgagagtcaa atattctctg tagactatga aaaaagtaa cagatatcac    2220
gatctaagtg ttatcccaat ccattcatca tgagttcctt aaagaagatt ctcggtctga    2280
aggggaaagg taagaaatct aagaaattag ggatcgcacc acccccttat gaagaggaca    2340
ctagcatgga gtatgctccg agcgctccaa ttgacaaatc ctattttgga gttgacgaga    2400
tggacaccta tgatccgaat caattaagat atgagaaatt cttctttaca gtgaaaatga    2460
cggttagatc taatcgtccg ttcagaacat actcagatgt ggcagccgct gtatcccatt    2520
gggatcacat gtacatcgga atggcaggga aacgtccctt ctacaaaatc ttggcttttt    2580
tgggttcttc taatctaaag gccactccag cggtattggc agatcaaggt caaccagagt    2640
atcacactca ctgcgaaggc agggcttatt tgccacatag gatgggaag accccctccca    2700
tgctcaatgt accagagcac ttcagaagac cattcaatat aggtctttac aagggaacga    2760
ttgagctcac aatgaccatc tacgatgatg agtcactgga agcagctcct atgatctggg    2820
atcatttcaa ttcttccaaa tttttctgatt tcagagagaa ggccttaatg tttggcctga    2880
ttgtcgagaa aaaggcatct ggagcgtggg tcctggattc tatcagccac ttcaaatgag    2940
ctagtctaac ttctagcttc tgaacaatcc ccggtttact cagtctctcc taattccagc    3000
ctctcgaaca actaatatcc tgtctttct atccctatga aaaaactaa cagagatcga    3060
tctgtttacg cgtcactatg aagtgccttt tgtacttagc cttttattc attggggtga    3120
attgcaagtt caccatagtt tttccacaca accaaaaagg aaactggaaa atgttccttt    3180
ctaattacca ttattgcccg tcaagctcag atttaaattg gcataatgac ttaataggca    3240
cagccataca agtcaaaatg cccaagagtc acaaggctat tcaagcagac ggttggatgt    3300
gtcatgcttc caaatgggtc tactacttgtg atttccgctg gtatgaccg aagtatataa    3360
cacagtccat ccgatccttc actccatctg tagaacaatg caaggaaagc attgaacaaa    3420
cgaaacaagg aacttggctg aatccaggct tccctcctca aagttgtgga tatgcaactg    3480
tgacggatgc cgaagcagtg attgtccagg tgactcctca ccatgtgctg gttgatgaat    3540
acacagagga atgggttgat tcacagttca tcaacgagaa atgcagcaat tacatatgcc    3600
ccactgtcca taactctaca acctggcatt ctgactataa ggtcaaaggg ctatgtgatt    3660
ctaacctcat ttccatggac atcaccttct tctcagagga cggagagcta tcatccctgg    3720
gaaaggaggg cacagggttc agaagtaact actttgctta tgaaactgga ggcaaggcct    3780
gcaaaatgca atactgcaag cattgggga g tcagactccc atcaggtgtc tggttcgaga    3840
tggctgataa ggatcctcttt gctgcagcca gattccctga atgcccagaa gggtcaagta    3900
tctctgctcc atctcagacc tcagtggatg taagtctaat tcaggacgtt gagaggatct    3960
tggattattc cctctgccaa gaaacctgga gcaaaatcag agcgggtctt ccaatctctc    4020
cagtggatct cagctatctt gctcctaaaa acccaggaac cggtcctgct ttcaccataa    4080
tcaatggtac cctaaaatac tttgagacca gatacatgca agtcgatatt gctgctccaa    4140
tcctctcaag aatggtcgga atgatcagtg gaactaccac agaaagggaa ctgtgggatg    4200
actgggcacc atatgaagac gtggaaattg gacccaatgg agttctgagg accagttcag    4260
gatataagtt tccttttatac atgattggac atggtatgtt ggactccgat cttcatctta    4320
gctcaaaggc tcaggtgttc gaacatcctc acattcaaga cgctgcttcg caacttccctg    4380
atgatgagag tttattttttt ggtgatactg ggctatccaa aaatccaatc gagcttgtag    4440
aaggttggtt cagtagttgg aaaagctcta ttgcctcttt tttctttatc ataggggttaa    4500
tcattggact attcttggtt ctccgagttg gtatccatct ttgcattaaa ttaaagcaca    4560
ccaagaaaag acagatttat acagacatag agatgaaccg aacttggaag taactcaaat    4620
cctgctaggt atgaaaaaaa ctaacagata tcacgctcga gcgtacgcca ccatgttcgt    4680
gtttctggtg ctgctgcctc tggtgagctc ccagtgcgtg aacctgacca caaggaccca    4740
gctgccccct gcctatacca attccttcac acggggcgtg tactatcccg acaaggtgtt    4800
ccggagcagc gtgctgcact ccacacagga tctgtttctg ccttttcttt ctaacgtgac    4860
ctggttccac gccatccacg tgagcggcac caatggcaca aagcggttcg acaatccagt    4920
gctgccctttt aacgatggcg tgtacttcgc ctccaccgag aagtctaaca tcatcagagg    4980
ctggatcttt ggcaccacac tggacagcaa gacacagtcc ctgctgatcg tgaacaatgc    5040
caccaacgtg gtcatcaagg tgtgcgagtt ccagttttgt aatgatccat tcctgggcgt    5100
gtactatcac aagaacaata gtcttggat ggagagcgag tttcgcgtgt attcctctgc    5160
caacaattgc acatttgagt acgtgtccca gcccttcctg atggacctgg agggcaagca    5220
gggcaatttc aagaacctga gggagttcgt gtttaagaat atcgatggct acttcaaaat    5280
ctactccaag cacacccaa tcaacctggt gcgcgacctg ccacagggct tctctgcct    5340
ggagccactg gtggatctgc ccatcggcat caacatcacc cggtttcaga cactgctggc    5400
cctgcacaga agctacctga caccaggcga cagctcctct ggatgaccg caggagcagc    5460
agcctactat gtgggctatc tgcagcccag gaccttcctg ctgaagtaca acgagaatgg    5520
caccatcaca gacgccgtgg attgcgccct ggatcccctg tctgagacca gtgtacact    5580
gaagagctt accgtggaga agggatcta tcagacaagt aatttcagtg tgcagcctac    5640
cgagtccatc gtgcgctttc caatatcac aaacctgtgc cctttggcg aggtgttcaa    5700
cgcaaccgc ttcgccagcg tgtacgcctg gaataggaag cgcatctcca actgcgtggc    5760
cgactattct gtgctgtaca acagcgcctc cttctctacc tttaagtgct atggcgtgag    5820
ccccacaaag ctgaatgacc tgtgctttac caacgtgtac gccgattcct tcgtgatcag    5880
gggcgacgag gtgcgccaga tcgccaccag acagacaggc aagatcgcag actacaatta    5940
taagctgcct gacgatttca ccggctgcgt gatcgcctgg aactctaaca atctggatag    6000
caaagtgggc ggcaactaca attatctgta ccggctgttt agaaagtcta atctgaagcc    6060
attcgagagg gacatctcca cagaaatcta ccaggccggc tctaccccct gcaatggcgt    6120
ggagggcttt aactgttatt tccctctgca gagctacggt ttccagccaa caaacggcgt    6180
gggctatcag ccctaccgcg tggttgtgct gtctttcgag ctgctgcacg cacctgcaac    6240
agtgtgcgga ccaaagaaga gcaccaatct ggtgaagaac aagtgcgtga acttcaactt    6300
caacggacta accggaacag gcgtgctgac cgagtccaac aagaagttcc tgcctttcca    6360
gcagttcggc agggacatcg cagataccac agacgccgtg cgcgaccctc agaccctgga    6420
gatcctggac atcacaccat gctccttcgg cggcgtgtct gtgatcacac caggcaccaa    6480
tacaagcaac caggtggccg tgctgtatca ggacgtgaat tgtaccgagg tgccagtggc    6540
```

```
aatccacgca gatcagctga cccctacatg gcgggtgtac tctaccggca gcaacgtgtt   6600
ccagacaaga gccggatgcc tgatcggagc agagcacgtg aacaatagct atgagtgcga   6660
catccctatc ggcgccggca tctgtgcctc ctaccagacc cagacaaact ccccaaggtc   6720
tgtgggagat gaggccgaag actttgtgga agtccacctg cctgatgtgc ataaccaggt   6780
gtctggcgtc gacctgggac tgccaaattg gggcaagtac gtgctgctga gtgctggagc   6840
actgactgcc ctgatgctga tcattttcct gatgacctgc tgtcggcgcg tgaacagaag   6900
tgagcccact cagcacaatc tgcgaggaac cgggagagaa gtgtcagtca cacctcagag   6960
cgggaaaatc attagtagtt gggaatcaca taaaagcggg ggcgagacca ggctgtgagc   7020
tagccagatt cttcatgttt ggaccaaatc aacttgtgat accatgctca aagaggcctc   7080
aattatattt gagtttttaa tttttatgaa aaaaactaac agcaatcatg gaagtccacg   7140
attttgagac cgacgagttc aatgatttca atgaagatga ctatgccaca agagaattcc   7200
tgaatcccga tgagcgcatg acgtacttga atcatgctga ttacaatttg aattctcctc   7260
taattagtga tgatattgac aatttgatca ggaaattcaa ttctcttccg attccctcga   7320
tgtgggatag taagaactgg gatggagttc ttgagatgtt aacatcatgt caagccaatc   7380
ccatctcaac atctcagatg cataaatgga tgggaagttg gttaatgtct gataatcatg   7440
atgccagtca agggtatagt tttttacatg aagtggacaa agaggcagaa ataacatttg   7500
acgtggtgga gaccttcatc cgcggctggg gcaacaaacc aattgaatac atcaaaaagg   7560
aaagatggac tgactcattc aaaattctcg cttatttgtg tcaaaagttt ttggacttac   7620
acaagttgac attaatctta aatgctgtct ctgaggtgga attgctcaac ttggcgagga   7680
cttttcaaagg caaagtcaga gaagttctc atggaacgaa catatgcagg attagggttc   7740
ccagcttggg tcctactttt atttcagaag gatgggctta cttcaagaaa cttgatattc   7800
taatggaccg aaacttttctg ttaatggtca aagatgtgat tatagggagg atgcaaacgg   7860
tgctatccat ggtatgtaga atagacaacc tgttctcaga gcaagacatc ttctcccttc   7920
taaatatcta cagaattgga gataaaattg tggagaggca gggaaatttt tcttatgact   7980
tgattaaaat ggtggaaccg atatgcaact tgaagctgat gaaattagca agagaatcaa   8040
ggccctttagt cccacaattc cctcattttg aaaatcatat caagacttct gttgatgaag   8100
gggcaaaaat tgaccgaggt ataagattcc tccatgatca gataatgagt gtgaaaacag   8160
tggatctcac actggtgatt tatggatcgt tcagacattg gggtcatcct tttatagatt   8220
attacactgg actagaaaaa ttacattccc aagtaaccat gaagaaagat attgatgtgt   8280
catatgcaaa agcacttgca agtgatttag ctcggattgt tctatttcaa cagttcaatg   8340
atcataaaaa gtggttcgtg aatggagact tgctccctca tgatcatccc tttaaaagtc   8400
atgttaaaga aaatacatgg cccacagctg ctcaagttca agattttgga gataaatggc   8460
atgaacttcc gctgattaaa tgttttgaaa tacccgactt actagaccca tcgataatat   8520
actctgacaa aagtcattca atgaataggt cagaggtgtt gaaacatgtc cgaatgaatc   8580
cgaacactcc tatccctagt aaaaaggtgt tgcagactat gttggacaca aaggctacca   8640
attggaaaga atttcttaaa gagattgatg agaagggctt agatgatgat gatctaatta   8700
ttggtcttaa aggaaaggag agggaactga agttggcagg tagattttttc tccctaatgt   8760
cttggaaatt gcgagaatac tttgtaatta ccgaatattt gataaagact catttcgttcc   8820
ctatgtttaa aggcctgaca atggcggacg atctaactgc agtcattaaa aagatgttag   8880
attcctcatc cggccaagga ttgaagtcat atgaggcaat ttgcatagcc aatcacattg   8940
attacgaaaa atgaataac caccaaagga agttatcaaa cggccagtg ttccgagtta   9000
tgggccagtt cttaggttat ccatcctaa tcgagagaac tcatgaattt tttgagaaaa   9060
gtcttatata ctacaatgga agaccagact tgatgcgtat tcacaacaac acactgatca   9120
attcaacctc ccaacgagtt tgttggcaag gacaagaggg tggactggaa ggtctacgcc   9180
aaaaaggatg gactatcctc aatctactgg ttattcaaag agaggctaaa atcagaaaca   9240
ctgctgtcaa agtcttggca caaggtgata atcaagttat ttgcacacag tataaaacga   9300
agaaatcgag aaacgttgta gaattacagg gtgctctcaa tcaaatggtt tctaataatg   9360
agaaaattat gactgcaatc aaaataggga cagggaagtt aggacttttg ataaatgacg   9420
atgagactat gcaatctgca gattacttga attatgaaaa aataccgatt ttccgtggag   9480
tgattagagg gttagagacc aagagatggt cacgagtgac ttgtgtcacc aatgaccaaa   9540
tacccacttg tgctaatata atgagctcag ttttccacaa tgctctccca gtagctcatt   9600
ttgctgagaa cccaatcaat gccatgatac agtacaatta ttttgggaca tttgctagac   9660
tcttgttgat gatgcatgat cctgctcttc gtcaatcatt gtatgaagtt caagataaga   9720
taccgggctt gcacagttct actttcaaat acgccatgtt gtatttggac ccttccattg   9780
gaggagtgtc gggcatgtct ttgtccaggt ttttgattag agccttccca gatcccgtaa   9840
cagaaagtct ctcattctgg agattcatcc atgtacatgc tcgaagtgag catctgaagg   9900
agatgagtgc agtatttgga aaccccgaga tagccaagtt tcgataaact cacatagaca   9960
agctagtaga agatccaacc tctctgaaca tcgctatggg aatgagtcca gcgaacttgt  10020
taaagactga ggttaaaaaa tgcttaatcg aatcaagaca aaccatcagg aaccaggtga  10080
ttaaggatgc aaccatatat ttgtatcatg aagaggatcg gctcagaagt ttcttatggt  10140
caataaaatcc tctgttccct agattttaa gtgaattcaa atcaggcact ttttgggag  10200
tcgcagacgg gctcatcagt ctatttcaaa attctcgtac tattcggaac tcctttaaga  10260
aaagtcatca tagggaattg gatgatttga ttgtgaggag tgaggtatcc tctttgacac  10320
atttagggaa acttcatttg agaagggat catgtaaaat gtggacatgt tcagctactc  10380
atgctgacac attaagatac aaatcctggg gccgtacagt tattgggaca actgtaccccc  10440
atccattaga aatgttgggt ccacaacatc gaaaagagac tccttgtgca ccatgtaaca  10500
catcagggtt caattatgtt tctgtgcatt gtccagacgg gatccatgac gtctttagtt  10560
cacggggacc attgcctgct tatctagggt ctaaaacatc tgaatctaca tctatttgc  10620
agccttggga aagggaaagc aaagtcccac tgattaaaag agctacacgt cttagagatg  10680
ctatctcttg gtttgttgaa cccgactcta aactagcaat gactatactt tctaacatcc  10740
actctttaac aggcgaagaa tggaccaaaa ggcagcatgg gttcaaaaga cagggtctg  10800
cccttcatag gttttcgaca tctcggatga gccatggtgg gttcgcatct cagagcactg  10860
cagcattgac caggttgatg gcaactacag acaccatgag ggatctggga gatcagaatt  10920
tcgactttttt attccaagca acgttgctct atgctcaaat taccaccact gttgcaagag  10980
acggatggat caccagttgt acagatcatt atcatattgc ctgtaagtcc tgtttgagac  11040
ccatagaaga gatcacccctg gactcaagta tggactacac gccccagat gtatcccatg  11100
tgctgaagac atggaggaat ggggaaggtt cgtgggaca agagataaaa cagatctatc  11160
ctttagaagg gaattggaag aatttagcac tgctgagca atcctatcaa gtcggcagat  11220
gtataggttt tctatatgga gacttggcgt atagaaaatc tactcatgcc gaggacagtt  11280
```

```
ctctatttcc tctatctata caaggtcgta ttagaggtcg aggtttctta aaagggttgc  11340
tagacggatt aatgagagca agttgctgcc aagtaataca ccggagaagt ctggctcatt  11400
tgaagaggcc ggccaacgca gtgtacggag gtttgattta cttgattgat aaattgagtg  11460
tatccacctcc attcctttct cttactagat caggacctat tagagacgaa ttagaaacga  11520
ttccccacaa gatcccaacc tcctatccga caagcaaccg tgtatatggg gtgattgtca  11580
gaaattactt caaataccaa tgccgtctaa ttgaaaaggg aaaatacaga tcacattatt  11640
cacaattatg gttattctca gatgtcttat ccatagactt cattggacca ttctctattt  11700
ccaccaccct cttgcaaatc ctatacaagc catttttatc tgggaaagat aagaatgagt  11760
tgagagagct ggcaaatctt tcttcattgc taagatcagg agaggggtgg gaagacatac  11820
atgtgaaatt cttcaccaag gacatattat tgtgtccaga ggaaatcaga catgcttgca  11880
agttcgggat tgctaaggat aataataaag acatgagcta tccccccttgg ggaagggaat  11940
ccagagggac aattacaaca atccctgttt attatacgac caccccttac ccaaagatgc  12000
tagagatgcc tccaagaatc caaaatcccc tgctgtccgg aatcaggttg gccaattac  12060
caactggcgc tcattataaa attcggagta tattacatgg aatggaatc cattacaggg  12120
acttcttgag ttgtggagac ggctccggag ggatgactgc tgcattacta cgagaaaatg  12180
tgcatagcag aggaatattc aatagtctgt tagaattatc agggtcagtc atgcgaggcg  12240
cctctcctga gcccccagt gccctagaaa ctttaggagg agataaatcg agatgtgtaa  12300
atggtgaaac atgttgggaa tatccatctg acttatgtga cccaaggact tgggactatt  12360
tcctccgact caaagcaggc ttggggcttc aaattgattt aattgtaatg gatatgaag  12420
ttcgggattc ttctactagc ctgaaaattg agacgaatgt tagaaattat gtgcaccgga  12480
ttttggatga gcaaggagtt ttaatctaca agacttatgg aacatatatt tgtgagagcg  12540
aaaagaatgc agtaacaatc cttggtccca tgttcaagac ggtcgactta gttcaaacag  12600
aatttagtag ttctcaaacg tctgaagtat atatggtatg taaaggtttg aagaaattaa  12660
tcgatgaacc caatcccgat tggtcttcca tcaatgaatc ctggaaaaac ctgtacgcat  12720
tccagtcatc agaacaggaa tttgccagag caaagaaggt tagtacatac tttaccttga  12780
caggtattcc ctcccaattc attcctgatc cttttgtaaa cattgagact atgctacaaa  12840
tattcggagt accccacggg gtgtctcatg cggctgcctt aaaatcatct gatagacctg  12900
cagatttatt gaccattagc cttttttata tggcgattat atcgtattat aacatcaatc  12960
atatcagagt aggaccgata cctccgaacc ccccatcaga tggaattgca caaatgtgg  13020
ggatcgctat aactggtata agcttttggc tgagtttgat ggagaaagac attccactat  13080
atcaacagtg tttagcagtt atccagcaat cattcccgat taggtgggag gctgtttcag  13140
taaaaggagg atacaagcag aagtggagta ctagaggtga tgggctccca aaagataccc  13200
gaacttcaga ctccttggcc ccaatcggga actggatcag atctctgaa ttggtccgaa  13260
accaagttcg tctaaatcca ttcaatgaga tcttgttcaa tcagctatgt cgtacagtgg  13320
ataatcattt gaaatggtca aatttgcgaa gaaacacagg aatgattgaa tggatcaata  13380
gacgaatttc aaaagaagac cggtctatac tgatgttgaa gagtgaccta cacgaggaaa  13440
actcttggag agattaaaaa atcatgagga gactccaaac tttaagtatg aaaaaaactt  13500
tgatccttaa gaccctcttg tggtttttat tttttatctg gttttgtggt cttcgt       13556

SEQ ID NO: 21            moltype = DNA length = 13607
FEATURE                  Location/Qualifiers
misc_feature             1..13607
                         note = VSV vector: Convac V2 South Africa
source                   1..13607
                         mol_type = other DNA
                         organism = synthetic construct
SEQUENCE: 21
acgaagacaa acaaaccatt attatcatta aaaggctcag gagaaacttt aacagtaatc    60
aaaatgtctg ttacagtcaa gagaatcatt gacaacacag tcatagttcc aaaacttcct   120
gcaaatgagg atcagtgga ataccggca gattacttca gaaaatcaaa ggagattcct   180
ctttacatca atactacaaa aagtttgtca gatctaagag gatatgtcta ccaaggcctg   240
aaatccggaa atgtatcaat catacatgtc aacagctact tgtatggagc attaaaggac   300
atccggggta agttggataa agattggtca agtttcggaa taaacatcgg aaagcaggg   360
gatacaatcg gaatatttga ccttgtatcc ttgaaagccc tggacggcgt acttccagat   420
ggagtatcgg atgcttccag aaccagcgca gatgacaat ggttgccttt gtatctactt   480
ggcttataca gagtgggcag aacacaaatg cctgaataca gaaaaagct catggatggc   540
ctgacaaatc aatgcaaaat gatcaatgaa cagtttgaac ctcttgtgcc agaaggtcgt   600
gacattttttg atgtgtgggg aaatgacagt aattacacaa aaattgtcgc tgcagtggac   660
atgttcttcc acatgttcaa aaaacatgaa tgtgcctcgt tcagatacgg aactattgtt   720
tccagattca aagattgtgc tgcattggca acatttggac acctctgcaa aataaccgga   780
atgtctacag aagatgtaac gacctggatc ttgaaccgag aagttgcaga tgaaatggtc   840
caaatgatgc ttccaggcca agaaattgac aaggccgatt catacatgcc ttatttgatc   900
gactttggat tgtcttctaa gtctccatat tcttccgtca aaaacctgc cttccacttc   960
tgggggcaat tgcagctct tctgctcaga tccaccagga caaggaatgc ccgacagtt   1020
gatgacattg agtatacatc tcttactaca gcaggttttgt tgtacgctta tgcagtagga   1080
tcctctgccg acttggcaca acagttttgt gttggagata caaatacac tccagatgat   1140
agtaccggag gattgacgac taatgcaccg ccacaaggca gagatgtggt cgaatggctc   1200
ggatggtttg aagatcaaaa cagaaaaccg actcctgata tgtgcagta tgcgaaaaga   1260
gcagtcatgt cactcaaggg cctaagagag aagacaattg gcaagtcagaa   1320
tttgacaaat gacccctataa ttctcagatc accattatat tattatgcta catatgaaaa   1380
aaactaacag atatcatgga taatctcaca aaagttcgtg agtatctcaa gtccattct   1440
cgtctggatc aggcggtagg agagatagat gagatcgaag cacaacgagc tgaaaagtcc   1500
aattatgagt tgttccaaga ggatggagtg aagagcata ctaagccctc ttattttcag   1560
gcagcagatg attctgacac aagaatctgaa ccagaaattg aagacaatca aggtttgtat   1620
gcaccagatc cagaagctga gcaagttgaa ggctttatac aggggcctt agatgactat   1680
gcagatgagg aagtggatgt tgtatttact tcggactgga acaagcctga gcttgaatct   1740
gacgagcatg gaaagacctt acggttgaca tcgccagagg gttaagtgg agagcagaaa   1800
tcccagtggc tttcgacgat taaagcagtc gtgcaaagtc ccaaatactg gaatctgca   1860
gagtgcacat ttgaagcatc gggagaaggg gtcattatga aggagcgcca gataactccg   1920
```

```
gatgtatata aggtcactcc agtgatgaac acacatccgt cccaatcaga agcagtatca   1980
gatgtttggt ctctctcaaa gacatccatg actttccaac ccaagaaagc aagtcttcag   2040
cctctcacca tatccttgga tgaattgttc tcatctagag gagagttcat ctctgtcgga   2100
ggtgacggac gaatgtctca taaagaggcc atcctgctcg gcctgagata caaaaagttg   2160
tacaatcagg cgagagtcaa atattctctg tagactatga aaaaaagtaa cagatatcac   2220
gatctaagtg ttatcccaat ccattcatca tgagttcctt aaagaagatt ctcggtctga   2280
aggggaaagg taagaaatct aagaaattag ggatcgcacc accccttat gaagaggaca   2340
ctagcatgga gtatgctccg agcgctccaa ttgacaaatc ctattttgga gttgacgaga   2400
tggacaccta tgatccgaat caattaagat atgagaaatt cttctttaca gtgaaaatga   2460
cggttagatc taatcgtccg ttcagaacat actcagatgt ggcagccgct gtatcccatt   2520
gggatcacat gtacatcgga atggcaggga acgtcccctt ctacaaaatc ttggcttttt   2580
tgggttcttc taatctaaag gccactccag cggtattggc agatcaaggt caaccagagt   2640
atcacactca ctgcgaaggc agggcttatt tgccacatag gatggggaag acccctccca   2700
tgctcaatgt accagagcac ttcagaagac cattcaatat aggtctttac aagggaacga   2760
ttgagctcac aatgaccatc tacgatgatg agtcactcga agcagctcct atgatctggg   2820
atcatttcaa ttcttccaaa ttttctgatt tcagagagaa ggcctaaatg tttggcctga   2880
ttgtcgagaa aaaggcatct ggagcgtggg tcctggattc tatcagccac ttcaaatgag   2940
ctagtctaac ttctagcttc tgaacaatcc ccggtttact cagtctctcc taattccagc   3000
ctctcgaaca actaatatcc tgtcttttct atccctatga aaaaaactaa cagagatcga   3060
tctgtttacg cgtcactatg aagtgccctt tgtacttagc cttttattc attggggtga   3120
attgcaagtt caccatagtt tttccacaca accaaaaagg aaactggaaa aatgttcctt   3180
ctaattacca ttattgcccg tcaagctcag atttaaattg gcataatgac ttaataggca   3240
cagccataca agtcaaaatg cccaagagtc acaaggctat tcaagcagac ggttggatgt   3300
gtcatgcttc caaatgggtc actacttgtg atttccgctg gtatgaccg aagtatataa   3360
cacagtccat ccgatccttc actccatctg tagaacaatg caaggaaagc attgaacaaa   3420
cgaaacaagg aacttggctg aatccaggct tccctcctca aggttgtgga tatgcaactg   3480
tgacggatgc cgaagcagtg attgtccagg tgactcctca ccatgtgctg gttgatgaat   3540
acacaggaga atgggttgat tcacagttca tcaacgaaaa atgcagcaat tacatatgcc   3600
ccactgtcca taactctaca acctggcatt ctgactaaa ggtcaaaggg ctatgtgatt   3660
ctaacctcat ttccatggac atcaccttct tctcagagga cggagcta tcatccctgg   3720
gaaaggaggg cacagggttc agaagtaact actttgctta tgaaactgga ggcaaggcct   3780
gcaaaatgca atactgcaag cattggggag tcagactccc atcaggtgtc tggttcgaga   3840
tggctgataa ggatctcttt gctgcagcca gattccctga tgcccagaa gggtcaagta   3900
tctctgctcc atctcagacc tcagtggatg taagtctaat tcaggacgtt gagaggatct   3960
tggattattc cctctgccaa gaaacctgga gcaaaatcag agcgggtctt ccaatctctc   4020
cagtggatct cagctatctt gctcctaaaa acccaggaac cggtcctgct ttcaccataa   4080
tcaatggtac cctaaaatac tttgagacca gatacatcag agtcgatatt gctgctccaa   4140
tcctctcaag aatggtcgga atgatcagtg gaactaccag agaaagggaa ctgtgggatg   4200
actgggcacc atatgaagac gtggaaattg gacccaatgg agttctgagg accagttcga   4260
gatataagtt tcctttatac atgattggac atggtatgtt ggactccgat cttcatctta   4320
gctcaaaggc tcaggtgttc gaacatcctc acattcaaga cgctgcttcg caacttcctg   4380
atgatgagag tttatttttt ggtgatactg gctatccaa aaatccaatc gagcttgtag   4440
aaggttggtt cagtagttgg aaaagctcta ttgcctctt tttctttatc ataggggtaa   4500
tcattggact attcttggtt ctccgagttg gtatccatct ttgcattaaa ttaaagcaca   4560
ccaagaaaag acagatttat acagacatag agatgaaccg acttggaaag taactcaaat   4620
cctgctaggt atgaaaaaaa ctaacagata tcacgctcga gcgtacgcca ccatgttcgt   4680
gtttctggtg ctgctgcctc tggtgagctc ccagtgcgtg aacttcacca caaggaccca   4740
gctgccccct gcctatacca attccttcac acgggggcgtg tactatcccg acaaggtgtt   4800
ccggagcagc gtgctgcact ccacacagga tctgtttctg cctttctttt ctaacgtgac   4860
ctggttccac gccatccacg tgagcggcac caatggcaca aagcggttcg ccaatccagt   4920
gctgcccttt aacgatggcg tgtacttcgc ctccaccgag aagtctaaca tcatcagagg   4980
ctggatcttt ggcaccacac tggacagcaa gacacagtcc ctgctgatcg tgaacaatgc   5040
caccaacgtg gtcatcaagg tgtgcgagtt ccagttttgt aatgatccat tcctgggcgt   5100
gtactatcac aagaacaata agtccttgat ggagagcgag tttcgcgtgt attcctctgc   5160
caacaattgc acatttgagt acgtgtccca gccccttcctg atggacctgg agggcaagca   5220
gggcaatttc aagaacctga gggagttcgt gtttaagaat atcgatggct acttcaaaat   5280
ctactccaag cacacccccaa tcaacctggt gcgcggcctg ccacagggct ctctgcct   5340
ggagccactg gtggatctgc ccatcggcat caacatcacc cggtttcaga cactgctggc   5400
cctgcacaga agctacctga caccaggcga cagctcctct ggatggaccg caggagcagc   5460
agcctactat gtgggctatc tgcagcccag gaccttcctg ctgaagtaca acgagaatgg   5520
caccatcaca gacgccgtgg attgcgccct ggatccctg tctgagacca gtgtacact   5580
gaagagcttt accgtggaga agggcatcta tcagacaagc aatttcaggg tgcagcctac   5640
cgagtccatc gtgcgctttc caatatcac aaacctgtgc ccttttggcg aggtgttcaa   5700
cgcaacccgc ttcgccagcg tgtacgcctg gaataggaag catcctcca actgcgtggc   5760
cgactattct gtgctgtaca acagcgcctc cttctctacc tttaagtgct atggcgtgag   5820
ccccacaaag ctgaatgacc tgtgctttac caacgtgtac gccgattcct tcgtgatcag   5880
gggcgacgag gtgcgccaga tcgcaccagg acagacaggc aatatcgcag actacaatta   5940
taagctgcct gacgatttca ccggctgcgt gatcgcctgg aactctaaca tctggatag   6000
caaagtgggc ggcaactaca attatctgta ccggctgttt agaaagtcta atctgaagcc   6060
attcgagagg gacatctcca cagaaatcta ccaggccggc tctaccccct gcaatgggcgt   6120
gaagggcttt aactgttatt tccctctgca gagctacggc ttccagccaa catatggcgt   6180
gggctatcag ccctaccgcg tggtggtgct gtcttttgag ctgctgcacg cacctgcaac   6240
agtgtgcgga ccaaagaaga gcaccaatct ggtgaagaac aagtgcgtga acttcaactt   6300
caacgggctg accggaacag gtgtgctgac cgagtccaac aagaagttcc tgcctttca   6360
gcagttcggc agggacatcg cagataccac agacgccgtg cgcgaccctc agaccctgga   6420
gatcctggac atcaccaccat gctccttcgg cggcgtgtct gtgatcacac caggcaccaa   6480
tacaagcaac caggtggccg tgctgtatca gggcgtgaat gtaccgaggt gccagtggc   6540
aatccacgca gatcagctga ccccctacatg gcgggtgtac tctaccggca gcaacgtgtt   6600
ccagacaaga gccggatgcc tgatcggagc agagcacgtg aacaatagct atgagtgcga   6660
```

```
catccctatc ggcgccggca tctgtgcctc ctaccagacc cagacaaact ccccagaatc   6720
aagcgtgatt cctctggtcc atccactgga agatccctcc acagtgttca aagacggaga   6780
tgaggccgaa gactttgtgg aagtccacct gcctgatgtg cataaccagg tgtctggcgt   6840
cgacctggga ctgccaaatt ggggcaagta cgtgctgctg agtgctggag cactgactgc   6900
cctgatgctg atcattttcc tgatgacctg ctgtcggcgc gtgaacagaa gtgagcccac   6960
tcagcacaat ctgcgaggaa ccgggagaga agtgtcagtc acacctcaga gcgggaaaat   7020
cattagtagt tgggaatcac ataaaagcgg gggcgagacc aggctgtgag ctagccagat   7080
tcttcatgtt tggaccaaat caacttgtga taccatgctc aaagaggcct caattatatt   7140
tgagttttta atttttatga aaaaaactaa cagcaatcat ggaagtccac gattttgaga   7200
ccgacgagtt caatgatttc aatgaagatg actatgccac aagagaattc ctgaatcccg   7260
atgagcgcat gacgtacttg aatcatgctg attacaattt gaattctcct ctaattagtg   7320
atgatattga caatttgatc aggaaattca attctcttcc gattccctcg atgtgggata   7380
gtaagaactg ggatggagtt cttgagatgt taacatcatg tcaagccaat cccatctcaa   7440
catctcagat gcataaatgg atgggaagtt ggttaatgtc tgataatcat gatgccagtc   7500
aagggtatag ttttttacat gaagtggaca aagaggcaga aataacattt gacgtggtgg   7560
agaccttcat ccgcggctgg ggcaacaaac caattgaata catcaaaaag gaaagatgga   7620
ctgactcatt caaaattctc gcttatttgt gtcaaaagtt tttggactta cacaagttga   7680
cattaatctt aaatgctgtc tctgaggtgg aattgctcaa cttggcgagg actttcaaag   7740
gcaaagtcag aagaagttct catgaacga acatatgcag gattagggtt cccagccttgg   7800
gtcctacttt tatttcagaa ggatgggctt acttcaagaa acttgatatt ctaatggacc   7860
gaaactttct gttaatggtc aaagatgtga ttataggag gatgcaaacg tgctatcca    7920
tggtatgtag aatagacaac ctgttctcag agcaagacat cctctccctt ctaaatatct   7980
acagaattgg agataaaatt gtggagaggc agggaaattt ttcttatgac ttgattaaaa   8040
tggtggaacc gatatgcaac ttgaagctga tgaaattagc aagagaatca aggcctttag   8100
tcccacaatt ccctcatttt gaaaatcata tcaagacttc tgttgatgaa ggggcaaaaa   8160
ttgaccgagg tataagattc ctccatgatc agataatgag tgtgaaaaca gtggatctca   8220
cactggtgat ttatggatcg ttcagacatt gggtcatcc ttttatagat tattacactg    8280
gactagaaaa attacattcc caagtaacca tgaagaaaga tattgatgtg tcatatgcaa   8340
aagcacttgc aagtgattta gctcggattg ttctatttca acagttcaat gatcataaaa   8400
agtggttcgt gaatggagac ttgctccctc atgatcatcc ctttaaaagt catgttaaag   8460
aaaatacatg gcccacagct gctcaagttc aagattttgg agataaatgg catgaacttc   8520
cgctgattaa atgttttgaa atacccgact tactagaccc atcgataata tactctgaca   8580
aaagtcattc aatgaatagg tcagaggtgt gaaacatgt ccgaatgaat ccgaacactc     8640
ctatccctag taaaaaggtg ttgcagacta tgttggacac aaaggctacc aattggaaag   8700
aatttcttaa agagattgat gagaagggct tagatgatga tgatctaatt attggtctta   8760
aaggaaagga gagggaactg aagttggcag gtagattttt ctcccctaatg tcttggaaat   8820
tgcgagaata ctttgtaatt accgaatatt tgataaagac tcatttcgtc cctatgttta   8880
aaggcctgac aatggcggac gatctaactg cagtcattaa aaagatgtta gattcctcat   8940
ccggccaagg attgaagtca tatgaggcaa tttgcatagc caatcacatt gattacgaaa   9000
aatgaataa ccaccaaagg aagttatcaa acgcccagt gttccgagtt atgggccagt     9060
tcttaggtta tccatcctta atcgagagaa ctcatgaatt ttttgagaaa agtcttatat   9120
actacaatgg aagaccagac ttgatgcgtg ttcacaacaa cacactgatc aattcaacct   9180
cccaacgagt ttgttggcaa ggacaagagg gtggactgga aggtctacgg caaaaaggat   9240
ggactatcct caatctactg gttattcaaa gagaggctaa aatcagaaac actgctgtca   9300
aagtcttggc acaaggtgat aatcaagtta tttgcacaca gtataaaacg aagaaatcga   9360
gaaacgttgt agaattacag ggtgctctca atcaaatggt ttctaataat gagaaaatta   9420
tgactgcaat caaaataggg acagggaagt taggactttt gataaatgac gatgagacta   9480
tgcaatctgc agattacttg aattatgaaa aaataccgat tttccgtgga gtgattagag   9540
ggttagagac caagagatgg tcacgagtga cttgtgtcac caatgaccaa ataccccactt  9600
gtgctaatat aatgagctca gtttccacaa atgctctcac cgtagctcat tttgctgaga   9660
acccaatcaa tgccatgata cagtacaatt attttgggac atttgctaga tcttgttga    9720
tgatgcatga tcctgctctt cgtcaatcat tgtatgaagt tcaagataag ataccgggct   9780
tgcacagttc tactttcaaa tacgccatgt tgtatttgga cccttccatt ggaggagtgt   9840
cgggcatgtc tttgtccagg ttttttgatta gagccttccc agatcccgta acagaaagtc   9900
tctcattctg gagattcatc catgtacatg ctcgaagtga gcatctgaag gagatgagtg   9960
cagtatttgg aaaccccgag atagccaagt ttcgaataac tcacatagac aagctagtag  10020
aagatccaac ctctctgaac atcgctatgg gaatgagtcc agcgaacttg ttaaagactg  10080
aggttaaaaa atgcttaatc gaatcaagac aaaccatcag gaaccaggtg attaaggatg  10140
caaccatata tttgtatcat gaagaggatc ggctcagaag tttcttatgg tcaataaatc  10200
ctctgttccc tagatttta agtgaattca aatcaggcac tttttttggga gtcgcagacg  10260
ggctcatcag tctatttcaa aattctcgta ctattcggaa ctcctttaag aaaaagtatc  10320
ataggaatt ggatgatttg attgtgagga gtgaggtatc ctcttgaca catttaggga    10380
aacttcattt gagaagggga tcatgtaaaa tgtggacatg ttcagctact catgctgaca  10440
cattaagata caaatcctgg ggccgtacag ttattgggac aactgtaccc catccattag  10500
aaatgttggg tccacaacat cgaaaagaga ctccttgtgc accatgtaac acatcagggt  10560
tcaattatgt ttctgtgcat tgtccagacg ggatccatga cgtctttagt tcacggggac  10620
cattgcctgc ttatctaggg tctaaaacat ctgaatctac atctattttg cagccttggg  10680
aaaggggaaag caaagtccca ctgattaaaa gactacacg tcttagagat gctatctctt  10740
ggtttgttga acccgactct aaactagcaa tgactatact ttctaacatc cactctttaa  10800
caggcgaaga atggaccaaa aggcagcatg ggttcaaaag aacagggtct gcccttcata  10860
ggttttcgac atctcggatg agccatgtgt ggttcgcatc tcagagcact gcagcattga  10920
ccaggttgat ggcaactaca gacaccatga gggatctggg agatcagaat tcgactttt   10980
tattccaagc aacgttgctc tatgctcaaa ttaccaccac tgttgcaaga acggatgga   11040
tcaccagttg tacagatcat tatcatattg cctgtaactc ctgtttgaga catagaaag   11100
agatcaccct ggactcaagt atggactaca cgccccaga tgtatcccat gtgctgaaga  11160
catggaggaa tggggaaggt tcgtggggac aagagataaa acagatctat cctttagaag  11220
ggaattggaa gaatttagca cctgctgagc aatcctatca agtcggcaga tgtataggtt  11280
ttctatatgg agacttggcg tatagaaaat ctactcatgc cgaggacagt tctctatttc  11340
ctctatctat acaaggtcgt attagaggtc gaggtttctt aaaagggttg ctagacggat  11400
```

-continued

```
taatgagagc aagttgctgc caagtaatac accggagaag tctggctcat ttgaagaggc  11460
cggccaacgc agtgtacgga ggtttgattt acttgattga taaattgagt gtatcacctc  11520
cattcctttc tcttactaga tcaggaccta ttagagacga attagaaacg attccccaca  11580
agatcccaac ctcctatccg acaagcaacc gtgatatggg ggtgattgtc agaaattact  11640
tcaaatacca atgccgtcta attgaaaagg gaaaatacag atcacattat tcacaattat  11700
ggttattctc agatgtctta tccatagact tcattggacc attctctatt tccaccaccc  11760
tcttgcaaat cctatacaag ccattttat ctgggaaaga taagaatgag ttgagagagc  11820
tggcaaatct ttcttcattg ctaagatcag gagaggggtg ggaagacata catgtgaaat  11880
tcttcaccaa ggacatatta ttgtgtccag aggaaatcag acatgcttgc aagttcggga  11940
ttgctaagga taataataaa gacatgagct atccccttg gggaagggaa tccagaggga  12000
caattacaac aatccctgtt tattatacga ccacccctta cccaaagatg ctagagatgc  12060
ctccaagaat ccaaaatccc ctgctgtccg gaatcaggtt gggccaatta ccaactggcg  12120
ctcattataa aattcggagt atattacatg gaatgggaat ccattacagg gacttcttga  12180
gttgtggaga cggctccgga gggatgactg ctgcattact acgagaaaat gtgcatagca  12240
gaggaatatt caatagtctg ttagaattat cagggtcagt catgcgaggc gcctctcctg  12300
agcccccag tgcctagaa actttaggag gagataaatc gagatgtgta aatggtgaaa  12360
catgttggga atatccatct gacttatgtg acccaaggac ttgggactat ttcctccgac  12420
tcaaagcagg cttggggctt caaattgatt taattgtaat ggatatggaa gttcgggatt  12480
cttctactag cctgaaaatt gagacgaatg ttagaaatta tgtgcaccgg attttggatg  12540
agcaaggagt tttaatctac aagacttatg gaacatatat ttgtgagagc gaaaagaatg  12600
cagtaacaat ccttggtccc atgttcaaga cggtcgacta gttcaaaca gaatttagta  12660
gttctcaaac gtctgaagta tatatggtat gtaaaggttt gaagaaatta atcgatgaac  12720
ccaatcccga ttggtcttcc atcaatgaat cctggaaaaa cctgtacgca ttccagtcat  12780
cagaacagga atttgccaga gcaaagaagg ttagtacata ctttaccttg acaggtattc  12840
cctcccaatt cattcctgat ccttttgtaa acattgagac tatgctacaa atattcggag  12900
tacccacggg tgtgtctcat gcggctgcct taaaatcatc tgatagacct gcagatttat  12960
tgaccattag cctttttat atggcgatta tcgtatta taacatcaat catatcgag  13020
taggaccgat acctccgaac ccccatcag atggaattgc acaaaatgtg gggatcgcta  13080
taactggtat aagcttttgg ctgagtttga tggagaaaga cattccacta tatcaacagt  13140
gtttagcagt tatccagcaa tcattcccga ttaggtggga ggctgtttca gtaaaaggag  13200
gatacaagca gaagtggagt actagaggtg atgggctccc aaaagatacc cgaacttcag  13260
actccttggc cccaatcggg aactggatca gatctctgga attggtccga aaccaagttc  13320
gtctaaatcc attcaatgag atcttgttca atcagctatg tcgtacagtg gataatcatt  13380
tgaaatggtc aaatttgcga agaaacacag gaatgattga atggatcaat agacgaattt  13440
caaaagaaga ccggtctata ctgatgttga gagtgacct acacgaggaa aactcttgga  13500
gagattaaaa aatcatgagg agactccaaa ctttaagtat gaaaaaaact ttgatcctta  13560
agaccctctt gtggttttta tttttatct ggttttgtgg tcttcgt           13607
```

SEQ ID NO: 22 moltype = DNA length = 13506
FEATURE Location/Qualifiers
misc_feature 1..13506
  note = VSV vector: Convac V3 China
source 1..13506
  mol_type = other DNA
  organism = synthetic construct
SEQUENCE: 22

```
acgaagacaa acaaaccatt attatcatta aaaggctcag gagaaacttt aacagtaatc  60
aaaatgtctg ttacagtcaa gagaatcatt gacaacacag tcatagttcc aaaacttcct  120
gcaaatgagg atcagtggga ataccggca gattacttca gaaaatcaaa ggagattcct  180
ctttacatca atactacaaa aagtttgtca gatctaagag gatatgtcta ccaaggcctc  240
aaatccggaa atgtatcaat catacatgtc aacagctact tgtatggagc attaaaggac  300
atccggggta gtttggataa agattggtca agtttcggaa taaacatcgg gaaagcaggg  360
gatacaatcg gaatatttga ccttgtatcc ttgaaagccc tggacggcgt acttccagat  420
ggagtatcgg atgcttccag aaccagcgca gatgacaaat ggttgccttt gtatctactt  480
ggcttataca gagtgggcag aacacaaatg cctgaataca gaaaaaagct catggatggg  540
ctgacaaatc aatgcaaaat gatcaatgaa cagtttgaac ctcttgtgcc agaaggtcgt  600
gacattttg atgtgtgggg aaatgacagt aattacacaa aaattgtcgc tgcagtggac  660
atgttcttcc acatgttcaa aaaacatgaa tgtgcctcgt tcagatacgg aactattgtt  720
tccagattca aagattgtgc tgcattggca acatttggac acctctgcaa aataaccgga  780
atgtctacag aagatgtaac gacctgatc ttgaaccgaa aagttgcaga tgaaatgctc  840
caaatgatgc ttccaggcca agaaattgac aaggccgatt catacatgcc ttatttgatc  900
gactttggat tgtcttctaa gtctccatat tcttccgtca aaaaccctgc cttccacttc  960
tgggggcaat tgacagctct tctgctcaga tccaccagag caaggaatgc ccgacagcct  1020
gatgcattg agtatacatc tcttactaca gcaggttttgt tgtacgctta tgcagtagga  1080
tcctctgccg acttggcaca acagttttgt gttggagata caaatacac tccagatgat  1140
agtaccggag gattgacgac taatgcaccg ccacaaggca gagatgtggt cgaatggctc  1200
ggatggtttg aagatcaaaa cagaaaaccg actcctgata tgatgcagta tgcgaaaaga  1260
gcagtcatgt cactgcaagg cctaagagag aagacaattg caagtatgc taagtcagaa  1320
tttgacaaat gaccctataa ttctcagatc acctattata tattatgcta catatgaaaa  1380
aaactaacag atatcatgga taatctcaca aaagttcgtg agtatctcaa gtcctattct  1440
cgtctggatc aggcggtagg agagatagat gagatcgaag cacaacgagc tgaaaagtcc  1500
aattatgagt tgttccaaga ggatggagtg gaagagcata ctaagccctc ttattttcag  1560
gcagcagatg attctgacac agaatctgaa ccagaaattg aagacaatca ggtttgtat  1620
gcaccagatc cagaagctga caagttgaa ggctttatac aggggccttt agatgactat  1680
gcagatgagg aagtggatgt tgtatttact tcggactgga aacagcctga gcttgaatct  1740
gacgagcatg gaaagacctt acggttgaca tcgccagagg gttaagtgg agagcagaaa  1800
tcccagtggc tttcgacgat taagcagtc gtgcaaagtg ccaaatactg gaatctggca  1860
gagtgcacat ttgaagcatc gggagaaggg gtcattatga aggagcgcca gataactccg  1920
gatgtatata aggtcactcc agtgatgaac acacatccgt cccaatcaga agcagtatca  1980
```

```
gatgtttggt ctctctcaaa gacatccatg actttccaac ccaagaaagc aagtcttcag  2040
cctctcacca tatccttgga tgaattgttc tcatctagag gagagttcat ctctgtcgga  2100
ggtgacggac gaatgtctca taaagaggcc atcctgctcg gcctgagata caaaaagttg  2160
tacaatcagg cgagagtcaa atattctctg tagactatga aaaaagtaa cagatatcac   2220
gatctaagtg ttatcccaat ccattcatca tgagttcctt aaagaagatt ctcggtctga  2280
aggggaaagg taagaaatct aagaaattag ggatcgcacc accccttat gaagaggaca   2340
ctagcatgga gtatgctccg agcgctccaa ttgacaaatc ctattttgga gttgacgaga  2400
tggcaccta tgatccgaat caattaagat atgagaaatt cttctttaca gtgaaaatga   2460
cggttagatc taatcgtccg ttcagaacat actcagatgt ggcagccgct gtatcccatt  2520
gggatcacat gtacatcgga atggcaggga aacgtcccct ctacaaaatc ttggcttttt  2580
tgggttcttc taatctaaag gccactccag cggtattggc agatcaaggt caaccagagt  2640
atcacactca ctgcgaaggc agggcttatt tgccacatag gatgggaag ccccctccca   2700
tgctcaatgt accagagcac ttcagaagac cattcaatat aggtctttac aagggaacga  2760
ttgagctcac aatgaccatc tacgatgatg agtcactgga agcagctcct atgatctggg  2820
atcatttcaa ttcttccaaa ttttctgatt tcagagagaa ggccttaatg tttggcctga  2880
ttgtcgagaa aaaggcatct ggagcgtggg tcctggattc tatcagccac ttcaaatgag  2940
ctagtctaac ttctagcttc tgaacaatcc ccggtttact cagtctctcc taattccagc  3000
ctctcgaaca actaatatcc tgtctttct atccctatga aaaaaactaa cagagatcga   3060
tctgtttacg cgtcactatg aagtgccttt tgtacttagc cttttattc attggggtga   3120
attgcaagtt caccactagt tttccacaca accaaaaagg aaactggaaa aatgttcctt  3180
ctaattacca ttattgcccg tcaagctcag atttaaattg gcataatgac ttaataggca  3240
cagccataca agtcaaaatg cccaagagtc acaaggctat tcaagcagac ggttggatgt  3300
gtcatgcttc caaatgggtc actacttgtg atttccgctg gtatggaccg aagtatataa  3360
cacagtccat ccgatccttc actccatctg tagaacaatg caaggaaagc attgaacaaa  3420
cgaaacaagg aacttggctg aatccaggct tccctcctca aagttgtgga tatgcaactg  3480
tgacggatgc cgaagcagtg atttgtccagg tgactcctca ccatgtgctg gttgatgaat  3540
acacaggaga atgggttgat tcacagttca tcaacggaaa atgcagcaat tacatatgcc  3600
ccactgtcca taactctaca acctggcatt ctgactataa ggtcaaaggg ctatgtgatt  3660
ctaacctcat ttccatggac atcaccttct tctcagagga cggagagcta tcatccctgg  3720
gaaaggaggg cacagggttc agaagtaact actttgctta tgaaactgga ggcaaggcct  3780
gcaaaatgca atactgcaag cattgggag  tcagactccc atcaggtgtc tggttcgaga  3840
tggctgataa ggatctcttt gctgcagcca gattccctga atgcccagaa gggtcaagta  3900
tctctgctcc atctcagacc tcagtggatg taagtctaat tcaggacgtt gagaggatct  3960
tggattattc cctctgccaa gaaacctgga gcaaaatcag agcgggtctt ccaatctctc  4020
cagtcgatct cagctatctt gctcctaaaa acccaggaac cggtcctgct ttcaccataa  4080
tcaatggtac cctaaaatac tttgagacca gatacatcag agtcgatatt gctgctccaa  4140
tcctctcaag aatggtcgga atgatcagtg gaactaccac agaaagggaa ctgtgggatg  4200
actgggcacc atatgaagac gtggaaattg gacccaatgg agttctgagg accagttcag  4260
gataaagtt tccttatac atgattggac atggtatgt ggactccgat cttcatctta    4320
gctcaaaggc tcaggtgttc gaacatcctc acattcaaga cgctgcttcg caacttcctg  4380
atgatgagag tttatttttt ggtgatactg gctatccaa aaatccaatc gagcttgtag   4440
aaggttggtt cagtagttgg aaaagctcta ttgcctcttt tttctttatc ataggttaa   4500
tcattggact attcttggtt ctccgagttg gtatccatct ttgcattaaa ttaaagcaca  4560
ccaagaaaag acagatttat acagacatag agatgaaccg acttggaaag taactcaaat  4620
cctgctaggt atgaaaaaaa ctaacagata tcacgctcga ggccaccatg ttcgtgtttc  4680
tggtgctgct gcctctggtg agctcccagt gcgtgaacct gaccacaagg acccagctgc  4740
ccctgcctta taccaattcc ttcacacggg gcgtgtacta tcccgacaag tgttccggaa  4800
gcagcgtgct gcactccaca caggatctgt ttctgccttt ctttctaac gtgacctggt   4860
tccacgccat ccacgtgagc ggcaccaatg gcacaaagcg gttcgacaat ccagtgctgc  4920
cctttaacga tggcgtgtac ttcgcctcca ccgagaagtc taacatcatc agaggctgga  4980
tctttggcac cacactggac agcaagacac agtccctgct gatcgtgaac aatgccacaa  5040
acgtggtcat caaggtgtgc gagttccagt tttgtaatga tccattcctg ggcgtgtact  5100
atcacaagaa caataagtct tggatggaga gcgagtttcg cgtgtattcc tctgccaaca  5160
attgcacatt tgagtacgtg tcccagcccct tcctgatgga cctggagggc aagcagggca  5220
atttcaagaa cctgagggag ttcgtgttta agaatatcga tggctacttc aaaatctact  5280
ccaagcacac cccaatcaac ctggtgcgcg acctgccaca gggcttctct gccctggagc  5340
cactggtgga tctgccatc ggcatcaaca tcacccggtt tcagacactg ctggccctgc   5400
acagaagcta cctgacacca ggcgacagct cctctgatg gaccgcagga gcagcagcct   5460
actatgtggg ctatctgcag cccaggacct tcctgctgaa gtacaacgag aatggcacca  5520
tcacagacgc cgtggattgc gccctggatc cctgtctga gaccaagtgt acactgaaga   5580
gctttaccgt ggagaagggc atctatcaga caagcaattt cagggtgcag cctaccgagt  5640
ccatcgtgcg ctttcccaat atcacaaacc tgtgcccttt tggcgaggtg ttcaacgcaa  5700
cccgcttcgc cagcgtgtac gcctggaata ggaagcgcat ctccaactgc gtggccgact  5760
attctgtgct gtacaacagc gcctccttct caccttttaa gtgctatggc gtgagcccca  5820
caaagctgaa tgacctgtgc tttaccaacg tgtacgccga ttccttcgtg atcaggggcg  5880
acgaggtgcg ccagatcgca ccaggacaga caggcaagat cgcagactac aattataagc  5940
tgcctgacga ttt caccggc tgcgtgatcg cctggaactc taacaatctg gatagcaaag  6000
tgggcggcaa ctacaattat ctgtaccggc tgtttagaaa gtctaatctg aagccattcg  6060
agagggacat ctccacagaa atctaccagg ccggctccac ccctgcaat ggcgtggagg   6120
gctttaactg ttatttccct ctgcagagct acggcttcca gccaacaaac ggcgtgggct  6180
atcagcccta ccgcgtggtg gtgctgtctt ttgagctgct gcacgcacct gcaacagtgt  6240
gcggaccaaa gaagagcacc aatctggtga agaacaagtg cgtgaacttc aacttcaacg  6300
gactgaccgg aacaggcgtg ctgaccgagt ccaacaagaa gttcctgcct tttcagcagt  6360
tcggcaggga catcgcagat accacagacg ccgtgcgaga cccccagacc ctggagatcc  6420
tggacatcac accatgctcc ttcggcggcg tgtctgtgat cacaccaggc accaataca   6480
gcaaccaggt ggccgtgctg tatcaggacg tgaattgtac cgaggtgcca gtggcaatcc  6540
acgcagatca gctgaccccct acatggcggg tgtactctac cggcagcaac gtgttccaga  6600
caagagccgg atgcctgatc ggagcagagc acgtgaacaa tagctatgag tgcgacatcc  6660
ctatcggcgc cggcatctgt gcctcctacc agacccctga caaactcccca aggtctggat  6720
```

```
ccggctacat ccccgaggcc cccagagacg gccaggccta cgtgcggaag gacggcgagt  6780
gggtactgct cagcaccttc ctgggcagca gttggaaaag ctccatcgcc tccttttcct  6840
ttatcatcgg cctgatcatc ggactgttcc tggtgctccg cgtgggtatc cacctgtgca  6900
tcaagctgaa gcacaccaag aaaagacaga tttatacaga catcgagatg aaccgacttg  6960
gaaagtaagc tagccagatt cttcatgttt ggaccaaatc aacttgtgat accatgctca  7020
aagaggcctc aattatattt gagttttaa tttttatgaa aaaaactaac agcaatcatg  7080
gaagtccacg attttgagac cgacgagttc aatgatttca atgaagatga ctatgccaca  7140
agagaattcc tgaatcccga tgagcgcatg acgtacttga atcatgctga ttacaatttg  7200
aattctcctc taattagtga tgatattgac aatttgatca ggaaattcaa ttctcttccg  7260
attccctcga tgtgggatag taagaactgg gatggagttc ttgagatgtt aacatcatgt  7320
caagccaatc ccatctcaac atctcagatg cataaatgga tgggaagttg gttaatgtct  7380
gataatcatg atgccagtca agggtatagt tttttacatg aagtggacaa agaggcagaa  7440
ataacatttg acgtggtgga gaccttcatc cgcggctggg gcaacaaacc aattgaatac  7500
atcaaaaagg aaagatggac tgactcattc aaaattctcg cttatttgtg tcaaaagttt  7560
ttggacttac acaagttgac attaatctta aatgctgtct ctgaggtgga attgctcaac  7620
ttggcgagga ctttcaaagg caagtcaga agaagttctc atggaacgaa catatgcagg  7680
attagggttc ccagcttggg tcctactttt atttcagaag gatgggctta cttcaagaaa  7740
cttgatattc taatgaccg aaacttttctg ttaatggtca aagatgtgat taggggagg  7800
atgcaaacgg tgctatccat ggtatgtaga atagacaacc tgttctcaga gcaagcatc  7860
ttctcccttc taaatatcta cagaattgga gataaaattg tggagaggca gggaaatttt  7920
tcttatgact tgattaaaat ggtggaaccg atatgcaact gaagctgat gaaattagca  7980
agagaatcaa ggcctttagt cccacaattc cctcattttg aaaatcatat caagacttct  8040
gttgatgaag gggcaaaaat tgaccgaggt ataagattcc tccatgatca gataatgagt  8100
gtgaaaacag tggatctcac actggtgatt tatggatcgt tcagacattg gggtcatcct  8160
tttatagatt attacactgg actagaaaaa ttacattccc aagtaaccat gaagaaagat  8220
attgatgtgt catatgcaaa agcacttgca agtgatttag ctcggattgt tctatttcaa  8280
cagttcaatg atcataaaaa gtggttcgtg aatggagact tgctccctca tgatcatccc  8340
tttaaaagtc atgttaaaga aaatacatgg cccacagctg ctcaagttca agattttgga  8400
gataaatggc atgaacttcc gctgattaaa tgttttgaaa tacccgactt actagaccca  8460
tcgataatat actctgacaa aagtcattca atgaataggt cagaggtgtt gaaacatgtc  8520
cgaatgaatc cgaacactcc tatccctagt aaaaaggtgt tgcagactat gttgacaca  8580
aaggctacca attggaaaga atttcttaaa gagattgatg agaagggctt agatgatgat  8640
gatctaatta ttggtcttaa aggaaaggag agggaactga agttggcagg tagatttttc  8700
tccctaatgt cttggaaatt gcgagaatac tttgtaatta ccgaatattt gataaagact  8760
catttcgtcc ctatgtttaa aggcctgaca atggcggacg atctaactgc agtcattaaa  8820
aagatgttag attcctcatc cggccaagga ttgaagtcat atgaggcaat tgcatagcc  8880
aatcacattg ttacgaaaaa atggaataac caccaaagga agttatcaaa cggcccagtg  8940
ttccgagtta tgggccagtt cttaggttat ccatccttaa tcgagagaac tcatgaattt  9000
tttgagaaaa gtcttatata ctacaatgga agaccagact tgatgcgtgt tcacaacaac  9060
acactgatca attcaacctc ccaacgagtt tgttggcaag gacaagaggg tggactggaa  9120
ggtctacggc aaaaaggatg gactatcctc aatctactgg ttattcaaag agaggctaaa  9180
atcagaaaca ctgctgtcaa agtcttggca caaggtgata atcaagttat ttgcacacag  9240
tataaaacga agaaatcgag aaacgttgta gaattacagg gtgctctcaa tcaaatggtt  9300
tctaataatg agaaaattat gactgcaatc aaaataggga cagggaagtt aggacttttg  9360
ataaatgacg atgagactat gcaatctgca gattacttga attatggaaa ataccgatt  9420
ttccgtggag tgattagagg gttagagacc aagagatggt cacgagtgac ttgtgtcacc  9480
aatgaccaaa tacccacttg tgctaatata atgagctcag tttccacaaa tgctctcacc  9540
gtagtccatt ttgctgagaa cccaatcaat gccatgatac agtacaatta ttttgggaca  9600
tttgctagac tcttgttgat gatgcatgat cctgctcttc gtcaatcatt gtatgaagtt  9660
caagataaga taccgggctt gcacagttct actttcaaat acgccatgtt gtatttggac  9720
ccttccattg gaggagtgtc gggcatgtct ttgtccagat ttttgattag agccttccca  9780
gatcccgtaa cagaaagtct ctcattctgg agattcatcc atgtacatgc tcgaagtgag  9840
catctgaagg agatgagtgc agtatttgga accccgaga tagccaagtt tcgataact  9900
cacatagaca agctagtaga agatccaacc tctctgaaca tcgctatggg aatgagtcca  9960
gcgaacttgt taaagactga ggttaaaaaa tgcttaatcg aatcaagaca aaccatcagg  10020
aaccaggtga ttaaggatgc aaccatatat ttgtatcatg aagaggatcg gctcagaagt  10080
ttcttatggt caataaatcc tctgttccct agattttaa gtgaattcaa atcaggcact  10140
tttttgggag tcgcagacgg gctcatcagt ctattttcaaa attctcgtac tattcggaac  10200
tccttaaga aaaagtatca tagggaattg gatgatttga ttgtgaggag tgaggtatcc  10260
tctttgacac attttaggga acttcatttg agaaggggat catgtaaaat gtggacatgt  10320
tcagctactc atgctgacac attaagatac aaatcctggg gccgtacagt tattgggaca  10380
actgtacccc atccattaga aatgttgggt ccacaacatc gaaaagagac tccttgtgca  10440
ccatgtaaca catcagggtt caattatgtt tctgtgcatt gtccagacgg gatccatgac  10500
gtctttagtt cacggggacc attgcctgct tatctagggt ctaaaacatc tgaatctaca  10560
tctattttgc agccttggga aaggggaagc aaagtcccac tgattaaaag agctacacgt  10620
cttagagatg ctatctcttg gtttgttgaa cccgactcta aactagcaat gactatactt  10680
tctaacatcc actctttaac aggcgaagaa tggaccaaaa ggcagcatgg gttcaaagaa  10740
acagggtctg cccttcatag gttttcgaca tctcggatga gccatggtgg gttcgcatct  10800
cagagcacag cagcattgac caggttgatg gcaactacag acaccatgag ggatctggga  10860
gatcagaatt tcgacttttt attccaagca acgttgctct atgctcaaat taccaccact  10920
gttgcaagag acgatggat caccagttgt acagatcatt atcatattgc ctgtaagtcc  10980
tgtttgagac ccatagaaga gatcacccctg gactcaagta tggactacac gccccccgat  11040
gtatcccatg tgctgaaagc atggaggaat ggggaaggtt cgtggggaca agagataaaa  11100
cagatctatc cttgtaagg gaattggaag aatttagcaa atcctatcaa  11160
gtcggcagat gtataggttt tctatatgga gacttggcgt atagaaaatc tactcatgcc  11220
gaggacagtt ctctatttcc tctatctata caaggtcgta ttagaggtcg aggtttctta  11280
aaagggttgc tagacggatt aatgagagca agttgctgcc aagtaataca ccggagaagt  11340
ctggctcatt tgaagaggcc ggccaacgca gtgtacggag gtttgattta cttgattgat  11400
aaattgagtg tatcacctcc attcctttct cttactagat caggacctat tagagacgaa  11460
```

```
ttagaaacga ttccccacaa gatcccaacc tcctatccga caagcaaccg tgatatgggg   11520
gtgattgtca gaaattactt caaataccaa tgccgtctaa ttgaaaaggg aaaatacaga   11580
tcacattatt cacaattatg gttattctca gatgtcttat ccatagactt cattggacca   11640
ttctctattt ccaccaccct cttgcaaatc ctatacaagc catttttatc tgggaaagat   11700
aagaatgagt tgagagagct ggcaaatgtt tcttcattgc taagatcagg agaggggtgg   11760
gaagacatac atgtgaaatt cttcaccaag gacatattat tgtgtccaga ggaaatcaga   11820
catgcttgca agttcgggat tgctaaggat aataataaag acatgagcta tccccttgg    11880
ggaagggaat ccagagggac aattacaaca atccctgttt attatacgac caccccttac   11940
ccaaagatgc tagagatgcc tccaagaatc caaaatcccc tgctgtccgg aatcaggttg   12000
ggccaattac caactggcgc tcattataaa attcggagta tattacatgg aatgggaatc   12060
cattacaggg acttcttgag ttgtggagac ggctccggag ggatgactgc tgcattacta   12120
cgagaaaatg tgcatagcag aggaatattc aatagtctgt tagaattatc agggtcagtc   12180
atgcgaggcg cctctcctga gccccccagt gccctagaaa cttaggagg agataaatcg     12240
agatgtgtaa atggtgaaac atgttgggaa tatccatctg acttatgtga cccaaggact   12300
tgggactatt tcctccgact caaagcaggc ttggggcttc aaattgattt aattgtaatg   12360
gatatgaagt tcgggattc ttctactagc ctgaaaattg agacgaatgt tagaaattat    12420
gtgcaccgga ttttggatga gcaaggagtt ttaatctaca agacttatgg aacatatatt   12480
tgtgagagcg aaaagaatgc agtaacaatc cttggtccca tgttcaagac ggtcgactta   12540
gttcaaacag aatttagtag ttctcaaacg tctgaagtat atatggtatg taaaggtttg   12600
aagaaattaa tcgatgaacc caatcccgat tggtcttcca tcaatgaatc ctggaaaaac   12660
ctgtacgcat tccagtcatc agaacaggaa tttgccagag caaagaaggt tagtacatac   12720
tttaccttga caggtattcc ctcccaattc attcctgatc cttttgtaaa cattgagact   12780
atgctacaaa tattcggagt acccacgggt gtgtctcatg cggctgcctt aaaatcatct   12840
gatagacctg cagatttatt gaccattagc ctttttata tggcgattat atcgtattat   12900
aacatcaatc atatcagagt aggaccgata cctccgaacc ccccatcaga tggaattgca   12960
caaaatgtgg ggatcgctat aactggtata agcttttgcc tgagtttgat ggagaaagac   13020
attccactat atcaacagtg tttagcagtt atccagcaat cattcccgat taggtgggga   13080
gctgtttcag taaaaggagg ataacaagcag aagtggagta ctagaggtga tgggctccca   13140
aaagataccc gaacttcaga ctccttggcc ccaatcggga actggatcag atctctgaaa   13200
ttggtccgaa accaagttcg tctaaatcca ttcaatgaga tcttgttcaa tcagctatgt   13260
cgtacagtgg ataatcattt gaaatggtca aatttgcgaa gaaacacagg aatgattgaa   13320
tggatcaata dagaaatttc aaaagaagac cggtctatac tgatgttgaa gagtgaccta   13380
cacgaggaaa actcttggag agattaaaaa atcatgagga gactccaaac tttaagtatg   13440
aaaaaaactt tgatccttaa gaccctcttg tggttttat ttttatctg gttttgtggt       13500
cttcgt                                                            13506
```

SEQ ID NO: 23         moltype = DNA  length = 13503
FEATURE             Location/Qualifiers
misc_feature       1..13503
                      note = VSV vector: Convac V3 South Africa
source             1..13503
                      mol_type = other DNA
                      organism = synthetic construct
SEQUENCE: 23

```
acgaagacaa acaaaccatt attatcatta aaaggctcag gagaaacttt aacagtaatc     60
aaaatgtctg ttacagtcaa gagaatcatt gacaacacag tcatagttcc aaaacttcct    120
gcaaatgagg atccagtgga atacccggca gattacttca gaaaatcaaa ggagattcct    180
ctttacatca atactacaaa aagtttgtca gatctaagag gatatgtcta ccaaggcctc    240
aaatccggaa atgtatcaat catacatgtc aacagctact tgtatggagc attaaaggac    300
atccggggta agttggataa agattggtca gtttcggaa taaacatcgg gaaagcaggg    360
gatacaatcg gaatattga ccttgtatcc ttgaaagccc tggacggcgt acttccagat    420
ggagtatcgg atgcttccag aaccagcgca gatgacaaat ggttgccttt gtatctactt    480
ggcttataca gagtgggcag aacacaaatg cctgaataca gaaaaagct catggatggg    540
ctgacaaatc aatgcaaaat gatcaatgaa cagtttgaac ctcttgtgcc agaaggtcgt   600
gacattttg atgtgtgggg aaatgacagt aattacacaa aaattgtcgc tgcagtggac    660
atgttcttcc acatgttcaa aaaacatgaa tgtgcctcgt tcagatacgg aactattgtt    720
tccagattca aagattgtgc tgcattggca acatttggac acctgcaa ataaccgga      780
atgtctacag aagatgtaac gacctggatc ttgaaccgag aagttgcaga tgaaatggtc    840
caaatgatgc ttcaggcca agaaattgac aaggcgatt catcatgc ttatttgatc       900
gactttggat tgtcttctaa gtctccatat tcttccgtca aaaaccctgc cttccacttc    960
tgggggcaat tgacagctct tctgctcaga tccaccagag caaggaatgc ccgacagcct   1020
gatgacattg agtatacatc tcttactaca gcaggtttgt tgtacgctta tgcagtagga   1080
tcctctgccg acttggcaca acagttttgt gttggagata caaatacac tccagatgat   1140
agtaccggag gattgacgac taatgcaccg ccacaaggca gatgtgtgt cgaatggtca   1200
ggatggttg aagatcaaaa cagaaaaccg actcctgata tgatgcagta tgcgaaaaga   1260
gcagtcatgt cactgcaagg cctaagagag aagacaattg gcaagtatgc taagtcagaa   1320
tttgacaaat gacccctata ttctcagatc acctattata tattatgcta catatgaaaa   1380
aaactaacag atatcatgga taatctcaca aaagtcgtg agtatctcaa gtcctattct    1440
cgtctggatc aggcggtagg agagatagat gagatcgaag cacaacgagc tgaaagtcc   1500
aattatgagt tgttccaaga ggatggagtg gaagagcata ctaagcccte ttattttcag   1560
gcagcagatg attctgacac agaatctgaa ccagaaattg aagacaatca ggtttgtat    1620
gcaccagatc cagaagctga gcaagttgaa ggctttatac aggggccttt agatgactat   1680
gcagatgagg aagtggatgt tgtatttact tcggactgga aacagcctga gcttgaatct   1740
gacgagctga aaagaccttt acgggttgaca tcgcagaaga gtttaagtgg agacagaaa   1800
tcccagtggc tttcgacgat taaagcagtc gtgcaaagtg ccaaatactg gaatctggca   1860
gagtgcacat ttgaagcatc gggagaaggg tcattatga aggagcgcca gataactccg   1920
gatgtatata aggtcactcc agtgatgaac acacatccgt cccaatcaga agcagtcatca   1980
gatgttttggt ctctctcaaa gacatccatg acttccaaac caagaaagc aagtcttcag    2040
cctctcacca tatccttgga tgaattgttc tcatctagag gagagttcat ctctgtcgga   2100
```

```
ggtgacggac gaatgtctca taaagaggcc atcctgctcg gcctgagata caaaaagttg  2160
tacaatcagg cgagagtcaa atattctctg tagactatga aaaaaagtaa cagatatcac  2220
gatctaagtg ttatcccaat ccattcatca tgagttcctt aaagaagatt ctcggtctga  2280
aggggaaagg taagaaatct aagaaattag ggatcgcacc acccccttat gaagaggaca  2340
ctagcatgga gtatgctccg agcgctccaa ttgacaaatc ctattttgga gttgacgaga  2400
tggacaccta tgatccgaat caattaagat atgagaaatt cttctttaca gtgaaaatga  2460
cggttagatc taatcgtccg ttcagaacat actcagatgt ggcagccgct gtatcccatt  2520
gggatcacat gtacatcgga atggcaggga aacgtccctt ctacaaaatc ttggctttt  2580
tgggttcttc taatctaaag gccactccag cggtattggc agatcaaggt caaccagagt  2640
atcacactca ctgcgaaggc agggcttatt tgccacatag gatggggaag accccctcca  2700
tgctcaatgt accagagcac ttcagaagac cattcaatat aggtctttac aagggaacga  2760
ttgagctcac aatgaccatc tacgatgatg agtcactgga agcagctcct atgatctggg  2820
atcatttcaa ttcttccaaa tttttctgatt tcagagagaa ggccttaatg tttggcctga  2880
ttgtcgagaa aaaggcatct ggagcgtggg tcctggattc tatcagccac ttcaaatgag  2940
ctagtctaac ttctagcttc tgaacaatcc ccggtttact cagtctctcc taattcagc  3000
ctctcgaaca actaatatcc tgtcttttct atccctatga aaaaactaa cagagatcga  3060
tctgtttacg cgtcactatg aagtgccttt tgtacttagc ctttttattc attggggtga  3120
attgcaagtt caccatagtt tttccacaca accaaaaagg aaactggaaa aatgttcctt  3180
ctaattacca ttattgcccg tcaagctcag atttaaattg gcataatgac ttaataggca  3240
cagccataca agtcaaaatg cccaagagtc acaaggctat tcaagcagac ggttggatgt  3300
gtcatgcttc caaatgggtc actacttgtg atttccgctg gtatggaccg aagtatataa  3360
cacagtccat ccgatccttc atcccatctg tagaacaatg caaggaaagc attgaacaaa  3420
cgaaacaagg aacttggctg aatccaggct tccctcctca aagttgtgga tatgcaactg  3480
tgacggatgc cgaagcagtg attgtccagg tgactcctca ccatgtgctg gttgatgaat  3540
acacaggaga atgggttgat tcacagttca tcaacgaaa atgcagcaat tacatatgcc  3600
ccactgtcca taactctaca acctggcatt ctgactataa ggtcaaaggg ctatgtgatt  3660
ctaacctcat ttccatggac atcaccttct tctcagagga cggagagcta tcatccctgg  3720
gaaaggaggg cacagggttc agaagtaact actttgctta tgaaactgga ggcaaggcct  3780
gcaaaatgca atactgcaag cattgggag tcagactccc atcaggtgtc tggttcgaga  3840
tggctgataa ggatctcttt gctgcagcca gattccctga atgcccagaa gggtcaagta  3900
tctctgctcc atctcagacc tcagtggatg taagtctaat tcaggacgtt gagaggatct  3960
tggattattc cctctgccaa gaaacctgga gcaaaatcag agcgggtctt ccaatctctc  4020
cagtggatct cagctatctt gctcctaaaa cccaggaac cggtcctgct ttcaccataa  4080
tcaatggtac cctaaaatac tttgagacca gatcatcaga agtcgatatt gctgctccaa  4140
tcctctcaag aatggtcgga atgatcagtg gaactaccac agaaagggaa ctgtgggatg  4200
actgggcacc atatgaagac gtggaaattg gacccaatgg agttctgagg accagttcag  4260
gatataagtt tccttatac atgattggac atggtatgtt ggactccgat cttcatctta  4320
gctcaaaggc tcaggtgttc gaacatcctc acattcaaga cgctgcttcg caacttcctg  4380
atgatggaa tttattttt ggtgatactg gctatccaaa aaatccaatc gagcttgtag  4440
aaggttggtt cagtagttgg aaaagctcta ttgcctcttt tttctttatc ataggggttaa  4500
tcattggact attcttggtt ctccgagttg gtatccatct ttgcattaaa ttaaagcaca  4560
ccaagaaaag acagatttat acagacatag agatgaaccg acttggaaag taactcaaat  4620
cctgctaggt atgaaaaaaa ctaacagata tcacgctgga ggccaccatg ttcgtgtttc  4680
tggtgctgct gcctctggtg agctcccagt gcgtgaactt caccacaagg acccagctgc  4740
cccctgccta taccaattcc ttcacacggg gcgtgtacta tcccgacaag gtgttccgga  4800
gcagcgtgct gcactccaca caggatctgt ttctgccttt ctttttctaac gtgacctggt  4860
tccacgccat ccacgtgagc ggcaccaatg gcacaaagcg gttcgccaat ccagtgctgc  4920
cctttaacga tggcgtgtac ttcgcctcca ccgagaagtc taacatcatc agaggctgga  4980
tctttggcac cacactggac agcaagacac agtccctgct gatcgtgaac aatgccacca  5040
acgtggtcat caaggtgtgc gagttccagt tttgtaatga tccattcctg ggcgtgtact  5100
atcacaagaa caataagtct tggatggaga gcgagtttcg cgtgtattcc tctgccaaca  5160
attgcacatt tgagtacgtg tcccagcccc tcctgatgaa cctggagggc aagcagggca  5220
atttcaagaa cctgagggag ttcgtgttta agaatatcga tggctacttc aaaatctact  5280
ccaagcacac cccaatcaac ctggtgcgcg gcctgccaca gggcttctct gccctggagc  5340
cactggtgga tctgcccatc ggcatcaaca tcacccggtt tcagacactg ctggccctgc  5400
acagaagcta cctgacacca ggcgacagct cctctctgat gaccgcagga gcagcagcct  5460
actatgtggg ctatctgcag cccaggacct tcctgctgaa gtacaacgag aatggcacca  5520
tcacagacgc cgtggattgc gccctggatc ccctgtctga gaccaagtgt acactgaaga  5580
gcttcaccgt ggagaagggc atctatcaga agcaatttg cagggtgcag cctaccaggt  5640
ccatcgtgcg ctttcccaat atcacaaacc tgtgcccttt tggcgaggt ttcaacgcaa  5700
cccgcttcgc cagcgtgtac gcctggaata ggaagcgcat ctccaactgc gtggccgact  5760
attctgtgct gtacaacagc gcctccttct ctacctttaa gtgctatggc gtgagcccca  5820
caaagctgaa tgacctgtgc tttaccaacg tgtacgccga ttccttcgtg atcagggcg  5880
acgaggtgcg ccagatcgca ccaggacaga caggacaga aattatagc cgcagactac aattataagc  5940
tgcctgacga tttcaccggc tgcgtgatcg cctggaactc taacaatctg gatagcaaag  6000
tgggcggcaa ctacaattat ctgtaccgcc tgtttagaaa gtcaatctg aagccattcg  6060
agagggacat ctccacagaa atctaccagg ccggctctac ccctgcaat ggcgtgaagg  6120
gctttaactg ttatttccct ctgcagagct acggcttcca gccaacatat ggcgtgggct  6180
atcagccta ccgcgtggtg gtgctgtctt ttgagctgct gcacgcacct gccacagtgt  6240
gcggaccaaa gaagagcacc aatctggtga agaacaagtg cgtgaacttc aacttcaacg  6300
gactgaccgg aacaggcgtg ctgaccgagt ccaacaagaa gttcctgcct ttcagcagt  6360
tcggcaggga catcgcagat accacagacg ccgtgcgcga ccctcagacc ctggagatcc  6420
tggacatcac cccatgctcc ttcggcgcg tgtctgtgat cacaccaggc accaataca  6480
gcaaccaggt ggccgtgctg tatcaggacg tgaattgcac cgaggtgcca gtggccataa  6540
acgcagatca gctgacccct acatggcggg tgtactctac cggcagcaac gtgttccaga  6600
caagagccgg atgcctgatc ggagcagagc acgtgaacaa tagctatgag tgcgacatcc  6660
ctatcggcgc cggcatctgt gcctcctacc agacccagac aaactcccca aggggatccg  6720
gctacatccc cgaggcccc agagacggcc aggcctacgt gcgaaggac ggcgagtggg  6780
tactgctcag caccttcctg ggcagcagtt ggaaaaagct catcgcctcc ttttcttta  6840
```

```
tcatcggcct gatcatcgga ctgttcctgg tgctccgcgt gggtatccac ctgtgcatca   6900
agctgaagca caccaagaaa agacagattt atacagacat cgagatgaac cgacttggaa   6960
agtaagctag ccagattctt catgtttgga ccaaatcaac ttgtgatacc atgctcaaag   7020
aggcctcaat tatatttgag ttttttaattt ttatgaaaaa aactaacagc aatcatggaa   7080
gtccacgatt ttgagaccga cgagttcaat gatttcaatg aagatgacta tgccacaaga   7140
gaattcctga atcccgatga gcgcatgacg tacttgaatc atgctgatta caatttgaat   7200
tctcctctaa ttagtgatga tattgacaat ttgatcagga aattcaattc tcttccgatt   7260
ccctcgatgt gggatagtaa gaactgggat ggagttcttg agatgttaac atcatgtcaa   7320
gccaatccca tctcaacatc tcagatgcat aaatggatgg gaagttggtt aatgtctgat   7380
aatcatgatg ccagtcaagg gtatagtttt ttacatgaag tggacaaaga ggcagaaata   7440
acatttgacg tggtggagac cttcatccgc ggctggggca acaaaccaat tgaatacatc   7500
aaaaaggaaa gatggactga ctcattcaaa attctcgctt atttgtgtca aaagtttttg   7560
gacttacaca agttgacatt aatcttaaat gctgtctctg aggtggaatt gctcaacttg   7620
gcgaggactt tcaaaggcaa agtcagaaga agttctcatg gaacgaacat atgcaggatt   7680
agggttccca gcttgggtcc tacttttatt tcagaaggat gggcttactt caagaaactt   7740
gatattctaa tggaccgaaa cttttctgtta atggtcaaag atgtgattat agggaggatg   7800
caaacggtgc tatccatggt atgtagaata gacaacctgt tctcagagca agacatcttc   7860
tcccttctaa atatctacag aattggagat agaggcaggg aaattttttct                7920
tatgacttga ttaaaatggt ggaaccgata tgcaacttga agctgatgaa attagcaaga   7980
gaatcaaggc cttagtccc acaattccct cattttgaaa atcatatcaa gacttctgtt   8040
gatgaagggg caaaaattga ccgaggtata agattcctcc atgatcagat aatgagtgtg   8100
aaaacagtgg atctcacact ggtgatttat ggatcgttca gacattgggg tcatcctttt   8160
atagattatt acactggact agaaaaatta cattcccaag taaccatgaa gaaagatatt   8220
gatgtgtcat atgcaaaagc acttgcaagt gatttagctc ggattgttct atttcaacag   8280
ttcaatgatc ataaaaagtg gttcgtgaat ggagacttgc tccctcatga tcatccctttt   8340
aaaagtcatg ttaaagaaaa tacatggccc acagctgctc aagttcaaga ttttggagat   8400
aaatggcatg aacttccgct gattaaatgt tttgaaatac ccgacttact agacccatcg   8460
ataatatact ctgacaaaag tcattcaatg aataggtcag aggtgttgaa acatgtccga   8520
atgaatccga acactcctat ccctagtaaa aaggtgttgc agactatgtt ggacacaaag   8580
gctaccaatt ggaagaatt tcttaaagag attgatgaga agggcttaga tgatgatgat   8640
ctaattattg gtcttaaagg aaaggagagg gaactgaagt tggcaggtag attttttctcc   8700
ctaatgtctt ggaaattgcg agaatacttt gtaattaccg aatatttgat aaagactcat   8760
ttcgtcccta tgtttaaagg cctgacaatg gcggacgatc taactgcagt cattaaaaag   8820
atgttagatt cctcatccgg ccaaggattg aagtcatatg aggcaatttg catgccaat   8880
cacattgatt acgaaaaatg gaataaccac caaaggaagt tatcaaacgg cccagtgttc   8940
cgagttatgg gccagttctt aggttatcca tccttaatcg agagaactca tgaatttttt   9000
gagaaaagtc ttatatacta caatggaaga ccagacttga tgcgtgttca caacaacaca   9060
ctgatcaatt caacctccca acgagtttgt tggcaaggac aagagggtgg actggaaggt   9120
ctacgcaaa aaggatggac tatcctcaat ctactggtta ttcaaagaga ggctaaaatc   9180
agaaacactg ctgtcaaagt cttggcacaa ggtgataatc aagttatttg cacacagtat   9240
aaaacgaaga aatcgagaaa cgttgtagaa ttacagggtg ctctcaatca aatggtttct   9300
aataatgaga aaattatgac tgcaatcaaa atagggacag ggaagttagg acttttgata   9360
aatgacgatg agactatgca atctgcagat tacttgaatt atggaaaat accgattttc   9420
cgtggagtga ttagagggtt agagaccaag agatggtcac gagtgacttg tgtcaccaat   9480
gaccaaatac ccacttgtgc taatataatg agctcagttt ccacaaatgc tctcaccgta   9540
gctcattttg ctgagaaccc aatcaatgcc atgatacagt acaattattt tgggacattt   9600
gctagactct tgttgatgat gcatgatcct gctcttcgtc aatcattgta tgaagttcaa   9660
gataagatac cgggcttgca cagttctact ttcaaatacg ccatgttgta tttggacccct   9720
tccattggag gagtgtcggg catgtctttg tccaggtttt tgattagagc cttcccagat   9780
cccgtaacag aaagtctctc attctggaga ttcatccatg tacatgctcg aagtgagcat   9840
ctgaaggaga tgagtgcagt attttggaaac cccgagatag ccaagtttcg aataactcac   9900
atagacaagc tagtagaaga tccaacctct ctgaacatcg ctatgggaat gagtccagcg   9960
aacttgttaa agactgaggt taaaaaatgc ttaatcgaat caagacaaac catcaggaac  10020
caggtgatta aggatgcaac catatatttg tatcatgaag aggatcggct cagaagtttc  10080
ttatggtcaa taaatcctct gttccctaga tttttaagtg aattcaaatc aggcacttttt  10140
ttgggagtcg cagacgggct catcagtcta tttcaaaatt ctcgtactat tcggaactcc  10200
tttaagaaaa agtatcatag ggaattggat gatttgattg tgaggagtga ggtatcctct  10260
ttgacacatt tagggaaact tcatttgaga aggggatcat gtaaaatgtg gacatgttca  10320
gctactcatg ctgacacatt aagatacaaa tcctggggcc atacagttat tgggacaact  10380
gtaccccatc cattagaaca gttgggtcca caacatcgaa aagagactcc ttgtgcacca  10440
tgtaacacat cagggttcaa ttatgttcct gtgcattgtc cagacggggat ccatgacgtc  10500
tttagttcac ggggaccatt gcctgcttat ctagggtcta aaacatctga atctacatct  10560
atttgcagc ttgggaaag ggaaagcaaa gtcccactga ttaaaagagc tacacgtctt  10620
agagatgcta tctcttggtt tgttgaaccc gactctaaac tagcaatgac tatactttct  10680
aacatccact ctttaacagg cgaagaatgg accaaaaggc agcatggggtt caaaagaaca  10740
gggtctgccc ttcataggtt ttcgacatct cggatgagcc atggtgggtt cgcatctcag  10800
agcactgcag cattgaccag gttgatggca actacagaca ccatgaggga tctgggagat  10860
cagaatttcg actttttatt ccaagcaacg ttgctctatg ctcaaattac caccactgtt  10920
gcaagagacg atgatgatcac cagttgtaca gatcattaca atattgcctg taagtcctgt  10980
ttgagaccca tagaagagat caccctggac tcaagtatgg actacacgcc cccagatgta  11040
tcccatgtgc tgaagacatg gaggaatggg gaaggttcgt ggggacaaga gataaaacag  11100
atctatcctt tagaagggaa ttggaagaat ttagcacctg ctgagcaatc ctatcaagtc  11160
ggcagatgta taggttttct atatgggac ttggcgtata gaaatctac tcatgccgag  11220
gacagtttctc tatttcctct atctatacaa ggtcgtatta gaggtcgagg tttcttaaaa  11280
gggttgctag acgattaat gagagcaagt gctgccaag taatacaccg gagaagtctg  11340
gctcatttga gaggccggc caacgcagtg tacgaggtt tgatttactt gattgataaa  11400
ttgagtgtat cacctccatt cctttctctt actagatcag gacctattag agacgaatta  11460
gaaacgattc cccacaagat cccaacctcc tatccgacaa gcaaccgtga tatgggggtg  11520
attgtcagaa attacttcaa ataccaatgc cgtctaattg aaaaggaaa atacagatca  11580
```

```
cattattcac aattatggtt attctcagat gtcttatcca tagacttcat tggaccattc  11640
tctatttcca ccaccctctt gcaaatccta tacaagccat ttttatctgg gaaagataag  11700
aatgagttga gagagctggc aaatctttct tcattgctaa gatcaggaga ggggtgggaa  11760
gacatacatg tgaaattctt caccaaggac atattattgt gtccagagga aatcagacat  11820
gcttgcaagt tcgggattgc taaggataat aataaagaca tgagctatcc cccttgggga  11880
agggaatcca gagggacaat tacaacaatc cctgtttatt atacgaccac cccttaccca  11940
aagatgctag agatgcctcc aagaatccaa aatcccctgc tgtccggaat caggttgggc  12000
caattaccaa ctggcgctca ttataaaatt cggagtatat tacatggaat gggaatccat  12060
tacagggact tcttgagttg tggagacggc tccggaggga tgactgctgc attactacga  12120
gaaaatgtgc atagcagagg aatattcaat agtctgttag aattatcagg gtcagtcatg  12180
cgaggcgcct ctcctgagcc ccccagtgcc ctagaaactt taggaggaga taaatcgaga  12240
tgtgtaaatg gtgaaacatg ttgggaatat ccatctgact tatgtgaccc aaggacttgg  12300
gactatttcc tccgactcaa agcaggcttg gggcttcaaa ttgatttaat tgtaatggat  12360
atggaagttc gggattcttc tactagcctg aaaattgaga cgaatgttag aaattatgtg  12420
caccggattt tggatgagca aggagtttta atctacaaga cttatggaac atatatttgt  12480
gagagcgaaa agaatgcagt aacaatcctt ggtcccatgt tcaagacggt cgacttagtt  12540
caaacagaat ttagtagttc tcaaacgtct gaagtatata tggtatgtaa aggtttgaag  12600
aaattaatcg atgaacccaa tcccgattgg tcttccatca atgaatcctg gaaaaacctg  12660
tacgcattcc agtcatcaga acaggaattt gccagagcaa agaaggttag tacatacttt  12720
accttgacag gtattccctc ccaattcatt cctgatcctt ttgtaaacat tgagactatg  12780
ctacaaatat tcggagtacc cacgggtgtg tctcatgcgg ctgccttaaa atcatctgat  12840
agacctgcag atttattgac cattagcctt ttttatatgg cgattatatc gtattataac  12900
atcaatcata tcagagtagg accgatacct ccgaaccccc catcagatgg aattgcacaa  12960
aatgtgggga tcgctataac tggtataagc ttttggctga gtttgatgga gaaagacatt  13020
ccactatatc aacagtgttt agcagttatc cagcaatcat tcccgattag gtgggaggct  13080
gtttcagtaa aaggaggata caagcagaag tggagtacta gaggtgatgg gctcccaaaa  13140
gatacccgaa cttcagactc cttggcccca atcgggaact ggatcagatc tctggaattg  13200
gtccgaaacc aagttcgtct aaatccattc aatgagatct tgttcaatca gctatgtcgt  13260
acagtggata atcatttgaa atggtcaaat ttgcgaagaa acacaggaat gattgaatgg  13320
atcaatagac gaatttcaaa agaagaccgg tctatactga tgttgaagag tgacctacac  13380
gaggaaaact cttggagaga ttaaaaaatc atgaggagac tccaaacttt aagtatgaaa  13440
aaaactttga tccttaagac cctcttgtgg tttttatttt ttatctggtt ttgtggtctt  13500
cgt                                                                13503
```

```
SEQ ID NO: 24          moltype = DNA  length = 13484
FEATURE                Location/Qualifiers
misc_feature           1..13484
                       note = VSV vector: Convac V4 China
source                 1..13484
                       mol_type = other DNA
                       organism = synthetic construct
SEQUENCE: 24
acgaagacaa acaaaccatt attatcatta aaaggctcag gagaaacttt aacagtaatc  60
aaaatgtctg ttacagtcaa gagaatcatt gacaacacag tcatagttcc aaaacttcct  120
gcaaatgagg atccagtgga atacccggca gattacttca gaaaatcaaa ggagattcct  180
ctttacatca atactacaaa aagtttgtca gatctaagag gatatgtcta ccaaggcctc  240
aaatccggaa atgtatcaat catacatgtc aacagctact tgtatggagc attaaaggac  300
atccggggta agttggataa agattggtca agtttcggaa taaacatcgg gaaagcaggg  360
gatacaatcg gaatatttga ccttgtatcc ttgaaagccc tggacggcgt acttccagat  420
ggagtatcgg atgcttccag aaccagcgca gatgacaaat ggttgccttt gtatctactt  480
ggcttataca gagtgggcag aacacaaatg cctgaataca gaaaaaagct catggatggg  540
ctgacaaatc aatgcaaaat gatcaatgaa cagtttgaac ctcttgtgcc agaaggtcgt  600
gacatttttg atgtgtgggg aaatgacagt aattacacaa aaattgtcgc tgcagtggac  660
atgttcttcc acatgttcaa aaaacatgaa tgtgcctcgt tcagatacgg aactattgtt  720
tccagattca aagattgtgc tgcattggca acatttggac acctctgcaa aataaccgga  780
atgtctacag aagatgtaac gacctggatc ttgaaccgag aagttgcaga tgaaatggtc  840
caaatgatgc ttccaggcca agaaattgac aaggccgatt catacatgcc ttatttgatc  900
gactttggat tgtcttctaa gtctccatat tcttccgtca aaaaccctgc cttccacttc  960
tgggggcaat tgacagctct tctgctcaga tccaccagag caaggaatgc ccgacagcct  1020
gatgacattg agtatacatc tcttactaca gcaggtttgt tgtacgctta tgcagtagga  1080
tcctctgccg acttggcaca acagttttgt gttggagata acaaatacac tccagatgat  1140
agtaccggag gattgacgac taatgcaccg ccacaaggca gagatgtggt cgaatggctc  1200
ggatggtttg aagatcaaaa cagaaaaccg actcctgata tgatgcagta tgcgaaaaga  1260
gcagtcatgt cactgcaagg cctaagagag aagacaattg gcaagtatgc taagtcagaa  1320
tttgacaaat gaccctataa ttctcagatc acctattata tattatgcta catatgaaaa  1380
aaactaacag atatcatgga taatctcaca aaagttcgtg agtatctcaa gtcctattct  1440
cgtctggatc aggcggtagg agagatagat gagatcgaag cacaacgagc tgaaaagtcc  1500
aattatgagt tgttccaaga ggatggagtg gaagagcata ctaagccctc ttattttcag  1560
gcagcagatg attctgacac agaatctgaa ccagaaattg aagacaatca aggtttgtat  1620
gcaccagatc cagaagctga gcaagttgaa ggctttatac aggggccttt agatgactat  1680
gcagatgagg aagtggatgt tgtatttact tcggactgga aacagcctga gcttgaatct  1740
gacgagcatg gaaagacctt acggttgaca tcgccagagg gtttaagtgg agagcagaaa  1800
tcccagtggc tttcgacgat taaagcagtc gtgcaaagtg ccaaatactg gaatctggca  1860
gagtgcacat ttgaagcatc gggagaaggg gtcattatga aggagcgcca gataactccg  1920
gatgtatata aggtcactcc agtgatgaac acacatccgt cccaatcaga agcagtatca  1980
gatgtttggt ctctctcaaa gacatccatg actttccaac ccaagaaagc aagtcttcag  2040
cctctcacca tatccttgga tgaattgttc tcatctagag gagagttcat ctctgtcgga  2100
ggtgacggac gaatgtctca taaagaggcc atcctgctcg gcctgagata caaaaagttg  2160
tacaatcagg cgagagtcaa atattctctg tagactatga aaaaaagtaa cagatatcac  2220
```

```
gatctaagtg ttatcccaat ccattcatca tgagttcctt aaagaagatt ctcggtctga   2280
aggggaaagg taagaaatct aagaaattag ggatcgcacc accccttat gaagaggaca    2340
ctagcatgga gtatgctccg agcgctccaa ttgacaaatc ctattttgga gttgacgaga   2400
tggcacccta tgatccgaat caattaagat atgagaaatt cttctttaca gtgaaaatga   2460
cggttagatc taatcgtccg ttcagaacat actcagatgt ggcagccgct gtatcccatt   2520
gggatcacat gtacatcgga atggcaggga aacgtcccct ctacaaaatc ttggcttttt   2580
tgggttcttc taatctaaag gccactccag cggtattggc agatcaaggt caaccagagt   2640
atcacactca ctgcgaaggc agggcttatt tgccacatag gatggggaag acccctccca   2700
tgctcaatgt accagagcac ttcagaagac cattcaatat aggtctttac aagggaacga   2760
ttgagctcac aatgaccatc tacgatgatg agtcactgga agcagctcct atgatctgaa   2820
atcatttcaa ttcttccaaa ttttctgatt tcagagagaa ggccttaatg tttggcctga   2880
ttgtcgagaa aaaggcatct ggagcgtggg tcctggattc tatcagccac ttcaaatgag   2940
ctagtctaac ttctagcttc tgaacaatcc ccggtttact cagtctctcc taattccagc   3000
ctctcgaaca actaatatcc tgtcttttct atccctatga aaaaaactaa cagagatcga   3060
tctgtttacg cgtgccacca tgttcgtgtt tctggtgctg ctgcctctgg tgagctccca   3120
gtgcgtgaac ctgaccacaa ggaccagct gccccctgcc tataccaatt ccttcacacg    3180
gggcgtgtac tatcccgaca aggtgttccg gagcagcgtg ctgcactcca cacaggatct   3240
gttttctgcct ttcttttcta acgtgacctg gttccacgcc atccacgtga gcggcaccaa  3300
tggcacaaag cggttcgaca atccagtgct gcccttttaac gatggcgtgt acttcgcctc  3360
caccgagaag tctaacatca tcagaggctg gatctttggc accacactgg acagcaagac   3420
acagtccctg ctgatcgtga acaatgccac caacgtggtc atcaaggtgt gcgagttcca   3480
gttttgtaat gatccattcc tgggcgtgta ctatcacaag acaataagt cttggatgga    3540
gagcgagttt cgcgtgtatt cctctgccaa caattgcaca tttgagtacg tgtcccagcc   3600
cttcctgatg gacctggagg gcaagcaggg caatttcaag aacctgaggg agttcgtgtt   3660
taagaatatc gatggctact tcaaaatcta ctccaagcac accccaatca acctggtgcg   3720
cgacctgcca cagggcttct ctgccctgga gccactggtg gatctgccca tcggcatcaa   3780
catcacccgg tttcagacac tgctggccct gcacagaagc tacctgacac caggcgacag   3840
ctcctctgga tggaccgcag gagcagcagc ctactatgtg ggctatctgc agcccaggac   3900
cttcctgctg aagtacaacg agaatggcac catcacagac gccgtggatt gcgccctgga   3960
tcccctgtct gagaccaagt gtacactgaa gagctttacc gtggagaagg gcatctatca   4020
gacaagcaat ttcagggtgc agcctaccga gtccatcgtg cgctttccca atatcacaaa   4080
cctgtgccct tttggcgagg tgttcaacgc aacccgcttc gccagcgtgt acgcctggaa   4140
taggaagcgc atctccaact gcgtggccga ctattctgtg ctgtacaaca cgcctcctt    4200
ctctaccttt aagtgctatg gcgtgagccc cacaaagctc aatgacctgt gctttaccaa   4260
cgtgtacgcc gattccttcg tgatcagggg cgacgaggtg cgccagatcg caccaggaca   4320
gacaggcaag atcgcagact acaattataa gctgcctgac gatttcaccg gctgcgtgat   4380
cgcctggaac tctaacaatc tggatagcaa agtgggcggc aactacaatt atctgtaccg   4440
gctgtttaga aagtctaatc tgaagccatt cgagagggac atctccacag aaatctacca   4500
ggccgctct accccctgca atggcgtgga gggctttaac tgttattcc ctctgcagag     4560
ctacggcttc cagccaacaa acggcgtggg ctatcagccc taccgcgtgg tggtgctgtc   4620
ttttgagctg ctgcacgcac ctgcaacagt gtgcggacca aagaagagca ccaatctggt   4680
gaagaacaag tgcgtgaact tcaacttcaa cggactgacc ggaacaggcg tgctgaccga   4740
gtccaacaag aagttcctgc cttttcagca gttcggcagg gacatcgcag ataccacaga   4800
cgccgtgcgc gaccctcaga ccctggagat cctggacatc acaccatgct ccttcggcgg   4860
cgtgtctgtg atcacaccag gcaccaatac aagcaaccag gtggccgtgc tgtatcagga   4920
cgtgaattgt accgaggtgc cagtggcaat ccacgcagat cagctgaccc ctacatggcg   4980
ggtgtactct accggcagca acgtgttcca gacaagagcc ggatgcctga tcggagcaga   5040
gcacgtgaac aatagctatg agtgcgacat ccctatcggc gccggcatct gtgcctccta   5100
ccagacccag acaaactccc caaggtctgt gggcgataca ggcctgtcca agaatcaat    5160
cgagctggta gagggctggt tcagcagttg aaaagctcc atcgcctcct ttttctttat    5220
catcgcctg atcatcggac tgttcctggt gctccgcgtg ggtatccatc tgtgcatcaa    5280
gctgaagcac accaagaaaa gacagattta tacagacatc gagatgaacc gcctgggaaa   5340
gggatccggc tccggcgagg caggggaag tctactaaca tgcggggacg tggaggaaaa    5400
tccccggcccc atgaagtgcc ttttgtactt agccttttta ttcattgggg tgaattcaa    5460
gttcaccata gttttccac aaaccaaaa aggaaactgg aaaaatgttc cttctaatta     5520
ccattattgc ccgtcaagct cagatttaaa ttggcataat gacttaatag gcacagccat   5580
acaagtcaaa atgcccaaga gtcacaaggc tattcaagca gacggttgga tgtgtcatgc   5640
ttccaaatgg gtcactactt gtgatttccg ctggtatgga ccgaagtata taacacagtc   5700
catccgatcc ttcactccat ctgtagaaca atgcaaggaa agcattgaac aaacgaaaca   5760
aggaacttgg ctgaatccag gcttccctcc tcaaagttgt ggatatgcaa ctgtgacgaa   5820
tgccgaagca gtgattgtcc aggtgactcc tcaccatgtg ctggttgatg aatacacagg   5880
agaatgggtt gattcacagt tcatcaacgg aaaatgcagc aattacatat gccccactgt   5940
ccataactct acaacctggc attctgacta taagtcaaa gggctatgtg attctaacct    6000
catttccatg gacatcacct tctttctcaga ggacgaggag ttcatccc tgggaaagga   6060
gggcacaggg ttcagaagta actactttgc ttatgaaact ggaggcaagg cctgcaaaat   6120
gcaatactgc aagcattggg gagtcagact cccatcaggt gtctggttcg agatggctga   6180
taaggatctc tttgctgcag ccagattccc tgaatgccca gaagggtcaa gtatctctgc   6240
tccatctcag acctcagtgg atgtaagtct aattcaggac gttgagagga tcttggatta   6300
ttccctctgc caagaaacct ggagcaaat cagagcggct cttccaatct ctccagtga    6360
tctcagctat cttgctccta aaacccagg aaccggtcct gctttcacca taatcaatgg   6420
tacccctaaa acttttgaga ccagatacat cagagtcgat attgctgctc caatcctctc   6480
aagaatggtc ggaatgatca gtggaactac cacagaaagg gaactgtggg atgactgggc   6540
accatatgaa gacgtggaaa ttggacccaa tggagttctg aggaccagtt caggatataa   6600
gttccttta tacatgattg gacatgtgat gttggactcc gatcttcatc ttagctcaaa   6660
ggctcaggtg ttcgaacatc ctcacattca agacgctgct tcgcaacttc ctgatgatga   6720
gagtttattt tttggtgata ctgggctatc caaaaatcca atcgagctg tagaaggttg    6780
gttcagtagt tggaaaagct ctattgcctc ttttttcttt atcatagggt taatcattgg   6840
actattcttg gttctccgag ttggtatcca tctttgcatt aaattaaagc acaccaagaa   6900
aagacagatt tatacagaca tagagatgaa ccgacttgga aagtaagcta gccagattct   6960
```

```
tcatgtttgg accaaatcaa cttgtgatac catgctcaaa gaggcctcaa ttatatttga   7020
gttttaatt tttatgaaaa aaactaacag caatcatgga agtccacgat tttgagaccg   7080
acgagttcaa tgatttcaat gaagatgact atgccacaag agaattcctg aatcccgatg  7140
agcgcatgac gtacttgaat catgctgatt acaatttgaa ttctcctcta attagtgatg  7200
atattgacaa tttgatcagg aaattcaatt ctcttccgat tccctcgatg tgggatagta  7260
agaactggga tggagttctt gagatgttaa catcatgtca agccaatccc atctcaacat  7320
ctcagatgca taaatggatg ggaagttggt taatgtctga taatcatgat gccagtcaag  7380
ggtatagttt tttacatgaa gtggacaaag aggcagaaat aacatttgac gtggtggaga  7440
ccttcatccg cggctgggc aacaaaccaa ttgaatacat caaaaaggaa agatggactg   7500
actcattcaa aattctcgct tatttgtgtc aaaagttttt ggacttacac aagttgacat  7560
taatcttaaa tgctgtctct gaggtggaat tgctcaactt ggcgaggact ttcaaaggca  7620
aagtcagaag aagttctcat ggaacgaaca tatgcaggat tagggttccc agcttgggtc  7680
ctactttat ttcagaagga tgggcttact tcaagaaact tgatattcta atggaccgaa   7740
actttctgtt aatggtcaaa gatgtgatta tagggaggat gcaaacggtg ctatccatgg  7800
tatgtagaat agacaacctg ttctcagagc aagacatctt ctcccttcta aatatctaca  7860
gaattgagaa taaaattgtg gagaggcagg gaaattttc ttatgacttg attaaaatgg   7920
tggaaccgat atgcaacttg aagctgatga aattagcaag agaatcaagg cctttagtcc  7980
cacaattccc tcattttgaa aatcatatca agacttctgt tgatgaaggg gcaaaaattg  8040
accgaggtat aagattcctc catgatcaga taatgagtgt gaaaacagtg gatctcacac  8100
tggtgattta tggatcgttc agacattggg gtcatccttt tatagattat tacactggac  8160
tagaaaaatt acattcccaa gtaaccatga agaaagatat tgatgtgtca tatgcaaaag  8220
cacttgcaag tgatttagct cggattgttc tatttcaaca gttcaatgat cataaaaagt  8280
ggttcgtgaa tggagacttg ctccctcatg atcatccctt taaaagtcat gttaaagaaa  8340
atacatggcc cacagctgct caagttcaag attttggaga taaatggcat gaacttccgc  8400
tgattaaatg ttttgaaata cccgacttac tagacccatc gataatatac tctgacaaaa  8460
gtcattcaat gaataggtca gaggtgttga acatgtccg aatgaatccg aacactccta   8520
tccctagtaa aaaggtgttg cagactatgt tggacacaaa ggctaccaat tggaaagaat  8580
ttcttaaaga gattgatgag aagggcttag atgatgatga tctaattatt ggtcttaaag  8640
gaaaggagg ggaactgaag ttggcaggta gattttttctc cctaatgtct tggaaattgc   8700
gagaatactt tgtaattacc gaatatttga taaagactca tttcgtccct atgtttaaag  8760
gcctgacaat ggcggacgat ctaactgcag tcattaaaaa gatgttagat tcctcatccg  8820
gccaaggatt gaagtcatat gaggcaattt gcatagccaa tcacattgat tacgaaaaat  8880
ggaataacca ccaaaggaag ttatcaaacg gcccagtgtt ccgagttatg gccagttct    8940
taggttatcc atccttaatc gagagaactc atgaattttt tgagaaaagt cttatatact  9000
acaatggaag accagacttg atgcgtgttc acaacaacac actgatcaat tcaacctccc  9060
aacgagtttg ttggcaagga caagagggtg gactggaagg tctacggcaa aaaggatgga  9120
ctatcctcaa tctactggtt attcaaagag aggctaaaat cagaaacact gctgtcaaag  9180
tcttggcaca aggtgataat caagttattt gcacacagta taaaacgaag aaatcgagaa  9240
acgttgtaga attacagggt gctctcaatc aaatggtttc taataatgag aaaattatga  9300
ctgcaatcaa aataggggaca gggaagttag gactttttgat aaatgacgat gagactatgc  9360
aatctgcaga ttacttgaat tatggaaaaa taccgatttt ccgtggagtg attagagggg  9420
tagagaccaa gagatggtca cgagtgactt gtgtcaccaa tgaccaaata cccacttgtg  9480
ctaatataat gagctcagtt tccacaaatg ctctcaccgt agctcatttt gctgagaacc  9540
caatcaatgc catgatacag tacaattatt ttgggacatt tgctagactc ttgttgatga  9600
tgcatgatcc tgctcttcgt caatcattgt atgaagttca agataagata ccgggcttgc  9660
acagttctac ttcaaatac gccatgttgt atttggaccc ttccattgga ggagtgtcgg   9720
gcatgtcttt gtccaggttt ttgattagag ccttcccaga tcccgtaaca gaaagtctct  9780
cattctggag attcatccat gtacatgctc gaagtgagca tctgaaggag atgagtcag   9840
tatttggaaa ccccgagata gccaagtttc gaataactca catagacaag ctagtagaag  9900
atccaacctc tctgaacatc gctatgggaa tgagtccagc gaacttgtta aagactgagg  9960
ttaaaaatg cttaatcgaa tcaagacaaa ccatcaggaa ccaggtgatt aaggatgcaa  10020
ccatatattt gtatcatgaa gaggatcggc tcagaagttt cttatggtca ataaatcctc  10080
tgttccctag atttttaagt gaattcaaat caggcacttt tttgggagtc gcagacgggc  10140
tcatcagtct atttcaaaat tctcgtacta ttcggaactc cttaagaaa aagtatcata   10200
gggaattgga tgatttgatt gtgaggagtg aggtatcctc tttgacacat ttagggaaac  10260
ttcatttgag aagggggatca tgtaaaatgt ggacatgttc agctactcat gctgacacat  10320
taagatacaa atcctgggc cgtacagtta ttgggacaac tgtacccat ccattagaaa    10380
tgttgggtcc acaacatcga aaagagactc cttgtgcacc atgtaacaca tcagggttca  10440
attatgtttc tgtgcattgt ccagacggga tcttagttca cggggaccat  10500
tgcctgctta tctagggtct aaaacatctg aatctacatc tattttgcag ccttgggaaa  10560
gggaaagcaa agtcccactg attaaaagag ctacacgtct tagagatgct atctcttggt  10620
ttgttgaacc cgactctaaa ctagcaatga ctatacttc taacatccac tctttaacag   10680
gcgaagaatg gaccaaaagg cagcatgggt tcaaagaac agggtctgcc cttcataggt   10740
tttcgacatc tcggatgagc catgtgggt tcgcatctca gagcactgca gcattgacca  10800
ggttgatggc aactcagac accatgaggg atctgggaga tcagaatttc gacttttat    10860
tccaagcaac gttgctctat gctcaaatta ccaccactgt tgcaagagac ggatgggatc  10920
ccagttgtac agatcattat catattgcct gtaagtcctg tttgagaccc atagaagaga  10980
tcaccctgga ctcaagtatg gactacacgc ccccagatgt atcccatgtg ctgaagacat  11040
gggaggatgg ggaaggttcg tggggacaag agataaaaca gatctatcct ttagaaggga  11100
attggaagaa tttagcacct gctgagcaat cctatcaagt cggcagatgt ataggttttc  11160
tatatgagga cttggcgtat agaaaatcta ctcatgccga ggacagtcct ctatttcctc  11220
tatctataca aggtcgtatt agaggtcgag gtttcttaaa aggggttgcta gacggattaa  11280
tgagagcaag ttgctgccaa gtaatacacc ggagaagtct ggctcatttg aagaggccgg  11340
ccaacgcagt gtacggaggt ttgatttact tgattagtgta tcacctccat  11400
tcctttctct tactagatca ggacctatta gagcgaatt agaacgatt ccccacaaga   11460
tcccaacctc ctatccgaca agcaaccgtg atatgggggt gattgtcaga aattacttca  11520
aataccaatg ccgtcaatt gaaaagggaa atacagatc acattattca caattatggt   11580
tattctcaga tgtcttatcc atagacttca ttggaccatt ctctatttcc accacctct   11640
tgcaaatcct atacaagcca tttttatctg ggaaagataa gaatgagttg agagagctgg  11700
```

```
caaatctttc ttcattgcta agatcaggag aggggtggga agacatacat gtgaaattct  11760
tcaccaagga catattattg tgtccagagg aaatcagaca tgcttgcaag ttcgggattg  11820
ctaaggataa taataaagac atgagctatc cccccttgggg aagggaatcc agagggacaa  11880
ttacaacaat ccctgtttat tatacgacca ccccttaccc aaagatgcta gagatgcctc  11940
caagaatcca aaatcccctg ctgtccggaa tcaggttggg ccaattacca actggcgctc  12000
attataaaat tcggagtata ttacatggaa tgggaatcca ttacagggac ttcttgagtt  12060
gtggagacgg ctccggaggg atgactgctg cattactacg agaaaatgtg catagcagag  12120
gaatattcaa tagtctgtta gaattatcag ggtcagtcat gcgaggcgcc tctcctgagc  12180
cccccagtgc cctagaaact ttaggaggag ataaatcgag atgtgtaaat ggtgaaacat  12240
gttgggaata tccatctgac ttatgtgacc caaggacttg ggactatttc ctccgactca  12300
aagcaggctt ggggcttcaa attgatttaa ttgtaatgga tatggaagtt cgggattctt  12360
ctactagcct gaaaattgag acgaatgtta gaaattatgt gcaccggatt ttggatgagc  12420
aaggagtttt aatctacaag acttatggaa catatatttg tgagagcgaa aagaatgcag  12480
taacaatcct tggtcccatg ttcaagacgg tcgacttagt tcaaacagaa tttagtagtt  12540
ctcaaacgtc tgaagtatat atggtatgta aaggtttgaa gaaattaatc gatgaaccca  12600
atcccgattg gtcttccatc aatgaatcct ggaaaaacct gtacgcattc cagtcatcag  12660
aacaggaatt tgccagagca aagaaggtta gtacatactt taccttgaca ggtattccct  12720
cccaattcat tcctgatcct tttgtaaaca ttgagactat gctacaaata ttcggagtac  12780
ccacgggtgt gtctcatgcg gctgccttaa aatcatctga tagacctgca gatttattga  12840
ccattagcct tttttatatg gcgattatat cgtattataa catcaatcat atcagagtag  12900
gaccgatacc tccgaacccc ccatcagatg gaattgcaca aaatgtgggg atcgctataa  12960
ctggtataag cttttggctg agtttgatgg agaaagacat tccactatat caacagtgtt  13020
tagcagttat ccagcaatca ttcccgatta ggtgggaggc tgtttcagta aaaggaggat  13080
acaagcagaa gtggagtact agaggtgatg ggctcccaaa agatacccga acttcagact  13140
ccttggcccc aatcgggaac tggatcagat ctctggaatt ggtccgaaac caagttcgtc  13200
taaatccatt caatgagatc ttgttcaatc agctatgtcg tacagtggat aatcatttga  13260
aatggtcaaa tttgcgaaga aacacaggaa tgattgaatg gatcaataga cgaatttcaa  13320
aagaagaccg gtctatactg atgttgaaga gtgacctaca cgaggaaaac tcttggagag  13380
attaaaaaat catgaggaga ctccaaactt taagtatgaa aaaaactttg atccttaaga  13440
ccctcttgtg gtttttattt tttatctggt tttgtggtct tcgt                  13484

SEQ ID NO: 25          moltype = DNA  length = 13484
FEATURE                Location/Qualifiers
misc_feature           1..13484
                       note = VSV vector: Convac V4 South Africa
source                 1..13484
                       mol_type = other DNA
                       organism = synthetic construct
SEQUENCE: 25
acgaagacaa acaaaccatt attatcatta aaaggctcag gagaaacttt aacagtaatc  60
aaaatgtctg ttacagtcaa gagaatcatt gacaacacag tcatagttcc aaaacttcct  120
gcaaatgagg atccagtgga atacccggca gattacttca gaaaatcaaa ggagattcct  180
ctttacatca atactacaaa aagtttgtca gatctaagag gatatgtcta ccaaggcctc  240
aaatccggaa atgtatcaat catacatgtc aacagctact tgtatggagc attaaaggac  300
atccggggta agttggataa agattggtca agtttcggaa taaacatcgg gaaagcaggg  360
gatacaatcg gaatatttga ccttgtatcc ttgaaagccc tggacggcgt acttccagat  420
ggagtatcgg atgcttccag aaccagcgca gatgacaaat ggttgccttt gtatctactt  480
ggcttataca gagtgggcag aacacaaatg cctgaataca gaaaaaagct catggatggg  540
ctgacaaatc aatgcaaaat gatcaatgaa cagtttgaac ctcttgtgcc agaaggtcgt  600
gacatttttg atgtgtgggg aaatgacagt aattacacaa aaattgtcgc tgcagtggac  660
atgttcttcc acatgttcaa aaaacatgaa tgtgcctcgt tcagatacgg aactattgtt  720
tccagattca aagattgtgc tgcattggca acatttggac acctctgcaa aataaccgga  780
atgtctacag aagatgtaac gacctggatc ttgaaccgag aagttgcaga tgaaatggtc  840
caaatgatgc ttccaggcca agaaattgac aaggccgatt catacatgcc ttatttgatc  900
gactttggat tgtcttctaa gtctccatat tcttccgtca aaaaccctgc cttccacttc  960
tgggggcaat tgacagctct tctgctcaga tccaccagag caaggaatgc ccgacagcct  1020
gatgacattg agtatacatc tcttactaca gcaggtttgt tgtacgctta tgcagtagga  1080
tcctctgccg acttggcaca acagttttgt gttggagata acaaatacac tccagatgat  1140
agtaccggag gattgacgac taatgcaccg ccacaaggca gagatgtggt cgaatggctc  1200
ggatggtttg aagatcaaaa cagaaaaccg actcctgata tgatgcagta tgcgaaaaga  1260
gcagtcatgt cactgcaagg cctaagagag aagacaattg gcaagtatgc taagtcagaa  1320
tttgacaaat gaccctataa ttctcagatc acctattata tattatgcta catatgaaaa  1380
aaactaacag atatcatgga taatctcaca aaagttcgtg agtatctcaa gtcctattct  1440
cgtctggatc aggcggtagg agagatagat gagatcgaag cacaacgagc tgaaaagtcc  1500
aattatgagt tgttccaaga ggatggagtg gaagagcata ctaagccctc ttattttcag  1560
gcagcagatg attctgacac agaatctgaa ccagaaattg aagacaatca aggtttgtat  1620
gcaccagatc cagaagctga gcaagttgaa ggctttatac aggggccttt agatgactat  1680
gcagatgagg aagtggatgt tgtatttact tcggactgga aacagcctga gcttgaatct  1740
gacgagcatg gaaagacctt acggttgaca tcgccagagg gtttaagtgg agagcagaaa  1800
tcccagtggc tttcgacgat taaagcagtc gtgcaaagtg ccaaatactg gaatctggca  1860
gagtgcacat ttgaagcatc gggagaaggg gtcattatga aggagcgcca gataactccg  1920
gatgtatata aggtcactcc agtgatgaac acacatccgt cccaatcaga agcagtatca  1980
gatgtttggt ctctctcaaa gacatccatg actttccaac ccaagaaagc aagtcttcag  2040
cctctcacca tatccttgga tgaattgttc tcatctagag gagagttcat ctctgtcgga  2100
ggtgacggac gaatgtctca taaagaggcc atcctgctcg gcctgagata caaaaagttg  2160
tacaatcagg cgagagtcaa atattctctg tagactatga aaaaaagtaa cagatatcac  2220
gatctaagtg ttatcccaat ccattcatca tgagttcctt aaagaagatt ctcggtctga  2280
aggggaaagg taagaaatct aagaaattag ggatcgcacc accccctat gaagaggaca  2340
ctagcatgga gtatgctccg agcgctccaa ttgacaaatc ctattttgga gttgacgaga  2400
```

```
tggacaccta tgatccgaat caattaagat atgagaaatt cttctttaca gtgaaaatga  2460
cggttagatc taatcgtccg ttcagaaacat actcagatgt ggcagccgct gtatcccatt  2520
gggatcacat gtacatcgga atggcaggga aacgtcccct ctacaaaatc ttggctttt   2580
tgggttcttc taatctaaag gccactccag cggtattggc agatcaaggt caaccagagt  2640
atcacactca ctgcgaaggc agggcttatt tgccacatag gatggggaag accccctccca 2700
tgctcaatgt accagagcac ttcagaagac cattcaatat aggtctttac aagggaacga  2760
ttgagctcac aatgaccatc tacgatgatg agtcactgga agcagctcct atgatctggg  2820
atcatttcaa ttcttccaaa ttttctgatt tcagagagaa ggccttaatg tttggcctga  2880
ttgtcgagaa aaaggcatct ggagcgtggg tcctggattc tatcagccac ttcaaatgag  2940
ctagtctaac ttctagcttc tgaacaatcc ccggtttact cagtctctcc taattccagc  3000
ctctcgaaca actaatatcc tgtctttct atccctatga aaaaactaa cagagatcga   3060
tctgtttacg cgtgccacca tgttcgtgtt tctggtgctg ctgcctctgg tgagctccca  3120
gtgcgtgaac ttcaccacaa ggaccagct gcccctgcc tataccaatt ccttcacacg   3180
gggcgtgtac tatcccgaca aggtgttccg gagcagcgtc ctgcactcca cacaggatct  3240
gtttctgcct ttctttttcta acgtgacctg gttccacgcc atccacgtga gcggcaccaa  3300
tggcacaaag cggttcgcca atccagtgct gcccttaaac gatggcgtgt acttcgcctc  3360
caccgagaag tctaacatca tcagaggctg gatctttggc accacactgg acagcaagac  3420
acagtccctg ctgatcgtga acaatgccac caacgtgatc ctgcactcca cacaggatct  3480
gttttgtaat gatccattcc tgggcgtgta ctatcacaag aacaataagt cttggatgga  3540
gagcgagttt cgcgtgtatt cctctgccaa caattgcaca tttgagtacg tgtcccagcc  3600
cttcctgatg gacctggagg gcaagcaggg caatttcaag aacctgaggg agttcgtgtt  3660
taagaatatc gatgcgctact tcaaaatcta ctccaagcac acccaatca acctggtgcg  3720
cggcctgcca cagggcttct ctgccctgga gccactggtg gatctgccca tcggcatcaa  3780
catcacccgg tttcagacac tgctggccct gcacagaagc tacctgacac caggcgacag  3840
ctcctctgga tggaccgcag gagcagcagc ctactatgtg ggctatctgc agcccaggac  3900
cttcctgctg aagtacaacg aagaatggcac catcacagac gccgtggatt ggcgcctgga  3960
tccctgtct gagaccaagt gtacactgaa gagctttacc gtggagaagg gcatccatca   4020
gacaagcaat tcagggtgc agcctaccga gtccatcgtg cgctttccca atatcacaaa   4080
cctgtgccct tttggcgagg tgttcaacgc aacccgcttc gccagcgtgt acgcctgaa   4140
taggaagcga atctccaact gcgtgccga ctattctgtg ctgtacaaca gcgcctcctt   4200
ctctacctttt aagtgctatg gcgtgagccc cacaaagctg aatgacctgt gctttaccaa  4260
cgtgtacgcc gattccttcg tgatcagggg cgacgaggtg cgccagatcg caccaggaca  4320
gacaggcaat atcgcagact acaattataa gctgcctgac gatttcaccg gctgcgtgat  4380
cgcctggaac tctaacaatc tggatagcaa agtgggcggc aactacaatt atctgtaccg  4440
gctgtttaga aagtctaatc tgaagccatt cgagagggac atctccacag aaatctacca  4500
ggccggctct accccctgca atggcgtgaa gggctttaac tgttatttcc ctctgcagag  4560
ctacggcttc cagccaacat atggcgtggg ctatcagccc taccgcgtgg tggtgctgtc  4620
tttttgagctg ctgcacgcac ctgcaacagt gtgcggacca aagaagagca ccaatctggt  4680
gaagaacaag tgcgtgaact tcaacttcaa cggactgaca ggaacaggcg tgctgaccga  4740
gtccaacaag aagttcctgc cttttcagca gttcggcagg gacatcgcag ataccacaga  4800
cgccgtgcgc gaccctcaga ccctggagat cctggacatc acaccatgct ccttcggcgg  4860
cgtgtctgtg atcacaccag gcaccaatac aagcaaccag gtggccgtgc tgtatcaggg  4920
cgtgaattgt accgaggtgc cagtggcaat ccacgcagat cagctgaccc ctacatgcga  4980
ggtgtactct accggcagca acgtgttcca gacaagagcc ggatgcctga tcggagcaga  5040
gcacgtgaac aatagctatg agtgcgacat ccctatcggc gccggcatct gtgcctccta  5100
ccagacccag acaaactccc caaggtctgt gggcgataca ggcctgtcca agaatccaat  5160
cgagctggta gagggctggt tcagcagttg gaaaagctcc atcgcctcct tttctttat   5220
catcggcctg atcatcggac tgttcctggt gctccgcgtg ggtatccacc tgtgcatcaa  5280
gctgaagcac accaagaaaa gacagattta tacagacatc gagatgaacc gcctgggaaa  5340
gggatccggc tccggcgagg caggggaag tctactaaca tgcggggacg tggaggaaaa  5400
tcccgcccc atgaagtgcc ttttgtactt agccttttta ttcattgggg tgaattgcaa  5460
gttcaccata gttttccac acaaccaaaa aggaaactgg aaaaatgttc cttctaatta   5520
ccattattgc ccgtcaagct cagatttaaa ttggcataat gacttaatag gcacagccat  5580
acaagtcaaa atgcccaaga gtcacaaggc tattcaagca gacggttgga tgtgtcatgc  5640
ttccaaatgg gtcactactt gtgatttccg ctggtatgga ccgaagtata taacacagtc  5700
catccgatcc ttcactccat ctgtagaaca atgcaaggaa agcattgaac aaacgaaaca  5760
aggaacttgg ctgaatccag gcttccctcc tcaaagttgt ggatatgcaa ctgtgacgga  5820
tgccgaagca gtgattgtcc aggtgactcc tcaccatgtg ctggttgatg aatacacagg  5880
agaatgggtt gattcacagt tcatcaacgg aaaatgcagc aattacatat gccccactgt  5940
ccataactct acaacctggc attctgacta taggtcaaa gggctatgtg attctaacct  6000
catttccatg gacatcacct tcttctcaga ggacggagag ctatcatccc tgggaaagga  6060
gggcacaggg ttcagaagta actactttgc ttatgaaact ggaggcaagg cctgcaaat   6120
gcaatactgc aagcattggg gagtcagact cccatcaggt gtctggttcg agatggctga  6180
taaggatctc ttttgctgcag ccagattccc tgaatgccca gaagggtcaa gtatctctgc  6240
tccatctcag acctcagtgg atgtaagtct aattcaggac gttgagagga tcttggatta  6300
ttccctctgc caagaaacct ggagcaaaat cagagcgggt cttccaatct ctccagtgga  6360
tctcagctat cttgctccta aaacccagg aaccggtcct gctttcacca taatcaatgg  6420
taccctaaaa tactttgaga ccagatacat cagtcgat attgctgtc caatcctctc    6480
aagaatggtc ggaatgatca gtgaactac cacagaaagg gaactgtggg atgactgggc  6540
accatatgaa gacgtggaaa ttggacccaa tggattctg aggaccagtt caggatataa   6600
gtttcctta tacatgattg dacatggtat gttggactcc gatcttcatc ttagctcaaa   6660
ggctcaggtg ttcgaacatc ctcacattca agacgctgct tcgcaacttc ctgatgatga  6720
gagtttatttt tttggtgata ctgggctatc caaaaatcca atcgagctg tagaaggttg   6780
gttcagtagt tggaaagct ctattgcctc tttttcttt atcatagggt taatcattgg    6840
actattcttg gttctccgag ttggtatcca tctttgcatt aaattaaagc acaccaagaa   6900
aagacagatt tatacagaca tagagatgaa ccgacttgga aagtaagcta gccagattct   6960
tcatgtttgg accaaatcaa cttgtgatac catgctcaaa gaggcctcaa ttatatttga  7020
gtttttaatt tttatgaaaa aaactaacag caatcatgga agtccacgat tttgagaccg   7080
acgagttcaa tgatttcaat gaagatgact atgccacaag agaattcctg aatcccgatg   7140
```

```
agcgcatgac gtacttgaat catgctgatt acaatttgaa ttctcctcta attagtgatg   7200
atattgacaa tttgatcagg aaattcaatt ctcttccgat tccctcgatg tgggatagta   7260
agaactggga tggagttctt gagatgttaa catcatgtca agccaatccc atctcaacat   7320
ctcagatgca taaatggatg ggaagttggt taatgtctga taatcatgat gccagtcaag   7380
ggtatagttt tttacatgaa gtggacaaag aggcagaaat aacatttgac gtggtggaga   7440
ccttcatccg cggctgggc aacaaaccaa ttgaatacat caaaaaggaa agatggactg    7500
actcattcaa aattctcgct tatttgtgtc aaaagttttt ggacttacac aagttgacat   7560
taatcttaaa tgctgtctct gaggtggaat tgctcaactt ggcgaggact ttcaaaggca   7620
aagtcagaag aagttctcat ggaacgaaca tatgcaggat tagggttccc agcttgggtc   7680
ctacttttat ttcagaagga tgggcttact tcaagaaact tgatattcta atggaccgaa   7740
actttctgtt aatggtcaaa gatgtgatta tagggaggat gcaaacggtg ctatccatgg   7800
tatgtagaat agacaacctg ttctcagagc aagcatctt ctcccttcta aatatctaca    7860
gaattggaga taaaattgtg gagaggcagg aaattttttc ttatgacttg attaaaatgg   7920
tggaaccgat atgcaacttg aagctgatga aattagcaag agaatcaagg cctttagtcc   7980
cacaattccc tcattttgaa aatcatatca agacttctgt tgatgaaggg gcaaaaattg   8040
accgaggtat aagattcctc catgatcaga taatgagtgt gaaaacagtg gatctcacac   8100
tggtgattta tggatcgttc agacattggg gtcatccttt tatagattat tacactggac   8160
tagaaaaatt acattcccaa gtaaccatga agaaagatat tgatgtgtca tatgcaaaag   8220
cacttgcaag tgatttagct cggattgttc tatttcaaca gttcaatgat cataaaaagt   8280
ggttcgtgaa tggagacttg ctccctcatg atcatccctt taaaagtcat gttaaagaaa   8340
atacatggcc cacagctgct caagttcaag attttggaga taaatggcat gaacttccgc   8400
tgattaaatg ttttgaaata cccgacttac tagacccatc gataatatac tctgacaaaa   8460
gtcattcaat gaataggtca gaggtgttga aacatgtccg aatgaatccg aacactccta   8520
tccctagtaa aaaggtgttg cagactatgt tggacacaaa ggctaccaat tggaaagaat   8580
ttcttaaaga gattgatgag aagggcttag atgatgatga tctaattatt ggtcttaaag   8640
gaaaggagag ggaactgaag ttggcaggta gatttttctc cctaatgtct tggaaattgc   8700
gagaatactt tgtaattacc gaatatttga taaagactca tttcgtccct atgtttaaag   8760
gcctgacaat ggcggacgat ctaactgcag tcattaaaaa gatgttagat tcctcatccg   8820
gccaaggatt gaagtcatat gaggcaattt gcatagccaa tcacattgat tacgaaaaat   8880
ggaataacca ccaaaggaag ttatcaaacg gcccagtgtt ccgagttatg ggccagttct   8940
taggttatcc atccttaatc gagagaactc atgaatttt tgagaaaagt cttatatact    9000
acaatggaag accagacttg atgcgtgttc acaacaacac actgatcaat tcaacctccc   9060
aacgagtttg ttggcaagga caagagggtg gactggaagg tctacggcaa aaaggatgga   9120
ctatcctcaa tctactggtt attcaaagag aggctaaaat cagaaacact gctgtcaaag   9180
tcttggcaca aggtgataat caagttattt gcacacagta taaaacgaag aaatcgagaa   9240
acgttgtaga attacagggt gctctcaatc aaatggtttc taataatgag aaaattatga   9300
ctgcaatcaa aataggaaca gggaagttag gacttttgat aaatgacgat gagactatgc   9360
aatctgcaga ttacttgaat tatggaaaaa taccgatttt ccgtgagtg attagagggt    9420
tagagaccaa gagatggtca cgagtgactt gtgtcaccaa tgaccaaata cccacttgtg   9480
ctaatatataat gagctcagtt tccacaaatg ctctcaccgt agctcatttt gctgagaacc   9540
caatcaatgc catgatacag tacaattatt tgggacatt tgctagactc ttgttgatga    9600
tgcatgatcc tgctcttcgt caatcattgt atgaagttca agataagata ccgggcttgc   9660
acagttctac tttcaaatac gccattgtt attggaccc ttccattgga ggagtgtcgg     9720
gcatgtcttt gtccaggttt ttgattagag ccttcccaga tcccgtaaca gaaagtctct   9780
cattctggag attcatccat gtacatgctc gaagtgagca tctgaaggag atgagtgcag   9840
tatttggaaa ccccgagata gccaagtttc gaataactca catagacaag ctagtagaag   9900
atccaacctc tctgaacatc gctatgggaa tgagtccgaa caacttgtta aagactgagg   9960
ttaaaaaatg cttaatcgaa tcaagacaaa ccatcaggaa ccaggtgatt aaggatgcaa  10020
ccatatattt gtatcatgaa gaggatcggc tcagaagttt cttatggtca ataaatcctc  10080
tgttccctag atttttaagt gaattcaaat caggcacttt tttgggagtc gcagacgggc  10140
tcatcagtct atttcaaaat tctcgtacta ttcggaactc ctttaagaaa aagtatcata  10200
gggaattgga tgatttgatt gtgaggagtg aggtatcctc tttgacacat ttagggaaac  10260
ttcatttgag aagggatca tgtaaaatgt ggacatgttc agctactcat gctgacacat    10320
taagatacaa atcctgggc cgtacagtta ttgggacaac tgtacccat ccattagaaa     10380
tgttggtcc acaacatcga aaagagactc cttgtgcacc atgtaacaca tcagggttca   10440
attatgtttc tgtgcattgt ccagacggga tccatgacgt cttagttca cggggaccat    10500
tgcctgctta tctagggtct aaaacatctg aatctcacatc tattttgcag ccttgggaaa  10560
gggaaagcaa agtcccactg attaaaagag ctacacgtct tagagatgct atctcttggt  10620
ttgttgaacc cgactctaaa ctagcaatga ctatactttc taacatccac tcttttaacag  10680
gcgaagaatg gaccaaaagg cagcatgggt tcaaaagaac agggtctgcc ttcataggt    10740
tttcgacatc tcggatgagc catggtgggt tcgcatctca gagcactgca gcattgacca  10800
ggttgatggc aactacagac accatgaggg atctgggaga tcagaatttc gacttttat    10860
tccaagcaac gttgctctat gctcaaatta ccaccactgt gcaagagac ggatggatca    10920
ccagttgtac agatcattat catattgcct gtaagtcctg tttgagaccc ataagaagag 10980
tcaccctgga ctcaagtatg gactacacgc cccagatgt atccatgtg ctgaagacat     11040
ggaggaatgg ggaaggttcg tgggacaag agataaaaca gatctatcct ttagaaggga  11100
attggaagaa tttagcacct gctgagcaat cctatcaagt cggcagatgt ataggttttc  11160
tatatggga cttggcgtat agaaaatcta ttcatgccga ggacagttct ctattcctc     11220
tatctataca aggtcgtatt agaggtcgag gttcttaaa agggttgcta gacggattaa   11280
tgagagcaag ttgctgccaa gtaatacacc ggagaagtct ggctcatttg aagaggccgg  11340
ccaacgcagt gtacggaggt ttgatttact tgattgataa attgagtgta tcacctccat  11400
tcctttctct tactagatca ggacctatta gagcgaatt agaacgatt ccccacaaga    11460
tcccaaccctc ctatccgaca agcaaccgtg atatgggggt gattgtcaga aattacttca  11520
aataccaatg ccgtctaatt gaaaaaggaa aatacagatc acattattca caattatgtt  11580
tattctcaga tgtcttatcc atagacttca ttggaccatt ctctatttcc accaccctct  11640
tgcaaatcct atacaagcca tttttatctg ggaaagataa gaatgagttg agagagctgg  11700
caaatcttc ttcattgcta agatcaggag aggggtggga agacatacat gtgaaattct    11760
tcaccaagga catattattg tgtccagagg aaatcagaca tgcttgcaag ttcgggattg  11820
ctaaggataa taataaagac atgagctatc ccccttgggg aagggaatcc agaggacaa   11880
```

```
ttacaacaat ccctgtttat tatacgacca ccccttaccc aaagatgcta gagatgcctc  11940
caagaatcca aaatcccctg ctgtccggaa tcaggttggg ccaattacca actggcgctc  12000
attataaaat tcggagtata ttacatggaa tgggaatcca ttacagggac ttcttgagtt  12060
gtggagacgg ctccggaggg atgactgctg cattactacg agaaaatgtg catagcagag  12120
gaatattcaa tagtctgtta gaattatcag ggtcagtcat gcgaggcgcc tctcctgagc  12180
cccccagtgc cctagaaact ttaggaggag ataaatcgag atgtgtaaat ggtgaaacat  12240
gttgggaata tccatctgac ttatgtgacc caaggacttg ggactatttc ctccgactca  12300
aagcaggctt ggggcttcaa attgatttaa ttgtaatgga tatggaagtt cgggattctt  12360
ctactagcct gaaaattgag acgaatgtta gaaattatgt gcaccggatt ttggatgagc  12420
aaggagtttt aatctacaag acttatggaa catatatttg tgagagcgaa aagaatgcag  12480
taacaatcct tggtcccatg ttcaagacgg tcgacttagt tcaaacagaa tttagtagtt  12540
ctcaaacgtc tgaagtatat atggtatgta aaggtttgaa gaaattaatc gatgaaccca  12600
atcccgattg gtcttccatc aatgaatcct ggaaaaacct gtacgcattc cagtcatcag  12660
aacaggaatt tgccagagca aagaaggtta gtacatactt taccttgaca ggtattccct  12720
cccaattcat tcctgatcct tttgtaaaca ttgagactat gctacaaata ttcggagtac  12780
ccacgggtgt gtctcatgcg gctgccttaa aatcatctga tagacctgca gatttattga  12840
ccattagcct tttttatatg gcgattatat cgtattataa catcaatcat atcagagtag  12900
gaccgatacc tccgaacccc ccatcagatg gaattgcaca aaatgtgggg atcgctataa  12960
ctggtataag cttttggctg agtttgatgg agaaagacat tccactatat caacagtgtt  13020
tagcagttat ccagcaatca ttcccgatta ggtgggaggc tgtttcagta aaaggaggat  13080
acaagcagaa gtggagtact agaggtgatg ggctcccaaa agatacccga acttcagact  13140
ccttggcccc aatcgggaac tggatcagat ctctggaatt ggtccgaaac caagttcgtc  13200
taaatccatt caatgagatc ttgttcaatc agctatgtcg tacagtggat aatcatttga  13260
aatggtcaaa tttgcgaaga aacacaggaa tgattgaatg gatcaataga cgaatttcaa  13320
aagaagaccg gtctatactg atgttgaaga gtgacctaca cgaggaaaac tcttggagag  13380
attaaaaaat catgaggaga ctccaaactt taagtatgaa aaaaactttg atccttaaga  13440
ccctcttgtg gtttttattt tttatctggt tttgtggtct tcgt                  13484
```

```
SEQ ID NO: 26           moltype = DNA  length = 12156
FEATURE                 Location/Qualifiers
misc_feature            1..12156
                        note = VSV vector: Convac V5 China
source                  1..12156
                        mol_type = other DNA
                        organism = synthetic construct
SEQUENCE: 26
acgaagacaa acaaaccatt attatcatta aaaggctcag gagaaacttt aacagtaatc  60
aaaatgtctg ttacagtcaa gagaatcatt gacaacacag tcatagttcc aaaacttcct  120
gcaaatgagg atccagtgga atacccggca gattacttca gaaaatcaaa ggagattcct  180
ctttacatca atactacaaa aagtttgtca gatctaagag gatatgtcta ccaaggcctc  240
aaatccggaa atgtatcaat catacatgtc aacagctact tgtatggagc attaaaggac  300
atccggggta agttggataa agattggtca agtttcggaa taaacatcgg gaaagcaggg  360
gatacaatcg gaatatttga ccttgtatcc ttgaaagccc tggacggcgt acttccagat  420
ggagtatcgg atgcttccag aaccagcgca gatgacaaat ggttgccttt gtatctactt  480
ggcttataca gagtgggcag aacacaaatg cctgaataca gaaaaaagct catggatggg  540
ctgacaaatc aatgcaaaat gatcaatgaa cagtttgaac ctcttgtgcc agaaggtcgt  600
gacatttttg atgtgtgggg aaatgacagt aattacacaa aaattgtcgc tgcagtggac  660
atgttcttcc acatgttcaa aaaacatgaa tgtgcctcgt tcagatacgg aactattgtt  720
tccagattca aagattgtgc tgcattggca acatttggac acctctgcaa aataaccgga  780
atgtctacag aagatgtaac gacctggatc ttgaaccgag aagttgcaga tgaaatggtc  840
caaatgatgc ttccaggcca agaaattgac aaggccgatt catacatgcc ttatttgatc  900
gactttggat tgtcttctaa gtctccatat tcttccgtca aaaaccctgc cttccacttc  960
tgggggcaat tgacagctct tctgctcaga tccaccagag caaggaatgc ccgacagcct  1020
gatgacattg agtatacatc tcttactaca gcaggtttgt tgtacgctta tgcagtagga  1080
tcctctgccg acttggcaca acagttttgt gttggagata acaaatacac tccagatgat  1140
agtaccggag gattgacgac taatgcaccg ccacaaggca gagatgtggt cgaatggctc  1200
ggatggtttg aagatcaaaa cagaaaaccg actcctgata tgatgcagta tgcgaaaaga  1260
gcagtcatgt cactgcaagg cctaagagag aagacaattg gcaagtatgc taagtcagaa  1320
tttgacaaat gaccctataa ttctcagatc acctattata tattatgcta catatgaaaa  1380
aaactaacag atatcatgga taatctcaca aaagttcgtg agtatctcaa gtcctattct  1440
cgtctggatc aggcggtagg agagatagat gagatcgaag cacaacgagc tgaaaagtcc  1500
aattatgagt tgttccaaga ggatggagtg gaagagcata ctaagccctc ttattttcag  1560
gcagcagatg attctgacac agaatctgaa ccagaaattg aagacaatca aggtttgtat  1620
gcaccagatc cagaagctga gcaagttgaa ggctttatac aggggccttt agatgactat  1680
gcagatgagg aagtggatgt tgtatttact tcggactgga aacagcctga gcttgaatct  1740
gacgagcatg gaaagacctt acggttgaca tcgccagagg gtttaagtgg agagcagaaa  1800
tcccagtggc tttcgacgat taaagcagtc gtgcaaagtg ccaaatactg gaatctggca  1860
gagtgcacat ttgaagcatc gggagaaggg gtcattatga aggagcgcca gataactccg  1920
gatgtatata aggtcactcc agtgatgaac acacatccgt cccaatcaga agcagtatca  1980
gatgtttggt ctctctcaaa gacatccatg actttccaac ccaagaaagc aagtcttcag  2040
cctctcacca tatccttgga tgaattgttc tcatctagag gagagttcat ctctgtcgga  2100
ggtgacggac gaatgtctca taaagaggcc atcctgctcg gcctgagata caaaaagttg  2160
tacaatcagg cgagagtcaa atattctctg tagactatga aaaaaagtaa cagatatcac  2220
gatctaagtg ttatcccaat ccattcatca tgagttcctt aaagaagatt ctcggtctga  2280
aggggaaagg taagaaatct aagaaattag ggatcgcacc accccctat gaagaggaca  2340
ctagcatgga gtatgctccg agcgctccaa ttgacaaatc ctattttgga gttgacgaga  2400
tggacaccta tgatccgaat caattaagat atgagaaatt cttctttaca gtgaaaatga  2460
cggttagatc taatcgtccg ttcagaacat actcagatgt ggcagccgct gtatcccatt  2520
gggatcacat gtacatcgga atggcaggga aacgtccctt ctacaaaatc ttggcttttt  2580
```

```
tgggttcttc taatctaaag gccactccag cggtattggc agatcaaggt caaccagagt     2640
atcacactca ctgcgaaggc agggcttatt tgccacatag gatggggaag acccctccca     2700
tgctcaatgt accagagcac ttcagaagac cattcaatat aggtctttac aagggaacga     2760
ttgagctcac aatgaccatc tacgatgatg agtcactgga agcagctcct atgatctggg     2820
atcatttcaa ttcttccaaa tttctgatt tcagagagaa ggcttaatg tttggcctga      2880
ttgtcgagaa aaaggcatct ggagcgtggg tcctggattc tatcagccac ttcaaatgag    2940
ctagtctaac ttctagcttc tgaacaatcc ccggtttact cagtctctcc taattccagc    3000
ctctcgaaca actaatatcc tgtcttttct atccctatga aaaaaactaa cagagatcga    3060
tctgtttacg cgtcactatg aagtgccttt tgtacttagc ctttttattc attggggtga    3120
attgcaagtt caccatagtt tttccacaca accaaaaagg aaactggaaa aatgttcctt    3180
ctaattacca ttattgcccg tcaagctcag atttaaattg gcataatgac ttaataggca    3240
cagccataca agtcaaaatg cccaagagtc acaaggctat tcaagcagac ggttggatgt    3300
gtcatgcttc caaatgggtc actacttgtg atttccgctg gtatggaccg aagtatataa    3360
cacagtccat ccgatccttc actccatctg tagaaacagg caaggaaagc attgaacaaa    3420
cgaaacaagg aacttggctg aatccaggct tccctcctca aagttgtgga tatgcaactg    3480
tgacggatgc cgaagcagtg attgtccagg tgactcctca ccatgtgctg gttgatgaat    3540
acacaggaga atgggttgat tcacagttca tcaacgaaa atgcagcaat tacatatgcc      3600
ccactgtcca taactctaca acctggcatt ctgactataa ggtcaaaggg ctatgtgatt    3660
ctaacctcat ttccatggac atcaccttct tctcagagga cggagagcta tcatccctgg    3720
gaaaggaggg cacagggttc agaagtaact actttgctta tgaaactgga ggcaaggcct    3780
gcaaaatgca atactgcaag cattgggag tcagactccc atcaggtgtc tggttcgaga     3840
tggctgataa ggatctcttt gctgcagcca gattccctga atgcccagaa gggtcaagta   3900
tctctgctcc atctcagacc tcagtggatg taagtctaat tcaggacgtt gagaggatct    3960
tggattattc cctctgccaa gaaacctgga gcaaaatcag agcgggtctt ccaatctctc    4020
cagtggatct cagctatctt gctcctaaaa acccaggaac cggtcctgct ttcaccataa   4080
tcaatggtac cctaaaatac tttgagacca gatacatcag agtcgatatt gctgctccaa   4140
tcctctcaag aatggtcgga atgatcagtg gaactaccac agaaagggaa ctgtgggatg   4200
actgggcacc atatgaagac gtggaaattg gacccaatgg agttctgagg accagttcag    4260
gatataagtt tcctttatac atgattggac atggtatgtt ggactccgat cttcatctta   4320
gctcaaaggc tcaggtgttc gaacatcctc acattcaaga cgctgcttcg caacttcctg    4380
atgatgagag tttatttttt ggtgatactg ggctatccaa aaatccaatc gagcttgtag   4440
aaggttggtt cagtagttgg aaaagctcta ttgcctcttt tttctttatc ataggggttaa   4500
tcattggact attcttggtt ctccgagttg gtatccatct ttgcattaaa ttaaagcaca    4560
ccaagaaaag acagattat acagacatag agatgaaccg acttggaaag taactcaaat     4620
cctgctaggt atgaaaaaaa ctaacagata tcacgctcga ggccaccatg aagtgcctgt   4680
tgtacttagc cttcctgttc atcggggtga attgccgctt tcccaatatc acaaacctgt    4740
gcccttttgg cgaggtgttc aacgcaaccc gcttcgccag cgtgtacgcc tggaatagga    4800
agcgcatctc caactgcgtg gccgactatt ctgtgctgta caacagcgcc tccttctcta   4860
cctttaagtg ctatggcgtg agccccacaa agctgaatga cctgtgcttt accaacgtgt   4920
acgccgattc cttcgtgatc aggggcgacg aggtgcgcca gatcgcacca ggacagacag    4980
gcaagatcgc agactacaat tataagctgc ctgacgattt caccggctgc gtgatcgcct   5040
ggaactctaa caatctggat agcaaagtgg gcggcaacta caattatctg taccggctgt   5100
ttagaaagtc taatctgaag ccattcgaga gggacatctc cacagaaatc taccaggccg   5160
gctctacccc ctgcaatggc gtggagggct ttaactgtta ttttcctctg cagagctacg   5220
gcttccagcc aacaaacggc gtgggctatc agccctaccg cgtggtggtg ctgtctttg    5280
agctgctgca cgcaccctgca acagtgtgcg gaccaaagaa gagcaccaat ctggtgaaga   5340
acaagtgcgt gaacttcaac ggctctctgg atcggctaca tccccgaggc cccagagacg   5400
gccaggccta cgtgcggaag acgggcagt gggtactgct cagcaccttc ctgggcagca    5460
gttgaaaaag ctccatcgcc tcctttttct ttatcatcgg cctgatcatc ggactgttcc    5520
tggtgctccg cgtgggtatc cacctgtgca tcaagctgaa gcacaccaag aaaagacaga    5580
tttatacaga catcgagatg aaccgacttg gaaagtaagc tagccagatt cttcatgttt    5640
ggaccaaatc aacttgtgat accatgctca aagaggcctc aatttatttt gagttttaa    5700
tttttatgaa aaaaactaac agcaatcatg gaagtccacg attttgagac cgacgagttc   5760
aatgatttca atgaagatga ctatgccaca agagaattcc tgaatcccga tgagcgcatg   5820
acgtacttga atcatgctga ttacaatttg aattctcctc taattagtga tgatattgac    5880
aatttgatca ggaaattcaa ttctcttccg attccctcga tgtgggatag taagaactgg   5940
gatggagttc ttgagatgtt aacatcatgt caagccaatc ccatctcaac atctcagatg   6000
cataaatgga tgggaagttg gttaatgtct gataatcatg atgccagtca agggtatagt   6060
tttttacatg aagtggacaa agaggcagaa ataacatttg acgtggtgga gaccttcatc    6120
cgcggctggg gcaacaaacc aattgaatac atcaaaaagg aagatggac tgactcattc   6180
aaaattctcg cttatttgtg tcaaaagttt tggacttac acaagttgac attaatctta   6240
aatgctgtct ctgaggtgga attgctcaac ttggcgagga ctttcaaagg caaagtcaga    6300
agaagttctc atggaacgaa catatgcagg attagggttc ccagcttggg tcctacttt     6360
atttcagaag gatgggctta cttcaagaaa cttgatgaccg aaacttttctg              6420
ttaatggtca aagatgtgat tatagggagg atgcaaacgg tgctatccat ggtatgtaga    6480
atagacaacc tgttctcaga gcaagacatc ttctcccttc taaatatcta cagaattgga    6540
gataaaattg tggagaggca gggaaatttt tcttatgact tgattaaaat ggtggaaccg    6600
atatgcaact tgaagctgat gaaattagca agagaatcaa ggcctttagt cccacaattc    6660
cctcattttg aaaatcatat caagacttct gttgatgaag gggcaaaatt tgaccgaggt    6720
ataagattcc tccatgatca gataatgagt gtgaaaacag tggatctcac actggtgatt   6780
tatgatcgt tcagacattg gggtcatcct tttatagatt attacactgg actagaaaaa    6840
ttacattccc aagtaaccat gaagaaagat ttgatgtgt catatgcaaa agcacttgca    6900
agtgatttag ctcggattgt tctatttcaa cagttcaatg atcataaaaa gtggttcgtg    6960
aatggagact tgctccctca tgatcatccc tttaaaagtc atgttaaaga aaatacatgg    7020
cccacagctg ctcaagttca agatttttgga gataaatggc atgaacttcc gctgattaaa   7080
tgttttgaaa tacccgactt actagaccca tcgataatat actctgacaa aagtcattca   7140
atgaataggc cagaggtgtt gaaacatgtc cgaatgaatc cgaacactcc tatccctagt   7200
aaaaaggtgt tgcagactat gttggacaca aaggctacca attggaaaga atttcttaaa    7260
gagattgatg agaagggctt agatgatgat gatctaatta ttggtcttaa aggaaaggag    7320
```

```
agggaactga agttggcagg tagattttc tccctaatgt cttggaaatt gcgagaatac  7380
tttgtaatta ccgaatattt gataaagact catttcgtcc ctatgtttaa aggcctgaca  7440
atggcggacg atctaactgc agtcattaaa aagatgttag attcctcatc cggccaagga  7500
ttgaagtcat atgaggcaat ttgcatagcc aatcacattg attacgaaaa atggaataac  7560
caccaaagga agttatcaaa cggcccagtg ttccgagttg tgggccagtt cttaggttat  7620
ccatccttaa tcgagagaac tcatgaattt tttgagaaaa gtcttatata ctacaatgga  7680
agaccagact tgatgcgtgt tcacaacaac acactgatca attcaacctc ccaacgagtt  7740
tgttggcaag gacaagaggg tggactggaa ggtctacggc aaaaaggatg gactatcctc  7800
aatctactgg ttattcaaag agaggctaaa atcagaaaca ctgctgtcaa agtcttggca  7860
caaggtgata atcaagttat ttgcacacag tataaaacga agaaatcgag aaacgttgta  7920
gaattacagg gtgctctcaa tcaaatggtt tctaataatg agaaaattat gactgcaatc  7980
aaaatagggg cagggaagtt aggacttttg ataaatgacg atgagactat gcaatctgca  8040
gattacttga attatggaaa ataccgatt tccgtggag tgattagagg gttagagacc  8100
aagagatggt cacgagtgac ttgtgtcacc aatgaccaaa tacccacttg tgctaatata  8160
atgagctcag tttccacaaa tgctctcacc gtagctcatt ttgctgagaa cccaatcaat  8220
gccatgatac agtacaatta ttttgggaca tttgctagac tcttgttgat gatgcatgat  8280
cctgctcttc gtcaatcatt gtatgaagtt caagataaga taccgggctt gcacagttct  8340
actttcaaat acgccatgtt gtatttggac ccttccattg gaggagtgtc gggcatgtct  8400
ttgtccaggt ttttgattag agccttccca gatcccgtaa cagaaagtct ctcattctgg  8460
agattcatcc atgtacatgc tcgaagtgag catctgaagg agatgagtgc agtatttgga  8520
aaccccgaga tagccaagtt tcgaataact cacatagaca agctagtaga agatccaacc  8580
tctctgaaca tcgctatggg aatgagtcca gcgaacttgt taaagactga ggttaaaaaa  8640
tgcttaatcg aatcaagaca aaccatcagg aaccaggtga ttaaggatgc aaccatatat  8700
ttgtatcatg aagaggatcg gctcagaagt ttcttatggt caataaatcc tctgttccct  8760
agattttaa gtgaattcaa atcaggcact ttttgggag tcgcagacgg gctcatcagt  8820
ctatttcaaa attctcgtac tattcggaac tcctttaaga aaaagtatca tagggaattg  8880
gatgatttga ttgtgaggag tgaggtatcc tctttgacac atttagggaa acttcatttg  8940
agaagggat catgtaaaat gtggacatgt tcagctactc atgctgacac attaagatac  9000
aaatcctggg gccgtacagt tattgggaca actgtacccc atccattaga aatgttgggt  9060
ccacaacatc gaaaagagac tccttgtgca ccatgataca catcagggtt caattatgtt  9120
tctgtgcatt gtccagacgg gatccatgac gtctttagtt cacggggacc attgcctgct  9180
tatctagggt ctaaaacatc tgaatctaca tctattttgc agccttggga aagggaaagc  9240
aaagtcccac tgattaaaag agctacacgt cttagagatg ctatctcttg gtttgttgaa  9300
cccgactcta aactagcat gactatactt tctaacatcc actctttaac aggcgaagaa  9360
tggaccaaaa ggcagcatgg gttcaaagaa acagggtctg cccttcatag gttttcgaca  9420
tctcggatga gccatggtgg gttcgcatct cagagcactg cagcattgac caggttgatg  9480
gcaactacag acaccatgag ggatctggga gatcagaatt tcgactttt attccaagca  9540
acgttgctct atgctcaaat taccaccact gttgcaagag acggatggat caccagttgt  9600
acagatcatt atcatattgc ctgtaagtcc tgtttgagac ccatagaaga gatcaccctg  9660
gactcaagta tggactacac gccccccagat gtatcccatg tgctgaagac atggaggaat  9720
ggggaaggtt cgtggggaca agagataaaa cagatctatc ctttagaagg gaattggaag  9780
aatttagcac ctgctgagca atcctatcaa gtcggcagat gtataggttt tctatatgga  9840
gacttggcgt ataaaatc tactcatgcc gaggacagtt ctctatttcc tctatctata  9900
caaggtcgta ttagaggtcg aggttctta aaagggttgc tagacggatt aatgagagca  9960
agttgctgcc aagtaataca ccggagaagt ctggctcatt tgaagaggcc ggccaacgca  10020
gtgtacggag gttgatta cttgattgat aaattgagtg tatcacctcc attcctttct  10080
cttactagat caggacctat tagagacgaa ttagaaacga ttcccacaa gatcccaacc  10140
tcctatccga caagcaaccg tgatatgggg gtgattgtca gaaattactt caaatcacaa  10200
tgccgtctaa ttgaaaaggg aaaatacaga tcacattatt cacaattatg gttattctca  10260
gatgtcttat ccatagactt cattggacca ttctctattt ccaccaccct cttgcaaatc  10320
ctatacaagc catttttatc tgggaaagat aagaatgatt tgaagagagct ggcaaatctt  10380
tcttcattgc taagatcagg agaggggtgg gaagacatac atgtgaaatt cttcaccaag  10440
gacatattat tgtgtccaga ggaaatcaga catgcttgca agttcggat tgctaaggat  10500
aataataaag acatgagcta tccccttgg ggaagggaat ccagagggac aattacaaca  10560
atccctgtt attatacgac caccccttac ccaaagatgc tagagatgcc tccaagaatc  10620
caaaatcccc tgctgtccgg aatcaggttg ggccaattca caactggcgc tcattataaa  10680
attcggagta tattacatgg aatgggaatc cattacaggg acttcttgag ttgtggagac  10740
ggctccggag ggatgactgc tgcattacta cgagaaaatg tgcatagcag aggaatattc  10800
aatagtctgt tagaattatc agggtcagtc atgcgaggcg cctctcctga gccccccagt  10860
gccctagaaa cttaggagg agataaatcg agatgtgaa atggtgggaa atgttgggaa  10920
tatccatctg acttatgtga cccaaggact tgggactatt tcctccgact caaagcaggc  10980
ttgggcttc aaattgatt aattgtaatg gatatgaag ttcggattc ttctactagc  11040
ctgaaaattg agacgaatgt tagaaattat gtgcaccgga ttttgatga gcaaggagtt  11100
ttaatctaca agacttatgg aacatatatt tgtgagagca agtaacaatc  11160
cttggtccca tgttcaagac ggtcgactta gttcaaacag aatttagtag ttctcaaacg  11220
tctgaagtat atatggtatg taaggttttg aagaaattaa tcgatgaacc caatcccgat  11280
tggtcttcca tcaatgaatc ctggaaaaac ctgtacgcat tccagtcatc agaacaggaa  11340
tttgccagag caaagaaggt tagtacatac tttaccttga caggtattcc ctcccaattc  11400
attcctgatc cttttgtaaa cattgagact atgctacaaa tattcggagt acccacgggt  11460
gtgtctcatg cggctgcctt aaaatcatct gatagacctg cagatttatt gaccattagc  11520
cttttttata tggcgattat atcgtattat aacatcaatc atatcagagt aggaccgata  11580
cctccgaacc ccccatcaga tggaattgca caaaatgtgg ggatcgctat aactggtata  11640
agcttttggc tgagtttgat ggagaaagac attccactat atcaacagtg tttagcagtt  11700
atccagcaat cattcccgat taggtgggag gctgttttcag taaaggagg atacaagcag  11760
aagtgggagta ctagaggtga tgggctccca aagatacccc gaacttcaga ctccttggcc  11820
ccaatcggga actggatcag atctctggaa ttggtccgaa accaagttcg tctaaatcca  11880
ttcaatgaga tcttgttcaa tcagctatgt cgtacagtgg ataatcattt gaatggtcca  11940
aatttgcgaa gaaacacagg aatgattgaa tggatcaata gacgaattc aaaagaagac  12000
cggtctatac tgatgttgaa gagtgaccta cacgaggaaa actcttggag agattaaaaa  12060
```

```
atcatgagga gactccaaac tttaagtatg aaaaaaactt tgatccttaa gaccctcttg  12120
tggtttttat tttttatctg gttttgtggt cttcgt                             12156

SEQ ID NO: 27          moltype = DNA  length = 12156
FEATURE                Location/Qualifiers
misc_feature           1..12156
                       note = VSV vector: Convac V5 South Africa
source                 1..12156
                       mol_type = other DNA
                       organism = synthetic construct
SEQUENCE: 27
acgaagacaa acaaaccatt attatcatta aaaggctcag gagaaacttt aacagtaatc  60
aaaatgtctg ttacagtcaa gagaatcatt gacaacacag tcatagttcc aaaacttcct  120
gcaaatgagg atccagtgga atacccggca gattacttca gaaaatcaaa ggagattcct  180
ctttacatca atactacaaa aagtttgtca gatctaagag gatatgtcta ccaaggcctc  240
aaatccggaa atgtatcaat catacatgtc aacagctact tgtatggagc attaaaggac  300
atccggggta agttggataa agattggtca agtttcggaa taaacatcgg gaaagcaggg  360
gatacaatcg gaatatttga ccttgtatcc ttgaaagccc tggacggcgt acttccagat  420
ggagtatcgg atgcttccag aaccagcgca gatgacaaat ggttgccttt gtatctactt  480
ggcttataca gagtgggcag aacacaaatg cctgaataca gaaaaaagct catggatggg  540
ctgacaaatc aatgcaaaat gatcaatgaa cagtttgaac ctcttgtgcc agaaggtcgt  600
gacatttttg atgtgtgggg aaatgacagt aattacacaa aaattgtcgc tgcagtggac  660
atgttcttcc acatgttcaa aaaacatgaa tgtgcctcgt tcagatacgg aactattgtt  720
tccagattca aagattgtgc tgcattggca acatttggac acctctgcaa aataaccgga  780
atgtctacag aagatgtaac gacctggatc ttgaaccgag aagttgcaga tgaaatggtc  840
caaatgatgc ttccaggcca agaaattgac aaggccgatt catacatgcc ttatttgatc  900
gactttggat tgtcttctaa gtctccatat tcttccgtca aaaaccctgc cttccacttc  960
tgggggcaat tgacagctct tctgctcaga tccaccagag caaggaatgc ccgacagcct  1020
gatgacattg agtatacatc tcttactaca gcaggtttgt tgtacgctta tgcagtagga  1080
tcctctgccg acttggcaca acagttttgt gttggagata acaaatacac tccagatgat  1140
agtaccggag gattgacgac taatgcaccg ccacaaggca gagatgtggt cgaatggctc  1200
ggatggtttg aagatcaaaa cagaaaaccg actcctgata tgatgcagta tgcgaaaaga  1260
gcagtcatgt cactgcaagg cctaagagag aagacaattg gcaagtatgc taagtcagaa  1320
tttgacaaat gaccctataa ttctcagatc acctattata tattatgcta catatgaaaa  1380
aaactaacag atatcatgga taatctcaca aaagttcgtg agtatctcaa gtcctattct  1440
cgtctggatc aggcggtagg agagatagat gagatcgaag cacaacgagc tgaaaagtcc  1500
aattatgagt tgttccaaga ggatggagtg gaagagcata ctaagccctc ttattttcag  1560
gcagcagatg attctgacac agaatctgaa ccagaaattg aagacaatca aggtttgtat  1620
gcaccagatc cagaagctga gcaagttgaa ggctttatac aggggccttt agatgactat  1680
gcagatgagg aagtggatgt tgtatttact tcggactgga aacagcctga gcttgaatct  1740
gacgagcatg gaaagacctt acggttgaca tcgccagagg gtttaagtgg agagcagaaa  1800
tcccagtggc tttcgacgat taaagcagtc gtgcaaagtg ccaaatactg gaatctggca  1860
gagtgcacat ttgaagcatc gggagaaggg gtcattatga aggagcgcca gataactccg  1920
gatgtatata aggtcactcc agtgatgaac acacatccgt cccaatcaga agcagtatca  1980
gatgtttggt ctctctcaaa gacatccatg actttccaac ccaagaaagc aagtcttcag  2040
cctctcacca tatccttgga tgaattgttc tcatctagag gagagttcat ctctgtcgga  2100
ggtgacggac gaatgtctca taaagaggcc atcctgctcg gcctgagata caaaaagttg  2160
tacaatcagg cgagagtcaa atattctctg tagactatga aaaaaagtaa cagatatcac  2220
gatctaagtg ttatcccaat ccattcatca tgagttcctt aaagaagatt ctcggtctga  2280
aggggaaagg taagaaatct aagaaattag ggatcgcacc acccccttat gaagaggaca  2340
ctagcatgga gtatgctccg agcgctccaa ttgacaaatc ctattttgga gttgacgaga  2400
tggacaccta tgatccgaat caattaagat atgagaaatt cttctttaca gtgaaaatga  2460
cggttagatc taatcgtccg ttcagaacat actcagatgt ggcagccgct gtatcccatt  2520
gggatcacat gtacatcgga atggcaggga aacgtccctt ctacaaaatc ttggcttttt  2580
tgggttcttc taatctaaag gccactccag cggtattggc agatcaaggt caaccagagt  2640
atcacactca ctgcgaaggc agggcttatt tgccacatag gatggggaag acccctccca  2700
tgctcaatgt accagagcac ttcagaagac cattcaatat aggtctttac aagggaacga  2760
ttgagctcac aatgaccatc tacgatgatg agtcactgga agcagctcct atgatctggg  2820
atcatttcaa ttcttccaaa ttttctgatt tcagagagaa ggccttaatg tttggcctga  2880
ttgtcgagaa aaaggcatct ggagcgtggg tcctggattc tatcagccac ttcaaatgag  2940
ctagtctaac ttctagcttc tgaacaatcc ccggtttact cagtctctcc taattccagc  3000
ctctcgaaca actaatatcc tgtcttttct atccctatga aaaaaactaa cagagatcga  3060
tctgtttacg cgtcactatg aagtgccttt tgtacttagc ctttttattc attggggtga  3120
attgcaagtt caccatagtt tttccacaca accaaaaagg aaactggaaa aatgttcctt  3180
ctaattacca ttattgcccg tcaagctcag atttaaattg gcataatgac ttaataggca  3240
cagccataca agtcaaaatg cccaagagtc acaaggctat tcaagcagac ggttggatgt  3300
gtcatgcttc caaatgggtc actacttgtg atttccgctg gtatggaccg aagtatataa  3360
cacagtccat ccgatccttc actccatctg tagaacaatg caaggaaagc attgaacaaa  3420
cgaaacaagg aacttggctg aatccaggct tccctcctca aagttgtgga tatgcaactg  3480
tgacggatgc cgaagcagtg attgtccagg tgactcctca ccatgtgctg gttgatgaat  3540
acacaggaga atgggttgat tcacagttca tcaacggaaa atgcagcaat tacatatgcc  3600
ccactgtcca taactctaca acctggcatt ctgactataa ggtcaaaggg ctatgtgatt  3660
ctaacctcat ttccatggac atcaccttct tctcagagga cggagagcta tcatccctgg  3720
gaaaggaggg cacagggttc agaagtaact actttgctta tgaaactgga ggcaaggcct  3780
gcaaaatgca atactgcaag cattggggag tcagactccc atcaggtgtc tggttcgaga  3840
tggctgataa ggatctcttt gctgcagcca gattccctga atgcccagaa gggtcaagta  3900
tctctgctcc atctcagacc tcagtggatg taagtctaat tcaggacgtt gagaggatct  3960
tggattattc cctctgccaa gaaacctgga gcaaaatcag agcgggtctt ccaatctctc  4020
cagtggatct cagctatctt gctcctaaaa acccaggaac cggtcctgct ttcaccataa  4080
```

-continued

```
tcaatggtac cctaaaatac tttgagacca gatacatcag agtcgatatt gctgctccaa 4140
tcctctcaag aatggtcgga atgatcagtg gaactaccac agaaagggaa ctgtgggatg 4200
actgggcacc atatgaagac gtggaaattg acccaatgga agttctgagg accagttcag 4260
gatataagtt tcctttatac atgattggac atggtatgtt ggactccgat cttcatctta 4320
gctcaaaggc tcaggtgttc gaacatcctc acattcaaga cgctgcttcg caacttcctg 4380
atgatgagag tttatttttt ggtgatactg ggctatccaa aaatccaatc gagcttgtag 4440
aaggttggtt cagtagttgg aaaagctcta ttgcctcttt tttctttatc ataggggttaa 4500
tcattggact attcttggtt ctccgagttg gtatccatct ttgcattaaa ttaaagcaca 4560
ccaagaaaag acagatttat acagacatag agatgaaccg acttggaaag taactcaaat 4620
cctgctaggt atgaaaaaaa ctaacagata tcacgctcga ggccaccatg aagtgcctgt 4680
tgtacttagc cttcctgttc atcggggtga attgccgctt tcccaatatc acaaacctgt 4740
gccctttgg cgaggtgttc aacgcaaccc gcttcgccag cgtgtacgcc tggaatagga 4800
agcgcatctc caactgcgtg gccgactatt ctgtgctgta caacagcgcc tccttctcta 4860
cctttaagtg ctatggcgtg agccccacaa agctgaatga cctgtgcttt accaacgtgt 4920
acgccgattc cttcgtgatc aggggcgacg aggtgcgcca gatcgcacca ggacagacag 4980
gcaatatcgc agactacaat tataagctgc ctgacgattt caccggctgc gtgatcgcct 5040
ggaactctaa caatctggat agcaaagtgg gcggcaacta caattatctg taccggctgt 5100
ttagaaagtc taatctgaag ccattcgaga gggacatctc cacagaaatc taccaggccg 5160
gctctacccc ctgcaatggc gtgaagggct ttaactgtta tttccctctg cagagctacg 5220
gcttccagcc aacatatggc gtgggctatc agccctaccg cgtggtggtg ctgtcttttg 5280
agctgctgca cgcacctgca acagtgtgcg gaccaaagaa gagcaccaat ctggtgaaga 5340
acaagtgcgt gaacttcaac ggctctggat ccggactacat ccccgaggcc cccagagacg 5400
gccaggccta cgtgcggaag gacgcgcagt gggtactgct cagcaccttc ctgggcagca 5460
gttgaaaaag ctccatcgcc tcctttttct ttatcatcgg cctgatcatc ggactgttcc 5520
tggtgctccg cgtgggtatc cacctgtgca tcaagctgaa gcacaccaag aaaagacaga 5580
tttatacaga catcgagatg aaccgacttg gaaagtaagc cagatt cttcatgttt 5640
ggaccaaatc aacttgtgat accatgctca aagaggcctc aatttatattt gagtttttaa 5700
tttttatgaa aaaactaac agcaatcatg gaagtccacg atttttgagac cgacgagttc 5760
aatgattca atgaagatga ctatgccaca agagaattcc tgaatcccga tgagcgcatg 5820
acgtacttga atcatgctga ttacaatttg aattctcctc taattagtga tgatattgac 5880
aatttgatca ggaaattcaa ttctcttccg attccctcga tgtgggatag taagaactgc 5940
gatggagttc ttgagatgtt aacatcatgt caagccaatc ccatctcaac atctcagatg 6000
cataaatgga tgggaagttg gttaatgtct gataatcatg atgccagtca agggtatagt 6060
tttttacatg aagtggacaa agaggcagaa ataacatttg acgtggtgga gaccttcatc 6120
cgcggctgtg gcaacaaacc aattgaatac atcaaaaagg aaagatgac tgactcattc 6180
aaaattctcg cttatttgtg tcaaaagttt ttggacttac acaagttgac attaatctta 6240
aatgctgtct ctgaggtgga attgctcaac ttggcgagga ctttcaaagg caaagtcaga 6300
agaagttctc atggaacgaa catatgcagg attagggttc ccagcttggg tcctactttt 6360
atttcagaag gatgggctta cttcaagaaa cttgatattc taatggaccg aaactttctg 6420
ttaatggtca aagatgtgat tatagggagg atgcaaacgg tgctatccat ggtatgtaga 6480
atagacaacc tgttctcaga gcaagacatc ttctcccttc taaatatcta cagaattgga 6540
gataaaattg tggagaggca gggaaatttt tcttatgact tgattaaaat ggtggaaccg 6600
atatgcaagt tgaagctgat gaaattagca agagaatgca ggcctttagt cccacaattc 6660
cctcatttg aaaatcatat caagacttct gttgatgaag gggcaaaaat tgaccgaggt 6720
ataagattcc tccatgatca gataatgagt gtgaaaacag tggatctcac actggtgatt 6780
tatggatcgt tcagacattg gggtcatcct tttatagatt attacactgg actagaaaaa 6840
ttacattccc aagtaaccat gaagaaagat attgatgtgt catatgcaaa agcacttgca 6900
agtgatttag ctcggattgt tctatttcaa cagttcaatg atcataaaaa gtggttcgtg 6960
aatggagact tgctccctca tgatcatccc tttaaaagtc atgttaaaga aaatacatgg 7020
cccacagctg ctcaagttca agattttgga gataaatggc atgaacttcc gctgattaaa 7080
tgttttgaaa tacccgactt actagaccca tcgataatat actctgacaa aagtcattca 7140
atgaataggt cagaggtgtt gaaacatgtc cgaatgaatc cgaacactcc tatccctagt 7200
aaaaaggtgt tgcagactat gttggacaca aaggctacca attggaaaga atttcttaaa 7260
gagattgatg agaagggctt agatgatgat gatctaatta ttggtcttaa aggaaaggag 7320
agggaactga agttggcagg tagatttttc tccctaatgt cttggaaatt gcgagaatac 7380
tttgtaatta ccgaatattt gataaagact catttcgtcc ctatgtttaa aggcctgaca 7440
atggcggacg atctaactgc agtcattaaa aagatgttag attcctcatc cggccaagga 7500
ttgaagtcat atgaggcaat ttgcatagcc aatcacattg attacgaaaa atggaataac 7560
caccaaagga agttatcaaa cggcccagtg ttccgagtta tgggccagtt cttaggttat 7620
ccatccttaa tcgagagaac tcatgaattt tttgagaaaa tgtcttatata ctacaatgga 7680
agaccagact tgatgcgtgt tcacaacaac acactgatca attcaacctc caacgagtt 7740
tgttggcaag acaagaggg tggactgaa ggtctacggc aaaaaggatg gactatcctc 7800
aatctactgg ttattcaaag agaggctaaa atcagaaaca ctgctgtcaa agtcttggca 7860
caaggtgata atcaagttat ttgcacacag tataaaacga agaaatcgaa aacgttgtta 7920
gaattacagg gtgctctcaa tcaaatggtt tctaataatg agaaaattat gactgcaatc 7980
aaaatagga agggggaagtt aggactttg ataaatgacg atgagactat gcaatctgca 8040
gattacttga attatggaaa aataccgatt ttccgtggag tgattagagg ttagagacc 8100
aagagatggt cacgagtgac ttgtgtcacc aatgaccaaa tacccacttg tgctaatata 8160
atgagctcag tttccacaaa tgctctcacc gtagctcatt ttgctgagaa cccaatcaat 8220
gccatgatac agtacaatta ttttgggaca tttgctagac tcttgttgat gatgcatgat 8280
cctgctcttc gtcaatcatt gtatgaagtt caagataaga taccgggctt gcacagttct 8340
actttcaaat acgccatgtt gtatttggac ccttccattg gaggagtgtc gggcatgtct 8400
ttgtccaggt ttttgattag agccttccca gatccccgtaa cagaaagtct ctcattctgg 8460
agattcactc atgtgacatgc tcgaagtgag catctgaagg agatgactga agtatttgga 8520
aaccccgaga tagccaagtt tcgataact cacatagaca agctagtaga agatccaacc 8580
tctctgaaca tcgctatggg aatgagtcca gcgaacttgt taaagactga ggttaaaaaa 8640
tgcttaatcg aatcaagaca aaccatcagg aaccaggtga ttaaggatgc aaccatatat 8700
ttgtatcatg aagaggatcg gctcagaagt ttcttatggt caataaatcc tctgttccct 8760
agattttta gtgaattcaa atcaggcact tttttgggag tcgcagacgg gctcatcagt 8820
```

```
ctatttcaaa attctcgtac tattcggaac tcctttaaga aaagtcatca tagggaattg   8880
gatgatttga ttgtgaggag tgaggtatcc tctttgacac atttaggaa  acttcatttg   8940
agaaggggat catgtaaaat gtggacatgt tcagctactc atgctgacac attaagatac   9000
aaatcctggg gccgtacagt tattgggaca actgtacccc atccattaga aatgttgggt   9060
ccacaacatc gaaaagagac tccttgtgca ccatgtaaca catcagggtt caattatgtt   9120
tctgtgcatt gtccgacgg  gatccatgac gtctttagtt cacggggacc attgcctgct   9180
tatctagggt ctaaaacatc tgaatctaca tctattttgc agccttggga aagggaaagc   9240
aaagtcccac tgattaaaag agctacacgt cttagagatg ctatctcttg gtttgttgaa   9300
cccgactcta aactaccaat gactatactt tctaacatcc actctttaac aggcgaagaa   9360
tggaccaaaa ggcagcatgg gttcaaaaga acagggtctg cccttcatag gttttcgaca   9420
tctcggatga gccatggtgg gttcgcatct cagagcactg cagcattgac caggttgatg   9480
gcaactacag acaccatgag ggatctggga gatcagaatt tcgactttt  attccaagca   9540
acgttgctct atgctcaaat taccaccact gttgcaagag acggatggat caccagttgt   9600
acagatcatt atcatattgc ctgtaagtcc tgtttgagac ccatagaaga gatcacccgt   9660
gactcaagta tggactacac gcccccagat gtatcccatg tgctgaagac atggaggaat   9720
gggggaaggtt cgtggggaca agagataaaa cagatctatc ctttagaagg gaattggaag   9780
aatttagcac ctgctgagca atcctatcaa gtcggcagat gtataggttt tctatatgga   9840
gacttggcgt atagaaaatc tactcatgcc gaggacagtt ctctattttcc tctatctata   9900
caaggtcgta ttagaggtcg aggtttctta aaagggttgc tagacggatt aatgagagca   9960
agttgctgcc aagtaataca ccggagaagt ctggctcatt tgaagaggcc ggccaacgca  10020
gtgtacggag gtttgattta cttgattgat aaattgagtg tatcacctcc attcctttct  10080
cttactagat caggacctat tagagacgaa ttagaaacga ttccccacaa gatcccaacc  10140
tcctatccga caagcaaccg tgatatgggg gtgattgtca gaaattactt caaatccaa   10200
tgccgtctaa ttgaaaaggg aaaatacaga tcacattatt cacaattatg gttattctca  10260
gatgtcttat ccatagactt cattggacca ttctctattt ccaccaccct cttgcaaatc  10320
ctatacaagc catttttatc tgggaaagat aagaatgaat tgaagagagct ggcaaatctt  10380
tcttcattgc taagatcagg agaggggtgg gaagacatac atgtgaaatt cttcaccaag  10440
gacatattat tgtgtccaga ggaaatcaga catgcttgca agtcgggat  tgctaaggat  10500
aataataaag acatgagcta tcccccttgg ggaagggaat ccagagggac aattacaaca  10560
atccctgttt attatacgac cacccttac  ccaaagatgc tagagatgcc tccaagaatc  10620
caaaatcccc tgctgtccgg aatcaggttg ggccaattac caactggcgc tcattataaa  10680
attcggagta tattacatgg aatgggaatc cattacaggg acttcttgag ttgtggagac  10740
ggctccggag ggatgactgc tgcattacta cgagaaaatg tgcatagcag aggaatattc  10800
aatagtctgt tagaattatc agggtcagtc atgcgaggcc cctctcctga gccccccagt  10860
gccctagaaa ctttaggagg agataaatcg agatgtgaa  atggtgaaac atgttgggaa  10920
tatccatctg acttatgtga cccaaggact tgggactatt tcctccgact caaagcaggc  10980
ttgggggcttc aaattgattt aattgtaatg gatatgaag  ttcgggattc ttctactagc  11040
ctgaaaattg agacgaatgt tagaaattat gtgcaccgga ttttgatga  gcaaggagtt  11100
ttaatctaca agacttatgg aaacatatatt tgtgagagca aaaagaatgc agtaacaatc  11160
cttggtccca tgttcaagac ggtcgactta gttcaaacag aatttagtag ttctcaaacg  11220
tctgaagtat atatgtgtatg taaaggtttg aagaaattaa tcgatgaacc caatcccgat  11280
tggtcttcca tcaatgaatc ctggaaaaac ctgtacgcat tccagtcatc agaacaggaa  11340
tttgccagag caaagaaggt tagtacatac tttaccttga caggtattcc ctcccaattc  11400
attcctgatc ctttttgtaaa cattgagact atgctacaaa tattcggagt ccccacgggt  11460
gtgtctcatg cggctgcctt aaaatcatct gatagacctg cagatttatt gaccattagc  11520
cttttttata tggcgattat atcgtattat aacatcaatc atatcagagt aggaccgata  11580
cctccgaacc ccccatcaga tggaattgca caaaatgtgg ggatcgctat aactggtata  11640
agcttttggc tgagtttgat ggagaaagac attccactat atcaacagtg tttagcagtt  11700
atccagcaat cattcccgat taggtgggag gctgtttcag taaaaggagg atacaagcag  11760
aagtggagta ctagaggtga tgggctccca aaagataccc gaacttcaga ctccttggcc  11820
ccaatcggca actggatcag atctctggaa ttggtccgaa accaagttcg tctaaatcca  11880
ttcaatgaga tcttgttcaa tcagctatgt cgtacagtgg ataatcattt gaaatggtca  11940
aatttgcgaa gaaacacagg aatgattgaa tggatcaata gacgaatttc aaaagaagac  12000
cggtctatac tgatgttgaa gagtgaccta cacgaggaaa actcttggag agattaaaaa  12060
atcatgagga gactccaaac tttaagtatg aaaaaaactt tgatccttaa gaccctcttg  12120
tggttttttat tttttatctg gttttgtggt cttcgt                            12156

SEQ ID NO: 28              moltype = AA  length = 682
FEATURE                    Location/Qualifiers
REGION                     1..682
                           note = SARS-CoV-2 spike protein (S) (682 aa)
source                     1..682
                           mol_type = protein
                           organism = synthetic construct
SEQUENCE: 28
MFVFLVLLPL VSSQCVNLTT RTQLPPAYTN SFTRGVYYPD KVFRSSVLHS TQDLFLPFFS     60
NVTWFHAIHV SGTNGTKRFD NPVLPFNDGV YFASTEKSNI IRGWIFGTTL DSKTQSLLIV    120
NNATNVVIKV CEFQFCNDPF LGVYYHKNNK SWMESEFRVY SSANNCTFEY VSQPFLMDLE    180
GKQGNFKNLR EFVFKNIDGY FKIYSKHTPI NLVRDLPQGF SALEPLVDLP IGINITRFQT    240
LLALHRSYLT PGDSSSGWTA GAAAYYVGYL QPRTFLLKYN ENGTITDAVD CALDPLSETK    300
CTLKSFTVEK GIYQTSNFRV QPTESIVRFP NITNLCPFGE VFNATRFASV YAWNRKRISN    360
CVADYSVLYN SASFSTFKCY GVSPTKLNDL CFTNVYADSF VIRGDEVRQI APGQTGKIAD    420
YNYKLPDDFT GCVIAWNSNN LDSKVGGNYN YLYRLFRKSN LKPFERDIST EIYQAGSTPC    480
NGVEGFNCYF PLQSYGFQPT NGVGYQPYRV VVLSFELLHA PATVCGPKKS TNLVKNKCVN    540
FNFNGLTGTG VLTESNKKFL PFQQFGRDIA DTTDAVRDPQ TLEILDITPC SFGGVSVITP    600
GTNTSNQVAV LYQDVNCTEV PVAIHADQLT PTWRVYSTGS NVFQTRAGCL IGAEHVNNSY    660
ECDIPIGAGI CASYQTQTNS PR                                              682

SEQ ID NO: 29              moltype = AA  length = 1273
```

-continued

```
FEATURE                Location/Qualifiers
REGION                 1..1273
                       note = SARS-CoV-2 spike protein (S) (1273 aa)
source                 1..1273
                       mol_type = protein
                       organism = synthetic construct
SEQUENCE: 29
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                     1273

SEQ ID NO: 30          moltype = AA  length = 781
FEATURE                Location/Qualifiers
REGION                 1..781
                       note = WuS1-RABVG (781 aa)
source                 1..781
                       mol_type = protein
                       organism = synthetic construct
SEQUENCE: 30
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRSVGDEAED FVEVHLPDVH NQVSGVDLGL PNWGKYVLLS  720
AGALTALMLI IFLMTCCRRV NRSEPTQHNL RGTGREVSVT PQSGKIISSW ESHKSGGETR  780
L                                                                  781

SEQ ID NO: 31          moltype = AA  length = 682
FEATURE                Location/Qualifiers
REGION                 1..682
                       note = WuS1-RABVG (682 aa)
source                 1..682
                       mol_type = protein
                       organism = synthetic construct
SEQUENCE: 31
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PR                                           682

SEQ ID NO: 32          moltype = AA  length = 525
FEATURE                Location/Qualifiers
REGION                 1..525
                       note = SARS-CoV-2 nucleocapsid protein (N)
source                 1..525
```

```
                              mol_type = protein
                              organism = synthetic construct
SEQUENCE: 32
MATLLRSLAL FKRNKDKPPI TSGSGGAIRG IKHIIIVPIP GDSSITTRSR LLDRLVRLIG    60
NPDVSGPKLT GALIGILSLF VESPGQLIQR ITDDPDVSIR LLEVVQSDQS QSGLTFASRG   120
TNMEDEADQY FSHDDPISSD QSRFGWFGNK EISDIEVQDP EGFNMILGTI LAQIWVLLAK   180
AVTAPDTAAD SELRRWIKYT QQRRVVGEFR LERKWLDVVR NRIAEDLSLR RFMVALILDI   240
KRTPGNKPRI AEMICDIDTY IVEAGLASFI LTIKFGIETM YPALGLHEFA GELSTLESLM   300
NLYQQMGETA PYMVILENSI QNKFSAGSYP LLWSYAMGVG VELENSMGGL NFGRSYFDPA   360
YFRLGQEMVR RSAGKVSSTL ASELGITAED ARLVSEIAMH TTEDKISRAV GPRQAQVSFL   420
HGDQSENELP RLGGKEDRRV KQSRGEARES YRETGPSRAS DARAAHLPTG TPLDIDTATE   480
SSQDPQDSRR SADALLRLQA MAGISEEQGS DTDTPIVYND RNLLD                  525

SEQ ID NO: 33                 moltype = DNA   length = 19
FEATURE                       Location/Qualifiers
misc_feature                  1..19
                              note = Synthesized
source                        1..19
                              mol_type = other DNA
                              organism = synthetic construct
SEQUENCE: 33
cttaatgcgc cgctacagg                                                  19

SEQ ID NO: 34                 moltype = DNA   length = 18
FEATURE                       Location/Qualifiers
misc_feature                  1..18
                              note = Synthesized
source                        1..18
                              mol_type = other DNA
                              organism = synthetic construct
SEQUENCE: 34
atgtgctgcg attaatta                                                   18

SEQ ID NO: 35                 moltype = DNA   length = 19
FEATURE                       Location/Qualifiers
misc_feature                  1..19
                              note = Synthesized
source                        1..19
                              mol_type = other DNA
                              organism = synthetic construct
SEQUENCE: 35
tgtgctgatt aagtgtaag                                                  19

SEQ ID NO: 36                 moltype = DNA   length = 17
FEATURE                       Location/Qualifiers
misc_feature                  1..17
                              note = Synthesized
source                        1..17
                              mol_type = other DNA
                              organism = synthetic construct
SEQUENCE: 36
gttttcccag tcacgac                                                    17

SEQ ID NO: 37                 moltype = DNA   length = 48
FEATURE                       Location/Qualifiers
misc_feature                  1..48
                              note = Synthesized
source                        1..48
                              mol_type = other DNA
                              organism = synthetic construct
SEQUENCE: 37
aaacgacggc cagtggaatt ccgttaatac gactcactat aggaaagg                  48

SEQ ID NO: 38                 moltype = DNA   length = 34
FEATURE                       Location/Qualifiers
misc_feature                  1..34
                              note = Synthesized
source                        1..34
                              mol_type = other DNA
                              organism = synthetic construct
SEQUENCE: 38
ggttgcgcgc cgttgactca ctatagggagt tagg                                34

SEQ ID NO: 39                 moltype = DNA   length = 39
FEATURE                       Location/Qualifiers
misc_feature                  1..39
                              note = Synthesized
source                        1..39
                              mol_type = other DNA
```

```
                        organism = synthetic construct
SEQUENCE: 39
gagagcgcgc atcgaaatta atacgactca ctatagata                              39

SEQ ID NO: 40           moltype = DNA  length = 39
FEATURE                 Location/Qualifiers
misc_feature            1..39
                        note = Synthesized
source                  1..39
                        mol_type = other DNA
                        organism = synthetic construct
SEQUENCE: 40
gagacgtacg cgtaatacga ctcactatag gggagaggg                              39

SEQ ID NO: 41           moltype = DNA  length = 19
FEATURE                 Location/Qualifiers
misc_feature            1..19
                        note = Synthesized
source                  1..19
                        mol_type = other DNA
                        organism = synthetic construct
SEQUENCE: 41
taatacatag ggtaatggg                                                    19

SEQ ID NO: 42           moltype = DNA  length = 46
FEATURE                 Location/Qualifiers
misc_feature            1..46
                        note = Synthesized
source                  1..46
                        mol_type = other DNA
                        organism = synthetic construct
SEQUENCE: 42
gtgtcgtctc gcgcgtgcgg ccgcgctagc cagcttgggt ctccct                      46

SEQ ID NO: 43           moltype = DNA  length = 45
FEATURE                 Location/Qualifiers
misc_feature            1..45
                        note = Synthesized
source                  1..45
                        mol_type = other DNA
                        organism = synthetic construct
SEQUENCE: 43
gtgtcgtctc tgggtaagga tagtgtcgtc tctggggtaa ggata                       45

SEQ ID NO: 44           moltype = DNA  length = 53
FEATURE                 Location/Qualifiers
misc_feature            1..53
                        note = Synthesized
source                  1..53
                        mol_type = other DNA
                        organism = synthetic construct
SEQUENCE: 44
gtgtggtctc tgaggatagt tcagtgtggt ctctggtcgg taaggatagt tca              53

SEQ ID NO: 45           moltype = DNA  length = 37
FEATURE                 Location/Qualifiers
misc_feature            1..37
                        note = Synthesized
source                  1..37
                        mol_type = other DNA
                        organism = synthetic construct
SEQUENCE: 45
gagaaggttt gagaacgcgt ctcggtacgc cgggttt                                37

SEQ ID NO: 46           moltype = DNA  length = 34
FEATURE                 Location/Qualifiers
misc_feature            1..34
                        note = Synthesized
source                  1..34
                        mol_type = other DNA
                        organism = synthetic construct
SEQUENCE: 46
tgtcacggat atccatcctg ctcttgtcct gtcc                                   34

SEQ ID NO: 47           moltype = DNA  length = 36
FEATURE                 Location/Qualifiers
misc_feature            1..36
                        note = Synthesized
source                  1..36
```

```
                            mol_type = other DNA
                            organism = synthetic construct
SEQUENCE: 47
cagtccaccg gtgtcacgga tatccctaat cctgct                              36

SEQ ID NO: 48               moltype = DNA   length = 30
FEATURE                     Location/Qualifiers
misc_feature                1..30
                            note = Synthesized
source                      1..30
                            mol_type = other DNA
                            organism = synthetic construct
SEQUENCE: 48
ggattaggga tatccgagat ggccacactt                                     30

SEQ ID NO: 49               moltype = DNA   length = 36
FEATURE                     Location/Qualifiers
misc_feature                1..36
                            note = Synthesized
source                      1..36
                            mol_type = other DNA
                            organism = synthetic construct
SEQUENCE: 49
aagtgtggcc atctcggata tccctaatcc tgctct                              36

SEQ ID NO: 50               moltype = DNA   length = 21
FEATURE                     Location/Qualifiers
misc_feature                1..21
                            note = Synthesized
source                      1..21
                            mol_type = other DNA
                            organism = synthetic construct
SEQUENCE: 50
tggccacact tttaaggagc t                                              21

SEQ ID NO: 51               moltype = DNA   length = 20
FEATURE                     Location/Qualifiers
misc_feature                1..20
                            note = Synthesized
source                      1..20
                            mol_type = other DNA
                            organism = synthetic construct
SEQUENCE: 51
ccaccggatc ctgatgtaat                                                20

SEQ ID NO: 52               moltype = DNA   length = 20
FEATURE                     Location/Qualifiers
misc_feature                1..20
                            note = Synthesized
source                      1..20
                            mol_type = other DNA
                            organism = synthetic construct
SEQUENCE: 52
ctggccttac cttcgcatca                                                20

SEQ ID NO: 53               moltype = DNA   length = 25
FEATURE                     Location/Qualifiers
misc_feature                1..25
                            note = Synthesized
source                      1..25
                            mol_type = other DNA
                            organism = synthetic construct
SEQUENCE: 53
aggattagcc agttttatcc tgact                                          25

SEQ ID NO: 54               moltype = DNA   length = 17
FEATURE                     Location/Qualifiers
misc_feature                1..17
                            note = Synthesized
source                      1..17
                            mol_type = other DNA
                            organism = synthetic construct
SEQUENCE: 54
agaagccagg agctaca                                                   17

SEQ ID NO: 55               moltype = DNA   length = 36
FEATURE                     Location/Qualifiers
misc_feature                1..36
                            note = Synthesized
```

```
                           source             1..36
                                              mol_type = other DNA
                                              organism = synthetic construct
SEQUENCE: 55
gtagtgtgcg atcgcgtgcg agaggccaga acaaca                                      36

SEQ ID NO: 56              moltype = DNA   length = 60
FEATURE                    Location/Qualifiers
misc_feature               1..60
                                              note = Synthesized
source                     1..60
                                              mol_type = other DNA
                                              organism = synthetic construct
SEQUENCE: 56
gtgtacgcgt tccgccagaa caacagtgta cgcgttcctg acggagaggc cagaacaaca            60

SEQ ID NO: 57              moltype = DNA   length = 82
FEATURE                    Location/Qualifiers
misc_feature               1..82
                                              note = Synthesized
source                     1..82
                                              mol_type = other DNA
                                              organism = synthetic construct
SEQUENCE: 57
gtgtgcggcc gctatagcgt aagttttttta taacaatggt gtgcggccgc tatagcgatc          60
tcctaagttt tttataacaa tg                                                     82

SEQ ID NO: 58              moltype = DNA   length = 67
FEATURE                    Location/Qualifiers
misc_feature               1..67
                                              note = Synthesized
source                     1..67
                                              mol_type = other DNA
                                              organism = synthetic construct
SEQUENCE: 58
gtgtgcggcc gttataacaa tggtgtgcgg ccgctataac gcgtttccta agttttttat           60
aacaatg                                                                      67

SEQ ID NO: 59              moltype = DNA   length = 83
FEATURE                    Location/Qualifiers
misc_feature               1..83
                                              note = Synthesized
source                     1..83
                                              mol_type = other DNA
                                              organism = synthetic construct
SEQUENCE: 59
gtgtgcggcc gctataacgt aagttttttta taacaatggt gtgcggccgc tataacgcgt          60
ttcctaagtt ttttataaca atg                                                    83

SEQ ID NO: 60              moltype = DNA   length = 19
FEATURE                    Location/Qualifiers
misc_feature               1..19
                                              note = Synthesized
source                     1..19
                                              mol_type = other DNA
                                              organism = synthetic construct
SEQUENCE: 60
gacaacccag gacaggagc                                                         19

SEQ ID NO: 61              moltype = DNA   length = 20
FEATURE                    Location/Qualifiers
misc_feature               1..20
                                              note = Synthesized
source                     1..20
                                              mol_type = other DNA
                                              organism = synthetic construct
SEQUENCE: 61
actctcaatg ttcctccgcc                                                        20

SEQ ID NO: 62              moltype = DNA   length = 20
FEATURE                    Location/Qualifiers
misc_feature               1..20
                                              note = Synthesized
source                     1..20
                                              mol_type = other DNA
                                              organism = synthetic construct
SEQUENCE: 62
gccattcctg gacttgggaa                                                        20
```

```
SEQ ID NO: 63              moltype = DNA   length = 31
FEATURE                    Location/Qualifiers
misc_feature               1..31
                           note = Synthesized
source                     1..31
                           mol_type = other DNA
                           organism = synthetic construct
SEQUENCE: 63
gtgtgcggcc gcaggttgta ctaggtgggt c                                    31

SEQ ID NO: 64              moltype = DNA   length = 20
FEATURE                    Location/Qualifiers
misc_feature               1..20
                           note = Synthesized
source                     1..20
                           mol_type = other DNA
                           organism = synthetic construct
SEQUENCE: 64
agtgattgcc tcccaaggtc                                                 20

SEQ ID NO: 65              moltype = DNA   length = 18
FEATURE                    Location/Qualifiers
misc_feature               1..18
                           note = Synthesized
source                     1..18
                           mol_type = other DNA
                           organism = synthetic construct
SEQUENCE: 65
tgagttcgtg agctttcg                                                   18

SEQ ID NO: 66              moltype = DNA   length = 22
FEATURE                    Location/Qualifiers
misc_feature               1..22
                           note = Synthesized
source                     1..22
                           mol_type = other DNA
                           organism = synthetic construct
SEQUENCE: 66
tctctgtaga ccgtagtgcc ca                                              22

SEQ ID NO: 67              moltype = DNA   length = 19
FEATURE                    Location/Qualifiers
misc_feature               1..19
                           note = Synthesized
source                     1..19
                           mol_type = other DNA
                           organism = synthetic construct
SEQUENCE: 67
caaccccga caaccagag                                                   19

SEQ ID NO: 68              moltype = DNA   length = 20
FEATURE                    Location/Qualifiers
misc_feature               1..20
                           note = Synthesized
source                     1..20
                           mol_type = other DNA
                           organism = synthetic construct
SEQUENCE: 68
caccctaaa ggagacaccg                                                  20

SEQ ID NO: 69              moltype = DNA   length = 44
FEATURE                    Location/Qualifiers
misc_feature               1..44
                           note = Synthesized
source                     1..44
                           mol_type = other DNA
                           organism = synthetic construct
SEQUENCE: 69
gtgtgaatct caagtgtgaa gacttcatgc atcatgggtc tcaa                      44

SEQ ID NO: 70              moltype = DNA   length = 16
FEATURE                    Location/Qualifiers
misc_feature               1..16
                           note = Synthesized
source                     1..16
                           mol_type = other DNA
                           organism = synthetic construct
SEQUENCE: 70
gagcgagcaa actact                                                     16
```

```
SEQ ID NO: 71              moltype = DNA  length = 20
FEATURE                    Location/Qualifiers
misc_feature               1..20
                           note = Synthesized
source                     1..20
                           mol_type = other DNA
                           organism = synthetic construct
SEQUENCE: 71
cccaagtatg ttgcaaccca                                                     20

SEQ ID NO: 72              moltype = DNA  length = 22
FEATURE                    Location/Qualifiers
misc_feature               1..22
                           note = Synthesized
source                     1..22
                           mol_type = other DNA
                           organism = synthetic construct
SEQUENCE: 72
tcgagcacta gcatagtcta ca                                                  22

SEQ ID NO: 73              moltype = DNA  length = 31
FEATURE                    Location/Qualifiers
misc_feature               1..31
                           note = Synthesized
source                     1..31
                           mol_type = other DNA
                           organism = synthetic construct
SEQUENCE: 73
gtgttctaga tcagagcgac cttacatagg a                                        31

SEQ ID NO: 74              moltype = DNA  length = 36
FEATURE                    Location/Qualifiers
misc_feature               1..36
                           note = Synthesized
source                     1..36
                           mol_type = other DNA
                           organism = synthetic construct
SEQUENCE: 74
gtgtcgtctc tatgtcacca caacgagacc ggtgcg                                   36

SEQ ID NO: 75              moltype = DNA  length = 20
FEATURE                    Location/Qualifiers
misc_feature               1..20
                           note = Synthesized
source                     1..20
                           mol_type = other DNA
                           organism = synthetic construct
SEQUENCE: 75
cttgatcggg ttgctagcca                                                     20

SEQ ID NO: 76              moltype = DNA  length = 20
FEATURE                    Location/Qualifiers
misc_feature               1..20
                           note = Synthesized
source                     1..20
                           mol_type = other DNA
                           organism = synthetic construct
SEQUENCE: 76
ccagggaatg tatgggggaa                                                     20

SEQ ID NO: 77              moltype = DNA  length = 20
FEATURE                    Location/Qualifiers
misc_feature               1..20
                           note = Synthesized
source                     1..20
                           mol_type = other DNA
                           organism = synthetic construct
SEQUENCE: 77
atgcttccaa caggcgtgta                                                     20

SEQ ID NO: 78              moltype = DNA  length = 21
FEATURE                    Location/Qualifiers
misc_feature               1..21
                           note = Synthesized
source                     1..21
                           mol_type = other DNA
                           organism = synthetic construct
SEQUENCE: 78
```

```
gttgcctata aaggggtcc c                                           21

SEQ ID NO: 79            moltype = DNA  length = 18
FEATURE                  Location/Qualifiers
misc_feature             1..18
                         note = Synthesized
source                   1..18
                         mol_type = other DNA
                         organism = synthetic construct
SEQUENCE: 79
ggggtccaat tacaggca                                              18

SEQ ID NO: 80            moltype = DNA  length = 40
FEATURE                  Location/Qualifiers
misc_feature             1..40
                         note = Synthesized
source                   1..40
                         mol_type = other DNA
                         organism = synthetic construct
SEQUENCE: 80
gtgttccatc ttgtgttcta gactatattg gttccatctt                      40

SEQ ID NO: 81            moltype = DNA  length = 55
FEATURE                  Location/Qualifiers
misc_feature             1..55
                         note = Synthesized
source                   1..55
                         mol_type = other DNA
                         organism = synthetic construct
SEQUENCE: 81
gcagagacgc gtctttttttt ataacaatgg cagagacgcg tcttttataa caatg    55

SEQ ID NO: 82            moltype = DNA  length = 56
FEATURE                  Location/Qualifiers
misc_feature             1..56
                         note = Synthesized
source                   1..56
                         mol_type = other DNA
                         organism = synthetic construct
SEQUENCE: 82
gctataacgc gtatcttttt tataacaatg gctataacgc gtattttata acaatg    56

SEQ ID NO: 83            moltype = DNA  length = 49
FEATURE                  Location/Qualifiers
misc_feature             1..49
                         note = Synthesized
source                   1..49
                         mol_type = other DNA
                         organism = synthetic construct
SEQUENCE: 83
tatcactctg tgtttttata acaatgtatc actctgtttt ataacaatg            49

SEQ ID NO: 84            moltype = DNA  length = 20
FEATURE                  Location/Qualifiers
misc_feature             1..20
                         note = Synthesized
source                   1..20
                         mol_type = other DNA
                         organism = synthetic construct
SEQUENCE: 84
gtatgctcga gtccctcacg                                            20

SEQ ID NO: 85            moltype = DNA  length = 20
FEATURE                  Location/Qualifiers
misc_feature             1..20
                         note = Synthesized
source                   1..20
                         mol_type = other DNA
                         organism = synthetic construct
SEQUENCE: 85
tctctcgtga ccttgttgct                                            20

SEQ ID NO: 86            moltype = DNA  length = 21
FEATURE                  Location/Qualifiers
misc_feature             1..21
                         note = Synthesized
source                   1..21
                         mol_type = other DNA
                         organism = synthetic construct
```

```
SEQUENCE: 86
acggctgctg aaaatgttag g                                              21

SEQ ID NO: 87              moltype = DNA  length = 20
FEATURE                    Location/Qualifiers
misc_feature               1..20
                           note = Synthesized
source                     1..20
                           mol_type = other DNA
                           organism = synthetic construct
SEQUENCE: 87
agttcaagcc tagttcgcct                                                20

SEQ ID NO: 88              moltype = DNA  length = 20
FEATURE                    Location/Qualifiers
misc_feature               1..20
                           note = Synthesized
source                     1..20
                           mol_type = other DNA
                           organism = synthetic construct
SEQUENCE: 88
aggcttgaga cctctgtcct                                                20

SEQ ID NO: 89              moltype = DNA  length = 20
FEATURE                    Location/Qualifiers
misc_feature               1..20
                           note = Synthesized
source                     1..20
                           mol_type = other DNA
                           organism = synthetic construct
SEQUENCE: 89
atgaaacaag ggcagcatgc                                                20

SEQ ID NO: 90              moltype = DNA  length = 20
FEATURE                    Location/Qualifiers
misc_feature               1..20
                           note = Synthesized
source                     1..20
                           mol_type = other DNA
                           organism = synthetic construct
SEQUENCE: 90
agaagaggac gagggactgg                                                20

SEQ ID NO: 91              moltype = DNA  length = 19
FEATURE                    Location/Qualifiers
misc_feature               1..19
                           note = Synthesized
source                     1..19
                           mol_type = other DNA
                           organism = synthetic construct
SEQUENCE: 91
cgggttatga tcggtgat                                                  19

SEQ ID NO: 92              moltype = DNA  length = 20
FEATURE                    Location/Qualifiers
misc_feature               1..20
                           note = Synthesized
source                     1..20
                           mol_type = other DNA
                           organism = synthetic construct
SEQUENCE: 92
ttgttgcgtg atcccgatga                                                20

SEQ ID NO: 93              moltype = DNA  length = 20
FEATURE                    Location/Qualifiers
misc_feature               1..20
                           note = Synthesized
source                     1..20
                           mol_type = other DNA
                           organism = synthetic construct
SEQUENCE: 93
tcaatgctct aagccaccca                                                20

SEQ ID NO: 94              moltype = DNA  length = 20
FEATURE                    Location/Qualifiers
misc_feature               1..20
                           note = Synthesized
source                     1..20
                           mol_type = other DNA
```

```
                                    organism = synthetic construct
SEQUENCE: 94
tcggcagcaa caacatctca                                                    20

SEQ ID NO: 95           moltype = DNA  length = 20
FEATURE                 Location/Qualifiers
misc_feature            1..20
                        note = Synthesized
source                  1..20
                        mol_type = other DNA
                        organism = synthetic construct
SEQUENCE: 95
ccctacctct agtgtggggt                                                    20

SEQ ID NO: 96           moltype = DNA  length = 20
FEATURE                 Location/Qualifiers
misc_feature            1..20
                        note = Synthesized
source                  1..20
                        mol_type = other DNA
                        organism = synthetic construct
SEQUENCE: 96
acggacctaa gctgtgcaaa                                                    20

SEQ ID NO: 97           moltype = DNA  length = 52
FEATURE                 Location/Qualifiers
misc_feature            1..52
                        note = Synthesized
source                  1..52
                        mol_type = other DNA
                        organism = synthetic construct
SEQUENCE: 97
ctcgcgatat cctgccctcg cgatcgccta attgcggaac cctaatcctg cc               52

SEQ ID NO: 98           moltype = DNA  length = 21
FEATURE                 Location/Qualifiers
misc_feature            1..21
                        note = Synthesized
source                  1..21
                        mol_type = other DNA
                        organism = synthetic construct
SEQUENCE: 98
gccctaggtg gttaggcatt a                                                  21

SEQ ID NO: 99           moltype = DNA  length = 41
FEATURE                 Location/Qualifiers
misc_feature            1..41
                        note = Synthesized
source                  1..41
                        mol_type = other DNA
                        organism = synthetic construct
SEQUENCE: 99
ccttacccaa ctttgtttgg tggccggcat agtcccagcc t                            41

SEQ ID NO: 100          moltype = DNA  length = 18
FEATURE                 Location/Qualifiers
misc_feature            1..18
                        note = Synthesized
source                  1..18
                        mol_type = other DNA
                        organism = synthetic construct
SEQUENCE: 100
tcagcaaaaa acccctca                                                      18

SEQ ID NO: 101          moltype = DNA  length = 36
FEATURE                 Location/Qualifiers
misc_feature            1..36
                        note = Synthesized
source                  1..36
                        mol_type = other DNA
                        organism = synthetic construct
SEQUENCE: 101
ggttgcgcgc atccggatat agttcctcct ttggtt                                  36

SEQ ID NO: 102          moltype = DNA  length = 34
FEATURE                 Location/Qualifiers
misc_feature            1..34
                        note = Synthesized
source                  1..34
```

```
                        mol_type = other DNA
                        organism = synthetic construct
SEQUENCE: 102
gaccatgatt acgccagcgg ccgcatccgg atat                              34

SEQ ID NO: 103          moltype = DNA  length = 24
FEATURE                 Location/Qualifiers
misc_feature            1..24
                        note = Synthesized
source                  1..24
                        mol_type = other DNA
                        organism = synthetic construct
SEQUENCE: 103
agcggataac aatttcacac agga                                         24

SEQ ID NO: 104          moltype = DNA  length = 24
FEATURE                 Location/Qualifiers
misc_feature            1..24
                        note = Synthesized
source                  1..24
                        mol_type = other DNA
                        organism = synthetic construct
SEQUENCE: 104
tattaccgcc tttgagtgag ctga                                         24

SEQ ID NO: 105          moltype = DNA  length = 20
FEATURE                 Location/Qualifiers
misc_feature            1..20
                        note = Synthesized
source                  1..20
                        mol_type = other DNA
                        organism = synthetic construct
SEQUENCE: 105
cttttttacgg ttcctggcct                                             20

SEQ ID NO: 106          moltype = DNA  length = 19
FEATURE                 Location/Qualifiers
misc_feature            1..19
                        note = Synthesized
source                  1..19
                        mol_type = other DNA
                        organism = synthetic construct
SEQUENCE: 106
acatttcccc gaaaagtgc                                               19
```